US012747249B2

(12) United States Patent
Ernst et al.

(10) Patent No.: US 12,747,249 B2
(45) **Date of Patent: *Sep. 29, 2026**

(54) EIF4A-INHIBITING COMPOUNDS AND METHODS RELATED THERETO

(71) Applicant: SJP Biotec GmbH, Meilen (CH)

(72) Inventors: Justin T. Ernst, San Diego, CA (US); Siegfried H. Reich, La Jolla, CA (US); Paul A. Sprengeler, Escondido, CA (US); Chinh Viet Tran, San Diego, CA (US); Garrick Kenneth Packard, San Diego, CA (US); Alan X. Xiang, Irvine, CA (US); Christian Nilewski, La Jolla, CA (US); Theo Michels, San Diego, CA (US)

(73) Assignee: SJP Biotec GmbH, Zürich (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/324,616

(22) Filed: May 26, 2023

(65) Prior Publication Data

US 2023/0295179 A1 Sep. 21, 2023

Related U.S. Application Data

(60) Continuation of application No. 17/720,529, filed on Apr. 14, 2022, now abandoned, which is a continuation of application No. 16/804,937, filed on Feb. 28, 2020, now Pat. No. 11,440,917, which is a continuation of application No. 15/917,973, filed on Mar. 12, 2018, now Pat. No. 10,577,378, which is a division of application No. 15/358,761, filed on Nov. 22, 2016, now Pat. No. 9,957,277.

(60) Provisional application No. 62/334,149, filed on May 10, 2016, provisional application No. 62/259,828, filed on Nov. 25, 2015.

(51) Int. Cl.

| | |
|---|---|
| ***C07D 491/048*** | (2006.01) |
| ***C07D 307/93*** | (2006.01) |
| ***C07D 333/78*** | (2006.01) |
| ***C07D 491/153*** | (2006.01) |
| ***C07D 491/16*** | (2006.01) |
| ***C07D 491/20*** | (2006.01) |
| ***C07D 498/14*** | (2006.01) |
| ***C07D 519/00*** | (2006.01) |

(52) U.S. Cl.

CPC ....... *C07D 491/048* (2013.01); *C07D 307/93* (2013.01); *C07D 333/78* (2013.01); *C07D 491/153* (2013.01); *C07D 491/16* (2013.01); *C07D 491/20* (2013.01); *C07D 498/14* (2013.01); *C07D 519/00* (2013.01)

(58) Field of Classification Search

CPC .................................................. C07D 491/048

See application file for complete search history.

(56) References Cited

U.S. PATENT DOCUMENTS

| | | | | |
|---|---|---|---|---|
| 8,404,088 | B2 | 3/2013 | Porco et al. | |
| 9,957,277 | B2 | 5/2018 | Ernst et al. | |
| 10,577,378 | B2 * | 3/2020 | Ernst ........................ | A61P 43/00 |
| 11,440,917 | B2 | 9/2022 | Ernst et al. | |
| 2009/0082371 | A1 | 3/2009 | Lu | |
| 2012/0238766 | A1 | 9/2012 | Porco et al. | |
| 2017/0137400 | A1 | 5/2017 | Marion et al. | |
| 2017/0145026 | A1 | 5/2017 | Ernst et al. | |
| 2018/0298017 | A1 | 10/2018 | Emst et al. | |
| 2020/0339590 | A1 | 10/2020 | Ernst et al. | |
| 2023/0071483 | A1 | 3/2023 | Ernst et al. | |

FOREIGN PATENT DOCUMENTS

| | | | |
|---|---|---|---|
| CA | 2567404 | A1 | 12/2005 |
| CA | 2744309 | A1 | 6/2010 |
| DE | 19934952 | A1 | 2/2000 |

(Continued)

OTHER PUBLICATIONS

Bartlett "Exploiting Chemical Diversity for Drug Discovery" Edited by Paul A Bartlett and Michael Entzeroth, The Royal Society of Chemistry, 2006, pp. 113-118.*

"Find ETDs Home >> Thesis Resources >> Find ETDs" Online: "https://ndltd.org/thesis-resources/find-etds/" Accessed Jan. 31, 2023.*

Irwin "ZINC—A Free Database of Commercially Available Compounds for Virtual Screening" J. Chem. Inf. Model. 2005, 45, 177-182.*

Kim "PubChem in 2021: new data content and improved web interfaces" Nucleic Acids Research, 2021, vol. 49, Database issue Published online Nov. 5, 2020.*

STN Registry/Zregistry (CAS Registrysm) Sep. 2016 2 pages.*

Modelska (Cell Death & Disease (2015), 6(1), e1603).*

Pelletier (Cancer Res. 2015, 75(2): 250-263).*

(Continued)

*Primary Examiner* — Nizal S Chandrakumar

(74) *Attorney, Agent, or Firm* — Mintz Levin Cohn Ferris Glovsky and Popeo P.C.

(57) ABSTRACT

The present invention provides synthesis, pharmaceutically acceptable formulations and uses of compounds in accordance with Formula I, or a stereoisomer, tautomer or pharmaceutically acceptable salt thereof.

(I)

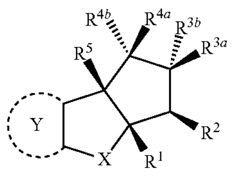

For Formula I compounds X, Y, $R^1$, $R^2$, $R^{3a}$, $R^{3b}$, $R^{4a}$, $R^{4b}$ and $R^5$ are as defined in the specification. The inventive Formula I compounds are inhibitors of eIF4A and find utility in any number of therapeutic applications, including but not limited to treatment of inflammation and various cancers.

4 Claims, No Drawings

(56) References Cited

FOREIGN PATENT DOCUMENTS

| | | | |
|---|---|---|---|
| EP | 1693059 | A1 | 8/2006 |
| EP | 3380101 | B1 | 1/2021 |
| FR | 3023290 | A1 | 1/2016 |
| NO | 2013016658 | A1 | 1/2013 |
| WO | 2005054457 | A1 | 6/2005 |
| WO | 2005092876 | A1 | 10/2005 |
| WO | 2006007634 | A1 | 1/2006 |
| WO | 2007139749 | A2 | 12/2007 |
| WO | 2011140334 | A2 | 11/2011 |
| WO | 2011140334 | A3 | 3/2012 |
| WO | 2012066002 | A1 | 5/2012 |
| WO | 2013170257 | A1 | 11/2013 |
| WO | 2015007714 | A1 | 1/2015 |
| WO | 2015075165 | A1 | 5/2015 |
| WO | 2016001441 | A1 | 1/2016 |
| WO | 2017091585 | A1 | 6/2017 |
| WO | 2019170257 | A1 | 9/2019 |

OTHER PUBLICATIONS

Damia, European Journal of Cancer 2009, 45, 2768-2781.*
Ocana, Nat. Rev. Clin. Oncol. 2011, 8, 200-209.*
Jorden, ZCommunications >> World Alzheimer Day:, Dec. 20, 2015.*
Sharma, Nature Reviews Cancer Apr. 2010, vol. 10, 241-253.*
Modelska, Cell Death and Disease (2015) 6, e1603.*
International Preliminary Report on Patentability received for PCT International Application No. PCT/US2016/063353, mailed on Jun. 7, 2018, 7 pages.
International Search Report received for PCT Patent International Application No. PCT/US2016/063353, mailed on Apr. 5, 2017, 10 pages.
Alachkar. (2013) "Silvestrol Exhibits Significant in Vivo and in Vitro Antileukemic Activities and Inhibits FL T3 and miR-155 Expressions in Acute Myeloid Leukemia", Journal of Hematology & Oncology, 6(21):1-12.
Alinari et al. (2012) "Dual Targeting of the Cyclin/Rb/E2F and Mitochondrial Pathways in Mantle Cell Lymphoma with the Translation Inhibitor Silvestrol", Clinical Cancer Research, 18(17):4600-4611.
Andreou et al. (Sep. 2012) "The DEAD-Box Helicase eIF4A: Paradigm or the Odd One Out?", RNA Biology, 10(1):19-32.
Bhat et al. (Apr. 2015) "Targeting the Translation Machinery in Cancer", Nature Reviews Drug Discovery, 14(4):261-278.
Bordeleau et al. (2008) "Therapeutic Suppression of Translation Initiation Modulates Chemosensitivity in a Mouse Lymphoma Model", The Journal of Clinical Investigation, 118(7):2651-2660.
Borisov et al. (Mar. 2007) "Nenitzescu Synthesis of Carbamate Indole Derivatives from N,N'-Bis (methoxycarbonyl)-p-benzoquinone Diimine", Russian Journal of Organic Chemistry, 43(3):414-416.
Boussemart et al. (Sep. 4, 2014) "elF4F is a Nexus of Resistance to Anti-BRAF and Anti-MEK Cancer Therapies", Nature, 513:105-109.
Bruce et al. (May 28, 1999) "Synthesis of the Carbocyclic Analogue of (±)-Rocaglamide", Tetrahedron Letters, 40(22):4279-4282.
Cencic et al. (Apr. 2009) "Antitumor Activity and Mechanism of Action of the Cyclopenta[b]benzofuran, Silvestrol", Plos One, 4(4):e5223 (14 pages).
Chambers et al. (Mar. 2013) "Synthesis of Biotinylated Episilvestrol: Highly Selective Targeting of the Translation Factors eIF4AI/II", Organic Letters, 15(6):1406-1409.
Chambers et al. (Jan. 15, 2016) "Total Synthesis of a Biotinylated Rocaglate: Selective Targeting of the Translation Factors eIF4AI/II", Bioorganic & Medicinal Chemistry Letters, 26(2):262-264.
Crown et al. (2004) "Docetaxel and Paclitaxel in the Treatment of Breast Cancer: A Review of Clinical Experience", The Oncologist, 9(suppl 2):24-32.
Damia et al. (2009) "Contemporary Pre-Clinical Development of Anticancer Agents—What are the Optimal Preclinical Models?", European Journal of Cancer, 45:2768-2781.
Harms et al. (May 21, 2014) "eIF4B, eIF4G and RNA Regulate eIF4A Activity in Translation Initiation by Modulating the eIF4A Conformational Cycle", Nucleic Acid Research, 42(12):7911-7922.
Hong-Sen et al. (2008) "Competitive Intramolecular Reductive Cross-Coupling Reaction Between Ketone-Ester and Ketone-Cyano Promoted by Sml2", Journal of Shanxi University, 215-217.
Johnson et al. (2001) "Relationships Between Drug Activity in NCI Preclinical in Vitro and in Vivo Models and Early Clinical Trials", British Journal of Cancer, 84(10):1424-1431.
Jorden Danica. (Sep. 22, 2015) "World Alzheimer Day: French Doctor Denounces Routine Alzheimer Medications", ZCommunications, 4 pages.
Koeffler et al. (Nov. 1991) "Molecular Mechanisms of Cancer", Conferences and Reviews, 155(5):505-514.
Kogure et al. (Sep. 26, 2013) "Therapeutic Potential of the Translation Inhibitor Silvestro! in Hepatocellular Cancer", Plos One, Article No. e76136, 8(9):1-14.
Li et al. (2016) "Co-Targeting Translation and Proteasome Rapidly Kills Colon Cancer Cells with Mutant RAS/RAF via ER Stress", Oncotarget, 8(6):1-13.
Lin et al. (2012) "Targeting Synthetic Lethal Interactions Between Myc and the eIF4F Complex Impedes Tumorigenesis", Cell reports, 1:325-333.
Li-Weber Min. (Oct. 15, 2015) "Molecular Mechanisms and Anti-Cancer Aspects of the Medicinal Phytochemicals Rocaglamides (=flavaglines)", International Journal of Cancer, 137(8):1791-1799.
Luan et al. (2015) "Rocaglamide Overcomes Tumor Necrosis Factor-Related Apoptosis-Inducing Ligand Resistance In Hepatocellular Carcinoma Cells by Attenuating the Inhibition of Caspase-8 Through Cellular FLICE-Like-Inhibitor Protein Downregulation", Molecular Medicine Reports, 11:203-211.
Lucas et al. (2009) "The Novel Plant-Derived Agent Silvestrol has B-Cell Selective Activity in Chronic Lymphocytic Leukemia and Acute Lymphoblastic Leukemia in Vitro and in Vivo", Blood, 113(19):4655-4666.
Marintchev et al. (Feb. 6, 2009) "Topology and Regulation of the Human eIF4A/4G/4H Helicase Complex in Translation Initiation", Cell, 136(3):447-460.
Mi et al. (2006) "Rocaglaol Induces Apoptosis and Cell Cycle Arrest in LNCaP Cells", Anticancer Research, 26(2A):947-952.
Modelska et al. (2015) "The Malignant Phenotype in Breast Cancer is Driven by eIF4A1-Mediated Changes in the Translational Landscape", Cell Death and Disease, 6:13 pages.
Mokhtari et al. (2017) "Combination Therapy in Combating Cancer", Oncotarget, 8(23):38022-38043.
Nguyen et al. (Aug. 1, 2018) "FGFR1-Activated Translation of WNT Pathway Components with Structured 5' UTRs is Vulnerable to Inhibition of EIF4A-Dependent Translation Initiation", The Journal of Cancer Research, 78 (15):4229-4240.
Oblinger et al. (2016) "Components of the eIF4F Complex are Potential Therapeutic Targets for Malignant Peripheral Nerve Sheath Tumors and Vestibular Schwannomas", Neuro-Oncology, 18(9):1-13.
Ocana et al. (2011) "Preclinical Development of Molecular-Targeted Agents for Cancer", Nature Reviews Clinical Oncology, 8:200-209.
Parsyan et al. (Apr. 2012) "mRNA Helicases: The Tacticians of Translational Control", Nature Reviews Molecular Cell Biology, 12(4):235-245.
Pelletier et al. (2015) "Targeting The eiF4F Translation Initiation Complex: A Critical Nexus for Cancer Development", Cancer Research, 75(2):250-263.
Pubchem. (Oct. 20, 2014) "7-oxa-11-azatricyclo[6.4.0.02,6]dodeca-1(8),2(6), 9, 11-tetraen-12-ylmethanamine", PubChem CID 82405096, 6 pages.
Pubchem. (Oct. 26, 2006) "N, N-Dimethyl-1alpha-Phenyl-3beta, 3aalpha-Dihydroxy-4,6-Dimethoxy-8aalpha-(4-Methoxyphenyl)-1,2,3,3a,8,8a-Hexahydrocyclopenta[A]Indene-2beta-Carboxamide", PubChem CID 11691869, 7 Pages.

(56) References Cited

OTHER PUBLICATIONS

Raza et al. (Dec. 2015) "Translational Dysregulation in Cancer: eIF4A Isoforms and Sequence Determinants of eIF4A Dependence", Biochemical Society Transactions, 43(6):1227-1233.
Roche et al. (Sep. 2010) "Biomimetic Photocycloaddition of 3-Hydroxyflavones: Synthesis and Evaluation of Rocaglate Derivatives as Inhibitors of Eukaryotic Translation", Angewandte Chemie, 49(37):6533-6538.
Rodrigo et al. (Nov. 30, 2012) "Synthesis of Rocaglamide Hydroxamates and Related Compounds as Eukaryotic Translation Inhibitors: Synthetic and Biological Studies", Journal of Medicinal Chemistry, 55(1):558-562.
Santagata et al. (2013) "Tight Coordination of Protein Translation and Heat Shock Factor 1 Activation Supports the Anabolic Malignant State", Science, 341(6143):1-21.
Sharma et al. (Apr. 2010) "Cell Line-Based Platforms to Evaluate the Therapeutic Efficacy of Candidate Anticancer Agents", Nature Reviews Cancer, 10:241-253.
Sugowdz et al. (1973) "Photochemical Synthesis. VI.The Formation of Benzosemibullvalene Derivatives in the Photoaddition of Diphenylacetylene to Methyl 2-Naphthoate, A Degenerate Thermal Isomerization of the Benzosemibullvalene Skeleton", Australian Journal of Chemistry, 26(1):147-171.
Suzuki et al. (Mar. 4, 2008) "PDCD4 Inhibits Translation Initiation by Binding to eIF4A Using Both its MA3 Domains", PNAS, 105(9):3274-3279.
Thuaud et al. (Dec. 13, 2010) "Novel Flavaglines Displaying Improved Cytotoxicity", Journal of Medicinal Chemistry, 54(1):411-415.
Trost et al. (Nov. 1, 1990) "An Unusual Oxidative Cyclization. A Synthesisand Absolute Stereochemical Assignment of (−)-Rocaglamide", Journal of the American Chemical Society, 112(24): 9022-9024.
Venkatesh et al. (Feb. 2000) "Role of the Development Scientist in Compound Lead Selection and Optimization", Journal of Pharmaceutical Sciences, 89(2):145-154.
Wang et al. (2016) "Chinese Herb Derived-Rocaglamide A is a Potent Inhibitor of Pancreatic Cancer Cells", American Journal of Translational Research, 8(2):1047-1054.
Wang et al. (2016) "Synthesis of Aza-Rocaglates via ESIPT-Mediated (3+2) Photocydoaddition", Chemistry: A European Journal, 22:12006-12010.
Wolfe et al. (Sep. 4, 2014) "RNA G-Quadruplexes Cause eIF4A-Dependent Oncogene Translation in Cancer", Nature, 513(7516):65-70.

* cited by examiner

EIF4A-INHIBITING COMPOUNDS AND METHODS RELATED THERETO

CROSS-REFERENCE TO RELATED PATENT APPLICATIONS

This application is a continuation of U.S. application Ser. No. 17/720,529 filed on Apr. 14, 2022, which is a continuation of U.S. application Ser. No. 16/804,937, filed on Feb. 28, 2020, now U.S. Pat. No. 11,440,917, issued on Sep. 13, 2022, which is a continuation of U.S. application Ser. No. 15/917,973, filed on Mar. 12, 2018, now U.S. Pat. No. 10,577,378, issued on Mar. 3, 2020, which is a divisional of U.S. application Ser. No. 15/358,761, filed on Nov. 22, 2016, now U.S. Pat. No. 9,957,277, issued on May 1, 2018, which claims the benefit of U.S. Provisional Application No. 62/334,149, filed on May 10, 2016 and U.S. Provisional Application No. 62/259,828, filed on Nov. 25, 2015. The entire contents of these applications are incorporated herein by reference in their entireties.

FIELD

The present invention generally relates to compounds having activity as inhibitors of eukaryotic initiation factor 4A (eIF4A), such as eIF4AI and eIF4AII, as well as to related compositions and methods for utilizing the inventive compounds as therapeutic agents for treatment of eIF4A dependent diseases, including the treatment of cancer.

BACKGROUND

Translation is the process where the sequence of an mRNA directs the synthesis of a specific protein. The translation of most cellular mRNA, and especially those that contain highly structured 5'-UTRs or an IRES element, depends on the formation of a functional eIF4F (eukaryotic initiation factor 4F) complex consisting of eIF4A, eIF4E and eIF4G. A. Marintchev et al., *Cell,* 2009; 136, 447-460. These eIF4 proteins are involved in the initiation phase of translation and help catalyze the recruitment of mRNA to the 40S ribosomal subunit to form the 48S initiation complex. eIF4F recognizes the cap structure at the 5'-end of mRNA through eIF4E, unwinds the secondary structure of the 5'-UTR region through the helicase activity of eIF4A, and binds the 43S complex through interactions between eIF4G and eIF3. A. Parsyan et al., *Nature Reviews, Molecular Cell Biology,* 2011; 12, 235-245.

The translation initiation factor eIF4A is a member of the "DEAD box" family of ATP-dependent helicases that acts as an RNA dependent ATPase and ATP-dependent RNA helicase to facilitate mRNA binding to the ribosome as part of the eIF4F complex. eIF4A consists of two distinct domains connected through a short linker that are both required for function. The enzymatic activity of eIF4A is stimulated by formation of a stable complex with eIF4G. The helicase activity of eIF4A either alone or as part of the eIF4F complex is increased through a transient interaction with eIF4B. eIF4A exists as a free form (eIF4$A_f$) and as a subunit of eIF4F (eIF4$A_c$) and is thought to cycle through the eIF4F complex during initiation. When bound in the eIF4F complex, eIF4$A_c$ is ~20-fold more efficient as an RNA helicase than when found alone, leading to the proposal that eIF4$A_c$ is the functional helicase for translation initiation. The helicase activity of eIF4F (via eIF4$A_c$) is thought to unwind local secondary structure in the 5'UTR of mRNAs to facilitate cap-dependent ribosome recruitment. See, e.g., U. Harms et al., *Nucleic Acids Research,* 2014; 1-12; A. Andreou et al., *RNA Biology,* 2013; 10, 19-32.

There are three eIF4A family members: eIF4AI, eIF4AII, and eIF4AIII. eIF4AI and eIF4AII show 90-95% similarity at the amino acid level, are involved in translation and are essential for growth and development. In addition to its role in translation initiation, isoform eIF4AII also has been implicated in microRNA mediated mRNA silencing. eIF4AIII is 65% similar to the other two isoforms and is involved in nonsense-mediated decay. All three eIF4A isoforms are members of the DEAD-box putative RNA helicase protein family that are characterized by seven highly conserved amino acid sequence motifs implicated in RNA remodeling. These proteins are involved in virtually all aspects of cellular RNA metabolism, including ribosome biogenesis, splicing, translation, and mRNA degradation.

eIF4A selectively regulates the translation of a subset of mRNAs. This selectivity is a result of structural elements and sequence recognition motifs found within the 5'-UTR of the mRNA. Translation inhibition can also be regulated by the tumor suppressor programmed cell death 4 (PDCD4). PDCD4 is a negative regulator of translation that binds and sequesters eIF4A. The association of PDCD4 with eIF4A induces a conformational change that prevents eIF4G from binding with eIF4A inhibiting translation initiation. C. Suzuki et al., *PNAS,* 2008; 105, 3274-3279.

Regulation of translation is an increasingly important field as it has implications in a range of diseases. Translation initiation is rate limiting and is dependent on the eukaryotic initiation factors. Alterations in the expression of eIF4A or factors (i.e. eIF4E, eIF4B and PDCD4) that alter its activity have been observed in many cancers. eIF4E is a well-established oncogene that regulates the translation of oncogenic mRNAs with long or structured 5'-UTRs. Overexpression of eIF4A, eIF4E and eIF4B has been associated with poor prognosis in disease indications including lymphoma, lung, colon, liver, ovarian and breast cancer. Decreased expression of PDCD4 has been linked to the development and progression of several types of cancer including lung, colon and liver. High levels of PDCD4 have been associated with good outcomes in certain types of breast cancer. See M. Bhat, *Nature Reviews Drug Discovery,* 2014; 14 261-278; A Modelska et al., *Cell Death and Disease,* 2015; 6, e1603.

Accordingly, while advances have been made in this field there remains a significant need in the art for compounds that specifically inhibit eFI4A activity, particularly with regard to eIF4A's role in regulation of cancer pathways, as well as for associated composition and methods. The present invention fulfills this need and provides further related advantages.

SUMMARY

The present invention is directed to compounds that inhibit or modulate the activity of eIF4A, as well as stereoisomers, tautomers and pharmaceutically acceptable salts of such compounds. The present invention also is directed to pharmaceutically acceptable compositions containing such compounds and associated methods for treating conditions that would benefit from eIF4A inhibition, such as cancer.

In one embodiment the invention is directed to compounds according to Formula I

I

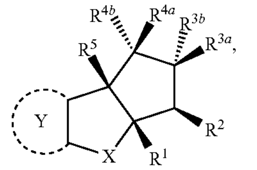

or stereoisomers, tautomers, or pharmaceutically acceptable salts thereof, wherein:

X is $CR^6R^7$, O, S, NH, $N(C_1\text{-}C_8)$alkyl, C(O), $C{=}CR^6R^7$, N(CO)R, S(O) or $S(O)_2$;

Y is a 5-membered heteroaryl or a 6-membered aryl or heteroaryl;

$R^1$ and $R^2$ independently are aryl, heterocyclyl, heteroaryl or cycloalkyl;

$R^{3a}$, $R^{3b}$, $R^{4a}$ and $R^{4b}$ independently are H, halogen, CN, $C_1$-$C_8$(alkyl), ($C_1$-$C_8$)haloalkyl, $C_2$-$C_8$(alkenyl), ($C_2$-$C_8$)alkynyl, $OR^9$, $NHR^9$, $NR^9R^9$, [($C_1$-$C_8$)alkylene]$OR^9$, [($C_1$-$C_8$)alkylene]$NHR^9$, [($C_1$-$C_8$)alkylene]$NR^9R^9$, $C(O)R^8$, $C(O)NHR^9$, $C(O)NR^9R^9$, C(O)[($C_1$-$C_8$)alkylene]$NHR^9$, C(O)[($C_1$-$C_8$)alkylene]$NR^9R^9$, $CO_2R^9$, $C(S)NHR^9$, $C(S)NR^9R^9$, $SR^9$, $S(O)R^9$, $SO_2R^9$, $SO_2NHR^9$, $SO_2NR^9R^9$, $NH(CO)R^8$, $NR^9(CO)R^8$, $NH(CO)NHR^9$, $NH(CO)NR^9R^9$, $NR^9(CO)NHR^9$, $NR^9(CO)NR^9R^9$, $P(O)(OH)(OR^9)$, $P(O)(OR^9)(OR^9)$, aryl, heteroaryl, cycloalkyl or heterocyclyl;

$R^{3a}$ and $R^{3b}$, and $R^{4a}$ and $R^{4b}$ independently combine to form oxo or alkenyl, or a cycloalkyl or heterocyclyl ring; or $R^{3a}$ and $R^{4a}$, $R^{3b}$ and $R^{4b}$ or $R^{4a}$ and $R^5$ together with the carbon atom to which they are attached form a cycloalkyl or heterocyclyl ring; or $R^2$ and $R^{3a}$ together with the carbon atom to which they are attached form a bicyclic ring system;

$R^5$ is H, halogen, OH, CN, $N_3$, $SR^9$, ($C_1$-$C_8$)alkyl, ($C_1$-$C_8$)haloalkyl, O($C_1$-$C_8$)alkyl, O($C_1$-$C_8$)haloalkyl, ($C_2$-$C_8$)alkynyl, NHC(O)($C_1$-$C_8$)alkyl or heteroaryl;

$R^6$ and $R^7$ independently are H, CN, halogen, $OR^9$, $SR^9$, ($C_1$-$C_8$)alkyl, $NH(R^9)$ or $NR^9R^9$;

$R^8$ is H, ($C_1$-$C_8$)alkyl, ($C_1$-$C_8$)haloalkyl, O($C_1$-$C_8$)alkyl, O($C_1$-$C_8$)haloalkyl, cycloalkyl, O(cycloalkyl), heterocyclyl, O(heterocyclyl), aryl, O(aryl), heteroaryl or O(heteroaryl);

$R^9$ is H, ($C_1$-$C_8$)alkyl, ($C_1$-$C_8$)haloalkyl, cycloalkyl, heterocyclyl, [($C_1$-$C_8$)alkylene]heterocyclyl, aryl, [($C_1$-$C_8$)alkylene] aryl or heteroaryl;

wherein the two $R^9$'s together with the nitrogen atom to which they are attached of $NR^9R^9$, [($C_1$-$C_8$)alkylene]$NR^9R^9$, $C(O)NR^9R^9$, C(O)[($C_1$-$C_8$)alkylene]$NR^9R^9$, $C(S)NR^9R^9$, $SO_2NR^9R^9$, $NH(CO)NR^9R^9$ or $NR^9(CO)NR^9R^9$, optionally form a heterocyclyl ring;

wherein any alkyl, alkenyl, cycloalkyl, heterocyclyl, heteroaryl or aryl is optionally substituted with 1, 2, or 3 groups selected from OH, CN, SH, $SO_2NH_2$, $SO_2$($C_1$-$C_4$)alkyl, $SO_2NH$($C_1$-$C_4$)alkyl, halogen, $NH_2$, NH($C_1$-$C_4$)alkyl, N[($C_1$-$C_4$)alkyl]$_2$, $C(O)NH_2$, COOH, COOMe, acetyl, ($C_1$-$C_8$)alkyl, O($C_1$-$C_8$)alkyl, O($C_1$-$C_8$)haloalkyl, ($C_2$-$C_8$)alkenyl, ($C_2$-$C_8$)alkynyl, haloalkyl, thioalkyl, cyanomethylene, alkylaminyl, $NH_2$—C(O)-alkylene, NH(Me)—C(O)-alkylene, $CH_2$—C(O)-lower alkyl, C(O)-lower alkyl, alkylcarbonylaminyl, $CH_2$—[CH(OH)]$_m$—$(CH_2)_p$—OH, $CH_2$—[CH(OH)]$_m$—$(CH_2)_p$—$NH_2$ or $CH_2$-aryl-alkoxy;

or wherein any alkyl, cycloalkyl or heterocyclyl is optionally substituted with oxo;

"m" and "p" are 1, 2, 3, 4, 5 or 6; and wherein when Y is a 6-membered aryl then X is not 0.

In one embodiment the 6-membered aryl or heteroaryl

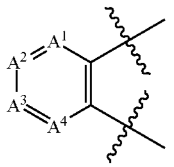

wherein $A^1$ is N or $CR^{10}$;

$A^2$ is N or $CR^{11}$;

$A^3$ is N or $CR^{12}$;

$A^4$ is N or $CR^{13}$; and $R^{10}$, $R^{11}$, $R^{12}$ and $R^{13}$ independently are H, halogen, $C_1$-$C_8$(alkyl), ($C_1$-$C_8$)haloalkyl, C(O)O($C_1$-$C_8$)alkyl, C(O)($C_1$-$C_8$)alkyl, $SO_2$($C_1$-$C_8$)alkyl, $C_2$-$C_8$(alkenyl), ($C_2$-$C_8$)alkynyl, $OR^9$, $NHR^9$, $NR^9R^9$, CN, [($C_1$-$C_8$)alkylene]$OR^9$, [($C_1$-$C_8$)alkylene]$NHR^9$, [($C_1$-$C_8$)alkylene]$NR^9R^9$, $C(O)R^8$, $C(O)NHR^9$, $C(O)NR^9R^9$, C(O)[($C_1$-$C_8$)alkylene]$NHR^9$, C(O)[($C_1$-$C_8$)alkylene]$NR^9R^9$, $CO_2R^9$, $C(S)NHR^9$, $C(S)NR^9R^9$, $SR^9$, $S(O)R^9$, $SO_2R^9$, $SO_2NHR^9$, $SO_2NR^9R^9$, $NH(CO)R^8$, $NR^9(CO)R^8$, $NH(CO)NHR^9$, $NH(CO)NR^9R^9$, $NR^9(CO)NHR^9$, $NR^9(CO)NR^9R^9$, $P(O)(OH)(OR^9)$, $P(O)(OR^9)(OR^9)$, aryl, heteroaryl, cycloalkyl or heterocyclyl.

In one embodiment the 5-membered heteroaryl is

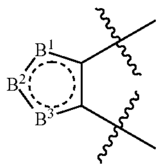

wherein any two of $B^1$, $B^2$ and $B^3$ are $CR^{14}$ and N and the remaining B ring atom is $N(R^{15})$ or S, wherein $R^{14}$ is H, CN, halogen, $OR^9$, $SR^9$, ($C_1$-$C_8$)alkyl, C(O)O($C_1$-$C_8$)alkyl, C(O)($C_1$-$C_8$)alkyl, $SO_2$($C_1$-$C_8$)alkyl, $SO_2NR^9R^9$, $C(O)NR^9R^9$, $NR^9R^9$ or $NR^9C(O)R$, and $R^{15}$ is H or ($C_1$-$C_8$)alkyl.

The present invention also provides a pharmaceutical composition comprising (i) a therapeutically effective amount of at least one compound according to Formula I or a stereoisomer, a tautomer or a pharmaceutically acceptable salt thereof; (ii) in combination with a pharmaceutically acceptable carrier, diluent or excipient.

Also provided by the present invention is a method for attenuating or inhibiting the activity of eIF4A in at least one cell overexpressing eIF4A, comprising contacting the at least one cell with a compound according to claim 1 or a stereoisomer, tautomer or pharmaceutically acceptable salt thereof.

According to the inventive method at least one cell is a colon cancer cell, a gastric cancer cell, a thyroid cancer cell, a lung cancer cell, a leukemia cell, a B-cell lymphoma, a T-cell lymphoma, a hairy cell lymphoma, Hodgkins lymphoma cell, non-Hodgkins lymphoma cell, Burkitt's lymphoma cell, a pancreatic cancer cell, a melanoma cell, a multiple melanoma cell, a brain cancer cell, a CNS cancer cell, a renal cancer cell, a prostate cancer cell, an ovarian cancer cell, or a breast cancer cell.

According to yet another embodiment the invention provides a method for treating a eIF4A dependent condition in a mammal in need thereof comprising administering to the mammal (i) a therapeutically effective amount of at least one compound according to claim 1 or a stereoisomer, tautomer or pharmaceutically acceptable salt thereof, or (ii) a pharmaceutical composition in accordance with the invention.

Compounds and pharmaceutically acceptable formulations in accordance with the invention are useful for treating an eIF4A dependent condition such as colon cancer, colorectal cancer, gastric cancer, thyroid cancer, lung cancer, leukemia, B-cell lymphoma, T-cell lymphoma, hairy cell lymphoma, Hodgkins lymphoma, non-Hodgkins lymphoma, Burkitt's lymphoma, pancreatic cancer, melanoma, multiple melanoma, brain cancer, CNS cancer, renal cancer, prostate cancer, ovarian cancer or breast cancer.

The above embodiments and other aspects of the invention are readily apparent in the detailed description that follows. Various references are set forth herein which describe in more detail certain background information, procedures, compounds and/or compositions, and are each hereby incorporated by reference in their entirety.

DETAILED DESCRIPTION

In the following description certain specific details are set forth in order to provide a thorough understanding of various embodiments of the invention. However, one skilled in the art will understand that the invention may be practiced without these details. Unless the context requires otherwise, throughout the present specification and claims, the word "comprise" and variations thereof, such as, "comprises" and "comprising" are to be construed in an open, inclusive sense (i.e., as "including, but not limited to").

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Definitions

As used herein, and unless noted to the contrary, the following terms and phrases have the meaning noted below.

"Amino" refers to the —$NH_2$ substituent.

"Aminocarbonyl" refers to the —C(O)$NH_2$ substituent.

"Carboxyl" refers to the —$CO_2$H substituent.

"Carbonyl" refers to a —C(O)—, —(CO)— or —C(O)— group. All notations are used interchangeably within the specification.

"Cyano" refers to the —C≡N substituent.

"Cyanoalkylene" refers to the -(alkylene)C° N substituent.

"Acetyl" refers to the —C(O)$CH_3$ substituent.

"Hydroxy" or "hydroxyl" refers to the —OH substituent.

"Hydroxyalkylene" refers to the -(alkylene)OH substituent.

"Oxo" refers to a ═O substituent.

"Thio" or "thiol" refer to a —SH substituent.

"Alkyl" refers to a saturated, straight or branched hydrocarbon chain radical consisting solely of carbon and hydrogen atoms, having from one to twelve carbon atoms ($C_1$-$C_{12}$ alkyl), from one to eight carbon atoms ($C_1$-$C_5$ alkyl) or from one to six carbon atoms ($C_1$-$C_6$ alkyl), and which is attached to the rest of the molecule by a single bond. Exemplary alkyl groups include methyl, ethyl, n-propyl, 1-methylethyl (isopropyl), n-butyl, n-pentyl, 1,1-dimethylethyl (t-butyl), 3-methylhexyl, 2-methylhexyl, and the like.

"Lower alkyl" has the same meaning as alkyl defined above but having from one to four carbon atoms ($C_1$-$C_4$ alkyl).

"Alkenyl" refers to an unsaturated alkyl group having at least one double bond and from two to twelve carbon atoms ($C_2$-$C_{12}$ alkenyl), from two to eight carbon atoms ($C_2$-$C_8$ alkenyl) or from two to six carbon atoms ($C_2$-$C_6$ alkenyl), and which is attached to the rest of the molecule by a single bond, e.g., ethenyl, propenyl, butenyl, pentenyl, hexenyl, and the like.

"Alkynyl" refers to an unsaturated alkyl group having at least one triple bond and from two to twelve carbon atoms ($C_2$-$C_{12}$ alkynyl), from two to ten carbon atoms ($C_2$-$C_{10}$ alkynyl) from two to eight carbon atoms ($C_2$-$C_8$ alkynyl) or from two to six carbon atoms ($C_2$-$C_6$ alkynyl), and which is attached to the rest of the molecule by a single bond, e.g., ethynyl, propynyl, butynyl, pentynyl, hexynyl, and the like.

"Alkylene" or "alkylene chain" refers to a straight or branched divalent hydrocarbon (alkyl) chain linking the rest of the molecule to a radical group, consisting solely of carbon and hydrogen, respectively. Alkylenes can have from one to twelve carbon atoms, e.g., methylene, ethylene, propylene, n-butylene, and the like. The alkylene chain is attached to the rest of the molecule through a single or double bond. The points of attachment of the alkylene chain to the rest of the molecule can be through one carbon or any two carbons within the chain. "Optionally substituted alkylene" refers to alkylene or substituted alkylene.

"Alkenylene" refers to divalent alkene. Examples of alkenylene include without limitation, ethenylene (—CH═CH—) and all stereoisomeric and conformational isomeric forms thereof. "Substituted alkenylene" refers to divalent substituted alkene. "Optionally substituted alkenylene" refers to alkenylene or substituted alkenylene.

"Alkynylene" refers to divalent alkyne. Examples of alkynylene include without limitation, ethynylene, propynylene. "Substituted alkynylene" refers to divalent substituted alkyne.

"Alkoxy" refers to a radical of the formula —$OR_a$ where $R_a$ is an alkyl having the indicated number of carbon atoms as defined above. Examples of alkoxy groups include without limitation —O-methyl (methoxy), —O-ethyl (ethoxy), —O-propyl (propoxy), —O-isopropyl (iso propoxy) and the like.

"Alkylaminyl" refers to a radical of the formula —$NHR_a$ or —$NR_aR_a$ where each $R_a$ is, independently, an alkyl radical having the indicated number of carbon atoms as defined above.

"Cycloalkylaminyl" refers to a radical of the formula —$NHR_a$ or —$NR_aR_a$ where $R_a$ is a cycloalkyl radical as defined herein.

"Alkylcarbonylaminyl" refers to a radical of the formula —NHC(O)$R_a$ or —$NR_a$C(O)$R_a$, where $R_a$ is an alkyl radical having the indicated number of carbon atoms as defined herein.

"Cycloalkylcarbonylaminyl" refers to a radical of the formula —NHC(O)$R_a$ or —$NR_a$C(O)$R_a$ where $R_a$ is a cycloalkyl radical as defined herein.

"Alkylaminocarbonyl" refers to a radical of the formula —C(O)NHR$_a$ or —C(O)NR$_a$R$_a$, where each R$_a$ is independently, an alkyl radical having the indicated number of carbon atoms as defined herein.

"Cyclolkylaminocarbonyl" refers to a radical of the formula —C(O)NHR$_a$, where R$_a$ is a cycloalkyl radical as defined herein.

"Aryl" refers to a hydrocarbon ring system radical comprising hydrogen, 6 to 18 carbon atoms and at least one aromatic ring. Exemplary aryls are hydrocarbon ring system radical comprising hydrogen and 6 to 9 carbon atoms and at least one aromatic ring; hydrocarbon ring system radical comprising hydrogen and 9 to 12 carbon atoms and at least one aromatic ring; hydrocarbon ring system radical comprising hydrogen and 12 to 15 carbon atoms and at least one aromatic ring; or hydrocarbon ring system radical comprising hydrogen and 15 to 18 carbon atoms and at least one aromatic ring. For purposes of this invention, the aryl radical may be a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. "Optionally substituted aryl" refers to a aryl group or a substituted aryl group.

"Arylene" denotes divalent aryl, and "substituted arylene" refers to divalent substituted aryl.

"Aralkyl" or "araalkylene" may be used interchangeably and refer to a radical of the formula —R$_b$—R$_c$ where R$_b$ is an alkylene chain as defined herein and R$_c$ is one or more aryl radicals as defined herein, for example, benzyl, diphenylmethyl and the like.

"Cycloalkyl" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, three to nine carbon atoms, three to eight carbon atoms, three to seven carbon atoms, three to six carbon atoms, three to five carbon atoms, a ring with four carbon atoms, or a ring with three carbon atoms. The cycloalkyl ring may be saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]heptanyl, and the like.

"Cycloalkylalkylene" or "cycloalkylalkyl" may be used interchangeably and refer to a radical of the formula —R$_b$R$_e$ where R$_b$ is an alkylene chain as defined herein and R$_e$ is a cycloalkyl radical as defined herein. In certain embodiments, R$_b$ is further substituted with a cycloalkyl group, such that the cycloalkylalkylene comprises two cycloalkyl moieties.

Cyclopropylalkylene and cyclobutylalkylene are exemplary cycloalkylalkylene groups, comprising at least one cyclopropyl or at least one cyclobutyl group, respectively.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo (bromine), chloro (chlorine), fluoro (fluorine), or iodo (iodine).

"Haloalkyl" refers to an alkyl radical having the indicated number of carbon atoms, as defined herein, wherein one or more hydrogen atoms of the alkyl group are substituted with a halogen (halo radicals), as defined above. The halogen atoms can be the same or different.

Exemplary haloalkyls are trifluoromethyl, difluoromethyl, trichloromethyl, 2,2,2-trifluoroethyl, 1,2-difluoroethyl, 3-bromo-2-fluoropropyl, 1,2-dibromoethyl, and the like.

"Heterocyclyl", heterocycle", or "heterocyclic ring" refers to a stable 3- to 18-membered saturated or unsaturated radical which consists of two to twelve carbon atoms and from one to six heteroatoms, for example, one to five heteroatoms, one to four heteroatoms, one to three heteroatoms, or one to two heteroatoms selected from the group consisting of nitrogen, oxygen and sulfur. Exemplary heterocycles include without limitation stable 3-15 membered saturated or unsaturated radicals, stable 3-12 membered saturated or unsaturated radicals, stable 3-9 membered saturated or unsaturated radicals, stable 8-membered saturated or unsaturated radicals, stable 7-membered saturated or unsaturated radicals, stable 6-membered saturated or unsaturated radicals, or stable 5-membered saturated or unsaturated radicals.

Unless stated otherwise specifically in the specification, the heterocyclyl radical may be a monocyclic, bicyclic, tricyclic or tetracyclic ring system, which may include fused, spiro or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of non-aromatic heterocyclyl radicals include, but are not limited to, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, thietanyl, trithianyl, tetrahydropyranyl, thiomorpholinyl, thiamorpholinyl, 1-oxo-thiomorpholinyl, and 1,1-dioxo-thiomorpholinyl. Heterocyclyls include heteroaryls as defined herein, and examples of aromatic heterocyclyls are listed in the definition of heteroaryls below.

"Heterocyclylalkyl" or "heterocyclylalkylene" refers to a radical of the formula —R$_b$R$_f$ where R$_b$ is an alkylene chain as defined herein and R$_f$ is a heterocyclyl radical as defined above, and if the heterocyclyl is a nitrogen-containing heterocyclyl, the heterocyclyl may be attached to the alkyl radical at the nitrogen atom.

"Heteroaryl" or "heteroarylene" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a stable 5-12 membered ring, a stable 5-10 membered ring, a stable 5-9 membered ring, a stable 5-8 membered ring, a stable 5-7 membered ring, or a stable 6 membered ring that comprises at least 1 heteroatom, at least 2 heteroatoms, at least 3 heteroatoms, at least 4 heteroatoms, at least 5 heteroatoms or at least 6 heteroatoms.

Heteroaryls may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. The heteroatom may be a member of an aromatic or non-aromatic ring, provided at least one ring in the heteroaryl is aromatic. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl).

"Heteroarylalkyl" or "heteroarylalkylene" refers to a radical of the formula —$R_bR_g$ where $R_b$ is an alkylene chain as defined above and $R_g$ is a heteroaryl radical as defined above.

"Thioalkyl" refers to a radical of the formula —SR where $R_a$ is an alkyl radical as defined above containing one to twelve carbon atoms, at least 1-10 carbon atoms, at least 1-8 carbon atoms, at least 1-6 carbon atoms, or at least 1-4 carbon atoms.

"Heterocyclylaminyl" refers to a radical of the formula —$NHR_f$ where $R_f$ is a heterocyclyl radical as defined above.

"Thione" refers to a =S group attached to a carbon atom of a saturated or unsaturated ($C_3$-$C_8$)cyclic or a ($C_1$-$C_8$) acyclic moiety.

"Sulfoxide" refers to a —S(O)— group in which the sulfur atom is covalently attached to two carbon atoms.

"Sulfone" refers to a —$S(O)_2$— or —($SO_2$)— group in which a hexavalent sulfur is attached to each of the two oxygen atoms through double bonds and is further attached to two carbon atoms through single covalent bonds.

The term "oxime" refers to a —C($R_a$)—N—$OR_a$ radical where $R_a$ is hydrogen, lower alkyl, an alkylene or arylene group as defined above.

The compound of the invention can exist in various isomeric forms, as well as in one or more tautomeric forms, including both single tautomers and mixtures of tautomers. The term "isomer" is intended to encompass all isomeric forms of a compound of this invention, including tautomeric forms of the compound.

Some compounds described here can have asymmetric centers and therefore exist in different enantiomeric and diastereomeric forms. A compound of the invention can be in the form of an optical isomer or a diastereomer. Accordingly, the invention encompasses compounds of the invention and their uses as described herein in the form of their optical isomers, diastereoisomers and mixtures thereof, including a racemic mixture. Optical isomers of the compounds of the invention can be obtained by known techniques such as asymmetric synthesis, chiral chromatography, or via chemical separation of stereoisomers through the employment of optically active resolving agents.

Unless otherwise indicated "stereoisomer" means one stereoisomer of a compound that is substantially free of other stereoisomers of that compound. Thus, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

If there is a discrepancy between a depicted structure and a name given to that structure, then the depicted structure controls. Additionally, if the stereochemistry of a structure or a portion of a structure is not indicated with, for example, bold or dashed lines, the structure or portion of the structure is to be interpreted as encompassing all stereoisomers of it. In some cases, however, where more than one chiral center exists, the structures and names may be represented as single enantiomers to help describe the relative stereochemistry. Those skilled in the art of organic synthesis will know if the compounds are prepared as single enantiomers from the methods used to prepare them.

In this description a "pharmaceutically acceptable salt" is a pharmaceutically acceptable, organic or inorganic acid or base salt of a compound of the invention. Representative pharmaceutically acceptable salts include, e.g., alkali metal salts, alkali earth salts, ammonium salts, water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts. A pharmaceutically acceptable salt can have more than one charged atom in its structure. In this instance the pharmaceutically acceptable salt can have multiple counterions. Thus, a pharmaceutically acceptable salt can have one or more charged atoms and/or one or more counterions.

The terms "treat", "treating" and "treatment" refer to the amelioration or eradication of a disease or symptoms associated with a disease. In certain embodiments, such terms refer to minimizing the spread or worsening of the disease resulting from the administration of one or more prophylactic or therapeutic agents to a patient with such a disease. In the context of the present invention the terms "treat", "treating" and "treatment" also refer to:

(i) preventing the disease or condition from occurring in a mammal, in particular, when such mammal is predisposed to the condition but has not yet been diagnosed as having it;

(ii) inhibiting the disease or condition, i.e., arresting its development;

(iii) relieving the disease or condition, i.e., causing regression of the disease or condition; or (iv) relieving the symptoms resulting from the disease or condition, i.e., relieving pain without addressing the underlying disease or condition. As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians. The term "effective amount" refers to an amount of a compound of the invention or other active ingredient sufficient to provide a therapeutic or prophylactic benefit in the treatment or prevention of a disease or to delay or minimize symptoms associated with a disease. Further, a therapeutically effective amount with respect to a compound of the invention means that amount of therapeutic agent alone, or in combination with other therapies, that provides a therapeutic benefit in the treatment or prevention of a disease. Used in connection with a compound of the invention, the term can encompass an amount that improves overall therapy, reduces or avoids symptoms or causes of disease, or enhances the therapeutic efficacy or synergies with another therapeutic agent.

The terms "modulate", "modulation" and the like refer to the ability of a compound to increase or decrease the function, or activity of, for example, eukaryotic initiation factor 4A (eIF4A), such as eIF4AI and eIF4AII. "Modulation", in its various forms, is intended to encompass inhibition, antagonism, partial antagonism, activation, agonism and/or partial agonism of the activity associated with eIF4A. eIF4A inhibitors are compounds that bind to, partially or totally block stimulation, decrease, prevent, delay activation, inactivate, desensitize, or down regulate signal transduction. The ability of a compound to modulate eIF4A activity can be demonstrated in an enzymatic assay or a cell-based assay.

A "patient" or subject" includes an animal, such as a human, cow, horse, sheep, lamb, pig, chicken, turkey, quail, cat, dog, mouse, rat, rabbit or guinea pig. The animal can be a mammal such as a non-primate and a primate (e.g., monkey and human). In one embodiment, a patient is a human, such as a human infant, child, adolescent or adult.

The term "prodrug" refers to a precursor of a drug, a compound which upon administration to a patient, must undergo chemical conversion by metabolic processes before becoming an active pharmacological agent. Exemplary prodrugs of compounds in accordance with Formula I are esters, acetamides, and amides.

Compounds of the Invention

The present invention is directed to compounds according to Formula I,

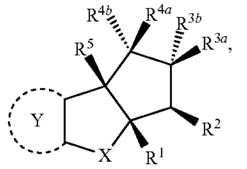

or stereoisomers, tautomers or pharmaceutically acceptable salts thereof.

In one embodiment X is $CR^6R^7$ or O. In another embodiment X is $CH_2$ or O.

In one embodiment Y is a 6-membered heteroaryl wherein $A^1$ is N, $A^2$ is $CR^{11}$, $A^3$ is $CR^{12}$ and $A^4$ is $CR^{13}$, wherein $R^{11}$, $R^{12}$ and $R^{13}$ independently are H, CN, halogen or $OR^9$.

In another embodiment Y is a 6-membered heteroaryl wherein $A^2$ is N, $A^1$ is $CR^{10}$, $A^3$ is $CR^{12}$ and $A^4$ is $CR^{13}$, wherein $R^{10}$, $R^{12}$ and $R^{13}$ independently are H, CN, halogen or $OR^9$. In another embodiment Y is a 6-membered heteroaryl wherein $A^3$ is N, $A^1$ is $CR^{10}$, $A^2$ is $CR^{11}$ and $A^4$ is $CR^{13}$, wherein $R^{10}$, $R^{11}$ and $R^{13}$ independently are H, CN, halogen or $OR^9$.

In another embodiment Y is a 6-membered heteroaryl wherein $A^4$ is N, $A^1$ is $CR^{10}$, $A^2$ is $CR^{11}$ and $A^3$ is $CR^{12}$, wherein $R^{10}$, $R^{11}$ and $R^{12}$ independently are H, CN, halogen or $OR^9$.

In another embodiment Y is a 6-membered heteroaryl wherein $A^2$ and $A^4$ are N, $A^1$ is $CR^{10}$ and $A^3$ is $CR^{12}$, wherein $R^{10}$ and $R^{12}$ independently are H, CN, halogen or $OR^9$. In one embodiment Y is a 5-membered heteroaryl wherein $B^1$ and $B^3$ are N or S and $B^2$ is $CR^{14}$, wherein $R^{14}$ is H, CN, halogen or $OR^9$.

In another embodiment Y is a 5-membered heteroaryl wherein $B^1$ is N, $B^2$ is $NR^{15}$ and $B^3$ is $CR^{14}$, wherein $R^{14}$ is H and $R^{15}$ is $OR^9$ or $C_1$-$C_6$(alkyl).

In another embodiment $R^1$ and $R^2$ are aryl.

In another embodiment $R^{3a}$, $R^{3b}$, $R^{4a}$ and $R^{4b}$ independently are H, halogen, $C_1$-$C_8$(alkyl), ($C_1$-$C_8$)haloalkyl, OH, CN, [($C_1$-$C_8$)alkylene]$OR^9$, [($C_1$-$C_8$)alkylene]$NHR^9$, [($C_1$-$C_8$)alkylene]$NR^9R^9$, C(O)$NH_2$, C(O)$NHR^9$, C(O)$NR^9R^9$, C(O)$R^9$, $CO_2R^9$, C(S)$NH_2$, S(O)$R^9$, $SO_2R^9$, $SO_2NHR^9$, $SO_2NR^9R^9$, heteroaryl or cycloalkyl, wherein $R^9$ is a $C_1$-$C_8$(alkyl) or ($C_1$-$C_8$)haloalkyl, or wherein the two $R^9$'s together with the nitrogen atom to which they are attached of [($C_1$-$C_8$)alkylene]$NR^9R^9$, C(O)$NR^9R^9$ or $SO_2NR^9R^9$, optionally form a heterocyclyl ring.

In another embodiment $R^{3b}$ is [($C_1$-$C_8$)alkylene]$NHR^9$ or [($C_1$-$C_8$)alkylene]$NR^9R^9$, wherein $R^9$ is $C_1$-$C_8$(alkyl) or ($C_1$-$C_8$)haloalkyl, or wherein the two $R^9$'s together with the nitrogen atom to which they are attached of [($C_1$-$C_8$)alkylene]$NR^9R^9$ optionally form a heterocyclyl ring.

In another embodiment $R^{4b}$ is OH.

In another embodiment $R^{4a}$ and $R^{4b}$ combine to form oxo or alkenyl.

In another embodiment $R^{3a}$ and $R^{4a}$, $R^{3b}$ and $R^{4b}$ or $R^{4a}$ and $R^5$ together with the carbon atom to which they are attached form a cycloalkyl or heterocyclyl ring;

In another embodiment $R^5$ is OH.

In another embodiment $R^6$ and $R^7$ are H or $C_1$-$C_8$(alkyl).

In another embodiment $R^9$ is H or $C_1$-$C_8$(alkyl). In another embodiment $R^9$ is $CH_3$.

In another embodiment, the compounds according to Formula I are selected from

Rac-(5aR,6S,7R,8R,8aS)-8,8a-dihydroxy-3-methoxy-5a-(4-methoxyphenyl)-N,N-dimethyl-6-phenyl-5a,7,8,8a-tetrahydro-6H-cyclopenta[4,5]furo[3,2-b]pyridine-7-carboxamide (Cpd. No. 1F), (5aR,6S,7R,8R,8aS)-3-cyano-5a-(4-cyanophenyl)-8,8a-dihydroxy-N,N-dimethyl-6-phenyl-5a,7,8,8a-tetrahydro-6H-cyclopenta[4,5]furo[3,2-b]pyridine-7-carboxamide (Cpd. No. 2F), (5aR,6S,7R,8R,8aS)-3-chloro-5a-(4-cyanophenyl)-8,8a-dihydroxy-N,N-dimethyl-6-phenyl-5a,7,8,8a-tetrahydro-6H-cyclopenta[4,5]furo[3,2-b]pyridine-7-carboxamide (Cpd. No. 3F), (5aR,6S,7R,8R,8aS)-3-cyano-8,8a-dihydroxy-5a-(4-methoxyphenyl)-N,N-dimethyl-6-phenyl-5a,7,8,8a-tetrahydro-6H-cyclopenta[4,5]furo[3,2-b]pyridine-7-carboxamide (Cpd. No. 4F), (5aR,6S,7R,8R,8aS)-3-chloro-8,8a-dihydroxy-5a-(4-methoxyphenyl)-N,N-dimethyl-6-phenyl-5a,7,8,8a-tetrahydro-6H-cyclopenta[4,5]furo[3,2-b]pyridine-7-carboxamide (Cpd. No. 5F), (5aR,6S,7R,8R,8aS)-5a-(4-cyanophenyl)-8,8a-dihydroxy-3-methoxy-N,N-dimethyl-6-phenyl-5a,7,8,8a-tetrahydro-6H-cyclopenta[4,5]furo[3,2-b]pyridine-7-carboxamide (Cpd. No. 6F), (5aR,6S,7R,8R,8aS)-3-chloro-8,8a-dihydroxy-N,N-dimethyl-6-phenyl-5a-(p-tolyl)-5a,7,8,8a-tetrahydro-6H-cyclopenta[4,5]furo[3,2-b]pyridine-7-carboxamide (Cpd. No. 7F), (5aR,6S,7R,8R,8aS)-3-chloro-8,8a-dihydroxy-N,N-dimethyl-6-phenyl-5a-(4-(trifluoromethyl)phenyl)-5a,7,8,8a-tetrahydro-6H-cyclopenta[4,5]furo[3,2-b]pyridine-7-carboxamide (Cpd. No. 8F), (5aR,6S,7R,8R,8aS)-5a-(4-cyanophenyl)-8,8a-dihydroxy-N,N-dimethyl-6-phenyl-5a,7,8,8a-tetrahydro-6H-cyclopenta[4,5]furo[3,2-b]pyridine-7-carboxamide (Cpd. No. 9F), (5aR,6S,7R,8R,8aS)-3-chloro-5a-(4-fluorophenyl)-8,8a-dihydroxy-N,N-dimethyl-6-phenyl-5a,7,8,8a-tetrahydro-6H-cyclopenta[4,5]furo[3,2-b]pyridine-7-carboxamide (Cpd. No. 10F), (5aR,6S,7R,8R,8aS)-3-chloro-5a-(4-chlorophenyl)-8,8a-dihydroxy-N,N-dimethyl-6-phenyl-5a,7,8,8a-tetrahydro-6H-cyclopenta[4,5]furo[3,2-b]pyridine-7-carboxamide (Cpd. No. 11F), (5aR,6S,7R,8R,8aS)-3-chloro-8,8a-dihydroxy-N,N-dimethyl-5a-(4-(methylsulfonyl)phenyl)-6-phenyl-5a,7,8,8a-tetrahydro-6H-cyclopenta[4,5]furo[3,2-b]pyridine-7-carboxamide (Cpd. No. 12F), Rac-(1R,2R,3S,3aR,8bS)-6-cyano-3a-(4-cyanophenyl)-1,8b-dihydroxy-N,N-dimethyl-3-phenyl-2,3,3a,8b-tetrahydro-1H-benzo[b]cyclopenta[d]thiophene-2-carboxamide (Cpd. No. 13F), Rac-(5aR,6S,7R,8R,8aS)-3-cyano-5a-(4-cyanophenyl)-8,8a-dihydroxy-N,N-dimethyl-6-phenyl-5a,7,8,8a-tetrahydro-6H-cyclopenta[4,5]furo[3,2-c]pyridine-7-carboxamide (Cpd. No. 14F), Rac-(4bS,5R,6R,7S,7aR)-7a-(4-cyanophenyl)-4b,5-dihydroxy-2-methoxy-N,N-dimethyl-7-phenyl-4b,6,7,7a-tetrahydro-5H-cyclopenta[4,5]furo[2,3-b]pyridine-6-carboxamide (Cpd. No. 15F), (5aR,6S,7R,8R,8aS)-3-chloro-5a-(4-(difluoromethyl)phenyl)-8,8a-dihydroxy-N,N-dimethyl-6-phenyl-5a,7,8,8a-tetrahydro-6H-cyclopenta[4,5]furo[3,2-b]pyridine-7-carboxamide (Cpd. No. 16F), (5aR,6S,7R,8R,8aS)-3-chloro-8,8a-dihydroxy-N,N-dimethyl-6-phenyl-5a-(4-(trifluoromethoxy)phenyl)-5a,7,8,8a-tetrahydro-6H-cyclopenta[4,5]furo[3,2-b]pyridine-7-carboxamide (Cpd. No. 17F), (5aR,6S,7R,8R,8aS)-3-chloro-5a-(4-cyanophenyl)-8,8a-dihydroxy-6-phenyl-5a,7,8,8a-tetrahydro-6H-cyclopenta[4,5]furo[3,2-b]pyridine-7-carboxamide (Cpd. No. 18F), Rac-(5aR,6S,7R,8R,8aS)-5a-(4-cyanophenyl)-8,8a-dihydroxy-1-methoxy-N,N-dimethyl-6-phenyl-5a,7,8,8a-tetrahydro-6H-cyclopenta[4,5]furo[3,2-c]pyridine-7-carboxamide (Cpd. No. 19F), (5aR,6S,7R,8R,8aS)-3-chloro-5a-(4-cyanophenyl)-8,8a-dihydroxy-N-methyl-6-phenyl-5a,7,8,8a-tetrahydro-6H-cyclopenta[4,5]furo[3,2-b]pyridine-7-carboxamide (Cpd. No. 20F), Rac-methyl (4aR,5S,6R,7R,7aS)-4a-(4-cyanophenyl)-7,7a-dihydroxy-2-methyl-5-phenyl-2,4a,5,6,7,7a-hexahydrocyclopenta[4,5]furo[3,2-c]pyrazole-6-carboxylate (Cpd. No. 21F), Rac-(5aR,6S,7R,8S,8aS)-3-chloro-5a-(4-cyanophenyl)-8,8a-dihydroxy-N,N-dimethyl-6-phenyl-5a,7,8,8a-tetrahydro-6H-cyclopenta[4,5]furo[3,2-b]pyridine-7-sulfonamide (Cpd. No. 22F), (4aR,5S,6R,7R,7aS)-4a-(4-cyanophenyl)-7,7a-dihydroxy-N,N,2-trimethyl-5-phenyl-2,4a,5,6,7,7a-hexahydrocyclopenta[4,5]furo[3,2-c]pyrazole-6-carboxamide (Cpd. No. 23F), Rac-methyl (5aR,6R,6aS,7aS,7bR)-3-chloro-5a-(4-cyanophenyl)-7b-hydroxy-6-phenyl-5a,7,7a,7b-tetrahydrocyclopropa[4',5']cyclopenta[1',2':4,5]furo[3,2-b]pyridine-6a(6H)-carboxylate (Cpd. No. 24F), Rac-methyl (5aR,6R,6aS,7aS,7bR)-3-chloro-5a-(4-cyanophenyl)-7b-hydroxy-6-phenyl-5a,7,7a,7b-tetrahydrocyclopropa[4',5']cyclopenta[1',2':4,5]furo[3,2-b]pyridine-6a(6H)-carboxylate (Cpd. No. 25F), Rac-4-((5aR,6S,7R,8R,8aS)-3-chloro-8,8a-dihydroxy-7-(oxazol-2-yl)-6-phenyl-6,7,8,8a-tetrahydro-5aH-cyclopenta[4,5]furo[3,2-b]pyridin-5a-yl)benzonitrile (Cpd. No. 26F), Rac-(5aR,6S,7R,8R,8aS)-5a-(4-bromophenyl)-3-chloro-8,8a-dihydroxy-6-phenyl-5a,7,8,8a-tetrahydro-6H-cyclopenta[4,5]furo[3,2-b]pyridine-7-carbothioamide (Cpd. No. 27F), Rac-(5aR,6S,7R,8R,8aS)-5a-(4-bromophenyl)-3-chloro-8,8a-dihydroxy-6-phenyl-5a,7,8,8a-tetrahydro-6H-cyclopenta[4,5]furo[3,2-b]pyridine-7-carbothioamide (Cpd. No. 28F), Rac-(5aR,6S,7R,8R,8aS)-5a-(4-cyanophenyl)-3,8,8a-trihydroxy-N,N-dimethyl-6-phenyl-2-(trifluoromethyl)-5a,7,8,8a-tetrahydro-6H-cyclopenta[4,5]furo[3,2-b]pyridine-7-carboxamide (Cpd. No. 29F), Rac-4-((5aR,6S,7S,8R,8aS)-7-(aminomethyl)-3-chloro-8,8a-dihydroxy-6-phenyl-6,7,8,8a-tetrahydro-5aH-cyclopenta[4,5]furo[3,2-b]pyridin-5a-yl)benzonitrile (Cpd. No. 30F), Rac-(5aR,6R,6aS,7aS,7bR)-3-chloro-5a-(4-cyanophenyl)-7b-hydroxy-N,N-dimethyl-6-phenyl-5a,7,7a,7b-tetrahydrocyclopropa[4',5']cyclopenta[1',2':4,5]furo[3,2-b]pyridine-6a(6H)-carboxamide (Cpd. No. 31F), Rac-(5aR,6S,7R,8aR)-3-chloro-5a-(4-cyanophenyl)-8a-hydroxy-N,N-dimethyl-8-oxo-6-phenyl-5a,7,8,8a-tetrahydro-6H-cyclopenta[4,5]furo[3,2-b]pyridine-7-carboxamide (Cpd. No. 32F), Rac-(5aR,6S,7R,8R,8aS)-3-chloro-5a-(4-cyanophenyl)-8,8a-dihydroxy-N,N,8-trimethyl-6-phenyl-5a,7,8,8a-tetrahydro-6H-cyclopenta[4,5]furo[3,2-b]pyridine-7-carboxamide (Cpd. No. 33Fa) and Rac-(5aR,6S,7R,8S,8aS)-3-chloro-5a-(4-cyanophenyl)-8,8a-dihydroxy-N,N,8-trimethyl-6-phenyl-5a,7,8,8a-tetrahydro-6H-cyclopenta[4,5]furo[3,2-b]pyridine-7-carboxamide (Cpd. No. 33Fb), Rac-(5aR,6S,8aR)-5a-(4-bromophenyl)-3-chloro-8-methylene-6-phenyl-5a,6,7,8-tetrahydro-8aH-cyclopenta[4,5]furo[3,2-b]pyridin-8a-ol (Cpd. No. 34F), Rac-(5aR,6R,8aS)-5a-(4-bromophenyl)-3-chloro-8a-hydroxy-8-methoxy-N,N-dimethyl-6-phenyl-5a,8a-dihydro-6H-cyclopenta[4,5]furo[3,2-b]pyridine-7-carboxamide (Cpd. No. 35F), Rac-(4aR,5S,6R,7R,7aS)-3-chloro-4a-(4-cyanophenyl)-7,7a-dihydroxy-N,N,2-trimethyl-5-phenyl-2,4a,5,6,7,7a-hexahydrocyclopenta[4,5]furo[3,2-c]pyrazole-6-carboxamide (Cpd. No. 36F), Rac-(4aR,5S,6R,7R,7aS)-4a-(4-bromophenyl)-3-chloro-7,7a-dihydroxy-N,N,2-trimethyl-5-phenyl-2,4a,5,6,7,7a-hexahydrocyclopenta[4,5]furo[3,2-c]pyrazole-6-carboxamide (Cpd. No. 37F), Rac-(5aR,6S,8R,8aS)-5a-(4-bromophenyl)-3-chloro-6-phenyl-6,7-dihydrospiro[cyclopenta[4,5]furo[3,2-b]pyridine-8,2'-oxetan]-8a(5aH)-ol (Cpd. No. 38F), Rac-4-((5aR,6S,7S,8R,8aS)-3-chloro-8,8a-dihydroxy-7-((methylamino)methyl)-6-phenyl-6,7,8,8a-tetrahydro-5aH-cyclopenta[4,5]furo[3,2-b]pyridin-5a-yl)benzonitrile (Cpd. No. 39F), Rac-4-((5aR,6S,7R,8R,8aS)-3-chloro-7-((dimethylamino)methyl)-8,8a-dihydroxy-6-phenyl-6,7,8,8a-tetrahydro-5aH-cyclopenta[4,5]furo[3,2-b]pyridin-5a-yl)benzonitrile (Cpd. No. 40Fa), rac-4-((5aR,6S,7S,8R,8aS)-3-chloro-7-((dimethylamino)methyl)-8,8a-dihydroxy-6-phenyl-6,7,8,8a-tetrahydro-5aH-cyclopenta[4,5]furo[3,2-b]pyridin-5a-yl)benzonitrile (Cpd. No. 40Fb), and rac-4-((5aR,6S,7S,8S,8aS)-3-chloro-7-((dimethylamino)methyl)-8,8a-dihydroxy-6-phenyl-6,7,8,8a-tetrahydro-5aH-cyclopenta[4,5]furo[3,2-b]pyridin-5a-yl)benzonitrile (Cpd. No. 40Fc)

Rac-4-((5aR,6S,7R,8R,8aS)-3-chloro-8,8a-dihydroxy-6-phenyl-7-(pyrrolidin-1-ylmethyl)-6,7,8,8a-tetrahydro-5aH-cyclopenta[4,5]furo[3,2-b]pyridin-5a-yl)benzonitrile (Cpd. No. 41Fa), rac-4-((5aR,6S,7S,8R,8aS)-3-chloro-8,8a-dihydroxy-6-phenyl-7-(pyrrolidin-1-ylmethyl)-6,7,8,8a-tetrahydro-5aH-cyclopenta[4,5]furo[3,2-b]pyridin-5a-yl)benzonitrile (Cpd. No. 41Fb), and rac-4-((5aR,6S,7S,8S,8aS)-3-chloro-8,8a-dihydroxy-6-phenyl-7-(pyrrolidin-1-ylmethyl)-6,7,8,8a-tetrahydro-5aH-cyclopenta[4,5]furo[3,2-b]pyridin-5a-yl)benzonitrile (Cpd. No. 41Fc), Rac-(1R,2R,3S,3aR,8bS)-8b-azido-1-hydroxy-6-methoxy-3a-(4-methoxyphenyl)-N,N-dimethyl-3-phenyl-2,3-dihydro-1H-cyclopenta[b]benzofuran-2-carboxamide (Cpd. No. 42F), Rac-methyl (5aR,6S,7R,8R,8aS)-5a-(4-bromophenyl)-3-chloro-8a-fluoro-8-hydroxy-6-phenyl-5a,7,8,8a-tetrahydro-6H-cyclopenta[4,5]furo[3,2-b]pyridine-7-carboxylate (Cpd. No. 43F), Rac-(1R,2R,3S,3aR,8bS)-8b-amino-1-hydroxy-6-methoxy-3a-(4-methoxyphenyl)-N,N-dimethyl-3-phenyl-2,3,3a,8b-tetrahydro-1H-cyclopenta[b]benzofuran-2-carboxamide (Cpd. No. 44F), Rac-(1R,2R,3S,3aR,8bS)-8b-acetamido-1-hydroxy-6-methoxy-3a-(4-methoxyphenyl)-N,N-dimethyl-3-phenyl-2,3,3a,8b-tetrahydro-1H-cyclopenta[b]benzofuran-2-carboxamide (Cpd. No. 45F), Rac-dimethyl 2-[[(5aR,6S,7R,8aR)-5a-(4-bromophenyl)-3-chloro-8a-hydroxy-8-oxo-6-phenyl-6,7-dihydrocyclopenta[4,5]furo[1,2-b]pyridin-7-yl]methyl]propanedioate (Cpd. No. 46F), Rac-(5aR,6S,8S,8aR)-5a-(4-bromophenyl)-3-chloro-8a-hydroxy-6-phenyl-5a,7,8,8a-tetrahydro-6H-cyclopenta[4,5]furo[3,2-b]pyridine-8-carbonitrile (Cpd. No. 47F), Rac-(5aR,6S,8aR)-5a-(4-bromophenyl)-3-chloro-8-ethynyl-6-phenyl-5a,6,7,8-tetrahydro-8aH-cyclopenta[4,5]furo[3,2-b]pyridin-8a-ol (Cpd. No. 48F), Rac-methyl (5aR,6S,7R,8R,8aR)-5a-(4-bromophenyl)-3-chloro-8-cyano-8a-hydroxy-6-phenyl-5a,7,8,8a-tetrahydro-6H-cyclopenta[4,5]furo[3,2-b]pyridine-7-carboxylate (Cpd. No. 49F), Rac-methyl (5aR,6S,7R,8R,8aR)-3-chloro-8-cyano-5a-(4-cyanophenyl)-8a-hydroxy-6-phenyl-5a,7,8,8a-tetrahydro-6H-cyclopenta[4,5]furo[3,2-b]pyridine-7-carboxylate (Cpd. No. 50F), Rac-(5aR,6S,7R,8R,8aR)-3-chloro-8-cyano-5a-(4-cyanophenyl)-8a-hydroxy-N,N-dimethyl-6-phenyl-5a,7,8,8a-tetrahydro-6H-cyclopenta[4,5]furo[3,2-b]pyridine-7-carboxamide (Cpd. No. 51F), Rac-(5aR,6S,7R,8R,8aR)-3-chloro-8-cyano-5a-(4-cyanophenyl)-8a-hydroxy-6-phenyl-5a,7,8,8a-tetrahydro-6H-cyclopenta[4,5]furo[3,2-b]pyridine-7-carboxamide (Cpd. No. 52F), Rac-(3aR,3bS,8aR,9R,9aR)-8a-(4-bromophenyl)-6-chloro-3b-hydroxy-9-phenyl-1,3a,3b,8a,9,9a-hexahydro-2H-oxazolo[4",5":4',5']cyclopenta[1',2':4,5]furo[3,2-b]pyridin-2-one (Cpd. No. 53F), Rac-4-((3aR,3bS,8aR,9R,9aR)-6-chloro-3b-hydroxy-2-oxo-9-phenyl-1,2,3a,3b,9,9a-hexahydro-8aH-oxazolo[4",5":4',5']cyclopenta[1',2':4,5]furo[3,2-b]pyridin-8a-yl)benzonitrile (Cpd. No. 54F), Rac-(5aR,6S,7S,8R,8aS)-5a-(4-bromophenyl)-3-chloro-7-(hydroxymethyl)-6-phenyl-5a,6,7,8-tetrahydro-8aH-cyclopenta[4,5]furo[3,2-b]pyridine-8,8a-diol (Cpd. No. 55F), Rac-4-((5aR,6S,7S,8R,8aS)-3-chloro-8,8a-dihydroxy-7-(hydroxymethyl)-6-phenyl-6,7,8,8a-tetrahydro-5aH-cyclopenta[4,5]furo[3,2-b]pyridin-5a-yl)benzonitrile (Cpd. No. 56F), Rac-(5aR,6S,7R,8R,8aS)-5a-(4-bromophenyl)-3-chloro-7-methyl-6-phenyl-5a,6,7,8-tetrahydro-8aH-cyclopenta[4,5]furo[3,2-b]pyridine-8,8a-diol (Cpd. No. 57F), Rac-methyl (5aR,6S,8S,8aS)-5a-(4-bromophenyl)-3-chloro-7-fluoro-8,8a-dihydroxy-6-phenyl-5a,7,8,8a-tetrahydro-6H-cyclopenta[4,5]furo[3,2-b]pyridine-7-carboxylate (Cpd. No. 58F), Rac-methyl (5aR,6S,8S,8aS)-3-chloro-5a-(4-cyanophenyl)-7-fluoro-8,8a-dihydroxy-6-phenyl-5a,7,8,8a-tetrahydro-6H-cyclopenta[4,5]furo[3,2-b]pyridine-7-carboxylate (Cpd. No. 59F), Rac-(2aS,3S,3aR,8bS,8cR)-3a-(4-bromophenyl)-6-chloro-3-phenyl-2a,3,3a,8c-tetrahydrooxeto[3",2":4',5']cyclopenta[1',2':4,5]furo[3,2-b]pyridin-8b(2H)-ol (Cpd. No. 60F), Rac-(2aS,3S,3aR,8bS,8cR)-3a-(4-bromophenyl)-6-chloro-3-phenyl-2a,3,3a,8c-tetrahydrooxeto[3",2":4',5']cyclopenta[1',2':4,5]furo[3,2-b]pyridin-8b(2H)-ol (Cpd. No. 61F), Rac-(5aR,6S,7S,8R,8aS)-5a-(4-bromophenyl)-3-chloro-7-(methoxymethyl)-6-phenyl-5a,6,7,8-tetrahydro-8aH-cyclopenta[4,5]furo[3,2-b]pyridine-8,8a-diol (Cpd. No. 62F), Rac-(1aS,3S,3aR,8bS)-3a-(4-bromophenyl)-6-chloro-3-phenyl-1a,2,3,3a-tetrahydro-oxireno[2",3":1',5']cyclopenta[1',2':4,5]furo[3,2-b]pyridine (Cpd. No. 63F), (4bS,5R,6R,7S,7aR)-7a-(4-Cyanophenyl)-4b,5-dihydroxy-4-methoxy-N,N-dimethyl-7-phenyl-4b,6,7,7a-tetrahydro-5H-cyclopenta[4,5]furo[2,3-c]pyridine-6-carboxamide (Cpd. No. 64F), Rac-4-((4bS,5R,6S,7S,7aR)-6-(aminomethyl)-4b,5-dihydroxy-4-methoxy-7-phenyl-5,6,7,7a-tetrahydro-4bH-cyclopenta[4,5]furo[2,3-c]pyridin-7a-yl)benzonitrile (Cpd. No. 65F), 4-((4bS,5R,6S,7S,7aR)-6-((Dimethylamino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 66F), 4-((4bS,5R,6S,7S,7aR)-4b,5-Dihydroxy-4-methoxy-7-phenyl-6-(piperazin-1-ylmethyl)-4b,5,6,7-tetrahydro-7aH-cyclopenta[4,5]furo[2,3-c]pyridin-7a-yl)benzonitrile (Cpd. No. 67F), Rac-4-((4bS,5R,6S,7S,7aR)-4b,5-dihydroxy-4-methoxy-6-((4-methylpiperazin-1-yl)methyl)-7-phenyl-4b,5,6,7-tetrahydro-7aH-cyclopenta[4,5]furo[2,3-c]pyridin-7a-yl)benzonitrile (Cpd. No. 68F), Rac-4-((4bS,5R,6S,7S,7aR)-4b,5-dihydroxy-4-methoxy-6-((methylamino)methyl)-7-phenyl-4b,5,6,7-tetrahydro-7aH-cyclopenta[4,5]furo[2,3-c]pyridin-7a-yl)benzonitrile (Cpd. No. 69F), Rac-4-((4bS,5R,6S,7S,7aR)-6-((ethylamino)methyl)-4b,5-dihydroxy-4-methoxy-7-phenyl-4b,5,6,7-tetrahydro-7aH-cyclopenta[4,5]furo[2,3-c]pyridin-7a-yl)cyclohexa-1,3-diene-1-carbonitrile (Cpd. No. 70F), Rac-4-((4bS,5R,6S,7S,7aR)-6-(azetidin-1-ylmethyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 71F), Rac-4-((4bS,5R,6S,7S,7aR)-4b,5-dihydroxy-4-methoxy-7-phenyl-6-(pyrrolidin-1-ylmethyl)-4b,5,6,7-tetrahydro-7aH-cyclopenta[4,5]furo[2,3-c]pyridin-7a-yl)benzonitrile (Cpd. No. 72F), 4-((4bS,5R,6S,7S,7aR)-6-((Diethylamino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 73F), Rac-4-((4bS,5R,6S,7S,7aR)-6-((ethyl(methyl)amino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 74F), Rac-4-((4bS,5R,6S,7S,7aR)-4b,5-dihydroxy-6-(((2-hydroxyethyl)(methyl)amino)methyl)-4-methoxy-7-phenyl-4b,5,6,7-tetrahydro-7aH-cyclopenta[4,5]furo[2,3-c]pyridin-7a-yl)benzonitrile (Cpd. No. 75F), Rac-4-((4bS,5R,6S,7S,7aR)-6-((benzyl(methyl)amino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 76F), Rac-4-((4bS,5R,6S,7S,7aR)-6-((benzylamino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 77F), Rac-4-((5R,6S,7S,7aR)-4b,5-dihydroxy-4-methoxy-7-phenyl-6-(((pyridin-3-ylmethyl)amino)methyl)-4b,5,6,7-tetrahydro-7aH-cyclopenta[4,5]furo[2,3-c]pyridin-7a-yl)benzonitrile (Cpd. No. 78F), Rac-4-((4bS,5R,6S,7S,7aR)-4b,5-dihydroxy-6-(((2-hydroxyethyl)amino)methyl)-4-methoxy-7-phenyl-5,6,7,7a-tetrahydro-4bH-cyclopenta[4,5]furo[2,3-c]pyridin-7a-yl)benzonitrile (Cpd. No. 79F), Rac-(4aR,5S,6R,7R,7aS)-4a-(4-cyanophenyl)-7,7a-dihydroxy-2-isopropyl-N,N-dimethyl-5-phenyl-2,4a,5,6,7,7a-hexahydrocyclopenta[4,5]furo[3,2-c]pyrazole-6-carboxamide (Cpd. No. 80F), 4-((3aR,4R,4aR,9bS,9cR)-9b-Hydroxy-9-methoxy-2-oxo-4-phenyl-2,3,3a,4,9b,9c-hexahydro-4aH-oxazolo[4",5":4',5']cyclopenta[1',2':4,5]furo[2,3-c]pyridin-4a-yl)benzonitrile (Cpd. No. 81F), Rac-(4aR,5S,6R,7R,7aS)-3-cyano-4a-(4-cyanophenyl)-7,7a-dihydroxy-N,N,2-trimethyl-5-phenyl-2,4a,5,6,7,7a-hexahydrocyclopenta[4,5]furo[3,2-c]pyrazole-6-carboxamide (Cpd. No. 82F), 4-((5aR,6S,7R,8S,8aS)-3-Chloro-8,8a-dihydroxy-6-phenyl-7-(pyrrolidin-1-ylsulfonyl)-6,7,8,8a-tetrahydro-5aH-cyclopenta[4,5]furo[3,2-b]pyridin-5a-yl)benzonitrile (Cpd. No. 83F), Rac-(5aR,6S,7R,8S,8aS)-5a-(4-bromophenyl)-3-chloro-7-(methylsulfonyl)-6-phenyl-5a,6,7,8-tetrahydro-8aH-cyclopenta[4,5]furo[3,2-b]pyridine-8,8a-diol (Cpd. No. 84F), Rac-4-((5aR,6S,7R,8S,8aS)-3-chloro-8,8a-dihydroxy-7-(methylsulfonyl)-6-phenyl-6,7,8,8a-tetrahydro-5aH-cyclopenta[4,5]furo[3,2-b]pyridin-5a-yl)benzonitrile (Cpd. No. 85F), (5aR,6S,7R,8S,8aS)-5a-(4-Cyanophenyl)-8,8a-dihydroxy-7-(methylsulfonyl)-6-phenyl-5a,7,8,8a-tetrahydro-6H-cyclopenta[4,5]furo[3,2-b]pyridine-3-carbonitrile (Cpd. No. 86F), Rac-((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)(morpholino)methanone (Cpd. No. 87F), Rac-(4bS,5R,6R,7S,7aR)-7a-(4-bromophenyl)-4b,5-dihydroxy-4-methoxy-N-methyl-7-phenyl-N-(2,2,2-trifluoroethyl)-4b,6,7,7a-tetrahydro-5H-cyclopenta[4,5]furo[2,3-c]pyridine-6-carboxamide (Cpd. No. 88F), Rac-(4bS,5R,6R,7S,7aR)-7a-(4-bromophenyl)-N-cyclopropyl-4b,5-dihydroxy-4-methoxy-7-phenyl-4b,6,7,7a-tetrahydro-5H-cyclopenta[4,5]furo[2,3-c]pyridine-6-carboxamide (Cpd. No. 89F), Rac-(4bS,5R,6R,7S,7aR)-7a-(4-bromophenyl)-4b,5-dihydroxy-4-methoxy-7-phenyl-N-(2,2,2-trifluoroethyl)-4b,6,7,7a-tetrahydro-5H-cyclopenta[4,5]furo[2,3-c]pyridine-6-carboxamide (Cpd. No. 90F), Rac-(5aR,6S,8S,8aS)-5a-(4-bromophenyl)-3-chloro-7,7-difluoro-6-phenyl-5a,6,7,8-tetrahydro-8aH-cyclopenta[4,5]furo[3,2-b]pyridine-8,8a-diol (Cpd. No. 91F), Rac-(5aR,6R,8R,8aS)-5a-(4-bromophenyl)-3-chloro-6-phenyl-5a,6-dihydrospiro[cyclopenta[4,5]furo[3,2-b]pyridine-7,1'-cyclopropane]-8,8a(8H)-diol (Cpd. No. 92F), Rac-(5aR,6S,7R,8S,8aS)-7-(benzylsulfonyl)-5a-(4-bromophenyl)-3-chloro-6-phenyl-5a,6,7,8-tetrahydro-8aH-cyclopenta[4,5]furo[3,2-b]pyridine-8,8a-diol (Cpd. No. 93F), Rac-4-((5aR,6S,7R,8S,8aS)-7-(benzylsulfonyl)-3-chloro-8,8a-dihydroxy-6-phenyl-6,7,8,8a-tetrahydro-5aH-cyclopenta[4,5]furo[3,2-b]pyridin-5a-yl)benzonitrile (Cpd. No. 94F), (4bS,5R,6R,7S,7aR)-7a-(4-Cyanophenyl)-4b,5-dihydroxy-N,N-dimethyl-7-phenyl-4b,6,7,7a-tetrahydro-5H-cyclopenta[4,5]furo[2,3-c]pyridine-6-carboxamide (Cpd. No. 95F), Rac-(4bS,5R,6R,7S,7aR)-4-cyano-7a-(4-cyanophenyl)-4b,5-dihydroxy-N,N-dimethyl-7-phenyl-4b,6,7,7a-tetrahydro-5H-cyclopenta[4,5]furo[2,3-c]pyridine-6-carboxamide (Cpd. No. 96F), Rac-(4bS,5R,6R,7S,7aR)-7a-(4-bromophenyl)-4-chloro-4b,5-dihydroxy-N,N-dimethyl-7-phenyl-4b,6,7,7a-tetrahydro-5H-cyclopenta[4,5]furo[2,3-c]pyridine-6-carboxamide (Cpd. No. 97F), (4bS,5R,6R,7S,7aR)-4-Chloro-7a-(4-cyanophenyl)-4b,5-dihydroxy-N,N-dimethyl-7-phenyl-4b,6,7,7a-tetrahydro-5H-cyclopenta[4,5]furo[2,3-c]pyridine-6-carboxamide (Cpd. No. 98F), Rac-(4aR,5S,6R,7R,7aS)-4a-(4-cyanophenyl)-7,7a-dihydroxy-2-(4-methoxybenzyl)-N,N-dimethyl-5-phenyl-2,4a,5,6,7,7a-hexahydrocyclopenta[4,5]furo[3,2-c]pyrazole-6-carboxamide (Cpd. No. 99F), Rac-(4aR,5S,6R,7R,7aS)-4a-(4-cyanophenyl)-7,7a-dihydroxy-N,N-dimethyl-5-phenyl-2,4a,5,6,7,7a-hexahydrocyclopenta[4,5]furo[3,2-c]pyrazole-6-carboxamide (Cpd. No. 100F), Rac-(4bS,5S,6R,7S,7aR)-7a-(4-bromophenyl)-4-methoxy-6-(methylsulfonyl)-7-phenyl-5,6,7,7a-tetrahydro-4bH-cyclopenta[4,5]furo[2,3-c]pyridine-4b,5-diol (Cpd. No. 101F), 4-((4bS,5S,6R,7S,7aR)-4b,5-dihydroxy-4-methoxy-6-(methylsulfonyl)-7-phenyl-4b,5,6,7-tetrahydro-7aH-cyclopenta[4,5]furo[2,3-c]pyridin-7a-yl)benzonitrile (Cpd. No. 102F), 4-((4bS,5R,6S,7S,7aR)-6-((dimethylamino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 103F), (5aR,6S,7R,8R,8aS)-3-chloro-5a-(4-cyanophenyl)-8,8a-dihydroxy-N,N-dimethyl-6-phenyl-5a,7,8,8a-tetrahydro-6H-cyclopenta[4,5]furo[3,2-b]pyridine-7-carboxamide (Cpd. No. 104F), (5aR,6S,7S,8R,8aS)-5a-(4-cyanophenyl)-7-((dimethylamino)methyl)-8,8a-dihydroxy-6-phenyl-5a,7,8,8a-tetrahydro-6H-cyclopenta[4,5]furo[3,2-b]pyridine-3-carbonitrile (Cpd. No. 105F), (4bS,5R,6S,7S,7aR)-7a-(4-(difluoromethyl)phenyl)-6-((dimethylamino)methyl)-4-methoxy-7-phenyl-5,6,7,7a-tetrahydro-4bH-cyclopenta[4,5]furo[2,3-c]pyridine-4b,5-diol (Cpd. No. 106F), (4bS,5R,6S,7S,7aR)-6-((dimethylamino)methyl)-4-methoxy-7-phenyl-7a-(4-(trifluoromethyl)phenyl)-5,6,7,7a-tetrahydro-4bH-cyclopenta[4,5]furo[2,3-c]pyridine-4b,5-diol (Cpd. No. 107F), (5aR,6S,7R,8R,8aS)-3-chloro-5a-(4-(difluoromethyl)phenyl)-7-((dimethylamino)methyl)-6-phenyl-5a,6,7,8-tetrahydro-8aH-cyclopenta[4,5]furo[3,2-b]pyridine-8,8a-diol (Cpd. No. 108F), (5aR,6S,7S,8R,8aS)-3-chloro-7-((dimethylamino)methyl)-6-phenyl-5a-(4-(trifluoromethyl)phenyl)-5a,6,7,8-tetrahydro-8aH-cyclopenta[4,5]furo[3,2-b]pyridine-8,8a-diol (Cpd. No. 109F), 4-((4bS,5R,6S,7S,7aR)-4b,5-dihydroxy-4-methoxy-6-(morpholinomethyl)-7-phenyl-4b,5,6,7-tetrahydro-7aH-cyclopenta[4,5]furo[2,3-c]pyridin-7a-yl)benzonitrile (Cpd. No. 110F), Rac-(4bS,5R,6R,7S,7aR)-7a-(4-bromophenyl)-N-(2,2-difluoroethyl)-4b,5-dihydroxy-4-methoxy-N-methyl-7-phenyl-4b,6,7,7a-tetrahydro-5H-cyclopenta[4,5]furo[2,3-c]pyridine-6-carboxamide (Cpd. No. 111F), 4-((4bS,5R,6S,7S,7aR)-6-(((2,2-difluoroethyl)(methyl)amino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 112F), 4-((4bS,5R,6S,7S,7aR)-6-((4,4-difluoropiperidin-1-yl)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 113F), Rac-((1R,5S)-8-azabicyclo[3.2.1]octan-8-yl)((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)methanone (Cpd. No. 114F), 4-((4bS,5R,6S,7S,7aR)-6-(((2,2-difluoroethyl)amino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 115F), Rac-(4bS,5R,6R,7S,7aR)-7a-(4-bromophenyl)-N-(2,2-difluoroethyl)-4b,5-dihydroxy-4-methoxy-7-phenyl-4b,6,7,7a-tetrahydro-5H-cyclopenta[4,5]furo[2,3-c]pyridine-6-carboxamide (Cpd. No. 116F), Rac-(4bS,5S,6R,7S,7aR)-7a-(4-bromophenyl)-4-methoxy-7-phenyl-6-((2,2,2-trifluoroethyl)sulfonyl)-5,6,7,7a-tetrahydro-4bH-cyclopenta[4,5]furo[2,3-c]pyridine-4b,5-diol (Cpd. No. 117F), Rac-4-((4bS,5S,6R,7S,7aR)-4b,5-dihydroxy-4-methoxy-7-phenyl-6-(phenylsulfonyl)-4b,5,6,7-tetrahydro-7aH-cyclopenta[4,5]furo[2,3-c]pyridin-7a-yl)benzonitrile (Cpd. No. 118F), Rac-4-((4bS,5S,6R,7S,7aR)-4b,5-dihydroxy-4-methoxy-7-phenyl-6-(pyridin-2-ylsulfonyl)-4b,5,6,7-tetrahydro-7aH-cyclopenta[4,5]furo[2,3-c]pyridin-7a-yl)benzonitrile (Cpd. No. 119F), 4-((4bR,5R,7S,7aR)-4b-hydroxy-5-(hydroxymethyl)-4-methoxy-7-phenyl-4b,5,6,7-tetrahydro-7aH-cyclopenta[4,5]furo[2,3-c]pyridin-7a-yl)benzonitrile (Cpd. No. 120F), Rac-((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)(3,3-difluoroazetidin-1-yl)methanone (Cpd. No. 121F), 4-((4bS,5R,6S,7S,7aR)-6-((3,3-difluoroazetidin-1-yl)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 122F), Rac-(5aR,6S,7R,8S,8aS)-3-chloro-5a-(4-cyanophenyl)-8,8a-dihydroxy-N-methyl-6-phenyl-5a,7,8,8a-tetrahydro-6H-cyclopenta[4,5]furo[3,2-b]pyridine-7-sulfonamide (Cpd. No. 123F), Rac-(5aR,6S,7R,8S,8aS)-5a-(4-bromophenyl)-3-chloro-8,8a-dihydroxy-N-methyl-6-phenyl-5a,7,8,8a-tetrahydro-6H-cyclopenta[4,5]furo[3,2-b]pyridine-7-sulfonamide (Cpd. No. 124F), Rac-(5aR,6S,7R,8S,8aS)-3-chloro-5a-(4-cyanophenyl)-8,8a-dihydroxy-N-methyl-6-phenyl-5a,7,8,8a-tetrahydro-6H-cyclopenta[4,5]furo[3,2-b]pyridine-7-sulfonamide (Cpd No. 125F), 4-((4bS,5S,6R,7S,7aR)-4b,5-dihydroxy-4-methoxy-6-(morpholinosulfonyl)-7-phenyl-4b,5,6,7-tetrahydro-7aH-cyclopenta[4,5]furo[2,3-c]pyridin-7a-yl)benzonitrile (Cpd. No. 126F), Rac-(5aR,6S,8R,8aS)-5a-(4-bromophenyl)-3-chloro-6-phenyl-5a,6,7,8-tetrahydro-8aH-cyclopenta[4,5]furo[3,2-b]pyridine-8,8a-diol (Cpd. No. 127F), Rac-4-((5aR,6S,8R,8aS)-3-chloro-8,8a-dihydroxy-6-phenyl-6,7,8,8a-tetrahydro-5aH-cyclopenta[4,5]furo[3,2-b]pyridin-5a-yl)benzonitrile (Cpd. No. 128F), Rac-(5aR,6S,8aR)-5a-(4-bromophenyl)-3-chloro-8a-hydroxy-6-phenyl-5a,6,7,8a-tetrahydro-8H-cyclopenta[4,5]furo[3,2-b]pyridin-8-one (Cpd. No. 129F), Rac-(5aR,6S,8S,8aS)-5a-(4-bromophenyl)-3-chloro-6-phenyl-5a,6,7,8-tetrahydro-8aH-cyclopenta[4,5]furo[3,2-b]pyridine-8,8a-diol (Cpd. No. 130F), Rac-4-((5aR,6S,8S,8aS)-3-chloro-8,8a-dihydroxy-6-phenyl-6,7,8,8a-tetrahydro-5aH-cyclopenta[4,5]furo[3,2-b]pyridin-5a-yl)benzonitrile (Cpd. No. 131F), Rac-N-((5aR,6S,8aS)-5a-(4-bromophenyl)-3-chloro-8a-hydroxy-6-phenyl-5a,6,7,8a-tetrahydro-8H-cyclopenta[4,5]furo[3,2-b]pyridin-8-ylidene)-4-methylbenzenesulfonohydrazide (Cpd. No. 132F), Rac-(5aR,6S,8aR)-5a-(4-bromophenyl)-3-chloro-6-phenyl-5a,6-dihydro-8aH-cyclopenta[4,5]furo[3,2-b]pyridin-8a-ol (Cpd. No. 133F), Rac-methyl (4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylate (Cpd. No. 134F), Rac-((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)(4,4-difluoropiperidin-1-yl)methanone (Cpd. No. 135F), Rac-methyl (5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridine-7-carboxylate (Cpd. No. 136F), Rac-(5aR,6S,7R,8R,8aS)-5a-(4-bromophenyl)-3-chloro-8,8a-dihydroxy-1-methoxy-N,N-dimethyl-6-phenyl-5a,7,8,8a-tetrahydro-6H-cyclopenta[4,5]furo[3,2-c]pyridine-7-carboxamide (Cpd. No. 137F), Rac-(5aR,6S,7S,8R,8aS)-5a-(4-bromophenyl)-3-chloro-7-((dimethylamino)methyl)-1-methoxy-6-phenyl-5a,6,7,8-tetrahydro-8aH-cyclopenta[4,5]furo[3,2-c]pyridine-8,8a-diol (Cpd. No. 138F), (5aR,6S,7S,8R,8aS)-5a-(4-cyanophenyl)-7-((dimethylamino)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 139F), 4-((5aR,6S,7S,8R,8aS)-3-chloro-7-((dimethylamino)methyl)-8,8a-dihydroxy-1-methoxy-6-phenyl-6,7,8,8a-tetrahydro-5aH-cyclopenta[4,5]furo[3,2-c]pyridin-5a-yl)benzonitrile (Cpd. No. 140F), Rac-4-((5aR,6S,7S,8R,8aS)-7-((dimethylamino)methyl)-8,8a-dihydroxy-1-methoxy-6-phenyl-6,7,8,8a-tetrahydro-5aH-cyclopenta[4,5]furo[3,2-c]pyridin-5a-yl)benzonitrile (Cpd. No. 141F), Rac-(5aR,6S,7S,8R,8aS)-3-chloro-5a-(4-chlorophenyl)-7-((dimethylamino)methyl)-1-methoxy-6-phenyl-5a,6,7,8-tetrahydro-8aH-cyclopenta[4,5]furo[3,2-c]pyridine-8,8a-diol (Cpd. No. 142F), Rac-(5aR,6S,7S,8R,8aS)-3-chloro-5a-(4-(difluoromethyl)phenyl)-7-((dimethylamino)methyl)-1-methoxy-6-phenyl-5a,6,7,8-tetrahydro-8aH-cyclopenta[4,5]furo[3,2-c]pyridine-8,8a-diol (Cpd. No. 143F), Rac-(5aR,6S,7S,8R,8aS)-3-chloro-7-((dimethylamino)methyl)-1-methoxy-6-phenyl-5a-(4-(trifluoromethyl)phenyl)-5a,6,7,8-tetrahydro-8aH-cyclopenta[4,5]furo[3,2-c]pyridine-8,8a-diol (Cpd. No. 144F), (5aR,6S,7S,8R,8aS)-5a-(4-chlorophenyl)-7-((dimethylamino)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 145F), Rac-(5aR,6S,7S,8R,8aS)-5a-(4-(difluoromethyl)phenyl)-7-((dimethylamino)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 146F), (5aR,6S,7S,8R,8aS)-7-((dimethylamino)methyl)-8,8a-dihydroxy-1-methoxy-6-phenyl-5a-(4-(trifluoromethyl)phenyl)-5a,7,8,8a-tetrahydro-6H-cyclopenta[4,5]furo[3,2-c]pyridine-3-carbonitrile (Cpd. No. 147F), Rac-(5aR,6S,7S,8R,8aS)-5a-(4-(difluoromethyl)phenyl)-7-((dimethylamino)methyl)-1-methoxy-6-phenyl-5a,6,7,8-tetrahydro-8aH-cyclopenta[4,5]furo[3,2-c]pyridine-8,8a-diol (Cpd. No. 148F), Rac-(5aR,6S,7S,8R,8aS)-7-((dimethylamino)methyl)-1-methoxy-6-phenyl-5a-(4-(trifluoromethyl)phenyl)-5a,6,7,8-tetrahydro-8aH-cyclopenta[4,5]furo[3,2-c]pyridine-8,8a-diol (Cpd. No. 149F), Rac-4-((5aR,6S,7S,8R,8aS)-7-((dimethylamino)methyl)-8,8a-dihydroxy-1-methoxy-3-(methylamino)-6-phenyl-6,7,8,8a-tetrahydro-5aH-cyclopenta[4,5]furo[3,2-c]pyridin-5a-yl)benzonitrile (Cpd. No. 150F), (5aR,6S,7S,8R,8aS)-5a-(4-Cyanophenyl)-8,8a-dihydroxy-1-methoxy-7-(morpholinomethyl)-6-phenyl-5a,7,8,8a-tetrahydro-6H-cyclopenta[4,5]furo[3,2-c]pyridine-3-carbonitrile (Cpd. No. 151F), Rac-4-((5aR,6S,7S,8R,8aS)-3-chloro-8,8a-dihydroxy-1-methoxy-7-(morpholinomethyl)-6-phenyl-6,7,8,8a-tetrahydro-5aH-cyclopenta[4,5]furo[3,2-c]pyridin-5a-yl)benzonitrile (Cpd. No. 152F), Rac-(5aR,6S,7S,8R,8aS)-5a-(4-cyanophenyl)-7-((3,3-difluoropyrrolidin-1-yl)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 153F), Rac-(5aR,6S,7S,8R,8aS)-5a-(4-cyanophenyl)-7-((3,3-difluoropiperidin-1-yl)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 154F), Rac-(5aR,6S,7S,8R,8aS)-7-((tert-butylamino)methyl)-5a-(4-cyanophenyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 155F), Rac-(5aR,6S,7S,8R,8aS)-5a-(4-bromophenyl)-7-((4-fluoropiperidin-1-yl)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 156aF), Rac-4-((5aR,6S,7S,8R,8aS)-3-chloro-7-((4-fluoropiperidin-1-yl)methyl)-8,8a-dihydroxy-1-methoxy-6-phenyl-6,7,8,8a-tetrahydro-5aH-cyclopenta[4,5]furo[3,2-c]pyridin-5a-yl)benzonitrile (Cpd. No. 156bF), Rac-(5aR,6S,7S,8R,8aS)-5a-(4-cyanophenyl)-7-((4-fluoropiperidin-1-yl)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 156cF), Rac-(5aR,6S,7S,8R,8aS)-5a-(4-bromophenyl)-7-((4,4-difluoropiperidin-1-yl)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 157aF), Rac-4-((5aR,6S,7S,8R,8aS)-3-chloro-7-((4,4-difluoropiperidin-1-yl)methyl)-8,8a-dihydroxy-1-methoxy-6-phenyl-6,7,8,8a-tetrahydro-5aH-cyclopenta[4,5]furo[3,2-c]pyridin-5a-yl)benzonitrile (Cpd. No. 157bF), Rac-(5aR,6S,7S,8R,8aS)-5a-(4-cyanophenyl)-7-((4,4-difluoropiperidin-1-yl)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 157cF), Rac-(5aR,6S,7S,8R,8aS)-5a-(4-bromophenyl)-8,8a-dihydroxy-1-methoxy-6-phenyl-7-(pyrrolidin-1-ylmethyl)-5a,7,8,8a-tetrahydro-6H-cyclopenta[4,5]furo[3,2-c]pyridine-3-carbonitrile (Cpd. No. 158aF), Rac-4-((5aR,6S,7S,8R,8aS)-3-chloro-8,8a-dihydroxy-1-methoxy-6-phenyl-7-(pyrrolidin-1-ylmethyl)-6,7,8,8a-tetrahydro-5aH-cyclopenta[4,5]furo[3,2-c]pyridin-5a-yl)benzonitrile (Cpd. No. 158bF), Rac-(5aR,6S,7S,8R,8aS)-5a-(4-cyanophenyl)-8,8a-dihydroxy-1-methoxy-6-phenyl-7-(pyrrolidin-1-ylmethyl)-5a,7,8,8a-tetrahydro-6H-cyclopenta[4,5]furo[3,2-c]pyridine-3-carbonitrile (Cpd. No. 158cF), Rac-(5aR,6S,7S,8R,8aS)-5a-(4-bromophenyl)-7-((diethylamino)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 159aF), Rac-4-((5aR,6S,7S,8R,8aS)-3-chloro-7-((diethylamino)methyl)-8,8a-dihydroxy-1-methoxy-6-phenyl-6,7,8,8a-tetrahydro-5aH-cyclopenta[4,5]furo[3,2-c]pyridin-5a-yl)benzonitrile (Cpd. No. 159bF), Rac-(5aR,6S,7S,8R,8aS)-5a-(4-cyanophenyl)-7-((diethylamino)methyl)-8,8a-dihydroxy-1-methoxy-6-phenyl-5a, 7,8,8a-tetrahydro-6H-cyclopenta[4,5]furo[3,2-c]pyridine-3-carbonitrile (Cpd. No. 159cF), Rac-(5aR,6S,7R,8S,8aS)-5a-(4-bromophenyl)-3-chloro-6-phenyl-7-(pyridin-2-ylthio)-5a,6,7,8-tetrahydro-8aH-cyclopenta[4,5]furo[3,2-b]pyridine-8,8a-diol (Cpd. No. 160aF), Rac-(5aR,6S,7R,8R,8aS)-5a-(4-bromophenyl)-3-chloro-6-phenyl-7-(pyridin-2-ylthio)-5a,6,7,8-tetrahydro-8aH-cyclopenta[4,5]furo[3,2-b]pyridine-8,8a-diol (Cpd. No. 160bF), Rac-methyl (1aS,2R,3S,3aR,8bS)-3a-(4-bromophenyl)-6-chloro-3-phenyl-1a,2,3,3a-tetrahydro-oxireno[2",3":1',5']cyclopenta[1',2':4,5]furo[3,2-b]pyridine-2-carboxylate (Cpd. No. 161F), Rac-(5aR,6S,8R,8aR)-5a-(4-bromophenyl)-3-chloro-8-(hydroxymethyl)-6-phenyl-5a,6,7,8-tetrahydro-8aH-cyclopenta[4,5]furo[3,2-b]pyridin-8a-ol (Cpd. No. 162F), Rac-(5aR,6S,7R,8S,8aS)-5a-(4-bromophenyl)-3-chloro-6-phenyl-7-(pyridin-2-ylsulfonyl)-5a,6,7,8-tetrahydro-8aH-cyclopenta[4,5]furo[3,2-b]pyridine-8,8a-diol (Cpd. No. 163F), Rac-4-((5aR,6S,7R,8S,8aS)-3-chloro-8,8a-dihydroxy-6-phenyl-7-(pyridin-2-ylsulfonyl)-6,7,8,8a-tetrahydro-5aH-cyclopenta[4,5]furo[3,2-b]pyridin-5a-yl)benzonitrile (Cpd. No. 164F), Rac-(5aR,6S,8S,8aR)-8-(aminomethyl)-5a-(4-bromophenyl)-3-chloro-6-phenyl-5a,6,7,8-tetra-hydro-8aH-cyclopenta[4,5]furo[3,2-b]pyridin-8a-ol (Cpd. No. 165), Rac-(5aR,6S,8S,8aR)-5a-(4-bromophenyl)-3-chloro-8-(hydroxymethyl)-6-phenyl-5a,6,7,8-tetrahydro-8aH-cyclopenta[4,5]furo[3,2-b]pyridin-8a-ol (Cpd. No. 166F), Rac-4-((5aR,6S,8R,8aR)-3-chloro-8a-hydroxy-8-(hydroxymethyl)-6-phenyl-6,7,8,8a-tetrahydro-5aH-cyclopenta[4,5]furo[3,2-b]pyridin-5a-yl)benzonitrile (Cpd. No. 167F), Rac-4-((5aR,6S,8S,8aR)-3-chloro-8a-hydroxy-8-(hydroxymethyl)-6-phenyl-6,7,8,8a-tetrahydro-5aH-cyclopenta[4,5]furo[3,2-b]pyridin-5a-yl)benzonitrile (Cpd. No. 168F), Rac-(2aR,3S,3aR,8bS,8cR)-3a-(4-bromophenyl)-6-chloro-8b-hydroxy-3-phenyl-3,3a,8b,8c-tetrahydrooxeto[3",2":4',5']cyclopenta[1',2':4,5]furo[3,2-b]pyridin-2(2aH)-one (Cpd. No. 169F), Rac-(4bR,5R,6R,7S,7aR)-5-(aminomethyl)-7a-(4-bromophenyl)-6-(hydroxymethyl)-4-methoxy-7-phenyl-5,6,7,7a-tetrahydro-4bH-cyclopenta[4,5]furo[2,3-c]pyridin-4b-ol (Cpd. No. 170F), Rac-4-((4bR,5R,6R,7S,7aR)-5-(aminomethyl)-4b-hydroxy-6-(hydroxymethyl)-4-methoxy-7-phenyl-4b,5,6,7-tetrahydro-7aH-cyclopenta[4,5]furo[2,3-c]pyridin-7a-yl)benzonitrile (Cpd. No. 171F), Rac-(4bR,5R,7S,7aR)-5-(aminomethyl)-7a-(4-bromophenyl)-4-methoxy-7-phenyl-5,6,7,7a-tetrahydro-4bH-cyclopenta[4,5]furo[2,3-c]pyridin-4b-ol (Cpd. No. 172F), Rac-4-((4bR,5R,7S,7aR)-5-(aminomethyl)-4b-hydroxy-4-methoxy-7-phenyl-4b,5,6,7-tetrahydro-7aH-cyclopenta[4,5]furo[2,3-c]pyridin-7a-yl)benzonitrile (Cpd. No. 173F), Rac-(5aR,6S,8R,8aR)-8-(aminomethyl)-5a-(4-bromophenyl)-3-chloro-6-phenyl-5a,6,7,8-tetrahydro-8aH-cyclopenta[4,5]furo[3,2-b]pyridin-8a-ol (Cpd. No. 174F), Rac-4-((5aR,6S,8R,8aR)-8-(aminomethyl)-3-chloro-8a-hydroxy-6-phenyl-6,7,8,8a-tetrahydro-5aH-cyclopenta[4,5]furo[3,2-b]pyridin-5a-yl)benzonitrile (Cpd. No. 175F), Rac-(5aR,6S,8R,8aR)-8-(aminomethyl)-5a-(4-cyanophenyl)-8a-hydroxy-6-phenyl-5a,7,8,8a-tetrahydro-6H-cyclopenta[4,5]furo[3,2-b]pyridine-3-carbonitrile (Cpd. No. 176F), Rac-(5aR,6S,8R,8aR)-5a-(4-bromophenyl)-3-chloro-8-(morpholinomethyl)-6-phenyl-5a,6,7,8-tetrahydro-8aH-cyclopenta[4,5]furo[3,2-b]pyridin-8a-ol (Cpd. No. 177F), Rac-4-((5aR,6S,8R,8aR)-3-chloro-8a-hydroxy-8-(morpholinomethyl)-6-phenyl-6,7,8,8a-tetrahydro-5aH-cyclopenta[4,5]furo[3,2-b]pyridin-5a-yl)benzonitrile (Cpd. No. 178F), Rac-(4bR,5R,6R,7S,7aR)-7a-(4-bromophenyl)-6-(hydroxymethyl)-4-methoxy-5-(morpholinomethyl)-7-phenyl-5,6,7,7a-tetrahydro-4bH-cyclopenta[4,5]furo[2,3-c]pyridin-4b-ol (Cpd. No. 179F), Rac-4-((4bR,5R,6R,7S,7aR)-4b-hydroxy-6-(hydroxymethyl)-4-methoxy-5-(morpholino-methyl)-7-phenyl-4b,5,6,7-tetrahydro-7aH-cyclopenta[4,5]furo[2,3-c]pyridin-7a-yl)benzonitrile (Cpd. No. 180F), Rac-(4bR,5R,6R,7S,7aR)-7a-(4-bromophenyl)-5-(((2,2-difluoroethyl)amino)methyl)-6-(hydroxymethyl)-4-methoxy-7-phenyl-5,6,7,7a-tetrahydro-4bH-cyclopenta[4,5]furo[2,3-c]pyridin-4b-ol (Cpd. No. 181F), Rac-4-((4bR,5R,6R,7S,7aR)-5-(((2,2-difluoroethyl)amino)methyl)-4b-hydroxy-6-(hydroxyl-methyl)-4-methoxy-7-phenyl-4b,5,6,7-tetrahydro-7aH-cyclopenta[4,5]furo[2,3-c]pyridin-7a-yl)benzonitrile (Cpd. No. 182F), Rac-(4bR,5R,6R,7S,7aR)-7a-(4-bromophenyl)-6-(hydroxymethyl)-4-methoxy-5-((4-methylpiperazin-1-yl)methyl)-7-phenyl-5,6,7,7a-tetrahydro-4bH-cyclopenta[4,5]furo[2,3-c]pyridin-4b-ol (Cpd. No. 183F), Rac-4-((4bR,5R,6R,7S,7aR)-4b-hydroxy-6-(hydroxymethyl)-4-methoxy-5-((4-methyl-piperazin-1-yl)methyl)-7-phenyl-4b,5,6,7-tetrahydro-7aH-cyclopenta[4,5]furo[2,3-c]pyridin-7a-yl)benzonitrile (Cpd. No. 184F), Rac-(4bR,5R,6R,7S,7aR)-7a-(4-bromophenyl)-6-(hydroxymethyl)-4-methoxy-5-((oxetan-3-ylamino)methyl)-7-phenyl-5,6,7,7a-tetrahydro-4bH-cyclopenta[4,5]furo[2,3-c]pyridin-4b-ol (Cpd. No. 185F), Rac-4-((4bR,5R,6R,7S,7aR)-4b-hydroxy-6-(hydroxymethyl)-4-methoxy-5-((oxetan-3-ylamino)-methyl)-7-phenyl-4b,5,6,7-tetrahydro-7aH-cyclopenta[4,5]furo[2,3-c]pyridin-7a-yl)-benzonitrile (Cpd. No. 186F), Rac-(4bR,5R,6R,7S,7aR)-7a-(4-bromophenyl)-6-(hydroxymethyl)-4-methoxy-7-phenyl-5-(((pyridin-4-ylmethyl)amino)methyl)-5,6,7,7a-tetrahydro-4bH-cyclopenta[4,5]furo[2,3-c]pyridin-4b-ol (Cpd. No. 187F), Rac-4-((4bR,5R,6R,7S,7aR)-4b-hydroxy-6-(hydroxymethyl)-4-methoxy-7-phenyl-5-(((pyridin-4-ylmethyl)amino)methyl)-4b,5,6,7-tetrahydro-7aH-cyclopenta[4,5]furo[2,3-c]pyridin-7a-yl)benzonitrile (Cpd. No. 188F), Rac-4-((5aR,6S,7R,8S,8aS)-3-chloro-8,8a-dihydroxy-6-phenyl-7-(pyridin-2-ylthio)-6,7,8,8a-tetrahydro-5aH-cyclopenta[4,5]furo[3,2-b]pyridin-5a-yl)benzonitrile (Cpd. No. 189F), Rac-(5aR,6S,8aS)-5a-(4-bromophenyl)-3-chloro-8-ethynyl-8,8a-dihydroxy-N,N-dimethyl-6-phenyl-5a,7,8,8a-tetrahydro-6H-cyclopenta[4,5]furo[3,2-b]pyridine-7-carboxamide (Cpd. No. 190F), Rac-(5aR,6S,8aS)-5a-(4-bromophenyl)-3-chloro-8,8a-dihydroxy-N,N-dimethyl-6-phenyl-8-(prop-1-yn-1-yl)-5a,7,8,8a-tetrahydro-6H-cyclopenta[4,5]furo[3,2-b]pyridine-7-carboxamide (Cpd. No. 191F), Rac-(4bR,7S,7aR)-7a-(4-bromophenyl)-4b-hydroxy-4-methoxy-N,N-dimethyl-5-oxo-7-phenyl-4b,6,7,7a-tetrahydro-5H-cyclopenta[4,5]furo[2,3-c]pyridine-6-carboxamide (Cpd. No. 192F), Rac-methyl (4bS,5R,6R,7aR)-4b,5-dihydroxy-7a-(4-iodophenyl)-4-methoxy-7-phenyl-4b,6,7,7a-tetrahydro-5H-cyclopenta[4,5]furo[2,3-c]pyridine-6-carboxylate (Cpd. No. 193F), Rac-4-((4bS,5R,6S,7S,7aR)-6-((4-acetylpiperazin-1-yl)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 194F), Rac-(5aR,6S,7S,8R,8aS)-5a-(4-bromophenyl)-3-chloro-7-(((2,2-difluoroethyl)amino)methyl)-1-methoxy-6-phenyl-5a,6,7,8-tetrahydro-8aH-cyclopenta[4,5]furo[3,2-c]pyridine-8,8a-diol (Cpd. No. 195F), Rac-4-((5aR,6S,7S,8R,8aS)-3-chloro-7-(((2,2-difluoroethyl)amino)methyl)-8,8a-dihydroxy-1-methoxy-6-phenyl-6,7,8,8a-tetrahydro-5aH-cyclopenta[4,5]furo[3,2-c]pyridin-5a-yl)benzonitrile (Cpd. No. 196F), Rac-(5aR,6S,7S,8R,8aS)-5a-(4-cyanophenyl)-7-(((2,2-difluoroethyl)amino)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 197F), 4-((5aR,6S,7S,8R,8aS)-3-chloro-8,8a-dihydroxy-1-methoxy-7-((4-methylpiperazin-1-yl)methyl)-6-phenyl-6,7,8,8a-tetrahydro-5aH-cyclopenta[4,5]furo[3,2-c]pyridin-5a-yl)benzonitrile (Cpd. No. 198aF), Rac-(5aR,6S,7S,8R,8aS)-5a-(4-cyanophenyl)-8,8a-dihydroxy-1-methoxy-7-((4-methylpiperazin-1-yl)methyl)-6-phenyl-5a,7,8,8a-tetrahydro-6H-cyclopenta[4,5]furo[3,2-c]pyridine-3-carbonitrile (Cpd. No. 198bF), Rac-(5aR,6S,7R,8R,8aR)-5a-(4-bromophenyl)-3-chloro-7-(hydroxymethyl)-1-methoxy-8-(morpholinomethyl)-6-phenyl-5a,6,7,8-tetrahydro-8aH-cyclopenta[4,5]furo[3,2-c]pyridin-8a-ol (Cpd. No. 199F), Rac-(5aR,6S,7R,8R,8aR)-5a-(4-cyanophenyl)-8a-hydroxy-7-(hydroxymethyl)-1-methoxy-8-(morpholinomethyl)-6-phenyl-5a,7,8,8a-tetrahydro-6H-cyclopenta[4,5]furo[3,2-c]pyridine-3-carbonitrile (Cpd. No. 200F), Rac-(4bR,5R,6R,7S,7aR)-5-((2-oxa-6-azaspiro[3.3]heptan-6-yl)methyl)-7a-(4-bromophenyl)-6-(hydroxymethyl)-4-methoxy-7-phenyl-5,6,7,7a-tetrahydro-4bH-cyclopenta[4,5]furo[2,3-c]pyridin-4b-ol (Cpd. No. 201F), Rac-4-((4bR,5R,6R,7S,7aR)-5-((2-oxa-6-azaspiro[3.3]heptan-6-yl)methyl)-4b-hydroxy-6-(hydroxymethyl)-4-methoxy-7-phenyl-4b,5,6,7-tetrahydro-7aH-cyclopenta[4,5]furo[2,3-c]pyridin-7a-yl)benzonitrile (Cpd. No. 202F), Rac-(4bR,5R,6R,7S,7aR)-7a-(4-bromophenyl)-6-(hydroxymethyl)-4-methoxy-5-((((1-methyl-1H-pyrazol-5-yl)methyl)amino)methyl)-7-phenyl-5,6,7,7a-tetrahydro-4bH-cyclopenta[4,5]furo[2,3-c]pyridin-4b-ol (Cpd. No. 203F), Rac-4-((4bR,5R,6R,7S,7aR)-4b-hydroxy-6-(hydroxymethyl)-4-methoxy-5-((((1-methyl-1H-pyrazol-5-yl)methyl)amino)methyl)-7-phenyl-4b,5,6,7-tetrahydro-7aH-cyclopenta[4,5]furo[2,3-c]pyridin-7a-yl)benzonitrile (Cpd. No. 204F), Rac-(4bR,5R,6R,7S,7aR)-7a-(4-bromophenyl)-5-((dimethylamino)methyl)-6-(hydroxymethyl)-4-methoxy-7-phenyl-5,6,7,7a-tetrahydro-4bH-cyclopenta[4,5]furo[2,3-c]pyridin-4b-ol (Cpd. No. 205F), Rac-4-((4bR,5R,6R,7S,7aR)-5-((dimethylamino)methyl)-4b-hydroxy-6-(hydroxymethyl)-4-methoxy-7-phenyl-4b,5,6,7-tetrahydro-7aH-cyclopenta[4,5]furo[2,3-c]pyridin-7a-yl)benzonitrile (Cpd. No. 206F), Rac-(5aR,6S,7S,8R,8aS)-5a-(4-cyanophenyl)-7-((3,3-difluoroazetidin-1-yl)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 207aF), Rac-4-((5aR,6S,7S,8R,8aS)-3-chloro-7-((3,3-difluoroazetidin-1-yl)methyl)-8,8a-dihydroxy-1-methoxy-6-phenyl-6,7,8,8a-tetrahydro-5aH-cyclopenta[4,5]furo[3,2-c]pyridin-5a-yl)benzonitrile (Cpd. No. 207bF), Rac-(5aR,6S,7S,8R,8aS)-5a-(4-cyanophenyl)-7-(((2,2-difluoroethyl)(methyl)amino)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 208aF), Rac-4-((5aR,6S,7S,8R,8aS)-3-chloro-7-(((2,2-difluoroethyl)(methyl)amino)methyl)-8,8a-dihydroxy-1-methoxy-6-phenyl-6,7,8,8a-tetrahydro-5aH-cyclopenta[4,5]furo[3,2-c]pyridin-5a-yl)benzonitrile (Cpd. No. 208bF), Rac-(5aR,6S,7R,8R,8aR)-5a-(4-bromophenyl)-3-chloro-8-((dimethylamino)methyl)-7-(hydroxymethyl)-1-methoxy-6-phenyl-5a,6,7,8-tetrahydro-8aH-cyclopenta[4,5]furo[3,2-c]pyridin-8a-ol (Cpd. No. 209F), Rac-(5aR,6S,7R,8R,8aR)-5a-(4-cyanophenyl)-8-((dimethylamino)methyl)-8a-hydroxy-7-(hydroxymethyl)-1-methoxy-6-phenyl-5a,7,8,8a-tetrahydro-6H-cyclopenta[4,5]furo[3,2-c]pyridine-3-carbonitrile (Cpd. No. 210F), Rac-(5aR,6S,7S,8R,8aS)-5a-(4-cyanophenyl)-7-((3-fluoroazetidin-1-yl)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 211aF), Rac-4-((5aR,6S,7S,8R,8aS)-3-chloro-7-((3-fluoroazetidin-1-yl)methyl)-8,8a-dihydroxy-1-methoxy-6-phenyl-6,7,8,8a-tetrahydro-5aH-cyclopenta[4,5]furo[3,2-c]pyridin-5a-yl)benzonitrile (Cpd. No. 211bF), (5aR,6S,7S,8R,8aS)-7-(Azetidin-1-ylmethyl)-5a-(4-cyanophenyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 212F), Rac-(5aR,6S,7R,8R,8aR)-5a-(4-cyanophenyl)-8-((4,4-difluoropiperidin-1-yl)methyl)-8a-hydroxy-7-(hydroxymethyl)-1-methoxy-6-phenyl-5a,7,8,8a-tetrahydro-6H-cyclopenta[4,5]furo[3,2-c]pyridine-3-carbonitrile (Cpd. No. 213F), Rac-(5aR,6S,7S,8R,8aS)-5a-(4-bromophenyl)-3-chloro-7-((3,3-dimethylmorpholino)methyl)-6-phenyl-5a,6,7,8-tetrahydro-8aH-cyclopenta[4,5]furo[3,2-b]pyridine-8,8a-diol (Cpd. No. 214F), Rac-((5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridin-7-yl)(3-(difluoromethyl)azetidin-1-yl)methanone (Cpd. No. 215F), Rac-((5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridin-7-yl)(3-(difluoromethyl)azetidin-1-yl)methanone (Cpd. No. 216F), Rac-4-((5aR,6S,7S,8R,8aS)-3-chloro-7-((3-(difluoromethyl)azetidin-1-yl)methyl)-8,8a-dihydroxy-1-methoxy-6-phenyl-6,7,8,8a-tetrahydro-5aH-cyclopenta[4,5]furo[3,2-c]pyridin-5a-yl)benzonitrile (Cpd. No. 217F), Rac-(5aR,6S,7S,8R,8aS)-5a-(4-cyanophenyl)-7-((3-(difluoromethyl)azetidin-1-yl)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 218F), Rac-((5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridin-7-yl)(1,1-difluoro-4-azaspiro[2.3]hexan-4-yl)methanone (Cpd. No. 219F), Rac-(5aR,6S,7S,8R,8aS)-5a-(4-bromophenyl)-3-chloro-7-((1,1-difluoro-4-azaspiro[2.3]hexan-4-yl)methyl)-1-methoxy-6-phenyl-5a,6,7,8-tetrahydro-8aH-cyclopenta[4,5]furo[3,2-c]pyridine-8,8a-diol (Cpd. No. 220F), Rac-(5aR,6S,7S,8R,8aS)-5a-(4-cyanophenyl)-7-((1,1-difluoro-4-azaspiro[2.3]hexan-4-yl)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 221F), Rac-4-((5aR,6S,7S,8R,8aS)-3-chloro-7-((1,1-difluoro-4-azaspiro[2.3]hexan-4-yl)methyl)-8,8a-dihydroxy-1-methoxy-6-phenyl-6,7,8,8a-tetrahydro-5aH-cyclopenta[4,5]furo[3,2-c]pyridin-5a-yl)benzonitrile (Cpd. No. 222F), Rac-(5aR,6S,7S,8R,8aS)-5a-(4-bromophenyl)-3-chloro-1-methoxy-7-((methylamino)methyl)-6-phenyl-5a,6,7,8-tetrahydro-8aH-cyclopenta[4,5]furo[3,2-c]pyridine-8,8a-diol (Cpd. No. 223F), Rac-4-((5aR,6S,7S,8R,8aS)-3-chloro-8,8a-dihydroxy-1-methoxy-7-((methylamino)methyl)-6-phenyl-6,7,8,8a-tetrahydro-5aH-cyclopenta[4,5]furo[3,2-c]pyridin-5a-yl)benzonitrile (Cpd. No. 224F), Rac-(5aR,6S,7S,8R,8aS)-5a-(4-cyanophenyl)-8,8a-dihydroxy-1-methoxy-7-((methylamino)methyl)-6-phenyl-5a,7,8,8a-tetrahydro-6H-cyclopenta[4,5]furo[3,2-c]pyridine-3-carbonitrile (Cpd. No. 225F), Rac-(4bR,5R,6R,7S,7aR)-7a-(4-bromophenyl)-5-((tert-butylamino)methyl)-6-(hydroxymethyl)-4-methoxy-7-phenyl-5,6,7,7a-tetrahydro-4bH-cyclopenta[4,5]furo[2,3-c]pyridin-4b-ol (Cpd. No. 226F), Rac-(5aR,6S,7R,8S,8aR)-5a-(4-bromophenyl)-3-chloro-7-((dimethylamino)methyl)-8a-hydroxy-6-phenyl-5a,7,8,8a-tetrahydro-6H-cyclopenta[4,5]furo[3,2-b]pyridine-8-carbonitrile (Cpd. No. 227F), Rac-(5aR,6S,7R,8S,8aR)-3-chloro-5a-(4-cyanophenyl)-7-((dimethylamino)methyl)-8a-hydroxy-6-phenyl-5a,7,8,8a-tetrahydro-6H-cyclopenta[4,5]furo[3,2-b]pyridine-8-carbonitrile (Cpd. No. 228F), Rac-(5aR,6S,7R,8R,8aS)-5a-(4-bromophenyl)-8,8a-dihydroxy-1,3-dimethoxy-N,N-dimethyl-6-phenyl-5a,7,8,8a-tetrahydro-6H-cyclopenta[4,5]furo[3,2-c]pyridine-7-carboxamide (Cpd. No. 229F), Rac-(5aR,6S,7S,8R,8aS)-5a-(4-bromophenyl)-7-((dimethylamino)methyl)-1,3-dimethoxy-6-phenyl-5a,6,7,8-tetrahydro-8aH-cyclopenta[4,5]furo[3,2-c]pyridine-8,8a-diol (Cpd. No. 230F), 4-((5aR,6S,7S,8R,8aS)-7-((dimethylamino)methyl)-8,8a-dihydroxy-1,3-dimethoxy-6-phenyl-6,7,8,8a-tetrahydro-5aH-cyclopenta[4,5]furo[3,2-c]pyridin-5a-yl)benzonitrile (Cpd. No. 231F), Rac-4-((5aR,6S,7S,8R,8aS)-7-((diethylamino)methyl)-8,8a-dihydroxy-1,3-dimethoxy-6-phenyl-6,7,8,8a-tetrahydro-5aH-cyclopenta[4,5]furo[3,2-c]pyridin-5a-yl)benzonitrile (Cpd. No. 232F), 4-((4bS,5R,6S,7S,7aR)-4b,5-dihydroxy-4-methoxy-6-((methyl(2,2,2-trifluoroethyl)amino)methyl)-7-phenyl-4b,5,6,7-tetrahydro-7aH-cyclopenta[4,5]furo[2,3-c]pyridin-7a-yl)benzonitrile (Cpd. No. 233F), Rac-(4bR,5R,7S,7aR)-7a-(4-(aminomethyl)phenyl)-5-(hydroxymethyl)-4-methoxy-7-phenyl-5,6,7,7a-tetrahydro-4bH-cyclopenta[4,5]furo[2,3-c]pyridin-4b-ol (Cpd. No. 234F), Rac-((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)(2-oxa-6-azaspiro[3.3]heptan-6-yl)methanone (Cpd. No. 235F), Rac-4-((4bS,5R,6S,7S,7aR)-6-((2-oxa-6-azaspiro[3.3]heptan-6-yl)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 236F), Rac-(4bS,5R,6R,7S,7aR)-7a-(4-bromophenyl)-4b,5-dihydroxy-4-methoxy-N-methyl-N-(oxetan-3-yl)-7-phenyl-4b,6,7,7a-tetrahydro-5H-cyclopenta[4,5]furo[2,3-c]pyridine-6-carboxamide (Cpd. No. 237F), Rac-4-((4bS,5R,6S,7S,7aR)-4b,5-dihydroxy-4-methoxy-6-((methyl(oxetan-3-yl)amino)methyl)-7-phenyl-4b,5,6,7-tetrahydro-7aH-cyclopenta[4,5]furo[2,3-c]pyridin-7a-yl)benzonitrile (Cpd. No. 238F), Rac-(4bS,5R,6R,7S,7aR)-7a-(4-bromophenyl)-4b,5-dihydroxy-4-methoxy-N-(oxetan-3-yl)-7-phenyl-4b,6,7,7a-tetrahydro-5H-cyclopenta[4,5]furo[2,3-c]pyridine-6-carboxamide (Cpd. No. 239F), Rac-4-((4bS,5R,6S,7S,7aR)-4b,5-dihydroxy-4-methoxy-6-((oxetan-3-ylamino)methyl)-7-phenyl-4b,5,6,7-tetrahydro-7aH-cyclopenta[4,5]furo[2,3-c]pyridin-7a-yl)benzonitrile (Cpd. No. 240F), Rac-4-((4bS,5R,6S,7S,7aR)-4b,5-dihydroxy-4-methoxy-6-((((1-methyl-1H-pyrazol-5-yl)methyl)amino)methyl)-7-phenyl-4b,5,6,7-tetrahydro-7aH-cyclopenta[4,5]furo[2,3-c]pyridin-7a-yl)benzonitrile (Cpd. No. 241F), Rac-4-((4bS,5R,6S,7S,7aR)-4b,5-dihydroxy-4-methoxy-6-((((1-methyl-1H-pyrazol-5-yl)methyl)amino)methyl)-7-phenyl-4b,5,6,7-tetrahydro-7aH-cyclopenta[4,5]furo[2,3-c]pyridin-7a-yl)benzonitrile (Cpd. No. 242F), 4-((4bS,5R,6S,7S,7aR)-6-((tert-butyl(methyl)amino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 243F), Rac-4-((4bS,5R,6S,7S,7aR)-6-((cyclopropylamino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 244F), Rac-(4bS,5R,6R,7S,7aR)-7a-(4-bromophenyl)-N-cyclopropyl-4b,5-dihydroxy-4-methoxy-N-methyl-7-phenyl-4b,6,7,7a-tetrahydro-5H-cyclopenta[4,5]furo[2,3-c]pyridine-6-carboxamide (Cpd. No. 245F), Rac-4-((4bS,5R,6S,7S,7aR)-6-((cyclopropyl(methyl)amino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 246F), Rac-(4bS,5R,6R,7S,7aR)-7a-(4-bromophenyl)-N-(2-fluoroethyl)-4b,5-dihydroxy-4-methoxy-N-methyl-7-phenyl-4b,6,7,7a-tetrahydro-5H-cyclopenta[4,5]furo[2,3-c]pyridine-6-carboxamide (Cpd. No. 247F), 4-((4bS,5R,6S,7S,7aR)-6-(((2-fluoroethyl)(methyl)amino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 248F), Rac-(4bS,5R,6R,7S,7aR)-7a-(4-bromophenyl)-4b,5-dihydroxy-4-methoxy-N-methyl-N-((1-methyl-1H-pyrazol-5-yl)methyl)-7-phenyl-4b,6,7,7a-tetrahydro-5H-cyclopenta[4,5]furo[2,3-c]pyridine-6-carboxamide (Cpd. No. 249F), 4-((4bS,5R,6S,7S,7aR)-4b,5-dihydroxy-4-methoxy-6-((methyl((1-methyl-1H-pyrazol-5-yl)methyl)amino)methyl)-7-phenyl-4b,5,6,7-tetrahydro-7aH-cyclopenta[4,5]furo[2,3-c]pyridin-7a-yl)benzonitrile (Cpd. No. 250F), Rac-(4bS,5R,6R,7S,7aR)-7a-(4-bromophenyl)-4b,5-dihydroxy-N-(2-hydroxy-2-methylpropyl)-4-methoxy-N-methyl-7-phenyl-4b,6,7,7a-tetrahydro-5H-cyclopenta[4,5]furo[2,3-c]pyridine-6-carboxamide (Cpd. No. 251F), 4-((4bS,5R,6S,7S,7aR)-4b,5-dihydroxy-6-(((2-hydroxy-2-methylpropyl)(methyl)amino)methyl)-4-methoxy-7-phenyl-4b,5,6,7-tetrahydro-7aH-cyclopenta[4,5]furo[2,3-c]pyridin-7a-yl)benzonitrile (Cpd. No. 252F), Rac-(4bS,5R,6R,7S,7aR)-7a-(4-bromophenyl)-4b,5-dihydroxy-N-(2-hydroxy-2-methylpropyl)-4-methoxy-7-phenyl-4b,6,7,7a-tetrahydro-5H-cyclopenta[4,5]furo[2,3-c]pyridine-6-carboxamide (Cpd. No. 253F), 4-((4bS,5R,6S,7S,7aR)-4b,5-dihydroxy-6-(((2-hydroxy-2-methylpropyl)amino)methyl)-4-methoxy-7-phenyl-4b,5,6,7-tetrahydro-7aH-cyclopenta[4,5]furo[2,3-c]pyridin-7a-yl)benzonitrile (Cpd. No. 254F), Rac-(4bS,5R,6S,7S,7aR)-6-((dimethylamino)methyl)-4-methoxy-7-phenyl-7a-(p-tolyl)-5,6,7,7a-tetrahydro-4bH-cyclopenta[4,5]furo[2,3-c]pyridine-4b,5-diol (Cpd. No. 255F), (4bS,5R,6S,7S,7aR)-6-((dimethylamino)methyl)-4-methoxy-7-phenyl-7a-(p-tolyl)-5,6,7,7a-tetrahydro-4bH-cyclopenta[4,5]furo[2,3-c]pyridine-4b,5-diol (Cpd. No. 256F), Rac-((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)(piperidin-1-yl)methanone (Cpd. No. 257F), 4-((4bS,5R,6S,7S,7aR)-4b,5-dihydroxy-4-methoxy-7-phenyl-6-(piperidin-1-ylmethyl)-4b,5,6,7-tetrahydro-7aH-cyclopenta[4,5]furo[2,3-c]pyridin-7a-yl)benzonitrile (Cpd. No. 258F), Rac-4-((4bS,5R,6S,7S,7aR)-6-(((2-fluoroethyl)amino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 259F), Rac-((4bS,5R,6R,7S,7aR)-7a-(4-bromophenyl)-4b,5-dihydroxy-4-methoxy-N-(2-methoxyethyl)-N-methyl-7-phenyl-4b,6,7,7a-tetrahydro-5H-cyclopenta[4,5]furo[2,3-c]pyridine-6-carboxamide (Cpd. No. 260F), 4-((4bS,5R,6S,7S,7aR)-4b,5-dihydroxy-4-methoxy-6-(((2-methoxyethyl)(methyl)amino)methyl)-7-phenyl-4b,5,6,7-tetrahydro-7aH-cyclopenta[4,5]furo[2,3-c]pyridin-7a-yl)benzonitrile (Cpd. No. 261F), Rac-(4bS,5R,6R,7S,7aR)-7a-(4-bromophenyl)-4b,5-dihydroxy-4-methoxy-N-(2-methoxyethyl)-7-phenyl-4b,6,7,7a-tetrahydro-5H-cyclopenta[4,5]furo[2,3-c]pyridine-6-carboxamide (Cpd. No. 262F), 4-((4bS,5R,6S,7S,7aR)-4b,5-dihydroxy-4-methoxy-6-(((2-methoxyethyl)amino)methyl)-7-phenyl-4b,5,6,7-tetrahydro-7aH-cyclopenta[4,5]furo[2,3-c]pyridin-7a-yl)benzonitrile hydrochloride (Cpd. No. 263F), Rac-((1R,5S)-3-oxa-8-azabicyclo[3.2.1]octan-8-yl)((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)methanone (Cpd. No. 264F), 4-((4bS,5R,6S,7S,7aR)-6-(((1R,5S)-3-oxa-8-azabicyclo[3.2.1]octan-8-yl) methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 265F), Rac-((1R,5S)-3-oxa-6-azabicyclo[3.1.1]heptan-6-yl)((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)methanone (Cpd. No. 266F), Rac-4-((4bS,5R,6S,7S,7aR)-6-(((1R,5S)-3-oxa-6-azabicyclo[3.1.1]heptan-6-yl)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 267F), 4-((4bS,5R,6S,7S,7aR)-6-(((1R,5S)-8-azabicyclo[3.2.1]octan-8-yl)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 268F), Rac-(3aR,4R,4aR,9bS,9cR)-4a-(4-(difluoromethyl)phenyl)-9b-hydroxy-9-methoxy-4-phenyl-3,3a,4,4a,9b,9c-hexahydro-2H-oxazolo[4",5":4',5']cyclopenta[1',2':4,5]furo[2,3-c]pyridin-2-one (Cpd. No. 269F), Rac-(4bS,5R,6R,7R,7aR)-6-amino-7a-(4-(difluoromethyl)phenyl)-4-methoxy-7-phenyl-5,6,7,7a-tetrahydro-4bH-cyclopenta[4,5]furo[2,3-c]pyridine-4b,5-diol (Cpd. No. 270F), Rac-((4bS,5R,6R,7S,7aR)-7a-(4-chlorophenyl)-4b,5-dihydroxy-4-methoxy-N,N-dimethyl-7-phenyl-4b,6,7,7a-tetrahydro-5H-cyclopenta[4,5]furo[2,3-c]pyridine-6-carboxamide (Cpd. No. 271F), (4bS,5R,6S,7S,7aR)-7a-(4-Chlorophenyl)-6-((dimethylamino)methyl)-4-methoxy-7-phenyl-5,6,7,7a-tetrahydro-4bH-cyclopenta[4,5]furo[2,3-c]pyridine-4b,5-diol (Cpd. No. 272F), Rac-(6-oxa-3-azabicyclo[3.1.1]heptan-3-yl)((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)methanone (Cpd. No. 273F), 4-((4bS,5R,6S,7S,7aR)-6-((6-oxa-3-azabicyclo[3.1.1]heptan-3-yl)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 274F), Rac-(3aR,4S,4aR,9bS,9cR)-4a-(4-bromophenyl)-9b-hydroxy-9-methoxy-4-phenyl-3,3a,4,4a,9b,9c-hexahydro-2H-furo[3",2":4',5']cyclopenta[1',2':4,5]furo[2,3-c]pyridin-2-one (Cpd. No. 275F), Rac-4-((4bS,5R,6R,7S,7aR)-6-(2-(dimethylamino)ethyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 276F), Rac-(4bS,5R,6R,7S,7aR)-7a-(4-bromophenyl)-4b,5-dihydroxy-4-methoxy-N-methyl-7-phenyl-N-(pyridin-3-ylmethyl)-4b,6,7,7a-tetrahydro-5H-cyclopenta[4,5]furo[2,3-c]pyridine-6-carboxamide (Cpd. No. 277F), 4-((4bS,5R,6S,7S,7aR)-4b,5-dihydroxy-4-methoxy-6-((methyl(pyridin-3-ylmethyl)amino)methyl)-7-phenyl-4b,5,6,7-tetrahydro-7aH-cyclopenta[4,5]furo[2,3-c]pyridin-7a-yl)benzonitrile (Cpd. No. 278F), Rac-((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)(3,3-difluoropyrrolidin-1-yl)methanone (Cpd. No. 279F), 4-((4bS,5R,6S,7S,7aR)-6-((3,3-difluoropyrrolidin-1-yl)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 280F), Rac-((4bS,5R,6R,7S,7aR)-4b,5-dihydroxy-4-methoxy-7-phenyl-7a-(4-(trifluoromethyl)phenyl)-4b,6,7,7a-tetrahydro-5H-cyclopenta[4,5]furo[2,3-c]pyridin-6-yl)(morpholino)methanone (Cpd. No. 281F), (4bS,5R,6S,7S,7aR)-4-Methoxy-6-(morpholinomethyl)-7-phenyl-7a-(4-(trifluoromethyl)phenyl)-5,6,7,7a-tetrahydro-4bH-cyclopenta[4,5]furo[2,3-c]pyridine-4b,5-diol (Cpd. No. 282F), Rac-(4bS,5R,6S,7S,7aR)-4-methoxy-6-((4-methylpiperazin-1-yl)methyl)-7-phenyl-7a-(4-(trifluoromethyl)phenyl)-5,6,7,7a-tetrahydro-4bH-cyclopenta[4,5]furo[2,3-c]pyridine-4b,5-diol (Cpd. No. 283F), (4bS,5R,6S,7S,7aR)-4-Methoxy-6-((4-methylpiperazin-1-yl)methyl)-7-phenyl-7a-(4-(trifluoromethyl)phenyl)-5,6,7,7a-tetrahydro-4bH-cyclopenta[4,5]furo[2,3-c]pyridine-4b,5-diol (Cpd. No. 284F), Rac-(4bS,5R,6R,7S,7aR)-N-(2,2-difluoroethyl)-4b,5-dihydroxy-4-methoxy-7-phenyl-7a-(4-(trifluoromethyl)phenyl)-4b,6,7,7a-tetrahydro-5H-cyclopenta[4,5]furo[2,3-c]pyridine-6-carboxamide (Cpd. No. 285F), (4bS,5R,6S,7S,7aR)-6-(((2,2-Difluoroethyl)amino)methyl)-4-methoxy-7-phenyl-7a-(4-(trifluoromethyl)phenyl)-5,6,7,7a-tetrahydro-4bH-cyclopenta[4,5]furo[2,3-c]pyridine-4b,5-diol (Cpd. No. 286F), Rac-4-((4bS,5R,7S,7aR)-4b,5-dihydroxy-4-methoxy-5-(morpholinomethyl)-7-phenyl-4b,5,6,7-tetrahydro-7aH-cyclopenta[4,5]furo[2,3-c]pyridin-7a-yl)benzonitrile (Cpd. No. 287F), (5aR,6S,7S,8R,8aS)-5a-(4-Cyanophenyl)-7-((3,3-difluoroazetidin-1-yl)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 288F), Rac-(4bR,7S,7aR)-4-methoxy-5-(morpholinomethyl)-7-phenyl-7a-(4-(trifluoromethyl)phenyl)-5,6,7,7a-tetrahydro-4bH-cyclopenta[4,5]furo[2,3-c]pyridin-4b-ol (Cpd. No. 289F), 4-((4bS,5R,6S,7S,7aR)-6-((tert-butylamino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 290F), 4-((4bS,5R,6S,7S,7aR)-4b,5-dihydroxy-4-methoxy-7-phenyl-6-(((2,2,2-trifluoroethyl)amino)methyl)-4b,5,6,7-tetrahydro-7aH-cyclopenta[4,5]furo[2,3-c]pyridin-7a-yl)benzonitrile (Cpd. No. 291F), Rac-(5aR,6S,7S,8R,8aS)-7-(aminomethyl)-5a-(4-bromophenyl)-3-chloro-1-methoxy-6-phenyl-5a,6,7,8-tetrahydro-8aH-cyclopenta[4,5]furo[3,2-c]pyridine-8,8a-diol (Cpd. No. 292F), Rac-(5aR,6S,7S,8R,8aS)-7-(aminomethyl)-5a-(4-cyanophenyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 293F), Rac-4-((5aR,6S,7S,8R,8aS)-7-(aminomethyl)-3-chloro-8,8a-dihydroxy-1-methoxy-6-phenyl-6,7,8,8a-tetrahydro-5aH-cyclopenta[4,5]furo[3,2-c]pyridin-5a-yl)benzonitrile (Cpd. No. 294F), and Rac-(5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridine-7-carboxylic acid (Cpd. No. 295F).

In another embodiment, the compounds according to Formula I are selected from (5aR,6S,7S,8R,8aS)-7-((Dimethylamino)methyl)-8,8a-dihydroxy-1-methoxy-6-phenyl-5a-(4-(trifluoromethyl)phenyl)-5a,7,8,8a-tetrahydro-6H-cyclopenta[4,5]furo[3,2-c]pyridine-3-carbonitrile (Cpd. No. 147F), 4-((5aR,6S,7S,8R,8aS)-3-Chloro-8,8a-dihydroxy-1-methoxy-7-((4-methylpiperazin-1-yl)methyl)-6-phenyl-6,7,8,8a-tetrahydro-5aH-cyclopenta[4,5]furo[3,2-c]pyridin-5a-yl)benzonitrile (Cpd. No. 198aF), (5aR,6S,7S,8R,8aS)-7-(Azetidin-1-ylmethyl)-5a-(4-cyanophenyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 212F), (5aR,6S,7S,8R,8aS)-5a-(4-Chlorophenyl)-7-((dimethylamino)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 145F), Rac-(5aR,6S,7S,8R,8aS)-3-chloro-7-((dimethylamino)methyl)-1-methoxy-6-phenyl-5a-(4-(trifluoromethyl)phenyl)-5a,6,7,8-tetrahydro-8aH-cyclopenta[4,5]furo[3,2-c]pyridine-8,8a-diol (Cpd. No. 144F), Rac-(5aR,6S,7S,8R,8aS)-3-chloro-5a-(4-(difluoromethyl)phenyl)-7-((dimethylamino)methyl)-1-methoxy-6-phenyl-5a,6,7,8-tetrahydro-8aH-cyclopenta[4,5]furo[3,2-c]pyridine-8,8a-diol (Cpd. No. 143F), Rac-(5aR,6S,7S,8R,8aS)-3-chloro-5a-(4-chlorophenyl)-7-((dimethylamino)methyl)-1-methoxy-6-phenyl-5a,6,7,8-tetrahydro-8aH-cyclopenta[4,5]furo[3,2-c]pyridine-8,8a-diol (Cpd. No. 142F), Rac-4-((5aR,6S,7S,8R,8aS)-3-chloro-7-(((2,2-difluoroethyl)amino)methyl)-8,8a-dihydroxy-1-methoxy-6-phenyl-6,7,8,8a-tetrahydro-5aH-cyclopenta[4,5]furo[3,2-c]pyridin-5a-yl)benzonitrile (Cpd. No. 196F), (5aR,6S,7S,8R,8aS)-5a-(4-Cyanophenyl)-7-((dimethylamino)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 139F), Rac-4-((5aR,6S,7S,8R,8aS)-3-chloro-7-((3,3-difluoroazetidin-1-yl)methyl)-8,8a-dihydroxy-1-methoxy-6-phenyl-6,7,8,8a-tetrahydro-5aH-cyclopenta[4,5]furo[3,2-c]pyridin-5a-yl)benzonitrile (Cpd. No. 207bF), Rac-4-((5aR,6S,7S,8R,8aS)-3-chloro-8,8a-dihydroxy-1-methoxy-7-(morpholinomethyl)-6-phenyl-6,7,8,8a-tetrahydro-5aH-cyclopenta[4,5]furo[3,2-c]pyridin-5a-yl)benzonitrile (Cpd. No. 152F), Rac-4-((5aR,6S,7S,8R,8aS)-3-chloro-7-((4,4-difluoropiperidin-1-yl)methyl)-8,8a-dihydroxy-1-methoxy-6-phenyl-6,7,8,8a-tetrahydro-5aH-cyclopenta[4,5]furo[3,2-c]pyridin-5a-yl)benzonitrile (Cpd. No. 157bF), Rac-4-((5aR,6S,7S,8R,8aS)-3-chloro-8,8a-dihydroxy-1-methoxy-6-phenyl-7-(pyrrolidin-1-ylmethyl)-6,7,8,8a-tetrahydro-5aH-cyclopenta[4,5]furo[3,2-c]pyridin-5a-yl)benzonitrile (Cpd. No. 158bF), 4-((5aR,6S,7S,8R,8aS)-7-((Dimethylamino)methyl)-8,8a-dihydroxy-1,3-dimethoxy-6-phenyl-6,7,8,8a-tetrahydro-5aH-cyclopenta[4,5]furo[3,2-c]pyridin-5a-yl)benzonitrile (Cpd. No. 231F), Rac-4-((5aR,6S,7S,8R,8aS)-3-chloro-7-((diethylamino)methyl)-8,8a-dihydroxy-1-methoxy-6-phenyl-6,7,8,8a-tetrahydro-5aH-cyclopenta[4,5]furo[3,2-c]pyridin-5a-yl)benzonitrile (Cpd. No. 159bF), 4-((5aR,6S,7S,8R,8aS)-3-Chloro-7-((dimethylamino)methyl)-8,8a-dihydroxy-1-methoxy-6-phenyl-6,7,8,8a-tetrahydro-5aH-cyclopenta[4,5]furo[3,2-c]pyridin-5a-yl)benzonitrile (Cpd. No. 140F), Rac-(5aR,6S,7S,8R,8aS)-5a-(4-(difluoromethyl)phenyl)-7-((dimethylamino)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 146F), (5aR,6S,7S,8R,8aS)-5a-(4-Cyanophenyl)-8,8a-dihydroxy-1-methoxy-7-(morpholinomethyl)-6-phenyl-5a,7,8,8a-tetrahydro-6H-cyclopenta[4,5]furo[3,2-c]pyridine-3-carbonitrile (Cpd. No. 151F), Rac-(5aR,6S,7S,8R,8aS)-5a-(4-cyanophenyl)-7-(((2,2-difluoroethyl)amino)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 197F), Rac-(5aR,6S,7S,8R,8aS)-5a-(4-cyanophenyl)-7-((3,3-difluoroazetidin-1-yl)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 207aF), Rac-(5aR,6S,7S,8R,8aS)-5a-(4-cyanophenyl)-7-((4,4-difluoropiperidin-1-yl)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 157cF), Rac-(5aR,6S,7S,8R,8aS)-5a-(4-cyanophenyl)-7-((3,3-difluoropyrrolidin-1-yl)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 153F), Rac-(5aR,6S,7S,8R,8aS)-5a-(4-cyanophenyl)-7-((diethylamino)methyl)-8,8a-dihydroxy-1-methoxy-6-phenyl-5a, 7,8,8a-tetrahydro-6H-cyclopenta[4,5]furo[3,2-c]pyridine-3-carbonitrile (Cpd. No. 159cF), Rac-(5aR,6S,7S,8R,8aS)-5a-(4-cyanophenyl)-8,8a-dihydroxy-1-methoxy-6-phenyl-7-(pyrrolidin-1-ylmethyl)-5a,7,8,8a-tetrahydro-6H-cyclopenta[4,5]furo[3,2-c]pyridine-3-carbonitrile (Cpd. No. 158cF), Rac-4-((4bR,5R,6R,7S,7aR)-4b-hydroxy-6-(hydroxymethyl)-4-methoxy-5-(morpholino-methyl)-7-phenyl-4b,5,6,7-tetrahydro-7aH-cyclopenta[4,5]furo[2,3-c]pyridin-7a-yl)benzonitrile (Cpd. No. 180F), Rac-4-((4bR,5R,6R,7S,7aR)-5-((dimethylamino)methyl)-4b-hydroxy-6-(hydroxymethyl)-4-methoxy-7-phenyl-4b,5,6,7-tetrahydro-7aH-cyclopenta[4,5]furo[2,3-c]pyridin-7a-yl)benzonitrile (Cpd. No. 206F), 4-((4bS,5R,6S,7S,7aR)-6-((Dimethylamino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 66F), (4bS,5R,6S,7S,7aR)-7a-(4-Chlorophenyl)-6-((dimethylamino)methyl)-4-methoxy-7-phenyl-5,6,7,7a-tetrahydro-4bH-cyclopenta[4,5]furo[2,3-c]pyridine-4b,5-diol (Cpd. No. 272F), (4bS,5R,6S,7S,7aR)-7a-(4-(Difluoromethyl)phenyl)-6-((dimethylamino)methyl)-4-methoxy-7-phenyl-5,6,7,7a-tetrahydro-4bH-cyclopenta[4,5]furo[2,3-c]pyridine-4b,5-diol (Cpd. No. 106F), and (4bS,5R,6S,7S,7aR)-6-((Dimethylamino)methyl)-4-methoxy-7-phenyl-7a-(4-(trifluoromethyl)phenyl)-5,6,7,7a-tetrahydro-4bH-cyclopenta[4,5]furo[2,3-c]pyridine-4b,5-diol (Cpd. No. 107F).

In another embodiment the compounds according to Formula I are selected from those presented in Table 1.

The inventive compounds according to Formula I may be isotopically-labeled by having one or more atoms replaced by an atom having a different atomic mass or mass number. Examples of isotopes that can be incorporated into compounds of according to Formula I include isotopes of hydrogen, carbon, nitrogen, oxygen, phosphorous, fluorine, chlorine, or iodine. Illustrative of such isotopes are $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These radiolabeled compounds can be used to measure the biodistribution, tissue concentration and the kinetics of transport and excretion from biological tissues including a subject to which such a labeled compound is administered. Labeled compounds are also used to determine therapeutic effectiveness, the site or mode of action, and the binding affinity of a candidate therapeutic to a pharmacologically important target. Certain radioactive-labeled compounds according to Formula I, therefore, are useful in drug and/or tissue distribution studies. The radioactive isotopes tritium, i.e. $^{3}H$, and carbon-14, i.e. $^{14}C$, are particularly useful for this purpose in view of their ease of incorporation and ready means of detection.

Substitution with heavier isotopes such as deuterium, i.e. $^{2}H$, affords certain therapeutic advantages resulting from the greater metabolic stability, for example, increased in vivo half-life of compounds containing deuterium. Substitution of hydrogen with deuterium may reduce dose required for therapeutic effect, and hence may be preferred in a discovery or clinical setting.

Substitution with positron emitting isotopes, such as $^{11}C$, $^{18}F$, $^{15}O$ and $^{13}N$, provides labeled analogs of the inventive compounds that are useful in Positron Emission Tomography (PET) studies, e.g., for examining substrate receptor occupancy. Isotopically-labeled compounds according to Formula I, can generally be prepared by conventional techniques known to those skilled in the art or by processes analogous to those described in the Preparations and Examples section as set out below using an appropriate isotopic-labeling reagent.

Embodiments of the invention disclosed herein are also meant to encompass the in vivo metabolic products of compounds according to Formula I. Such products may result from, for example, the oxidation, reduction, hydrolysis, amidation, esterification, and like processes primarily due to enzymatic activity upon administration of a compound of the invention.

Accordingly, the invention includes compounds that are produced as by-products of enzymatic or non-enzymatic activity on an inventive compound following the administration of such a compound to a mammal for a period of time sufficient to yield a metabolic product. Metabolic products, particularly pharmaceutically active metabolites are typically identified by administering a radiolabeled compound of the invention in a detectable dose to a subject, such as rat, mouse, guinea pig, monkey, or human, for a sufficient period of time during which metabolism occurs, and isolating the metabolic products from urine, blood or other biological samples that are obtained from the subject receiving the radiolabeled compound.

The invention also provides pharmaceutically acceptable salt forms of Formula I compounds. Encompassed within the scope of the invention are both acid and base addition salts that are formed by contacting a pharmaceutically suitable acid or a pharmaceutically suitable base with a compound of the invention.

To this end, a "pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

Similarly, a "pharmaceutically acceptable base addition salt" refers to those salts which retain the biological effectiveness and properties of the free acids, which are not biologically or otherwise undesirable. These salts are prepared by addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

Compounds of the invention or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

The term "tautomer" refers to a proton shift from one atom of a molecule to another atom of the same molecule.

The inventive compounds are synthesized using conventional synthetic methods, and more specifically using the general methods noted below.

Pharmaceutical Formulations

In one embodiment, a compounds according Formulae I are formulated as pharmaceutically acceptable compositions that contain a Formulae I compound in an amount effective to treat a particular disease or condition of interest upon administration of the pharmaceutical composition to a mammal. Pharmaceutical compositions in accordance with the present invention can comprise a Formulae I compound in combination with a pharmaceutically acceptable carrier, diluent or excipient.

In this regard, a "pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

Further, a "mammal" includes humans and both domestic animals such as laboratory animals and household pets (e.g., cats, dogs, swine, cattle, sheep, goats, horses, rabbits), and non-domestic animals such as wildlife and the like.

The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see Remington: The Science and Practice of Pharmacy, 20th Edition (Philadelphia College of Pharmacy and Science, 2000). The composition to be administered will, in any event, contain a therapeutically effective amount of a compound of the invention, or a pharmaceutically acceptable salt thereof, for treatment of a disease or condition of interest in accordance with the teachings of this invention.

A pharmaceutical composition of the invention may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example, inhalatory administration. When intended for oral administration, the pharmaceutical composition is preferably in either solid or liquid form, where semi-solid, semi-liquid, suspension and gel forms are included within the forms considered herein as either solid or liquid.

As a solid composition for oral administration the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of the invention intended for either parenteral or oral administration should contain an amount of a compound of the invention such that a suitable dosage will be obtained.

The pharmaceutical composition of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device.

The pharmaceutical composition of the invention may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the invention in solid or liquid form may include an agent that binds to the compound of the invention and thereby assists in the delivery of the compound. Suitable agents that may act in this capacity include a monoclonal or polyclonal antibody, a protein or a liposome.

The pharmaceutical composition of the invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients.

Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

The pharmaceutical compositions of the invention may be prepared by any methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

In certain embodiments a pharmaceutical composition comprising a compound of Formula I is administered to a mammal in an amount sufficient to inhibit eIF4A activity upon administration, and preferably with acceptable toxicity to the same. eIF4A activity of Formula I compounds can be determined by one skilled in the art, for example, as described in the Examples below. Appropriate concentrations and dosages can be readily determined by one skilled in the art.

Therapeutic Use

The compounds of the invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy.

"Effective amount" or "therapeutically effective amount" refers to that amount of a compound of the invention which, when administered to a mammal, preferably a human, is sufficient to effect treatment, as defined below, of a eIF4A related condition or disease in the mammal, preferably a human. The amount of a compound of the invention which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

Compounds of the invention or pharmaceutically acceptable salt thereof may also be administered simultaneously with, prior to, or after administration of one or more other therapeutic agents. Such combination therapy includes administration of a single pharmaceutical dosage formulation which contains a compound of the invention and one or more additional active agents, as well as administration of the compound of the invention and each active agent in its own separate pharmaceutical dosage formulation. For example, a compound of the invention and the other active agent can be administered to the patient together in a single oral dosage composition such as a tablet or capsule, or each agent administered in separate oral dosage formulations. Where separate dosage formulations are used, the compounds of the invention and one or more additional active agents can be administered at essentially the same time, i.e., concurrently, or at separately staggered times, i.e., sequentially; combination therapy is understood to include all these regimens.

In certain embodiments the disclosed compounds are useful for inhibiting the activity of eIF4A and/or can be useful in analyzing eIF4A signaling activity in model systems and/or for preventing, treating, or ameliorating a symptom associated with a disease, disorder, or pathological condition involving eIF4A, preferably one afflicting humans. A compound which inhibits the activity of eIF4A will be useful in preventing, treating, ameliorating, or reducing the symptoms or progression of diseases of uncontrolled cell growth, proliferation and/or survival, inappropriate cellular immune responses, or inappropriate cellular inflammatory responses or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by eIF4A, such as, for example, haematological tumors, solid tumors, and/or metastases thereof, including leukaemias and myelodysplastic syndrome, Waldenstrom macroglobulinemia, and malignant lymphomas, for example, B-cell lymphoma, T-cell lymphoma, hairy cell lymphoma, Hodgkin's lymphoma, non-Hodgin's lymphoma, and Burkitt's lymphoma, head and neck tumors including brain tumors and brain metastases, tumors of the thorax including non-small cell and small cell lung tumors, gastrointestinal tumors, endocrine tumors, mammary and other gynecological tumors, urological tumors including renal, bladder and prostate tumors, skin tumors, and sarcomas, and/or metastases thereof.

Furthermore, the inventive compounds and their pharmaceutical compositions are candidate therapeutics for the prophylaxis and/or therapy of cytokine related diseases, such as inflammatory diseases, allergies, or other conditions associated with proinflammatory cytokines. Exemplary inflammatory diseases include without limitation, chronic or acute inflammation, inflammation of the joints such as chronic inflammatory arthritis, rheumatoid arthritis, psoriatic arthritis, osteoarthritis, juvenile rheumatoid arthritis, Reiter's syndrome, rheumatoid traumatic arthritis, rubella arthritis, acute synovitis and gouty arthritis; inflammatory skin diseases such as sunburn, psoriasis, erythrodermic psoriasis, pustular psoriasis, eczema, dermatitis, acute or chronic graft formation, atopic dermatitis, contact dermatitis, urticaria and scleroderma; inflammation of the gastrointestinal tract such as inflammatory bowel disease, Crohn's disease and related conditions, ulcerative colitis, colitis, and diverticulitis; nephritis, urethritis, salpingitis, oophoritis, endomyometritis, spondylitis, systemic lupus erythematosus and related disorders, multiple sclerosis, asthma, meningitis, myelitis, encephalomyelitis, encephalitis, phlebitis, thrombophlebitis, respiratory diseases such as asthma, bronchitis, chronic obstructive pulmonary disease (COPD), inflammatory lung disease and adult respiratory distress syndrome, and allergic rhinitis; endocarditis, osteomyelitis, rheumatic fever, rheumatic pericarditis, rheumatic endocarditis, rheumatic myocarditis, rheumatic mitral valve disease, rheumatic aortic valve disease, prostatitis, prostatocystitis, spondoarthropathies ankylosing spondylitis, synovitis, tenosynovotis, myositis, pharyngitis, polymyalgia rheumatica, shoulder tendonitis or bursitis, gout, pseudo gout, vasculitides, inflammatory diseases of the thyroid selected from granulomatous thyroiditis, lymphocytic thyroiditis, invasive fibrous thyroiditis, acute thyroiditis; Hashimoto's thyroiditis, Kawasaki's disease, Raynaud's phenomenon, Sjogren's syndrome, neuroinflammatory disease, sepsis, conjunctivitis, keratitis, iridocyclitis, optic neuritis, otitis, lymphoadenitis, nasopaharingitis, sinusitis, pharyngitis, tonsillitis, laryngitis, epiglottitis, bronchitis, pneumonitis, stomatitis, gingivitis. oesophagitis, gastritis, peritonitis, hepatitis, cholelithiasis, cholecystitis, glomerulonephritis, goodpasture's disease, crescentic glomerulonephritis, pancreatitis, endomyometritis, myometritis, metritis, cervicitis, endocervicitis, exocervicitis, parametritis, tuberculosis, vaginitis, vulvitis, silicosis, sarcoidosis, pneumoconiosis, pyresis, inflammatory polyarthropathies, psoriatric arthropathies, intestinal fibrosis, bronchiectasis and enteropathic arthropathies.

Yet further, the inventive compounds and their pharmaceutical compositions are candidate therapeutics for the prophylaxis and/or therapy of fibrotic diseases, such as various forms of fibrosis, fibromas or any disease giving rise to fibrosis whether as a main or a secondary symptom. Exemplary fibrotic diseases include without limitation, viral hepatitis, hepatic fibrosis, liver fibrosis, renal fibrosis, schistosomiasis, steatohepatitis (alcoholic or non-alcoholic (NASH)), cirrhosis, idiopathic pulmonary fibrosis (IPF), systemic sclerosis (scleroderma), nephrogenic systemic fibrosis (NSF), diabetes, untreated hypertension, heart attack, hypertension, atherosclerosis, restenosis, macular degeneration, retinal and vitreal retinopathy, keloids, hypertrophic scars, Crohn's disease and Alzheimer's disease.

Although inflammation is the unifying pathogenic process of these diseases, current therapies only treat the symptoms of the disease and not the underlying cause of inflammation. The compositions of the present invention are useful for the treatment and/or prophylaxis of inflammatory diseases and related complications and disorders.

Accordingly, certain embodiments are directed to a method for treating a eIF4A dependent condition in a mammal in need thereof, the method comprising administering an effective amount of a pharmaceutical composition as described above (i.e., a pharmaceutical composition comprising any one or more compounds of Formula I) to a mammal.

As described above deregulation of protein synthesis is a common event in human cancers. A key regulator of translational control is eIF4E whose activity is a key determinant of tumorigenicity. Inhibitors of eIF4A are suitable candidate therapeutics for treating cell proliferative disorders such as cancer. A wide variety of cancers, including solid tumors, lymphomas and leukemias, are amenable to the compositions and methods disclosed herein. Types of cancer that may be treated include, but are not limited to: adenocarcinoma of the breast, prostate, and colon; all forms of bronchogenic carcinoma of the lung; myeloid; melanoma; hepatoma; neuroblastoma; papilloma; apudoma; choristoma; branchioma; malignant carcinoid syndrome; carcinoid heart disease; and carcinoma (e.g., Walker, basal cell, basosquamous, Brown-Pearce, ductal, Ehrlich tumor, Krebs 2, merkel cell, mucinous, non-small cell lung, oat cell, papillary, scirrhous, bronchiolar, bronchogenic, squamous cell, and transitional cell). Additional types of cancers that may be treated include: histiocytic disorders; leukemia; histiocytosis malignant; Hodgkin's disease; immunoproliferative small; non-Hodgkin's lymphoma; T-cell lymphoma, B-cell lymphoma, hairy cell lymphoma, Burkitt's lymphoma, plasmacytoma; reticuloendotheliosis; melanoma; chondroblastoma; chondroma; chondrosarcoma; fibroma; fibrosarcoma; giant cell tumors; histiocytoma; lipoma; liposarcoma; mesothelioma; myxoma; myxosarcoma; osteoma; osteosarcoma; chordoma; craniopharyngioma; dysgerminoma; hamartoma; mesenchymoma; mesonephroma; myosarcoma; ameloblastoma; cementoma; odontoma; teratoma; thymoma; trophoblastic tumor.

Other cancers that can be treated using the inventive compounds include without limitation adenoma; cholangioma; cholesteatoma; cyclindroma; cystadenocarcinoma; cystadenoma; granulosa cell tumor; gynandroblastoma; hepatoma; hidradenoma; islet cell tumor; Leydig cell tumor; papilloma; sertoli cell tumor; theca cell tumor; leimyoma; leiomyosarcoma; myoblastoma; myomma; myosarcoma; rhabdomyoma; rhabdomyosarcoma; ependymoma; ganglioneuroma; glioma; medulloblastoma; meningioma; neurilemmoma; neuroblastoma; neuroepithelioma; neurofibroma; neuroma; paraganglioma; paraganglioma nonchromaffin.

In one embodiment the inventive compounds are candidate therapeutic agents for the treatment of cancers such as angiokeratoma; angiolymphoid hyperplasia with eosinophilia; angioma sclerosing; angiomatosis; glomangioma; hemangioendothelioma; hemangioma; hemangiopericytoma; hemangiosarcoma; lymphangioma; lymphangiomyoma; lymphangiosarcoma; pinealoma; carcinosarcoma; chondrosarcoma; cystosarcoma phyllodes; fibrosarcoma; hemangiosarcoma; leiomyosarcoma; leukosarcoma; liposarcoma; lymphangiosarcoma; myosarcoma; myxosarcoma; ovarian carcinoma; rhabdomyosarcoma; sarcoma; neoplasms; nerofibromatosis; and cervical dysplasia.

In a particular embodiment the present disclosure provides methods for treating colon cancer, colorectal cancer, gastric cancer, thyroid cancer, lung cancer, leukemia, acute myeloid leukemia, pancreatic cancer, melanoma, multiple melanoma, brain cancer, primary and secondary CNS cancer, including malignant glioma and glioblastoma, renal cancer, prostate cancer, including castration-resistant prostate cancer, ovarian cancer, or breast cancer, including triple negative, HER2 positive, and hormone receptor positive breast cancers. According to such a method, a therapeutically effective amount of at least one compound according to Formula I or a stereoisomer, tautomer or pharmaceutically acceptable salt thereof can be administered to a subject who has been diagnosed with a cell proliferative disease, such as a cancer. Alternatively, a pharmaceutical composition comprising at least one compound according to Formula I or a stereoisomer, tautomer or pharmaceutically acceptable salt thereof can be administered to a subject who has been diagnosed with cancer.

In certain embodiments the compounds in accordance with the invention are administered to a subject with cancer in conjunction with other conventional cancer therapies such as radiation treatment or surgery. Radiation therapy is well-known in the art and includes X-ray therapies, such as gamma-irradiation, and radiopharmaceutical therapies.

In certain embodiments the inventive eIF4A inhibitor compounds are used with at least one anti-cancer agent. Anti-cancer agents include chemotherapeutic drugs. A chemotherapeutic agent includes, but is not limited to, an inhibitor of chromatin function, a topoisomerase inhibitor, a microtubule inhibiting drug, a DNA damaging agent, an antimetabolite (such as folate antagonists, pyrimidine analogs, purine analogs, and sugar-modified analogs), a DNA synthesis inhibitor, a DNA interactive agent (such as an intercalating agent), and a DNA repair inhibitor.

Illustrative chemotherapeutic agents include, without limitation, the following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, Cytoxan, dactinomycin, daunorubicin, doxorubicin, epirubicin, hexamethylmelamineoxaliplatin, iphosphamide, melphalan, merchlorehtamine, mitomycin, mitoxantrone, nitrosourea, plicamycin, procarbazine, taxol, taxotere, temozolamide, teniposide, triethylenethiophosphoramide and etoposide (VP 16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP470, genistein) and growth factor inhibitors (vascular endothelial growth factor (VEGF) inhibitors, fibroblast growth factor (FGF) inhibitors); angiotensin receptor blocker; nitric oxide donors; anti-sense oligonucleotides; antibodies (trastuzumab, rituximab); chimeric antigen receptors; cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin, irinotecan (CPT-11) and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers, toxins such as Cholera toxin, ricin, *Pseudomonas* exotoxin, *Bordetella pertussis* adenylate cyclase toxin, or diphtheria toxin, and caspase activators; and chromatin disruptors.

In certain embodiments an eIF4A inhibitor in accordance with the present invention is used simultaneously, in the same formulation or in separate formulations, or sequentially with an additional agent(s) as part of a combination therapy regimen.

eIF4A inhibitors according to Formula I including their corresponding salts and pharmaceutically acceptable compositions of Formula I compounds are also effective as therapeutic agents for treating or preventing cytokine mediated disorders, such as inflammation in a patient, preferably in a human. In one embodiment, a compound or composition in accordance with the invention is particularly useful for treating or preventing a disease selected from chronic or acute inflammation, chronic inflammatory arthritis, rheumatoid arthritis, psoriasis, COPD, inflammatory bowel disease, septic shock, Crohn's disease, ulcerative colitis, multiple sclerosis and asthma.

The inventive compounds their corresponding salts and pharmaceutically acceptable compositions are candidate therapeutics for treating brain related disorders which include without limitation autism, Fragile X-syndrome, Parkinson's disease and Alzheimer's disease. Treatment is effected by administering to a subject in need of treatment a Formula I compound, its pharmaceutically acceptable salt form, or a pharmaceutically acceptable composition of a Formula I compound or its salt.

The invention also supports the use of the inventive compounds or a pharmaceutically acceptable formulation of the inventive compound as an inhibitor of eIF4A activity. Such inhibition is achieved by contacting a cell expressing eIF4A with a compound or a pharmaceutically acceptable formulation, to lower or inhibit eIF4A activity, to provide therapeutic efficacy for a eIF4A dependent condition in a mammal in need thereof.

Therapeutically effective dosages of a compound according to Formula I or a composition of a Formula I compound will generally range from about 1 to 2000 mg/day, from about 10 to about 1000 mg/day, from about 10 to about 500 mg/day, from about 10 to about 250 mg/day, from about 10 to about 100 mg/day, or from about 10 to about 50 mg/day. The therapeutically effective dosages may be administered in one or multiple doses. It will be appreciated, however, that specific doses of the compounds of the invention for any particular patient will depend on a variety of factors such as age, sex, body weight, general health condition, diet, individual response of the patient to be treated, time of administration, severity of the disease to be treated, the activity of particular compound applied, dosage form, mode of application and concomitant medication. The therapeutically effective amount for a given situation will readily be determined by routine experimentation and is within the skills and judgment of the ordinary clinician or physician. In any case the compound or composition will be administered at dosages and in a manner which allows a therapeutically effective amount to be delivered based upon patient's unique condition.

General Synthetic Methods

General Method ("GM") 1:

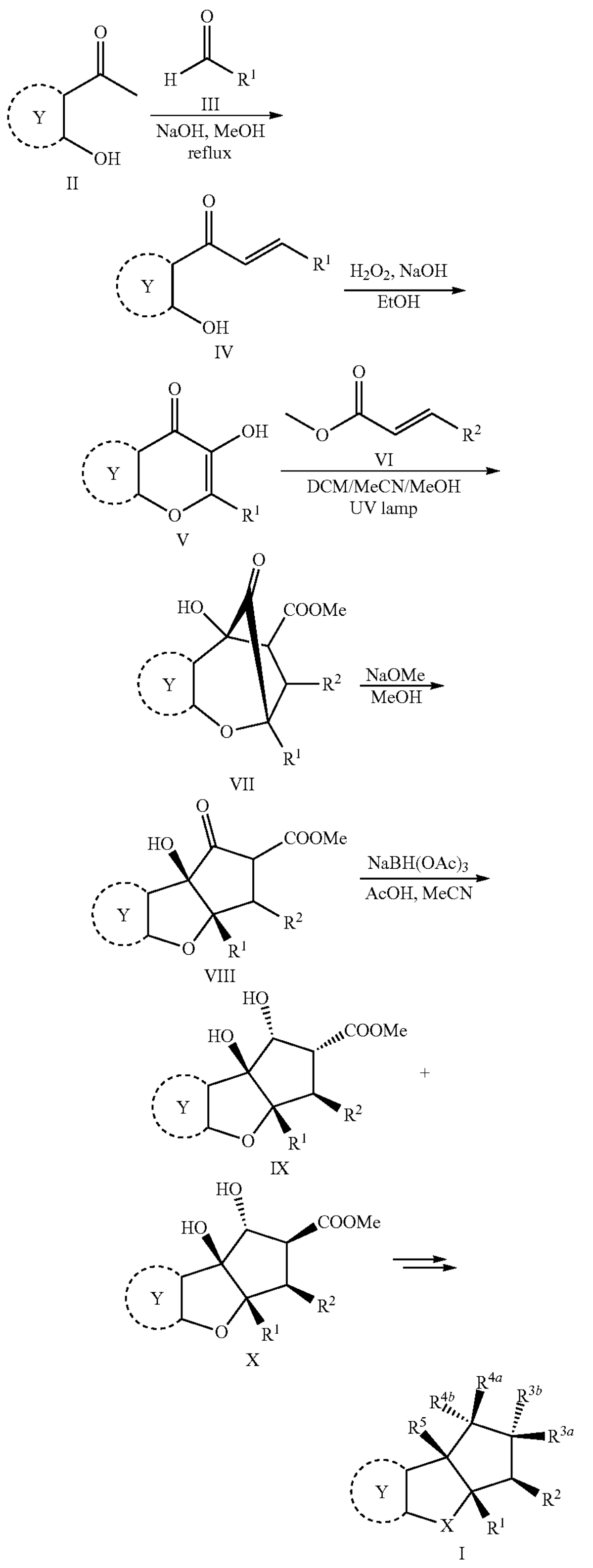

The formation of I (X is O) is accomplished by a multi-step synthetic sequence starting with compound II.-

Condensation of compounds II and III, followed by treatment with hydrogen peroxide and sodium hydroxide in ethanol gives intermediate V. Hydroxyflavone V is submitted to a sequence of photocycloaddition, ketol rearrangement, and directed stereoselective reduction to give a diastereoisomeric mixture of flavagline IX and X. Deprotection and/or further functional group manipulation, if necessary, generate compound I (X is O). Compound I in its enantiomeric pure form is finally obtained via chiral HPLC separation.

General Method 2:

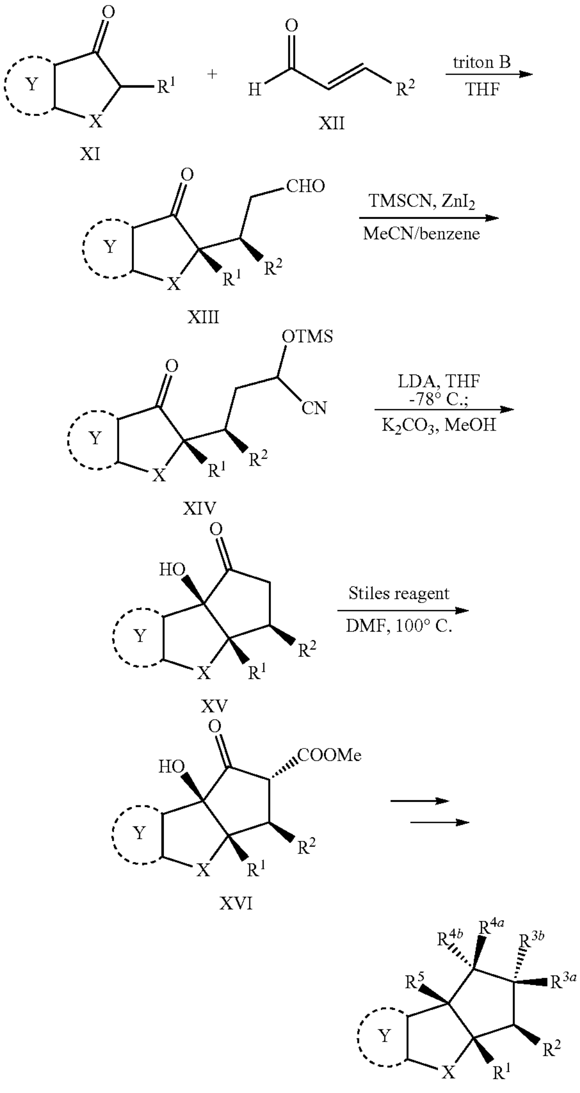

XI XII XIII XIV XV XVI I

Alternatively, the formation of compound I (X is as defined in the specification) is accomplished by the synthetic sequence described immediately above. In this synthesis, Michael addition of compound XI to compound XII yields the desired syn-arranged product XIII. Aldehyde XIII is subjected to trimethylsilyl cyanide to yield the cyanohydrin XIV. Formation of acyloin XV is initiated by addition of lithium diisopropylamide to XIV, followed by deprotection of the resulting mixture with potassium carbonate. Treatment of XV with excess of Stiles reagent in dimethylformamide at 100° C. results in the formation of the ketoester XVI. Deprotection and/or further functional group manipulation, if necessary, generates compound I. Compound I in its enantiomeric pure form is finally obtained via chiral HPLC separation.

General Method 3:

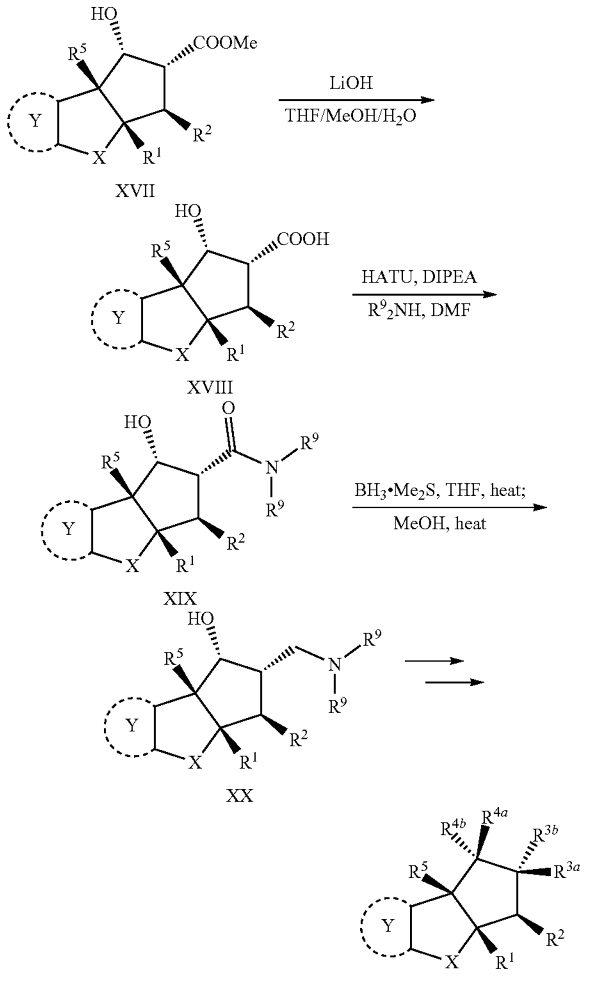

XVII XVIII XIX XX I

The formation of I ($R^{3a}$=H, and $R^{3b}$=—$CH_2NR^9_2$) is accomplished by a multi-step synthetic sequence starting with compound XVII. Ester hydrolysis of compounds XVII, followed by amide coupling with $NHR^9_2$ gives intermediate XIX. Amide XIX is reduced with borane upon heating to provide amine XX. Deprotection and/or further functional group manipulation, if necessary, generate compound I ($R^{3a}$=H, and $R^{3b}$=—$CH_2NR^9_2$). Compound I in its enantiomeric pure form is finally obtained via chiral HPLC separation.

General Method 4:

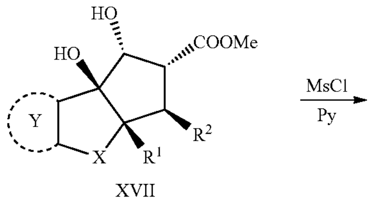

XVII

-continued

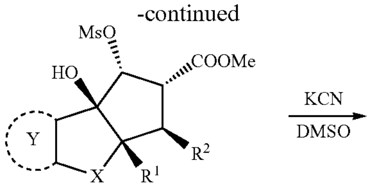

XXI

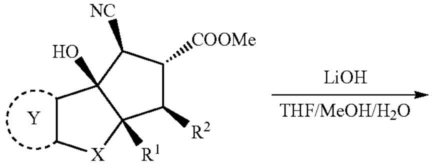

XXII

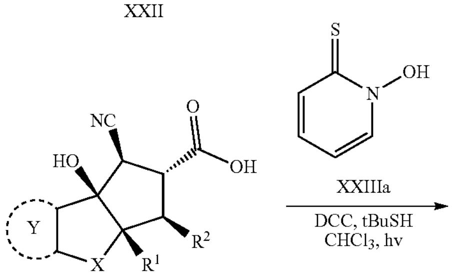

XXIII

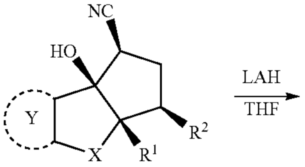

XXIV

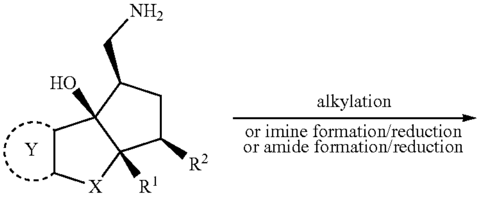

XXV

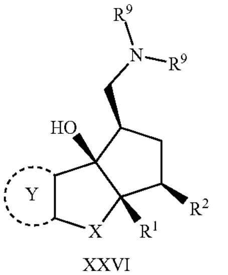

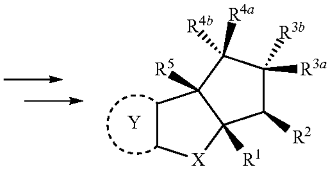

I

XXVI

The formation of I ($R^{3a}$, $R^{3b}$ and $R^{4b}$=H, and $R^{4a}$=—$CH_2NR^9{}_2$) is accomplished by a multi-step synthetic sequence starting with compound XVII. Compound XVII is treated with methanesulfonyl chloride in pyridine to form mesylate XXI. Stereoselective replacement of the mesylate moiety with a cyano group is accomplished with potassium cyanide. The resulting cyano ester XXII is hydrolyzed, followed by Barton's radical decarboxylation to produce nitrile XXIV. The cyano moiety is reduced to primary amine with lithium aluminum hydride. Functionalization of the primary amino group to generate amine XXVI is accomplished via standard alkylation, imine formation/reduction or amide formation/reduction methods. Deprotection and/or further functional group manipulation, if necessary, generate compound I ($R^{3a}$, $R^{3b}$ and $R^{4b}$=H, and $R^{4a}$=—$CH_2NR^9{}_2$). Compound I in its enantiomeric pure form is finally obtained via chiral HPLC separation.

General Method 5:

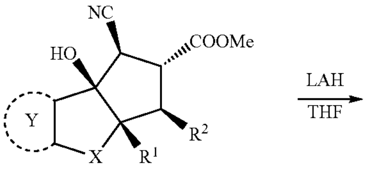

XXII

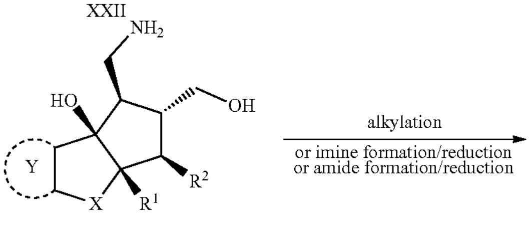

XXVII

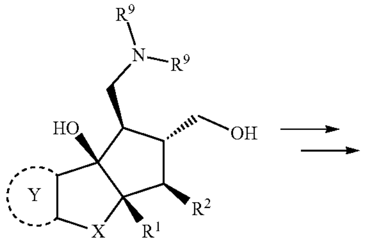

XXVIII

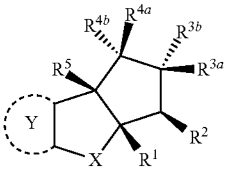

I

The formation of I ($R^{3a}$ and $R^{4b}$=H, $R^{3b}$=—$CH_2OH$ and $R^{4a}$=—$CH_2NR^9{}_2$) is accomplished by a multi-step synthetic sequence starting with compound XXII. Compound XXII is reduced with lithium aluminum hydride to generate compound XXVII. Functionalization of the primary amino group to generate amine XXVIII is accomplished via standard alkylation, imine formation/reduction or amide formation/reduction methods. Deprotection and/or further functional group manipulation, if necessary, generate compound I ($R^{3a}$ and $R^{4b}$=H, $R^{3b}$—$CH_2OH$ and $R^{4a}$=—$CH_2NR^9{}_2$). Compound I in its enantiomeric pure form is finally obtained via chiral HPLC separation.

General Method 6:

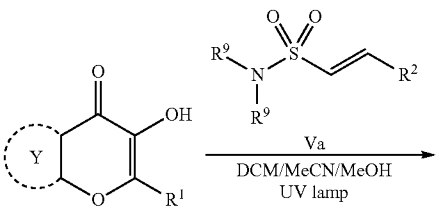

V

-continued

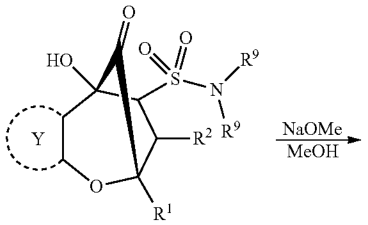

XXIX

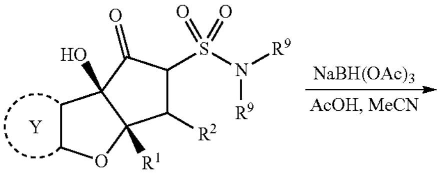

XXX

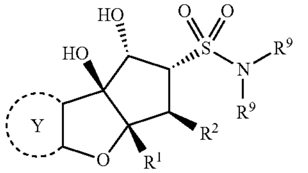

XXXI

+

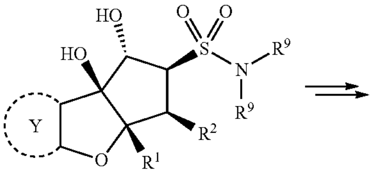

XXXII

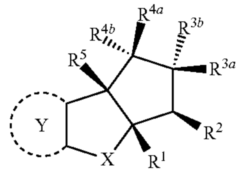

I

The formation of I ($R^{3a}$ or $R^{3b}$=—$SO_2NR^9R^9$) is accomplished by a multi-step synthetic sequence starting with hydroxyflavone V. V is submitted to a sequence of photocycloaddition, ketol rearrangement, and directed stereoselective reduction to give a diastereoisomeric mixture of flavagline XXXI and XXXII. Deprotection and/or further functional group manipulation, if necessary, generates compound I ($R^{3a}$ or $R^{3b}$=$SO_2NR^9R^9$). Compound I in its enantiomeric pure form is finally obtained via chiral HPLC separation.

General Method 7:

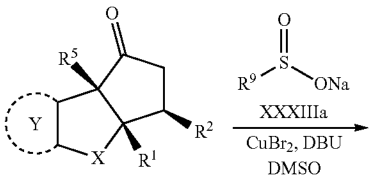

XXXIII

-continued

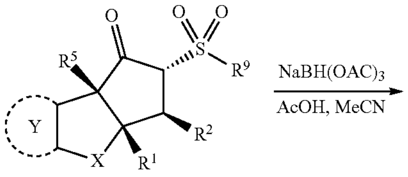

XXXIV

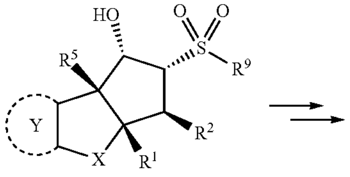

XXXV

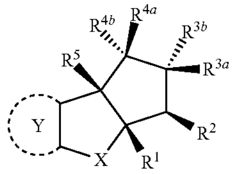

I

The formation of compound I ($R^{3a}$=H and $R^{3b}$=—$SO_2R^9$) is accomplished by a multi-step synthetic sequence starting with compound XXXIII. XXXIII is submitted to sodium sulfonate XXXIIIa in the presence of copper(II) bromide and 1,8-diazabicyclo[5.4.0]undec-7-ene to give XXXIV. XXXIV is reduced to give XXXV via sodium triacetylborohydride. Deprotection and/or further functional group manipulation, if necessary, generates compound I ($R^{3a}$=H and $R^{3b}$=$SO_2R^9$). Compound I in its enantiomeric pure form is finally obtained via chiral HPLC separation.

Compound I ($R^{3a}$=H and $R^{3b}$=—$SO_2R^9$) can also be used to form compound I ($R^{3a}$=H and $R^{3b}$=—$SO_2NR^9R^9$) using conventional methods known in the chemical art.

General Method 8:

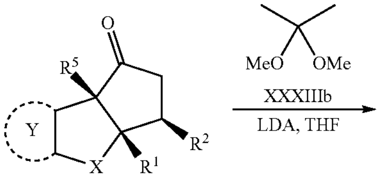

XXXIII

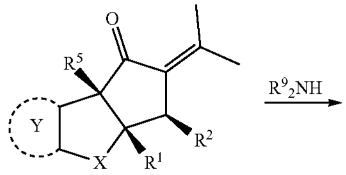

XXXVI

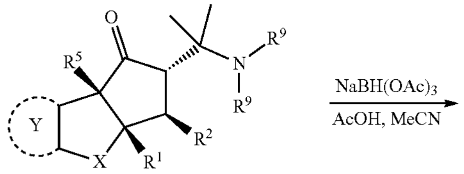

XXXVII

-continued

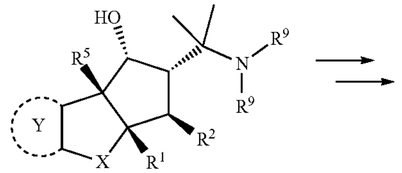

XXXVIII

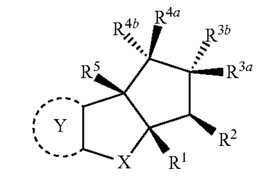

I

The formation of compound I ($R^{3a}$=H and $R^{3b}$=—C$(CH_3)_2NR^9{}_2$) is accomplished by a multi-step synthetic sequence starting with compound XXXIII. XXXIII is treated with lithium diisopropylamide followed by dimethyl acetal XXXIIIb to generate enone XXXVI. XXXVI is then treated with a nucleophile to give the Michael adduct XXXVII. The ketone group is reduced via sodium triacetylborohydride to produce compound XXXVIII. Deprotection and/or further functional group manipulation, if necessary, generates compound I ($R^{3a}$=H and $R^{3b}$=C$(CH_3)_2NR^9{}_2$). Compound I in its enantiomeric pure form is finally obtained via chiral HPLC separation.

General Method 9:

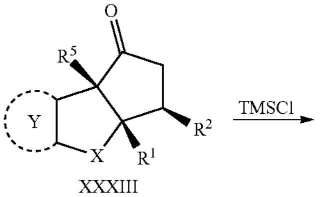

XXXIII

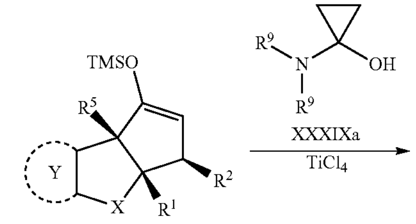

XXXIX

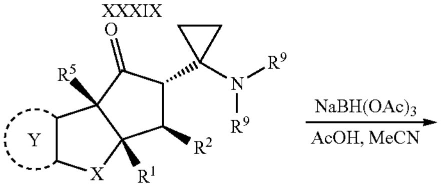

XL

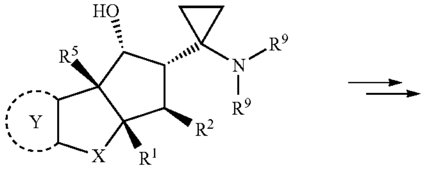

XLI

-continued

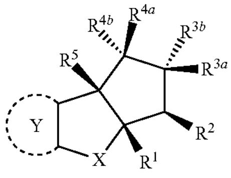

I

The formation of compound I ($R^{3a}$=H and $R^{3b}$=—C$(CH_2)_2NR^9{}_2$) is accomplished by a multi-step synthetic sequence starting with compound XXXIII. The trimethylsilyl enol ether of XXXIII reacts with compound XXXIXa in the presence of titanium tetrachloride to generate compound XL. XL is reduced via sodium triacetylborohydride to produce compound XLI. Deprotection and/or further functional group manipulation, if necessary, generates compound I ($R^{3a}$=H and $R^{3b}$=C$(CH_2)_2NR^9{}_2$). Compound I in its enantiomeric pure form is finally obtained via chiral HPLC separation.

General Method 10:

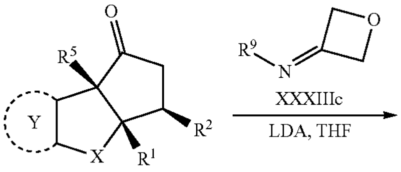

XXXIII

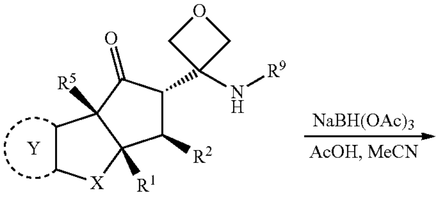

XLII

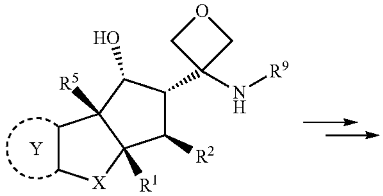

XLIII

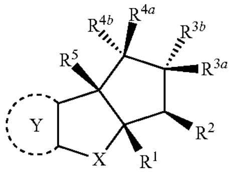

I

The formation of compound I ($R^{3a}$=H and $R^{3b}$=—C$(CH_2OCH_2)NHR^9$) is accomplished by a multi-step synthetic sequence starting with compound XXXIII. The enolate of XXXIII reacts with compound XXXIIIc to generate compound XLII. XLII is reduced via sodium triacetylborohydride to produce compound XLIII. Deprotection and/or further functional group manipulation, if necessary, generates compound I ($R^{3a}$=H and $R^{3b}$=C$(CH_2OCH_2)NHR^9$). Compound I in its enantiomeric pure form is finally obtained via chiral HPLC separation.

General Method 11:

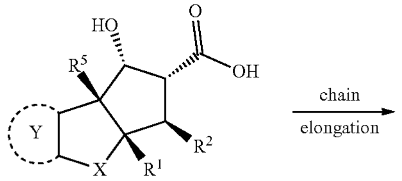

XVIII

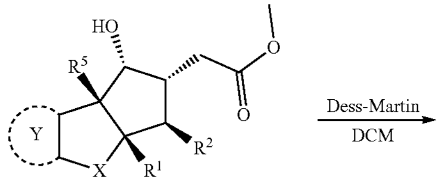

XLIV

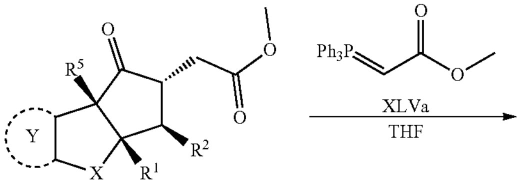

XLV

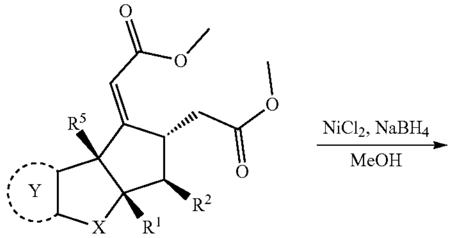

XLVI

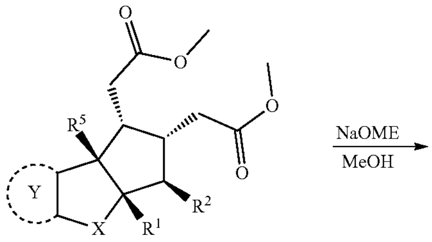

XLVII

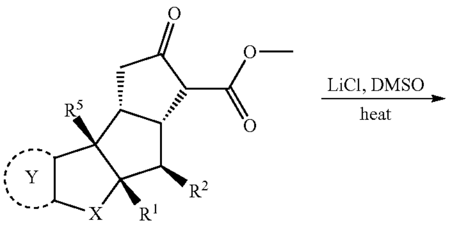

XLVIII

-continued

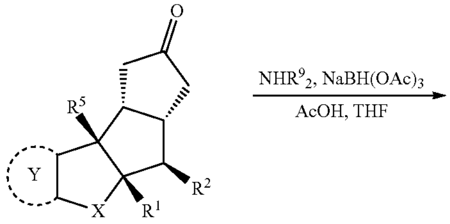

XLIX

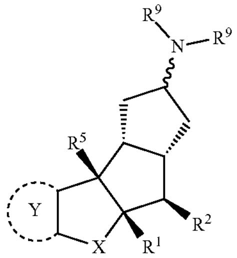

L

The formation of compound L is accomplished by a multi-step synthetic sequence starting with compound XVIII. One-carbon chain extention of XVIII via standard procedures generates ester XLIV. XLIV is oxidized followed by treatment with ylide XLVa to produce olefin XLVI. Reduction of the olefin followed by Dieckmann condensation gives rise to compound XLVIII. Decarboxylation of XLVIII followed by reductive amination generates compound L. Compound L in its diastereomeric and enantiomeric pure form is finally obtained via reverse phase HPLC and chiral HPLC separation.

General Method 12:

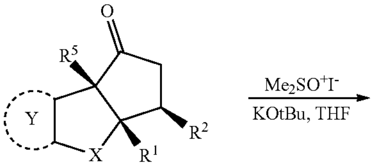

XXXIII

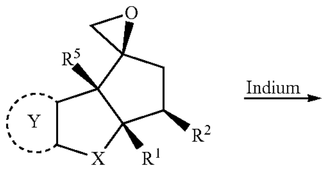

LI

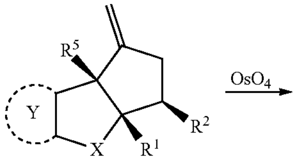

LII

-continued

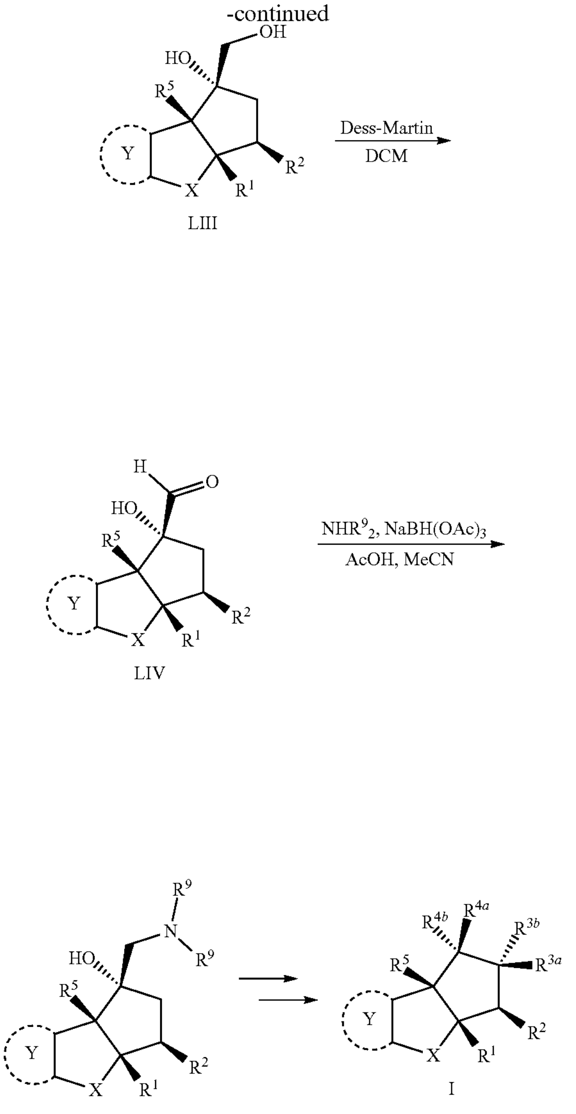

LIII

LIV

LV

I

The formation of compound I ($R^{4a}$=—$CH_2NR^9_2$ and $R^{4b}$=OH) is accomplished by a multi-step synthetic sequence starting with compound XXXIII. XXXIII is converted to olefin LII followed by dihydroxylation in the presence of osmium tetroxide to generate LIII. The primary hydroxyl group of LIII is selectively oxidized, followed by reductive amination to yield amine LV. Deprotection and/or further functional group manipulation, if necessary, generates compound I ($R^{4a}$=—$CH_2NR^9_2$ and $R^{4b}$=OH). Compound I in its enantiomeric pure form is finally obtained via chiral HPLC separation.

In the above methods, it is understood that if protecting groups are used during the synthesis of intermediates, or if a Formula I compound contains one or more protecting groups, then such protecting groups are removed by methods known in the chemical art. Other functional group transformations, such as the conversion of atom X from S to $S(O)_2$, from C═O to C═$CR^6R^7$, from NH to N($C_1$-$C_8$) alkyl, and the conversion of an intermediate or a Formula I compound to a pharmaceutically acceptable salt are carried out using conventional methods known in the chemical art.

EXAMPLES

Example 1

Rac-(5aR,6S,7R,8R,8aS)-8,8a-dihydroxy-3-methoxy-5a-(4-methoxyphenyl)-N,N-dimethyl-6-phenyl-5a,7,8,8a-tetrahydro-6H-cyclopenta[4,5]furo[3,2-b]pyridine-7-carboxamide (Cpd. No. 1F)

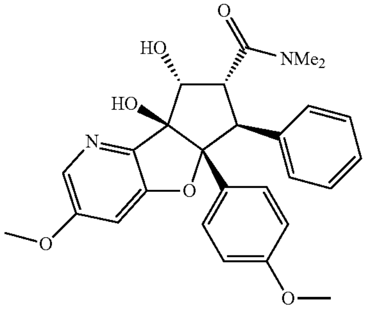

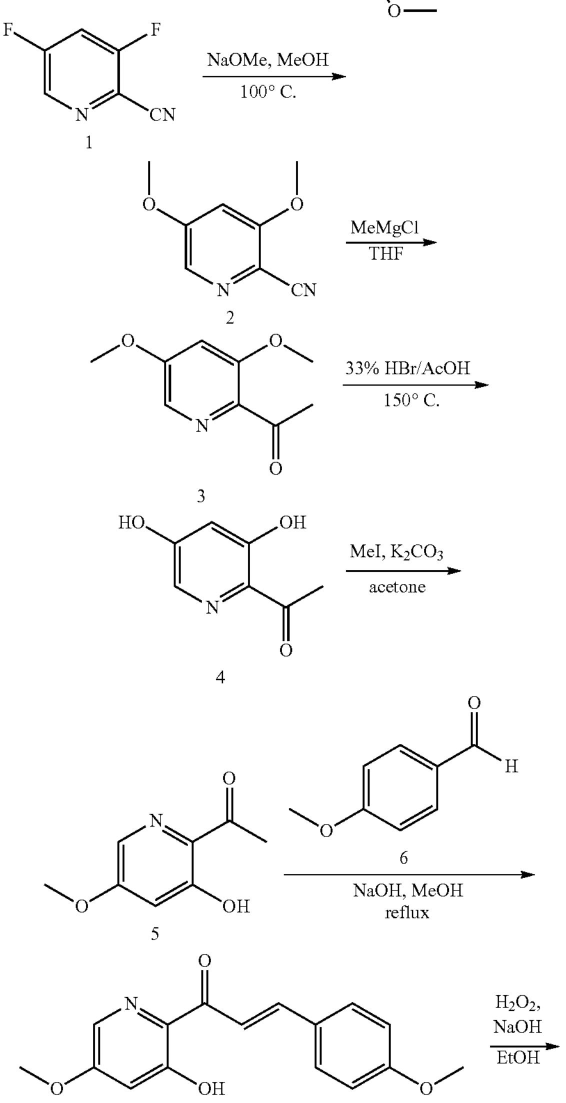

1

2

3

4

5

6

7

-continued

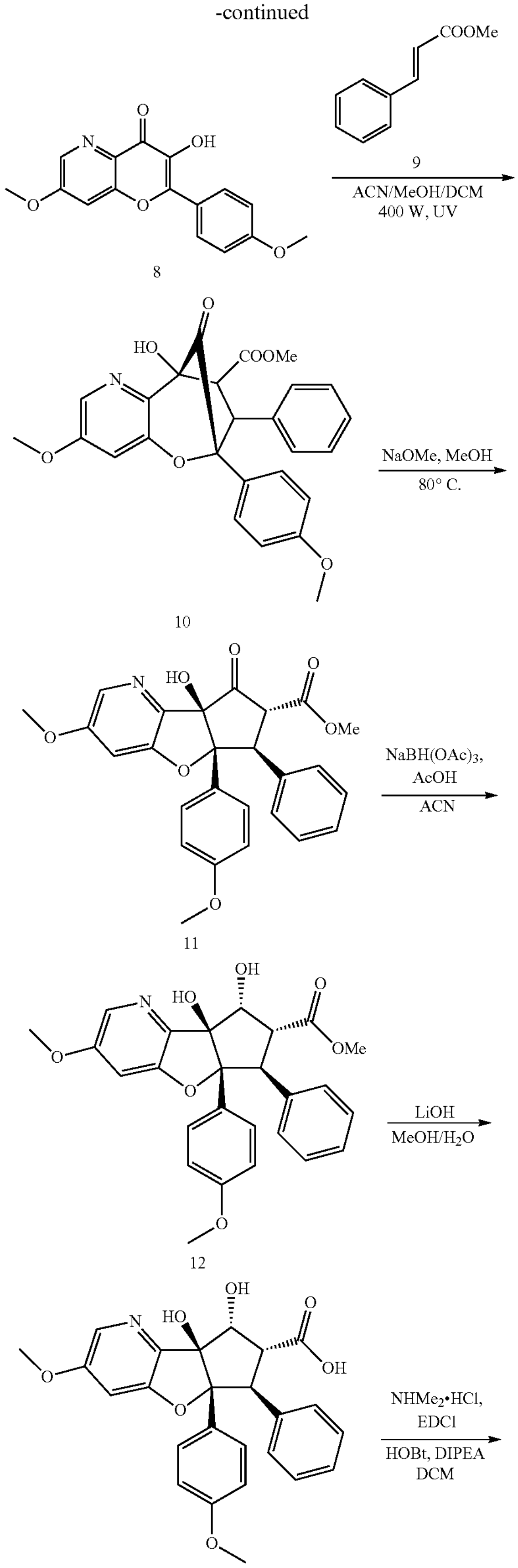

9

8

10

11

12

13

-continued

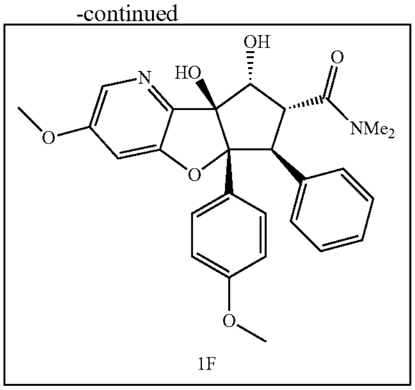

1F

Synthesis of 3,5-dimethoxypicolinonitrile (2)

To a solution of 3,5-difluoropicolinonitrile (1, 50 g, 0.36 mol) in methanol (80 mL), sodium methoxide (30% in methanol, 150 mL, 0.83 mol) was added. The reaction mixture was refluxed at 100° C. for 12 h. After completion, the solvent was removed under reduced pressure and the crude was treated with saturated ammonium chloride solution (50 mL) to get precipitate. The precipitated solid was filtered, washed with water and dried under vacuum to afford 3,5-dimethoxypicolinonitrile (2) as a white solid. Yield: 42 g, 72%; MS (ESI) m/z 165.23[M+1]$^+$.

Synthesis of 1-(3,5-dimethoxypyridin-2-yl)ethan-1-one (3)

To a solution of 3,5-dimethoxypicolinonitrile (2, 42 g, 256 mmol) in dry tetrahydrofuran (100 mL) at −20° C., methyl magnesium chloride (255.8 mL, 767.53 mmol) was added dropwise over a period of 30 min. The reaction mass was slowly brought to room temperature and stirred for an additional 12 h. After completion, the reaction mass was quenched with 6 M hydrochloric acid and extracted with ethyl acetate. The organic layer was washed with 1 M sodium hydroxide solution and water, dried over anhydrous sodium sulfate, filtered and concentrated under reduced pressure to afford 1-(3,5-dimethoxypyridin-2-yl)ethan-1-one (3) as a yellow oil. Yield: 30.0 g, 64.72%; MS (ESI) m/z 181.61[M+1]$^+$.

Synthesis of 1-(3,5-dihydroxypyridin-2-yl)ethan-1-one (4)

A sealed tube was charged with 1-(3,5-dimethoxypyridin-2-yl)ethan-1-one (3, 30.0 g, 165.9 mmol) and hydrobromic acid (33% in acetic acid, 300 mL) was added and the reaction mixture was heated at 150° C. for 16 h. After completion, volatiles were removed under reduced pressure and the crude was neutralized to pH ~8 using 10% sodium hydroxide and ethyl acetate (300 mL) was added. The solution was passed through a bed of celite and the bed was washed with ethyl acetate (100 mL). The organic layer was separated from the combined filtrate and dried over anhydrous sodium sulfate, filtered and concentrated under reduced pressure to afford 1-(3,5-dihydroxypyridin-2-yl)ethan-1-one (4) as a brown oil. Yield: 9.0 g, 35%; MS (ESI) m/z 152.0[M−1]$^-$.

Synthesis of 1-(3-hydroxy-5-methoxypyridin-2-yl)ethan-1-one (5)

To a solution of 1-(3,5-dihydroxypyridin-2-yl)ethan-1-one (4, 9.0 g, 58.8 mmol) in acetone (100 mL) at 0° C., potassium carbonate (24.3 g, 176.4 mmol) was added followed by addition of methyl iodide. The reaction mixture was stirred at room temperature for 6 h. After completion, the solvent was distilled off and water (20 mL) was added. The reaction mass was extracted with 5% methanol in dichloromethane (100 mL). The organic layer was washed with water and brine, dried over anhydrous sodium sulfate, filtered and concentrated to afford 1-(3-hydroxy-5-methoxypyridin-2-yl)ethan-1-one (5) as an off-white solid. Yield: 8.5 g, crude.

Synthesis of (E)-1-(3-hydroxy-5-methoxypyridin-2-yl)-3-(4-methoxyphenyl)prop-2-en-1-one (7)

To a solution of 1-(3-hydroxy-5-methoxypyridin-2-yl)ethan-1-one (5, 8.5 g, 50.8 mmol) and sodium hydroxide (6.1 g, 152.0 mmol) in methanol (50 mL), 4-methoxybenzaldehyde (6, 6.9 g, 50.8 mmol) was added. The reaction was heated to reflux for 4 h. After completion, the reaction mass was cooled to room temperature. The solid was filtered, washed with water and then dried under vacuum to afford (E)-1-(3-hydroxy-5-methoxypyridin-2-yl)-3-(4-methoxyphenyl)prop-2-en-1-one (7) as a yellow solid. Yield: 9.0 g, crude; MS (ESI) m/z 286.23[M+1]$^+$.

Synthesis of 3-hydroxy-7-methoxy-2-(4-methoxyphenyl)-4H-pyrano[3,2-b]pyridin-4-one (8)

To a solution of (E)-1-(3-hydroxy-5-methoxypyridin-2-yl)-3-(4-methoxyphenyl)prop-2-en-1-one (7, 9.0 g, 31.5 mmol) and sodium hydroxide (3.78 g, 94.7 mmol) in methanol (50 mL) at 0° C., hydrogen peroxide (10.73 mL, 94.7 mmol) was added. The reaction mass was stirred for 6 h at room temperature (exotherm was observed). After completion, the reaction mass was cooled and neutralized to pH ~7 by the addition of 6 M hydrogen chloride. The precipitated solid was filtered and dried under vacuum to afford of 3-hydroxy-7-methoxy-2-(4-methoxyphenyl)-4H-pyrano[3,2-b]pyridin-4-one (8) as a yellow solid. Yield: 3.5 g, 37%; MS (ESI) m/z 452.19[M+1]$^+$.

Synthesis of rac-methyl (7S,8S,9R)-9-hydroxy-3-methoxy-6-(4-methoxyphenyl)-10-oxo-7-phenyl-6,7,8,9-tetrahydro-6,9-methanooxepino[3,2-b]pyridine-8-carboxylate (10)

A solution of 3-hydroxy-7-methoxy-2-(4-methoxyphenyl)-4H-pyrano[3,2-b]pyridin-4-one (8, 3.5 g, 11.3 mmol) and methyl cinnamate (9, 19 g, 111.7 mmol) in dichloromethane (200 mL), acetonitrile (100 mL) and methanol (100 mL) was placed in a UV reactor flask. The reaction mixture was irradiated for 15 h under 400 watts UV light. After completion, the solvent was removed under reduced pressure and the residue was purified over a plug of silica gel eluting the compound with ethyl acetate. The desired fractions were concentrated under reduced pressure to afford rac-methyl (7S,8S,9R)-9-hydroxy-3-methoxy-6-(4-methoxyphenyl)-10-oxo-7-phenyl-6,7,8,9-tetrahydro-6,9-methanooxepino[3,2-b]pyridine-8-carboxylate (10). Yield: 3.0 g, crude.

Synthesis of rac-methyl (5aR,6S,7R,8aR)-8a-hydroxy-3-methoxy-5a-(4-methoxyphenyl)-8-oxo-6-phenyl-5a,7,8,8a-tetrahydro-6H-cyclopenta[4,5]furo[3,2-b]pyridine-7-carboxylate (11)

The crude compound rac-methyl (7S,8S,9R)-9-hydroxy-3-methoxy-6-(4-methoxyphenyl)-10-oxo-7-phenyl-6,7,8,9-tetrahydro-6,9-methanooxepino[3,2-b]pyridine-8-carboxylate (10, 3.0 g)) was suspended in methanol (30 mL) and treated with 25% sodium methoxide in methanol (30 mL). The reaction was heated at 80° C. for 2 h. After completion, the solvent was removed under reduced pressure. The crude was diluted with ammonium chloride solution and extracted with ethyl acetate. The organic phase was separated, dried over sodium sulphate and concentrated under reduced pressure to afford rac-methyl (5aR,6S,7R,8aR)-8a-hydroxy-3-methoxy-5a-(4-methoxyphenyl)-8-oxo-6-phenyl-5a,7,8,8a-tetrahydro-6H-cyclopenta[4,5]furo[3,2-b]pyridine-7-carboxylate (11, 3.0 g, crude).

Synthesis of rac-methyl (5aR,6S,7R,8R,8aS)-8,8a-dihydroxy-3-methoxy-5a-(4-methoxyphenyl)-6-phenyl-5a,7,8,8a-tetrahydro-6H-cyclopenta[4,5]furo[3,2-b]pyridine-7-carboxylate (12)

To a solution of sodium triacetoxyborohydride (8.27 g, 3.9 mmol), rac-methyl (5aR,6S,7R,8aR)-8a-hydroxy-3-methoxy-5a-(4-methoxyphenyl)-8-oxo-6-phenyl-5a,7,8,8a-tetrahydro-6H-cyclopenta[4,5]furo[3,2-b]pyridine-7-carboxylate (11, 3.0 g, 6.5 mmol) in acetonitrile (50 mL), acetic acid (3.9 g, 66.5 mmol) was added. The resulting mixture was stirred for 4 h at room temperature. After completion, the reaction mixture was partitioned between saturated aqueous sodium bicarbonate solution and ethyl acetate. The organic layer was separated, dried over sodium sulphate, filtered and concentrated under reduced pressure to get the crude. The crude was purified by silica gel column chromatography eluting with 50% ethyl acetate in hexanes. The desired fractions were concentrated to afford rac-methyl (5aR,6S,7R,8R,8aS)-8,8a-dihydroxy-3-methoxy-5a-(4-methoxyphenyl)-6-phenyl-5a,7,8,8a-tetrahydro-6H-cyclopenta[4,5]furo[3,2-b]pyridine-7-carboxylate (12). Yield: 1.2 g, 39.86%; MS (ESI) m/z 464.29[M+1]$^+$.

Synthesis of rac-(5aR,6S,7R,8R,8aS)-8,8a-dihydroxy-3-methoxy-5a-(4-methoxyphenyl)-6-phenyl-5a, 7,8,8a-tetrahydro-6H-cyclopenta[4,5]furo[3,2-b]pyridine-7-carboxylic acid (13)

To a solution of rac-methyl (5aR,6S,7R,8R,8aS)-8,8a-dihydroxy-3-methoxy-5a-(4-methoxyphenyl)-6-phenyl-5a,7,8,8a-tetrahydro-6H-cyclopenta[4,5]furo[3,2-b]pyridine-7-carboxylate (12, 1.2 g, 2.5 mmol) in methanol and water (3:1, 20 mL), lithium hydroxide (1.49 g, 62.2 mmol) was added and the reaction was stirred for 16 h at room temperature. After completion, the reaction mass was cooled to 0° C. and acidified with 1 M hydrochloric acid to pH 2-3. The precipitate was filtered and dried under vacuum to afford rac-(5aR,6S,7R,8R,8aS)-8,8a-dihydroxy-3-methoxy-5a-(4-methoxyphenyl)-6-phenyl-5a,7,8,8a-tetrahydro-6H-cyclopenta[4,5]furo[3,2-b]pyridine-7-carboxylic acid (13) as an off-white solid. Yield: 0.9 g, 77.33%; MS (ESI) m/z 450.28[M+1]$^+$.

Synthesis of rac-(5aR,6S,7R,8R,8aS)-8,8a-dihydroxy-3-methoxy-5a-(4-methoxyphenyl)-N,N-dimethyl-6-phenyl-5a,7,8,8a-tetrahydro-6H-cyclopenta[4,5]furo[3,2-b]pyridine-7-carboxamide (Cpd. No. 1F)

To a solution of rac-(5aR,6S,7R,8R,8aS)-8,8a-dihydroxy-3-methoxy-5a-(4-methoxyphenyl)-6-phenyl-5a,7,8,8a-tetrahydro-6H-cyclopenta[4,5]furo[3,2-b]pyridine-7-carboxylic acid (13, 0.9 g, 2.0 mmol) in dichloromethane (30 mL) at 0°

C., 1-ethyl-3-(3-dimethylaminopropyl)carbodiimide (1.15 g, 6.0 mmol), hydroxybenzotriazole (0.8 g, 6.0 mmol) and N,N-diisopropylethylamine (1.55 g, 12.0 mmol) were added and the mixture was stirred for 5 min. Dimethylamine hydrochloride (0.814 g, 10.02 mmol) was then added at the same temperature and the reaction was stirred for 12 h at room temperature. After completion, the reaction mass was diluted with dichloromethane and washed with cold water. The organic layer was separated and dried over sodium sulphate, filtered and concentrated to give the crude. The crude was purified by silica gel column chromatography eluting with 70-90% ethyl acetate in hexanes to afford rac-(5aR,6S,7R,8R,8aS)-8,8a-dihydroxy-3-methoxy-5a-(4-methoxyphenyl)-N,N-dimethyl-6-phenyl-5a,7,8,8a-tetrahydro-6H-cyclopenta[4,5]furo[3,2-b]pyridine-7-carboxamide (Cpd. No. 1F) as an off-white solid. Yield: 0.077 g, 7.33%; MS (ESI) m/z 477.22[M+1]$^+$; $^1$H NMR (400 MHz, DMSO-d$_6$) δ 7.89 (d, J=2.4 Hz, 1H), 7.20 (d, J=2.4 Hz, 1H), 7.09-7.00 (m, 4H), 6.94-6.98 (m, 1H), 6.86 (d, J=7.2 Hz, 2H), 6.64 (d, J=9.2 Hz, 2H), 5.61 (s, 1H), 5.05 (d, J=5.2 Hz, 1H), 4.84 (t, J=6 Hz, 1H), 4.31 (d, J=13.2 Hz, 1H), 4.09 (dd, J=13.2, 6.4 Hz, 1H), 3.86 (s, 3H), 3.61 (s, 3H), 3.22 (s, 3H), 2.74 (s, 3H).

Example 2

(5aR,6S,7R,8R,8aS)-3-cyano-5a-(4-cyanophenyl)-8,8a-dihydroxy-N,N-dimethyl-6-phenyl-5a,7,8,8a-tetrahydro-6H-cyclopenta[4,5]furo[3,2-b]pyridine-7-carboxamide (Cpd. No. 2F)

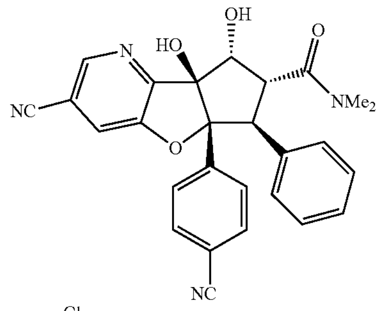

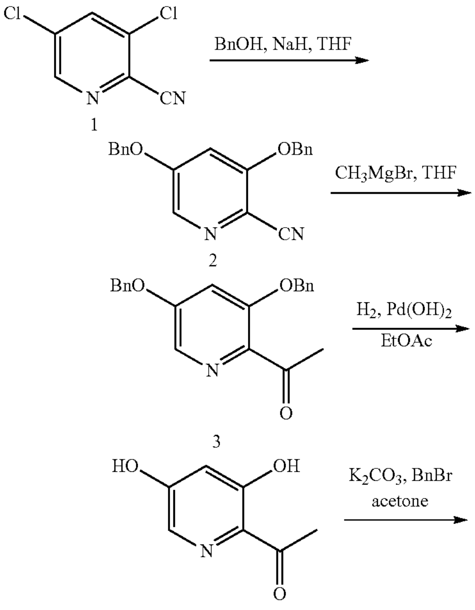

1
2
3
4

-continued

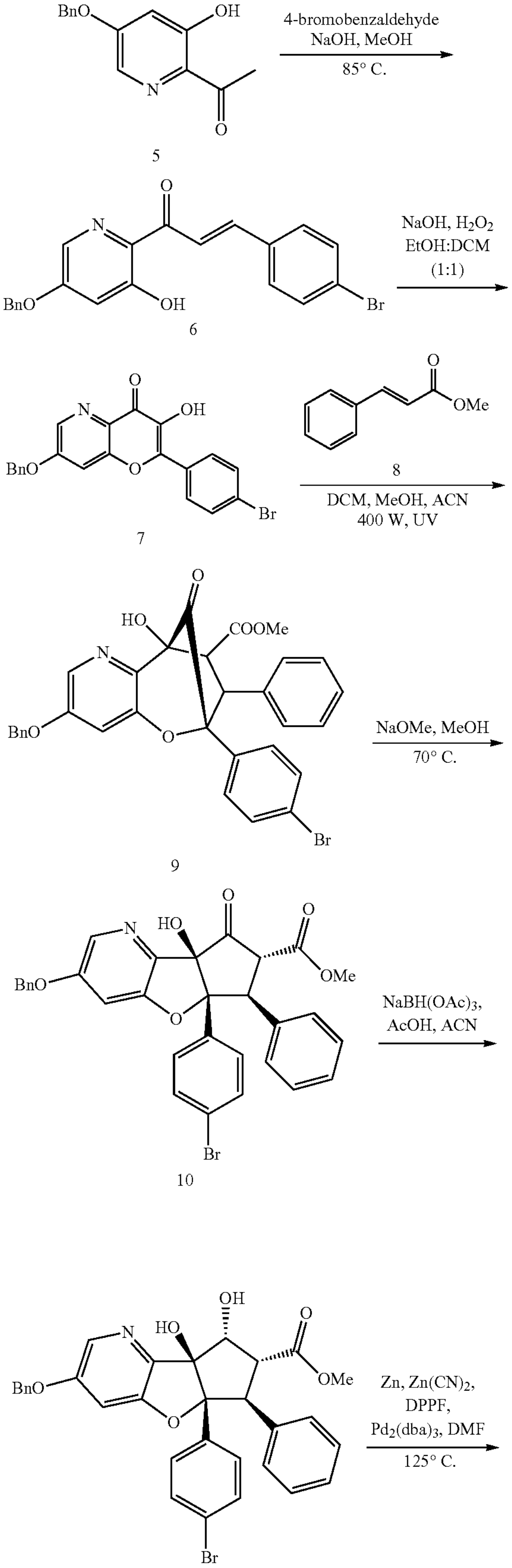

5
6
7
9
10
11

-continued

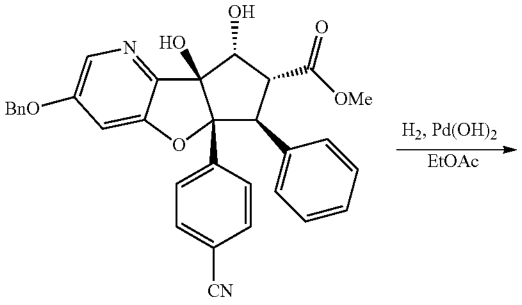

12

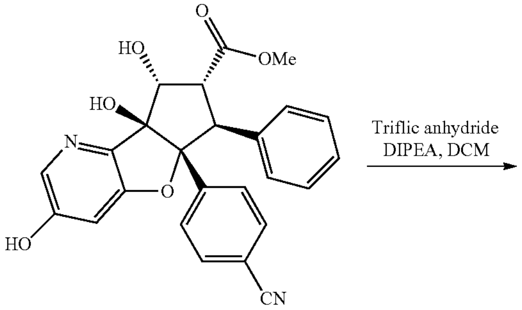

13

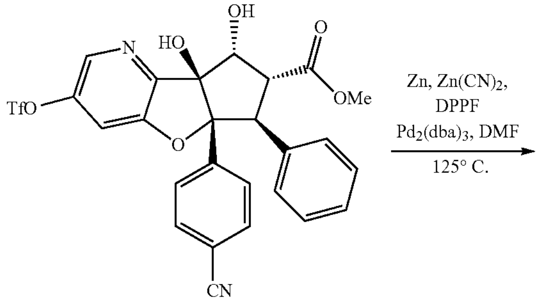

14

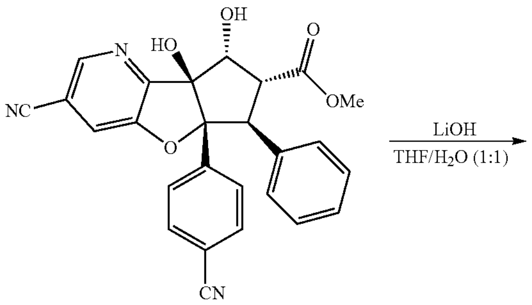

15

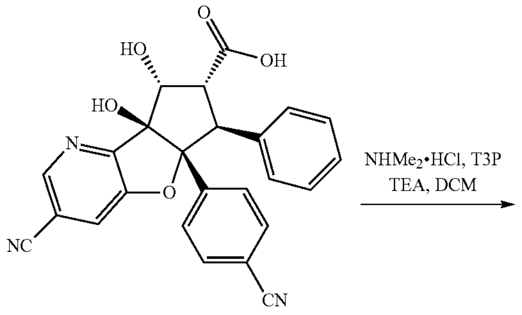

16

-continued

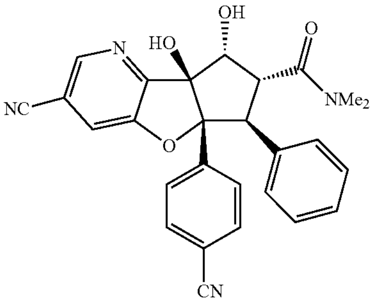

2F

Synthesis of 3,5-bis(benzyloxy)picolinonitrile (2)

To a solution of 3,5-dichloropicolinonitrile (1, 65.0 g, 377.2 mmol) in tetrahydrofuran (500 mL) under nitrogen, sodium hydride (27.2 g, 1.13 mol) was added at 0° C. The suspension was stirred at room temperature for 30 minutes. Benzyl alcohol (81.37 mL, 755 mmol) was added and the reaction was stirred for another 3 h. After completion, the reaction mass was treated with saturated ammonium chloride solution at 0° C. The residue was dissolved in ethyl acetate (1000 mL), separated the organic layer and washed with water (2×200 mL) then with brine (100 mL). The organics were separated and dried over anhydrous sodium sulfate before concentration to dryness and triturated with pentane. The precipitated solid was filtered and dried under vacuum to afford 3,5-bis(benzyloxy)picolinonitrile (2) as an off-white solid. Yield: 130.0 g, crude; MS (ESI) m/z 317.21 $[M+1]^+$.

Synthesis of 1-(3,5-bis(benzyloxy)pyridin-2-yl) ethan-1-one (3)

To a solution of 3,5-bis(benzyloxy)picolinonitrile (2, 70.0 g, 221.5 mmol) in dry tetrahydrofuran (500 mL), methyl magnesium bromide (78.37 mL, 664.5 mmol) was added dropwise over a period of 30 min at −30° C. The reaction mass was slowly brought to room temperature and stirred for 2 h. After completion, the reaction mass was treated with 6M hydrogen chloride and stirred for 2 h. The crude was extracted with ethyl acetate. The organic layer was washed with 1M sodium hydroxide solution, water, dried over anhydrous sodium sulfate, filtered and concentrated under reduced pressure to afford 1-(3,5-bis(benzyloxy)pyridin-2-yl)ethan-1-one (3) as a yellow oil. Yield: 82.0 g, 93.75%; MS (ESI) m/z 334.16$[M+1]^+$.

Synthesis of 1-(3,5-dihydroxypyridin-2-yl)ethan-1-one (4)

To a solution of 1-(3,5-bis(benzyloxy)pyridin-2-yl)ethan-1-one (3, 82.0 g, 246.2 mmol) in ethyl acetate (500 mL), palladium hydroxide (34.47 g, 246.2 mmol, 50% wet) was added. The reaction was flushed twice with hydrogen gas and stirred at room temperature for 16 h under hydrogen pressure. After completion, the reaction mass was passed through a bed of celite and the filtrate was concentrated under reduced pressure to afford 1-(3,5-dihydroxypyridin-2-yl)ethan-1-one (4) as a brown oil. Yield: 40.0 g, 88.8%; MS (ESI) m/z 152.13$[M-1]^-$.

Synthesis of 1-(5-(benzyloxy)-3-hydroxypyridin-2-yl)ethan-1-one (5)

To a solution of 1-(3,5-dihydroxypyridin-2-yl)ethan-1-one (4, 40.0 g, 261.4 mmol) in acetone (250 mL), potassium carbonate (72.15 g, 522.8 mmol) was added under nitrogen. Benzyl bromide (21.7 mL, 182.9 mmol) was added and reaction was stirred for another 3 h. After completion, volatiles were removed under reduced pressure and crude residue was dissolved in ethyl acetate (200 mL) and washed with water (2×150 mL) and brine (150 mL). The organics were separated and dried over anhydrous sodium sulfate before concentration to dryness and triturated with pentane. The solid was filtered and dried under vacuum to afford 1-(5-(benzyloxy)-3-hydroxypyridin-2-yl)ethan-1-one (5) as a brown solid. Yield: 50.0 g, 94.1%; MS (ESI) m/z 244.04 $[M+1]^+$.

Synthesis of (E)-1-(5-(benzyloxy)-3-hydroxypyridin-2-yl)-3-(4-bromophenyl)prop-2-en-1-one (6)

To a solution of 1-(5-(benzyloxy)-3-hydroxypyridin-2-yl)ethan-1-one (5, 50.0 g, 205.6 mmol) and sodium hydroxide (24.69 g, 617.28 mmol) in methanol (100 mL), 4-bromobenzaldehyde (38.06 g, 205.7 mmol) was added and the reaction mixture was heated at 85° C. for 2 h. After completion, reaction mass was cooled and solid was filtered, washed with water and dried under vacuum to afford of (E)-1-(5-(benzyloxy)-3-hydroxypyridin-2-yl)-3-(4-bromophenyl)prop-2-en-1-one (6) as a yellow solid. Yield: 50.2 g, 59.64%; MS (ESI) m/z 410.05 $[M+1]^+$.

Synthesis of 7-(benzyloxy)-2-(4-bromophenyl)-3-hydroxy-4H-pyrano[3,2-b]pyridin-4-one (7)

To a solution of (E)-1-(5-(benzyloxy)-3-hydroxypyridin-2-yl)-3-(4-bromophenyl)prop-2-en-1-one (6, 20.0 g, 48.8 mmol) and sodium hydroxide (13.7 g, 342.2 mmol) in ethanol: dichloromethane (1:1, 100 mL), hydrogen peroxide (15.11 mL, 684.5 mmol) was added at room temperature. The reaction mass was stirred for 1 h (exotherm was observed). After completion, reaction mass was cooled and neutralized by addition of 6M hydrogen chloride. The precipitated solid was filtered and dried under vacuum to afford 7-(benzyloxy)-2-(4-bromophenyl)-3-hydroxy-4H-pyrano[3,2-b]pyridin-4-one (7) as a yellow solid. Yield: 11.0 g, 53%; MS (ESI) m/z 424.03$[M+1]^+$.

Synthesis of rac-methyl (7S,8S,9R)-3-(benzyloxy)-6-(4-bromophenyl)-9-hydroxy-10-oxo-7-phenyl-6,7,8,9-tetrahydro-6,9-methanooxepino[3,2-b]pyridine-8-carboxylate (9)

A solution of 7-(benzyloxy)-2-(4-bromophenyl)-3-hydroxy-4H-pyrano[3,2-b]pyridin-4-one (7, 11.0 g, 25.94 mmol) and methyl cinnamate (8, 42.28 g, 259.4 mmol) in dichloromethane (200 mL), acetonitrile (100 mL) and methanol (100 mL) was placed in a UV reactor flask. The reaction mixture was irradiated under 400 watts UV light for 15 h. After completion, the solvent was removed under reduced pressure and the residue was purified over a plug of silica gel eluting the compound with ethyl acetate. The desired fractions were concentrated under reduced pressure to afford rac-methyl (7S,8S,9R)-3-(benzyloxy)-6-(4-bromophenyl)-9-hydroxy-10-oxo-7-phenyl-6,7,8,9-tetrahydro-6,9-methanooxepino[3,2-b]pyridine-8-carboxylate (9, 11.2 g, crude).

Synthesis of rac-methyl (5aR,6S,7R,8aR)-3-(benzyloxy)-5a-(4-bromophenyl)-8a-hydroxy-8-oxo-6-phenyl-5a,7,8,8a-tetrahydro-6H-cyclopenta[4,5]furo[3,2-b]pyridine-7-carboxylate (10)

The crude compound rac-methyl (7S,8S,9R)-3-(benzyloxy)-6-(4-bromophenyl)-9-hydroxy-10-oxo-7-phenyl-6,7,8,9-tetrahydro-6,9-methanooxepino[3,2-b]pyridine-8-carboxylate (9, 11.2 g) was suspended in methanol (100 mL) and treated with 25% sodium methoxide in methanol (110 mL) and heated the mixture to 70° C. for 1 h. After completion, the solvent was removed under reduced pressure and crude was treated with ammonium chloride solution and extracted with ethyl acetate. The organic phase was separated, dried over sodium sulphate and concentrated under reduced pressure to afford rac-methyl (5aR,6S,7R,8aR)-3-(benzyloxy)-5a-(4-bromophenyl)-8a-hydroxy-8-oxo-6-phenyl-5a,7,8,8a-tetrahydro-6H-cyclopenta[4,5]furo[3,2-b]pyridine-7-carboxylate (10). Yield: 11.0 g, crude.

Synthesis of rac-methyl (5aR,6S,7R,8R,8aS)-3-(benzyloxy)-5a-(4-bromophenyl)-8,8a-dihydroxy-6-phenyl-5a,7,8,8a-tetrahydro-6H-cyclopenta[4,5]furo[3,2-b]pyridine-7-carboxylate (11)

The above crude compound (10, 11.0 g, crude) was charged to a solution of sodium triacetoxyborohydride (23.4 g, 112.4 mmol) in acetonitrile (80 mL) and acetic acid (11.3 mL, 188.33 mmol) and the resulting mixture was stirred for 4 h at room temperature. After completion, reaction mixture was partitioned between saturated aqueous sodium bicarbonate solution and ethyl acetate. The organic layer was separated, dried over sodium sulphate and concentrated under reduced pressure to get the crude. The crude was purified by silica gel column chromatography eluting with 50% ethyl acetate in hexanes. The desired fractions were concentrated to afford rac-methyl (5aR,6S,7R,8R,8aS)-3-(benzyloxy)-5a-(4-bromophenyl)-8,8a-dihydroxy-6-phenyl-5a,7,8,8a-tetrahydro-6H-cyclopenta[4,5]furo[3,2-b]pyridine-7-carboxylate (11) as a light yellow solid. Yield: 5.7 g, 51.77%; MS (ESI) m/z 588.38$[M+1]^+$.

Synthesis of rac-methyl (5aR,6S,7R,8R,8aS)-3-(benzyloxy)-5a-(4-cyanophenyl)-8,8a-dihydroxy-6-phenyl-5a,7,8,8a-tetrahydro-6H-cyclopenta[4,5]furo[3,2-b]pyridine-7-carboxylate (12)

To a solution of rac-methyl (5aR,6S,7R,8R,8aS)-3-(benzyloxy)-5a-(4-bromophenyl)-8,8a-dihydroxy-6-phenyl-5a,7,8,8a-tetrahydro-6H-cyclopenta[4,5]furo[3,2-b]pyridine-7-carboxylate (11, 5.0 g, 8.50 mmol) in dimethylformamide, zinc cyanide (6.12 g, 52.0 mmol) and zinc (0.055 g, 0.84 mmol) were added at room temperature and degassed the mixture with argon for 15 min. 1,1'-Bis(diphenylphosphino)ferrocene (0.124 g, 0.169 mmol), tris(dibenzylideneacetone)dipalladium (0.233 g, 0.254 mmol) were added to the reaction, degassing was continued for 5 min and heated the reaction mixture at 125° C. for 2 h. After completion, the reaction was cooled to room temperature and passed through a bed of celite. The filtrate was concentrated and treated with ice-cold water, the precipitated solid was filtered and dried under vacuum to afford rac-methyl (5aR,6S,7R,8R,8aS)-3-(benzyloxy)-5a-(4-cyanophenyl)-8,8a-dihydroxy-6-phenyl-5a,7,8,8a-tetrahydro-6H-cyclopenta[4,5]furo[3,2-b]pyridine-7-carboxylate (12) as a yellow solid. Yield: 4.4 g, 96.9%; MS (ESI) m/z 535.13 $[M+1]^+$.

Synthesis of rac-methyl (5aR,6S,7R,8R,8aS)-5a-(4-cyanophenyl)-3,8,8a-trihydroxy-6-phenyl-5a,7,8,8a-tetrahydro-6H-cyclopenta[4,5]furo[3,2-b]pyridine-7-carboxylate (13)

To a solution of rac-methyl (5aR,6S,7R,8R,8aS)-3-(benzyloxy)-5a-(4-cyanophenyl)-8,8a-dihydroxy-6-phenyl-5a,7,8,8a-tetrahydro-6H-cyclopenta[4,5]furo[3,2-b]pyridine-7-carboxylate (12, 2.5 g, 4.61 mmol) in ethyl acetate (50 mL), palladium hydroxide (1.66 g, 11.6 mmol, 50% wet) was added at room temperature. The reaction was flushed with hydrogen gas twice and stirred at room temperature for 16 h under hydrogen pressure. After completion, the reaction mass was passed through a bed of celite and the filtrate was concentrated under reduced pressure to afford rac-methyl (5aR,6S,7R,8R,8aS)-5a-(4-cyanophenyl)-3,8,8a-trihydroxy-6-phenyl-5a,7,8,8a-tetrahydro-6H-cyclopenta[4,5]furo[3,2-b]pyridine-7-carboxylate (13) as a brown oil. Yield: 2.01 g, 96.9%; MS (ESI) m/z 443.15$[M-1]^-$.

Synthesis of rac-methyl (5aR,6S,7R,8R,8aS)-5a-(4-cyanophenyl)-8,8a-dihydroxy-6-phenyl-3-(((trifluoromethyl)sulfonyl)oxy)-5a, 7,8,8a-tetrahydro-6H-cyclopenta[4,5]furo[3,2-b]pyridine-7-carboxylate (14)

To a solution of rac-methyl (5aR,6S,7R,8R,8aS)-5a-(4-cyanophenyl)-3,8,8a-trihydroxy-6-phenyl-5a,7,8,8a-tetrahydro-6H-cyclopenta[4,5]furo[3,2-b]pyridine-7-carboxylate (13, 2.01 g, 4.52 mmol) in dichloromethane (100 mL) under nitrogen, N,N-diisopropylethylamine (0.57 g, 4.41 mmol) was added at −78° C. followed by addition of triflic anhydride (0.765 mL, 3.78 mmol). The reaction was stirred at −78° C. for 45 min. After completion, the reaction mass was treated with saturated sodium bicarbonate solution at 0° C. The crude was extracted with dichloromethane (100 mL) and the organic layer was washed with water (2×50 mL) then with brine (50 mL). The organics were separated and dried over anhydrous sodium sulfate before concentration to dryness and triturated with pentane. The precipitated solid was filtered and dried under vacuum to afford rac-methyl (5aR,6S,7R,8R,8aS)-5a-(4-cyanophenyl)-8,8a-dihydroxy-6-phenyl-3-(((trifluoromethyl)sulfonyl)oxy)-5a,7,8,8a-tetrahydro-6H-cyclopenta[4,5]furo[3,2-b]pyridine-7-carboxylate (14) as a yellow solid. Yield: 2.01 g, 77.9%; MS (ESI) m/z 577.1 [M+1]*.

Synthesis of rac-methyl (5aR,6S,7R,8R,8aS)-3-cyano-5a-(4-cyanophenyl)-8,8a-dihydroxy-6-phenyl-5a,7,8,8a-tetrahydro-6H-cyclopenta[4,5]furo[3,2-b]pyridine-7-carboxylate (15)

To a solution of rac-methyl (5aR,6S,7R,8R,8aS)-5a-(4-cyanophenyl)-8,8a-dihydroxy-6-phenyl-3-(((trifluoromethyl)sulfonyl)oxy)-5a,7,8,8a-tetrahydro-6H-cyclopenta[4,5]furo[3,2-b]pyridine-7-carboxylate (14, 2.0 g, 3.48 mmol) in dimethylformamide, zinc cyanide (2.4 g, 20.09 mmol) and zinc (0.027 g, 0.418 mmol) were added at room temperature and the reaction mixture was degassed with argon for 15 min. 1,1'-Bis(diphenylphosphino)ferrocene (51.0 mg, 0.006 mmol) and tris(dibenzylideneacetone)dipalladium (95 mg, 0.104 mmol) were added to the reaction, continued degassing for 5 min and heated the reaction mixture at 125° C. for 2 h. After completion, the reaction was cooled to room temperature and passed through bed of celite.

Filtrate was concentrated and treated with ice-cold water, the precipitated solid was filtered and dried under vacuum to afford rac-methyl (5aR,6S,7R,8R,8aS)-3-cyano-5a-(4-cyanophenyl)-8,8a-dihydroxy-6-phenyl-5a,7,8,8a-tetrahydro-6H-cyclopenta[4,5]furo[3,2-b]pyridine-7-carboxylate (15) as a yellow solid. Yield: 1.9 g, crude; MS (ESI) m/z 454.38$[M+1]^+$.

Synthesis of rac-(5aR,6S,7R,8R,8aS)-3-cyano-5a-(4-cyanophenyl)-8,8a-dihydroxy-6-phenyl-5a, 7,8,8a-tetrahydro-6H-cyclopenta[4,5]furo[3,2-b]pyridine-7-carboxylic acid (16)

To a solution of rac-methyl (5aR,6S,7R,8R,8aS)-3-cyano-5a-(4-cyanophenyl)-8,8a-dihydroxy-6-phenyl-5a,7,8,8a-tetrahydro-6H-cyclopenta[4,5]furo[3,2-b]pyridine-7-carboxylate (15, 1.9 g, 3.29 mmol) in tetrahydrofuran:water (3:1, 12 mL), lithium hydroxide (0.237 g, 9.87 mmol) was added and the reaction was stirred for 6 h at room temperature. After completion, the reaction mass was cooled to 0° C. and acidified with 1M hydrogen chloride to pH ~3. The precipitated solid was filtered and dried under vacuum to afford rac-(5aR,6S,7R,8R,8aS)-3-cyano-5a-(4-cyanophenyl)-8,8a-dihydroxy-6-phenyl-5a,7,8,8a-tetrahydro-6H-cyclopenta[4,5]furo[3,2-b]pyridine-7-carboxylic acid (16) as a yellow solid. Yield: 0.55 g, 31%; MS (ESI) m/z 438.32$[M-1]^-$.

Synthesis of (5aR,6S,7R,8R,8aS)-3-cyano-5a-(4-cyanophenyl)-8,8a-dihydroxy-N,N-dimethyl-6-phenyl-5a,7,8,8a-tetrahydro-6H-cyclopenta[4,5]furo[3,2-b]pyridine-7-carboxamide (Cpd. No. 2F)

To a solution of rac-(5aR,6S,7R,8R,8aS)-3-cyano-5a-(4-cyanophenyl)-8,8a-dihydroxy-6-phenyl-5a,7,8,8a-tetrahydro-6H-cyclopenta[4,5]furo[3,2-b]pyridine-7-carboxylic acid (16, 0.5 g, 1.1 mmol) in dichloromethane (10 mL), triethylamine (0.46 mL, 3.4 mmol) and dimethylamine·hydrogen chloride (0.139 g, 1.17 mmol) were added at 0° C. The mixture was stirred for 5 min and treated with propylphosphonic anhydride (0.139 mL, 1.7 mmol, 50% in ethyl acetate) at same temperature and the reaction was stirred for 4 h at room temperature. After completion, reaction mass was diluted with dichloromethane and washed with cold water. The organic layer was dried over sodium sulphate, filtered and concentrated to give the crude. The crude was purified by silica gel column chromatography eluting with 70-90% ethyl acetate in hexanes to afford rac-(5aR,6S,7R,8R,8aS)-3-cyano-5a-(4-cyanophenyl)-8,8a-dihydroxy-N,N-dimethyl-6-phenyl-5a,7,8,8a-tetrahydro-6H-cyclopenta[4,5]furo[3,2-b]pyridine-7-carboxamide (rac-Cpd. No. 2F) as a white solid. The enantiomers were separated by chiral preparative HPLC [chiralpak IB (4.6×250) mm]. Yield: 160 mg, 30%; Peak 1 (Cpd. No. 2F, 35 mg), $[\alpha]_D$−202.0° (c 0.1, $CHCl_3$), $R_t$=5.99 min, ee >99%; MS (ESI) m/z 467.37$[M+1]^+$; UPLC: 98.66%; $^1H$ NMR (400 MHz, DMSO-$d_6$) δ 8.63 (d, J=1.6 Hz, 1H), 8.05 (d, J=1.6 Hz, 1H), 7.5 (d, J=8.4 Hz, 2H), 7.33 (d, J=8.4 Hz, 2H), 7.03 (t, J=7.2 Hz, 2H), 6.95 (t, J=8.8 Hz, 3H), 6.37 (s, 1H), 5.45 (d, J=5.6 Hz, 1H), 4.76 (t, J=5.2 Hz, 1H), 4.70 (d, J=13.2 Hz, 1H), 4.36 (dd, J=13.6, 4.8 Hz, 1H), 3.28 (s, 3H), 2.79 (s, 3H); Peak-2 (26 mg), $[\alpha]_D$+2420 (c 0.1, $CHCl_3$), $R_t$=8.46 min, ee >95%; MS (ESI) m/z 467.37$[M+1]^+$; UPLC: 99.95%; $^1H$ NMR (400 MHz, DMSO-$d_6$) δ 8.63 (d, J=1.6 Hz, 1H), 8.05 (d, J=1.6 Hz, 1H), 7.5 (d, J=8.4 Hz, 2H), 7.33 (d, J=8.4 Hz, 2H), 7.03 (t, J=7.2 Hz, 2H), 6.95 (t, J=9.2 Hz, 3H), 6.37 (s, 1H), 5.46 (d, J=6 Hz, 1H), 4.76 (t, J=5.2 Hz, 1H), 4.70 (d, J=13.2 Hz, 1H), 4.37 (dd, J=13.2, 4.4 Hz, 1H), 3.28 (s, 3H), 2.78 (s, 3H).

Example 3

(5aR,6S,7R,8R,8aS)-3-chloro-5a-(4-cyanophenyl)-8,8a-dihydroxy-N,N-dimethyl-6-phenyl-5a,7,8,8a-tetrahydro-6H-cyclopenta[4,5]furo[3,2-b]pyridine-7-carboxamide (Cpd. No. 3F)

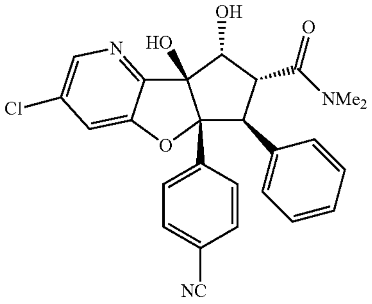

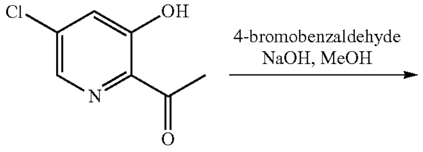

1

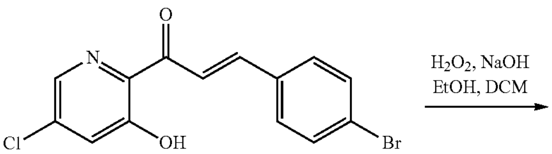

2

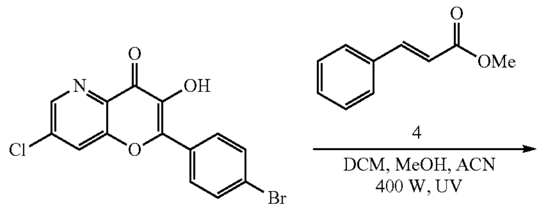

3

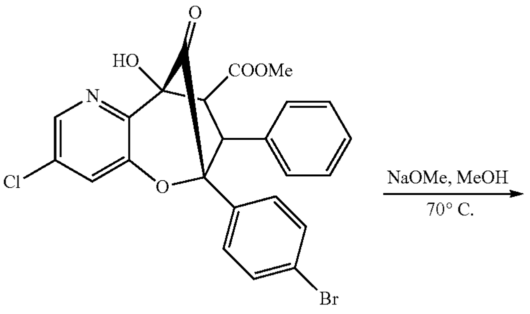

5

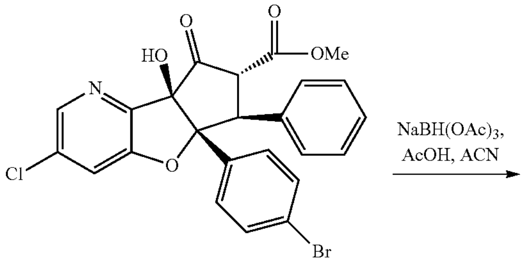

6

-continued

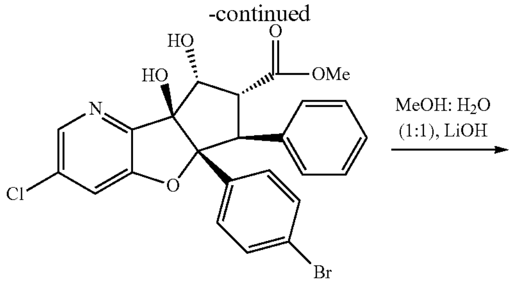

7

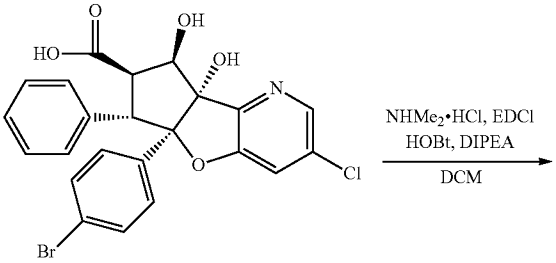

8

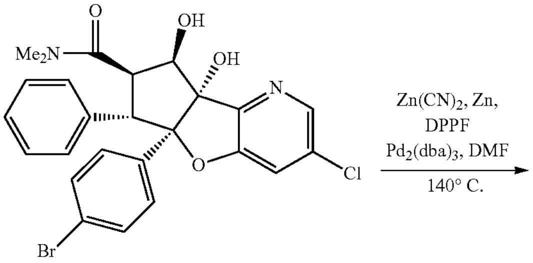

9

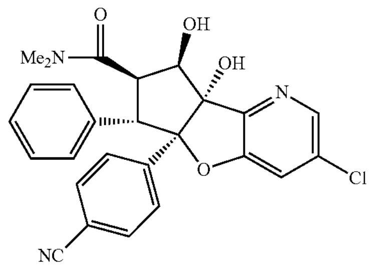

3F

Synthesis of (E)-3-(4-bromophenyl)-1-(5-chloro-3-hydroxypyridin-2-yl)prop-2-en-1-one (2)

To a solution of 1-(5-chloro-3-hydroxypyridin-2-yl)ethan-1-one (1, 10.0 g, 58.47 mmol) and sodium hydroxide (7.0 g, 175.0 mmol) in methanol (100 mL), 4-bromobenzaldehyde (10.75 g, 58.47 mmol) was added and the reaction heated to reflux for 30 minutes. After completion, reaction mass was cooled and solid was filtered, washed with water and dried under high vacuum to afford of (E)-3-(4-bromophenyl)-1-(5-chloro-3-hydroxypyridin-2-yl)prop-2-en-1-one (2) as a yellow solid. Yield: 12.0 g, 63%; MS (ESI) m/z 338.95[M+1]$^+$.

Synthesis of 2-(4-bromophenyl)-7-chloro-3-hydroxy-4H-pyrano[3,2-b]pyridin-4-one (3)

To a solution of (E)-3-(4-bromophenyl)-1-(5-chloro-3-hydroxypyridin-2-yl)prop-2-en-1-one (12.0 g, 35.3 mmol)

and sodium hydroxide (10.0 g, 249.3 mmol) in ethanol (120 mL) and dichloromethane (40 mL), hydrogen peroxide (8.97 mL, 94.7 mmol) was added at room temperature. The reaction mass was stirred for 1 h at room temperature (exotherm was observed). After completion, reaction mass was cooled and neutralized to pH ~7 by addition of 6M hydrogen chloride. The precipitated solid was filtered and dried under vacuum to afford 2-(4-bromophenyl)-7-chloro-3-hydroxy-4H-pyrano[3,2-b]pyridin-4-one (3) as a pale yellow solid. Yield: 4.0 g, 33%; MS (ESI) m/z 354.10$[M+1]^+$.

Synthesis of rac-methyl (7S,8S,9R)-6-(4-bromophenyl)-3-chloro-9-hydroxy-10-oxo-7-phenyl-6,7,8,9-tetrahydro-6,9-methanooxepino[3,2-b]pyridine-8-carboxylate (5)

A solution of 2-(4-bromophenyl)-7-chloro-3-hydroxy-4H-pyrano[3,2-b]pyridin-4-one (3, 4.0 g, 11.39 mmol) and methyl cinnamate (4, 18.46 g, 113.9 mmol) in dichloromethane (200 mL), acetonitrile (100 mL) and methanol (100 mL) was placed in a UV reactor flask. The reaction mixture was irradiated under 400 watts UV light for 15 h. After completion, the solvent was removed under reduced pressure and the residue was purified over a plug of silica gel eluting the compound with ethyl acetate. The desired fractions were concentrated under reduced pressure to afford rac-methyl (7S,8S,9R)-6-(4-bromophenyl)-3-chloro-9-hydroxy-10-oxo-7-phenyl-6,7,8,9-tetrahydro-6,9-methanooxepino[3,2-b]pyridine-8-carboxylate (5, 6.0 g, crude).

Synthesis of rac-methyl (5aR,6S,7R,8aR)-5a-(4-bromophenyl)-3-chloro-8a-hydroxy-8-oxo-6-phenyl-5a,7,8,8a-tetrahydro-6H-cyclopenta[4,5]furo[3,2-b]pyridine-7-carboxylate (6)

The crude compound rac-methyl (7S,8S,9R)-6-(4-bromophenyl)-3-chloro-9-hydroxy-10-oxo-7-phenyl-6,7,8,9-tetrahydro-6,9-methanooxepino[3,2-b]pyridine-8-carboxylate (5, 6.0 g) was suspended in methanol (30 mL) and treated with 25% sodium methoxide in methanol (30 mL) and heated the mixture to 70° C. for 1 h. After completion, the solvent was removed under reduced pressure and crude was treated with ammonium chloride solution and extracted with ethyl acetate. The organic phase was separated, dried over sodium sulphate and concentrated under reduced pressure to afford rac-methyl (5aR,6S,7R,8aR)-5a-(4-bromophenyl)-3-chloro-8a-hydroxy-8-oxo-6-phenyl-5a,7,8,8a-tetrahydro-6H-cyclopenta[4,5]furo[3,2-b]pyridine-7-carboxylate (6, 5.0 g, crude).

Synthesis of rac-methyl (5aR,6S,7R,8R,8aS)-5a-(4-bromophenyl)-3-chloro-8,8a-dihydroxy-6-phenyl-5a,7,8,8a-tetrahydro-6H-cyclopenta[4,5]furo[3,2-b]pyridine-7-carboxylate (7)

The above crude compound (6, 5.0 g, 9.74 mmol) was charged to a solution of sodium triacetoxyborohydride (12.6 g, 58.4 mmol) in acetonitrile (30 mL) and acetic acid (3.6 mL, 97.2 mmol) and the resulting mixture was stirred for 4 h at room temperature. After completion, reaction mixture was partitioned between saturated aqueous sodium bicarbonate solution and ethyl acetate. The organic layer was separated, dried over sodium sulphate and concentrated under reduced pressure to get the crude. The crude was purified by silica gel column chromatography eluting with 50% ethyl acetate in hexanes. The desired fractions were concentrated under reduced pressure to afford rac-methyl (5aR,6S,7R,8R,8aS)-5a-(4-bromophenyl)-3-chloro-8,8a-dihydroxy-6-phenyl-5a,7,8,8a-tetrahydro-6H-cyclopenta[4,5]furo[3,2-b]pyridine-7-carboxylate (7) as an off-white solid. Yield: 3.3 g, 66%; MS (ESI) m/z 516.01$[M-1]^-$.

Synthesis of rac-(5aR,6S,7R,8R,8aS)-5a-(4-bromophenyl)-3-chloro-8,8a-dihydroxy-6-phenyl-5a, 7,8,8a-tetrahydro-6H-cyclopenta[4,5]furo[3,2-b]pyridine-7-carboxylic acid (8)

To a solution of rac-methyl (5aR,6S,7R,8R,8aS)-5a-(4-bromophenyl)-3-chloro-8,8a-dihydroxy-6-phenyl-5a,7,8,8a-tetrahydro-6H-cyclopenta[4,5]furo[3,2-b]pyridine-7-carboxylate (7, 3.3 g, 6.4 mmol) in methanol:water (3:1, 11 mL), lithium hydroxide (3.68 g, 153.6 mmol) was added and the reaction was stirred for 3 h at room temperature. After completion, the reaction mass was cooled to 0° C. and acidified with 5M hydrogen chloride to pH ~3. The solid precipitated was filtered and dried under high vacuum to afford rac-(5aR,6S,7R,8R,8aS)-5a-(4-bromophenyl)-3-chloro-8,8a-dihydroxy-6-phenyl-5a,7,8,8a-tetrahydro-6H-cyclopenta[4,5]furo[3,2-b]pyridine-7-carboxylic acid (8) as an off-white solid. Yield: 3.2 g, crude; MS (ESI) m/z 502.02$[M+1]^+$.

Synthesis of rac-(5aR,6S,7R,8R,8aS)-5a-(4-bromophenyl)-3-chloro-8,8a-dihydroxy-N,N-dimethyl-6-phenyl-5a,7,8,8a-tetrahydro-6H-cyclopenta[4,5]furo[3,2-b]pyridine-7-carboxamide (9)

To a solution of rac-(5aR,6S,7R,8R,8aS)-5a-(4-bromophenyl)-3-chloro-8,8a-dihydroxy-6-phenyl-5a,7,8,8a-tetrahydro-6H-cyclopenta[4,5]furo[3,2-b]pyridine-7-carboxylic acid (8, 3.2 g, 6.39 mmol) in dichloromethane (30 mL), 1-ethyl-3-(3-dimethylaminopropyl)carbodiimide hydrogen chloride (3.6 g, 19.16 mmol), hydroxybenzotriazole (2.8 g, 19.16 mmol) and N,N-diisopropylethylamine (7.3 mL, 41.9 mmol) were added at 0° C. and stirred the mixture for 5 min. Dimethylamine hydrogen chloride (2.8 g, 34.9 mmol) was then added at same temperature and the reaction was stirred for 12 h at room temperature. After completion, reaction mass was diluted with dichloromethane and washed with cold water. The organic layer was separated and dried over sodium sulphate, filtered and concentrated to give crude. The crude was purified by silica gel column chromatography eluting with 70-90% ethyl acetate in hexanes to afford rac-(5aR,6S,7R,8R,8aS)-5a-(4-bromophenyl)-3-chloro-8,8a-dihydroxy-N,N-dimethyl-6-phenyl-5a,7,8,8a-tetrahydro-6H-cyclopenta[4,5]furo[3,2-b]pyridine-7-carboxamide (9) as a white solid. Yield: 2.9 g, 76%; MS (ESI) m/z 529.05 $[M+1]^+$.

Synthesis of (5aR,6S,7R,8R,8aS)-3-chloro-5a-(4-cyanophenyl)-8,8a-dihydroxy-N,N-dimethyl-6-phenyl-5a,7,8,8a-tetrahydro-6H-cyclopenta[4,5]furo[3,2-b]pyridine-7-carboxamide (Cpd. No. 3F)

To a solution of (5aR,6S,7R,8R,8aS)-5a-(4-bromophenyl)-3-chloro-8,8a-dihydroxy-N,N-dimethyl-6-phenyl-5a,7,8,8a-tetrahydro-6H-cyclopenta[4,5]furo[3,2-b]pyridine-7-carboxamide (9, 1.5 g, 2.84 mmol) in dimethylformamide (25 mL), zinc cyanide (6.0 g, 17.0 mmol) and zinc (0.022 g, 0.34 mmol) were added and degassed the mixture with argon for 15 min. 1,1'-Bis(diphenylphosphino)ferrocene (0.041 g, 0.056 mmol), tris(dibenzylideneacetone)dipalladium (0.078 g, 0.085 mmol) were added to the above reaction and degassing was continued for another 5 min followed by heating the reaction mixture at 140° C. for 1 h. After completion, the reaction was cooled to room temperature and passed through a bed of celite. Filtrate was concentrated and treated with ice-cold water, the precipitated solid was filtered and the crude was purified by reverse phase prep HPLC. Desired fractions were concentrated under vacuum to afford rac-(5aR,6S,7R,8R,8aS)-3-chloro-5a-(4-cyanophenyl)-8,8a-dihydroxy-N,N-dimethyl-6-phenyl-5a,7,8,8a-tetrahydro-6H-cyclopenta[4,5]furo[3,2-b]pyridine-7-carboxamide (rac-Cpd. No. 3F) as an off-white solid. The enantiomers were separated by chiral preparative HPLC [chiralpak IB (4.6×250) mm]. Yield: 1.1 g (85%); Peak 1 (Cpd. No. 3F, 40 mg), $[\alpha]_D$−180.5° (c 0.1, $CHCl_3$), $R_t$=7.95 min, ee >99%; MS (ESI) m/z 476.35$[M+1]^+$; UPLC: 98.31%; $^1H$ NMR (400 MHz, DMSO-d6) δ 8.21 (d, J=2.0 Hz, 1H), 7.73 (d, J=2.0 Hz, 1H), 7.50 (d, J=8.4 Hz, 2H), 7.34 (d, J=8.6 Hz, 2H), 7.03 (t, J=7.2 Hz, 2H), 6.97-6.91 (m, 3H), 6.15 (s, 1H), 5.34 (d, J=5.6 Hz, 1H), 4.73 (t, J=5.2 Hz, 1H), 4.66 (d, J=13.2 Hz, 1H), 4.34 (dd, J=13.2, 5.2 Hz, 1H), 3.28 (s, 3H), 2.78 (s, 3H). Peak 2 (41 mg), $[\alpha]_D$+1800 (c 0.1, $CHCl_3$), $R_t$=15.19 min, ee >98.5%; MS (ESI) m/z 476.35 $[M+1]^+$; UPLC: 98.76%; $^1H$ NMR (400 MHz, DMSO-$d_6$) δ 8.21 (d, J=2.0 Hz, 1H), 7.73 (d, J=2.0 Hz, 1H), 7.50 (d, J=8.4 Hz, 2H), 7.33 (d, J=8.6 Hz, 2H), 7.03 (t, J=7.2 Hz, 2H), 6.97-6.91 (m, 3H), 6.15 (s, 1H), 5.34 (d, J=5.8 Hz, 1H), 4.73 (t, J=5.4 Hz, 1H), 4.66 (d, J=13.2 Hz, 1H), 4.34 (dd, J=13.2, 5.4 Hz, 1H), 3.28 (s, 3H), 2.78 (s, 3H).

Example 4

(5aR,6S,7R,8R,8aS)-3-cyano-8,8a-dihydroxy-5a-(4-methoxyphenyl)-N,N-dimethyl-6-phenyl-5a,7,8,8a-tetrahydro-6H-cyclopenta[4,5]furo[3,2-b]pyridine-7-carboxamide (Cpd. No. 4F)

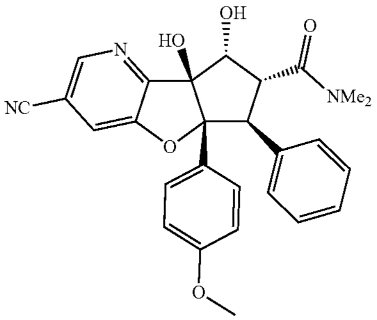

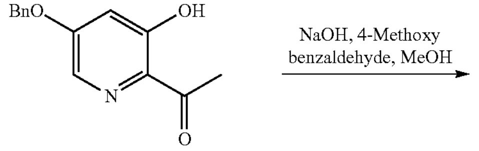

1

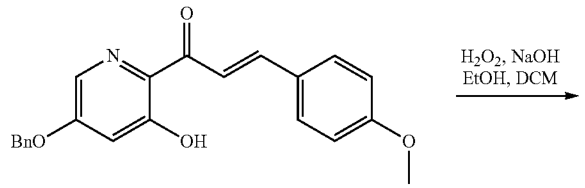

2

-continued

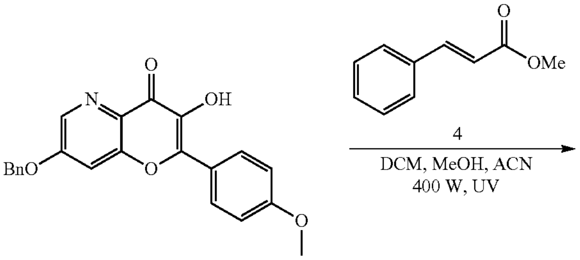

3

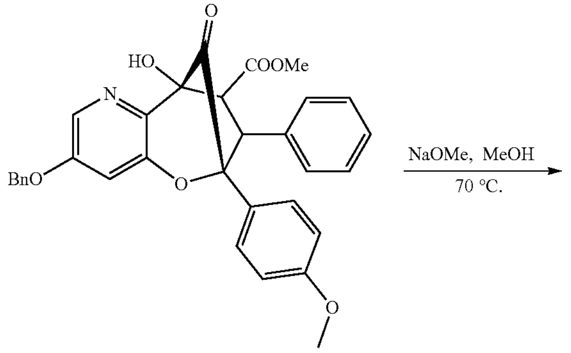

5

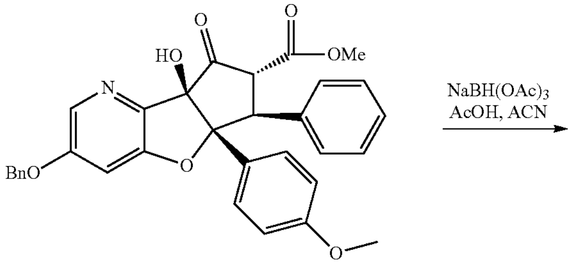

6

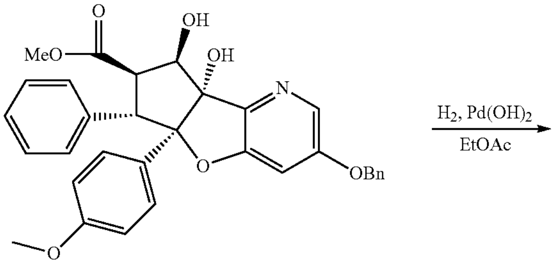

7

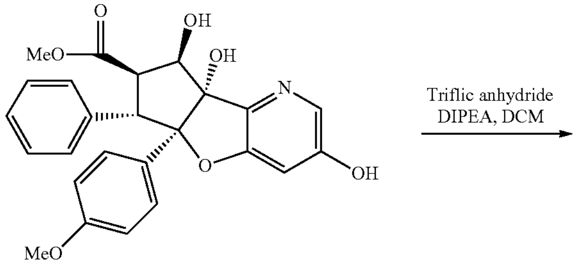

8

-continued

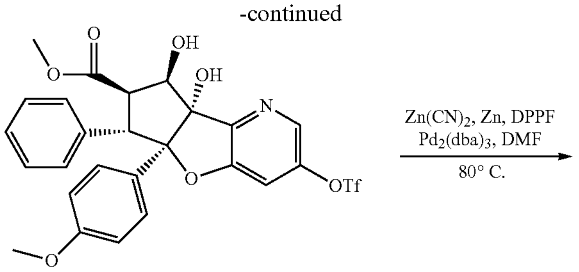

9

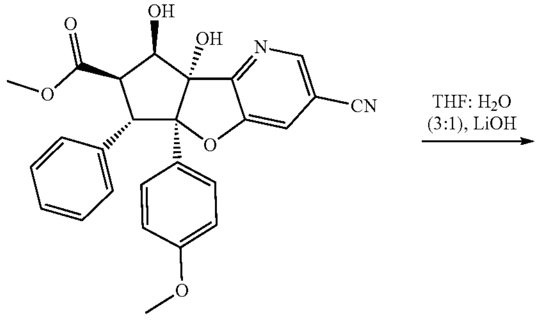

10

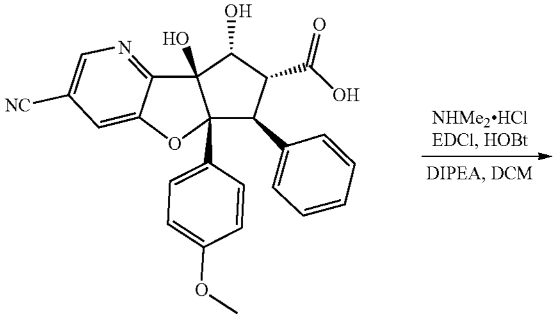

11

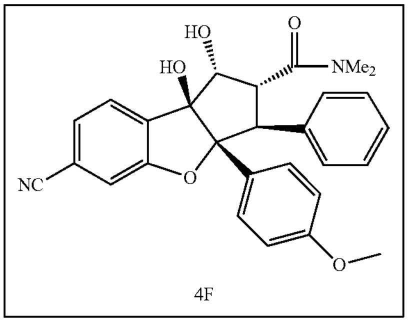

4F

Synthesis of (E)-1-(5-(benzyloxy)-3-hydroxypyridin-2-yl)-3-(4-methoxyphenyl)prop-2-en-1-one (2)

To a solution of 1-(5-(benzyloxy)-3-hydroxypyridin-2-yl)ethan-1-one (42.0 g, 172.8 mmol) and sodium hydroxide (20.97 g, 518.5 mmol) in methanol (200 mL), 4-methoxybenzaldehyde (31.97 g, 172.8 mmol) was added and the reaction was heated to reflux for 30 minutes. After completion, reaction mass was cooled and solid was filtered, washed with water and dried under vacuum to afford of (E)-1-(5-(benzyloxy)-3-hydroxypyridin-2-yl)-3-(4-methoxyphenyl)prop-2-en-1-one as a yellow solid. Yield: 62.3 g, crude; MS (ESI) m/z 362.32[M+1]$^+$.

Synthesis of 7-(benzyloxy)-3-hydroxy-2-(4-methoxyphenyl)-4H-pyrano[3,2-b]pyridin-4-one (3)

To a solution of (E)-1-(5-(benzyloxy)-3-hydroxypyridin-2-yl)-3-(4-methoxyphenyl)prop-2-en-1-one (2, 54.0 g, 149 mmol) and sodium hydroxide (47.8 g, 1.19 mol) in ethanol (300 mL), hydrogen peroxide (27.6 mL, 747 mmol) was added at room temperature. The reaction mass was stirred for 1 h (exotherm was observed). After completion, reaction mass was cooled and neutralized to pH ~7 by addition of 6M hydrogen chloride at 0° C. The precipitated solid was filtered and dried under vacuum to afford 7-(benzyloxy)-3-hydroxy-2-(4-methoxyphenyl)-4H-pyrano[3,2-b]pyridin-4-one as a pale yellow solid. Yield: 20.5 g, 36%; MS (ESI) m/z 376.11 [M+1]$^+$.

Synthesis of rac-methyl (7S,8S,9R)-3-(benzyloxy)-9-hydroxy-6-(4-methoxyphenyl)-10-oxo-7-phenyl-6,7,8,9-tetrahydro-6,9-methanooxepino[3,2-b]pyridine-8-carboxylate (5)

A solution of 7-(benzyloxy)-3-hydroxy-2-(4-methoxyphenyl)-4H-pyrano[3,2-b]pyridin-4-one (18.0 g, 48.0 mmol) and methyl cinnamate (4, 77.8 g, 480.0 mmol) in dichloromethane (200 mL) acetonitrile (100 mL) and methanol (100 mL) was placed in a UV reactor flask. The reaction mixture was irradiated with 400 watts UV light for 15 h. After completion, the solvent was removed under reduced pressure and the residue was purified over a plug of silica gel, eluting the compound with ethyl acetate. The desired fractions were concentrated under reduced pressure to afford rac-methyl (7S,8S,9R)-3-(benzyloxy)-9-hydroxy-6-(4-methoxyphenyl)-10-oxo-7-phenyl-6,7,8,9-tetrahydro-6,9-methanooxepino[3,2-b]pyridine-8-carboxylate (5, 15.0 g, crude).

Synthesis of rac-methyl (5aR,6S,7R,8aR)-3-(benzyloxy)-8a-hydroxy-5a-(4-methoxyphenyl)-8-oxo-6-phenyl-5a,7,8,8a-tetrahydro-6H-cyclopenta[4,5]furo[3,2-b]pyridine-7-carboxylate (6)

The crude compound rac-methyl (7S,8S,9R)-3-(benzyloxy)-9-hydroxy-6-(4-methoxyphenyl)-10-oxo-7-phenyl-6,7,8,9-tetrahydro-6,9-methanooxepino[3,2-b]pyridine-8-carboxylate (5, 15.0 g) was suspended in methanol (30 mL) and treated with 25% sodium methoxide in methanol (30 mL) and heated the mixture to 70° C. for 1 h. After completion, the solvent was removed under reduced pressure and crude was treated with ammonium chloride solution and extracted with ethyl acetate. The organic phase was dried over sodium sulphate and concentrated under reduced pressure to afford rac-methyl (5aR,6S,7R,8aR)-3-(benzyloxy)-8a-hydroxy-5a-(4-methoxyphenyl)-8-oxo-6-phenyl-5a,7,8,8a-tetrahydro-6H-cyclopenta[4,5]furo[3,2-b]pyridine-7-carboxylate (6, 12.5 g, crude).

Synthesis of rac-methyl (5aR,6S,7R,8R,8aS)-3-(benzyloxy)-8,8a-dihydroxy-5a-(4-methoxyphenyl)-6-phenyl-5a,7,8,8a-tetrahydro-6H-cyclopenta[4,5]furo[3,2-b]pyridine-7-carboxylate (7)

The above crude compound (6, 12.5 g, 6.0 mmol) was added to a solution of sodium triacetoxyborohydride (14.8 g, 4.21 mmol) in acetonitrile (130 mL) and acetic acid (13.93 mL, 23.27 mmol) and the resulting mixture was stirred for 6 h at room temperature. After completion, reaction mixture was partitioned between saturated aqueous sodium bicarbonate solution and ethyl acetate. The organic layer was separated, dried over sodium sulphate and concentrated under reduced pressure to get the crude. The crude was purified by silica gel column chromatography eluting with 50%-70% ethyl acetate in hexanes. The desired fractions were concentrated under reduced pressure to afford rac-methyl (5aR,6S,7R,8R,8aS)-3-(benzyloxy)-8,8a-dihydroxy-5a-(4-methoxyphenyl)-6-phenyl-5a,7,8,8a-tetrahydro-6H-cyclopenta[4,5]furo[3,2-b]pyridine-7-carboxylate (7) as a pale brown solid. Yield: 4.5 g, 35%; MS (ESI) m/z 540.25 $[M+1]^+$.

Synthesis of rac-methyl (5aR,6S,7R,8R,8aS)-3,8,8a-trihydroxy-5a-(4-methoxyphenyl)-6-phenyl-5a,7,8,8a-tetrahydro-6H-cyclopenta[4,5]furo[3,2-b]pyridine-7-carboxylate (8)

To a solution of rac-methyl (5aR,6S,7R,8R,8aS)-3-(benzyloxy)-8,8a-dihydroxy-5a-(4-methoxyphenyl)-6-phenyl-5a,7,8,8a-tetrahydro-6H-cyclopenta[4,5]furo[3,2-b]pyridine-7-carboxylate (7, 3.0 g, 5.55 mmol) in ethyl acetate (300 mL) at room temperature palladium hydroxide (0.195 g, 2.78 mmol, 50% wet) was added. The reaction was flushed with hydrogen gas twice and stirred under hydrogen pressure at room temperature for 16 h. After completion, the reaction mass was passed through bed of celite and filtrate was concentrated under reduced pressure to afford rac-methyl (5aR,6S,7R,8R,8aS)-3,8,8a-trihydroxy-5a-(4-methoxyphenyl)-6-phenyl-5a,7,8,8a-tetrahydro-6H-cyclopenta[4,5]furo[3,2-b]pyridine-7-carboxylate (8) as a brown solid. Yield: 2.8 g, 94%; MS (ESI) m/z 450.17$[M+1]^+$.

Synthesis of rac-methyl (5aR,6S,7R,8R,8aS)-8,8a-dihydroxy-5a-(4-methoxyphenyl)-6-phenyl-3-(((trifluoromethyl)sulfonyl)oxy)-5a, 7,8,8a-tetrahydro-6H-cyclopenta[4,5]furo[3,2-b]pyridine-7-carboxylate (9)

To a solution of rac-methyl (5aR,6S,7R,8R,8aS)-3,8,8a-trihydroxy-5a-(4-methoxyphenyl)-6-phenyl-5a,7,8,8a-tetrahydro-6H-cyclopenta[4,5]furo[3,2-b]pyridine-7-carboxylate (8, 2.2 g, 4.8 mmol) and N,N-diisopropylethylamine (0.94 g, 7.3 mmol) in dichloromethane (300 mL) was added under nitrogen at −78° C. triflic anhydride (1.79 g, 6.36 mmol) was added slowly. The reaction was stirred for 30 min at −78° C. and brought to room temperature and stirred for 1 h. After completion, the reaction mass was treated with saturated sodium bicarbonate solution at 0° C. The residue was dissolved in dichloromethane (300 mL) separated the organic layer and washed with water (2×50 mL) then with brine solution (50 mL).

The organic layer was separated and dried over anhydrous sodium sulfate before concentration to dryness. The solid was triturated with pentane, filtered and dried under vacuum to afford rac-methyl (5aR,6S,7R,8R,8aS)-8,8a-dihydroxy-5a-(4-methoxyphenyl)-6-phenyl-3-(((trifluoromethyl)sulfonyl)oxy)-5a,7,8,8a-tetrahydro-6H-cyclopenta[4,5]furo[3,2-b]pyridine-7-carboxylate (9) as a brown solid. Yield: 2.5 g, 87.8%; MS (ESI) m/z 582.05$[M+1]^+$.

Synthesis of rac-methyl (5aR,6S,7R,8R,8aS)-3-cyano-8,8a-dihydroxy-5a-(4-methoxyphenyl)-6-phenyl-5a,7,8,8a-tetrahydro-6H-cyclopenta[4,5]furo[3,2-b]pyridine-7-carboxylate (10)

To a solution of rac-methyl (5aR,6S,7R,8R,8aS)-8,8a-dihydroxy-5a-(4-methoxyphenyl)-6-phenyl-3-(((trifluoromethyl)sulfonyl)oxy)-5a,7,8,8a-tetrahydro-6H-cyclopenta[4,5]furo[3,2-b]pyridine-7-carboxylate (9, 0.5 g, 0.86 mmol) in dimethylformamide at room temperature, zinc cyanide (0.6 g, 5.13 mmol) and zinc (0.067 g, 0.10 mmol) were added and degassed the reaction with argon for 15 min. 1,1'-Bis(diphenylphosphino)ferrocene (0.023 g, 0.025 mmol), tris(dibenzylideneacetone)dipalladium (0.025 g, 0.034 mmol) were added to the reaction and degassing was continued with argon for 5 min followed by heating at 85° C. for 1 h. After completion, the reaction was cooled to room temperature and passed through a bed of celite. Filtrate was concentrated and treated with ice-cold water. The precipitated solid was filtered and purified by reverse phase prep HPLC. Desired fractions were concentrated to dryness under vacuum to afford rac-methyl (5aR,6S,7R,8R,8aS)-3-cyano-8,8a-dihydroxy-5a-(4-methoxyphenyl)-6-phenyl-5a,7,8,8a-tetrahydro-6H-cyclopenta[4,5]furo[3,2-b]pyridine-7-carboxylate (10) as a yellow solid. Yield: 150 mg, 38%; MS (ESI) m/z 459.19$[M+1]^+$.

Synthesis of rac-(5aR,6S,7R,8R,8aS)-3-cyano-8,8a-dihydroxy-5a-(4-methoxyphenyl)-6-phenyl-5a, 7,8,8a-tetrahydro-6H-cyclopenta[4,5]furo[3,2-b]pyridine-7-carboxylic acid (11)

To a solution of rac-methyl (5aR,6S,7R,8R,8aS)-3-cyano-8,8a-dihydroxy-5a-(4-methoxyphenyl)-6-phenyl-5a,7,8,8a-tetrahydro-6H-cyclopenta[4,5]furo[3,2-b]pyridine-7-carboxylate (10, 0.42 g, 0.91 mmol) in tetrahydrofuran:water (3:1, 12 mL), lithium hydroxide (0.066 g, 2.75 mmol) was added and the reaction was stirred for 6 h at room temperature. After completion, the reaction mass was cooled to 0° C. and acidified with 1M citric acid to pH ~5. The precipitated solid was filtered and dried under vacuum to afford rac-(5aR,6S,7R,8R,8aS)-3-cyano-8,8a-dihydroxy-5a-(4-methoxyphenyl)-6-phenyl-5a,7,8,8a-tetrahydro-6H-cyclopenta[4,5]furo[3,2-b]pyridine-7-carboxylic acid (11) as an off-white solid. Yield: 0.3 g, 73.7%; MS (ESI) m/z 445.19 $[M+1]^+$.

Synthesis of (5aR,6S,7R,8R,8aS)-3-cyano-8,8a-dihydroxy-5a-(4-methoxyphenyl)-N,N-dimethyl-6-phenyl-5a,7,8,8a-tetrahydro-6H-cyclopenta[4,5]furo[3,2-b]pyridine-7-carboxamide (Cpd. No. 4F)

To a solution of rac-(5aR,6S,7R,8R,8aS)-3-cyano-8,8a-dihydroxy-5a-(4-methoxyphenyl)-6-phenyl-5a,7,8,8a-tetrahydro-6H-cyclopenta[4,5]furo[3,2-b]pyridine-7-carboxylic acid (11, 0.3 g, 0.67 mmol) in dichloromethane (30 mL), 1-ethyl-3-(3-dimethylaminopropyl)carbodiimide (0.388 g, 2.02 mmol), hydroxybenzotriazole (0.27 g, 2.02 mmol) and N,N-diisopropylethylamine (0.52 mg, 4.05 mmol) were added at 0° C. and stirred the mixture for 5 min. Dimethylamine-hydrogen chloride (0.274 g, 3.78 mmol) was then added at same temperature and the mixture was stirred for 12 h at room temperature. After completion, reaction mass was diluted with dichloromethane and washed with cold water. The organic layer was separated and dried over sodium sulphate, filtered and concentrated to give crude. The crude was purified by silica gel column chromatography eluting with 70-90% ethyl acetate in hexanes to afford rac-(5aR,6S,7R,8R,8aS)-3-cyano-8,8a-dihydroxy-5a-(4-methoxyphenyl)-N,N-dimethyl-6-phenyl-5a,7,8,8a-tetrahydro-6H-cyclopenta[4,5]furo[3,2-b]pyridine-7-carboxamide (rac-Cpd. No. 4F) as a white solid. The enantiomers were separated by chiral preparative HPLC [chiralpak IB (4.6×250) mm]. Yield: 250 mg, 75.9%; Peak 1 (Cpd. No. 4F, 35 mg), $[\alpha]_D$−172.0° (c 0.1, $CHCl_3$), $R_t$=6.54 min, ee >99%; MS (ESI) m/z 472.33[M+1]$^+$; UPLC: 98.98%; $^1$H NMR (400 MHz, DMSO-$d_6$) δ 8.60 (s, 1H), 8.00 (s, 1H), 7.07-7.00 (m, 4H), 6.97 (d, J=7.0 Hz, 1H), 6.91 (d, J=7.2 Hz, 2H), 6.60 (d, J=8.8 Hz), 6.09 (s, 1H), 5.34 (d, J=5.4 Hz, 1H), 4.76 (s, 1H), 4.54 (d, J=12.8 Hz, 1H), 4.25 (dd, J=13.5, 5.2 Hz, 1H), 3.59 (s, 3H), 3.26 (s, 3H), 2.77 (s, 3H); Peak-2 (35 mg), $[\alpha]_D$+152.0° (c 0.1, $CHCl_3$), $R_t$=10.65 min, ee >99%; MS (ESI) m/z 472.34[M+1]$^+$; UPLC: 99.58%; $^1$H NMR (400 MHz, DMSO-$d_6$) δ 8.60 (d, J=1.4 Hz, 1H), 8.00 (d, J=1.4 Hz, 1H), 7.05-7.01 (m, 4H), 6.97 (d, J=7.2 Hz, 1H), 6.91 (d, J=7.4 Hz, 2H), 6.61 (d, J=8.8 Hz, 2H), 6.09 (s, 1H), 5.34 (d, J=5.6 Hz, 1H), 4.76 (t, J=5.2 Hz, 1H), 4.54 (d, J=13.2 Hz, 1H), 4.25 (dd, J=13.2, 5.2 Hz, 1H), 3.59 (s, 3H), 3.26 (s, 3H), 2.77 (s, 3H).

Example 5

(5aR,6S,7R,8R,8aS)-3-chloro-8,8a-dihydroxy-5a-(4-methoxyphenyl)-N,N-dimethyl-6-phenyl-5a,7,8,8a-tetrahydro-6H-cyclopenta[4,5]furo[3,2-b]pyridine-7-carboxamide (Cpd. No. 5F)

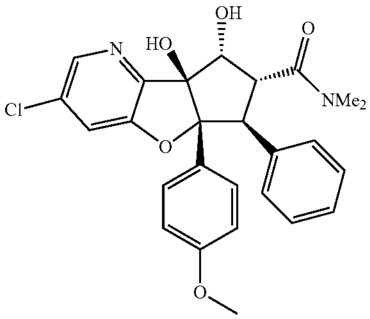

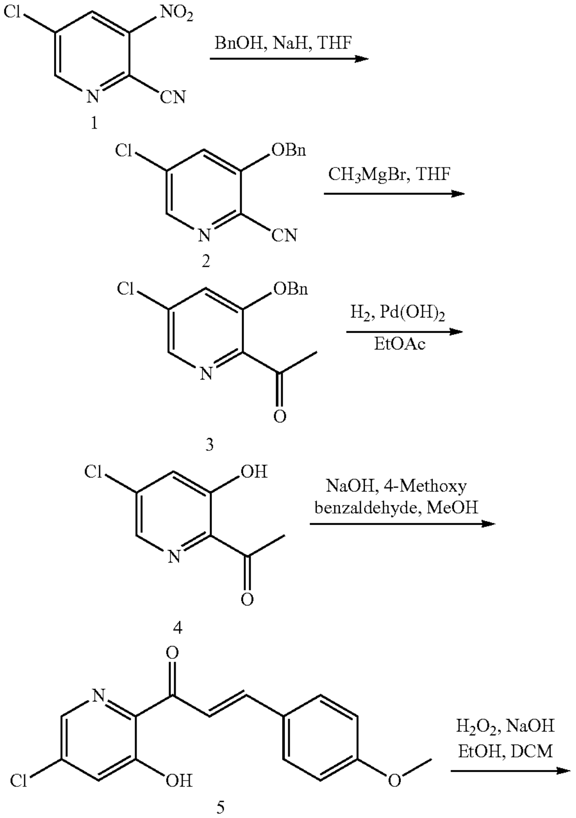

-continued

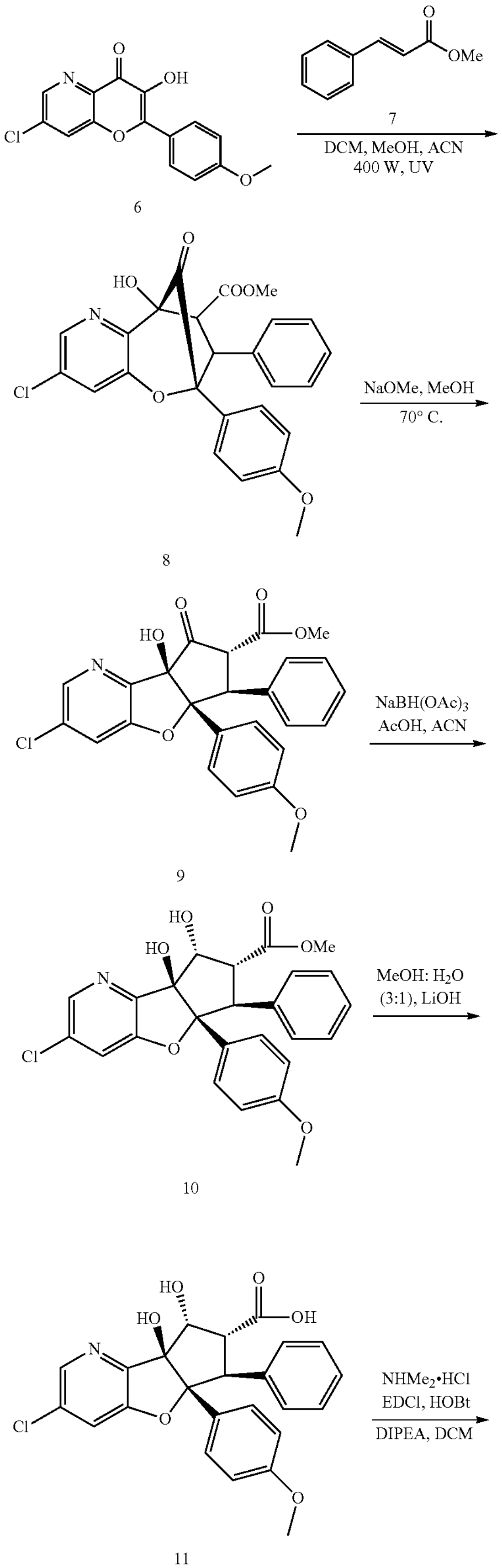

-continued

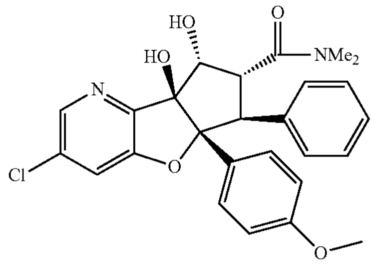

5F

Synthesis of 3-(benzyloxy)-5-chloropicolinonitrile (2)

To a solution of 5-chloro-3-nitropicolinonitrile (1, 25.0 g, 273.2 mmol) in tetrahydrofuran (250 mL) under nitrogen sodium hydride (11.0 g, 273.2 mmol) was added at room temperature. The suspension was stirred for 30 minutes and then benzyl alcohol (29.5 mL, 273.2 mmol) was added and stirring was continued for another 3 h. After completion, the reaction mass was cooled to 0° C. and treated with saturated ammonium chloride solution. The mixture was diluted with ethyl acetate (200 mL) and organic layer was separated, washed with water (2×50 mL) and brine (50 mL). The organic layer was dried over anhydrous sodium sulfate and solvent was removed under reduced pressure to get crude. The crude was treated with pentane (100 mL) to get solid which was filtered and dried under vacuum to afford 3-(benzyloxy)-5-chloropicolinonitrile (2) as brownish solid. Yield: 28.0 g, 84%; MS (ESI) m/z 245.09$[M+1]^+$.

Synthesis of 1-(3-(benzyloxy)-5-chloropyridin-2-yl)ethan-1-one (3)

To a solution of 3-(benzyloxy)-5-chloropicolinonitrile (2, 28.0 g, 114.0 mmol) in dry tetrahydrofuran (250 mL), methyl magnesium bromide (114.0 mL, 344.0 mmol) was added dropwise at −30° C. over a period of 30 min. The reaction mass was slowly brought to room temperature and stirred for 2 h. After completion, the reaction mixture was treated with 6M hydrogen chloride (pH ~3) and stirred for another 2 h. The mixture was extracted with ethyl acetate (200 mL) and layers were separated. The organic layer was washed with 1M sodium hydroxide solution (50 mL), water (50 mL), dried over anhydrous sodium sulfate and concentrated under reduced pressure to afford 1-(3-(benzyloxy)-5-chloropyridin-2-yl)ethan-1-one (3) as a yellow oil. Yield: 19.0 g, 29.9%; MS (ESI) m/z 262.10$[M+1]^+$.

Synthesis of 1-(5-chloro-3-hydroxypyridin-2-yl)ethan-1-one (4)

To a solution of 1-(3-(benzyloxy)-5-chloropyridin-2-yl)ethan-1-one (19.0 g, 72.7 mmol) in ethylacetate palladium hydroxide (50% wet) (10.0 g, 36.3 mmol) was added at room temperature. The reaction was purged with hydrogen gas twice and stirred under hydrogen pressure for 16 h. After completion, the reaction mass was passed through bed of celite and filtrate was concentrated under reduced pressure to afford 1-(5-chloro-3-hydroxypyridin-2-yl)ethan-1-one as a brown oil. Yield: 8.0 g, 64.5%; MS (ESI) m/z 170.03$[M-1]^-$.

Synthesis of (E)-1-(5-chloro-3-hydroxypyridin-2-yl)-3-(4-methoxyphenyl)prop-2-en-1-one (5)

To a solution of 1-(5-chloro-3-hydroxypyridin-2-yl)ethan-1-one (4, 8.0 g, 46.3 mmol) and sodium hydroxide (5.6 g, 140.0 mmol) in methanol (50 mL), mmol) 4-methoxybenzaldehyde (6.9 mL, 56.1 mmol) was added and the reaction was heated to reflux for 30 minutes. After completion, reaction mass was cooled and solid was filtered, washed with water and then dried under high vacuum to afford of (E)-1-(5-chloro-3-hydroxypyridin-2-yl)-3-(4-methoxyphenyl)prop-2-en-1-one (5) as a yellow solid. Yield: 10.5 g, 77.7%; MS (ESI) m/z 290.02$[M+1]^+$.

Synthesis of 7-chloro-3-hydroxy-2-(4-methoxyphenyl)-4H-pyrano[3,2-b]pyridin-4-one (6)

To a solution of (E)-1-(5-chloro-3-hydroxypyridin-2-yl)-3-(4-methoxyphenyl)prop-2-en-1-one (5, 10.5 g, 36.3 mmol) and sodium hydroxide (10.0 g, 254.3 mmol) in ethanol (100 mL), hydrogen peroxide (10.73 mL, 94.7 mmol) was added at room temperature. The reaction mass was stirred for 1 h at room temperature (exotherm was observed). After completion, reaction mass was cooled and neutralized to pH ~7 by addition of 6M hydrogen chloride. The precipitated solid was filtered and dried under vacuum to afford 7-chloro-3-hydroxy-2-(4-methoxyphenyl)-4H-pyrano[3,2-b]pyridin-4-one (6) as a brick red solid. Yield: 6.5 g, 59%; MS (ESI) m/z 304.17$[M+1]^+$ Synthesis of rac-methyl (7S,8S,9R)-3-chloro-9-hydroxy-6-(4-methoxyphenyl)-10-oxo-7-phenyl-6,7,8,9-tetrahydro-6,9-methanooxepino[3,2-b]pyridine-8-carboxylate (8)

A solution of 7-chloro-3-hydroxy-2-(4-methoxyphenyl)-4H-pyrano[3,2-b]pyridin-4-one (6, 6.5 g, 21.4 mmol) and methyl cinnamate (7, 34.7 g, 214.5 mmol) in dichloromethane (200 mL), acetonitrile (100 mL) and methanol (100 mL) was placed in a UV reactor. The reaction mixture was irradiated under 400 watts UV light for 15 h. After completion, the solvent was removed under reduced pressure and the residue was purified over a plug of silica gel eluting the compound with ethyl acetate. The desired fractions were concentrated under reduced pressure to afford rac-methyl (7S,8S,9R)-3-chloro-9-hydroxy-6-(4-methoxyphenyl)-10-oxo-7-phenyl-6,7,8,9-tetrahydro-6,9-methanooxepino[3,2-b]pyridine-8-carboxylate (8, 4.0 g, crude).

Synthesis of rac-methyl (5aR,6S,7R,8aR)-3-chloro-8a-hydroxy-5a-(4-methoxyphenyl)-8-oxo-6-phenyl-5a,7,8,8a-tetrahydro-6H-cyclopenta[4,5]furo[3,2-b]pyridine-7-carboxylate (9)

The crude compound rac-methyl (7S,8S,9R)-3-chloro-9-hydroxy-6-(4-methoxyphenyl)-10-oxo-7-phenyl-6,7,8,9-tetrahydro-6,9-methanooxepino[3,2-b]pyridine-8-carboxylate (8, 4.0 g) was suspended in methanol (30 mL) and treated with 25% sodium methoxide in methanol (30 mL) and the mixture was heated to 70° C. for 1 h. After completion, the solvent was removed under reduced pressure and crude was treated with ammonium chloride solution and extracted with ethyl acetate. The organic phase was separated, dried over sodium sulphate and concentrated under reduced pressure to afford rac-methyl (5aR,6S,7R,8aR)-3-chloro-8a-hydroxy-5a-(4-methoxyphenyl)-8-oxo-6-phenyl-5a,7,8,8a-tetrahydro-6H-cyclopenta[4,5]furo[3,2-b]pyridine-7-carboxylate (9, 2.8 g, crude).

Synthesis of rac-methyl (5aR,6S,7R,8R,8aS)-3-chloro-8,8a-dihydroxy-5a-(4-methoxyphenyl)-6-phenyl-5a,7,8,8a-tetrahydro-6H-cyclopenta[4,5]furo[3,2-b]pyridine-7-carboxylate (10)

The above crude compound (9, 2.8 g, 6.0 mmol) was added to a solution of sodium triacetoxyborohydride (8.9 g, 42.1 mmol) in acetonitrile (30 mL) and acetic acid (3.6 mL, 60.2 mmol) mixture, the resulting reaction mass was stirred for 4 h at room temperature. After completion, the reaction mixture was partitioned between saturated aqueous sodium bicarbonate solution (50 mL) and ethyl acetate (100 mL). The organic layer was separated, dried over sodium sulphate and concentrated under reduced pressure to get the crude. The crude was purified by silica gel column chromatography eluting with 50% ethyl acetate in hexanes. The desired fractions were concentrated to afford rac-methyl (5aR,6S,7R,8R,8aS)-3-chloro-8,8a-dihydroxy-5a-(4-methoxyphenyl)-6-phenyl-5a,7,8,8a-tetrahydro-6H-cyclopenta[4,5]furo[3,2-b]pyridine-7-carboxylate (10) as a yellow solid. Yield: 0.7 g, 25%; MS (ESI) m/z 468.11[M+1]$^+$

Synthesis of rac-(5aR,6S,7R,8R,8aS)-3-chloro-8,8a-dihydroxy-5a-(4-methoxyphenyl)-6-phenyl-5a, 7,8,8a-tetrahydro-6H-cyclopenta[4,5]furo[3,2-b]pyridine-7-carboxylic acid (11)

To a solution of rac-methyl (5aR,6S,7R,8R,8aS)-3-chloro-8,8a-dihydroxy-5a-(4-methoxyphenyl)-6-phenyl-5a,7,8,8a-tetrahydro-6H-cyclopenta[4,5]furo[3,2-b]pyridine-7-carboxylate (10, 0.7 g, 1.48 mmol) in methanol:water (3:1, 12 mL), lithium hydroxide (0.539 g, 22.48 mmol) was added and the reaction was stirred for 6 h at room temperature. After completion, the reaction mass was cooled to 0° C. and acidified with 1M hydrogen chloride to pH ~3. The solid precipitated was filtered and dried under vacuum to afford rac-(5aR,6S,7R,8R,8aS)-3-chloro-8,8a-dihydroxy-5a-(4-methoxyphenyl)-6-phenyl-5a,7,8,8a-tetrahydro-6H-cyclopenta[4,5]furo[3,2-b]pyridine-7-carboxylic acid (11) as an off-white solid. Yield: 0.4 g, 58.9%; MS (ESI) m/z 452.11 [M−1]$^-$.

Synthesis of (5aR,6S,7R,8R,8aS)-3-chloro-8,8a-dihydroxy-5a-(4-methoxyphenyl)-N,N-dimethyl-6-phenyl-5a,7,8,8a-tetrahydro-6H-cyclopenta[4,5]furo[3,2-b]pyridine-7-carboxamide (Cpd. No. 5F)

To a solution of rac-(5aR,6S,7R,8R,8aS)-3-chloro-8,8a-dihydroxy-5a-(4-methoxyphenyl)-6-phenyl-5a,7,8,8a-tetrahydro-6H-cyclopenta[4,5]furo[3,2-b]pyridine-7-carboxylic acid (11, 0.4 g, 0.88 mmol) in dichloromethane (30 mL), 1-ethyl-3-(3-dimethylaminopropyl)carbodiimide (0.508 g, 2.6 mmol), hydroxybenzotriazole (0.35 g, 2.6 mmol) and N,N-diisopropylethylamine (0.9 mL, 5.29 mmol) were added at 0° C. and stirred the mixture for 5 min. Dimethylamine-hydrogen chloride (0.357 g, 4.41 mmol) was then added at same temperature and the reaction was stirred for 12 h at room temperature. After completion, reaction mass was diluted with dichloromethane (25 mL) and washed with cold water. The organic layer was separated and dried over sodium sulphate, filtered and concentrated to give crude compound. The crude was purified by silica gel column chromatography eluting with 70-90% ethyl acetate in hexanes to afford rac-(5aR,6S,7R,8R,8aS)-3-chloro-8,8a-dihydroxy-5a-(4-methoxyphenyl)-N,N-dimethyl-6-phenyl-5a,7,8,8a-tetrahydro-6H-cyclopenta[4,5]furo[3,2-b]pyridine-7-carboxamide (rac-Cpd. No. 5F) as a white solid. The enantiomers were separated using chiralpak IB (4.6×250) mm column. Yield: 100 mg, 23.5%; Peak 1 (Cpd. No. 5F, 30 mg), $[\alpha]_D$−179.0° (c 0.1, $CHCl_3$), $R_t$=6.87 min, ee >99%; MS (ESI) m/z 481.33[M+1]$^+$; UPLC: 99.92%; $^1$H NMR (400 MHz, DMSO-$d_6$) δ 8.18 (d, J=2.0 Hz, 1H), 7.68 (d, J=2.0 Hz, 1H), 7.04-7.02 (m, 4H), 6.95 (t, J=7.6 Hz, 1H), 6.89 (d, J=7.6 Hz, 2H), 6.61 (d, J=8.8 Hz, 2H), 5.87 (s, 1H), 5.22 (d, J=5.6 Hz, 1H), 4.75 (t, J=5.6 Hz, 1H), 4.48 (d, J=13.2 Hz, 1H), 4.19 (dd, J=13.2, 6.0 Hz, 1H), 3.60 (s, 3H), 3.25 (s, 3H), 2.76 (s, 3H). Peak-2 (50 mg), $[\alpha]_D$+180.0° (c 0.1, $CHCl_3$), $R_t$=12.16 min, ee >99%; MS (ESI) m/z 481.33 [M+1]$^+$; UPLC: 99.26%; $^1$H NMR (400 MHz, DMSO-$d_6$) δ 8.18 (d, J=2.0 Hz, 1H), 7.68 (d, J=2.0 Hz, 1H), 7.04-7.02 (m, 4H), 6.95 (t, J=7.4 Hz, 1H), 6.89 (d, J=7.6 Hz, 2H), 6.61 (d, J=8.8 Hz, 2H), 5.88 (s, 1H), 5.22 (d, J=5.5 Hz, 1H), 4.75 (t, J=5.6 Hz, 1H), 4.48 (d, J=13.6 Hz, 1H), 4.18 (dd, J=13.6, 5.6 Hz, 1H), 3.60 (s, 3H), 3.25 (s, 3H), 2.76 (s, 3H).

Example 6

(5aR,6S,7R,8R,8aS)-5a-(4-cyanophenyl)-8,8a-dihydroxy-3-methoxy-N,N-dimethyl-6-phenyl-5a,7,8,8a-tetrahydro-6H-cyclopenta[4,5]furo[3,2-b]pyridine-7-carboxamide (Cpd. No. 6F)

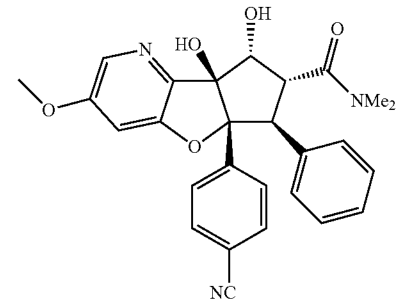

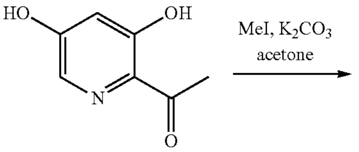

1

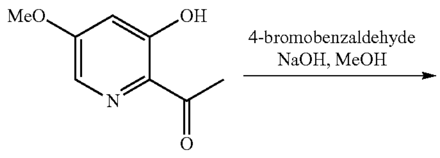

2

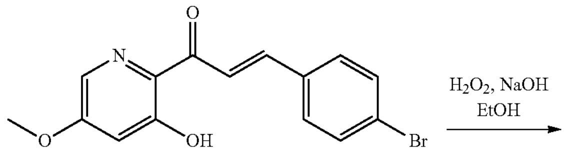

3

-continued

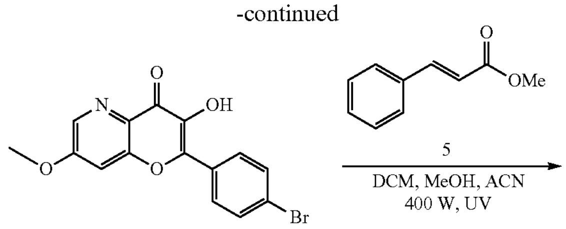

4

5

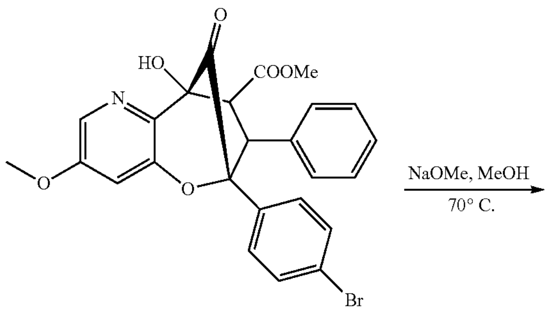

6

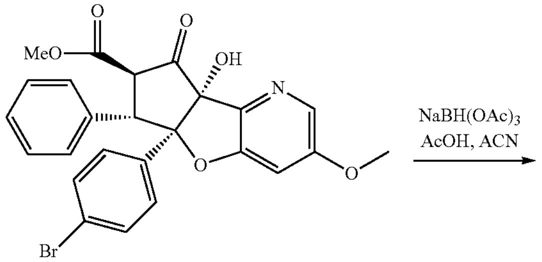

7

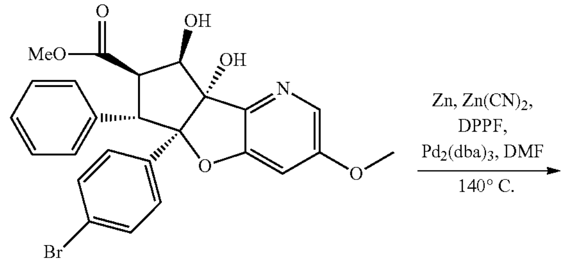

8

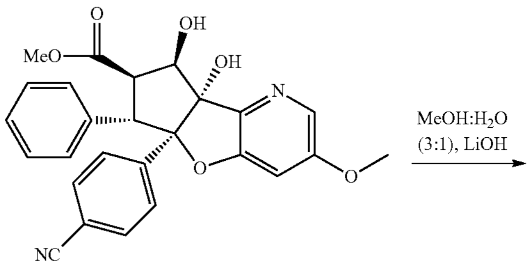

9

-continued

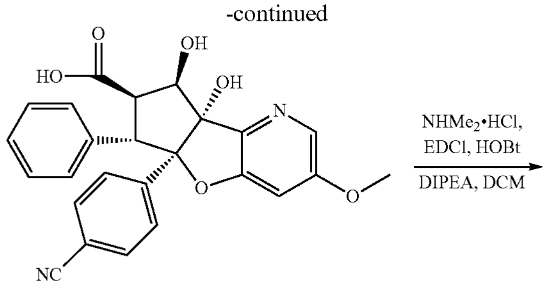

10

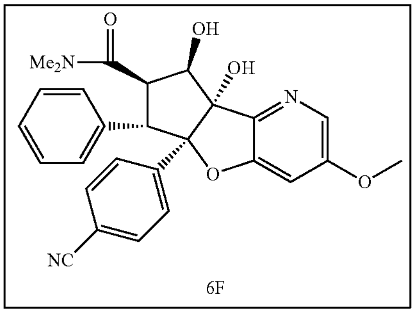

6F

Synthesis of 1-(3-hydroxy-5-methoxypyridin-2-yl) ethan-1-one (2)

To a solution of 1-(3,5-dihydroxypyridin-2-yl)ethan-1-one (1, 14.0 g, 92.2 mmol) in acetone (50 mL) potassium carbonate (12.7 g, 276.3 mmol) was added under nitrogen atmosphere. Methyl iodide (13.07 g, 92.10 mmol) was added to the above suspension and the reaction was stirred for 6 h at room temperature. After completion, volatiles were removed and the crude residue was dissolved in ethyl acetate (100 mL) and washed with water (2×50 mL) and brine solution (50 mL). The organic layer was separated and dried over anhydrous sodium sulfate. The crude was triturated with pentane. The precipitated solid which was filtered and dried under vacuum to afford 1-(3-hydroxy-5-methoxypyridin-2-yl)ethan-1-one (2) as a brownish solid. Yield: 8.0 g, 52%.

Synthesis of (E)-3-(4-bromophenyl)-1-(3-hydroxy-5-methoxypyridin-2-yl)prop-2-en-1-one (3)

To a solution of 1-(3-hydroxy-5-methoxypyridin-2-yl) ethan-1-one (2, 8.0 g, 47.8 mmol) and sodium hydroxide (5.74 g, 143.6 mmol) in methanol (120 mL), 4-bromobenzaldehyde (8.85 g, 47.8 mmol) was added and the mixture was heated to reflux for 2 h. After completion, the reaction mass was cooled and the solid obtained was filtered, washed with water and dried under vacuum to afford of (E)-3-(4-bromophenyl)-1-(3-hydroxy-5-methoxypyridin-2-yl)prop-2-en-1-one (3) as a yellow solid. Yield: 14.0 g, 87.7%; MS (ESI) m/z 334.01[M+1]$^+$.

Synthesis of 2-(4-bromophenyl)-3-hydroxy-7-methoxy-4H-pyrano[3,2-b]pyridin-4-one (4)

To a solution of (E)-3-(4-bromophenyl)-1-(3-hydroxy-5-methoxypyridin-2-yl)prop-2-en-1-one (3, 14.0 g, 36.3 mmol) and sodium hydroxide (11.73 g, 126.1 mmol) in ethanol (200 mL) hydrogen peroxide (23.25 mL, 126.1 mmol) was added at room temperature. The reaction mass was stirred for 1 h (exotherm was observed). After completion, reaction mass was cooled and neutralized to pH ~7 by addition of 6M hydrogen chloride. The precipitated solid was filtered and dried under vacuum to afford 2-(4-bromophenyl)-3-hydroxy-7-methoxy-4H-pyrano[3,2-b]pyridin-4-one (4) as a pale yellow solid. Yield: 12.0 g, 82.53%; MS (ESI) m/z 348.05$[M+1]^+$.

Synthesis of rac-methyl (7S,8S,9R)-6-(4-bromophenyl)-9-hydroxy-3-methoxy-10-oxo-7-phenyl-6,7,8,9-tetrahydro-6,9-methanooxepino[3,2-b]pyridine-8-carboxylate (6)

A solution of 2-(4-bromophenyl)-3-hydroxy-7-methoxy-4H-pyrano[3,2-b]pyridin-4-one (4, 6.0 g, 17.24 mmol) and methyl cinnamate (5, 27.9 g, 172.4 mmol) in dichloromethane (200 mL), acetonitrile (100 mL) and methanol (100 mL) was placed in a UV reactor flask. The reaction mixture was irradiated under 400 watts UV light for 15 h. After completion, the solvent was removed under reduced pressure and the residue was purified over a plug of silica gel eluting the compound with ethyl acetate. The desired fractions were concentrated under reduced pressure to afford rac-methyl (7S,8S,9R)-6-(4-bromophenyl)-9-hydroxy-3-methoxy-10-oxo-7-phenyl-6,7,8,9-tetrahydro-6,9-methanooxepino[3,2-b]pyridine-8-carboxylate (6, 3.5 g, crude).

Synthesis of rac-methyl (5aR,6S,7R,8aR)-5a-(4-bromophenyl)-8a-hydroxy-3-methoxy-8-oxo-6-phenyl-5a,7,8,8a-tetrahydro-6H-cyclopenta[4,5]furo[3,2-b]pyridine-7-carboxylate (7)

The crude compound rac-methyl (7S,8S,9R)-6-(4-bromophenyl)-9-hydroxy-3-methoxy-10-oxo-7-phenyl-6,7,8,9-tetrahydro-6,9-methanooxepino[3,2-b]pyridine-8-carboxylate (6, 3.5 g) was suspended in methanol (20 mL) and treated with 25% sodium methoxide in methanol (20 mL) and heated the mixture to 70° C. for 1 h. After completion, the solvent was removed under reduced pressure and crude was treated with ammonium chloride solution and extracted with ethyl acetate. The organic phase was separated, dried over sodium sulphate and concentrated under reduced pressure to rac-methyl (5aR,6S,7R,8aR)-5a-(4-bromophenyl)-8a-hydroxy-3-methoxy-8-oxo-6-phenyl-5a,7,8,8a-tetrahydro-6H-cyclopenta[4,5]furo[3,2-b]pyridine-7-carboxylate (7, 3.5 g, crude).

Synthesis of rac-methyl (5aR,6S,7R,8R,8aS)-5a-(4-bromophenyl)-8,8a-dihydroxy-3-methoxy-6-phenyl-5a, 7,8,8a-tetrahydro-6H-cyclopenta[4,5]furo[3,2-b]pyridine-7-carboxylate (8)

The above crude compound (7, 3.5 g, 7.6 mmol) was charged to a solution of sodium triacetoxyborohydride (9.72 g, 4.58 mmol) in acetonitrile (30 mL) and acetic acid (4.57 mL, 60.2 mmol) and the resulting mixture was stirred for 4 h at room temperature. After completion, reaction mixture was partitioned between saturated aqueous sodium bicarbonate solution and ethyl acetate. The organic layer was separated, dried over sodium sulphate and concentrated under reduced pressure to get the crude. The crude was purified by silica gel column chromatography eluting with 50% ethyl acetate in hexanes. The desired fractions were concentrated to afford rac-methyl (5aR,6S,7R,8R,8aS)-5a-(4-bromophenyl)-8,8a-dihydroxy-3-methoxy-6-phenyl-5a, 7,8,8a-tetrahydro-6H-cyclopenta[4,5]furo[3,2-b]pyridine-7-carboxylate (8) as pale yellow solid. Yield: 0.8 g, 23.5%; MS (ESI) m/z 510.03$[M-1]^-$.

Synthesis of rac-methyl (5aR,6S,7R,8R,8aS)-5a-(4-cyanophenyl)-8,8a-dihydroxy-3-methoxy-6-phenyl-5a, 7,8,8a-tetrahydro-6H-cyclopenta[4,5]furo[3,2-b]pyridine-7-carboxylate (9)

To a mixture of rac-methyl (5aR,6S,7R,8R,8aS)-5a-(4-bromophenyl)-8,8a-dihydroxy-3-methoxy-6-phenyl-5a,7,8,8a-tetrahydro-6H-cyclopenta[4,5]furo[3,2-b]pyridine-7-carboxylate (8, 0.8 g, 1.56 mmol) in dimethylformamide at room temperature, zinc cyanide (1.123 g, 9.59 mmol) and zinc (0.022 g, 0.18 mmol) were added and degassed the mixture with argon for 15 min. 1,1'-Bis(diphenylphosphino) ferrocene (0.041 g, 0.313 mmol) and tris(dibenzylideneacetone)dipalladium (0.078 g, 0.470 mmol) were added to the above reaction and mixture was degassed with argon for 5 min and then heated at 140° C. for 2 h. After completion, the reaction was cooled to room temperature and passed through a bed of celite. The filtrate was concentrated and treated with ice-cold water. The precipitated solid was filtered and the crude product was triturated with n-pentane. The solid was filtered and dried under vacuum to afford rac-methyl (5aR, 6S,7R,8R,8aS)-5a-(4-cyanophenyl)-8,8a-dihydroxy-3-methoxy-6-phenyl-5a,7,8,8a-tetrahydro-6H-cyclopenta[4,5]furo[3,2-b]pyridine-7-carboxylate (9) as a brown solid. Yield: 0.75 g, crude; MS (ESI) m/z 459.35$[M+1]^+$.

Synthesis of rac-(5aR,6S,7R,8R,8aS)-5a-(4-cyanophenyl)-8,8a-dihydroxy-3-methoxy-6-phenyl-5a, 7,8,8a-tetrahydro-6H-cyclopenta[4,5]furo[3,2-b]pyridine-7-carboxylic acid (10)

To a solution of rac-methyl (5aR,6S,7R,8R,8aS)-5a-(4-cyanophenyl)-8,8a-dihydroxy-3-methoxy-6-phenyl-5a,7,8,8a-tetrahydro-6H-cyclopenta[4,5]furo[3,2-b]pyridine-7-carboxylate (9, 0.75 g, 1.63 mmol) in methanol:water (3:1, 12 mL), lithium hydroxide (0.411 g, 9.81 mmol) was added and the reaction was stirred for 6 h at room temperature. After completion, the reaction mass was cooled to 0° C. and acidified with 1M citric acid to pH ~5. The precipitated solid was filtered and dried under vacuum to afford rac-(5aR,6S, 7R,8R,8aS)-5a-(4-cyanophenyl)-8,8a-dihydroxy-3-methoxy-6-phenyl-5a,7,8,8a-tetrahydro-6H-cyclopenta[4,5]furo[3,2-b]pyridine-7-carboxylic acid (10) as an off-white solid. Yield: 0.6 g, crude; MS (ESI) m/z 445.35$[M+1]^+$.

Synthesis of (5aR,6S,7R,8R,8aS)-5a-(4-cyanophenyl)-8,8a-dihydroxy-3-methoxy-N,N-dimethyl-6-phenyl-5a, 7,8,8a-tetrahydro-6H-cyclopenta[4,5]furo[3,2-b]pyridine-7-carboxamide (Cpd. No. 6F)

To a solution of rac-(5aR,6S,7R,8R,8aS)-5a-(4-cyanophenyl)-8,8a-dihydroxy-3-methoxy-6-phenyl-5a,7,8,8a-tetrahydro-6H-cyclopenta[4,5]furo[3,2-b]pyridine-7-carboxylic acid (10, 0.6 g, 1.35 mmol) in dichloromethane (30 mL), 1-ethyl-3-(3-dimethylaminopropyl)carbodiimide (0.77 g, 4.05 mmol), hydroxybenzotriazole (0.54 g, 4.05 mmol) and N,N-diisopropylethylamine (1.04 g, 8.10 mmol) were added at 0° C. and the mixture was stirred for 5 min. Dimethylamine hydrochloride (0.55 g, 6.75 mmol) was then added and the reaction mixture was stirred for 12 h at room temperature. After completion, reaction mass was diluted with dichloromethane and washed with cold water. The organic layer was dried over sodium sulphate, filtered and concentrated to give crude. The crude was purified by reverse phase prep HPLC to afford rac-(5aR,6S,7R,8R,8aS)-5a-(4-cyanophenyl)-8,8a-dihydroxy-3-methoxy-N,N-dimethyl-6-phenyl-5a,7,8,8a-tetrahydro-6H-cyclopenta[4,5]

furo[3,2-b]pyridine-7-carboxamide (rac-Cpd. No. 6F) as a white solid. The enantiomers were separated by chiral preparative HPLC [chiralpak IB (4.6×250) mm]. Yield: 110 mg, 17%; Peak 1 (Cpd. No. 6F, 54 mg), $[\alpha]_D$−106° (c 0.1, $CHCl_3$), $R_t$=6.86 min, ee >99%; MS (ESI) m/z 472.37[M+1]$^+$; UPLC: 96.33%; $^1H$ NMR (400 MHz, DMSO-d6) S 7.9 (d, J=2.0 Hz, 1H), 7.50 (d, J=8.5 Hz, 2H), 7.34 (d, J=8.5 Hz, 2H), 7.21 (d, J=2.4 Hz, 1H), 7.05 (s, 1H), 7.02 (d, J=7.5 Hz, 1H), 6.96 (d, J=7.2 Hz, 1H), 6.90 (d, J=7.4 Hz, 2H), 5.88 (s, 1H), 5.16 (brs, 1H), 4.77 (brs, 1H), 4.54 (d, J=13.2 Hz, 1H), 4.25 (dd, J=13.2, 5.8 Hz, 1H), 3.86 (s, 3H), 3.26 (s, 3H), 2.77 (s, 3H). Peak 2 (45 mg), $[\alpha]_D$+147.1° (c 0.1, $CHCl_3$), $R_t$=12.85 min, ee >99%; MS (ESI) m/z 472.37[M+1]$^+$; UPLC: 99.95%; $^1H$ NMR (400 MHz, DMSO-d6) δ 7.9 (d, J=2.4 Hz, 1H), 7.52 (d, J=8.6 Hz, 2H), 7.35 (d, J=8.4 Hz, 2H), 7.22 (d, J=2.2 Hz, 1H), 7.05 (s, 1H), 7.03 (d, J=7.6 Hz, 1H), 6.97 (d, J=7.2 Hz, 1H), 6.91 (d, J=7.4 Hz, 2H), 5.88 (s, 1H), 5.17 (brs, 1H), 4.78 (d, J=5.6 Hz, 1H), 4.55 (d, J=13.2 Hz, 1H), 4.27 (dd, J=13.2, 5.6 Hz 1H), 3.86 (s, 3H), 3.26 (s, 3H), 2.77 (s, 3H).

Example 7

(5aR,6S,7R,8R,8aS)-3-chloro-8,8a-dihydroxy-N,N-dimethyl-6-phenyl-5a-(p-tolyl)-5a,7,8,8a-tetrahydro-6H-cyclopenta[4,5]furo[3,2-b]pyridine-7-carboxamide (Cpd. No. 7F)

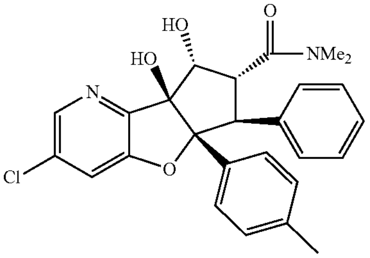

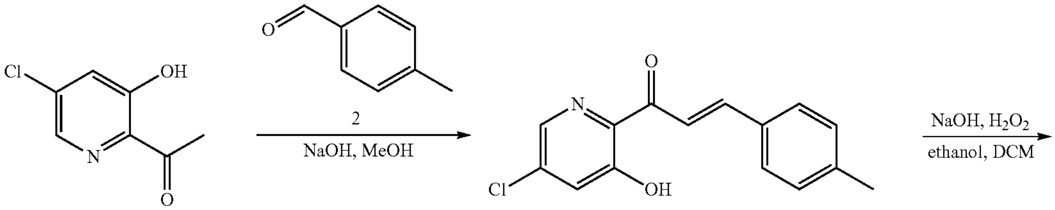

1

3

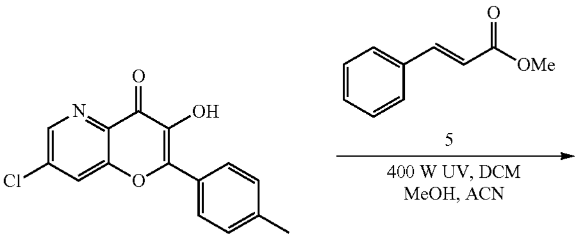

4

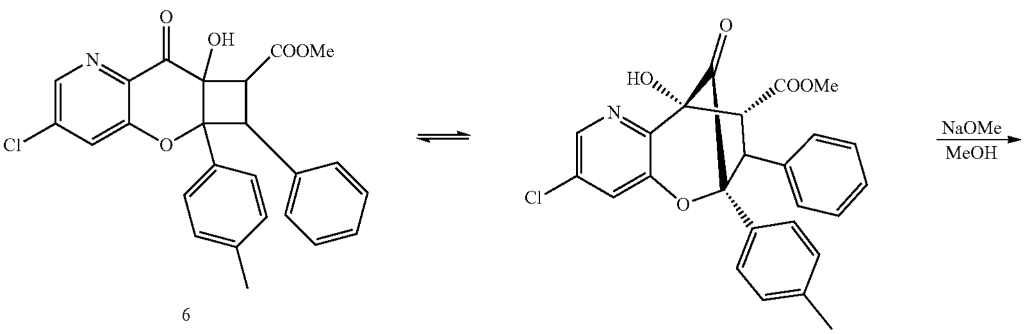

6

6a

-continued

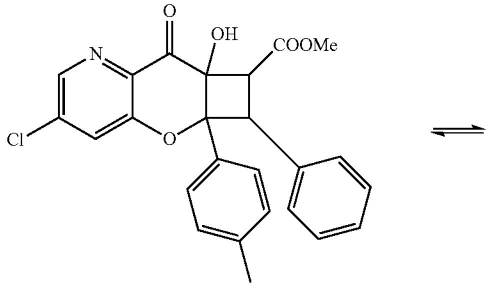

6

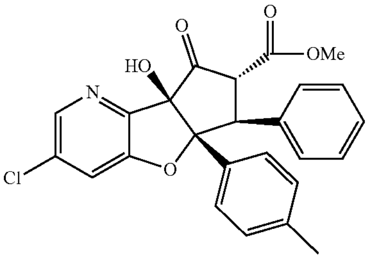

7

NaBH(OAc)$_3$,
AcOH, ACN

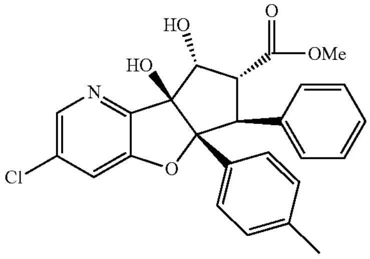

8

LiOH, THF
$H_2O$

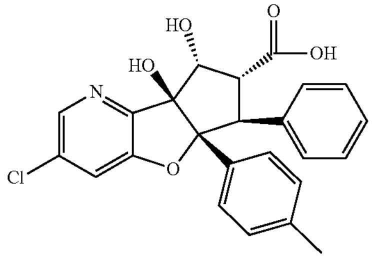

9

$NHMe_2$•HCl, EDCl
HOBt, DIPEA DCM

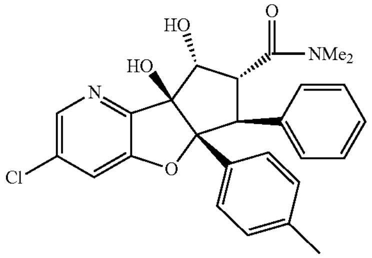

7F

Synthesis of (E)-1-(5-chloro-3-hydroxypyridin-2-yl)-3-(p-tolyl)prop-2-en-1-one (3)

To a solution of 1-(5-chloro-3-hydroxypyridin-2-yl) ethan-1-one (1, 6.0 g, 34.9 mmol) in methanol (30 mL), sodium hydroxide (4.19 g, 104.9 mmol) and 4-methylbenzaldehyde (2, 4.19 g, 34.9 mmol) were added. The reaction mixture was heated at 85° C. for 2 h. After completion, reaction mass was cooled and obtained solid was filtered, washed with water and dried under vacuum to afford of (E)-1-(5-chloro-3-hydroxypyridin-2-yl)-3-(p-tolyl)prop-2-en-1-one (3) as yellow solid. Yield: 5.0 g, 52.08%; MS (ESI) m/z 274.13[M+1]$^+$.

Synthesis of 7-chloro-3-hydroxy-2-(p-tolyl)-4H-pyrano[3,2-b]pyridin-4-one (4)

To a solution of (E)-1-(5-chloro-3-hydroxypyridin-2-yl)-3-(p-tolyl)prop-2-en-1-one (3, 5.0 g, 18.3 mmol) in ethanol/dichloromethane (1:1, 20 mL), sodium hydroxide (6.45 g, 161.15 mmol) was added followed by addition of 30% hydrogen peroxide (4.8 mL, 161.15 mmol) at room temperature. The reaction mass was stirred for 1 h (exotherm was observed). After completion, reaction mass was cooled and neutralized by addition of 6 M hydrogen chloride. The precipitated solid was filtered and dried under vacuum to afford 7-chloro-3-hydroxy-2-(p-tolyl)-4H-pyrano[3,2-b]pyridin-4-one (4) as brown solid. Yield: 1.66 g, 25%; MS (ESI) m/z 288.14[M+1]$^+$.

Synthesis of rac-methyl 3-chloro-7a-hydroxy-8-oxo-6-phenyl-5a-(p-tolyl)-5a,6,7a,8-tetrahydro-7H-cyclobuta[5,6]pyrano[3,2-b]pyridine-7-carboxylate (6/6a)

A solution of 7-chloro-3-hydroxy-2-(p-tolyl)-4H-pyrano[3,2-b]pyridin-4-one (4, 1.3 g, 4.5 mmol) and methyl cinnamate (5, 6.99 g, 45.1 mmol) in dichloromethane (200 mL), acetonitrile (100 mL) and methanol (100 mL) was placed in a UV reactor flask. The reaction mixture was irradiated for 15 h under 400 watts UV light. After completion, the solvent was removed under reduced pressure and the residue was purified by Combi-flash (12 g, RediSep column) using ethyl acetate as eluent. The desired fractions were concentrated under reduced pressure to afford rac-methyl 3-chloro-7a-hydroxy-8-oxo-6-phenyl-5a-(p-tolyl)-5a,6,7a,8-tetrahydro-7H-cyclobuta[5,6]pyrano[3,2-b]pyridine-7-carboxylate (6/6a). Yield: 1.1 g, crude.

Synthesis of rac-methyl (5aR,6S,7R,8aR)-3-chloro-8a-hydroxy-8-oxo-6-phenyl-5a-(p-tolyl)-5a,7,8,8a-tetrahydro-6H-cyclopenta[4,5]furo[3,2-b]pyridine-7-carboxylate (7)

The crude rac-methyl 3-chloro-7a-hydroxy-8-oxo-6-phenyl-5a-(p-tolyl)-5a,6,7a,8-tetrahydro-7H-cyclobuta[5,6]pyrano[3,2-b]pyridine-7-carboxylate (6, 1.1 g) was suspended in methanol (10 mL) and sodium methoxide (25% in methanol, 10 mL) was added. The reaction mixture was heated to 90° C. for 1 h. After completion, the solvent was removed under reduced pressure and the reaction was quenched with ammonium chloride solution and extracted with ethyl acetate. The organic phase was separated, dried over anhydrous sodium sulphate and concentrated under reduced pressure to afford rac-methyl (5aR,6S,7R,8aR)-3-chloro-8a-hydroxy-8-oxo-6-phenyl-5a-(p-tolyl)-5a,7,8,8a-tetrahydro-6H-cyclopenta[4,5]furo[3,2-b]pyridine-7-carboxylate (7). Yield: 0.9 g; crude.

Synthesis of rac-methyl (5aR,6S,7R,8R,8aS)-3-chloro-8,8a-dihydroxy-6-phenyl-5a-(p-tolyl)-5a,7,8,8a-tetrahydro-6H-cyclopenta[4,5]furo[3,2-b]pyridine-7-carboxylate (8)

To a solution of rac-methyl (5aR,6S,7R,8aR)-3-chloro-8a-hydroxy-8-oxo-6-phenyl-5a-(p-tolyl)-5a,7,8,8a-tetrahydro-6H-cyclopenta[4,5]furo[3,2-b]pyridine-7-carboxylate (7, 0.9 g) in acetonitrile (10 mL), sodium triacetoxyborohydride (2.54 g, 11.9 mmol) and acetic acid (1.1 mL, 20.0 mmol) were added. The resulting mixture was stirred for 16 h at room temperature. After completion, reaction mixture was partitioned between saturated aqueous sodium bicarbonate solution and ethyl acetate. The organic layer was separated, dried over anhydrous sodium sulphate and concentrated under reduced pressure to get the crude. The crude was purified by Combi-flash (4 g, RediSep column) using 70% ethyl acetate in hexanes as eluent. The desired fractions were concentrated to afford rac-methyl (5aR,6S,7R,8R,8aS)-3-chloro-8,8a-dihydroxy-6-phenyl-5a-(p-tolyl)-5a,7,8,8a-tetrahydro-6H-cyclopenta[4,5]furo[3,2-b]pyridine-7-carboxylate (8) as light yellow solid. Yield: 0.25 g, 27%; MS (ESI) m/z 452.33[M+1]$^+$.

Synthesis of rac-(5aR,6S,7R,8R,8aS)-3-chloro-8,8a-dihydroxy-6-phenyl-5a-(p-tolyl)-5a, 7,8,8a-tetrahydro-6H-cyclopenta[4,5]furo[3,2-b]pyridine-7-carboxylic acid (9)

To a solution of rac-methyl (5aR,6S,7R,8R,8aS)-3-chloro-8,8a-dihydroxy-6-phenyl-5a-(p-tolyl)-5a,7,8,8a-tetrahydro-6H-cyclopenta[4,5]furo[3,2-b]pyridine-7-carboxylate (8, 0.25 g, 0.55 mmol) in tetrahydrofuran and water (3:1, 4.0 mL), lithium hydroxide (0.26 g, 11.0 mmol) was added and the reaction was stirred for 6 h at room temperature. After completion, the reaction mass was cooled to 0° C. and acidified with 1M hydrogen chloride to pH ~3. The precipitated solid was filtered and washed with water and dried under vacuum to afford rac-(5aR,6S,7R,8R,8aS)-3-chloro-8,8a-dihydroxy-6-phenyl-5a-(p-tolyl)-5a,7,8,8a-tetrahydro-6H-cyclopenta[4,5]furo[3,2-b]pyridine-7-carboxylic acid (9) as yellow solid. Yield: 0.13 g, 54.0%; MS (ESI) m/z 438.32[M+1]$^+$.

Synthesis of (5aR,6S,7R,8R,8aS)-3-chloro-8,8a-dihydroxy-N,N-dimethyl-6-phenyl-5a-(p-tolyl)-5a,7,8,8a-tetrahydro-6H-cyclopenta[4,5]furo[3,2-b]pyridine-7-carboxamide (Cpd. No. 7F)

To a solution of rac-(5aR,6S,7R,8R,8aS)-3-chloro-8,8a-dihydroxy-6-phenyl-5a-(p-tolyl)-5a,7,8,8a-tetrahydro-6H-cyclopenta[4,5]furo[3,2-b]pyridine-7-carboxylic acid (9, 0.13 g, 29.7 mmol) in dichloromethane (5.0 mL), 1-ethyl-3-(3-dimethylaminopropyl)carbodiimide hydrochloride (0.046 g, 0.50 mmol), 1-hydroxybenzotriazole (0.067 g, 0.49 mmol) and N,N-diisopropylethylamine (0.15 mL, 0.49 mmol) were added at 0° C. and stirred the mixture for 5 min. Dimethylamine hydrochloride (0.032 g, 0.34 mmol) was then added at same temperature and the mixture was stirred at room temperature for 16 h. After completion, reaction mass was diluted with dichloromethane and washed with cold water. The organic layer was separated and dried over sodium sulphate, filtered and concentrated to give crude. The crude was purified by Combi-flash (4 g, RediSep column) using 70% ethyl acetate in hexanes as eluent. The desired fractions were concentrated under reduced pressure to afford rac-(5aR,6S,7R,8R,8aS)-3-chloro-8,8a-dihydroxy-N,N-dimethyl-6-phenyl-5a-(p-tolyl)-5a,7,8,8a-tetrahydro-6H-cyclopenta[4,5]furo[3,2-b]pyridine-7-carboxamide (rac-Cpd. No. 7F) as white solid. Yield: 0.07 mg, 50%, MS (ESI) m/z 465.32[M+1]$^+$. The enantiomers were separated by chiral preparative HPLC [chiralpak IB (4.6×250) mm]. Peak 1 (13 mg); $[\alpha]_D$+212.0° (c 0.1, $CHCl_3$); $R_t$=10.18 min, ee >95%; MS (ESI) m/z 465.32[M+1]$^+$; UPLC 97.1%; $^1$H NMR (400 MHz, DMSO-$d_6$) δ 8.18 (d, J=2.0 Hz, 1H), 7.69 (d, J=2.0 Hz, 1H), 7.11-6.94 (m, 5H), 6.90 (d, J=8.2 Hz, 2H), 6.86 (d, J=8.2 Hz, 2H), 5.88 (s, 1H), 5.23 (t, J=5.5, 1H), 4.77 (t, J=5.6 Hz, 1H), 4.51 (d, J=13.2 Hz, 1H), 4.23-4.18 (dd, J=13.2, 5.6 Hz, 1H), 3.25 (s, 3H), 2.76 (s, 3H), 2.11 (s, 3H). Peak-2 (Cpd. No. 7F, 9 mg); $[\alpha]_D$−191.1° (c 0.1, $CHCl_3$); $R_t$=22.4 min, ee >99%; MS (ESI) m/z 465.32[M+1]$^+$; UPLC 99.8%; $^1$H NMR (400 MHz, DMSO-$d_6$) δ 8.18 (d, J=2.0 Hz, 1H), 7.69 (d, J=2.0 Hz, 1H), 7.03-6.94 (m, 5H), 6.90 (d, J=8.2 Hz, 2H), 6.86 (d, J=8.2 Hz, 2H), 5.88 (s, 1H), 5.23 (d, J=5.6, 1H), 4.77 (t, J=5.6 Hz, 1H), 4.50 (d, J=13.2 Hz, 1H), 4.23-4.18 (dd, J=13.2, 5.6 Hz, 1H), 3.25 (s, 3H), 2.76 (s, 3H), 2.11 (s, 3H).

Example 8

(5aR,6S,7R,8R,8aS)-3-chloro-8,8a-dihydroxy-N,N-dimethyl-6-phenyl-5a-(4-(trifluoromethyl)phenyl)-5a,7,8,8a-tetrahydro-6H-cyclopenta[4,5]furo[3,2-b]pyridine-7-carboxamide (Cpd. No. 8F)

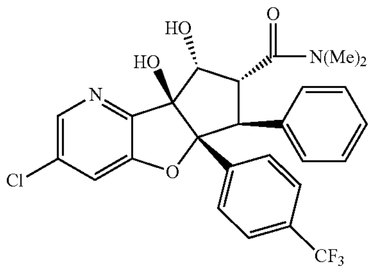

-continued
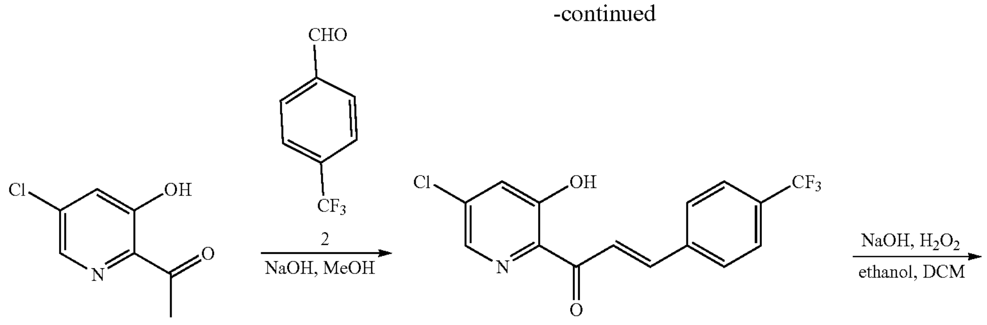
2
1 3
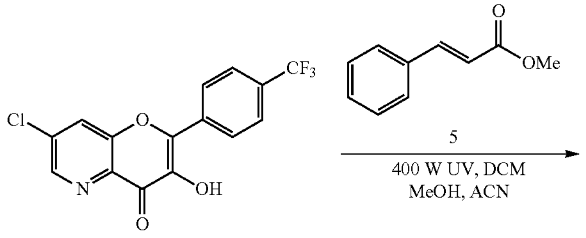
5
4
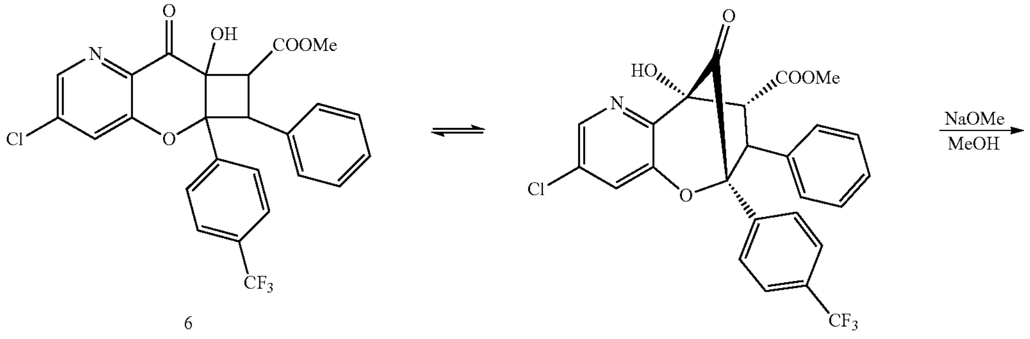
6 6a
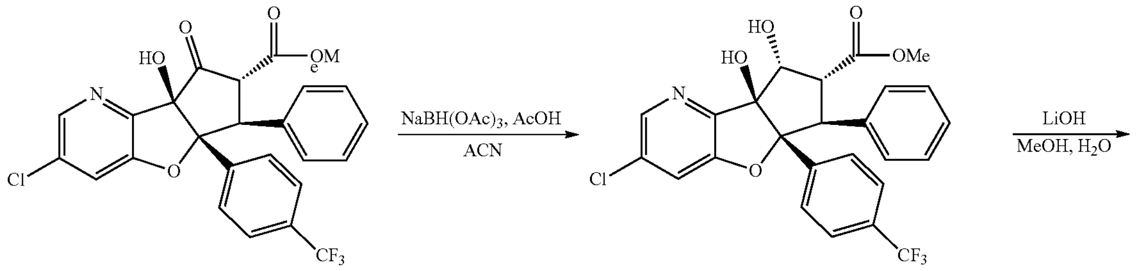
7 8
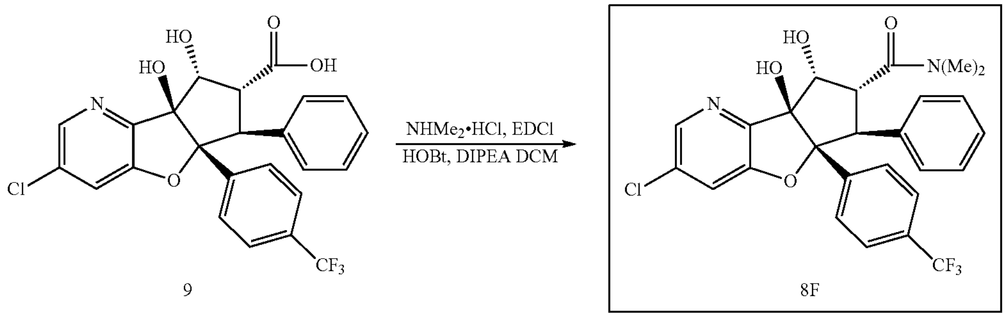
9 8F Synthesis of (E)-1-(5-chloro-3-hydroxypyridin-2-yl)-3-(4-(trifluoromethyl)phenyl)prop-2-en-1-one (3)

To a solution of 1-(5-chloro-3-hydroxypyridin-2-yl)ethan-1-one (1, 6.0 g, 35.08 mmol) in methanol (20 mL), sodium hydroxide (4.2 g, 105.24 mmol) and 4-(trifluoromethyl)benzaldehyde (2, 6.1 g, 35.8 mmol) were added. The reaction mixture was heated at 90° C. for 1 h. After completion, reaction mass was cooled and precipitated solid was filtered, washed with water and dried under vacuum to afford of (E)-1-(5-chloro-3-hydroxypyridin-2-yl)-3-(4-(trifluoromethyl)phenyl)prop-2-en-1-one (3) as yellow solid. Yield: 6.0 g, 55%; MS (ESI) m/z 328.26[M+1]$^+$.

Synthesis of 7-chloro-3-hydroxy-2-(4-(trifluoromethyl)phenyl)-4H-pyrano[3,2-b]pyridin-4-one (4)

To a solution of (E)-1-(5-chloro-3-hydroxypyridin-2-yl)-3-(4-(trifluoromethyl)phenyl)prop-2-en-1-one (3, 6.0 g, 18.3 mmol) in ethanol/dichloromethane (1:1, 200 mL), 10% sodium hydroxide (50.1 mL, 128.4 mmol) was added followed by addition of 30% hydrogen peroxide (12.5 mL, 128.4 mmol) at room temperature. The reaction mass was stirred for 30 min (exotherm was observed). After completion, reaction mass was cooled and neutralized with 6 M hydrogen chloride to pH ~7, then dichloromethane was distilled off and precipitated solid was filtered and washed with ethanol and n-pentane. Solid dried under vacuum to afford 7-chloro-3-hydroxy-2-(4-(trifluoromethyl)phenyl)-4H-pyrano[3,2-b]pyridin-4-one (4) as light orange solid. Yield: 3.5 g, 56%; MS (ESI) m/z 342.06[M+1]$^+$.

Synthesis of rac-methyl (6R,7S,8S,9R)-3-chloro-9-hydroxy-10-oxo-7-phenyl-6-(4-(trifluoromethyl)phenyl)-6,7,8,9-tetrahydro-6,9-methanooxepino[3,2-b]pyridine-8-carboxylate (6/6a)

A solution of 7-chloro-3-hydroxy-2-(4-(trifluoromethyl)phenyl)-4H-pyrano[3,2-b]pyridin-4-one (4, 3.0 g, 8.79 mmol) and methyl cinnamate (5, 14.2 g, 87.9 mmol) in dichloromethane (200 mL), acetonitrile (100 mL) and methanol (100 mL) was placed in a UV reactor flask. The reaction mixture was irradiated for 24 h under 400 watts UV light. After completion, the solvent was removed under reduced pressure and the residue was purified by Combiflash (24 g RediSep column) using ethyl acetate as eluent. The desired fractions were concentrated under reduced pressure to afford rac-methyl (6R,7S,8S,9R)-3-chloro-9-hydroxy-10-oxo-7-phenyl-6-(4-(trifluoromethyl)phenyl)-6,7,8,9-tetrahydro-6,9-methanooxepino[3,2-b]pyridine-8-carboxylate (6/6a) as brown sticky solid. Yield: 3.0 g, crude; MS (ESI) m/z 504.39[M+1]$^+$.

Synthesis of rac-methyl (5aR,6S,7R,8aR)-3-chloro-8a-hydroxy-8-oxo-6-phenyl-5a-(4-(trifluoromethyl)phenyl)-5a, 7,8,8a-tetrahydro-6H-cyclopenta[4,5]furo[3,2-b]pyridine-7-carboxylate (7)

The crude rac-methyl (6R,7S,8S,9R)-3-chloro-9-hydroxy-10-oxo-7-phenyl-6-(4-(trifluoromethyl)phenyl)-6,7,8,9-tetrahydro-6,9-methanooxepino[3,2-b]pyridine-8-carboxylate (6/6a, 3.0 g, 5.96 mmol) was suspended in methanol (30 mL) and treated with sodium methoxide (25% in methanol, 30 mL) and heated the mixture at 90° C. for 3 h. After completion, the solvent was removed under reduced pressure. The crude was diluted with ammonium chloride solution and extracted with ethyl acetate. The organic phase was separated, dried over anhydrous sodium sulphate and concentrated under reduced pressure to afford rac-methyl (5aR,6S,7R,8aR)-3-chloro-8a-hydroxy-8-oxo-6-phenyl-5a-(4-(trifluoromethyl)phenyl)-5a,7,8,8a-tetrahydro-6H-cyclopenta[4,5]furo[3,2-b]pyridine-7-carboxylate (7) as brown sticky solid. Yield: 2.5 g, crude; MS (ESI) m/z 504.10[M+1]$^+$.

Synthesis of rac-methyl (5aR,6S,7R,8R,8aS)-3-chloro-8,8a-dihydroxy-6-phenyl-5a-(4-(trifluoromethyl)phenyl)-5a, 7,8,8a-tetrahydro-6H-cyclopenta[4,5]furo[3,2-b]pyridine-7-carboxylate (8)

To a solution of rac-methyl (5aR,6S,7R,8aR)-3-chloro-8a-hydroxy-8-oxo-6-phenyl-5a-(4-(trifluoromethyl)phenyl)-5a,7,8,8a-tetrahydro-6H-cyclopenta[4,5]furo[3,2-b]pyridine-7-carboxylate (7, 2.5 g, 4.97) in acetonitrile (250 mL), sodium triacetoxyborohydride (6.0 g, 29.82 mmol) and acetic acid (3.0 mL, 49.7 mmol) were added at 0° C. The resulting mixture was stirred for 10 h at room temperature. After completion, reaction mixture was partitioned between saturated aqueous sodium bicarbonate solution and ethyl acetate. The organic layer was separated, dried over anhydrous sodium sulphate and concentrated under reduced pressure to get the crude. The crude was purified by Combiflash (12 g RediSep column) using 70% ethyl acetate in hexanes as eluent. The desired fractions were concentrated to afford rac-methyl (5aR,6S,7R,8R,8aS)-3-chloro-8,8a-dihydroxy-6-phenyl-5a-(4-(trifluoromethyl)phenyl)-5a,7,8,8a-tetrahydro-6H-cyclopenta[4,5]furo[3,2-b]pyridine-7-carboxylate (8) as off white solid. Yield: 1.1 g, 44%; MS (ESI) m/z 506.8[M+1]$^+$.

Synthesis of rac-(5aR,6S,7R,8R,8aS)-3-chloro-8,8a-dihydroxy-6-phenyl-5a-(4-(trifluoromethyl)phenyl)-5a, 7,8,8a-tetrahydro-6H-cyclopenta[4,5]furo[3,2-b]pyridine-7-carboxylic acid (9)

To a solution of rac-methyl (5aR,6S,7R,8R,8aS)-3-chloro-8,8a-dihydroxy-6-phenyl-5a-(4-(trifluoromethyl)phenyl)-5a,7,8,8a-tetrahydro-6H-cyclopenta[4,5]furo[3,2-b]pyridine-7-carboxylate (8, 1.1 g, 2.1 mmol) in methanol and water (3:1, 13 mL), lithium hydroxide (2.19 g, 52.2 mmol) was added and the reaction was stirred for 3 h at room temperature. After completion, the reaction mass was cooled to 0° C. and acidified with 6 M hydrogen chloride to pH ~6. The precipitated solid was filtered and dried under vacuum to afford rac-(5aR,6S,7R,8R,8aS)-3-chloro-8,8a-dihydroxy-6-phenyl-5a-(4-(trifluoromethyl)phenyl)-5a,7,8,8a-tetrahydro-6H-cyclopenta[4,5]furo[3,2-b]pyridine-7-carboxylic acid (9) as off white solid. Yield: 900 mg, 85%; MS (ESI) m/z 492.5[M+1]$^+$ Synthesis of (5aR,6S,7R,8R,8aS)-3-chloro-8,8a-dihydroxy-N,N-dimethyl-6-phenyl-5a-(4-(trifluoromethyl)phenyl)-5a, 7,8,8a-tetrahydro-6H-cyclopenta[4,5]furo[3,2-b]pyridine-7-carboxamide (Cpd. No. 8F)

To a solution of rac-(5aR,6S,7R,8R,8aS)-3-chloro-8,8a-dihydroxy-6-phenyl-5a-(4-(trifluoromethyl)phenyl)-5a,7,8,8a-tetrahydro-6H-cyclopenta[4,5]furo[3,2-b]pyridine-7-carboxylic acid (9, 0.90 g, 1.83 mmol) in dichloromethane (50 mL), 1-ethyl-3-(3-dimethylaminopropyl)carbodiimide hydrochloride (1.0 g, 5.4 mmol), 1-hydroxybenzotriazole (0.74 g, 5.4 mmol) and N,N-diisopropylethylamine (1.9 mL, 10.9 mmol) were added at 0° C. and stirred the mixture for 5 min. Dimethylamine hydrochloride (0.74 g, 9.1 mmol) was then added at same temperature and the mixture was stirred for 20 h at room temperature After completion, reaction mass was diluted with dichloromethane and washed with cold water. The organic layer was separated and dried over anhydrous sodium sulphate, filtered and concentrated to give crude. The crude was purified by Combi-flash (4 g RediSep column) using 5% methanol in dichloromethane as eluent. The desired fractions were concentrated to afford rac-(5aR,6S,7R,8R,8aS)-3-chloro-8,8a-dihydroxy-N,N-dimethyl-6-phenyl-5a-(4-(trifluoromethyl)phenyl)-5a,7,8,8a-tetrahydro-6H-cyclopenta[4,5]furo[3,2-b]pyridine-7-carboxamide (Cpd. No. 8F) as off white solid. Yield: 0.5 g, 53%; the enantiomers were separated by chiral preparative HPLC [chiralpak ID (4.6×250) mm]. Peak 1 (50 mg); $[\alpha]_D$+212.0° (c 0.1, $CHCl_3$); $R_t$=6.26 min, ee >99%; MS (ESI) m/z 519.30[M+1]$^+$; UPLC 97%; $^1$H NMR (400 MHz, DMSO-$d_6$) δ 8.21 (d, J=2.0 Hz, 1H), 7.74 (d, J=2.0 Hz, 1H), 7.35 (dd, J=13.6 Hz, 8.9 Hz, 4H), 7.04-7.00 (m, 2H), 6.96-6.91 (m, 3H), 6.13 (s, 1H), 5.34 (d, J=5.6 Hz, 1H), 4.77 (t, J=5.4 Hz, 1H), 4.64 (d, J=13.2 Hz, 1H), 4.34 (dd, J=13.2, 5.2 Hz, 1H), 3.28 (s, 3H), 2.78 (s, 3H). Peak-2 (Cpd. No. 8F, 50 mg); $[\alpha]_D$−194.5° (c 0.1, $CHCl_3$); $R_t$=12.49 min, ee >99%; MS (ESI) m/z 519.31[M+1]$^+$; UPLC 99%; $^1$H NMR (400 MHz, DMSO-$d_6$) δ:8.21 (d, J=2.0 Hz, 1H), 7.74 (d, J=2.0 Hz, 1H), 7.35 (dd, J=13.6 Hz, 8.9 Hz, 4H), 7.04-7.00 (m, 2H), 6.96-6.91 (m, 3H), 6.13 (s, 1H), 5.34 (d, J=5.6 Hz, 1H), 4.77 (t, J=5.4 Hz, 1H), 4.64 (d, J=13.2 Hz, 1H), 4.34 (dd, J=13.2, 5.2 Hz, 1H), 3.28 (s, 3H), 2.78 (s, 3H).

Example 9

(5aR,6S,7R,8R,8aS)-5a-(4-cyanophenyl)-8,8a-dihydroxy-N,N-dimethyl-6-phenyl-5a,7,8,8a-tetrahydro-6H-cyclopenta[4,5]furo[3,2-b]pyridine-7-carboxamide (Cpd. No. 9F)

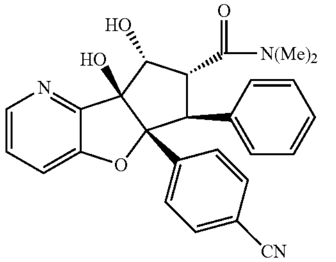

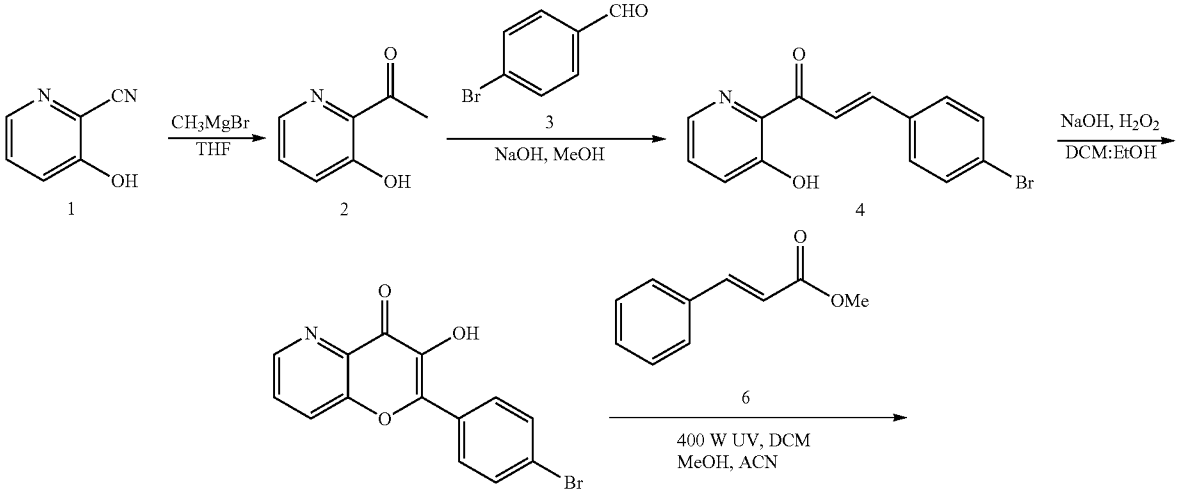

1

2

4

5

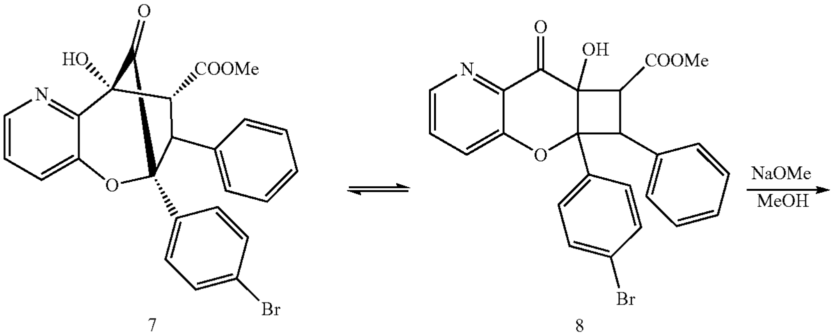

7

8

-continued

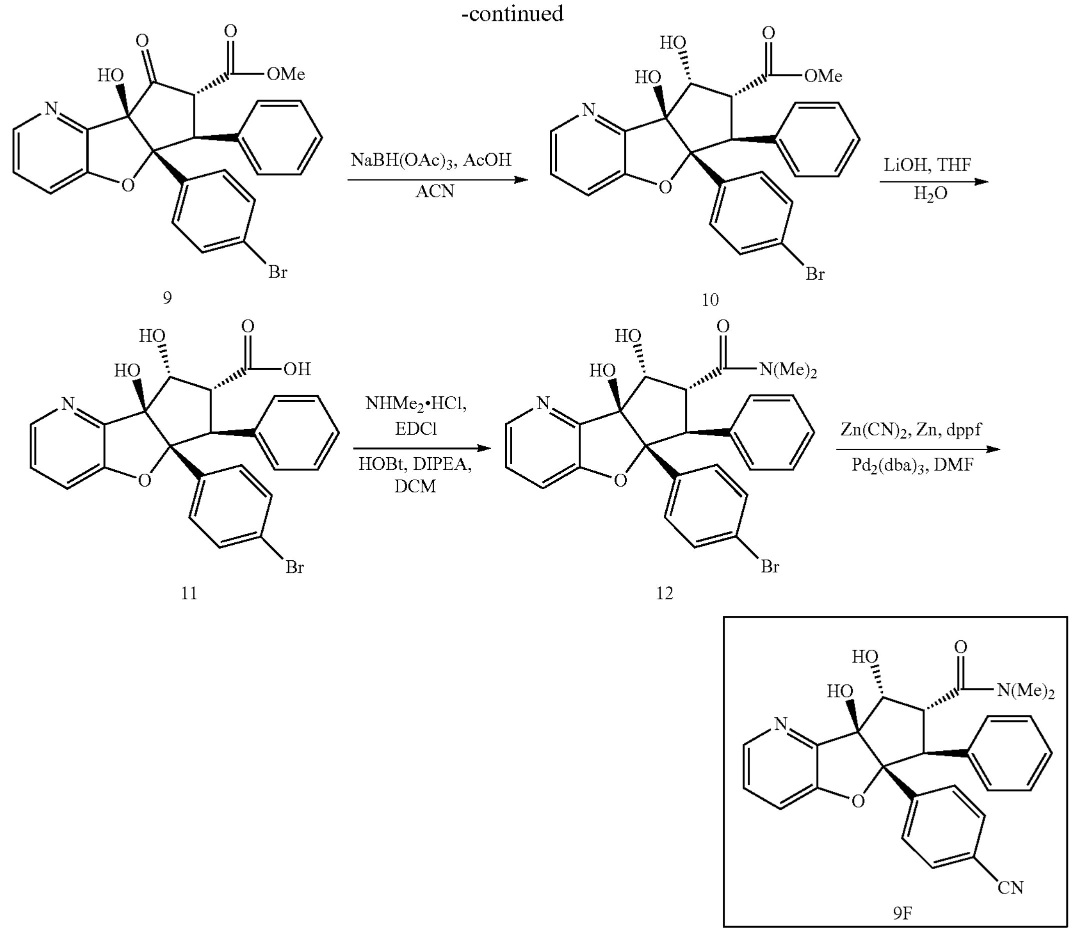

9 10 11 12 9F

Synthesis of 1-(3-hydroxypyridin-2-yl)ethan-1-one (2)

To a solution of 3-hydroxypicolinonitrile (1, 7.0 g, 58.2 mmol) in dry tetrahydrofuran (100 mL), 3 M methyl magnesium bromide in diethyl ether (58.0 mL, 174.84 mmol) was added drop wise over a period of 30 min at 0° C. The reaction mass was slowly brought to room temperature and stirred for 2 h. After completion, the reaction mass was treated with 6 M hydrogen chloride upto pH~3 and stirred for 2 h. Then extracted the crude with ethyl acetate. The organic layer was washed with aqueous sodium hydroxide, dried over anhydrous sodium sulphate, filtered and concentrated under reduced pressure to afford 1-(3-hydroxypyridin-2-yl)ethan-1-one (2) as yellow solid. Yield: 6.5 g, 81.3%, crude.

Synthesis of (E)-3-(4-bromophenyl)-1-(3-hydroxypyridin-2-yl)prop-2-en-1-one (4)

To a solution of 1-(3-hydroxypyridin-2-yl)ethan-1-one (2, 6.5 g, 47.4 mmol) in methanol (50 mL), sodium hydroxide (5.7 g, 142.1 mmol) was added followed by addition of 4-bromobenzaldehyde (3, 10.5 g, 56.8 mmol) and the reaction mixture was heated at 90° C. for 1 h. After completion, reaction mass was cooled and obtained solid was filtered, washed with water and dried under vacuum to afford of (E)-3-(4-bromophenyl)-1-(3-hydroxypyridin-2-yl)prop-2-en-1-one (4) as light yellow solid. Yield: 10.2 g, 70.7%; MS (ESI) m/z 304.09[M+1]$^+$.

Synthesis of 2-(4-bromophenyl)-3-hydroxy-4H-pyrano[3,2-b]pyridin-4-one (5)

To a solution of (E)-3-(4-bromophenyl)-1-(3-hydroxypyridin-2-yl)prop-2-en-1-one (4, 10.0 g, 46.03 mmol) in dichloromethane and ethanol (1:1, 50 mL), 10% sodium hydroxide (92.0 mL, 322.2 mmol) was added followed by addition of 30% hydrogen peroxide (25 mL, 322.2 mmol) at room temperature. The reaction mass was stirred for 1 h (exotherm was observed). After completion, reaction mass was cooled and neutralized with 6 M hydrogen chloride to pH ~7. The solvents were concentrated to half volume, the precipitated solid was filtered and dried under vacuum to afford 2-(4-bromophenyl)-3-hydroxy-4H-pyrano[3,2-b]pyridin-4-one (5) as yellow solid. Yield: 3.7 g, 26.4%; MS (ESI) m/z 318.19[M+1]$^+$.

Synthesis of rac-methyl 5a-(4-bromophenyl)-7a-hydroxy-8-oxo-6-phenyl-5a,6,7a,8-tetrahydro-7H-cyclobuta[5,6]pyrano[3,2-b]pyridine-7-carboxylate (7/8)

A solution of 2-(4-bromophenyl)-3-hydroxy-4H-pyrano[3,2-b]pyridin-4-one (5, 3.7 g, 11.6 mmol) and methyl cinnamate (6, 13.2 g, 81.4 mmol) in dichloromethane (200 mL), acetonitrile (50 mL) and methanol (50 mL) was placed in a UV reactor flask. The reaction mixture was irradiated for 24 h under 400 watts UV light. After completion, the solvent was removed under reduced pressure. The crude was purified by Combi-flash (24 g, RediSep column) using 80% ethyl acetate in hexanes as eluent. The desired fractions were concentrated under reduced pressure to afford rac-methyl 5a-(4-bromophenyl)-7a-hydroxy-8-oxo-6-phenyl-5a,6,7a,8-tetrahydro-7H-cyclobuta[5,6]pyrano[3,2-b]pyridine-7-carboxylate (7/8) as yellow solid. Yield: 3.5 g, crude.

Synthesis of rac-methyl (5aR,6S,7R,8aR)-5a-(4-bromophenyl)-8a-hydroxy-8-oxo-6-phenyl-5a,7,8,8a-tetrahydro-6H-cyclopenta[4,5]furo[3,2-b]pyridine-7-carboxylate (9)

The crude rac-methyl 5a-(4-bromophenyl)-7a-hydroxy-8-oxo-6-phenyl-5a,6,7a,8-tetrahydro-7H-cyclobuta[5,6]pyrano[3,2-b]pyridine-7-carboxylate (7/8, 3.5 g) was suspended in methanol (20 mL) and treated with sodium methoxide (25% in methanol, 13.1 mL) and heated the mixture to 90° C. for 3 h. After completion, the solvent was removed under reduced pressure, diluted the mixture with ammonium chloride solution and extracted with ethyl acetate. The organic phase was separated, dried over sodium sulphate and concentrated under reduced pressure to afford rac-methyl (5aR,6S,7R,8aR)-5a-(4-bromophenyl)-8a-hydroxy-8-oxo-6-phenyl-5a,7,8,8a-tetrahydro-6H-cyclopenta[4,5]furo[3,2-b]pyridine-7-carboxylate (9) as yellow solid. Yield: 3.0 g, crude.

Synthesis of rac-methyl (5aR,6S,7R,8R,8aS)-5a-(4-bromophenyl)-8,8a-dihydroxy-6-phenyl-5a,7,8,8a-tetrahydro-6H-cyclopenta[4,5]furo[3,2-b]pyridine-7-carboxylate (10)

To a solution of sodium triacetoxyborohydride (5.6 g, 31.2 mmol), rac-methyl (5aR,6S,7R,8aR)-5a-(4-bromophenyl)-8a-hydroxy-8-oxo-6-phenyl-5a,7,8,8a-tetrahydro-6H-cyclopenta[4,5]furo[3,2-b]pyridine-7-carboxylate (9, 2.5 g) in acetonitrile (30 mL), acetic acid (3.13 g, 52.05 mmol) was added. The resulting mixture was stirred for 4 h at room temperature. After completion, reaction mixture was partitioned between saturated aqueous sodium bicarbonate solution and ethyl acetate. The organic layer was separated, dried over sodium sulphate and concentrated under reduced pressure to get the crude. The crude was purified by Combi-flash (12 g, RediSep column) using 50%-70% ethyl acetate in hexanes as eluent. The desired fractions were concentrated under reduced pressure to afford rac-methyl (5aR,6S,7R,8R,8aS)-5a-(4-bromophenyl)-8,8a-dihydroxy-6-phenyl-5a,7,8,8a-tetrahydro-6H-cyclopenta[4,5]furo[3,2-b]pyridine-7-carboxylate (10) as yellow solid. Yield: 0.9 g, 37%; MS (ESI) m/z 482.19$[M+1]^+$.

Synthesis of rac-(5aR,6S,7R,8R,8aS)-5a-(4-bromophenyl)-8,8a-dihydroxy-6-phenyl-5a, 7,8,8a-tetrahydro-6H-cyclopenta[4,5]furo[3,2-b]pyridine-7-carboxylic acid (11)

To a solution of rac-methyl (5aR,6S,7R,8R,8aS)-5a-(4-bromophenyl)-8,8a-dihydroxy-6-phenyl-5a,7,8,8a-tetrahydro-6H-cyclopenta[4,5]furo[3,2-b]pyridine-7-carboxylate (10, 0.9 g, 1.87 mmol) in tetrahydrofuran and water (3:1, 30 mL), lithium hydroxide (0.80 g, 37.3 mmol) was added and the reaction was stirred for 16 h at room temperature. After completion, the reaction mass was cooled to 0° C. and acidified with 6M hydrogen chloride to pH ~3. The precipitated solid was filtered and dried under vacuum to afford rac-(5aR,6S,7R,8R,8aS)-5a-(4-bromophenyl)-8,8a-dihydroxy-6-phenyl-5a,7,8,8a-tetrahydro-6H-cyclopenta[4,5]furo[3,2-b]pyridine-7-carboxylic acid (11) as light yellow solid. Yield: 0.75 g, 86%; MS (ESI) m/z 466.15$[M-1]^-$.

Synthesis of rac-(5aR,6S,7R,8R,8aS)-5a-(4-bromophenyl)-8,8a-dihydroxy-N,N-dimethyl-6-phenyl-5a,7,8,8a-tetrahydro-6H-cyclopenta[4,5]furo[3,2-b]pyridine-7-carboxamide (12)

To a solution of rac-(5aR,6S,7R,8R,8aS)-5a-(4-bromophenyl)-8,8a-dihydroxy-6-phenyl-5a,7,8,8a-tetrahydro-6H-cyclopenta[4,5]furo[3,2-b]pyridine-7-carboxylic acid (11, 0.75 g, 1.60 mmol) in dichloromethane (15 mL), 1-ethyl-3-(3-dimethylaminopropyl)carbodiimide hydrochloride (0.614 g, 3.2 mmol), 1-hydroxybenzotriazole (0.43 g, 3.20 mmol) and N,N-diisopropylethylamine (0.85 mL, 4.8 mmol) were added at 0° C. and stirred the mixture for 5 min. Dimethylamine hydrochloride (0.21 g, 3.20 mmol) was then added at same temperature and the mixture was stirred for 16 h at room temperature. After completion, reaction mass was diluted with dichloromethane and washed with cold water. The organic layer was separated and dried over sodium sulphate, filtered and concentrated to give crude. The crude was purified by Combi-flash (12 g, RediSep column) using 70% ethyl acetate in hexanes as eluent. The desired fractions were concentrated to afford rac-(5aR,6S,7R,8R,8aS)-5a-(4-bromophenyl)-8,8a-dihydroxy-N,N-dimethyl-6-phenyl-5a,7,8,8a-tetrahydro-6H-cyclopenta[4,5]furo[3,2-b]pyridine-7-carboxamide (12) as light yellow solid. Yield: 0.450 g, 56%; MS (ESI) m/z 495.21 $[M+1]^+$.

Synthesis of (5aR,6S,7R,8R,8aS)-5a-(4-cyanophenyl)-8,8a-dihydroxy-N,N-dimethyl-6-phenyl-5a,7,8,8a-tetrahydro-6H-cyclopenta[4,5]furo[3,2-b]pyridine-7-carboxamide (Cpd. No. 9F)

To a solution of rac-(5aR,6S,7R,8R,8aS)-5a-(4-bromophenyl)-8,8a-dihydroxy-N,N-dimethyl-6-phenyl-5a,7,8,8a-tetrahydro-6H-cyclopenta[4,5]furo[3,2-b]pyridine-7-carboxamide (12, 0.25 g, 0.504 mmol) in N,N-dimethylformamide (20.0 mL), zinc cyanide (0.335 g, 3.24 mmol) and zinc (0.001 g, 0.014 mmol) were added at room temperature and degassed the mixture with argon for 15 min. 1,1'-Bis(diphenylphosphino)ferrocene (0.007 g, 0.010 mmol), tris(dibenzylideneacetone)dipalladium (0.014 g, 0.015 mmol) were added to the reaction and degassing was continued for another 5 min. The reaction mixture was heated at 140° C. for 5 h. After completion, the reaction was cooled to room temperature and passed through celite bed. The filtrate was diluted with ethyl acetate and washed with water. The organic layer was separated, dried over sodium sulphate and concentrated under reduced pressure to get the crude. The crude was purified by Combi-flash (4 g, RediSep column) using 80%-100% ethyl acetate in hexanes as eluent. The desired fractions were concentrated under reduced pressure to afford rac-(5aR,6S,7R,8R,8aS)-5a-(4-cyanophenyl)-8,8a-dihydroxy-N,N-dimethyl-6-phenyl-5a,7,8,8a-tetrahydro-6H-cyclopenta[4,5]furo[3,2-b]pyridine-7-carboxamide (rac-Cpd. No. 9F) as white solid. The enantiomers were separated by chiral preparative HPLC [chiralpak IA (4.6×250) mm]. Yield: 210 mg, 93%; Peak 1 (25 mg), $[\alpha]_D$+136° (c 0.23, $CHCl_3$), $R_t$=7.70 min, ee >99%; MS (ESI) m/z 442.40$[M+1]^+$; UPLC: 98.86%; $^1H$ NMR (400 MHz, DMSO-$d_6$) δ 8.18 (d, J=1.6 Hz, 1H), 7.50 (d, J=8.4 Hz, 3H), 7.36-7.29 (m, 3H), 7.05-7.01 (m, 2H), 6.97-6.91 (m, 3H), 6.05 (s, 1H), 5.25 (d, J=5.6 Hz, 1H), 4.79 (t, J=5.2 Hz, 1H), 4.58 (d, J=13.2 Hz, 1H), 4.30 (dd, J=13.2, 5.2 Hz, 1H), 3.28 (s, 3H), 2.77 (s, 3H); Peak-2 (Cpd. No. 9F, 38 mg), $[\alpha]_D$-166° (c 0.24, $CHCl_3$), $R_t$=13.92 min, ee >95%; MS (ESI) m/z 442.4[M+1]$^+$; UPLC: 98.93%; $^1H$ NMR (400 MHz, DMSO-$d_6$) δ 8.18 (d, J=1.6 Hz, 1H), 7.50 (d, J=8.4 Hz, 3H), 7.36-7.29 (m, 3H), 7.05-7.01 (m, 2H), 6.97-6.91 (m, 3H), 6.05 (s, 1H), 5.25 (d, J=5.6 Hz, 1H), 4.79 (t, J=5.2 Hz, 1H), 4.58 (d, J=13.2 Hz, 1H), 4.30 (dd, J=13.2, 5.2 Hz, 1H), 3.28 (s, 3H), 2.77 (s, 3H).
Example 10
(5aR,6S,7R,8R,8aS)-3-chloro-5a-(4-fluorophenyl)-8,8a-dihydroxy-N,N-dimethyl-6-phenyl-5a,7,8,8a-tetrahydro-6H-cyclopenta[4,5]furo[3,2-b]pyridine-7-carboxamide (Cpd. No. 10F)
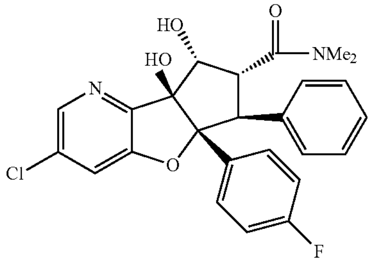
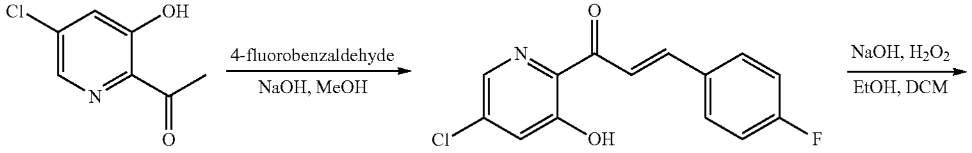
1
2
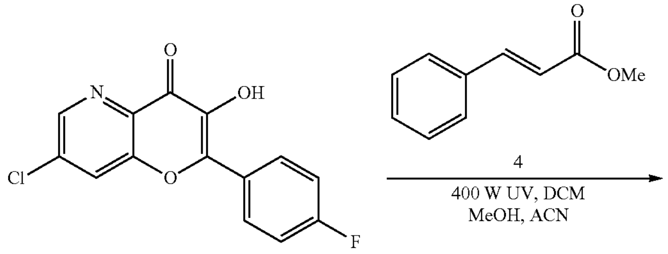
3
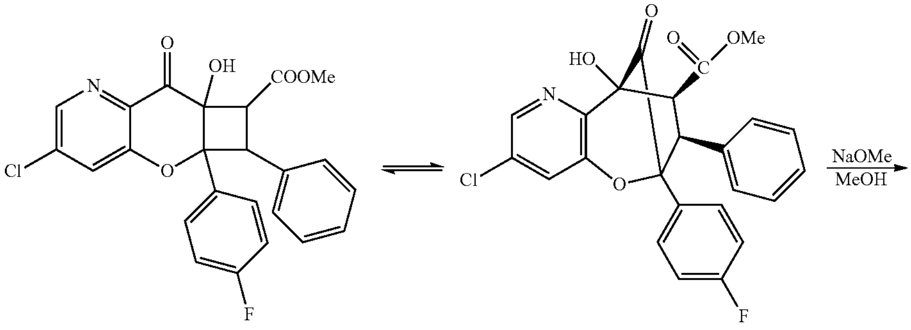
5
5a
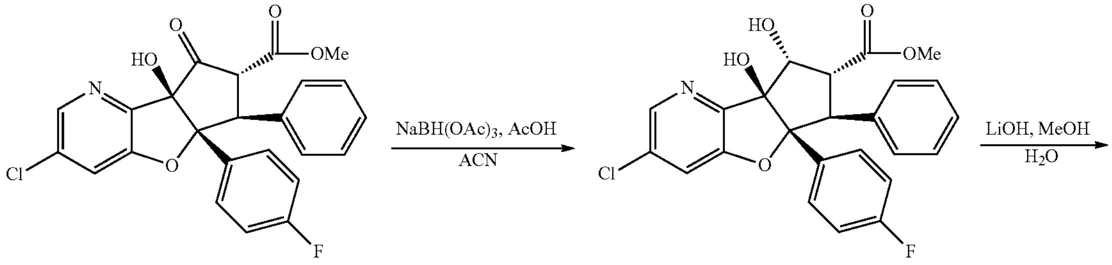
6
7

-continued

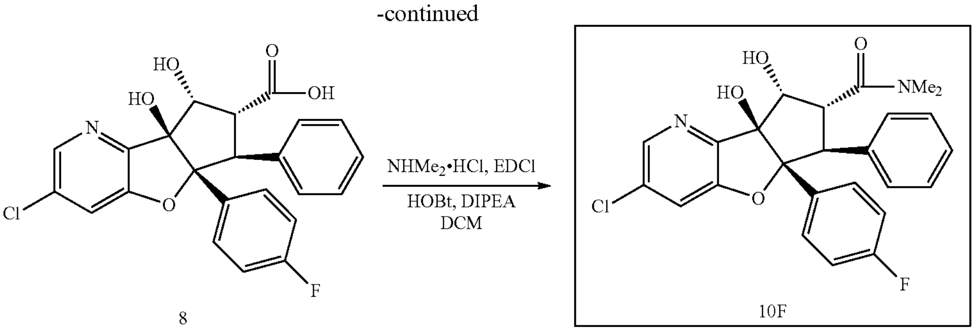

8

10F

Synthesis of (E)-1-(5-chloro-3-hydroxypyridin-2-yl)-3-(4-fluorophenyl)prop-2-en-1-one (2)

To a solution of 1-(5-chloro-3-hydroxypyridin-2-yl) ethan-1-one (1, 5.0 g, 29.23 mmol) in methanol (25 mL), sodium hydroxide (3.5 g, 87.71 mmol) was added followed by addition of 4-fluorobenzaldehyde (4.35 g, 35.08 mmol) and the reaction mixture was heated at 80° C. for 1 h. After completion, reaction mass was cooled and precipitated solid was filtered, washed with water and dried under vacuum to afford of (E)-1-(5-chloro-3-hydroxypyridin-2-yl)-3-(4-fluorophenyl)prop-2-en-1-one (2) as pale yellow solid. Yield: 4.2 g, 51.8%; MS (ESI) m/z 276.16[M−1]$^-$.

Synthesis of 7-chloro-2-(4-fluorophenyl)-3-hydroxy-4H-pyrano[3,2-b]pyridin-4-one (3)

To a solution of (E)-1-(5-chloro-3-hydroxypyridin-2-yl)-3-(4-fluorophenyl)prop-2-en-1-one (2, 3.0 g, 10.81 mmol) in ethanol/dichloromethane (1:1, 100 mL), 10% sodium hydroxide solution (30.0 mL, 75.81 mmol) was added followed by addition of hydrogen peroxide (30% solution, 6.7 mL, 54.1 mmol) at room temperature. The reaction mass was stirred for 1 h (exotherm was observed). After completion, reaction mass was poured on ice cold water and neutralized by addition of 6 M hydrogen chloride and extracted with dichloromethane (100 mL). The organic layer was separated, dried over sodium sulphate, filtered and concentrated under reduced pressure to get crude. The crude was triturated with diethylether and n-pentane to afford 7-(chloro)-2-(4-fluoroophenyl)-3-hydroxy-4H-pyrano[3,2-b]pyridin-4-one (3) as yellow solid. Yield: 2.5 g, 79.6%; MS (ESI) m/z 290.07[M−1]$^-$.

Synthesis of rac-methyl 3-chloro-5a-(4-fluorophenyl)-7a-hydroxy-8-oxo-6-phenyl-5a,6,7a,8-tetrahydro-7H-cyclobuta[5,6]pyrano[3,2-b]pyridine-7-carboxylate (5/5a)

A solution of 7-(chloro)-2-(4-fluoroophenyl)-3-hydroxy-4H-pyrano[3,2-b]pyridin-4-one (3, 2.5 g, 8.59 mmol) and methyl cinnamate (4, 13.9 g, 85.7 mmol) in dichloromethane (200 mL), acetonitrile (100 mL) and methanol (100 mL) was placed in a UV reactor flask. The reaction mixture was irradiated under 400 watts UV light for 16 h. After completion, the solvent was removed under reduced pressure. The residue was purified by Combi-flash (24 g, RediSep column) using ethyl acetate as eluent. The desired fractions were concentrated under reduced pressure to afford rac-methyl 3-chloro-5a-(4-fluorophenyl)-7a-hydroxy-8-oxo-6-phenyl-5a,6,7a,8-tetrahydro-7H-cyclobuta[5,6]pyrano[3,2-b]pyridine-7-carboxylate (5/5a). Yield: 2.5 g, crude.

Synthesis of rac-methyl (5aR,6S,7R,8aR)-3-chloro-5a-(4-fluorophenyl)-8a-hydroxy-8-oxo-6-phenyl-5a,7,8,8a-tetrahydro-6H-cyclopenta[4,5]furo[3,2-b]pyridine-7-carboxylate (6)

The crude rac-methyl 3-(chloro)-5a-(4-fluoroophenyl)-7a-hydroxy-8-oxo-6-phenyl-5a,6,7a,8-tetrahydro-7H-cyclobuta[5,6]pyrano[3,2-b]pyridine-7-carboxylate (5, 1.3 g) was suspended in methanol (15 mL) and treated with sodium methoxide (25% in methanol, 15 mL) and heated the mixture at 80° C. for 1 h. After completion, the solvent was removed under reduced pressure and the reaction was treated with ammonium chloride solution and extracted with ethyl acetate. The organic phase was separated, dried over sodium sulphate and concentrated under reduced pressure to afford rac-methyl (5aR,6S,7R,8aR)-3-chloro-5a-(4-fluorophenyl)-8a-hydroxy-8-oxo-6-phenyl-5a,7,8,8a-tetrahydro-6H-cyclopenta[4,5]furo[3,2-b]pyridine-7-carboxylate (6). Yield: 1.4 g, crude.

Synthesis of rac-methyl (5aR,6S,7R,8R,8aS)-3-chloro-5a-(4-fluorophenyl)-8,8a-dihydroxy-6-phenyl-5a, 7,8,8a-tetrahydro-6H-cyclopenta[4,5]furo[3,2-b]pyridine-7-carboxylate (7)

To a solution of sodium triacetoxyborohydride (1.8 g, 2.86 mmol), rac-methyl (5aR,6S,7R,8aR)-3-(chloro)-5a-(4-fluorophenyl)-8a-hydroxy-8-oxo-6-phenyl-5a,7,8,8a-tetrahydro-6H-cyclopenta[4,5]furo[3,2-b]pyridine-7-carboxylate (6, 1.3 g) in acetonitrile (50 mL), acetic acid (1.7 mL, 28.69 mmol) was added. The resulting mixture was stirred for 4 h at room temperature. After completion, reaction mixture was partitioned between saturated aqueous sodium bicarbonate solution and ethyl acetate. The organic layer was separated, dried over sodium sulphate and concentrated under reduced pressure to get the crude. The crude was purified by Combi-flash (4 g, RediSep column) using 50% ethyl acetate in hexanes as eluent. The desired fractions were concentrated under reduced pressure to afford rac-methyl (5aR,6S,7R,8R,8aS)-3-chloro-5a-(4-fluorophenyl)-8,8a-dihydroxy-6-phenyl-5a,7,8,8a-tetrahydro-6H-cyclopenta[4,5]furo[3,2-b]pyridine-7-carboxylate (7) as light yellow solid. Yield: 0.32 g, 24.6%; MS (ESI) m/z 456.17[M+1]$^+$.

Synthesis of rac-(5aR,6S,7R,8R,8aS)-3-chloro-5a-(4-fluorophenyl)-8,8a-dihydroxy-6-phenyl-5a, 7,8, 8a-tetrahydro-6H-cyclopenta[4,5]furo[3,2-b]pyridine-7-carboxylic acid (8)

To a solution of rac-methyl (5aR,6S,7R,8R,8aS)-3-chloro-5a-(4-fluoroophenyl)-8,8a-dihydroxy-6-phenyl-5a,7, 8,8a-tetrahydro-6H-cyclopenta[4,5]furo[3,2-b]pyridine-7-carboxylate (7, 0.30 g, 0.65 mmol) in methanol and water (3:1, 12 mL), lithium hydroxide (0.158 g, 6.59 mmol) was added and the reaction was stirred for 6 h at room temperature. After completion, the reaction mass was cooled to 0° C. and acidified with 6 M hydrogen chloride to pH ~3. The precipitated solid was filtered and dried under vacuum to afford rac-(5aR,6S,7R,8R,8aS)-3-chloro-5a-(4-fluorophenyl)-8,8a-dihydroxy-6-phenyl-5a,7,8,8a-tetrahydro-6H-cyclopenta[4,5]furo[3,2-b]pyridine-7-carboxylic acid (8) as yellow solid. Yield: 0.25 g, 86.2%; MS (ESI) m/z 442.20 $[M+1]^+$.

Synthesis of (5aR,6S,7R,8R,8aS)-3-chloro-5a-(4-fluorophenyl)-8,8a-dihydroxy-N,N-dimethyl-6-phenyl-5a, 7,8,8a-tetrahydro-6H-cyclopenta[4,5]furo[3,2-b]pyridine-7-carboxamide (Cpd. No. 10F)

To a solution of rac-(5aR,6S,7R,8R,8aS)-3-chloro-5a-(4-fluorophenyl)-8,8a-dihydroxy-6-phenyl-5a,7,8,8a-tetrahydro-6H-cyclopenta[4,5]furo[3,2-b]pyridine-7-carboxylic acid (8, 0.25 g, 0.566 mmol) in dichloromethane (10 mL), 1-ethyl-3-(3-dimethylaminopropyl)carbodiimide hydrochloride (0.32 g, 1.70 mmol), 1-hydroxybenzotriazole (0.23 g, 1.70 mmol) and N,N-diisopropylethylamine (0.6 mL, 3.4 mmol) were added at 0° C. and stirred the mixture for 5 min. Dimethylamine hydrochloride (0.23 g, 2.83 mmol) was then added at same temperature and the mixture was stirred for 16 h at 40° C. After completion, reaction mass was diluted with dichloromethane and washed with cold water. The organic layer was separated and dried over sodium sulphate, filtered and concentrated to give crude. The crude was purified by Combi-flash (12 g, RediSep column) using 5% methanol in dichloromethane as eluent. The desired fractions were concentrated under reduced pressure to afford rac-(5aR,6S,7R,8R,8aS)-3-chloro-5a-(4-fluorophenyl)-8,8a-dihydroxy-N,N-dimethyl-6-phenyl-5a,7,8,8a-tetrahydro-6H-cyclopenta[4,5]furo[3,2-b]pyridine-7-carboxamide (rac-Cpd. No. 10F). The enantiomers were separated by chiral preparative HPLC [chiralpak ID (4.6×250) mm]. Yield: 100 mg, 38%; Peak 1 (26 mg); $[\alpha]_D$+182.2° (c 0.3, $CHCl_3$); $R_t$=5.88 min, ee >99%; MS (ESI) m/z 469.34$[M+1]^+$; UPLC: 99.07%; $^1$H NMR (400 MHz, DMSO-$d_6$) δ 8.20 (d, J=1.9 Hz, 1H), 7.70 (d, J=1.9 Hz, 1H), 7.16-7.13 (m, 2H), 7.02 (t, J=7.2 Hz, 2H), 6.97-6.93 (m, 1H), 6.90-6.87 (m, 4H), 6.01 (s, 1H), 5.28 (d, J=5.6 Hz, 1H), 4.75 (t, J=5.5 Hz, 1H), 4.53 (d, J=13.3 Hz, 1H), 4.22 (dd, J=13.2, 5.4 Hz, 1H), 3.26 (s, 3H), 2.77 (s, 3H). Peak-2 (Cpd. No. 10F, 34 mg); $[\alpha]_D$−201.4° (c 0.29, $CHCl_3$); $R_t$=10.86 min, ee >99%; MS (ESI) m/z 469.34 $[M+1]^+$; UPLC: 99.78%; $^1$H NMR (400 MHz, DMSO-$d_6$) δ 8.20 (d, J=1.9 Hz, 1H), 7.70 (d, J=1.9 Hz, 1H), 7.16-7.13 (m, 2H), 7.03 (t, J=7.2 Hz, 2H), 6.97-6.82 (m, 4H), 6.01 (s, 1H), 5.28 (d, J=5.6 Hz, 1H), 4.75 (t, J=5.5 Hz, 1H), 4.53 (d, J=13.2 Hz, 1H), 4.22 (dd, J=13.3, 5.4 Hz, 1H), 3.26 (s, 3H), 2.77 (s, 3H).

Example 11

(5aR,6S,7R,8R,8aS)-3-chloro-5a-(4-chlorophenyl)-8,8a-dihydroxy-N,N-dimethyl-6-phenyl-5a,7,8,8a-tetrahydro-6H-cyclopenta[4,5]furo[3,2-b]pyridine-7-carboxamide (Cpd. No. 11F)

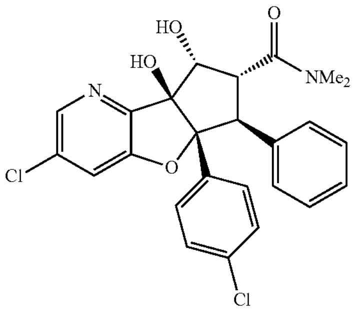

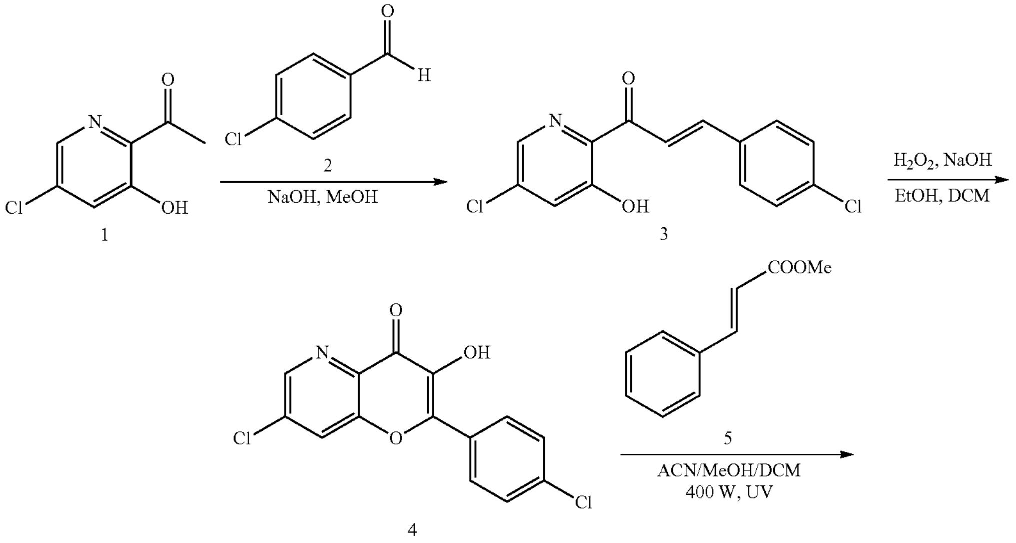

-continued

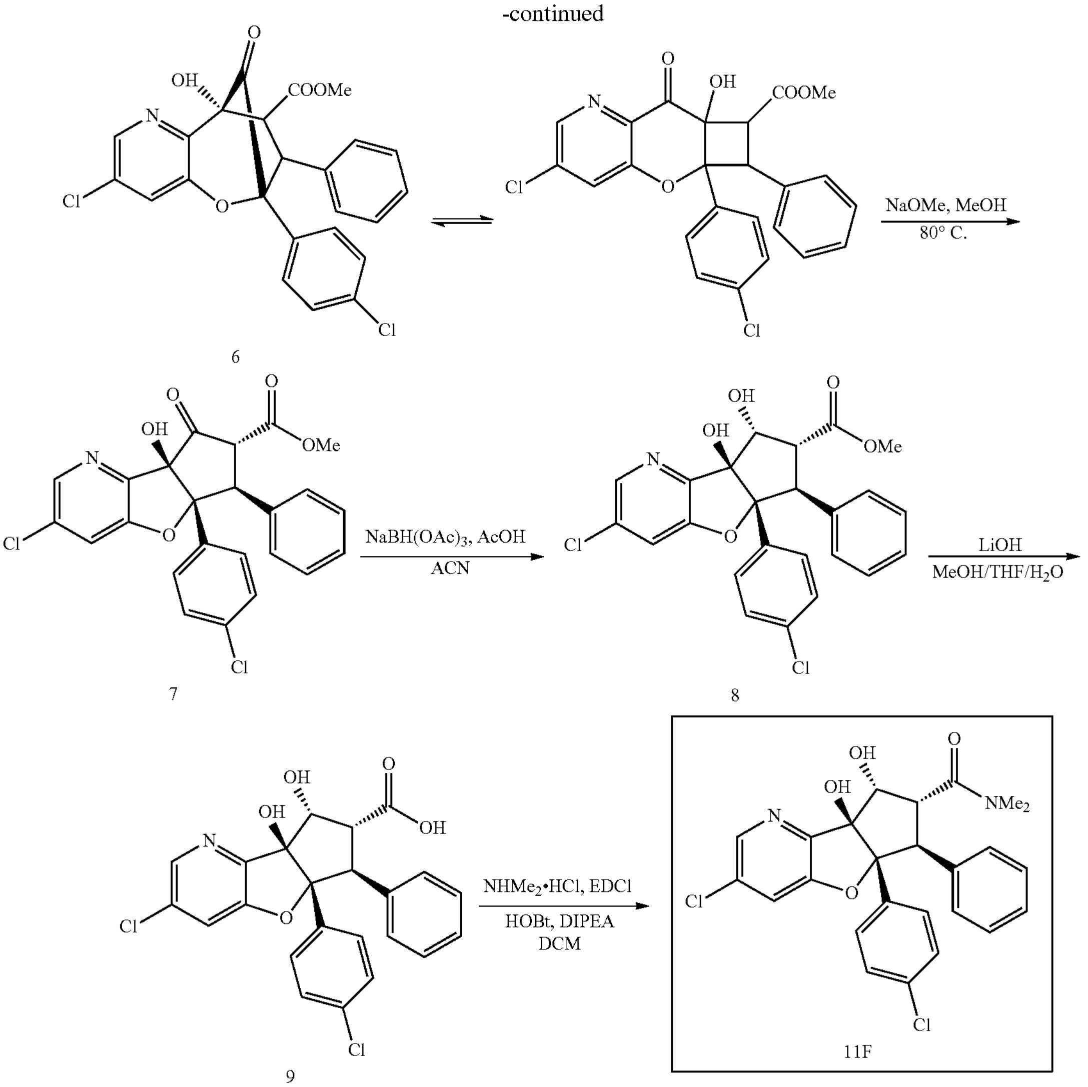

6 7 8 9 11F

Synthesis of (E)-1-(5-chloro-3-hydroxypyridin-2-yl)-3-(4-chlorophenyl)prop-2-en-1-one (3)

To a solution of 1-(5-chloro-3-hydroxypyridin-2-yl) ethan-1-one (1, 4.0 g, 23.4 mmol) in methanol (20 mL), sodium hydroxide (2.8 g, 70.2 mmol) was added followed by addition of 4-chlorobenzaldehyde (2, 3.3 g, 23.4 mmol). The reaction was heated to reflux for 10 min. After completion, the reaction mass was cooled to room temperature and diluted with water (20 mL). The precipitated solid was filtered, washed with water, n-pentane and dried under vacuum to afford (E)-1-(5-chloro-3-hydroxypyridin-2-yl)-3-(4-chlorophenyl)prop-2-en-1-one (3) as yellow solid. Yield: 6.1 g, 89.0%; MS (ESI) m/z 292.15$[M-1]^-$.

Synthesis of 7-chloro-2-(4-chlorophenyl)-3-hydroxy-4H-pyrano[3,2-b]pyridin-4-one (4)

To a solution of (E)-1-(5-chloro-3-hydroxypyridin-2-yl)-3-(4-chlorophenyl)prop-2-en-1-one (3, 7.0 g, 23.9 mmol) in ethanol (400 mL) and dichloromethane (66 mL) at 0° C., 10% aqueous sodium hydroxide (6.7 g, 167.2 mmol) was added followed by the addition of 30% aqueous hydrogen peroxide (37.5 mL, 334.4 mmol). The reaction mass was stirred for 30 min at room temperature (exotherm was observed). After completion, the reaction mass was cooled and neutralized to pH ~7 by the addition of 6 M hydrogen chloride. The mixture was extracted with ethyl acetate (100 mL) and the organic layer was washed with water and brine, dried over anhydrous sodium sulfate, filtered and concentrated. The solid obtained was triturated with ethanol, filtered and dried under vacuum to afford 7-chloro-2-(4-chlorophenyl)-3-hydroxy-4H-pyrano[3,2-b]pyridin-4-one (4) as light yellow solid. Yield: 2.81 g, 38.2%; MS (ESI) m/z 308.04$[M+1]^+$.

Synthesis of rac-methyl 3-chloro-5a-(4-chlorophenyl)-7a-hydroxy-8-oxo-6-phenyl-5a,6,7a,8-tetrahydro-7H-cyclobuta[5,6]pyrano[3,2-b]pyridine-7-carboxylate (6)

A solution of 7-chloro-2-(4-chlorophenyl)-3-hydroxy-4H-pyrano[3,2-b]pyridin-4-one (4, 2.8 g, 9.12 mmol) and methyl cinnamate (5, 14.7 g, 91.2 mmol) in dichloromethane (200 mL), acetonitrile (100 mL) and methanol (100 mL) was placed in a UV reactor flask. The reaction mixture was irradiated for 8 h under 400 watts UV light. After completion, solvent was removed under reduced pressure and the residue was purified over a plug of silica gel eluting the compound with ethyl acetate. The desired fractions were concentrated under reduced pressure to afford rac-methyl 3-chloro-5a-(4-chlorophenyl)-7a-hydroxy-8-oxo-6-phenyl-5a,6,7a,8-tetrahydro-7H-cyclobuta[5,6]pyrano[3,2-b]pyridine-7-carboxylate (6) as brown solid. Yield: 3.1 g, crude.

Synthesis of rac-methyl (5aR,6S,7R,8aR)-3-chloro-5a-(4-chlorophenyl)-8a-hydroxy-8-oxo-6-phenyl-5a,7,8,8a-tetrahydro-6H-cyclopenta[4,5]furo[3,2-b]pyridine-7-carboxylate (7)

The crude rac-methyl 3-chloro-5a-(4-chlorophenyl)-7a-hydroxy-8-oxo-6-phenyl-5a,6,7a,8-tetrahydro-7H-cyclobuta[5,6]pyrano[3,2-b]pyridine-7-carboxylate (6, 3.1 g, 6.6 mmol) was suspended in methanol (30 mL) and treated with 25% sodium methoxide in methanol (20 mL). The reaction was heated at 80° C. for 2 h. After completion, the solvent was removed under reduced pressure and crude was diluted with aqueous ammonium chloride solution and extracted with ethyl acetate. The organic phase was separated, dried over sodium sulphate and concentrated under reduced pressure to afford rac-methyl (5aR,6S,7R,8aR)-3-chloro-5a-(4-chlorophenyl)-8a-hydroxy-8-oxo-6-phenyl-5a,7,8,8a-tetrahydro-6H-cyclopenta[4,5]furo[3,2-b]pyridine-7-carboxylate (7). Yield: 2.35 g, crude.

Synthesis of rac-methyl (5aR,6S,7R,8R,8aS)-3-chloro-5a-(4-chlorophenyl)-8,8a-dihydroxy-6-phenyl-5a, 7,8,8a-tetrahydro-6H-cyclopenta[4,5]furo[3,2-b]pyridine-7-carboxylate (8)

To a solution of sodium triacetoxyborohydride (6.23 g, 29.4 mmol), rac-methyl (5aR,6S,7R,8aR)-3-chloro-5a-(4-chlorophenyl)-8a-hydroxy-8-oxo-6-phenyl-5a,7,8,8a-tetrahydro-6H-cyclopenta[4,5]furo[3,2-b]pyridine-7-carboxylate (7, 2.3 g, 4.9 mmol) in acetonitrile (60 mL), acetic acid (3.0 g, 49.0 mmol) was added. The resulting mixture was stirred for 18 h at room temperature. After completion, the reaction mixture was partitioned between saturated aqueous sodium bicarbonate solution and ethyl acetate. The organic layer was separated and dried over sodium sulphate, filtered and concentrated to give crude. The crude was purified by silica gel column chromatography using 60% ethyl acetate in hexanes as eluent. The desired fractions were concentrated under reduced pressure to afford rac-methyl (5aR,6S,7R,8R,8aS)-3-chloro-5a-(4-chlorophenyl)-8,8a-dihydroxy-6-phenyl-5a,7,8,8a-tetrahydro-6H-cyclopenta[4,5]furo[3,2-b]pyridine-7-carboxylate (8) as white solid. Yield: 1.1 g, 25.6%; MS (ESI) m/z 472.15$[M+1]^+$.

Synthesis of rac-(5aR,6S,7R,8R,8aS)-3-chloro-5a-(4-chlorophenyl)-8,8a-dihydroxy-6-phenyl-5a, 7,8,8a-tetrahydro-6H-cyclopenta[4,5]furo[3,2-b]pyridine-7-carboxylic acid (9)

To a solution of rac-methyl (5aR,6S,7R,8R,8aS)-3-chloro-5a-(4-chlorophenyl)-8,8a-dihydroxy-6-phenyl-5a,7,8,8a-tetrahydro-6H-cyclopenta[4,5]furo[3,2-b]pyridine-7-carboxylate (8, 1.0 g, 2.12 mmol) in methanol, tetrahydrofuran and water (3:2:1, 18 mL), lithium hydroxide (0.89 g, 21.2 mmol) was added and the reaction was stirred for 3 h at room temperature. After completion, the reaction mass was cooled to 0° C. and acidified with 1 M hydrochloric acid to pH ~2-3. The precipitate was filtered and dried under vacuum to afford rac-(5aR,6S,7R,8R,8aS)-3-chloro-5a-(4-chlorophenyl)-8,8a-dihydroxy-6-phenyl-5a,7,8,8a-tetrahydro-6H-cyclopenta[4,5]furo[3,2-b]pyridine-7-carboxylic acid (9) as white solid. Yield: 0.55 g, 56.7%; MS (ESI) m/z 458.14$[M+1]^+$.

Synthesis of (5aR,6S,7R,8R,8aS)-3-chloro-5a-(4-chlorophenyl)-8,8a-dihydroxy-N,N-dimethyl-6-phenyl-5a,7,8,8a-tetrahydro-6H-cyclopenta[4,5]furo[3,2-b]pyridine-7-carboxamide (Cpd. No. 11F)

To a solution of rac-(5aR,6S,7R,8R,8aS)-3-chloro-5a-(4-chlorophenyl)-8,8a-dihydroxy-6-phenyl-5a,7,8,8a-tetrahydro-6H-cyclopenta[4,5]furo[3,2-b]pyridine-7-carboxylic acid (9, 0.3 g, 0.65 mmol) in dichloromethane (8 mL) at 0° C., 1-ethyl-3-(3-dimethylaminopropyl) carbodiimide (0.30 g, 1.95 mmol), hydroxybenzotriazole (0.29 g, 1.95 mmol) and N,N-diisopropylethylamine (0.51 g, 3.94 mmol) were added and the mixture was stirred for 5 min. Dimethylamine hydrochloride (0.27 g, 3.2 mmol) was then added at the same temperature and the reaction was stirred for 48 h at room temperature. After completion, the reaction mass was diluted with dichloromethane and washed with cold water. The organic layer was separated and dried over sodium sulphate, filtered and concentrated to give crude. The crude was purified by silica gel column chromatography using 2-3% dichloromethane in methanol as eleunt. The desired fractions were concentrated under reduced pressure to afford rac-(5aR,6S,7R,8R,8aS)-3-chloro-5a-(4-chlorophenyl)-8,8a-dihydroxy-N,N-dimethyl-6-phenyl-5a,7,8,8a-tetrahydro-6H-cyclopenta[4,5]furo[3,2-b]pyridine-7-carboxamide (rac-Cpd. No. 11F) as white solid. The enantiomers were separated by chiral preparative HPLC [chiralpak IB (4.6×250) mm]. Peak 1 (64 mg), $[\alpha]_D$+212.3° (c 0.1, $CHCl_3$), $R_t$=9.727 min, ee >99% $^1$H NMR (400 MHz, DMSO-$d_6$) δ: 8.20 (d, J=2.0 Hz, 1H), 7.70 (d, J=2.0 Hz, 1H), 7.14 (d, J=8.8 Hz, 2H), 7.05 (m, 4H), 6.95 (d, J=7.2 Hz, 1H), 6.91 (d, J=7.4 Hz, 2H), 6.04 (s, 1H), 5.28 (d, J=5.7 Hz, 1H), 4.7 (t, J=5.4 Hz, 1H), 4.57 (d, J=13.2 Hz, 1H), 4.25 (dd, J=13.2, 5.2 Hz, 1H), 3.26 (s, 3H), 2.77 (s, 3H); MS (ESI) m/z 529.35 $[M+1]^+$; UPLC: 99.92%. Peak-2 (Cpd. No. 11F, 68 mg), $[\alpha]_D$−209.6° (c 0.1, $CHCl_3$), $R_t$=23.133 min, ee >99%. $^1$H NMR (400 MHz, DMSO-$d_6$) δ: 8.20 (d, J=2.0 Hz, 1H), 7.70 (d, J=2.0 Hz, 1H), 7.13 (d, J=8.8 Hz, 2H), 7.03 (m, 4H), 6.95 (d, J=7.4 Hz, 1H1), 6.91 (d, J=7.4 Hz, 2H), 6.04 (s, 1H), 5.29 (d, J=5.6 Hz, 1H), 4.73 (t, J=5.4 Hz, 1H), 4.57 (d, J=13.2 Hz, 1H), 4.25 (dd, J=13.2, 5.2 Hz, 1H), 3.26 (s, 3H), 2.77 (s, 3H); MS (ESI) m/z 529.34 $[M+1]^+$; UPLC: 99.83%.

Example 12
(5aR,6S,7R,8R,8aS)-3-chloro-8,8a-dihydroxy-N,N-dimethyl-5a-(4-(methylsulfonyl)phenyl)-6-phenyl-5a,7,8,8a-tetrahydro-6H-cyclopenta[4,5]furo[3,2-b]pyridine-7-carboxamide (Cpd. No. 12F)
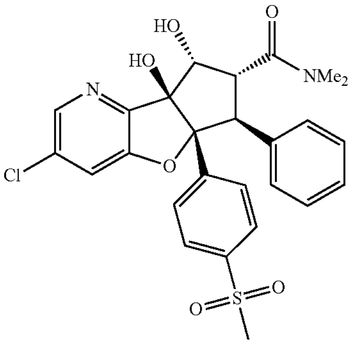
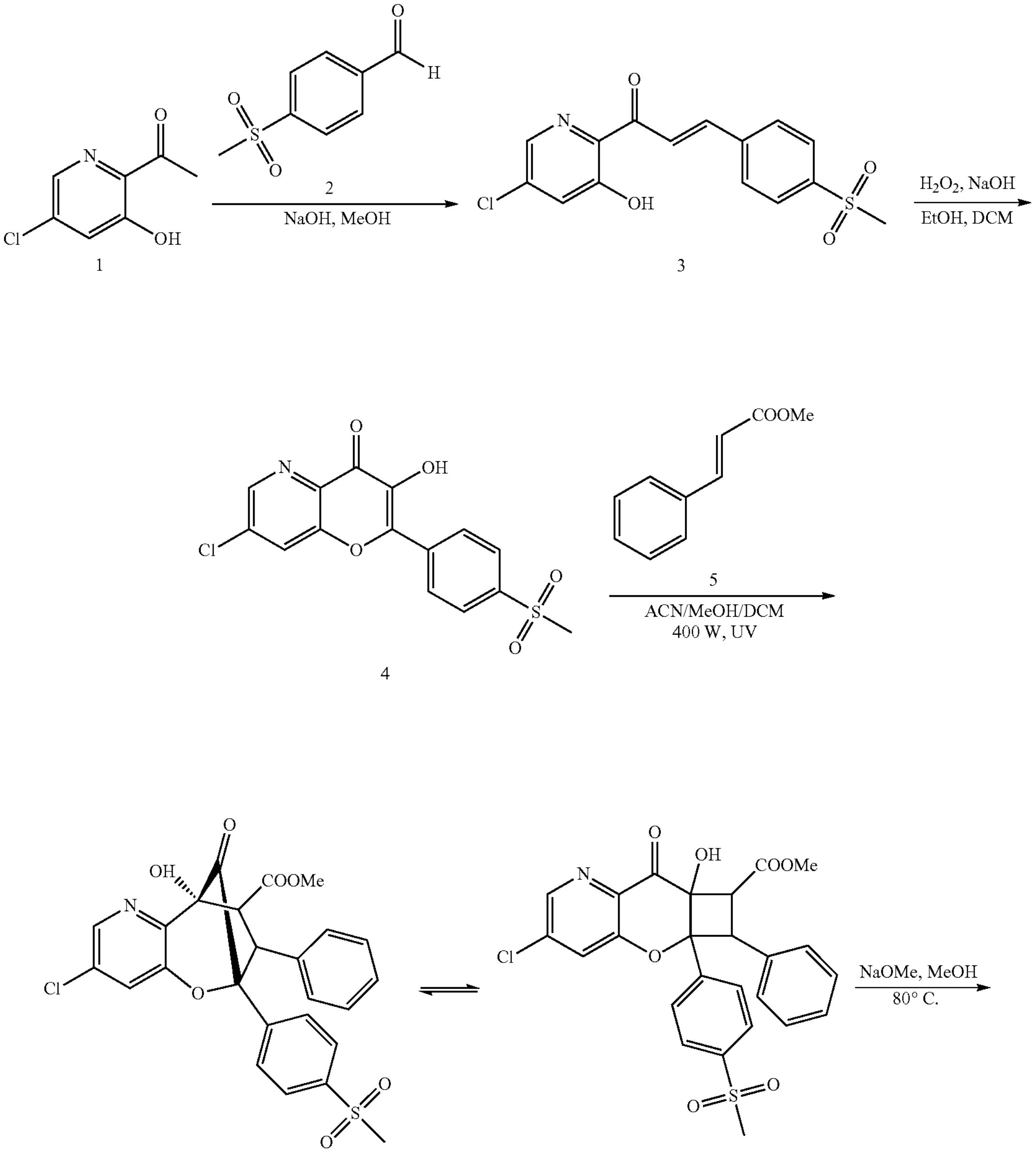
1
3
4
6

-continued

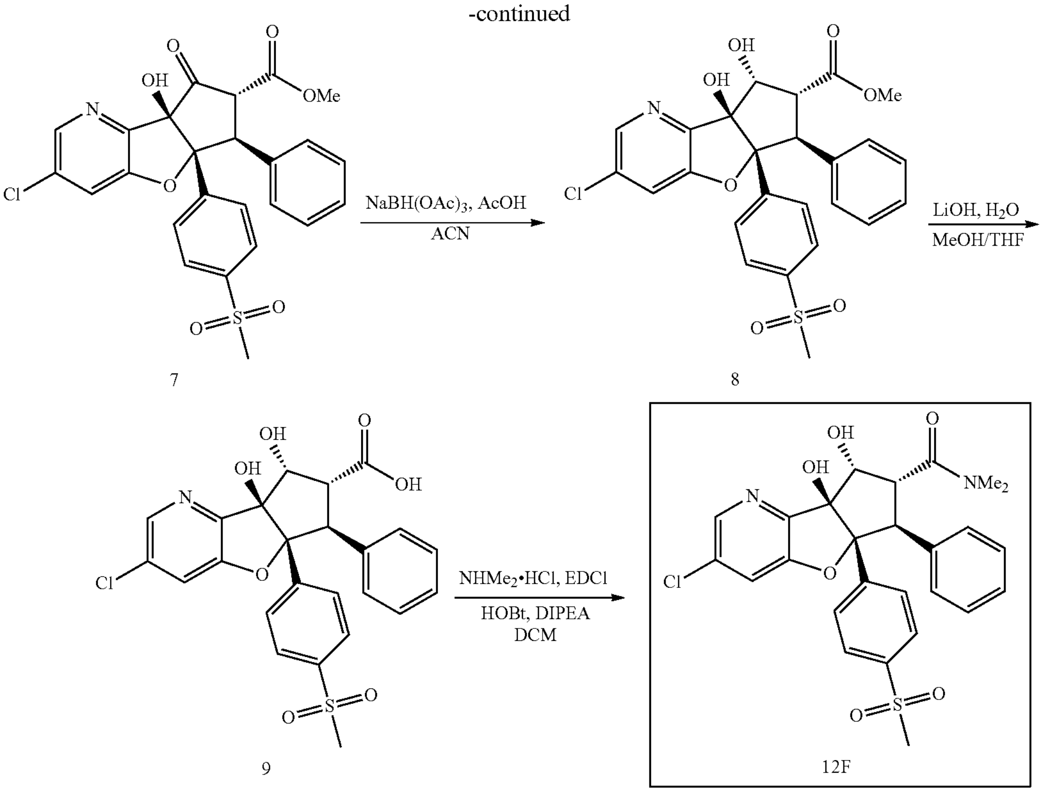

7 8 9 12F

Synthesis of (E)-1-(5-chloro-3-hydroxypyridin-2-yl)-3-(4-(methylsulfonyl)phenyl)prop-2-en-1-one (3)

To a solution of 1-(5-chloro-3-hydroxypyridin-2-yl) ethan-1-one (1, 4.0 g, 23.4 mmol) in methanol (20 mL), sodium hydroxide (2.8 g, 70.2 mmol) was added followed by addition of 4-(methylsulfonyl)benzaldehyde (2, 4.3 g, 23.4 mmol). The reaction was heated to reflux for 30 min. After completion, the reaction mass was cooled to room temperature and diluted with water (20 mL). The precipitated solid was filtered, washed with water, n-pentane and dried under vacuum to afford (E)-1-(5-chloro-3-hydroxypyridin-2-yl)-3-(4-(methylsulfonyl)phenyl)prop-2-en-1-one (3) as yellow solid. Yield: 5.3 g, 68.0%; MS (ESI) m/z 338.15[M+1]$^+$.

Synthesis of 7-chloro-3-hydroxy-2-(4-(methylsulfonyl)phenyl)-4H-pyrano[3,2-b]pyridin-4-one (4)

To a solution of (E)-1-(5-chloro-3-hydroxypyridin-2-yl)-3-(4-(methylsulfonyl)phenyl)prop-2-en-1-one (3, 5.3 g, 15.7 mmol) in ethanol (30 mL) and dichloromethane (6 mL) at 0° C., 10% aq. sodium hydroxide (4.4 g, 110.1 mmol) was added followed by the addition of 30% hydrogen peroxide (11.3 mL, 110.1 mmol). The reaction mass was stirred for 30 min at room temperature (exotherm was observed). After completion, the reaction mass was cooled and neutralized to pH ~7 by the addition of 6 M hydrogen chloride. The mixture was extracted with ethyl acetate (100 mL). The organic layer was washed with water and brine, dried over anhydrous sodium sulfate, filtered and concentrated. The solid obtained was triturated with n-pentane and ethanol, filtered and dried under vacuum to afford 7-chloro-3-hydroxy-2-(4-(methylsulfonyl)phenyl)-4H-pyrano[3,2-b]pyridin-4-one (4) as light brown solid. Yield: 0.80 g, 15.3%; MS (ESI) m/z 352.13[M+1]$^+$.

Synthesis of rac-methyl 3-chloro-7a-hydroxy-5a-(4-(methylsulfonyl)phenyl)-8-oxo-6-phenyl-5a,6,7a,8-tetrahydro-7H-cyclobuta[5,6]pyrano[3,2-b]pyridine-7-carboxylate (6)

A solution of 7-chloro-3-hydroxy-2-(4-(methylsulfonyl) phenyl)-4H-pyrano[3,2-b]pyridin-4-one (4, 1.9 g, 5.4 mmol) and methyl cinnamate (5, 8.8 g, 54.1 mmol) in dichloromethane (200 mL), acetonitrile (100 mL) and methanol (100 mL) was placed in a UV reactor flask. The reaction mixture was irradiated under 400 watts UV light for 8 h. After completion, solvent was removed under reduced pressure and the residue was purified over a plug of silica gel eluting the compound with ethyl acetate. The desired fractions were concentrated under reduced pressure to afford rac-methyl 3-chloro-7a-hydroxy-5a-(4-(methylsulfonyl) phenyl)-8-oxo-6-phenyl-5a,6,7a,8-tetrahydro-7H-cyclobuta [5,6]pyrano[3,2-b]pyridine-7-carboxylate (6) as brown solid. Yield: 2.5 g, crude.

Synthesis of rac-methyl (5aR,6S,7R,8aR)-3-chloro-8a-hydroxy-5a-(4-(methylsulfonyl)phenyl)-8-oxo-6-phenyl-5a,7,8,8a-tetrahydro-6H-cyclopenta[4,5]furo [3,2-b]pyridine-7-carboxylate (7)

The crude rac-methyl 3-chloro-7a-hydroxy-5a-(4-(methylsulfonyl)phenyl)-8-oxo-6-phenyl-5a,6,7a,8-tetrahydro-7H-cyclobuta[5,6]pyrano[3,2-b]pyridine-7-carboxylate (6, 2.5 g, 4.8 mmol) was suspended in methanol (30 mL) and treated with 25% sodium methoxide in methanol (15 mL) followed by heating at 80° C. for 2 h. After completion, the solvent was removed under reduced pressure. The crude was diluted with ammonium chloride solution and extracted with ethyl acetate. The organic phase was separated, dried over sodium sulphate and concentrated under reduced pressure to afford rac-methyl (5aR,6S,7R,8aR)-3-chloro-8a-hydroxy-5a-(4-(methylsulfonyl)phenyl)-8-oxo-6-phenyl-5a,7,8,8a-tetrahydro-6H-cyclopenta[4,5]furo[3,2-b]pyridine-7-carboxylate (7). Yield: 1.6 g, crude.

Synthesis of rac-methyl (5aR,6S,7R,8R,8aS)-3-chloro-8,8a-dihydroxy-5a-(4-(methylsulfonyl)phenyl)-6-phenyl-5a,7,8,8a-tetrahydro-6H-cyclopenta[4,5]furo[3,2-b]pyridine-7-carboxylate (8)

To a solution of sodium triacetoxyborohydride (3.96 g, 18.8 mmol), rac-methyl (5aR,6S,7R,8aR)-3-chloro-8a-hydroxy-5a-(4-(methylsulfonyl)phenyl)-8-oxo-6-phenyl-5a,7,8,8a-tetrahydro-6H-cyclopenta[4,5]furo[3,2-b]pyridine-7-carboxylate (7, 1.6 g, 3.1 mmol) in acetonitrile (30 mL), acetic acid (1.87 g, 31.2 mmol) was added. The resulting mixture was stirred for 12 h at room temperature. After completion, the reaction mixture was partitioned between saturated aqueous sodium bicarbonate solution and ethyl acetate. The organic layer was separated and dried over sodium sulphate, filtered and concentrated to give crude. The crude was purified by silica gel column chromatography using 2-3% dichloromethane in methanol as eluent. The desired fractions were concentrated to afford rac-methyl (5aR,6S,7R,8R,8aS)-3-chloro-8,8a-dihydroxy-5a-(4-(methylsulfonyl)phenyl)-6-phenyl-5a,7,8,8a-tetrahydro-6H-cyclopenta[4,5]furo[3,2-b]pyridine-7-carboxylate (8) as brown solid. Yield: 0.6 g, 37.5%; MS (ESI) m/z 516.1[M+1]$^+$.

Synthesis of rac-(5aR,6S,7R,8R,8aS)-3-chloro-8,8a-dihydroxy-5a-(4-(methylsulfonyl)phenyl)-6-phenyl-5a, 7,8,8a-tetrahydro-6H-cyclopenta[4,5]furo[3,2-b]pyridine-7-carboxylic acid (9)

To a solution of rac-methyl (5aR,6S,7R,8R,8aS)-3-chloro-8,8a-dihydroxy-5a-(4-(methylsulfonyl)phenyl)-6-phenyl-5a,7,8,8a-tetrahydro-6H-cyclopenta[4,5]furo[3,2-b]pyridine-7-carboxylate (8, 0.6 g, 1.16 mmol) in methanol, tetrahydrofuran and water (2:1:1, 12 mL), lithium hydroxide (0.27 g, 11.16 mmol) was added and the reaction was stirred for 2 h at room temperature. After completion, the reaction mass was cooled to 0° C. and acidified with 1 M hydrochloric acid to pH ~2-3. The precipitate was filtered and dried under vacuum to afford rac-(5aR,6S,7R,8R,8aS)-3-chloro-8,8a-dihydroxy-5a-(4-(methylsulfonyl)phenyl)-6-phenyl-5a,7,8,8a-tetrahydro-6H-cyclopenta[4,5]furo[3,2-b]pyridine-7-carboxylic acid (9) as off white solid. Yield: 0.45 g, 77.5%; MS (ESI) m/z 502.04[M+1]$^+$.

Synthesis of (5aR,6S,7R,8R,8aS)-3-chloro-8,8a-dihydroxy-N,N-dimethyl-5a-(4-(methylsulfonyl)phenyl)-6-phenyl-5a,7,8,8a-tetrahydro-6H-cyclopenta[4,5]furo[3,2-b]pyridine-7-carboxamide (Cpd. No. 12F)

To a solution of rac-(5aR,6S,7R,8R,8aS)-3-chloro-8,8a-dihydroxy-5a-(4-(methylsulfonyl)phenyl)-6-phenyl-5a,7,8,8a-tetrahydro-6H-cyclopenta[4,5]furo[3,2-b]pyridine-7-carboxylic acid (9, 0.3 g, 0.59 mmol) in dichloromethane (8 mL) at 0° C., 1-ethyl-3-(3-dimethylaminopropyl) carbodiimide (0.28 g, 1.79 mmol), hydroxybenzotriazole (0.27 g, 1.79 mmol) and N,N-diisopropylethylamine (0.46 g, 3.59 mmol) were added and the mixture was stirred for 10 min. Dimethylamine hydrochloride (0.24 g, 2.99 mmol) was then added at the same temperature and the reaction was stirred for 32 h at room temperature. After completion, the reaction mass was diluted with dichloromethane and washed with cold water. The organic layer was separated and dried over sodium sulphate, filtered and concentrated to give crude. The crude was purified by silica gel column chromatography using 2-3% dichloromethane in methanol as eluent. The desired fractions were concentrated under reduced pressure to afford rac-(5aR,6S,7R,8R,8aS)-3-chloro-8,8a-dihydroxy-N,N-dimethyl-5a-(4-(methylsulfonyl)phenyl)-6-phenyl-5a,7,8,8a-tetrahydro-6H-cyclopenta[4,5]furo[3,2-b]pyridine-7-carboxamide (rac-Cpd. No. 12F) as off white solid. The enantiomers were separated by chiral preparative HPLC [chiralpak IB (4.6×250) mm]. Yield: 0.16 g, (racemic mixture). Peak 1 (47 mg), $[\alpha]_D$=196.10 (c 0.1, $CHCl_3$), $R_t$=8.089 min, ee >99%. $^1$H NMR (400 MHz, DMSO-$d_6$) δ: 8.21 (d, J=2.0 Hz, 1H), 7.74 (d, J=2.0 Hz, 1H), 7.58 (d, J=8.4 Hz, 2H), 7.41 (d, J=8.4 Hz, 2H), 7.04 (t, J=7.2 Hz, 2H), 6.96 (t, J=9.6 Hz, 3H), 6.16 (bs, 1H), 5.38 (bs, 1H), 4.77 (d, J=5.2 Hz, 1H), 4.64 (d, J=13.6 Hz, 1H), 4.35 (dd, J=13.2, 5.2 Hz, 1H), 3.28 (s, 3H), 3.03 (s, 3H), 2.78 (s, 3H); MS (ESI) m/z 529.35[M+1]$^+$; UPLC: 99.92%. Peak-2 (Cpd. No. 12F, 44 mg), $[\alpha]_D$−173.2° (c 0.1, $CHCl_3$), $R_t$=16.147 min, ee >99%. $^1$H NMR (400 MHz, DMSO-$d_6$) δ: 8.21 (d, J=2.0 Hz, 1H), 7.74 (d, J=2.0 Hz, 1H), 7.58 (d, J=8.4 Hz, 2H), 7.41 (d, J=8.4 Hz, 2H), 7.04 (t, J=7.2 Hz, 2H), 6.96 (t, J=9.6 Hz, 3H), 6.18 (bs, 1H), 5.36 (bs, 1H), 4.77 (d, J=5.2 Hz, 1H), 4.64 (d, J=13.2 Hz, 1H), 4.35 (dd, J=13.2, 5.2 Hz, 1H), 3.28 (s, 3H), 3.03 (s, 3H), 2.98 (s, 3H); MS (ESI) m/z 529.34[M+1]$^+$ Example 13

Rac-(1R,2R,3S,3aR,8bS)-6-cyano-3a-(4-cyanophenyl)-1,8b-dihydroxy-N,N-dimethyl-3-phenyl-2,3,3a,8b-tetrahydro-1H-benzo[b]cyclopenta[d]thiophene-2-carboxamide (Cpd. No. 13F)

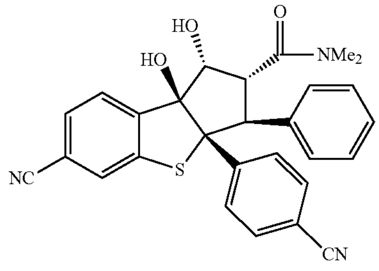

-continued
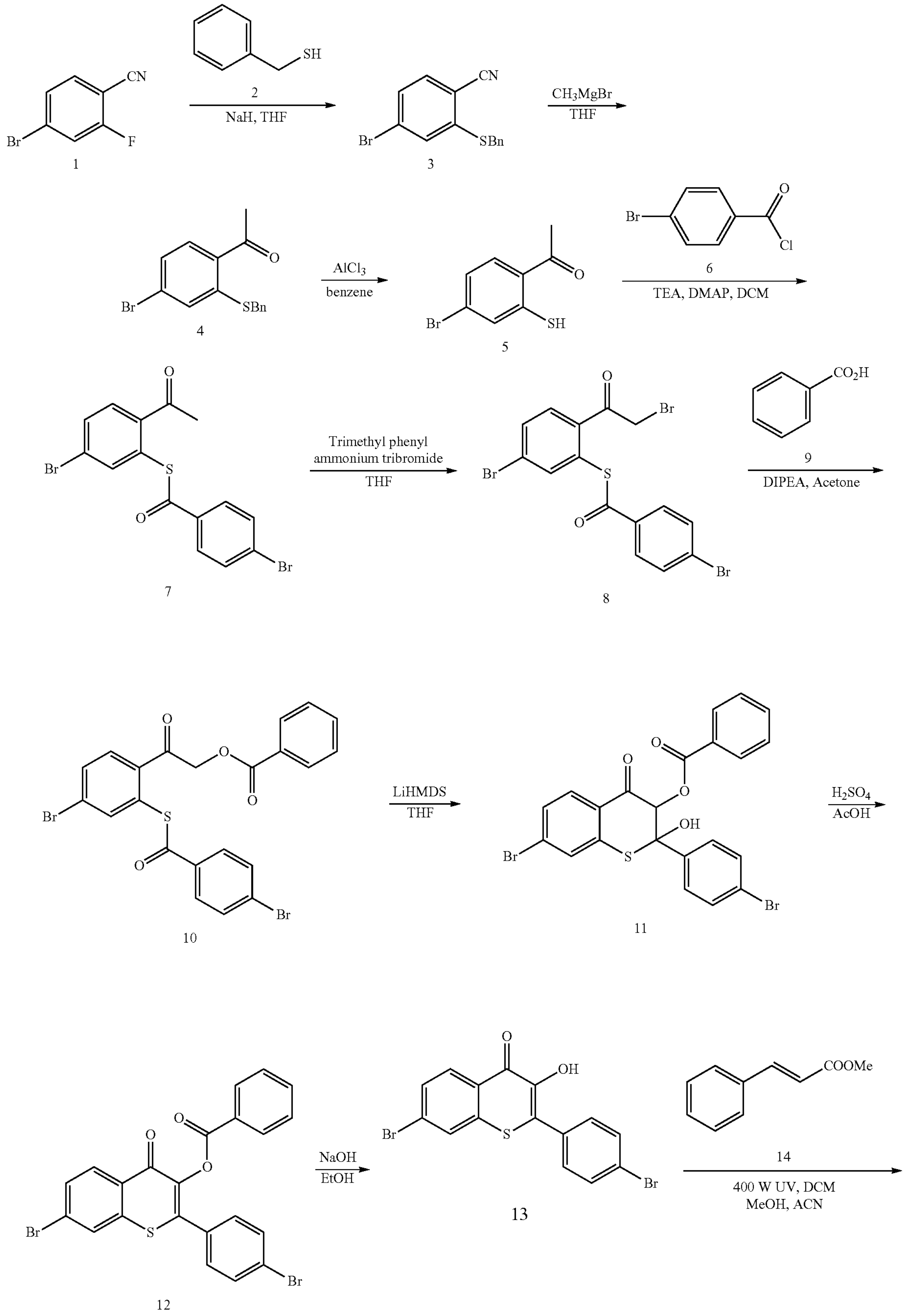

-continued

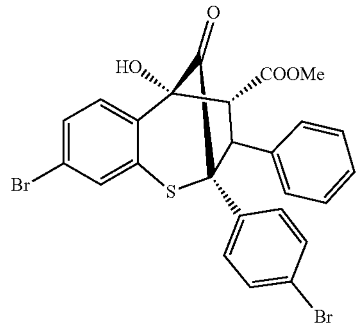

15

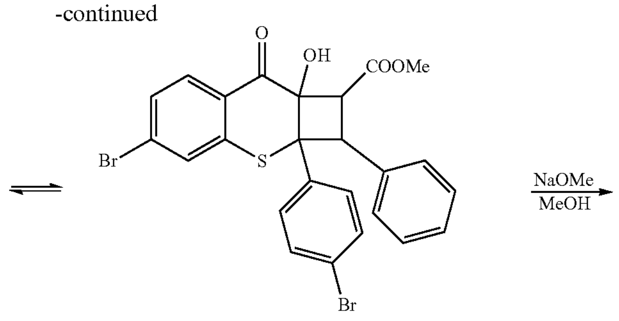

16

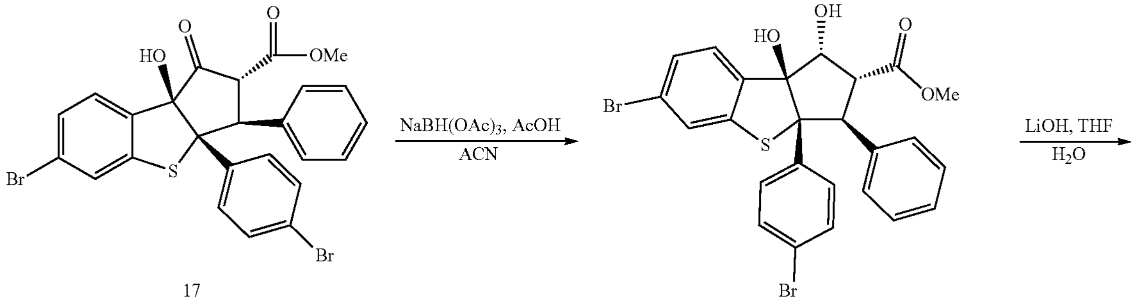

17

18

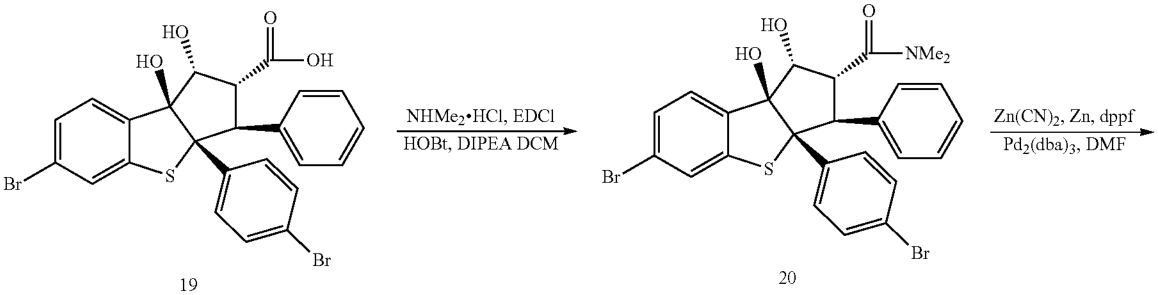

19

20

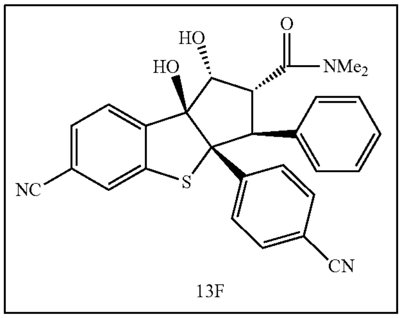

13F

Synthesis of 2-(benzylthio)-4-bromobenzonitrile (3)

To a stirred suspension of sodium hydride (30.15 g, 753.7 mmol) in tetrahydrofuran (1500 mL), benzyl mercaptan (2, 62.4 g, 502.6 mmol) was added slowly at 0° C. and stirred for 15 min. 4-Bromo-2-fluorobenzonitrile (1, 100.0 g, 502.6 mmol) was added slowly at same temperature and then reaction mixture was stirred at room temperature for 1 h. After completion, reaction mass was treated with saturated ammonium chloride solution and extracted with ethyl acetate. The organic layer was separated and dried over anhydrous sodium sulphate, filtered and concentrated under reduced pressure to afford 2-(benzylthio)-4-bromobenzonitrile (3) as yellow solid. Yield: 19.3 g, 62%; MS (ESI) m/z 302.01[M−1]$^-$.

Synthesis of 1-(2-(benzylthio)-4-bromophenyl) ethan-1-one (4)

To a solution of 2-(benzylthio)-4-bromobenzonitrile (3, 90.0 g, 297.0 mmol) in tetrahydrofuran (1000 mL), 3 M methyl magnesium bromide in diethyl ether (290.4 mL, 891.0 mmol) was added drop wise at −10° C. The reaction mass was slowly brought to room temperature and stirred for 16 h. After completion, the reaction mass was acidified with saturated 6 M hydrogen chloride solution and then extracted with ethyl acetate. The organic layer was dried over anhydrous sodium sulphate, filtered and concentrated under reduced pressure to afford 1-(2-(benzylthio)-4-bromophenyl)ethan-1-one (4) as brown solid. Yield: 74.0 g, Crude Synthesis of 1-(4-bromo-2-mercaptophenyl)ethan-1-one (5)

To a solution of aluminum trichloride (74.79 g, 562.50 mmol) in benzene (1200 mL), 1-(2-(benzylthio)-4-bromophenyl)ethan-1-one (4, 60.0 gm, 187.5 mmol) was added at 0° C. The reaction mass was slowly brought to room temperature and stirred for 2 h. After completion, the reaction mass was basified by 1 N sodium hydroxide solution to pH ~8-9 and then washed with ethyl acetate. Then aqueous layer was acidified by 1 M hydrogen chloride solution to pH ~5-6 and then extracted with dichloromethane. The organic layer was dried over anhydrous sodium sulphate, filtered and concentrated under reduced pressure to afford 1-(4-bromo-2-mercaptophenyl)ethan-1-one (5) as yellow solid. Yield: 31.5 g, 73.2%; MS (ESI) m/z 229.09 $[M-1]^-$.

Synthesis of S-(2-acetyl-5-bromophenyl) 4-bromobenzothioate (7)

To a solution of 1-(4-bromo-2-mercaptophenyl)ethan-1-one (5, 21.5 g, 93.4 mmol) in dichloromethane (200 mL), triethylamine (39.2 g, 28.04 mmol) and N,N-dimethylaminopyridine (1.1 g, 9.3 mmol) were added at 0° C., followed by slow addition of 4-bromobenzoyl chloride (6, 30.7 g, 140.2 mmol). The reaction mixture was stirred at room temperature for 1 h. After completion, reaction mass was quenched with cold water and extracted with dichloromethane. The organic layer was dried over anhydrous sodium sulphate, filtered and concentrated under reduced pressure to get the solid which was triturated with pentane to afford S-(2-acetyl-5-bromophenyl) 4-bromobenzothioate (7) as brown solid. Yield: 27.9 g, 72.4%; MS (ESI) m/z 411.04 $[M-1]^-$.

Synthesis of S-(5-bromo-2-(2-bromoacetyl)phenyl)-4-bromobenzothioate (8)

To a solution of S-(2-acetyl-5-bromophenyl) 4-bromobenzothioate (7, 27.0 g, 67.0 mmol) in tetrahydrofuran (300 mL), trimethylphenylammonium tribromide (33.2 g, 88.0 mmol) was added at room temperature. The reaction mass was stirred at 60° C. for 16 h. After completion, reaction mass was cooled and water was added followed by extraction with ethyl acetate. The organic layer was dried over anhydrous sodium sulphate, filtered and concentrated under reduced pressure to afford S-(5-bromo-2-(2-bromoacetyl)phenyl) 4-bromobenzothioate (8) as yellow solid. Yield: 12.5 g, crude.

Synthesis of 2-(4-bromo-2-((4-bromobenzoyl)thio)phenyl)-2-oxoethyl benzoate (10)

To a solution of benzoic acid (9, 2.98 g, 24.48 mmol) in acetone (750 mL), N,N-diisopropylethylamine (3.15 g, 24.48 mmol) was added and mixture was stirred at room temperature for 15 min. The mixture was cooled to 0° C. and S-(5-Bromo-2-(2-bromoacetyl)phenyl)-4-bromobenzothioate (8, 12.0 g, 24.48 mmol) was added. The reaction mass was slowly brought to room temperature and stirred for 2 h. After completion, the solvent was removed under reduced pressure and the residue was diluted with water and extracted with dichloromethane. The organic layer was dried over anhydrous sodium sulphate, filtered and concentrated under reduced pressure. The crude was purified by column chromatography on silica gel (100-200 mesh) using 10% ethyl acetate in hexanes as eluent. The desired fractions were concentrated under reduced pressure to afford 2-(4-bromo-2-((4-bromobenzoyl)thio)phenyl)-2-oxoethyl benzoate (10) as yellow solid. Yield: 4.0 g, crude.

Synthesis of 7-bromo-2-(4-bromophenyl)-2-hydroxy-4-oxothiochroman-3-yl benzoate (11)

To a solution of 2-(4-bromo-2-((4-bromobenzoyl)thio)phenyl)-2-oxoethyl benzoate (10, 4.0 g, 7.53 mmol) in tetrahydrofuran (250 mL), 1 M lithium bis(trimethylsilyl)amide in tetrahydrofuran (22.5 ml, 3.0 mmol) was added at −78° C. The reaction mass was slowly brought to room temperature and stirred for 30 min. After completion, reaction mixture was quenched with saturated ammonium chloride solution and extracted with ethyl acetate. The organic layer was dried over anhydrous sodium sulphate, filtered and concentrated under reduced pressure to afford 7-bromo-2-(4-bromophenyl)-2-hydroxy-4-oxothiochroman-3-yl benzoate (11) as brown solid. Yield: 3.2 g, crude.

Synthesis of 7-bromo-2-(4-bromophenyl)-4-oxo-4H-thiochromen-3-yl benzoate (12)

To a solution of 7-bromo-2-(4-bromophenyl)-2-hydroxy-4-oxothiochroman-3-yl benzoate (11, 3.2 g, 6.2 mmol) in acetic acid (6.4 mL, 2 volumes), sulphuric acid (3.2 mL, 1 volumes) was added drop wise and stirred the mixture for 4 h at room temperature. After completion, crushed ice was added to the reaction and the precipitated solid was filtered, washed with cold water and dried under reduced pressure to afford 7-bromo-2-(4-bromophenyl)-4-oxo-4H-thiochromen-3-yl benzoate (12) as brown solid. Yield: 3.0 g, crude.

Synthesis of 7-bromo-2-(4-bromophenyl)-3-hydroxy-4H-thiochromen-4-one (13)

To a solution of 7-bromo-2-(4-bromophenyl)-4-oxo-4H-thiochromen-3-yl benzoate (12, 3.0 g, 5.8 mmol) in ethanol (10 mL), 10% sodium hydroxide solution (8.9 g, 2.4 mmol) was added and the reaction mixture was stirred for 3 h at 90° C. After completion, the reaction mass was cooled to room temperature and acidified with 1 M hydrogen chloride to pH ~6. The precipitated solid was filtered and dried under vacuum to afford 7-bromo-2-(4-bromophenyl)-3-hydroxy-4H-thiochromen-4-one (13) as brown solid. Yield: 0.8 g, 34%; MS (ESI) m/z 408.98$[M-1]^-$.

Synthesis of rac-methyl (2S,3S,4S,5R)-8-bromo-2-(4-bromophenyl)-5-hydroxy-10-oxo-3-phenyl-2,3,4,5-tetrahydro-2,5-methanobenzo[b]thiepine-4-carboxylate (15/16)

A solution of 7-bromo-2-(4-bromophenyl)-3-hydroxy-4H-thiochromen-4-one (13, 0.8 g, 1.95 mmol) and methyl cinnamate (14, 3.16 g, 19.5 mmol) in dichloromethane (200 mL), acetonitrile (100 mL) and methanol (100 mL) was placed in a UV reactor flask. The reaction mixture was irradiated at 400 watts UV light for 15 h. After completion, the solvent was removed under reduced pressure and the crude was purified by Combi-flash (12 g, RediSep column)

using ethyl acetate as eluent. The desired fractions were concentrated under reduced pressure to afford rac-methyl (2S,3S,4S,5R)-8-bromo-2-(4-bromophenyl)-5-hydroxy-10-oxo-3-phenyl-2,3,4,5-tetrahydro-2,5-methanobenzo[b]thiepine-4-carboxylate (15/16). Yield: 0.6 g, crude.

Synthesis of rac-methyl (2R,3S,3aR,8bS)-6-bromo-3a-(4-bromophenyl)-8b-hydroxy-1-oxo-3-phenyl-2,3,3a,8b-tetrahydro-1H-benzo[b]cyclopenta[d]thiophene-2-carboxylate (17)

The crude methyl (2S,3S,4S,5R)-8-bromo-2-(4-bromophenyl)-5-hydroxy-10-oxo-3-phenyl-2,3,4,5-tetrahydro-2,5-methanobenzo[b]thiepine-4-carboxylate (15, 16, 0.60 g) was suspended in methanol (6 mL) and treated with 25% sodium methoxide in methanol (6 mL). The mixture was then heated at 90° C. for 3 h. After completion, the solvent was removed under reduced pressure and crude was treated with ammonium chloride solution and extracted with ethyl acetate. The organic phase was dried over anhydrous sodium sulphate and concentrated under reduced pressure to afford rac-methyl (2R,3S,3aR,8bS)-6-bromo-3a-(4-bromophenyl)-8b-hydroxy-1-oxo-3-phenyl-2,3,3a,8b-tetrahydro-1H-benzo[b]cyclopenta[d]thiophene-2-carboxylate (17). Yield: 450 mg, crude.

Synthesis of rac-methyl (1R,2R,3S,3aR,8bS)-6-bromo-3a-(4-bromophenyl)-1,8b-dihydroxy-3-phenyl-2,3,3a,8b-tetrahydro-1H-benzo[b]cyclopenta[d]thiophene-2-carboxylate (18)

To a solution of rac-methyl (2R,3S,3aR,8bS)-6-bromo-3a-(4-bromophenyl)-8b-hydroxy-1-oxo-3-phenyl-2,3,3a,8b-tetrahydro-1H-benzo[b]cyclopenta[d]thiophene-2-carboxylate (17, 0.45 g, 0.78 mmol) in acetonitrile (10.0 mL), sodium triacetoxyborohydride (0.99 g, 4.71 mmol) and acetic acid (0.47 mL, 7.85 mmol) were added. The resulting mixture was stirred at room temperature for 6 h. After completion, reaction mixture was partitioned between saturated aqueous sodium bicarbonate solution and ethyl acetate. The organic layer was separated, dried over anhydrous sodium sulphate and concentrated under reduced pressure to get crude. The crude was purified by Combi-flash (4 g, RediSep column) using 30-40% ethyl acetate in hexanes as eluent. The desired fractions were concentrated under reduced pressure to afford rac-methyl (1R,2R,3S,3aR,8bS)-6-bromo-3a-(4-bromophenyl)-1,8b-dihydroxy-3-phenyl-2,3,3a,8b-tetrahydro-1H-benzo[b]cyclopenta[d]thiophene-2-carboxylate (18). Yield: 0.12 g, 26%, MS (ESI) m/z 572.98 $[M-1]^-$.

Synthesis of rac-(R,2R,3S,3aR,8bS)-6-bromo-3a-(4-bromophenyl)-1,8b-dihydroxy-3-phenyl-2,3,3a,8b-tetrahydro-1H-benzo[b]cyclopenta[d]thiophene-2-carboxylic acid (19)

To a solution of rac-methyl (1R,2R,3S,3aR,8bS)-6-bromo-3a-(4-bromophenyl)-1,8b-dihydroxy-3-phenyl-2,3,3a,8b-tetrahydro-1H-benzo[b]cyclopenta[d]thiophene-2-carboxylate (18, 0.12 g, 0.2 mmol) in tetrahydrofuran:water (7:3, 10 mL), lithium hydroxide (0.10 g, 4.18 mmol) was added and the reaction was stirred for 6 h at room temperature. After completion, the reaction mass was cooled to 0° C. and acidified with 1 M hydrogen chloride to pH ~3. The solid precipitated was filtered and dried under vacuum to afford rac-(1R,2R,3S,3aR,8bS)-6-bromo-3a-(4-bromophenyl)-1,8b-dihydroxy-3-phenyl-2,3,3a,8b-tetrahydro-1H-benzo[b]cyclopenta[d]thiophene-2-carboxylic acid (19) as white solid. Yield: 0.10 g, 86%, MS (ESI) m/z 559.05$[M-1]^-$.

Synthesis of rac-(1R,2R,3S,3aR,8bS)-6-bromo-3a-(4-bromophenyl)-1,8b-dihydroxy-N,N-dimethyl-3-phenyl-2,3,3a,8b-tetrahydro-1H-benzo[b]cyclopenta[d]thiophene-2-carboxamide (20)

To a solution of rac-(1R,2R,3S,3aR,8bS)-6-bromo-3a-(4-bromophenyl)-1,8b-dihydroxy-3-phenyl-2,3,3a,8b-tetrahydro-1H-benzo[b]cyclopenta[d]thiophene-2-carboxylic acid (19, 0.10 g, 0.17 mmol) in dichloromethane (10 mL), 1-ethyl-3-(3-dimethylaminopropyl)carbodiimide (0.133 g, 0.69 mmol), hydroxybenzotriazole (0.095 g, 0.7 mmol) and N,N-diisopropylethylamine (0.32 mL, 1.8 mmol) were added at 0° C. and stirred the mixture for 5 min. Dimethylamine hydrochloride (0.10 g, 1.16 mmol) was then added at same temperature and the reaction was stirred at room temperature for 12 h. After completion, reaction mass was diluted with dichloromethane (25 mL) and washed with cold water. The organic layer was separated and dried over anhydrous sodium sulphate, filtered and concentrated under reduced pressure. The crude was purified by Combi-flash (4 g, RediSep column) using 50% ethyl acetate in hexanes as eluent. The appropriate fractions were concentrated under reduced pressure to afford rac-(1R,2R,3S,3aR,8bS)-6-bromo-3a-(4-bromophenyl)-1,8b-dihydroxy-N,N-dimethyl-3-phenyl-2,3,3a,8b-tetrahydro-1H-benzo[b]cyclopenta[d]thiophene-2-carboxamide (20) as white solid. Yield: 80.0 mg, 77%, MS (ESI) m/z 588.10$[M+1]^+$.

Synthesis of rac-(1R,2R,3S,3aR,8bS)-6-cyano-3a-(4-cyanophenyl)-1,8b-dihydroxy-N,N-dimethyl-3-phenyl-2,3,3a,8b-tetrahydro-1H-benzo[b]cyclopenta[d]thiophene-2-carboxamide (Cpd. No. 13F)

To a mixture of rac-(1R,2R,3S,3aR,8bS)-6-bromo-3a-(4-bromophenyl)-1,8b-dihydroxy-N,N-dimethyl-3-phenyl-2,3,3a,8b-tetrahydro-1H-benzo[b]cyclopenta[d]thiophene-2-carboxamide (20, 0.07 g, 0.11 mmol) in dimethylformamide (2 mL) at room temperature, zinc cyanide (0.083 g, 0.71 mmol) and zinc powder (0.011 g, 0.017 mmol) were added and degassed the mixture with argon for 15 min. 1,1'-Bis (diphenylphosphino) ferrocene (0.013 g, 0.002 mmol) and tris(dibenzylideneacetone)dipalladium (0.032 g, 0.003 mmol) were added to the above reaction and degassing was continued for another 5 min followed by heating the reaction at 140° C. for 3 h. After completion, the reaction was cooled to room temperature and passed through celite bed. Filtrate was concentrated under reduced pressure and treated with ice-cold water, the solid precipitated was filtered and purified by Combi-flash (4 g, RediSep column) using 40% ethyl acetate in hexanes as eluent to afford rac-(1R,2R,3S,3aR,8bS)-6-cyano-3a-(4-cyanophenyl)-1,8b-dihydroxy-N,N-dimethyl-3-phenyl-2,3,3a,8b-tetrahydro-1H-benzo[b]cyclopenta[d]thiophene-2-carboxamide (Cpd. No. 13F) as white solid. Yield: 0.018 mg, 31%. MS (ESI) m/z 482.38$[M+1]^+$; UPLC 95.7%; $^1H$ NMR (400 MHz, DMSO-$d_6$) δ: 7.90 (d, J=4.0 Hz, 1H), 7.82 (d, J=8.0 Hz, 1H), 7.60-7.57 (m, 3H), 7.26 (d, J=8.4 Hz, 2H), 7.07-7.06 (m, 3H), 6.78-6.76 (m, 2H), 6.08 (s, 1H), 5.91 (d, J=6.5 Hz, 1H), 5.00 (dd, J=8.3, 6.8 Hz, 1H), 4.32 (d, J=12.2 Hz, 1H), 3.95 (dd, J=12.0, 8.8 Hz, 1H), 3.13 (s, 3H), 2.69 (s, 3H).

Example 14
Rac-(5aR,6S,7R,8R,8aS)-3-cyano-5a-(4-cyanophenyl)-8,8a-dihydroxy-N,N-dimethyl-6-phenyl-5a,7,8,8a-tetrahydro-6H-cyclopenta[4,5]furo[3,2-c]pyridine-7-carboxamide (Cpd. No. 14F)
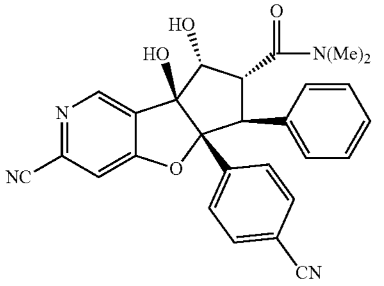
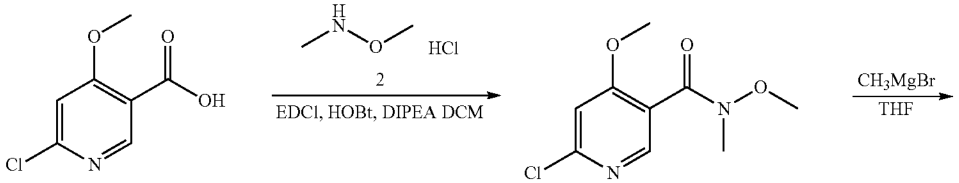
1 3
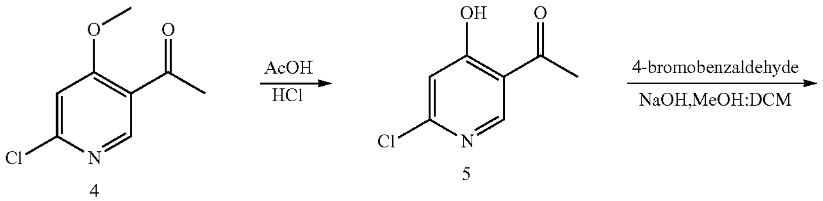
4 5
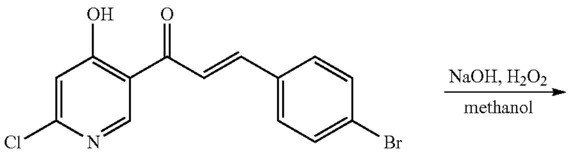
6
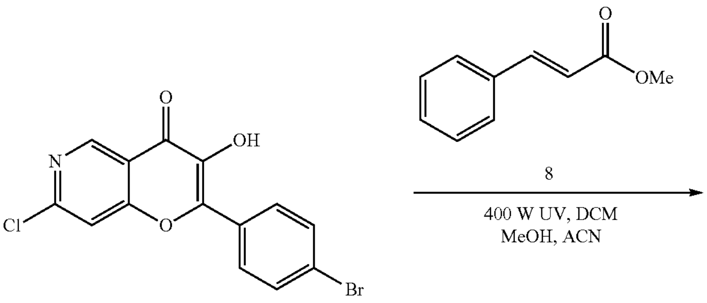
7

-continued

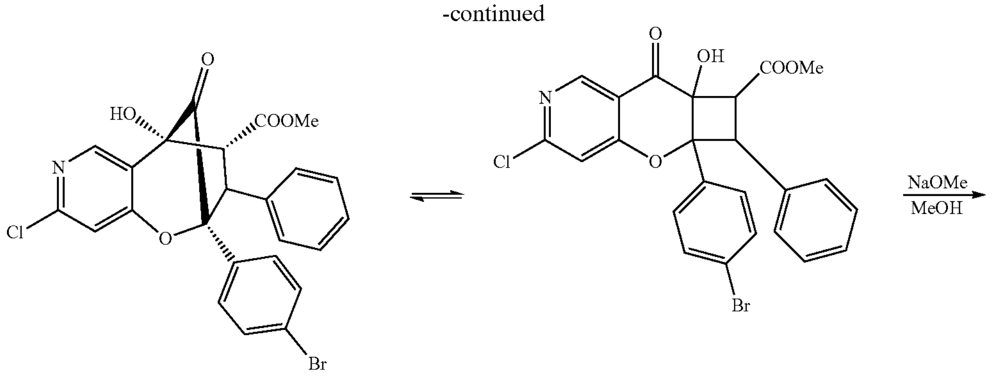

9

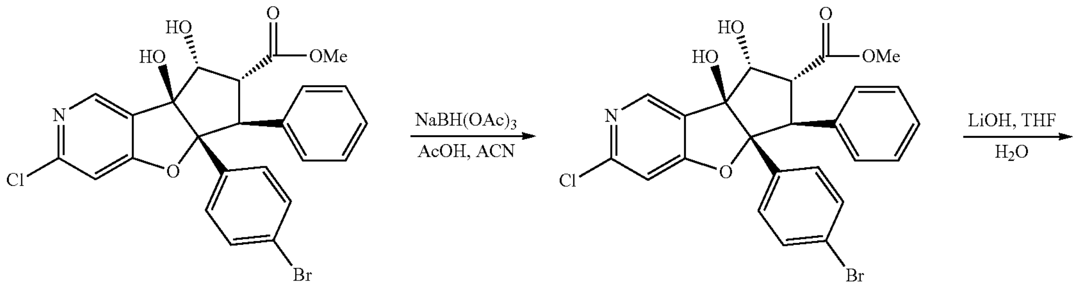

10 11

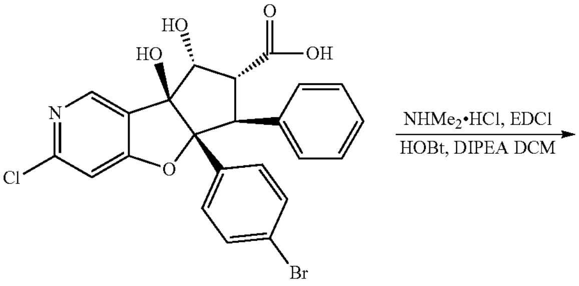

12

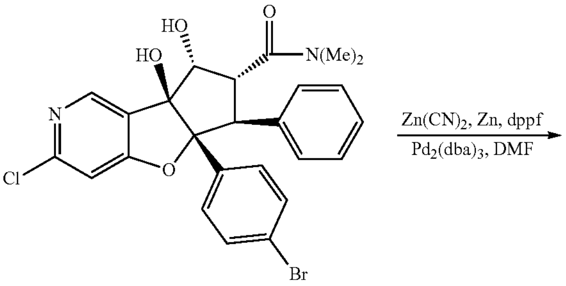

13

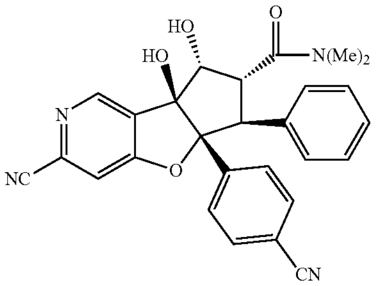

14F

Synthesis of 6-chloro-N,4-dimethoxy-N-methylnicotinamide (3)

To a solution of 6-chloro-4-methoxynicotinic acid (1, 25.0 g, 133.6 mmol) in dichloromethane (300 mL), 1-ethyl-3-(3-dimethylaminopropyl)carbodiimide hydrochloride (38.44 g, 200.5 mmol), 1-hydroxybenzotriazole (30.40 g, 200.4 mmol) and N,N-diisopropylethylamine (69.8 mL, 400.8 mmol) were added at 0° C. and stirred the mixture for 5 min. N,O-dimethylhydroxylamine hydrochloride (2, 19.56 g, 200.53 mmol) was then added at same temperature and the reaction was stirred for 16 h at room temperature. After completion, reaction mass was diluted with dichloromethane and washed with cold water. The organic layer was separated and dried over sodium sulphate, filtered and concentrated to give crude. The crude was re-crystallised in ethanol to afford 6-chloro-N,4-dimethoxy-N-methylnicotinamide (3) as white solid. Yield: 19.3 g, 62%; MS (ESI) m/z 231.17 $[M+1]^+$.

Synthesis of 1-(6-chloro-4-methoxypyridin-3-yl)ethan-1-one (4)

To a solution of 6-chloro-N,4-dimethoxy-N-methylnicotinamide (3, 17.0 g, 73.9 mmol) in dry tetrahydrofuran (200 mL), methyl magnesium bromide (26.43 mL, 221.7 mmol) was added drop wise over a period of 30 min at 0° C. The reaction mass was slowly brought to room temperature and stirred for 2 h. After completion, the reaction mass was treated with saturated ammonium chloride solution and then extracted with ethyl acetate. The organic layer was dried over anhydrous sodium sulfate, filtered and concentrated under reduced pressure to afford 1-(6-chloro-4-methoxy-pyridin-3-yl)ethan-1-one (4) as yellow solid. Yield: 12.0 g, 87%; MS (ESI) m/z 186.17[M+1]$^+$.

Synthesis of 1-(6-chloro-4-hydroxypyridin-3-yl) ethan-1-one (5)

To a solution of 1-(6-chloro-4-methoxypyridin-3-yl) ethan-1-one (4, 10.0 g, 54.0 mmol) in acetic acid (30.0 mL), 6 M hydrogen chloride (60.0 mL) was added. The reaction mixture was refluxed at 100° C. for 16 h. After completion, the reaction mass was concentrated under reduced pressure and diluted with water, cooled to 0° C. and basified with 10% NaOH solution to pH ~9-10 and extracted with ethyl acetate. The organic layer was concentrated to recover starting material. The aqueous layer was cooled to 0° C. and acidified with 6 M hydrogen chloride. The precipitated solid was filtered and dried to afford 1-(6-chloro-4-hydroxypyridin-3-yl)ethan-1-one (5) as brown solid. Yield: 6.3 g, 68.4%; MS (ESI) m/z 170.08 [M−1]$^-$.

Synthesis of (E)-3-(4-bromophenyl)-1-(6-chloro-4-hydroxypyridin-3-yl)prop-2-en-1-one (6)

To a solution of 1-(6-chloro-4-hydroxypyridin-3-yl) ethan-1-one (5, 5.5 g, 32.0 mmol) in methanol: dichloromethane (50:20 mL), sodium hydroxide (3.84 g, 96.0 mmol) was added followed by addition of 4-bromobenzaldehyde (6.5 g, 35.0 mmol) and the reaction mixture was heated at 90° C. for 1 h. After completion, reaction mass was cooled and obtained solid was filtered, washed with water and dried under vacuum to afford of (E)-3-(4-bromophenyl)-1-(6-chloro-4-hydroxypyridin-3-yl)prop-2-en-1-one (6) as yellow solid. Yield: 10.5 g, 95%; MS (ESI) m/z 338.08 [M+1]$^+$.

Synthesis of 2-(4-bromophenyl)-7-chloro-3-hydroxy-4H-pyrano[3,2-c]pyridin-4-one (7)

To a solution of (E)-3-(4-bromophenyl)-1-(6-chloro-4-hydroxypyridin-3-yl)prop-2-en-1-one (6, 10.0 g, 29.0 mmol) in methanol (150 mL), 10% sodium hydroxide (36 mL, 88.0 mmol) was added followed by addition of hydrogen peroxide (6.57 mL, 58.0 mmol) at room temperature. The reaction mass was stirred for 1 h (exotherm was observed). After completion, reaction mass was cooled and neutralized with 6 M hydrogen chloride to pH ~7. The precipitated solid was filtered and dried under vacuum to afford 2-(4-bromophenyl)-7-chloro-3-hydroxy-4H-pyrano [3,2-c]pyridin-4-one (7) as yellow solid. Yield: 3.1 g, 30%; MS (ESI) m/z 350.08[M−1]$^-$.

Synthesis of rac-methyl (2S,3S,4S,5R)-2-(4-bromophenyl)-8-chloro-5-hydroxy-10-oxo-3-phenyl-2,3,4,5-tetrahydro-2,5-methanooxepino[3,2-c]pyridine-4-carboxylate (9)

A solution of 2-(4-bromophenyl)-7-chloro-3-hydroxy-4H-pyrano[3,2-c]pyridin-4-one (7, 3.1 g, 8.5 mmol) and methyl cinnamate (8, 13.82 g, 85.0 mmol) in dichloromethane (200 mL), acetonitrile (100 mL) and methanol (100 mL) was placed in a UV reactor flask. The reaction mixture was irradiated for 24 h under 400 watts UV light. After completion, the solvent was removed under reduced pressure and the residue was purified over a plug of silica gel eluting the compound with ethyl acetate. The desired fractions were concentrated under reduced pressure to afford rac-methyl (2S,3S,4S,5R)-2-(4-bromophenyl)-8-chloro-5-hydroxy-10-oxo-3-phenyl-2,3,4,5-tetrahydro-2,5-methanooxepino[3,2-c]pyridine-4-carboxylate (9). Yield: 3.1 g, crude.

Synthesis of rac-methyl (5aR,6S,7R,8aR)-5a-(4-bromophenyl)-3-chloro-8a-hydroxy-8-oxo-6-phenyl-5a, 7,8,8a-tetrahydro-6H-cyclopenta[4,5]furo[3,2-c] pyridine-7-carboxylate (10)

The crude rac-methyl (2S,3S,4S,5R)-2-(4-bromophenyl)-8-chloro-5-hydroxy-10-oxo-3-phenyl-2,3,4,5-tetrahydro-2,5-methanooxepino[3,2-c]pyridine-4-carboxylate (9, 3.1 g) was suspended in methanol (30 mL) and treated with sodium methoxide (25% in methanol, 20 mL) and heated the mixture to 90° C. for 3 h. After completion, the solvent was removed under reduced pressure, diluted the mixture with ammonium chloride solution and extracted with ethyl acetate. The organic phase was separated, dried over sodium sulphate and concentrated under reduced pressure to afford rac-methyl (5aR,6S,7R,8aR)-5a-(4-bromophenyl)-3-chloro-8a-hydroxy-8-oxo-6-phenyl-5a,7,8,8a-tetrahydro-6H-cyclopenta[4,5]furo[3,2-c]pyridine-7-carboxylate (10). Yield: 2.2 g, crude.

Synthesis of rac-methyl (5aR,6S,7R,8R,8aS)-5a-(4-bromophenyl)-3-chloro-8,8a-dihydroxy-6-phenyl-5a, 7,8,8a-tetrahydro-6H-cyclopenta[4,5]furo[3,2-c] pyridine-7-carboxylate (11)

To a solution of sodium triacetoxyborohydride (5.2 g, 24.0 mmol), rac-methyl (5aR,6S,7R,8aR)-5a-(4-bromophenyl)-3-chloro-8a-hydroxy-8-oxo-6-phenyl-5a,7,8,8a-tetrahydro-6H-cyclopenta[4,5]furo[3,2-c]pyridine-7-carboxylate (10, 2.1 g) in acetonitrile (50 mL), acetic acid (2.4 mL, 40.0 mmol) was added. The resulting mixture was stirred for 4 h at room temperature. After completion, reaction mixture was partitioned between saturated aqueous sodium bicarbonate solution and ethyl acetate. The organic layer was separated, dried over sodium sulphate and concentrated under reduced pressure to get the crude. The crude was purified by silica gel column chromatography eluting with 30% ethyl acetate in hexanes. The desired fractions were concentrated to afford rac-methyl (5aR,6S,7R,8R,8aS)-5a-(4-bromophenyl)-3-chloro-8,8a-dihydroxy-6-phenyl-5a,7,8,8a-tetrahydro-6H-cyclopenta[4,5]furo[3,2-c]pyridine-7-carboxylate (11) as off white solid. Yield: 1.21 g, 57.6%; MS (ESI) m/z 516.22 [M+1]$^+$.

Synthesis of rac-(5aR,6S,7R,8R,8aS)-5a-(4-bromophenyl)-3-chloro-8,8a-dihydroxy-6-phenyl-5a,7,8, 8a-tetrahydro-6H-cyclopenta[4,5]furo[3,2-c]pyridine-7-carboxylic acid (12)

To a solution of rac-methyl (5aR,6S,7R,8R,8aS)-5a-(4-bromophenyl)-3-chloro-8,8a-dihydroxy-6-phenyl-5a,7,8, 8a-tetrahydro-6H-cyclopenta[4,5]furo[3,2-c]pyridine-7-carboxylate (11, 1.2 g, 2.3 mmol) in tetrahydrofuran and water (3:1, 15 mL), lithium hydroxide (0.55 g, 23.0 mmol) was added and the reaction was stirred for 16 h at room temperature. After completion, the reaction mass was cooled to 0° C. and acidified with 1M hydrogen chloride to pH ~3. The precipitated solid was filtered and dried under vacuum to afford rac-(5aR,6S,7R,8R,8aS)-5a-(4-bromophenyl)-3-chloro-8,8a-dihydroxy-6-phenyl-5a,7,8,8a-tetrahydro-6H-cyclopenta[4,5]furo[3,2-c]pyridine-7-carboxylic acid (12) as off white solid. Yield: 1.05 g, 90%; MS (ESI) m/z 502.06[M+1]$^+$.

Synthesis of rac-(5aR,6S,7R,8R,8aS)-5a-(4-bromophenyl)-3-chloro-8,8a-dihydroxy-N,N-dimethyl-6-phenyl-5a,7,8,8a-tetrahydro-6H-cyclopenta[4,5]furo[3,2-c]pyridine-7-carboxamide (13)

To a solution of rac-(5aR,6S,7R,8R,8aS)-5a-(4-bromophenyl)-3-chloro-8,8a-dihydroxy-6-phenyl-5a,7,8,8a-tetrahydro-6H-cyclopenta[4,5]furo[3,2-c]pyridine-7-carboxylic acid (12, 0.7 g, 13.9 mmol) in dichloromethane (50 mL), 1-ethyl-3-(3-dimethylaminopropyl)carbodiimide hydrochloride (0.8 g, 4.17 mmol), 1-hydroxybenzotriazole (0.63 g, 4.17 mmol) and N,N-diisopropylethylamine (1.43 mL, 8.3 mmol) were added at 0° C. and stirred the mixture for 5 min. Dimethylamine hydrochloride (0.56 g, 6.9 mmol) was then added at same temperature and the mixture was stirred for 16 h at 40° C. After completion, reaction mass was diluted with dichloromethane and washed with cold water. The organic layer was separated and dried over sodium sulphate, filtered and concentrated to give crude. The crude was purified by silica gel column chromatography eluting with 70% ethyl acetate in hexanes. The desired fractions were concentrated to afford rac-(5aR,6S,7R,8R,8aS)-5a-(4-bromophenyl)-3-chloro-8,8a-dihydroxy-N,N-dimethyl-6-phenyl-5a,7,8,8a-tetrahydro-6H-cyclopenta[4,5]furo[3,2-c]pyridine-7-carboxamide (13) as white solid. Yield: 0.52 g, 71%; MS (ESI) m/z 523.21 [M+1]$^+$.

Synthesis of rac-(5aR,6S,7R,8R,8aS)-3-cyano-5a-(4-cyanophenyl)-8,8a-dihydroxy-N,N-dimethyl-6-phenyl-5a,7,8,8a-tetrahydro-6H-cyclopenta[4,5]furo[3,2-c]pyridine-7-carboxamide (Cpd. No. 14F)

To a solution of rac-(5aR,6S,7R,8R,8aS)-5a-(4-bromophenyl)-3-chloro-8,8a-dihydroxy-N,N-dimethyl-6-phenyl-5a,7,8,8a-tetrahydro-6H-cyclopenta[4,5]furo[3,2-c]pyridine-7-carboxamide (13, 0.5 g, 0.94 mmol) in N,N-dimethylformamide (10.0 mL), zinc cyanide (0.66 g, 5.6 mmol) and zinc (0.007 g, 0.11 mmol) were added at room temperature and degassed the mixture with argon for 15 min. 1,1'-Bis(diphenylphosphino)ferrocene (0.013 g, 0.018 mmol), tris(dibenzylideneacetone)dipalladium (0.026 g, 0.028 mmol) were added to the reaction and degassing was continued for another 5 min. The reaction mixture was heated at 150° C. for 2 h. After completion, the reaction was cooled to room temperature and passed through celite bed. The filtrate was diluted with ethyl acetate and washed with water. The organic layer was separated, dried over sodium sulphate and concentrated under reduced pressure to get the crude. The crude was purified by silica gel column chromatography eluting with 70% ethyl acetate in hexanes. The desired fractions were concentrated under reduced pressure to afford rac-(5aR,6S,7R,8R,8aS)-3-cyano-5a-(4-cyanophenyl)-8,8a-dihydroxy-N,N-dimethyl-6-phenyl-5a,7,8,8a-tetrahydro-6H-cyclopenta[4,5]furo[3,2-c]pyridine-7-carboxamide (Cpd. No. 14F) as white solid. Yield: 0.15 g, 34%; MS (ESI) m/z 467.20 [M+1]$^+$. $^1$H NMR (400 MHz, DMSO-$d_6$) 8.64 (s, 1H), 7.97 (s, 1H), 7.60 (d, J=8.8 Hz, 2H), 7.38 (d, J=8.4 Hz, 2H), 7.06-6.98 (m, 3H), 6.84 (d, J=6.8 Hz, 2H), 6.13 (s, 1H), 5.98 (d, J=6.4 Hz, 1H), 4.95 (t, J=6.8 Hz, 1H), 4.27-4.14 (m, 2H), 3.23 (s, 3H), 2.73 (s, 3H).

Example 15

Rac-(4bS,5R,6R,7S,7aR)-7a-(4-cyanophenyl)-4b,5-dihydroxy-2-methoxy-N,N-dimethyl-7-phenyl-4b,6,7,7a-tetrahydro-5H-cyclopenta[4,5]furo[2,3-b]pyridine-6-carboxamide (Cpd. No. 15F)

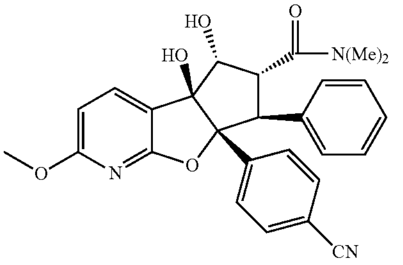

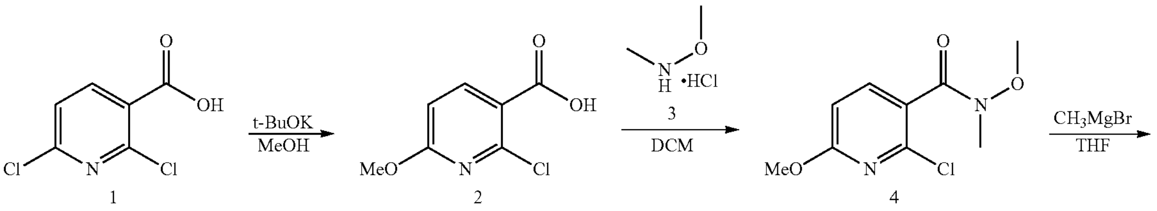

-continued
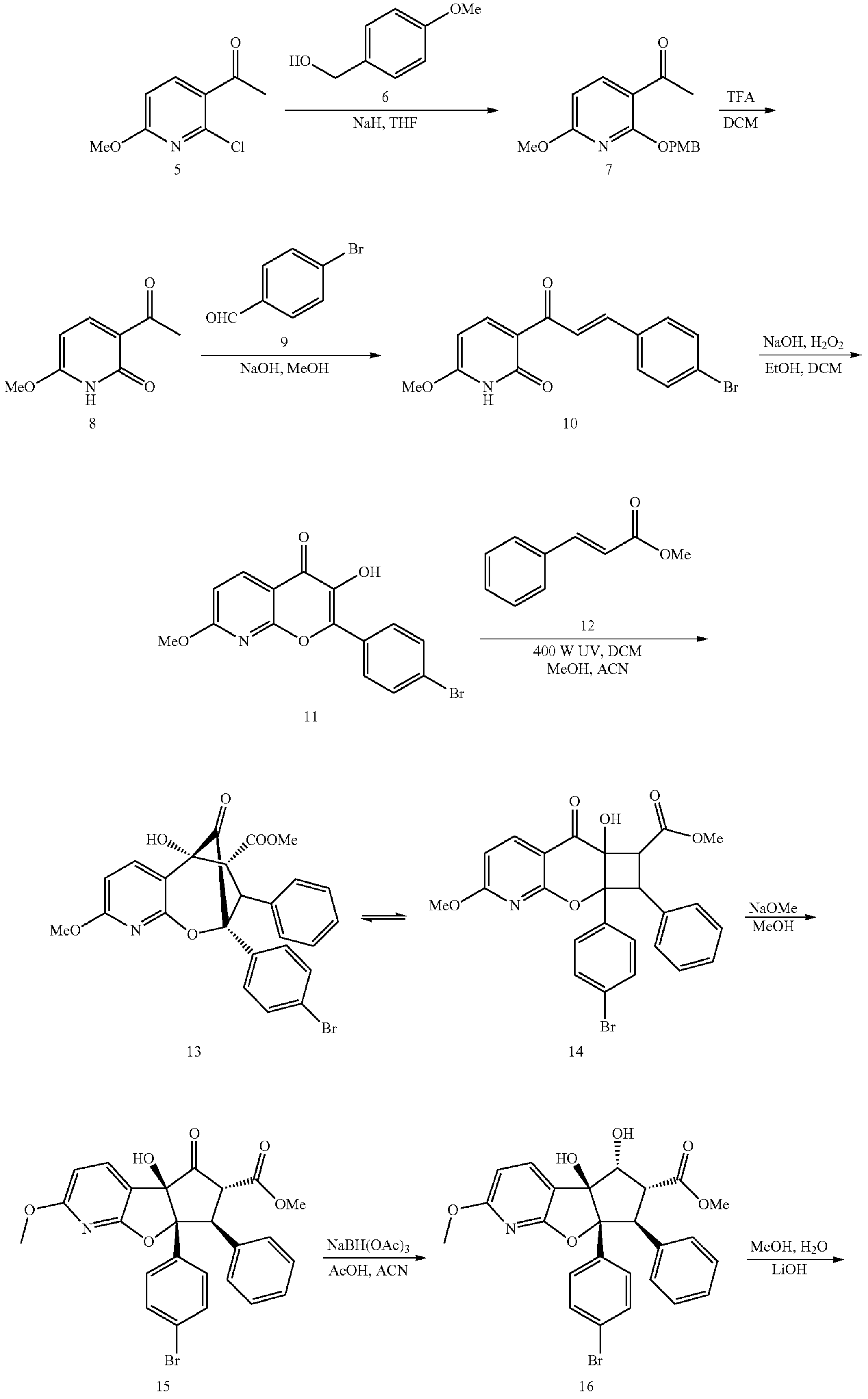

-continued

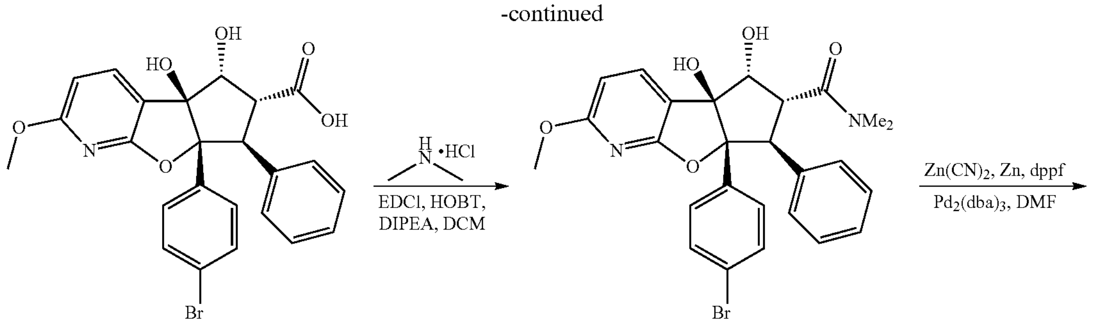

17 18

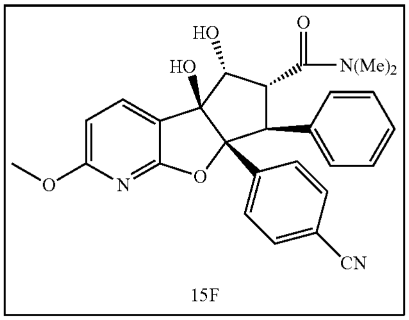

15F

Synthesis of 2-chloro-6-methoxynicotinic acid (2)

To a suspension of 2,6-dichloronicotinic acid (1, 20.0 g, 105.2 mmol) in methanol (250 mL) under nitrogen, potassium tert-butoxide (35.0 g, 316.0 mol) was added at room temperature. The reaction mixture was allowed to stir at 80° C. for 24 h. After completion, solvent was removed under reduced pressure and crude was treated with 6 M hydrogen chloride. Precipitated solid was filtered and dried under vacuum to afford 2-chloro-6-methoxynicotinic acid (2) as white solid. Yield: 20.0 g, crude; MS (ESI) m/z 188.06[M+1]$^+$.

Synthesis of 2-chloro-N,6-dimethoxy-N-methylnicotinamide (4)

To a solution of 2-chloro-6-methoxynicotinic acid (2, 20.0 g, 107.52 mmol) in dichloromethane (400 mL), 1-ethyl-3-(3-dimethylaminopropyl)carbodiimide hydrochloride (30.6 g, 161.0 mmol), 1-hydroxybenzotriazole (21.6 g, 161.0 mmol) and N,N-diisopropylethylamine (46.6 mL, 322.5 mmol) were added at 0° C. and stirred the mixture for 5 min. N,O-dimethylhydroxylamine hydrochloride (3, 12.4 g, 129.0 mmol) was then added at same temperature and the reaction was stirred at room temperature for 4 h. After completion, reaction mass was diluted with dichloromethane and washed with cold water. The organic layer was separated and dried over anhydrous sodium sulphate, filtered and concentrated to afford 2-chloro-N,6-dimethoxy-N-methylnicotinamide (4) as yellow solid. Yield: 18.0 g, 58.3%; MS (ESI) m/z 231.15[M+1]$^+$.

Synthesis of 1-(2-chloro-6-methoxypyridin-3-yl) ethan-1-one (5)

To a solution of 2-chloro-N,6-dimethoxy-N-methylnicotinamide (4, 18.0 g, 78.2 mmol) in dry tetrahydrofuran (200 mL), 3 M methyl magnesium bromide in diethyl ether (52.0 mL, 156.5 mmol) was added drop wise over a period of 30 min at 0° C. The reaction mass was slowly brought to room temperature and stirred for 2 h. After completion, the reaction mass was treated with saturated ammonium chloride solution and then extracted with ethyl acetate. The organic layer was dried over anhydrous sodium sulphate, filtered and concentrated under reduced pressure to afford 1-(2-chloro-6-methoxypyridin-3-yl)ethan-1-one (5) as yellow solid. Yield: 14.0 g, crude; MS (ESI) m/z 186.14[M+1]$^+$.

Synthesis of 1-(6-methoxy-2-((4-methoxybenzyl) oxy)pyridin-3-yl)ethan-1-one (7)

To a solution of 1-(2-chloro-6-methoxypyridin-3-yl) ethan-1-one (5, 14.0 g, 75.6 mmol) in tetrahydrofuran (100 mL) under nitrogen, sodium hydride (4.5 g, 113.4 mol) was added at 0° C. and stirred for 10 min. 4-methoxybenzyl alcohol (6, 11.0 mL, 75.6 mmol) was added drop wise over a period of 30 min at 0° C. and stirred at room temperature for 2 h. After completion, the reaction mass was diluted with water (200 mL) and then extracted with ethyl acetate (2×150 mL). The organic layer was dried over anhydrous sodium sulphate, filtered and concentrated under reduced pressure to get the crude. The crude was purified by column chromatography on silica gel (100-200 mesh) using 20% ethyl acetate in hexanes as eluent. The desired fractions were concentrated under reduced pressure to afford 1-(6-methoxy-2-((4-methoxybenzyl)oxy)pyridin-3-yl)ethan-1-one (7) as yellow solid. Yield: 10.5 g, 48.3%; MS (ESI) m/z 288.23[M+1]$^+$.

Synthesis of 3-acetyl-6-methoxypyridin-2(1H)-one (8)

To a cool solution of 1-(6-methoxy-2-((4-methoxybenzyl) oxy)pyridin-3-yl)ethan-1-one (7, 10.5 g, 36.6 mmol) in dichloromethane (100 mL), trifluoroacetic acid (2.0 mL) was added at 0° C. and the reaction mixture was stirred at room temperature for 2 h. After completion, saturated solution of sodium bicarbonate was added to the reaction mixture and extracted with dichloromethane. The organic layer was dried over anhydrous sodium sulphate, filtered and concentrated under reduced pressure to afford 3-acetyl-6-methoxypyridin-2(1H)-one (8) as yellow solid. Yield: 5.0 g, crude; MS (ESI) m/z 168.17[M+1]$^+$.

Synthesis of (E)-3-(3-(4-bromophenyl)acryloyl)-6-methoxypyridin-2(1H)-one (10)

To a solution of 3-acetyl-6-methoxypyridin-2(1H)-one (8, 4.5 g, 26.4 mmol) in methanol (30.0 mL), sodium hydroxide (3.17 g, 79.4 mmol) and 4-bromobenzaldehyde (9, 5.3 g, 29.1 mmol) were added. The reaction mixture was heated at 80° C. for 2 h. After completion, reaction mass was cooled and obtained solid was filtered, washed with water and dried under vacuum to afford (E)-3-(3-(4-bromophenyl)acryloyl)-6-methoxypyridin-2(1H)-one (10) as yellow solid. Yield: 8.5 g, crude; MS (ESI) m/z 332.11[M−1]$^-$.

Synthesis of 2-(4-bromophenyl)-3-hydroxy-7-methoxy-4H-pyrano[2,3-b]pyridin-4-one (11)

To a solution (E)-3-(3-(4-bromophenyl)acryloyl)-6-methoxypyridin-2(1H)-one (10, 6 g, 17.8 mmol) in ethanol/dichloromethane (1:1, 200 mL), sodium hydroxide (10%, 50 mL, 124.6 mmol) was added followed by addition of 30% hydrogen peroxide (14.1 mL, 124.6 mmol) at room temperature. The reaction mass was stirred for 2 h (excessive exotherm was observed so precaution must be taken). After completion, reaction mass was cooled to 0° C. and pH was adjusted to 8 using 6 M hydrochloric acid. The solvents were removed under reduced pressure and solid was filtered. The solid was suspended in ethanol and neutralized by addition of 6 M hydrogen chloride (pH ~6) at 0° C. The precipitated solid was filtered and dried under vacuum to afford 2-(4-bromophenyl)-3-hydroxy-7-methoxy-4H-pyrano[2,3-b]pyridin-4-one (11) as yellow solid. Yield: 3.2 g, 41%; MS (ESI) m/z 348.16[M+1]$^+$.

Synthesis of rac-methyl (2S,4R,5R)-2-(4-bromophenyl)-5-hydroxy-8-methoxy-10-oxo-3-phenyl-2,3,4,5-tetrahydro-2,5-methanooxepino[2,3-b]pyridine-4-carboxylate (13/14)

A solution of 2-(4-bromophenyl)-3-hydroxy-7-methoxy-4H-pyrano[2,3-b]pyridin-4-one (11, 3.0 g, 8.6 mmol) and methyl cinnamate (12, 1.4 g, 86.4 mmol) in dichloromethane (200 mL), acetonitrile (100 mL) and methanol (100 mL) was placed in a UV reactor flask. The reaction mixture was irradiated for 16 h under 400 watts UV light. After completion, the solvent was removed under reduced pressure and the residue was purified by Combi-flash (12 g, RediSep) using ethyl acetate as eluent. The desired fractions were concentrated under reduced pressure to afford rac-methyl (2S,4R,5R)-2-(4-bromophenyl)-5-hydroxy-8-methoxy-10-oxo-3-phenyl-2,3,4,5-tetrahydro-2,5-methanooxepino[2,3-b]pyridine-4-carboxylate (13/14) as yellow solid. Yield: 1.3 g, crude. MS(ESI) m/z 508.33[M−1]$^-$.

Synthesis of rac-methyl (4bR,6R,7S,7aR)-7a-(4-bromophenyl)-4b-hydroxy-2-methoxy-5-oxo-7-phenyl-4b,6,7,7a-tetrahydro-5H-cyclopenta[4,5]furo[2,3-b]pyridine-6-carboxylate (15)

The crude rac-methyl (2S,4R,5R)-2-(4-bromophenyl)-5-hydroxy-8-methoxy-10-oxo-3-phenyl-2,3,4,5-tetrahydro-2,5-methanooxepino[2,3-b]pyridine-4-carboxylate (13/14, 1.3 g) was suspended in methanol (13.0 mL) and treated with sodium methoxide (25% in methanol, 13.0 mL) and heated the mixture to 80° C. for 2 h. After completion, the solvent was removed under reduced pressure and the reaction was diluted with ammonium chloride solution and extracted with ethyl acetate. The organic phase was separated, dried over anhydrous sodium sulphate, filtered and concentrated under reduced pressure to afford rac-methyl (4bR,6R,7S,7aR)-7a-(4-bromophenyl)-4b-hydroxy-2-methoxy-5-oxo-7-phenyl-4b,6,7,7a-tetrahydro-5H-cyclopenta[4,5]furo[2,3-b]pyridine-6-carboxylate (15) as brown solid. Yield: 1.1 g, crude; MS (ESI) m/z 508.33[M−1]$^-$.

Synthesis of rac-methyl (4bS,5R,6R,7S,7aR)-7a-(4-bromophenyl)-4b,5-dihydroxy-2-methoxy-7-phenyl-4b,6,7,7a-tetrahydro-5H-cyclopenta[4,5]furo[2,3-b]pyridine-6-carboxylate (16)

To a solution of rac-methyl (4bR,6R,7S,7aR)-7a-(4-bromophenyl)-4b-hydroxy-2-methoxy-5-oxo-7-phenyl-4b,6,7,7a-tetrahydro-5H-cyclopenta[4,5]furo[2,3-b]pyridine-6-carboxylate (15, 1.0 g, 2.1 mmol) in acetonitrile (20.0 mL), sodium triacetoxyborohydride (2.7 g, 12.9 mmol) and acetic acid (1.23 mL, 22.0 mmol) were added. The resulting mixture was stirred for 4 h at room temperature. After completion, reaction mixture was partitioned between saturated aqueous sodium bicarbonate solution and ethyl acetate. The organic layer was separated, dried over anhydrous sodium sulphate, filtered and concentrated under reduced pressure to afford rac-methyl (4bS,5R,6R,7S,7aR)-7a-(4-bromophenyl)-4b,5-dihydroxy-2-methoxy-7-phenyl-4b,6,7,7a-tetrahydro-5H-cyclopenta[4,5]furo[2,3-b]pyridine-6-carboxylate (16) as white solid. Yield: 120 mg, 12%; MS (ESI) m/z 512.32[M+1]$^+$.

Synthesis of rac-(4bS,5R,6R,7S,7aR)-7a-(4-bromophenyl)-4b,5-dihydroxy-2-methoxy-7-phenyl-4b,6,7,7a-tetrahydro-5H-cyclopenta[4,5]furo[2,3-b]pyridine-6-carboxylic acid (17)

To a solution of rac-methyl (4bS,5R,6R,7S,7aR)-7a-(4-bromophenyl)-4b,5-dihydroxy-2-methoxy-7-phenyl-4b,6,7,7a-tetrahydro-5H-cyclopenta[4,5]furo[2,3-b]pyridine-6-carboxylate (16, 110 mg, 0.21 mmol) in methanol and water (2:1, 6.0 mL), lithium hydroxide (20.0 mg, 0.86 mmol) was added and the reaction was stirred for 16 h at room temperature. After completion, the reaction mass was cooled to 0° C. and acidified with 1 M hydrogen chloride to pH ~3. The precipitated solid was filtered and dried under vacuum to afford rac-(4bS,5R,6R,7S,7aR)-7a-(4-bromophenyl)-4b,5-dihydroxy-2-methoxy-7-phenyl-4b,6,7,7a-tetrahydro-5H-cyclopenta[4,5]furo[2,3-b]pyridine-6-carboxylic acid (17) as brown solid. Yield: 100 mg, 93%; MS (ESI) m/z 496.16 [M−1]$^-$.

Synthesis of rac-(4bS,5R,6R,7S,7aR)-7a-(4-bromophenyl)-4b,5-dihydroxy-2-methoxy-N,N-dimethyl-7-phenyl-4b,6,7,7a-tetrahydro-5H-cyclopenta[4,5]furo[2,3-b]pyridine-6-carboxamide (18)

To a solution of rac-(4bS,5R,6R,7S,7aR)-7a-(4-bromophenyl)-4b,5-dihydroxy-2-methoxy-7-phenyl-4b,6,7,7a-tetrahydro-5H-cyclopenta[4,5]furo[2,3-b]pyridine-6-carboxylic acid (17, 100 mg, 0.20 mmol) in dichloromethane (10.0 mL), 1-ethyl-3-(3-dimethylaminopropyl)carbodiimide hydrochloride (96.0 mg, 0.50 mmol), 1-hydroxybenzotriazole (76.0 mg, 0.50 mmol) and N,N-diisopropylethylamine (0.213 mL, 1.2 mmol) were added at 0° C. and stirred the mixture for 5 min. Dimethylamine hydrochloride (81.0 mg, 1.0 mmol) was then added at same temperature and the mixture was stirred for 6 h at room temperature. After completion, reaction mass was diluted with dichloromethane and washed with cold water. The organic layer was separated and dried over anhydrous sodium sulphate, filtered and concentrated to give crude. The crude was purified by Combi-flash (4 g, RediSep) using 70% ethyl acetate in hexanes as eluent. The desired fractions were concentrated under reduced pressure to afford rac-(4bS,5R,6R,7S,7aR)-7a-(4-bromophenyl)-4b,5-dihydroxy-2-methoxy-N,N-dimethyl-7-phenyl-4b,6,7,7a-tetrahydro-5H-cyclopenta[4,5]furo[2,3-b]pyridine-6-carboxamide (18) as off white solid. Yield: 40.0 mg, 37.9%; MS (ESI) m/z 525.28[M+1]$^+$.

Synthesis of rac-(4bS,5R,6R,7S,7aR)-7a-(4-cyanophenyl)-4b,5-dihydroxy-2-methoxy-N,N-dimethyl-7-phenyl-4b,6,7,7a-tetrahydro-SH-cyclopenta[4,5]furo[2,3-b]pyridine-6-carboxamide (Cpd. No. 15F)

To a solution of rac-(4bS,5R,6R,7S,7aR)-7a-(4-bromophenyl)-4b,5-dihydroxy-2-methoxy-N,N-dimethyl-7-phenyl-4b,6,7,7a-tetrahydro-5H-cyclopenta[4,5]furo[2,3-b]pyridine-6-carboxamide (18, 40.0 mg, 0.076 mmol) in N,N-dimethylformamide (5.0 mL), zinc cyanide (18.0 mg, 0.152 mmol) and zinc (25.0 mg, 0.38 mmol) were added at room temperature and degassed the mixture with argon for 15 min. 1,1'-Bis(diphenylphosphino)ferrocene (4.0 mg, 0.015 mmol), tris(dibenzylideneacetone) dipalladium (7.1 mg, 0.015 mmol) were added to the reaction and degassing was continued for another 5 min. The reaction mixture was heated at 140° C. for 6 h. After completion, the reaction was cooled to room temperature and passed through celite bed. The filtrate was diluted with ethyl acetate and washed with water. The organic layer was separated, dried over anhydrous sodium sulphate, filtered and concentrated under reduced pressure to get the crude. The crude was purified by reverse phase HPLC and the desired fractions were concentrated under reduced pressure to afford rac-(4bS,5R,6R,7S,7aR)-7a-(4-cyanophenyl)-4b,5-dihydroxy-2-methoxy-N,N-dimethyl-7-phenyl-4b,6,7,7a-tetrahydro-5H-cyclopenta[4,5]furo[2,3-b]pyridine-6-carboxamide (Cpd. No. 15F) as off white solid. Yield: 8.0 mg, 23%; MS (ESI) m/z 472.44[M+1]$^+$; $^1$H NMR (400 MHz, DMSO-$d_6$) δ 7.75 (d, J=8.0 Hz, 1H), 7.58 (d, J=8.4 Hz, 2H), 7.40 (d, J=8.1 Hz, 2H), 7.06-6.97 (m, 3H), 6.85 (d, J=7.12 Hz, 2H), 6.46 (d, J=8.0 Hz, 1H), 5.69 (d, J=6.0 Hz, 1H), 5.57 (s, 1H), 4.92 (t, J=7.7 Hz, 1H), 4.26 (d, J=13.1 Hz, 1H), 4.12 (dd, J=13.0, 8.0 Hz, 1H), 3.88 (s, 3H), 3.22 (s, 3H), 2.72 (s, 3H).

Example 16

(5aR,6S,7R,8R,8aS)-3-chloro-5a-(4-(difluoromethyl)phenyl)-8,8a-dihydroxy-N,N-dimethyl-6-phenyl-5a,7,8,8a-tetrahydro-6H-cyclopenta[4,5]furo[3,2-b]pyridine-7-carboxamide (Cpd. No. 16F)

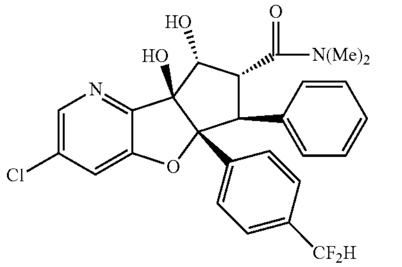

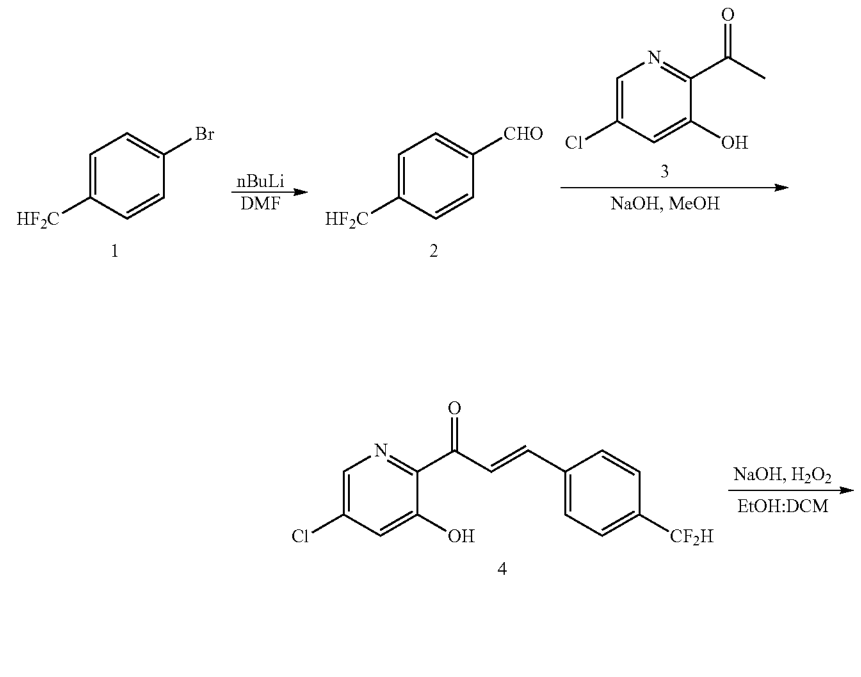

-continued

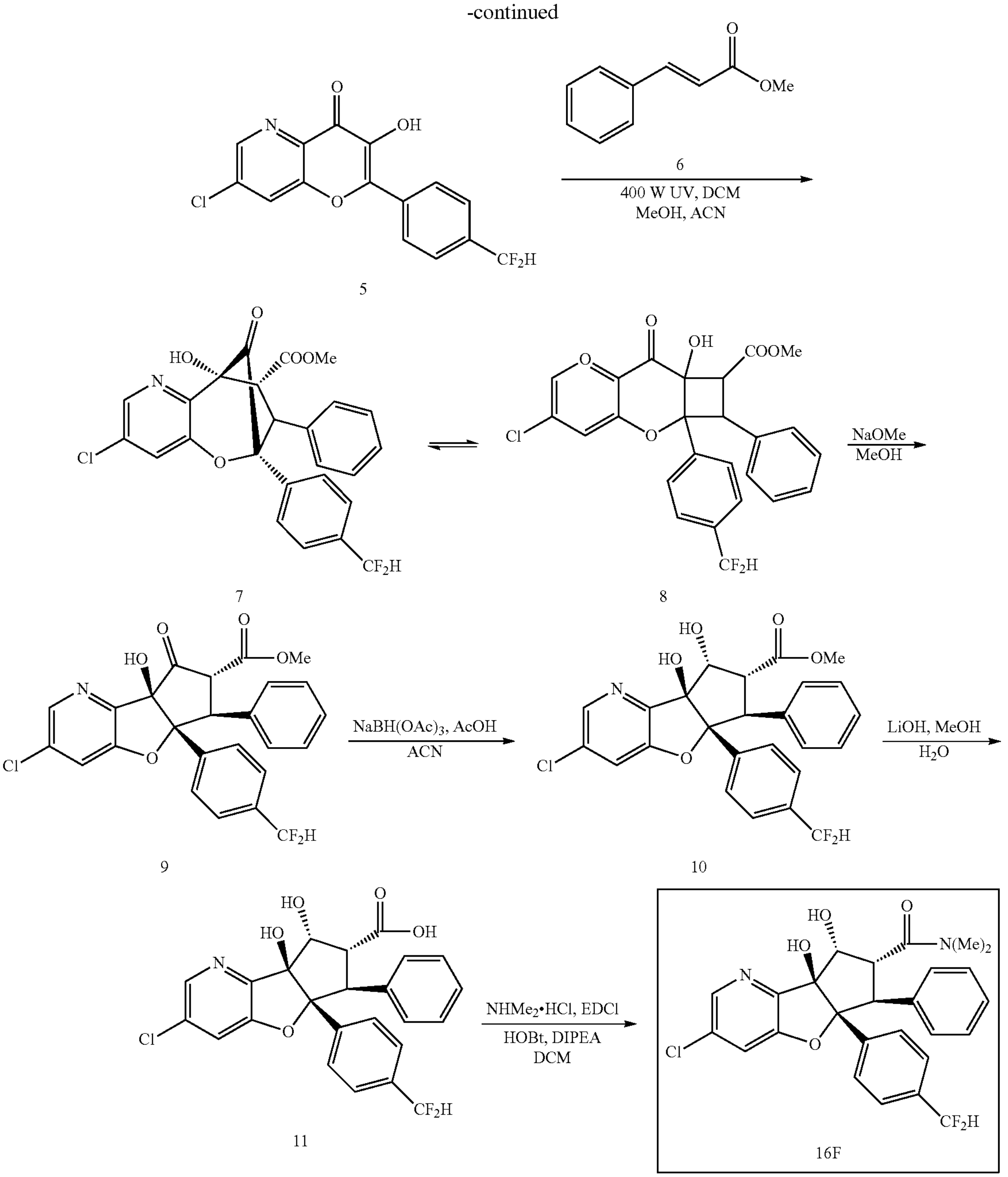

5 7 8 9 10 11 16F

Synthesis of 4-(difluoromethyl)benzaldehyde (2)

To a solution of 1-bromo-4-(difluoromethyl)benzene (1, 20.0 g, 96.6 mmol) in dry tetrahydrofuran (200 mL), n-butyl lithium in hexane (2.5 M, 38.6 mL, 96.6 mmol) was added drop wise over a period of 30 min at −78° C. The reaction mass was stirred for 1 h at −78° C. and N,N-dimethylformamide (35.3 mL, 579.6 mmol) was added at same temperature and reaction was stirred for 1 h. After completion, the reaction mass was brought to 0° C. and treated with saturated ammonium chloride solution and extracted with ethyl acetate. The organic layer was dried over anhydrous sodium sulphate, filtered and concentrated under reduced pressure. The crude was purified by Combi-flash (12 g, RediSep column) using 2% ethyl acetate in hexanes as eluent. The desired fraction were concentrated below 30° C. under reduced pressure to afford 4-(difluoromethyl)benzaldehyde (2) as light yellow liquid (Used freshly prepared compound, highly unstable). Yield: 9.0 g, 59.7%; MS (ESI) m/z: poor ionization.

Synthesis of (E)-1-(5-chloro-3-hydroxypyridin-2-yl)-3-(4-(difluoromethyl)phenyl)prop-2-en-1-one (4)

To a solution of 1-(5-chloro-3-hydroxypyridin-2-yl) ethan-1-one (3, 10.4 g, 60.8 mmol) in methanol (50 mL), sodium hydroxide (7.3 g, 182.4 mmol) and 4-(difluoromethyl)benzaldehyde (2, 9.5 g, 60.8 mmol) were added and the reaction mixture was heated at 90° C. for 1 h. After completion, reaction mass was cooled and obtained solid was filtered, washed with water and dried under vacuum to afford (E)-1-(5-chloro-3-hydroxypyridin-2-yl)-3-(4-(difluoromethyl)phenyl)prop-2-en-1-one (4) as yellow solid. Yield: 20.0 g, crude; MS (ESI) m/z 308.3[M−1]$^-$.

Synthesis of 7-chloro-2-(4-(difluoromethyl)phenyl)-3-hydroxy-4H-pyrano[3,2-b]pyridin-4-one (5)

To a solution of (E)-1-(5-chloro-3-hydroxypyridin-2-yl)-3-(4-(difluoromethyl)phenyl)prop-2-en-1-one (4, 20.0 g, 64.7 mmol) in ethanol: dichloromethane (150 mL), 10% sodium hydroxide (129 mL, 323.6 mmol) was added followed by addition of hydrogen peroxide (26.5 mL, 226.4 mmol) at room temperature. The reaction mass was stirred for 1 h (exotherm was observed). After completion, reaction mixture was cooled and neutralized with 6 M hydrogen chloride to pH ~7. The solvents were distilled off and precipitated solid was filtered and dried under vacuum to afford 7-chloro-2-(4-(difluoromethyl)phenyl)-3-hydroxy-4H-pyrano[3,2-b]pyridin-4-one (5) as yellow solid. Yield: 3.0 g, 13%; MS (ESI) m/z 322.17[M−1]$^-$.

Synthesis of rac-methyl (6S,7S,8S,9R)-3-chloro-6-(4-(difluoromethyl)phenyl)-9-hydroxy-10-oxo-7-phenyl-6,7,8,9-tetrahydro-6,9-methanooxepino[3,2-b]pyridine-8-carboxylate (7/8)

A solution of 7-chloro-2-(4-(difluoromethyl)phenyl)-3-hydroxy-4H-pyrano[3,2-b]pyridin-4-one (5, 3.0 g, 8.5 mmol) and methyl cinnamate (6, 13.82 g, 85.0 mmol) in dichloromethane (200 mL), acetonitrile (100 mL) and methanol (100 mL) was placed in a UV reactor flask. The reaction mixture was irradiated for 16 h under 400 watts UV light. After completion, the solvent was removed under reduced pressure and the crude was purified by Combi-flash (12 g, RediSep column) using ethyl acetate as eluent. The desired fractions were concentrated under reduced pressure to afford rac-methyl (6S,7S,8S,9R)-3-chloro-6-(4-(difluoromethyl)phenyl)-9-hydroxy-10-oxo-7-phenyl-6,7,8,9-tetrahydro-6,9-methanooxepino[3,2-b]pyridine-8-carboxylate (7/8) as brown solid. Yield: 3.0 g, crude.

Synthesis of rac-methyl (5aR,6S,7R,8aR)-3-chloro-5a-(4-(difluoromethyl)phenyl)-8a-hydroxy-8-oxo-6-phenyl-5a,7,8,8a-tetrahydro-6H-cyclopenta[4,5]furo[3,2-b]pyridine-7-carboxylate (9)

The crude methyl (6S,7S,8S,9R)-3-chloro-6-(4-(difluoromethyl)phenyl)-9-hydroxy-10-oxo-7-phenyl-6,7,8,9-tetrahydro-6,9-methanooxepino[3,2-b]pyridine-8-carboxylate (7, 8, 3.0 g) was suspended in methanol (30 mL) and treated with sodium methoxide (25% in methanol, 25 mL) and heated the mixture to 90° C. for 3 h. After completion, the solvent was removed under reduced pressure and mixture was diluted with ammonium chloride solution and extracted with ethyl acetate. The organic phase was separated, dried over anhydrous sodium sulphate, filtered and concentrated under reduced pressure to afford rac-methyl (5aR,6S,7R,8aR)-3-chloro-5a-(4-(difluoromethyl)phenyl)-8a-hydroxy-8-oxo-6-phenyl-5a,7,8,8a-tetrahydro-6H-cyclopenta[4,5]furo[3,2-b]pyridine-7-carboxylate (9) as brown solid. Yield: 2.5 g, crude.

Synthesis of rac-methyl (5aR,6S,7R,8R,8aS)-3-chloro-5a-(4-(difluoromethyl)phenyl)-8,8a-dihydroxy-6-phenyl-5a, 7,8,8a-tetrahydro-6H-cyclopenta[4,5]furo[3,2-b]pyridine-7-carboxylate (10)

To a solution of sodium triacetoxyborohydride (5.2 g, 24.0 mmol), methyl (5aR,6S,7R,8aR)-3-chloro-5a-(4-(difluoromethyl)phenyl)-8a-hydroxy-8-oxo-6-phenyl-5a,7,8,8a-tetrahydro-6H-cyclopenta[4,5]furo[3,2-b]pyridine-7-carboxylate (9, 2.5 g) in acetonitrile (50 mL), acetic acid (2.4 mL, 40.0 mmol) was added. The resulting mixture was stirred at room temperature for 4 h. After completion, reaction mixture was partitioned between saturated aqueous sodium bicarbonate solution and ethyl acetate. The organic layer was separated, dried over sodium sulphate and concentrated under reduced pressure to get the crude. The crude was purified by Combi-flash (12 g, RediSep) using 30% ethyl acetate in hexanes as eluent. The desired fractions were concentrated under reduced pressure to afford rac-methyl (5aR,6S,7R,8R,8aS)-3-chloro-5a-(4-(difluoromethyl)phenyl)-8,8a-dihydroxy-6-phenyl-5a,7,8,8a-tetrahydro-6H-cyclopenta[4,5]furo[3,2-b]pyridine-7-carboxylate (10) as off white solid. Yield: 1.0 g, 33%; MS (ESI) m/z 486.29[M−1]$^-$.

Synthesis of rac-(5aR,6S,7R,8R,8aS)-3-chloro-5a-(4-(difluoromethyl)phenyl)-8,8a-dihydroxy-6-phenyl-5a,7,8,8a-tetrahydro-6H-cyclopenta[4,5]furo[3,2-b]pyridine-7-carboxylic acid (11)

To a solution of rac-methyl (5aR,6S,7R,8R,8aS)-3-chloro-5a-(4-(difluoromethyl)phenyl)-8,8a-dihydroxy-6-phenyl-5a,7,8,8a-tetrahydro-6H-cyclopenta[4,5]furo[3,2-b]pyridine-7-carboxylate (10, 1.2 g, 2.3 mmol) in methanol and water (3:1, 16 mL), lithium hydroxide (0.55 g, 23.0 mmol) was added and the reaction was stirred at room temperature for 16 h. After completion, the reaction mass was cooled to 0° C. and acidified with 1 M hydrogen chloride to pH ~3. The precipitated solid was filtered and dried under vacuum to afford rac-(5aR,6S,7R,8R,8aS)-3-chloro-5a-(4-(difluoromethyl)phenyl)-8,8a-dihydroxy-6-phenyl-5a,7,8,8a-tetrahydro-6H-cyclopenta[4,5]furo[3,2-b]pyridine-7-carboxylic acid (11) as off yellow solid. Yield: 1.05 g, 93%; MS (ESI) m/z 472.2[M−1]$^-$.

Synthesis of (5aR,6S,7R,8R,8aS)-3-chloro-5a-(4-(difluoromethyl)phenyl)-8,8a-dihydroxy-N,N-dimethyl-6-phenyl-5a,7,8,8a-tetrahydro-6H-cyclopenta[4,5]furo[3,2-b]pyridine-7-carboxamide (Cpd. No. 16F)

To a solution of rac-(5aR,6S,7R,8R,8aS)-3-chloro-5a-(4-(difluoromethyl)phenyl)-8,8a-dihydroxy-6-phenyl-5a,7,8,8a-tetrahydro-6H-cyclopenta[4,5]furo[3,2-b]pyridine-7-carboxylic acid (11, 0.6 g, 13.9 mmol) in dichloromethane (50 mL), 1-ethyl-3-(3-dimethylaminopropyl)carbodiimide hydrochloride (0.72 g, 3.7 mmol), 1-hydroxybenzotriazole (0.513 g, 6.33 mmol) and N,N-diisopropylethylamine (1.34 mL, 7.59 mmol) were added at 0° C. and stirred the mixture for 5 min. Dimethylamine hydrochloride (0.514 g, 6.33 mmol) was then added at same temperature and the mixture was stirred for 16 h at 40° C. After completion, reaction mass was diluted with dichloromethane and washed with cold water. The organic layer was separated and dried over anhydrous sodium sulphate, filtered and concentrated to give crude.

The crude was purified by Combi-flash (4 g, RediSep) using 70% ethyl acetate in hexanes as eluent. The desired fractions were concentrated under reduced pressure to afford rac-(5aR,6S,7R,8R,8aS)-3-chloro-5a-(4-(difluoromethyl)phenyl)-8,8a-dihydroxy-N,N-dimethyl-6-phenyl-5a,7,8,8a-tetrahydro-6H-cyclopenta[4,5]furo[3,2-b]pyridine-7-carboxamide (rac-Cpd. No. 16F) as white solid. The enantiomers were separated by chiral preparative HPLC [chiralpak ID (4.6×250) mm]. Yield: 400 mg, 63.5%; Peak 1 (116 mg), $[\alpha]_D$+218.2° (c 0.25, $CHCl_3$), $R_t$=8.37 min, ee >99%; MS (ESI) m/z 501.40[M+1]$^+$; UPLC: 99.38%; $^1H$ NMR (400 MHz, DMSO-$d_6$) δ 8.20 (d, J=2.0 Hz, 1H), 7.72 (d, J=2.0 Hz, 1H), 7.28-7.22 (m, 4H), 7.03-6.91 (m, 5H), 6.85 (t, J=56.0 Hz, 1H), 6.06 (s, 1H), 5.30 (d, J=5.6 Hz, 1H), 4.76 (t, J=5.6 Hz, 1H), 4.60 (d, J=13.2 Hz, 1H), 4.30 (dd, J=13.2, 5.2 Hz, 1H), 3.28 (s, 3H), 2.78 (s, 3H); Peak-2 (Cpd. No. 16F, 129 mg), $[\alpha]_D$−190° (c 0.28, $CHCl_3$), $R_t$=18.28 min, ee >99%; MS (ESI) m/z 501.40[M+1]$^+$; UPLC: 99.29%; $^1H$ NMR (400 MHz, DMSO-$d_6$) δ 8.20 (d, J=2.0 Hz, 1H), 7.72 (d, J=2.0 Hz, 1H), 7.28 (dd, J=16.8 Hz, 8.4 Hz, 4H), 7.03-6.91 (m, 5H), 6.85 (t, J=56.0 Hz, 1H), 6.06 (s, 1H), 5.30 (d, J=5.6 Hz, 1H), 4.76 (t, J=5.6 Hz, 1H), 4.60 (d, J=13.2 Hz, 1H), 4.30 (dd, J=13.2, 5.2 Hz, 1H), 3.28 (s, 3H), 2.79 (s, 3H).

Example 17

(5aR,6S,7R,8R,8aS)-3-chloro-8,8a-dihydroxy-N,N-dimethyl-6-phenyl-5a-(4-(trifluoromethoxy)phenyl)-5a,7,8,8a-tetrahydro-6H-cyclopenta[4,5]furo[3,2-b]pyridine-7-carboxamide (Cpd. No. 171F)

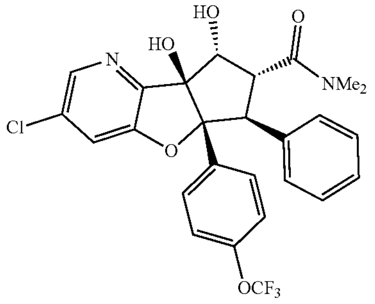

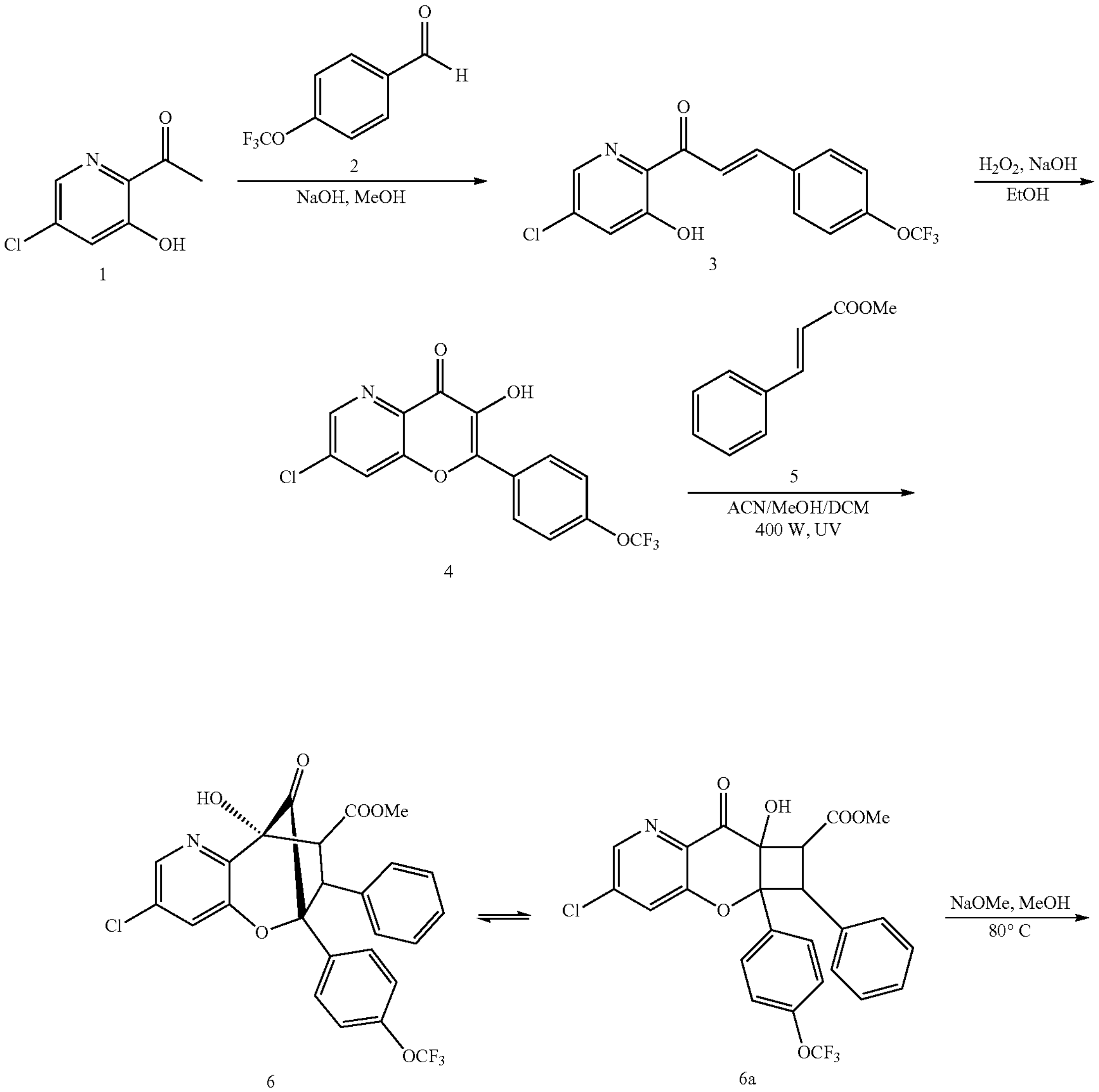

-continued

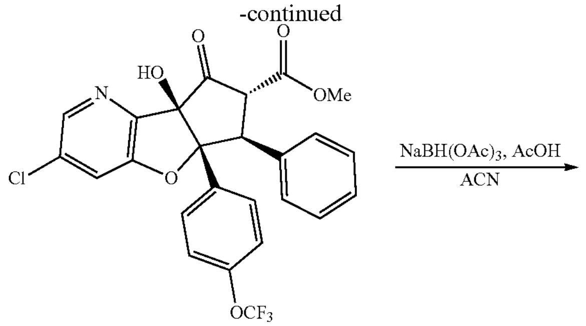

7

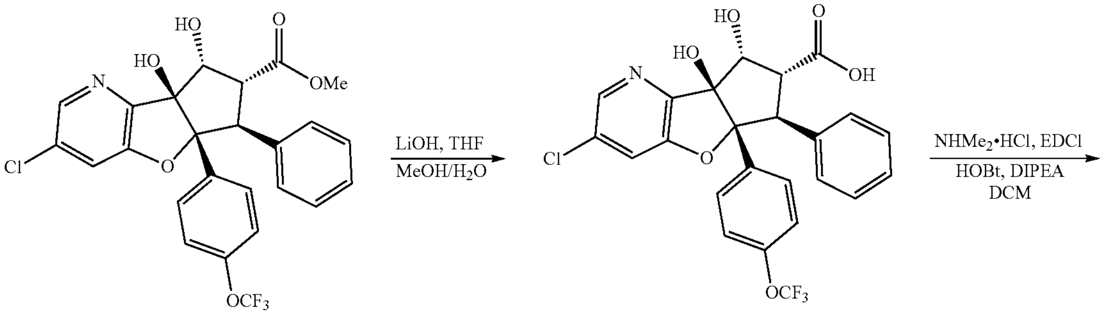

8 9

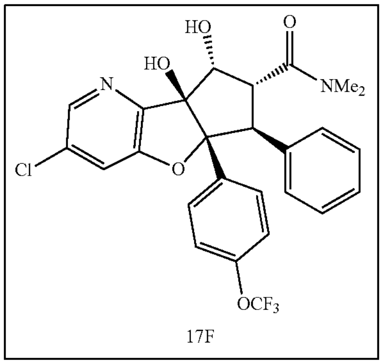

17F

Synthesis of (E)-1-(5-chloro-3-hydroxypyridin-2-yl)-3-(4-(trifluoromethoxy)phenyl)prop-2-en-1-one (3)

To a solution of 1-(5-chloro-3-hydroxypyridin-2-yl)ethan-1-one (1, 7.0 g, 40.7 mmol) and 4-(trifluoromethoxy)benzaldehyde (2, 7.75 g, 40.7 mmol) in methanol (35 mL), sodium hydroxide (4.89 g, 122.3 mmol) was added and the mixture was heated to refluxed for 30 min. After completion, the reaction mass was cooled to room temperature and diluted with water (50 mL). The precipitated solid was filtered, washed with water, n-pentane and dried under vacuum to afford (E)-1-(5-chloro-3-hydroxypyridin-2-yl)-3-(4-(trifluoromethoxy)phenyl)prop-2-en-1-one (3) as yellow solid. Yield: 7.1 g, 50.0%; MS (ESI) m/z 342.18$[M-1]^-$.

Synthesis of 7-chloro-3-hydroxy-2-(4-(trifluoromethoxy)phenyl)-4H-pyrano[3,2-b]pyridin-4-one (4)

To a solution of (E)-1-(5-chloro-3-hydroxypyridin-2-yl)-3-(4-(trifluoromethoxy)phenyl)prop-2-en-1-one (3, 5.0 g, 14.5 mmol) in ethanol (50 mL) at 0° C., 10% aqueous sodium hydroxide (4.01 g, 101.5 mmol) was added followed by the addition of 30% aqueous hydrogen peroxide (11.15 mL, 101.5 mmol). The reaction mass was stirred for 30 min at room temperature (exotherm was observed). After completion, the reaction mass was cooled and neutralized by the addition of 6 M hydrogen chloride to pH ~7. The solid obtained was filtered, washed with ethanol, pentane and dried under vacuum to afford 7-chloro-3-hydroxy-2-(4-(trifluoromethoxy)phenyl)-4H-pyrano[3,2-b]pyridin-4-one (4) as white solid. Yield: 2.8 g, 51%; MS (ESI) m/z 356.14$[M+1]^+$.

Synthesis of rac-methyl (7S,8S,9R)-3-chloro-9-hydroxy-10-oxo-7-phenyl-6-(4-(trifluoromethoxy)phenyl)-6,7,8,9-tetrahydro-6,9-methanooxepino[3,2-b]pyridine-8-carboxylate (6/6a)

A solution of 7-chloro-3-hydroxy-2-(4-(trifluoromethoxy)phenyl)-4H-pyrano[3,2-b]pyridin-4-one (4, 2.8 g, 7.8 mmol) and methyl cinnamate (5, 12.69 g, 7.8 mmol) in dichloromethane (200 mL), acetonitrile (100 mL) and methanol (100 mL) was placed in a UV reactor flask. The reaction mixture was irradiated under 400 watts UV light for 24 h. After completion, solvent was removed under reduced pressure and the residue was purified over a plug of silica gel eluting the compound with 5% methanol in dichloromethane. The desired fractions were concentrated under reduced pressure to afford rac-methyl (7S,8S,9R)-3-chloro-9-hydroxy-10-oxo-7-phenyl-6-(4-(trifluoromethoxy)phenyl)-6,7,8,9-tetrahydro-6,9-methanooxepino[3,2-b]pyridine-8-carboxylate (6/6a) as brown solid. Yield: 3.0 g, crude.

Synthesis of rac-methyl (5aR,6S,7R,8aR)-3-chloro-8a-hydroxy-8-oxo-6-phenyl-5a-(4-(trifluoromethoxy)phenyl)-5a, 7,8,8a-tetrahydro-6H-cyclopenta[4,5]furo[3,2-b]pyridine-7-carboxylate (7)

The crude rac-methyl (7S,8S,9R)-3-chloro-9-hydroxy-10-oxo-7-phenyl-6-(4-(trifluoromethoxy)phenyl)-6,7,8,9-tetrahydro-6,9-methanooxepino[3,2-b]pyridine-8-carboxylate (6/6a, 3.0 g, 5.7 mmol) was suspended in methanol (60 mL) and treated with 25% sodium methoxide in methanol (12.4 mL). The reaction was heated at 80° C. for 4 h. After completion, the solvent was removed under reduced pressure. The crude was diluted with ammonium chloride solution and extracted with ethyl acetate. The organic phase was separated, dried over sodium sulphate and concentrated under reduced pressure to afford rac-methyl (5aR,6S,7R,8aR)-3-chloro-8a-hydroxy-8-oxo-6-phenyl-5a-(4-(trifluoromethoxy)phenyl)-5a,7,8,8a-tetrahydro-6H-cyclopenta[4,5]furo[3,2-b]pyridine-7-carboxylate (7) as brown solid. Yield: 3.0 g, crude.

Synthesis of rac-methyl (5aR,6S,7R,8R,8aS)-3-chloro-8,8a-dihydroxy-6-phenyl-5a-(4-(trifluoromethoxy)phenyl)-5a, 7,8,8a-tetrahydro-6H-cyclopenta[4,5]furo[3,2-b]pyridine-7-carboxylate (8)

A solution of rac-methyl (5aR,6S,7R,8aR)-3-chloro-8a-hydroxy-8-oxo-6-phenyl-5a-(4-(trifluoromethoxy)phenyl)-5a,7,8,8a-tetrahydro-6H-cyclopenta[4,5]furo[3,2-b]pyridine-7-carboxylate (7, 3.0 g, 5.7 mmol) in acetonitrile (60 mL) was cooled at 0° C., to this solution acetic acid (3.46 g, 57.7 mmol) and sodium triacetoxyborohydride (7.3 g, 34.6 mmol) were added. The resulting mixture was stirred for 12 h at room temperature. After completion, the reaction mixture was partitioned between saturated aqueous sodium bicarbonate solution and ethyl acetate. The organic layer was separated and dried over sodium sulphate, filtered and concentrated to give crude. The crude was purified by silica gel column chromatography using 2-3% in methanol in dichloromethane as eluent. The desired fractions were concentrated to afford rac-methyl (5aR,6S,7R,8R,8aS)-3-chloro-8,8a-dihydroxy-6-phenyl-5a-(4-(trifluoromethoxy)phenyl)-5a,7,8,8a-tetrahydro-6H-cyclopenta[4,5]furo[3,2-b]pyridine-7-carboxylate (8) as white solid. Yield: 0.6 g, 20.0%; MS (ESI) m/z 522.2[M+1]$^+$.

Synthesis of rac-(5aR,6S,7R,8R,8aS)-3-chloro-8,8a-dihydroxy-6-phenyl-5a-(4-(trifluoromethoxy)phenyl)-5a, 7,8,8a-tetrahydro-6H-cyclopenta[4,5]furo[3,2-b]pyridine-7-carboxylic acid (9)

To a solution of rac-methyl (5aR,6S,7R,8R,8aS)-3-chloro-8,8a-dihydroxy-6-phenyl-5a-(4-(trifluoromethoxy)phenyl)-5a,7,8,8a-tetrahydro-6H-cyclopenta[4,5]furo[3,2-b]pyridine-7-carboxylate (8, 0.6 g, 1.15 mmol) in methanol, tetrahydrofuran and water (2:1:1, 12 mL), lithium hydroxide (0.27 g, 11.5 mmol) was added and the reaction was stirred for 6 h at room temperature. After completion, the reaction mass was concentrated and cooled to 0° C. and acidified with 1 M hydrochloric acid to pH ~2-3. The precipitated solid was filtered and dried under vacuum to afford rac-(5aR,6S,7R,8R,8aS)-3-chloro-8,8a-dihydroxy-6-phenyl-5a-(4-(trifluoromethoxy)phenyl)-5a,7,8,8a-tetrahydro-6H-cyclopenta[4,5]furo[3,2-b]pyridine-7-carboxylic acid (9) as off white solid. Yield: 0.45 g, 77%; MS (ESI) m/z 506.19[M−1]$^-$.

Synthesis of (5aR,6S,7R,8R,8aS)-3-chloro-8,8a-dihydroxy-N,N-dimethyl-6-phenyl-5a-(4-(trifluoromethoxy)phenyl)-5a, 7,8,8a-tetrahydro-6H-cyclopenta[4,5]furo[3,2-b]pyridine-7-carboxamide (Cpd. No. 17F)

To a solution of rac-(5aR,6S,7R,8R,8aS)-3-chloro-8,8a-dihydroxy-6-phenyl-5a-(4-(trifluoromethoxy)phenyl)-5a,7,8,8a-tetrahydro-6H-cyclopenta[4,5]furo[3,2-b]pyridine-7-carboxylic acid (9, 0.3 g, 0.59 mmol) in dichloromethane (10 mL) at 0° C., 1-ethyl-3-(3-dimethylaminopropyl) carbodiimide (0.275 g, 1.77 mmol), hydroxybenzotriazole (0.271 g, 1.77 mmol) and N,N-diisopropylethylamine (0.58 mL, 3.54 mmol) were added and the mixture was stirred for 5 min. Dimethylamine hydrochloride (0.241 g, 2.95 mmol) was then added at the same temperature and the mixture was stirred for 16 h at room temperature. After completion, the reaction mass was diluted with dichloromethane and washed with cold water. The organic layer was separated and dried over sodium sulphate, filtered and concentrated to give crude. The crude was purified by silica gel column chromatography using 2-3% methanol in dichloromethane as eluent. The desired fractions were concentrated to afford rac-(5aR,6S,7R,8R,8aS)-3-chloro-8,8a-dihydroxy-N,N-dimethyl-6-phenyl-5a-(4-(trifluoromethoxy)phenyl)-5a,7,8,8a-tetrahydro-6H-cyclopenta[4,5]furo[3,2-b]pyridine-7-carboxamide (rac-Cpd. No. 17F) as off white solid. The enantiomers were separated by chiral preparative HPLC [chiralpak IB (4.6×250) mm]. Yield: 0.15 g, (racemic mixture). Peak 1 (79 mg), $[\alpha]_D$+2110 (c 0.1, $CHCl_3$), $R_t$=5.982 min, ee >99%. $^1$H NMR (400 MHz, DMSO-$d_6$) δ: 8.20 (d, J=2.0 Hz, 1H), 7.71 (d, J=2.0 Hz, 1H), 7.24 (d, J=8.8 Hz, 2H), 7.04-6.98 (m, 4H), 6.94 (t, J=7.2 Hz, 1H), 6.89 (d, J=7.6 Hz, 2H), 6.10 (s, 1H), 5.31 (d, J=5.6 Hz, 1H), 4.76 (t, J=5.4 Hz, 1H), 4.55 (d, J=13.6 Hz, 1H), 4.25 (dd, J=13.2, 5.2 Hz, 1H), 3.26 (s, 3H), 2.77 (s, 3H); MS (ESI) m/z 535.36 [M+1]$^+$; UPLC: 98.9%. Peak-2 (Cpd. No. 17F, 67 mg), $[\alpha]_D$−217.4° (c 0.1, $CHCl_3$), $R_t$=12.093 min, ee >99%. $^1$H NMR (400 MHz, DMSO-$d_6$) δ 8.20 (d, J=2.0 Hz, 1H), 7.71 (d, J=2.0 Hz, 1H), 7.24 (d, J=8.8 Hz, 2H), 7.04-6.98 (m, 4H), 6.95 (t, J=6.8 Hz, 1H), 6.89 (d, J=7.6 Hz, 2H), 6.10 (s, 1H), 5.31 (d, J=5.6 Hz, 1H), 4.76 (t, J=5.4 Hz, 1H), 4.55 (d, J=13.2 Hz, 1H), 4.25 (dd, J=13.2, 5.2 Hz, 1H), 3.26 (s, 3H), 2.77 (s, 3H); MS (ESI) m/z 535.39[M+1]$^+$; UPLC: 99.57%.

Example 18

(5aR,6S,7R,8R,8aS)-3-chloro-5a-(4-cyanophenyl)-8,8a-dihydroxy-6-phenyl-5a,7,8,8a-tetrahydro-6H-cyclopenta[4,5]furo[3,2-b]pyridine-7-carboxamide (Cpd. No. 18F)

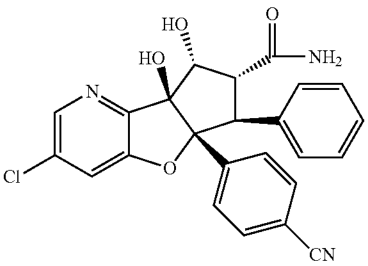

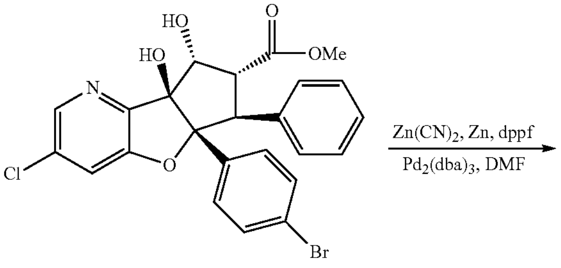

1

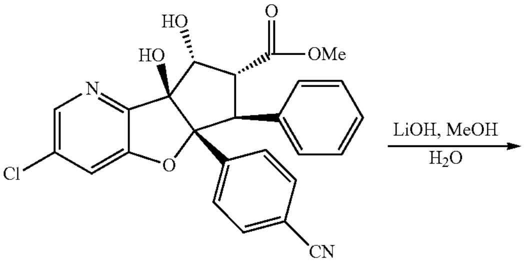

2

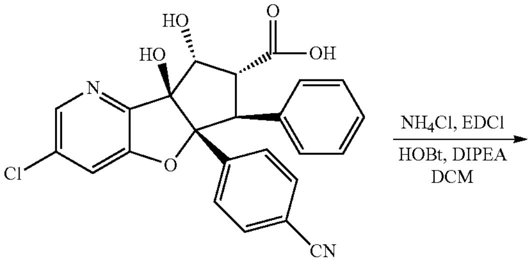

3

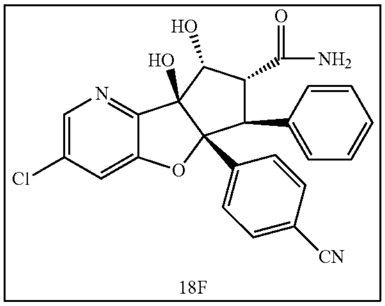

18F

Synthesis of rac-methyl (5aR,6S,7R,8R,8aS)-3-chloro-5a-(4-cyanophenyl)-8,8a-dihydroxy-6-phenyl-5a, 7,8,8a-tetrahydro-6H-cyclopenta[4,5]furo[3,2-b]pyridine-7-carboxylate (2)

To a solution of rac-methyl (5aR,6S,7R,8R,8aS)-5a-(4-bromophenyl)-3-chloro-8,8a-dihydroxy-6-phenyl-5a,7,8,8a-tetrahydro-6H-cyclopenta[4,5]furo[3,2-b]pyridine-7-carboxylate (1, 0.45 g, 0.87 mmol) in N,N-dimethylformamide (5 mL), zinc cyanide (0.113 g, 0.96 mmol) and zinc (0.28 g, 0.43 mmol) were added at room temperature and degassed the mixture with argon for 15 min. 1,1'-Bis(diphenylphosphino)ferrocene (0.012 g, 0.017 mmol), tris(dibenzylideneacetone)dipalladium (0.023 g, 0.026 mmol) were added to the reaction and degassing was continued for 5 min. The reaction mixture was heated at 125° C. for 3 h. After completion, the reaction was cooled to room temperature and passed through celite bed. The filtrate was concentrated to get the crude. The crude was purified by Combi-flash (12 g, RediSep column) using 70% ethyl acetate in hexanes as eluent. The desired fractions were concentrated under reduced pressure to afford rac-methyl (5aR,6S,7R,8R,8aS)-3-chloro-5a-(4-cyanophenyl)-8,8a-dihydroxy-6-phenyl-5a,7,8,8a-tetrahydro-6H-cyclopenta[4,5]furo[3,2-b]pyridine-7-carboxylate (2) as white solid. Yield: 0.31 g, 77.5%; MS (ESI) m/z 463.15[M+1]$^+$.

Synthesis of rac-(5aR,6S,7R,8R,8aS)-3-chloro-5a-(4-cyanophenyl)-8,8a-dihydroxy-6-phenyl-5a, 7,8,8a-tetrahydro-6H-cyclopenta[4,5]furo[3,2-b]pyridine-7-carboxylic acid (3)

To a solution of rac-methyl (5aR,6S,7R,8R,8aS)-3-chloro-5a-(4-cyanophenyl)-8,8a-dihydroxy-6-phenyl-5a,7,8,8a-tetrahydro-6H-cyclopenta[4,5]furo[3,2-b]pyridine-7-carboxylate (2, 0.3 g, 0.649 mmol) in methanol and water (3:1, 10 mL), lithium hydroxide (0.077 g, 3.246 mmol) was added and the reaction was stirred for 6 h at room temperature. After completion, the reaction mass was cooled to 0° C. and acidified with 5% citric acid to pH ~6. The precipitated solid was filtered and dried under vacuum to afford rac-(5aR,6S,7R,8R,8aS)-3-chloro-5a-(4-cyanophenyl)-8,8a-dihydroxy-6-phenyl-5a,7,8,8a-tetrahydro-6H-cyclopenta[4,5]furo[3,2-b]pyridine-7-carboxylic acid (3) as white solid. Yield: 0.21 g, 72.4%; MS (ESI) m/z 449.0[M+1]$^+$.

Synthesis of (5aR,6S,7R,8R,8aS)-3-chloro-5a-(4-cyanophenyl)-8,8a-dihydroxy-6-phenyl-5a,7,8,8a-tetrahydro-6H-cyclopenta[4,5]furo[3,2-b]pyridine-7-carboxamide (Cpd. No. 18F)

To a solution of rac-(5aR,6S,7R,8R,8aS)-3-chloro-5a-(4-cyanophenyl)-8,8a-dihydroxy-6-phenyl-5a,7,8,8a-tetrahydro-6H-cyclopenta[4,5]furo[3,2-b]pyridine-7-carboxylic acid (3, 0.18 g, 0.401 mmol) in dichloromethane (5 mL), 1-ethyl-3-(3-dimethylaminopropyl)carbodiimide hydrochloride (0.16 g, 0.803 mmol), 1-hydroxybenzotriazole (0.108 g, 0.803 mmol) and N,N-diisopropylethylamine (0.2 mL, 1.20 mmol) were added at 0° C. and stirred the mixture for 5 min. Ammonium chloride (0.21 g, 4.01 mmol) was then added at same temperature and the mixture was stirred at room temperature for 16 h. After completion, reaction mass was diluted with dichloromethane and washed with cold water. The organic layer was separated and dried over anhydrous sodium sulphate, filtered and concentrated to give crude. The crude was purified by Combi-flash (4 g, RediSep column) using 70% ethyl acetate in hexanes as eluent. The desired fractions were concentrated under reduced pressure to afford rac-(5aR,6S,7R,8R,8aS)-3-chloro-5a-(4-cyanophenyl)-8,8a-dihydroxy-6-phenyl-5a,7,8,8a-tetrahydro-6H-cyclopenta[4,5]furo[3,2-b]pyridine-7-carboxamide (rac-Cpd. No. 18F) as off white solid. Yield: 0.14 g, 78.2%; MS (ESI) m/z 448.12$[M+1]^+$. The enantiomers were separated by chiral preparative HPLC [chiralpak IB (4.6×250) mm]. Yield: 140 mg, 78%; Peak-1 (Cpd. No. 18F, 5 mg); $[\alpha]_D$−184.2° (c 0.27, DMSO); $R_t$=6.41 min, ee >99%; MS (ESI) m/z 448.38$[M+1]^+$; UPLC 97.6%; $^1H$ NMR (400 MHz, DMSO-$d_6$)[8] 8.20 (d, J=1.8 Hz, 1H), 7.70 (d, J=1.8 Hz, 1H), 7.51 (d, J=8.4 Hz, 2H), 7.25 (d, J=8.4 Hz, 2H), 7.10-6.96 (m, 5H), 6.16 (s, 1H), 5.31 (d, J=4.5 Hz, 1H), 4.58-4.55 (m, 1H), 3.97 (dd, J=14.0, 4.1 Hz, 1H). Peak-2 (7 mg); $[\alpha]_D$+128.8° (c 0.26, DMSO); $R_t$=11.06 min, ee >99%; MS (ESI) m/z 448.37$[M+1]^+$; UPLC 99.2%; $^1H$ NMR (400 MHz, DMSO-$d_6$) δ 8.20 (d, J=1.9 Hz, 1H), 7.70 (d, J=1.9 Hz, 1H), 7.51 (d, J=8.5 Hz, 2H), 7.25 (d, J=8.5 Hz, 2H), 7.09-6.96 (m, 5H), 6.16 (s, 1H), 5.31 (d, J=4.5 Hz, 1H), 4.57 (m, J=7.8 Hz, 2H), 3.97 (dd, J=13.8, 4.2 Hz, 1H).

Example 19

Rac-(5aR,6S,7R,8R,8aS)-5a-(4-cyanophenyl)-8,8a-dihydroxy-1-methoxy-N,N-dimethyl-6-phenyl-5a,7,8,8a-tetrahydro-6H-cyclopenta[4,5]furo[3,2-c]pyridine-7-carboxamide (Cpd. No. 19F)

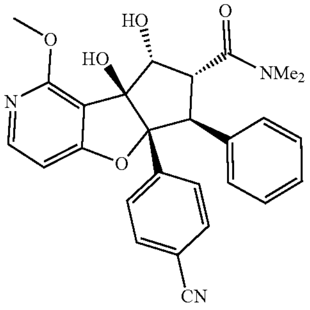

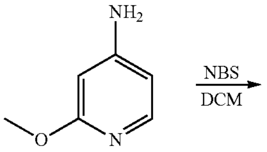

1

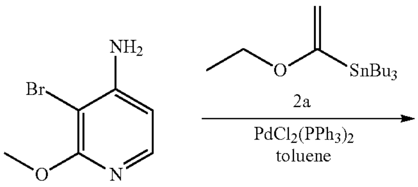

2

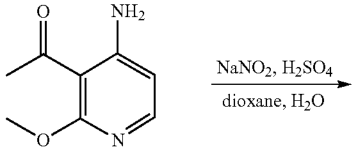

3

-continued

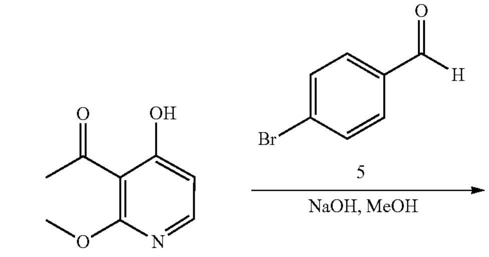

4

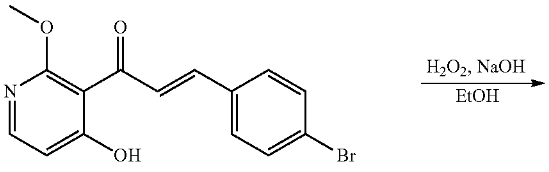

6

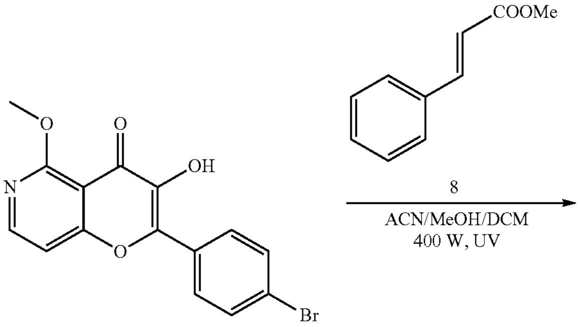

7

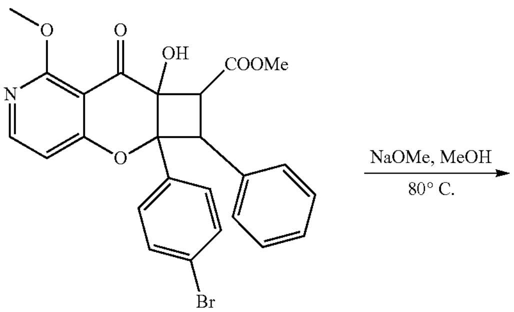

9

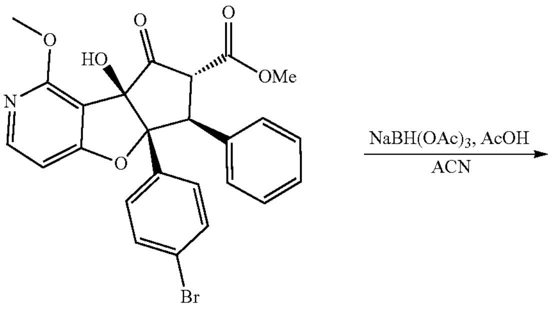

10

-continued

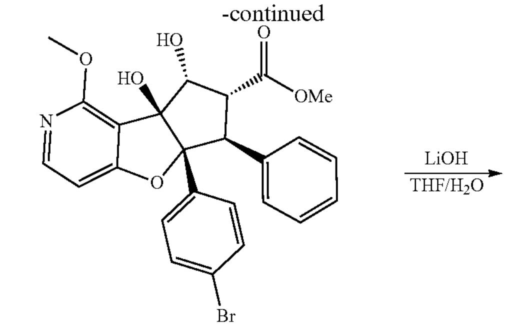

11

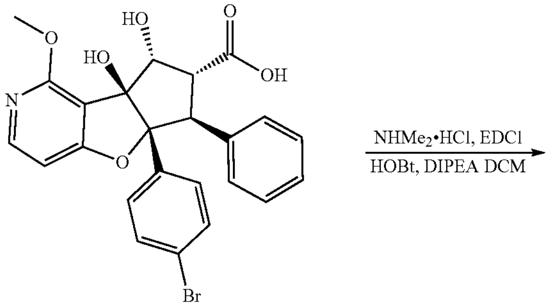

12

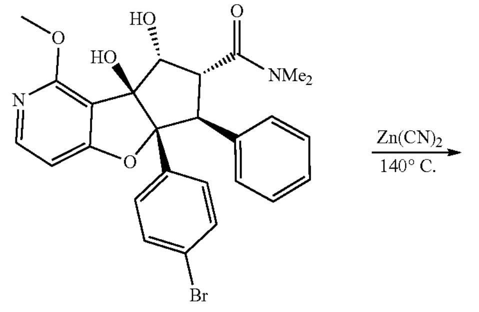

13

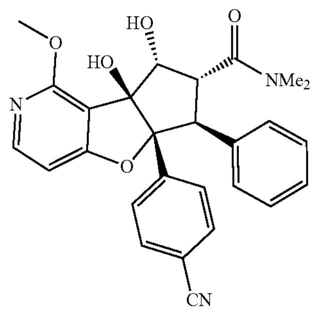

19F

Synthesis of 3-bromo-2-methoxypyridin-4-amine (2)

To a solution of 2-methoxypyridin-4-amine (1, 20.0 g, 161.2 mmol) in dichloromethane (200 mL) at 0° C., N-bromo succinimide (26.6 g, 161.2 mmol) was added and the reaction mixture was stirred at 0° C. for 30 min. After completion, the mixture was quenched with ice cold water (100 mL) and the reaction mass was extracted with dichloromethane (300 mL). The organic layer was washed with water and brine, dried over anhydrous sodium sulfate, filtered and concentrated. The crude was triturated with n-pentane and diethyl ether to afford 3-bromo-2-methoxypyridin-4-amine (2) as yellow solid. Yield: 30.0 g, 92%; MS (ESI) m/z 203.09[M+1]$^+$.

Synthesis of 1-(4-amino-2-methoxypyridin-3-yl) ethan-1-one (3)

To a solution of 3-bromo-2-methoxypyridin-4-amine (2, 25.0 g, 123.7 mmol) in toluene (250 mL), tributyl(1-ethoxyvinyl)stannane (2a, 67.01 g, 185.0 mmol) were added at room temperature and the reaction mixture was degassed with argon for 15 min. Bis(triphenylphosphine)palladium (II) chloride (8.6 g, 12.3 mmol) was added to the reaction, continued degassing for 5 min and heated the reaction mixture at 100° C. for 16 h. After completion, the reaction mass was diluted with ethyl acetate (300 mL) and washed with water. The organic layer was separated and dried over sodium sulphate, filtered and concentrated to give crude. The crude was treated with 1N hydrochloric acid (100 mL) and the reaction mixture was stirred at room temperature for 1 h. The mixture was then basified with Sodium bicarbonate solution up to pH~7 and extracted with ethyl acetate (300 mL) and washed with water. The organic layer was separated and dried over sodium sulphate, filtered and concentrated to give crude. The crude was purified by silica gel column chromatography eluting with 10% ethyl acetate in hexane. The desired fractions were concentrated to afford 1-(4-amino-2-methoxypyridin-3-yl) ethan-1-one (3) as off white solid. Yield: 10.0 g, 65%; MS (ESI) m/z 167.16[M+1]$^+$.

Synthesis of 1-(4-hydroxy-2-methoxypyridin-3-yl) ethan-1-one (4)

To a solution of 1-(4-amino-2-methoxypyridin-3-yl) ethan-1-one (3, 10.0 g, 59.8 mmol) in 1,4-dioxane (250 mL) at 0° C., 50% aq. sulfuric acid solution (117.3 g, 1196.9 mmol) was added drop wise over a period of 30 min. A solution of sodium nitrite in water (16.5 g, 239.5 mmol) was added drop wise at 0° C. and heated the reaction mixture at 50° C. for 1 h. After completion, the reaction mass was quenched with 10% sodium hydroxide solution to pH ~7 and extracted with ethyl acetate (200 mL). The organic layer was separated and washed water, dried over anhydrous sodium sulfate, filtered and concentrated under reduced pressure. The crude was purified by silica gel column chromatography eluting with 5% ethyl acetate in hexane. The desired fractions were concentrated to afford 1-(4-hydroxy-2-methoxypyridin-3-yl)ethan-1-one (4) as yellow solid. Yield: 3.7 g, 37.2%; MS (ESI) m/z: no ionization

Synthesis of (E)-3-(4-bromophenyl)-1-(4-hydroxy-2-methoxypyridin-3-yl)prop-2-en-1-one (6)

To a solution of 1-(4-hydroxy-2-methoxypyridin-3-yl) ethan-1-one (4, 3.7 g, 22.1 mmol) in methanol (40 mL), sodium hydroxide (2.6 g, 66.3 mmol) was added followed by addition of 4-bromobenzaldehyde (5, 4.0 g, 22.1 mmol). The reaction was heated to reflux for 30 min. After completion, the reaction mass was cooled to room temperature and the mixture was diluted with water (20 mL). The precipitated solid was filtered, washed with water, n-pentane and dried under vacuum to afford (E)-3-(4-bromophenyl)-1-(4-hydroxy-2-methoxypyridin-3-yl)prop-2-en-1-one (6) as yellow solid. Yield: 5.0 g, 68.0%; MS (ESI) m/z 334.10[M+1]$^+$.

Synthesis of 2-(4-bromophenyl)-3-hydroxy-5-methoxy-4H-pyrano[3,2-c]pyridin-4-one (7)

To a solution of (E)-3-(4-bromophenyl)-1-(4-hydroxy-2-methoxypyridin-3-yl)prop-2-en-1-one (6, 6.0 g, 18.0 mmol) in ethanol (60 mL) and dichloromethane (10 mL) at 0° C., 10% aq. sodium hydroxide (50 mL, 126.6 mmol) was added followed by addition of 30% aq. hydrogen peroxide (4.2 mL, 126.6 mmol). The reaction mass was stirred for 30 min at room temperature (exotherm was observed). After completion, the reaction mass was cooled and neutralized to pH ~7 by the addition of 6 M hydrogen chloride. The mixture was extracted with ethyl acetate (100 mL) and the organic layer was washed with water and brine, dried over anhydrous sodium sulfate, filtered and concentrated. The solid obtained was triturated with n-pentane and ethanol, filtered and dried under vacuum to afford of 2-(4-bromophenyl)-3-hydroxy-5-methoxy-4H-pyrano[3,2-c]pyridin-4-one (7) as yellow solid. Yield: 2.0 g, 32.2%; MS (ESI) m/z 348.07 $[M+1]^+$.

Synthesis of methyl 5a-(4-bromophenyl)-7a-hydroxy-1-methoxy-8-oxo-6-phenyl-5a,6,7a,8-tetrahydro-7H-cyclobuta[5,6]pyrano[3,2-c]pyridine-7-carboxylate (9)

A solution of 2-(4-bromophenyl)-3-hydroxy-5-methoxy-4H-pyrano[3,2-c]pyridin-4-one (7, 2.0 g, 5.7 mmol) and methyl cinnamate (8, 9.34 g, 50.7 mmol) in dichloromethane (200 mL), acetonitrile (100 mL) and methanol (100 mL) was placed in a UV reactor flask. The reaction mixture was irradiated for 8 h under 400 watts UV light. After completion, solvent was removed under reduced pressure and the residue was purified over a plug of silica gel eluting the compound with ethyl acetate. The desired fractions were concentrated under reduced pressure to afford methyl 5a-(4-bromophenyl)-7a-hydroxy-1-methoxy-8-oxo-6-phenyl-5a,6,7a,8-tetrahydro-7H-cyclobuta[5,6]pyrano[3,2-c]pyridine-7-carboxylate (9) as yellow sticky mass. Yield: 1.7 g, crude.

Synthesis of rac-methyl (5aR,6S,7R,8aR)-5a-(4-bromophenyl)-8a-hydroxy-1-methoxy-8-oxo-6-phenyl-5a,7,8,8a-tetrahydro-6H-cyclopenta[4,5]furo[3,2-c]pyridine-7-carboxylate (10)

The crude methyl 5a-(4-bromophenyl)-7a-hydroxy-1-methoxy-8-oxo-6-phenyl-5a,6,7a,8-tetrahydro-7H-cyclobuta[5,6]pyrano[3,2-c]pyridine-7-carboxylate (9, 1.7 g, 3.3 mmol) was suspended in methanol (20 mL) and treated with 25% sodium methoxide in methanol (15 mL). The reaction was heated at 80° C. for 2 h. After completion, the solvent was removed under reduced pressure. The crude was diluted with ammonium chloride solution and extracted with ethyl acetate. The organic phase was separated, dried over sodium sulphate and concentrated under reduced pressure to afford rac-methyl (5aR,6S,7R,8aR)-5a-(4-bromophenyl)-8a-hydroxy-1-methoxy-8-oxo-6-phenyl-5a,7,8,8a-tetrahydro-6H-cyclopenta[4,5]furo[3,2-c]pyridine-7-carboxylate (10). Yield: 1.6 g, crude.

Synthesis of rac-methyl (5aR,6S,7R,8R,8aS)-5a-(4-bromophenyl)-8,8a-dihydroxy-1-methoxy-6-phenyl-5a,7,8,8a-tetrahydro-6H-cyclopenta[4,5]furo[3,2-c]pyridine-7-carboxylate (11)

To a solution of sodium triacetoxyborohydride (3.99 g, 18.8 mmol), rac-methyl (5aR,6S,7R,8aR)-5a-(4-bromophenyl)-8a-hydroxy-1-methoxy-8-oxo-6-phenyl-5a,7,8,8a-tetrahydro-6H-cyclopenta[4,5]furo[3,2-c]pyridine-7-carboxylate (10, 1.6 g, 3.1 mmol) in acetonitrile (20 mL), acetic acid (1.77 g, 31.5 mmol) was added. The resulting mixture was stirred for 12 h at room temperature. After completion, the reaction mixture was partitioned between saturated aqueous sodium bicarbonate solution and ethyl acetate. The organic layer was separated, dried over sodium sulphate, filtered and concentrated under reduced pressure to get the crude. The crude was purified by prep HPLC purification and lyophilized to afford rac-methyl (5aR,6S,7R,8R,8aS)-5a-(4-bromophenyl)-8,8a-dihydroxy-1-methoxy-6-phenyl-5a,7,8,8a-tetrahydro-6H-cyclopenta[4,5]furo[3,2-c]pyridine-7-carboxylate (11) as yellowish solid. Yield: 0.03 g, 2.0%; MS (ESI) m/z 512.1$[M+1]^+$.

Synthesis of rac-(5aR,6S,7R,8R,8aS)-5a-(4-bromophenyl)-8,8a-dihydroxy-1-methoxy-6-phenyl-5a,7,8,8a-tetrahydro-6H-cyclopenta[4,5]furo[3,2-c]pyridine-7-carboxylic acid (12)

To a solution of rac-methyl (5aR,6S,7R,8R,8aS)-5a-(4-bromophenyl)-8,8a-dihydroxy-1-methoxy-6-phenyl-5a,7,8,8a-tetrahydro-6H-cyclopenta[4,5]furo[3,2-c]pyridine-7-carboxylate (11, 0.03 g, 0.06 mmol) in tetrahydrofuran and water (3:1, 4 mL), lithium hydroxide (0.015 g, 0.06 mmol) was added and the reaction was stirred for 2 h at room temperature. After completion, the reaction mass was cooled to 0° C. and acidified with 1 M hydrochloric acid to pH ~2-3. The precipitate was filtered and dried under vacuum to afford rac-(5aR,6S,7R,8R,8aS)-5a-(4-bromophenyl)-8,8a-dihydroxy-1-methoxy-6-phenyl-5a,7,8,8a-tetrahydro-6H-cyclopenta[4,5]furo[3,2-c]pyridine-7-carboxylic acid (12) as yellow solid. Yield: 0.02 g, 69.3%; MS (ESI) m/z 498.24$[M+1]^+$.

Synthesis of rac-(5aR,6S,7R,8R,8aS)-5a-(4-bromophenyl)-8,8a-dihydroxy-1-methoxy-N,N-dimethyl-6-phenyl-5a,7,8,8a-tetrahydro-6H-cyclopenta[4,5]furo[3,2-c]pyridine-7-carboxamide (13)

To a solution of rac-(5aR,6S,7R,8R,8aS)-5a-(4-bromophenyl)-8,8a-dihydroxy-1-methoxy-6-phenyl-5a,7,8,8a-tetrahydro-6H-cyclopenta[4,5]furo[3,2-c]pyridine-7-carboxylic acid (12, 0.02 g, 0.04 mmol) in dichloromethane (2 mL) at 0° C., 1-ethyl-3-(3-dimethylaminopropyl) carbodiimide (0.019 g, 0.12 mmol), hydroxybenzotriazole (0.018 g, 0.12 mmol) and N,N-diisopropylethylamine (0.04 g, 0.24 mmol) were added and the mixture was stirred for 5 min. Dimethylamine hydrochloride (0.016 g, 0.20 mmol) was then added at the same temperature and the reaction was stirred for 16 h at room temperature. After completion, the reaction mass was diluted with dichloromethane and washed with cold water. The organic layer was separated and dried over sodium sulphate, filtered and concentrated to give crude. The crude was purified by silica gel column chromatography eluting with 2-3% dichloromethane in methanol. The desired fractions were concentrated to afford rac-(5aR,6S,7R,8R,8aS)-5a-(4-bromophenyl)-8,8a-dihydroxy-1-methoxy-N,N-dimethyl-6-phenyl-5a,7,8,8a-tetrahydro-6H-cyclopenta[4,5]furo[3,2-c]pyridine-7-carboxamide (13) as yellow sticky mass. Yield: 0.02 g, 95%; MS (ESI) m/z 525.15 $[M+1]^+$;

Synthesis of rac-(5aR,6S,7R,8R,8aS)-5a-(4-cyanophenyl)-8,8a-dihydroxy-1-methoxy-N,N-dimethyl-6-phenyl-5a,7,8,8a-tetrahydro-6H-cyclopenta[4,5]furo[3,2-c]pyridine-7-carboxamide (Cpd. No. 19F)

To a solution of rac-(5aR,6S,7R,8R,8aS)-5a-(4-bromophenyl)-8,8a-dihydroxy-1-methoxy-N,N-dimethyl-6-phenyl-5a,7,8,8a-tetrahydro-6H-cyclopenta[4,5]furo[3,2-c]pyridine-7-carboxamide (13, 0.02 g, 0.04 mmol) in N,N-dimethylformamide (1.0 mL), zinc cyanide (0.026 g, 0.22 mmol) and zinc (0.001 g, 0.004 mmol) were added at room temperature and the reaction mixture was degassed with argon for 15 min. 1,1'-Bis(diphenylphosphino)ferrocene (0.5 mg, 0.0001 mmol) and tris(dibenzylideneacetone) dipalladium (1.0 mg, 0.0001 mmol) were added to the reaction, continued degassing for 5 min and heated the reaction mixture at 140° C. for 4 h. After completion, the reaction mass was diluted with ethyl acetate and washed with cold water. The organic layer was separated and dried over sodium sulphate, filtered and concentrated to give crude. The crude was purified by prep HPLC and lyophilized to afford rac-(5aR,6S,7R,8R,8aS)-5a-(4-cyanophenyl)-8,8a-dihydroxy-1-methoxy-N,N-dimethyl-6-phenyl-5a,7,8,8a-tetrahydro-6H-cyclopenta[4,5]furo[3,2-c]pyridine-7-carboxamide (Cpd. No. 19F) as white solid. Yield: 3.5 mg, 20%; MS (ESI) m/z 472.44[M+1]$^+$; 1H NMR (400 MHz, DMSO-$d_6$) δ 8.04 (d, J=5.6 Hz, 1H), 7.50 (d, J=8.8 Hz, 2H), 7.33 (d, J=8.4 Hz, 2H), 7.03 (t, J=8.0 Hz, 2H), 6.96 (t, J=7.2 Hz, 1H), 6.90 (d, J=7.6 Hz, 2H), 6.83 (d, J=5.6 Hz, 1H), 5.61 (s, 1H), 5.10 (bs, 1H), 4.75 (d, J=5.2 Hz, 1H), 4.44 (d, J=13.6 Hz, 1H), 4.26 (dd, J=13.6, 5.2 Hz, 1H), 3.85 (s, 3H), 3.28 (s, 3H), 2.77 (s, 3H).

Example 20

(5aR,6S,7R,8R,8aS)-3-chloro-5a-(4-cyanophenyl)-8,8a-dihydroxy-N-methyl-6-phenyl-5a,7,8,8a-tetrahydro-6H-cyclopenta[4,5]furo[3,2-b]pyridine-7-carboxamide (Cpd. No. 20F)

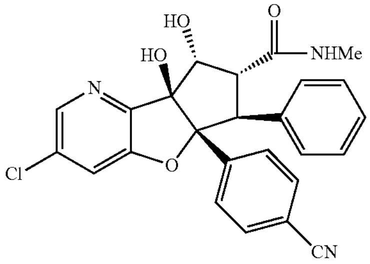

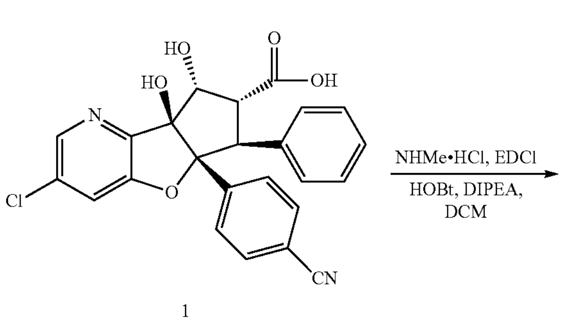

1

-continued

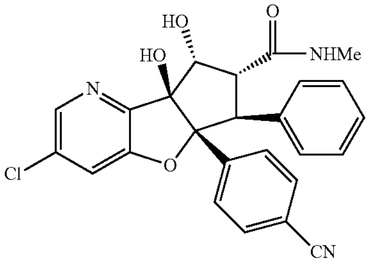

20F

Synthesis of (5aR,6S,7R,8R,8aS)-3-chloro-5a-(4-cyanophenyl)-8,8a-dihydroxy-N-methyl-6-phenyl-5a,7,8,8a-tetrahydro-6H-cyclopenta[4,5]furo[3,2-b]pyridine-7-carboxamide Cpd. No. 20F)

To a solution of rac-(5aR,6S,7R,8R,8aS)-3-chloro-5a-(4-cyanophenyl)-8,8a-dihydroxy-6-phenyl-5a,7,8,8a-tetrahydro-6H-cyclopenta[4,5]furo[3,2-b]pyridine-7-carboxylic acid (1, 0.13 g, 0.29 mmol) in dichloromethane (10 mL), 1-ethyl-3-(3-dimethylaminopropyl)carbodiimide hydrochloride (0.13 g, 0.87 mmol), 1-hydroxybenzotriazole (0.12 g, 0.87 mmol) and N,N-diisopropylethylamine (0.5 mL, 2.9 mmol) were added at 0° C. and stirred the mixture for 5 min. Methylamine hydrochloride (0.097 g, 1.45 mmol) was then added at same temperature and the mixture was stirred for 16 h at 40° C. After completion, reaction mass was diluted with dichloromethane and washed with cold water. The organic layer was separated and dried over sodium sulphate, filtered and concentrated under reduced pressure to afford rac-(5aR,6S,7R,8R,8aS)-3-chloro-5a-(4-cyanophenyl)-8,8a-dihydroxy-N-methyl-6-phenyl-5a,7,8,8a-tetrahydro-6H-cyclopenta[4,5]furo[3,2-b]pyridine-7-carboxamide (rac-Cpd. No. 20F) as brown solid. Yield: 120 mg, 90%. The enantiomers were separated by chiral preparative HPLC [chiralpak IC (4.6×250) mm]. Peak 1 (22 mg); $[\alpha]_D$+51.4° (c 0.14, $CHCl_3$); $R_t$=5.66 min, ee >99%; MS (ESI) m/z 462.41 [M+1]$^+$; UPLC: 99.09%; $^1$H NMR (400 MHz, DMSO-$d_6$) δ 8.20 (d, J=2.0 Hz, 1H), 8.17 (q, J=4.3 Hz, 1H), 7.71 (d, J=2.0 Hz, 1H), 7.51 (d, J=8.5 Hz, 2H), 7.25 (d, J=8.5 Hz, 2H), 7.08-6.96 (m, 5H), 6.19 (s, 1H), 5.29 (d, J=4.5 Hz, 1H), 4.61 (d, J=14.0 Hz, 1H), 4.52 (t, J=4.4 Hz, 1H), 3.95 (dd, J=14.0, 4.4 Hz, 1H), 2.55 (d, J=4.5 Hz, 3H). Peak-2 (Cpd. No. 20F, 18 mg); $[\alpha]_D$−178° (c 0.13, $CHCl_3$); $R_t$=7.24 min, ee >99%; MS (ESI) m/z 462.42[M+1]$^+$; UPLC: 99.61%; $^1$H NMR (400 MHz, DMSO-$d_6$) δ 8.20 (d, J=2.0 Hz, 1H), 8.17 (q, J=4.3 Hz, 1H), 7.71 (d, J=1.9 Hz, 1H), 7.51 (d, J=8.5 Hz, 2H), 7.25 (d, J=8.5 Hz, 2H), 7.08-6.96 (m, 5H), 6.19 (s, 1H), 5.29 (d, J=4.5 Hz, 1H), 4.61 (d, J=14.0 Hz, 1H), 4.52 (t, J=4.4 Hz, 1H), 3.96 (dd, J=14.0, 4.4 Hz, 1H), 2.56 (d, J=4.6 Hz, 3H).

Example 21

Rac-methyl (4aR,5S,6R,7R,7aS)-4a-(4-cyanophenyl)-7,7a-dihydroxy-2-methyl-5-phenyl-2,4a,5,6,7,7a-hexahydrocyclopenta[4,5]furo[3,2-c]pyrazole-6-carboxylate (Cpd. No. 21F)

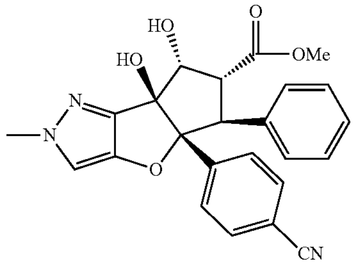

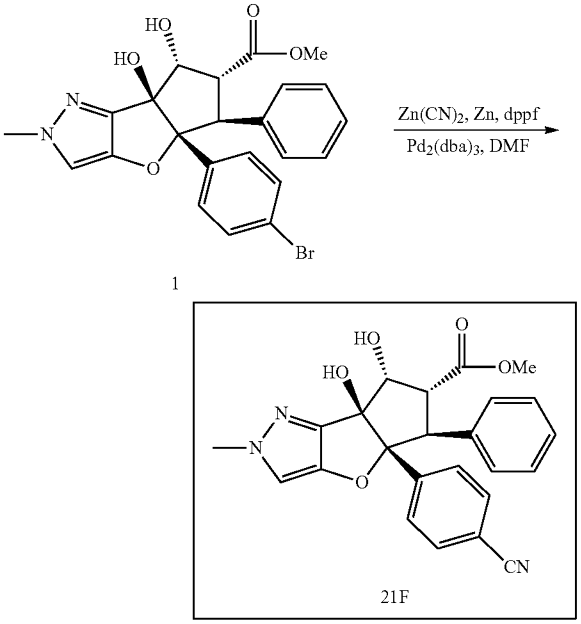

1

21F

Synthesis of rac-methyl (4aR,5S,6R,7R,7aS)-4a-(4-cyanophenyl)-7,7a-dihydroxy-2-methyl-5-phenyl-2,4a,5,6,7,7a-hexahydrocyclopenta[4,5]furo[3,2-c]pyrazole-6-carboxylate (Cpd. No. 21F)

To a solution of rac-methyl (4aR,5S,6R,7R,7aS)-4a-(4-bromophenyl)-7,7a-dihydroxy-2-methyl-5-phenyl-2,4a,5,6,7,7a-hexahydrocyclopenta[4,5]furo[3,2-c]pyrazole-6-carboxylate (1, 0.018 g, 0.037 mmol) in N,N-dimethylformamide (1.0 mL), zinc cyanide (0.026 g, 0.22 mmol) and zinc (0.001 g, 0.004 mmol) were added at room temperature and degassed the mixture with argon for 15 min. 1,1'-Bis(diphenylphosphino)ferrocene (0.001 g, 0.0007 mmol), tris(dibenzylideneacetone)dipalladium (0.002 g, 0.0009 mmol) were added to the reaction and degassing was continued for another 5 min. The reaction mixture was heated at 140° C. for 2 h. After completion, the reaction mass was diluted with ethyl acetate and washed with cold water. The organic layer was separated and dried over sodium sulphate, filtered and concentrated to give crude. The crude was purified by silica gel column chromatography using 2-3% methanol in dichloromethane as eluent. The desired fractions were concentrated to afford rac-(4aR,5S,6R,7R,7aS)-3-chloro-4a-(4-cyanophenyl)-7,7a-dihydroxy-N,N,2-trimethyl-5-phenyl-2,4a,5,6,7,7a-hexahydrocyclopenta[4,5]furo[3,2-c]pyrazole-6-carboxamide (Cpd. No. 21F) as white solid. Yield: 0.004 g, 25%; (racemic mixture). $^1H$ NMR (400 MHz, DMSO-$d_6$) δ 7.49 (d, J=8.4 Hz, 2H), 7.32 (s, 1H), 7.27 (d, J=8.4 Hz, 2H), 7.07-6.98 (m, 3H), 6.87 (d, J=7.2 Hz, 2H), 5.77 (s, 1H), 5.71 (brs, 1H), 4.66 (d, J=4.8 Hz, 1H), 4.35 (d, J=14.0 Hz, 1H), 4.05 (dd, J=14.0, 6.0 Hz, 1H), 3.79 (s, 3H), 3.54 (s, 3H); MS (ESI) m/z 432.4[M+1]$^+$.

Example 22

Rac-(5aR,6S,7R,8S,8aS)-3-chloro-5a-(4-cyanophenyl)-8,8a-dihydroxy-N,N-dimethyl-6-phenyl-5a,7,8,8a-tetrahydro-6H-cyclopenta[4,5]furo[3,2-b]pyridine-7-sulfonamide (Cpd. No. 22F)

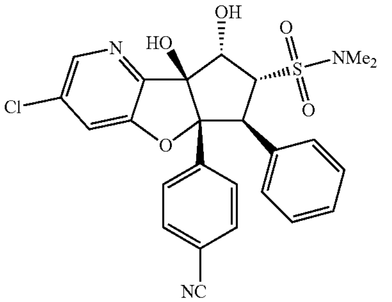

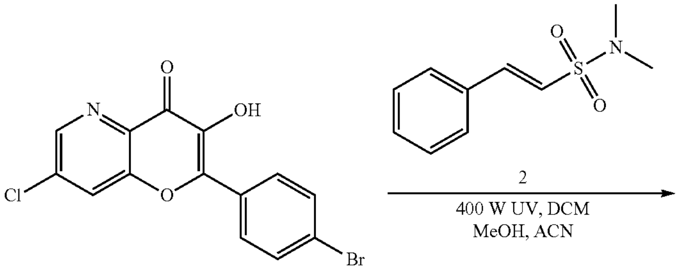

2

1

-continued

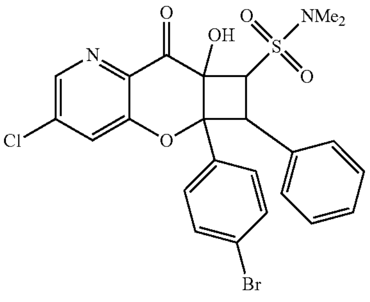

3

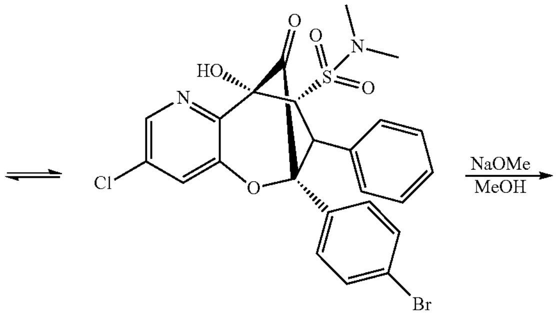

3a

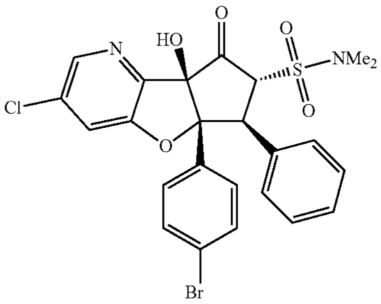

4

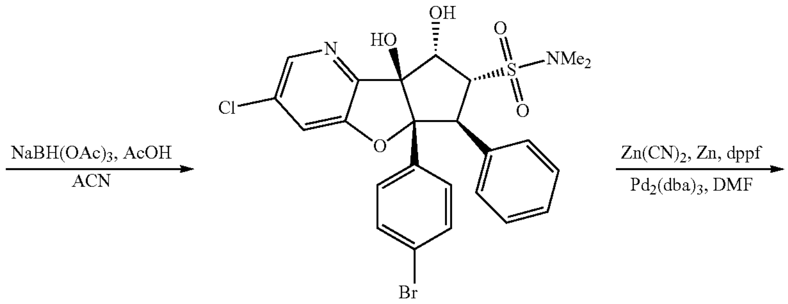

5

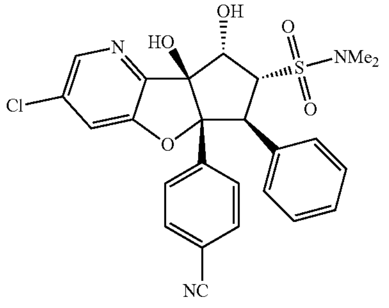

22F

Synthesis of rac-5a-(4-bromophenyl)-3-chloro-7a-hydroxy-N,N-dimethyl-8-oxo-6-phenyl-5a,6,7a,8-tetrahydro-7H-cyclobuta[5,6]pyrano[3,2-b]pyridine-7-sulfonamide (3/3a)

A solution of 2-(4-bromophenyl)-7-chloro-3-hydroxy-4H-pyrano[3,2-b]pyridin-4-one (1, 1.5 g, 4.27 mmol) and (E)-N,N-dimethyl-2-phenylethene-1-sulfonamide (2, 4.50 g, 21.4 mmol) in dichloromethane (200 mL), acetonitrile (100 mL) and methanol (100 mL) was placed in a UV reactor flask. The reaction mixture was irradiated for 3 day under 400 watts UV light. After completion, the solvent was removed under reduced pressure. The crude was purified by Combi-flash (4 g, RediSep column) using ethyl acetate as eluent. The desired fractions were concentrated under reduced pressure to afford rac-5a-(4-bromophenyl)-3-chloro-7a-hydroxy-N,N-dimethyl-8-oxo-6-phenyl-5a,6,7a,8-tetrahydro-7H-cyclobuta[5,6]pyrano[3,2-b]pyridine-7-sulfonamide (3/3a) as brown solid. Yield: 0.7 g, Crude.

Synthesis of rac-(5aR,6S,7R,8aR)-5a-(4-bromophenyl)-3-chloro-8a-hydroxy-N,N-dimethyl-8-oxo-6-phenyl-5a,7,8,8a-tetrahydro-6H-cyclopenta[4,5]furo[3,2-b]pyridine-7-sulfonamide (4)

The crude rac-5a-(4-bromophenyl)-3-chloro-7a-hydroxy-N,N-dimethyl-8-oxo-6-phenyl-5a,6,7a,8-tetrahydro-7H-cyclobuta[5,6]pyrano[3,2-b]pyridine-7-sulfonamide (3, 0.7 g) was suspended in methanol (20 mL) and treated with sodium methoxide (25% in methanol, 10 mL) and heated the mixture to 80° C. for 2 h. After completion, the solvent was removed under reduced pressure and the reaction was treated with ammonium chloride solution and extracted with ethyl acetate. The organic phase was separated, dried over sodium sulphate and concentrated under reduced pressure to afford rac-(5aR,6S,7R,8aR)-5a-(4-bromophenyl)-3-chloro-8a-hydroxy-N,N-dimethyl-8-oxo-6-phenyl-5a,7,8,8a-tetrahydro-6H-cyclopenta[4,5]furo[3,2-b]pyridine-7-sulfonamide (4) as brown solid. Yield: 0.35 g, crude Synthesis of rac-(5aR,6S,7R,8S,8aS)-5a-(4-bromophenyl)-3-chloro-8,8a-dihydroxy-N,N-dimethyl-6-phenyl-5a,7,8,8a-tetrahydro-6H-cyclopenta[4,5]furo[3,2-b]pyridine-7-sulfonamide (5)

To a solution of sodium triacetoxyborohydride (1.27 g, 3.73 mmol) and rac-(5aR,6S,7R,8aR)-5a-(4-bromophenyl)-3-chloro-8a-hydroxy-N,N-dimethyl-8-oxo-6-phenyl-5a,7,8,8a-tetrahydro-6H-cyclopenta[4,5]furo[3,2-b]pyridine-7-sulfonamide (4, 0.35 g, 0.622 mmol) in acetonitrile (20 mL), acetic acid (4.0 mL, 6.22 mmol) was added. The resulting mixture was stirred for 15 h at room temperature. After completion, reaction mixture was partitioned between saturated aqueous sodium bicarbonate solution and ethyl acetate. The organic layer was separated, dried over sodium sulphate and concentrated under reduced pressure to get the crude. The crude was purified by Combi-flash (4 g, RediSep column) using 50% ethyl acetate in hexanes as eluent. The obtained compound was purified by reverse phase HPLC. The desired fractions were concentrated under reduced pressure to afford rac-(5aR,6S,7R,8S,8aS)-5a-(4-bromophenyl)-3-chloro-8,8a-dihydroxy-N,N-dimethyl-6-phenyl-5a,7,8,8a-tetrahydro-6H-cyclopenta[4,5]furo[3,2-b]pyridine-7-sulfonamide (5) as light yellow solid. Yield: 0.04 g, 10%. MS (ESI) m/z 565.06[M+1]$^+$.

Synthesis of rac-(5aR,6S,7R,8S,8aS)-3-chloro-5a-(4-cyanophenyl)-8,8a-dihydroxy-N,N-dimethyl-6-phenyl-5a,7,8,8a-tetrahydro-6H-cyclopenta[4,5]furo[3,2-b]pyridine-7-sulfonamide (Cpd. No. 22F)

To a solution of rac-(5aR,6S,7R,8S,8aS)-5a-(4-bromophenyl)-3-chloro-8,8a-dihydroxy-N,N-dimethyl-6-phenyl-5a,7,8,8a-tetrahydro-6H-cyclopenta[4,5]furo[3,2-b]pyridine-7-sulfonamide (0.03 g, 0.053 mmol) in N,N-dimethylformamide, zinc cyanide (0.005 g, 0.063 mmol) and zinc (0.001 g, 0.0053 mmol) were added at room temperature and degassed the mixture with argon for 15 min. 1,1'-Bis(diphenylphosphino)ferrocene (0.001 g, 0.001 mmol), tris(dibenzylideneacetone)dipalladium (0.002 g, 0.002 mmol) were added to the reaction and degassing was continued for 5 min. The reaction mixture was heated at 140° C. for 1 h. After completion, the reaction was cooled to room temperature and passed through celite bed. The filtrate was purified by Combi-flash (4 g, RediSep column) using 10% methanol in dichloromethane as eluent. Finally the compound was purified through reverse phase HPLC. The desired fractions were concentrated under reduced pressure to afford rac-(5aR,6S,7R,8S,8aS)-3-chloro-5a-(4-cyanophenyl)-8,8a-dihydroxy-N,N-dimethyl-6-phenyl-5a,7,8,8a-tetrahydro-6H-cyclopenta[4,5]furo[3,2-b]pyridine-7-sulfonamide (Cpd. No. 22F) as off white solid. Yield: 0.002 g, 7.3%; MS (ESI) m/z 512.45[M+1]$^+$. $^1$H NMR (400 MHz, DMSO-$d_6$) δ 8.20 (d, J=1.9 Hz, 1H), 7.69 (d, J=1.9 Hz, 1H), 7.49 (dd, J=14.6 Hz, 8.9 Hz, 4H), 7.14 (d, J=7.2 Hz, 2H), 7.08-6.99 (m, 3H), 6.44 (s, 1H), 5.97 (d, J=6.2 Hz, 1H), 4.95 (dd, J=13.8, 4.0 Hz, 1H), 4.65 (t, J=6.0 Hz, 1H), 4.58 (d, J=13.6, Hz, 1H), 2.46 (s, 6H).

Example 23

(4aR,5S,6R,7R,7aS)-4a-(4-cyanophenyl)-7,7a-dihydroxy-N,N,2-trimethyl-5-phenyl-2,4a,5,6,7,7a-hexahydrocyclopenta[4,5]furo[3,2-c]pyrazole-6-carboxamide (Cpd. No. 23F)

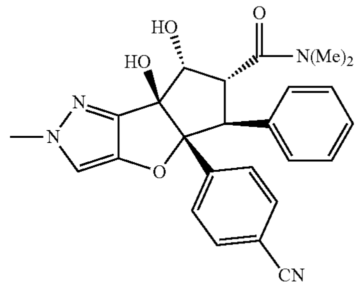

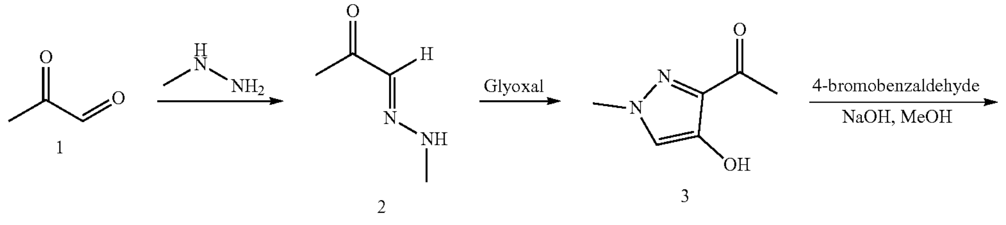

-continued
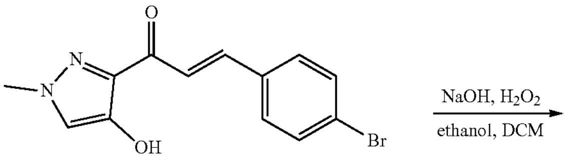
4
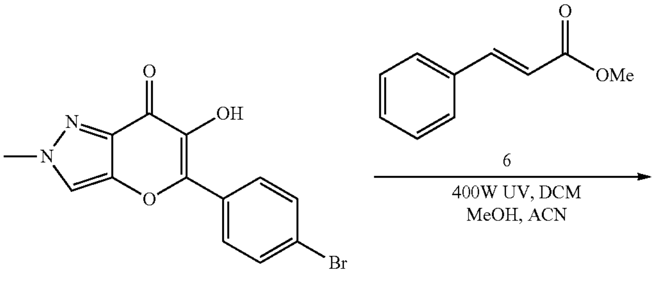
5
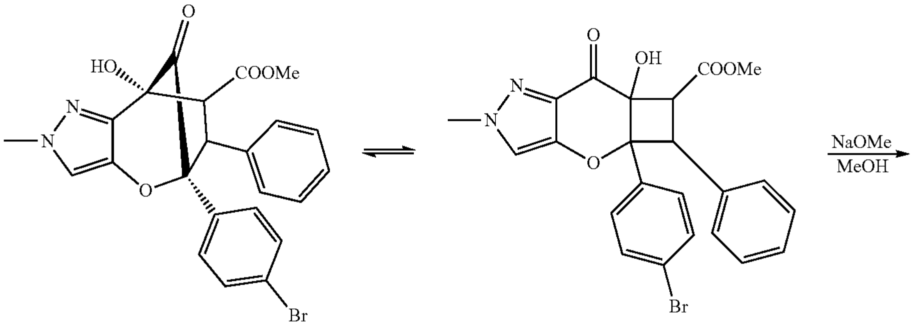
7
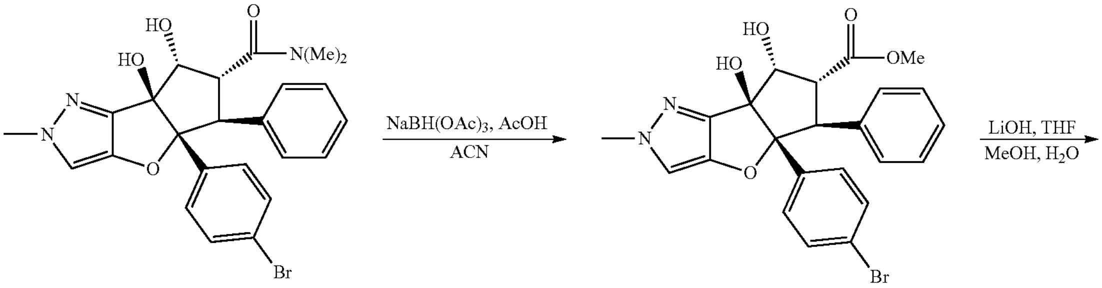
8 9
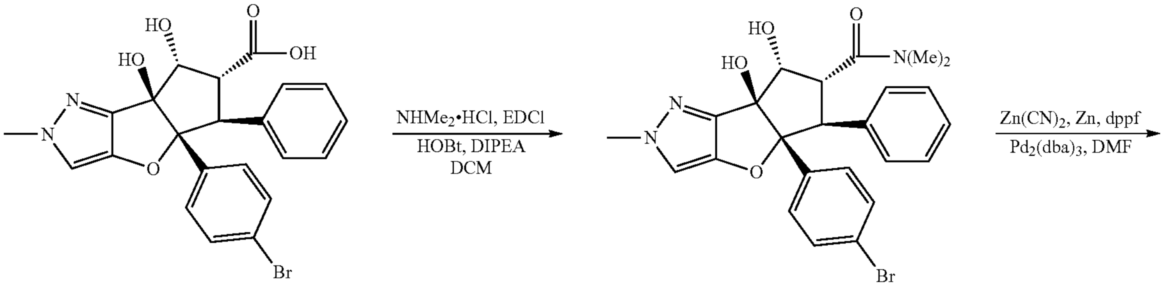
10 11

-continued

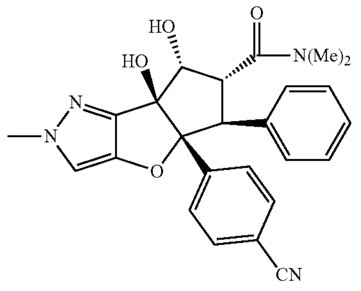

23F

Synthesis of (E)-1-(2-methylhydrazono)propan-2-one (2)

To a solution of 2-oxopropanal (1, 56.0 g, 777.3 mmol, 35% aqueous solution) in acetic acid (100 mL), methylhydrazine (36.0 g, 777.3 mmol, 80% aqueous solution) was added at 0° C. The reaction was stirred at room temperature for 16 h and then heated at 100° C. for 6 h. After completion, reaction mixture was diluted with ethyl acetate and washed with cold water. The organic layer was separated and dried over sodium sulphate, filtered and concentrated under reduced pressure to give crude. The crude was purified by silica gel column chromatography using 20% ethyl acetate in hexanes as eluent. The desired fractions were concentrated to afford (E)-1-(2-methylhydrazono)propan-2-one (2) as brown solid. Yield: 13.0 g, 16.8%; MS (ESI) m/z 101.02 $[M+1]^+$.

Synthesis of 1-(4-hydroxy-1-methyl-1H-pyrazol-3-yl)ethan-1-one (3)

To glyoxal (38.0 mL, 260.0 mmol, 40% aqueous solution), (E)-1-(2-methylhydrazono)propan-2-one (2, 13.0 g, 130.0 mmol) was added and the mixture was stirred at 110° C. for 2 h. After completion, reaction mixture was diluted with ethyl acetate and washed with cold water. The organic layer was separated and dried over sodium sulphate, filtered and concentrated to give crude. The crude was purified by silica gel column chromatography using 30% ethyl acetate in hexanes as eluent. The desired fractions were concentrated to afford 1-(4-hydroxy-1-methyl-1H-pyrazol-3-yl) ethan-1-one (3) as brown solid. Yield: 12.0 g, 65.9%; MS (ESI) m/z 141.04$[M+1]^+$.

Synthesis of (E)-3-(4-bromophenyl)-1-(4-hydroxy-1-methyl-1H-pyrazol-3-yl)prop-2-en-1-one (4)

To a solution of 1-(4-hydroxy-1-methyl-1H-pyrazol-3-yl) ethan-1-one (3, 12.0 g, 85.7 mmol) in methanol (70 mL), sodium hydroxide (10.28 g, 257.1 mmol) was added followed by addition of 4-bromobenzaldehyde (15.77 g, 85.7 mmol) and the reaction mixture was heated at 90° C. for 30 min. After completion, reaction mass was cooled to room temperature and the precipitated solid was filtered, washed with water and dried under vacuum to afford of (E)-3-(4-bromophenyl)-1-(4-hydroxy-1-methyl-1H-pyrazol-3-yl) prop-2-en-1-one (4) as yellow solid. Yield: 24.5 g, 98%; MS (ESI) m/z 307 $[M+1]^+$.

Synthesis of 5-(4-bromophenyl)-6-hydroxy-2-methylpyrano[3,2-c]pyrazol-7(2H)-one (5)

To a solution of (E)-3-(4-bromophenyl)-1-(4-hydroxy-1-methyl-1H-pyrazol-3-yl)prop-2-en-1-one (4, 24.0 g, 78.4 mmol) in ethanol (240 mL) and dichloromethane (100 mL), 10% aqueous sodium hydroxide solution (219 mL, 549.0 mmol) was added followed by addition of hydrogen peroxide (62.57 mL, 549.0 mmol, 30%) at room temperature. The reaction mass was stirred for 1 h (exotherm was observed). After completion, reaction mass was cooled and neutralized with 6 M hydrogen chloride to pH ~7. The precipitated solid was filtered and dried under vacuum to afford 5-(4-bromophenyl)-6-hydroxy-2-methylpyrano[3,2-c]pyrazol-7(2H)-one (5) as brown solid. Yield: 11.1 g, 44.4%; MS (ESI) m/z 319.09$[M-1]^-$.

Synthesis of rac-methyl (6S,7S,8R)-5-(4-bromophenyl)-8-hydroxy-2-methyl-9-oxo-6-phenyl-5,6,7,8-tetrahydro-2H-5,8-methanooxepino[3,2-c]pyrazole-7-carboxylate (7)

A solution of 5-(4-bromophenyl)-6-hydroxy-2-methylpyrano[3,2-c]pyrazol-7(2H)-one (5, 11.0 g, 34.3 mmol) and methyl cinnamate (6, 55.6 g, 34.3 mmol) in dichloromethane (200 mL), acetonitrile (100 mL) and methanol (100 mL) was placed in a UV reactor flask. The reaction mixture was irradiated for 8 h under 400 watts UV light. After completion, the solvent was removed under reduced pressure and the residue was purified over a plug of silica gel eluting the compound with 5% methanol in dichloromethane. The desired fractions were concentrated under reduced pressure to afford rac-methyl (6S,7S,8R)-5-(4-bromophenyl)-8-hydroxy-2-methyl-9-oxo-6-phenyl-5,6,7,8-tetrahydro-2H-5,8-methanooxepino[3,2-c]pyrazole-7-carboxylate (7). Yield: 18.1 g, crude.

Synthesis of rac-methyl (4aR,5S,6R,7aR)-4a-(4-bromophenyl)-7a-hydroxy-2-methyl-7-oxo-5-phenyl-2,4a,5,6,7,7a-hexahydrocyclopenta[4,5]furo[3,2-c]pyrazole-6-carboxylate (8)

The crude rac-methyl (6S,7S,8R)-5-(4-bromophenyl)-8-hydroxy-2-methyl-9-oxo-6-phenyl-5,6,7,8-tetrahydro-2H-5,8-methanooxepino[3,2-c]pyrazole-7-carboxylate (7, 18.0 g) was suspended in methanol (100 mL) and treated with sodium methoxide (25% in methanol, 90 mL) and heated the mixture to 90° C. for 3 h. After completion, the solvent was removed under reduced pressure, diluted the mixture with ammonium chloride solution and extracted with ethyl acetate. The organic phase was separated, dried over sodium sulphate and concentrated under reduced pressure to afford rac-methyl (4aR,5S,6R,7aR)-4a-(4-bromophenyl)-7a-hydroxy-2-methyl-7-oxo-5-phenyl-2,4a,5,6,7,7a-hexahydrocyclopenta[4,5]furo[3,2-c]pyrazole-6-carboxylate (8). Yield: 14.0 g, crude.

Synthesis of rac-methyl (4aR,5S,6R,7R,7aS)-4a-(4-bromophenyl)-7,7a-dihydroxy-2-methyl-5-phenyl-2,4a,5,6,7,7a-hexahydrocyclopenta[4,5]furo[3,2-c]pyrazole-6-carboxylate (9)

To a solution of sodium triacetoxyborohydride (18.4 g, 87.1 mmol), rac-methyl (4aR,5S,6R,7aR)-4a-(4-bromophenyl)-7a-hydroxy-2-methyl-7-oxo-5-phenyl-2,4a,5,6,7,7a-hexahydrocyclopenta[4,5]furo[3,2-c]pyrazole-6-carboxylate (8, 7.0 g) in acetonitrile (100 mL), acetic acid (9 mL, 145.0 mmol) was added. The resulting mixture was stirred for 18 h at room temperature. After completion, reaction mixture was partitioned between saturated aqueous sodium bicarbonate solution and ethyl acetate. The organic layer was separated, dried over sodium sulphate and concentrated under reduced pressure to get the crude. The crude was purified by silica gel column chromatography using 80% ethyl acetate in hexanes as eluent. The desired fractions were concentrated to afford rac-methyl (4aR,5S,6R,7R,7aS)-4a-(4-bromophenyl)-7,7a-dihydroxy-2-methyl-5-phenyl-2,4a,5,6,7,7a-hexahydrocyclopenta[4,5]furo[3,2-c]pyrazole-6-carboxylate (9) as off white solid. Yield: 1.4 g, 20.0%; MS (ESI) m/z 485.06[M+1]$^+$.

Synthesis of rac-(4aR,5S,6R,7R,7aS)-4a-(4-bromophenyl)-7,7a-dihydroxy-2-methyl-5-phenyl-2,4a,5,6,7,7a-hexahydrocyclopenta[4,5]furo[3,2-c]pyrazole-6-carboxylic acid (10)

To a solution of rac-methyl (4aR,5S,6R,7R,7aS)-4a-(4-bromophenyl)-7,7a-dihydroxy-2-methyl-5-phenyl-2,4a,5,6,7,7a-hexahydrocyclopenta[4,5]furo[3,2-c]pyrazole-6-carboxylate (9, 1.3 g, 2.68 mmol) in methanol: tetrahydrofuran: water (3:2:1, 18 mL), lithium hydroxide (1.12 g, 23.0 mmol) was added and the reaction was stirred for 3 h at room temperature. After completion, the reaction mass was cooled to 0° C. and acidified with 1 M hydrogen chloride to pH ~3. The precipitated solid was filtered and dried under vacuum to afford rac-(4aR,5S,6R,7R,7aS)-4a-(4-bromophenyl)-7,7a-dihydroxy-2-methyl-5-phenyl-2,4a,5,6,7,7a-hexahydrocyclopenta[4,5]furo[3,2-c]pyrazole-6-carboxylic acid (10) as white solid. Yield: 1.21 g, 95.4%; MS (ESI) m/z 471.19 [M+1]$^+$.

Synthesis of rac-(4aR,5S,6R,7R,7aS)-4a-(4-bromophenyl)-7,7a-dihydroxy-N,N,2-trimethyl-5-phenyl-2,4a,5,6,7,7a-hexahydrocyclopenta[4,5]furo[3,2-c]pyrazole-6-carboxamide (11)

To a solution of rac-(4aR,5S,6R,7R,7aS)-4a-(4-bromophenyl)-7,7a-dihydroxy-N,N,2-trimethyl-5-phenyl-2,4a,5,6,7,7a-hexahydrocyclopenta[4,5]furo[3,2-c]pyrazole-6-carboxamide (10, 1.2 g, 2.55 mmol) in dichloromethane (30 mL), 1-ethyl-3-(3-dimethylaminopropyl)carbodiimide hydrochloride (1.18 g, 7.65 mmol), 1-hydroxybenzotriazole (1.17 g, 7.65 mmol) and N,N-diisopropylethylamine (2.45 mL, 15.3 mmol) were added at 0° C. and stirred the mixture for 5 min. Dimethylamine hydrochloride (1.04 g, 12.7 mmol) was then added at same temperature and the mixture was stirred for 16 h at 40° C. After completion, reaction mass was diluted with dichloromethane and washed with cold water. The organic layer was separated and dried over sodium sulphate, filtered and concentrated to give crude. The crude was purified by silica gel column chromatography using 3% methanol in dichloromethane as eluent. The desired fractions were concentrated to afford rac-(4aR,5S,6R,7R,7aS)-4a-(4-bromophenyl)-7,7a-dihydroxy-N,N,2-trimethyl-5-phenyl-2,4a,5,6,7,7a-hexahydrocyclopenta[4,5]furo[3,2-c]pyrazole-6-carboxamide (11) as white solid. Yield: 1.0 g, 78.7%; MS (ESI) m/z 498.09[M+1]$^+$.

Synthesis of (4aR,5S,6R,7R,7aS)-4a-(4-cyanophenyl)-7,7a-dihydroxy-N,N,2-trimethyl-5-phenyl-2,4a,5,6,7,7a-hexahydrocyclopenta[4,5]furo[3,2-c]pyrazole-6-carboxamide (Cpd. No. 23F)

To a solution of rac-(4aR,5S,6R,7R,7aS)-4a-(4-bromophenyl)-7,7a-dihydroxy-N,N,2-trimethyl-5-phenyl-2,4a,5,6,7,7a-hexahydrocyclopenta[4,5]furo[3,2-c]pyrazole-6-carboxamide (11, 0.5 g, 1.0 mmol) in N,N-dimethylformamide (10.0 mL), zinc cyanide (0.71 g, 6.0 mmol) and zinc (0.008 g, 0.12 mmol) were added at room temperature and degassed the mixture with argon for 15 min. 1,1'-Bis(diphenylphosphino)ferrocene (0.011 g, 0.012 mmol), tris(dibenzylideneacetone)dipalladium (0.027 g, 0.03 mmol) were added to the reaction and degassing was continued for another 5 min. The reaction mixture was heated at 140° C. for 3 h. After completion, the reaction mass was diluted with ethyl acetate and washed with cold water. The organic layer was separated and dried over sodium sulphate, filtered and concentrated to give crude. The crude was purified by silica gel column chromatography using 2-3% methanol in dichloromethane as eluent. The desired fractions were concentrated to afford rac-(4aR,5S,6R,7R,7aS)-4a-(4-cyanophenyl)-7,7a-dihydroxy-N,N,2-trimethyl-5-phenyl-2,4a,5,6,7,7a-hexahydrocyclopenta[4,5]furo[3,2-c]pyrazole-6-carboxamide (rac-Cpd. No. 23F) as white solid. The enantiomers were separated by chiral preparative HPLC [chiralpak IB (4.6×250) mm]. Yield: 0.26 g, (racemic mixture). Peak 1 (Cpd. No. 23F, 100 mg), $[\alpha]_D$−100.5° (c 0.1, $CHCl_3$), $R_t$=4.419 min, ee >99%. $^1$H NMR (400 MHz, DMSO-$d_6$) δ: 7.53 (d, J=8.8 Hz, 2H), 7.35 (s, 1H), 7.32 (d, J=8.4 Hz, 2H), 7.03-6.94 (m, 3H), 6.80 (d, J=6.8 Hz, 2H), 5.64 (s, 1H), 5.21 (d, J=6.2 Hz, 1H), 4.81 (t, J=6.8 Hz, 1H), 4.42 (d, J=13.4 Hz, 1H), 4.07 (dd, J=13.4, 7.6 Hz, 1H), 3.81 (s, 3H), 3.20 (s, 3H), 2.73 (s, 3H); MS (ESI) m/z 445.5[M+1]$^+$. Peak-2 (95 mg), $[\alpha]_D$+95.5° (c 0.1, $CHCl_3$), $R_t$=7.878 min, ee >99%. $^1$H NMR (400 MHz, DMSO-$d_6$) δ: 7.53 (d, J=8.6 Hz, 2H), 7.35 (s, 1H), 7.32 (d, J=8.4 Hz, 2H), 6.99 (m, 3H), 6.80 (d, J=7.0 Hz, 2H), 5.64 (s, 1H), 5.21 (d, J=6.28 Hz, 1H), 4.81 (t, J=7.0 Hz, 1H), 4.42 (d, J=13.2 Hz, 1H), 4.07 (dd, J=13.3, 7.6 Hz, 1H), 3.81 (s, 3H), 3.20 (s, 3H), 2.73 (s, 3H); MS (ESI) m/z 445.5[M+1]$^+$.

Example 24

Rac-methyl (5aR,6R,6aS,7aS,7bR)-3-chloro-5a-(4-cyanophenyl)-7b-hydroxy-6-phenyl-5a,7,7a,7b-tetrahydrocyclopropa[4',5']cyclopenta[1',2':4,5]furo[3,2-b]pyridine-6a(6H)-carboxylate (Cpd. No. 24F)

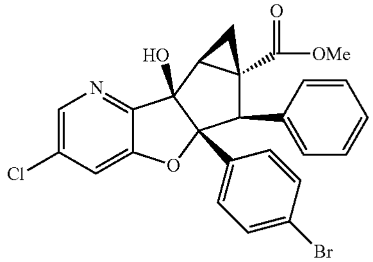

-continued

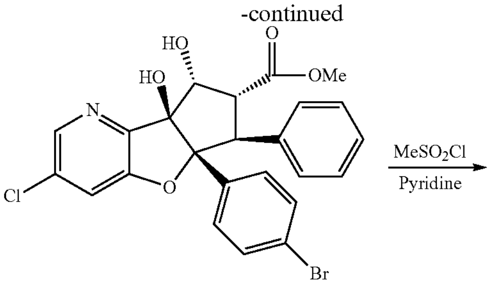

1

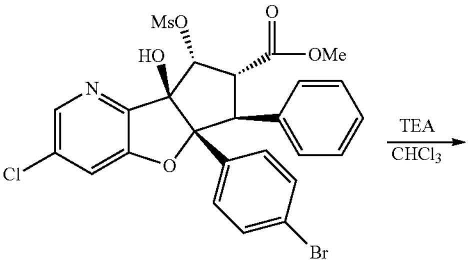

2

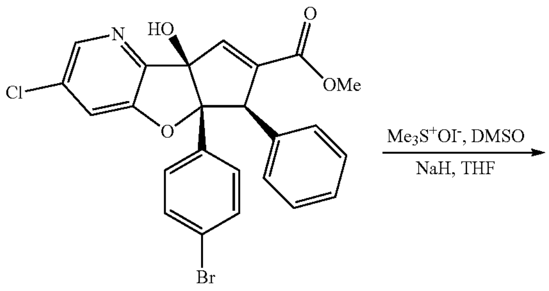

3

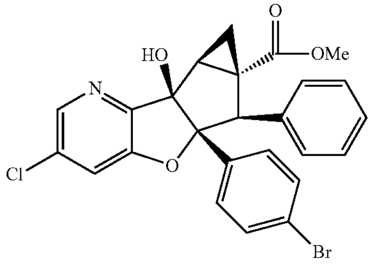

24F

Synthesis of rac-methyl (5aR,6S,7R,8R,8aS)-5a-(4-bromophenyl)-3-chloro-8a-hydroxy-8-((methylsulfonyl)oxy)-6-phenyl-5a,7,8,8a-tetrahydro-6H-cyclopenta[4,5]furo[3,2-b]pyridine-7-carboxylate (2)

To a solution of rac-methyl (5aR,6S,7R,8R,8aS)-5a-(4-bromophenyl)-3-chloro-8,8a-dihydroxy-6-phenyl-5a,7,8,8a-tetrahydro-6H-cyclopenta[4,5]furo[3,2-b]pyridine-7-carboxylate (1, 1.3 g, 2.5 mmol) in pyridine (5 mL) under nitrogen, methanesulphonyl chloride (0.3 mL, 3.7 mmol) was added at room temperature. The reaction mixture was stirred at room temperature for 6 h. After completion, the reaction mixture was diluted with ethyl acetate (50 mL) and washed with water (20 mL) and brine (20 mL). The organic layer was dried over anhydrous sodium sulphate and concentrated under reduced pressure to get crude. The crude was triturated with n-pentane and diethyl-ether. The precipitated solid was filtered and dried under vacuum to afford rac-methyl (5aR,6S,7R,8R,8aS)-5a-(4-bromophenyl)-3-chloro-8a-hydroxy-8-((methylsulfonyl)oxy)-6-phenyl-5a,7,8,8a-tetrahydro-6H-cyclopenta[4,5]furo[3,2-b]pyridine-7-carboxylate (2) as yellow solid. Yield: 1.4 g, 93.5%; MS (ESI) m/z 594.18[M+1]$^+$.

Synthesis of rac-methyl (5aR,6R,8aR)-5a-(4-bromophenyl)-3-chloro-8a-hydroxy-6-phenyl-5a,8a-dihydro-6H-cyclopenta[4,5]furo[3,2-b]pyridine-7-carboxylate (3)

To a solution of rac-methyl (5aR,6S,7R,8R,8aS)-5a-(4-bromophenyl)-3-chloro-8a-hydroxy-8-((methylsulfonyl)oxy)-6-phenyl-5a,7,8,8a-tetrahydro-6H-cyclopenta[4,5]furo[3,2-b]pyridine-7-carboxylate (2, 1.3 g, 2.18 mmol) in chloroform (10 mL), triethylamine (5 mL) was added at room temperature. The reaction mixture was stirred at 85° C. for 16 h. After completion of reaction, water (50 mL) was added and then extracted with ethyl acetate (60 mL). The organic layer was washed with brine and dried over anhydrous sodium sulphate, filtered and concentrated under reduced pressure to get the crude. The crude was purified by Combi-flash (4 g, RediSep column) using 30% ethyl acetate in hexanes as eluent. The desired fractions were concentrated to afford rac-methyl (5aR,6R,8aR)-5a-(4-bromophenyl)-3-chloro-8a-hydroxy-6-phenyl-5a,8a-dihydro-6H-cyclopenta[4,5]furo[3,2-b]pyridine-7-carboxylate (3) as white solid. Yield: 0.65 g, 60%; MS (ESI) m/z 498.18[M+1]$^+$.

Synthesis of rac-methyl (5aR,6R,6aS,7aS,7bR)-5a-(4-bromophenyl)-3-chloro-7b-hydroxy-6-phenyl-5a,7,7a,7b-tetrahydrocyclopropa[4',5']cyclopenta[1',2':4,5]furo[3,2-b]pyridine-6a(6H)-carboxylate (Cpd. No. 24F)

To a solution of sodium hydride (72 mg, 1.8 mmol) in dimethyl sulfoxide (15 mL) under nitrogen, trimethylsulfoxonium iodide (0.42 g, 1.92 mmol) was added at room temperature and allowed to stir at room temperature for 1 h. Then rac-methyl (5aR,6R,8aR)-5a-(4-bromophenyl)-3-chloro-8a-hydroxy-6-phenyl-5a,8a-dihydro-6H-cyclopenta[4,5]furo[3,2-b]pyridine-7-carboxylate (600 mg, 1.2 mmol) in dimethyl sulfoxide:tetrahydrofuran (1:1) was added to above suspension at 0° C. and the reaction mixture was stirred at room temperature for 16 h. After completion, water (30 mL) was added and then extracted with ethyl acetate (50 mL). The organic layer was washed with brine and dried over anhydrous sodium sulphate, filtered and concentrated under reduced pressure to get the crude. The crude containing starting material and desired product at same retention factor ($R_f$) on TLC and LCMS, was purified by reverse phase HPLC. The desired fractions were concentrated to afford rac-methyl (5aR,6R,6aS,7aS,7bR)-5a-(4-bromophenyl)-3-chloro-7b-hydroxy-6-phenyl-5a,7,7a,7b-tetrahydrocyclopropa[4',5']cyclopenta[1',2':4,5]furo[3,2-b]pyridine-6a(6H)-carboxylate (Cpd. No. 24F) as white solid. Yield: 58 mg, 10%; MS (ESI) m/z 512.34[M+1]$^+$; $^1$H NMR (400 MHz, DMSO-$d_6$) δ 8.32 (s, 1H), 7.79 (s, 1H), 7.26 (d, J=8.2 Hz, 2H), 7.18-7.11 (m, 5H), 7.02 (d, J=8.24 Hz, 2H), 6.18 (s, 1H), 4.53 (s, 1H), 3.48 (s, 3H), 2.58 (d, J=5.0 Hz, 1H), 1.94 (t, J=8 Hz, 1H), 1.87 (t, J=3.76 Hz, 1H).

Example 25

Rac-methyl (5aR,6R,6aS,7aS,7bR)-3-chloro-5a-(4-cyanophenyl)-7b-hydroxy-6-phenyl-5a,7,7a,7b-tetrahydrocyclopropa[4',5']cyclopenta[1',2':4,5]furo[3,2-b]pyridine-6a(6H)-carboxylate (Cpd. No. 25F)

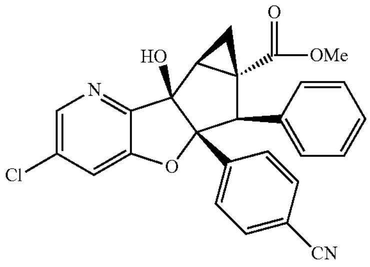

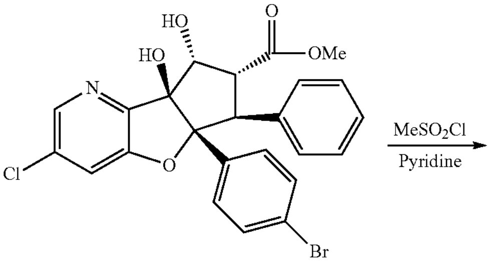

1

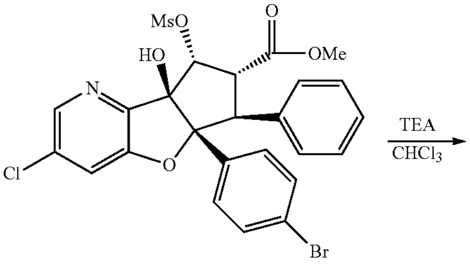

2

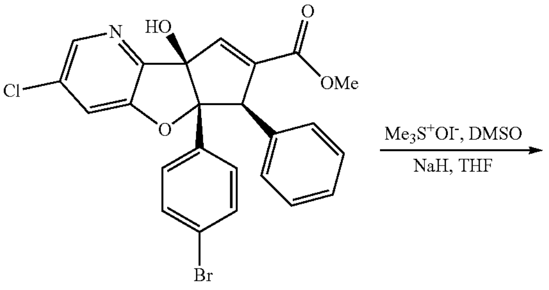

3

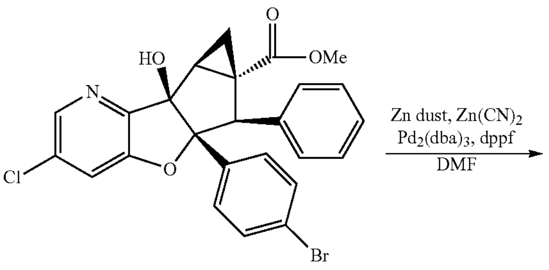

4

-continued

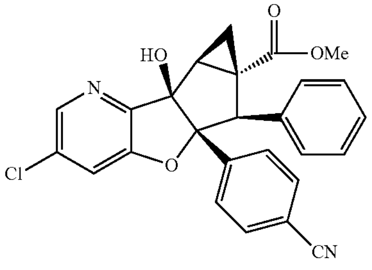

25F

Synthesis of rac-methyl (5aR,6S,7R,8R,8aS)-5a-(4-bromophenyl)-3-chloro-8a-hydroxy-8-((methylsulfonyl)oxy)-6-phenyl-5a,7,8,8a-tetrahydro-6H-cyclopenta[4,5]furo[3,2-b]pyridine-7-carboxylate (2)

To a solution of rac-methyl (5aR,6S,7R,8R,8aS)-5a-(4-bromophenyl)-3-chloro-8,8a-dihydroxy-6-phenyl-5a,7,8,8a-tetrahydro-6H-cyclopenta[4,5]furo[3,2-b]pyridine-7-carboxylate (1, 1.3 g, 2.5 mmol) in pyridine (5 mL) under nitrogen, methanesulphonyl chloride (0.3 mL, 3.7 mmol) was added at room temperature. The reaction mixture was stirred at room temperature for 6 h. After completion, the reaction mixture was diluted with ethyl acetate (50 mL) and washed with water (20 mL) and brine (20 mL). The organic layer was dried over anhydrous sodium sulphate and concentrated under reduced pressure to get crude. The crude was triturated with n-pentane and diethyl-ether. The precipitated solid was filtered and dried under vacuum to afford rac-methyl (5aR,6S,7R,8R,8aS)-5a-(4-bromophenyl)-3-chloro-8a-hydroxy-8-((methylsulfonyl)oxy)-6-phenyl-5a,7,8,8a-tetrahydro-6H-cyclopenta[4,5]furo[3,2-b]pyridine-7-carboxylate (2) as yellow solid. Yield: 1.4 g, 93.5%; MS (ESI) m/z 594.18[M+1]$^+$.

Synthesis of rac-methyl (5aR,6R,8aR)-5a-(4-bromophenyl)-3-chloro-8a-hydroxy-6-phenyl-5a,8a-dihydro-6H-cyclopenta[4,5]furo[3,2-b]pyridine-7-carboxylate (3)

To a solution of rac-methyl (5aR,6S,7R,8R,8aS)-5a-(4-bromophenyl)-3-chloro-8a-hydroxy-8-((methylsulfonyl)oxy)-6-phenyl-5a,7,8,8a-tetrahydro-6H-cyclopenta[4,5]furo[3,2-b]pyridine-7-carboxylate (2, 1.3 g, 2.18 mmol) in chloroform (10 mL), triethylamine (5 mL) was added at room temperature. The reaction mixture was stirred at 85° C. for 16 h. After completion of reaction, water (50 mL) was added and then extracted with ethyl acetate (60 mL). The organic layer was washed with brine and dried over anhydrous sodium sulphate, filtered and concentrated under reduced pressure to get the crude. The crude was purified by Combi-flash (4 g, RediSep column) using 30% ethyl acetate in hexanes as eluent. The desired fractions were concentrated to afford rac-methyl (5aR,6R,8aR)-5a-(4-bromophenyl)-3-chloro-8a-hydroxy-6-phenyl-5a,8a-dihydro-6H-cyclopenta[4,5]furo[3,2-b]pyridine-7-carboxylate (3) as white solid. Yield: 0.65 g, 60%; MS (ESI) m/z 498.18[M+1]$^+$.

Synthesis of rac-methyl (5aR,6R,6aS,7aS,7bR)-5a-(4-bromophenyl)-3-chloro-7b-hydroxy-6-phenyl-5a,7,7a, 7b-tetrahydrocyclopropa[4',5']cyclopenta[1',2':4,5]furo[3,2-b]pyridine-6a(6H)-carboxylate (4)

To a solution of sodium hydride (72 mg, 1.8 mmol) in dimethyl sulfoxide (15 mL) under nitrogen, trimethylsulfoxonium iodide (0.42 g, 1.92 mmol) was added at room temperature and allowed to stir at room temperature for 1 h. Then rac-methyl (5aR,6R,8aR)-5a-(4-bromophenyl)-3-chloro-8a-hydroxy-6-phenyl-5a,8a-dihydro-6H-cyclopenta[4,5]furo[3,2-b]pyridine-7-carboxylate (600 mg, 1.2 mmol) in dimethyl sulfoxide:tetrahydrofuran (1:1) was added to above suspension at 0° C. and the reaction mixture was stirred at room temperature for 16 h. After completion, water (30 mL) was added and then extracted with ethyl acetate (50 mL). The organic layer was washed with brine and dried over anhydrous sodium sulphate, filtered and concentrated under reduced pressure to get the crude. The crude containing starting material and desired product at same retention factor ($R_f$) on TLC and LCMS, was purified by reverse phase HPLC. The desired fractions were concentrated to afford rac-methyl (5aR,6R,6aS,7aS,7bR)-5a-(4-bromophenyl)-3-chloro-7b-hydroxy-6-phenyl-5a,7,7a,7b-tetrahydrocyclopropa[4',5']cyclopenta[1',2':4,5]furo[3,2-b]pyridine-6a(6H)-carboxylate (4) as white solid. Yield: 58 mg, 10%; MS (ESI) m/z 512.34[M+1]$^+$; UPLC: 99.85%; $^1$H NMR (400 MHz, DMSO-$d_6$) δ 8.32 (s, 1H), 7.79 (s, 1H), 7.26 (d, J=8.2 Hz, 2H), 7.18-7.11 (m, 5H), 7.02 (d, J=8.24 Hz, 2H), 6.18 (s, 1H), 4.53 (s, 1H), 3.48 (s, 3H), 2.58 (d, J=5.0 Hz, 1H), 1.94 (t, J=8 Hz, 1H), 1.87 (t, J=3.76 Hz, 1H).

Synthesis of rac-methyl (5aR,6R,6aS,7aS,7bR)-3-chloro-5a-(4-cyanophenyl)-7b-hydroxy-6-phenyl-5a,7,7a, 7b-tetrahydrocyclopropa[4',5']cyclopenta[1',2':4,5]furo[3,2-b]pyridine-6a(6H)-carboxylate (Cpd. No. 25F)

To a solution of rac-methyl (5aR,6R,6aS,7aS,7bR)-5a-(4-bromophenyl)-3-chloro-7b-hydroxy-6-phenyl-5a,7,7a,7b-tetrahydrocyclopropa[4',5']cyclopenta[1',2':4,5]furo[3,2-b]pyridine-6a(6H)-carboxylate (4, 20 mg, 0.039 mmol) in N,N-dimethylformamide (10.0 mL), zinc cyanide (10 mg, 0.156 mmol) and zinc (9 mg, 0.078 mmol) were added at room temperature and degassed the mixture with argon for 15 min. 1,1'-Bis(diphenylphosphino)ferrocene (1.0 mg, 0.018 mmol), tris(dibenzylideneacetone) dipalladium (1.0 mg, 0.00078 mmol) were added to the reaction and degassing was continued for another 5 min. The reaction mixture was heated at 130° C. for 6 h. After completion, the reaction was cooled to room temperature and passed through celite bed. The filtrate was diluted with ethyl acetate and washed with water. The organic layer was separated, dried over sodium sulphate and concentrated under reduced pressure to get the crude containing desired product and dicyano (side product). The crude was purified by reverse phase HPLC. The desired fractions were concentrated under reduced pressure to afford rac-methyl (5aR,6R,6aS,7aS,7bR)-3-chloro-5a-(4-cyanophenyl)-7b-hydroxy-6-phenyl-5a,7,7a,7b-tetrahydrocyclopropa[4',5']cyclopenta[1',2':4,5]furo[3,2-b]pyridine-6a(6H)-carboxylate (Cpd. No. 25F) as white solid. Yield: 3 mg, 15.7%; MS (ESI) m/z 459.40[M+1]$^+$; UPLC: 97.51%; $^1$H NMR (400 MHz, DMSO-$d_6$) δ 8.34 (d, J=1.9 Hz, 1H), 7.82 (d, J=1.9 Hz, 1H), 7.55 (d, J=8.6 Hz, 2H), 7.27 (d, J=8.5 Hz, 2H), 7.19-7.09 (m, 5H), 6.28 (s, 1H), 4.59 (s, 1H), 3.48 (s, 3H), 3.17 (d, J=5.2 Hz, 1H), 1.98 (t, J=5.5 Hz, 1H), 1.90 (t, J=8.7 Hz, 1H).

Example 26

Rac-4-((5aR,6S,7R,8R,8aS)-3-chloro-8,8a-dihydroxy-7-(oxazol-2-yl)-6-phenyl-6,7,8,8a-tetrahydro-5aH-cyclopenta[4,5]furo[3,2-b]pyridin-5a-yl)benzonitrile (Cpd. No. 26F)

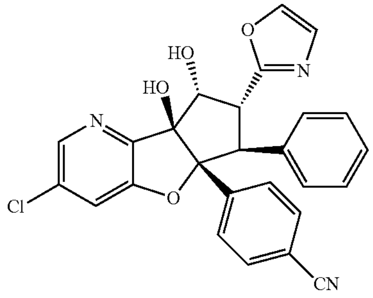

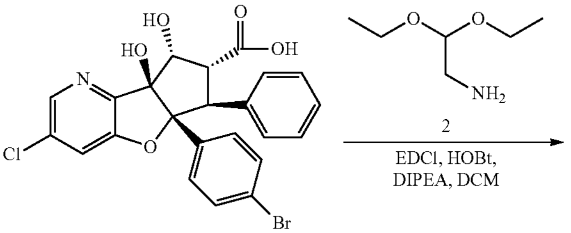

1

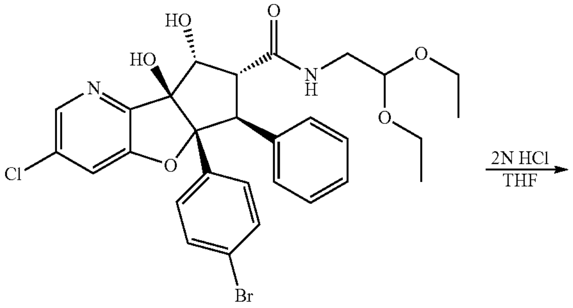

3

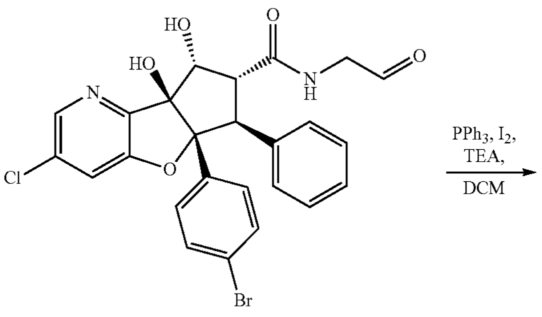

4

-continued

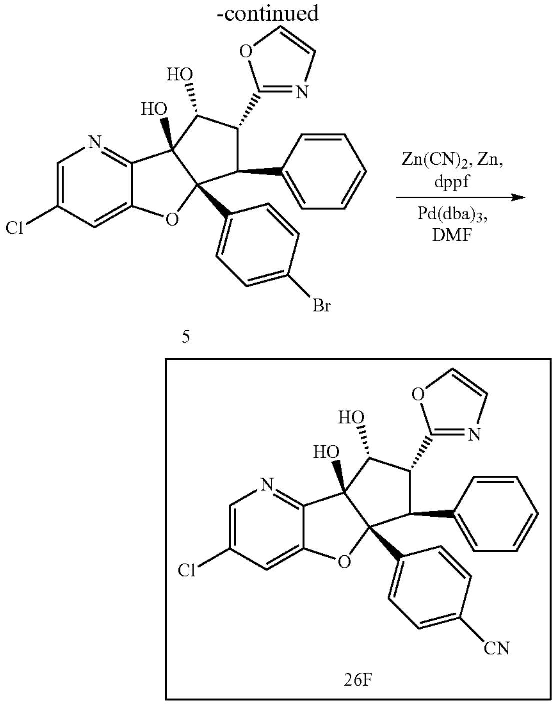

5

26F

Synthesis of rac-(5aR,6S,7R,8R,8aS)-5a-(4-bromophenyl)-3-chloro-N-(2,2-diethoxyethyl)-8,8a-dihydroxy-6-phenyl-5a, 7,8,8a-tetrahydro-6H-cyclopenta[4,5]furo[3,2-b]pyridine-7-carboxamide (3)

To a solution of rac-(5aR,6S,7R,8R,8aS)-5a-(4-bromophenyl)-3-chloro-8,8a-dihydroxy-6-phenyl-5a,7,8,8a-tetrahydro-6H-cyclopenta[4,5]furo[3,2-b]pyridine-7-carboxylic acid (1, 1.4 g, 2.7 mmol) in dichloromethane (20 mL), 1-ethyl-3-(3-dimethylaminopropyl) carbodiimide hydrochloride (1.6 g, 8.3 mmol), 1-hydroxybenzotriazole (1.13 g, 8.3 mmol) and N,N-diisopropylethylamine (2.88 mL, 16.0 mmol) were added at 0° C. and stirred the mixture for 5 min. 2,2-diethoxyethan-1-amine (2, 2.35 g, 13.0 mmol) was then added at same temperature and the reaction was stirred at 35° C. for 16 h. After completion, reaction mass was diluted with dichloromethane and washed with cold water. The organic layer was separated and dried over anhydrous sodium sulphate, filtered and concentrated to give crude. The crude was purified by Combi-flash (12 g, RediSep column) using 2% methanol in dichloromethane as eluent. The desired fractions were concentrated under reduced pressure to afford rac-(5aR,6S,7R,8R,8aS)-5a-(4-bromophenyl)-3-chloro-N-(2,2-diethoxyethyl)-8,8a-dihydroxy-6-phenyl-5a,7,8,8a-tetrahydro-6H-cyclopenta[4,5]furo[3,2-b]pyridine-7-carboxamide (3) as light brown oil. Yield: 1.1 g, 64%; MS (ESI) m/z 617.12[M+1]$^+$.

Synthesis of rac-(5aR,6S,7R,8R,8aS)-5a-(4-bromophenyl)-3-chloro-8,8a-dihydroxy-N-(2-oxoethyl)-6-phenyl-5a,7,8,8a-tetrahydro-6H-cyclopenta[4,5]furo[3,2-b]pyridine-7-carboxamide (4)

To a solution of rac-(5aR,6S,7R,8R,8aS)-5a-(4-bromophenyl)-3-chloro-N-(2,2-diethoxyethyl)-8,8a-dihydroxy-6-phenyl-5a,7,8,8a-tetrahydro-6H-cyclopenta[4,5]furo[3,2-b]pyridine-7-carboxamide (3, 1.0 g, 1.6 mmol) in tetrahydrofuran (5.0 mL), 2N hydrochloric acid (5.0 mL) was added. The reaction mixture was stirred for 4 h at room temperature. After completion, the reaction mass diluted with ethyl acetate and organic layer was separated and dried over anhydrous sodium sulphate, filtered and concentrated under reduced pressure to afford rac-(5aR,6S,7R,8R,8aS)-5a-(4-bromophenyl)-3-chloro-8,8a-dihydroxy-N-(2-oxoethyl)-6-phenyl-5a,7,8,8a-tetrahydro-6H-cyclopenta[4,5]furo[3,2-b]pyridine-7-carboxamide (4) as white solid. Yield: 0.91 g, crude, MS (ESI) m/z 543.23[M+1]$^+$.

Synthesis of rac-(5aR,6S,7R,8R,8aS)-5a-(4-bromophenyl)-3-chloro-7-(oxazol-2-yl)-6-phenyl-5a,6,7,8-tetrahydro-8aH-cyclopenta[4,5]furo[3,2-b]pyridine-8,8a-diol (5)

To a solution of rac-(5aR,6S,7R,8R,8aS)-5a-(4-bromophenyl)-3-chloro-8,8a-dihydroxy-N-(2-oxoethyl)-6-phenyl-5a,7,8,8a-tetrahydro-6H-cyclopenta[4,5]furo[3,2-b]pyridine-7-carboxamide (4, 0.9 g, 1.6 mmol) in dichloromethane (20.0 mL), triphenyl phosphine (0.87 g, 3.0 mmol), iodine (0.83 g, 3.3 mmol) and triethylamine (0.86 mL, 6.4 mmol) were added. The reaction mixture was stirred at room temperature for 16 h. After completion, the reaction mass diluted with dichloromethane and organic layer was washed with water (2×20 mL) and brine (20 mL). The organics layer was separated and dried over anhydrous sodium sulphate before concentration to dryness. The crude was purified by Combi-flash (4 g, RediSep column) using 2% methanol in dichloromethane as eluent. The desired fractions were concentrated to afford rac-(5aR,6S,7R,8R,8aS)-5a-(4-bromophenyl)-3-chloro-7-(oxazol-2-yl)-6-phenyl-5a,6,7,8-tetrahydro-8aH-cyclopenta[4,5]furo[3,2-b]pyridine-8,8a-diol (5) as off white solid. Yield: 0.18 g, 20%, MS (ESI) m/z 525.15[M+1]$^+$.

Synthesis of rac-4-((5aR,6S,7R,8R,8aS)-3-chloro-8,8a-dihydroxy-7-(oxazol-2-yl)-6-phenyl-6,7,8,8a-tetrahydro-5aH-cyclopenta[4,5]furo[3,2-b]pyridin-5a-yl)benzonitrile (Cpd. No. 26F)

To a solution of rac-(5aR,6S,7R,8R,8aS)-5a-(4-bromophenyl)-3-chloro-7-(oxazol-2-yl)-6-phenyl-5a,6,7,8-tetrahydro-8aH-cyclopenta[4,5]furo[3,2-b]pyridine-8,8a-diol (5, 0.06 g, 0.095 mmol) in N,N-dimethylformamide (1.0 mL), zinc cyanide (0.012 g, 0.1 mmol) and zinc (0.014 g, 0.19 mmol) were added at room temperature and degassed the mixture with argon for 15 min. 1,1'-Bis(diphenylphosphino)ferrocene (0.0013 g, 0.0019 mmol), tris(dibenzylideneacetone)dipalladium (0.0026 g, 0.0028 mmol) were added to the reaction and degassing was continued for another 5 min. The reaction mixture was heated at 150° C. for 2 h. After completion, the reaction was cooled to room temperature and passed through celite bed. The filtrate was diluted with ethyl acetate and washed with water. The organic layer was separated, dried over sodium sulphate and concentrated under reduced pressure to get the crude. The crude was purified by Combi-flash (4 g, RediSep column) using 2% methanol in dichloromethane as eluent. The desired fractions were concentrated under reduced pressure. The compound obtained was further given for reverse phase HPLC. The desired fractions were collected and were lyophilized to afford rac-4-((5aR,6S,7R,8R,8aS)-3-chloro-8,8a-dihydroxy-7-(oxazol-2-yl)-6-phenyl-6,7,8,8a-tetrahydro-5aH-cyclopenta[4,5]furo[3,2-b]pyridin-5a-yl)benzonitrile (Cpd. No. 26F) as white solid. Yield: 0.012 g, 27%; MS (ESI) m/z 472.40[M+1]$^+$. UPLC: 99.63%; $^1$H NMR (400 MHz, DMSO-$d_6$) δ 8.20 (d, J=2.0 Hz, 1H), 7.94 (s, 1H), 7.74 (d, J=2.0 Hz, 1H), 7.49 (d, J=8.5 Hz, 2H), 7.35 (d, J=8.5 Hz, 2H), 7.04-6.94 (m, 6H), 6.36 (brs, 1H), 5.60 (brs, J=5.0 Hz, 1H), 4.85 (d, J=14.0 Hz, 1H), 4.68 (dd, J=14.0, 4.2 Hz, 1H), 4.60 (d, J=4.1 Hz, 1H).

Example 27

Rac-(5aR,6S,7R,8R,8aS)-5a-(4-bromophenyl)-3-chloro-8,8a-dihydroxy-6-phenyl-5a,7,8,8a-tetrahydro-6H-cyclopenta[4,5]furo[3,2-b]pyridine-7-carbothioamide (Cpd. No. 27F)

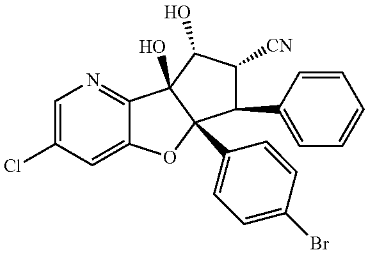

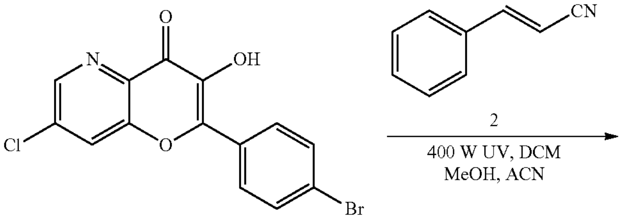

1

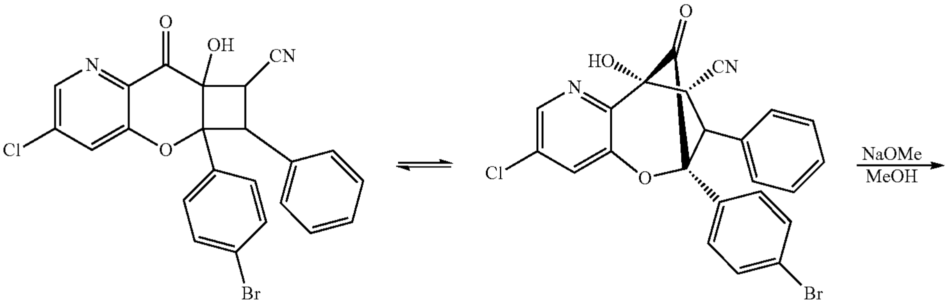

3 3a

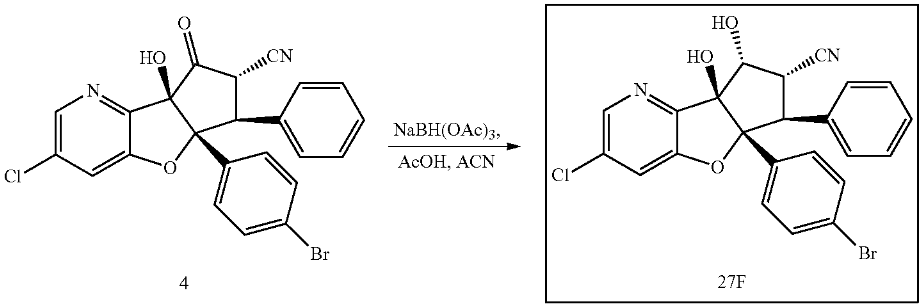

4 27F

Synthesis of rac-5a-(4-bromophenyl)-3-chloro-7a-hydroxy-8-oxo-6-phenyl-5a,6,7a,8-tetrahydro-7H-cyclobuta[5,6]pyrano[3,2-b]pyridine-7-carbonitrile (3/3a)

A solution of 2-(4-bromophenyl)-7-chloro-3-hydroxy-4H-pyrano[3,2-b]pyridin-4-one (1, 5.0 g, 14.25 mmol) and cinnamonitrile (2, 18.3 g, 142.4 mmol) in dichloromethane (200 mL), acetonitrile (100 mL) and methanol (100 mL) was placed in a UV reactor flask. The reaction mixture was irradiated for 16 h under 400 watts UV light. After comple tion, the solvent was removed under reduced pressure and the residue was purified by Combi-flash (24 g RediSep column) using ethyl acetate as eluent. The desired fractions were concentrated under reduced pressure to afford rac-5a-(4-bromophenyl)-3-chloro-7a-hydroxy-8-oxo-6-phenyl-5a,6,7a,8-tetrahydro-7H-cyclobuta[5,6]pyrano[3,2-b]pyridine-7-carbonitrile (3/3a) as brown solid. Yield: 6.0 g; crude.

Synthesis of rac-(5aR,6S,7S,8aR)-5a-(4-bromophenyl)-3-chloro-8a-hydroxy-8-oxo-6-phenyl-5a,7,8,8a-tetrahydro-6H-cyclopenta[4,5]furo[3,2-b]pyridine-7-carbonitrile (4)

The crude rac-5a-(4-bromophenyl)-3-chloro-7a-hydroxy-8-oxo-6-phenyl-5a,6,7a,8-tetrahydro-7H-cyclobuta[5,6]pyrano[3,2-b]pyridine-7-carbonitrile (3, 6.0 g) was suspended in methanol (60 mL) and treated with sodium methoxide (25% in methanol, 60 mL) and heated the mixture to 70° C. for 1 h. After completion, the solvent was removed under reduced pressure and the reaction was quenched with ammonium chloride solution and extracted with ethyl acetate. The organic phase was separated, dried over sodium sulphate and concentrated under reduced pressure to afford rac-(5aR,6S,7S,8aR)-5a-(4-bromophenyl)-3-chloro-8a-hydroxy-8-oxo-6-phenyl-5a,7,8,8a-tetrahydro-6H-cyclopenta[4,5]furo[3,2-b]pyridine-7-carbonitrile (4) as brown solid. Yield: 6.0 g, crude.

Synthesis of rac-(5aR,6S,7S,8R,8aS)-5a-(4-bromophenyl)-3-chloro-8,8a-dihydroxy-6-phenyl-5a,7,8,8a-tetrahydro-6H-cyclopenta[4,5]furo[3,2-b]pyridine-7-carbonitrile (Cpd. No. 27F)

To a solution of sodium triacetoxyborohydride (7.95 g, 37.5 mmol) and rac-(5aR,6S,7S,8aR)-5a-(4-bromophenyl)-3-chloro-8a-hydroxy-8-oxo-6-phenyl-5a,7,8,8a-tetrahydro-6H-cyclopenta[4,5]furo[3,2-b]pyridine-7-carbonitrile carboxylate (4, 6.0 g) in acetonitrile (70 mL), acetic acid (7.5 mL, 125 mmol) was added. The resulting mixture was stirred at room temperature for 16 h. After completion, reaction mixture was partitioned between saturated aqueous sodium bicarbonate solution and ethyl acetate. The organic layer was separated, dried over sodium sulphate and concentrated under reduced pressure to get the crude. The crude was purified by reverse phase HPLC. The desired fractions were concentrated under reduced pressure to afford rac-(5aR,6S,7S,8R,8aS)-5a-(4-bromophenyl)-3-chloro-8,8a-dihydroxy-6-phenyl-5a,7,8,8a-tetrahydro-6H-cyclopenta[4,5]furo[3,2-b]pyridine-7-carbonitrile (Cpd. No. 27F) as light yellow solid. Yield: 4.6 g, 76.0%; MS (ESI) m/z 483.35[M+1]$^+$. UPLC 97.0%; $^1$H NMR (400 MHz, DMSO-$d_6$) δ 8.24 (d, J=1.9 Hz, 1H), 7.72 (d, J=1.9 Hz, 1H), 7.23 (d, J=8.6 Hz, 2H), 7.18-7.14 (m, 4H), 7.12-7.06 (m, 3H), 6.43 (d, J=6.2 Hz, 1H), 6.29 (s, 1H), 4.58 (t, J=3.5 Hz, 1H), 4.49 (dd, J=14.0, 4.0 Hz, 1H), 4.39 (d, J=14.0 Hz, 1H).

Example 28

Rac-(5aR,6S,7R,8R,8aS)-5a-(4-bromophenyl)-3-chloro-8,8a-dihydroxy-6-phenyl-5a,7,8,8a-tetrahydro-6H-cyclopenta[4,5]furo[3,2-b]pyridine-7-carbothioamide (Cpd. No. 28F)

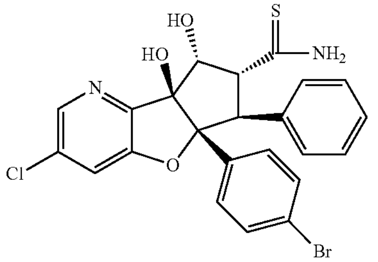

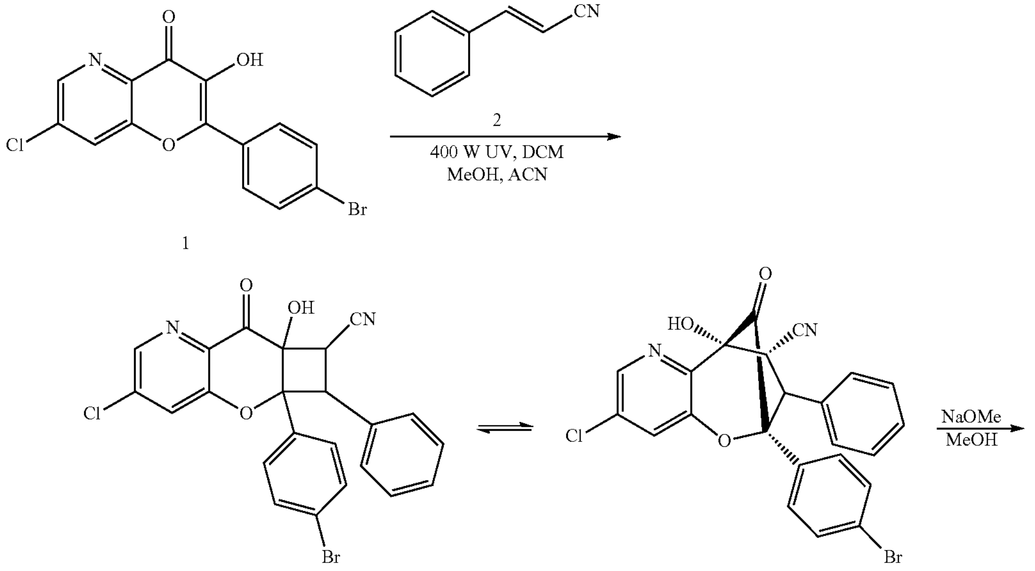

1

3

3a

-continued

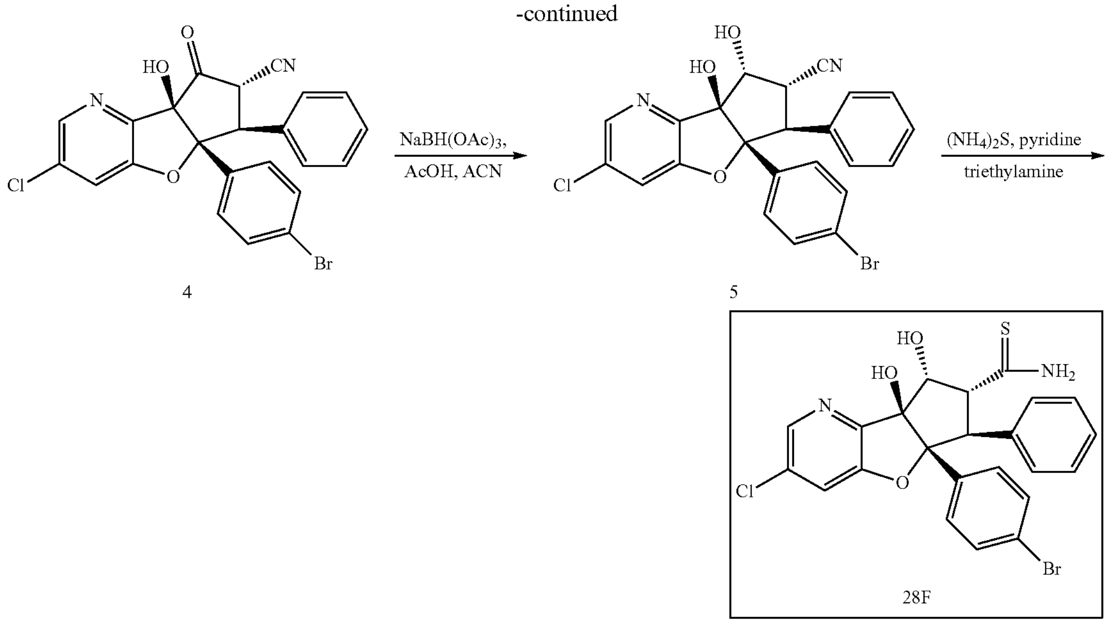

4 5 28F

Synthesis of rac-5a-(4-bromophenyl)-3-chloro-7a-hydroxy-8-oxo-6-phenyl-5a,6,7a,8-tetrahydro-7H-cyclobuta[5,6]pyrano[3,2-b]pyridine-7-carbonitrile (3/3a)

A solution of 2-(4-bromophenyl)-7-chloro-3-hydroxy-4H-pyrano[3,2-b]pyridin-4-one (1, 5.0 g, 14.25 mmol) and cinnamonitrile (2, 18.3 g, 142.4 mmol) in dichloromethane (200 mL), acetonitrile (100 mL) and methanol (100 mL) was placed in a UV reactor flask. The reaction mixture was irradiated for 16 h under 400 watts UV light. After completion, the solvent was removed under reduced pressure and the residue was purified by Combi-flash (24 g RediSep column) using ethyl acetate as eluent. The desired fractions were concentrated under reduced pressure to afford rac-5a-(4-bromophenyl)-3-chloro-7a-hydroxy-8-oxo-6-phenyl-5a,6,7a,8-tetrahydro-7H-cyclobuta[5,6]pyrano[3,2-b]pyridine-7-carbonitrile (3/3a) as brown solid. Yield: 6.0 g; crude.

Synthesis of rac-(5aR,6S,7S,8aR)-5a-(4-bromophenyl)-3-chloro-8a-hydroxy-8-oxo-6-phenyl-5a,7,8,8a-tetrahydro-6H-cyclopenta[4,5]furo[3,2-b]pyridine-7-carbonitrile (4)

The crude rac-5a-(4-bromophenyl)-3-chloro-7a-hydroxy-8-oxo-6-phenyl-5a,6,7a,8-tetrahydro-7H-cyclobuta[5,6]pyrano[3,2-b]pyridine-7-carbonitrile (3, 6.0 g) was suspended in methanol (60 mL) and treated with sodium methoxide (25% in methanol, 60 mL) and heated the mixture to 70° C. for 1 h. After completion, the solvent was removed under reduced pressure and the reaction was quenched with ammonium chloride solution and extracted with ethyl acetate. The organic phase was separated, dried over sodium sulphate and concentrated under reduced pressure to afford rac-(5aR,6S,7S,8aR)-5a-(4-bromophenyl)-3-chloro-8a-hydroxy-8-oxo-6-phenyl-5a,7,8,8a-tetrahydro-6H-cyclopenta[4,5]furo[3,2-b]pyridine-7-carbonitrile (4) as brown solid. Yield: 6.0 g, crude.

Synthesis of rac-(5aR,6S,7S,8R,8aS)-5a-(4-bromophenyl)-3-chloro-8,8a-dihydroxy-6-phenyl-5a,7,8,8a-tetrahydro-6H-cyclopenta[4,5]furo[3,2-b]pyridine-7-carbonitrile (5)

To a solution of sodium triacetoxyborohydride (7.95 g, 37.5 mmol) and rac-(5aR,6S,7S,8aR)-5a-(4-bromophenyl)-3-chloro-8a-hydroxy-8-oxo-6-phenyl-5a,7,8,8a-tetrahydro-6H-cyclopenta[4,5]furo[3,2-b]pyridine-7-carbonitrile (4, 6.0 g) in acetonitrile (70 mL), acetic acid (7.5 mL, 125 mmol) was added. The resulting mixture was stirred at room temperature for 16 h. After completion, reaction mixture was partitioned between saturated aqueous sodium bicarbonate solution and ethyl acetate. The organic layer was separated, dried over sodium sulphate and concentrated under reduced pressure to get the crude. The crude was purified by reverse phase HPLC. The desired fractions were concentrated under reduced pressure to afford rac-(5aR,6S,7S,8R,8aS)-5a-(4-bromophenyl)-3-chloro-8,8a-dihydroxy-6-phenyl-5a,7,8,8a-tetrahydro-6H-cyclopenta[4,5]furo[3,2-b]pyridine-7-carbonitrile (5) as light yellow solid. Yield: 4.6 g, 76.0%; MS (ESI) m/z 483.35$[M+1]^+$. UPLC 97.0%; $^1H$ NMR (400 MHz, DMSO-$d_6$) δ 8.24 (d, J=1.9 Hz, 1H), 7.72 (d, J=1.9 Hz, 1H), 7.23 (d, J=8.6 Hz, 2H), 7.18-7.14 (m, 4H), 7.12-7.06 (m, 3H), 6.43 (d, J=6.2 Hz, 1H), 6.29 (s, 1H), 4.58 (t, J=3.5 Hz, 1H), 4.49 (dd, J=14.0, 4.0 Hz, 1H), 4.39 (d, J=14.0 Hz, 1H).

Synthesis of rac-(5aR,6S,7R,8R,8aS)-5a-(4-bromophenyl)-3-chloro-8,8a-dihydroxy-6-phenyl-5a,7,8,8a-tetrahydro-6H-cyclopenta[4,5]furo[3,2-b]pyridine-7-carbothioamide (Cpd. No. 28F)

A flask containing pyridine (3 mL) was charged with rac-(5aR,6S,7S,8R,8aS)-5a-(4-bromophenyl)-3-chloro-8,8a-dihydroxy-6-phenyl-5a,7,8,8a-tetrahydro-6H-cyclopenta[4,5]furo[3,2-b]pyridine-7-carbonitrile (5, 0.5 g, 1.03 mmol) and triethylamine (0.15 mL, 1.14 mmol) was added at room temperature. The mixture was cooled to 0° C. and ammonium sulphide (40-48% by wt solution in water) (0.2 mL, 1.14 mmol) was added and stirred for 5 min. The reaction mixture was heated at 50° C. for 7 h. After completion, reaction mass was diluted with dichloromethane and washed with 1 M hydrogen chloride. The organic layer was dried over sodium sulphate, filtered and concentrated to give crude. The crude was purified by Combi-flash (4 g, RediSep column) using 70-90% ethyl acetate in hexanes as eluent. The desired fraction were concentrated to afford rac-(5aR,6S,7R,8R,8aS)-5a-(4-bromophenyl)-3-chloro-8,8a-dihydroxy-6-phenyl-5a,7,8,8a-tetrahydro-6H-cyclopenta[4,5]furo[3,2-b]pyridine-7-carbothioamide (Cpd. No. 28F) as white solid. Yield: 76 mg, 14.2%; MS (ESI) m/z 517.31 $[M+1]^+$; UPLC 97.3%; $^1H$ NMR (400 MHz, DMSO-$d_6$) δ 9.67 (s, 1H), 9.21 (s, 1H), 8.19 (d, J=1.9 Hz, 1H), 7.67 (d, J=2.0 Hz, 1H), 7.21 (d, J=8.6 Hz, 2H), 7.09-6.99 (m, 7H), 6.20 (brs, 1H), 5.56 (brs, 1H), 4.79 (d, J=14.3 Hz, 1H), 4.48 (d, J=3.9 Hz, 1H), 4.37 (dd, J=14.2, 3.9 Hz, 1H).

Example 29

Rac-(5aR,6S,7R,8R,8aS)-5a-(4-cyanophenyl)-3,8,8a-trihydroxy-N,N-dimethyl-6-phenyl-2-(trifluoromethyl)-5a,7,8,8a-tetrahydro-6H-cyclopenta[4,5]furo[3,2-b]pyridine-7-carboxamide (Cpd. No. 29F)

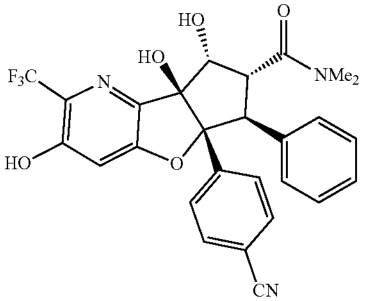

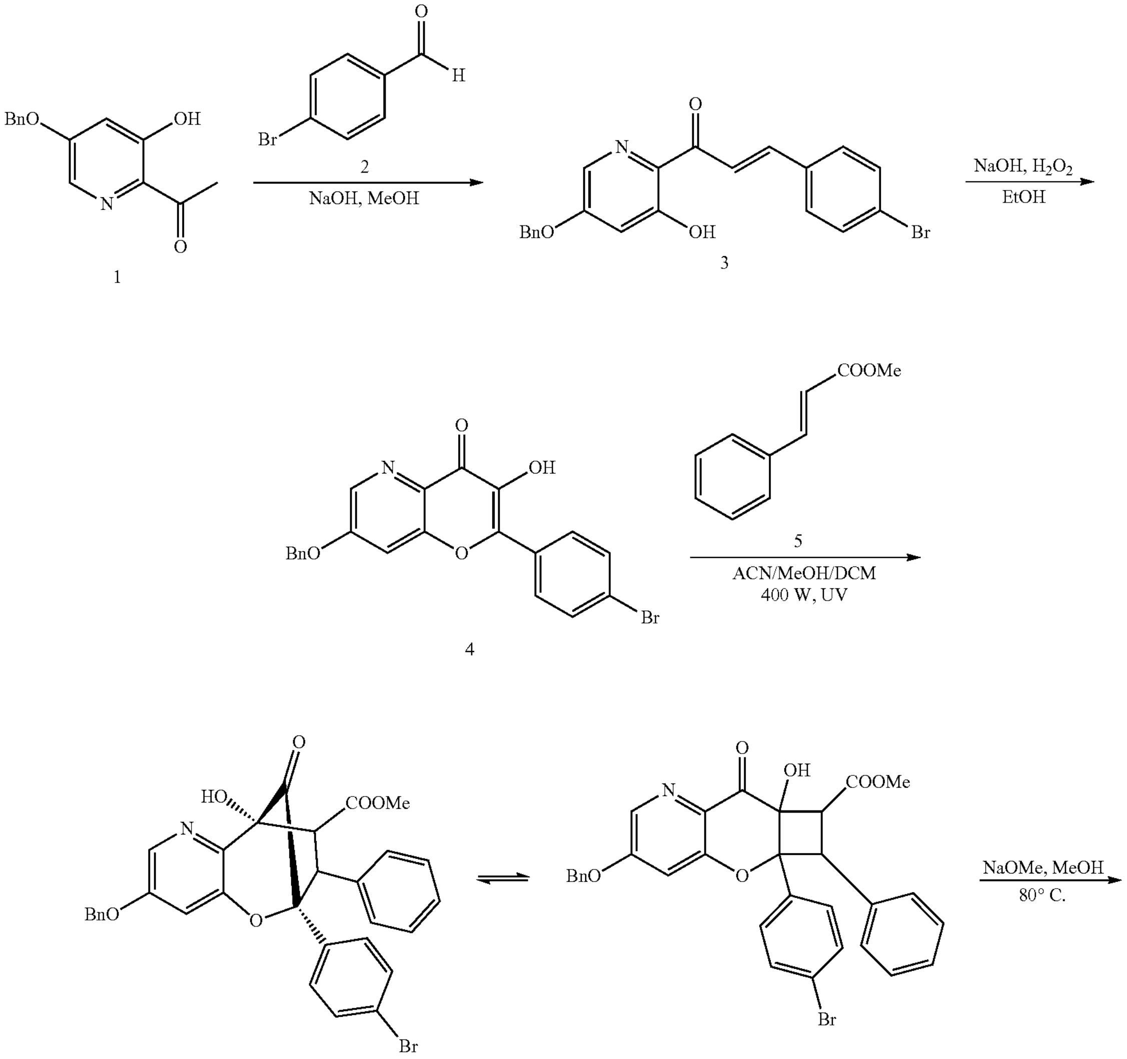

-continued

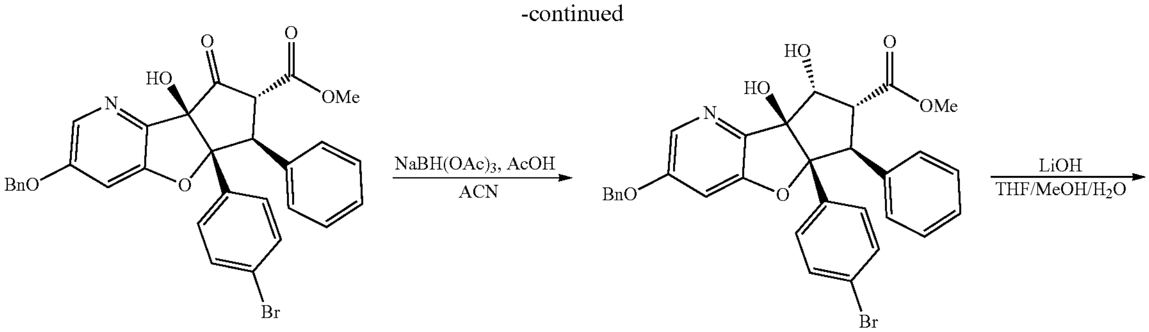

7 8

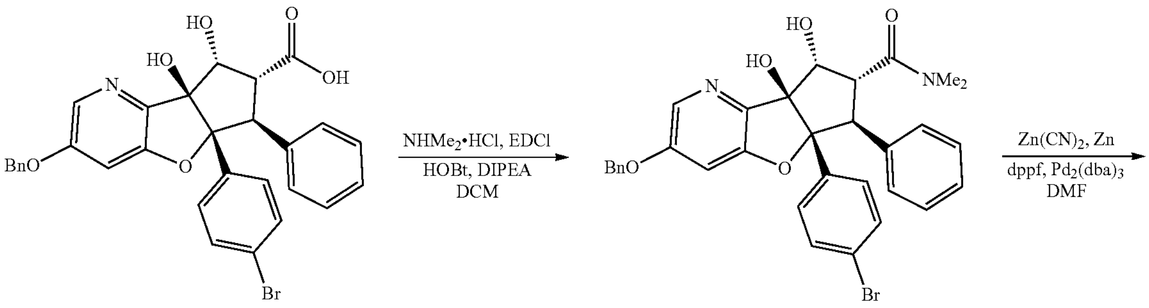

9 10

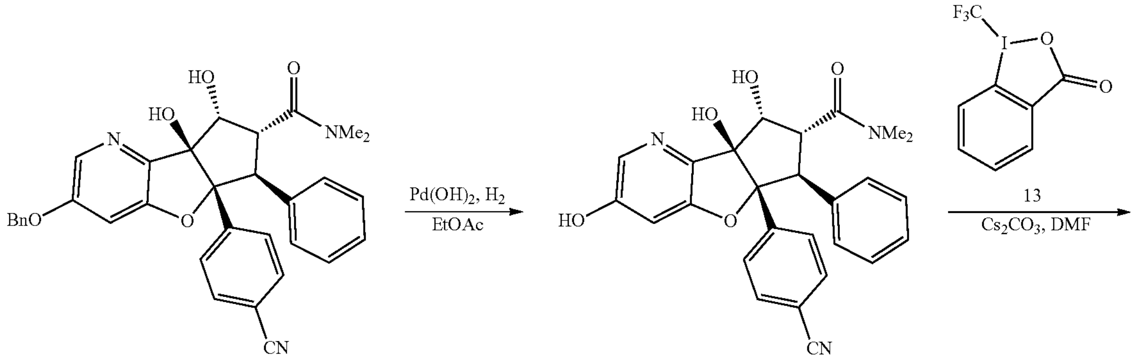

11 12

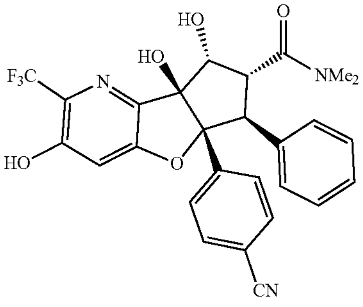

29F

Synthesis of (E)-1-(5-(benzyloxy)-3-hydroxypyridin-2-yl)-3-(4-bromophenyl)prop-2-en-1-one (3)

To a solution of 1-(5-(benzyloxy)-3-hydroxypyridin-2-yl) ethan-1-one (1, 7.80 g, 32.06 mmol) and 4-bromobenzaldehyde (2, 5.83 g, 32.06 mmol) in methanol (40 mL), sodium hydroxide (3.84 g, 96.18 mmol) was added. The reaction was heated to reflux for 30 min. After completion, the reaction mass was cooled to room temperature and diluted with water (50 mL). The precipitated solid was filtered, washed with water, n-pentane and dried under vacuum to afford (E)-1-(5-(benzyloxy)-3-hydroxypyridin-2-yl)-3-(4-bromophenyl)prop-2-en-1-one (3) as yellow solid. Yield: 12.0 g, 89.21%; MS (ESI) m/z 408.30[M−1]$^-$.

Synthesis of 7-(benzyloxy)-2-(4-bromophenyl)-3-hydroxy-4H-pyrano[3,2-b]pyridin-4-one (4)

To a solution of (E)-1-(5-(benzyloxy)-3-hydroxypyridin-2-yl)-3-(4-bromophenyl)prop-2-en-1-one (3, 12.0 g, 29.33 mmol) in ethanol (100 mL) at 0° C., 10% aqueous sodium hydroxide (8.21 g, 205.3 mmol) was added followed by the addition of 30% aqueous hydrogen peroxide (23.26 mL, 205.3 mmol). The reaction mass was stirred for 30 min at room temperature (exotherm was observed). After completion, the reaction mass was cooled and neutralized to pH ~7 by the addition of 6 M hydrogen chloride. The solid obtained was filtered, washed with ethanol, pentane and dried under vacuum to afford 7-(benzyloxy)-2-(4-bromophenyl)-3-hydroxy-4H-pyrano[3,2-b]pyridin-4-one (4) as white solid. Yield: 5.0 g, 40%; MS (ESI) m/z 424.14[M+1]$^+$.

Synthesis of rac-methyl (7S,8S,9R)-3-(benzyloxy)-6-(4-bromophenyl)-9-hydroxy-10-oxo-7-phenyl-6,7,8,9-tetrahydro-6,9-methanooxepino[3,2-b]pyridine-8-carboxylate (6)

A solution of 7-(benzyloxy)-2-(4-bromophenyl)-3-hydroxy-4H-pyrano[3,2-b]pyridin-4-one (4, 5.0 g, 11.78 mmol) and methyl cinnamate (5, 19.11 g, 117.8 mmol) in dichloromethane (250 mL), acetonitrile (125 mL) and methanol (125 mL) was placed in a UV reactor flask. The reaction mixture was irradiated for 24 h under 400 watts UV light. After completion, solvent was removed under reduced pressure and the residue was purified over a plug of silica gel eluting the compound with 5% methanol in dichloromethane. The desired fractions were concentrated under reduced pressure to afford rac-methyl (7S,8S,9R)-3-(benzyloxy)-6-(4-bromophenyl)-9-hydroxy-10-oxo-7-phenyl-6,7,8,9-tetrahydro-6,9-methanooxepino[3,2-b]pyridine-8-carboxylate (6) as brown solid. Yield: 6.4 g, crude.

Synthesis of rac-methyl (5aR,6S,7R,8aR)-3-(benzyloxy)-5a-(4-bromophenyl)-8a-hydroxy-8-oxo-6-phenyl-5a,7,8,8a-tetrahydro-6H-cyclopenta[4,5]furo[3,2-b]pyridine-7-carboxylate (7)

The crude rac-methyl (7S,8S,9R)-3-(benzyloxy)-6-(4-bromophenyl)-9-hydroxy-10-oxo-7-phenyl-6,7,8,9-tetrahydro-6,9-methanooxepino[3,2-b]pyridine-8-carboxylate (6, 6.4 g, 10.91 mmol) was suspended in methanol (120 mL) and treated with 25% sodium methoxide in methanol (23.57 mL). The reaction was heated at 80° C. for 4 h. After completion, the solvent was removed under reduced pressure. The crude was diluted with ammonium chloride solution and extracted with ethyl acetate. The organic phase was separated, dried over sodium sulphate and concentrated under reduced pressure to afford rac-methyl (5aR,6S,7R,8aR)-3-(benzyloxy)-5a-(4-bromophenyl)-8a-hydroxy-8-oxo-6-phenyl-5a,7,8,8a-tetrahydro-6H-cyclopenta[4,5]furo[3,2-b]pyridine-7-carboxylate (7) as brown solid. Yield: 5.3 g, crude.

Synthesis of rac-methyl (5aR,6S,7R,8R,8aS)-3-(benzyloxy)-5a-(4-bromophenyl)-8,8a-dihydroxy-6-phenyl-5a,7,8,8a-tetrahydro-6H-cyclopenta[4,5]furo[3,2-b]pyridine-7-carboxylate (8)

A solution of rac-methyl (5aR,6S,7R,8aR)-3-(benzyloxy)-5a-(4-bromophenyl)-8a-hydroxy-8-oxo-6-phenyl-5a,7,8,8a-tetrahydro-6H-cyclopenta[4,5]furo[3,2-b]pyridine-7-carboxylate (7, 5.3 g, 9.03 mmol) in acetonitrile (110 mL) was cooled at 0° C., acetic acid (5.42 g, 90.37 mmol) and sodium triacetoxyborohydride (11.49 g, 54.22 mmol) were added. The resulting mixture was stirred for 12 h at room temperature. After completion, the reaction mixture was partitioned between saturated aqueous sodium bicarbonate solution and ethyl acetate. The organic layer was separated and dried over sodium sulphate, filtered and concentrated to give crude. The crude was purified by silica gel column chromatography eluting with 2-3% in methanol in dichloromethane. The desired fractions were concentrated to afford rac-methyl (5aR,6S,7R,8R,8aS)-3-(benzyloxy)-5a-(4-bromophenyl)-8,8a-dihydroxy-6-phenyl-5a,7,8,8a-tetrahydro-6H-cyclopenta[4,5]furo[3,2-b]pyridine-7-carboxylate (8) as white solid. Yield: 2.5 g, 47.0%; MS (ESI) m/z 588.2[M+1]$^+$.

Synthesis of rac-(5aR,6S,7R,8R,8aS)-3-(benzyloxy)-5a-(4-bromophenyl)-8,8a-dihydroxy-6-phenyl-5a, 7,8,8a-tetrahydro-6H-cyclopenta[4,5]furo[3,2-b]pyridine-7-carboxylic acid (9)

To a solution of rac-methyl (5aR,6S,7R,8R,8aS)-3-(benzyloxy)-5a-(4-bromophenyl)-8,8a-dihydroxy-6-phenyl-5a,7,8,8a-tetrahydro-6H-cyclopenta[4,5]furo[3,2-b]pyridine-7-carboxylate (8, 0.5 g, 0.849 mmol) in methanol, tetrahydrofuran and water (2:1:1, 10 mL), lithium hydroxide (0.20 g, 8.49 mmol) was added and the reaction was stirred for 6 h at room temperature. After completion, the solvent was evaporated and crude was cooled to 0° C. followed by acidifying with 1 M hydrochloric acid to pH 2-3. The precipitated solid was filtered and dried under vacuum to afford rac-(5aR,6S,7R,8R,8aS)-3-(benzyloxy)-5a-(4-bromophenyl)-8,8a-dihydroxy-6-phenyl-5a,7,8,8a-tetrahydro-6H-cyclopenta[4,5]furo[3,2-b]pyridine-7-carboxylic acid (9) as white solid. Yield: 0.42 g, 86%; MS (ESI) m/z 572.14[M−1]$^-$.

Synthesis of rac-(5aR,6S,7R,8R,8aS)-3-(benzyloxy)-5a-(4-bromophenyl)-8,8a-dihydroxy-N,N-dimethyl-6-phenyl-5a,7,8,8a-tetrahydro-6H-cyclopenta[4,5]furo[3,2-b]pyridine-7-carboxamide (10)

To a solution of rac-(5aR,6S,7R,8R,8aS)-3-(benzyloxy)-5a-(4-bromophenyl)-8,8a-dihydroxy-6-phenyl-5a,7,8,8a-tetrahydro-6H-cyclopenta[4,5]furo[3,2-b]pyridine-7-carboxylic acid (9, 0.42 g, 0.73 mmol) in dichloromethane (8 mL) at 0° C., 1-ethyl-3-(3-dimethylaminopropyl) carbodiimide (0.34 g, 2.19 mmol), hydroxybenzotriazole (0.33 g, 2.19 mmol) and N,N-diisopropylethylamine (0.78 mL, 4.38 mmol) were added and the mixture was stirred for 5 min. Dimethylamine hydrochloride (0.298 g, 3.65 mmol) was then added at the same temperature and the reaction was stirred for 16 h at room temperature. After completion, the reaction mass was diluted with dichloromethane and washed with cold water. The organic layer was separated and dried over sodium sulphate, filtered and concentrated to give crude. The crude was purified by silica gel column chromatography eluting with 2-3% methanol in dichloromethane. The desired fractions were concentrated to afford rac-(5aR,6S,7R,8R,8aS)-3-(benzyloxy)-5a-(4-bromophenyl)-8,8a-dihydroxy-N,N-dimethyl-6-phenyl-5a,7,8,8a-tetrahydro-6H-cyclopenta[4,5]furo[3,2-b]pyridine-7-carboxamide (10) as yellow solid. Yield: 0.35 g, 79.7%; MS (ESI) m/z 601.3[M+1]$^+$.

Synthesis of rac-(5aR,6S,7R,8R,8aS)-3-(benzyloxy)-5a-(4-cyanophenyl)-8,8a-dihydroxy-N,N-dimethyl-6-phenyl-5a,7,8,8a-tetrahydro-6H-cyclopenta[4,5]furo[3,2-b]pyridine-7-carboxamide (11)

To a solution of rac-(5aR,6S,7R,8R,8aS)-3-(benzyloxy)-5a-(4-bromophenyl)-8,8a-dihydroxy-N,N-dimethyl-6-phenyl-5a,7,8,8a-tetrahydro-6H-cyclopenta[4,5]furo[3,2-b] pyridine-7-carboxamide (10, 0.35 g, 0.582 mmol) in N,N-dimethylformamide (7.0 mL), zinc cyanide (0.409 g, 3.49 mmol) and zinc (0.0045 g, 0.06 mmol) were added at room temperature and degassed the mixture with argon for 15 min. 1,1'-Bis(diphenylphosphino)ferrocene (0.008 g, 0.0116 mmol), tris(dibenzylideneacetone)dipalladium (0.015 g, 0.0174 mmol) were added to the reaction and degassing was continued for another 5 min. The reaction mixture was heated at 140° C. for 4 h. After completion, the reaction mass was diluted with ethyl acetate and washed with cold water. The organic layer was separated and dried over sodium sulphate, filtered and concentrated to give crude. The crude was purified by silica gel column chromatography using 2-3% methanol in dichloromethane as eluent. The desired fractions were concentrated to afford rac-(5aR,6S,7R,8R,8aS)-3-(benzyloxy)-5a-(4-cyanophenyl)-8,8a-dihydroxy-N,N-dimethyl-6-phenyl-5a,7,8,8a-tetrahydro-6H-cyclopenta[4,5]furo[3,2-b]pyridine-7-carboxamide (11) as white solid. Yield: 0.26 g, 81.76%; MS (ESI) m/z 548.29 $[M+1]^+$.

Synthesis of rac-(5aR,6S,7R,8R,8aS)-5a-(4-cyanophenyl)-3,8,8a-trihydroxy-N,N-dimethyl-6-phenyl-5a,7,8,8a-tetrahydro-6H-cyclopenta[4,5]furo[3,2-b] pyridine-7-carboxamide (12)

To a solution of rac-(5aR,6S,7R,8R,8aS)-3-(benzyloxy)-5a-(4-cyanophenyl)-8,8a-dihydroxy-N,N-dimethyl-6-phenyl-5a,7,8,8a-tetrahydro-6H-cyclopenta[4,5]furo[3,2-b] pyridine-7-carboxamide (11, 0.26 g, 0.474 mmol) in ethyl acetate (6.0 mL) and palladium hydroxide (0.13 g, 0.949 mmol, 50% wet) was added. The reaction was flushed with hydrogen gas twice and stirred at room temperature for 16 h under hydrogen pressure. After completion, the reaction mass was passed through celite bed and filtrate was concentrated under reduced pressure to afford rac-(5aR,6S,7R,8R,8aS)-5a-(4-cyanophenyl)-3,8,8a-trihydroxy-N,N-dimethyl-6-phenyl-5a,7,8,8a-tetrahydro-6H-cyclopenta[4,5] furo[3,2-b]pyridine-7-carboxamide (12) as off white solid. Yield: 0.17 g, 78.34%; MS (ESI) m/z 456.32$[M-1]^-$.

Synthesis of rac-(5aR,6S,7R,8R,8aS)-5a-(4-cyanophenyl)-3,8,8a-trihydroxy-N,N-dimethyl-6-phenyl-2-(trifluoromethyl)-5a, 7,8,8a-tetrahydro-6H-cyclopenta[4,5]furo[3,2-b]pyridine-7-carboxamide (Cpd. No. 29F)

To a solution of rac-(5aR,6S,7R,8R,8aS)-5a-(4-cyanophenyl)-3,8,8a-trihydroxy-N,N-dimethyl-6-phenyl-5a,7,8,8a-tetrahydro-6H-cyclopenta[4,5]furo[3,2-b]pyridine-7-carboxamide (12, 0.15 g, 0.327 mmol) in N,N-dimethylformamide (5.0 mL), cesium carbonate (0.27 g, 0.819 mmol) and 1-(trifluoromethyl)-1-benzo[d][1,2]iodaoxol-3(1H)-one (13, 0.31 g, 0.393 mmol) were added at room temperature and reaction mixture was stirred at room temperature for 2 h. After completion, the reaction mass was diluted with ethyl acetate and washed with cold water. The organic layer was separated and dried over sodium sulphate, filtered and concentrated to give crude. The crude was purified by silica gel column chromatography using 2-3% methanol in dichloromethane as eluent. The desired fractions were concentrated to afford rac-(5aR,6S,7R,8R,8aS)-5a-(4-cyanophenyl)-3,8,8a-trihydroxy-N,N-dimethyl-6-phenyl-2-(trifluoromethyl)-5a,7,8,8a-tetrahydro-6H-cyclopenta[4,5]furo[3,2-b]pyridine-7-carboxamide (Cpd. No. 29F) as yellow solid. Yield: 0.18 g, 10%; MS (ESI) m/z 526.4$[M+1]^+$; $^1H$ NMR (400 MHz, DMSO-$d_6$) δ 11.16 (s, 1H), 7.48 (d, J=7.6 Hz, 2H), 7.31 (d, J=7.4 Hz, 2H), 7.03-7.06 (m, 3H), 6.90-6.98 (m, 3H), 6.03 (s, 1H), 5.32 (d, J=4.4 Hz, 1H), 4.64-4.71 (m, 2H), 4.34 (d, J=10.8 Hz, 1H), 3.27 (s, 3H), 2.78 (s, 3H).

Example 30

Rac-4-((5aR,6S,7S,8R,8aS)-7-(aminomethyl)-3-chloro-8,8a-dihydroxy-6-phenyl-6,7,8,8a-tetrahydro-5aH-cyclopenta[4,5]furo[3,2-b]pyridin-5a-yl)benzonitrile (Cpd. No. 30F)

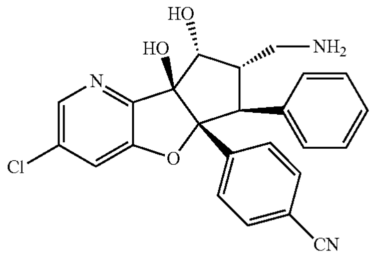

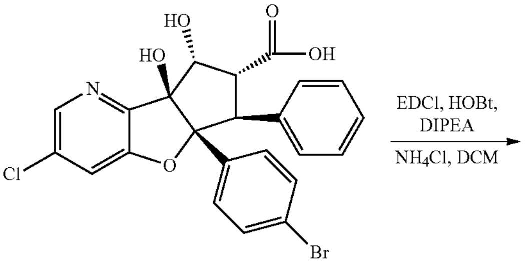

1

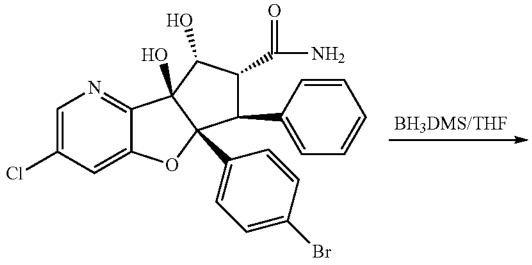

2

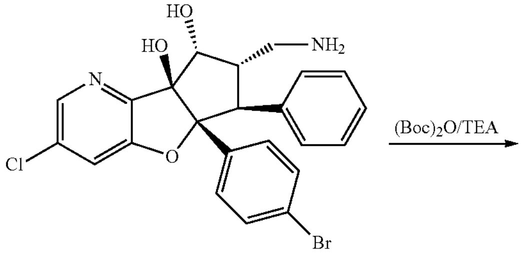

3

-continued

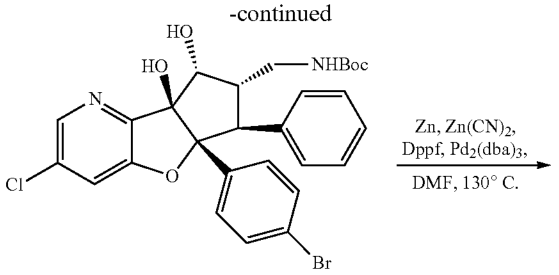

4

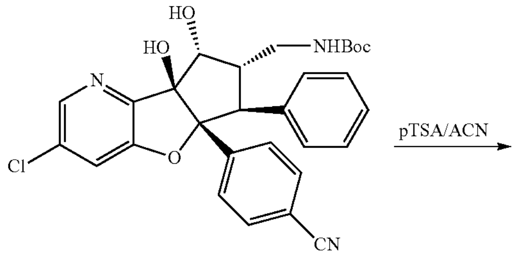

5

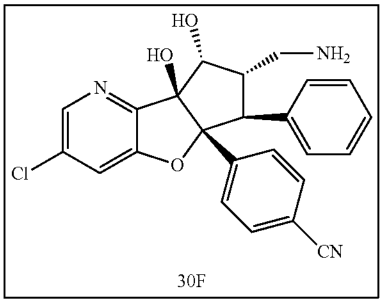 [SMILES: N#Cc1ccc([C@@]23Oc4cc(Cl)cnc4[C@]2(O)[C@H](O)[C@H](CN)[C@H]3c2ccccc2)cc1]

30F

Synthesis of rac-(5aR,6S,7R,8R,8aS)-5a-(4-bromophenyl)-3-chloro-8,8a-dihydroxy-6-phenyl-5a,7,8,8a-tetrahydro-6H-cyclopenta[4,5]furo[3,2-b]pyridine-7-carboxamide (2)

To a solution of rac-(5aR,6S,7R,8R,8aS)-5a-(4-bromophenyl)-3-chloro-8,8a-dihydroxy-6-phenyl-5a,7,8,8a-tetrahydro-6H-cyclopenta[4,5]furo[3,2-b]pyridine-7-carboxylic acid (1, 1.80 g, 3.50 mmol) in dichloromethane (30 mL), 1-ethyl-3-(3-dimethylaminopropyl)carbodiimide (1.33 g, 7.00 mmol), hydroxybenzotriazole (1.06 g, 7.00 mmol) and diisopropylethylamine (1.80 mL, 10.00 mmol) were added at 0° C. and stirred the mixture for 5 min. Ammonium chloride (1.90 g, 3.50 mmol) was then added and the reaction mixture was stirred for 16 h at room temperature. After completion, the reaction mass was diluted with dichloromethane and washed with cold water. The organic layer was dried over sodium sulphate, filtered and concentrated to give crude. The crude was purified by triturating the solid with ethanol and n-pentane, filtered and dried under vacuum to afford rac-(5aR,6S,7R,8R,8aS)-5a-(4-bromophenyl)-3-chloro-8,8a-dihydroxy-6-phenyl-5a,7,8,8a-tetrahydro-6H-cyclopenta[4,5]furo[3,2-b]pyridine-7-carboxamide (2) as white solid. Yield: 1.10 g, 64%; MS (ESI) m/z 501.26[M+1]$^+$.

Synthesis of rac-(5aR,6S,7S,8R,8aS)-7-(aminomethyl)-5a-(4-bromophenyl)-3-chloro-6-phenyl-5a,6,7,8-tetrahydro-8aH-cyclopenta[4,5]furo[3,2-b]pyridine-8,8a-diol (3)

To a solution of rac-(5aR,6S,7R,8R,8aS)-5a-(4-bromophenyl)-3-chloro-8,8a-dihydroxy-6-phenyl-5a,7,8,8a-tetrahydro-6H-cyclopenta[4,5]furo[3,2-b]pyridine-7-carboxamide (2, 0.60 g, 1.20 mmol) in tetrahydrofuran (20 mL), borane dimethylsulfide complex (0.91 mL, 12.00 mmol) was added at 0° C. The reaction mixture was then heated at 60-70° C. for 5 h. After completion, reaction mass was quenched with methanol at 0° C. The solvents were removed under reduced pressure to afford rac-(5aR,6S,7S,8R,8aS)-7-(aminomethyl)-5a-(4-bromophenyl)-3-chloro-6-phenyl-5a,6,7,8-tetrahydro-8aH-cyclopenta[4,5]furo[3,2-b]pyridine-8,8a-diol (3) as brown liquid. Yield: 0.50 g, (crude); MS (ESI) m/z 487.11[M+1]$^+$.

Synthesis of rac-tert-butyl (((5aR,6S,7S,8R,8aS)-5a-(4-bromophenyl)-3-chloro-8,8a-dihydroxy-6-phenyl-5a,7,8,8a-tetrahydro-6H-cyclopenta[4,5]furo[3,2-b]pyridin-7-yl)methyl)carbamate (4)

To a solution of rac-(5aR,6S,7S,8R,8aS)-7-(aminomethyl)-5a-(4-bromophenyl)-3-chloro-6-phenyl-5a,6,7,8-tetrahydro-8aH-cyclopenta[4,5]furo[3,2-b]pyridine-8,8a-diol (3, 0.306 g, 0.64 mmol) in dichloromethane (15 mL), triethylamine (0.178 mL, 1.28 mmol) and di-tert-butyl dicarbonate (0.167 g, 0.768 mmol) were added at room temperature. The reaction mixture was stirred for 3 h at room temperature. After completion, reaction mass was diluted with dichloromethane and washed with cold water. The organic layer was dried over sodium sulphate, filtered and concentrated under reduced pressure to give crude. The crude was purified by silica gel column chromatography using 30% ethyl acetate in hexanes as eluent. The desired fractions were concentrated under reduced pressure to afford rac-tert-butyl (((5aR,6S,7S,8R,8aS)-5a-(4-bromophenyl)-3-chloro-8,8a-dihydroxy-6-phenyl-5a,7,8,8a-tetrahydro-6H-cyclopenta[4,5]furo[3,2-b]pyridin-7-yl)methyl)carbamate (4) as white solid. Yield: 0.125 g, 33.46%; MS (ESI) m/z 587.11[M+1]$^+$.

Synthesis of rac-tert-butyl (((5aR,6S,7S,8R,8aS)-3-chloro-5a-(4-cyanophenyl)-8,8a-dihydroxy-6-phenyl-5a,7,8,8a-tetrahydro-6H-cyclopenta[4,5]furo[3,2-b]pyridin-7-yl)methyl)carbamate (5)

To a mixture of rac-tert-butyl (((5aR,6S,7S,8R,8aS)-5a-(4-bromophenyl)-3-chloro-8,8a-dihydroxy-6-phenyl-5a,7,8,8a-tetrahydro-6H-cyclopenta[4,5]furo[3,2-b]pyridin-7-yl)methyl)carbamate (4, 0.12 g, 0.20 mmol) in N,N-dimethylformamide (10 mL) at room temperature, zinc cyanide (24 mg, 0.20 mmol) and zinc dust (26 mg, 0.40 mmol) were added and the mixture was degassed with argon for 15 min. 1,1'-Bis(diphenylphosphino)ferrocene (2.90 mg, 0.004 mmol) and tris(dibenzylideneacetone)dipalladium (5.70 mg, 0.006 mmol) were added to the above reaction and the mixture was degassed with argon for additional 5 min followed by heating at 130° C. for 3 h. After completion, the reaction mixture was cooled to room temperature and passed through a celite bed. Filtrate was concentrated and treated with ice-cold water, the solid precipitated was filtered and crude was purified by silica gel column chromatography using 30% ethyl acetate in hexanes as eluent. The solvent was removed under reduced pressure to afford rac-tert-butyl (((5aR,6S,7S,8R,8aS)-3-chloro-5a-(4-cyanophenyl)-8,8a-dihydroxy-6-phenyl-5a,7,8,8a-tetrahydro-6H-cyclopenta[4,5]furo[3,2-b]pyridin-7-yl)methyl)carbamate (5) as white solid. Yield: 0.11 g, 90%; MS (ESI) m/z 534.31[M+1]$^+$.

Synthesis of rac-4-((5aR,6S,7S,8R,8aS)-7-(aminomethyl)-3-chloro-8,8a-dihydroxy-6-phenyl-6,7,8,8a-tetrahydro-5aH-cyclopenta[4,5]furo[3,2-b]pyridin-5a-yl)benzonitrile (Cpd. No. 30F)

To a solution of rac-tert-butyl (((5aR,6S,7S,8R,8aS)-3-chloro-5a-(4-cyanophenyl)-8,8a-dihydroxy-6-phenyl-5a,7, 8,8a-tetrahydro-6H-cyclopenta[4,5]furo[3,2-b]pyridin-7-yl) methyl)carbamate (5, 0.11 g, 0.20 mmol) in acetonitrile (5 mL), p-toluenesulfonic acid (0.039 g, 0.20 mmol) was added and the reaction was stirred at 35° C. for 16 h. After completion, the reaction mixture was concentrated and crude was purified by reverse phase HPLC to afford rac-4-((5aR,6S,7S,8R,8aS)-7-(aminomethyl)-3-chloro-8,8a-dihydroxy-6-phenyl-6,7,8,8a-tetrahydro-5aH-cyclopenta[4,5]furo[3,2-b]pyridin-5a-yl)benzonitrile (Cpd. No. 30F) as white solid. Yield: 55 mg, 60%; MS (ESI) m/z 434.40[M+1]$^+$; $^1$H NMR (400 MHz, DMSO-$d_6$) δ 8.18 (d, J=2.0 Hz, 1H), 7.63 (d, J=2.0 Hz, 1H), 7.48 (d, J=8.4 Hz, 2H), 7.32 (d, J=8.6 Hz, 2H), 7.10-6.99 (m, 5H), 6.04 (s, 1H), 4.54 (d, J=4.4 Hz, 1H), 3.95 (d, J=14 Hz, 1H), 3.12-3.07 (m, 1H), 2.66 (m, 2H).

Example 31

Rac-(5aR,6R,6aS,7aS,7bR)-3-chloro-5a-(4-cyanophenyl)-7b-hydroxy-N,N-dimethyl-6-phenyl-5a,7,7a,7b-tetrahydrocyclopropa[4',5']cyclopenta[1',2':4,5]furo[3,2-b]pyridine-6a(6H)-carboxamide (Cpd. No. 31F)

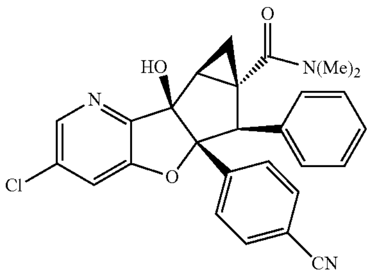

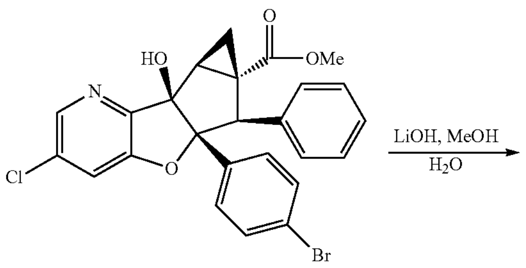

1

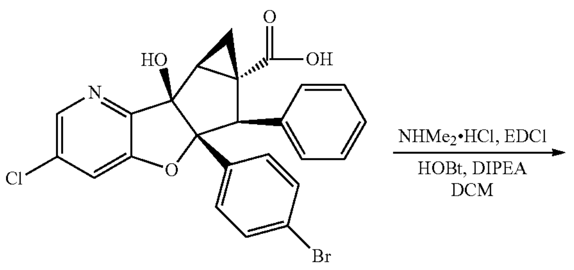

2

-continued

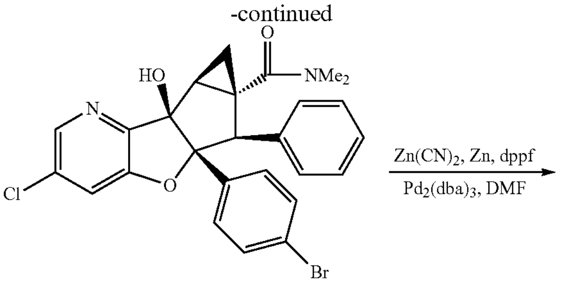

3

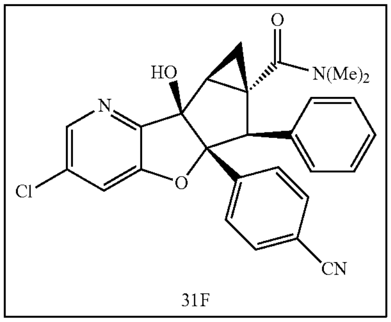

31F

Synthesis of rac-(5aR,6R,6aS,7aS,7bR)-5a-(4-bromophenyl)-3-chloro-7b-hydroxy-6-phenyl-5a,7,7a,7b-tetrahydrocyclopropa[4',5']cyclopenta[1',2':4,5]furo[3,2-b]pyridine-6a(6H)-carboxylic acid (2)

To a solution of rac-methyl (5aR,6R,6aS,7aS,7bR)-5a-(4-bromophenyl)-3-chloro-7b-hydroxy-6-phenyl-5a,7,7a,7b-tetrahydrocyclopropa[4',5']cyclopenta[1',2':4,5]furo[3,2-b]pyridine-6a(6H)-carboxylate (1, 38.0 mg, 0.074 mmol) in methanol and water (3:1, 7 mL), lithium hydroxide (18.0 mg, 0.74 mmol) was added and the reaction was stirred for 16 h at room temperature. After completion, methanol was removed under reduced pressure and crude was diluted with water and acidified with 1 M hydrogen chloride to pH ~3 followed by extraction with ethyl acetate (20 mL). The organic layer was separated, dried over sodium sulphate and concentrated under reduced pressure to afford rac-(5aR,6R,6aS,7aS,7bR)-5a-(4-bromophenyl)-3-chloro-7b-hydroxy-6-phenyl-5a,7,7a,7b-tetrahydrocyclopropa[4',5']cyclopenta[1',2':4,5]furo[3,2-b]pyridine-6a(6H)-carboxylic acid (2) as off white solid. Yield: 23.0 mg, 62%; MS (ESI) m/z 496.15[M−1]$^-$.

Synthesis of rac-(5aR,6R,6aS,7aS,7bR)-5a-(4-bromophenyl)-3-chloro-7b-hydroxy-N,N-dimethyl-6-phenyl-5a,7,7a,7b-tetrahydrocyclopropa[4',5']cyclopenta[1',2':4,5]furo[3,2-b]pyridine-6a(6H)-carboxamide (3)

To a solution of rac-(5aR,6R,6aS,7aS,7bR)-5a-(4-bromophenyl)-3-chloro-7b-hydroxy-6-phenyl-5a,7,7a,7b-tetrahydrocyclopropa[4',5']cyclopenta[1',2':4,5]furo[3,2-b]pyridine-6a(6H)-carboxylic acid (2, 20.0 mg, 0.04 mmol) in dichloromethane (2 mL), 1-ethyl-3-(3-dimethylaminopropyl)carbodiimide hydrochloride (23.0 mg, 0.12 mmol), 1-hydroxybenzotriazole (16.0 mg, 0.12 mmol) and N,N-diisopropylethylamine (0.042 mL, 0.24 mmol) were added at 0° C. and stirred the mixture for 5 min. Dimethylamine hydrochloride (16.0 mg, 0.20 mmol) was then added at same temperature and the mixture was stirred for 16 h at 40° C.

After completion, reaction mass was diluted with dichloromethane and washed with cold water. The organic layer was separated and dried over sodium sulphate, filtered and concentrated to give crude. The crude was purified by Combi-flash (4 g, RediSep column) using 30% ethyl acetate in hexanes as eluent. The desired fractions were concentrated under reduced pressure to afford rac-(5aR,6R,6aS,7aS,7bR)-5a-(4-bromophenyl)-3-chloro-7b-hydroxy-N,N-dimethyl-6-phenyl-5a,7,7a,7b-tetrahydrocyclopropa[4',5']cyclopenta[1',2':4,5]furo[3,2-b]pyridine-6a(6H)-carboxamide (3) as yellow solid. Yield: 30 mg, crude; MS (ESI) m/z 525.20[M+1]$^+$.

Synthesis of rac-(5aR,6R,6aS,7aS,7bR)-3-chloro-5a-(4-cyanophenyl)-7b-hydroxy-N,N-dimethyl-6-phenyl-5a,7,7a,7b-tetrahydrocyclopropa[4',5']cyclopenta[1',2':4,5]furo[3,2-b]pyridine-6a(6H)-carboxamide (Cpd. No. 31F)

To a solution of rac-(5aR,6R,6aS,7aS,7bR)-5a-(4-bromophenyl)-3-chloro-7b-hydroxy-N,N-dimethyl-6-phenyl-5a,7,7a,7b-tetrahydrocyclopropa[4',5']cyclopenta[1',2':4,5]furo[3,2-b]pyridine-6a(6H)-carboxamide (3, 30.0 mg, 0.05 mmol) in N,N-dimethylformamide (5.0 mL), zinc cyanide (17.0 mg, 0.14 mmol) and zinc (7.0 mg, 0.11 mmol) were added at room temperature and degassed the mixture with argon for 15 min. 1,1'-Bis(diphenylphosphino)ferrocene (1.0 mg, 0.001 mmol), tris(dibenzylideneacetone)dipalladium (1.0 mg, 0.001 mmol) were added to the reaction and degassing was continued for another 5 min. The reaction mixture was heated at 130° C. for 2 h. After completion, the reaction was cooled to room temperature and passed through celite bed. The filtrate was diluted with ethyl acetate and washed with water. The organic layer was separated, dried over sodium sulphate and concentrated under reduced pressure to get the crude. Desired and dicyano compound (side product) were purified by reverse phase prep HPLC. The desired fractions were concentrated under reduced pressure to afford rac-(5aR,6R,6aS,7aS,7bR)-3-chloro-5a-(4-cyanophenyl)-7b-hydroxy-N,N-dimethyl-6-phenyl-5a,7,7a,7b-tetrahydrocyclopropa[4',5']cyclopenta[1',2':4,5]furo[3,2-b]pyridine-6a(6H)-carboxamide (Cpd. No. 31F) as white solid. Yield: 2.5 mg, 1.9%; MS (ESI) m/z 472.48[M+1]$^+$. UPLC: 97.91%; $^1$H NMR (400 MHz, DMSO-$d_6$) δ 8.36 (d, J=1.9 Hz, 1H), 7.81 (d, J=1.8 Hz, 1H), 7.55 (d, J=8.5 Hz, 2H), 7.31 (d, J=8.5 Hz, 2H), 7.23-7.19 (m, 2H), 7.15-7.07 (m, 3H), 6.18 (brs, 1H), 4.44 (s, 1H), 2.57 (s, 6H), 2.38 (s, 1H), 1.74 (t, J=6.2 Hz, 1H), 1.51 (t, J=7.6 Hz, 1H).

Example 32

Rac-(5aR,6S,7R,8aR)-3-chloro-5a-(4-cyanophenyl)-8a-hydroxy-N,N-dimethyl-8-oxo-6-phenyl-5a,7,8,8a-tetrahydro-6H-cyclopenta[4,5]furo[3,2-b]pyridine-7-carboxamide (Cpd. No. 32F)

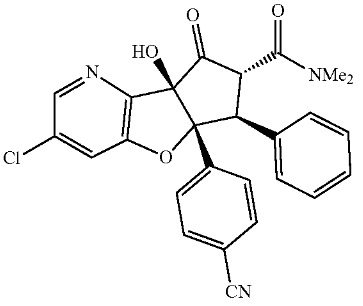

-continued

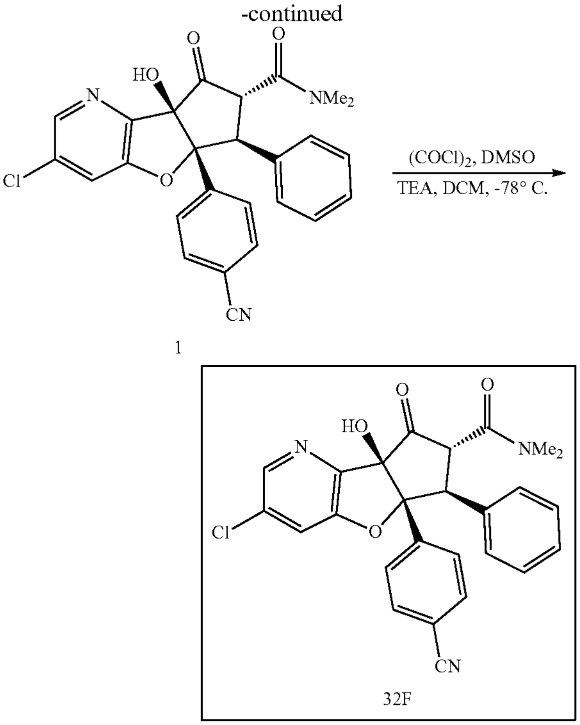

1

32F

Synthesis of rac-(5aR,6S, 7R, 8aR)-3-chloro-5a-(4-cyanophenyl)-8a-hydroxy-N,N-dimethyl-8-oxo-6-phenyl-5a,7,8,8a-tetrahydro-6H-cyclopenta[4,5]furo[3,2-b]pyridine-7-carboxamide (Cpd. No. 26)

To a solution of oxalyl chloride (0.044 mL, 0.525 mmol) in dry dichloromethane (1.0 mL) under nitrogen, dimethylsulphoxide (0.052 mL, 0.735 mmol) was added drop wise at −78° C. The reaction mixture was stirred for 30 min and a solution of rac-(5aR,6S,7R,8R,8aS)-3-chloro-5a-(4-cyanophenyl)-8,8a-dihydroxy-N,N-dimethyl-6-phenyl-5a,7,8,8a-tetrahydro-6H-cyclopenta[4,5]furo[3,2-b]pyridine-7-carboxamide (1, 0.1 g, 0.210 mmol) in dichloromethane (1.0 mL) was added and stirring was continued for another 2 h at the same temperature and then the mixture was treated with triethylamine (0.58 mL, 4.20 mmol). The reaction mass was slowly brought to room temperature and stirred for 15 min. The mixture was diluted with water (10 mL) and dichloromethane (20 mL). The organic layer was washed with water and brine, dried over anhydrous sodium sulfate, filtered and concentrated. The crude was purified by silica gel column chromatography using 50% ethyl acetate in hexanes as eluent. The desired fractions were concentrated under reduced pressure to afford rac-(5aR,6S,7R,8aR)-3-chloro-5a-(4-cyanophenyl)-8a-hydroxy-N,N-dimethyl-8-oxo-6-phenyl-5a,7,8,8a-tetrahydro-6H-cyclopenta[4,5]furo[3,2-b]pyridine-7-carboxamide (Cpd. No. 32F) as an off-white solid. Yield: 0.01 g, 38% (racemic mixture); MS (ESI) m/z 474.46[M+1]$^+$; $^1$H NMR (400 MHz, DMSO-$d_6$) δ 8.33 (d, J=2.0 Hz, 1H), 8.03 (d, J=2.0 Hz, 1H), 7.66 (d, J=8.6 Hz, 2H), 7.39 (d, J=8.6 Hz, 2H), 7.11-7.06 (m, 3H), 7.02-6.88 (m, 3H), 4.92 (d, J=13.0 Hz, 1H), 4.30 (d, J=13.0 Hz, 1H), 3.29 (s, 3H), 2.76 (s, 3H).

Example 33

Rac-(5aR,6S,7R,8R,8aS)-3-chloro-5a-(4-cyanophenyl)-8,8a-dihydroxy-N,N,8-trimethyl-6-phenyl-5a,7,8,8a-tetrahydro-6H-cyclopenta[4,5]furo[3,2-b]pyridine-7-carboxamide (Cpd. No. 33Fa) and Rac-(5aR,6S,7R,8S,8aS)-3-chloro-5a-(4-cyanophenyl)-8,8a-dihydroxy-N,N,8-trimethyl-6-phenyl-5a,7,8,8a-tetrahydro-6H-cyclopenta[4,5]furo[3,2-b]pyridine-7-carboxamide (Cpd. No. 33Fb)

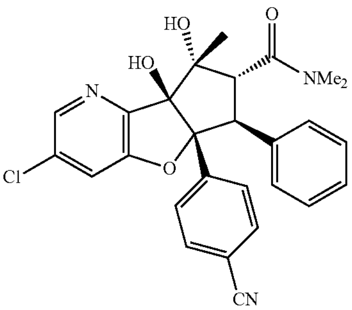

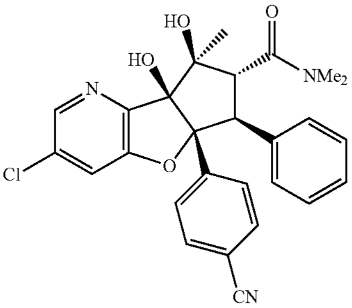

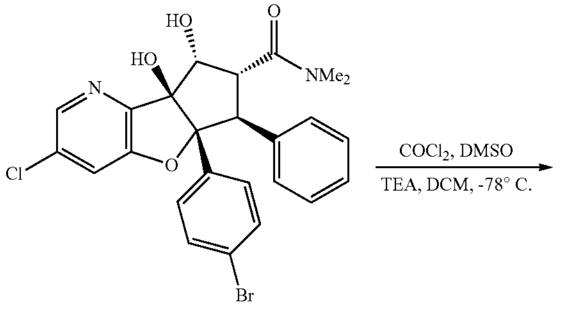

1

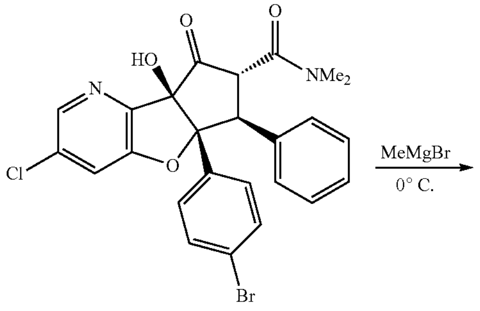

2

-continued

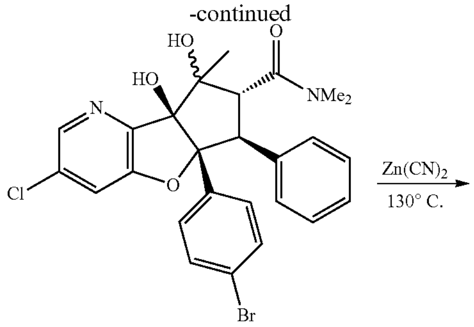

3

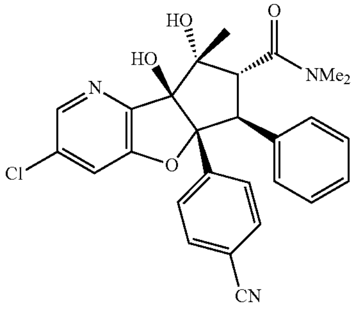

33Fa

+

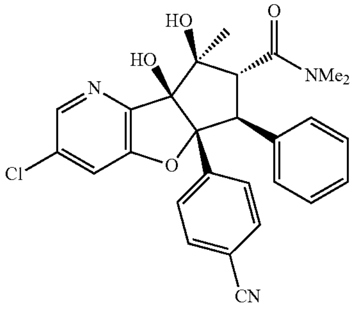

33Fb

Synthesis of rac-(5aR,6S,7R,8aR)-5a-(4-bromophenyl)-3-chloro-8a-hydroxy-N,N-dimethyl-8-oxo-6-phenyl-5a,7,8,8a-tetrahydro-6H-cyclopenta[4,5]furo[3,2-b]pyridine-7-carboxamide (2)

To a solution of oxalyl chloride (0.607 mL, 7.08 mmol) in dry dichloromethane (7.5 mL) under nitrogen at −78° C., dimethyl sulfoxide (0.704 mL, 9.91 mmol) was added dropwise. The reaction mixture was stirred for 30 min and a solution of (5aR,6S,7R,8R,8aS)-5a-(4-bromophenyl)-3-chloro-8,8a-dihydroxy-N,N-dimethyl-6-phenyl-5a,7,8,8a-tetrahydro-6H-cyclopenta[4,5]furo[3,2-b]pyridine-7-carboxamide (1, 1.50 g, 2.83 mmol) in dichloromethane (20 mL) was added at −78° C. The reaction was stirred for another 2 h at same temperature and then triethylamine (3.95 mL, 28.31 mmol) was added. The reaction mass was slowly brought to room temperature and stirred for 15 min. The mixture was diluted with water (20 mL) and dichloromethane (40 mL). The organic layer was washed with water and brine, dried over anhydrous sodium sulfate, filtered and concentrated. The crude was purified by silica gel column chromatography using 50% ethyl acetate in hexanes as eluent. The desired fractions were concentrated under reduced pressure to afford rac-(5aR,6S,7R,8aR)-5a-(4-bromophenyl)-3-chloro-8a-hydroxy-N,N-dimethyl-8-oxo-6-phenyl-5a,7,8,8a-tetrahydro-6H-cyclopenta[4,5]furo[3,2-b]pyridine-7-carboxamide (2) as an off-white solid. Yield: 0.5 g, 33%; MS (ESI) m/z 525.19[M−1]$^-$.

Synthesis of rac-(5aR,6S,7R,8aS)-5a-(4-bromophenyl)-3-chloro-8,8a-dihydroxy-N,N,8-trimethyl-6-phenyl-5a,7,8,8a-tetrahydro-6H-cyclopenta[4,5]furo[3,2-b]pyridine-7-carboxamide (3)

To a solution of rac-(5aR,6S,7R,8aR)-5a-(4-bromophenyl)-3-chloro-8a-hydroxy-N,N-dimethyl-8-oxo-6-phenyl-5a,7,8,8a-tetrahydro-6H-cyclopenta[4,5]furo[3,2-b]pyridine-7-carboxamide (2, 0.3 g, 0.568 mmol) in dry diethyl ether (5.0 mL), methyl magnesium bromide (3.8 mL, 11.37 mmol) was added dropwise at 0° C. over a period of 5 min. The reaction mass was slowly brought to room temperature and stirred for 6 h. After completion, the reaction mixture was treated with saturated aqueous solution of ammonium chloride and extracted with ethyl acetate (20 mL). The organic layer was washed with water and brine, dried over anhydrous sodium sulfate, filtered and concentrated to afford rac-(5aR,6S,7R,8aS)-5a-(4-bromophenyl)-3-chloro-8,8a-dihydroxy-N,N,8-trimethyl-6-phenyl-5a,7,8,8a-tetrahydro-6H-cyclopenta[4,5]furo[3,2-b]pyridine-7-carboxamide (3) as yellow semi solid (mixture of diastereomers). Yield: 0.3 g, crude; MS (ESI) m/z 543.34[M+1]$^+$.

Synthesis of rac-(5aR,6S,7R,8R,8aS)-3-chloro-5a-(4-cyanophenyl)-8,8a-dihydroxy-N,N,8-trimethyl-6-phenyl-5a,7,8,8a-tetrahydro-6H-cyclopenta[4,5]furo[3,2-b]pyridine-7-carboxamide (Cpd. No. 33Fa) and Rac-(5aR,6S,7R,8S,8aS)-3-chloro-5a-(4-cyanophenyl)-8,8a-dihydroxy-N,N,8-trimethyl-6-phenyl-5a,7,8,8a-tetrahydro-6H-cyclopenta[4,5]furo[3,2-b]pyridine-7-carboxamide (Cpd. No. 33Fb)

To a solution afford rac-(5aR,6S,7R,8aS)-5a-(4-bromophenyl)-3-chloro-8,8a-dihydroxy-N,N,8-trimethyl-6-phenyl-5a,7,8,8a-tetrahydro-6H-cyclopenta[4,5]furo[3,2-b]pyridine-7-carboxamide (3, 0.3 g, 0.55 mmol) in dimethylformamide (25 mL), zinc cyanide (0.37 g, 3.3 mmol) and zinc (0.004 g, 0.066 mmol) were added and degassed the mixture with argon for 15 min. 1,1'-Bis(diphenylphosphino)ferrocene (0.041 g, 0.011 mmol), tris(dibenzylideneacetone)dipalladium (0.078 g, 0.016 mmol) were added to the above reaction and degassing was continued for another 5 min followed by heating the reaction mixture at 130° C. for 1 h. After completion, the reaction was cooled to room temperature and passed through a bed of celite. The filtrate was concentrated and treated with ice-cold water, the precipitated solid was filtered and the crude was purified by reverse phase prep HPLC and lyophilized to afford rac-(5aR,6S,7R,8R,8aS)-3-chloro-5a-(4-cyanophenyl)-8,8a-dihydroxy-N,N,8-trimethyl-6-phenyl-5a,7,8,8a-tetrahydro-6H-cyclopenta[4,5]furo[3,2-b]pyridine-7-carboxamide (Cpd. No. 33Fa) and Rac-(5aR,6S,7R,8S,8aS)-3-chloro-5a-(4-cyanophenyl)-8,8a-dihydroxy-N,N,8-trimethyl-6-phenyl-5a,7,8,8a-tetrahydro-6H-cyclopenta[4,5]furo[3,2-b]pyridine-7-carboxamide (Cpd. No. 33Fb)

Cpd. No. 33Fa: Yield: 0.005 g (off white solid), 1.5%; MS (ESI) m/z 490.52[M+1]$^+$; $^1$H NMR (400 MHz, DMSO-$d_6$) δ 8.12 (d, J=2.0 Hz, 1H), 7.66 (d, J=2.0 Hz, 1H), 7.47 (d, J=8.6 Hz, 2H), 7.35 (d, J=8.4 Hz, 2H), 7.06 (m, 2H), 6.96 (m, 3H), 6.06 (s, 1H), 4.82 (m, 2H), 4.32 (d, J=13.2 Hz, 1H), 3.40 (s, 3H), 2.88 (s, 3H), 1.46 (s, 3H).

Cpd. No. 33Fb: Yield: 0.005 g (off white solid), 1.5%; MS (ESI) m/z 490.52[M+1]$^+$; $^1$H NMR (400 MHz, DMSO-$d_6$) δ 8.28 (d, J=2.0 Hz, 1H), 7.28 (d, J=2.0 Hz, 1H), 7.60 (d, J=8.6 Hz, 2H), 7.49 (d, J=8.3 Hz, 2H), 7.05 (m, 3H), 6.80 (d, J=13.0 Hz, 2H), 5.92 (brs, 2H), 4.07 (d, J=13.8 Hz, 1H), 3.93 (d, J=13.8 Hz, 1H), 3.45 (s, 3H), 2.78 (s, 3H), 1.24 (s, 3H).

Example 34

Rac-(5aR,6S,8aR)-5a-(4-bromophenyl)-3-chloro-8-methylene-6-phenyl-5a,6,7,8-tetrahydro-8aH-cyclopenta[4,5]furo[3,2-b]pyridin-8a-ol (Cpd. No. 34F)

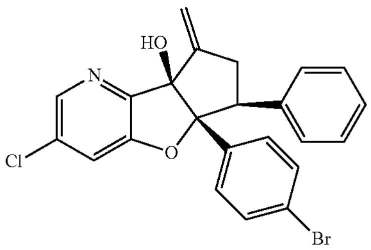

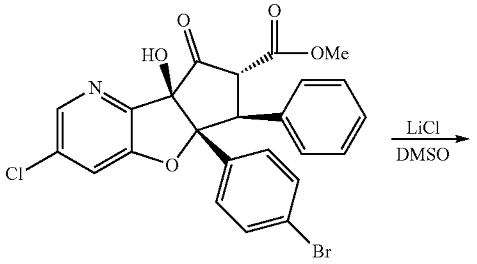

1

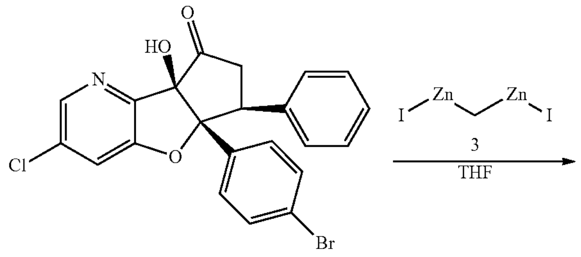

2

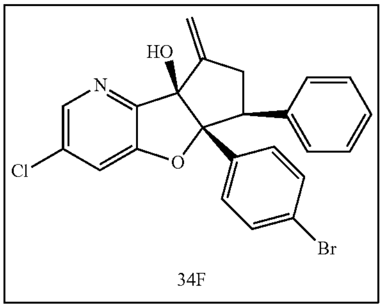

34F

Synthesis of rac-(5aR,6S,8aR)-5a-(4-bromophenyl)-3-chloro-8a-hydroxy-6-phenyl-5a,6,7,8a-tetrahydro-8H-cyclopenta[4,5]furo[3,2-b]pyridin-8-one (2)

To a solution of rac-methyl (5aR,6S,7R,8aR)-5a-(4-bromophenyl)-3-chloro-8a-hydroxy-8-oxo-6-phenyl-5a,7,8,8a-tetrahydro-6H-cyclopenta[4,5]furo[3,2-b]pyridine-7-carboxylate (1, 3.0 g, 5.8 mmol) in dimethylsulfoxide (60 mL), lithium chloride (27.2 g, 1.13 mol) was added and stirred the mixture at 150° C. for 24 h. After completion, ice cooled water was added and precipitated solid was filtered. The solid was dissolved in dichloromethane (100 mL), washed with water (2×30 mL) and brine (20 mL). The organics layer was separated and dried over anhydrous sodium sulphate before concentration to dryness. The crude was purified by Combi-flash (12 g, RediSep column) using 20% ethyl acetate in hexanes as eluent. The desired fractions were concentrated under reduced pressure to afford rac-(5aR,6S,8aR)-5a-(4-bromophenyl)-3-chloro-8a-hydroxy-6-phenyl-5a,6,7,8a-tetrahydro-8H-cyclopenta[4,5]furo[3,2-b]pyridin-8-one (2) as off white solid. Yield: 0.85 g, 32.6%; MS (ESI) m/z 455.92$[M+1]^+$.

Synthesis of rac-(5aR,6S,8aR)-5a-(4-bromophenyl)-3-chloro-8-methylene-6-phenyl-5a,6,7,8-tetrahydro-8aH-cyclopenta[4,5]furo[3,2-b]pyridin-8a-ol (Cpd. No. 34F)

To a solution of rac-(5aR,6S,8aR)-5a-(4-bromophenyl)-3-chloro-8a-hydroxy-6-phenyl-5a,6,7,8a-tetrahydro-8H-cyclopenta[4,5]furo[3,2-b]pyridin-8-one (2, 0.1 g, 0.021 mmol) in dry tetrahydrofuran (2.0 mL), freshly prepared bis(iodozincio)methane (3, 0.17 g, 0.43 mmol) was added drop wise at 0° C. The reaction mass was stirred for 1.5 h at room temperature. After completion, the reaction mass was treated with saturated solution of ammonium chloride and extracted with diethyl ether. The organic layer was dried over anhydrous sodium sulphate, filtered and concentrated under reduced pressure. The crude was purified by Combi-flash (4 g, RediSep column) using 10% ethyl acetate in hexanes as eluent to afford rac-(5aR,6S,8aR)-5a-(4-bromophenyl)-3-chloro-8-methylene-6-phenyl-5a,6,7,8-tetrahydro-8aH-cyclopenta[4,5]furo[3,2-b]pyridin-8a-ol (Cpd. No. 34F) as white solid. Yield: 0.03 g, 30.0%; MS (ESI) m/z 453.93$[M+1]^+$; $^1H$ NMR (400 MHz, DMSO-$d_6$) δ 8.27 (d, J=1.8 Hz, 1H), 7.80 (d, J=1.8 Hz, 1H), 7.36 (d, J=8.4 Hz, 2H), 7.14-7.06 (m, 5H), 6.95-6.93 (m, 2H), 5.98 (s, 1H), 5.79 (s, 1H), 5.42 (s, 1H), 3.47 (dd, J=13.4, 8.2 Hz, 1H), 3.15 (dd, J=17.0, 13.2 Hz, 1H), 2.80 (dd, J=17.4, 8.2 Hz, 1H).

Example 35

Rac-(5aR,6R,8aS)-5a-(4-bromophenyl)-3-chloro-8a-hydroxy-8-methoxy-N,N-dimethyl-6-phenyl-5a,8a-dihydro-6H-cyclopenta[4,5]furo[3,2-b]pyridine-7-carboxamide (Cpd. No. 35F)

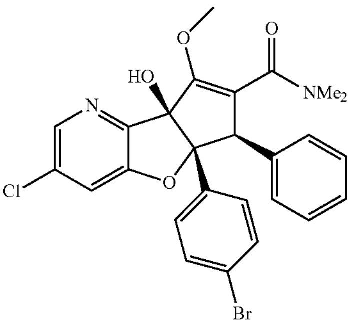

-continued

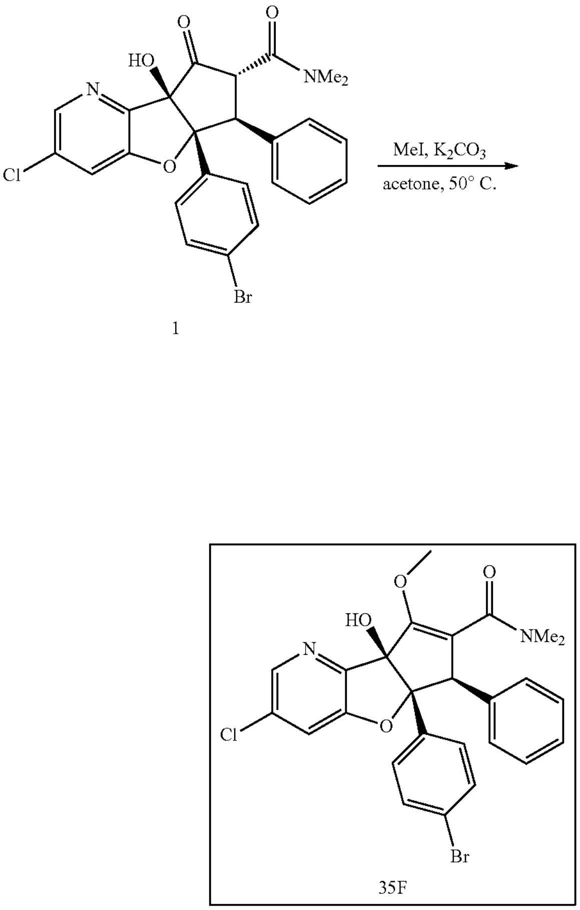

1

35F

Synthesis of rac-(5aR,6R,8aS)-5a-(4-bromophenyl)-3-chloro-8a-hydroxy-8-methoxy-N,N-dimethyl-6-phenyl-5a,8a-dihydro-6H-cyclopenta[4,5]furo[3,2-b]pyridine-7-carboxamide (Cpd. No. 35F)

To a solution of rac-(5aR,6S,7R,8aR)-5a-(4-bromophenyl)-3-chloro-8a-hydroxy-N,N-dimethyl-8-oxo-6-phenyl-5a,7,8,8a-tetrahydro-6H-cyclopenta[4,5]furo[3,2-b]pyridine-7-carboxamide (1, 0.200 g, 0.37 mmol) in acetone (5 mL), potassium carbonate (0.102 g, 0.74 mmol) and methyl iodide (0.035 mL, 0.55 mmol) were added and reaction mixture was heated at 50° C. for 16 hours. After completion, reaction mixture was cooled and water (25 mL) was added followed by extraction with ethyl acetate (100 mL). The organic layer was dried over anhydrous sodium sulfate, filtered and concentrated. The crude was purified by silica gel column chromatography using 1% methanol in dichloromethane as eluent. The desired fractions were concentrated to afford rac-(5aR,6R,8aS)-5a-(4-bromophenyl)-3-chloro-8a-hydroxy-8-methoxy-N,N-dimethyl-6-phenyl-5a,8a-dihydro-6H-cyclopenta[4,5]furo[3,2-b]pyridine-7-carboxamide (Cpd. No. 35F) as off white solid. Yield: 0.11 g, 54%; MS (ESI) m/z 541.44$[M+1]^+$; $^1H$ NMR (400 MHz, DMSO-$d_6$) δ 8.29 (d, J=2.0 Hz, 1H), 7.83 (d, J=1.6 Hz, 1H), 7.25 (d, J=8.4 Hz, 2H), 7.12 (d, J=8.8 Hz, 2H), 7.10-6.88 (m, 3H), 6.90 (d, J=6.0 Hz, 2H), 6.64 (s, 1H), 4.35 (s, 1H), 4.08 (s, 3H), 3.12 (s, 3H), 2.73 (s, 3H).

Example 36

Rac-(4aR,5S,6R,7R,7aS)-3-chloro-4a-(4-cyanophenyl)-7,7a-dihydroxy-N,N,2-trimethyl-5-phenyl-2,4a,5,6,7,7a-hexahydrocyclopenta[4,5]furo[3,2-c]pyrazole-6-carboxamide (Cpd. No. 36F)

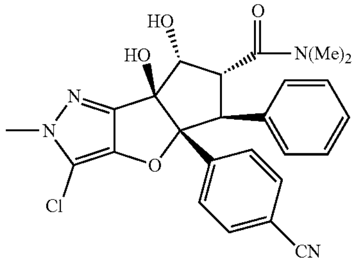

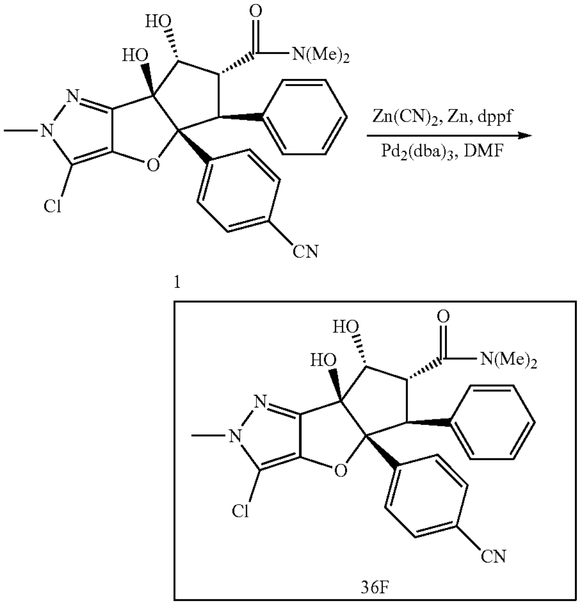

1

36F

Synthesis of rac-(4aR,5S,6R,7R,7aS)-3-chloro-4a-(4-cyanophenyl)-7,7a-dihydroxy-N,N,2-trimethyl-5-phenyl-2,4a,5,6,7,7a-hexahydrocyclopenta[4,5]furo[3,2-c]pyrazole-6-carboxamide (Cpd. No. 36F)

To a solution of rac-(4aR,5S,6R,7R,7aS)-4a-(4-bromophenyl)-3-chloro-7,7a-dihydroxy-N,N,2-trimethyl-5-phenyl-2,4a,5,6,7,7a-hexahydrocyclopenta[4,5]furo[3,2-c]pyrazole-6-carboxamide (1, 0.04 g, 0.07 mmol) in N,N-dimethylformamide (1.0 mL), zinc cyanide (0.052 g, 0.45 mmol) and zinc (0.001 g, 0.008 mmol) were added at room temperature and degassed the mixture with argon for 15 min. 1,1'-Bis(diphenylphosphino)ferrocene (0.001 g, 0.001 mmol), tris(dibenzylideneacetone)dipalladium (0.002 g, 0.002 mmol) were added to the reaction and degassing was continued for another 5 min. The reaction mixture was heated at 140° C. for 2 h. After completion, the reaction mass was diluted with ethyl acetate and washed with cold water. The organic layer was separated and dried over sodium sulphate, filtered and concentrated to give crude. The crude was purified by silica gel column chromatography using 2-3% methanol in dichloromethane as eluent. The desired fractions were concentrated to afford rac-(4aR,5S,6R,7R,7aS)-3-chloro-4a-(4-cyanophenyl)-7,7a-dihydroxy-N,N,2-trimethyl-5-phenyl-2,4a,5,6,7,7a-hexahydrocyclopenta[4,5]furo[3,2-c]pyrazole-6-carboxamide (Cpd. No. 36F) as white solid. The crude was purified by Prep HPLC. Yield: 0.013 g, 36% (racemic mixture); MS (ESI) m/z 479.5 $[M+1]^+$; $^1H$ NMR (400 MHz, DMSO-$d_6$) δ 7.54 (d, J=8.6 Hz, 2H), 7.32 (d, J=8.6 Hz, 2H), 7.01 (m, 3H), 6.81 (d, J=7.2 Hz, 2H), 5.85 (s, 1H), 5.48 (d, J=6.2 Hz, 1H), 4.78 (t, J=6.8 Hz, 1H), 4.45 (d, J=13.4 Hz, 1H), 4.11 (dd, J=13.4, 7.36 Hz, 1H), 3.78 (s, 3H), 3.20 (s, 3H), 2.74 (s, 3H).

Example 37

Rac-(4aR,5S,6R,7R,7aS)-4a-(4-bromophenyl)-3-chloro-7,7a-dihydroxy-N,N,2-trimethyl-5-phenyl-2,4a,5,6,7,7a-hexahydrocyclopenta[4,5]furo[3,2-c]pyrazole-6-carboxamide (Cpd. No. 37F)

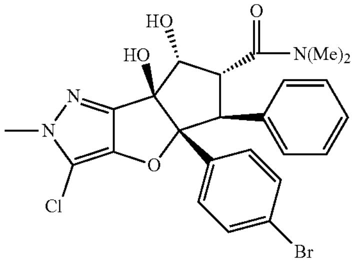

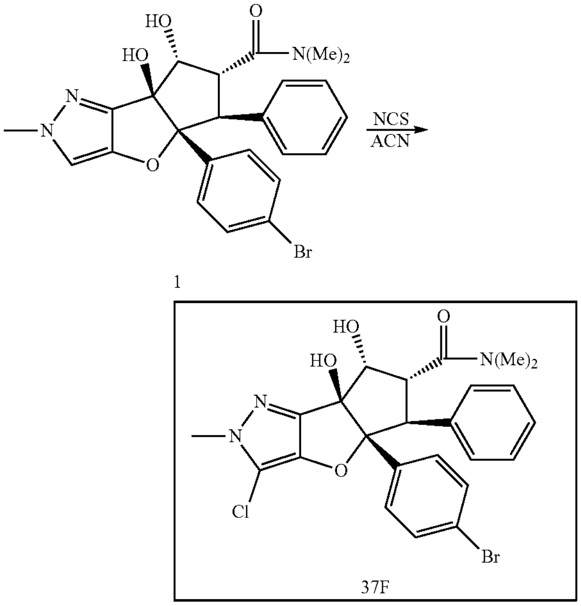

1

37F

Synthesis of rac-(4aR,5S,6R,7R,7aS)-4a-(4-bromophenyl)-3-chloro-7,7a-dihydroxy-N,N,2-trimethyl-5-phenyl-2,4a,5,6,7,7a-hexahydrocyclopenta[4,5]furo[3,2-c]pyrazole-6-carboxamide (Cpd. No. 37F)

To a solution of rac-(4aR,5S,6R,7R,7aS)-4a-(4-bromophenyl)-7,7a-dihydroxy-N,N,2-trimethyl-5-phenyl-2,4a,5,6,7,7a-hexahydrocyclopenta[4,5]furo[3,2-c]pyrazole-6-carboxamide (1, 0.1 g, 0.2 mmol) in acetonitrile (3 mL), N-chlorosuccinimide (0.04 g, 0.30 mmol) was added and the reaction was stirred at 45° C. for 4 h. After completion, reaction mass was diluted with ethyl acetate and washed with cold water. The organic layer was separated and dried over sodium sulphate, filtered and concentrated to give crude. The crude was purified by silica gel column chromatography using 5% methanol in dichloromethane as eluent. The desired fractions were concentrated to afford rac-(4aR,5S,6R,7R,7aS)-4a-(4-bromophenyl)-3-chloro-7,7a-dihydroxy-N,N,2-trimethyl-5-phenyl-2,4a,5,6,7,7a-hexahydrocyclopenta[4,5]furo[3,2-c]pyrazole-6-carboxamide (Cpd. No. 37F) as white solid. Yield: 0.055 g, 51.8%; (racemic mixture); MS (ESI) m/z 532.5[M+1]$^+$; $^1$H NMR (400 MHz, DMSO-d$_6$) δ 7.27 (d, J=8.6 Hz, 2H), 7.04 (m, 5H), 6.81 (d, J=7.2 Hz, 2H), 5.74 (s, 1H), 5.41 (d, J=6.2 Hz, 1H), 4.77 (t, J=6.9 Hz, 1H), 4.38 (d, J=13.2 Hz, 1H), 4.03 (dd, J=13.2, 7.6 Hz, 1H), 3.78 (s, 3H), 3.19 (s, 3H), 2.73 (s, 3H).

Example 38

Rac-(5aR,6S,8R,8aS)-5a-(4-bromophenyl)-3-chloro-6-phenyl-6,7-dihydrospiro[cyclopenta[4,5]furo[3,2-b]pyridine-8,2'-oxetan]-8a(5aH)-ol (Cpd. No. 38F)

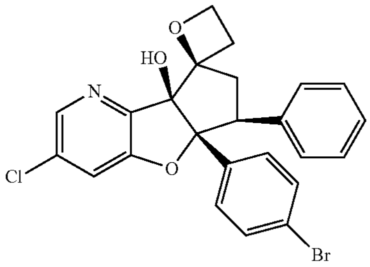

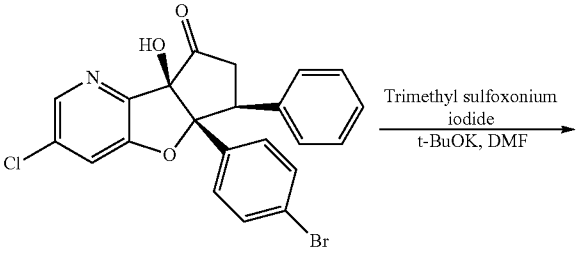

1

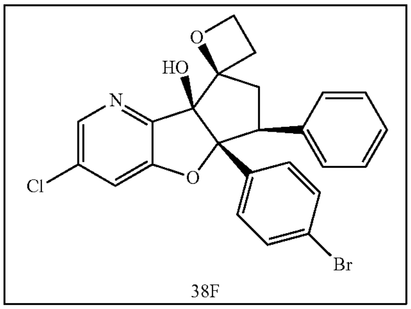

38F

Synthesis of rac-(5aR,6S,8R,8aS)-5a-(4-bromophenyl)-3-chloro-6-phenyl-6,7-dihydrospiro[cyclopenta[4,5]furo[3,2-b]pyridine-8,2'-oxetan]-8a(5aH)-ol (Cpd. No. 38F)

To a solution of trimethyl sulfoxonium iodide (2, 0.96 g, 4.3 mmol) in N,N-dimethylformamide (10 mL), potassium tert-butoxide (0.49 g, 4.3 mmol) was added and stirred for 30 minutes at 50° C. A solution of rac-(5aR,6S,8aR)-5a-(4-bromophenyl)-3-chloro-8a-hydroxy-6-phenyl-5a,6,7,8a-tetrahydro-8H-cyclopenta[4,5]furo[3,2-b]pyridin-8-one (1, 0.35 g, 1.0 mmol) in N,N-dimethylformamide was added to the above mixture at 50° C. and reaction was stirred for 16 h at 50° C. After completion, the reaction mixture was cooled and diluted with ethyl acetate and washed with cold water. The organic layer was separated and dried over anhydrous sodium sulphate, filtered and concentrated to give crude. The crude was purified by Combi-flash (12 g, RediSep column) using 10% ethyl acetate in hexanes as eluent. The desired fractions were concentrated under reduced pressure to afford rac-(5aR,6S,8R,8aS)-5a-(4-bromophenyl)-3-chloro-6-phenyl-6,7-dihydrospiro[cyclopenta[4,5]furo[3,2-b]pyridine-8,2'-oxetan]-8a(5aH)-ol (Cpd. No. 38F) as white solid. Yield: 0.032 g, 8.6%; MS (ESI) m/z 483.92[M+1]$^+$; $^1$H NMR (400 MHz, DMSO-d$_6$) δ 8.30 (d, J=2.0 Hz, 1H), 7.80 (d, J=2.0 Hz, 1H), 7.25 (d, J=8.6 Hz, 2H), 7.14 (d, J=8.7 Hz, 2H), 7.10-6.99 (m, 5H), 5.78 (s, 1H), 4.62-4.57 (m, 2H), 3.62-3.51 (m, 2H), 2.78-2.72 (m, 1H), 2.66-2.53 (m, 1H).

Example 39

Rac-4-((5aR,6S,7S,8R,8aS)-3-chloro-8,8a-dihydroxy-7-((methylamino)methyl)-6-phenyl-6,7,8,8a-tetrahydro-5aH-cyclopenta[4,5]furo[3,2-b]pyridin-5a-yl)benzonitrile (Cpd. No. 39F)

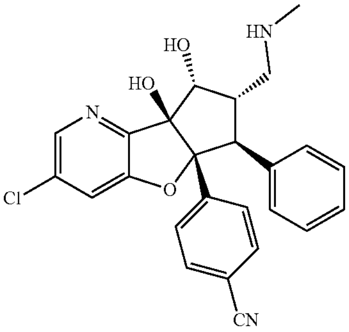

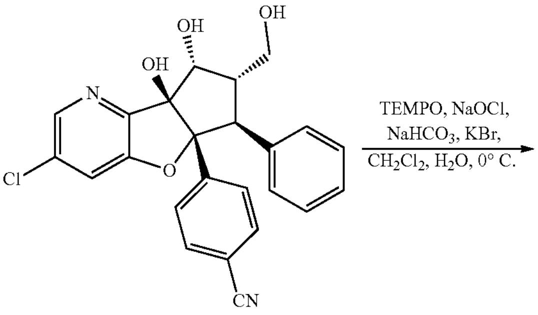

1

-continued

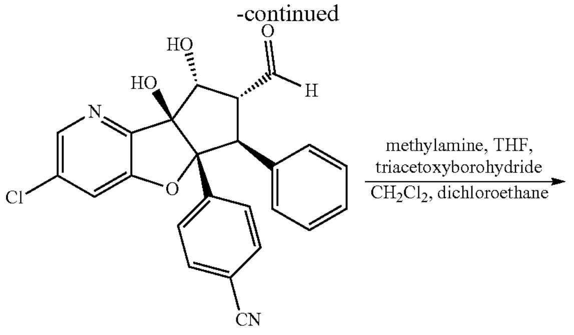

2

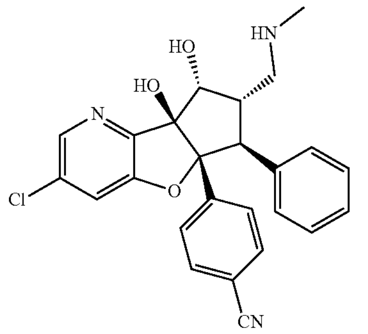

39F

Synthesis of rac-4-((5aR,6S,7R,8R,8aS)-3-chloro-7-formyl-8,8a-dihydroxy-6-phenyl-6,7,8,8a-tetrahydro-5aH-cyclopenta[4,5]furo[3,2-b]pyridin-5a-yl)benzonitrile (2)

To a vigorously stirred solution of rac-4-((5aR,6S,7S,8R,8aS)-3-chloro-8,8a-dihydroxy-7-(hydroxymethyl)-6-phenyl-6,7,8,8a-tetrahydro-5aH-cyclopenta[4,5]furo[3,2-b]pyridin-5a-yl)benzonitrile (1, 272 mg, 0.630 mmol) in dichloromethane (100 mL) at 0° C. was added saturated aqueous sodium bicarbonate (30 mL), 0.5 M potassium bromide in water (1.25 mL, 0.63 mmol) and then TEMPO (4.9 mg, 0.030 mmol). The resulting slightly orange biphasic mixture was stirred vigorously at 0° C. for 10 min and then aqueous solution of sodium hypochlorite in water (0.34 mL of 10-15% available chlorine) was added dropwise. The resulting orange biphasic mixture was stirred vigorously at 0° C. for 15 min. More sodium hypochlorite (0.34 mL of 10-15% available chlorine) was added and stirring at 0° C. was continued for an additional 20 min. The layers were separated in separatory funnel. The aqueous layer was extracted once with dichloromethane. The combined organics were dried over sodium sulfate, filtered, and concentrated on a rotary evaporator down to ~5 mL. This solution of rac-4-((5aR,6S,7R,8R,8aS)-3-chloro-7-formyl-8,8a-dihydroxy-6-phenyl-6,7,8,8a-tetrahydro-5aH-cyclopenta[4,5]furo[3,2-b]pyridin-5a-yl)benzonitrile (2) was used in the next reaction without further manipulation or purification. MS (ESI) m/z 433.1[M+1]$^+$.

Synthesis of rac-4-((5aR,6S,7S,8R,8aS)-3-chloro-8,8a-dihydroxy-7-((methylamino)methyl)-6-phenyl-6,7,8,8a-tetrahydro-5aH-cyclopenta[4,5]furo[3,2-b]pyridin-5a-yl)benzonitrile (Cpd. No. 39F)

To a stirred solution of rac-4-[(5aR,6S,7R,8R,8aS)-3-chloro-7-formyl-8,8a-dihydroxy-6-phenyl-7,8-dihydro-6H-cyclopenta[4,5]furo[1,2-b]pyridin-5a-yl]benzonitrile (2, 135 mg, 0.310 mmol) in DICHLOROMETHANE (2.5 mL) was added sequentially: 1,2-DICHLOROETHANE (5 mL), methylamine (2 M in TETRAHYDROFURAN) (0.31 mL, 0.62 mmol), and then sodium triacetoxyborohydride (132 mg, 0.62 mmol). The resulting mixture was capped and stirred at room temperature for 1.5 h. Saturated aqueous Sodium bicarbonate (2 mL) was added with vigorous stirring. The layers were separated in a separatory funnel and the aqueous layer extracted once with DICHLOROMETHANE. The combined organics were evaporated to dryness, dissolved in DMSO and methanol, filtered, and purified via preparatory HPLC (15-35% acetonitrile in water with 0.1% TRIFLUOROACETIC ACID). Fractions containing the desired product were loaded onto a Strata X-C ion exchange column from Phenomenex. The column was eluted sequentially with water, acetonitrile, methanol, and then 5% ammonium hydroxide in methanol. Fractions containing the desired product were combined, concentrated on a rotary evaporator and dried under high vacuum to afford rac-4-((5aR,6S,7S,8R,8aS)-3-chloro-8,8a-dihydroxy-7-((methylamino)methyl)-6-phenyl-6,7,8,8a-tetrahydro-5aH-cyclopenta[4,5]furo[3,2-b]pyridin-5a-yl)benzonitrile (Cpd. No. 39F) as an off-white solid. Yield: 34 mg, 24%; MS (ESI) m/z 448.1[M+1]$^+$; $^1$H NMR (400 MHz, DMSO-$d_6$) δ 8.18 (d, J=2.0 Hz, 1H), 7.64 (d, J=2.0 Hz, 1H), 7.52-7.46 (m, 2H), 7.37-7.31 (m, 2H), 7.13-6.96 (m, 5H), 6.07 (s, 1H), 4.50 (d, J=4.1 Hz, 1H), 4.00 (d, J=14.1 Hz, 1H), 3.21 (ddt, J=13.0, 8.1, 3.6 Hz, 1H), 2.69 (dd, J=12.0, 8.5 Hz, 1H), 2.24 (s, 3H).

Example 40

Rac-4-((5aR,6S,7R,8R,8aS)-3-chloro-7-((dimethylamino)methyl)-8,8a-dihydroxy-6-phenyl-6,7,8,8a-tetrahydro-5aH-cyclopenta[4,5]furo[3,2-b]pyridin-5a-yl)benzonitrile (Cpd. No. 40Fa), rac-4-((5aR,6S,7S,8R,8aS)-3-chloro-7-((dimethylamino)methyl)-8,8a-dihydroxy-6-phenyl-6,7,8,8a-tetrahydro-5aH-cyclopenta[4,5]furo[3,2-b]pyridin-5a-yl)benzonitrile (Cpd. No. 40Fb), and rac-4-((5aR,6S,7S,8S,8aS)-3-chloro-7-((dimethylamino)methyl)-8,8a-dihydroxy-6-phenyl-6,7,8,8a-tetrahydro-5aH-cyclopenta[4,5]furo[3,2-b]pyridin-5a-yl)benzonitrile (Cpd. No. 40Fc)

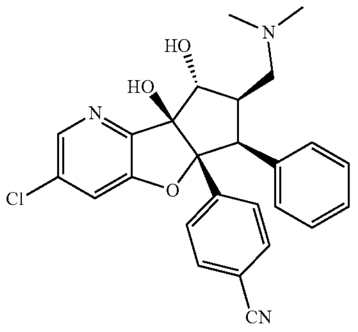

-continued

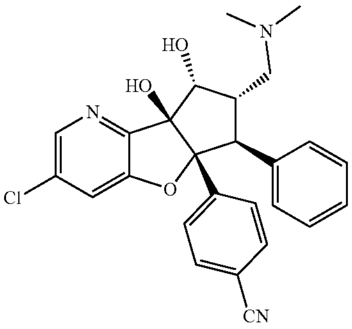

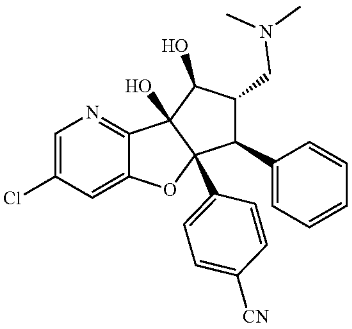

-continued

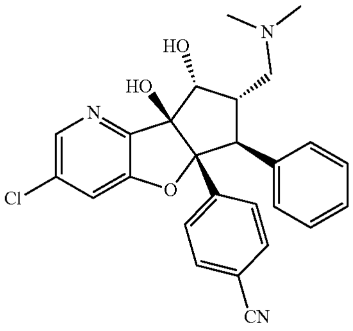

40Fb

+

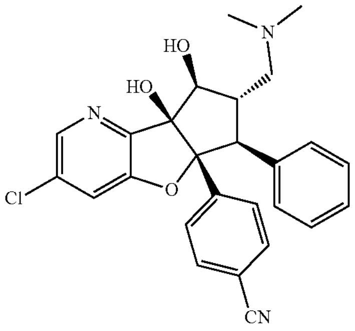

40Fc

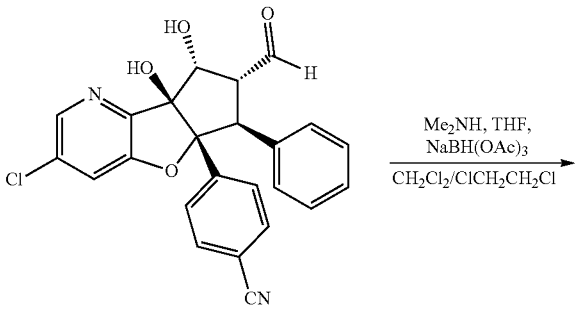

1

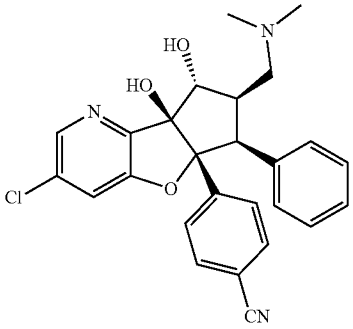

40Fa

+

Synthesis of rac-4-((5aR,6S,7R,8R,8aS)-3-chloro-7-((dimethylamino)methyl)-8,8a-dihydroxy-6-phenyl-6,7,8,8a-tetrahydro-5aH-cyclopenta[4,5]furo[3,2-b]pyridin-5a-yl)benzonitrile (Cpd. No. 40Fa), rac-4-((5aR,6S,7S,8R,8aS)-3-chloro-7-((dimethylamino)methyl)-8,8a-dihydroxy-6-phenyl-6,7,8,8a-tetrahydro-5aH-cyclopenta[4,5]furo[3,2-b]pyridin-5a-yl)benzonitrile (Cpd. No. 40Fb), and rac-4-((5aR,6S,7S,8S,8aS)-3-chloro-7-((dimethylamino)methyl)-8,8a-dihydroxy-6-phenyl-6,7,8,8a-tetrahydro-5aH-cyclopenta[4,5]furo[3,2-b]pyridin-5a-yl)benzonitrile (Cpd. No. 40Fc)

To a stirred solution of rac-4-((5aR,6S,7R,8R,8aS)-3-chloro-7-formyl-8,8a-dihydroxy-6-phenyl-6,7,8,8a-tetrahydro-5aH-cyclopenta[4,5]furo[3,2-b]pyridin-5a-yl)benzonitrile (1, 135 mg, 0.31 mmol) in dichloromethane (2.5 mL) was added sequentially: 1,2-dichloroethane (5 mL), dimethylamine (2 M in tetrahydrofuran) (0.31 mL, 0.62 mmol), and then sodium triacetoxyborohydride (132 mg, 0.62 mmol). The resulting mixture was capped and stirred at room temperature for 1.5 h. Saturated aqueous sodium bicarbonate (2 mL) was added with vigorous stirring. The layers were separated in a separatory funnel and the aqueous layer extracted once with dichloromethane. The combined organics were evaporated to dryness, dissolved in dimethyl sulfoxide and methanol, filtered, and purified via preparatory HPLC (15-37% acetonitrile in water with 0.1% trifluoroacetic acid). Fractions containing the desired products were loaded onto a Strata X-C ion exchange column from Phenomenex. The column was eluted sequentially with water, acetonitrile, methanol, and then 5% ammonium hydroxide in methanol. Fractions containing the desired product were combined, concentrated on a rotary evaporator and dried under high vacuum to afford rac-4-((5aR,6S,7R,8R,8aS)-3-chloro-7-((dimethylamino)methyl)-8,8a-dihydroxy-6-phenyl-6,7,8,8a-tetrahydro-5aH-cyclopenta[4,5]furo[3,2-b]pyridin-5a-yl)benzonitrile (Cpd. No. 40Fa) as a white solid. Yield: 4 mg, 3%; MS (ESI) m/z 462.1[M+1]$^+$; $^1$H NMR (400 MHz, DMSO-$d_6$) δ 8.24 (d, J=2.0 Hz, 1H), 7.57-7.46 (m, 5H), 7.31-7.26 (m, 2H), 7.24-7.12 (m, 3H), 6.80 (s, 1H), 4.40 (d, J=11.7 Hz, 1H), 4.08 (d, J=7.1 Hz, 1H), 2.43 (tdd, J=11.0, 6.9, 4.0 Hz, 1H), 1.99 (s, 7H), 1.90 (t, J=11.3 Hz, 1H). And rac-4-((5aR,6S,7S,8R,8aS)-3-chloro-7-((dimethylamino)methyl)-8,8a-dihydroxy-6-phenyl-6,7,8,8a-tetrahydro-5aH-cyclopenta[4,5]furo[3,2-b]pyridin-5a-yl)benzonitrile (Cpd. No. 40Fb) as a white solid. Yield: 30 mg, 21%; MS (ESI) m/z 462.1[M+1]$^+$; $^1$H NMR (400 MHz, DMSO-$d_6$) δ 8.18 (d, J=2.0 Hz, 1H), 7.63 (d, J=2.0 Hz, 1H), 7.51-7.46 (m, 2H), 7.39-7.33 (m, 2H), 7.12-6.97 (m, 5H), 6.12 (s, 1H), 5.33 (s, 1H), 4.44 (d, J=3.8 Hz, 1H), 3.94 (d, J=14.0 Hz, 1H), 3.22 (ddt, J=13.8, 10.1, 3.4 Hz, 1H), 2.61 (dd, J=12.3, 10.0 Hz, 1H), 2.21 (s, 6H), 1.98 (dd, J=12.4, 2.9 Hz, 1H). And rac-4-((5aR,6S,7S,8S,8aS)-3-chloro-7-((dimethylamino)methyl)-8,8a-dihydroxy-6-phenyl-6,7,8,8a-tetrahydro-5aH-cyclopenta[4,5]furo[3,2-b]pyridin-5a-yl)benzonitrile (Cpd. No. 40Fc) as a white solid. Yield: 8 mg, 6%; MS (ESI) m/z 462.1[M+1]$^+$; $^1$H NMR (400 MHz, DMSO-$d_6$) δ 8.32 (d, J=2.0 Hz, 1H), 7.81 (d, J=2.1 Hz, 1H), 7.68-7.62 (m, 2H), 7.46 (d, J=7.7 Hz, 2H), 7.06 (dd, J=4.8, 1.9 Hz, 3H), 6.81-6.74 (m, 2H), 6.18 (s, 1H), 5.51 (s, 1H), 4.50 (d, J=6.0 Hz, 1H), 3.00 (d, J=13.3 Hz, 1H), 2.68-2.58 (m, 1H), 2.22-2.13 (m, 1H), 2.07 (s, 6H), 2.02 (dd, J=12.6, 4.0 Hz, 1H).

Example 41

Rac-4-((5aR,6S,7R,8R,8aS)-3-chloro-8,8a-dihydroxy-6-phenyl-7-(pyrrolidin-1-ylmethyl)-6,7,8,8a-tetrahydro-5aH-cyclopenta[4,5]furo[3,2-b]pyridin-5a-yl)benzonitrile (Cpd. No. 41Fa), rac-4-((5aR,6S,7S,8R,8aS)-3-chloro-8,8a-dihydroxy-6-phenyl-7-(pyrrolidin-1-ylmethyl)-6,7,8,8a-tetrahydro-5aH-cyclopenta[4,5]furo[3,2-b]pyridin-5a-yl)benzonitrile (Cpd. No. 41Fb), and rac-4-((5aR,6S,7S,8S,8aS)-3-chloro-8,8a-dihydroxy-6-phenyl-7-(pyrrolidin-1-ylmethyl)-6,7,8,8a-tetrahydro-5aH-cyclopenta[4,5]furo[3,2-b]pyridin-5a-yl)benzonitrile (Cpd. No. 41Fc)

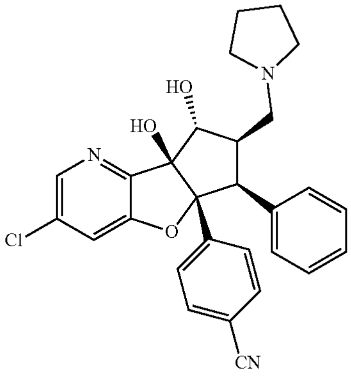

-continued

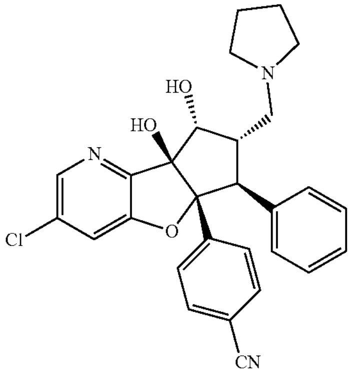

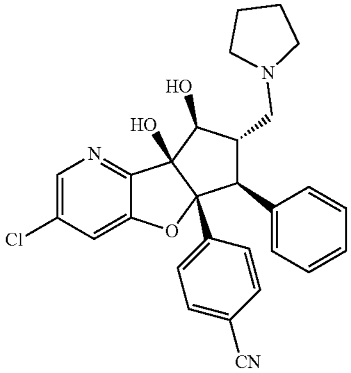

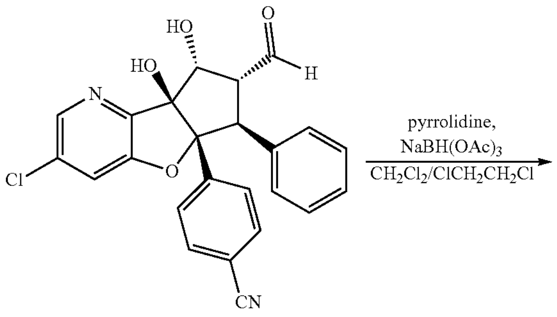

1

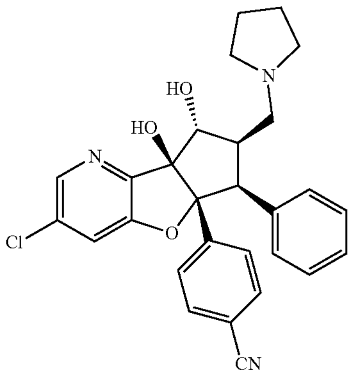

41Fa

+

-continued

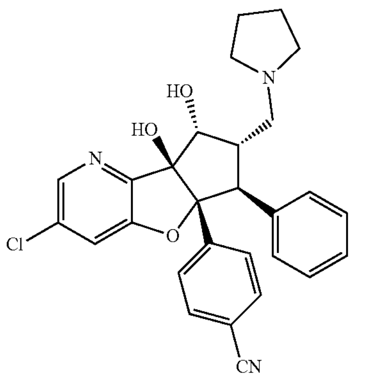

41Fb

+

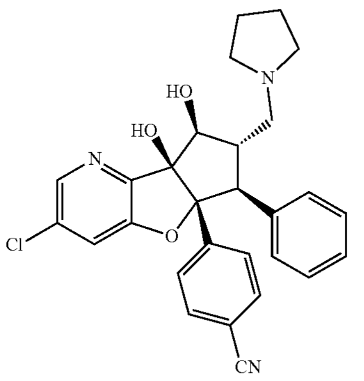

41Fc

Synthesis of rac-4-((5aR,6S,7R,8R,8aS)-3-chloro-8,8a-dihydroxy-6-phenyl-7-(pyrrolidin-1-ylmethyl)-6,7,8,8a-tetrahydro-5aH-cyclopenta[4,5]furo[3,2-b]pyridin-5a-yl)benzonitrile (Cpd. No. 41Fa), rac-4-((5aR,6S,7S,8R,8aS)-3-chloro-8,8a-dihydroxy-6-phenyl-7-(pyrrolidin-1-ylmethyl)-6,7,8,8a-tetrahydro-5aH-cyclopenta[4,5]furo[3,2-b]pyridin-5a-yl)benzonitrile (Cpd. No. 41Fb), and rac-4-((5aR,6S,7S,8S,8aS)-3-chloro-8,8a-dihydroxy-6-phenyl-7-(pyrrolidin-1-ylmethyl)-6,7,8,8a-tetrahydro-5aH-cyclopenta[4,5]furo[3,2-b]pyridin-5a-yl)benzonitrile (Cpd. No. 41Fc)

To a stirred solution of rac-4-((5aR,6S,7R,8R,8aS)-3-chloro-7-formyl-8,8a-dihydroxy-6-phenyl-6,7,8,8a-tetrahydro-5aH-cyclopenta[4,5]furo[3,2-b]pyridin-5a-yl)benzonitrile (1, 200 mg, 0.46 mmol) in dichloromethane (3 mL) was added sequentially: 1,2-dichloroethane (3 mL), pyrrolidine (65 mg, 0.92 mmol) in 1,2-dichloroethane (1 mL) and then sodium triacetoxyborohydride (195 mg, 0.92 mmol). The resulting mixture was capped and stirred at room temperature for 1 h. Saturated aqueous sodium bicarbonate (2 mL) was added with vigorous stirring. The layers were separated in a separatory funnel and the aqueous layer extracted once with dichloromethane. The combined organics were evaporated to dryness, dissolved in dimethyl sulfoxide and methanol, filtered, and purified via preparatory HPLC (15-37% acetonitrile in water with 0.1% trifluoroacetic acid). Fractions containing the desired products were loaded onto a Strata X-C ion exchange column from Phenomenex. The column was eluted sequentially with water, acetonitrile, methanol, and then 5% ammonium hydroxide in methanol. Fractions containing the desired product were concentrated on a rotary evaporator and lyophilized to dryness from 50% acetonitrile in water to afford rac-4-((5aR,6S,7R,8R,8aS)-3-chloro-8,8a-dihydroxy-6-phenyl-7-(pyrrolidin-1-ylmethyl)-6,7,8,8a-tetrahydro-5aH-cyclopenta[4,5]furo[3,2-b]pyridin-5a-yl)benzonitrile (Cpd. No. 41Fa) as a slightly yellow solid. Yield: 10 mg, 4%; MS (ESI) m/z 488.2[M+1]$^+$; $^1$H NMR (400 MHz, DMSO-d$_6$) δ 8.24 (d, J=1.9 Hz, 1H), 7.59-7.44 (m, 5H), 7.33-7.25 (m, 2H), 7.23-7.10 (m, 3H), 6.80 (s, 1H), 5.09 (s, 1H), 4.40 (d, J=11.7 Hz, 1H), 4.11 (d, J=7.0 Hz, 1H), 2.47-2.39 (m, 1H), 2.39-2.30 (m, 2H), 2.24-2.05 (m, 4H), 1.64 (d, J=4.8 Hz, 4H). And rac-4-((5aR,6S,7S,8R,8aS)-3-chloro-8,8a-dihydroxy-6-phenyl-7-(pyrrolidin-1-ylmethyl)-6,7,8,8a-tetrahydro-5aH-cyclopenta[4,5]furo[3,2-b]pyridin-5a-yl)benzonitrile (Cpd. No. 41Fb) as a white solid. Yield: 30 mg, 13%; MS (ESI) m/z 488.2[M+1]$^+$; $^1$H NMR (400 MHz, DMSO-d$_6$) δ 8.17 (dd, J=2.0, 0.6 Hz, 1H), 7.63 (dd, J=2.0, 0.6 Hz, 1H), 7.52-7.46 (m, 2H), 7.38-7.32 (m, 2H), 7.12-6.96 (m, 5H), 6.11 (d, J=0.6 Hz, 1H), 5.46 (s, 1H), 4.47 (d, J=3.9 Hz, 1H), 3.97 (d, J=14.1 Hz, 1H), 3.23 (ddt, J=13.6, 9.6, 3.2 Hz, 1H), 2.83 (dd, J=12.2, 9.6 Hz, 1H), 2.62-2.53 (m, 2H), 2.48-2.40 (m, 2H), 2.20 (dd, J=12.2, 2.8 Hz, 1H), 1.74-1.63 (m, 4H). And rac-4-((5aR,6S,7S,8S,8aS)-3-chloro-8,8a-dihydroxy-6-phenyl-7-(pyrrolidin-1-ylmethyl)-6,7,8,8a-tetrahydro-5aH-cyclopenta[4,5]furo[3,2-b]pyridin-5a-yl)benzonitrile (Cpd. No. 41Fc) as a white solid. Yield: 10 mg, 4%; MS (ESI) m/z 488.2[M+1]$^+$; $^1$H NMR (400 MHz, DMSO-d$_6$) δ 8.32 (d, J=2.1 Hz, 1H), 7.81 (d, J=2.0 Hz, 1H), 7.68-7.61 (m, 2H), 7.46 (d, J=8.0 Hz, 2H), 7.06 (dd, J=4.8, 1.9 Hz, 3H), 6.77 (dd, J=6.7, 2.9 Hz, 2H), 6.13 (s, 1H), 5.52 (s, 1H), 4.52 (d, J=5.9 Hz, 1H), 3.02 (d, J=13.3 Hz, 1H), 2.69-2.57 (m, 1H), 2.47-2.18 (m, 711), 1.58 (d, J=6.2 Hz, 4H).

Example 42

Rac-(1R,2R,3S,3aR,8bS)-8b-azido-1-hydroxy-6-methoxy-3a-(4-methoxyphenyl)-N,N-dimethyl-3-phenyl-2,3-dihydro-1H-cyclopenta[b]benzofuran-2-carboxamide (Cpd. No. 42F)

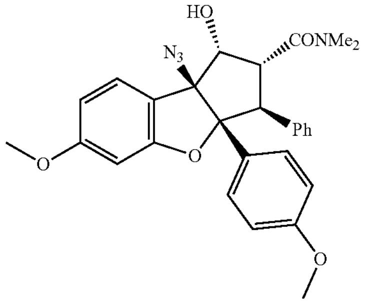

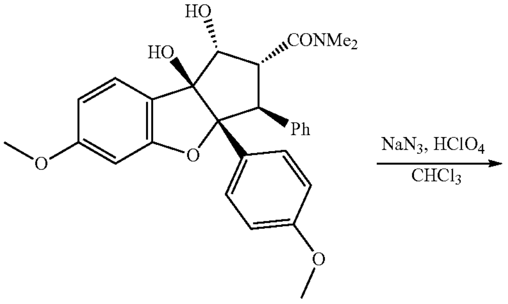

1

-continued

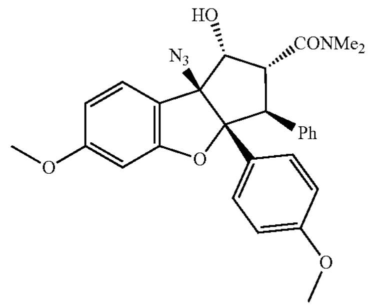

42F

Synthesis of rac-(R,2R,3S,3aR,8bS)-8b-azido-1-hydroxy-6-methoxy-3a-(4-methoxyphenyl)-N,N-dimethyl-3-phenyl-2,3-dihydro-1H-cyclopenta[b]benzofuran-2-carboxamide (Cpd. No. 42F)

To a solution of rac-(1R,2R,3S,3aR,8bS)-1,8b-dihydroxy-6-methoxy-3a-(4-methoxyphenyl)-N,N-dimethyl-3-phenyl-2,3-dihydro-1H-cyclopenta[b]benzofuran-2-carboxamide (150 mg, 0.32 mmol) in chloroform (1.5 mL) was added sodium azide (61 mg, 0.95 mmol), followed by perchloric acid (0.08 mL, 0.95 mmol). The orange solution was stirred at 25° C. for 90 m. The reaction mixture was then poured carefully into a solution of saturated sodium bicarbonate (10 mL). The heterogeneous solution was extracted with dichloromethane (3×5 mL). The organic material was washed with brine and dried over magnesium sulfate, filtered, and solvent removed under reduced pressure. Purification by silica gel chromatography eluting with hexanes and ethyl acetate afforded rac-(1R,2R,3S,3aR,8bS)-8b-azido-1-hydroxy-6-methoxy-3a-(4-methoxyphenyl)-N,N-dimethyl-3-phenyl-2,3-dihydro-1H-cyclopenta[b]benzofuran-2-carboxamide (Cpd. No. 42F) as a white solid. Yield 89%. MS (ESI) m/z 501.2[M+1]$^+$; NMR (400 MHz, $CD_3OD$) S 7.54 (d, J=4.8 Hz, 1H), 7.12-7.04 (m, 5H), 6.77-6.73 (m, 4H), 6.69-6.65 (m, 2H), 4.82 (d, J=5.1 Hz, 1H), 4.28 (d, J=8.1 Hz, 1H), 4.04 (dd, J=7.8, 4.8 Hz, 1H), 3.87 (s, 3H), 3.77 (s, 3H). 3.24-2.64 (bs, 6H)

Example 43

Rac-methyl (5aR,6S,7R,8R,8aS)-5a-(4-bromophenyl)-3-chloro-8a-fluoro-8-hydroxy-6-phenyl-5a,7,8,8a-tetrahydro-6H-cyclopenta[4,5]furo[3,2-b]pyridine-7-carboxylate (Cpd. No. 43F)

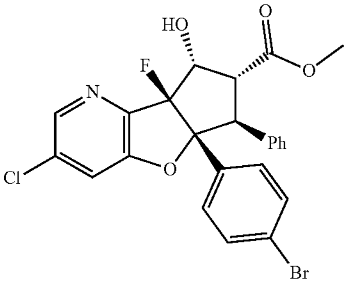

-continued

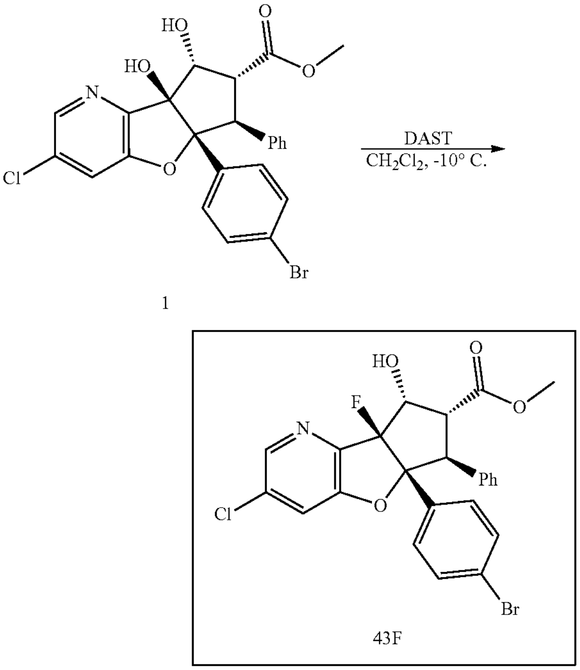

1

43F

Synthesis of rac-methyl (5aR,6S,7R,8R,8aS)-5a-(4-bromophenyl)-3-chloro-8a-fluoro-8-hydroxy-6-phenyl-5a,7,8,8a-tetrahydro-6H-cyclopenta[4,5]furo[3,2-b]pyridine-7-carboxylate (Cpd. No. 43F)

Dissolved rac-methyl (5aR,6S,7R,8R,8aS)-5a-(4-bromophenyl)-3-chloro-8,8a-dihydroxy-6-phenyl-5a,7,8,8a-tetrahydro-6H-cyclopenta[4,5]furo[3,2-b]pyridine-7-carboxylate (50 mg, 0.10 mmol) in dichloromethane (1 mL). The solution was cooled to −10° C. and (diethylamino)sulfur trifluoride (47 mg, 0.29 mmol) was added. The mixture was stirred at −10° C. for 3 h and then quenched with a few drops of methanol. Saturated aqueous ammonium chloride (5 mL) and dichloromethane (5 mL) were added. The layers were separated and the aqueous material was extracted with dichloromethane (3×5 mL). The combined organic material was washed with brine, dried over magnesium sulfate, filtered and solvent removed under reduced pressure. Purification by silica gel chromatography afforded rac-methyl (5aR,6S,7R,8R,8aS)-5a-(4-bromophenyl)-3-chloro-8a-fluoro-8-hydroxy-6-phenyl-5a,7,8,8a-tetrahydro-6H-cyclopenta[4,5]furo[3,2-b]pyridine-7-carboxylate (Cpd. No. 43F) as a white solid. Yield 24%. MS (ESI) m/z 501.9[M+1]$^+$; $^1$H NMR (400 MHz, Chloroform-d) δ 8.33 (d, J=1.8 Hz, 1H), 7.51 (dd, J=1.4, 1.4 Hz, 1H), 7.36-7.23 (m, 3H), 7.20-7.06 (m, 3H), 6.99 (dt, J=8.6, 1.6 Hz, 2H), 6.85-6.78 (m, 2H), 5.40 (ddd, J=16.9, 7.1, 1.1 Hz, 1H), 4.19 (dd, J=14.0, 1.9 Hz, 1H), 3.94 (dtd, J=14.0, 7.2, 1.2 Hz, 1H), 3.64 (d, J=1.2 Hz, 3H).

Example 44

Rac-(1R,2R,3S,3aR,8bS)-8b-amino-1-hydroxy-6-methoxy-3a-(4-methoxyphenyl)-N,N-dimethyl-3-phenyl-2,3,3a,8b-tetrahydro-1H-cyclopenta[b]benzofuran-2-carboxamide (Cpd. No. 44F)

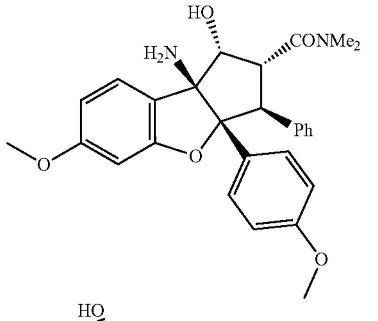

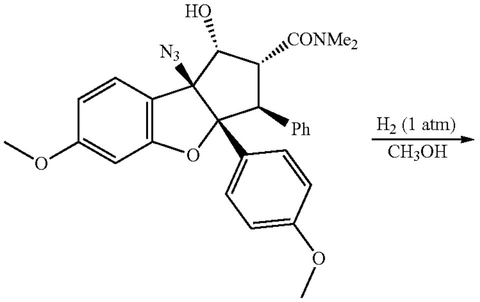

1

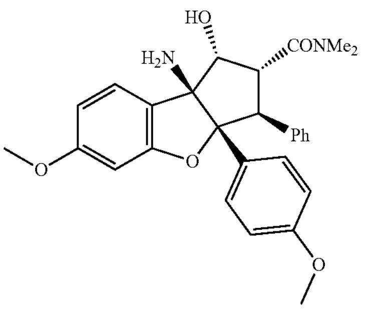

44F

Synthesis of Rac-(1R,2R,3S,3aR,8bS)-8b-amino-1-hydroxy-6-methoxy-3a-(4-methoxyphenyl)-N,N-dimethyl-3-phenyl-2,3,3a,8b-tetrahydro-1H-cyclopenta[b]benzofuran-2-carboxamide (Cpd. No. 44F)

To a solution of rac-(1R,2R,3S,3aR,8bS)-8b-azido-1-hydroxy-6-methoxy-3a-(4-methoxyphenyl)-N,N-dimethyl-3-phenyl-2,3,3a,8b-tetrahydro-1H-cyclopenta[b]benzofuran-2-carboxamide (55 mg, 0.11 mmol) in methanol (1 mL) was added palladium on carbon (2 mg, 0.11 mmol). The solution was sparged with hydrogen gas for 1 min then stirred at room temperature under an atmosphere of hydrogen. After 6 h the reaction mixture was filtered through celite, the filter cake was washed several times with methanol. The solvent was removed under reduced pressure and purification via reverse phase HPLC yielded rac-(1R,2R,3S,3aR,8bS)-8b-amino-1-hydroxy-6-methoxy-3a-(4-methoxyphenyl)-N,N-dimethyl-3-phenyl-2,3,3a,8b-tetrahydro-1H-cyclopenta[b]benzofuran-2-carboxamide (Cpd. No. 44F) as an off-white solid. Yield 48%. MS (ESI) m/z 342.9[M+1]$^+$; NMR (400 MHz, $CD_3OD$) δ 7.65 (d, J=5.1 Hz, 1H), 7.07-7.01 (m, 5H) 6.86 (d, J=7.1 Hz, 1H), 6.81 (d, J=1.2 Hz, 1H), 6.67 (dd, J=5.1, 1.2 Hz, 1H), 5.15 (d, J=5.7 Hz, 1H), 4.64 (d, J=7.5 Hz), 4.36 (dd, J=7.5, 5.7 Hz, 1H), 3.86 (s, 3H), 3.74 (s, 3H), 3.28 (s, 3H), 2.91 (s, 3H)

Example 45

Rac-(1R,2R,3S,3aR,8bS)-8b-acetamido-1-hydroxy-6-methoxy-3a-(4-methoxyphenyl)-N,N-dimethyl-3-phenyl-2,3,3a,8b-tetrahydro-1H-cyclopenta[b]benzofuran-2-carboxamide (Cpd. No. 45F)

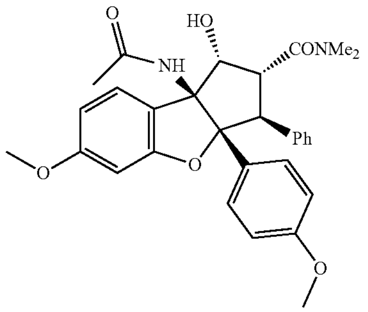

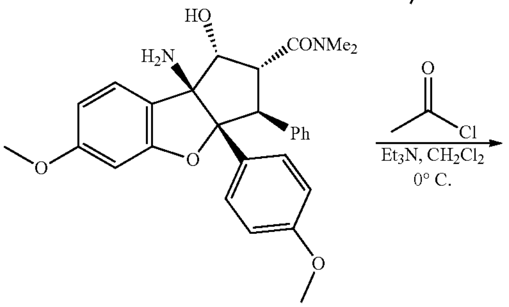

1

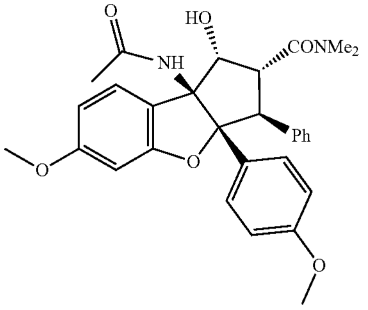

45F

Synthesis of rac-(R,2R,3S,3aR,8bS)-8b-acetamido-1-hydroxy-6-methoxy-3a-(4-methoxyphenyl)-N,N-dimethyl-3-phenyl-2,3,3a,8b-tetrahydro-1H-cyclopenta[b]benzofuran-2-carboxamide (Cpd. No. 45F)

A solution of rac-(1R,2R,3S,3aR,8bS)-8b-amino-1-hydroxy-6-methoxy-3a-(4-methoxyphenyl)-N,N-dimethyl-3-phenyl-2,3,3a,8b-tetrahydro-1H-cyclopenta[b]benzofuran-2-carboxamide (10 mg, 0.02 mmol) in dichloromethane (0.4 ml) and triethylamine (0.01 ml, 0.07 mmol) was added acetyl chloride (0.01 ml, 0.07 mmol) dropwise via micropipette. After 1 h the mixture was diluted with dichloromethane and poured onto saturated aqueous sodium bicarbonate (5 mL), and the aqueous material was extracted with dichloromethane (3×5 mL). The combine organic material was washed with brine (30 ml), dried over magnesium sulfate, filtered and solvent removed under reduced pressure. The product was purified via reverse phase HPLC to afford rac-(1R,2R,3S,3aR,8bS)-8b-acetamido-1-hydroxy-6-methoxy-3a-(4-methoxyphenyl)-N,N-dimethyl-3-phenyl-2,3,3a,8b-tetrahydro-1H-cyclopenta[b]benzofuran-2-carboxamide (Cpd. No. 45F). Yield: 62%. MS (ESI) m/z 517.3 $[M+1]^+$; $^1H$ NMR (400 MHz, Chloroform-d) δ 7.59 (d, J=8.5 Hz, 1H), 7.12-6.99 (m, 6H), 6.83 (dd, J=6.5, 3.1 Hz, 2H), 6.79-6.73 (m, 2H), 6.64 (d, J=2.3 Hz, 1H), 6.52 (dd, J=8.5, 2.4 Hz, 1H) 5.72 (s, 1H), 5.32 (d, J=9.7 Hz, 1H), 4.60 (d, J=13.1 Hz, 1H), 4.02 (dd, J=13.2, 9.6 Hz, 1H), 3.84 (2, 3H), 3.75 (s, 3H), 3.38-3.18 (bs, 3H), 2.89-2.96 (bs, 3H), 2.11-1.92 (m, 1H).

Example 46

Rac-dimethyl 2-[[(5aR,6S,7R,8aR)-5a-(4-bromophenyl)-3-chloro-8a-hydroxy-8-oxo-6-phenyl-6,7-dihydrocyclopenta[4,5]furo[1,2-b]pyridin-7-yl]methyl] propanedioate (Cpd. No. 46F)

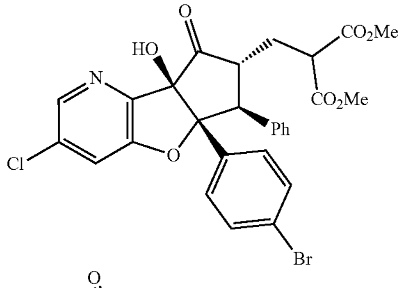

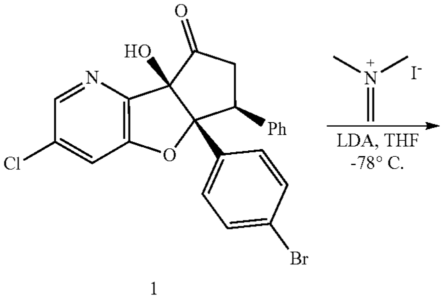

1

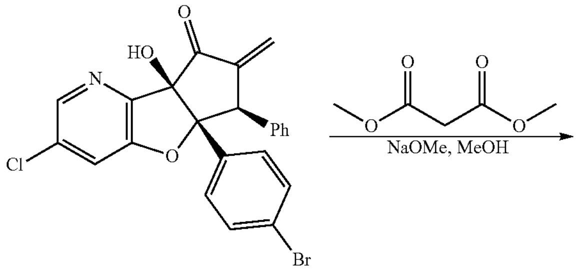

2

-continued

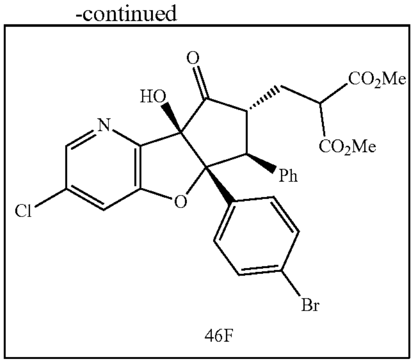

46F

Synthesis of rac-4-((5aR,6R,8aR)-3-chloro-8a-hydroxy-7-methylene-8-oxo-6-phenyl-6,7,8,8a-tetrahydro-5aH-cyclopenta[4,5]furo[3,2-b]pyridin-5a-yl) benzonitrile (2)

Rac-(5aR,6S,8aR)-5a-(4-bromophenyl)-3-chloro-8a-hydroxy-6-phenyl-6,7-dihydrocyclopenta[4,5]furo[1,2-b]pyridin-8-one (95 mg, 0.21 mmol) was stirred in anhydrous tetrahydrofuran (3 mL) at −78° C. and (diisopropylamino) lithium (0.44 mL, 0.85 mmol) was added dropwise. After 15 minutes solid dimethyl(methylene)ammonium iodide (192 mg, 1.04 mmol) was added in 1 portion. The mixture was allowed to gradually warm to room temperature. After 3 h at this temperature the reaction mixture was diluted reaction with ethyl acetate (20 mL) and poured onto saturated aqueous sodium bicarbonate (30 mL). The layers were separated and aqueous material extracted with ethyl acetate (3×15 mL). The combine organic material was washed with brine, dried over magnesium sulfate, filtered, and solvent removed under reduced pressure. Purification via silica gel chromatography eluting with hexanes and ethyl acetate afforded rac-(5aR,6R,8aR)-5a-(4-bromophenyl)-3-chloro-8a-hydroxy-7-methylene-6-phenyl-6H-cyclopenta[4,5]furo[1,2-b]pyridin-8-one (2) as a brown residue. Yield 56%. MS (ESI) m/z 415.1 $[M+1]^+$.

Synthesis of rac-dimethyl 2-[[(5aR,6S,7R,8aR)-5a-(4-bromophenyl)-3-chloro-8a-hydroxy-8-oxo-6-phenyl-6,7-dihydrocyclopenta[4,5]furo[1,2-b]pyridin-7-yl]methyl]propanedioate (Cpd. No. 46F)

Rac-(5aR,6R,8aR)-5a-(4-bromophenyl)-3-chloro-8a-hydroxy-7-methylene-6-phenyl-6H-cyclopenta[4,5]furo[1,2-b]pyridin-8-one (11 mg, 0.02 mmol) and dimethyl malonate (0.01 mL, 0.11 mmol) were dissolved in dry methanol (0.5 mL). Sodium methoxide (0.01 mL, 0.07 mmol) was added dropwise via syringe and the solution was stirred at room temperature. After 2 h the reaction was neutralized by the addition of 2 drops of 6 M hydrochloric acid. The mixture was diluted with water (5 mL), and was extracted with ethyl acetate (3×5 mL). The combined organic material was dried over magnesium sulfate, filtered and solvent removed under reduced pressure. Purification via reverse phase HPLC afforded rac-dimethyl 2-[[(5aR,6S,7R,8aR)-5a-(4-bromophenyl)-3-chloro-8a-hydroxy-8-oxo-6-phenyl-6,7-dihydrocyclopenta[4,5]furo[1,2-b]pyridin-7-yl]methyl]propanedioate (Cpd. No. 46F) as an off-white solid. Yield: 71%. MS (ESI) m/z 602.3$[M+1]^+$; 1H NMR (400 MHz, Chloroform-d) δ 8.26 (s, 1H), 7.57 (s, 1H), 7.39-7.22 (m, 6H), 7.22-7.09

(m, 4H), 6.98-6.90 (m, 2H), 6.86-6.79 (m, 2H) 3.80 (dd, J=9.1, 6.1 Hz, 2H), 3.74-3.54 (m, 8H), 3.42-3.27 (m, 3H), 2.10-1.96 (m, 2H).

Example 47

Rac-(5aR,6S,8S,8aR)-5a-(4-bromophenyl)-3-chloro-8a-hydroxy-6-phenyl-5a,7,8,8a-tetrahydro-6H-cyclopenta[4,5]furo[3,2-b]pyridine-8-carbonitrile (Cpd. No. 47F)

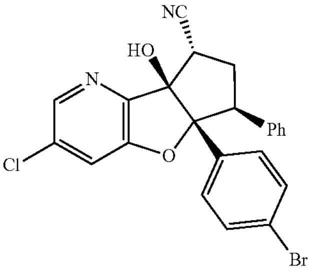

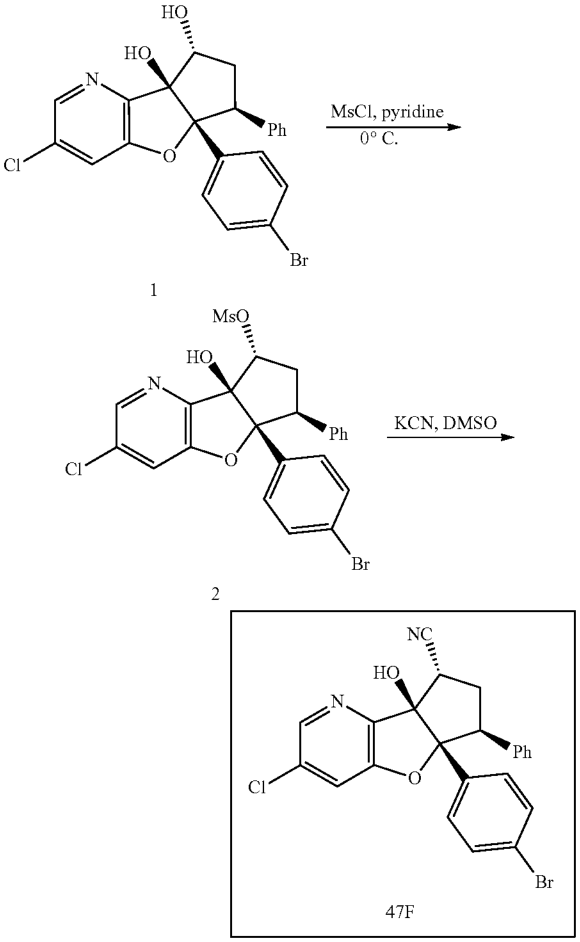

1

2

47F

Synthesis of rac-(5aR,6S,8R,8aS)-5a-(4-bromophenyl)-3-chloro-8a-hydroxy-6-phenyl-5a, 7,8,8a-tetrahydro-6H-cyclopenta[4,5]furo[3,2-b]pyridin-8-yl methanesulfonate (2)

To a solution of rac-(5aR,6S,8R,8aS)-5a-(4-bromophenyl)-3-chloro-6-phenyl-5a,6,7,8-tetrahydro-8aH-cyclopenta[4,5]furo[3,2-b]pyridine-8,8a-diol (1, 558 mg, 10.9 mmol) in pyridine (9 mL) at 0° C. was added methanesulfonyl chloride (0.10 ml, 1.31 mmol). The reaction was allowed to reach room temperature and stirred 16 h. An additional 0.05 ml of methanesulfonyl chloride was added and the reaction stirred an additional 24 h, at which point the reaction mixture was poured onto water and ethyl acetate. The aqueous material was extracted with ethyl acetate (3×15 ml), and the combined organic were washed with 3 M aqueous copper sulfate (30 ml), brine (30 ml), dried over magnesium sulfate, filtered and solvent removed under reduced pressure. The crude residue was purified by silica gel chromatography eluting with hexanes and ethyl acetate to afford rac-(5aR,6S,8R,8aS)-5a-(4-bromophenyl)-3-chloro-8a-hydroxy-6-phenyl-5a,7,8,8a-tetrahydro-6H-cyclopenta[4,5]furo[3,2-b]pyridin-8-yl methanesulfonate (2) as an off-white residue. Yield 39%. MS (ESI) m/z 538.1[M+1]$^+$.

Synthesis of rac-(5aR,6S,8S,8aR)-5a-(4-bromophenyl)-3-chloro-8a-hydroxy-6-phenyl-5a, 7,8,8a-tetrahydro-6H-cyclopenta[4,5]furo[3,2-b]pyridine-8-carbonitrile (Cpd. No. 47F)

To a solution of rac-(5aR,6S,8R,8aS)-5a-(4-bromophenyl)-3-chloro-8a-hydroxy-6-phenyl-5a,7,8,8a-tetrahydro-6H-cyclopenta[4,5]furo[3,2-b]pyridin-8-yl methanesulfonate (2, 242 mg, 0.45 mmol) in dimethyl sulfoxide (2 mL) was added potassium cyanide (294 mg, 4.51 mmol) at room temperature. After 2.5 h the mixture was diluted with acetonitrile, filtered through celite, placed in a test tube and purified by reverse phase HPLC to afford rac-(5aR,6S,8S,8aR)-5a-(4-bromophenyl)-3-chloro-8a-hydroxy-6-phenyl-5a,7,8,8a-tetrahydro-6H-cyclopenta[4,5]furo[3,2-b]pyridine-8-carbonitrile (Cpd. No. 47F). Yield: 85%; MS (ESI) m/z 468.1 [M+1]$^+$; $^1$H NMR (400 MHz, $CDCl_3$) δ 7.68 (dd, J=1.9, 0.5 Hz, 1H), 7.35 (dd, J=1.9, 0.6 Hz, 1H), 7.37-7.20 (m, 1H), 7.22-7.04 (m, 1H), 7.15 (s, 1H), 7.08-6.94 (m, 3H), 4.81 (s, 1H), 4.18-4.06 (m, 1H), 3.88 (dd, J=7.5, 3.7 Hz, 1H), 2.95 (ddd, J=13.1, 11.8, 7.6 Hz, 1H), 2.67-2.53 (m, 2H), 2.06-1.97 (m, 1H), 1.25 (td, J=7.1, 0.6 Hz, 1H).

Example 48

Rac-(5aR,6S,8aR)-5a-(4-bromophenyl)-3-chloro-8-ethynyl-6-phenyl-5a,6,7,8-tetrahydro-8aH-cyclopenta[4,5]furo[3,2-b]pyridin-8a-ol (Cpd. No. 48F)

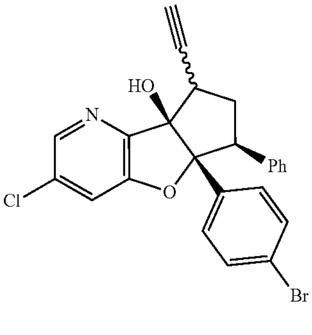

-continued

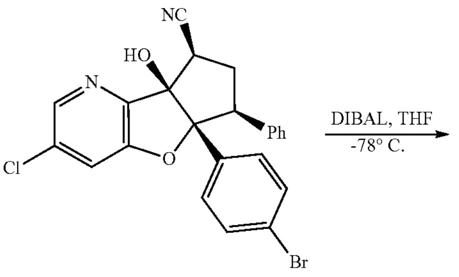

1

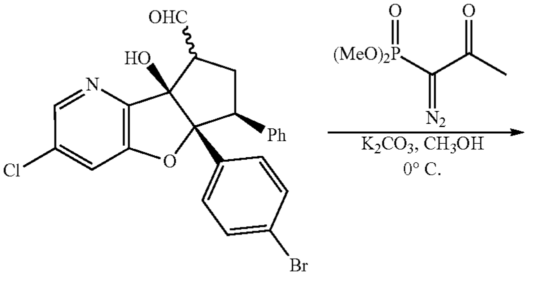

2

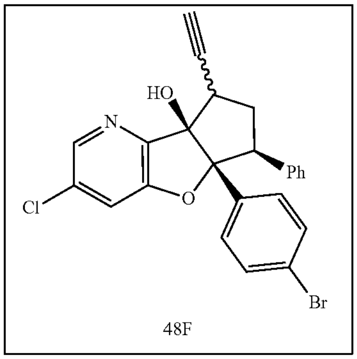

48F

Synthesis of rac-(5aR,6S,8aR)-5a-(4-bromophenyl)-3-chloro-8a-hydroxy-6-phenyl-5a,7,8,8a-tetrahydro-6H-cyclopenta[4,5]furo[3,2-b]pyridine-8-carbaldehyde (2)

To a solution of rac-(5aR,6S,8R,8aR)-5a-(4-bromophenyl)-3-chloro-8a-hydroxy-6-phenyl-5a,7,8,8a-tetrahydro-6H-cyclopenta[4,5]furo[3,2-b]pyridine-8-carbonitrile (75 mg, 0.16 mmol) in dichloromethane (1 ml) at −78° C. was added a solution of diisobutylaluminum hydride (0.32 mL, 0.32 mmol) dropwise. After 30 m the reaction was warmed to room temperature, stirred for 30 m, then cooled to 0° C. and quenched by the dropwise addition of 3 M hydrochloric acid. The reaction was diluted with ethyl acetate (10 mL) and saturated aqueous Rochelle's salt (10 mL). The layers were separated and the aqueous material was extracted with ethyl acetate (2×10 mL). The combined organic material was washed with saturated aqueous Rochelle's salt (10 mL), brine (20 mL), dried over magnesium sulfate, filtered, and solvent was removed under reduced pressure. Purification by silica gel chromatography eluting with hexanes and ethyl acetate afforded an inseparable mixture of epimeric aldehydes that was carried on to the following step without further purification. MS (ESI) m/z 470.0[M+1]$^+$.

Synthesis of rac-(5aR,6S,8aR)-5a-(4-bromophenyl)-3-chloro-8-ethynyl-6-phenyl-5a,6,7,8-tetrahydro-8aH-cyclopenta[4,5]furo[3,2-b]pyridin-8a-ol (Cpd. No. 48)

A solution containing a mixture of epimeric aldehydes at c-8 rac-(5aR,6S,8aR)-5a-(4-bromophenyl)-3-chloro-8a-hydroxy-6-phenyl-5a,7,8,8a-tetrahydro-6H-cyclopenta[4,5]furo[3,2-b]pyridine-8-carbaldehyde (50 mg) and methanol (1 ml) was cooled to 0° C. and 1-diazo-1dimethoxyphosphoryl-propane-2-one (Homer-Wadsworth-Emmons reagent, 0.76 ml, 0.53 mmol) was added followed by potassium carbonate (208 mg, 0.64 mmol). The mixture was stirred for 3 h and solvent was removed under reduced pressure. The residue was taken up in dichloromethane (5 ml) and saturated aqueous sodium bicarbonate (5 ml). The layers were separated and the aqueous layer was extracted with dichloromethane (2×5 ml). The combined organic material was washed with brine, dried over magnesium sulfate, filtered, and solvent removed under reduced pressure. The residue was purified via reverse phase HPLC to afford a 3:1 mixture of alkynes rac-(5aR,6S,8aR)-5a-(4-bromophenyl)-3-chloro-8-ethynyl-6-phenyl-5a,6,7,8-tetrahydro-8aH-cyclopenta[4,5]furo[3,2-b]pyridin-8a-ol (Cpd. No. 48). MS (ESI) m/z 468.2[M+1]$^+$; NMR (400 MHz, $CDCl_3$) Major diastereomer: δ 8.24 (d, J=1.9 Hz, 1H), 7.47 (dd, J=1.9, 0.5 Hz, 1H). 7.33-7.19 (m), 7.19-7.06 (m), 7.06-6.98 (m), 6.98-6.90 (m), 3.70-3.56 (m, 2H), 2.77-2.59 (m, 3H). Minor diastereomer: δ 8.20 (d, J=1.9 Hz, 1H), 7.57 (dd, J=1.9, 0.5 Hz, 1H), 7.33-7.19 (m), 7.19-7.06 (m), 7.06-6.98 (m), 6.98-6.90 m) 4.28 (dd, J=11.7, 6.2 Hz, 1H), 3.82 (dt, J=6.6, 3.3 Hz, 1H), 2.49 (ddd, J=12.8, 6.3, 3.6 Hz, 1H), 2.12 (d, J=3.3 Hz, 1H).

Example 49

Rac-methyl (5aR,6S,7R,8R,8aR)-5a-(4-bromophenyl)-3-chloro-8-cyano-8a-hydroxy-6-phenyl-5a,7,8,8a-tetrahydro-6H-cyclopenta[4,5]furo[3,2-b]pyridine-7-carboxylate (Cpd. No. 49F)

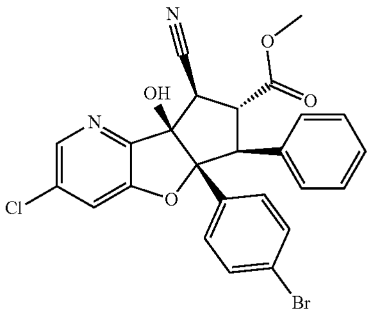

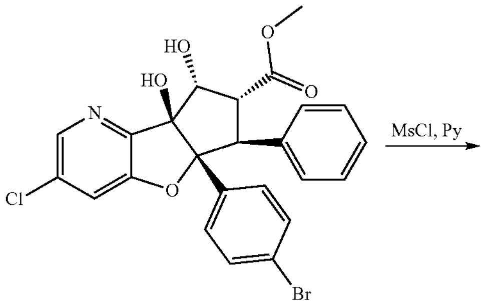

1

-continued

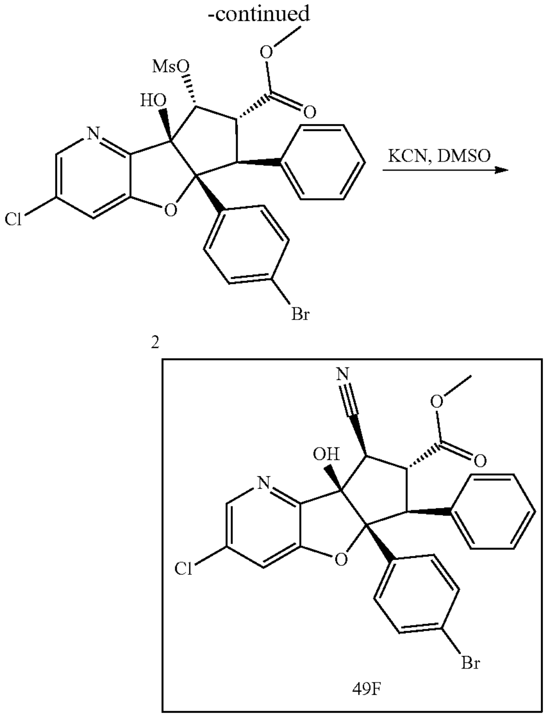

2

49F

Synthesis of rac-methyl (5aR,6S,7R,8R,8aS)-5a-(4-bromophenyl)-3-chloro-8a-hydroxy-8-((methylsulfonyl)oxy)-6-phenyl-5a,7,8,8a-tetrahydro-6H-cyclopenta[4,5]furo[3,2-b]pyridine-7-carboxylate (2)

To a solution of rac-methyl (5aR,6S,7R,8R,8aS)-5a-(4-bromophenyl)-3-chloro-8,8a-dihydroxy-6-phenyl-5a,7,8,8a-tetrahydro-6H-cyclopenta[4,5]furo[3,2-b]pyridine-7-carboxylate (1, 200 mg, 0.39 mmol) in pyridine (4 mL) was added methanesulfonyl chloride (0.04 mL, 0.46 mmol) dropwise. The reaction was stirred at room temperature overnight. More methanesulfonyl chloride (0.04 mL, 0.46 mmol) was added dropwise. The reaction was stirred at room temperature over the weekend. The resulting mixture was concentrated, re-diluted with dichloromethane and washed with water. The combined organics were dried over magnesium sulfate, filtered and concentrated. The crude was purified via flash chromatography (silica, ethyl acetate/hexane=0-40%) to afford rac-methyl (5aR,6S,7R,8R,8aS)-5a-(4-bromophenyl)-3-chloro-8a-hydroxy-8-((methylsulfonyl)oxy)-6-phenyl-5a,7,8,8a-tetrahydro-6H-cyclopenta[4,5]furo[3,2-b]pyridine-7-carboxylate (2) as a white solid. Yield: 201 mg, 87%; MS (ESI) m/z 596.1[M+1]$^+$; $^1$H NMR (300 MHz, DMSO-$d_6$) δ 8.35 (d, J=2.0 Hz, 1H), 7.87 (d, J=2.0 Hz, 1H), 7.36-7.22 (m, 2H), 7.20-7.04 (m, 5H), 7.03-6.91 (m, 2H), 6.76 (s, 1H), 5.76 (s, 1H), 5.69 (d, J=5.9 Hz, 1H), 4.47 (dd, J=14.3, 6.0 Hz, 1H), 4.26 (d, J=14.3 Hz, 1H), 3.57 (s, 3H), 3.15 (s, 3H).

Synthesis of rac-methyl (5aR,6S,7R,8R,8aR)-5a-(4-bromophenyl)-3-chloro-8-cyano-8a-hydroxy-6-phenyl-5a,7,8,8a-tetrahydro-6H-cyclopenta[4,5]furo[3,2-b]pyridine-7-carboxylate (Cpd. No. 49F)

Rac-methyl (5aR,6S,7R,8R,8aS)-5a-(4-bromophenyl)-3-chloro-8a-hydroxy-8-((methylsulfonyl)oxy)-6-phenyl-5a,7,8,8a-tetrahydro-6H-cyclopenta[4,5]furo[3,2-b]pyridine-7-carboxylate (2, 81 mg, 0.14 mmol) and potassium cyanide (18 mg, 0.27 mmol) were dissolved in dimethylsulfoxide (0.50 mL). The reaction was stirred at room temperature for 4 h. The mixture was purified on reverse phase HPLC (acetonitrile/water=15-75%) to afford rac-methyl (5aR,6S,7R,8R,8aR)-5a-(4-bromophenyl)-3-chloro-8-cyano-8a-hydroxy-6-phenyl-5a,7,8,8a-tetrahydro-6H-cyclopenta[4,5]furo[3,2-b]pyridine-7-carboxylate (Cpd. No. 49F) as a pink solid. Yield: 45 mg, 63%; MS (ESI) m/z 527.0[M+1]$^+$; $^1$H NMR (300 MHz, DMSO-$d_6$) δ 8.37 (d, J=2.0 Hz, 1H), 7.88 (d, J=2.0 Hz, 1H), 7.38 (d, J=8.7 Hz, 2H), 7.19-7.03 (m, 4H), 6.93 (d, J=9.6 Hz, 2H), 6.81 (s, 1H), 4.29-4.08 (m, 2H), 3.76 (d, J=12 Hz, 1H), 3.54 (s, 3H).

Example 50

Rac-methyl (5aR,6S,7R,8R,8aR)-3-chloro-8-cyano-5a-(4-cyanophenyl)-8a-hydroxy-6-phenyl-5a,7,8,8a-tetrahydro-6H-cyclopenta[4,5]furo[3,2-b]pyridine-7-carboxylate (Cpd. No. 50F)

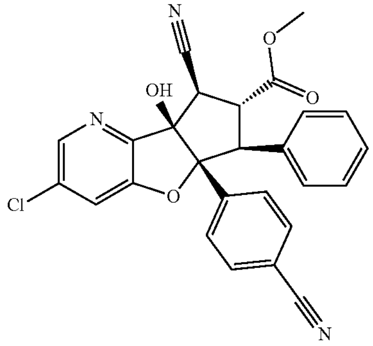

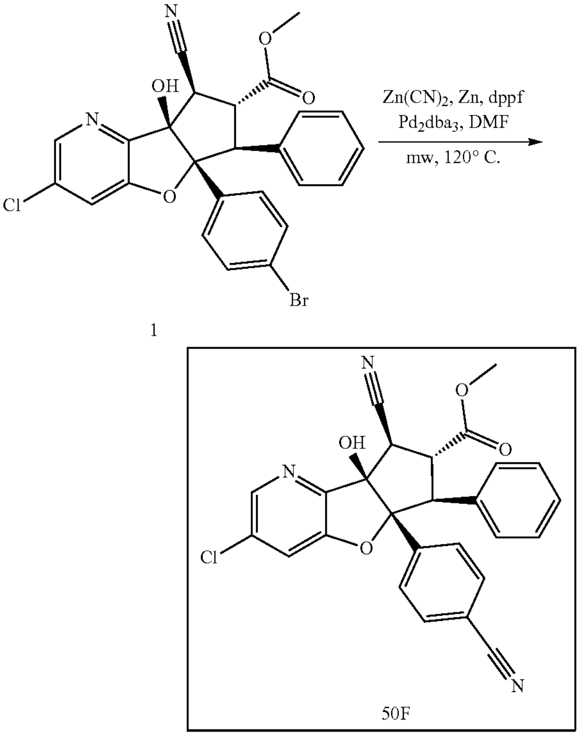

1

50F

Synthesis of rac-methyl (5aR,6S,7R,8R,8aR)-3-chloro-8-cyano-5a-(4-cyanophenyl)-8a-hydroxy-6-phenyl-5a,7,8,8a-tetrahydro-6H-cyclopenta[4,5]furo[3,2-b]pyridine-7-carboxylate (Cpd. No. 50F)

A suspension of rac-methyl (5aR,6S,7R,8R,8aR)-5a-(4-bromophenyl)-3-chloro-8-cyano-8a-hydroxy-6-phenyl-5a,7,8,8a-tetrahydro-6H-cyclopenta[4,5]furo[3,2-b]pyridine-7-carboxylate (1, 450 mg, 0.86 mmol), zinc (30 mg, 0.47 mmol) and zinc cyanide (322 mg, 2.74 mmol) in N,N-dimethylformamide (10 mL) and water (1 mL) was purged with argon for 5 min. Dppf (45 mg, 0.08 mmol) and tris(dibenzylideneacetone)dipalladium(0) (47 mg, 0.05 mmol) were added. The reaction was microwaved at 120° C. for 1 h. The mixture was diluted with dichloromethane and washed with water. The combined organics were dried over magnesium sulfate, filtered and concentrated. The crude was purified via flash chromatography (silica, ethyl acetate/hexanes=0-35%) to afford rac-methyl (5aR,6S,7R,8R,8aR)-3-chloro-8-cyano-5a-(4-cyanophenyl)-8a-hydroxy-6-phenyl-5a,7,8,8a-tetrahydro-6H-cyclopenta[4,5]furo[3,2-b]pyridine-7-carboxylate (Cpd. No. 50F) as a white solid. Yield: 400 mg, 99%; MS (ESI) m/z 472.3[M+1]$^+$; $^1$H NMR (400 MHz, DMSO-$d_6$) δ 8.38 (d, J=2.0 Hz, 1H), 7.90 (d, J=2.0 Hz, 1H), 7.76-7.57 (m, 2H), 7.38 (d, J=8.1 Hz, 2H), 7.07 (dt, J=4.9, 1.8 Hz, 3H), 6.98-6.93 (m, 2H), 6.89 (s, 1H), 4.34-4.22 (m, 2H), 3.89-3.79 (m, 1H), 3.54 (s, 3H).

Example 51

Rac-(5aR,6S,7R,8R,8aR)-3-chloro-8-cyano-5a-(4-cyanophenyl)-8a-hydroxy-N,N-dimethyl-6-phenyl-5a,7,8,8a-tetrahydro-6H-cyclopenta[4,5]furo[3,2-b]pyridine-7-carboxamide (Cpd. No. 51F)

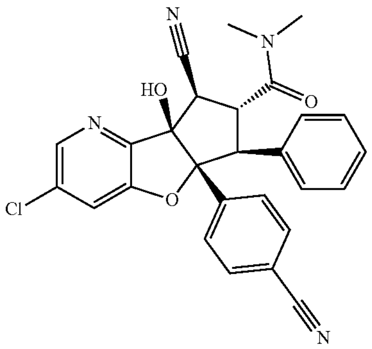

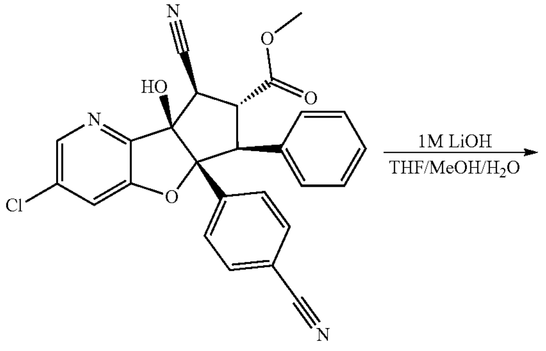

1

-continued

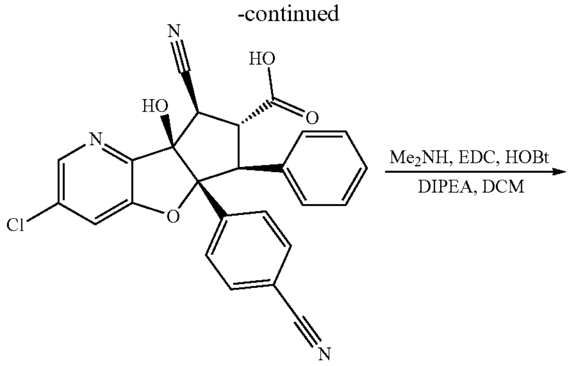

2

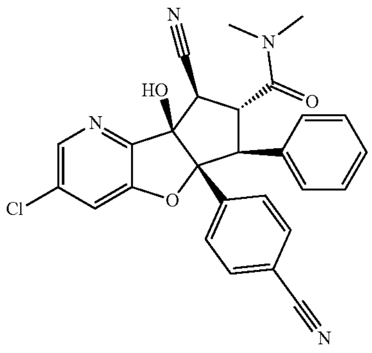

51F

Synthesis of rac-(5aR,6S,7R,8R,8aR)-3-chloro-8-cyano-5a-(4-cyanophenyl)-8a-hydroxy-6-phenyl-5a,7,8,8a-tetrahydro-6H-cyclopenta[4,5]furo[3,2-b]pyridine-7-carboxylic acid (2)

To a solution of rac-methyl (5aR,6S,7R,8R,8aR)-3-chloro-8-cyano-5a-(4-cyanophenyl)-8a-hydroxy-6-phenyl-5a,7,8,8a-tetrahydro-6H-cyclopenta[4,5]furo[3,2-b]pyridine-7-carboxylate (15 mg, 0.03 mmol) in tetrahydrofuran (1 mL) and methanol (1 mL) was added 2 M lithium hydroxide (1 mL, 2 mmol). The reaction was stirred at room temperature for 5 m. The reaction was acidified with 1 M hydrochloric acid and the organic volatiles were evaporated. The mixture was diluted with water and extracted with dichloromethane. The combined organics were dried over magnesium sulfate, filtered and concentrated. The crude was used for next step without further purification. Yield: 15 mg, crude; MS (ESI) m/z 458.2[M+1]$^+$.

Synthesis of rac-(5aR,6S,7R,8R,8aR)-3-chloro-8-cyano-5a-(4-cyanophenyl)-8a-hydroxy-N,N-dimethyl-6-phenyl-5a,7,8,8a-tetrahydro-6H-cyclopenta[4,5]furo[3,2-b]pyridine-7-carboxamide (Cpd. No. 51F)

To a solution of rac-(5aR,6S,7R,8R,8aR)-3-chloro-8-cyano-5a-(4-cyanophenyl)-8a-hydroxy-6-phenyl-5a,7,8,8a-tetrahydro-6H-cyclopenta[4,5]furo[3,2-b]pyridine-7-carboxylic acid (2, 30 mg, 0.07 mmol), N-(3-dimethylaminopropyl)-N'-ethylcarbodiimide hydrochloride (39 mg, 0.20 mmol), 1-hydroxybenzotriazole hydrate (31 mg, 0.20 mmol) in dichloromethane (4 mL) at 0° C. was added N,N-diisopropylethylamine (0.08 mL, 0.46 mmol) and N-methylmethanamine hydrochloride (11 mg, 0.13 mmol). The reaction was stirred at room temperature overnight. The mixture was diluted with dichloromethane and washed with aqueous saturated sodium bicarbonate solution. The combined organics were dried over magnesium sulfate, filtered and concentrated. The crude was purified via column chromatography (silica, ethyl acetate/hexane=0-60%), followed by reverse phase HPLC (acetonitrile/water=15-60%) to afford rac-(5aR,6S,7R,8R,8aR)-3-chloro-8-cyano-5a-(4-cyanophenyl)-8a-hydroxy-N,N-dimethyl-6-phenyl-5a,7,8,8a-tetrahydro-6H-cyclopenta[4,5]furo[3,2-b]pyridine-7-carboxamide (Cpd. No. 51F) as a white solid. Yield: 13.7 mg, 43%; MS (ESI) m/z 485.5[M+1]$^+$; $^1$H NMR (400 MHz, DMSO-d$_6$) δ 8.37 (d, J=2.0 Hz, 1H), 7.91 (d, J=2.0 Hz, 1H), 7.73-7.65 (m, 2H), 7.47 (d, J=8.1 Hz, 2H), 7.13-7.04 (m, 3H), 6.91 (s, 1H), 6.88-6.81 (m, 2H), 4.48 (dd, J=12.7, 10.4 Hz, 1H), 3.97-3.85 (m, 2H), 3.26 (s, 3H), 2.76 (s, 3H).

Example 52

Rac-(5aR,6S,7R,8R,8aR)-3-chloro-8-cyano-5a-(4-cyanophenyl)-8a-hydroxy-6-phenyl-5a,7,8,8a-tetrahydro-6H-cyclopenta[4,5]furo[3,2-b]pyridine-7-carboxamide (Cpd. No. 52F)

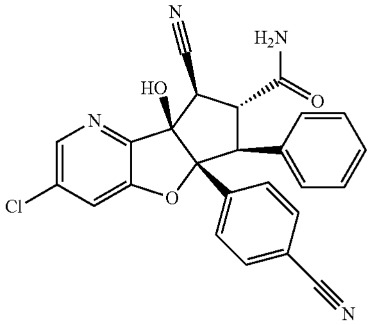

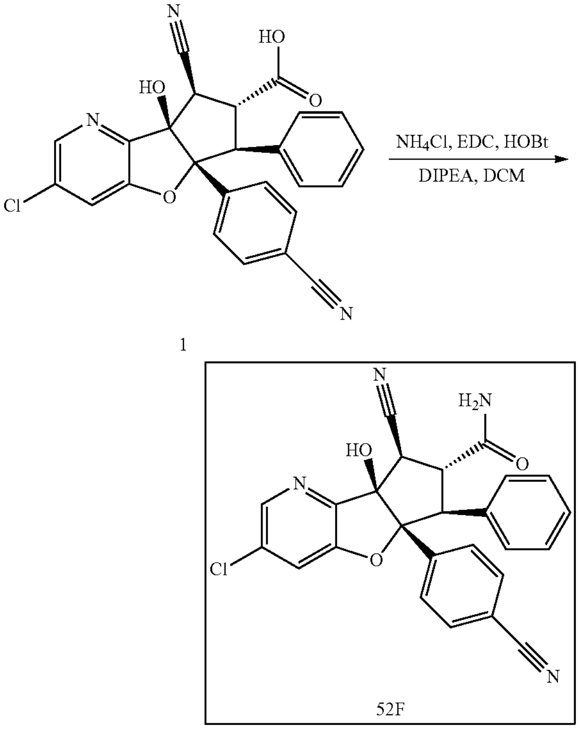

1

52F

Synthesis of rac-(5aR,6S,7R,8R,8aR)-3-chloro-8-cyano-5a-(4-cyanophenyl)-8a-hydroxy-6-phenyl-5a,7,8,8a-tetrahydro-6H-cyclopenta[4,5]furo[3,2-b]pyridine-7-carboxamide (Cpd. No. 52F)

To a solution of rac-(5aR,6S,7R,8R,8aR)-3-chloro-8-cyano-5a-(4-cyanophenyl)-8a-hydroxy-6-phenyl-5a,7,8,8a-tetrahydro-6H-cyclopenta[4,5]furo[3,2-b]pyridine-7-carboxylic acid (30 mg, 0.07 mmol), N-(3-dimethylaminopropyl)-N'-ethylcarbodiimide hydrochloride (38 mg, 0.20 mmol), 1-hydroxybenzotriazole hydrate (30 mg, 0.20 mmol) and ammonium chloride (9 mg, 0.16 mmol) in dichloromethane (4 mL) was added N,N-diisopropylethylamine (0.09 mL, 0.52 mmol). The reaction was stirred at room temperature overnight. The mixture was diluted with dichloromethane and washed with aqueous saturated sodium bicarbonate solution. The combined organics were dried over magnesium sulfate, filtered and concentrated. The crude was purified via column chromatography (silica, ethyl acetate/hexane=0-50%) to afford rac-(5aR,6S,7R,8R,8aR)-3-chloro-8-cyano-5a-(4-cyanophenyl)-8a-hydroxy-6-phenyl-5a,7,8,8a-tetrahydro-6H-cyclopenta[4,5]furo[3,2-b]pyridine-7-carboxamide (Cpd. No. 52F) as a white solid. Yield: 16 mg, 53%; MS (ESI) m/z 457.1[M+1]$^+$; H NMR (400 MHz, DMSO-d$_6$) δ 8.39 (d, J=2.0 Hz, 1H), 7.95-7.87 (m, 2H), 7.74 (d, J=8.2 Hz, 2H), 7.35 (d, J=8.6 Hz, 3H), 7.09 (dd, J=5.0, 1.9 Hz, 3H), 6.95 (dd, J=6.8, 2.9 Hz, 2H), 6.90 (d, J=0.6 Hz, 1H), 4.06 (dd, J=13.3, 10.8 Hz, 1H), 3.89 (d, J=10.7 Hz, 1H), 3.62 (d, J=13.3 Hz, 1H).

Example 53

Rac-(3aR,3bS,8aR,9R,9aR)-8a-(4-bromophenyl)-6-chloro-3b-hydroxy-9-phenyl-1,3a,3b,8a,9,9a-hexahydro-2H-oxazolo[4",5":4',5']cyclopenta[1',2':4,5]furo[3,2-b]pyridin-2-one (Cpd. No. 53F)

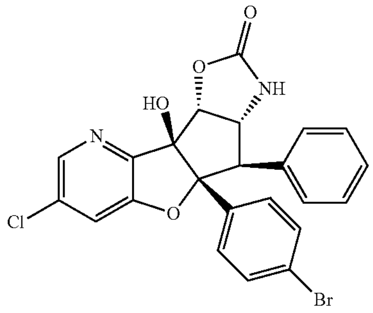

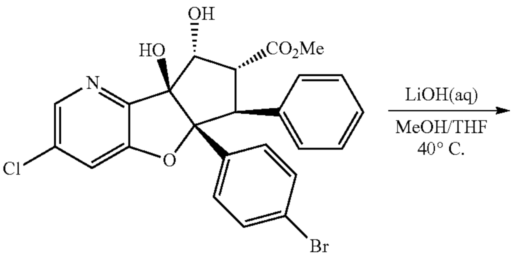

1

-continued

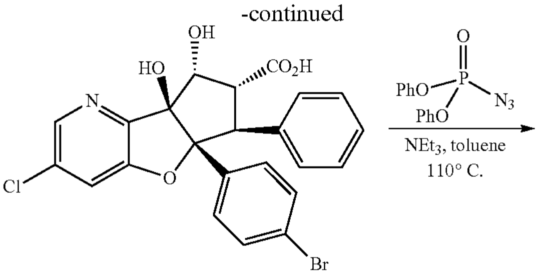

2

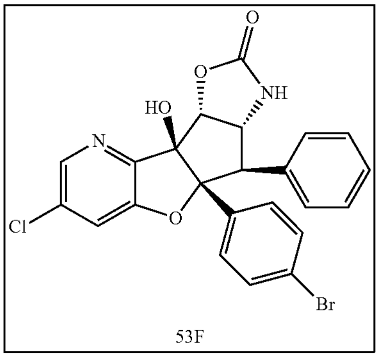

53F

Synthesis of rac-(5aR,6S,7R,8R,8aS)-5a-(4-bromophenyl)-3-chloro-8,8a-dihydroxy-6-phenyl-5a, 7,8, 8a-tetrahydro-6H-cyclopenta[4,5]furo[3,2-b]pyridine-7-carboxylic acid (2)

To rac-methyl (5aR,6S,7R,8R,8aS)-5a-(4-bromophenyl)-3-chloro-8,8a-dihydroxy-6-phenyl-5a,7,8,8a-tetrahydro-6H-cyclopenta[4,5]furo[3,2-b]pyridine-7-carboxylate (1, 111 mg, 0.22 mmol) in tetrahydrofuran (1 mL) and methanol (1 mL) at room temperature was added 2 M lithium hydroxide (1.6 mL, 3.2 mmol) and the mixture was stirred at 40° C. After 1 h the mixture was cooled down to room temperature and stirred for another 1.5 h. The mixture was acidified with 2 M hydrochloric acid (1.8 mL) and diluted with ethyl acetate and water. The aqueous phase was extracted with ethyl acetate thrice, and the combined organic phases were dried (sodium sulfate), filtered and concentrated. The crude material was pure by LCMS and used in the next step without further purification. Yield: 120 mg, crude; MS (ESI) m/z 502.0[M+1]$^+$.

Synthesis of rac-(3aR,3bS,8aR,9R,9aR)-8a-(4-bromophenyl)-6-chloro-3b-hydroxy-9-phenyl-1,3a,3b,8a, 9,9a-hexahydro-2H-oxazolo[4",5":4',5']cyclopenta [1',2':4,5]furo[3,2-b]pyridin-2-one (Cpd. No. 53F)

To crude rac-(5aR,6S,7R,8R,8aS)-5a-(4-bromophenyl)-3-chloro-8,8a-dihydroxy-6-phenyl-5a,7,8,8a-tetrahydro-6H-cyclopenta[4,5]furo[3,2-b]pyridine-7-carboxylic acid (2, 108 mg, 0.215 mmol) in toluene (2 mL) at room temperature were added molecular sieves (40 mg), diphenyl phosphoryl azide (60 μL, 0.28 mmol) and triethylamine (46 μL, 0.33 mmol) and the mixture was stirred at room temperature for 15 m, then at 110° C. for 2 h. Then the mixture was allowed to cool down to room temperature, diluted with dichloromethane, and washed with brine. The aqueous phase was extracted thrice with dichloromethane and the combined organic phases were washed with brine, then dried (sodium sulfate), filtered, and concentrated. Purification by column chromatography (silica, 0-10% methanol/dichloromethane) followed by repeated prep-HPLC (C18, acetonitrile/water+0.1% trifluoroacetic acid) gave rac-(3aR,3bS,8aR,9R,9aR)-8a-(4-bromophenyl)-6-chloro-3b-hydroxy-9-phenyl-1,3a,3b,8a,9,9a-hexahydro-2H-oxazolo[4",5":4',5']cyclopenta[1',2':4,5]furo[3,2-b]pyridin-2-one (Cpd. No. 53F) as a white fluffy solid. Yield: 24 mg, 22%; MS (ESI) 499.2[M+1]$^+$; $^1$H NMR (300 MHz, DMSO-d) δ 8.36 (d, J=2.0 Hz, 1H), 8.27 (bs, 1H), 7.84 (d, J=2.0 Hz, 1H), 7.37 (d, J=8.2 Hz, 2H), 7.17-7.11 (m, 3H), 7.07 (d, J=8.2 Hz, 2H), 7.01-6.69 (m, 2H), 6.33 (s, 1H), 5.49 (d, J=9.3 Hz, 1H), 4.91 (dd, J=9.3, 9.7 Hz, 1H), 3.53 (d, J=9.7 Hz, 1H).

Example 54

Rac-4-((3aR,3bS,8aR,9R,9aR)-6-chloro-3b-hydroxy-2-oxo-9-phenyl-1,2,3a,3b,9,9a-hexahydro-8aH-oxazolo[4",5":4',5']cyclopenta[1',2':4,5]furo[3,2-b]pyridin-8a-yl)benzonitrile (Cpd. No. 54F)

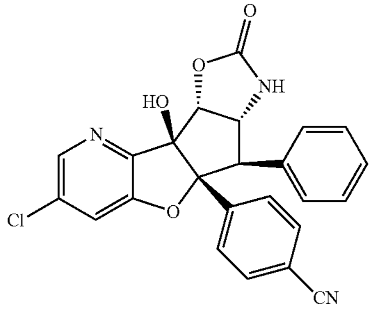

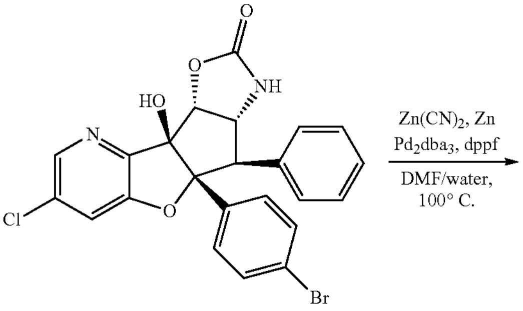

1

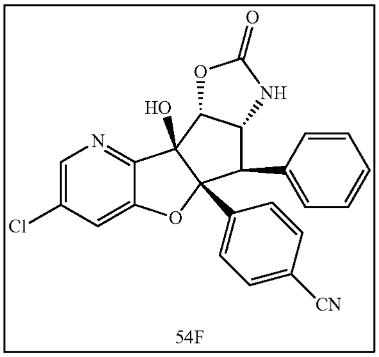

54F

Synthesis of rac-4-((3aR,3bS,8aR,9R,9aR)-6-chloro-3b-hydroxy-2-oxo-9-phenyl-1,2,3a,3b,9,9a-hexahydro-8aH-oxazolo[4",5":4',5']cyclopenta[1',2':4,5]furo[3,2-b]pyridin-8a-yl)benzonitrile (Cpd. No. 54F)

In a 0.5-2 mL microwave vial rac-(3aR,3bS,8aR,9R,9aR)-8a-(4-bromophenyl)-6-chloro-3b-hydroxy-9-phenyl-1,3a,3b,8a,9,9a-hexahydro-2H-oxazolo[4",5":4',5']cyclopenta[1',2':4,5]-furo[3,2-b]pyridin-2-one (1, 13.7 mg, 0.0274 mmol) was dissolved in N,N-dimethylformamide (1 mL) and water (0.1 mL). Zinc cyanide (10.8 mg, 0.092 mmol) and zinc (1 mg, 0.02 mmol) were added, and the mixture was degassed by bubbling argon through it for 5 min. 1,1'-Bis(diphenylphosphino)ferrocene (4.6 mg, 0.0083 mmol) and tris(dibenzylideneacetone)dipalladium(0) (3.8 mg, 0.0042 mmol) were added and the mixture was incubated at 100° C. for 30 min, then for another 15 min. Then the mixture was diluted with dichloromethane and washed with water. The aqueous phase was extracted with dichloromethane twice. Then the combined organic phases were dried (sodium sulfate), filtered and concentrated. Purification by HPLC (C18, Acetonitrile/water+0.1% trifluoroacetic acid) gave rac-4-((3aR,3bS,8aR,9R,9aR)-6-chloro-3b-hydroxy-2-oxo-9-phenyl-1,2,3a,3b,9,9a-hexahydro-8aH-oxazolo[4",5":4',5']cyclopenta[1',2':4,5]furo[3,2-b]pyridin-8a-yl)benzonitrile (Cpd. No. 54F) as an off-white solid. Yield: 5.6 mg, 46%; MS (ESI) 445.9[M+1]$^+$; $^1$H NMR (400 MHz, DMSO-$d_6$) δ 8.38 (d, J=2.0 Hz, 1H), 8.30 (s, 1H), 7.87 (d, J=2.0 Hz, 1H), 7.67 (d, J=8.7 Hz, 2H), 7.32 (d, J=8.7 Hz, 2H), 7.15-7.10 (m, 3H), 7.02-6.97 (m, 2H), 6.43 (s, 1H), 5.53 (d, J=8.9 Hz, 1H), 4.97 (dd, J=9.9, 8.9 Hz, 1H), 3.60 (d, J=9.9 Hz, 1H).

Example 55

Rac-(5aR,6S,7S,8R,8aS)-5a-(4-bromophenyl)-3-chloro-7-(hydroxymethyl)-6-phenyl-5a,6,7,8-tetrahydro-8aH-cyclopenta[4,5]furo[3,2-b]pyridine-8,8a-diol (Cpd. No. 55F)

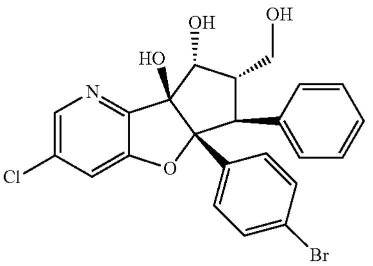

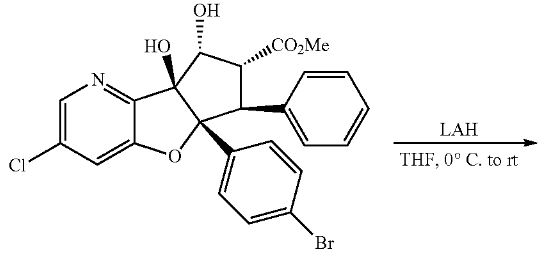

1

-continued

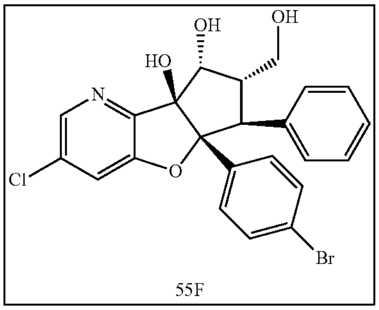

55F

Synthesis of rac-(5aR,6S,7S,8R,8aS)-5a-(4-bromophenyl)-3-chloro-7-(hydroxymethyl)-6-phenyl-5a,6,7,8-tetrahydro-8aH-cyclopenta[4,5]furo[3,2-b]pyridine-8,8a-diol (Cpd. No. 55F)

To a solution of rac-methyl (5aR,6S,7R,8R,8aS)-5a-(4-bromophenyl)-3-chloro-8,8a-dihydroxy-6-phenyl-5a,7,8,8a-tetrahydro-6H-cyclopenta[4,5]furo[3,2-b]pyridine-7-carboxylate (1, 320 mg, 0.619 mmol) in tetrahydrofuran (4 mL) at 0° C. was added lithium aluminum hydride (LAH) (27 mg, 0.71 mmol) and the mixture was stirred at 0° C. for 30 min, then warmed up to rt. After another 1.5 h another 13 mg (0.34 mmol) LAH were added, and stirring at room temperature was continued. After another 30 min another 13 mg (0.34 mmol) LAH were added. After 3 h (total reaction time) water and brine were carefully added, and the mixture was diluted with ethyl acetate. The phases were separated and the aq. phase was extracted with ethyl acetate thrice. The combined organic phases were washed with brine, then dried (sodium sulfate), filtered and concentrated. The crude product was purified by column chromatography (silica, methanol/dichloromethane, product eluted at 5% methanol). Yield: 165 mg, ca. 90% pure, ca. 49% yield; Ca. 25 mg of this material were repurified by HPLC (C18, acetonitrile/water+0.1% trifluoroacetic acid) to give rac-(5aR,6S,7S,8R,8aS)-5a-(4-bromophenyl)-3-chloro-7-(hydroxymethyl)-6-phenyl-5a,6,7,8-tetrahydro-8aH-cyclopenta[4,5]furo[3,2-b]pyridine-8,8a-diol (Cpd. No. 55F) as a fluffy white solid. MS (ESI) m/z 487.9[M+1]$^+$; $^1$H NMR (300 MHz, DMSO-d) S 8.17 (d, J=2.1 Hz, 1H), 7.61 (d, J=2.1 Hz, 1H), 7.21 (d, J=8.7 Hz, 2H), 7.14-6.97 (m, 7H), 4.50 (d, J=3.8 Hz, 1H), 3.88 (d, J=14.2 Hz, 1H), 3.55 (dd, J=10.6, 9.1 Hz, 1H), 3.43 (dd, J=10.6, 3.1 Hz, 1H), 3.21-3.09 (m, 1H).

Example 56

Rac-4-((5aR,6S,7S,8R,8aS)-3-chloro-8,8a-dihydroxy-7-(hydroxymethyl)-6-phenyl-6,7,8,8a-tetrahydro-5aH-cyclopenta[4,5]furo[3,2-b]pyridin-5a-yl)benzonitrile (Cpd. No. 56F)

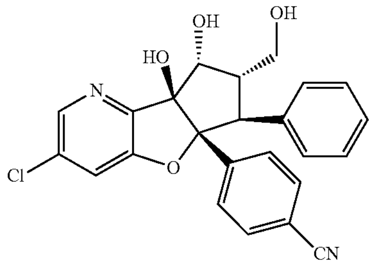

-continued

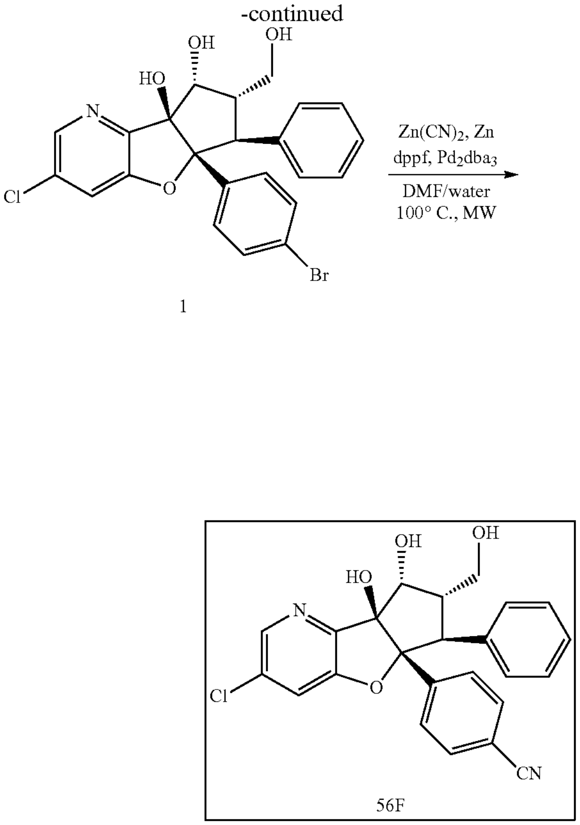

1

56F

Synthesis of rac-4-((5aR,6S,7S,8R,8aS)-3-chloro-8,8a-dihydroxy-7-(hydroxymethyl)-6-phenyl-6,7,8,8a-tetrahydro-5aH-cyclopenta[4,5]furo[3,2-b]pyridin-5a-yl)benzonitrile (Cpd. No. 56F)

In a 0.5-2 mL microwave vial rac-(5aR,6S,7S,8R,8aS)-5a-(4-bromophenyl)-3-chloro-7-(hydroxymethyl)-6-phenyl-5a,6,7,8-tetrahydro-8aH-cyclopenta[4,5]furo[3,2-b]pyridine-8,8a-diol (1, 24.7 mg, 0.0505 mmol) was dissolved in N,N-dimethylformamide (0.50 mL) and water (0.05 mL). Zinc cyanide (19 mg, 0.16 mmol) and zinc (1.8 mg, 0.028 mmol) were added, and the mixture was degassed by bubbling argon through it for 5 min. 1,1'-Bis(diphenylphosphino)ferrocene (2.7 mg, 0.0049 mmol) and tris(dibenzylideneacetone)dipalladium(0) (2.8 mg, 0.0030 mmol) were added, and the mixture was incubated at 100° C. for 30 min. Then the mixture was diluted with ethyl acetate and washed with water. The organic phase was dried (sodium sulfate), filtered and concentrated. Purification by column chromatography (silica, methanol/dichloromethane, product eluted at 5% methanol) and subsequently by HPLC (C18, acetonitrile/water+0.1% trifluoroacetic acid) gave rac-4-((5aR,6S,7S,8R,8aS)-3-chloro-8,8a-dihydroxy-7-(hydroxymethyl)-6-phenyl-6,7,8,8a-tetrahydro-5aH-cyclopenta[4,5]furo[3,2-b]pyridin-5a-yl)benzonitrile (Cpd. No. 56F). Yield: 15.5 mg, 71%; MS (ESI) m/z 435.3[M+1]$^+$; $^1$H NMR (300 MHz, DMSO-$d_6$) δ 8.19 (d, J=2.0 Hz, 1H), 7.64 (d, J=2.0 Hz, 1H), 7.49 (d, J=8.6 Hz, 2H), 7.32 (d, J=8.6 Hz, 2H), 7.14-6.96 (m, 5H), 4.52 (d, J=3.9 Hz, 1H), 3.94 (d, J=14.1 Hz, 1H), 3.57 (dd, J=10.7, 9.6 Hz, 1H), 3.45 (dd, J=10.7, 2.9 Hz, 1H), 3.26-3.14 (m, 1H).

Example 57

Rac-(5aR,6S,7R,8R,8aS)-5a-(4-bromophenyl)-3-chloro-7-methyl-6-phenyl-5a,6,7,8-tetrahydro-8aH-cyclopenta[4,5]furo[3,2-b]pyridine-8,8a-diol (Cpd. No. 57F)

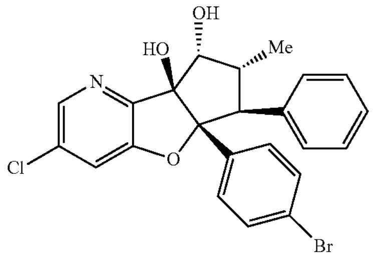

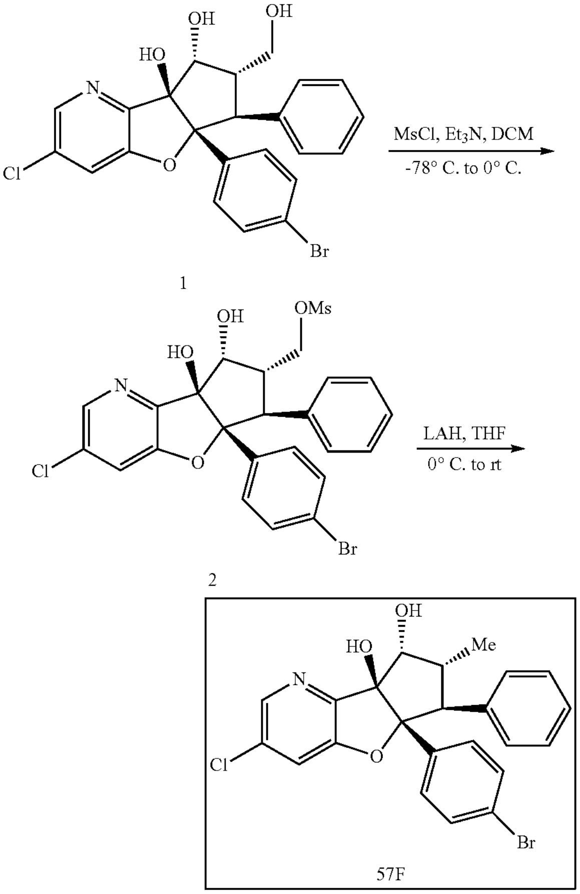

1

2

57F

Synthesis of rac-((5aR,6S,7S,8R,8aS)-5a-(4-bromophenyl)-3-chloro-8,8a-dihydroxy-6-phenyl-5a, 7,8,8a-tetrahydro-6H-cyclopenta[4,5]furo[3,2-b]pyridin-7-yl)methyl methanesulfonate (2)

In a flame-dried vial, rac-(5aR,6S,7S,8R,8aS)-5a-(4-bromophenyl)-3-chloro-7-(hydroxymethyl)-6-phenyl-5a,6,7,8-tetrahydro-8aH-cyclopenta[4,5]furo[3,2-b]pyridine-8,8a-diol (1, 60 mg, 0.12 mmol) was dissolved in dichloromethane (2 mL). Triethylamine (0.13 mL, 1.3 mmol) was added, and the mixture was cooled down to −78° C. Methanesulfonyl chloride (10.5 μL, 15.5 mg, 0.135 mmol) was added, and the mixture was stirred at −78° C. for 30 min, then warmed up to 0° C. Another 4 μL (6 mg, 0.05 mmol) methanesulfonyl chloride were added, and the mixture was stirred for another 5 min (conversion was monitored by TLC). Then the reaction was quenched with water and diluted with dichloromethane. The phases were separated and the organic phase was extracted with dichloromethane thrice. The combined organic phases were dried (sodium sulfate), filtered and concentrated. The so-obtained crude product 2 was used without further purification. MS (ESI) m/z 566.0 [M+1]$^+$.

Synthesis of rac-(5aR,6S,7R,8R,8aS)-5a-(4-bromophenyl)-3-chloro-7-methyl-6-phenyl-5a,6,7,8-tetrahydro-8aH-cyclopenta[4,5]furo[3,2-b]pyridine-8,8a-diol (Cpd. No. 57F)

In a flame-dried flask, rac-((5aR,6S,7S,8R,8aS)-5a-(4-bromophenyl)-3-chloro-8,8a-dihydroxy-6-phenyl-5a,7,8,8a-tetrahydro-6H-cyclopenta[4,5]furo[3,2-b]pyridin-7-yl) methyl methanesulfonate (2, ca. 69 mg, 0.12 mmol) was dissolved in tetrahydrofuran (1.2 mL) and cooled to 0° C. Lithium aluminum hydride (LAH) (5.1 mg, 0.13 mmol) was added, and the mixture was stirred at 0° C. After 20 min, another 6.5 mg (0.17 mmol) LAH were added, and the mixture was warmed up to room temperature After another 1 h 25 min another 6 mg (0.16 mmol) LAH were added. After 2.5 h (total reaction time) the mixture was cooled down to 0° C., and water was carefully added. The mixture was diluted with dichloromethane and filtered. Then the phases were separated and the aq. phase was extracted with dichloromethane thrice. The combined organic phases were dried (sodium sulfate), filtered and concentrated. The crude product was purified by repeated column chromatography (silica, methanol/dichloromethane, product eluted at 4% methanol, followed by ethyl acetate/hexane, product eluted at 50% ethyl acetate). The so-obtained product was repurified by HPLC (C18, acetonitrile/water+0.1% trifluoroacetic acid) to give rac-(5aR,6S,7R,8R,8aS)-5a-(4-bromophenyl)-3-chloro-7-methyl-6-phenyl-5a,6,7,8-tetrahydro-8aH-cyclopenta[4,5]furo[3,2-b]pyridine-8,8a-diol (Cpd. No. 57F) as a fluffy white solid. Yield: 6.5 mg, 11%, 2 steps; MS (ESI) m/z 472.1[M+1]$^+$; $^1$H NMR (500 MHz, DMSO-d$_6$) δ 8.17 (d, J=2 Hz, 1H), 7.60 (d, J=2 Hz, 1H), 7.20 (d, J=9 Hz, 2H), 7.22-7.19 (m, 4H), 7.04-7.01 (m, 3H), 4.27 (d, J=4 Hz, 1H), 3.80 (d, J=14 Hz, 1H), 3.13-3.07 (m, 1H), 0.96 (d, J=7 Hz, 3H).

Example 58

Rac-methyl (5aR,6S,8S,8aS)-5a-(4-bromophenyl)-3-chloro-7-fluoro-8,8a-dihydroxy-6-phenyl-5a,7,8,8a-tetrahydro-6H-cyclopenta[4,5]furo[3,2-b]pyridine-7-carboxylate (Cpd. No. 58F)

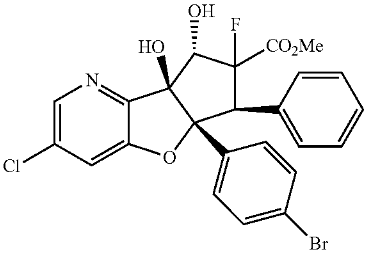

-continued

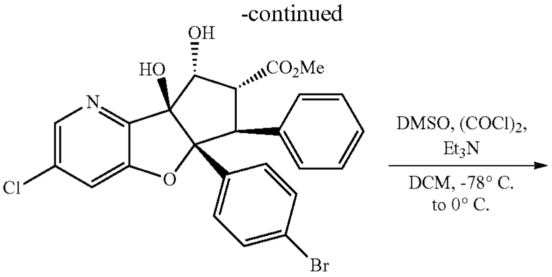

1

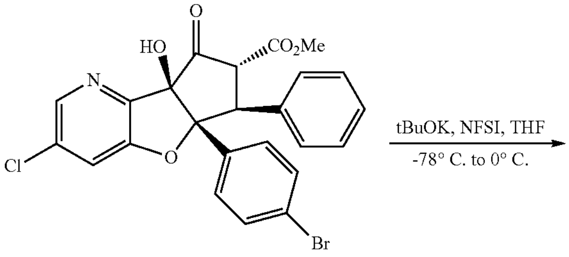

2

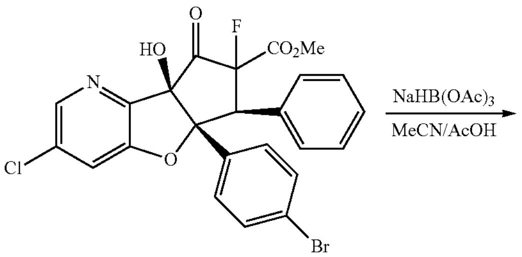

3

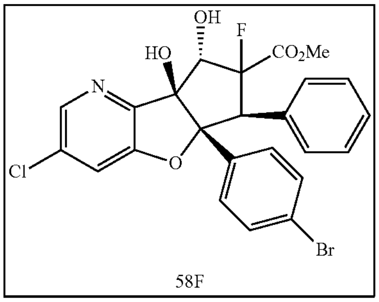

58F

Synthesis of rac-methyl (5aR,6S,7R,8aR)-5a-(4-bromophenyl)-3-chloro-8a-hydroxy-8-oxo-6-phenyl-5a, 7,8,8a-tetrahydro-6H-cyclopenta[4,5]furo[3,2-b]pyridine-7-carboxylate (2)

To oxalyl chloride (2 M in dichloromethane, 0.86 mL, 1.7 mmol) in dichloromethane (8 mL) at −78° C. was added dimethyl sulfoxide (0.14 mL, 0.15 g, 2.0 mmol) and the mixture was stirred for 10 min. Then rac-methyl (5aR,6S,7R,8R,8aS)-5a-(4-bromophenyl)-3-chloro-8,8a-dihydroxy-6-phenyl-5a,7,8,8a-tetrahydro-6H-cyclopenta[4,5]furo[3,2-b]pyridine-7-carboxylate (1, 726 mg, 1.40 mmol) in 8 mL dichloromethane was added and the mixture was stirred for 30 min. Then triethylamine (1.1 mL, 0.80 g, 7.9 mmol) was added and the mixture was allowed to warm up to room temperature within 1.5 h. Water was added, and the phases were separated. The aqueous phase was extracted with dichloromethane thrice, and the combined organic phases were dried (sodium sulfate), filtered and concentrated. The crude material was purified by column chromatography (silica, 0% to 100% ethyl acetate/hexane, then 0% to 10% methanol/dichloromethane). Yield: 217 mg, 38%; MS (ESI) m/z 514.1[M+1]$^+$.

Synthesis of rac-methyl (5aR,6S,8aR)-5a-(4-bromophenyl)-3-chloro-7-fluoro-8a-hydroxy-8-oxo-6-phenyl-5a,7,8,8a-tetrahydro-6H-cyclopenta[4,5]furo[3,2-b]pyridine-7-carboxylate (3)

The starting material rac-methyl (5aR,6S,7R,8aR)-5a-(4-bromophenyl)-3-chloro-8a-hydroxy-8-oxo-6-phenyl-5a,7,8,8a-tetrahydro-6H-cyclopenta[4,5]furo[3,2-b]pyridine-7-carboxylate (2, 88 mg, 0.17 mmol) was dissolved in tetrahydrofuran (1.2 mL) and cooled to −78° C. Potassium tert-butoxide (25 mg, 0.22 mmol) in 0.2 mL tetrahydrofuran was added dropwise, and the mixture was stirred at −78° C. for 10 min, then at 0° C. for 5 min, then cooled to −78° C. again. N-Fluorobenzenesulfonimide (70 mg, 0.22 mmol) in 0.3 mL tetrahydrofuran was added and the mixture was slowly warmed up to 0° C. within 2 h and stirred at this temp for another 1 h. Another 12 mg (0.038 mmol) N-fluorobenzenesulfonimide in 0.05 mL tetrahydrofuran were added and the reaction mixture was stirred for a few more minutes until the reaction was complete. Then 2 mL aqueous ammonium chloride solution was added, and the mixture was diluted with dichloromethane. The phases were separated, and the aqueous phase was extracted with dichloromethane thrice. The combined organic phases were dried (sodium sulfate), filtered and concentrated. The crude material contained the desired product (MS (ESI) m/z 532.1[M+1]$^+$) and was directly used in the next step.

Synthesis of rac-methyl (5aR,6S,8S,8aS)-5a-(4-bromophenyl)-3-chloro-7-fluoro-8,8a-dihydroxy-6-phenyl-5a,7,8,8a-tetrahydro-6H-cyclopenta[4,5]furo[3,2-b]pyridine-7-carboxylate (Cpd. No. 52)

The crude starting material rac-methyl (5aR,6S,8aR)-5a-(4-bromophenyl)-3-chloro-7-fluoro-8a-hydroxy-8-oxo-6-phenyl-5a,7,8,8a-tetrahydro-6H-cyclopenta[4,5]furo[3,2-b]pyridine-7-carboxylate (3, crude product from the previous step) was dissolved in acetonitrile (1.7 mL) and acetic acid (1.7 mL), and sodium triacetoxyborohydride (362 mg, 1.71 mmol) were added. The mixture was stirred at room temperature. After 15 min complete conversion was observed by LCMS. Water was carefully added, and the mixture was extracted with dichloromethane thrice. The combined organic phases were dried (sodium sulfate), filtered and concentrated. Purification by column chromatography (silica, ethyl acetate/hexane, product eluted at 55% ethyl acetate) gave 59 mg of material, which was repurified by HPLC (C18, acetonitrile/water+0.1% trifluoroacetic acid) to give rac-methyl (5aR,6S,8S,8aS)-5a-(4-bromophenyl)-3-chloro-7-fluoro-8,8a-dihydroxy-6-phenyl-5a,7,8,8a-tetrahydro-6H-cyclopenta[4,5]furo[3,2-b]pyridine-7-carboxylate (Cpd. No. 58F) as fluffy white solid. Yield: 39.5 mg, 43%, two steps; MS (ESI) m/z 534.2[M+1]$^+$; $^1$H NMR (500 MHz, DMSO-$d_6$) δ 8.23 (d, J=2 Hz, 1H), 7.46 (d, J=2 Hz, 1H), 7.35 (d, J=9 Hz, 2H), 7.27 (d, J=9 Hz, 2H), 7.21-7.14 (m, 5H), 5.33 (d, J=29 Hz, 1H), 4.48 (d, J=22 Hz, 1H), 3.30 (s, 3H).

Example 59

Rac-methyl (5aR,6S,8S,8aS)-3-chloro-5a-(4-cyanophenyl)-7-fluoro-8,8a-dihydroxy-6-phenyl-5a,7,8,8a-tetrahydro-6H-cyclopenta[4,5]furo[3,2-b]pyridine-7-carboxylate (Cpd. No. 59F)

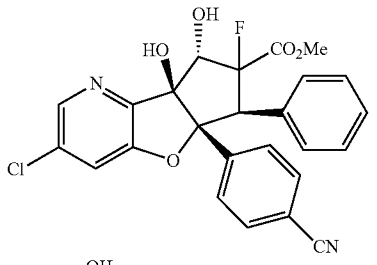

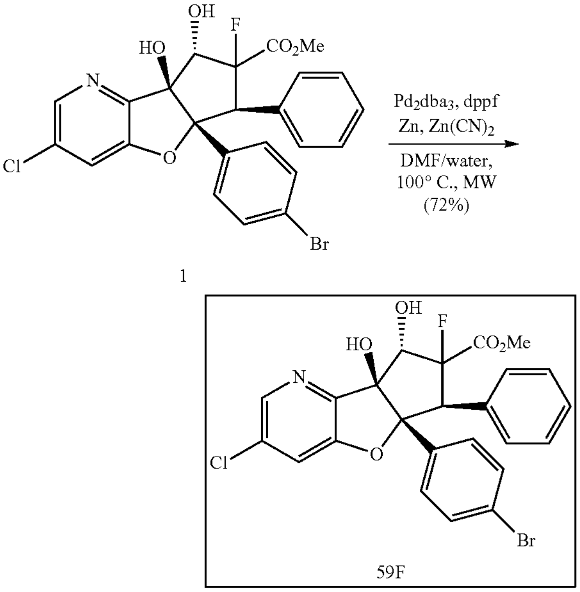

1

59F

Synthesis of rac-methyl (5aR,6S,8S,8aS)-3-chloro-5a-(4-cyanophenyl)-7-fluoro-8,8a-dihydroxy-6-phenyl-5a,7,8,8a-tetrahydro-6H-cyclopenta[4,5]furo[3,2-b]pyridine-7-carboxylate (Cpd. No. 59F)

In a 0.5-2 mL MW vial rac-methyl (5aR,6S,8S,8aS)-5a-(4-bromophenyl)-3-chloro-7-fluoro-8,8a-dihydroxy-6-phenyl-5a,7,8,8a-tetrahydro-6H-cyclopenta[4,5]furo[3,2-b]pyridine-7-carboxylate (1, 56 mg, 0.10 mmol) was dissolved in N,N-dimethylformamide (1.5 mL) and water (0.15 mL). Zinc cyanide (40 mg, 0.34 mmol) and zinc (2.7 mg, 0.042 mmol) were added, and the mixture was degassed by bubbling argon through it for 5 min. 1,1'-Bis(diphenylphosphino)ferrocene (11.6 mg, 0.0209 mmol) and tris(dibenzylideneacetone)dipalladium(0) (9.6 mg, 0.010 mmol) were added and the mixture was incubated at 100° C. for 30 min. Then the mixture was diluted with dichloromethane and washed with water. The aqueous phase was extracted with dichloromethane once more. Then the combined organic phases were dried (sodium sulfate), filtered and concentrated. Purification by column chromatography (silica, ethyl acetate/hexane, product eluted at 6% ethyl acetate) gave rac-methyl (5aR,6S,8S,8aS)-3-chloro-5a-(4-cyanophenyl)-7-fluoro-8,8a-dihydroxy-6-phenyl-5a,7,8,8a-tetrahydro-6H-cyclopenta[4,5]furo[3,2-b]pyridine-7-carboxylate (Cpd. No. 59F) as off-white solid. Yield: 36.5 mg, 72%; MS (ESI) m/z 481.0[M+1]$^+$; $^1$H NMR (400 MHz, DMSO-$d_6$) δ 8.25 (d, J=2.0 Hz, 1H), 7.60 (d, 8.6 Hz, 2H, AB-system), 7.56 (d, J=8.6 Hz, 2H, AB-system), 7.52 (d, J=2.0 Hz, 1H), 7.19-7.12 (m, 5H), 7.03 (s, 1H), 5.96 (d, J=7.4 Hz, 1H), 5.36 (dd, J=28.6, 7.4 Hz, 1H), 4.52 (d, J=22.8 Hz, 1H), 3.31 (s, 3H).

Example 60

Rac-(2aS,3S,3aR,8bS,8cR)-3a-(4-bromophenyl)-6-chloro-3-phenyl-2a,3,3a,8c-tetrahydrooxeto[3",2":4',5']cyclopenta[1',2':4,5]furo[3,2-b]pyridin-8b(2H)-ol (Cpd. No. 60F)

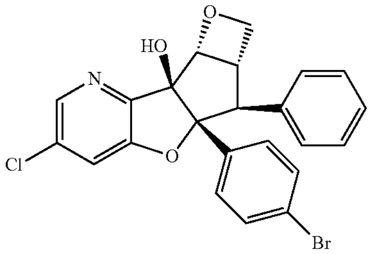

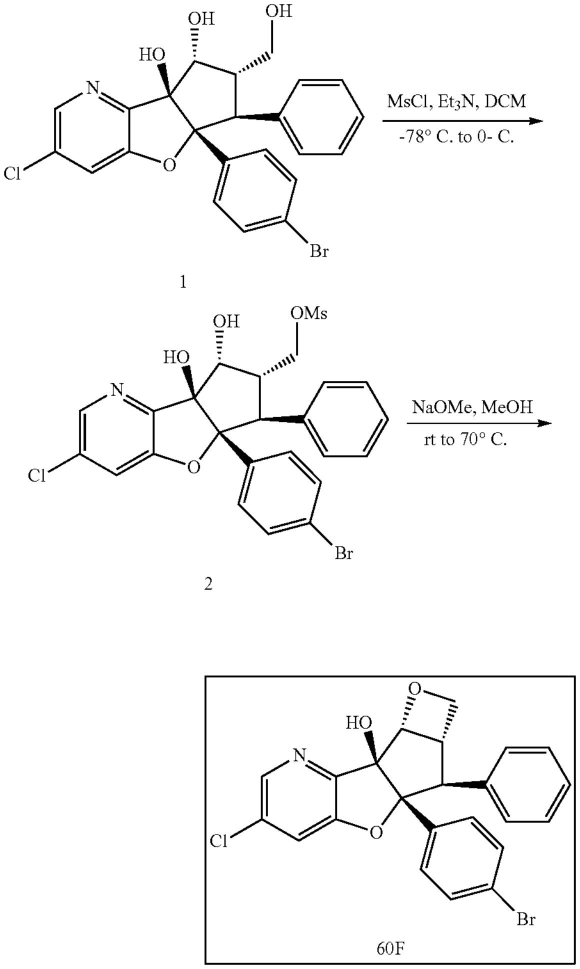

1

2

60F

Synthesis of rac-((5aR,6S,7S,8R,8aS)-5a-(4-bromophenyl)-3-chloro-8,8a-dihydroxy-6-phenyl-5a,7,8,8a-tetrahydro-6H-cyclopenta[4,5]furo[3,2-b]pyridin-7-yl)methyl methanesulfonate (2)

In a flame-dried vial, rac-(5aR,6S,7S,8R,8aS)-5a-(4-bromophenyl)-3-chloro-7-(hydroxymethyl)-6-phenyl-5a,6,7,8-tetrahydro-8aH-cyclopenta[4,5]furo[3,2-b]pyridine-8,8a-diol (1, 64 mg, 0.13 mmol) was dissolved in dichloromethane (2 mL). Triethylamine (0.14 mL, 0.14 g, 1.3 mmol) was added, and the mixture was cooled down to −78° C. Methanesulfonyl chloride (11.5 μL, 17.0 mg, 0.149 mmol) was added, and the mixture was stirred at −78° C. for 30 min, then warmed up to 0° C., and stirred for another 30 min. Then the reaction was quenched with water. The phases were separated and the aqueous phase was extracted with dichloromethane thrice. The combined organic phases were dried (sodium sulfate), filtered and concentrated. The crude product was directly used in the next step. MS (ESI) m/z 566.2[M+1]$^+$.

Synthesis of rac-(2aS,3S,3aR,8bS,8cR)-3a-(4-bromophenyl)-6-chloro-3-phenyl-2a,3,3a,8c-tetrahydrooxeto[3",2":4',5']cyclopenta[1',2':4,5]furo[3,2-b]pyridin-8b(2H)-ol (Cpd. No. 60F)

In a flame-dried vial, rac((5aR,6S,7S,8R,8aS)-5a-(4-bromophenyl)-3-chloro-8,8a-dihydroxy-6-phenyl-5a,7,8,8a-tetrahydro-6H-cyclopenta[4,5]furo[3,2-b]pyridin-7-yl) methyl methanesulfonate (2, crude product from previous step, ca. 74 mg, 0.13 mmol) was dissolved in methanol (2.6 mL) and cooled to 0° C. Sodium methanolate (25% in methanol, 0.30 mL, 1.3 mmol) was added, and the mixture was stirred at room temperature. After 20 min the mixture was warmed up to 50° C. After another 20 min the mixture was warmed up to 75° C. After another 30 min complete conversion was observed by LCMS. The mixture was allowed to cool down to room temperature, diluted with dichloromethane and washed with water. The aqueous phase was extracted with dichloromethane and the combined organic phases were dried (sodium sulfate), filtered and concentrated. Purification by column chromatography (silica, ethyl acetate/hexane, product eluted at 45% ethyl acetate) gave rac-(2aS,3S,3aR,8bS,8cR)-3a-(4-bromophenyl)-6-chloro-3-phenyl-2a,3,3a,8c-tetrahydrooxeto[3",2":4',5']cyclopenta[1',2':4,5]furo[3,2-b]pyridin-8b(2H)-ol (Cpd. No. 60F) as a white solid. Yield: 30.9 mg, 50%, two steps; MS (ESI) m/z 470.1[M+1]$^+$; $^1$H NMR (400 MHz, DMSO-$d_6$) δ 8.25 (d, J=2.0 Hz, 1H), 7.78 (d, J=2.0 Hz, 1H), 7.32 (d, J=8.8 Hz, 2H), 7.15-7.07 (m, 3H), 7.02 (d, J=8.8 Hz, 2H), 7.00-6.96 (m, 2H), 6.21 (s, 1H), 5.55 (d, J=6.1 Hz, 1H), 4.75 (dd, J=5.8, 5.8 Hz, 1H), 4.13 (d, J=8.0 Hz, 1H), 3.95 (dd, J=5.8, 2.9 Hz, 1H), 3.79-3.72 (m, 1H).

Example 61

Rac-(2aS,3S,3aR,8bS,8cR)-3a-(4-bromophenyl)-6-chloro-3-phenyl-2a,3,3a,8c-tetrahydrooxeto[3",2":4',5']cyclopenta[1',2':4,5]furo[3,2-b]pyridin-8b(2H)-ol (Cpd. No. 61F)

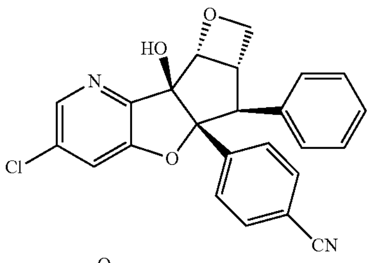

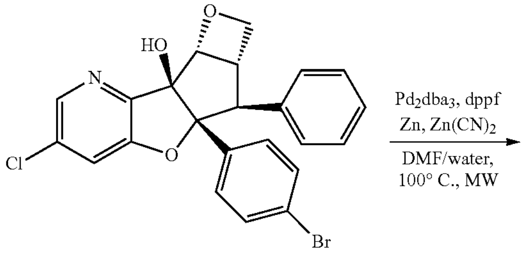

1

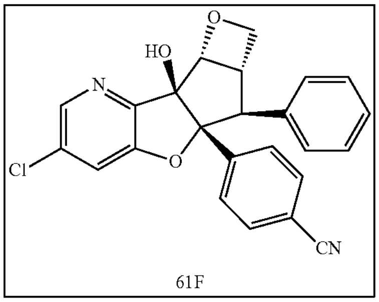

61F

Synthesis of rac-4-((2aS,3S,3aR,8bS,8cR)-6-chloro-8b-hydroxy-3-phenyl-2a,3,8b,8c-tetrahydrooxeto[3",2":4',5']cyclopenta[1',2':4,5]furo[3,2-b]pyridin-3a(2H)-yl)benzonitrile (Cpd. No. 61F)

In a 0.5-2 mL MW vial rac-(2aS,3S,3aR,8bS,8cR)-3a-(4-bromophenyl)-6-chloro-3-phenyl-2a,3,3a,8c-tetrahydrooxeto[3",2":4',5']cyclopenta[1',2':4,5]furo[3,2-b]pyridin-8b(2H)-ol (1, 21.8 mg, 0.046 mmol) was dissolved in N,N-dimethylformamide (0.7 mL) and water (0.07 mL). Zinc cyanide (18.2 mg, 0.155 mmol) and zinc (1.2 mg, 0.018 mmol) were added, and the mixture was degassed by bubbling argon through it for 5 min. 1,1'-Bis(diphenylphosphino)ferrocene (5.1 mg, 0.0092 mmol) and tris(dibenzylideneacetone)dipalladium(0) (4.2 mg, 0.0046 mmol) were added and the mixture was incubated at 100° C. for 30 min. Then the mixture was diluted with dichloromethane and washed with water. The aqueous phase was extracted with dichloromethane once more. Then the combined organic phases were dried (sodium sulfate), filtered and concentrated. Purification by column chromatography (silica, hexane/ethyl acetate, product eluted at 55% ethyl acetate) gave rac-(2aS,3S,3aR,8bS,8cR)-3a-(4-bromophenyl)-6-chloro-3-phenyl-2a,3,3a,8c-tetrahydrooxeto[3",2":4', 5']cyclopenta[1',2':4,5]furo[3,2-b]pyridin-8b(2H)-ol (Cpd. No. 61F) as a white solid. Yield: 7.8 mg, 40%; MS (ESI) m/z 417.0[M+1]$^+$; $^1$H NMR (400 MHz, DMSO-$d_6$) δ 8.27 (d, J=2.0 Hz, 1H), 7.83 (d, J=2.0 Hz, 1H), 7.61 (d, J=8.8 Hz, 2H), 7.26 (d, J=8.8 Hz, 2H), 7.14-7.08 (m, 3H), 7.00-6.96 (m, 2H), 6.30 (s, 1H), 5.58 (d, J=6.0 Hz, 1H), 4.76 (dd, J=5.8, 5.8 Hz, 1H), 4.19 (d, J=8.0 Hz, 1H), 3.95 (dd, J=5.8, 2.8 Hz, 1H), 3.84-3.78 (m, 1H).

Example 62

Rac-(5aR,6S,7S,8R,8aS)-5a-(4-bromophenyl)-3-chloro-7-(methoxymethyl)-6-phenyl-5a,6,7,8-tetrahydro-8aH-cyclopenta[4,5]furo[3,2-b]pyridine-8,8a-diol (Cpd. No. 62F)

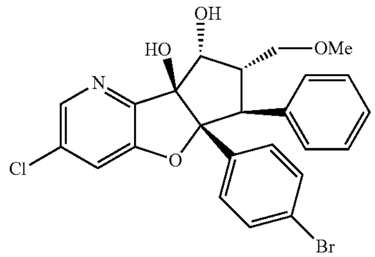

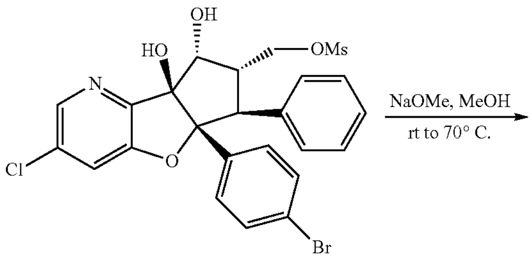

1

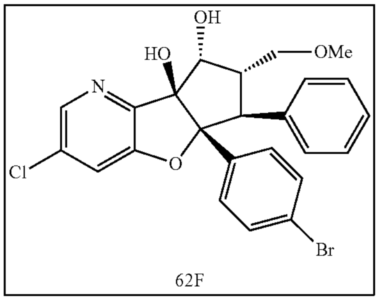

62F

+

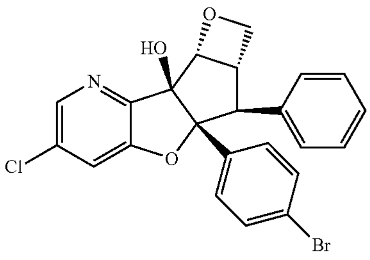

2

Synthesis of rac-(5aR,6S,7S,8R,8aS)-5a-(4-bromophenyl)-3-chloro-7-(methoxymethyl)-6-phenyl-5a,6,7,8-tetrahydro-8aH-cyclopenta[4,5]furo[3,2-b]pyridine-8,8a-diol (Cpd. No. 62F)

In a flame-dried vial, crude rac-((5aR,6S,7S,8R,8aS)-5a-(4-bromophenyl)-3-chloro-8,8a-dihydroxy-6-phenyl-5a,7,8,8a-tetrahydro-6H-cyclopenta[4,5]furo[3,2-b]pyridin-7-yl)-methyl methanesulfonate (1, ca. 266 mg, 0.469 mmol) was dissolved in methanol (9.4 mL) and cooled to 0° C. Sodium methanolate (25% in methanol, 1.1 mL, 4.8 mmol) was added, and the mixture was stirred at room temperature. After 20 min the mixture was warmed up to 50° C. After another 15 min the mixture was warmed up to 75° C. After another 25 min complete conversion was observed by LCMS. The mixture was allowed to cool down to room temperature, diluted with dichloromethane and washed with water. The aqueous phase was extracted with dichloromethane and the combined organic phases were dried (sodium sulfate), filtered and concentrated. Purification by column chromatography (silica, ethyl acetate/hexane) followed by repeated preparative TLC (silica, ethyl acetate/Hexane=2/1, then dichloromethane/Methanol=9/1) gave rac-(5aR,6S,7S,8R,8aS)-5a-(4-bromophenyl)-3-chloro-7-(methoxymethyl)-6-phenyl-5a,6,7,8-tetrahydro-8aH-cyclopenta[4,5]furo[3,2-b]pyridine-8,8a-diol (Cpd. No. 62F) as a white solid. Yield: 7.1 mg, 3%); MS (ESI) m/z 502.1[M+1]$^+$; $^1$H NMR (400 MHz, DMSO-$d_6$) δ 8.17 (d, 2.0 Hz, 1H), 7.61 (d, J=2.0 Hz, 1H), 7.21 (d, J=8.9 Hz, 2H), 7.13-17.08 (m, 4H), 7.06-6.99 (m, 3H), 6.02 (s, 1H), 5.30 (d, J=5.6 Hz, 1H), 4.42 (dd, J=5.6 Hz, 4.3 Hz, 1H), 3.88 (d, J=14.0 Hz, 1H), 3.52 (dd, J=9.2, 9.2 Hz, 1H), 3.30-3.18 (m, 2H), 3.23 (s, 3H).

Example 63

Rac-(1aS,3S,3aR,8bS)-3a-(4-bromophenyl)-6-chloro-3-phenyl-1a,2,3,3a-tetrahydro-oxireno[2",3":1',5']cyclopenta[1',2':4,5]furo[3,2-b]pyridine (Cpd. No. 63F)

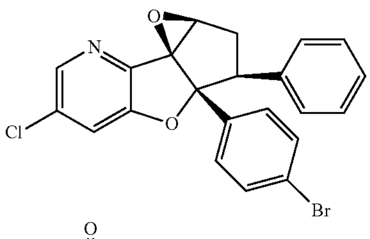

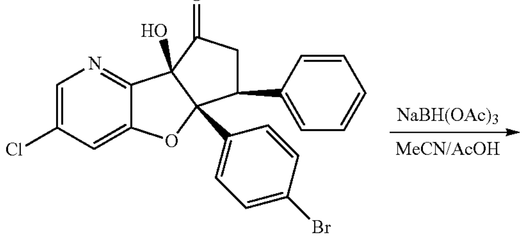

1

-continued

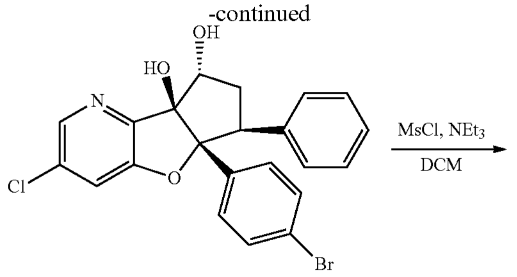

2

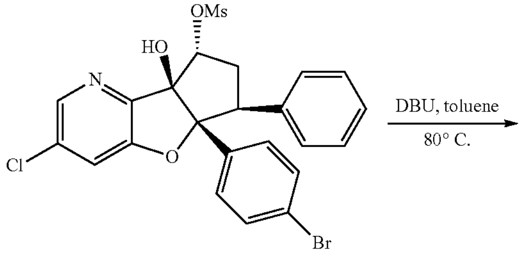

3

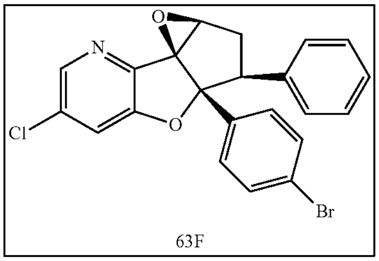

63F

Synthesis of rac-(5aR,6S,8R,8aS)-5a-(4-bromophenyl)-3-chloro-6-phenyl-5a,6,7,8-tetrahydro-8aH-cyclopenta[4,5]furo[3,2-b]pyridine-8,8a-diol (2)

The starting material rac-(5aR,6S,8aR)-5a-(4-bromophenyl)-3-chloro-8a-hydroxy-6-phenyl-5a,6,7,8a-tetrahydro-8H-cyclopenta[4,5]furo[3,2-b]pyridin-8-one (1, 200 mg, 0.438 mmol) was dissolved in acetonitrile (2.2 mL) and acetic acid (2.2 mL). Sodium triacetoxyborohydride (928 mg, 4.38 mmol) was added, and the resulting mixture was stirred at room temperature. After 30 min water was carefully added, and the mixture was extracted with dichloromethane three times. The combined organic phases were dried (sodium sulfate), filtered and concentrated. Purification by column chromatography (silica, ethyl acetate/hexane, product eluted at 50% ethyl acetate) gave rac-(5aR,6S,8R,8aS)-5a-(4-bromophenyl)-3-chloro-6-phenyl-5a,6,7,8-tetrahydro-8aH-cyclopenta[4,5]furo[3,2-b]pyridine-8,8a-diol (2) as off-white solid. Yield: 201 mg, 100%; MS (ESI) m/z 458.3[M+1]$^+$.

Synthesis of rac-(5aR,6S,8R,8aS)-5a-(4-bromophenyl)-3-chloro-8a-hydroxy-6-phenyl-5a,7,8,8a-tetrahydro-6H-cyclopenta[4,5]furo[3,2-b]pyridin-8-yl methanesulfonate (3)

In a flame-dried flask, rac-(5aR,6S,8R,8aS)-5a-(4-bromophenyl)-3-chloro-6-phenyl-5a,6,7,8-tetrahydro-8aH-cyclopenta[4,5]furo[3,2-b]pyridine-8,8a-diol (2, 20 mg, 0.044 mmol) were dissolved in dichloromethane (0.5 mL). Triethylamine (0.05 mL, 0.5 mmol) was added, and the mixture was cooled down to −78° C. Methanesulfonyl chloride (4.8

μL, 7.1 mg, 0.062 mmol) was added, and the mixture was stirred at −78° C. for 30 min, then warmed up to 0° C. Another 5 μL (7 mg, 0.06 mmol) methanesulfonyl chloride were added, followed by another 2 μL (3 mg, 0.03 mmol) methanesulfonyl chloride. After 1 h 10 min (total reaction time) the reaction was quenched with water and diluted with dichloromethane. The phases were separated, and the aqueous phase was extracted with dichloromethane thrice. The combined organic phases were dried (sodium sulfate), filtered and concentrated. The crude product was purified by column chromatography (silica, ethyl acetate/hexane, product eluted at 50% ethyl acetate) to give rac-(5aR,6S,8R,8aS)-5a-(4-bromophenyl)-3-chloro-8a-hydroxy-6-phenyl-5a,7,8,8a-tetrahydro-6H-cyclopenta[4,5]furo[3,2-b]pyridin-8-yl methanesulfonate (3). Yield: 17.7 mg, 76%, white solid.

Synthesis of rac-(1aS,3S,3aR,8bS)-3a-(4-bromophenyl)-6-chloro-3-phenyl-1a,2,3,3a-tetrahydro-oxireno[2",3":1',5']cyclopenta[1',2':4,5]furo[3,2-b]pyridine (Cpd. No. 63F)

In a flame-dried vial, rac-(5aR,6S,8R,8aS)-5a-(4-bromophenyl)-3-chloro-8a-hydroxy-6-phenyl-5a,7,8,8a-tetrahydro-6H-cyclopenta[4,5]furo[3,2-b]pyridin-8-yl methanesulfonate (3, 17.7 mg, 0.033 mmol) was dissolved in toluene (0.5 mL). 1,8-Diazabicyclo[5.4.0]undec-7-ene (25.0 μL, 25.5 mg, 0.168 mmol) was added, and the mixture was stirred at 50° C. for 45 min, and then warmed up to 65° C. After another 45 min the mixture was warmed up to 80° C. After another 45 min another 25 μL (25.5 mg, 0.168 mmol) 1,8-diazabicyclo[5.4.0]undec-7-ene were added, and stirring at 80° C. was continued for another 15 min. Then the mixture was cooled down to room temperature and the reaction was quenched with saturated ammonium chloride solution. The mixture was extracted with dichloromethane thrice, and the combined organic phases were dried (sodium sulfate), filtered and concentrated. Purification by column chromatography (silica, ethyl acetate/hexane, product eluted at 30% ethyl acetate) and subsequent preparative TLC (silica, ethyl acetate/hexane=1/1) gave rac-(1aS,3S,3aR,8bS)-3a-(4-bromophenyl)-6-chloro-3-phenyl-1a,2,3,3a-tetrahydro-oxireno[2",3":1',5']cyclopenta[1',2':4,5]furo[3,2-b]pyridine (Cpd. No. 63F) as a white solid. Yield: 4.0 mg, 28%; MS (ESI) m/z 440.0$[M+1]^+$; $^1H$ NMR (400 MHz, $CDCl_3$) δ 8.17 (d, J=1.9 Hz, 1H), 7.29 (d, J=1.9 Hz, 1H), 7.21 (d, J=8.9 Hz, 2H), 7.18-7.08 (m, 5H), 7.07-7.03 (m, 2H), 4.60 (dd, J=12.1, 9.3 Hz, 1H), 4.27 (d, J=3.7 Hz, 1H), 2.72 (ddd, J=14.8, 9.3, 3.7 Hz, 1H), 2.57 (dd, J=14.8, 12.1 Hz, 1H).

Example 64

(4bS,5R,6R,7S,7aR)-7a-(4-cyanophenyl)-4b,5-dihydroxy-4-methoxy-N,N-dimethyl-7-phenyl-4b,6,7,7a-tetrahydro-5H-cyclopenta[4,5]furo[2,3-c]pyridine-6-carboxamide (Cpd. No. 64F)

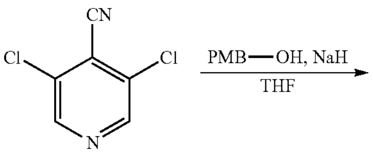

1

-continued

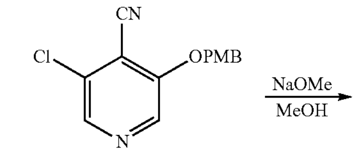

2

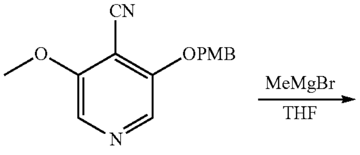

3

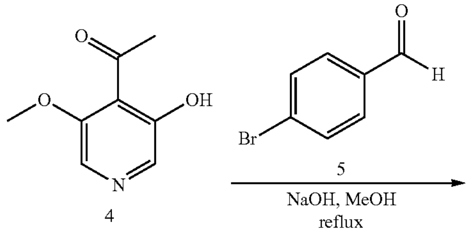

4

5

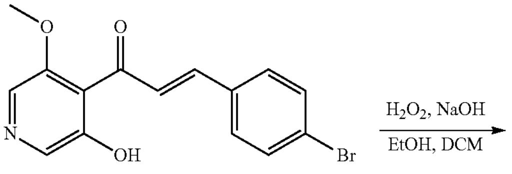

6

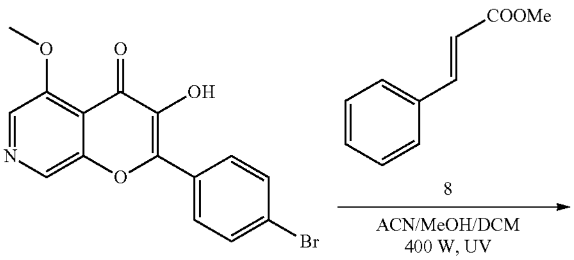

7

8

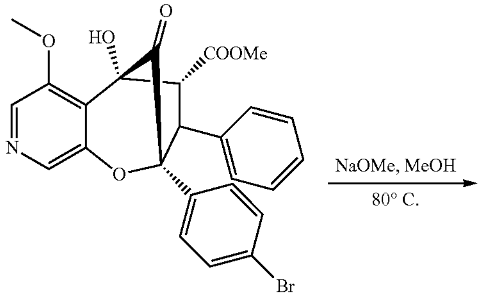

9

-continued

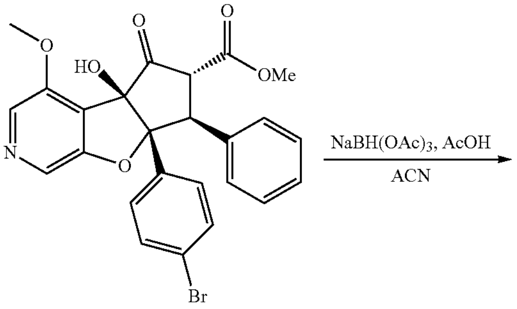

10

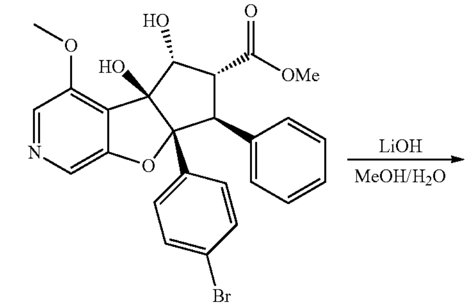

11

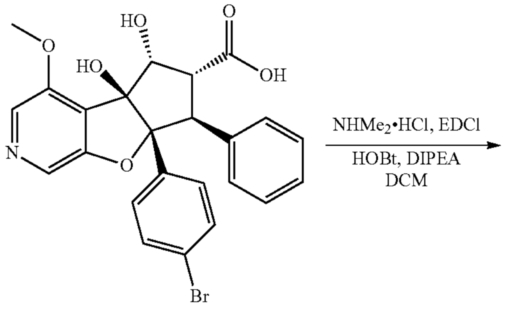

12

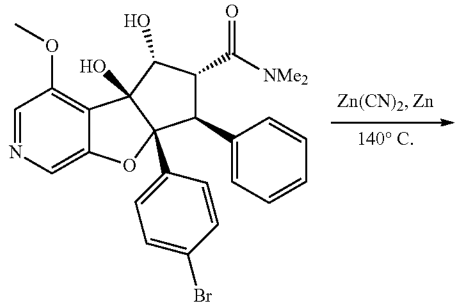

13

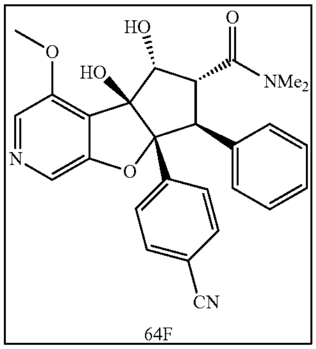

64F

Synthesis of 3-chloro-5-((4-methoxybenzyl)oxy) isonicotinonitrile (2)

To a solution of 3,5-dichloroisonicotinonitrile (1, 15.00 g, 87.20 mmol) in tetrahydrofuran (300 mL) at 0° C., 60% sodium hydride (6.90 g, 174.40 mmol) was added followed by addition of (4-methoxyphenyl)methanol (13.20 g, 95.70 mmol) and the reaction mixture was stirred at room temperature for 2 h. After completion, the mixture was quenched with ice cold water (100 mL) and the mixture was extracted with ethyl acetate (100 mL). The organic layer was washed with water and brine, dried over anhydrous sodium sulfate, filtered and concentrated to afford 3-chloro-5-((4-methoxybenzyl)oxy)isonicotinonitrile (2) as white solid. Yield: 18.0 g, 75%; MS (ESI) m/z 275.16[M+1]$^+$.

Synthesis of 3-methoxy-5-((4-methoxybenzyl)oxy) isonicotinonitrile (3)

To a solution of 3-chloro-5-((4-methoxybenzyl)oxy)isonicotinonitrile (2, 14.00 g, 51.10 mmol) in methanol (160 mL), sodium methoxide (25% in methanol, 20 mL) was added. The reaction mixture was refluxed at 80° C. for 2 h. After completion, solvent was removed under reduced pressure. The mixture was quenched with ice cold water (100 mL) and extracted with ethyl acetate (100 mL). The organic layer was washed with water and brine, dried over anhydrous sodium sulfate, filtered and concentrated. The crude was purified by silica gel column chromatography using 50% ethyl acetate in hexanes as eluents. The desired fractions were concentrated to afford 3-methoxy-5-((4-methoxybenzyl)oxy)isonicotinonitrile (3) as white solid. Yield: 6.3 g, 45%; MS (ESI) m/z 271.23[M+1]$^+$.

Synthesis of 1-(3-hydroxy-5-methoxypyridin-4-yl) ethan-1-one (4)

To a solution of 3-methoxy-5-((4-methoxybenzyl)oxy) isonicotinonitrile (3, 6.30 g, 23.30 mmol) in dry tetrahydrofuran (250 mL) at 0° C., methyl magnesium bromide (69.90 mL, 209.73 mmol) was added dropwise over a period of 30 min. The reaction mass was slowly brought to room temperature and stirred for additional 12 h. After completion, the reaction mass was quenched with 6 M hydrochloric acid to pH ~3 and stirred for 3 h. The mixture was diluted with ethyl acetate (100 mL), water (50 mL) and basified with $NaHCO_3$ up to pH~10. The organic layer was separated, washed with water, dried over anhydrous sodium sulfate, filtered and concentrated under reduced pressure. The crude was purified by silica gel column chromatography using 60% ethyl acetate in hexanes as eluent. The desired fractions were concentrated to afford 1-(3-hydroxy-5-methoxypyridin-4-yl)ethan-1-one (4) as light yellow solid. Yield: 2.0 g, 51.2%; MS (ESI) m/z 168.17[M+1]$^+$.

Synthesis of (E)-3-(4-bromophenyl)-1-(3-hydroxy-5-methoxypyridin-4-yl)prop-2-en-1-one (6)

To a solution of 1-(3-hydroxy-5-methoxypyridin-4-yl) ethan-1-one (4, 2.00 g, 11.90 mmol) in methanol (10 mL), sodium hydroxide (1.40 g, 35.90 mmol) was added followed by addition of 4-bromobenzaldehyde (5, 2.19 g, 11.90 mmol). The reaction was heated to reflux for 10 min. After completion, the reaction mass was cooled to room temperature, diluted with water (20 mL) and extracted with 5% methanol in dichloromethane (100 mL). The organic layer was dried over anhydrous sodium sulfate, filtered and concentrated. The solid obtained was triturated with pentane, filtered and dried under vacuum to afford (E)-3-(4-bromophenyl)-1-(3-hydroxy-5-methoxypyridin-4-yl)prop-2-en-1-one (6) as yellow solid. Yield: 3.2 g, 76.0%; MS (ESI) m/z 334.14[M+1]$^+$.

Synthesis of (2-(4-bromophenyl)-3-hydroxy-5-methoxy-4H-pyrano[2,3-c]pyridin-4-one (7)

To a solution of (E)-3-(4-bromophenyl)-1-(3-hydroxy-5-methoxypyridin-4-yl)prop-2-en-1-one (6, 4.60 g, 13.80 mmol) in ethanol (70 mL) and dichloromethane (10 mL) at 0° C., 10% aqueous sodium hydroxide solution (39 mL, 96.60 mmol) was added followed by the addition of 30% aqueous hydrogen peroxide (9.80 mL, 96.60 mmol). The reaction mass was stirred for 30 min at room temperature (exotherm was observed). After completion, the reaction mass was cooled and neutralized to pH ~7 by the addition of 6 M hydrogen chloride. The mixture was extracted with ethyl acetate (100 mL). The organic layer was washed with water and brine, dried over anhydrous sodium sulfate, filtered and concentrated. The solid obtained was triturated with ethanol, filtered and dried under vacuum to afford of (2-(4-bromophenyl)-3-hydroxy-5-methoxy-4H-pyrano[2,3-c]pyridin-4-one (7) as yellow solid. Yield: 1.4 g, 29.2%; MS (ESI) m/z 348.07[M+1]$^+$.

Synthesis of rac-methyl (2R,4R,5R)-2-(4-bromophenyl)-5-hydroxy-6-methoxy-10-oxo-3-phenyl-2,3,4,5-tetrahydro-2,5-methanooxepino[2,3-c]pyridine-4-carboxylate (9)

A solution of (2-(4-bromophenyl)-3-hydroxy-5-methoxy-4H-pyrano[2,3-c]pyridin-4-one (7, 1.40 g, 4.04 mmol) and methyl cinnamate (8, 6.53 g, 10.40 mmol) in dichloromethane (200 mL), acetonitrile (100 mL) and methanol (100 mL) was placed in a UV reactor flask. The reaction mixture was irradiated under 400 watts UV light for 18 h. After completion, solvent was removed under reduced pressure and the residue was purified over a plug of silica gel eluting the compound with ethyl acetate. The desired fractions were concentrated under reduced pressure to afford rac-methyl (2R,4R,5R)-2-(4-bromophenyl)-5-hydroxy-6-methoxy-10-oxo-3-phenyl-2,3,4,5-tetrahydro-2,5-methanooxepino[2,3-c]pyridine-4-carboxylate (9) as dark brown solid. Yield: 1.80 g, crude.

Synthesis of rac-methyl (4bR,6R,7S,7aR)-7a-(4-bromophenyl)-4b-hydroxy-4-methoxy-5-oxo-7-phenyl-4b,6,7,7a-tetrahydro-5H-cyclopenta[4,5]furo[2,3-c]pyridine-6-carboxylate (10)

The crude compound rac-methyl (2R,4R,5R)-2-(4-bromophenyl)-5-hydroxy-6-methoxy-10-oxo-3-phenyl-2,3,4,5-tetrahydro-2,5-methanooxepino[2,3-c]pyridine-4-carboxylate (9, 1.80 g) was suspended in methanol (25 mL) and treated with 25% sodium methoxide in methanol (15 mL). The reaction was heated at 80° C. for 3 h. After completion, the solvent was removed under reduced pressure. The crude was diluted with ammonium chloride solution and extracted with ethyl acetate. The organic phase was separated, dried over sodium sulphate and concentrated under reduced pressure to afford rac-methyl (4bR,6R,7S,7aR)-7a-(4-bromophenyl)-4b-hydroxy-4-methoxy-5-oxo-7-phenyl-4b,6,7,7a-tetrahydro-5H-cyclopenta[4,5]furo[2,3-c]pyridine-6-carboxylate (10) as brown solid. Yield: 1.4 g, crude.

Synthesis of rac-methyl (4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylate (11)

To a solution of sodium triacetoxyborohydride (3.40 g, 16.50 mmol), rac-methyl (4bR,6R,7S,7aR)-7a-(4-bromophenyl)-4b-hydroxy-4-methoxy-5-oxo-7-phenyl-4b,6,7,7a-tetrahydro-5H-cyclopenta[4,5]furo[2,3-c]pyridine-6-carboxylate (10, 1.40 g, 2.75 mmol) in acetonitrile (20 mL), acetic acid (1.65 g, 27.50 mmol) was added. The resulting mixture was stirred for 4 h at room temperature. After completion, the reaction mixture was partitioned between saturated aqueous sodium bicarbonate solution and ethyl acetate. The organic layer was separated, dried over sodium sulphate, filtered and concentrated under reduced pressure to get the crude. The crude was purified by silica gel column chromatography using 50% ethyl acetate in hexanes as eluents. The desired fractions were concentrated under reduced pressure to afford rac-methyl (4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylate (11) as brown solid. Yield: 0.70 g, 50.0%; MS (ESI) m/z 512.2[M+1]$^+$.

Synthesis of rac-(4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylic acid (12)

To a solution of rac-methyl (4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylate (11, 0.70 g, 1.30 mmol) in methanol and water (3:1, 20 mL), lithium hydroxide (0.32 g, 13.60 mmol) was added and the reaction was stirred for 2 h at room temperature. After completion, the reaction mass was cooled to 0° C. and acidified with 1 M hydrochloric acid to pH ~2-3. The precipitate was filtered and dried under vacuum to afford rac-(4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylic acid (12) as white solid. Yield: 0.53 g, 77.3%; MS (ESI) m/z 498.08[M+1]$^+$.

Synthesis of rac-(4bS,5R,6R,7S,7aR)-7a-(4-bromophenyl)-4b,5-dihydroxy-4-methoxy-N,N-dimethyl-7-phenyl-4b,6,7,7a-tetrahydro-5H-cyclopenta[4,5]furo[2,3-c]pyridine-6-carboxamide (13)

To a solution of rac-(4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylic acid (12, 0.53 g, 1.00 mmol) in dichloromethane (25 mL) at 0° C., 1-ethyl-3-(3-dimethylaminopropyl) carbodiimide (0.49 g, 3.10 mmol), hydroxybenzotriazole (0.48 g, 3.10 mmol) and N,N-diisopropylethylamine (0.82 g, 6.30 mmol) were added and the mixture was stirred for 5 min.

Dimethylamine hydrochloride (0.43 g, 5.20 mmol) was then added at the same temperature and the reaction was stirred for 28 h at room temperature. After completion, the reaction mass was diluted with dichloromethane and washed with cold water. The organic layer was separated and dried over sodium sulphate, filtered and concentrated to give crude. The crude was purified by silica gel column chromatography using 60-70% ethyl acetate in hexanes as eluent. The desired fractions were concentrated to afford rac-(4bS, 5R,6R,7S,7aR)-7a-(4-bromophenyl)-4b,5-dihydroxy-4-methoxy-N,N-dimethyl-7-phenyl-4b,6,7,7a-tetrahydro-5H-cyclopenta[4,5]furo[2,3-c]pyridine-6-carboxamide (13) as white solid. Yield: 0.38 g, 68%; MS (ESI) m/z 525.24[M+1]$^+$.

Synthesis of (4bS,5R,6R,7S,7aR)-7a-(4-cyanophenyl)-4b,5-dihydroxy-4-methoxy-N,N-dimethyl-7-phenyl-4b,6,7,7a-tetrahydro-5H-cyclopenta[4,5]furo[2,3-c]pyridine-6-carboxamide (Cpd. No. 64F)

To a solution of rac-(4bS,5R,6R,7S,7aR)-7a-(4-bromophenyl)-4b,5-dihydroxy-4-methoxy-N,N-dimethyl-7-phenyl-4b,6,7,7a-tetrahydro-5H-cyclopenta[4,5]furo[2,3-c]pyridine-6-carboxamide (13, 0.38 g, 0.73 mmol) in N,N-dimethylformamide (5.0 mL), zinc cyanide (0.51 g, 4.40 mmol) and zinc dust (0.005 g, 0.08 mmol) were added at room temperature and the reaction mixture was degassed with argon for 15 min. 1,1'-Bis(diphenylphosphino)ferrocene (8 mg, 0.0014 mmol) and tris(dibenzylideneacetone) dipalladium (19 mg, 0.021 mmol) were added to the reaction, degassed for additional 5 min and heated the mixture at 140° C. for 16 h. After completion, the reaction mass was diluted with ethyl acetate and washed with cold water. The organic layer was separated and dried over sodium sulphate, filtered and concentrated to give crude. The crude was purified by silica gel column chromatography using 2-3% methanol in dichloromethane as eluent. The desired fractions were concentrated to afford rac-methyl (4bS,5R,6R,7S,7aR)-7a-(4-cyanophenyl)-4b,5-dihydroxy-4-methoxy-N,N-dimethyl-7-phenyl-4b,6,7,7a-tetrahydro-5H-cyclopenta[4,5]furo[2,3-c]pyridine-6-carboxamide (rac-Cpd. No. 64F) as white solid. The enantiomers were separated by chiral preparative HPLC [chiralpak IB (4.6×250) mm]. Yield: 0.169 g, 49% (racemic mixture)

Peak 1 (31 mg), $[\alpha]_D$+89.60 (c 0.1, $CHCl_3$), $R_t$=7.796 min, ee >99% $^1H$ NMR (400 MHz, DMSO-$d_6$) δ 8.12 (s, 1H), 8.00 (s, 1H), 7.48 (d, J=8.5 Hz, 2H), 7.32 (d, J=8.5 Hz, 2H), 7.02 (t, J=7.3 Hz, 2H), 6.94 (m, 3H), 5.8 (s, 1H), 5.16 (d, J=5.4 Hz, 1H), 4.76 (t, J=5.2 Hz, 1H), 4.49 (d, J=13.4 Hz, 1H), 4.25 (dd, J=13.4, 5.1 Hz, 1H), 3.87 (s, 3H), 3.29 (s, 3H), 2.77 (s, 3H); MS (ESI) m/z 472.43 [M+1]$^+$; Purity: 99.32%

Peak-2 (Cpd. No. 64F, 26 mg), $[\alpha]_D$−89.5° (c 0.1, $CHCl_3$), $R_t$=10.192 min, ee >99% $^1H$ NMR (400 MHz, DMSO-$d_6$) δ 8.12 (s, 1H), 8.00 (s, 1H), 7.48 (d, J=8.5 Hz, 2H), 7.32 (d, J=8.5 Hz, 2H), 7.02 (t, J=7.3 Hz, 2H), 6.94 (m, 3H), 5.8 (s, 1H), 5.16 (d, J=5.4 Hz, 1H), 4.76 (t, J=5.2 Hz, 1H), 4.49 (d, J=13.4 Hz, 1H), 4.25 (dd, J=13.4, 5.1 Hz, 1H), 3.87 (s, 3H), 3.29 (s, 3H), 2.77 (s, 3H); MS (ESI) m/z 472.43 [M+1]$^+$; Purity: 99.04%.

Example 65

Rac-4-((4bS,5R,6S,7S,7aR)-6-(aminomethyl)-4b,5-dihydroxy-4-methoxy-7-phenyl-5,6,7,7a-tetrahydro-4bH-cyclopenta[4,5]furo[2,3-c]pyridin-7a-yl)benzonitrile (Cpd. No. 65F)

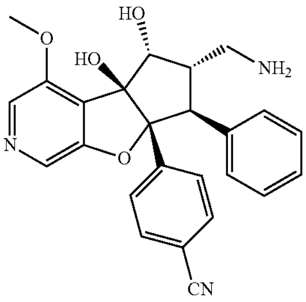

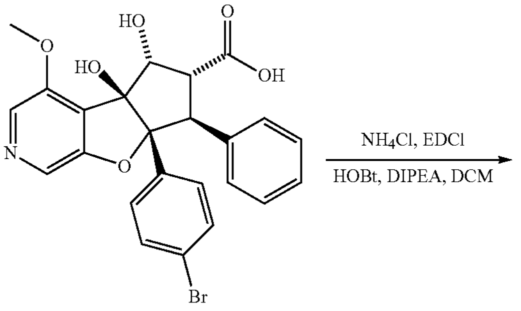

1

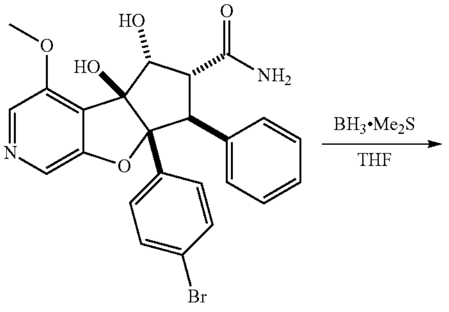

2

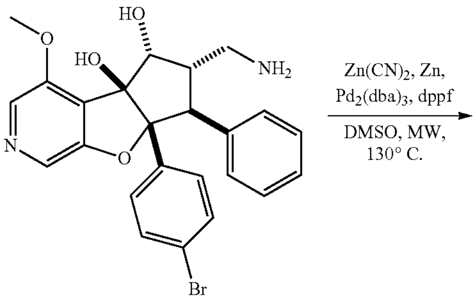

3

-continued

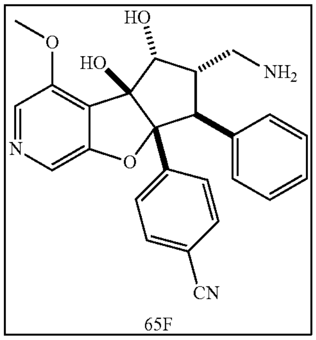

65F

Synthesis of rac-(4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxamide (2)

To a suspension of rac-(4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylic acid (1, 2.50 g, 5.02 mmol) in dichloromethane (30 mL) was added 1-(3-dimethylaminopropyl)-3-ethylcarbodiimide hydrochloride (1.92 g, 10.03 mmol), 1-hydroxybenzotriazole (1.36 g, 10.03 mmol) and N,N-diisopropylethylamine (1.95 g, 15.05 mmol). The mixture was stirred at 0° C. for 5 min, then ammonium chloride (322 mg, 6.02 mmol) was added and the mixture was stirred at 20° C. for 12 h. The mixture was diluted with water (20 mL) and extracted with dichloromethane (60 mL×2). The organic layer was dried and concentrated under reduced pressure to give a residue, which was purified by silica gel chromatography (dichloromethane:methanol=20:1 to 10:1) to afford rac-(4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxamide (2) as a light yellow solid. Yield: 2.00 g, 80%; MS (ESI) m/z 497.0 $[M+1]^+$; $^1H$ NMR (400 MHz, DMSO-$d_6$) δ 8.07 (s, 1H), 7.97 (s, 1H), 7.71 (s, 1H), 7.22 (d, J=8.4 Hz, 1H), 7.07-6.99 (m, 8H), 5.69 (s, 1H), 5.17 (d, J=4.0 Hz, 1H), 4.60 (t, J=4.4 Hz, 1H), 4.30 (d, J=14.0 Hz, 1H), 3.91-3.90 (m, 1H), 3.87 (s, 3H).

Synthesis of rac-(4bS,5R,6S,7S,7aR)-6-(aminomethyl)-7a-(4-bromophenyl)-4-methoxy-7-phenyl-5,6,7,7a-tetrahydro-4bH-cyclopenta[4,5]furo[2,3-c]pyridine-4b,5-diol (3)

To a suspension of rac-(4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxamide (2, 2.00 g, 4.02 mmol) in tetrahydrofuran (40 mL) was added borane dimethyl sulfide complex (10 M, 4.02 mL) at 0° C. and the mixture was heated to 60° C. for 0.5 h. The mixture was cooled to 0° C., quenched with methanol (20 mL) and concentrated under reduced pressure to give a crude product, which was triturated in hexane/dichloromethane (10/1, 20 mL) and filtered off solid to afford rac-(4bS,5R,6S,7S,7aR)-6-(aminomethyl)-7a-(4-bromophenyl)-4-methoxy-7-phenyl-5,6,7,7a-tetrahydro-4bH-cyclopenta[4,5]furo[2,3-c]pyridine-4b,5-diol (3) as a white solid. Yield: 1.20 g, 62%; MS (ESI) m/z 483.1$[M+1]^+$.

Synthesis of rac-4-((4bS,5R,6S,7S,7aR)-6-(aminomethyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 65F)

A mixture of rac-(4bS,5R,6S,7S,7aR)-6-(aminomethyl)-7a-(4-bromophenyl)-4-methoxy-7-phenyl-5,6,7,7a-tetrahydro-4bH-cyclopenta[4,5]furo[2,3-c]pyridine-4b,5-diol (3, 500 mg, 1.03 mmol), zinc powder (67 mg, 1.03 mmol), zinc cyanide (1.21 g, 10.34 mmol), tris(dibenzylideneacetone) dipalladium (95 mg, 103.4 umol) and 1,1'-bis(diphenylphosphino)ferrocene (57 mg, 103.4 umol) in dimethyl sulfoxide (4 mL) was stirred at 130° C. under nitrogen at microwave irradiate (150 Psi, 40 W) for 1 h. The reaction mixture was purified by silica gel chromatography (dichloromethane/methanol=20:1 to 10:1) to give the product, which was further purified by prep-HPLC (column: Phenomenex Gemini 150*25 mm*10 um; mobile phase: [water (0.05% ammonia hydroxide v/v)–acetonitrile]; B %: 40%-70%, 10 min) to afford rac-4-((4bS,5R,6S,7S,7aR)-6-(aminomethyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 65F) as a light yellow solid. Yield: 22 mg, 5%; MS (ESI) m/z 430.1 $[M+1]^+$; HPLC: 99.89%; $^1H$ NMR (400 MHz, DMSO-$d_6$) δ 8.06 (s, 1H), 7.98 (s, 1H), 7.50 (d, J=8.8 Hz, 2H), 7.36 (d, J=8.4 Hz, 2H), 7.08-7.04 (m, 2H), 7.01-6.99 (m, 3H), 5.68 (s, 1H), 4.59 (d, J=4.4 Hz, 1H), 3.89 (s, 3H), 3.77 (d, J=14.0 Hz, 1H), 3.06-2.90 (m, 1H), 2.67-2.60 (m, 2H).

Example 66

4-((4bS,5R,6S,7S,7aR)-6-((dimethylamino)methyl)-4b,5-dihydroxy-4-methoxy-7-phenyl-4b,5,6,7-tetrahydro-7aH-cyclopenta[4,5]furo[2,3-c]pyridin-7a-yl) benzonitrile (Cpd. No. 66F)

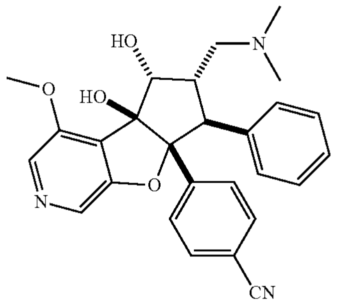

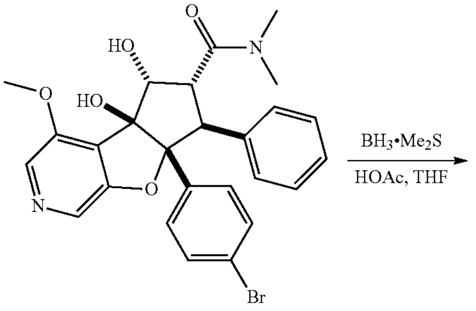

1

-continued

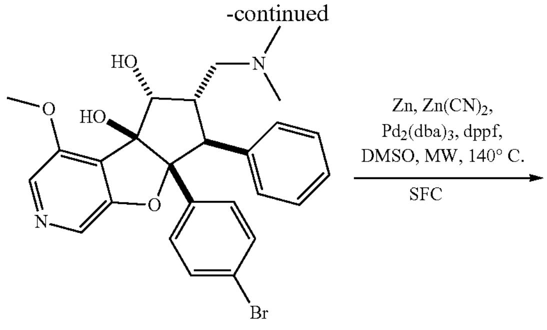

2

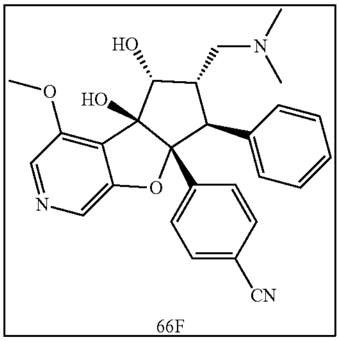

66F

Synthesis of rac-(4bS,5R,6S,7S,7aR)-7a-(4-bromophenyl)-6-((dimethylamino)methyl)-4-methoxy-7-phenyl-5,6,7,7a-tetrahydro-4bH-cyclopenta[4,5]furo[2,3-c]pyridine-4b,5-diol (2)

To a solution of rac-(4bS,5R,6R,7S,7aR)-7a-(4-bromophenyl)-4b,5-dihydroxy-4-methoxy-N,N-dimethyl-7-phenyl-4b,6,7,7a-tetrahydro-5H-cyclopenta[4,5]furo[2,3-c]pyridine-6-carboxamide (1, 500 mg, 0.95 mmol) dissolved in tetrahydrofuran (3 mL) was added borane dimethyl sulfide complex solution (10 M, 0.95 mL) at 0° C. and the mixture was stirred at 25° C. for 30 min, then the mixture was reflux at 60° C. for 2 h. TLC (dichloromethane/methanol=10:1) showed there was no starting material. The reaction mixture was quenched with acetic acid (2 mL) at 0° C. and the mixture was reflux at 60° C. for 1 h, LCMS showed there was desired product detected. The reaction mixture was concentrated and the residue was diluted with water (30 mL). The resulting mixture was extracted with ethyl acetate (10 mL×3). The water phase was adjusted pH=7-8 with saturated sodium bicarbonate and then extracted with ethyl acetate (10 mL×5). The combined organic layer was dried over anhydrous sodium sulfate and concentrated in vacuum to afford the product rac-(4bS,5R,6S,7S,7aR)-7a-(4-bromophenyl)-6-((dimethylamino)methyl)-4-methoxy-7-phenyl-5,6,7,7a-tetrahydro-4bH-cyclopenta[4,5]furo[2,3-c]pyridine-4b,5-diol (2) as a white solid. Yield: 400 mg, 79%; MS (ESI) m/z 510.8 $[M+1]^+$.

Synthesis of 4-((4bS,5R,6S,7S,7aR)-6-((dimethylamino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 66F)

To a solution of rac-(4bS,5R,6S,7S,7aR)-7a-(4-bromophenyl)-6-((dimethylamino)methyl)-4-methoxy-7-phenyl-5,6,7,7a-tetrahydro-4bH-cyclopenta[4,5]furo[2,3-c]pyridine-4b,5-diol (2, 150 mg, 0.29 mmol) dissolved in dimethyl sulfoxide (3 mL) was added zinc (19 mg, 0.29 mmol), zinc cyanide (344 mg, 2.93 mmol) at 25° C. and the reaction mixture was degassed with nitrogen for 15 min. 1,1'-Bis (diphenylphosphino)ferrocene (16 mg, 0.29 mmol) and tris (dibenzylideneacetone)dipalladium (17 mg, 0.029 mmol) was added and the mixture was stirred in microwave (100 w, 140° C., 150 psi) for 2 h. LCMS showed desired product. The reaction mixture was filtered and the filtrate was concentrated in vacuum. The crude was purified by column (dichloromethane/methanol=10:1) to afford rac-4-((4bS,5R,6S,7S,7aR)-6-((dimethylamino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile as a brown solid. Yield: 120 mg, 89%. The enantiomers were separated by SFC column: AD (250 mm×30 mm, 10 um); mobile phase: [0.1% ammonium hydroxide/isopropanl]; B %: 40%-40%, 4 min: 90 min). Peak 1 (Cpd. No. 66F, 17 mg), $[\alpha]_D$+2.988° (c 0.08, $CHCl_3$), $[\alpha]_D$+20.0780 (c 0.5, methanol); Rt=3.155 min, ee >98%; MS (ESI) m/z 458.2 $[M+1]^+$; HPLC: 98.46%; $^1H$ NMR (400 MHz, $CD_3OD$) δ 8.03 (s, 1H), 7.96 (s, 1H), 7.49 (d, J=8.8 Hz, 2H), 7.42 (d, J=8.4 Hz, 2H), 7.09-6.99 (m, 5H), 4.75 (d, J=4.8 Hz, 1H), 3.99 (s, 3H), 3.83 (d, J=14.4 Hz, 1H), 3.26-3.24 (m, 1H), 2.86-2.80 (m, 1H), 2.38 (s, 6H), 2.26-2.23 (m, 1H); Peak 2 (21 mg); $[\alpha]_D$−7.3940 (c 0.08, $CHCl_3$), $[\alpha]_D$−11.907° (c 0.5, methanol); Rt=3.607 min, ee >98%; MS (ESI) m/z 458.2 $[M+1]^+$; HPLC: 97.65%; $^1H$ NMR (400 MHz, $CD_3OD$) δ 8.03 (s, 1H), 7.96 (s, 1H), 7.49 (d, J=8.8 Hz, 2H), 7.42 (d, J=8.4 Hz, 2H), 7.09-6.99 (m, 5H), 4.75 (d, J=4.8 Hz, 1H), 3.99 (s, 3H), 3.83 (d, J=14.4 Hz, 1H), 3.28-3.24 (m, 1H), 2.86-2.80 (m, 1H), 2.47 (s, 6H), 2.25-2.21 (m, 1H).

Example 67

4-((4bS,5R,6S,7S,7aR)-4b,5-dihydroxy-4-methoxy-7-phenyl-6-(piperazin-1-ylmethyl)-4b,5,6,7-tetrahydro-7aH-cyclopenta[4,5]furo[2,3-c]pyridin-7a-yl)benzonitrile (Cpd. No. 67F)

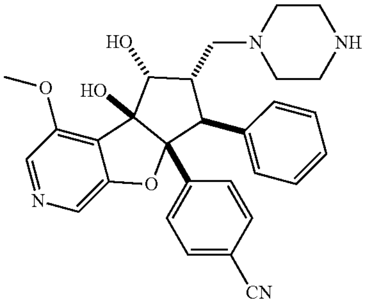

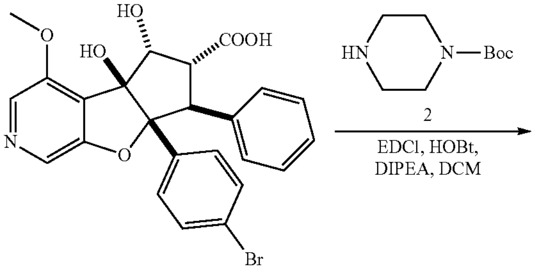

1

-continued

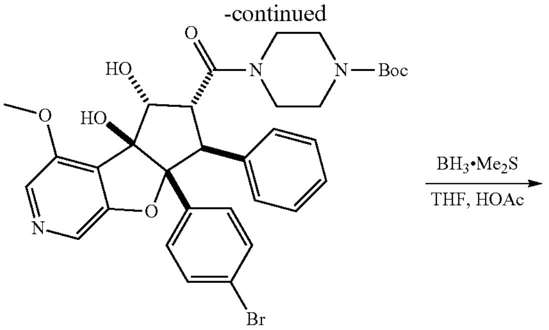

3

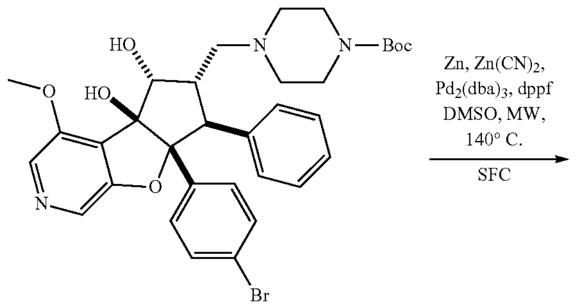

4

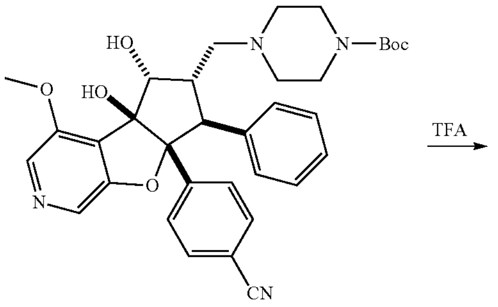

5

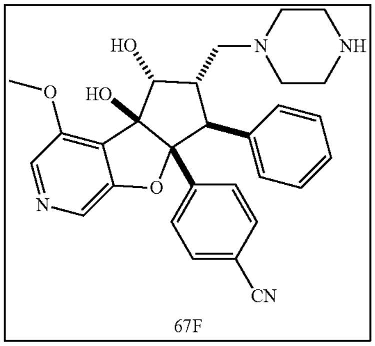 [SMILES: COc1cncc2c1[C@]1(O)[C@H](O)[C@H](CN3CCNCC3)[C@@H](c3ccccc3)[C@]1(c1ccc(C#N)cc1)O2]

67F

Synthesis of rac-tert-butyl 4-((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carbonyl)piperazine-1-carboxylate (3)

To a solution of rac-(4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylic acid (1, 1.50 g, 3.01 mmol) in dichloromethane (10 mL) was added 1-ethyl-3-(3-dimethylaminopropyl)carbodiimide hydrogen chloride (1.20 g, 6.02 mmol), 1-hydroxybenzotriazole (813 mg, 6.02 mmol) and N,N-diisopropylethylamine (1.60 g, 12.04 mmol, 2.1 mL) at 0° C. and the mixture was stirred at 0° C. for 30 min. Then tert-butyl piperazine-1-carboxylate (617 mg, 3.31 mmol) was added and the mixture was stirred at 25° C. for 12 h. LCMS showed there was desired product detected. The reaction mixture was diluted with dichloromethane (100 mL) and washed with water (100 mL×3). The resulting organic layer was dried over anhydrous sodium sulfate and concentrated in vacuum. The crude was purified by column (dichloromethane/methanol=20:1) to afford the product rac-tert-butyl 4-((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carbonyl)piperazine-1-carboxylate (3) as a yellow solid. Yield: 1.00 g, 47%; MS (ESI) m/z 668.1 $[M+1]^+$.

Synthesis of rac-tert-butyl 4-(((4bS,5R,6S,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)methyl)piperazine-1-carboxylate (4)

To a solution of rac-tert-butyl 4-((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carbonyl)piperazine-1-carboxylate (3, 1.00 g, 1.50 mmol) dissolved in tetrahydrofuran (10 mL) was added borane dimethyl sulfide complex solution (10 M, 1.50 mL) at 0° C. and the mixture was stirred at 25° C. for 30 min, then the mixture was reflux at 60° C. for 2 h. LCMS showed there was no starting material left. The reaction mixture was quenched with acetic acid (3 mL) at 0° C. and the mixture was reflux at 60° C. for 1 h. The reaction mixture was concentrated, washed with petroleum/ethyl acetate=2:1 (20 mL) and filtered. The filter cake was diluted with water (30 mL) and extracted with ethyl acetate (10 mL×2). The water phase was adjusted pH=7-8 with saturated sodium bicarbonate and then extracted with ethyl acetate (20 mL×3). The combined organic phase was dried with anhydrous sodium sulfate and concentrated in vacuum. The crude was purified by column (dichloromethane/methanol=20:1) to afford the product rac-tert-butyl 4-(((4bS,5R,6S,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)methyl)piperazine-1-carboxylate (4) as a white solid. Yield: 500 mg, 49%; MS (ESI) m/z 654.4 $[M+1]^+$.

Synthesis of tert-butyl 4-(((4bS,5R,6S,7S,7aR)-7a-(4-cyanophenyl)-4b,5-dihydroxy-4-methoxy-7-phenyl-4b,6,7,7a-tetrahydro-5H-cyclopenta[4,5]furo[2,3-c]pyridin-6-yl)methyl)piperazine-1-carboxylate (5)

To a solution of rac-tert-butyl 4-(((4bS,5R,6S,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)methyl)piperazine-1-carboxylate(4, 250 mg, 0.38 mmol) dissolved in dimethyl sulfoxide (3 mL) was added zinc (25 mg, 0.38 mmol), zinc cyanide (180 mg, 1.53 mmol) at 25° C. and the reaction mixture was degassed with nitrogen for 15 min. 1,1'-Bis(diphenylphosphino)ferrocene (21 mg, 0.038 mmol) and tris(dibenzylideneacetone)dipalladium (22 mg, 38.31 umol) were added and the mixture was stirred in microwave (100 w, 140° C., 150 psi) for 2 h. LCMS showed there was desired product detected. The reaction mixture was filtered and the filtrate was concentrated in vacuum. The crude was purified by column (dichloromethane/methanol=50:1) to afford rac-tert-butyl 4-(((4bS,5R,6S,7S,7aR)-7a-(4-cyanophenyl)-4b,5-dihydroxy-4-methoxy-7-phenyl-4b,6,7,7a-tetrahydro-5H-cyclopenta[4,5]furo[2,3-c]pyridin-6-yl)methyl)piperazine-1-carboxylate as a brown solid. Yield: 75 mg, crude. The enantiomers were separated by SFC column: OD (250 mm×30 mm, 10 um); mobile phase: [0.1% $NH_3H2O$, methanol]; B %: 25%-25%, 4.3 min; 200 min). Peak 1 (5, 16 mg), MS (ESI) m/z 599.3[M+1]$^+$; Peak 2 (19 mg); MS (ESI) m/z 599.3 [M+1]$^+$.

Synthesis of 4-((4bS,5R,6S,7S,7aR)-4b,5-dihydroxy-4-methoxy-7-phenyl-6-(piperazin-1-ylmethyl)-4b,5,6,7-tetrahydro-7aH-cyclopenta[4,5]furo[2,3-c]pyridin-7a-yl)benzonitrile (Cpd. No. 67F)

To a solution of tert-butyl 4-(((4bS,5R,6S,7S,7aR)-7a-(4-cyanophenyl)-4b,5-dihydroxy-4-methoxy-7-phenyl-4b,6,7,7a-tetrahydro-5H-cyclopenta[4,5]furo[2,3-c]pyridin-6-yl)methyl)piperazine-1-carboxylate(5, 65 mg, 0.11 mmol) in acetonitrile (1 mL) was added trifluoroacetic acid (112 mg, 0.65 mmol) at 25° C. The mixture was stirred at 25° C. for 1 h. LCMS showed desired product. The reaction mixture was adjusted pH=7-8 with saturated sodium bicarbonate. The crude was purified by prep-HPLC (column: Phenomenex Gemini C18 250×21.2 mm×5 um; mobile phase: [water (0.05% ammonia hydroxide v/v)—acetonitrile]; B %: 23%-53%, 12 min) to afford product 4-((4bS,5R,6S,7S,7aR)-4b,5-dihydroxy-4-methoxy-7-phenyl-6-(piperazin-1-ylmethyl)-4b,5,6,7-tetrahydro-7aH-cyclopenta[4,5]furo[2,3-c]pyridin-7a-yl)benzonitrile (Cpd. No. 67F). Yield: 20 mg, 36%. $[\alpha]_D$−5.430° (c 0.08, $CHCl_3$); $R_t$=3.515 min, ee >99%; MS (ESI) m/z 499.2 [M+1]$^+$; HPLC: 97.40%; $^1H$ NMR (400 MHz, DMSO-$d_6$) δ 8.04 (s, 1H), 7.96 (s, 1H), 7.48 (d, J=8.8 Hz, 2H), 7.37 (d, J=8.4 Hz, 2H), 7.07-7.06 (m, 2H), 7.02-6.88 (m, 3H), 5.74 (brs, 1H), 5.15 (brs, 1H), 4.50 (d, J=3.6 Hz, 1H), 3.88 (s, 3H), 3.80 (d, J=14.0 Hz, 1H), 3.35-3.27 (m, 1H), 2.72-2.70 (m, 4H), 2.70-2.68 (m, 2H), 2.26-2.23 (m, 2H), 2.06 (dd, J=12.4 Hz, 2.0 Hz, 1H).

Example 68

Rac-4-((4bS,5R,6S,7S,7aR)-4b,5-dihydroxy-4-methoxy-6-((4-methylpiperazin-1-yl)methyl)-7-phenyl-4b,5,6,7-tetrahydro-7aH-cyclopenta[4,5]furo[2,3-c]pyridin-7a-yl)benzonitrile (Cpd. No. 68F)

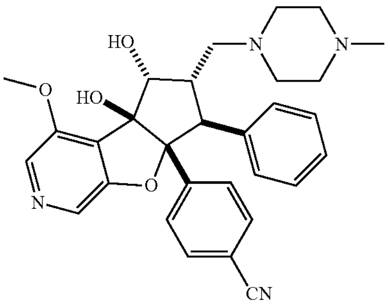

-continued

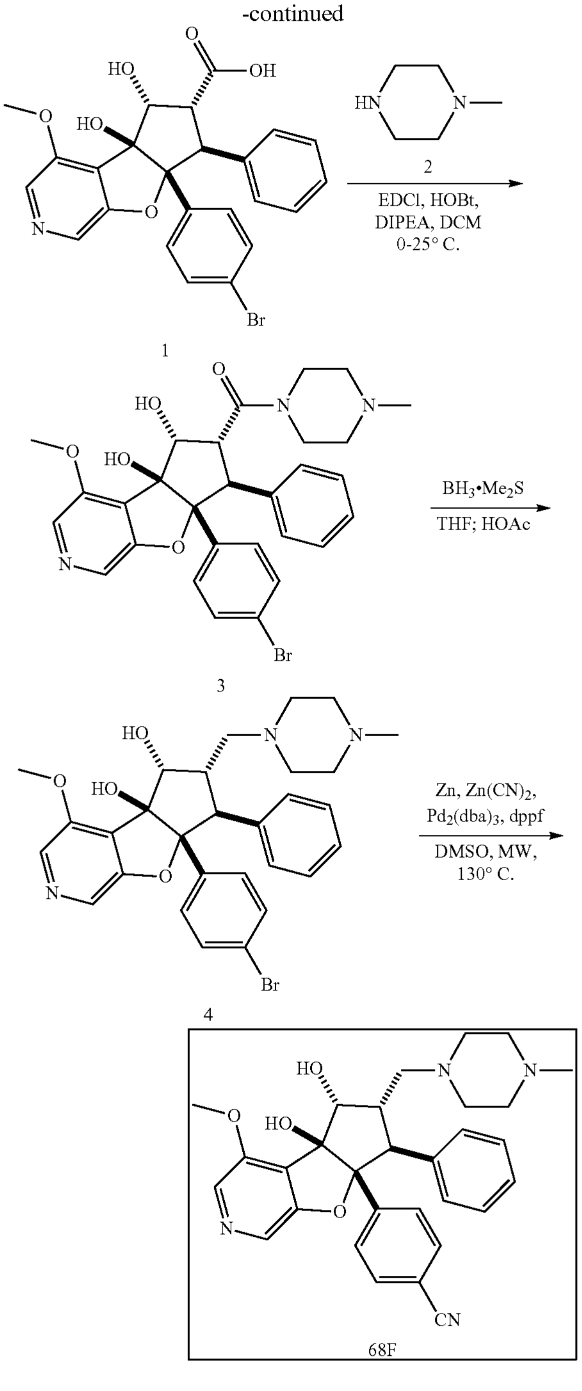

Synthesis of rac-((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)(4-methylpiperazin-1-yl)methanone (3)

To a solution of rac-(4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylic acid (1, 2.50 g, 5.02 mmol) in dichloromethane (30 mL) was added 1-(3-dimethylaminopropyl)-3-ethylcarbodiimide hydrochloride (1.92 g, 10.03 mmol), 1-hydroxybenzotriazole (1.36 g, 10.03 mmol) and N,N-diisopropylethylamine (1.95 g, 15.05 mmol) at 0° C. The mixture was stirred at 0° C. for 0.5 h. Then 1-methylpiperazine (2, 553 mg, 5.52 mmol, 0.61 mL) was added. The mixture was stirred at 20° C. for 11.5 h. The mixture was diluted with water (50 mL) and extracted with dichloromethane (50 mL×3). The combined organic layer was washed with brine (50 mL), dried over anhydrous sodium sulphate and concentrated. The residue was purified by column chromatography (dichloromethane/methanol=20:1 to 10:1) to afford rac-((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)(4-methylpiperazin-1-yl)methanone (3) as a white solid. Yield: 2.60 g, 89%; MS (ESI) m/z 580.1 $[M+1]^+$; $^1H$ NMR (400 MHz, DMSO-$d_6$) δ 8.10 (s, 1H), 7.99 (s, 1H), 7.20 (d, J=8.8 Hz, 2H), 7.11-7.01 (m, 4H), 6.99-6.89 (m, 3H), 5.72 (s, 1H), 5.17 (d, J=5.2 Hz, 1H), 4.68 (t, J=5.2 Hz, 1H), 4.47 (d, J=13.6 Hz, 1H), 4.21 (dd, J=13.6 Hz, 5.2 Hz, 1H), 3.95-3.85 (m, 1H), 3.88 (s, 3H), 3.72-3.62 (m, 1H), 3.55-3.45 (m, 1H), 3.32-3.24 (m, 1H), 2.62-2.53 (m, 1H), 2.44-2.31 (m, 2H), 2.23 (s, 3H), 2.16-2.06 (m, 1H).

Synthesis of rac-(4bS,5R,6S,7S,7aR)-7a-(4-bromophenyl)-4-methoxy-6-((4-methylpiperazin-1-yl)methyl)-7-phenyl-5,6,7,7a-tetrahydro-4bH-cyclopenta[4,5]furo[2,3-c]pyridine-4b,5-diol (4)

To a solution of rac-((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)(4-methylpiperazin-1-yl)methanone (3, 2.60 g, 4.48 mmol) in tetrahydrofuran (30 mL) was added borane dimethyl sulfide complex (10 M, 4.48 mL) at 0° C. The mixture was stirred at 0° C. for 0.5 h. Then the mixture was warmed to 70° C. and stirred at 70° C. for 1 h. The mixture was quenched with acetic acid (9 mL) and then stirred at 70° C. for 1 h. The mixture was concentrated and water (20 mL) was added. The mixture was washed with methyl t-butyl ether (30 mL×3).

The aqueous layer was adjusted to pH=8 with saturated sodium bicarbonate, extracted with ethyl acetate (50 mL×3). The combined organic layer was dried over sodium sulphate and concentrated to afford rac-(4bS,5R,6S,7S,7aR)-7a-(4-bromophenyl)-4-methoxy-6-((4-methylpiperazin-1-yl)methyl)-7-phenyl-5,6,7,7a-tetrahydro-4bH-cyclopenta[4,5]furo[2,3-c]pyridine-4b,5-diol (4) as a white solid. Yield: 2.00 g, 79%; MS (ESI) m/z 566.0 $[M+1]^+$; $^1H$ NMR (400 MHz, DMSO-$d_6$) δ 8.02 (s, 1H), 7.95 (s, 1H), 7.21 (d, J=8.8 Hz, 2H), 7.14-7.06 (m, 4H), 7.03-6.97 (m, 3H), 6.53 (s, 1H), 5.62 (s, 1H), 4.48 (d, J=4.0 Hz, 1H), 3.88 (s, 3H), 3.74 (d, J=14.0 Hz, 1H), 3.19-3.15 (m, 1H), 2.62-2.55 (m, 2H), 2.46-2.26 (m, 6H), 2.19 (s, 3H), 2.08-2.04 (m, 1H).

Synthesis of rac-4-((4bS,5R,6S,7S,7aR)-4b,5-dihydroxy-4-methoxy-6-((4-methylpiperazin-1-yl)methyl)-7-phenyl-4b,5,6,7-tetrahydro-7aH-cyclopenta[4,5]furo[2,3-c]pyridin-7a-yl)benzonitrile (Cpd. No. 68F)

A solution of rac-(4bS,5R,6S,7S,7aR)-7a-(4-bromophenyl)-4-methoxy-6-((4-methylpiperazin-1-yl)methyl)-7-phenyl-5,6,7,7a-tetrahydro-4bH-cyclopenta[4,5]furo[2,3-c]pyridine-4b,5-diol (4, 500 mg, 0.88 mmol), 1,1'-bis(diphenylphosphino)ferrocene (49 mg, 0.088 mmol), tris(dibenzylideneacetone)dipalladium(0) (81 mg, 0.088 mmol), zinc powder (58 mg, 0.88 mmol), zinc cyanide (518 mg, 4.41 mmol) in dimethyl sulfoxide (6 mL) was stirred under nitrogen at microwave (150 psi, 40 W) at 130° C. for 2 h. The mixture was filtered and the filtrate was purified by column chromatography (dichloromethane/methanol=100:1 to 10:1) to give the product which was then further purified by Prep-HPLC (column: Phenomenex Gemini C18 250*50 mm*10 um; mobile phase: [water (0.05% ammonia hydroxide v/v)–acetonitrile]; B %: 23%-48%, 30 min, 87% min) to afford rac-4-((4bS,5R,6S,7S,7aR)-4b,5-dihydroxy-4-methoxy-6-((4-methylpiperazin-1-yl)methyl)-7-phenyl-4b,5,6,7-tetrahydro-7aH-cyclopenta[4,5]furo[2,3-c]pyridin-7a-yl)benzonitrile (Cpd. No. 68F) as a white solid. Yield: 142 mg, 31%; MS (ESI) m/z 513.2 $[M+1]^+$; HPLC:100%; $^1H$ NMR (400 MHz, DMSO-$d_6$) δ 8.04 (s, 1H), 7.97 (s, 1H), 7.48 (d, J=8.8 Hz, 2H), 7.37 (d, J=8.4 Hz, 2H), 7.08-7.05 (m, 2H), 7.04-6.96 (m, 3H), 5.73 (s, 1H), 5.10 (d, J=2.4 Hz, 1H), 4.49 (s, 1H), 3.88 (s, 3H), 3.80 (d, J=14.0 Hz, 1H), 3.24-3.21 (m, 1H), 2.65-2.55 (m, 2H), 2.48-2.21 (m, 6H), 2.18 (s, 3H), 2.10-2.05 (m, 1H).

Example 69

Rac-4-((4bS,5R,6S,7S,7aR)-4b,5-dihydroxy-4-methoxy-6-((methylamino)methyl)-7-phenyl-4b,5,6,7-tetrahydro-7aH-cyclopenta[4,5]furo[2,3-c]pyridin-7a-yl)benzonitrile (Cpd. No. 69F)

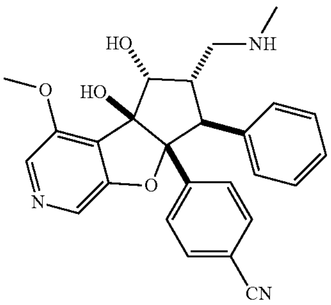

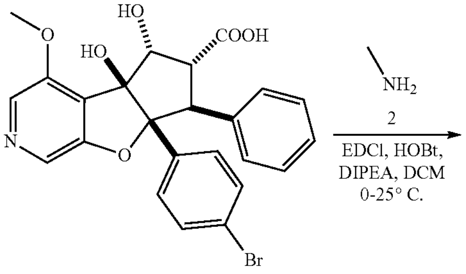

1

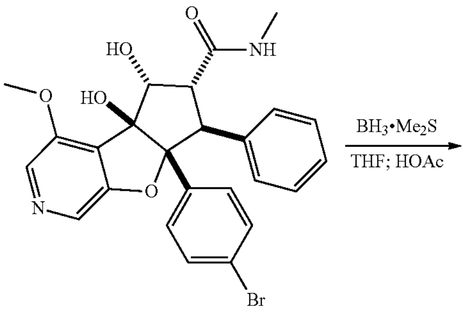

3

-continued

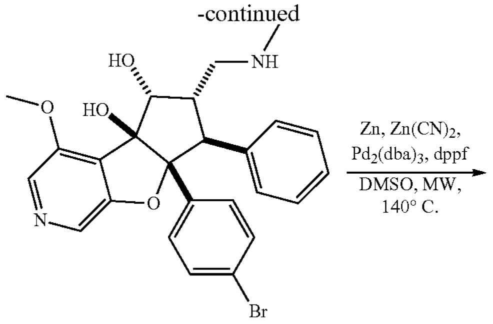

4

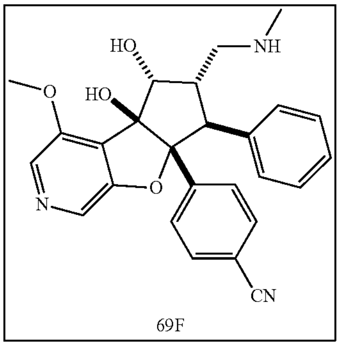

69F

Synthesis of rac-(4bS,5R,6R,7S,7aR)-7a-(4-bromophenyl)-4b,5-dihydroxy-4-methoxy-N-methyl-7-phenyl-4b,6,7,7a-tetrahydro-5H-cyclopenta[4,5]furo[2,3-c]pyridine-6-carboxamide (3)

To a solution of rac-(4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylic acid (1, 2.00 g, 4.01 mmol) in dichloromethane (10 mL) was added 1-ethyl-3-(3-dimethylaminopropyl)carbodiimide hydrogen chloride (1.54 g, 8.03 mmol), 1-hydroxybenzotriazole (1.08 g, 8.03 mmol) and N,N-diisopropylethylamine (2.07 g, 16.05 mmol, 2.8 mL) at 0° C. and the mixture was stirred at 0° C. for 30 minutes. Then methanamine (453.66 mg, 4.82 mmol, 33% in methanol) was added and the mixture was stirred at 25° C. for 12 h. LCMS showed there was desired product detected. The reaction mixture was diluted with dichloromethane (20 mL) and washed with water (60 mL×3). The organic phase was dried over anhydrous sodium sulfate and concentrated in vacuum. The crude was purified by column chromatography (dichloromethane/methanol=20:1) to afford the product rac-(4bS,5R,6R,7S,7aR)-7a-(4-bromophenyl)-4b,5-dihydroxy-4-methoxy-N-methyl-7-phenyl-4b,6,7,7a-tetrahydro-5H-cyclopenta[4,5]furo[2,3-c]pyridine-6-carboxamide (3) as a white solid. Yield: 1.86 g, 72% yield; MS (ESI) m/z 511.0 $[M+1]^+$.

Synthesis of rac-(4bS,5R,6S,7S,7aR)-7a-(4-bromophenyl)-4-methoxy-6-((methylamino)methyl)-7-phenyl-5,6,7,7a-tetrahydro-4bH-cyclopenta[4,5]furo[2,3-c]pyridine-4b,5-diol (4)

To a solution of rac-(4bS,5R,6R,7S,7aR)-7a-(4-bromophenyl)-4b,5-dihydroxy-4-methoxy-N-methyl-7-phenyl-4b,6,7,7a-tetrahydro-5H-cyclopenta[4,5]furo[2,3-c]pyridine-6-carboxamide (3, 1.86 g, 3.64 mmol) in tetrahydrofuran (40 mL) was added borane dimethyl sulfide complex solution (10 M, 3.64 mL) at 0° C. and the mixture was stirred at 25° C. for 30 min. Then the mixture was refluxed at 60° C. for 2 h. TLC (dichloromethane/methanol=10:1) showed there was no starting material left. The reaction mixture was quenched with acetic acid (5 mL) at 0° C. and the mixture was reflux at 60° C. for 1 h. The reaction mixture was concentrated and washed with petroleum/ethyl acetate=2:1 (30 mL) and filtered. The filter-cake was diluted with water (30 mL) and extracted with ethyl acetate (10 mL×2). The water phase was adjusted pH=7-8 with saturated sodium bicarbonate and then extracted with ethyl acetate (20 mL×3). The combined organic phase was dried over anhydrous sodium sulfate and concentrated in vacuum to afford the product rac-(4bS,5R,6S,7S,7aR)-7a-(4-bromophenyl)-4-methoxy-6-((methylamino)methyl)-7-phenyl-5,6,7,7a-tetrahydro-4bH-cyclopenta[4,5]furo[2,3-c]pyridine-4b,5-diol (4) as a white solid. Yield: 1.45 g, 69%; MS (ESI) m/z 497.0 $[M+1]^+$; $^1$H NMR (400 MHz, DMSO-$d_6$) δ 8.05 (s, 1H), 7.98 (s, 1H), 7.24 (d, J=8.8 Hz, 2H), 7.13-7.08 (m, 4H), 7.03-7.01 (m, 3H), 5.68 (s, 1H), 4.59 (d, J=4.0 Hz, 1H), 3.89 (s, 3H), 3.72 (d, J=14.4 Hz, 1H), 3.23-3.17 (m, 3H), 2.81-2.78 (m, 1H), 2.57-2.53 (m, 1H), 2.37 (s, 3H).

Synthesis of rac-4-((4bS,5R,6S,7S,7aR)-4b,5-dihydroxy-4-methoxy-6-((methylamino)methyl)-7-phenyl-4b,5,6,7-tetrahydro-7aH-cyclopenta[4,5]furo[2,3-c]pyridin-7a-yl)benzonitrile (Cpd. No. 69F)

To a solution of rac-(4bS,5R,6S,7S,7aR)-7a-(4-bromophenyl)-4-methoxy-6-((methylamino)methyl)-7-phenyl-5,6,7,7a-tetrahydro-4bH-cyclopenta[4,5]furo[2,3-c]pyridine-4b,5-diol (4, 300 mg, 0.60 mmol) in dimethyl sulfoxide (3 mL) was added zinc cyanide (283 mg, 2.41 mmol), zinc (79 mg, 1.21 mmol) at 25° C. and the reaction mixture was degassed with nitrogen for 15 min. 1,1'-Bis(diphenylphosphino)ferrocene (67 mg, 0.12 mmol) and tris(dibenzylideneacetone)dipalladium (110 mg, 0.12 mmol) was added and the mixture was stirred in microwave (100 w, 140° C., 150 psi) for 2 h. LCMS showed desired product. The reaction mixture was filtered and the filtrate was concentrated in vacuum. The crude was purified by column chromatography (dichloromethane/methanol=10:1), monitored by LCMS. Then the crude was purified by Prep-HPLC (Phenomenex Gemini C18 250×50 mm×10 um; mobile phase: [water (0.05% ammonia hydroxide v/v)—acetonitrile]; B %: 37%-62%, 30 min, 69% min) to afford the product rac-4-((4bS,5R,6S,7S,7aR)-4b,5-dihydroxy-4-methoxy-6-((methylamino)methyl)-7-phenyl-4b,5,6,7-tetrahydro-7aH-cyclopenta[4,5]furo[2,3-c]pyridin-7a-yl)benzonitrile (Cpd. No. 69F) as a white solid. Yield: 99 mg, 37%; MS (ESI) m/z 444.2 $[M+1]^+$; HPLC: 99.81%; $^1$H NMR (400 MHz, DMSO-$d_6$) δ 8.06 (s, 1H), 7.98 (s, 1H), 7.49 (d, J=8.0 Hz, 2H), 7.36 (d, J=8.4 Hz, 2H), 7.09-7.05 (m, 2H), 7.01-6.99 (m, 3H), 5.73 (s, 1H), 4.56 (d, J=3.6 Hz, 1H), 3.89 (s, 3H), 3.82 (d, J=14.0 Hz, 1H), 3.20-3.14 (m, 1H), 2.69-2.66 (m, 1H), 2.27 (s, 3H).

Example 70

Rac-4-((4bS,5R,6S,7S,7aR)-6-((ethylamino)methyl)-4b,5-dihydroxy-4-methoxy-7-phenyl-4b,5,6,7-tetrahydro-7aH-cyclopenta[4,5]furo[2,3-c]pyridin-7a-yl)cyclohexa-1,3-diene-1-carbonitrile (Cpd. No. 70F)

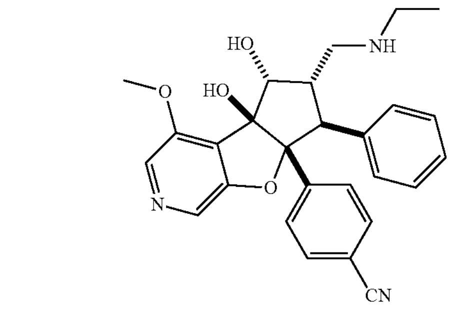

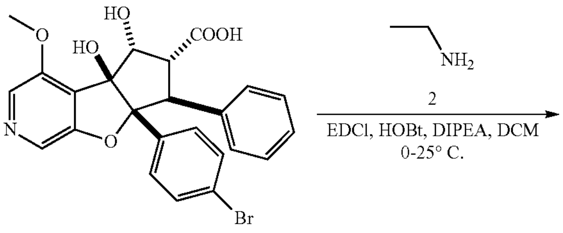

1

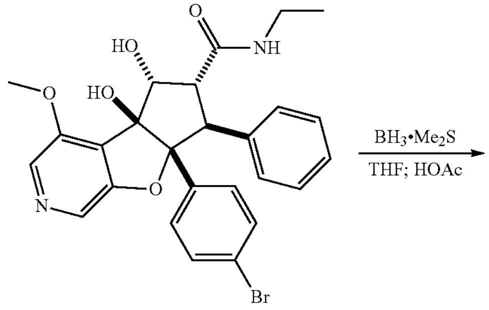

3

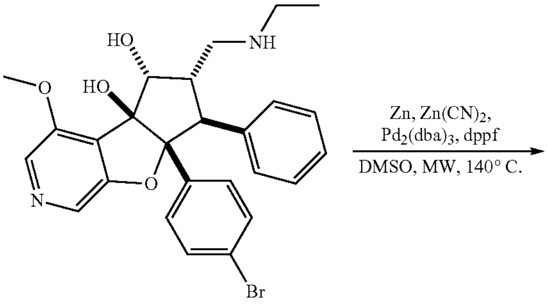

4

-continued

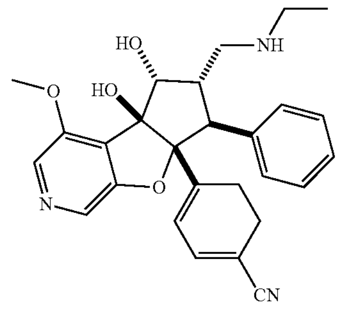

70F

Synthesis of rac-(4bS,5R,6R,7S,7aR)-7a-(4-bromophenyl)-N-ethyl-4b,5-dihydroxy-4-methoxy-7-phenyl-4b,6,7,7a-tetrahydro-5H-cyclopenta[4,5]furo[2,3-c]pyridine-6-carboxamide (3)

To a solution of rac-(4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylic acid (1, 2.00 g, 4.01 mmol) in dichloromethane (10 mL) was added 1-(3-dimethylaminopropyl)-3-ethylcarbodiimide hydrochloride (1.54 g, 8.02 mmol), 1-hydroxybenzotriazole (1.08 g, 8.02 mmol) and N,N-diisopropylethylamine (2.07 g, 16.04 mmol, 2.8 mL) and the mixture was stirred at 0° C. for 30 min. Then ethanamine (217 mg, 4.81 mmol) was added and the mixture was stirred at 25° C. for 12 h. LCMS showed there was desired product detected. The reaction mixture was diluted with dichloromethane (30 mL) and washed with water (100 mL×3). The organic phase was dried over anhydrous sodium sulfate and concentrated in vacuum. The crude was purified by column chromatography (dichloromethane/methanol=20:1) to afford the product rac-(4bS,5R,6R,7S,7aR)-7a-(4-bromophenyl)-N-ethyl-4b,5-dihydroxy-4-methoxy-7-phenyl-4b,6,7,7a-tetrahydro-5H-cyclopenta[4,5]furo[2,3-c]pyridine-6-carboxamide (3) as a white solid. Yield: 1.7 g, 78%; MS (ESI) m/z 525.0 $[M+1]^+$.

Synthesis of rac-(4bS,5R,6S,7S,7aR)-7a-(4-bromophenyl)-6-((ethylamino)methyl)-4-methoxy-7-phenyl-5,6,7,7a-tetrahydro-4bH-cyclopenta[4,5]furo[2,3-c]pyridine-4b,5-diol (4)

To a solution of rac-(4bS,5R,6R,7S,7aR)-7a-(4-bromophenyl)-N-ethyl-4b,5-dihydroxy-4-methoxy-7-phenyl-4b,6,7,7a-tetrahydro-5H-cyclopenta[4,5]furo[2,3-c]pyridine-6-carboxamide (3, 1.70 g, 3.24 mmol) in tetrahydrofuran (10 mL) was added borane dimethyl sulfide complex solution (10 M, 3.24 mL) at 0° C. and the mixture was stirred at 25° C. for 30 min. Then the mixture was reflux at 60° C. for 2 h. TLC (dichloromethane/methanol=10:1) showed there was no starting material left. The reaction mixture was quenched with acetic acid (5 mL) at 0° C. and the mixture was reflux at 60° C. for 1 h. The reaction mixture was concentrated, washed with petroleum/ethyl acetate=2:1 (30 mL) and filtered. The filter-cake was diluted with water (30 mL) and extracted with ethyl acetate (10 mL×2). The aqueous layer was adjusted pH=7-8 with saturated sodium bicarbonate, extracted with ethyl acetate (20 mL×3). The combined organic layer was dried over anhydrous sodium sulfate and concentrated in vacuum to afford the product rac-(4bS,5R, 6S,7S,7aR)-7a-(4-bromophenyl)-6-((ethylamino)methyl)-4-methoxy-7-phenyl-5,6,7,7a-tetrahydro-4bH-cyclopenta[4,5]furo[2,3-c]pyridine-4b,5-diol (4) as a yellow solid. Yield: 1.20 g, 69%; MS (ESI) m/z 511.0 $[M+1]^+$.

Synthesis of rac-4-((4bS,5R,6S,7S,7aR)-6-((ethylamino)methyl)-4b,5-dihydroxy-4-methoxy-7-phenyl-4b,5,6,7-tetrahydro-7aH-cyclopenta[4,5]furo[2,3-c]pyridin-7a-yl)cyclohexa-1,3-diene-1-carbonitrile (Cpd. No. 70F)

To a solution of rac-(4bS,5R,6S,7S,7aR)-7a-(4-bromophenyl)-6-((ethylamino)methyl)-4-methoxy-7-phenyl-5,6,7,7a-tetrahydro-4bH-cyclopenta[4,5]furo[2,3-c]pyridine-4b,5-diol (4, 500 mg, 0.98 mmol) in dimethyl sulfoxide (2 mL) was added zinc cyanide (459 mg, 3.91 mmol), zinc (64 mg, 0.98 mmol) and the reaction mixture was degassed with nitrogen for 15 min. 1,1'-Bis(diphenylphosphino)ferrocene (54 mg, 0.098 mmol) and tris(dibenzylideneacetone)dipalladium (56 mg, 0.098 mmol) was added and the mixture was stirred in microwave (100 w, 140° C., 150 psi) for 2 h. LCMS showed there was desired product detected. The reaction mixture was filtered and the filtrate was concentrated in vacuum. The residue was purified by column chromatography (dichloromethane/methanol=10:1) to give the crude which was further purified by Prep-HPLC (Phenomenex Gemini C18 250×50 mm×10 um; mobile phase: [water (0.05% ammonia hydroxide v/v)—acetonitrile]; B %: 37%-62%, 30 min, 69% min) to afford the product rac-4-((4bS,5R,6S,7S,7aR)-6-((ethylamino)methyl)-4b,5-dihydroxy-4-methoxy-7-phenyl-4b,5,6,7-tetrahydro-7aH-cyclopenta[4,5]furo[2,3-c]pyridin-7a-yl)cyclohexa-1,3-diene-1-carbonitrile (Cpd. No. 70F) as a white solid. Yield: 174 mg, 38%; MS (ESI) m/z 458.2 $[M+1]^+$; HPLC: 97.93%; $^1H$ NMR (400 MHz, DMSO-$d_6$) δ 8.06 (s, 1H), 7.98 (s, 1H), 7.49 (d, J=8.4 Hz, 2H), 7.37 (d, J=8.4 Hz, 2H), 7.10-7.05 (m, 2H), 7.01-6.88 (m, 3H), 5.68 (s, 1H), 4.55 (d, J=4.4 Hz, 1H), 3.89 (s, 3H), 3.83 (d, J=14.4 Hz, 1H), 3.17-3.13 (m, 1H), 2.55-2.53 (m, 1H), 2.51-2.50 (m, 1H), 2.49-2.46 (m, 1H), 0.97 (t, J=7.2 Hz, 3H).

Example 71

Rac-4-((4bS,5R,6S,7S,7aR)-6-(azetidin-1-ylmethyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 71F)

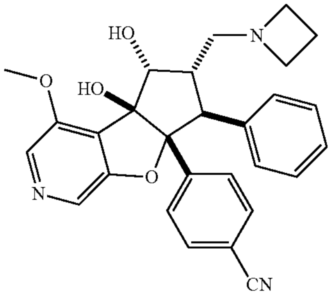

-continued

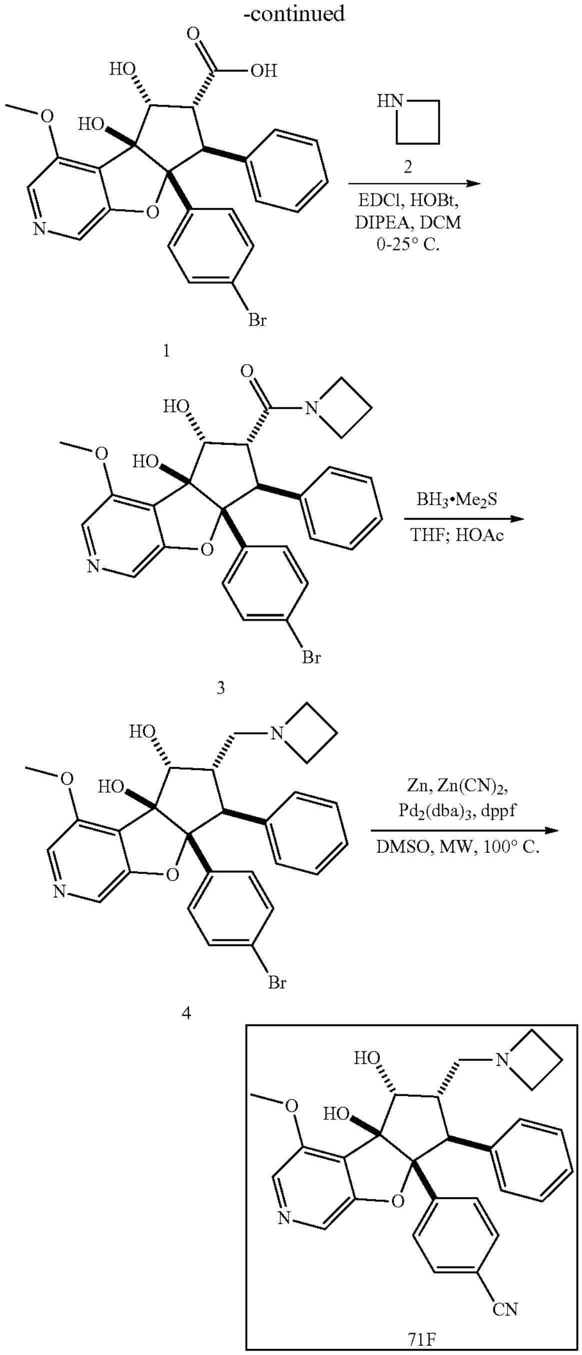

Synthesis of rac-azetidin-1-yl((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)methanone (3)

A mixture of rac-(4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylic acid (1, 3.00 g, 6.02 mmol), 1-hydroxybenzotriazole (3.25 g, 24.1 mmol), 1-ethyl-3-(3-dimethylaminopropyl)carbodiimide hydrogen chloride (2.31 g, 12.0 mmol) and N,N-diisopropylethylamine (1.56 g, 12.0 mmol, 2.1 mL) in dichloromethane (40 mL) was stirred at 0° C. for 15 min and 25°

C. for 30 min. Then azetidine (844 mg, 9.03 mmol, hydrogen chloride salt) was added and the mixture was stirred at 25° C. for 2 h. The mixture was diluted with water (40 mL), extracted with dichloromethane (40 mL×3). The combined extracts were washed with water (40 mL×2), brine (40 mL), evaporated in vacuo to get crude product. Chromatograph column (methanol/dichloromethane from 0% to 5%) gave rac-azetidin-1-yl((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)methanone (3) as a yellow solid. Yield: 2.50 g, 76%; MS(ESI+) m/z 537.0 $[M+1]^+$; $^1H$ NMR (DMSO-$d_6$, 400 MHz) δ 8.09 (s, 1H), 7.99 (s, 1H), 7.20 (d, J=8.8 Hz, 2H), 7.08-7.03 (m, 4H), 6.94-6.91 (m, 3H), 5.70 (s, 2H), 5.15 (d, J=5.2 Hz, 1H1), 4.66 (t, J=5.2 Hz, 1H), 4.54-4.50 (m, 1H), 4.39-4.35 (m, 2H), 3.88 (s, 3H), 3.88-3.80 (m, 3H), 2.33-2.19 (m, 2H).

Synthesis of rac-(4bS,5R,6S,7S,7aR)-6-(azetidin-1-ylmethyl)-7a-(4-bromophenyl)-4-methoxy-7-phenyl-5,6,7,7a-tetrahydro-4bH-cyclopenta[4,5]furo[2,3-c]pyridine-4b,5-diol (4)

To a mixture of rac-azetidin-1-yl((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)methanone (3, 1.50 g, 2.79 mmol) in tetrahydrofuran (20 mL) was added borane-methyl sulfide complex (10 M, 2.8 mL) drop-wise at 0° C. for 15 min and the mixture was stirred at 60° C. for 4 h. The desired product can be detected and no starting material by TLC. The mixture was cooled to 0° C., quenched with acetic acid (6 mL) drop-wise and stirred at 25° C. for 0.5 h and 60° C. for 1 h. The resulting solution was concentrated under reduced pressure to give the crude product. The crude product was dissolved in water (40 mL), extracted with methyl tert-butyl ether (40 mL×2). The water phase was adjusted pH=8 with sodium bicarbonate (solid), extracted with ethyl acetate (40 mL×3). The combined extracts were washed with water (40 mL×2), brine(40 mL), evaporated in vacuo to afford rac-(4bS,5R,6S,7S,7aR)-6-(azetidin-1-ylmethyl)-7a-(4-bromophenyl)-4-methoxy-7-phenyl-5,6,7,7a-tetrahydro-4bH-cyclopenta[4,5]furo[2,3-c]pyridine-4b,5-diol (4) as a white solid. Yield: 1.30 g, 88%; MS (ESI+) m/z 525.1 $[M+1]^+$. $^1H$ NMR (DMSO-$d_6$, 400 MHz) δ 8.01 (s, 1H), 7.95 (s, 1H), 7.21 (d, J=8.8 Hz, 2H), 7.12-7.08 (m, 4H), 7.03-6.96 (m, 3H), 5.60 (s, 1H), 4.46 (d, J=3.6 Hz, 1H), 3.88 (s, 3H), 3.77-3.72 (m, 1H), 3.11-3.05 (m, 4H), 2.95-2.85 (m, 1H), 2.67-2.51 (m, 2H), 1.93-1.88 (m, 2H).

Synthesis of rac-4-((4bS,5R,6S,7S,7aR)-6-(azetidin-1-ylmethyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 71F)

Rac-(4bS,5R,6S,7S,7aR)-6-(azetidin-1-ylmethyl)-7a-(4-bromophenyl)-4-methoxy-7-phenyl-5,6,7,7a-tetrahydro-4bH-cyclopenta[4,5]furo[2,3-c]pyridine-4b,5-diol (4, 300 mg, 573 umol), 1,1'-Bis(diphenylphosphino)ferrocene (64 mg, 114 umol), zinc (38 mg, 573 umol), zinc cyanide (673 mg, 5.73 mmol) and tris(dibenzylideneacetone)dipalladium (105 mg, 115 umol) in dimethyl sulphoxide (3 mL) was stirred at microwave (100° C., 140 W) for 2.5 h under nitrogen. The desired product can be detected by LCMS. The mixture was directly purified by column chromatography (methanol/dichloromethane from 0% to 10%) to give the crude product (100 mg as a brown oil). The crude was purified by Prep-HPLC (column: Phenomenex Gemini C18 250*21.2 mm*5 um; mobile phase: [water (0.05% ammonia hydroxide v/v)–acetonitrile]; B %: 32%-62%, 12 min) and lyophilized to give rac-4-((4bS,5R,6S,7S,7aR)-6-(azetidin-1-ylmethyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 71F). Yield: 10 mg, 4%; MS (ESI+) m/z 470.2 $[M+1]^+$; HPLC: 100%; $^1H$ NMR (DMSO-$d_6$, 400 MHz) δ 8.05 (s, 1H), 7.97 (s, 1H), 7.49 (d, J=8.4 Hz, 2H), 7.35 (d, J=8.8 Hz, 2H), 7.11-7.07 (m, 2H), 7.03-6.99 (m, 3H), 5.72 (s, 1H), 5.66 (brs, 1H), 4.48 (d, J=4.0 Hz, 1H), 3.88 (s, 3H), 3.82 (d, J=14.0 Hz, 1H), 3.14-3.08 (m, 4H), 2.95-2.85 (m, 1H), 2.70-2.60 (m, 1H), 2.38-2.36 (m, 1H), 1.92 (t, J=6.8 Hz, 2H).

Example 72

Rac-4-((4bS,5R,6S,7S,7aR)-4b,5-dihydroxy-4-methoxy-7-phenyl-6-(pyrrolidin-1-ylmethyl)-4b,5,6,7-tetrahydro-7aH-cyclopenta[4,5]furo[2,3-c]pyridin-7a-yl)benzonitrile (Cpd. No. 72F)

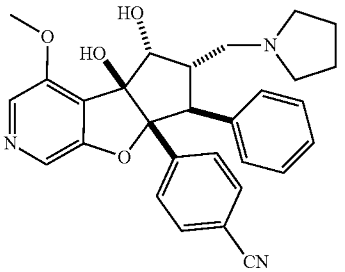

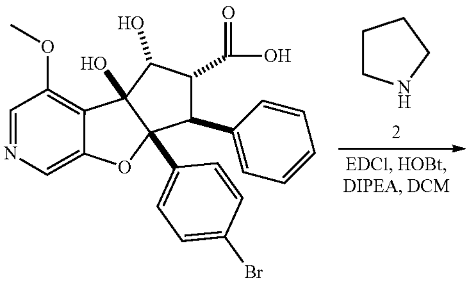

1

2

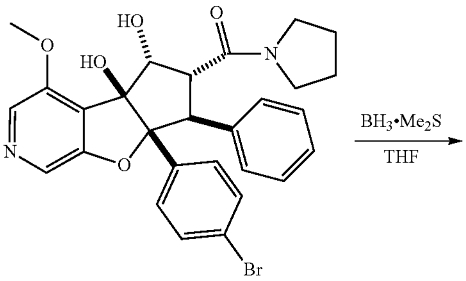

3

-continued

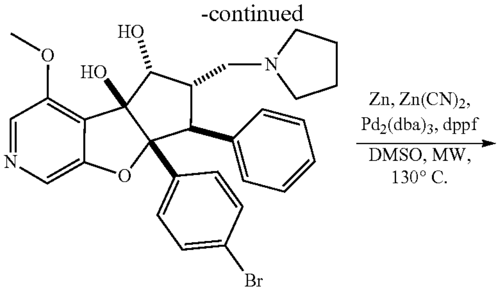

4

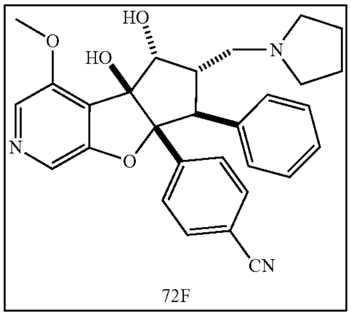

72F

Synthesis of rac-((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)(pyrrolidin-1-yl)methanone (3)

To a suspension of rac-(4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylic acid (1, 2.00 g, 4.01 mmol) in dichloromethane (30 mL) was added 1-(3-dimethylaminopropyl)-3-ethylcarbodiimide hydrochloride (1.54 g, 8.02 mmol), 1-hydroxybenzotriazole (1.08 g, 8.02 mmol) and N,N-diisopropylethylamine (2.07 g, 16.04 mmol) at 0° C. After stirred for 1 h at 25° C., pyrrolidine (570 mg, 8.02 mmol) was added and the reaction was stirred at 25° C. for 14 h. TLC (dichloromethane/methanol=20/1) indicated the RI was consumed. The reaction suspension was diluted with water (80 mL) and dichloromethane (80 mL). The insoluble was collected by filtration as the product as white solid. The suspension was extracted with dichloromethane (30 mL×3) and the combined organic layer was concentrated to give a residue. The residue was purified by column chromatography (dichloromethane/methanol=20/1) to afford the product rac-((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)(pyrrolidin-1-yl)methanone (3) as white solid. Yield: 2.2 g, 90%; MS (ESI) m/z 551.1 [M+1]$^+$.

Synthesis of rac-(4bS,5R,6S,7S,7aR)-7a-(4-bromophenyl)-4-methoxy-7-phenyl-6-(pyrrolidin-1-ylmethyl)-5,6,7,7a-tetrahydro-4bH-cyclopenta[4,5]furo[2,3-c]pyridine-4b,5-diol (4)

To a suspension of rac-((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)(pyrrolidin-1-yl)methanone (3, 2.20 g, 3.99 mmol) in tetrahydrofuran (40 mL) was added borane dimethyl sulfide complex (10 M, 1.99 mL) dropwise at 25° C. After 10 min, the suspension was heated at 65° C. for 3 h. LCMS indicated the reaction completed. The reaction was quenched by the addition of acetic acid (20 mL) dropwise at 25° C. and the resulting solution was stirred at 65° C. for 1 h. The solution was concentrated under reduced pressure and the residue was diluted with water (20 mL). It was extracted with methyl t-butyl ether (20 mL×2) and the resulting aqueous layer was neutralized by saturated aqueous sodium bicarbonate to pH=9. The aqueous layer was extracted with dichloromethane (20 mL×3). The combined organic layer was dried over anhydrous sodium sulfate, concentrated under reduced pressure to afford the desired product rac-(4bS,5R,6S,7S,7aR)-7a-(4-bromophenyl)-4-methoxy-7-phenyl-6-(pyrrolidin-1-ylmethyl)-5,6,7,7a-tetrahydro-4bH-cyclopenta[4,5]furo[2,3-c]pyridine-4b,5-diol (4) as white solid. Yield: 1.2 g, 51.8%; MS (ESI) m/z 537.1 [M+1]$^+$.

Synthesis of rac-4-((4bS,5R,6S,7S,7aR)-4b,5-dihydroxy-4-methoxy-7-phenyl-6-(pyrrolidin-1-ylmethyl)-4b,5,6,7-tetrahydro-7aH-cyclopenta[4,5]furo[2,3-c]pyridin-7a-yl)benzonitrile (Cpd. No. 72F)

A solution of rac-(4bS,5R,6S,7S,7aR)-7a-(4-bromophenyl)-4-methoxy-7-phenyl-6-(pyrrolidin-1-ylmethyl)-5,6,7,7a-tetrahydro-4bH-cyclopenta[4,5]furo[2,3-c]pyridine-4b,5-diol (4, 500 mg, 930 umol), 1,1'bis(diphenylphosphino)ferrocene (52 mg, 93 umol), tris(dibenzylideneacetone)dipalladium(0) (85 mg, 93 umol), zinc powder (61 mg, 930 umol), zinc cyanide (546 mg, 4.65 mmol) in dimethyl sulfoxide (2 mL) was stirred under nitrogen at microwave (150 psi, 40 W) at 140° C. for 2 h. The mixture was filtered and filtrate was purified by column chromatography (dichloromethane:methanol=100:1 to 10:1) to afford rac-4-((4bS,5R,6S,7S,7aR)-4b,5-dihydroxy-4-methoxy-7-phenyl-6-(pyrrolidin-1-ylmethyl)-4b,5,6,7-tetrahydro-7aH-cyclopenta[4,5]furo[2,3-c]pyridin-7a-yl)benzonitrile (Cpd. No. 72F) as a pink solid. Yield: 199 mg, 44%; MS (ESI) m/z 484.2 [M+1]$^+$; HPLC: 95.065%; $^1$H NMR (400 MHz, DMSO-d$_6$) δ 9.52 (brs, 1H), 8.10 (s, 1H), 8.03 (s, 1H), 7.53 (d, J=8.8 Hz, 2H), 7.41 (d, J=8.4 Hz, 2H), 7.15-7.03 (m, 5H), 5.92 (s, 1H), 5.36 (d, J=5.6 Hz, 1H), 4.72 (t, J=5.6 Hz, 1H), 3.91 (s, 3H), 3.82 (d, J=13.6 Hz, 2H), 3.70-3.59 (m, 1H), 3.54-3.42 (m, 1H), 3.17-3.04 (m, 2H), 2.95-2.86 (m, 1H), 2.10-1.88 (m, 4H).

Example 73

4-((4bS,5R,6S,7S,7aR)-6-((diethylamino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 73F)

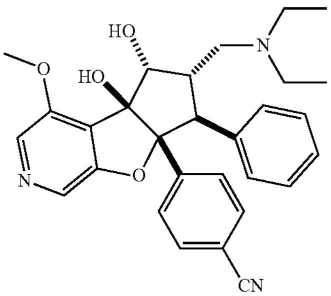

-continued

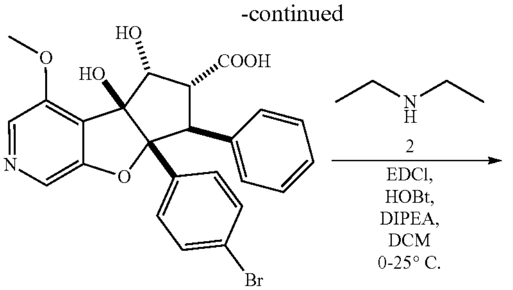

1

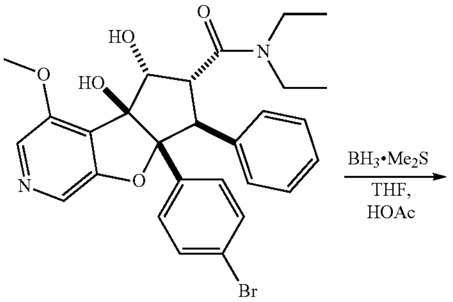

3

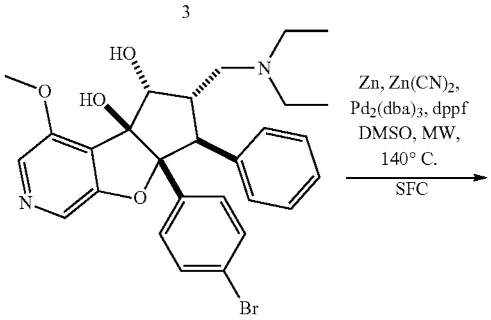

4

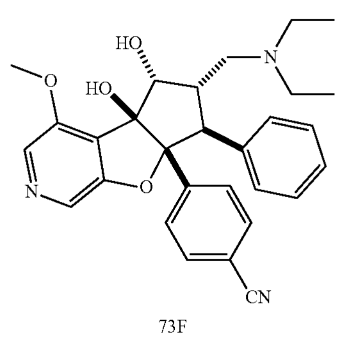

73F

Synthesis of rac-(4bS,5R,6R,7S,7aR)-7a-(4-bromophenyl)-N,N-diethyl-4b,5-dihydroxy-4-methoxy-7-phenyl-4b,6,7,7a-tetrahydro-5H-cyclopenta[4,5]furo[2,3-c]pyridine-6-carboxamide (3)

To a solution of rac-(4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylic acid (1, 1.50 g, 3.01 mmol) in dichloromethane (10 mL) was added 1-ethyl-3-(3-dimethylaminopropyl)carbodiimide hydrogen chloride (1.15 g, 6.02 mmol), 1-hydroxybenzotriazole (813 mg, 6.02 mmol) and N,N-diisopropylethylamine (2.33 g, 18.06 mmol, 3.15 mL) at 0° C. and the mixture was stirred at 0° C. for 30 minutes. Then N-ethylethanamine (495 mg, 4.51 mmol, hydrochloride) was added and the mixture was stirred at 25° C. for 12 h. LCMS showed there was desired product detected. The reaction mixture was washed with water (30 mL×3). The organic layer was dried over anhydrous sodium sulfate and concentrated in vacuum to give the crude. The crude was purified by column chromatography (dichloromethane:methanol=20:1) to afford the product rac-(4bS,5R,6R,7S,7aR)-7a-(4-bromophenyl)-N,N-diethyl-4b,5-dihydroxy-4-methoxy-7-phenyl-4b,6,7,7a-tetrahydro-5H-cyclopenta[4,5]furo[2,3-c]pyridine-6-carboxamide (3) as a yellow solid. Yield: 1.00 g, 54.82% yield; MS (ESI) m/z 555.1 $[M+1]^+$.

Synthesis of rac-(4bS,5R,6S,7S,7aR)-7a-(4-bromophenyl)-6-((diethylamino)methyl)-4-methoxy-7-phenyl-5,6,7,7a-tetrahydro-4bH-cyclopenta[4,5]furo[2,3-c]pyridine-4b,5-diol (4)

To a solution of rac-(4bS,5R,6R,7S,7aR)-7a-(4-bromophenyl)-N,N-diethyl-4b,5-dihydroxy-4-methoxy-7-phenyl-4b,6,7,7a-tetrahydro-5H-cyclopenta[4,5]furo[2,3-c]pyridine-6-carboxamide (3, 1.00 g, 1.81 mmol) dissolved in tetrahydrofuran (10 mL) was added borane dimethyl sulfide complex solution (10 mol/L, 1.81 mL) at 0° C. and the mixture was stirred at 25° C. for 30 min. Then the mixture was reflux at 60° C. for 2 h. LCMS showed there was no starting material. The reaction mixture was quenched with acetic acid (3 mL) at 0° C. and the mixture was reflux at 60° C. for 1 h. LCMS showed there was desired product detected. The reaction mixture was concentrated and the residue was washed with petroleum: ethyl acetate=2:1 (30 mL) and filtered. The filter cake was diluted with water (30 mL) and extracted with ethyl acetate (10 mL×2). The aqueous layer was adjusted pH=7-8 with saturated sodium bicarbonate solution and then extracted with ethyl acetate (20 mL×3). The combined organic layer was dried over anhydrous sodium sulfate, filtered and concentrated in vacuum to afford the product rac-(4bS,5R,6S,7S,7aR)-7a-(4-bromophenyl)-6-((diethylamino)methyl)-4-methoxy-7-phenyl-5,6,7,7a-tetrahydro-4bH-cyclopenta[4,5]furo[2,3-c]pyridine-4b,5-diol (4) as a white solid. Yield: 620 mg, 56.35%; MS (ESI) m/z 539.1 $[M+1]^+$.

Synthesis of 4-((4bS,5R,6S,7S,7aR)-6-((diethylamino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 73F)

A mixture of rac-(4bS,5R,6S,7S,7aR)-7a-(4-bromophenyl)-6-((diethylamino)methyl)-4-methoxy-7-phenyl-5,6,7,7a-tetrahydro-4bH-cyclopenta[4,5]furo[2,3-c]pyridine-4b,5-diol (4, 30 mg, 55.6 umol), zinc powder (4 mg, 55.6 umol), tris(dibenzylideneacetone)dipalladium(0) (5 mg, 5.56 umol), bis(diphenylphosphino)ferrocene (3 mg, 5.56 umol) and zinc cyanide (65 mg, 556 umol) in dimethyl sulfoxide (1 mL) was stirred at 130° C. under nitrogen in microwave (150 Psi, 40 W) for 1 h. The reaction mixture was directly purified by silica gel chromatography (dichloromethane: methanol=20:1 to 10:1) to give the product, which were separated by chiral Prep-HPLC (AD—3S_5_40_3.0 mL Column: Chiralpak AD—3 100×4.6 mm I.D, 3 um Mobile phase: 40% ethanol (0.05% DEA) in $CO_2$ Flow rate: 3.0 mL/min AD—3S_4_5_40_3 mL; Column: Chiralpak AD—3 100×4.6 mm I.D, 3 um Mobile phase: iso-propanol (0.05% DEA) in $CO_2$ from 5% to 40% Flow rate: 3 mL/min Wavelength: 220 nm) to afford two enantiomers. The two enantiomers were further purified by Prep-HPLC (column:

Phenomenex Gemini C18 250×21.2 mm×5 um; mobile phase: [water (0.05% ammonia hydroxide v/v)—acetonitrile]; B %: 41%-71%, 12 min) to give the two pure products 4-((4bS,5R,6S,7S,7aR)-6-((diethylamino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 73F); Peak 1 (Cpd. No. 73, 1.1 mg), Yield: 4.07%; $[\alpha]_D$−13.228° (c 0.08, $CHCl_3$), $R_t$=0.562 min, ee=100%; MS (ESI) m/z 486.2 $[M+1]^+$; HPLC: 99.90%; $^1$H NMR (400 MHz, DMSO-$d_6$) δ 8.05 (s, 1H), 7.97 (s, 1H), 7.49 (d, J=8.4 Hz, 2H), 7.37 (d, J=8.4 Hz, 2H), 7.09-7.05 (m, 2H), 7.02-6.99 (m, 3H), 5.71 (s, 1H), 5.20 (s, 1H), 4.50 (d, J=3.2 Hz, 1H), 3.88 (s, 3H), 3.84 (d, J=14.4 Hz, 1H), 3.20-3.16 (m, 1H), 2.62-2.52 (m, 3H), 2.49-2.44 (m, 2H), 2.30-2.25 (m, 1H), 0.94 (t, J=7.2 Hz, 6H); Peak 2 (Cpd. No. 73, 2.2 mg), Yield: 8.15%; $[\alpha]_D$+10.0960 (c 0.08, $CHCl_3$), +3.039° (c 0.08, methanol), $R_t$=1.317 min, ee=99.72%; MS (ESI) m/z 486.2 $[M+1]^+$; HPLC: 100%; $^1$H NMR (400 MHz, DMSO-$d_6$) δ: 8.05 (s, 1H), 7.97 (s, 1H), 7.49 (d, J=8.8 Hz, 2H), 7.37 (d, J=8.4 Hz, 2H), 7.09-7.05 (m, 2H), 7.02-6.99 (m, 3H), 5.73 (s, 1H), 5.22 (s, 1H), 4.50 (s, 1H), 3.88 (s, 3H), 3.84 (d, J=14.0 Hz, 1H), 3.31-3.25 (m, 1H), 2.62-2.58 (m, 3H), 2.49-2.44 (m, 2H), 2.30-2.25 (m, 1H), 0.94 (t, J=7.2 Hz, 6H).

Example 74

Rac-4-((4bS,5R,6S,7S,7aR)-6-((ethyl(methyl)amino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 74F)

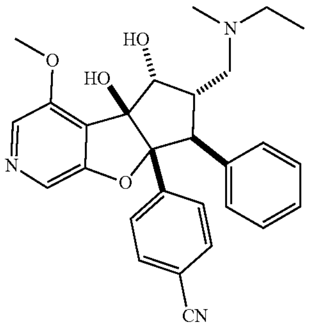

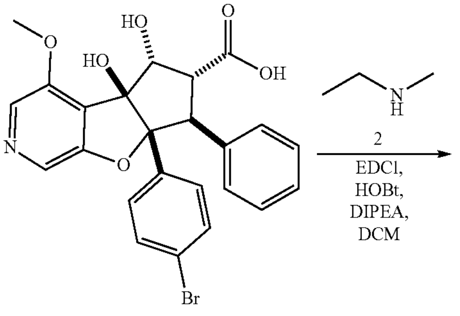

1

-continued

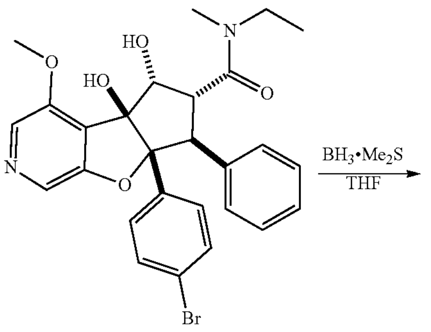

3

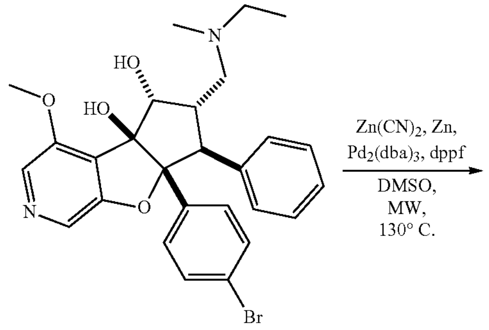

4

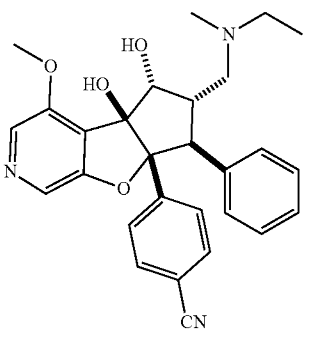

74F

Synthesis of rac-(4bS,5R,6R,7S,7aR)-7a-(4-bromophenyl)-N-ethyl-4b,5-dihydroxy-4-methoxy-N-methyl-7-phenyl-4b,6,7,7a-tetrahydro-5H-cyclopenta[4,5]furo[2,3-c]pyridine-6-carboxamide (3)

To a mixture of rac-(4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylic acid (1, 3.00 g, 6.02 mmol) in dichloromethane (45 mL) was added 1-(3-dimethylaminopropyl)-3-ethylcarbodiimide hydrochloride (2.31 g, 12.04 mmol), 1-hydroxybenzotriazole (1.63 g, 12.04 mmol) and N,N-diisopropylethylamine (2.33 g, 18.06 mmol). The mixture was stirred at 0° C. for 10 min, then N-methylethanamine (427 mg, 7.22 mmol) was added and the mixture was stirred at 20° C. for 12 h. The mixture was diluted with dichloromethane (20 mL) and washed with water (20 mL×2). The organic layer was dried and concentrated under reduced pressure to give a residue, which was purified by silica gel chromatography (dichloromethane:methanol=50:1 to 10:1) to afford rac-(4bS,5R,6R,7S,7aR)-7a-(4-bromophenyl)-N-ethyl-4b,5-dihydroxy-4-methoxy-N-methyl-7-phenyl-4b,6,7,7a-tetra-hydro-5H-cyclopenta[4,5]furo[2,3-c]pyridine-6-carboxamide (3) as a light yellow solid. Yield: 2.70 g, 83.15%; MS (ESI) m/z 539.0 $[M+1]^+$. $^1H$ NMR (400 MHz, DMSO-$d_6$) δ 8.10 (s, 1H), 7.99 (s, 1H), 7.22-7.20 (m, 2H), 7.08-7.05 (m, 4H), 7.04-7.02 (m, 1H), 6.89-6.57 (m, 2H), 5.69 (s, 1H), 5.11-5.08 (m, 1H), 4.75-4.71 (m, 1H), 4.49-4.41 (m, 1H), 4.16-4.11 (m, 1H), 3.88 (s, 3H), 3.70-3.56 (m, 1H), 3.26-3.23 (m, 4H), 1.30 (t, J=7.2 Hz, 1H), 0.95 (t, J=7.2 Hz, 2H).

Synthesis of rac-(4bS,5R,6S,7S,7aR)-7a-(4-bromophenyl)-6-((ethyl(methyl)amino)methyl)-4-methoxy-7-phenyl-5,6,7,7a-tetrahydro-4bH-cyclopenta[4,5]furo[2,3-c]pyridine-4b,5-diol (4)

To a solution of rac-(4bS,5R,6R,7S,7aR)-7a-(4-bromophenyl)-N-ethyl-4b,5-dihydroxy-4-methoxy-N-methyl-7-phenyl-4b,6,7,7a-tetrahydro-5H-cyclopenta[4,5]furo[2,3-c]pyridine-6-carboxamide (3, 2.70 g, 5.01 mmol) in tetrahydrofuran (50 mL) was added borane dimethyl sulfide complex (10 M, 5.0 mL) at 0° C. under the nitrogen atmosphere. The mixture was stirred at 0° C. for 30 min, then reflux at 65° C. for 2 h. TLC (dichloromethane: methanol=10:1) showed the starting material was consumed completely. The reaction mixture was cooled to 0° C. and quenched with acetic acid (10 mL). Then the mixture was stirred at 25° C. for 10 min and heated at 60° C. for 1 h. Removed solvent under reduce pressure, the residue was diluted with water (80 mL), washed with methyl tertiary butyl ether (40 mL×2). The water phase was adjusted pH to 8 with saturated sodium bicarbonate solution, extracted with ethyl acetate (50 mL×3). Combined the extracts, washed by brine(40 mL), dried over anhydrous sodium sulfate, filtrated and concentrated to give rac-(4bS,5R,6S,7S,7aR)-7a-(4-bromophenyl)-6-((ethyl(methyl)amino)methyl)-4-methoxy-7-phenyl-5,6,7,7a-tetrahydro-4bH-cyclopenta[4,5]furo[2,3-c]pyridine-4b,5-diol (4) as a white solid. Yield: 1.20 g, 61%; MS (ESI) m/z: 527.0 $[M+1]^+$; $^1H$ NMR (400 MHz, DMSO-$d_6$) δ 8.02 (s, 1H), 7.95 (s, 1H), 7.22-7.20 (m, 2H), 7.13-7.06 (m, 4H), 7.00-6.98 (m, 3H), 5.63 (s, 1H), 4.49 (d, J=4.0 Hz, 1H), 3.88 (s, 3H), 3.75 (d, J=14.0 Hz, 1H), 3.14-3.11 (m, 1H), 2.50-2.49 (m, 1H), 2.49-2.47 (m, 1H), 2.35-2.25 (m, 1H), 2.21 (s, 3H), 2.15-2.05 (m, 1H), 0.95 (t, J=7.2 Hz, 3H).

Synthesis of rac-4-((4bS,5R,6S,7S,7aR)-6-((ethyl(methyl)amino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 74F)

To a mixture of rac-(4bS,5R,6S,7S,7aR)-7a-(4-bromophenyl)-6-((ethyl(methyl)amino)methyl)-4-methoxy-7-phenyl-5,6,7,7a-tetrahydro-4bH-cyclopenta[4,5]furo[2,3-c]pyridine-4b,5-diol (4, 500 mg, 951.6 umol), tris(dibenzylideneacetone)dipalladium (87 mg, 95.16 umol), 1,1'-bis(diphenylphosphino)ferrocene (53 mg, 95.16 umol), Zinc (62 mg, 951.6 umol), zinc cyanide (447 mg, 3.81 mmol) were taken up into a microwave tube in dimethyl sulfoxide (5 mL) under nitrogen at 25° C. After addition, the sealed tube was heated at 130° C. for 2 h in microwave (40 W, 20 bar). The reaction mixture was purified by silica gel column chromatography (dichloromethane:methanol=20:1 to 10:1) to give the crude product, which was purification by trituration from methanol (5 mL) to give pure product rac-4-((4bS,5R,6S,7S,7aR)-6-((ethyl(methyl)amino)methyl)-4b,5-dihydroxy-4-methoxy-7-phenyl-4b,5,6,7-tetrahydro-7aH1-cyclopenta[4,5]furo[2,3-c]pyridin-7a-yl)benzonitrile (Cpd. No. 74F) as white solid. Yield: 138 mg, 30.5%; MS (ESI) m/z 472.2 $[M+1]^+$; HPLC: 99.23%; $^1H$ NMR (400 MHz, DMSO-$d_6$) δ 8.05 (s, 1H), 7.97 (s, 1H), 7.49 (d, J=8.8 Hz, 2H), 7.37 (d, J=8.8 Hz, 2H), 7.08-7.05 (m, 2H), 7.02-7.00 (m, 3H), 5.73 (s, 1H), 5.17 (bs, 1H), 4.50 (s, 1H), 3.88 (s, 3H), 3.82 (d, J=14.0 Hz, 1H), 2.60-2.57 (m, 1H), 2.49-2.47 (m, 1H), 2.31-2.30 (m, 1H), 2.22 (s, 3H), 2.12-2.11 (m, 1H), 0.97 (t, J=7.2 Hz, 3H).

Example 75

Rac-4-((4bS,5R,6S,7S,7aR)-4b,5-dihydroxy-6-(((2-hydroxyethyl)(methyl)amino)methyl)-4-methoxy-7-phenyl-4b,5,6,7-tetrahydro-7aH-cyclopenta[4,5]furo[2,3-c]pyridin-7a-yl)benzonitrile (Cpd. No. 75F)

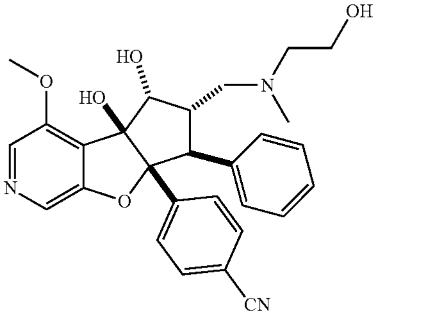

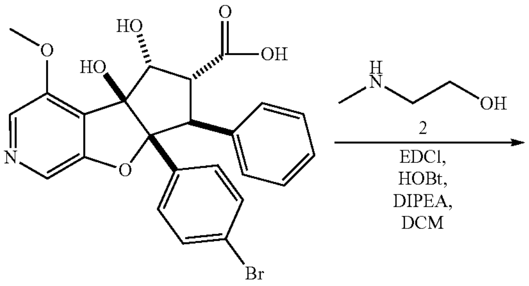

1

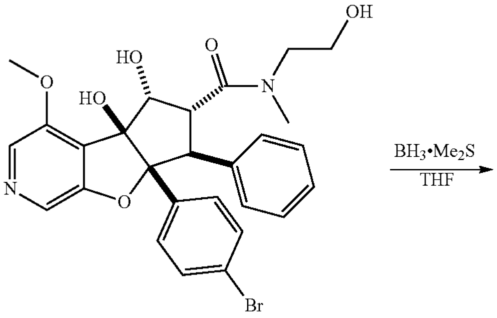

3

-continued

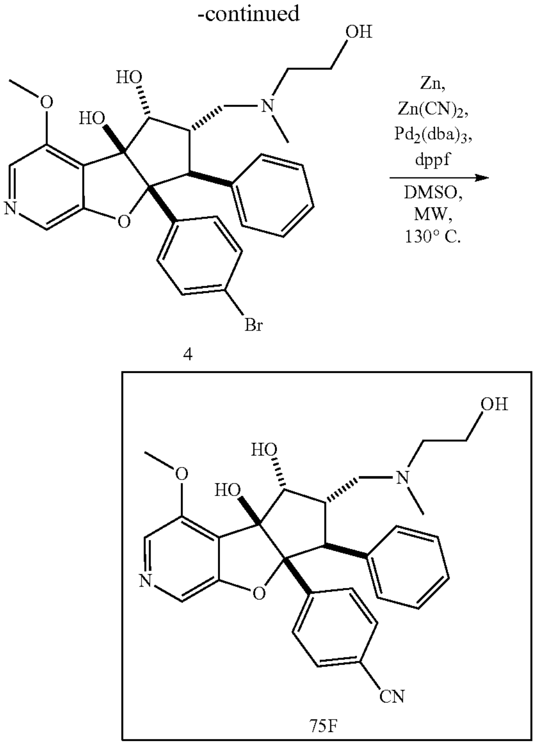

4

75F

Synthesis of rac-(4bS,5R,6R,7S,7aR)-7a-(4-bromophenyl)-4b,5-dihydroxy-N-(2-hydroxyethyl)-4-methoxy-N-methyl-7-phenyl-4b,6,7,7a-tetrahydro-5H-cyclopenta[4,5]furo[2,3-c]pyridine-6-carboxamide (3)

To a suspension of rac-(4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylic acid (1, 2.00 g, 4.01 mmol) in dichloromethane (20 mL) was added 1-(3-dimethylaminopropyl)-3-ethylcarbodiimide hydrochloride (1.54 g, 8.02 mmol), 1-hydroxybenzotriazole (1.08 g, 8.02 mmol) and N,N-diisopropylethylamine (2.07 g, 16.04 mmol) at 0° C. After stirred for 1 h at 25° C., 2-(methylamino)ethanol (602 mg, 8.02 mmol) was added and the reaction was stirred at 25° C. for 14 h. TLC (dichloromethane/methanol=20/1) indicated the starting material was consumed. The reaction suspension was diluted with water (80 mL) and extracted with dichloromethane (40 mL×3). The combined organic layer was concentrated to give a residue. The residue combined was purified by column chromatography (dichloromethane/methanol=10/1) to afford rac-(4bS,5R,6R,7S,7aR)-7a-(4-bromophenyl)-4b,5-dihydroxy-N-(2-hydroxyethyl)-4-methoxy-N-methyl-7-phenyl-4b,6,7,7a-tetrahydro-5H-cyclopenta[4,5]furo[2,3-c]pyridine-6-carboxamide (3) as white solid. Yield: 1.5 g, crude; MS (ESI) m/z 555.0 $[M+1]^+$.

Synthesis of rac-(4bS,5R,6S,7S,7aR)-7a-(4-bromophenyl)-6-(((2-hydroxyethyl)(methyl)amino)methyl)-4-methoxy-7-phenyl-5,6,7,7a-tetrahydro-4bH-cyclopenta[4,5]furo[2,3-c]pyridine-4b,5-diol (4)

To a suspension of rac-(4bS,5R,6R,7S,7aR)-7a-(4-bromophenyl)-4b,5-dihydroxy-N-(2-hydroxyethyl)-4-methoxy-N-methyl-7-phenyl-4b,6,7,7a-tetrahydro-5H-cyclopenta[4,5]furo[2,3-c]pyridine-6-carboxamide (3, 2.00 g, 3.60 mmol) in tetrahydrofuran (40 mL) was added borane dimethyl sulfide complex (10 M, 1.80 mL) dropwise at 25° C. After 10 min, the suspension was heated at 65° C. for 2 h. TLC (dichloromethane/methanol=10/1) indicated the reaction completed. The reaction was quenched by the addition of acetic acid (20 mL) at 25° C. dropwise and then the solution was stirred at 65° C. for 1 hr. The solution was concentrated under reduced pressure and the residue was diluted with dichloromethane (40 mL) and then neutralized by saturated aqueous sodium bicarbonate to pH=9. The organic layer was separated and the aqueous layer was extracted with dichloromethane (20 mL). The combined organic layer was dried over sodium sulfate, concentrated under reduced pressure to afford rac-(4bS,5R,6S,7S,7aR)-7a-(4-bromophenyl)-6-(((2-hydroxyethyl)(methyl)amino)methyl)-4-methoxy-7-phenyl-5,6,7,7a-tetrahydro-4bH-cyclopenta[4,5]furo[2,3-c]pyridine-4b,5-diol (4) as white solid. Yield: 1.8 g, crude; MS (ESI) m/z 541.1 $[M+1]^+$.

Synthesis of rac-4-((4bS,5R,6S,7S,7aR)-4b,5-dihydroxy-6-(((2-hydroxyethyl)(methyl)amino)methyl)-4-methoxy-7-phenyl-4b,5,6,7-tetrahydro-7aH-cyclopenta[4,5]furo[2,3-c]pyridin-7a-yl)benzonitrile (Cpd. No. 75F)

A mixture of rac-(4bS,5R,6S,7S,7aR)-7a-(4-bromophenyl)-6-(((2-hydroxyethyl)(methyl)amino)methyl)-4-methoxy-7-phenyl-5,6,7,7a-tetrahydro-4bH-cyclopenta[4,5]furo[2,3-c]pyridine-4b,5-diol (4, 450 mg, 831 umol), zinc cyanide (390 mg, 3.32 mmol), zinc (54 mg, 831 umol), tris(dibenzylideneacetone)dipalladium (76 mg, 83 umol) and 1,1'-Bis(diphenylphosphino)ferrocene (46 mg, 83 umol) in dimethylsulfoxide (5 mL) was stirred at 130° C. for 1.5 hr under nitrogen at microwave irradiation. The reaction was performed 2 batches in parallel and work up together. LCMS indicated the reaction completed and the desired product was main peak. The reaction mixture was poured onto silica gel in a column and eluted with dichloromethane~dichloromethane/methanol=10/1 (0.1% ammonia) to give the crude product which was further purified by prep-HPLC (column: Phenomenex Gemini 150*25 mm*10 um; mobile phase: [water (0.05% ammonia hydroxide v/v)–acetonitrile]; B %: 33%-63%, 10 min) to afford the pure product rac-4-((4bS,5R,6S,7S,7aR)-4b,5-dihydroxy-6-(((2-hydroxyethyl)(methyl)amino)methyl)-4-methoxy-7-phenyl-4b,5,6,7-tetrahydro-7aH-cyclopenta[4,5]furo[2,3-c]pyridin-7a-yl)benzonitrile (Cpd. No. 75F) as white solid. Yield: 205 mg, 25%; MS (ESI) m/z 541.1 $[M+1]^+$; HPLC: 99.08%; $^1H$ NMR (400 MHz, DMSO-$d_6$) δ 8.05 (s, 1H), 7.96 (s, 1H), 7.49 (d, J=8.8 Hz, 2H), 7.38 (d, J=8.8 Hz, 2H), 7.09-6.99 (m, 5H), 5.72 (s, 1H), 5.06 (brs, 1H), 4.54 (d, J=4.0 Hz, 1H), 4.49 (s, 1H), 3.88 (s, 3H), 3.80 (s, J=14.0 Hz, 1H), 3.48-3.44 (m, 2H), 3.27-3.19 (m, 1H), 2.60-2.53 (m, 2H), 2.31-2.27 (m, 4H), 2.14 (dd, J=12.4, 3.2 Hz, 1H).

Example 76

Rac-4-((4bS,5R,6S,7S,7aR)-6-((benzyl(methyl)amino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 76F)

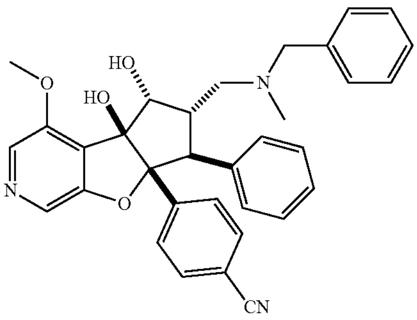

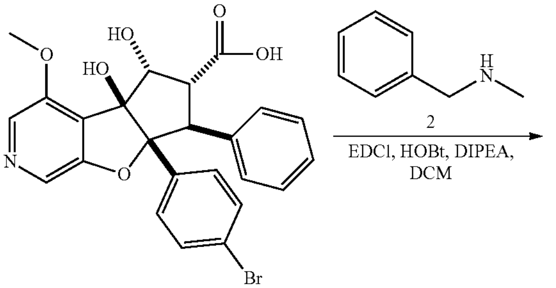

1

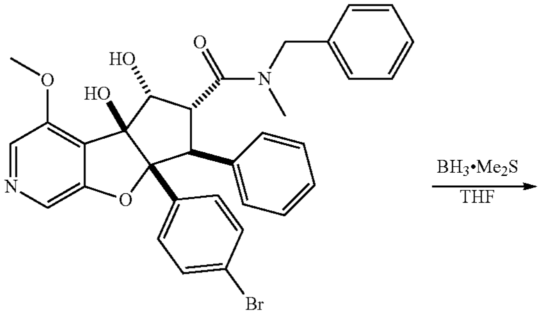

3

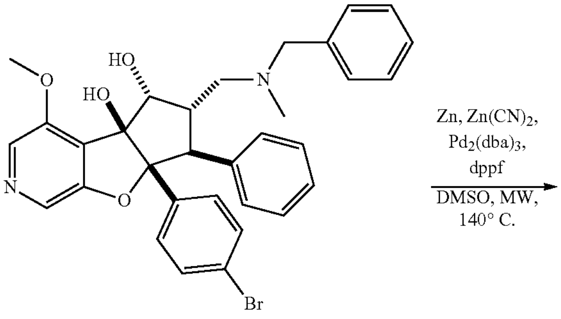

4

-continued

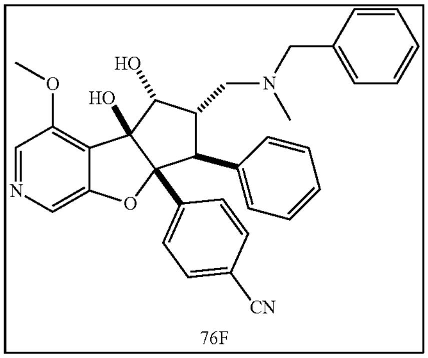

76F

Synthesis of rac-(4bS,5R,6R,7S,7aR)-N-benzyl-7a-(4-bromophenyl)-4b,5-dihydroxy-4-methoxy-N-methyl-7-phenyl-4b,6,7,7a-tetrahydro-5H-cyclopenta[4,5]furo[2,3-c]pyridine-6-carboxamide (3)

To a solution of rac-(4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylic acid (1, 2.5 g, 5.02 mmol) in dichloromethane (25 mL) was added carbodiimide hydrochloride (1.92 g, 10.04 mmol), hydroxybenzotriazole (1.36 g, 10.04 mmol) and diisopropylethylamine (2.60 g, 20.08 mmol) at 0° C. and the mixture was stirred at 0° C. for 30 minutes. Then 1-phenylethanamine (607.9 mg, 5.02 mmol) was added and the mixture was stirred at 25° C. for 12 h. LCMS showed there was desired product detected. The reaction mixture was diluted with dichloromethane (30 mL) and washed with water (100 mL×3). The organic phase was dried over anhydrous sodium sulfate and concentrated in vacuum to afford the product rac-(4bS,5R,6R,7S,7aR)-N-benzyl-7a-(4-bromophenyl)-4b,5-dihydroxy-4-methoxy-N-methyl-7-phenyl-4b,6,7,7a-tetrahydro-5H-cyclopenta[4,5]furo[2,3-c]pyridine-6-carboxamide (3) as a white solid. Yield: 2.76 g, crude; MS (ESI) m/z 601.3 $[M+1]^+$.

Synthesis of rac-(4bS,5R,6S,7S,7aR)-6-((benzyl(methyl)amino)methyl)-7a-(4-bromophenyl)-4-methoxy-7-phenyl-5,6,7,7a-tetrahydro-4bH-cyclopenta[4,5]furo[2,3-c]pyridine-4b,5-diol (4)

To a suspension of rac-(4bS,5R,6R,7S,7aR)-N-benzyl-7a-(4-bromophenyl)-4b,5-dihydroxy-4-methoxy-N-methyl-7-phenyl-4b,6,7,7a-tetrahydro-5H-cyclopenta[4,5]furo[2,3-c]pyridine-6-carboxamide (3, 2.70 g, 4.49 mmol) in tetrahydrofuran (40 mL) was added borane dimethyl sulfide complex (10 M, 3.59 mL) dropwise at 25° C. After 10 min, the suspension was heated at 65° C. for 1 h. TLC (dichloromethane/methanol=10/1) indicated the reaction completed. The reaction was quenched by the addition of acetic acid (20 mL) at 25° C. dropwise and then the solution was stirred at 65° C. for 1 hr. The solution was concentrated under reduced pressure and the residue was diluted with water (60 mL). The suspension was basified by solid sodium carbonate to pH=10. The mixture was extracted with dichloromethane (60 mL×2). The combined organic layer was dried over anhydrous sodium sulfate, concentrated under reduced pressure to afford the crude product rac-(4bS,5R,6S,7S,7aR)-6-((benzyl(methyl)amino)methyl)-7a-(4-bromophenyl)-4-methoxy-7-phenyl-5,6,7,7a-tetrahydro-4bH-cyclopenta[4,5]furo[2,3-c]pyridine-4b,5-diol (4) as white solid. Yield: 2.30 g, crude; MS (ESI) m/z 587.2 [M+1]$^+$.

Synthesis of rac-4-((4bS,5R,6S,7S,7aR)-6-((benzyl(methyl)amino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 76F)

A mixture of rac-(4bS,5R,6S,7S,7aR)-6-((benzyl(methyl)amino)methyl)-7a-(4-bromophenyl)-4-methoxy-7-phenyl-5,6,7,7a-tetrahydro-4bH-cyclopenta[4,5]furo[2,3-c]pyridine-4b,5-diol (4, 1.0 g, 1.70 mmol), zinc cyanide (800 mg, 6.81 mmol), zinc (111 mg, 1.70 mmol), tris(dibenzylideneacetone)dipalladium (156 mg, 0.17 mmol) and 1,1'-Bis(diphenylphosphino)ferrocene (94 mg, 0.17 mmol) in dimethylsulfoxide (10 mL) was stirred at 140° C. for 1.5 h under nitrogen at microwave (140° C., 1.5 h, 20 bar) irradiation. The reaction was performed 2 batches in parallel and work up together. LCMS indicated the desired product was main peak. The reaction mixture was poured onto silica gel in a column and eluted with dichloromethane ~ dichloromethane/methanol=10/1 (0.5% ammonia) to give the crude product which was purification again by prep-HPLC (column: Phenomenex Gemini 150*25 mm*10 um; mobile phase: [water (0.05% ammonia hydroxide v/v)–acetonitrile]; B %: 45%-70%, 26 MIN; 83% min) to afford the pure product rac-4-((4bS,5R,6S,7S,7aR)-6-((benzyl(methyl)amino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 76F) as white solid. Yield: 270 mg, 15%; MS (ESI) m/z 534.2 [M+1]$^+$; HPLC: 99.79%; $^1$H NMR (400 MHz, DMSO-$d_6$) δ 8.06 (s, 1H), 7.99 (s, 1H), 7.48 (d, J=8.4 Hz, 2H), 7.36-7.32 (m, 7H), 7.07-6.95 (m, 5H), 5.76 (s, 1H), 5.12 (d, J=4.8 Hz, 1H), 4.61 (s, 1H), 3.91 (s, 3H), 3.79 (d, J=14.0 Hz, 1H), 3.64 (d, J=13.2 Hz, 1H), 3.42 (d, J=13.2 Hz, 1H), 3.27-3.23 (m, 1H), 2.72-2.66 (m, 1H), 2.22-2.19 (m, 4H).

Example 77

Rac-4-((4bS,5R,6S,7S,7aR)-6-((benzylamino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 77F)

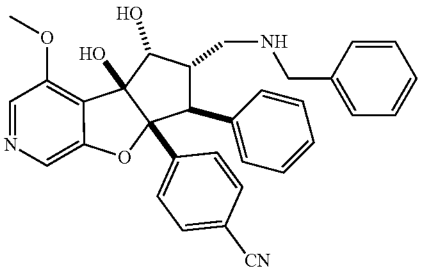

-continued

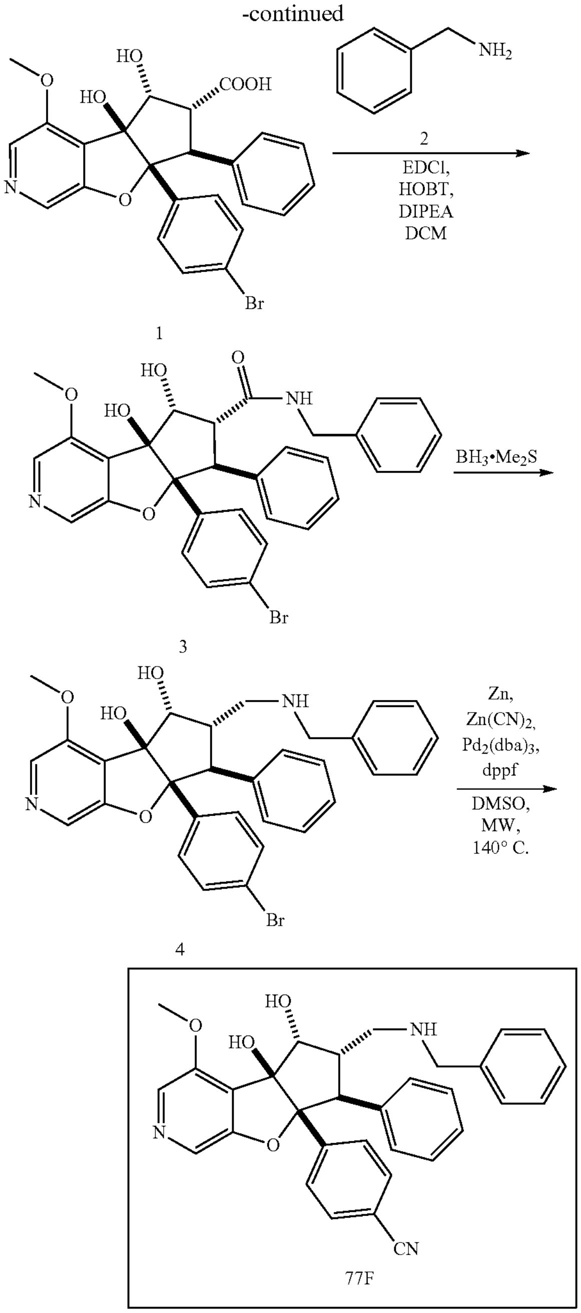

1

3

4

77F

Synthesis of rac-(4bS,5R,6R,7S,7aR)-N-benzyl-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxamide (3)

To a solution of rac-(4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylic acid (1, 2.50 g, 5.02 mmol) in dichloromethane (30 mL) was added 1-(3-dimethylaminopropyl)-3-ethylcarbodiimide hydrochloride (1.92 g, 10.03 mmol), 1-hydroxybenzotriazole (1.36 g, 10.03 mmol) and N,N-diisopropylethylamine (1.95 g, 15.05 mmol) at 0° C. The mixture was stirred at 0° C. for 0.5 h. Then phenylmethanamine (645.47 mg, 6.02 mmol) was added. The mixture was stirred at 20° C. for 11.5 h. The mixture was diluted with water (50 mL) and extracted with dichloromethane (50 mL×3). The combined organic layer was washed with brine (50 mL), dried over anhydrous sodium sulphate and concentrated. The residue was purified by column chromatography (dichloromethane: methanol=20:1 to 10:1) to afford rac-(4bS,5R,6R,7S,7aR)-N-benzyl-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxamide (3) as a white solid. Yield: 2.10 g, 71.21%; MS (ESI) m/z 587.0 $[M+1]^+$; $^1H$ NMR (400 MHz, DMSO-$d_6$) δ 8.71 (t, J=6.0 Hz, 1H), 8.09 (s, 1H), 7.99 (s, 1H), 7.27-7.18 (m, 5H), 7.15-6.98 (m, 9H), 5.72 (s, 1H), 5.17 (d, J=4.4 Hz, 1H), 4.63 (t, J=4.4 Hz, 1H), 4.41 (d, J=14.4 Hz, 1H), 4.32 (dd, J=15.2 Hz, 6.0 Hz, 1H), 4.20 (dd, J=15.2 Hz, 5.2 Hz, 1H), 3.99 (dd, J=14.4 Hz, 4.8 Hz, 1H), 3.88 (s, 3H).

Synthesis of rac-(4bS,5R,6S,7S,7aR)-6-((benzylamino)methyl)-7a-(4-bromophenyl)-4-methoxy-7-phenyl-5,6,7,7a-tetrahydro-4bH-cyclopenta[4,5]furo[2,3-c]pyridine-4b,5-diol (4)

To a solution of rac-(4bS,5R,6R,7S,7aR)-N-benzyl-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxamide (3, 2.10 g, 3.57 mmol) in tetrahydrofuran (30 mL) was added borane dimethyl sulfide complex (10 M, 3.57 mL) at 0° C. The mixture was stirred at 0° C. for 0.5 h. Then the mixture was warmed to 70° C. and stirred at 70° C. for 1 h. The mixture was quenched with acetic acid (9 mL) and then stirred at 70° C. for 1 h. The mixture was concentrated. Water (20 mL) was added. The mixture was washed with methyl t-butyl ether (30 mL×3). The aqueous layer was adjusted to pH=8 with saturated sodium bicarbonate, extracted with ethyl acetate (50 mL×3). The combined organic layer was dried over sodium sulphate and concentrated to afford rac-(4bS,5R,6S,7S,7aR)-6-((benzylamino)methyl)-7a-(4-bromophenyl)-4-methoxy-7-phenyl-5,6,7,7a-tetrahydro-4bH-cyclopenta[4,5]furo[2,3-c]pyridine-4b,5-diol (4) as a white solid. Yield: 1.00 g, 48.78%; MS (ESI) m/z 573.1 $[M+1]^+$.

Synthesis rac-4-((4bS,5R,6S,7S,7aR)-6-((benzylamino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 77F)

A solution of rac-(4bS,5R,6S,7S,7aR)-6-((benzylamino)methyl)-7a-(4-bromophenyl)-4-methoxy-7-phenyl-5,6,7,7a-tetrahydro-4bH-cyclopenta[4,5]furo[2,3-c]pyridine-4b,5-diol (4, 500 mg, 872 umol), 1,1'bis(diphenylphosphino) ferrocene (48 mg, 87 umol), tris(dibenzylideneacetone) dipalladium(0) (80 mg, 87 umol), zinc powder (57 mg, 872 umol), zinc cyanide (512 mg, 4.36 mmol) in dimethyl sulfoxide (6 mL) was stirred under nitrogen at microwave (150 psi, 40 W) at 130° C. for 2 h. The mixture was filtered and purified by column chromatography (dichloromethane: methanol=100:1 to 10:1) to give the product, which was further purified by prep-HPLC (column: Phenomenex Synergi Max-RP 250*50 mm*10 um; mobile phase: [water (0.05% ammonia hydroxide v/v)—acetonitrile]; B %: 40%-65%, 26 MIN; 73% min) to afford rac-4-((4bS,5R,6S,7S,7aR)-6-((benzylamino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 77F) as a gray solid. Yield: 205 mg, 45.25%; MS (ESI) m/z 520.5 $[M+1]^+$; HPLC: 99.69%; $^1H$ NMR (400 MHz, DMSO-$d_6$) δ 8.05 (s, 1H), 7.98 (s, 1H), 7.49 (d, J=8.4 Hz, 2H), 7.36 (d, J=8.4 Hz, 2H), 7.31-7.25 (m, 4H), 7.23-7.17 (m, 1H), 7.07-6.92 (m, 5H), 5.69 (s, 1H), 5.41 (brs, 1H), 4.59 (d, J=4.0 Hz, 1H), 3.89 (s, 3H), 3.79 (d, J=14.4 Hz, 1H), 3.68 (s, 2H), 3.22-3.12 (m, 1H), 2.71-2.63 (in, 1H).

Example 78

Rac-4-((5R,6S,7S,7aR)-4b,5-dihydroxy-4-methoxy-7-phenyl-6-(((pyridin-3-ylmethyl)amino)methyl)-4b,5,6,7-tetrahydro-7aH-cyclopenta[4,5]furo[2,3-c]pyridin-7a-yl)benzonitrile (Cpd. No. 78F)

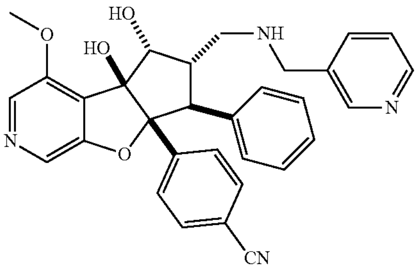

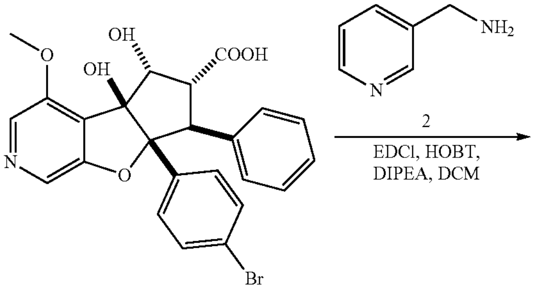

1

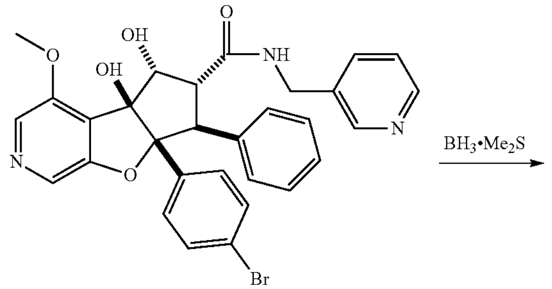

3

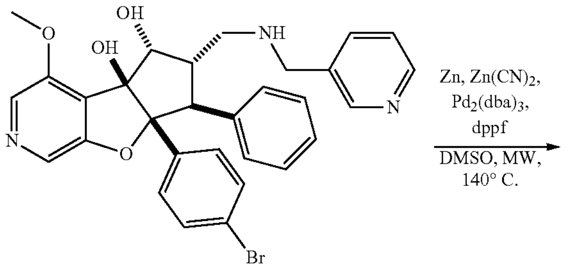

4

-continued

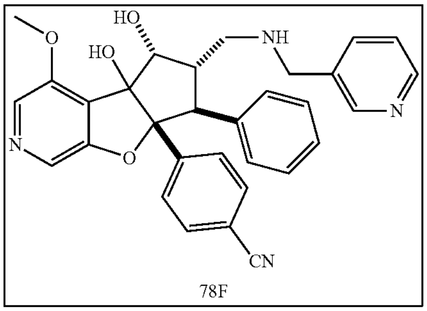

78F

Synthesis of rac-(4bS,5R,6R,7S,7aR)-7a-(4-bromophenyl)-4b,5-dihydroxy-4-methoxy-7-phenyl-N-(pyridin-3-ylmethyl)-4b,6,7,7a-tetrahydro-5H-cyclopenta[4,5]furo[2,3-c]pyridine-6-carboxamide (3)

To a suspension of rac-(4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylic acid (1, 5.00 g, 10.03 mmol) in dichloromethane (50 mL) was added 1-(3-dimethylaminopropyl)-3-ethylcarbodiimide hydrochloride (3.85 g, 20.06 mmol), hydroxybenzotriazole (2.71 g, 20.06 mmol) and N,N-diisopropylethylamine (5.19 g, 40.12 mmol) at 0° C. The mixture was stirred at 30° C. for 30 min, then 3-pyridylmethanamine (1.08 g, 10.03 mmol) was added at 30° C. and the mixture was stirred at 30° C. for 16 h. The solution was poured into water (50 mL) and filtered. The filter-cake was washed with dichloromethane (20 mL×3) to afford the crude product. The crude product was triturated with a mixture solution of dichloromethane:methanol=10:1 (30 mL) to give rac-(4bS,5R,6R,7S,7aR)-7a-(4-bromophenyl)-4b,5-dihydroxy-4-methoxy-7-phenyl-N-(pyridin-3-ylmethyl)-4b,6,7,7a-tetrahydro-5H-cyclopenta[4,5]furo[2,3-c]pyridine-6-carboxamide (3) as a white solid. Yield: 4.50 g, 73%; MS (ESI) m/z 588.0 $[M+1]^+$; $^1$H NMR (400 MHz, DMSO-$d_6$) δ 8.71 (t, J=6.0 Hz, 1H), 8.40 (d, J=2.8 Hz, 2H), 8.09 (s, 1H), 7.99 (s, 1H), 7.50-7.45 (m, 1H), 7.25-7.22 (m, 3H), 7.08-6.97 (m, 7H), 5.71 (s, 1H), 5.21 (d, J=4.8 Hz, 1H), 4.64 (t, J=4.4 Hz 1H), 4.41 (d, J=14.4 Hz, 1H), 4.31-4.25 (m, 2H), 3.98-3.96 (m, 11H), 3.88 (s, 3H).

Synthesis of rac-(4bS,5R,6S,7S,7aR)-7a-(4-bromophenyl)-4-methoxy-7-phenyl-6-(((pyridin-3-ylmethyl)amino)methyl)-5,6,7,7a-tetrahydro-4bH-cyclopenta[4,5]furo[2,3-c]pyridine-4b,5-diol (4)

To a solution of rac-(4bS,5R,6R,7S,7aR)-7a-(4-bromophenyl)-4b,5-dihydroxy-4-methoxy-7-phenyl-N-(pyridin-3-ylmethyl)-4b,6,7,7a-tetrahydro-5H-cyclopenta[4,5]furo[2,3-c]pyridine-6-carboxamide (3, 4.50 g, 7.65 mmol) in tetrahydrofuran was added borane dimethyl sulfide complex (10 M, 3.64 mL) at 0° C. The solution was stirred at 60° C. for 1 h, then quenched with acetic acid (3 mL) at 0° C. and then heated at 60° C. for 1 hr. The reaction mixture was concentrated in vacuum and diluted with water (100 mL) and washed with ethyl acetate (50 mL×2). The water phase was adjusted pH=7-8 with saturated sodium bicarbonate at 0° C. and then extracted with ethyl acetate (200 mL×3). The combined organic layer was dried over anhydrous sodium sulfate and concentrated in vacuum to give rac-(4bS,5R,6S,7S,7aR)-7a-(4-bromophenyl)-4-methoxy-7-phenyl-6-(((pyridin-3-ylmethyl)amino)methyl)-5,6,7,7a-tetrahydro-4bH-cyclopenta[4,5]furo[2,3-c]pyridine-4b,5-diol (4) as a white solid. Yield: 4.50 g, 99%; MS (ESI) m/z 576.0 $[M+1]^+$.

Synthesis of rac-4-((5R,6S,7S,7aR)-4b,5-dihydroxy-4-methoxy-7-phenyl-6-(((pyridin-3-ylmethyl)amino)methyl)-4b,5,6,7-tetrahydro-7aH-cyclopenta[4,5]furo[2,3-c]pyridin-7a-yl)benzonitrile (Cpd. No. 78F)

To a solution of rac-(4bS,5R,6S,7S,7aR)-7a-(4-bromophenyl)-4-methoxy-7-phenyl-6-(((pyridin-3-ylmethyl)amino)methyl)-5,6,7,7a-tetrahydro-4bH-cyclopenta[4,5]furo[2,3-c]pyridine-4b,5-diol (4, 1.30 g, 2.26 mmol) in dimethyl sulfoxide (10 mL) was added zinc cyanide (1.06 g, 9.04 mmol), zinc (296 mg, 4.52 mmol), 1,1'-Bis(diphenylphosphino)ferrocene (251 mg, 452.0 umol) and tris(dibenzylideneacetone)dipalladium (414 mg, 452.0 umol) under $N_2$. The sealed tube was heated at 130° C. for 3 h under microwave (40 w, 20 bar). The reaction solution was filtered. The filtrate was purified by column (dichloromethane:methanol=50:1) to afford the crude product. The crude product was further purified by Prep-HPLC to afford rac-4-((5R,6S,7S,7aR)-4b,5-dihydroxy-4-methoxy-7-phenyl-6-(((pyridin-3-ylmethyl)amino)methyl)-4b,5,6,7-tetrahydro-7aH-cyclopenta[4,5]furo[2,3-c]pyridin-7a-yl)benzonitrile (Cpd. No. 78F) as a white solid. Yield: 287 mg, 24.3%; MS (ESI) m/z 521.2 $[M+1]^+$; HPLC: 97.52%; $^1$H NMR (400 MHz, DMSO-$d_6$) δ 8.49 (s, 1H), 8.41 (d, J=4.4 Hz, 1H), 8.05 (s, 1H), 7.98 (s, 1H), 7.75-7.70 (m, 1H), 7.49 (d, J=8.4 Hz, 2H), 7.36 (d, J=8.4 Hz, 2H), 7.31-7.28 (m, 1H), 7.05-6.94 (m, 5H), 5.70 (s, 1H), 5.34 (brs, 1H), 4.59 (d, J=4.0 Hz, 1H), 3.89 (s, 3H), 3.78 (d, J=14.4 Hz, 1H), 3.71-3.68 (m, 2H), 3.19-3.15 (m, 1H), 2.69-2.63 (m, 1H), 2.46-2.43 (m, 1H).

Example 79

Rac-4-((4bS,5R,6S,7S,7aR)-4b,5-dihydroxy-6-(((2-hydroxyethyl)amino)methyl)-4-methoxy-7-phenyl-5,6,7,7a-tetrahydro-4bH-cyclopenta[4,5]furo[2,3-c]pyridin-7a-yl)benzonitrile (Cpd. No. 79F)

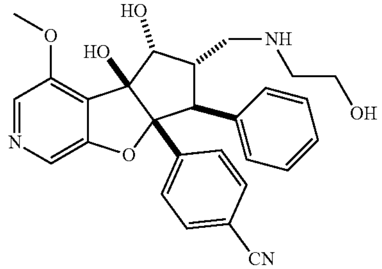

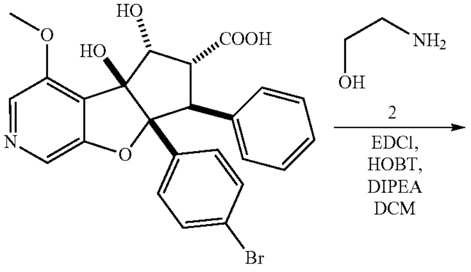

1

-continued

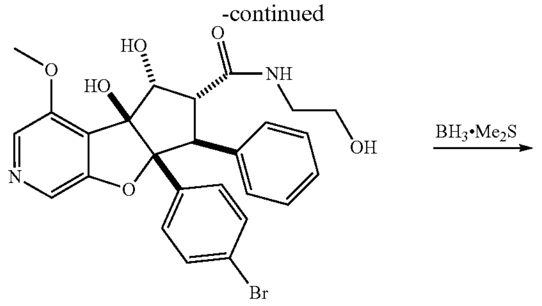

3

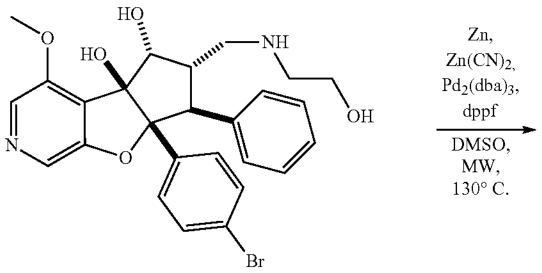

4

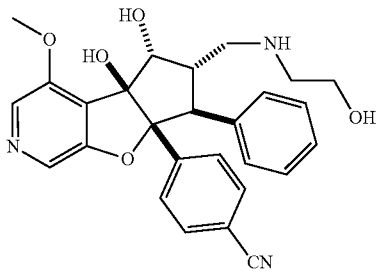

79F

Synthesis of rac-(4bS,5R,6R,7S,7aR)-7a-(4-bromophenyl)-4b,5-dihydroxy-N-(2-hydroxyethyl)-4-methoxy-7-phenyl-4b,6,7,7a-tetrahydro-5H-cyclopenta[4,5]furo[2,3-c]pyridine-6-carboxamide (3)

To a suspension of rac-(4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylic acid (1, 2.43 g, 4.88 mmol) in dichloromethane (30 mL) was added 1-(3-dimethylaminopropyl)-3-ethylcarbodiimide hydrochloride (1.87 g, 9.75 mmol), 1-hydroxybenzotriazole (1.32 g, 9.75 mmol) and N,N-diisopropylethylamine (3.15 g, 24.38 mmol) under nitrogen atmosphere at 0° C. After 10 min, 2-aminoethanol (358 mg, 5.86 mmol) was added and the mixture was stirred at 25° C. for 12 h. The mixture was diluted with dichloromethane (20 mL) and washed with water (20 mL×2). The organic layer was dried and concentrated under reduced pressure to give a residue, which was purified by silica gel chromatography (dichloromethane:methanol=50:1 to 10:1) to afford rac-(4bS,5R,6R,7S,7aR)-7a-(4-bromophenyl)-4b,5-dihydroxy-N-(2-hydroxyethyl)-4-methoxy-7-phenyl-4b,6,7,7a-tetrahydro-5H-cyclopenta[4,5]furo[2,3-c]pyridine-6-carboxamide (3) as a white solid. Yield: 1.40 g, 52.78%; MS (ESI) m/z 543.0 $[M+1]^+$. $^1$H NMR (400 MHz, DMSO-$d_6$) δ 8.29 (t, J=5.6 Hz, 1H), 8.08 (s, 1H), 7.98 (s, 1H), 7.22 (d, J=8.4 Hz, 2H), 7.08-6.98 (m, 7H), 5.67 (s, 1H), 5.05 (d, J=3.6 Hz, 1H), 4.66 (t, J=5.2 Hz, 1H), 4.57 (t, J=4.0 Hz, 1H), 4.34 (d, J=14.0 Hz, 1H), 3.97-3.93 (m, 1H), 3.87 (s, 3H), 3.33-3.20 (m, 2H), 3.11-3.07 (m, 2H).

Synthesis of rac-(4bS,5R,6S,7S,7aR)-7a-(4-bromophenyl)-6-(((2-hydroxyethyl)amino)methyl)-4-methoxy-7-phenyl-5,6,7,7a-tetrahydro-4bH-cyclopenta[4,5]furo[2,3-c]pyridine-4b,5-diol (4)

To a solution of rac-(4bS,5R,6R,7S,7aR)-7a-(4-bromophenyl)-4b,5-dihydroxy-N-(2-hydroxyethyl)-4-methoxy-7-phenyl-4b,6,7,7a-tetrahydro-5H-cyclopenta[4,5]furo[2,3-c]pyridine-6-carboxamide (3, 1.40 g, 2.59 mmol) in tetrahydrofuran (30 mL) was added borane dimethyl sulfide complex (10 M, 2.6 mL) at 0° C. under the nitrogen atmosphere. The mixture was stirred at 0° C. for 30 minutes and then reflux at 65° C. for 2 h. TLC (dichloromethane: methanol=10:1) showed the starting material was consumed completed. The reaction mixture was cooled to 0° C. and quenched with acetic acid (10 mL). Then the mixture was stirred at 25° C. for 10 minutes and heated at 60° C. for 1 hour. Removed solvents under reduce pressure, the residue was diluted by water (80 mL), extracted with methyl tertiary buthyl ether (40 mL×2). The water phase was adjusted pH to 8 with saturated sodium bicarbonate solution, and then extracted with ethyl acetate (50 mL×3). Combined the extracts, washed by brine(40 mL), dried over anhydrous sodium sulfate, filtrated and concentrated to give rac-(4bS,5R,6S,7S,7aR)-7a-(4-bromophenyl)-6-(((2-hydroxyethyl)amino)methyl)-4-methoxy-7-phenyl-5,6,7,7a-tetrahydro-4bH-cyclopenta[4,5]furo[2,3-c]pyridine-4b,5-diol (4) as a white solid. Yield: 794 mg, 56.96%; MS (ESI) m/z: 529.1 $[M+1]^+$.

Synthesis of rac-4-((4bS,5R,6S,7S,7aR)-4b,5-dihydroxy-6-(((2-hydroxyethyl)amino)methyl)-4-methoxy-7-phenyl-5,6,7,7a-tetrahydro-4bH-cyclopenta[4,5]furo[2,3-c]pyridin-7a-yl)benzonitrile (Cpd. No. 79F)

A mixture of rac-(4bS,5R,6S,7S,7aR)-7a-(4-bromophenyl)-6-(((2-hydroxyethyl)amino)methyl)-4-methoxy-7-phenyl-5,6,7,7a-tetrahydro-4bH-cyclopenta[4,5]furo[2,3-c]pyridine-4b,5-diol (4, 400 mg, 758.4 umol), tris(dibenzylideneacetone)Dipalladium (105 mg, 113.8 umol), 1,1'-bis(diphenylphosphino)ferrocene (63 mg, 113.8 umol), Zinc (50 mg, 758.4 umol), zinc cyanide (356 mg, 192.6 mmol) were taken into a microwave tube in DMSO (4 mL) under nitrogen atmosphere at 25° C. After addition, the sealed tube was heated at 135° C. for 2.5 h under microwave (40 W, 20 bar). The reaction mixture was purified by silica gel column chromatography (dichloromethane:methanol=20:1 to 10:1) to give the crude product, which was purification by trituration with methanol (5 mL) to give pure product rac-4-((4bS,5R,6S,7S,7aR)-4b,5-dihydroxy-6-(((2-hydroxyethyl)amino)methyl)-4-methoxy-7-phenyl-5,6,7,7a-tetrahydro-4bH-cyclopenta[4,5]furo[2,3-c]pyridin-7a-yl)benzonitrile (Cpd. No. 79F) as white solid. Yield: 76 mg, 20.97%; MS (ESI) m/z 474.2 $[M+1]^+$; HPLC: 99.19%; $^1$H NMR (400 MHz, DMSO-$d_6$) δ 8.09 (s, 1H), 8.03 (s, 1H), 7.56 (d, J=8.4 Hz, 2H), 7.36 (d, J=8.4 Hz, 2H), 7.13-7.04 (m, 4H), 5.88 (s, 1H), 5.20 (s, 1H), 4.71 (d, J=4.0 Hz, 1H), 3.91 (s, 3H), 3.78 (d, J=14.4 Hz, 1H), 3.70-3.60 (m, 2H), 3.07-2.99 (m, 3H), 2.74-2.67 (m, 1H).

Example 80
Rac-(4aR,5S,6R,7R,7aS)-4a-(4-cyanophenyl)-7,7a-dihydroxy-2-isopropyl-N,N-dimethyl-5-phenyl-2,4a,5,6,7,7a-hexahydrocyclopenta[4,5]furo[3,2-c]pyrazole-6-carboxamide (Cpd. No. 80F)
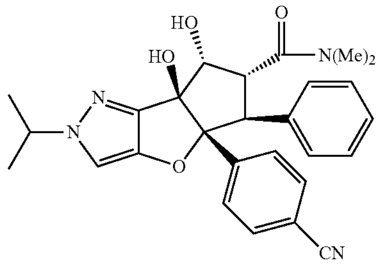
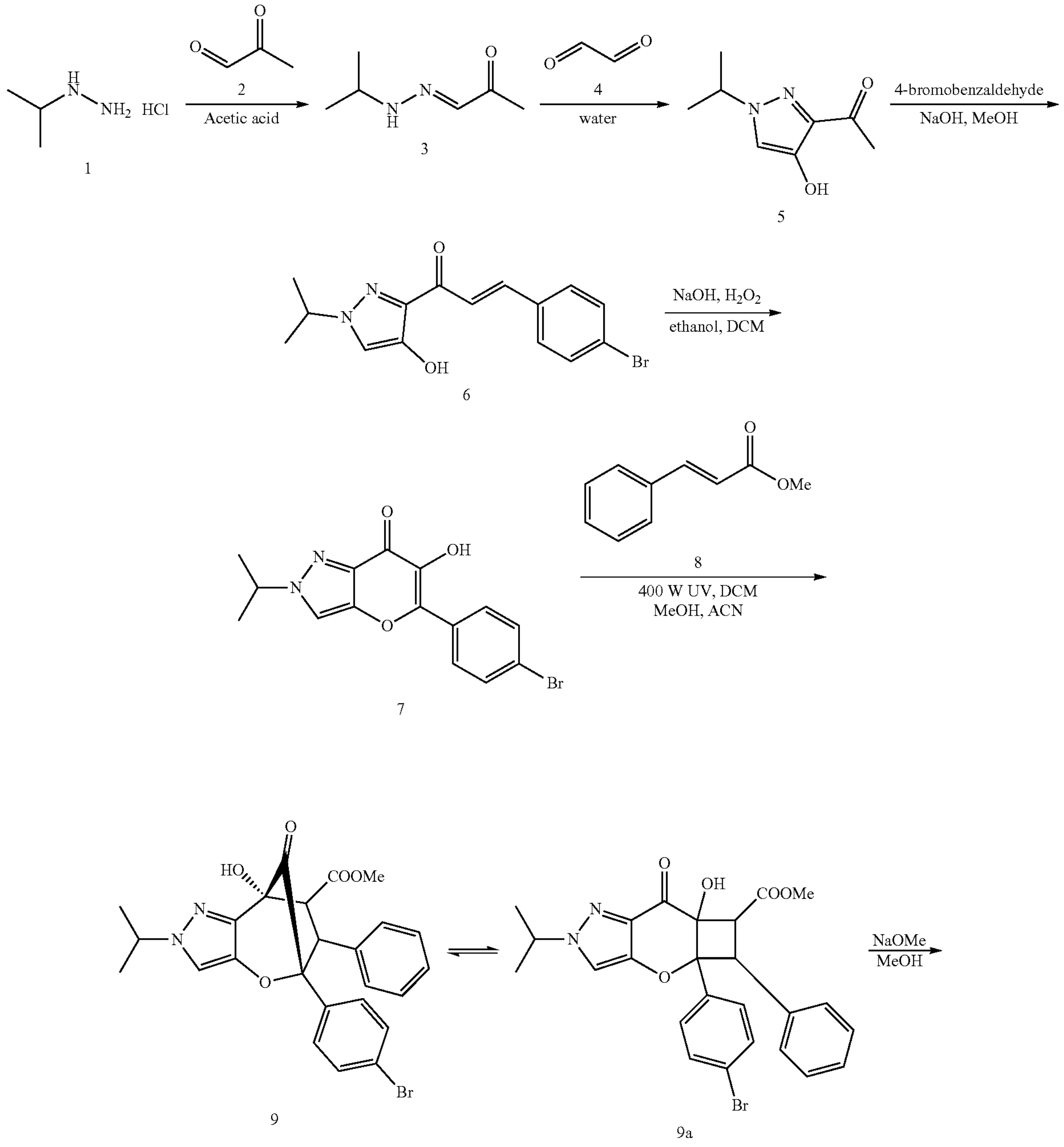

-continued

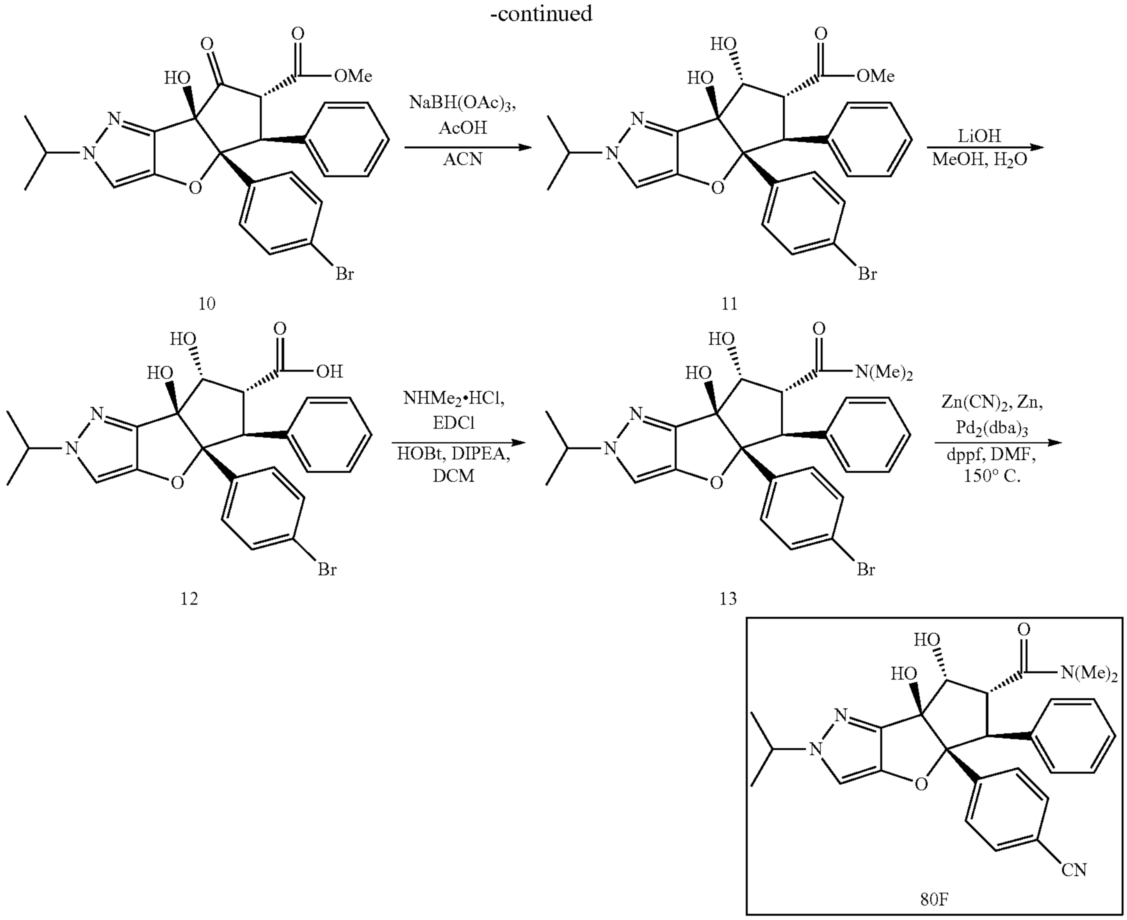

10 11 12 13 80F

Synthesis of (E)-1-(2-isopropylhydrazono) propan-2-one (3)

To a solution of isopropylhydrazine hydrochloride (1, 19.5 g, 177 mmol) in acetic acid (21.2 mL), 2-oxopropanal (2, 10.2 g, 141 mmol) was added at 0° C. The reaction was stirred 16 h at room temperature. After completion, the reaction mixture was partitioned between saturated aqueous sodium bicarbonate solution and ethyl acetate. The organic layer was separated, dried over anhydrous sodium sulphate and concentrated under reduced pressure to afford (E)-1-(2-isopropylhydrazono) propan-2-one (3) as orange solid. Yield: 13.0 g, 57%; MS (ESI) m/z poor ionization.

Synthesis of 1-(4-hydroxy-1-isopropyl-1H-pyrazol-3-yl) ethan-1-one (5)

To a solution of (E)-1-(2-isopropylhydrazono) propan-2-one (3, 13.1 g, 102 mmol) in water, oxalaldehyde (4, 5.93 g, 102 mmol) was added at room temperature. The reaction was stirred 3 h at room temperature. After completion, reaction mixture was diluted with dichloromethane and washed with cold water. The organic layer was separated and dried over anhydrous sodium sulphate, filtered and concentrated under reduced pressure to get the crude. The crude was purified by silica gel (100-200 mesh) column chromatography using 5% ethyl acetate in hexanes as eluent. The desired fractions were concentrated to afford 1-(4-hydroxy-1-isopropyl-1H-pyrazol-3-yl) ethan-1-one (5) as light yellow liquid. Yield: 3.5 g, 20%; MS (ESI) m/z 169 $[M+1]^+$.

Synthesis of (E)-3-(4-bromophenyl)-1-(4-hydroxy-1-isopropyl-1H-pyrazol-3-yl) prop-2-en-1-one (6)

To a solution of 1-(4-hydroxy-1-isopropyl-1H-pyrazol-3-yl)ethan-1-one (5, 3.5 g, 20.8 mmol) in methanol (17.5 mL), sodium hydroxide (2.5 g, 62.5 mmol) was added at room temperature followed by addition of 4-bromobenzaldehyde (3.8 g, 20.8 mmol). The reaction mixture was heated at 90° C. for 30 min. After completion, reaction mass was cooled to room temperature and the precipitated solid was filtered, washed with water and dried under vacuum to afford of (E)-3-(4-bromophenyl)-1-(4-hydroxy-1-isopropyl-1H-pyrazol-3-yl)prop-2-en-1-one (6) as yellow solid. Yield: 6.5 g, 93%; MS (ESI) m/z 333 $[M-1]^-$.

Synthesis 5-(4-bromophenyl)-6-hydroxy-2-isopropylpyrano [3,2-c]pyrazol-7(2H)-one (7)

To a solution of (E)-3-(4-bromophenyl)-1-(4-hydroxy-1-isopropyl-1H-pyrazol-3-yl)prop-2-en-1-one (6, 5.0 g, 14.97 mmol) in ethanol (50 mL) and dichloromethane (50 mL), 10% aqueous sodium hydroxide solution (41 mL, 104.3 mmol) was added followed by addition of hydrogen peroxide (11.8 mL, 104.3 mmol, 30%) at room temperature. The reaction mass was stirred for 2 h (exotherm was observed). After completion, reaction mass was cooled and neutralized with 6 M hydrogen chloride to pH ~7 and dichloromethane was distilled off. The precipitated solid was filtered and dried under vacuum to afford 5-(4-bromophenyl)-6-hydroxy-2-isopropylpyrano [3,2-c]pyrazol-7(2H)-one (7) as off white solid. Yield: 3.50 g, 67%; MS (ESI) m/z 347.24 $[M-1]^-$.

Synthesis of rac-methyl (6S,7S,8R)-5-(4-bromophenyl)-8-hydroxy-2-isopropyl-9-oxo-6-phenyl-5,6,7,8-tetrahydro-2H-5,8-methanooxepino[3,2-c]pyrazole-7-carboxylate (9&9a)

A solution of 5-(4-bromophenyl)-6-hydroxy-2-isopropylpyrano [3,2-c]pyrazol-7(2H)-one (7, 4.1 g, 11.78 mmol) and methyl cinnamate (8, 19.0 g, 117.8 mmol) in dichloromethane (200 mL), acetonitrile (100 mL) and methanol (100 mL) was placed in a UV reactor flask. The reaction mixture was irradiated for 12 h under 400 watts UV light. After completion, the solvent was removed under reduced pressure. The crude was purified by Combi-flash (40 g, RediSep column) using 5% methanol in dichloromethane as eluent. The desired fractions were concentrated under reduced pressure to afford rac-methyl (6S,7S,8R)-5-(4-bromophenyl)-8-hydroxy-2-isopropyl-9-oxo-6-phenyl-5,6,7,8-tetrahydro-2H-5,8-methanooxepino[3,2-c]pyrazole-7-carboxylate (9&9a). Yield: 4.0 g, crude.

Synthesis rac-methyl (4aR,5S,6R,7aR)-4a-(4-bromophenyl)-7a-hydroxy-2-isopropyl-7-oxo-5-phenyl-2,4a,5,6,7,7a-hexahydrocyclopenta[4,5]furo[3,2-c]pyrazole-6-carboxylate (10)

The crude rac-methyl (6S,7S,8R)-5-(4-bromophenyl)-8-hydroxy-2-isopropyl-9-oxo-6-phenyl-5,6,7,8-tetrahydro-2H-5,8-methanooxepino[3,2-c]pyrazole-7-carboxylate (9a, 4.0 g) was suspended in methanol (100 mL) and treated with sodium methoxide (25% in methanol, 40 mL) and heated the mixture to 80° C. for 3 h. After completion, the solvent was removed under reduced pressure, diluted the mixture with ammonium chloride solution and extracted with ethyl acetate. The organic phase was separated, dried over anhydrous sodium sulphate and concentrated under reduced pressure to afford rac-methyl (4aR,5S,6R,7aR)-4a-(4-bromophenyl)-7a-hydroxy-2-isopropyl-7-oxo-5-phenyl-2,4a,5,6,7,7a-hexahydrocyclopenta[4,5]furo[3,2-c]pyrazole-6-carboxylate (10). Yield: 4.0 g, crude.

Synthesis rac-methyl (4aR,5S,6R,7R,7aS)-4a-(4-bromophenyl)-7,7a-dihydroxy-2-isopropyl-5-phenyl-2,4a,5,6,7,7a-hexahydrocyclopenta[4,5]furo[3,2-c]pyrazole-6-carboxylate (11)

To a solution of sodium triacetoxyborohydride (10.0 g, 47.05 mmol), rac-methyl (4aR,5S,6R,7aR)-4a-(4-bromophenyl)-7a-hydroxy-2-isopropyl-7-oxo-5-phenyl-2,4a,5,6,7,7a-hexahydrocyclopenta[4,5]furo[3,2-c]pyrazole-6-carboxylate (10, 4.0 g, 7.84 mmol) in acetonitrile (40 mL), acetic acid (4.7 mL, 78.4 mmol) was added. The resulting mixture was stirred for 12 h at room temperature. After completion, reaction mixture was partitioned between saturated aqueous sodium bicarbonate solution and ethyl acetate. The organic layer was separated, dried over anhydrous sodium sulphate and concentrated under reduced pressure to get the crude. The crude was purified by Combi-flash (40 g, RediSep column) using 2% methanol in dichloromethane as eluent. The desired fractions were concentrated to afford rac-methyl (4aR,5S,6R,7R,7aS)-4a-(4-bromophenyl)-7,7a-dihydroxy-2-isopropyl-5-phenyl-2,4a,5,6,7,7a-hexahydrocyclopenta[4,5]furo[3,2-c]pyrazole-6-carboxylate (11) as off white solid. Yield: 1.0 g, 25%; MS (ESI) m/z 511.51 $[M-1]^-$.

Synthesis of rac-(4aR,5S,6R,7R,7aS)-4a-(4-bromophenyl)-7,7a-dihydroxy-2-isopropyl-5-phenyl-2,4a,5,6,7,7a-hexahydrocyclopenta[4,5]furo[3,2-c]pyrazole-6-carboxylic acid (12)

To a solution of rac-methyl (4aR,5S,6R,7R,7aS)-4a-(4-bromophenyl)-7,7a-dihydroxy-2-isopropyl-5-phenyl-2,4a,5,6,7,7a-hexahydrocyclopenta[4,5]furo[3,2-c]pyrazole-6-carboxylate (11, 1.0 g, 2.0 mmol) in methanol:water (3:1, 16 mL), lithium hydroxide (0.964 g, 40.16 mmol) was added and the reaction was stirred for 2 h at room temperature. After completion, methanol was distilled off, the reaction mass was cooled to 0° C. and acidified with 1 M hydrogen chloride to pH ~6. The precipitated solid was filtered and dried under vacuum to afford rac-(4aR,5S,6R,7R,7aS)-4a-(4-bromophenyl)-7,7a-dihydroxy-2-isopropyl-5-phenyl-2,4a,5,6,7,7a-hexahydrocyclopenta[4,5]furo[3,2-c]pyrazole-6-carboxylic acid (12) as white solid. Yield: 0.9 g, 93%; MS (ESI) m/z 497.23$[M-1]^-$.

Synthesis of rac-(4aR,5S,6R,7R,7aS)-4a-(4-bromophenyl)-7,7a-dihydroxy-2-isopropyl-N,N-dimethyl-5-phenyl-2,4a,5,6,7,7a-hexahydrocyclopenta[4,5]furo[3,2-c]pyrazole-6-carboxamide (13)

To a solution of rac-(4aR,5S,6R,7R,7aS)-4a-(4-bromophenyl)-7,7a-dihydroxy-2-isopropyl-5-phenyl-2,4a,5,6,7,7a-hexahydrocyclopenta[4,5]furo[3,2-c]pyrazole-6-carboxylic acid (12, 0.9 g, 1.807 mmol) in dichloromethane (20 mL), 1-ethyl-3-(3-dimethylaminopropyl)carbodiimide hydrochloride (1.0 g, 5.42 mmol), 1-hydroxybenzotriazole (0.732 g, 9.03 mmol) and N,N-diisopropylethylamine (1.9 mL, 10.85 mmol) were added at 0° C. and stirred the mixture for 5 min. Dimethylamine hydrochloride (0.734 g, 9.03 mmol) was then added at same temperature and the mixture was stirred for 16 h at 40° C. After completion, reaction mass was diluted with dichloromethane and washed with cold water. The organic layer was separated and dried over anhydrous sodium sulphate, filtered and concentrated under reduced pressure to get the crude. The crude was purified by Combi-flash (12 g, RediSep column) using 15% methanol in dichloromethane as eluent. The desired fractions were concentrated to afford rac-(4aR,5S,6R,7R,7aS)-4a-(4-bromophenyl)-7,7a-dihydroxy-2-isopropyl-N,N-dimethyl-5-phenyl-2,4a,5,6,7,7a-hexahydrocyclopenta[4,5]furo[3,2-c]pyrazole-6-carboxamide (13) as white solid. Yield: 0.6 g, 63%; MS (ESI) m/z 526.36$[M+1]^+$.

Synthesis of rac-(4aR,5S,6R,7R,7aS)-4a-(4-cyanophenyl)-7,7a-dihydroxy-2-isopropyl-N,N-dimethyl-5-phenyl-2,4a,5,6,7,7a-hexahydrocyclopenta[4,5]furo[3,2-c]pyrazole-6-carboxamide (Cpd. No. 80F)

To a solution of rac-(4aR,5S,6R,7R,7aS)-4a-(4-bromophenyl)-7,7a-dihydroxy-2-isopropyl-N,N-dimethyl-5-phenyl-2,4a,5,6,7,7a-hexahydrocyclopenta[4,5]furo[3,2-c]pyrazole-6-carboxamide (13, 0.4 g, 0.16 mmol) in N,N-dimethylformamide (10.0 mL), zinc cyanide (0.267 g, 2.28 mmol) and zinc (0.006 g, 0.09 mmol) were added at room temperature and degassed the mixture with argon for 15 min. 1,1'-Bis(diphenylphosphino)ferrocene (0.009 g, 0.015 mmol) and tris(dibenzylideneacetone)dipalladium (0.021 g, 0.022 mmol) were added to the reaction and degassing was continued for another 5 min. The reaction mixture was heated at 150° C. for 4 h. After completion, the reaction mass was diluted with ethyl acetate and washed with cold water. The organic layer was separated and dried over anhydrous sodium sulphate, filtered and concentrated under reduced pressure to get the crude. The crude was purified by Combi-flash (4.0 g, RediSep column) using 3% methanol in dichloromethane as eluent. The compound was re-purified through reverse HPLC. The desired fractions were concentrated to afford rac-(4aR,5S,6R,7R,7aS)-4a-(4-cyanophenyl)-7,7a-dihydroxy-2-isopropyl-N,N-dimethyl-5-phenyl-2,4a,5,6,7,7a-hexahydrocyclopenta[4,5]furo[3,2-c]pyrazole-6-carboxamide (Cpd. No. 80F) as white solid. Yield: 0.100 g, 28%. MS (ESI) m/z 473.48$[M+1]^+$; UPLC: 99.74%. $^1H$ NMR (400 MHz, DMSO-$d_6$) δ 7.52 (d, J=8.5 Hz, 2H), 7.42 (s, 1H), 7.33 (d, J=8.4 Hz, 2H), 7.02-6.94 (m, 3H), 6.81 (d, J=7.1 Hz, 2H), 5.63 (bs, 1H), 4.81 (d, J=7.3 Hz, 1H), 4.43-4.39 (m, 2H), 4.09 (dd, J=7.3 Hz, 13.3 Hz 1H), 3.21 (s, 3H), 2.73 (s, 3H), 1.44-1.41 (m, 6H).

Example 81

4-((3aR,4R,4aR,9bS,9cR)-9b-hydroxy-9-methoxy-2-oxo-4-phenyl-2,3,3a,4,9b,9c-hexahydro-4aH-oxazolo[4",5":4',5']cyclopenta[1',2':4,5]furo[2,3-c]pyridin-4a-yl)benzonitrile (Cpd. No. 81F)

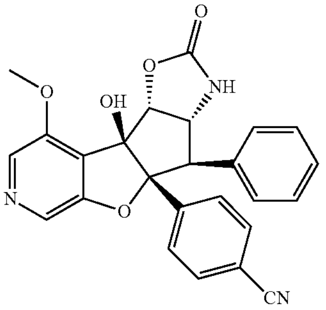

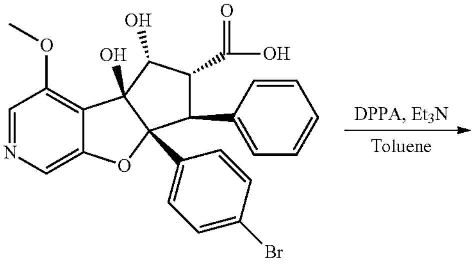

1

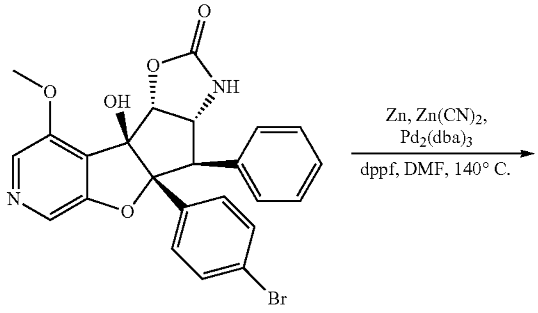

2

-continued

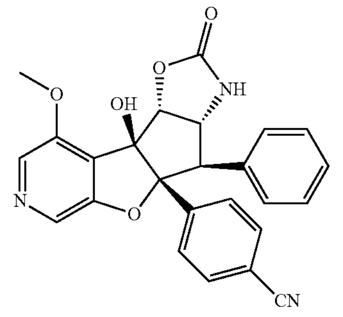

81F

Synthesis of rac-(3aR,4R,4aR,9bS,9cR)-4a-(4-bromophenyl)-9b-hydroxy-9-methoxy-4-phenyl-3,3a,4,4a,9b,9c-hexahydro-2H-oxazolo[4",5":4',5]cyclopenta[1',2':4,5]furo[2,3-c]pyridin-2-one (2)

To a solution of rac-(4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylic acid (1, 0.500 g, 1.00 mmol) in toluene (10 mL) under nitrogen, molecular sieve (0.125 g), diphenylphosphoryl azide (0.36 g, 1.30 mmol) and triethylamine (0.152 g, 1.50 mmol) were added to the reaction mixture and the reaction was stirred for 15 min at room temperature and then heated to reflux for 2 h. After completion, the reaction mass was diluted with dichloromethane and washed with cold water. The organic layer was separated and dried over anhydrous sodium sulphate, filtered and concentrated to give crude. The crude was purified by silica gel column chromatography using 0-5% methanol in dichloromethane as eluent. The desired fractions were concentrated to afford rac-(3aR,4R,4aR,9bS,9cR)-4a-(4-bromophenyl)-9b-hydroxy-9-methoxy-4-phenyl-3,3a,4,4a,9b,9c-hexahydro-2H-oxazolo[4",5":4',5']cyclopenta[1',2':4,5]furo[2,3-c]pyridin-2-one (2) as white solid. Yield: 0.450 g, 90%; MS (ESI) m/z 493.23 $[M-1]^-$.

Synthesis of 4-((3aR,4R,4aR,9bS,9cR)-9b-hydroxy-9-methoxy-2-oxo-4-phenyl-2,3,3a,4,9b,9c-hexahydro-4aH-oxazolo[4",5":4',5']cyclopenta[1',2':4,5]furo[2,3-c]pyridin-4a-yl)benzonitrile (Cpd. No. 81F)

To a solution of rac-(3aR,4R,4aR,9bS,9cR)-4a-(4-bromophenyl)-9b-hydroxy-9-methoxy-4-phenyl-3,3a,4,4a,9b,9c-hexahydro-2H-oxazolo[4",5":4',5']cyclopenta[1',2':4,5]furo[2,3-c]pyridin-2-one (2, 0.45 g, 0.910 mmol) in N,N-dimethylformamide (10 mL), zinc cyanide (0.64 g, 5.46 mmol) and zinc dust (0.007 g, 0.109 mmol) were added at room temperature and the reaction mixture was degassed with argon for 15 min. 1,1'-Bis(diphenylphosphino)ferrocene (0.010 g, 0.0182 mmol) and tris(dibenzylideneacetone) dipalladium (0.025 g, 0.0273 mmol) were added to the reaction, degassed for additional 5 min and mixture was heated at 140° C. for 2 h. After completion, the reaction mass was diluted with ethyl acetate and washed with cold water.

The organic layer was separated and dried over anhydrous sodium sulphate, filtered and concentrated to give crude. The crude was purified by silica gel column chromatography using 0-4% methanol in dichloromethane as eluent. The desired fractions were concentrated to afford rac-4-((3aR,4R,4aR,9bS,9cR)-9b-hydroxy-9-methoxy-2-oxo-4-phenyl-2,3,3a,4,9b,9c-hexahydro-4aH-oxazolo[4",5":4',5']cyclopenta[1',2':4,5]furo[2,3-c]pyridin-4a-yl)benzonitrile as white solid. Yield: 0.165 g, 41% (racemic) m/z 442.15 $[M+1]^+$. The enantiomers were separated using chiral preparative HPLC [chiralpak IC (4.6×250 mm, 5)]. n-Hexane/Ethano=40/60 (v/v). Peak 1 (Cpd. No. 81F, 85 mg), $[\alpha]_D$−54.7° (c 0.25, $CHCl_3$), $R_t$=4.510 min, ee: 99.28%, MS (ESI); m/z 442.15 $[M+1]^+$. $^1H$ NMR (400 MHz, DMSO-$d_6$) δ 8.31 (s, 1H), 8.22 (s, 1H), 8.16 (s, 1H), 7.63 (d, J=8.44 Hz, 2H), 7.31 (d, J=8.44 Hz, 2H), 7.14-7.10 (m, 3H), 7.00-6.98 (m, 2H), 6.12 (s, 1H), 5.43 (d, J=8.28 Hz, 1H), 4.99 (t, J=9.74 Hz, 1H), 3.97 (s, 3H), 3.50 (d, J=10.88 Hz, 1H). Peak 2 (72 mg), $[\alpha]_D$+69.6° (c 0.398, $CHCl_3$), $R_t$=8.676 min, ee: 99.68%; MS (ESI) m/z 442.15 $[M+1]^+$; $^1H$ NMR (400 MHz, DMSO-$d_6$) δ 8.31 (s, 1H), 8.22 (s, 1H), 8.16 (s, 1H), 7.63 (d, J=8.44 Hz, 2H), 7.31 (d, J=8.44 Hz, 2H), 7.15-7.11 (m, 3H), 7.00-6.98 (m, 2H), 6.12 (s, 1H), 5.43 (d, J=8.36 Hz, 1H), 4.99 (t, J=9.74 Hz, 1H), 3.97 (s, 3H), 3.50 (d, J=10.84 Hz, 1H).

Example 82

Rac-(4aR,5S,6R,7R,7aS)-3-cyano-4a-(4-cyanophenyl)-7,7a-dihydroxy-N,N,2-trimethyl-5-phenyl-2,4a,5,6,7,7a-hexahydrocyclopenta[4,5]furo[3,2-c]pyrazole-6-carboxamide (Cpd. No. 82F)

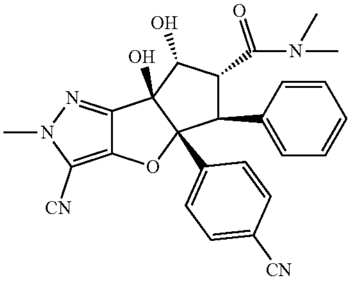

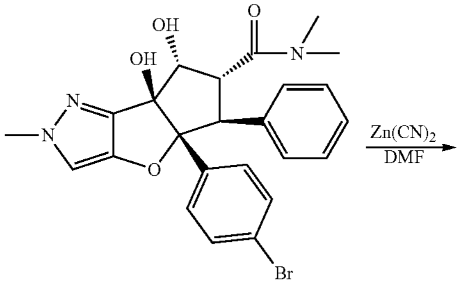

1

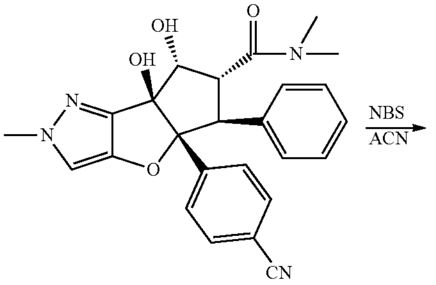

2

-continued

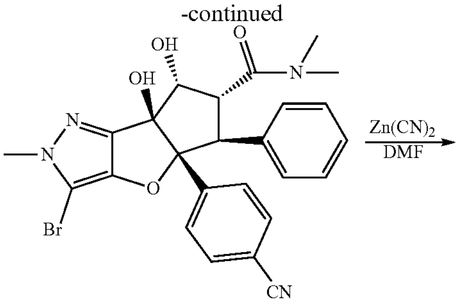

3

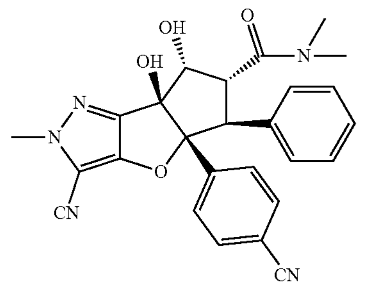

82F

Synthesis of rac-(4aR,5S,6R,7R,7aS)-4a-(4-cyanophenyl)-7,7a-dihydroxy-N,N,2-trimethyl-5-phenyl-2,4a,5,6,7,7a-hexahydrocyclopenta[4,5]furo[3,2-c]pyrazole-6-carboxamide (2)

To a solution of rac-(4aR,5S,6R,7R,7aS)-4a-(4-bromophenyl)-7,7a-dihydroxy-N,N,2-trimethyl-5-phenyl-2,4a,5,6,7,7a-hexahydrocyclopenta[4,5]furo[3,2-c]pyrazole-6-carboxamide (1, 0.30 g, 0.603 mmol) in N,N-dimethylformamide (10 mL), zinc cyanide (0.423 g, 0.362 mmol) and zinc dust (0.0047 g, 0.0724 mmol) were added at room temperature and the reaction mixture was degassed with argon for 15 min. 1,1'-Bis(diphenylphosphino)ferrocene (0.0068 g, 0.0120 mmol) and tris(dibenzylideneacetone)dipalladium (0.0165 g, 0.0181 mmol) were added to the reaction, degassed for additional 5 min and the mixture was heated at 140° C. for 8 h. After completion, the reaction mass was diluted with ethyl acetate and washed with cold water. The organic layer was separated and dried over anhydrous sodium sulphate, filtered and concentrated to give crude. The crude was purified by silica gel column chromatography using 2-3% methanol in dichloromethane as eluent. The desired fractions were concentrated to afford rac-(4aR,5S,6R,7R,7aS)-4a-(4-cyanophenyl)-7,7a-dihydroxy-N,N,2-trimethyl-5-phenyl-2,4a,5,6,7,7a-hexahydrocyclopenta[4,5]furo[3,2-c]pyrazole-6-carboxamide (2) as white solid. Yield: 0.180 g, 67%; MS (ESI) m/z 445.42$[M+1]^+$.

Synthesis of rac-(4aR,5S,6R,7R,7aS)-3-bromo-4a-(4-cyanophenyl)-7,7a-dihydroxy-N,N,2-trimethyl-5-phenyl-2,4a,5,6,7,7a-hexahydrocyclopenta[4,5]furo[3,2-c]pyrazole-6-carboxamide (3)

To a solution of rac-(4aR,5S,6R,7R,7aS)-4a-(4-cyanophenyl)-7,7a-dihydroxy-N,N,2-trimethyl-5-phenyl-2,4a,5,6,7,7a-hexahydrocyclopenta[4,5]furo[3,2-c]pyrazole-6-carboxamide, (2, 0.170 g, 0.382 mmol) in acetonitrile (6 ml), N-bromo succinimide (0.081 g, 0.458 mmol) was added.

The reaction mass was stirred for 1 h. After completion, the reaction mass was diluted with ethyl acetate and washed with cold water. The organic layer was separated and dried over anhydrous sodium sulphate, filtered and concentrated to give crude. The crude was purified by silica gel column chromatography using 2-4% methanol in dichloromethane as eluent. The desired fractions were concentrated to afford rac-(4aR,5S,6R,7R,7aS)-3-bromo-4a-(4-cyanophenyl)-7,7a-dihydroxy-N,N,2-trimethyl-5-phenyl-2,4a,5,6,7,7a-hexahydrocyclopenta[4,5]furo[3,2-c]pyrazole-6-carboxamide (3) as white solid. Yield: 0.10 g, 50%; MS (ESI) m/z 523.14 $[M+1]^+$.

Synthesis of rac-(4aR,5S,6R,7R,7aS)-3-cyano-4a-(4-cyanophenyl)-7,7a-dihydroxy-N,N,2-trimethyl-5-phenyl-2,4a,5,6,7,7a-hexahydrocyclopenta[4,5]furo[3,2-c]pyrazole-6-carboxamide (Cpd. No. 82F)

To a solution of rac-(4aR,5S,6R,7R,7aS)-3-bromo-4a-(4-cyanophenyl)-7,7a-dihydroxy-N,N,2-trimethyl-5-phenyl-2,4a,5,6,7,7a-hexahydrocyclopenta[4,5]furo[3,2-c]pyrazole-6-carboxamide (3, 0.10 g, 0.191 mmol) in N,N-dimethylformamide (4 mL), zinc cyanide (0.134 g, 1.14 mmol) and zinc dust (0.00149 g, 0.0229 mmol) were added at room temperature and the reaction mixture was degassed with argon for 15 min. 1,1'-Bis(diphenylphosphino)ferrocene (0.0021 g, 0.00383 mmol) and tris(dibenzylideneacetone)dipalladium (0.005 g, 0.00574 mmol) were added to the reaction, degassed for additional 5 min and mixture was heated at 140° C. for 7 h. After completion, the reaction mass was diluted with ethyl acetate and washed with cold water. The organic layer was separated and dried over anhydrous sodium sulphate, filtered and concentrated to give crude. The crude was purified by preparative HPLC afford rac-(4aR,5S,6R,7R,7aS)-3-cyano-4a-(4-cyanophenyl)-7,7a-dihydroxy-N,N,2-trimethyl-5-phenyl-2,4a,5,6,7,7a-hexahydrocyclopenta[4,5]furo[3,2-c]pyrazole-6-carboxamide (Cpd. No. 82F) as white solid. Yield: 0.007 g, 7%; MS (ESI) m/z 470.24 $[M+1]^+$. $^1H$ NMR (400 MHz, DMSO-$d_6$) δ 7.55 (d, J=7.64 Hz, 2H), 7.34 (d, J=8.40 Hz, 2H), 7.08-6.96 (m, 3H), 6.83 (d, J=7.12 Hz, 2H), 6.03 (s, 1H), 5.69 (bs, 1H), 4.81 (d, J=7.04 Hz, 1H), 4.45 (d, J=13.28 Hz, 1H), 4.20-4.11 (m, 1H), 3.98 (s, 3H), 3.21 (s, 3H), 2.74 (s, 3H).

Example 83

4-((5aR,6S,7R,8S,8aS)-3-chloro-8,8a-dihydroxy-6-phenyl-7-(pyrrolidin-1-ylsulfonyl)-6,7,8,8a-tetrahydro-5aH-cyclopenta[4,5]furo[3,2-b]pyridin-5a-yl)benzonitrile (Cpd. No. 83F)

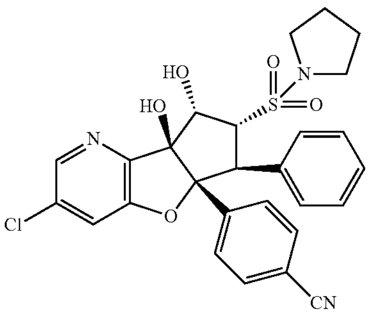 [SMILES: N#Cc1ccc([C@@]23Oc4cc(Cl)cnc4[C@]2(O)[C@H](O)[C@H](S(=O)(=O)N2CCCC2)[C@H]3c2ccccc2)cc1]

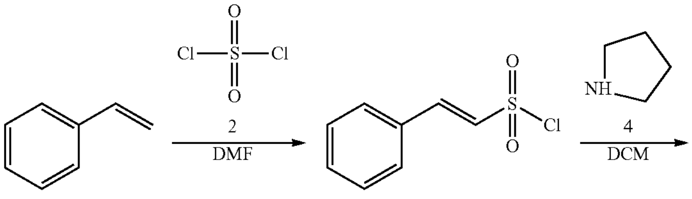

1

3

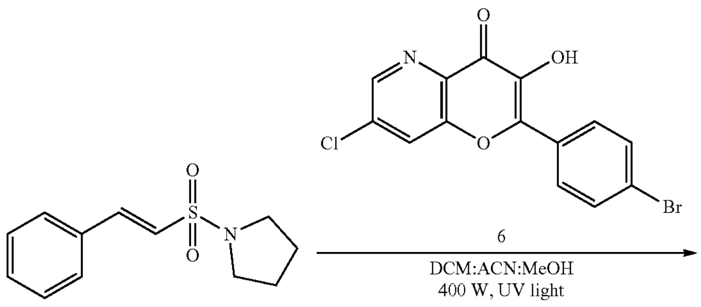

5

-continued

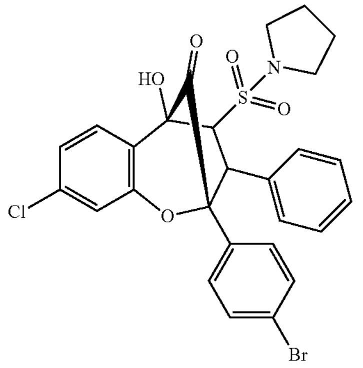

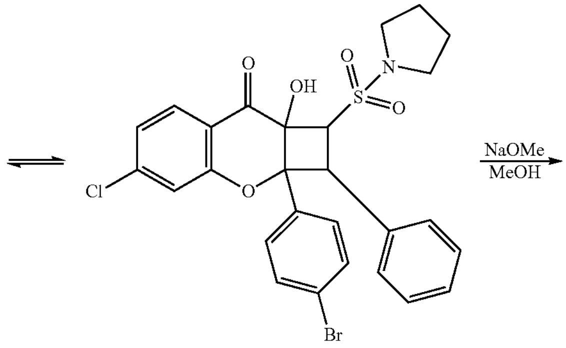

7 7a

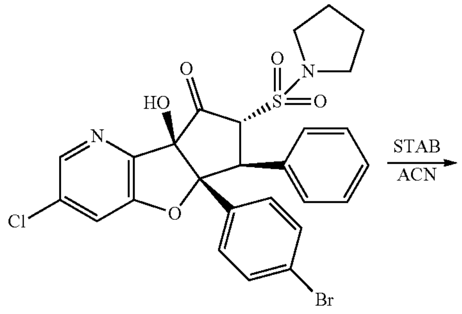

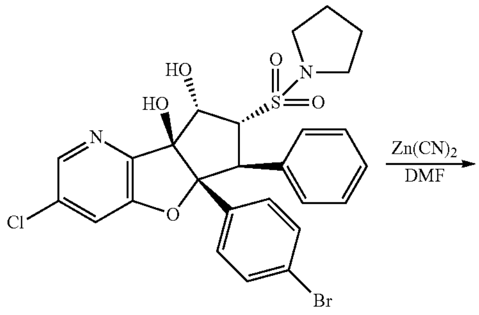

8 9

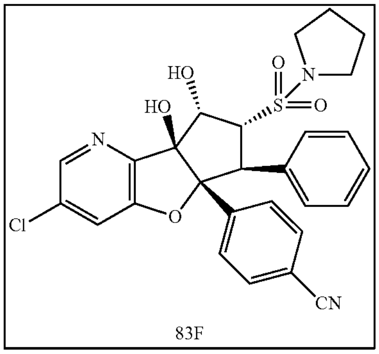

83F

Synthesis of (E)-2-phenylethene-1-sulfonyl chloride (3)

Sulfuryl dichloride (2, 77.70 mL, 960.1 mmol) was added drop wise to anhydrous dimethylformamide (80 mL) at 0° C. under nitrogen and the reaction mixture was stirred at room temperature for 30 min. Styrene (1, 50.0 g, 478.4 mmol) was added and the reaction mixture was heated at 90° C. for 2 h. After completion, the mixture was quenched with ice cold water (1000 ml), the precipitated solid was filtered and dried under vacuum to afford (E)-2-phenylethene-1-sulfonyl chloride (3) as light brown solid. Yield: 60.0 g crude.

Synthesis of (E)-1-(styrylsulfonyl)pyrrolidine (5)

To a solution of pyrrolidine (4, 23.2 g, 326.6 mmol) in dichloromethane (60 ml) at 0° C., triethylamine (113.6 mL, 816.8 mmol) and a solution of (E)-2-phenylethene-1-sulfonyl chloride (3 55.0 g, 272.2 mmol) in dichloromethane were added drop wise over a period of 15 min. The reaction mass was slowly brought to room temperature and stirred for additional 16 h. After completion, the reaction mass was diluted with dichloromethane (500 mL) and water (250 mL). The organic layer was separated, washed with water, dried over anhydrous sodium sulphate, filtered and concentrated under reduced pressure. The crude product was purified by silica gel column chromatography using 20% ethyl acetate in hexanes as eluent. The desired fractions were concentrated to afford (E)-1-(styrylsulfonyl)pyrrolidine (5) as Brown solid. Yield: 37.0 g, 64.0%; MS (ESI) m/z 238.19 $[M+1]^+$.

Synthesis of rac-(3S,4S,5R)-2-(4-bromophenyl)-8-chloro-5-hydroxy-3-phenyl-4-(pyrrolidin-1-ylsulfonyl)-2,3,4,5-tetrahydro-2,5-methanobenzo[b]oxepin-10-one (7)

A solution of 2-(4-bromophenyl)-7-chloro-3-hydroxy-4H-pyrano[3,2-b]pyridin-4-one (6, 4.0 g, 11.4 mmol) and (E)-1-(styrylsulfonyl)pyrrolidine (5, 27.0 g, 113.4 mmol) in dichloromethane (150 mL), acetonitrile (150 mL) and methanol (150 mL) was placed in a UV reactor flask. The reaction mixture was irradiated under 400 watts UV light for 72 h. After completion, solvent was removed under reduced pressure and the residue was purified over a plug of silica gel eluting the compound with ethyl acetate. The desired fractions were concentrated under reduced pressure to afford rac-(3S,4S,5R)-2-(4-bromophenyl)-8-chloro-5-hydroxy-3-phenyl-4-(pyrrolidin-1-ylsulfonyl)-2,3,4,5-tetrahydro-2,5-methanobenzo[b]oxepin-10-one (7) as yellow brown solid. Yield: 4.2 g, crude; MS (ESI) m/z 587.08[M−1]$^+$.

Synthesis of rac-(5aR,6S,7R,8aR)-5a-(4-bromophenyl)-3-chloro-8a-hydroxy-6-phenyl-7-(pyrrolidin-1-ylsulfonyl)-5a,6,7,8a-tetrahydro-8H-cyclopenta[4,5]furo[3,2-b]pyridin-8-one (8)

The crude compound rac-(3S,4S,5R)-2-(4-bromophenyl)-8-chloro-5-hydroxy-3-phenyl-4-(pyrrolidin-1-ylsulfonyl)-2,3,4,5-tetrahydro-2,5-methanobenzo[b]oxepin-10-one (7, 4.0 g, 6.8 mmol) was suspended in methanol (100 mL) and treated with 25% sodium methoxide in methanol (20 mL). The reaction was heated at 80° C. for 3 h. After completion, the solvent was removed under reduced pressure. The crude mixture was diluted with ammonium chloride solution and extracted with ethyl acetate. The organic phase was separated, dried over anhydrous sodium sulphate and concentrated under reduced pressure to afford rac-(5aR,6S,7R,8aR)-5a-(4-bromophenyl)-3-chloro-8a-hydroxy-6-phenyl-7-(pyrrolidin-1-ylsulfonyl)-5a,6,7,8a-tetrahydro-8H-cyclopenta[4,5]furo[3,2-b]pyridin-8-one (8) as brown solid. Yield: 4.0 g, crude.

Synthesis of rac-(5aR,6S,7R,8S,8aS)-5a-(4-bromophenyl)-3-chloro-6-phenyl-7-(pyrrolidin-1-ylsulfonyl)-5a,6,7,8-tetrahydro-8aH-cyclopenta[4,5]furo[3,2-b]pyridine-8,8a-diol (9)

To a solution of sodium triacetoxyborohydride (8.65 g, 40.8 mmol), rac-(5aR,6S,7R,8aR)-5a-(4-bromophenyl)-3-chloro-8a-hydroxy-6-phenyl-7-(pyrrolidin-1-ylsulfonyl)-5a,6,7,8a-tetrahydro-8H-cyclopenta[4,5]furo[3,2-b]pyridin-8-one (8, 4.0 g, 6.80 mmol) in acetonitrile (80 mL), acetic acid (4.08 mL, 68.0 mmol) was added. The resulting mixture was stirred for 16 h at room temperature. After completion, the reaction mixture was partitioned between saturated aqueous sodium bicarbonate solution and ethyl acetate. The organic layer was separated, dried over anhydrous sodium sulphate, filtered and concentrated under reduced pressure to get the crude. The crude was purified by silica gel column chromatography using 1-5% methanol in dichloromethane as eluents. The desired fractions were concentrated under reduced pressure to afford rac-(5aR,6S,7R,8S,8aS)-5a-(4-bromophenyl)-3-chloro-6-phenyl-7-(pyrrolidin-1-ylsulfonyl)-5a,6,7,8-tetrahydro-8aH-cyclopenta[4,5]furo[3,2-b]pyridine-8,8a-diol (9) as off white solid. Yield: 0.4 g, 10.0%; MS (ESI) m/z 591.27 [M+1]$^+$.

Synthesis of 4-((5aR,6S,7R,8S,8aS)-3-chloro-8,8a-dihydroxy-6-phenyl-7-(pyrrolidin-1-ylsulfonyl)-6,7,8,8a-tetrahydro-5aH-cyclopenta[4,5]furo[3,2-b]pyridin-5a-yl)benzonitrile (Cpd. No. 83F)

To a solution of rac-(5aR,6S,7R,8S,8aS)-5a-(4-bromophenyl)-3-chloro-6-phenyl-7-(pyrrolidin-1-ylsulfonyl)-5a,6,7,8-tetrahydro-8aH-cyclopenta[4,5]furo[3,2-b]pyridine-8,8a-diol (9, 0.35 g, 0.593 mmol) in N,N-dimethylformamide (7.0 mL), zinc cyanide (0.105 g, 0.889 mmol) and zinc dust (0.004 g, 0.059 mmol) were added at room temperature and the reaction mixture was degassed with argon for 15 min. 1,1'-Bis(diphenylphosphino)ferrocene (0.043 g, 0.059 mmol) and tris(dibenzylideneacetone)dipalladium (0.004 g, 0.0177 mmol) were added to the reaction, degassed for additional 5 min and mixture was heated at 135° C. for 4 h. After completion, the reaction mass was diluted with ethyl acetate and washed with cold water. The organic layer was separated and dried over anhydrous sodium sulphate, filtered and concentrated to give crude. The crude was purified by silica gel column chromatography using 2-3% methanol in dichloromethane as eluent. The desired fractions were concentrated to afford rac-4-((5aR,6S,7R,8S,8aS)-3-chloro-8,8a-dihydroxy-6-phenyl-7-(pyrrolidin-1-ylsulfonyl)-6,7,8,8a-tetrahydro-5aH-cyclopenta[4,5]furo[3,2-b]pyridin-5a-yl)benzonitrile as white solid. Yield: 0.1 g, 31% (racemic). The enantiomers were separated by chiral HPLC [Chiralpak IC (4.6×250)mm, 5μ] n-Hexane/EtOH=50/50(v/v). Peak 1 (22 mg), $[\alpha]_D$+118.00 (c 0.44, $CHCl_3$), $R_t$=9.946 min, ee: 99.8%; MS (ESI) m/z 538.14 [M+1]$^+$. $^1$H NMR (400 MHz, DMSO-$d_6$) δ 8.20 (d, J=1.92 Hz, 1H), 7.68 (d, J=1.92 Hz, 1H), 7.49 (bs, 4H), 7.14 (d, J=7.2 Hz, 2H), 7.04 (m, 3H), 6.44 (s, 1H), 5.93 (d, J=6.2 Hz, 1H), 4.93 (dd, J=13.58 Hz, 4.06 Hz, 1H), 4.67 (t, J=5.2 Hz, 1H), 4.60 (d, J=13.4 Hz, 1H), 3.11 (bs, 2H), 2.66 (bs, 2H), 1.60 (m, 4H). Peak 2 (Cpd. No. 83F, 19 mg), $[\alpha]_D$−120.9° (c 0.4, $CHCl_3$), $R_t$=13.664 min, ee: 99.9%; MS (ESI) m/z 538.14 [M+1]$^+$. $^1$H NMR (400 MHz, DMSO-$d_6$) δ 8.20 (d, J=1.92 Hz, 1H), 7.68 (d, J=1.92 Hz, 1H), 7.49 (m, 4H), 7.14 (d, J=7.2 Hz, 2H), 7.04 (m, 3H), 6.44 (s, 1H), 5.93 (d, J=6.2 Hz, 1H), 4.93 (dd, J=13.58 Hz, 4.06 Hz, 1H), 4.67 (t, J=5.2 Hz, 1H), 4.60 (d, J=13.4 Hz, 1H), 3.11 (bs, 2H), 2.66 (bs, 2H), 1.60 (m, 4H).

Example 84

Rac-(5aR,6S,7R,8S,8aS)-5a-(4-bromophenyl)-3-chloro-7-(methylsulfonyl)-6-phenyl-5a,6,7,8-tetrahydro-8aH-cyclopenta[4,5]furo[3,2-b]pyridine-8,8a-diol (Cpd. No. 84F)

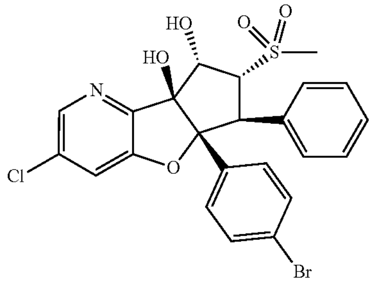

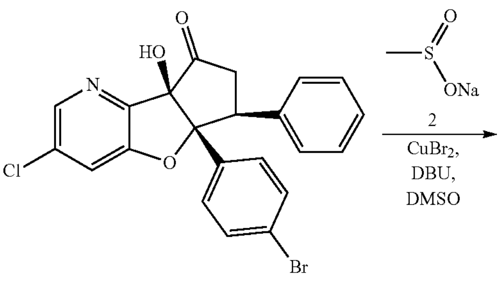

1

-continued

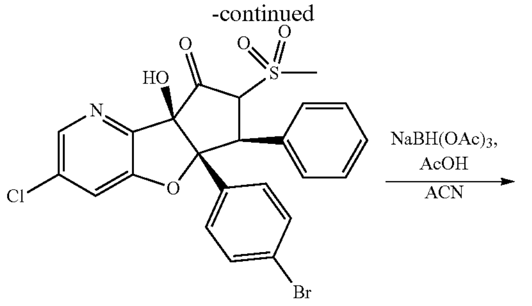

3

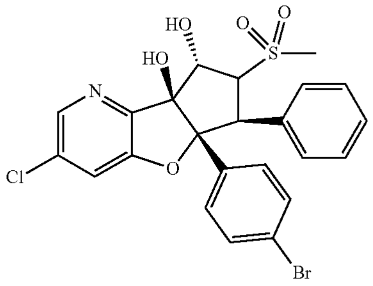

84F

Synthesis of rac-(5aR,6S,8aR)-5a-(4-bromophenyl)-3-chloro-8a-hydroxy-7-(methylsulfonyl)-6-phenyl-5a,6,7,8a-tetrahydro-8H-cyclopenta[4,5]furo[3,2-b]pyridin-8-one (3)

To a solution of 1,8-diazabicyclo[5.4.0]undec-7-ene (3.0 mL, 19.7 mmol) in dimethyl sulfoxide (10 mL), copper(II) bromide (51 mg, 0.23 mmol) was added at room temperature in presence of air. Rac-(5aR,6S,8aR)-5a-(4-bromophenyl)-3-chloro-8a-hydroxy-6-phenyl-5a,6,7,8a-tetrahydro-8H-cyclopenta[4,5]furo[3,2-b]pyridin-8-one (1, 1.5 g, 3.2 mmol) and sodium methanesulfinate (2, 3.36 g, 32.0 mmol) in dimethyl sulfoxide (10.0 mL) were added drop wise to above reaction mixture at room temperature in presence of air. The reaction mixture was stirred at room temperature for 1 h. After completion (monitored by MS), the reaction mass was diluted with ethyl acetate and washed with cold water. The organic layer was separated and dried over anhydrous sodium sulphate, filtered and concentrated under reduced pressure to afford rac-(5aR,6S,8aR)-5a-(4-bromophenyl)-3-chloro-8a-hydroxy-7-(methylsulfonyl)-6-phenyl-5a,6,7,8a-tetrahydro-8H-cyclopenta[4,5]furo[3,2-b]pyridin-8-one (3) as brown semi solid. Yield: 0.5 g, crude; MS (ESI) m/z 532 $[M-1]^-$.

Synthesis of rac-(5aR,6S,7R,8S,8aS)-5a-(4-bromophenyl)-3-chloro-7-(methylsulfonyl)-6-phenyl-5a,6,7,8-tetrahydro-8aH-cyclopenta[4,5]furo[3,2-b]pyridine-8,8a-diol (Cpd. No. 84F)

To a solution of sodium triacetoxyborohydride (1.19 g, 5.62 mmol) and rac-(5aR,6S,8aR)-5a-(4-bromophenyl)-3-chloro-8a-hydroxy-7-(methylsulfonyl)-6-phenyl-5a,6,7,8a-tetrahydro-8H-cyclopenta[4,5]furo[3,2-b]pyridin-8-one (3, 0.5 g, 0.938 mmol) in acetonitrile (25 mL), acetic acid (0.562 mL, 9.38 mmol) was added. The resulting mixture was stirred for 6 h at room temperature. After completion, reaction mixture was partitioned between saturated aqueous sodium bicarbonate solution and ethyl acetate. The organic layer was separated, dried over anhydrous sodium sulphate and concentrated under reduced pressure to get the crude. The crude was purified by Combi-flash (12 g, RediSep column) using 60% ethyl acetate in hexanes as eluent. The desired fractions were concentrated under reduced pressure to afford rac-(5aR,6S,7R,8S,8aS)-5a-(4-bromophenyl)-3-chloro-7-(methylsulfonyl)-6-phenyl-5a,6,7,8-tetrahydro-8aH-cyclopenta[4,5]furo[3,2-b]pyridine-8,8a-diol (Cpd. No. 84F) as white solid. Yield: 70 mg, 14%. MS (ESI) m/z 536.08 $[M+1]^+$; UPLC 99.8%; $^1H$ NMR (400 MHz, DMSO-d) δ: 8.21 (d, J=2.0 Hz, 1H), 7.67 (d, J=2.0 Hz, 1H), 7.24 (d, J=8.7 Hz, 2H), 7.19-7.16 (m, 4H) 7.08-7.01 (m, 3H), 6.33 (bs, 1H), 6.20 (bs, 1H), 4.83 (dd, J=4.0, 13.5 Hz, 1H), 4.77 (d, J=4.4 Hz, 1H), 4.56 (d, J=13.6 Hz, 1H), 2.84 (s, 3H).

Example 85

Rac-4-((5aR,6S,7R,8S,8aS)-3-chloro-8,8a-dihydroxy-7-(methylsulfonyl)-6-phenyl-6,7,8,8a-tetrahydro-5aH-cyclopenta[4,5]furo[3,2-b]pyridin-5a-yl) benzonitrile (Cpd. No. 85F)

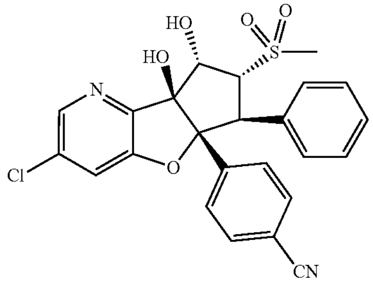

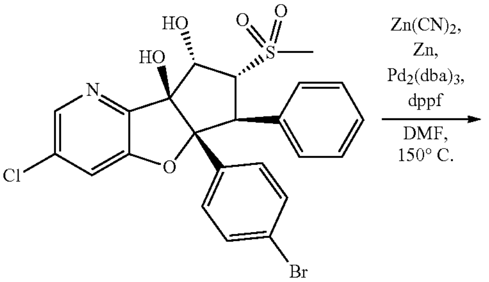

1

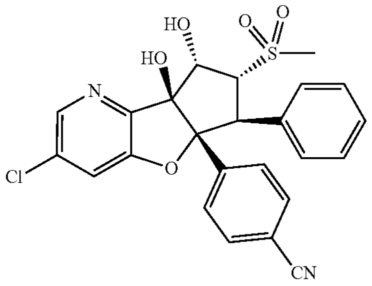

85F

Synthesis of rac-4-((5aR,6S,7R,8S,8aS)-3-chloro-8,8a-dihydroxy-7-(methylsulfonyl)-6-phenyl-6,7,8,8a-tetrahydro-5aH-cyclopenta[4,5]furo[3,2-b]pyridin-5a-yl)benzonitrile (Cpd. No. 85F)

To a solution of rac-(5aR,6S,7R,8S,8aS)-5a-(4-bromophenyl)-3-chloro-7-(methylsulfonyl)-6-phenyl-5a,6,7,8-tetrahydro-8aH-cyclopenta[4,5]furo[3,2-b]pyridine-8,8a-diol (1, 0.13 g, 0.242 mmol) in N,N-dimethylformamide (5.0 mL), zinc cyanide (0.033 g, 0.291 mmol) and zinc (0.0016 g, 0.024 mmol) were added at room temperature and degassed the mixture with argon for 15 min. 1,1'-Bis(diphenylphosphino)ferrocene (0.013 g, 0.024 mmol) and tris (dibenzylideneacetone)dipalladium (0.006 g, 0.007 mmol) were added to the reaction mixture and degassing was continued for another 5 min. The reaction mixture was heated at 150° C. for 2 h. After completion, the reaction was cooled to room temperature and passed through celite bed. The filtrate was diluted with ethyl acetate and washed with water. The organic layer was separated, dried over anhydrous sodium sulphate and concentrated under reduced pressure to get the crude. The crude containing monocyano and dicyano compounds were purified by reversed phase prep-HPLC to afford rac-4-((5aR,6S,7R,8S,8aS)-3-chloro-8,8a-dihydroxy-7-(methylsulfonyl)-6-phenyl-6,7,8,8a-tetrahydro-5aH-cyclopenta[4,5]furo[3,2-b]pyridin-5a-yl)benzonitrile as off white solid. Yield: 84 mg, 45%. The enantiomers were separated by chiral preparative HPLC [chiralpak ID (4.6×250) mm] using 0.1% DEA in n-Hexane/EtOH=70/30(v/v) mobile phase. Peak 1 (30 mg); $[\alpha]_D$+48.5° (c 0.25, $CHCl_3$); $R_t$=11.3 min, ee >99%; MS (ESI) m/z 483.08 $[M+1]^+$; UPLC: 99.70%; $^1H$ NMR (400 MHz, DMSO-$d_6$) δ: 8.22 (d, J=1.92 Hz, 1H), 7.71 (d, J=1.8 Hz, 1H), 7.52 (d, J=8.5 Hz, 2H), 7.44 (d, J=8.5 Hz, 2H), 7.18 (d, J=6.48 Hz, 2H), 7.07-7.00 (m, 3H), 6.45 (s, 1H), 6.26 (d, J=6.2 Hz, 1H), 4.94 (dd, J=4.0, 13.8 Hz, 1H), 4.78 (t, J=6.2 Hz, 1H), 4.61 (d, J=13.7 Hz, 1H), 2.86 (s, 3H). Peak-2 (Cpd. No. 85F, 33.0 mg); $[\alpha]_D$−46.6° (c 0.30, $CHCl_3$); $R_t$=17.2 min, ee >99%; MS (ESI) m/z 483.08 $[M+1]^+$; UPLC: 99.35%; $^1H$ NMR (400 MHz, DMSO-$d_6$) δ: 8.22 (d, J=1.8 Hz, 1H), 7.71 (d, J=1.8 Hz, 1H), 7.52 (d, J=8.4 Hz, 2H), 7.44 (d, J=8.5 Hz, 2H), 7.18 (d, J=6.6 Hz 2H), 7.07-7.00 (m, 3H), 6.45 (s, 1H), 6.26 (d, J=6.3 Hz, 1H), 4.94 (dd, J=4.0 Hz, 13.6 Hz, 1H), 4.78 (t, J=4.52 Hz, 1H), 4.62 (d, J=13.8 Hz, 1H), 2.86 (s, 3H).

Example 86

(5aR,6S,7R,8S,8aS)-5a-(4-cyanophenyl)-8,8a-dihydroxy-7-(methylsulfonyl)-6-phenyl-5a,7,8,8a-tetrahydro-6H-cyclopenta[4,5]furo[3,2-b]pyridine-3-carbonitrile (Cpd. No. 86F)

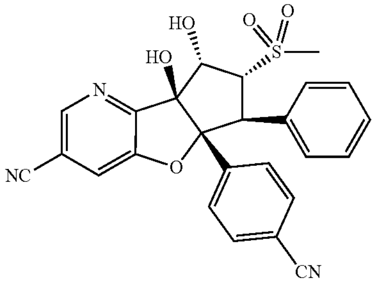

-continued

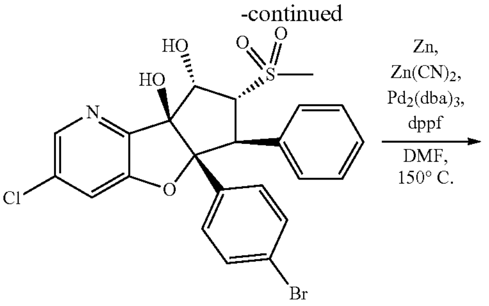

1

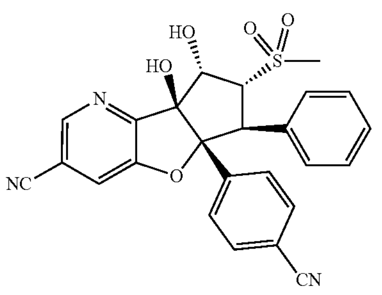

86F

Synthesis of (5aR,6S,7R,8S,8aS)-5a-(4-cyanophenyl)-8,8a-dihydroxy-7-(methylsulfonyl)-6-phenyl-5a, 7,8,8a-tetrahydro-6H-cyclopenta[4,5]furo[3,2-b] pyridine-3-carbonitrile (Cpd. No. 86F)

To a solution of rac-(5aR,6S,7R,8S,8aS)-5a-(4-bromophenyl)-3-chloro-7-(methylsulfonyl)-6-phenyl-5a,6,7,8-tetrahydro-8aH-cyclopenta[4,5]furo[3,2-b]pyridine-8,8a-diol (1, 0.13 g, 0.242 mmol) in N,N-dimethylformamide (5.0 mL), zinc cyanide (0.033 g, 0.291 mmol) and zinc (0.0016 g, 0.024 mmol) were added at room temperature and degassed the mixture with argon for 15 min. 1,1'-Bis(diphenylphosphino)ferrocene (0.013 g, 0.024 mmol) and tris (dibenzylideneacetone)dipalladium (0.006 g, 0.007 mmol) were added to the reaction mixture and degassing was continued for another 5 min. The reaction mixture was heated at 150° C. for 2 h. After completion, the reaction was cooled to room temperature and passed through celite bed. The filtrate was diluted with ethyl acetate and washed with water. The organic layer was separated, dried over anhydrous sodium sulphate and concentrated under reduced pressure to get the crude. The crude containing monocyano and dicyano compounds were purified by reversed phase prep-HPLC to afford rac-(5aR,6S,7R,8S,8aS)-5a-(4-cyanophenyl)-8,8a-dihydroxy-7-(methylsulfonyl)-6-phenyl-5a,7,8,8a-tetrahydro-6H-cyclopenta[4,5]furo[3,2-b]pyridine-3-carbonitrile (Cpd. No. 86) as off white solid. Yield: 15 mg, 20%; MS (ESI) m/z 474.11 $[M+1]^+$; UPLC 99.1%; $^1H$ NMR (400 MHz, DMSO-$d_6$) δ: 8.66 (d, J=1.4 Hz, 1H), 8.04 (d, J=1.4 Hz, 1H), 7.52 (d, J=8.6 Hz, 2H), 7.45 (d, J=8.4 Hz, 2H), 7.20 (d, J=6.6 Hz, 2H), 7.07-7.02 (m, 3H), 6.66 (s, 1H), 6.38 (d, J=6.3 Hz, 1H), 4.99 (dd, J=3.7 Hz, 13.8 Hz, 1H), 4.83-4.80 (m, 1H), 4.65 (d, J=13.7 Hz, 1H), 2.85 (s, 3H).

Example 87

Rac-((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)(morpholino)methanone (Cpd. No. 87F)

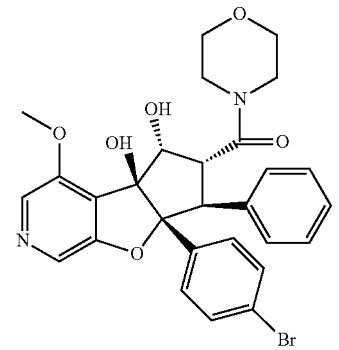

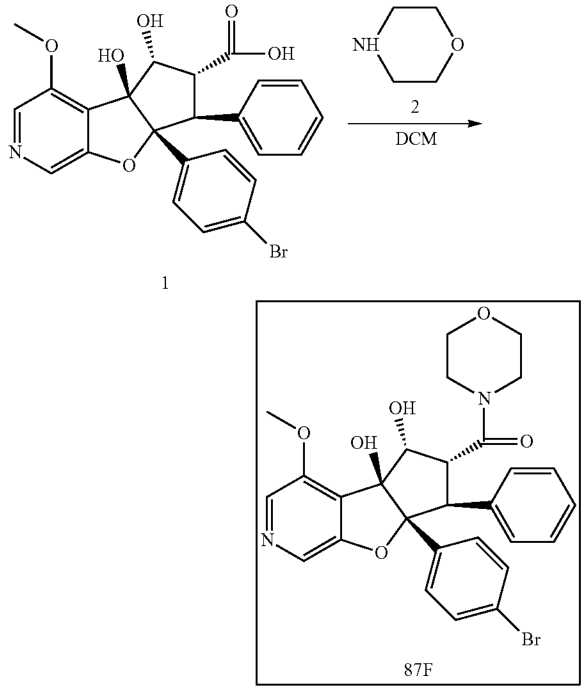

1

87F

Synthesis of rac-((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)(morpholino)methanone (Cpd. No. 87F)

To a solution of rac-(4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylic acid (1, 0.07 g, 0.1404 mmol) in dichloromethane (2 mL) at 0° C., 1-ethyl-3-(3-dimethylaminopropyl) carbodiimide (0.080 g, 0.4214 mmol), hydroxybenzotriazole (0.056 g, 0.4214 mmol) and N,N-diisopropylethylamine (0.126 g, 0.9832 mmol) were added and the mixture was stirred for 5 min. Morpholine (2, 0.006 g, 0.7023 mmol) was then added at the same temperature and the reaction was stirred for 16 h at room temperature. After completion, the reaction mass was diluted with dichloromethane and washed with cold water. The organic layer was separated and dried over anhydrous sodium sulphate, filtered and concentrated to give crude. The crude was purified by silica gel column chromatography using 0-5% methanol in dichloromethane as eluent. The desired fractions were concentrated to afford rac-((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)(morpholino)methanone (Cpd. No. 87F) as white solid. Yield: 0.04 g, 51%; MS (ESI) m/z 567.22 $[M+1]^+$. $^1H$ NMR (400 MHz, DMSO-$d_6$) δ 8.10 (s, 1H), 7.99 (s, 1H), 7.20 (d, J=8.56 Hz, 2H), 7.09-6.96 (m, 5H), 6.92 (d, J=7.36, 2H), 5.68 (s, 1H), 5.20 (d, J=5.48 Hz, 1H), 4.69 (bs, 1H), 4.45 (d, J=13.2 Hz, 1H), 3.88 (bs, 4H), 3.76-3.69 (m, 4H), 3.59 (bs, 1H), 3.45-3.42 (m, 2H), 3.11 (bs, 1H).

Example 88

Rac-(4bS,5R,6R,7S,7aR)-7a-(4-bromophenyl)-4b,5-dihydroxy-4-methoxy-N-methyl-7-phenyl-N-(2,2,2-trifluoroethyl)-4b,6,7,7a-tetrahydro-5H-cyclopenta[4,5]furo[2,3-c]pyridine-6-carboxamide (Cpd. No. 88F)

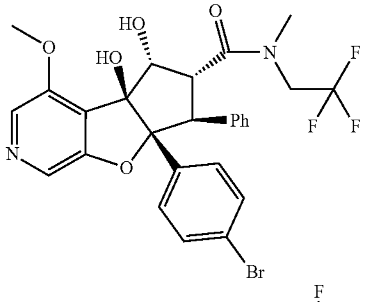

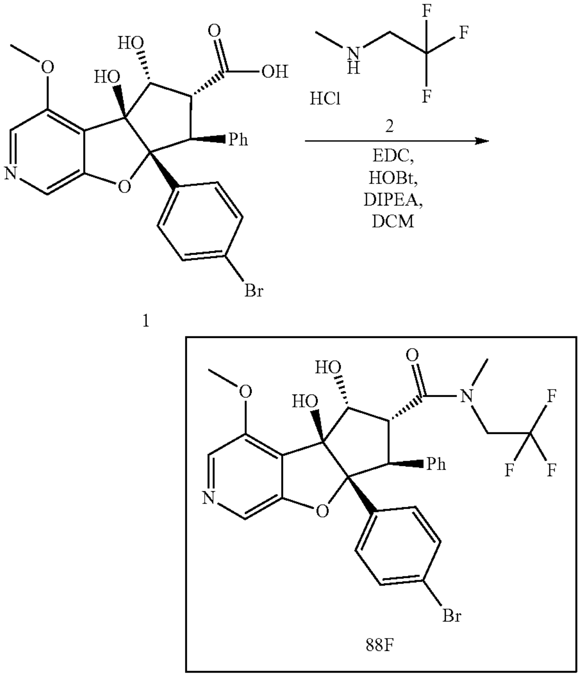

1

88F

Synthesis of rac-(4bS,5R,6R,7S,7aR)-7a-(4-bromophenyl)-4b,5-dihydroxy-4-methoxy-N-methyl-7-phenyl-N-(2,2,2-trifluoroethyl)-4b,6,7,7a-tetrahydro-5H-cyclopenta[4,5]furo[2,3-c]pyridine-6-carboxamide (Cpd. No. 88F)

To a solution of rac-(4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylic acid (1, 0.4 g, 0.8 mmol) in dichloromethane (20 mL), 1-ethyl-3-(3-dimethylaminopropyl)carbodiimide (0.37 g, 2.4 mmol), hydroxybenzotriazole (0.32 g, 2.4 mmol) and N,N-diisopropylethylamine (0.9 ml, 4.8 mmol) were added at 0° C. and stirred the mixture for 5 min. 2,2,2-trifluoro-N-methylethan-1-amine hydrochloride (0.39 g, 3.0 mmol) was then added and the reaction mixture was stirred for 3 h at room temperature. After completion, reaction mass was diluted with dichloromethane and washed with cold water. The organic layer was dried over anhydrous sodium sulphate, filtered and concentrated under reduce pressure to get the crude. The crude product was purified by Combi-flash (4.0 g, RediSep column) using 3% methanol in dichloromethane as eluent. The crude obtained was submitted for reverse phase prep HPLC. The desired fractions were lyophilized to afford rac-(4bS,5R,6R,7S,7aR)-7a-(4-bromophenyl)-4b,5-dihydroxy-4-methoxy-N-methyl-7-phenyl-N-(2,2,2-trifluoroethyl)-4b,6,7,7a-tetrahydro-5H-cyclopenta[4,5]furo[2,3-c]pyridine-6-carboxamide (Cpd. No. 88F) as white solid. Yield: 12 mg, 2.5%; MS (ESI) m/z 593.23 $[M+1]^+$ UPLC: 99.79%; $^1$H NMR (400 MHz, DMSO-d)$^6$ 8.11 (s, 1H), 8.00 (s, 1H), 7.22 (d, J=12.2 Hz, 2H), 7.14-7.03 (m, 4H), 6.97 (d, J=6.7 Hz, 1H), 6.92-6.85 (m, 2H), 5.76 (s, 1H), 5.23 (d, J=5.4 Hz, 1H), 4.81 (t, J=5.2 Hz, 1H), 4.44 (d, J=13.4 Hz, 1H), 4.31-4.23 (m, 2H), 3.97-3.88 (m, 1H), 3.88 (s, 3H), 3.42 (s, 3H).

Example 89

Rac-(4bS,5R,6R,7S,7aR)-7a-(4-bromophenyl)-N-cyclopropyl-4b,5-dihydroxy-4-methoxy-7-phenyl-4b,6,7,7a-tetrahydro-5H-cyclopenta[4,5]furo[2,3-c]pyridine-6-carboxamide (Cpd. No. 89F)

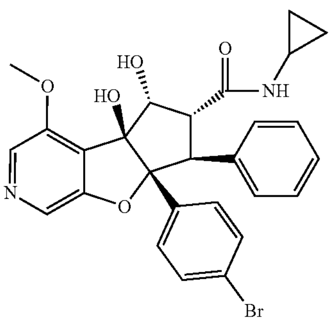

-continued

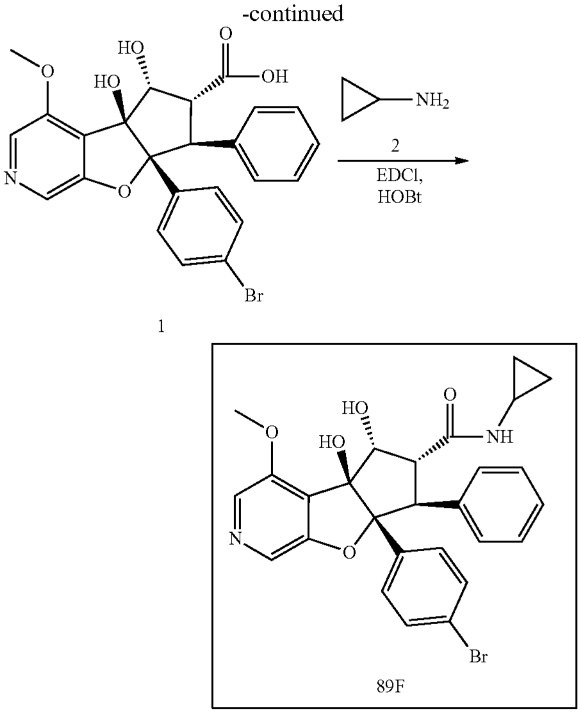

1

89F

Synthesis of rac-(4bS,5R,6R,7S,7aR)-7a-(4-bromophenyl)-N-cyclopropyl-4b,5-dihydroxy-4-methoxy-7-phenyl-4b,6,7,7a-tetrahydro-5H-cyclopenta[4,5]furo[2,3-c]pyridine-6-carboxamide (Cpd. No. 89F)

To a solution of rac-(4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylic acid (1, 1.50 g, 3.01 mmol) in dichloromethane (40 mL) at 0° C., 1-ethyl-3-(3-dimethylaminopropyl) carbodiimide (1.73 g, 9.05 mmol), hydroxybenzotriazole (1.38 g, 9.05 mmol) and N,N-diisopropylethylamine (2.72 g, 21.12 mmol) were added and the mixture was stirred for 5 min. Cyclopropylamine (2, 0.861 g, 15.09 mmol) was then added at the same temperature and the reaction was stirred for 16 h at room temperature. After completion, the reaction mass was diluted with dichloromethane and washed with cold water. The organic layer was separated and dried over anhydrous sodium sulphate, filtered and concentrated to give crude product. The crude product was purified by silica gel column chromatography using 0-5% methanol in dichloromethane as eluent. The desired fractions were concentrated to afford rac-(4bS,5R,6R,7S,7aR)-7a-(4-bromophenyl)-N-cyclopropyl-4b,5-dihydroxy-4-methoxy-7-phenyl-4b,6,7,7a-tetrahydro-5H-cyclopenta[4,5]furo[2,3-c]pyridine-6-carboxamide (Cpd. No. 89F) as white solid. Yield: 1.3 g, 86% MS (ESI) m/z 537.2 $[M+1]^+$. $^1$H NMR (400 MHz, DMSO-$d_6$) δ 8.28 (d, J=4.08 Hz, 1H), 8.08 (s, 1H), 7.98 (s, 1H), 7.22 (d, J=8.56 Hz, 2H), 7.08-6.95 (m, 7H), 5.65 (s, 1H), 5.08 (d, J=4.16 Hz, 1H), 4.54 (t, J=4.18 Hz, 1H), 4.34 (d, J=14.0 Hz, 1H), 3.87 (s, 3H), 3.78 (dd, J=14.16 Hz, 6.16 Hz, 1H), 2.55 (d, J=3.8 Hz, 1H), 0.55 (d, J=6.64 Hz, 2H), 0.43-0.40 (m, 1H), 0.28-0.26 (m, 1H).

Example 90

Rac-(4bS,5R,6R,7S,7aR)-7a-(4-bromophenyl)-4b,5-dihydroxy-4-methoxy-7-phenyl-N-(2,2,2-trifluoroethyl)-4b,6,7,7a-tetrahydro-5H-cyclopenta[4,5]furo[2,3-c]pyridine-6-carboxamide (Cpd. No. 90F)

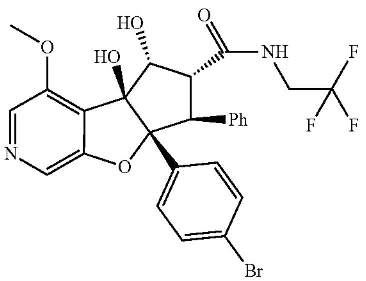

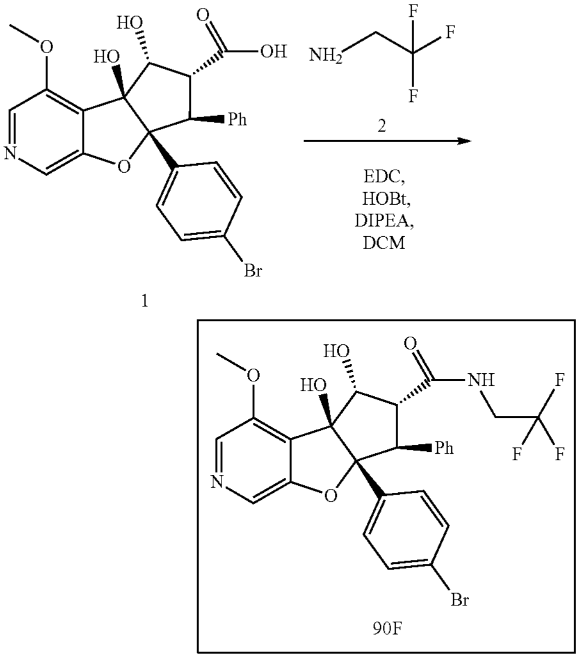

1

90F

Synthesis of rac-(4bS,5R,6R,7S,7aR)-7a-(4-bromophenyl)-4b,5-dihydroxy-4-methoxy-7-phenyl-N-(2,2,2-trifluoroethyl)-4b,6,7,7a-tetrahydro-5H-cyclopenta[4,5]furo[2,3-c]pyridine-6-carboxamide (Cpd. No. 90F)

To a solution of (4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylic acid (1, 0.5 g, 1.0 mmol) in dichloromethane (20 mL), 1-ethyl-3-(3-dimethylaminopropyl)carbodiimide (0.47 g, 3.0 mmol), hydroxybenzotriazole (0.40 g, 3.0 mmol) and N,N-diisopropylethylamine (0.9 ml, 5.0 mmol) were added at 0° C. and stirred the mixture for 5 min. 2,2,2-Trifluoroethan-1-amine (2, 0.30 g, 3.0 mmol) was added to above solution and the reaction mixture was stirred for 3 h at room temperature. After completion, reaction mass was diluted with dichloromethane and washed with cold water. The organic layer was dried over anhydrous sodium sulphate, filtered and concentrated under reduced pressure to get the crude. The crude was purified by Combi-flash (4 g RediSep column) using 3% methanol in dichloromethane as eluent. The crude compound was submitted for reverse phase prep HPLC. The desired fractions were lyophilized to afford rac-(4bS,5R,6R,7S,7aR)-7a-(4-bromophenyl)-4b,5-dihydroxy-4-methoxy-7-phenyl-N-(2,2,2-trifluoroethyl)-4b,6,7,7a-tetrahydro-5H-cyclopenta[4,5]furo[2,3-c]pyridine-6-carboxamide (Cpd. No. 90F) as white solid. Yield: 217 mg, 40%; MS (ESI) m/z 579.21 $[M+1]^+$, UPLC: 99.29%. $^1H$ NMR (400 MHz, DMSO-$d_6$) δ 8.78 (t, J=6.1 Hz, 1H), 8.09 (s, 1H), 7.98 (s, 1H), 7.23 (d, J=8.6 Hz, 2H), 7.06-7.02 (m, 4H), 6.98 (d, J=7.0 Hz, 1H), 6.94 (d, J=7.4 Hz, 2H), 5.67 (s, 1H), 5.08 (d, J=4.9 Hz, 1H), 4.63 (d, J=4.8 Hz, 1H), 4.37 (d, J=12.7 Hz, 1H), 3.96 (dd, J=4.8 Hz, 14.2 Hz, 1H), 3.90 (s, 3H), 3.80 (m, 1H).

Example 91

Rac-(5aR,6S,8S,8aS)-5a-(4-bromophenyl)-3-chloro-7,7-difluoro-6-phenyl-5a,6,7,8-tetrahydro-8aH-cyclopenta[4,5]furo[3,2-b]pyridine-8,8a-diol (Cpd. No. 91F)

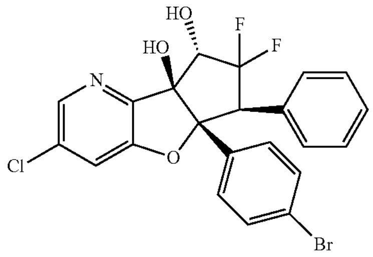

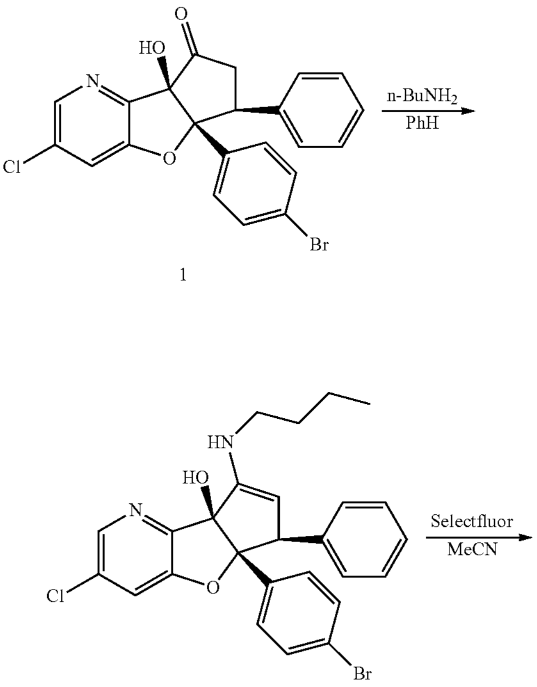

1

2

-continued

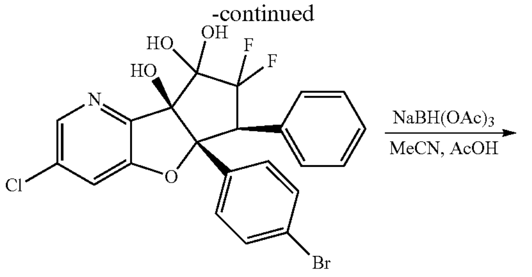

3

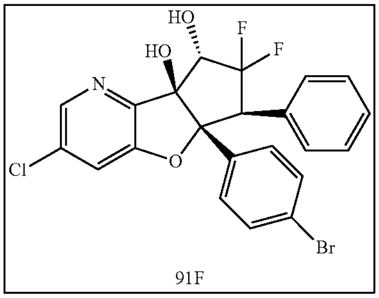

91F

Synthesis of rac-(5aR,6S,8aR)-5a-(4-bromophenyl)-8-(butylamino)-3-chloro-6-phenyl-5a,6-dihydro-8aH-cyclopenta[4,5]furo[3,2-b]pyridin-8a-ol (2)

To a solution of rac-(5aR,6S,8aR)-5a-(4-bromophenyl)-3-chloro-8a-hydroxy-6-phenyl-5a,6,7,8a-tetrahydro-8H-cyclopenta[4,5]furo[3,2-b]pyridin-8-one (1, 0.50 g, 1.09 mmol) in benzene (5.0 ml), trifluoroacetic acid (0.01 ml, cat) was added followed by addition of n-butyl amine (0.12 g, 1.64 mmol). The reaction mixture was stirred at 100° C. After completion, The mixture was diluted with ethyl acetate (100 mL) and water (50 mL). The organic layer was separated and washed with water, dried over anhydrous sodium sulfate, filtered and concentrated under reduced pressure to afford rac-(5aR,6S,8aR)-5a-(4-bromophenyl)-8-(butylamino)-3-chloro-6-phenyl-5a,6-dihydro-8aH-cyclopenta[4,5]furo[3,2-b]pyridin-8a-ol (2) as yellow solid. Yield: 0.6 g, 64%; MS (ESI) m/z 511.29 $[M+1]^+$.

Synthesis of rac-(5aR,6S,8aR)-5a-(4-bromophenyl)-3-chloro-7,7-difluoro-6-phenyl-6,7-dihydro-8H-cyclopenta[4,5]furo[3,2-b]pyridine-8,8,8a(5aH)-triol (3)

To a solution of rac-(5aR,6S,8aR)-5a-(4-bromophenyl)-8-(butylamino)-3-chloro-6-phenyl-5a,6-dihydro-8aH-cyclopenta[4,5]furo[3,2-b]pyridin-8a-ol (2, 0.6 g, 1.1 mmol) in acetonitrile (10 ml) at 0° C., selectfluor (0.83 g, 2.3 mmol) was added in one portion followed by sodium sulfate (0.6 g). The reaction mass was stirred for 12 h at 70° C. After completion, the mixture was diluted with ethyl acetate (100 mL) and water (50 mL). The organic layer was separated, washed with water, dried over anhydrous sodium sulfate, and concentrated under reduced pressure to afford rac-(5aR,6S,8aR)-5a-(4-bromophenyl)-3-chloro-7,7-difluoro-6-phenyl-6,7-dihydro-8H-cyclopenta[4,5]furo[3,2-b]pyridine-8,8,8a(5aH)-triol (3) as yellow solid. Yield: 0.37 g crude MS (ESI) m/z 509.95 $[M+1]^+$.

Synthesis of rac-(5aR,6S,8S,8aS)-5a-(4-bromophenyl)-3-chloro-7,7-difluoro-6-phenyl-5a,6,7,8-tetrahydro-8aH-cyclopenta[4,5]furo[3,2-b]pyridine-8,8a-diol (Cpd. No. 91F)

To a solution of rac-(5aR,6S,8aR)-5a-(4-bromophenyl)-3-chloro-7,7-difluoro-6-phenyl-6,7-dihydro-8H-cyclopenta[4,5]furo[3,2-b]pyridine-8,8,8a(5aH)-triol (3, 0.2 g, 0.407 mmol) in acetonitrile (5 mL) and acetic acid (0.5 ml, 8.14 mmol) was added sodium triacetoxyborohydride (0.51 g, 2.4 mmol). The resulting mixture was stirred for 24 h at room temperature. After completion, the reaction mixture was partitioned between saturated aqueous sodium bicarbonate solution and ethyl acetate. The organic layer was separated, dried over anhydrous sodium sulphate, and concentrated under reduced pressure to get the crude. The crude product was purified by preparative HPLC to afford rac-(5aR,6S,8S,8aS)-5a-(4-bromophenyl)-3-chloro-7,7-difluoro-6-phenyl-5a,6,7,8-tetrahydro-8aH-cyclopenta[4,5]furo[3,2-b]pyridine-8,8a-diol (Cpd. No. 91F) as white solid. Yield: 3 mg, 1.5%; MS (ESI) m/z 494.34 $[M+1]^+$; $^1H$ NMR (400 MHz, DMSO-$d_6$) δ 8.26 (d, J=2 Hz, 1H), 7.73 (d, J=2 Hz, 1H), 7.33 (d, J=8.8 Hz, 2H), 7.19 (m, 7H), 6.57 (d, J=5.6 Hz, 1H), 6.42 (s, 1H), 4.57 (m, 1H), 4.42 (m, 1H).

Example 92

Rac-(5aR,6R,8R,8aS)-5a-(4-bromophenyl)-3-chloro-6-phenyl-5a,6-dihydrospiro[cyclopenta[4,5]furo[3,2-b]pyridine-7,1'-cyclopropane]-8,8a(8H)-diol (Cpd. No. 92F)

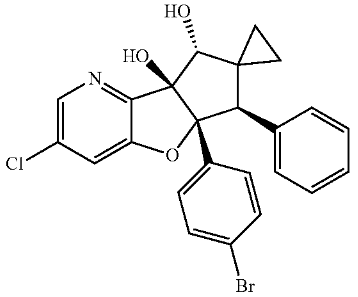

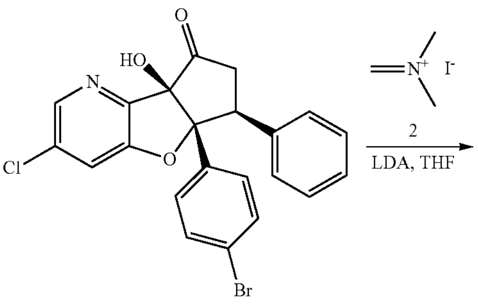

1

-continued

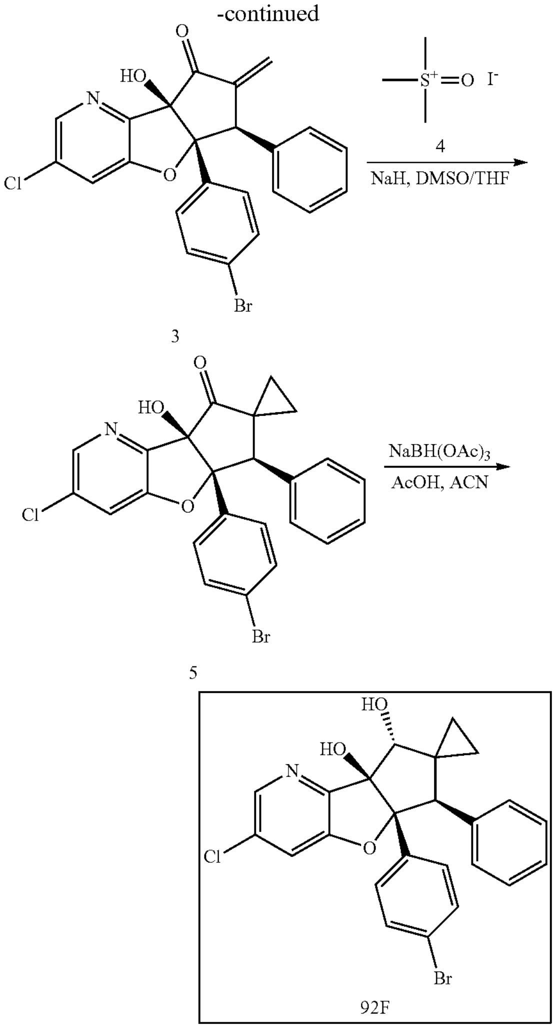

3

5

92F

Synthesis of rac-(5aR,6R,8aR)-5a-(4-bromophenyl)-3-chloro-8a-hydroxy-7-methylene-6-phenyl-5a,6,7,8a-tetrahydro-8H-cyclopenta[4,5]furo[3,2-b]pyridin-8-one (3)

A solution of rac-(5aR,6S,8aR)-5a-(4-bromophenyl)-3-chloro-8a-hydroxy-6-phenyl-5a,6,7,8a-tetrahydro-8H-cyclopenta[4,5]furo[3,2-b]pyridin-8-one (1, 0.150 g, 0.32 mmol) in tetrahydrofuran (3 mL) was cooled to 0° C. and lithium diisopropylamide (2.0 M in THF) (0.48 mL, 0.96 mmol) was added. The reaction mixture was stirred at the same temperature for 30 min. N-methyl-N-methylenemethanaminium iodide (2, 0.207 g, 1.12 mmol) was then added and reaction mixture was stirred at room temperature for 3 h. Reaction mixture was quenched with saturated ammonium chloride solution and extracted with ethyl acetate. The organic layer was dried over anhydrous sodium sulphate, filtered and concentrated to give crude product. Crude product obtained was purified by column chromatography using silica gel (100-200 mesh) and 0-10% ethyl acetate in hexane to afford rac-(5aR,6R,8aR)-5a-(4-bromophenyl)-3-chloro-8a-hydroxy-7-methylene-6-phenyl-5a,6,7,8a-tetrahydro-8H-cyclopenta[4,5]furo[3,2-b]pyridin-8-one (3) as off white solid. Yield: 0.075 g, 49%; MS (ESI) m/z 467.90 $[M+1]^+$.

Synthesis of rac-(5aR,6R,8aR)-5a-(4-bromophenyl)-3-chloro-8a-hydroxy-6-phenyl-5a,8a-dihydrospiro[cyclopenta[4,5]furo[3,2-b]pyridine-7,1'-cyclopropan]-8(6H)-one (5)

To a solution of rac-(5aR,6R,8aR)-5a-(4-bromophenyl)-3-chloro-8a-hydroxy-7-methylene-6-phenyl-5a,6,7,8a-tetrahydro-8H-cyclopenta[4,5]furo[3,2-b]pyridin-8-one (3, 0.200 g, 0.42 mmol) in DMSO (2 mL) was added sodium hydride (0.016 g, 0.42 mmol) and reaction mixture was stirred at room temperature for 15 minutes. A solution of trimethylsulfoxonium iodide (4, 0.092 g, 0.42 mmol) in DMSO:THF (1:1) (2 mL) was then added at 0° C. and the reaction mixture was stirred at 0° C. for 1 hour. The reaction mixture was quenched with water and extracted with ethyl acetate. The organic phase was dried over anhydrous sodium sulphate, filtered and concentrated to afford rac-(5aR,6R,8aR)-5a-(4-bromophenyl)-3-chloro-8a-hydroxy-6-phenyl-5a,8a-dihydrospiro[cyclopenta[4,5]furo[3,2-b]pyridine-7,1'-cyclopropan]-8(6H) one (5) as light brown sticky solid which was directly used for next reaction without purification. Yield: 0.180 g, crude; MS (ESI) m/z 481.93 $[M+1]^+$.

Synthesis of rac-(5aR,6R,8R,8aS)-5a-(4-bromophenyl)-3-chloro-6-phenyl-5a,6-dihydrospiro[cyclopenta[4,5]furo[3,2-b]pyridine-7,1'-cyclopropane]-8,8a(8H)-diol (Cpd. No. 92F)

To a solution of rac-(5aR,6R,8aR)-5a-(4-bromophenyl)-3-chloro-8a-hydroxy-6-phenyl-5a,8a-dihydrospiro[cyclopenta[4,5]furo[3,2-b]pyridine-7,1'-cyclopropan]-8(6H)-one (5, 0.180 g, 0.37 mmol) in acetonitrile (5 mL), at 0° C. were added acetic acid (0.22 mL, 3.7 mmol) and sodium triacetoxyborohydride (0.470 g, 2.22 mmol) and the reaction mixture was stirred at room temperature for 16 h. The reaction mixture was quenched with saturated sodium bicarbonate solution and extracted with ethyl acetate. The organic layer was washed with water, dried over anhydrous sodium sulphate, filtered and concentrated to give crude product. The crude product obtained was purified by preparative HPLC to afford rac-(5aR,6R,8R,8aS)-5a-(4-bromophenyl)-3-chloro-6-phenyl-5a,6-dihydrospiro[cyclopenta[4,5]furo[3,2-b]pyridine-7,1'-cyclopropane]-8,8a(8H)-diol (Cpd. No. 92F) as white solid. Yield: 0.035 g, 19.4%; MS (ESI) m/z 484.43 [M+1]+$^1$H NMR (400 MHz, DMSO-$d_6$) δ 8.18 (d, J=2.0 Hz, 1H), 7.56 (d, J=2.0 Hz, 1H), 7.24 (d, J=7.0 Hz, 2H), 7.14-7.07 (m, 3H), 7.01 (d, J=8.6 Hz, 2H), 6.92 (d, J=6.4 Hz, 2H), 6.03 (s, 1H), 5.17 (d, J=5.6 Hz, 1H), 4.84 (d, J=5.6 Hz, 1H), 3.43 (s, 1H), 0.56-0.49 (m, 2H), 0.36-0.29 (m, 1H), 0.13-0.06 (m, 1H).

Example 93

Rac-(5aR,6S,7R,8S,8aS)-7-(benzylsulfonyl)-5a-(4-bromophenyl)-3-chloro-6-phenyl-5a,6,7,8-tetrahydro-8aH-cyclopenta[4,5]furo[3,2-b]pyridine-8,8a-diol (Cpd. No. 93F)

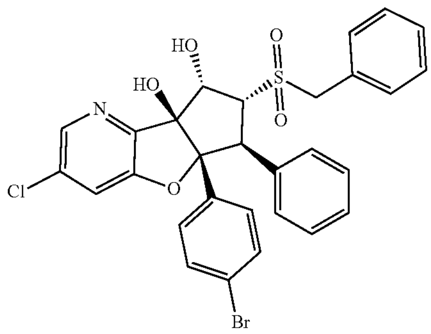

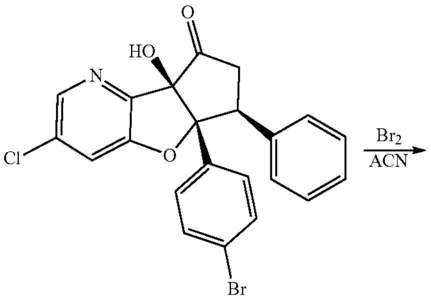

1

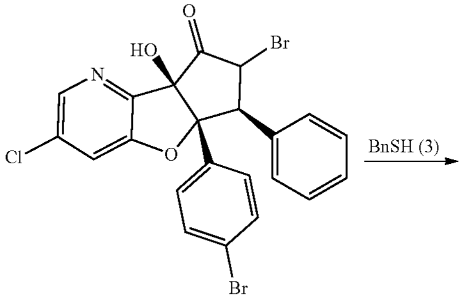

2

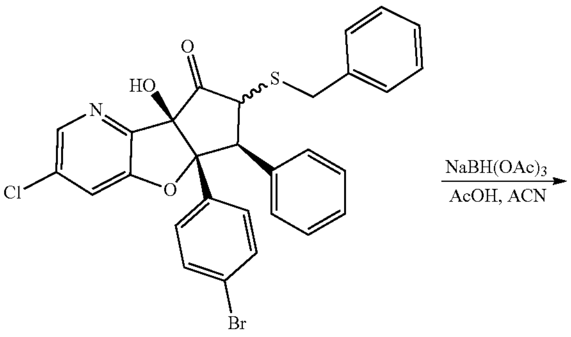

4

-continued

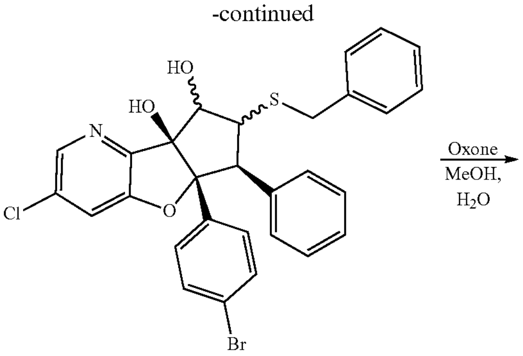

5

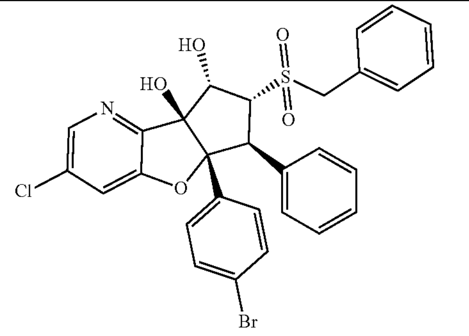

93F

Synthesis of rac-(5aR,6S,8aR)-7-bromo-5a-(4-bromophenyl)-3-chloro-8a-hydroxy-6-phenyl-5a,6,7,8a-tetrahydro-8H-cyclopenta[4,5]furo[3,2-b]pyridin-8-one (2)

Bromine (0.24 mL, 4.7 mmol) was added to a solution of rac-(5aR,6S,8aR)-5a-(4-bromophenyl)-3-chloro-8a-hydroxy-6-phenyl-5a,6,7,8a-tetrahydro-8H-cyclopenta[4,5]furo[3,2-b]pyridin-8-one (1, 2.0 g, 4.3 mmol) in acetonitrile (30 mL) at 0° C. The reaction mixture was then allowed to come to room temperature and stirred for 40 h. The reaction mixture was diluted with water and extracted with ethyl acetate. The organic layer was dried over anhydrous sodium sulphate, filtered and concentrated to give crude product which was purified by column chromatography using silica gel (100-200 mesh) and 0-30% ethyl acetate in hexane to afford rac-(5aR,6S,8aR)-7-bromo-5a-(4-bromophenyl)-3-chloro-8a-hydroxy-6-phenyl-5a,6,7,8a-tetrahydro-8H-cyclopenta[4,5]furo[3,2-b]pyridin-8-one (2) as yellow solid. Yield: 1.7 g, 73.9%; MS (ESI) m/z 532.13$[M-1]^-$.

Synthesis of rac-(5aR,6S,8aR)-7-(benzylthio)-5a-(4-bromophenyl)-3-chloro-8a-hydroxy-6-phenyl-5a,6,7,8a-tetrahydro-8H-cyclopenta[4,5]furo[3,2-b]pyridin-8-one (4)

The solution of rac-(5aR,6S,8aR)-7-bromo-5a-(4-bromophenyl)-3-chloro-8a-hydroxy-6-phenyl-5a,6,7,8a-tetrahydro-8H-cyclopenta[4,5]furo[3,2-b]pyridin-8-one (2, 0.200 g, 0.37 mmol) in benzyl mercaptan (3, 1 mL) was heated at 70° C. for 2 h. Reaction mixture was cooled to give rac-(5aR,6S,8aR)-7-(benzylthio)-5a-(4-bromophenyl)-3-chloro-8a-hydroxy-6-phenyl-5a,6,7,8a-tetrahydro-8H-cyclopenta[4,5]furo[3,2-b]pyridin-8-one (4) as yellow viscous liquid which was directly used for next reaction without purification. Yield: 0.200 g, crude; MS (ESI) m/z 578.03 $[M+1]^+$.

Synthesis of rac-(5aR,6S,8aS)-7-(benzylthio)-5a-(4-bromophenyl)-3-chloro-6-phenyl-5a,6,7,8-tetrahydro-8aH-cyclopenta[4,5]furo[3,2-b]pyridine-8,8a-diol (5)

To the solution of rac-(5aR,6S,8aR)-7-(benzylthio)-5a-(4-bromophenyl)-3-chloro-8a-hydroxy-6-phenyl-5a,6,7,8a-tetrahydro-8H-cyclopenta[4,5]furo[3,2-b]pyridin-8-one (4, 0.350 g, 0.6 mmol) in acetonitrile (10 mL) at 0° C. were added acetic acid (0.72 mL, 12.0 mmol) and sodium triacetoxy borohydride (1.5 g, 7.2 mmol). The reaction mixture was then stirred at room temperature for 16 h. The reaction mixture was then quenched with saturated sodium bicarbonate solution and extracted with ethyl acetate. The organic layer was washed with water, dried over anhydrous sodium sulphate, filtered and concentrated to give crude product which was purified by column chromatography using silica gel (100-200 mesh) and 0-30% ethyl acetate in hexane to afford rac-(5aR,6S,8aS)-7-(benzylthio)-5a-(4-bromophenyl)-3-chloro-6-phenyl-5a,6,7,8-tetrahydro-8aH-cyclopenta[4,5]furo[3,2-b]pyridine-8,8a-diol (5) as white solid. Yield: 0.150 g, crude; MS (ESI) m/z 580.03 $[M+1]^+$.

Synthesis of rac-(5aR,6S,7R,8S,8aS)-7-(benzylsulfonyl)-5a-(4-bromophenyl)-3-chloro-6-phenyl-5a,6,7,8-tetrahydro-8aH-cyclopenta[4,5]furo[3,2-b]pyridine-8,8a-diol (Cpd. No. 93F)

To a solution of rac-(5aR,6S,8aS)-7-(benzylthio)-5a-(4-bromophenyl)-3-chloro-6-phenyl-5a,6,7,8-tetrahydro-8aH-cyclopenta[4,5]furo[3,2-b]pyridine-8,8a-diol (5, 0.210 g, 0.36 mmol) in methanol (5 mL) at 0° C. was added a solution of oxone (0.274 g, 1.8 mmol) in water (5 mL) and reaction mixture was stirred at room temperature for 24 h. Reaction mixture was concentrated, diluted with water, and extracted with dichloromethane. The organic layer was washed with water, dried over anhydrous sodium sulphate, filtered and concentrated to give crude product, which was purified by column chromatography using silica gel (100-200 mesh) and 0-50% ethyl acetate in hexane to give mixture, which was purified by preparative HPLC to afford rac-(5aR,6S,7R,8S,8aS)-7-(benzylsulfonyl)-5a-(4-bromophenyl)-3-chloro-6-phenyl-5a,6,7,8-tetrahydro-8aH-cyclopenta[4,5]furo[3,2-b]pyridine-8,8a-diol (Cpd. No. 93F) as white solid. Yield: 0.026 g, 11.8%; MS (ESI) m/z 612.12 $[M+1]^+$; $^1H$ NMR (400 MHz, DMSO-$d_6$) δ 8.23 (s, 1H), 7.70 (s, 1H), 7.32-7.31 (m, 3H), 7.28-7.25 (m, 2H), 7.20 (d, J=8.7 Hz, 2H), 7.17-7.12 (m, 4H), 7.10-7.05 (m, 3H), 6.4 (bs, 2H), 4.94-4.87 (m, 2H), 4.64 (d, J=13.2 Hz, 1H), 4.38 (d, J=13.0 Hz, 1H) and 4.30 (d, J=12.9 Hz, 1H).

Example 94

Rac-4-((5aR,6S,7R,8S,8aS)-7-(benzylsulfonyl)-3-chloro-8,8a-dihydroxy-6-phenyl-6,7,8,8a-tetrahydro-5aH-cyclopenta[4,5]furo[3,2-b]pyridin-5a-yl)benzonitrile (Cpd. No. 94F)

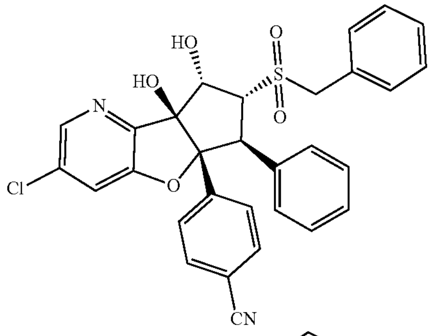

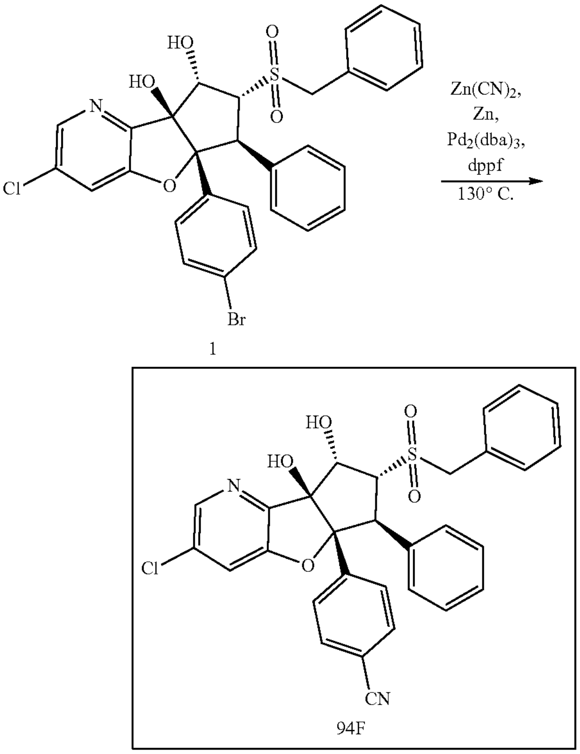

1

94F

Synthesis of rac-4-((5aR,6S,7R,8S,8aS)-7-(benzylsulfonyl)-3-chloro-8,8a-dihydroxy-6-phenyl-6,7,8,8a-tetrahydro-5aH-cyclopenta[4,5]furo[3,2-b]pyridin-5a-yl)benzonitrile (Cpd. No. 94F)

To a solution of rac-(5aR,6S,7R,8S,8aS)-7-(benzylsulfonyl)-5a-(4-bromophenyl)-3-chloro-6-phenyl-5a,6,7,8-tetrahydro-8aH-cyclopenta[4,5]furo[3,2-b]pyridine-8,8a-diol (1, 0.018 g, 0.029 mmol) in N,N-dimethylformamide (1 mL), zinc cyanide (0.020 g, 0.176 mmol) and zinc dust (0.0002 g, 0.0034 mmol) were added at room temperature and the reaction mixture was degassed with argon for 15 min. 1,1'-Bis(diphenylphosphino)ferrocene (0.0003 g, 0.000058 mmol) and tris(dibenzylideneacetone)dipalladium (0.0008 g, 0.00008 mmol) were added to the reaction, degassed for additional 5 min and reaction mixture was heated at 130° C. for 3 h. After completion, the reaction mass was diluted with ethyl acetate and washed with cold water. The organic layer was separated and dried over anhydrous sodium sulphate, filtered and concentrated to give crude product. The crude product was purified by preparative HPLC to afford rac-4-((5aR,6S,7R,8S,8aS)-7-(benzylsulfonyl)-3-chloro-8,8a-dihydroxy-6-phenyl-6,7,8,8a-tetrahydro-5aH-cyclopenta[4,5]furo[3,2-b]pyridin-5a-yl)benzonitrile (Cpd. No. 94F) as white solid. Yield: 0.008 g, 50%; MS (ESI) m/z 559.2 $[M+1]^+$. $^1H$ NMR (400 MHz, DMSO-$d_6$) δ 8.25 (s, 1H), 7.74 (s, 1H), 7.55 (d, J=8.4 Hz, 2H), 7.47 (d, J=8.4 Hz, 2H), 7.33-7.31 (m, 3H), 7.19 (d, J=6.4 Hz, 2H), 7.15-7.13 (m, 2H), 7.08-7.03 (m, 3H), 6.49 (s, 1H), 6.39 (d, J=6.2 Hz, 1H), 5.04 (dd, J=4.4 Hz, 1H), 4.91 (t, J=6 Hz, 1H), 4.70 (d, J=13.6 Hz, 1H), 4.40 (d, J=8.2 Hz, 1H), 4.32 (d, J=8.2 Hz, 1H).

Example 95

(4bS,5R,6R,7S,7aR)-7a-(4-cyanophenyl)-4b,5-dihydroxy-N,N-dimethyl-7-phenyl-4b,6,7,7a-tetrahydro-5H-cyclopenta[4,5]furo[2,3-c]pyridine-6-carboxamide (Cpd. No. 95F)

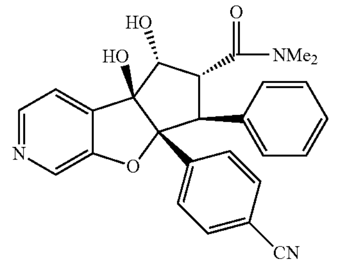

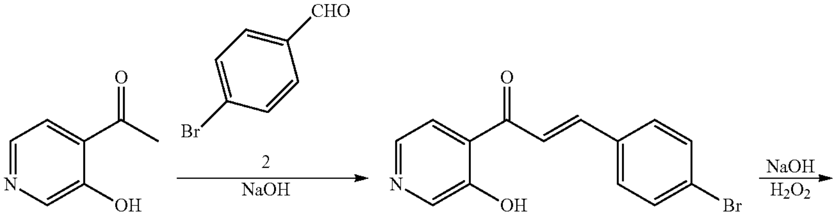

1 3

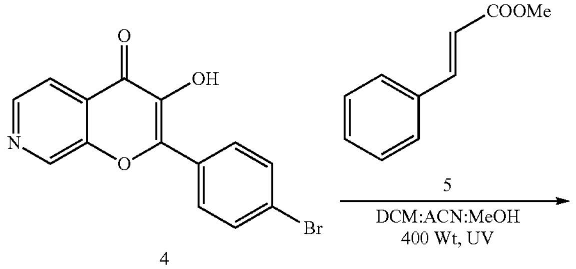

4

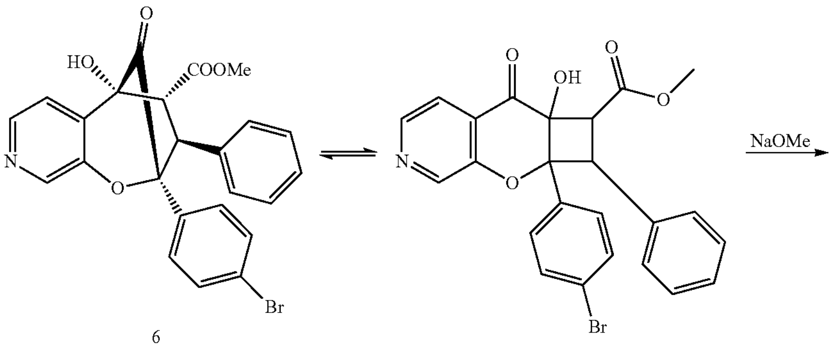

6 6a

-continued

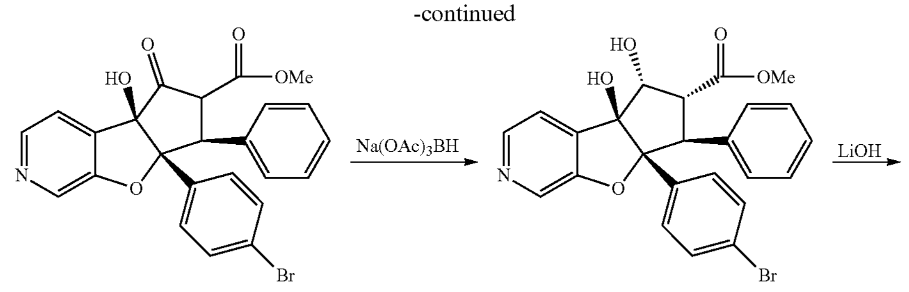

7 8

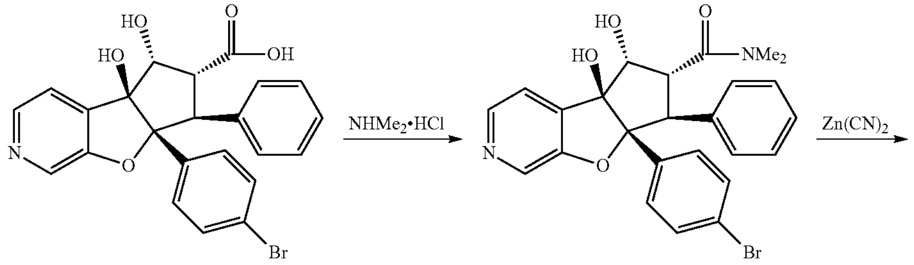

9 10

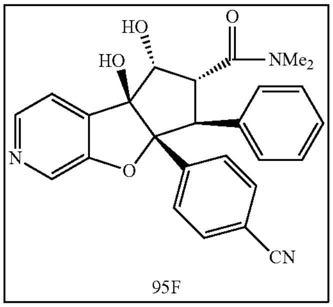

95F

Synthesis of (E)-3-(4-bromophenyl)-1-(3-hydroxy-pyridin-4-yl)prop-2-en-1-one (3)

To a solution of 1-(3-hydroxypyridin-4-yl)ethan-1-one (1, 3.0 g, 21.89 mmol) and 4-bromobenzaldehyde (2, 4.05 g, 21.89 mmol) in methanol (15 mL), sodium hydroxide (2.62 g, 65.67 mmol) was added and the mixture was heated to reflux for 30 min. After completion, the reaction mass was cooled to room temperature, the precipitated solid was filtered, washed with water, n-pentane and dried under vacuum to afford (E)-3-(4-bromophenyl)-1-(3-hydroxypyridin-4-yl)prop-2-en-1-one (3) as yellow solid. Yield: 6.0 g, 90.0%; MS (ESI) m/z 304.18 $[M+1]^+$.

Synthesis of 2-(4-bromophenyl)-3-hydroxy-4H-pyrano[2,3-c]pyridin-4-one (4)

To a solution of (E)-3-(4-bromophenyl)-1-(3-hydroxy-pyridin-4-yl)prop-2-en-1-one (3, 6.0 g, 19.72 mmol) in ethanol (120 mL) at 0° C., sodium hydroxide (5.52 g, 138.0 mmol) was added followed by the addition of 30% aqueous hydrogen peroxide (15.65 mL, 138.0 mmol).

The reaction mass was stirred for 30 min at 60° C. After completion, the reaction mass was cooled and neutralized by the addition of 6 M hydrogen chloride to pH ~7. The solid obtained was filtered, washed with cold ethanol, pentane and dried under vacuum to afford 2-(4-bromophenyl)-3-hydroxy-4H-pyrano[2,3-c]pyridin-4-one (4) as Pale yellow solid. Yield: 3.2 g, 51%; MS (ESI) m/z 316.16$[M-1]^-$.

Synthesis of rac-methyl (2S,3S,4S,5R)-2-(4-bromophenyl)-5-hydroxy-10-oxo-3-phenyl-2,3,4,5-tetrahydro-2,5-methanooxepino[2,3-c]pyridine-4-carboxylate (6)

A solution of 2-(4-bromophenyl)-3-hydroxy-4H-pyrano [2,3-c]pyridin-4-one (4, 3.5 g, 11.0 mmol) and methyl cinnamate (5, 17.84 g, 110.0 mmol) in dichloromethane (200 mL), acetonitrile (100 mL) and methanol (100 mL) was placed in a UV reactor flask. The reaction mixture was irradiated under 400 watts UV light for 24 h. After completion, solvent was removed under reduced pressure and the residue was purified over a plug of silica gel eluting the compound with 5% methanol in dichloromethane. The desired fractions were concentrated under reduced pressure to afford rac-methyl (2S,3S,4S,5R)-2-(4-bromophenyl)-5-hydroxy-10-oxo-3-phenyl-2,3,4,5-tetrahydro-2,5-methanooxepino[2,3-c]pyridine-4-carboxylate (6) as Yellow solid. Yield: 4.0 g, 77%; MS (ESI) m/z 510.05[M+31]+.

Synthesis of rac-methyl (4bR,7S,7aR)-7a-(4-bromophenyl)-4b-hydroxy-5-oxo-7-phenyl-4b,6,7,7a-tetrahydro-5H-cyclopenta[4,5]furo[2,3-c]pyridine-6-carboxylate (7)

A solution of rac-methyl (2S,3S,4S,5R)-2-(4-bromophenyl)-5-hydroxy-10-oxo-3-phenyl-2,3,4,5-tetrahydro-2,5-methanooxepino[2,3-c]pyridine-4-carboxylate (6, 4.0 g, 8.33 mmol) was suspended in methanol (40 mL) and treated with 25% sodium methoxide in methanol (4.5 mL). The reaction was heated at 80° C. for 4 h. After completion, the solvent was removed under reduced pressure. The crude was diluted with ammonium chloride solution and extracted with ethyl acetate. The organic phase was separated, dried over sodium sulphate and concentrated under reduced pressure to afford rac-methyl (4bR,7S,7aR)-7a-(4-bromophenyl)-4b-hydroxy-5-oxo-7-phenyl-4b,6,7,7a-tetrahydro-5H-cyclopenta[4,5]furo[2,3-c]pyridine-6-carboxylate (7) as white solid. Yield: 3.0 g, 75%; MS (ESI) m/z 480.04 $[M+1]^+$.

Synthesis of rac-methyl (4bS,5R,6R,7S,7aR)-7a-(4-bromophenyl)-4b,5-dihydroxy-7-phenyl-4b,6,7,7a-tetrahydro-5H-cyclopenta[4,5]furo[2,3-c]pyridine-6-carboxylate (8)

A solution of rac-methyl (4bR,7S,7aR)-7a-(4-bromophenyl)-4b-hydroxy-5-oxo-7-phenyl-4b,6,7,7a-tetrahydro-5H-cyclopenta[4,5]furo[2,3-c]pyridine-6-carboxylate (7, 3.0 g, 6.24 mmol) in acetonitrile (60 mL) was cooled at 0° C., acetic acid (3.74 g, 62.40 mmol) and sodium triacetoxyborohydride (13.54 g, 6.24 mmol) were added. The resulting mixture was stirred for 12 h at room temperature. After completion, the reaction mixture was partitioned between saturated aqueous sodium bicarbonate solution and ethyl acetate. The organic layer was separated and dried over sodium sulphate, filtered and concentrated to give crude. The crude was purified by silica gel column chromatography eluting with 2-3% in methanol in dichloromethane. The desired fractions were concentrated to afford rac-methyl (4bS,5R,6R,7S,7aR)-7a-(4-bromophenyl)-4b,5-dihydroxy-7-phenyl-4b,6,7,7a-tetrahydro-5H-cyclopenta[4,5]furo[2,3-c]pyridine-6-carboxylate (8) as Yellow solid. Yield: 1.5 g, 50.0%; MS (ESI) m/z 482.31 $[M+1]^+$.

Synthesis of rac-(4bS,5R,6R,7S,7aR)-7a-(4-bromophenyl)-4b,5-dihydroxy-7-phenyl-4b,6,7,7a-tetrahydro-5H-cyclopenta[4,5]furo[2,3-c]pyridine-6-carboxylic acid (9)

To a solution of rac-methyl (4bS,5R,6R,7S,7aR)-7a-(4-bromophenyl)-4b,5-dihydroxy-7-phenyl-4b,6,7,7a-tetrahydro-5H-cyclopenta[4,5]furo[2,3-c]pyridine-6-carboxylate (8, 1.0 g, 2.07 mmol) in methanol, tetrahydrofuran and water (2:1:1, 12 mL), lithium hydroxide (0.497 g, 20.7 mmol) was added and the reaction was stirred for 6 h at room temperature. After completion, the reaction mass was concentrated and cooled to 0° C. and acidified with 1 M hydrochloric acid to pH ~2-3. The precipitated solid was filtered and dried under vacuum to afford rac-(4bS,5R,6R,7S,7aR)-7a-(4-bromophenyl)-4b,5-dihydroxy-7-phenyl-4b,6,7,7a-tetrahydro-5H-cyclopenta[4,5]furo[2,3-c]pyridine-6-carboxylic acid (9) as white solid. Yield: 0.75 g, 77%; MS (ESI) m/z 468.25 $[M+1]^+$.

Synthesis of rac-(4bS,5R,6R,7S,7aR)-7a-(4-bromophenyl)-4b,5-dihydroxy-N,N-dimethyl-7-phenyl-4b,6,7,7a-tetrahydro-5H-cyclopenta[4,5]furo[2,3-c]pyridine-6-carboxamide (10)

To a solution of rac-(4bS,5R,6R,7S,7aR)-7a-(4-bromophenyl)-4b,5-dihydroxy-7-phenyl-4b,6,7,7a-tetrahydro-5H-cyclopenta[4,5]furo[2,3-c]pyridine-6-carboxylic acid (9, 0.75 g, 1.59 mmol) in dichloromethane (15 mL) at 0° C., 1-ethyl-3-(3-dimethylaminopropyl) carbodiimide (0.742 g, 4.78 mmol), hydroxybenzotriazole (0.732 g, 4.78 mmol) and N,N-diisopropylethylamine (1.71 mL, 9.57 mmol) were added and the mixture was stirred for 5 min. Dimethylamine hydrochloride (0.650 g, 7.9 mmol) was then added at the same temperature and the mixture was stirred for 16 h at room temperature. After completion, the reaction mass was diluted with dichloromethane and washed with cold water. The organic layer was separated and dried over sodium sulphate, filtered and concentrated to give crude. The crude was purified by silica gel column chromatography eluting with 2-3% methanol in dichloromethane. The desired fractions were concentrated to afford rac-(4bS,5R,6R,7S,7aR)-7a-(4-bromophenyl)-4b,5-dihydroxy-N,N-dimethyl-7-phenyl-4b,6,7,7a-tetrahydro-5H-cyclopenta[4,5]furo[2,3-c]pyridine-6-carboxamide (10) as off white solid; Yield: 0.50 g, 64%; MS (ESI) m/z 495.11 $[M+1]^+$.

Synthesis of (4bS,5R,6R,7S,7aR)-7a-(4-cyanophenyl)-4b,5-dihydroxy-N,N-dimethyl-7-phenyl-4b,6,7,7a-tetrahydro-SH-cyclopenta[4,5]furo[2,3-c]pyridine-6-carboxamide (Cpd. No. 95F)

To a solution of rac-(4bS,5R,6R,7S,7aR)-7a-(4-bromophenyl)-4b,5-dihydroxy-N,N-dimethyl-7-phenyl-4b,6,7,7a-tetrahydro-5H-cyclopenta[4,5]furo[2,3-c]pyridine-6-carboxamide (10, 0.200 g, 0.40 mmol) in N,N-dimethylformamide (4.0 mL), zinc cyanide (0.285 g, 2.42 mmol) and zinc (0.0031 g, 0.048 mmol) were added at room temperature and degassed the mixture with argon for 15 minute. 1,1'-Bis(diphenylphosphino)ferrocene (0.006 g, 0.008 mmol) and tris(dibenzylideneacetone)dipalladium (0.008 g, 0.012 mmol) were added to the reaction and degassing was continued for another 5 min. The reaction mixture was heated at 140° C. for 3 h. After completion, the reaction mass was diluted with ethyl acetate and washed with cold water. The organic layer was separated and dried over sodium sulphate, filtered and concentrated to give crude. The crude was purified by silica gel column chromatography eluting with 2-3% methanol in dichloromethane. The desired fractions were concentrated to afford rac-(4bS,5R,6R,7S,7aR)-7a-(4-cyanophenyl)-4b,5-dihydroxy-N,N-dimethyl-7-phenyl-4b,6,7,7a-tetrahydro-5H-cyclopenta[4,5]furo[2,3-c]pyridine-6-carboxamide as white solid. Yield: 0.11 g, 62%. (Racemic mixture); MS (ESI) m/z 442.36 $[M+1]^+$; The enantiomers were separated by chiral preparative HPLC [chiralpak IA (4.6×250) mm, 5μ]. Peak 1 (Cpd. No. 95F, 24 mg), $[\alpha]_D$−125.4° (c 0.23, $CHCl_3$), $R_t$=4.356 min, ee >99% $^1$H NMR (400 MHz, DMSO-$d_6$) δ 8.48 (s, 1H), 8.24 (d, J=4.76 Hz, 1H), 7.57 (d, J=8.52 Hz, 2H), 7.47 (d, J=5.00 Hz, 1H), 7.40 (d, J=8.48 Hz, 2H), 7.05 (m, 3H), 6.8 (d, J=7.08 Hz, 2H) 5.91 (s, 1H), 5.74 (d, J=6.08 Hz, 1H), 4.94 (t, J=7.04 Hz, 1H), 4.31 (d, J=13.2 Hz, 1H), 4.18 (dd, J=7.56 Hz, J=7.60 Hz, 1H), 3.23 (s, 3H), 2.73 (s, 3H); Peak-2 (24 mg), $[\alpha]_D$+122.3° (c 0.264, $CHCl_3$), $R_t$=14.114 min, ee >99% $^1$H NMR (400 MHz, DMSO-$d_6$) δ 8.48 (s, 1H), 8.24 (d, J=4.76 Hz, 1H), 7.57 (d, J=8.52 Hz, 2H), 7.47 (d, J=5.00 Hz, 1H), 7.40 (d, J=8.48 Hz, 2H), 7.05 (m, 3H), 6.8 (d, J=7.08 Hz, 2H), 5.91 (s, 1H), 5.74 (d, J=6.00 Hz, 1H), 4.94 (t, J=7.08 Hz, 1H), 4.31 (d, J=13.2 Hz, 1H), 4.19 (dd, J=7.60, 7.48 Hz, 1H), 3.23 (s, 3H), 2.73 (s, 3H).

Example 96

Rac-(4bS,5R,6R,7S,7aR)-4-cyano-7a-(4-cyanophenyl)-4b,5-dihydroxy-N,N-dimethyl-7-phenyl-4b,6,7,7a-tetrahydro-5H-cyclopenta[4,5]furo[2,3-c]pyridine-6-carboxamide (Cpd. No. 96F)

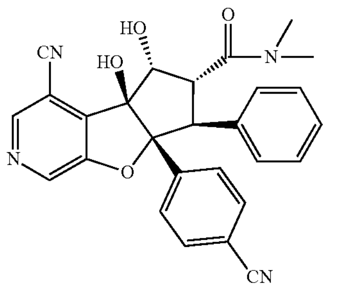

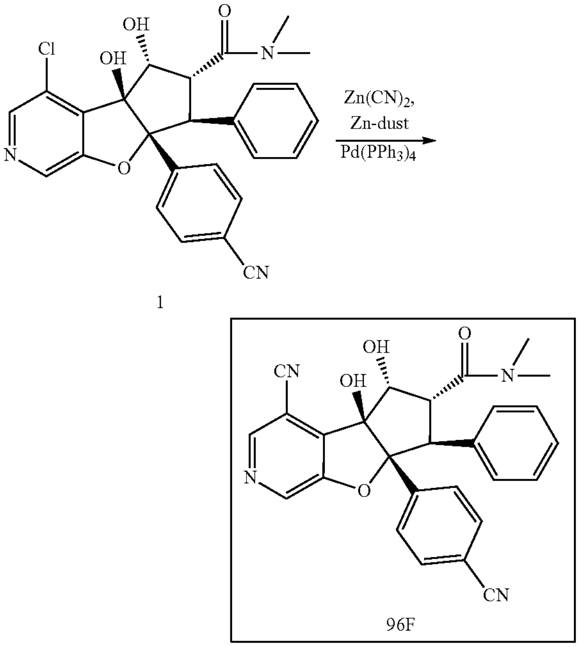

1

96F

Synthesis of rac-(4bS,5R,6R,7S,7aR)-4-cyano-7a-(4-cyanophenyl)-4b,5-dihydroxy-N,N-dimethyl-7-phenyl-4b,6,7,7a-tetrahydro-5H-cyclopenta[4,5]furo[2,3-c]pyridine-6-carboxamide (Cpd. No. 96F)

To a solution of rac-(4bS,5R,6R,7S,7aR)-4-chloro-7a-(4-cyanophenyl)-4b,5-dihydroxy-N,N-dimethyl-7-phenyl-4b,6,7,7a-tetrahydro-5H-cyclopenta[4,5]furo[2,3-c]pyridine-6-carboxamide (1, 0.2 g, 0.419 mmol) in N,N-dimethylformamide (4 mL), zinc cyanide (0.98 g, 8.3 mmol) and zinc dust (0.013 g, 0.201 mmol) were added at room temperature and the reaction mixture was degassed with argon for 15 minutes and tetrakis(triphenylphosphine)palladium (0) (0.132 g, 0.117 mmol) was added to the reaction mixture, degassed for additional 5 min and reaction mixture was heated at 140° C. for 3 h. After completion, the reaction mass was diluted with ethyl acetate and washed with cold water. The organic layer was separated and dried over anhydrous sodium sulphate, filtered and concentrated to give crude product. The crude product was purified by preparative HPLC. The desired fractions were concentrated and lyophilized to afford rac-(4bS,5R,6R,7S,7aR)-4-cyano-7a-(4-cyanophenyl)-4b,5-dihydroxy-N,N-dimethyl-7-phenyl-4b,6,7,7a-tetrahydro-5H-cyclopenta[4,5]furo[2,3-c]pyridine-6-carboxamide (Cpd. No. 96F) as white solid. Yield: 0.013 g, 6.6%; MS (ESI) m/z 467.27 $[M+1]^+$; $^1$H NMR (400 MHz, DMSO-$d_6$) δ 8.79 (s, 1H), 8.68 (s, 1H), 7.60 (d, J=8.4 Hz, 2H), 7.41 (d, J=8 Hz, 2H), 7.08-7.03 (m, 3H), 6.81 (d, J=6.8 Hz, 2H), 4.34 (d, J=7.6 Hz, 1H), 3.96-3.91 (m, 1H), 3.82 (d, J=13.2 Hz, 1H), 3.26 (s, 3H), 2.77 (s, 3H).

Example 97

Rac-(4bS,5R,6R,7S,7aR)-7a-(4-bromophenyl)-4-chloro-4b,5-dihydroxy-N,N-dimethyl-7-phenyl-4b,6,7,7a-tetrahydro-5H-cyclopenta[4,5]furo[2,3-c]pyridine-6-carboxamide (Cpd. No. 97F)

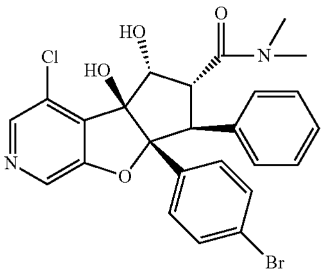

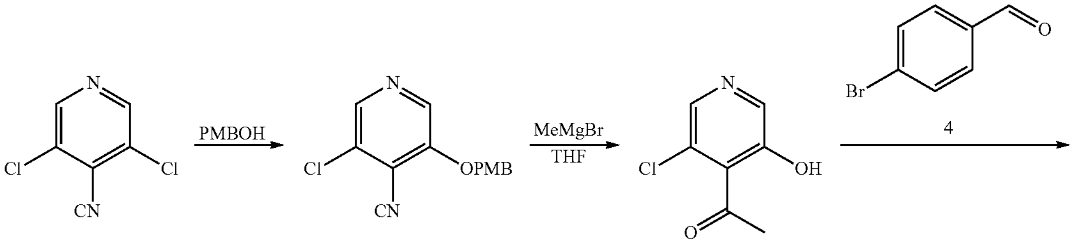

1 2 3

-continued
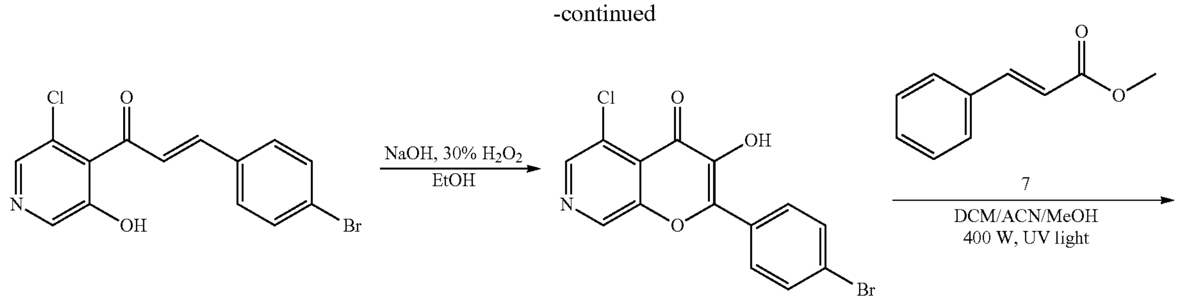
5 6
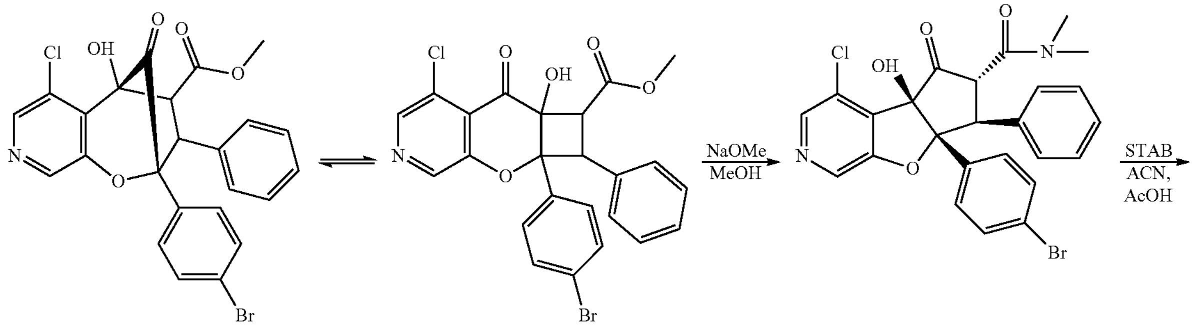
8 8a 9
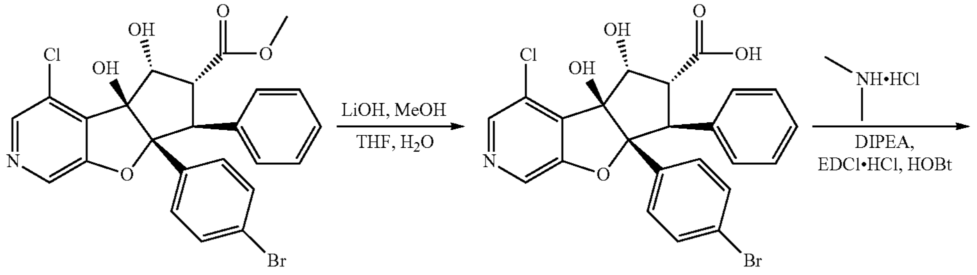
10 11
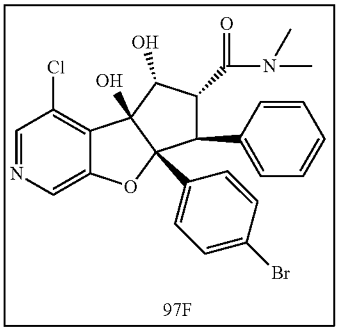
97F

Synthesis of 3-chloro-5-((4-methoxybenzyl) oxy) isonicotinonitrile (2)

To a solution of 3,5-dichloroisonicotinonitrile (1, 50.00 g, 289.0 mmol) in PGP-18 tetrahydrofuran (500 ml) at 0° C., 60% sodium hydride (13.87 g, 346.8 mmol) was added followed by addition of (4-methoxyphenyl)methanol (33.67 ml, 289.0 mmol) and the reaction mixture was stirred at room temperature for 10 min. After completion, the mixture was quenched with ice cold water (1000 ml), solid compound obtained was then filtered and dried to afford 3-chloro-5-((4-methoxybenzyl)oxy)isonicotinonitrile (2) as white solid. Yield: 85.0 g, 95%; MS (ESI) m/z 275.16 $[M+1]^+$.

Synthesis of 1-(3-chloro-5-hydroxypyridin-4-yl) ethan-1-one (3)

To a solution of 3-chloro-5-((4-methoxybenzyl)oxy)isonicotinonitrile (2, 10.0 g, 36.4 mmol) in dry tetrahydrofuran (60 ml) at 0° C., methyl magnesium bromide (109.4 mL, 328.4 mmol) was added drop wise over a period of 30 min. The reaction mass was slowly brought to room temperature and stirred for additional 12 h. After completion, the reaction mass was quenched with 6 M hydrochloric acid to pH ~3 and stirred for 3 h. The mixture was diluted with ethyl acetate (100 mL), water (50 mL) and basified with sodium bicarbonate up to pH~10. The organic layer was separated, washed with water, dried over anhydrous sodium sulfate, filtered and concentrated under reduced pressure. The crude product was purified by silica gel column chromatography using 25% ethyl acetate in hexanes as eluent. The desired fractions were concentrated to afford 1-(3-chloro-5-hydroxypyridin-4-yl) ethan-1-one (3) as light yellow solid. Yield: 2.94 g, 47%; MS (ESI) m/z 170.17$[M-1]^+$.

Synthesis of (E)-3-(4-bromophenyl)-1-(3-chloro-5-hydroxypyridin-4-yl) prop-2-en-1-one (5)

To a solution of 1-(3-chloro-5-hydroxypyridin-4-yl) ethan-1-one (3, 1.3 g, 7.57 mmol) in methanol (13 mL), sodium hydroxide (0.9 g, 22.7 mmol) was added followed by addition of 4-bromobenzaldehyde (4, 1.4 g, 7.57 mmol). The reaction was heated to reflux for 30 min. After completion, the reaction mass was cooled to room temperature then diluted with water (20 mL). Solid obtained was filtered and dried. The solid obtained was triturated with pentane, filtered and dried under vacuum to afford (E)-3-(4-bromophenyl)-1-(3-chloro-5-hydroxypyridin-4-yl)prop-2-en-1-one (5) as yellow solid. Yield: 2.5 g, 98%; MS (ESI) m/z 336.1$[M-1]^+$.

Synthesis of 2-(4-bromophenyl)-5-chloro-3-hydroxy-4H-pyrano [2,3-c] pyridin-4-one (6)

To a solution of (E)-3-(4-bromophenyl)-1-(3-chloro-5-hydroxypyridin-4-yl)prop-2-en-1-one (5, 2.5 g, 7.41 mmol) in ethanol (75 mL) at 0° C., sodium hydroxide (0.36 g, 8.90 mmol) was added followed by the addition of 30% aqueous hydrogen peroxide (5.88 mL, 51.9 mmol). The reaction mixture was heated at 60° C. for 30 min. After completion, the reaction mixture was cooled and neutralized to pH ~7 by the addition of 6 M hydrogen chloride. The solid obtained was filtered and dried to get crude compound. The crude product obtained was triturated with ethanol, filtered and dried under vacuum to afford 2-(4-bromophenyl)-5-chloro-3-hydroxy-4H-pyrano[2,3-c]pyridin-4-one (6) as yellow solid. Yield: 0.7 g, 26.0%; MS (ESI) m/z 351.3 $[M+1]^+$.

Synthesis of rac-methyl (3S,4S,5R)-2-(4-bromophenyl)-6-chloro-5-hydroxy-10-oxo-3-phenyl-2,3,4,5-tetrahydro-2,5-methanooxepino[2,3-c]pyridine-4-carboxylate (8)

A solution of 2-(4-bromophenyl)-5-chloro-3-hydroxy-4H-pyrano[2,3-c]pyridin-4-one (6, 4.0 g, 11.3 mmol) and methyl cinnamate (7, 21.0 g, 113.4 mmol) in dichloromethane (200 mL), acetonitrile (100 mL) and methanol (100 mL) was placed in a UV reactor flask. The reaction mixture was irradiated under 400 watts UV light for 18 h. After completion, solvent was removed under reduced pressure and the residue was purified over a plug of silica gel eluting the compound with ethyl acetate. The desired fractions were concentrated under reduced pressure to afford rac-methyl (3S,4S,5R)-2-(4-bromophenyl)-6-chloro-5-hydroxy-10-oxo-3-phenyl-2,3,4,5-tetrahydro-2,5-methanooxepino[2,3-c]pyridine-4-carboxylate (8) as yellow brown solid. Yield: 4.9 g, crude. MS (ESI) m/z 512.42$[M-1]^+$.

Synthesis of rac-methyl (4bR,6R,7S,7aR)-7a-(4-bromophenyl)-4-chloro-4b-hydroxy-5-oxo-7-phenyl-4b,6,7,7a-tetrahydro-5H-cyclopenta[4,5]furo[2,3-c]pyridine-6-carboxylate (9)

The crude compound rac-methyl (3S,4S,5R)-2-(4-bromophenyl)-6-chloro-5-hydroxy-10-oxo-3-phenyl-2,3,4,5-tetrahydro-2,5-methanooxepino[2,3-c]pyridine-4-carboxylate (8, 4.9 g) was suspended in methanol (100 mL) and treated with 25% sodium methoxide solution in methanol (20 mL). The reaction was heated at 80° C. for 3 h. After completion, the solvent was removed under reduced pressure. The crude was diluted with ammonium chloride solution and extracted with ethyl acetate. The organic layer was separated, dried over anhydrous sodium sulphate and concentrated under reduced pressure to afford of rac-methyl (4bR,6R,7S,7aR)-7a-(4-bromophenyl)-4-chloro-4b-hydroxy-5-oxo-7-phenyl-4b,6,7,7a-tetrahydro-5H-cyclopenta[4,5]furo[2,3-c]pyridine-6-carboxylate (9) as brown solid. Yield: 4.2 g, crude.

Synthesis of rac-methyl (4bS,5R,6R,7S,7aR)-7a-(4-bromophenyl)-4-chloro-4b,5-dihydroxy-7-phenyl-4b,6,7,7a-tetrahydro-5H-cyclopenta[4,5]furo[2,3-c]pyridine-6-carboxylate (10)

To a solution of rac-methyl (4bR,6R,7S,7aR)-7a-(4-bromophenyl)-4-chloro-4b-hydroxy-5-oxo-7-phenyl-4b,6,7,7a-tetrahydro-5H-cyclopenta[4,5]furo[2,3-c]pyridine-6-carboxylate (9, 4.0 g, 7.79 mmol) in acetonitrile (40 mL) and acetic acid (4.6 ml, 77.9 mmol), sodium triacetoxyborohydride (16.91 g, 77.9 mmol) was added. The resulting mixture was stirred at room temperature for 4 h. After completion, the reaction mixture was partitioned between saturated aqueous sodium bicarbonate solution and ethyl acetate. The organic layer was separated, dried over anhydrous sodium sulphate, filtered and concentrated under reduced pressure to get the crude product. The crude product was purified by silica gel column chromatography using 0-5% methanol in dichloromethane as eluent. The desired fractions were concentrated under reduced pressure to afford rac-methyl (4bS,5R,6R,7S,7aR)-7a-(4-bromophenyl)-4-chloro-4b,5-dihydroxy-7-phenyl-4b,6,7,7a-tetrahydro-5H-cyclopenta[4,5]

furo[2,3-c]pyridine-6-carboxylate (10) as off white solid. Yield: 1.7 g, 42.5%; MS (ESI) m/z 516.16 $[M+1]^+$.

Synthesis of rac-(4bS,5R,6R,7S,7aR)-7a-(4-bromophenyl)-4-chloro-4b,5-dihydroxy-7-phenyl-4b,6,7,7a-tetrahydro-5H-cyclopenta[4,5]furo[2,3-c]pyridine-6-carboxylic acid (11)

To a solution of rac-methyl (4bS,5R,6R,7S,7aR)-7a-(4-bromophenyl)-4-chloro-4b,5-dihydroxy-7-phenyl-4b,6,7,7a-tetrahydro-5H-cyclopenta[4,5]furo[2,3-c]pyridine-6-carboxylate (10, 1.75 g, 3.39 mmol) in methanol:THF:water (2:1:1, 50 mL), lithium hydroxide (1.63 g, 67.9 mmol) was added and the reaction was stirred for 2 h at room temperature. After completion, the reaction mixture was cooled to 0° C. and acidified with 1 M hydrochloric acid to pH ~2-3. The precipitate obtained was filtered and dried under vacuum to afford rac-(4bS,5R,6R,7S,7aR)-7a-(4-bromophenyl)-4-chloro-4b,5-dihydroxy-7-phenyl-4b,6,7,7a-tetrahydro-5H-cyclopenta[4,5]furo[2,3-c]pyridine-6-carboxylic acid (11) as white solid. Yield: 1.6 g, 94%; MS (ESI) m/z 502.1 $[M+1]^+$.

Synthesis of rac-(4bS,5R,6R,7S,7aR)-7a-(4-bromophenyl)-4-chloro-4b,5-dihydroxy-N,N-dimethyl-7-phenyl-4b,6,7,7a-tetrahydro-5H-cyclopenta[4,5]furo[2,3-c]pyridine-6-carboxamide (Cpd. No. 97F)

To a solution of rac-(4bS,5R,6R,7S,7aR)-7a-(4-bromophenyl)-4-chloro-4b,5-dihydroxy-7-phenyl-4b,6,7,7a-tetrahydro-5H-cyclopenta[4,5]furo[2,3-c]pyridine-6-carboxylic acid (11, 1.6 g, 3.19 mmol) in dichloromethane (20 mL) at 0° C., 1-ethyl-3-(3-dimethylaminopropyl) carbodiimide (1.8 g, 9.57 mmol), hydroxybenzotriazole (1.46 g, 9.57 mmol) and N,N-diisopropylethylamine (3.5 g, 19.1 mmol) were added and the mixture was stirred for 5 min. Dimethylamine hydrochloride (1.3 g, 15.9 mmol) was then added at the same temperature and the reaction was stirred for 16 h at room temperature. After completion, the reaction mass was diluted with dichloromethane and washed with cold water. The organic layer was separated and dried over anhydrous sodium sulphate, filtered and concentrated to give crude product. The crude product was purified by silica gel column chromatography using 0-5% methanol in dichloromethane as eluent. The desired fractions were concentrated to afford rac-(4bS,5R,6R,7S,7aR)-7a-(4-bromophenyl)-4-chloro-4b,5-dihydroxy-N,N-dimethyl-7-phenyl-4b,6,7,7a-tetrahydro-5H-cyclopenta[4,5]furo[2,3-c]pyridine-6-carboxamide (Cpd. No. 97F) as white solid. Yield: 0.8 g, 48%; MS (ESI) m/z 529.16 $[M+1]^+$; $^1H$ NMR (400 MHz, DMSO-$d_6$) δ 8.38 (s, 1H), 8.16 (s, 1H), 7.22 (d, J=8.8 Hz, 2H), 7.09-7.02 (m, 4H), 6.96-6.93 (m, 3H), 6.05 (s, 1H), 5.45 (s, 1H), 4.76 (d, J=3.6 Hz, 1H), 4.56 (d, J=13.2 Hz, 1H), 4.28 (m, 1H), 3.30 (s, 3H), 2.79 (s, 3H).

Example 98

(4bS,5R,6R,7S,7aR)-4-chloro-7a-(4-cyanophenyl)-4b,5-dihydroxy-N,N-dimethyl-7-phenyl-4b,6,7,7a-tetrahydro-5H-cyclopenta[4,5]furo[2,3-c]pyridine-6-carboxamide (Cpd. No. 98F)

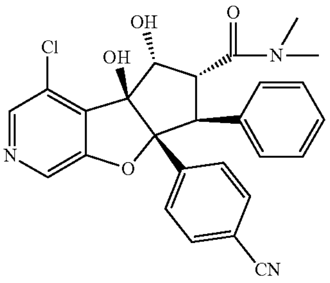

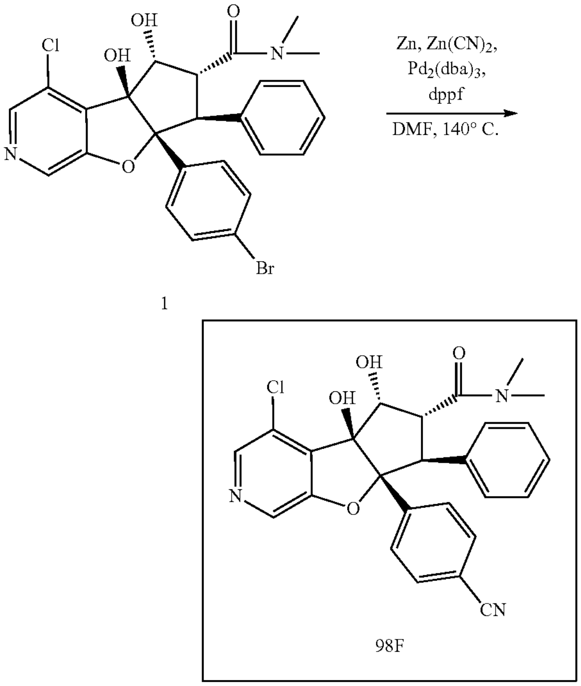

1

98F

Synthesis of (4bS,5R,6R,7S,7aR)-4-chloro-7a-(4-cyanophenyl)-4b,5-dihydroxy-N,N-dimethyl-7-phenyl-4b,6,7,7a-tetrahydro-5H-cyclopenta[4,5]furo[2,3-c]pyridine-6-carboxamide (Cpd. No. 98F)

To a solution of rac-(4bS,5R,6R,7S,7aR)-7a-(4-bromophenyl)-4-chloro-4b,5-dihydroxy-N,N-dimethyl-7-phenyl-4b,6,7,7a-tetrahydro-5H-cyclopenta[4,5]furo[2,3-c]pyridine-6-carboxamide (1, 0.6 g, 1.13 mmol) in N,N-dimethylformamide (10 mL), zinc cyanide (0.129 g, 0.568 mmol) and zinc dust (0.0088 g, 0.13 mmol) were added at room temperature and the reaction mixture was degassed with argon for 15 min. 1,1'-Bis(diphenylphosphino)ferrocene (0.012 g, 0.022 mmol) and tris(dibenzylideneacetone) dipalladium (0.065 g, 0.056 mmol) were added to the reaction, degassed for additional 5 min and reaction mixture was heated at 140° C. for 3 h. After completion, the reaction mixture was diluted with ethyl acetate and washed with cold water. The organic layer was separated and dried over anhydrous sodium sulphate, filtered and concentrated to give crude product. The crude product was purified by silica gel column chromatography using 2-3% methanol in dichloromethane as eluent. The desired fractions were concentrated to afford rac-(4bS,5R,6R,7S,7aR)-4-chloro-7a-(4-cyanophenyl)-4b,5-dihydroxy-N,N-dimethyl-7-phenyl-4b,6,7,7a-tetrahydro-5H-cyclopenta[4,5]furo[2,3-c]pyridine-6-carboxamide as white solid. Yield: 0.35 g, 65% (racemic mixture). The enantiomers were separated by chiral preparative HPLC [chiralpak IA (4.6×250) mm, 5μ]. n-Hexane/IPA=70/30(v/v); Peak 1 (84 mg), $[\alpha]_D$+76.50 (c 0.4, $CHCl_3$), $R_t$=12.226 min, ee:98.08% MS (ESI) m/z 476.24 $[M+1]^+$; $^1H$ NMR (400 MHz, DMSO-$d_6$) δ 8.41 (s, 1H), 8.18 (s, 1H), 7.49 (d, J=8.4 Hz, 2H), 7.34 (d, J=9.2 Hz, 2H), 7.08-7.01 (m, 2H), 6.96-6.93 (m, 3H), 6.14 (s, 1H), 5.50 (d, J=6 Hz, 1H), 4.77 (t, J=4.8 Hz, 1H), 4.61 (d, J=13.6 Hz, 1H), 4.35-4.31 (m, 1H), 2.80 (s, 3H), 2.50 (s, 3H). Peak-2 (Cpd. No. 98F, 74 mg); MS (ESI) m/z 476.24 $[M+1]^+[\alpha]_D$−78.0° (c 0.4, $CHCl_3$), $R_t$=17.345 min, ee:97.02%. $^1H$ NMR (400 MHz, DMSO-$d_6$) δ 8.41 (s, 1H), 8.18 (s, 1H), 7.49 (d, J=8.4 Hz, 2H), 7.34 (d, J=9.2 Hz, 2H), 7.08-7.01 (m, 2H), 6.96-6.93 (m, 3H), 6.14 (s, 1H), 5.50 (d, J=6 Hz, 1H), 4.77 (t, J=4.8 Hz, 1H), 4.61 (d, J=13.6 Hz, 1H), 4.35-4.31 (m, 1H), 2.80 (s, 3H), 2.50 (s, 3H).

Example 99

Rac-(4aR,5S,6R,7R,7aS)-4a-(4-cyanophenyl)-7,7a-dihydroxy-2-(4-methoxybenzyl)-N,N-dimethyl-5-phenyl-2,4a,5,6,7,7a-hexahydrocyclopenta[4,5]furo[3,2-c]pyrazole-6-carboxamide (Cpd. No. 99F)

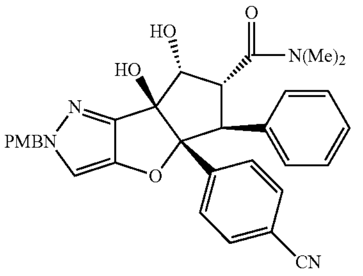

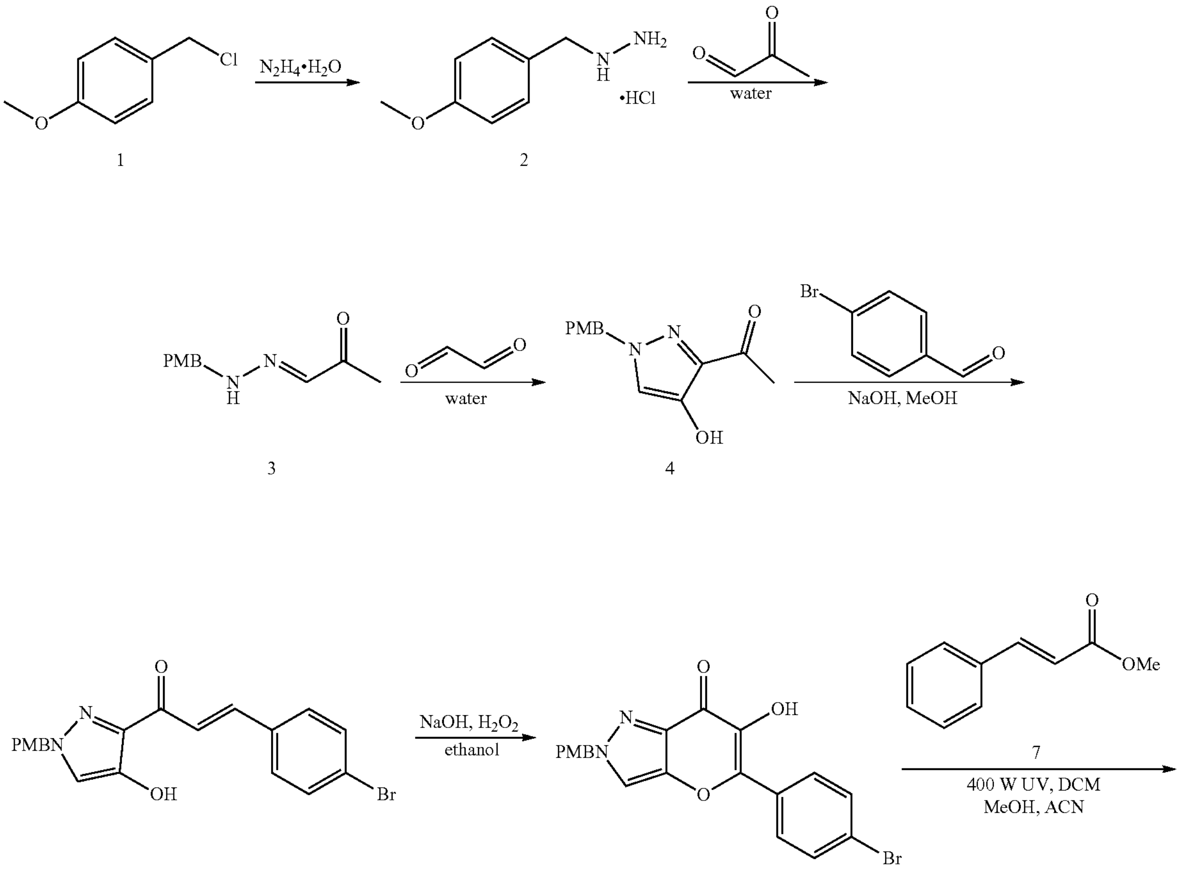

1

2

3

4

5

6

7

-continued

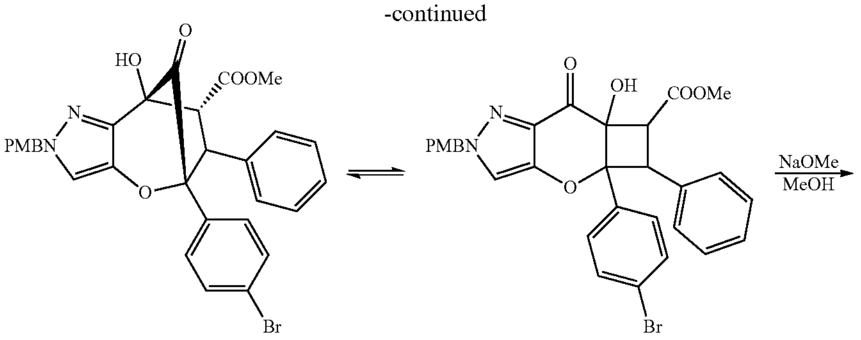

8 8a

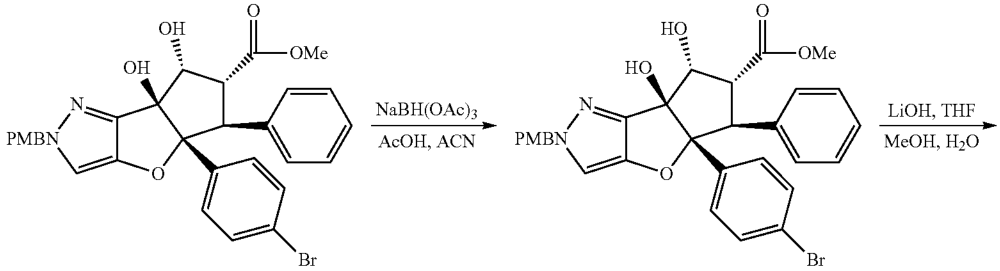

9 10

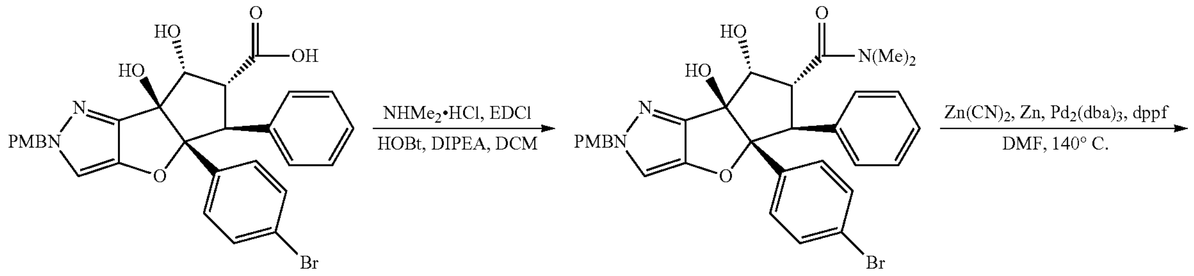

11 12

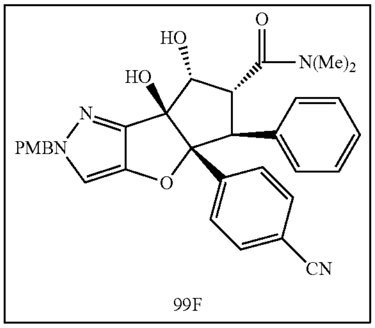

99F

Synthesis of (4-methoxybenzyl)hydrazine hydrochloride (2)

To a solution of 1-(chloromethyl)-4-methoxybenzene (1, 50.0 g, 320 mmol) in ethanol (1200 ml), hydrazine hydrate (36.0 g, 777.3 mmol, 80% aqueous solution) was added at 0° C. The reaction was stirred at 90° C. for 2 h. After completion the reaction mixture was concentrated under reduced pressure to give crude residue. Residue obtained was diluted with ethanol and acidified with 6 N hydrogen chloride to pH ~2. The precipitated solid was filtered and dried under vacuum to afford (4-methoxybenzyl) hydrazine hydrochloride (2) as yellow solid. Yield: 50.0 g. The crude product was used as such in next step. MS (ESI) m/z 153.1 $[M+1]^+$.

Synthesis of (E)-1-(2-(4-methoxybenzyl)hydrazono)propan-2-one (3)

The solution of (4-methoxybenzyl) hydrazine hydrochloride (2, 20.0 g, 106.0 mmol), and pyruvaldehyde (16.7 g, 260.0 mmol) in water (300 ml) was stirred at room temperature for 2 h. After completion, reaction mixture was diluted with dichloromethane and washed with cold water. The organic layer was separated and dried over anhydrous sodium sulphate, filtered and concentrated to afford (E)-1-(2-(4-methoxybenzyl)hydrazono)propan-2-one (3) as yellow solid. Yield: 18.9 g, 65.9%; MS (ESI) m/z 205.04$[M-1]^-$.

Synthesis of I-(4-hydroxy-1-(4-methoxybenzyl)-1H-pyrazol-3-yl)ethan-1-one (4)

The solution of (E)-1-(2-(4-methoxybenzyl)hydrazono)propan-2-one (3, 18.0 g, 87.0 mmol) and glyoxal (7.8 g, 260.0 mmol) in water (100 ml) was heated at 100° C. for 3 h. After completion, reaction mixture was diluted with dichloromethane and washed with cold water. The organic layer was separated and dried over anhydrous sodium sulphate, filtered and concentrated to give crude. The crude was purified by silica gel column chromatography eluting with 10% ethyl acetate in hexanes. The desired fractions were concentrated to afford 1-(4-hydroxy-1-(4-methoxybenzyl)-1H-pyrazol-3-yl) ethan-1-one (4) as light yellow solid. Yield: 6.4 g, 28.9%; MS (ESI) m/z 244.9[M−1]$^-$.

Synthesis of (E)-3-(4-bromophenyl)-1-(4-hydroxy-1-(4-methoxybenzyl)-1H-pyrazol-3-yl)prop-2-en-1-one (5)

To a solution of 1-(4-hydroxy-1-(4-methoxybenzyl)-1H-pyrazol-3-yl)ethan-1-one (4, 3.0 g, 12.19 mmol) in methanol (15 mL), sodium hydroxide (1.46 g, 36.5 mmol) was added followed by addition of 4-bromobenzaldehyde (2.24 g, 12.19 mmol) and the reaction mixture was heated at 90° C. for 30 min. After completion, reaction mixture was cooled to room temperature and the precipitated solid was filtered, washed with water and dried under vacuum to afford of (E)-3-(4-bromophenyl)-1-(4-hydroxy-1-(4-methoxybenzyl)-1H-pyrazol-3-yl)prop-2-en-1-one (5) as yellow solid. Yield: 3.5 g, 70%; MS (ESI) m/z 411[M−1]$^-$.

Synthesis of 5-(4-bromophenyl)-6-hydroxy-2-(4-methoxybenzyl) pyrano [3,2-c]pyrazol-7(2H)-one (6)

To a solution of (E)-3-(4-bromophenyl)-1-(4-hydroxy-1-(4-methoxybenzyl)-1H-pyrazol-3-yl)prop-2-en-1-one (5, 3.50 g, 8.49 mmol) in ethanol (20 mL), 10% aqueous sodium hydroxide solution (23 mL, 59.4 mmol) was added followed by addition of hydrogen peroxide (6.7 mL, 59.4 mmol, 30%) at room temperature. The reaction mixture was stirred for 2 h (exotherm was observed). After completion, reaction mixture was cooled and neutralized with 6 M hydrogen chloride to pH ~7. The precipitated solid was filtered and dried under vacuum to afford 5-(4-bromophenyl)-6-hydroxy-2-(4-methoxybenzyl) pyrano[3,2-c]pyrazol-7(2H)-one (6) as brown solid. Yield: 2.0 g, 55.4%; MS (ESI) m/z 425.31[M−1]$^-$.

Synthesis of rac-methyl (6S,7S,8R)-5-(4-bromophenyl)-8-hydroxy-2-(4-methoxybenzyl)-9-oxo-6-phenyl-5,6,7,8-tetrahydro-2H-5,8-methanooxepino [3,2-c] pyrazole-7-carboxylate (8)

A solution of 5-(4-bromophenyl)-6-hydroxy-2-(4-methoxybenzyl) pyrano[3,2-c]pyrazol-7(2H)-one (6, 8.0 g, 18.69 mmol) and methyl cinnamate (7, 30.4 g, 187.1 mmol) in dichloromethane (200 mL), acetonitrile (100 mL) and methanol (100 mL) was placed in a UV reactor flask. The reaction mixture was irradiated with 400 watts UV light for 8 h. After completion, the solvent was removed under reduced pressure and the residue was purified over a plug of silica gel eluting the compound with 0-5% methanol in dichloromethane. The desired fractions were concentrated under reduced pressure to afford rac-methyl (6S,7S,8R)-5-(4-bromophenyl)-8-hydroxy-2-(4-methoxybenzyl)-9-oxo-6-phenyl-5,6,7,8-tetrahydro-2H-5,8-methanooxepino[3,2-c]pyrazole-7-carboxylate (8). Yield: 6.0 g, crude, MS (ESI) m/z 587.1[M−1]$^-$.

Synthesis of rac-methyl (4aR,5S,6R,7aR)-4a-(4-bromophenyl)-7a-hydroxy-2-(4-methoxybenzyl)-7-oxo-5-phenyl-2,4a,5,6,7,7a-hexahydrocyclopenta[4,5]furo[3,2-c]pyrazole-6-carboxylate (9)

The crude rac-methyl (6S,7S,8R)-5-(4-bromophenyl)-8-hydroxy-2-(4-methoxybenzyl)-9-oxo-6-phenyl-5,6,7,8-tetrahydro-2H-5,8-methanooxepino[3,2-c]pyrazole-7-carboxylate (8, 6.00 g, crude) was suspended in methanol (50 mL) and treated with sodium methoxide (25% in methanol, 40 mL) and heated the mixture to 90° C. for 3 h. After completion, the solvent was removed under reduced pressure, diluted the mixture with ammonium chloride solution and extracted with ethyl acetate. The organic phase was separated, dried over anhydrous sodium sulphate and concentrated under reduced pressure to afford rac-methyl (4aR,5S,6R,7aR)-4a-(4-bromophenyl)-7a-hydroxy-2-(4-methoxybenzyl)-7-oxo-5-phenyl-2,4a,5,6,7,7a-hexahydrocyclopenta[4,5]furo[3,2-c]pyrazole-6-carboxylate (9). Yield: 6.1 g, crude, MS (ESI) m/z 587.3 [M−1]$^-$ Synthesis of rac-methyl (4aR,5S,6R,7R,7aS)-4a-(4-bromophenyl)-7,7a-dihydroxy-2-(4-methoxybenzyl)-5-phenyl-2,4a,5,6,7,7a-hexahydrocyclopenta[4,5]furo[3,2-c]pyrazole-6-carboxylate (10)

To a solution of rac-methyl (4aR,5S,6R,7aR)-4a-(4-bromophenyl)-7a-hydroxy-2-(4-methoxybenzyl)-7-oxo-5-phenyl-2,4a,5,6,7,7a-hexahydrocyclopenta[4,5]furo[3,2-c]pyrazole-6-carboxylate (9, 6.0 g, 10.2 mmol) in acetonitrile (80 mL) and acetic acid (6.1 mL, 102.0 mmol) sodium triacetoxyborohydride (13.0 g, 61.2 mmol) was added and resulting reaction mixture was stirred for 18 h at room temperature. After completion, the reaction mixture was partitioned between saturated aqueous sodium bicarbonate solution and ethyl acetate. The organic layer was separated, dried over anhydrous sodium sulphate and concentrated under reduced pressure to get the crude product. The crude product obtained was purified by silica gel column chromatography eluting with 2% methanol in dichloromethane. The desired fractions were concentrated to afford rac-methyl (4aR,5S,6R,7R,7aS)-4a-(4-bromophenyl)-7,7a-dihydroxy-2-(4-methoxybenzyl)-5-phenyl-2,4a,5,6,7,7a-hexahydrocyclopenta[4,5]furo[3,2-c]pyrazole-6-carboxylate (10) as off white solid. Yield: 0.49 g, 8.3%; MS (ESI) m/z 591.36 [M+1]$^+$.

Synthesis of rac-(4aR,5S,6R,7R,7aS)-4a-(4-bromophenyl)-7,7a-dihydroxy-2-(4-methoxybenzyl)-5-phenyl-2,4a,5,6,7,7a-hexahydrocyclopenta[4,5]furo[3,2-c]pyrazole-6-carboxylic acid (11)

To a solution of rac-methyl (4aR,5S,6R,7R,7aS)-4a-(4-bromophenyl)-7,7a-dihydroxy-2-(4-methoxybenzyl)-5-phenyl-2,4a,5,6,7,7a-hexahydrocyclopenta[4,5]furo[3,2-c]pyrazole-6-carboxylate (10, 0.47 g, 0.79 mmol) in methanol:tetrahydrofuran:water (3:2:1, 18 mL), lithium hydroxide (0.33 g, 7.9 mmol) was added and the reaction was stirred for 2 h at room temperature. After completion, the reaction mixture was cooled to 0° C. and acidified with 1 M hydrogen chloride to pH ~3. The precipitated solid was filtered and dried under vacuum to afford rac-(4aR,5S,6R,7R,7aS)-4a-

(4-bromophenyl)-7,7a-dihydroxy-2-(4-methoxybenzyl)-5-phenyl-2,4a,5,6,7,7a-hexahydrocyclopenta[4,5]furo[3,2-c]pyrazole-6-carboxylic acid (11) as white solid. Yield: 0.41 g, 89.4%, MS (ESI) m/z 577.09 $[M+1]^+$.

Synthesis of rac-(4aR,5S,6R,7R,7aS)-4a-(4-bromophenyl)-7,7a-dihydroxy-2-(4-methoxybenzyl)-N,N-dimethyl-5-phenyl-2,4a,5,6,7,7a-hexahydrocyclopenta[4,5]furo[3,2-c]pyrazole-6-carboxamide (12)

To a solution of rac-(4aR,5S,6R,7R,7aS)-4a-(4-bromophenyl)-7,7a-dihydroxy-2-(4-methoxybenzyl)-5-phenyl-2,4a,5,6,7,7a-hexahydrocyclopenta[4,5]furo[3,2-c]pyrazole-6-carboxylic acid (11, 0.4 g, 0.69 mmol) in dichloromethane (10 mL), 1-ethyl-3-(3-dimethylaminopropyl)carbodiimide hydrochloride (0.39 g, 2.07 mmol), 1-hydroxybenzotriazole (0.32 g, 2.07 mmol) and N,N-diisopropylethylamine (0.7 mL, 4.14 mmol) were added at 0° C. and stirred the mixture for 5 minutes. Dimethylamine hydrochloride (0.28 g, 3.48 mmol) was then added at same temperature and the reaction mixture was stirred for 16 h at 40° C. After completion, reaction mixture was diluted with dichloromethane and washed with cold water. The organic layer was separated and dried over anhydrous sodium sulphate, filtered and concentrated to give crude product. The crude product obtained was purified by silica gel column chromatography eluting with 3% methanol in dichloromethane. The desired fractions were concentrated to afford rac-(4aR,5S,6R,7R,7aS)-4a-(4-bromophenyl)-7,7a-dihydroxy-2-(4-methoxybenzyl)-N,N-dimethyl-5-phenyl-2,4a,5,6,7,7a-hexahydrocyclopenta[4,5]furo[3,2-c]pyrazole-6-carboxamide (12) as white solid. Yield: 0.26 g, 62.7%; MS (ESI) m/z 604.01 $[M+1]^+$.

Synthesis of rac-(4aR,5S,6R,7R,7aS)-4a-(4-cyanophenyl)-7,7a-dihydroxy-2-(4-methoxybenzyl)-N,N-dimethyl-5-phenyl-2,4a,5,6,7,7a-hexahydrocyclopenta[4,5]furo[3,2-c]pyrazole-6-carboxamide (Cpd. No. 99F)

To a solution of rac-(4aR,5S,6R,7R,7aS)-4a-(4-bromophenyl)-7,7a-dihydroxy-2-(4-methoxybenzyl)-N,N-dimethyl-5-phenyl-2,4a,5,6,7,7a-hexahydrocyclopenta[4,5]furo[3,2-c]pyrazole-6-carboxamide (12, 0.100 g, 0.16 mmol) in N,N-dimethylformamide (2.0 mL), zinc cyanide (0.11 g, 0.99 mmol) and zinc dust (0.002 g, 0.019 mmol) were added at room temperature and degassed the mixture with argon for 15 min. 1,1'-Bis(diphenylphosphino)ferrocene (2 mg, 0.003 mmol) and tris(dibenzylideneacetone)dipalladium (5 mg, 0.004 mmol) were added to the reaction mixture and degassing was continued for another 5 min. The reaction mixture was heated at 140° C. for 3 h. After completion, the reaction mixture was diluted with ethyl acetate and washed with cold water. The organic layer was separated and dried over anhydrous sodium sulphate, filtered and concentrated to give crude product. The crude product was purified by silica gel column chromatography using 2-3% methanol in dichloromethane as eluent. The desired fractions were concentrated to afford rac-(4aR,5S,6R,7R,7aS)-4a-(4-cyanophenyl)-7,7a-dihydroxy-2-(4-methoxybenzyl)-N,N-dimethyl-5-phenyl-2,4a,5,6,7,7a-hexahydrocyclopenta[4,5]furo[3,2-c]pyrazole-6-carboxamide (Cpd. No. 99F) as white solid. Yield: 0.068 g, 74.4% (Racemic) MS (ESI) m/z 551.49 $[M+1]^+$; $^1H$ NMR (400 MHz, DMSO-$d_6$) δ 7.51 (d, J=8.4 Hz, 2H), 7.40 (s, 1H), 7.33 (d, J=8.6 Hz, 2H), 7.24 (d, J=8.6 Hz, 2H), 7.02-6.94 (m, 3H), 6.88 (d, J=7.2 Hz, 2H), 6.81 (d, J=7.2 Hz, 2H), 5.69 (s, 1H), 5.22-5.14 (m, 3H), 4.79 (t, J=6.9 Hz, 1H), 4.44 (d, J=13.4 Hz, 1H), 4.10 (dd, J=13.4, 7.6 Hz, 1H), 3.72 (s, 3H), 3.21 (s, 3H), 2.74 (s, 3H).

Example 100

Rac-(4aR,5S,6R,7R,7aS)-4a-(4-cyanophenyl)-7,7a-dihydroxy-N,N-dimethyl-5-phenyl-2,4a,5,6,7,7a-hexahydrocyclopenta[4,5]furo[3,2-c]pyrazole-6-carboxamide (Cpd. No. 100F)

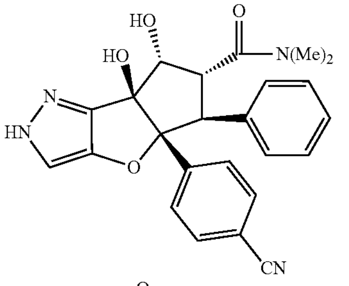

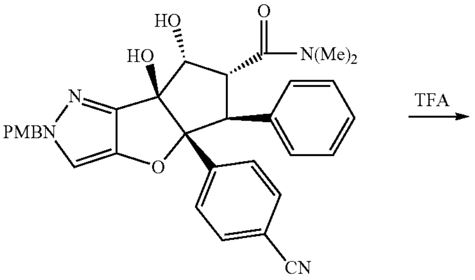

1

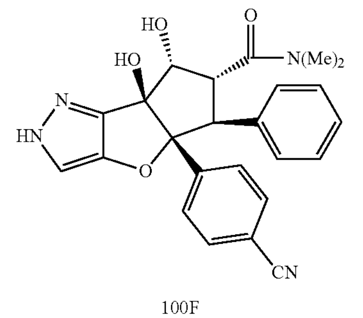

100F

Synthesis of rac-(4aR,5S,6R,7R,7aS)-4a-(4-cyanophenyl)-7,7a-dihydroxy-N,N-dimethyl-5-phenyl-2,4a,5,6,7,7a-hexahydrocyclopenta[4,5]furo[3,2-c]pyrazole-6-carboxamide (Cpd. No. 100F)

To compound rac-(4aR,5S,6R,7R,7aS)-4a-(4-cyanophenyl)-7,7a-dihydroxy-2-(4-methoxybenzyl)-N,N-dimethyl-5-phenyl-2,4a,5,6,7,7a-hexahydrocyclopenta[4,5]furo[3,2-c]pyrazole-6-carboxamide (1, 0.1 g, 0.18 mmol), trifluoroacetic acid (2 ml) was added at 0° C. and reaction mixture was heated at 100° C. for 2 h. After completion, reaction mixture was concentrated under reduced pressure to give crude product, which was purified by preparative HPLC. The desired fractions were concentrated to afford rac-(4aR,5S,6R,7R,7aS)-4a-(4-cyanophenyl)-7,7a-dihydroxy-N,N-dimethyl-5-phenyl-2,4a,5,6,7,7a-hexahydrocyclopenta[4,5]furo[3,2-c]pyrazole-6-carboxamide (Cpd. No. 100F) as white solid. Yield: 0.020 g, 25.4% (racemic mixture); MS (ESI) m/z 431.24 $[M+1]^+$; $^1H$ NMR (400 MHz, DMSO-$d_6$) δ 7.54 (d, J=8.5 Hz, 2H), 7.34 (d, J=8.3 Hz, 2H), 7.28 (s, 1H), 7.02-6.95 (m, 3H), 6.80 (d, J=6.96 Hz, 2H), 5.67 (s, 1H), 4.85 (d, J=7.84 Hz, 1H), 4.44 (d, J=13.2 Hz, 1H), 4.06 (dd, J=13.2, 7.6 Hz, 1H), 3.20 (s, 3H), 2.73 (s, 3H).

Example 101

Rac-(4bS,5S,6R,7S,7aR)-7a-(4-bromophenyl)-4-methoxy-6-(methylsulfonyl)-7-phenyl-5,6,7,7a-tetrahydro-4bH-cyclopenta[4,5]furo[2,3-c]pyridine-4b,5-diol (Cpd. No. 101F)

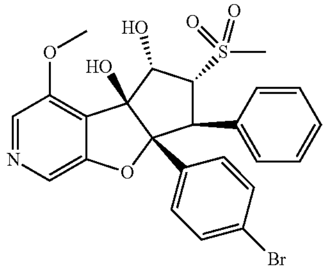

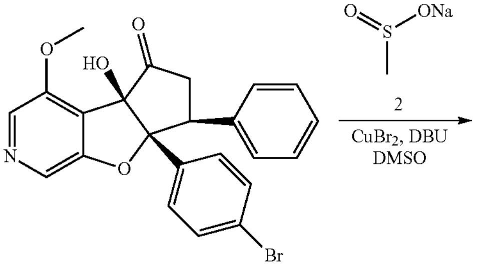

1

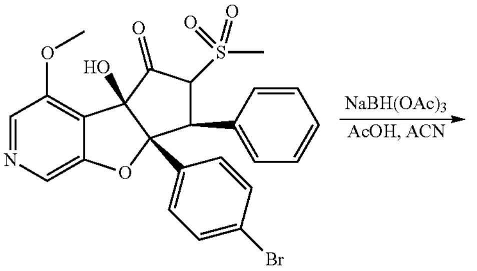

3

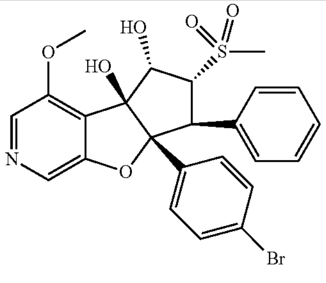

101F

Synthesis of rac-(4bR,7S,7aR)-7a-(4-bromophenyl)-4b-hydroxy-4-methoxy-6-(methylsulfonyl)-7-phenyl-4b,6,7,7a-tetrahydro-5H-cyclopenta[4,5]furo[2,3-c]pyridin-5-one (3)

To a solution of 1,8-diazabicyclo[5.4.0]undec-7-ene (0.36 mL, 2.37 mmol) in dimethyl sulfoxide (5.0 mL), copper(II) bromide (6.0 mg, 0.027 mmol) was added at room temperature in presence of air. Rac-(4bR,7S,7aR)-7a-(4-bromophenyl)-4b-hydroxy-4-methoxy-7-phenyl-4b,6,7,7a-tetrahydro-5H-cyclopenta[4,5]furo[2,3-c]pyridin-5-one (1, 0.18 g, 0.39 mmol) and sodium methanesulfinate (2, 0.404 g, 3.9 mmol) in dimethyl sulfoxide (5.0 mL) were added drop wise to above reaction mixture at room temperature in presence of air. The reaction mixture was stirred at room temperature for 1 h. After completion, (monitored by MS), the reaction mass was diluted with ethyl acetate and washed with cold water. The organic layer was separated and dried over anhydrous sodium sulphate, filtered and concentrated under reduced pressure to afford rac-(4bR,7S,7aR)-7a-(4-bromophenyl)-4b-hydroxy-4-methoxy-6-(methylsulfonyl)-7-phenyl-4b,6,7,7a-tetrahydro-5H-cyclopenta[4,5]furo[2,3-c]pyridin-5-one (3). Yield: 0.1 g, crude; MS (ESI) m/z 528 $[M-1]^-$.

Synthesis of rac-(4bS,5S,6R,7S,7aR)-7a-(4-bromophenyl)-4-methoxy-6-(methylsulfonyl)-7-phenyl-5,6,7,7a-tetrahydro-4bH-cyclopenta[4,5]furo[2,3-c]pyridine-4b,5-diol (Cpd. No. 101F)

To a solution of sodium triacetoxyborohydride (0.24 g, 1.13 mmol) and rac-(4bR,7S,7aR)-7a-(4-bromophenyl)-4b-hydroxy-4-methoxy-6-(methylsulfonyl)-7-phenyl-4b,6,7,7a-tetrahydro-5H-cyclopenta[4,5]furo[2,3-c]pyridin-5-one (3, 0.1 g, 0.18 mmol) in acetonitrile (10 mL), acetic acid (0.1 mL, 1.81 mmol) was added. The resulting mixture was stirred for 6 h at room temperature. After completion, reaction mixture was partitioned between saturated aqueous sodium bicarbonate solution and ethyl acetate. The organic layer was separated, dried over anhydrous sodium sulphate and concentrated under reduced pressure to get the crude. The crude was purified by Combi-flash (4.0 g, RediSep column) using 40% ethyl acetate in hexanes as eluent. The desired fractions were concentrated under reduced pressure to afford rac-(4bS,5S,6R,7S,7aR)-7a-(4-bromophenyl)-4-methoxy-6-(methylsulfonyl)-7-phenyl-5,6,7,7a-tetrahydro-4bH-cyclopenta[4,5]furo[2,3-c]pyridine-4b,5-diol (Cpd. No. 101F) as off white solid. Yield: 3.8 mg, 0.3%. MS (ESI) m/z 532.13 $[M+1]^+$; UPLC 99.5%; $^1H$ NMR (400 MHz, DMSO-$d_6$) δ 8.14 (s, 1H), 8.05 (s, 1H), 7.26 (d, J=8.84 Hz, 2H), 7.19 (d, J=8.72 Hz, 2H), 7.12-7.10 (m, 2H), 7.05-7.04 (m, 3H), 6.17 (bs, 1H), 6.07 (bs, 1H), 4.81 (d, J=3.12 Hz, 1H), 4.75 (dd, J=4.0 Hz, 13.8 Hz, 1H), 4.40 (d, J=13.8 Hz, 1H), 3.90 (s, 3H), 2.80 (s, 3H).

Example 102

4-((4bS,5S,6R,7S,7aR)-4b,5-dihydroxy-4-methoxy-6-(methylsulfonyl)-7-phenyl-4b,5,6,7-tetrahydro-7aH-cyclopenta[4,5]furo[2,3-c]pyridin-7a-yl)benzonitrile (Cpd. No. 102F)

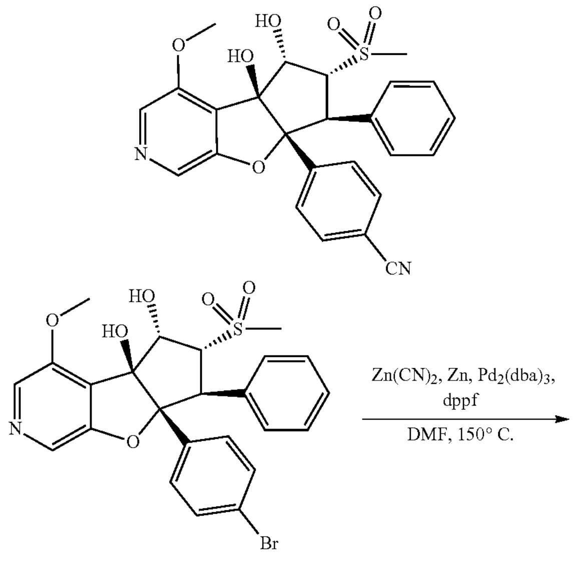

1

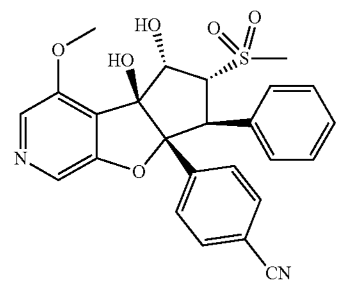

102F

Synthesis of 4-((4bS,5S,6R,7S,7aR)-4b,5-dihydroxy-4-methoxy-6-(methylsulfonyl)-7-phenyl-4b,5,6,7-tetrahydro-7aH-cyclopenta[4,5]furo[2,3-c]pyridin-7a-yl)benzonitrile (Cpd. No. 102F)

To a solution of rac-(4bS,5S,6R,7S,7aR)-7a-(4-bromophenyl)-4-methoxy-6-(methylsulfonyl)-7-phenyl-5,6,7,7a-tetrahydro-4bH-cyclopenta[4,5]furo[2,3-c]pyridine-4b,5-diol (1, 0.25 g, 0.47 mmol) in N,N-dimethylformamide (3.0 mL), zinc cyanide (0.081 g, 0.7 mmol) and zinc dust (0.003 g, 0.04 mmol) were added at room temperature and degassed the mixture with argon for 15 min. 1,1'-Bis(diphenylphosphino)ferrocene (0.008 g, 0.014 mmol) and tris(dibenzylideneacetone)dipalladium (0.012 g, 0.014 mmol) were added to the reaction mixture and degassing was continued for another 5 min. The reaction mixture was heated at 150° C. for 2 h. After completion, the reaction was cooled to room temperature and passed through celite bed. The filtrate was diluted with ethyl acetate and washed with water. The organic layer was separated, dried over anhydrous sodium sulphate and concentrated under reduced pressure to get the crude. The crude was purified by Combi-flash (12 g, RediSep column) using 70% ethyl acetate in hexanes as eluent. The desired fractions were concentrated under reduced pressure to afford rac-4-((4bS,5S,6R,7S,7aR)-4b,5-dihydroxy-4-methoxy-6-(methylsulfonyl)-7-phenyl-4b,5,6,7-tetrahydro-7aH-cyclopenta[4,5]furo[2,3-c]pyridin-7a-yl)benzonitrile as white solid. Yield: 110 mg, 48.8%. MS (ESI) m/z 479.19 $[M+1]^+$; UPLC 98.5%; The enantiomers were separated by chiral preparative HPLC [chiralpak ID (4.6×250) mm] using n-Hexane/EtOH=40/60(v/v) mobile phase. Peak 1 (Cpd. No. 102F, 27.0 mg); $[\alpha]_D$+34.8° (c 0.25, $CHCl_3$); $R_t$=7.65 min, ee >99%; MS (ESI) m/z 479.17 $[M+1]^+$; UPLC: 98.5%; $^1$H NMR (400 MHz, DMSO-$d_6$) δ: 8.08 (s, 1H), 8.01 (s, 1H), 7.52 (d, J=8.64 Hz, 2H), 7.44 (d, J=8.33 Hz, 2H), 7.14-7.12 (m, 2H), 7.05-7.00 (m, 3H), 6.17 (d, J=6.5 Hz, 1H), 6.07 (s, 1H), 4.86-4.80 (m, 2H), 4.46 (d, J=13.4 Hz, 1H), 3.88 (s, 3H), 2.85 (s, 3H). Peak-2 (20.0 mg); $[\alpha]_D$−31.5° (c 0.25, $CHCl_3$); $R_t$=12.5 min, ee >99%; MS (ESI) m/z 479.19 $[M+1]^+$; UPLC: 99.6%; $^1$H NMR (400 MHz, DMSO-$d_6$) δ: 8.08 (s, 1H), 8.00 (s, 1H), 7.52 (d, J=8.64 Hz, 2H), 7.45 (d, J=8.36 Hz, 2H), 7.14-7.12 (m, 2H), 7.04-7.02 (m, 3H), 6.17 (d, J=6.5 Hz, 1H), 6.07 (s, 1H), 4.86-4.80 (m, 2H), 4.46 (d, J=13.4 Hz, 1H), 3.88 (s, 3H), 2.85 (s, 3H).

Example 103

4-((4bS,5R,6S,7S,7aR)-6-((dimethylamino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No 103F)

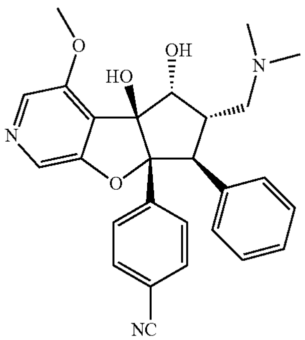

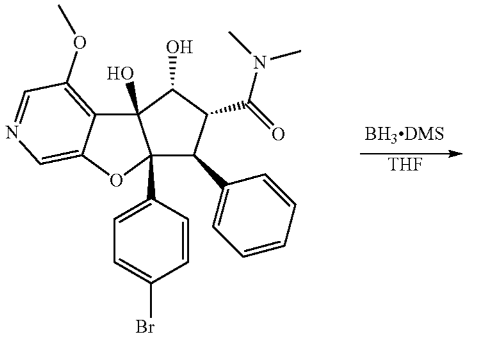

1

-continued

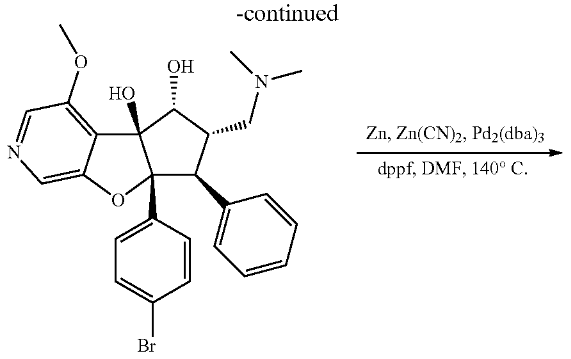

2

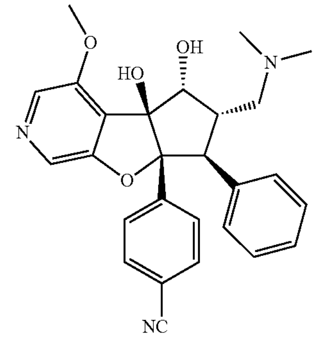

103F

Synthesis of rac-(4bS,5R,6S,7S,7aR)-7a-(4-bromophenyl)-6-((dimethylamino)methyl)-4-methoxy-7-phenyl-5,6,7,7a-tetrahydro-4bH-cyclopenta[4,5]furo[2,3-c]pyridine-4b,5-diol (2)

To a solution of rac-(4bS,5R,6R,7S,7aR)-7a-(4-bromophenyl)-4b,5-dihydroxy-4-methoxy-N,N-dimethyl-7-phenyl-4b,6,7,7a-tetrahydro-5H-cyclopenta[4,5]furo[2,3-c]pyridine-6-carboxamide (1, 0.80 g, 1.52 mmol) in dry tetrahydrofuran (20 mL) at 0° C., borane dimethyl sulphide complex (1.30 ml, 15.2 mmol) was added. The resulting mixture was stirred for 16 h at room temperature. After completion, the reaction mass was quenched with methanol at 0° C. and refluxed at 80° C. for 6 h. After completion, the reaction mass was concentrated to give crude product. The crude product was purified by silica gel column chromatography using 0-5% methanol in dichloromethane as eluent. The desired fractions were concentrated to afford rac-(4bS,5R,6S,7S,7aR)-7a-(4-bromophenyl)-6-((dimethylamino)methyl)-4-methoxy-7-phenyl-5,6,7,7a-tetrahydro-4bH-cyclopenta[4,5]furo[2,3-c]pyridine-4b,5-diol (2) as white solid. Yield: 0.41 g, 56.7%; MS (ESI) m/z 511.17 $[M+1]^+$.

Synthesis of 4-((4bS,5R,6S,7S,7aR)-6-((dimethylamino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 103F)

To a solution of rac-(4bS,5R,6S,7S,7aR)-7a-(4-bromophenyl)-6-((dimethylamino)methyl)-4-methoxy-7-phenyl-5,6,7,7a-tetrahydro-4bH-cyclopenta[4,5]furo[2,3-c]pyridine-4b,5-diol (2, 0.4 g, 1.04 mmol) in N,N-dimethylformamide (10 mL), zinc cyanide (0.45 g, 3.92 mmol) and zinc dust (0.026 g, 0.39 mmol) were added at room temperature and the reaction mixture was degassed with argon for 15 minute. 1,1'-Bis(diphenylphosphino)ferrocene (0.021 g, 0.039 mmol) and tris(dibenzylideneacetone)dipalladium (0.035 g, 0.039 mmol) were added to the reaction, degassed for additional 5 minute and heated the mixture at 140° C. for 3 h. After completion, the reaction mass was diluted with ethyl acetate and washed with cold water. The organic layer was separated and dried over sodium sulphate, filtered and concentrated to give crude. The crude was purified by silica gel column chromatography using 2-3% methanol in dichloromethane as eluent. The desired fractions were concentrated to afford rac-4-((4bS,5R,6S,7S,7aR)-6-((dimethylamino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile as white solid. Yield: 0.220 g, 62.8% (racemic). MS (ESI) m/z 458.31 $[M+1]^+$. The enantiomers were separated by chiral preparative HPLC [chiralpak ID (4.6×250) mm, 5μ]. Peak 1 (43 mg), $R_t$=10.667 min, ee=99.24%, $^1H$ NMR (400 MHz, DMSO-$d_6$) δ 8.04 (s, 1H), 7.96 (s, 1H), 7.49 (d, J=8.4 Hz, 2H), 7.37 (d, J=8.4 Hz, 2H), 7.09-7.05 (m, 2H), 7.01-6.97 (m, 3H), 5.73 (s, 1H), 4.48 (d, J=3.84 Hz, 1H), 3.87 (s, 3H), 3.78 (d, J=14.1 Hz, 1H), 3.19-3.12 (m, 1H), 2.20 (s, 6H), 1.97 (d, J=12.8 Hz, 1H), 1.89 (s, 2H). Peak 2 (Cpd. No. 103F, 38 mg), $[\alpha]_D$+25.0° (c 0.26, $CHCl_3$), $R_t$=13.904 min, ee >97%. $^1H$ NMR (400 MHz, DMSO-$d_6$) δ 8.04 (s, 1H), 7.96 (s, 1H), 7.49 (d, J=8.4 Hz, 2H), 7.37 (d, J=8.4 Hz 2H), 7.09-7.05 (m, 2H), 7.01-6.99 (m, 3H), 5.73 (s, 1H), 4.48 (d, J=3.96 Hz, 1H), 3.87 (s, 3H), 3.78 (d, J=14 Hz, 1H), 3.19-3.16 (m, 1H), 2.20 (s, 6H), 1.97 (d, J=12.8 Hz, 1H), 1.88 (s, 2H).

Example 104

(5aR,6S,7R,8R,8aS)-3-chloro-5a-(4-cyanophenyl)-8,8a-dihydroxy-N,N-dimethyl-6-phenyl-5a,7,8,8a-tetrahydro-6H-cyclopenta[4,5]furo[3,2-b]pyridine-7-carboxamide (Cpd. No. 104F)

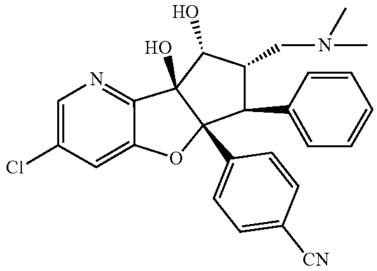

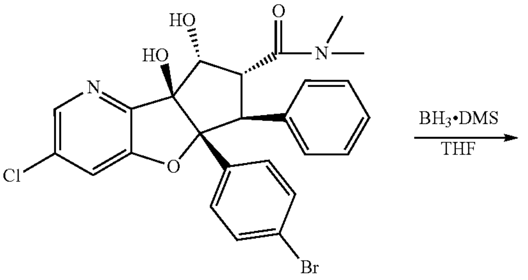

1

-continued

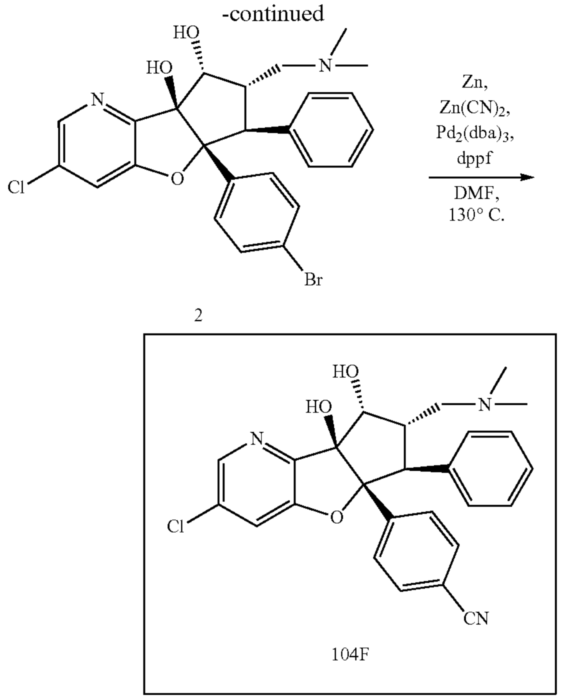

2

104F

Synthesis of rac-(5aR,6S,7S,8R,8aS)-5a-(4-bromophenyl)-3-chloro-7-((dimethylamino)methyl)-6-phenyl-5a,6,7,8-tetrahydro-8aH-cyclopenta[4,5]furo[3,2-b]pyridine-8,8a-diol (2)

To a solution of rac-(5aR,6S,7R,8R,8aS)-5a-(4-bromophenyl)-3-chloro-8,8a-dihydroxy-N,N-dimethyl-6-phenyl-5a,7,8,8a-tetrahydro-6H-cyclopenta[4,5]furo[3,2-b]pyridine-7-carboxamide (7, 2.0 g, 3.78 mmol) in dry tetrahydrofuran (30 ml) at 0° C., borane dimethyl sulphide complex (3.59 mL, 37.87 mmol) was added drop wise over a period of 5 min. The reaction mass was slowly brought to room temperature and stirred for additional 16 h. After completion, the reaction mass was quenched with methanol at 0° C. and heated to reflux for 5 h. After completion, solvent was removed under reduced pressure and the residue was purified over a plug of silica gel eluting the compound with 1-5% methanol in dichloromethane. The desired fractions were concentrated under reduced pressure to afford rac-(5aR,6S,7S,8R,8aS)-5a-(4-bromophenyl)-3-chloro-7-((dimethylamino)methyl)-6-phenyl-5a,6,7,8-tetrahydro-8aH-cyclopenta[4,5]furo[3,2-b]pyridine-8,8a-diol (8) as white solid. Yield: 1.2 g, 61.8%; MS (ESI) m/z 515.32 $[M+1]^+$.

Synthesis of 4-((5aR,6S,7S,8R,8aS)-3-chloro-7-((dimethylamino)methyl)-8,8a-dihydroxy-6-phenyl-6,7,8,8a-tetrahydro-5aH-cyclopenta[4,5]furo[3,2-b]pyridin-5a-yl)benzonitrile (Cpd. No. 104F)

To a solution of rac-(5aR,6S,7S,8R,8aS)-5a-(4-bromophenyl)-3-chloro-7-((dimethylamino)methyl)-6-phenyl-5a,6,7,8-tetrahydro-8aH-cyclopenta[4,5]furo[3,2-b]pyridine-8,8a-diol (8, 1.2 g, 2.32 mmol) in N,N-dimethylformamide (48 mL), zinc cyanide (0.273 g, 2.32 mmol) and zinc dust (0.304 g, 4.65 mmol) were added at room temperature and the reaction mixture was degassed with argon for 15 min. 1,1'-Bis(diphenylphosphino)ferrocene (0.025 g, 0.046 mmol) and tris(dibenzylideneacetone) dipalladium (0.064 g, 0.069 mmol) were added to the reaction, degassed for additional 5 min and mixture was heated at 130° C. for 4 h. After completion, the reaction mass was diluted with ethyl acetate and washed with cold water. The organic layer was separated and dried over anhydrous sodium sulphate, filtered and concentrated to give crude. The crude was purified by silica gel column chromatography using 2-3% methanol in dichloromethane as eluent. The desired fractions were concentrated to afford rac-4-((5aR,6S,7S,8R,8aS)-3-chloro-7-((dimethylamino)methyl)-8,8a-dihydroxy-6-phenyl-6,7,8,8a-tetrahydro-5aH-cyclopenta[4,5]furo[3,2-b]pyridin-5a-yl)benzonitrile (Cpd. No. 104F) as white solid. Yield: 0.49 g, 46.2% (racemic). MS (ESI) m/z 462.23 $[M+1]^+$. The enantiomers were separated by chiral HPLC [chiralpak IA (4.6×250) mm, 5μ], n-hexane/EtOH 20/80 V/V.

Peak-1 (137 mg), $[\alpha]_D$−110.4° (c 0.26, $CHCl_3$), $R_t$=4.580 min, ee: 98.5% MS (ESI) m/z 462.23 $[M+1]^+$. $^1H$ NMR (400 MHz, DMSO-$d_6$) δ 8.18 (d, J=1.60 Hz, 1H), 7.63 (d, J=1.68 Hz, 1H), 7.48 (d, J=8.42 Hz, 2H), 7.36 (d, J=8.40 Hz, 2H), 7.15-6.98 (m, 5H), 6.12 (s, 1H), 5.41 (bs, 1H), 4.45 (s, 1H), 3.93 (d, J=13.90 Hz, 1H), 3.24 (bs, 1H), 2.66 (s, 1H), 2.59 (s, 1H), 2.25 (s, 6H).

Peak-2 (133 mg), $[\alpha]_D$+105.4° (c 0.25, $CHCl_3$), $R_t$=12.693 min, ee: 99.9%, MS (ESI) m/z 462.23 $[M+1]^+$. $^1H$ NMR (400 MHz, DMSO-$d_6$) δ 8.18 (d, J=1.60 Hz, 1H), 7.63 (d, J=1.68 Hz, 1H), 7.48 (d, J=8.42 Hz, 2H), 7.36 (d, J=8.40 Hz, 2H), 7.15-6.98 (m, 5H), 6.12 (s, 1H), 5.41 (bs, 1H), 4.45 (s, 1H), 3.93 (d, J=13.90 Hz, 1H), 3.24 (bs, 1H), 2.66 (s, 1H), 2.59 (s, 1H), 2.25 (s, 6H).

Example 105

5aR,6S,7S,8R,8aS)-5a-(4-cyanophenyl)-7-((dimethylamino)methyl)-8,8a-dihydroxy-6-phenyl-5a,7,8,8a-tetrahydro-6H-cyclopenta[4,5]furo[3,2-b]pyridine-3-carbonitrile (Cpd. No. 105F)

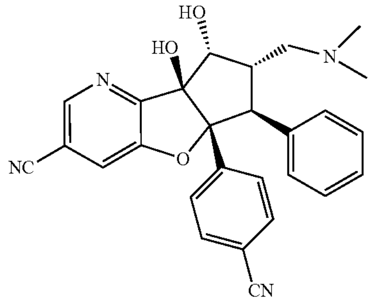

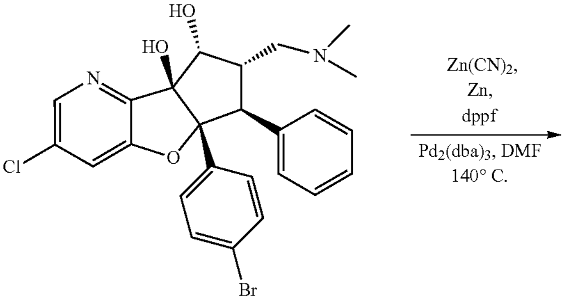

1

-continued

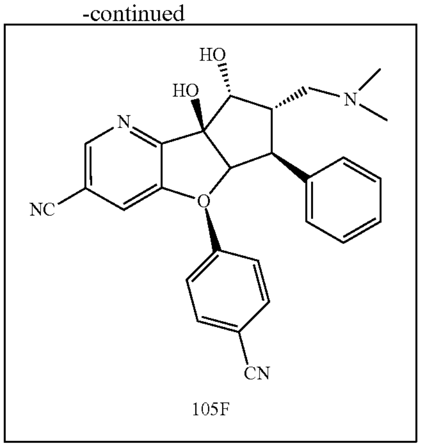

105F

Synthesis of 5aR,6S,7S,8R,8aS)-5a-(4-cyanophenyl)-7-((dimethylamino)methyl)-8,8a-dihydroxy-6-phenyl-5a,7,8,8a-tetrahydro-6H-cyclopenta[4,5]furo[3,2-b]pyridine-3-carbonitrile (Cpd. No. 105F)

To a solution of rac-(5aR,6S,7S,8R,8aS)-5a-(4-bromophenyl)-3-chloro-7-((dimethylamino)methyl)-6-phenyl-5a,6,7,8-tetrahydro-8aH-cyclopenta[4,5]furo[3,2-b]pyridine-8,8a-diol (1, 0.4 g, 0.77 mmol) in N,N-dimethylformamide (5.0 mL), zinc cyanide (0.099 g, 0.85 mmol) and zinc dust (0.099 g, 1.55 mmol) were added at room temperature and degassed the mixture with argon for 15 min. 1,1'-Bis(diphenylphosphino)ferrocene (0.011 g, 0.015 mmol), tris(dibenzylideneacetone)dipalladium (0.021 g, 0.023 mmol) were added to the reaction and degassing was continued for another 5 min. The reaction mixture was heated at 140° C. for 3 h. After completion, the reaction was cooled to room temperature and passed through celite bed. The filtrate was diluted with ethyl acetate and washed with water. The organic layer was separated, dried over sodium sulphate and concentrated under reduced pressure to get the crude. The crude was purified by combi-flash (12 g, RediSep column), using 0-15% methanol in dichloromethane as eluent. The desired fractions were concentrated under reduced pressure. The Compound was again repurified by reverse phase preparative HPLC. The desired fractions were lyophilized to give rac-(5aR,6S,7S,8R,8aS)-5a-(4-cyanophenyl)-7-((dimethylamino)methyl)-8,8a-dihydroxy-6-phenyl-5a,7,8,8a-tetrahydro-6H-cyclopenta[4,5]furo[3,2-b]pyridine-3-carbonitrile as white solid. The enantiomers were separated by chiral preparative HPLC [chiralpak IA (4.6×250) mm]; 0.1% TEA in n-Hexane/IPA=80/20(v/v); Yield: 120 mg, 34%; Peak 1 (Cpd. No. 105F, 7 mg), $[\alpha]_D$−71.9° (c 0.26, $CHCl_3$), $R_t$=22.203, ee >99%; MS (ESI) m/z 453.29 $[M+1]^+$; UPLC: 98.48%; $^1H$ NMR (400 MHz, DMSO-$d_6$) δ: 8.60 (s, 1H), 7.96 (s, 1H), 7.48 (d, J=8.3 Hz, 2H), 7.35 (d, J=8.2 Hz, 2H), 7.11-7.00 (m, 5H), 6.33 (s, 1H), 4.48 (d, J=2.84 Hz, 1H), 3.96 (d, J=13.8 Hz, 1H), 3.25 (m, 1H), 2.66-2.49 (m, 1H), 2.21 (s, 6H), 2.00-1.97 (d, J=11.0 Hz, 1H). Peak 2 (4 mg), $[\alpha]_D$+21.9° (c 0.266, $CHCl_3$), $R_t$=34.931, ee >98%; MS (ESI) m/z 453.29 $[M+1]^+$; UPLC: 99.54%; $^1H$ NMR (400 MHz, DMSO-$d_6$) δ: 8.60 (d, J=1.32 Hz, 1H), 7.96 (d, J=1.28 Hz, 1H), 7.48 (d, J=8.4 Hz, 2H), 7.35 (d, J=8.4 Hz, 2H), 7.11-6.98 (m, 5H), 6.32 (s, 1H), 5.46 (brs, 1H), 4.48 (d, J=3.3 Hz, 1H), 3.96 (d, J=13.9 Hz, 1H), 3.41-3.25 (m, 1H), 2.60-2.4 (m, 1H), 2.20 (s, 6H), 1.98 (d, J=10.3 Hz, 1H).

Example 106

(4bS,5R,6S,7S,7aR)-7a-(4-(difluoromethyl)phenyl)-6-((dimethylamino)methyl)-4-methoxy-7-phenyl-5,6,7,7a-tetrahydro-4bH-cyclopenta[4,5]furo[2,3-c]pyridine-4b,5-diol (Cpd. No. 106F)

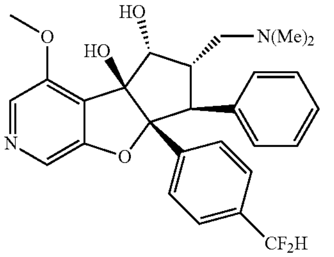

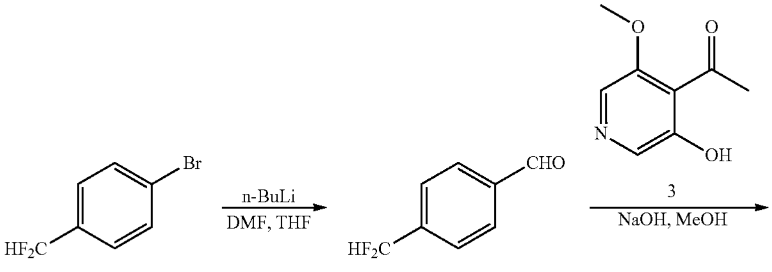

1 2

-continued
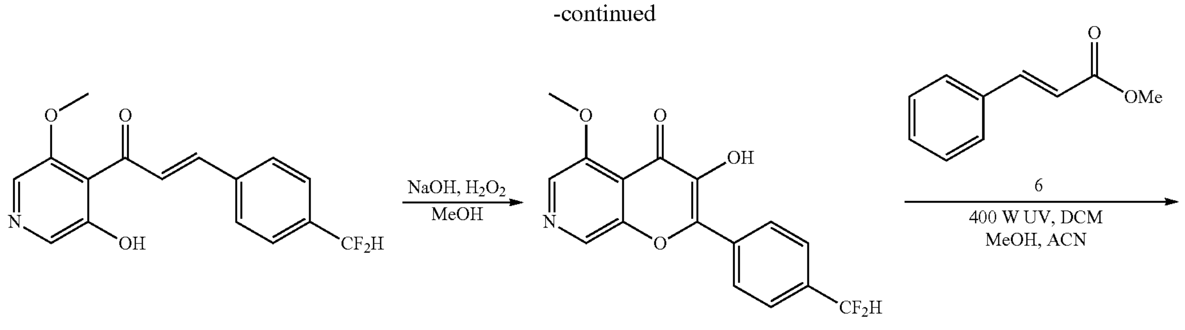
4 5
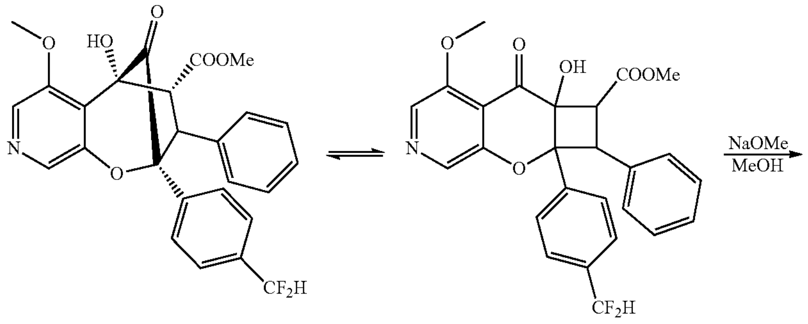
7 7a
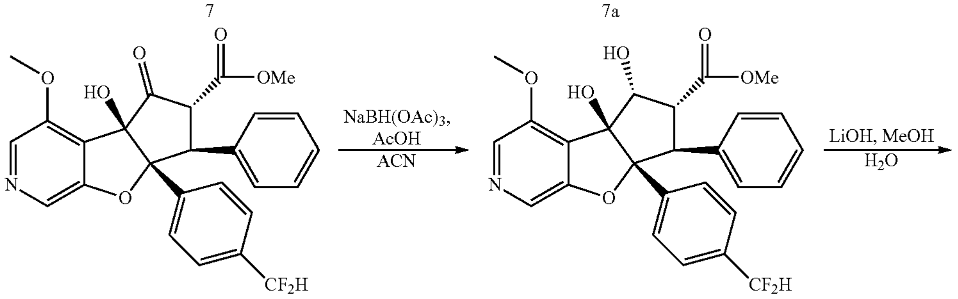
8 9
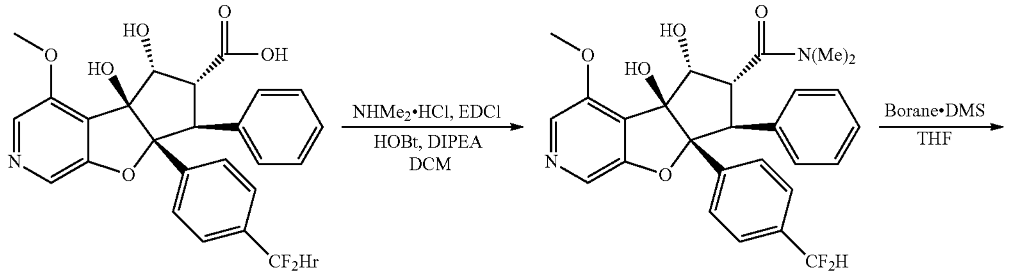
10 11
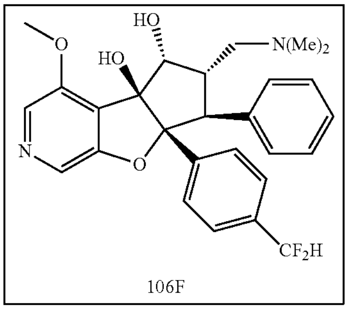
106F Synthesis of 4-(difluoromethyl)benzaldehyde (2)

To a solution of 1-bromo-4-(difluoromethyl)benzene (1, 35.0 g, 169.08 mmol) in dry tetrahydrofuran (300 mL), n-butyllithium in hexane (2.5 M, 67.0 mL, 169.08 mmol) was added drop wise over a period of 30 min at −78° C. The reaction mass was stirred for 1 h at −78° C. and N,N-dimethylformamide (38.48 mL, 507.24 mmol) was added at same temperature and the reaction was further stirred at −78° C. for 1 h. After completion, the reaction mixture was brought to 0° C. and treated with saturated ammonium chloride solution and extracted with ethyl acetate. The organic layer was dried over anhydrous sodium sulphate, filtered and concentrated under reduced pressure to get the crude. The crude was purified by Combi-flash (40 g, RediSep column) using 2% ethyl acetate in hexanes as eluent. The desired fraction were concentrated below 30° C. under reduced pressure to afford 4-(difluoromethyl)benzaldehyde (2) as light yellow liquid (highly unstable). Yield: 17.0 g, 64%; MS (ESI) m/z poor ionization.

Synthesis of (E)-3-(4-(difluoromethyl) phenyl)-1-(3-hydroxy-5-methoxypyridin-4-yl) prop-2-en-1-one (4)

To a solution of 1-(3-hydroxy-5-methoxypyridin-4-yl) ethan-1-one (3, 12.6 g, 75.4 mmol) in methanol (50 mL), sodium hydroxide (6.03 g, 150.0 mmol) and 4-(difluoromethyl)benzaldehyde (2, 11.7 g, 75.4 mmol) were added at 0° C. and the reaction mixture was stirred at room temperature for 1 h. After completion, the reaction mixture was cooled, water was added then neutralized to pH ~ 7 with 6M hydrogen chloride at 0° C., obtained solid was filtered, washed with excess water and dried under vacuum to afford (E)-3-(4-(difluoromethyl) phenyl)-1-(3-hydroxy-5-methoxypyridin-4-yl)prop-2-en-1-one (4) as yellow solid. Yield: 20.2 g, MS (ESI) m/z 304.13[M−1]$^-$.

Synthesis of 2-(4-(difluoromethyl) phenyl)-3-hydroxy-5-methoxy-4H-pyrano[2,3-c]pyridin-4-one (5)

To a solution of (E)-3-(4-(difluoromethyl)phenyl)-1-(3-hydroxy-5-methoxypyridin-4-yl)prop-2-en-1-one (4, 20.2 g, 65.5 mmol) in methanol (200 mL), 10% sodium hydroxide (65.6 mL, 163.9 mmol) was added followed by addition of hydrogen peroxide (18.6 mL, 163.9 mmol, 30%) at 0° C. The reaction mass was stirred for 45 min at 0° C. After completion the reaction mixture was and neutralized with 6 M hydrogen chloride to pH ~7. The solvent was distilled off and precipitated solid was filtered and dried under vacuum to afford 2-(4-(difluoromethyl) phenyl)-3-hydroxy-5-methoxy-4H-pyrano[2,3-c]pyridin-4-one (5) as pale yellow solid. Yield: 5.5 g, 26%; MS (ESI) m/z 318.23[M−1]$^-$.

Synthesis of rac-methyl (2S,3S,4S,5R)-2-(4-(difluoromethyl)phenyl)-5-hydroxy-6-methoxy-10-oxo-3-phenyl-2,3,4,5-tetrahydro-2,5-methanooxepino[2,3-c]pyridine-4-carboxylate (7,7a)

A solution of 2-(4-(difluoromethyl) phenyl)-3-hydroxy-5-methoxy-4H-pyrano[2,3-c]pyridin-4-one (5, 5.5 g, 17.24 mmol) and methyl cinnamate (6, 28.0 g, 172.4 mmol) in dichloromethane (200 mL), acetonitrile (100 mL) and methanol (100 mL) was placed in a UV reactor flask. The reaction mixture was irradiated for 16 h under 400 watts UV light. After completion, the solvent was removed under reduced pressure and the crude was purified by Combi-flash (40 g, RediSep column) using ethyl acetate as eluent. The desired fractions were concentrated under reduced pressure to afford rac-methyl (2S,3S,4S,5R)-2-(4-(difluoromethyl) phenyl)-5-hydroxy-6-methoxy-10-oxo-3-phenyl-2,3,4,5-tetrahydro-2,5-methanooxepino[2,3-c]pyridine-4-carboxylate (7,7a) as brown solid. Yield: 6.0 g, crude.

Synthesis of rac-methyl (4bR,6R,7S,7aR)-7a-(4-(difluoromethyl)phenyl)-4b-hydroxy-4-methoxy-5-oxo-7-phenyl-4b,6,7,7a-tetrahydro-5H-cyclopenta[4,5]furo[2,3-c]pyridine-6-carboxylate (8)

The crude rac-methyl (2S,3S,4S,5R)-2-(4-(difluoromethyl)phenyl)-5-hydroxy-6-methoxy-10-oxo-3-phenyl-2,3,4,5-tetrahydro-2,5-methanooxepino[2,3-c]pyridine-4-carboxylate (7,7a, 6.0 g) was suspended in methanol (60 mL) and treated with sodium methoxide (25% in methanol, 60 mL) and heated the mixture to 90° C. for 3 h. After completion, the solvent was removed under reduced pressure and mixture was diluted with ammonium chloride solution and extracted with ethyl acetate. The organic phase was separated, dried over anhydrous sodium sulphate, filtered and concentrated under reduced pressure to afford rac-methyl (4bR,6R,7S,7aR)-7a-(4-(difluoromethyl)phenyl)-4b-hydroxy-4-methoxy-5-oxo-7-phenyl-4b,6,7,7a-tetrahydro-5H-cyclopenta[4,5]furo[2,3-c]pyridine-6-carboxylate (8) as brown solid. Yield: 5.3 g, crude.

Synthesis of rac-methyl (4bS,5R,6R,7S,7aR)-7a-(4-(difluoromethyl)phenyl)-4b,5-dihydroxy-4-methoxy-7-phenyl-4b,6,7,7a-tetrahydro-5H-cyclopenta[4,5]furo[2,3-c]pyridine-6-carboxylate (9)

To a solution of sodium triacetoxyborohydride (14.0 g, 66.1 mmol), rac-methyl (4bR,6R,7S,7aR)-7a-(4-(difluoromethyl)phenyl)-4b-hydroxy-4-methoxy-5-oxo-7-phenyl-4b,6,7,7a-tetrahydro-5H-cyclopenta[4,5]furo[2,3-c]pyridine-6-carboxylate (8, 5.3 g, 11 mmol) in acetonitrile (50 mL), acetic acid (6.6 mL, 110.0 mmol) was added. The resulting mixture was stirred at room temperature for 4 h. After completion, reaction mixture was partitioned between saturated aqueous sodium bicarbonate solution and ethyl acetate. The organic layer was separated, dried over sodium sulphate and concentrated under reduced pressure to get the crude. The crude was purified by Combi-flash (40 g, RediSep) using 90% ethyl acetate in hexanes as eluent. The desired fractions were concentrated under reduced pressure to afford rac-methyl (4bS,5R,6R,7S,7aR)-7a-(4-(difluoromethyl)phenyl)-4b,5-dihydroxy-4-methoxy-7-phenyl-4b,6,7,7a-tetrahydro-5H-cyclopenta[4,5]furo[2,3-c]pyridine-6-carboxylate (9) as off white solid. Yield: 2.35 g, 44%; MS (ESI) m/z 482.22 [M−1]$^-$.

Synthesis of rac-(4bS,5R,6R,7S,7aR)-7a-(4-(difluoromethyl)phenyl)-4b,5-dihydroxy-4-methoxy-7-phenyl-4b,6,7,7a-tetrahydro-5H-cyclopenta[4,5]furo[2,3-c]pyridine-6-carboxylic acid (10)

To a solution of rac-methyl (4bS,5R,6R,7S,7aR)-7a-(4-(difluoromethyl)phenyl)-4b,5-dihydroxy-4-methoxy-7-phenyl-4b,6,7,7a-tetrahydro-5H-cyclopenta[4,5]furo[2,3-c]pyridine-6-carboxylate (9, 2.35 g, 4.86 mmol) in methanol and water (3:1, 24 mL), lithium hydroxide (1.16 g, 48.6 mmol) was added and the reaction was stirred at room temperature for 1 h. After completion, methanol was distilled off and reaction mass was cooled to 0° C. and acidified with 1 M hydrogen chloride to pH ~6. The precipitated solid was filtered and dried under vacuum to afford rac-(4bS,5R,6R,7S,7aR)-7a-(4-(difluoromethyl)phenyl)-4b,5-dihydroxy-4-methoxy-7-phenyl-4b,6,7,7a-tetrahydro-5H-cyclopenta[4,5]furo[2,3-c]pyridine-6-carboxylic acid (10) as off white solid. Yield: 1.97 g, 93%; MS (ESI) m/z 468.31[M−1]$^-$.

Synthesis of rac-(4bS,5R,6R,7S,7aR)-7a-(4-(difluoromethyl)phenyl)-4b,5-dihydroxy-4-methoxy-N,N-dimethyl-7-phenyl-4b,6,7,7a-tetrahydro-5H-cyclopenta[4,5]furo[2,3-c]pyridine-6-carboxamide (11)

To a solution of rac-(4bS,5R,6R,7S,7aR)-7a-(4-(difluoromethyl)phenyl)-4b,5-dihydroxy-4-methoxy-7-phenyl-4b,6,7,7a-tetrahydro-5H-cyclopenta[4,5]furo[2,3-c]pyridine-6-carboxylic acid (10, 0.6 g, 1.27 mmol) in dichloromethane (20 mL), 1-ethyl-3-(3-dimethylaminopropyl)carbodiimide hydrochloride (0.73 g, 3.83 mmol), 1-hydroxybenzotriazole (0.518 g, 3.83 mmol) and N,N-diisopropylethylamine (1.34 mL, 7.67 mmol) were added at 0° C. and stirred the mixture for 5 min. Dimethylamine hydrochloride (0.518 g, 6.39 mmol) was then added at same temperature and the mixture was stirred for 16 h at 40° C. After completion, reaction mass was diluted with dichloromethane and washed with cold water. The organic layer was separated and dried over anhydrous sodium sulphate, filtered and concentrated to give crude. The crude was purified by Combi-flash (12 g, RediSep) using 90% ethyl acetate in hexanes as eluent. The desired fractions were concentrated under reduced pressure to afford rac-(4bS,5R,6R,7S,7aR)-7a-(4-(difluoromethyl)phenyl)-4b,5-dihydroxy-4-methoxy-N,N-dimethyl-7-phenyl-4b,6,7,7a-tetrahydro-5H-cyclopenta[4,5]furo[2,3-c]pyridine-6-carboxamide (11) as off white solid. Yield: 0.59 g, 93%; MS (ESI) m/z 497.42 [M+1]$^+$.

Synthesis of (4bS,5R,6S,7S,7aR)-7a-(4-(difluoromethyl)phenyl)-6-((dimethylamino)methyl)-4-methoxy-7-phenyl-5,6,7,7a-tetrahydro-4bH-cyclopenta[4,5]furo[2,3-c]pyridine-4b,5-diol (Cpd. No. 106F)

To a solution of rac-(4bS,5R,6R,7S,7aR)-7a-(4-(difluoromethyl)phenyl)-4b,5-dihydroxy-4-methoxy-N,N-dimethyl-7-phenyl-4b,6,7,7a-tetrahydro-5H-cyclopenta[4,5]furo[2,3-c]pyridine-6-carboxamide (11, 0.59 g, 1.18 mmol) in tetrahydrofuran (15 mL), borane dimethyl sulphide (1.13 mL 11.8 mmol) was added at 0° C. and stirred the mixture for 2 h at 60° C. After completion, reaction mass was quenched with methanol (5.0 mL) and again heated for 10 h at 60° C. The reaction mixture was concentrated under reduced pressure to get the crude. The crude was purified by combi-flash (12 g, RediSep) using 20% methanol in dichloromethane as eluent. The desired fractions were concentrated to afford rac-(4bS,5R,6S,7S,7aR)-7a-(4-(difluoromethyl)phenyl)-6-((dimethylamino)methyl)-4-methoxy-7-phenyl-5,6,7,7a-tetrahydro-4bH-cyclopenta[4,5]furo[2,3-c]pyridine-4b,5-diol as white solid. Yield: 75 mg, 13%. The enantiomers were separated by chiral preparative HPLC [chiralpak IA (4.6×250) mm] Mobile phase: 0.1% TEA in n-Hexane/EtOH=85/15(v/v). Peak 1 (46 mg), $[\alpha]_D$+9.6° (c 0.250, $CHCl_3$), $R_t$=14.72, ee >99% MS (ESI) m/z 483.28 [M+1]$^+$ UPLC: 98.5%. $^1$H NMR (400 MHz, DMSO-$d_6$) δ: 8.04 (s, 1H), 7.95 (s, 1H), 7.33 (d, J=8.0 Hz, 2H), 7.21 (d, J=8.1 Hz, 2H), 7.07-7.03 (m, 2H), 6.97-6.90 (m, 3H), 6.83 (t, J=55.9 Hz, 1H), 5.64 (s, 1H), 4.52 (d, J=3.7 Hz, 1H), 3.87 (s, 3H), 3.76 (d, J=14.0 Hz, 1H), 3.19-3.15 (m, 1H), 2.65-2.61 (m, 2H), 2.22 (s, 6H), 1.98 (s, 1H). Peak 2 (Cpd. No. 106F, 29 mg), $[\alpha]_D$−2.4° (c 0.25, $CHCl_3$), $R_t$=26.39, ee >99% MS (ESI) m/z 483.33 [M+1]$^+$, UPLC: 99.3%. $^1$H NMR (400 MHz, DMSO-$d_6$) δ: 8.03 (s, 1H), 7.95 (s, 1H), 7.32 (d, J=8.2 Hz, 2H), 7.22 (d, J=8.1 Hz, 2H), 7.07-7.03 (m, 2H) 6.97-6.95 (m, 3H), 6.83 (t, J=55.8 Hz, 1H), 5.641 (s, 1H), 4.51 (d, J=4.2 Hz, 1H), 3.87 (s, 3H), 3.76 (d, J=14.1 Hz, 1H), 3.18 (t, J=11.0 Hz, 1H), 2.58-2.50 (m, 2H), 2.20 (s, 6H), 1.95 (d, J=4.2 Hz, 1H).

Example 107

(4bS,5R,6S,7S,7aR)-6-((dimethylamino)methyl)-4-methoxy-7-phenyl-7a-(4-(trifluoromethyl)phenyl)-5,6,7,7a-tetrahydro-4bH-cyclopenta[4,5]furo[2,3-c]pyridine-4b,5-diol (Cpd. No. 107F)

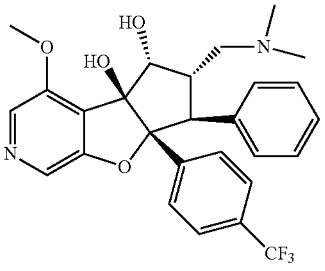

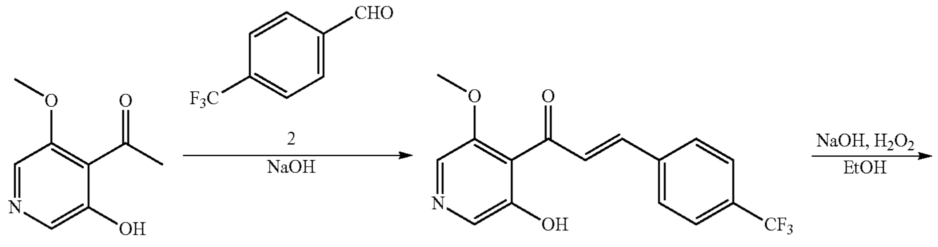

1

3

-continued
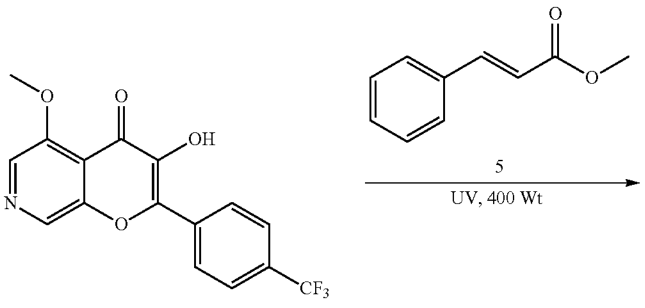
4
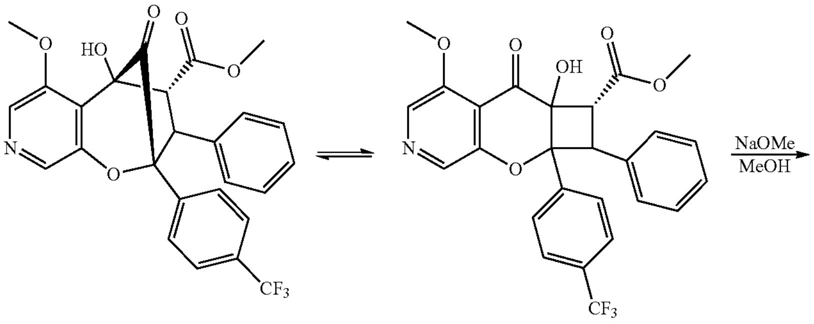
6 6a
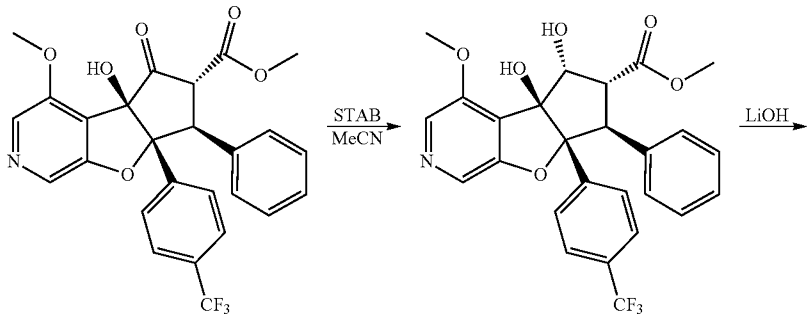
7 8
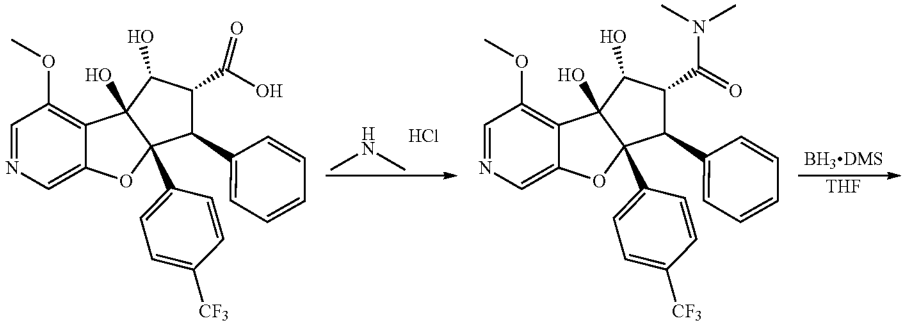
9 10

-continued

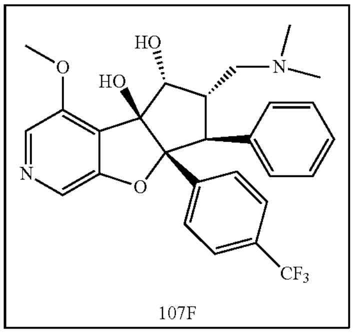

107F

Synthesis of (E)-1-(3-hydroxy-5-methoxypyridin-4-yl)-3-(4-(trifluoromethyl)phenyl) prop-2-en-1-one (3)

To a solution of 1-(3-hydroxy-5-methoxypyridin-4-yl) ethan-1-one (1, 10.0 g, 59.8 mmol) and 4-(trifluoromethyl) benzaldehyde (2, 10.41 g, 59.8 mmol) in methanol (50 mL), sodium hydroxide (7.17 g, 179.4 mmol) was added and the mixture was heated to reflux for 30 min. After completion, the reaction mass was cooled to room temperature, the solvent methanol was distilled off under reduced pressure and the residue was neutralized with 1N hydrochloric acid up to pH-7 at 0° C. The precipitated solid was filtered, washed with water, n-pentane and dried under vacuum to afford (E)-1-(3-hydroxy-5-methoxypyridin-4-yl)-3-(4-(trifluoromethyl) phenyl) prop-2-en-1-one (3) as yellow solid. Yield: 16.1 g, 83.0%; MS (ESI) m/z 324.22[M+1]$^+$.

Synthesis of 3-hydroxy-5-methoxy-2-(4-(trifluoromethyl) phenyl)-4H-pyrano[2,3-c]pyridin-4-one (4)

To a solution of (E)-1-(3-hydroxy-5-methoxypyridin-4-yl)-3-(4-(trifluoromethyl)phenyl)prop-2-en-1-one (3, 15.0 g, 46.4 mmol) in ethanol (150 mL) at 0° C., sodium hydroxide (2.22 g, 55.68 mmol) was added followed by the addition of 30% aqueous hydrogen peroxide (36.80 mL, 324.8 mmol). The reaction mass was stirred for 30 min at 60° C. After completion, the reaction mass was cooled and neutralized by the addition of 6 M hydrochloric acid to pH ~7. The solid obtained was filtered, washed with cold ethanol, pentane and dried under vacuum to afford 3-hydroxy-5-methoxy-2-(4-(trifluoromethyl) phenyl)-4H-pyrano [2,3-c]pyridin-4-one (4) as pale yellow solid. Yield: 3.2 g, 20%; MS (ESI) m/z 338.09[M+1]$^+$.

Synthesis of rac-methyl (3S,4S,5R)-5-hydroxy-6-methoxy-10-oxo-3-phenyl-2-(4-(trifluoromethyl) phenyl)-2,3,4,5-tetrahydro-2,5-methanooxepino[2,3-c]pyridine-4-carboxylate (6)

A solution of 3-hydroxy-5-methoxy-2-(4-(trifluoromethyl) phenyl)-4H-pyrano[2,3-c]pyridin-4-one (4, 3.2 g, 9.48 mmol) and methyl cinnamate (5, 15.38 g, 94.88 mmol) in dichloromethane (200 mL), acetonitrile (100 mL) and methanol (100 mL) was placed in a UV reactor flask. The reaction mixture was irradiated under 400 watts UV light for 24 h. After completion, solvent was removed under reduced pressure and the residue was purified over a plug of silica gel eluting the compound with 5% methanol in dichloromethane. The desired fractions were concentrated under reduced pressure to afford rac-methyl (3S,4S,5R)-5-hydroxy-6-methoxy-10-oxo-3-phenyl-2-(4-(trifluoromethyl)phenyl)-2,3,4,5-tetrahydro-2,5-methanooxepino[2,3-c]pyridine-4-carboxylate (6) as brown solid. Yield: 3.5 g, 74%; MS (ESI) m/z 499.39[M−1]$^-$.

Synthesis of rac-methyl (4bR,6R,7S,7aR)-4b-hydroxy-4-methoxy-5-oxo-7-phenyl-7a-(4-(trifluoromethyl)phenyl)-4b,6,7,7a-tetrahydro-5H-cyclopenta[4,5]furo[2,3-c]pyridine-6-carboxylate (7)

A solution of rac-methyl (3S,4S,5R)-5-hydroxy-6-methoxy-10-oxo-3-phenyl-2-(4-(trifluoromethyl)phenyl)-2,3,4,5-tetrahydro-2,5-methanooxepino[2,3-c]pyridine-4-carboxylate (6, 3.5 g, 7.0 mmol) was suspended in methanol (35 mL) and treated with 25% sodium methoxide in methanol (7.0 mL). The reaction was heated at 80° C. for 4 h. After completion, the solvent was removed under reduced pressure. The crude was diluted with ammonium chloride solution and extracted with ethyl acetate. The organic phase was separated, dried over sodium sulphate and concentrated under reduced pressure to afford rac-methyl (4bR,6R,7S,7aR)-4b-hydroxy-4-methoxy-5-oxo-7-phenyl-7a-(4-(trifluoromethyl)phenyl)-4b,6,7,7a-tetrahydro-5H-cyclopenta[4,5]furo[2,3-c]pyridine-6-carboxylate (7) as brown solid. Yield: 3.2 g, crude; MS (ESI) m/z 500.16[M+1]$^+$.

Synthesis of rac-methyl (4bS,5R,6R,7S,7aR)-4b,5-dihydroxy-4-methoxy-7-phenyl-7a-(4-(trifluoromethyl)phenyl)-4b,6,7,7a-tetrahydro-5H-cyclopenta[4,5]furo[2,3-c]pyridine-6-carboxylate (8)

A solution of rac-methyl (4bR,6R,7S,7aR)-4b-hydroxy-4-methoxy-5-oxo-7-phenyl-7a-(4-(trifluoromethyl)phenyl)-4b,6,7,7a-tetrahydro-5H-cyclopenta[4,5]furo[2,3-c]pyridine-6-carboxylate (7, 3.2 g, 6.40 mmol) in acetonitrile (60 mL) was cooled at 0° C., acetic acid (3.84 g, 64.07 mmol) and sodium triacetoxyborohydride (8.14 g, 38.44 mmol) were added. The resulting mixture was stirred for 12 h at room temperature. After completion, the reaction mixture was partitioned between saturated aqueous sodium bicarbonate solution and ethyl acetate. The organic layer was separated and dried over anhydrous sodium sulphate, filtered and concentrated to give crude. The crude was purified by silica gel column chromatography eluting with 2-3% in methanol in dichloromethane. The desired fractions were concentrated to afford rac-methyl (4bS,5R,6R,7S,7aR)-4b,5-dihydroxy-4-methoxy-7-phenyl-7a-(4-(trifluoromethyl) phenyl)-4b,6,7,7a-tetrahydro-5H-cyclopenta[4,5]furo[2,3-c]pyridine-6-carboxylate (8) as white solid. Yield: 1.2 g, 38.0%; MS (ESI) m/z 502.19[M+1]$^+$.

Synthesis of rac-(4bS,5R,6R,7S,7aR)-4b,5-dihydroxy-4-methoxy-7-phenyl-7a-(4-(trifluoromethyl)phenyl)-4b,6,7,7a-tetrahydro-5H-cyclopenta[4,5]furo[2,3-c]pyridine-6-carboxylic acid (9)

To a solution of rac-methyl (4bS,5R,6R,7S,7aR)-4b,5-dihydroxy-4-methoxy-7-phenyl-7a-(4-(trifluoromethyl)phenyl)-4b,6,7,7a-tetrahydro-5H-cyclopenta[4,5]furo[2,3-c]pyridine-6-carboxylate (8, 1.2 g, 2.39 mmol) in methanol, tetrahydrofuran and water (2:1:1, 12 mL), lithium hydroxide (0.574 g, 23.9 mmol) was added and the reaction was stirred for 6 h at room temperature. After completion, the reaction mass was concentrated and cooled to 0° C. and acidified with 1 M hydrochloric acid to pH ~2-3. The precipitated solid was filtered and dried under vacuum to afford rac-(4bS,5R,6R,7S,7aR)-4b,5-dihydroxy-4-methoxy-7-phenyl-7a-(4-(trifluoromethyl)phenyl)-4b,6,7,7a-tetrahydro-5H-cyclopenta[4,5]furo[2,3-c]pyridine-6-carboxylic acid (9) as off white solid. Yield: 0.90 g, 80%; MS (ESI) m/z 488.37 $[M+1]^+$.

Synthesis of rac-(4bS,5R,6R,7S,7aR)-4b,5-dihydroxy-4-methoxy-N,N-dimethyl-7-phenyl-7a-(4-(trifluoromethyl)phenyl)-4b,6,7,7a-tetrahydro-5H-cyclopenta[4,5]furo[2,3-c]pyridine-6-carboxamide (10)

To a solution of rac-(4bS,5R,6R,7S,7aR)-4b,5-dihydroxy-4-methoxy-7-phenyl-7a-(4-(trifluoromethyl)phenyl)-4b,6,7,7a-tetrahydro-5H-cyclopenta[4,5]furo[2,3-c]pyridine-6-carboxylic acid (9, 0.9 g, 1.84 mmol) in dichloromethane (18 mL) at 0° C., 1-ethyl-3-(3-dimethylaminopropyl) carbodiimide (0.859 g, 5.53 mmol), hydroxybenzotriazole (0.846 g, 5.53 mmol) and N,N-diisopropylethylamine (1.82 mL, 11.04 mmol) were added and the mixture was stirred for 5 min. Dimethylamine hydrochloride (0.750 g, 9.2 mmol) was then added at the same temperature and the mixture was stirred for 16 h at room temperature. After completion, the reaction mass was diluted with dichloromethane and washed with cold water. The organic layer was separated and dried over anhydrous sodium sulphate, filtered and concentrated to give crude product. The crude product was purified by silica gel column chromatography eluting with 2-3% methanol in dichloromethane. The desired fractions were concentrated to afford rac-(4bS,5R,6R,7S,7aR)-4b,5-dihydroxy-4-methoxy-N,N-dimethyl-7-phenyl-7a-(4-(trifluoromethyl)phenyl)-4b,6,7,7a-tetrahydro-5H-cyclopenta[4,5]furo[2,3-c]pyridine-6-carboxamide (10) as off white solid; Yield: 0.60 g, 64%; MS (ESI) m/z 515.22 $[M+1]^+$.

Synthesis of (4bS,5R,6S,7S,7aR)-6-((dimethylamino)methyl)-4-methoxy-7-phenyl-7a-(4-(trifluoromethyl)phenyl)-5,6,7,7a-tetrahydro-4bH-cyclopenta[4,5]furo[2,3-c]pyridine-4b,5-diol (Cpd. No. 107F)

To a solution rac-(4bS,5R,6R,7S,7aR)-4b,5-dihydroxy-4-methoxy-N,N-dimethyl-7-phenyl-7a-(4-(trifluoromethyl)phenyl)-4b,6,7,7a-tetrahydro-5H-cyclopenta[4,5]furo[2,3-c]pyridine-6-carboxamide (10, 0.6 g, 1.16 mmol) in tetrahydrofuran (12 mL), borane dimethylsulfide (1.10 ml, 11.66 mol) was added at 0° C. The reaction mixture was stirred at room temperature for 4.0 h. After completion, reaction mass was quenched with methanol at 0° C., then refluxed at 70° C. for 36 h The solvents were concentrated to give crude product. The crude product was purified by silica gel column chromatography eluting with 5-10% in methanol in dichloromethane. The desired fractions were concentrated to afford rac-(4bS,5R,6S,7S,7aR)-6-((dimethylamino)methyl)-4-methoxy-7-phenyl-7a-(4-(trifluoromethyl)phenyl)-5,6,7,7a-tetrahydro-4bH-cyclopenta[4,5]furo[2,3-c]pyridine-4b,5-diol as white solid; Yield: 0.310 g, 53% (racemic mixture), MS (ESI) m/z 501.27 $[M+1]^+$. The enantiomers were separated by chiral preparative HPLC [chiralpak IA (4.6×250)mm, 5] 0.1% diethyl amine in n-hexane/isopropanol 70/30 v/v; Peak 1 (42 mg), $[\alpha]_D$+34.1° (c 0.3, $CHCl_3$), $R_t$=7.587 min, ee=99.78%; $^1H$ NMR (400 MHz, DMSO-$d_6$) δ 8.05 (s, 1H), 7.96 (s, 1H), 7.42-7.37 (m, 4H), 7.08 (t, J=7.76 Hz, 2H), 7.00 (d, J=7.32 Hz, 2H), 5.70 (s, 1H), 5.14 (d, J=1.72 Hz, 1H), 4.51 (s, 1H), 3.88 (s, 3H), 3.79 (d, J=13.92 Hz, 1H), 3.20 (d, J=21.16 Hz 1H), 2.21 (s, 6H), 1.99 (s, 2H); Peak 2 (Cpd. No. 107F, 65 mg), $[\alpha]_D$−53.2° (c 0.27, $CHCl_3$), $R_t$=15.337 min, ee=99.60%; $^1H$ NMR (400 MHz, DMSO-$d_6$) δ 8.04 (s, 1H), 7.96 (s, 1H), 7.41-7.36 (m, 4H), 7.07 (t, J=7.76 Hz, 2H), 7.00 (d, J=7.32 Hz, 2H), 5.70 (s, 1H), 5.14 (s, 1H), 4.51 (d, J=3.16, 1H), 3.87 (s, 3H), 3.87 (d, J=14.04 Hz, 1H), 3.16 (s, 1H), 2.20 (s, 6H), 1.99 (d, J=9.4 Hz, 2H).

Example 108

(5aR,6S,7R,8R,8aS)-3-chloro-5a-(4-(difluoromethyl)phenyl)-7-((dimethylamino)methyl)-6-phenyl-5a,6,7,8-tetrahydro-8aH-cyclopenta[4,5]furo[3,2-b]pyridine-8,8a-diol (Cpd. No. 108F)

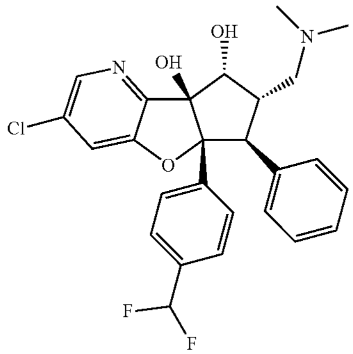

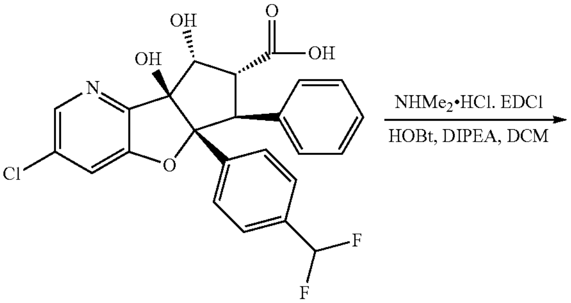

1

-continued

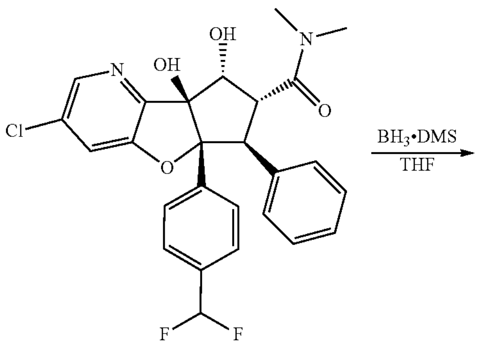

2

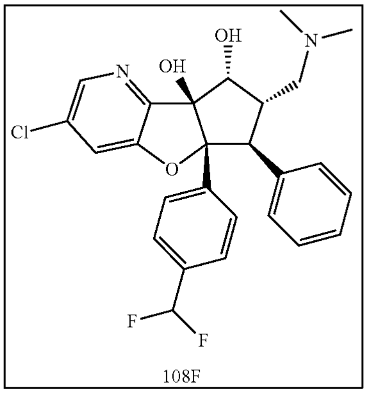

108F

Synthesis of rac-(5aR,6S,7R,8R,8aS)-3-chloro-5a-(4-(difluoromethyl)phenyl)-8,8a-dihydroxy-N,N-dimethyl-6-phenyl-5a,7,8,8a-tetrahydro-6H-cyclopenta[4,5]furo[3,2-b]pyridine-7-carboxamide (2)

To a solution of rac-(5aR,6S,7R,8R,8aS)-3-chloro-5a-(4-(difluoromethyl)phenyl)-8,8a-dihydroxy-6-phenyl-5a,7,8,8a-tetrahydro-6H-cyclopenta[4,5]furo[3,2-b]pyridine-7-carboxylic acid (1, 0.47 g, 1.00 mmol) in dichloromethane (15 mL) at 0° C., 1-ethyl-3-(3-dimethylaminopropyl)carbodiimide (0.576 g, 3.00 mmol), hydroxybenzotriazole (0.46 g, 3.00 mmol) and N,N-diisopropylethylamine (0.776 g, 6.00 mmol) were added and the mixture was stirred for 5 min. Dimethylamine hydrochloride (0.408 g, 5.0 mmol) was then added at the same temperature and the reaction was stirred for 16 h at room temperature. After completion, the reaction mass was diluted with dichloromethane and washed with water. The organic layer was separated and dried over anhydrous sodium sulphate, filtered and concentrated to give crude. The crude was purified by Combi-flash (4.0 g, RediSep) using 3% methanol in dichloromethane as eluent. The desired fractions were concentrated to afford rac-(5aR,6S,7R,8R,8aS)-3-chloro-5a-(4-(difluoromethyl)phenyl)-8,8a-dihydroxy-N,N-dimethyl-6-phenyl-5a,7,8,8a-tetrahydro-6H-cyclopenta[4,5]furo[3,2-b]pyridine-7-carboxamide (2) as light yellow solid. Yield: 0.35 g, 70%; MS (ESI) m/z 501.13 $[M+1]^+$.

Synthesis of (5aR,6S,7R,8R,8aS)-3-chloro-5a-(4-(difluoromethyl)phenyl)-7-((dimethylamino)methyl)-6-phenyl-5a,6,7,8-tetrahydro-8aH-cyclopenta[4,5]furo[3,2-b]pyridine-8,8a-diol (Cpd. No. 108F)

To a solution of rac-(5aR,6S,7R,8R,8aS) 3-chloro-5a-(4-(difluoromethyl)phenyl)-8,8a-dihydroxy-N,N-dimethyl-6-phenyl-5a,7,8,8a-tetrahydro-6H-cyclopenta[4,5]furo[3,2-b]pyridine-7-carboxamide (2, 0.35 g, 0.6796 mmol) in dry tetrahydrofuran (6.0 ml) at 0° C., borane dimethyl sulphide complex (0.66 mL, 6.796 mmol) was added at 0° C. The reaction mixture was heated at 60-70° C. for 5 h. After completion, the reaction mixture was quenched with methanol at 0° C. and again heated for 10 h at 60° C. The solvent was removed under reduced pressure and the residue was purified by Combi-flash (4.0 g, RediSep column) using 5% methanol in dichloromethane as eluent. The desired fraction were concentrated under reduced pressure to afford rac-(5aR,6S,7R,8R,8aS)-3-chloro-5a-(4-(difluoromethyl)phenyl)-7-((dimethylamino)methyl)-6-phenyl-5a,6,7,8-tetrahydro-8aH-cyclopenta[4,5]furo[3,2-b]pyridine-8,8a-diol as white solid. Yield: 80 mg, 23.53%; MS (ESI) m/z 487.15 $[M+1]^+$, UPLC: 98.5%. The enantiomers were separated by chiral preparative HPLC [chiralpak IA (4.6×250) mm]; n-Heaxane/EtOH=75/25(v/v); Peak 1 (Cpd. No. 108F, 2.2 mg); $R_t$=7.69, ee >99%; MS (ESI) m/z 487.22 $[M+1]^+$; UPLC: 98.6%; $^1$H NMR (400 MHz, DMSO-$d_6$) δ 8.16 (s, 1H), 7.60 (s, 1H), 7.31 (d, J=8.0 Hz, 2H), 7.22 (d, J=8.0 Hz, 2H), 7.11-6.96 (m, 5H), 6.82 (t, J=55.6 Hz, 1H), 6.00 (s, 1H), 4.47 (s, 1H), 3.89 (d, J=13.8 Hz, 1H), 2.73-2.61 (m, 2H), 2.12 (s, 6H), 2.00 (d, J=12.6 Hz, 1H), 1.90 (s, 1H). Peak-2 (2.1 mg); $R_t$=19.71, ee >95%; MS (ESI) m/z 487.23 $[M+1]^+$; UPLC: 99.0%. $^1$H NMR (400 MHz, DMSO-$d_6$) δ 8.16 (s, 1H), 7.61 (s, 1H), 7.31 (d, J=7.9 Hz, 2H), 7.22 (d, J=7.9 Hz, 2H), 7.06-6.99 (m, 5H), 6.83 (t, J=57.1 Hz, 1H), 6.02 (S, 1H), 4.47 (s, 1H), 3.89 (d, J=14.5 Hz, 1H), 2.70-2.61 (m, 2H), 2.23 (s, 6H), 2.02 (bs, 1H), 1.90 (s, 1H).

Example 109

(5aR,6S,7S,8R,8aS)-3-chloro-7-((dimethylamino)methyl)-6-phenyl-5a-(4-(trifluoromethyl)phenyl)-5a,6,7,8-tetrahydro-8aH-cyclopenta[4,5]furo[3,2-b]pyridine-8,8a-diol (Cpd. No. 109F)

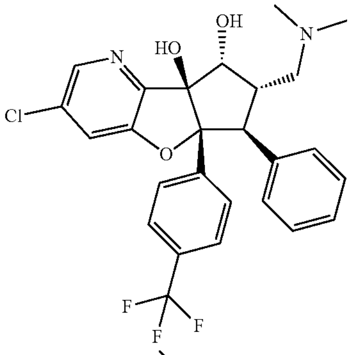

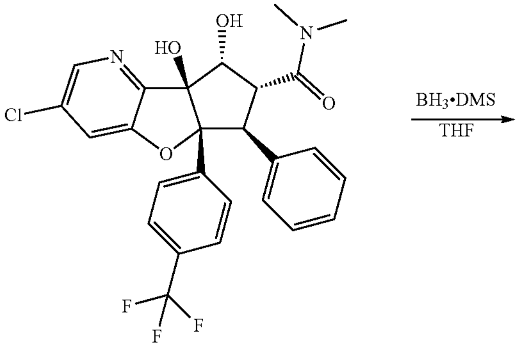

1

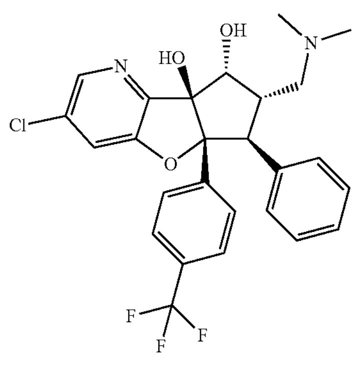

109F

Synthesis of (5aR,6S,7S,8R,8aS)-3-chloro-7-((dimethylamino)methyl)-6-phenyl-5a-(4-(trifluoromethyl)phenyl)-5a,6,7,8-tetrahydro-8aH-cyclopenta[4,5]furo[3,2-b]pyridine-8,8a-diol (Cpd. No. 109F)

To a solution of rac-(5aR,6S,7R,8R,8aS)-3-chloro-8,8a-dihydroxy-N,N-dimethyl-6-phenyl-5a-(4-(trifluoromethyl)phenyl)-5a,7,8,8a-tetrahydro-6H-cyclopenta[4,5]furo[3,2-b]pyridine-7-carboxamide (1, 0.20 g, 0.386 mmol) in tetrahydrofuran (5 mL), borane dimethyl sulphide (0.36 mL 3.86 mmol) was added at 0° C. and stirred the mixture for 3 h at 60° C. After completion, the reaction mixture was quenched with methanol (3.0 mL) and again heated for 10 h at 60° C. The reaction mixture was concentrated to give crude. The crude was purified by Combi-flash (12.0 g, RediSep column) using 20% methanol in dichloromethane as eluent. The desired fractions were concentrated to afford rac-(5aR,6S,7S,8R,8aS)-3-chloro-7-((dimethylamino)methyl)-6-phenyl-5a-(4-(trifluoromethyl)phenyl)-5a,6,7,8-tetrahydro-8aH-cyclopenta[4,5]furo[3,2-b]pyridine-8,8a-diol as off white solid. Yield: 32 mg, 16%. The enantiomers were separated by chiral preparative HPLC [chiralpak IA (4.6×250) mm] using n-Hexane/EtOH=70/30(v/v) mobile phase. Peak 1 (Cpd. No. 109F, 17 mg), $[\alpha]_D$−93.2° (c 0.25, $CHCl_3$), $R_t$=6.12, ee >99%. MS (ESI) m/z 505.19 $[M+1]^+$, UPLC: 97.06%. $^1H$ NMR (400 MHz, DMSO-$d_6$) &: 8.18 (d, J=1.8 Hz, 1H), 7.64 (d, J=1.8 Hz, 1H), 7.41-7.36 (m, 4H), 7.09-6.97 (m, 5H), 6.09 (s, 1H), 5.38 (bs, 1H), 4.47 (d, J=3.3 Hz, 1H), 3.92 (d, J=14.0 Hz, 1H), 3.21 (m, 1H), 2.66 (m, 1H), 2.26 (s, 6H), 2.05 (m, 1H). Peak 2 (11 mg), $[\alpha]_D$+99.1° (c 0.25, $CHCl_3$), $R_t$=12.18, ee >99%. MS (ESI) m/z 505.19 $[M+1]^+$, UPLC: 97.92%. $^1H$ NMR (400 MHz, DMSO-$d_6$) δ: 8.18 (d, J=1.84 Hz, 1H), 7.64 (d, J=1.8 Hz, 1H), 7.41-7.38 (m, 4H), 7.09-6.96 (m, 5H), 6.09 (s, 1H), 5.34 (bs, 1H), 4.47 (d, J=3.7 Hz, 1H), 3.92 (d, J=14.0 Hz, 1H), 3.23 (m, 1H), 2.61 (d, J=9.2 Hz, 1H), 2.29 (s, 6H), 2.02-2.00 (m, 1H).

Example 110

4-((4bS,5R,6S,7S,7aR)-4b,5-dihydroxy-4-methoxy-6-(morpholinomethyl)-7-phenyl-4b,5,6,7-tetrahydro-7aH-cyclopenta[4,5]furo[2,3-c]pyridin-7a-yl)benzonitrile (Cpd. No. 110F)

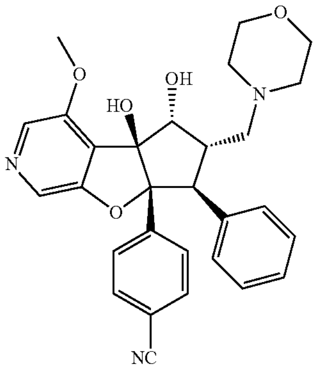

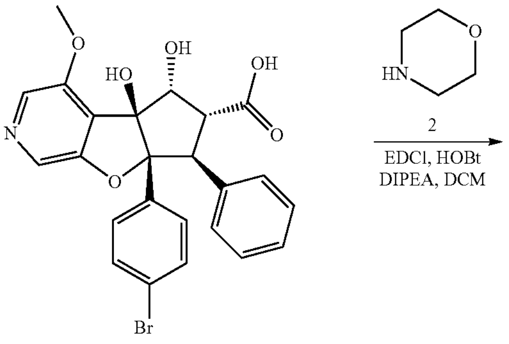

1

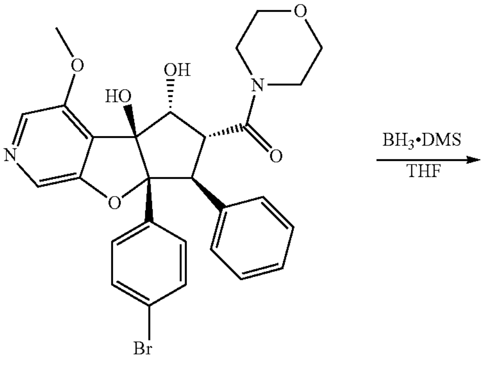

3

-continued

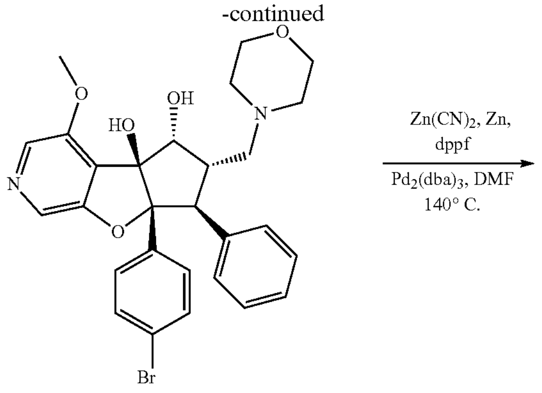

4

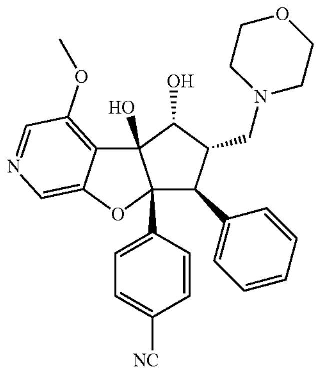

110F

Synthesis of rac-((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)(morpholino)methanone (3)

To a solution of rac-(4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylic acid (1, 1.2 g, 2.40 mmol) in dichloromethane (12 mL), 1-ethyl-3-(3-dimethylaminopropyl)carbodiimide hydrochloride (1.37 g, 7.22 mmol), 1-hydroxybenzotriazole (0.97 g, 7.22 mmol) and N,N-diisopropylethylamine (2.21 mL, 12.12 mmol) were added at 0° C. and stirred the mixture for 5 minutes. Morpholine (2, 0.63 g, 7.20 mmol) was added at same temperature and the mixture was stirred for 16 h at 40° C. After completion, reaction mass was diluted with dichloromethane and washed with cold water. The organic layer was separated and dried over anhydrous sodium sulphate, filtered and concentrated to give crude. The crude was purified by silica gel column chromatography eluting with 0-4% methanol in dichloromethane. The desired fractions were concentrated to afford rac-((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)(morpholino)methanone (3) as white solid. Yield: 0.91 g, 66%; MS (ESI) m/z 567 $[M+1]^+$.

Synthesis of rac-(4bS,5R,6S,7S,7aR)-7a-(4-bromophenyl)-4-methoxy-6-(morpholinomethyl)-7-phenyl-5,6,7,7a-tetrahydro-4bH-cyclopenta[4,5]furo[2,3-c]pyridine-4b, 5-diol (4)

To a solution of rac-((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)(morpholino)methanone (3, 0.8 g, 1.41 mmol) in dry tetrahydrofuran (20 mL) at 0° C., borane dimethyl sulphide complex (1.1 ml, 14.2 mmol) was added. The resulting mixture was stirred for 16 h at room temperature. After completion, the reaction mass was quenched with methanol at 0° C. and refluxed at 80° C. for 6 h. After completion, the reaction mass was concentrated to give crude. The crude was purified by silica gel column chromatography using 0-5% methanol in dichloromethane as eluent. The desired fractions were concentrated to rac-(4bS,5R,6S,7S,7aR)-7a-(4-bromophenyl)-4-methoxy-6-(morpholinomethyl)-7-phenyl-5,6,7,7a-tetrahydro-4bH-cyclopenta[4,5]furo[2,3-c]pyridine-4b,5-diol (4) as white solid. Yield: 0.65 g, 80%; MS (ESI) m/z 553.17 $[M+1]^+$.

Synthesis of 4-((4bS,5R,6S,7S,7aR)-4b,5-dihydroxy-4-methoxy-6-(morpholinomethyl)-7-phenyl-4b,5,6,7-tetrahydro-7aH-cyclopenta[4,5]furo[2,3-c]pyridin-7a-yl)benzonitrile (Cpd. No. 110F)

To a solution of rac-(4bS,5R,6S,7S,7aR)-7a-(4-bromophenyl)-4-methoxy-6-(morpholinomethyl)-7-phenyl-5,6,7,7a-tetrahydro-4bH-cyclopenta[4,5]furo[2,3-c]pyridine-4b,5-diol (4, 0.6 g, 1.00 mmol) in N,N-dimethylformamide (10 mL), zinc cyanide (0.76 g, 6.52 mmol) and zinc dust (0.07 g, 0.12 mmol) were added at room temperature and the reaction mixture was degassed with argon for 15 min. 1,1'-Bis(diphenylphosphino)ferrocene (0.006 g, 0.02 mmol) and tris(dibenzylideneacetone)dipalladium (0.003 g, 0.003 mmol) were added to the reaction, degassed for additional 5 min and heated the mixture at 140° C. for 3 h. After completion, the reaction mass was diluted with ethyl acetate and washed with cold water. The organic layer was separated and dried over sodium sulphate, filtered and concentrated to give crude. The crude was purified by silica gel column chromatography using 3-4% methanol in dichloromethane as eluent. The desired fractions were concentrated to afford rac-4-((4bS,5R,6S,7S,7aR)-4b,5-dihydroxy-4-methoxy-6-(morpholinomethyl)-7-phenyl-4b,5,6,7-tetrahydro-7aH-cyclopenta[4,5]furo[2,3-c]pyridin-7a-yl)benzonitrile as white solid. Yield: 0.30 g, 55% (racemic mixture). The enantiomers were separated by chiral preparative chiral HPLC [chiralpak IA (4.6×250) mm, 5μ], n-Hexane/EtOH=30/70 v/v. Peak-1 (Cpd. No. 110F, 69 mg), $[\alpha]_D$−4.0° (c 0.45, $CHCl_3$), $R_t$=5.548 min, ee >99.88%, $^1$H NMR (400 MHz, DMSO-$d_6$) δ 8.04 (s, 1H), 7.96 (s, 1H), 7.49 (d, J=7.2 Hz, 2H), 7.38 (d, J=8.0 Hz 2H), 7.09-7.00 (m, 5H), 5.70 (s, 1H), 5.10 (d, J=4.4 Hz, 1H), 4.50 (s, 1H), 3.88 (s, 3H), 3.81 (d, J=14.0 Hz, 1H), 3.61 (bs, 4H), 3.31 (bs, 1H), 2.62-2.50 (m, 4H), 2.33 (bs, 1H), 2.09 (d, J=12.0 Hz, 1H); MS (ESI) m/z 458.31 $[M+1]^+$; Peak-2 (60 mg), $[\alpha]_D$+4.3° (c 0.28, $CHCl_3$), $R_t$=8.285 min, ee >95.22%, $^1$H NMR (400 MHz, DMSO-d) δ 8.04 (s, 1H), 7.96 (s, 1H), 7.49 (d, J=7.2 Hz, 2H), 7.38 (d, J=8.0 Hz 2H), 7.09-7.00 (m, 5H), 5.70 (s, 1H), 5.10 (d, J=4.4 Hz, 1H), 4.50 (s, 1H), 3.88 (s, 3H), 3.81 (d, J=14.0 Hz, 1H), 3.61 (bs, 4H), 3.31(bs, 1H), 2.62-2.50 (m, 4H), 2.33 (bs, 1H), 2.09 (d, J=12.0 Hz, 1H); MS (ESI) m/z 458.31 $[M+1]^+$.

Example 111

Rac-(4bS,5R,6R,7S,7aR)-7a-(4-bromophenyl)-N-(2,2-difluoroethyl)-4b,5-dihydroxy-4-methoxy-N-methyl-7-phenyl-4b,6,7,7a-tetrahydro-5H-cyclopenta[4,5]furo[2,3-c]pyridine-6-carboxamide (Cpd. No. 111F)

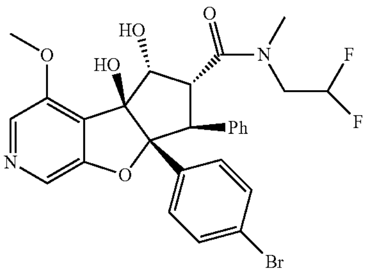

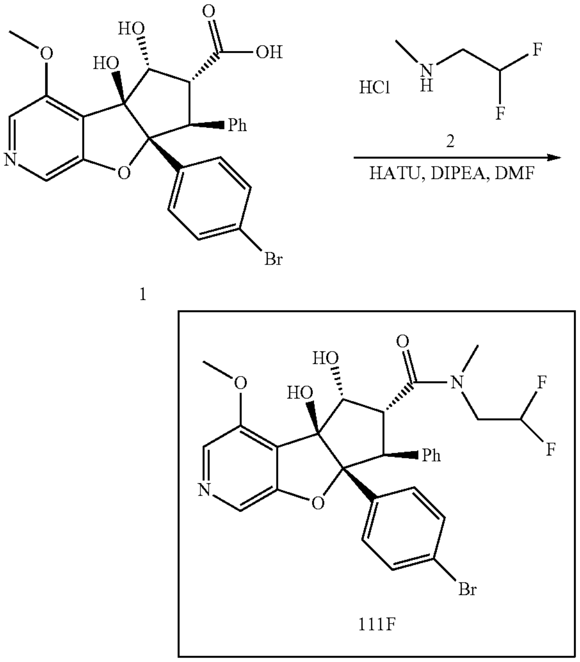

1

111F

Synthesis of rac-(4bS,5R,6R,7S,7aR)-7a-(4-bromophenyl)-N-(2,2-difluoroethyl)-4b,5-dihydroxy-4-methoxy-N-methyl-7-phenyl-4b,6,7,7a-tetrahydro-5H-cyclopenta[4,5]furo[2,3-c]pyridine-6-carboxamide (Cpd. No. 111F)

To a solution of rac-(4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylic acid (1, 1.0 g, 2.0 mmol) in N,N-dimethylformamide (20 mL), 1-[Bis(dimethylamino)methylene]-1H-1,2,3-triazolo[4,5-b]pyridinium 3-oxid hexafluorophosphate (2.29 g, 6.0 mmol) and N,N-diisopropylethylamine (1.8 ml, 10.0 mmol) were added at 0° C. and stirred the mixture for 5 min. 2,2-Difluoroethan-1-amine hydrochloride (2, 0.39 g, 3.0 mmol) was then added and the reaction mixture was stirred for 4 h at room temperature. After completion, reaction mass was diluted with ethylacetate and washed with cold water. The organic layer was dried over anhydrous sodium sulphate, filtered and concentrated to give crude. The crude was purified by Combi-flash (12 g, RediSep column) using 3% methanol in dichloromethane as eluent. Further purification was done on reverse phase preperative HPLC. The desired fractions were lyophilized to afford rac-(4bS,5R,6R,7S,7aR)-7a-(4-bromophenyl)-N-(2,2-difluoroethyl)-4b,5-dihydroxy-4-methoxy-N-methyl-7-phenyl-4b,6,7,7a-tetrahydro-5H-cyclopenta[4,5]furo[2,3-c]pyridine-6-carboxamide (Cpd. No. 111F) as brown solid. Yield: 0.6 g, 54%; MS (ESI) m/z 575.25 $[M+1]^+$, UPLC: 99.64%; $^1$H NMR (400 MHz, DMSO-$d_6$) δ 8.10 (s, 1H), 8.00 (s, 1H), 7.20 (d, J=8.5 Hz, 2H), 7.09-7.01 (m, 4H), 6.97 (d, J=7.01 Hz, 1H), 6.91 (d, J=7.4 Hz, 2H), 6.56-6.29 (m, 1H), 5.74 (s, 1H), 5.22 (d, J=5.5 Hz, 1H), 4.79 (t, J=5.4 Hz, 1H), 4.45 (d, J=10.0 Hz, 1H), 4.24 (dd, J=5.0 Hz, 13.6 Hz, 1H), 3.80 (s, 3H), 3.68-3.56 (m, 2H), 3.38 (s, 3H).

Example 112

4-((4bS,5R,6S,7S,7aR)-6-(((2,2-difluoroethyl)(methyl)amino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 121F)

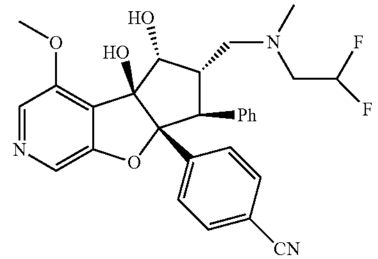

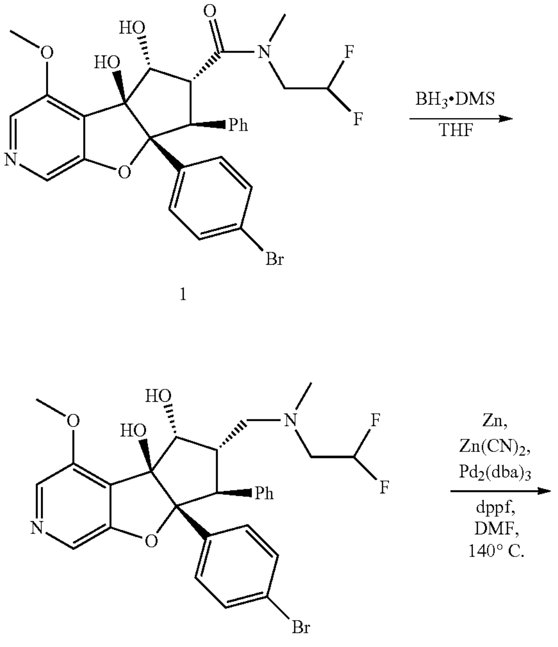

1

2

-continued

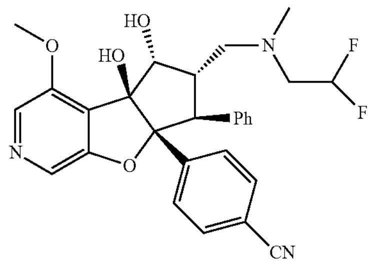

112F

Synthesis of rac-(4bS,5R,6S,7S,7aR)-7a-(4-bromophenyl)-6-(((2,2-difluoroethyl)(methyl)amino)methyl)-4-methoxy-7-phenyl-5,6,7,7a-tetrahydro-4bH-cyclopenta[4,5]furo[2,3-c]pyridine-4b,5-diol (2)

To a solution of rac-(4bS,5R,6R,7S,7aR)-7a-(4-bromophenyl)-N-(2,2-difluoroethyl)-4b,5-dihydroxy-4-methoxy-N-methyl-7-phenyl-4b,6,7,7a-tetrahydro-5H-cyclopenta[4,5]furo[2,3-c]pyridine-6-carboxamide (1, 0.6 g, 1.0 mmol) in tetrahydrofuran, borane dimethylsulfide (1.0 ml, 10.0 mmol) was added at 0° C. The reaction mixture was heated at 60° C. for 5 h. After completion, reaction mass was quenched with methanol at 0° C. and then heated at 80° C. for 6 h. The solvents were concentrated and compound was dried to afford rac-(4bS,5R,6S,7S,7aR)-7a-(4-bromophenyl)-6-(((2,2-difluoroethyl)(methyl)amino)methyl)-4-methoxy-7-phenyl-5,6,7,7a-tetrahydro-4bH-cyclopenta[4,5]furo[2,3-c]pyridine-4b,5-diol (2) as brown solid. Yield: 0.55 g, 95%; MS (ESI) m/z 559.57[M−1]$^-$, UPLC: 89.48%.

Synthesis of 4-((4bS,5R,6S,7S,7aR)-6-(((2,2-difluoroethyl)(methyl)amino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 112F)

To a mixture of rac-(4bS,5R,6S,7S,7aR)-7a-(4-bromophenyl)-6-(((2,2-difluoroethyl)(methyl)amino)methyl)-4-methoxy-7-phenyl-5,6,7,7a-tetrahydro-4bH-cyclopenta[4,5]furo[2,3-c]pyridine-4b,5-diol (2, 0.55 g, 0.98 mmol) in N,N-dimethylformamide (5.0 mL) at room temperature, zinc cyanide (690 mg, 5.89 mmol) and zinc dust (13 mg, 0.19 mmol) were added at room temperature and degassed the mixture with argon for 15 min. 1,1'-Bis(diphenylphosphino)ferrocene (16.0 mg, 0.029 mmol) and tris(dibenzylideneacetone)dipalladium (27.0 mg, 0.029 mmol) were added to the reaction mixture and degassing was continued for another 5 min. The reaction mixture was heated at 140° C. for 6 h. After completion, the reaction was cooled to room temperature and passed through celite bed. The filtrate was concentrated and treated with ice-cold water, the solid precipitated was filtered. The solid obtained was purified by Combi-flash (12 g, RediSep column) using 30% ethyl acetate in hexanes as eluent. The crude was submitted for reverse phase prep HPLC. The desired fractions were lyophilized to afford rac-4-((4bS,5R,6S,7S,7aR)-6-(((2,2-difluoroethyl)(methyl)amino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile as white solid. The enantiomers were separated by chiral preparative HPLC [chiralpak IB (4.6×250) mm] using 0.1% TEA in n-Hexane/IPA=80/20(v/v) Mobile phase. Yield: 0.12 g, 23%, Peak 1 (49 mg), $[\alpha]_D$+48.8° (c 0.24, $CHCl_3$), $R_t$=9.414 min, ee >99%. MS (ESI) m/z 508.29 [M+1]$^+$; UPLC: 99.36%. $^1$H NMR (400 MHz, DMSO-$d_6$) δ 8.08 (s, 1H), 7.95 (s, 1H), 7.47 (d, J=8.6 Hz, 2H), 7.37 (d, J=8.5 Hz, 2H), 7.09-6.98 (m, 5H), 6.33-6.06 (m, 1H), 4.56 (d, J=3.5 Hz, 1H), 3.86 (s, 3H), 3.75 (d, J=14.0 Hz, 1H), 3.31-2.87 (m, 2H), 2.66-2.60 (m, 3H), 2.53 (s, 3H). Peak 2 (Cpd. No. 112F, 49 mg), $[\alpha]_D$−10.8° (c 0.24, $CHCl_3$), $R_t$=14.357 min, ee >99%. MS (ESI) m/z 508.29 [M+1]$^+$; UPLC: 96.14%. $^1$H NMR (400 MHz, DMSO-$d_6$) δ 8.09 (s, 1H), 8.02 (s, 1H), 7.51 (d, J=7.8 Hz, 2H), 7.40 (d, J=7.1 Hz, 2H), 7.09-7.01 (m, 5H), 6.31-5.17 (m, 1H), 4.53 (d, J=7.0 Hz, 1H), 3.90 (s, 3H), 3.79 (d, J=13.8, 1H), 3.15-2.95 (m, 2H), 2.53 (s, 3H), 2.40 (s, 3H).

Example 113

4-((4bS,5R,6S,7S,7aR)-6-((4,4-difluoropiperidin-1-yl)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 113F)

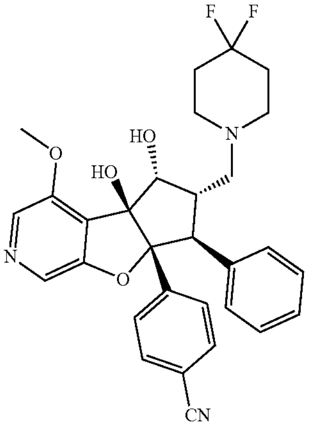

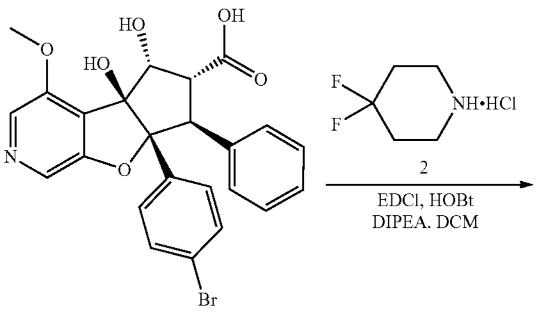

1

-continued

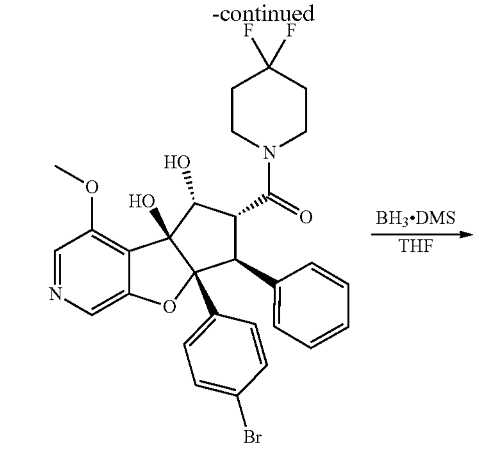

3

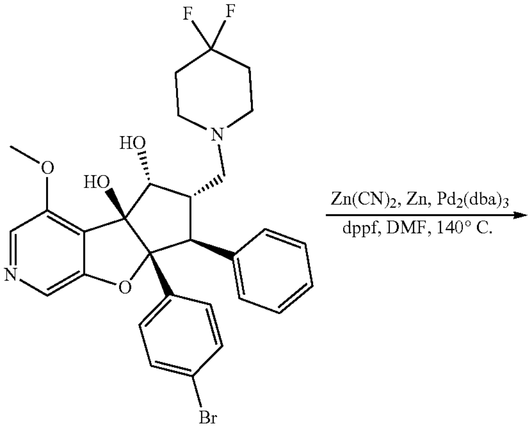

4

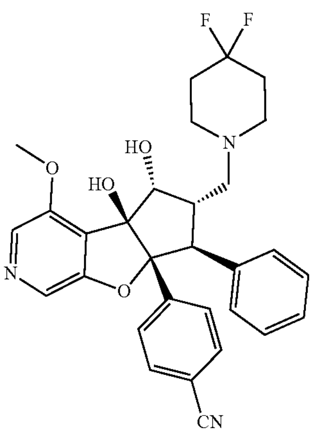

113F

Synthesis of rac-((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)(4,4-difluoropiperidin-1-yl)methanone (3)

To a solution of rac-(4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylic acid (1, 0.9 g, 1.8 mmol) in dichloromethane (10 mL), 1-ethyl-3-(3-dimethylaminopropyl)carbodiimide hydrochloride (1.03 g, 5.41 mmol), 1-hydroxybenzotriazole (0.72 g, 5.41 mmol) and N,N-diisopropylethylamine (1.65 mL, 9.12 mmol) were added at 0° C. and stirred for 5 minutes before 4,4-difluoropiperidine hydrochloride (2, 1.4 g, 9.12 mmol) was added at the same temperature and the mixture was stirred for 16 h at RT. After completion, the reaction mass was diluted with dichloromethane and washed with cold water. The organic layer was separated and dried over anhydrous sodium sulphate, filtered and concentrated to give crude product. The crude product was purified by silica gel column chromatography eluting with 0-4% methanol in dichloromethane. The desired fractions were concentrated to afford rac-((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)(4,4-difluoropiperidin-1-yl)methanone (3) as white solid. Yield: 0.67 g, 67%; MS (ESI) m/z 601.01[M+1]$^+$.

Synthesis of rac-(4bS,5R,6S,7S,7aR)-7a-(4-bromophenyl)-6-((4,4-difluoropiperidin-1-yl)methyl)-4-methoxy-7-phenyl-5,6,7,7a-tetrahydro-4bH-cyclopenta[4,5]furo[2,3-c]pyridine-4b, 5-diol (4)

To a solution of rac-((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)(4,4-difluoropiperidin-1-yl)methanone (3, 0.6 g, 1.00 mmol) in dry tetrahydrofuran (25 mL) at 0° C., borane dimethyl sulphide complex (1.0 ml, 10.2 mmol) was added. The resulting mixture was stirred for 16 h at room temperature. After completion, the reaction mass was quenched with methanol at 0° C. and reflux at 80° C. for 6 h. After completion, the reaction mass was concentrated to give crude product. The crude product was purified by silica gel column chromatography using 1-5% methanol in dichloromethane as eluent. The desired fractions were concentrated to rac-(4bS,5R,6S,7S,7aR)-7a-(4-bromophenyl)-6-((4,4-difluoropiperidin-1-yl)methyl)-4-methoxy-7-phenyl-5,6,7,7a-tetrahydro-4bH-cyclopenta[4,5]furo[2,3-c]pyridine-4b,5-diol (4) as white solid. Yield: 0.560 g, 95.7%; MS (ESI) m/z 587.17[M+1]$^+$.

Synthesis of 4-((4bS,5R,6S,7S,7aR)-6-((4,4-difluoropiperidin-1-yl)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 113F)

To a solution of rac-(4bS,5R,6S,7S,7aR)-7a-(4-bromophenyl)-6-((4,4-difluoropiperidin-1-yl)methyl)-4-methoxy-7-phenyl-5,6,7,7a-tetrahydro-4bH-cyclopenta[4,5]furo[2,3-c]pyridine-4b,5-diol (4, 0.50 g, 0.85 mmol) in N,N-dimethylformamide (10 mL), zinc cyanide (0.59 g, 5.12 mmol) and zinc dust (0.006 g, 0.10 mmol) were added at room temperature and the reaction mixture was degassed with argon for 15 min. 1,1'-Bis(diphenylphosphino)ferrocene (0.009 g, 0.0025 mmol) and tris(dibenzylideneacetone) dipalladium (0.023 g, 0.025 mmol) were added to the reaction, degassed for additional 5 min and heated the mixture at 140° C. for 4 h. After completion, the reaction mass was diluted with ethyl acetate and washed with cold water. The organic layer was separated and dried over anhydrous sodium sulphate, filtered and concentrated to give crude. The crude product was purified by silica gel column chromatography using 2-4% methanol in dichloromethane as eluent. The desired fractions were concentrated to afford rac-4-((4bS,5R,6S,7S,7aR)-6-((4,4-difluoropiperidin-1-yl)

methyl)-4b,5-dihydroxy-4-methoxy-7-phenyl-4b,5,6,7-tetrahydro-7aH-cyclopenta[4,5]furo[2,3-c]pyridin-7a-yl)benzonitrile as white solid. Yield: 0.325 g, 71% (racemic mixture). The enantiomers were separated by chiral preparative HPLC [chiralpak IC (4.6×250)mm, 5μ] in isocratic n-hexane/isopropanol 80/20 v/v. Peak-1 (79 mg), $[\alpha]_D$+10.0° (c 0.27, $CHCl_3$), $R_t$=10.477 min, ee=99.90%; $^1H$ NMR (400 MHz, DMSO-$d_6$) δ 8.04 (s, 1H), 7.97 (s, 1H), 7.49 (d, J=7.2 Hz, 2H), 7.39 (d, J=8.4 Hz, 2H), 7.09-6.98 (m, 5H), 5.73 (s, 1H), 5.08 (d, J=5.6 Hz, 1H), 4.51 (s, 1H), 3.88 (s, 3H), 3.80 (d, J=14.0 Hz, 1H), 3.32 (s, 1H), 2.70-2.49 (m, 5H), 2.15 (d, J=9.6 Hz, 1H), 1.97 (bs, 4H); MS (ESI) m/z 458.3[M+1]$^+$; Peak-2 (Cpd. No. 113F, 74 mg), $[\alpha]_D$−4.4° (c 0.27, $CHCl_3$), $R_t$=13.904 min, ee=99.42%; $^1H$ NMR (400 MHz, DMSO-$d_6$) δ 8.04 (s, 1H), 7.97 (s, 1H), 7.49 (d, J=7.2 Hz, 2H), 7.39 (d, J=8.4 Hz, 2H), 7.09-6.98 (m, 5H), 5.73 (s, 1H), 5.08 (d, J=5.6 Hz, 1H), 4.51 (s, 1H), 3.87 (s, 3H), 3.80 (d, J=14.0 Hz, 1H), 3.32 (s, 1H), 2.70-2.49 (m, 5H), 2.15 (d, J=9.6 Hz, 1H), 1.97 (bs, 4H); MS (ESI) m/z 458.31[M+1]$^+$.

Example 114

Rac-((1R,5S)-8-azabicyclo[3.2.1]octan-8-yl)((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)methanone (Cpd. No. 114F)

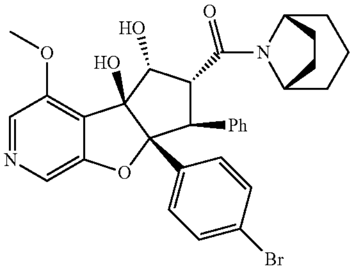

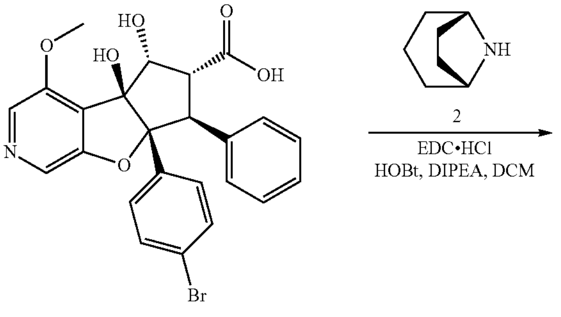

1

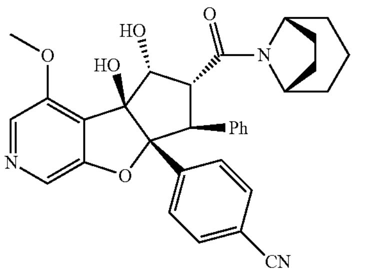

114F

Synthesis of rac-((1R,5S)-8-azabicyclo[3.2.1]octan-8-yl)((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)methanone (Cpd. No. 114F)

To a solution of rac-(4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylic acid (1, 0.05 g, 0.10 mmol) in dichloromethane (5.0 mL), 1-ethyl-3-(3-dimethylaminopropyl) carbodiimide (0.043 g, 0.32 mmol), hydroxybenzotriazole (0.04 g, 0.3 mmol) and N,N-diisopropylethylamine (0.09 mL, 0.5 mmol) were added at 0° C. and stirred the mixture for 5 min. 8-Azabicyclo[3.2.1]octane (0.016 g, 0.15 mmol) was then added at same temperature and the reaction was stirred at room temperature for 5 h. After completion, reaction mass was diluted with dichloromethane (20 mL) and washed with cold water. The organic layer was separated and dried over anhydrous sodium sulphate, filtered and concentrated under reduced pressure. The crude was purified by reverse phase HPLC to afford rac-((1R,5S)-8-azabicyclo[3.2.1]octan-8-yl)((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)methanone (Cpd. No. 114F) as white solid. Yield: 23.0 mg, 43%. MS (ESI) m/z 591.18[M+1]$^+$; UPLC 99.6%; $^1H$ NMR (400 MHz, DMSO-$d_6$, at High temperature VT (373K) δ: 8.11 (s, 1H), 8.01 (s, 1H), 7.21 (d, J=8.6 Hz, 2H), 7.11 (d, J=8.1 Hz, 2H), 7.05-6.94 (m, 5H), 4.70 (d, J=4.8 Hz, 1H), 4.52 (d, J=13.2 Hz, 1H), 4.09-4.05 (m, 1H), 3.92 (s, 3H), 2.01-1.78 (m, 8H), 1.60-1.55 (m, 4H).

Example 115

4-((4bS,5R,6S,7S,7aR)-6-(((2,2-difluoroethyl)amino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 115F)

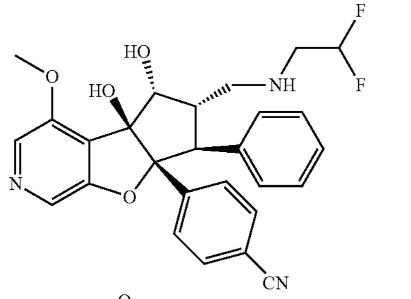

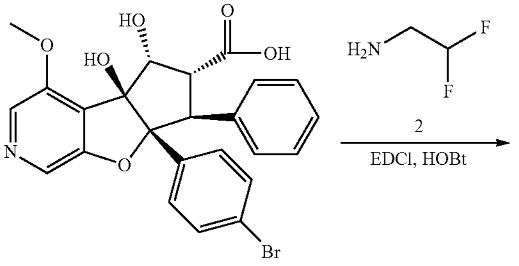

1

-continued

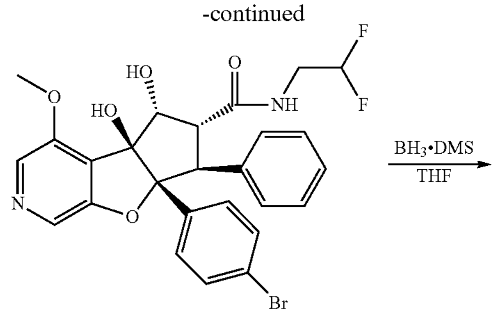

3

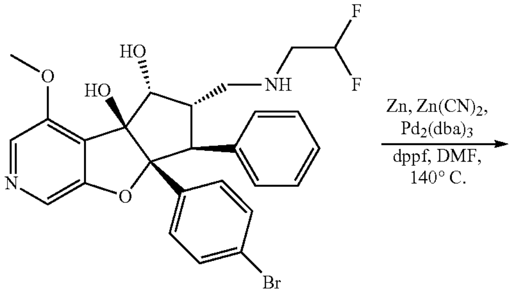

4

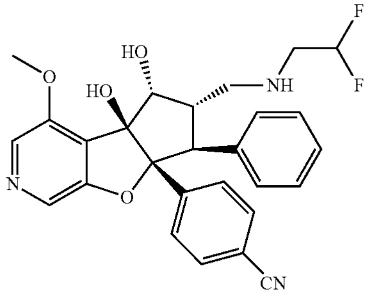

115F

Synthesis of rac-(4bS,5R,6R,7S,7aR)-7a-(4-bromophenyl)-N-(2,2-difluoroethyl)-4b,5-dihydroxy-4-methoxy-7-phenyl-4b,6,7,7a-tetrahydro-5H-cyclopenta[4,5]furo[2,3-c]pyridine-6-carboxamide (3)

To a solution of rac-(4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylic acid (1, 1.00 g, 2.01 mmol) in dichloromethane (20 mL) at 0° C., 1-ethyl-3-(3-dimethylaminopropyl) carbodiimide (1.15 g, 6.03 mmol), hydroxybenzotriazole (0.923 g, 6.03 mmol) and N,N-diisopropylethylamine (1.81 g, 14.08 mmol) were added and the mixture was stirred for 5 min. 2,2-difluoroethane-1-amine (2, 0.814 g, 10.06 mmol) was then added at the same temperature and the reaction was stirred for 16 h at room temperature. After completion, the reaction mass was diluted with dichloromethane and washed with cold water. The organic layer was separated and dried over anhydrous sodium sulphate, filtered and concentrated to give crude. The crude was purified by silica gel column chromatography using 0-3% methanol in dichloromethane as eluent. The desired fractions were concentrated to afford rac-(4bS,5R,6R,7S,7aR)-7a-(4-bromophenyl)-N-(2,2-difluoroethyl)-4b,5-dihydroxy-4-methoxy-7-phenyl-4b,6,7,7a-tetrahydro-5H-cyclopenta[4,5]furo[2,3-c]pyridine-6-carboxamide (3) as white solid. Yield: 1.00 g, 83%; MS (ESI) m/z 561.14[M+1]$^+$.

Synthesis of rac-(4bS,5R,6S,7S,7aR)-7a-(4-bromophenyl)-6-(((2,2-difluoroethyl)amino)methyl)-4-methoxy-7-phenyl-5,6,7,7a-tetrahydro-4bH-cyclopenta[4,5]furo[2,3-c]pyridine-4b, 5-diol (4)

To a solution of rac-(4bS,5R,6R,7S,7aR)-7a-(4-bromophenyl)-N-(2,2-difluoroethyl)-4b,5-dihydroxy-4-methoxy-7-phenyl-4b,6,7,7a-tetrahydro-5H-cyclopenta[4,5]furo[2,3-c]pyridine-6-carboxamide (3, 1.0 g, 1.78 mmol) in dry tetrahydrofuran (60 ml) at 0° C., borane dimethyl sulphide complex (1.35 g, 70.85 mmol) was added drop wise over a period of 5 min. The reaction mass was slowly brought to room temperature and stirred for additional 16 h. After completion, the reaction mass was quenched with methanol at 0° C. and heated to reflux for 5 h. After completion, solvent was removed under reduced pressure and the residue was purified over a plug of silica gel eluting the compound with 5% methanol in dichloromethane. The desired fractions were concentrated under reduced pressure to afford rac-(4bS,5R,6S,7S,7aR)-7a-(4-bromophenyl)-6-(((2,2-difluoroethyl)amino)methyl)-4-methoxy-7-phenyl-5,6,7,7a-tetrahydro-4bH-cyclopenta[4,5]furo[2,3-c]pyridine-4b,5-diol (4) as white solid. Yield: 0.8 g, 82%; MS (ESI) m/z 547.20[M+1]$^+$.

Synthesis of 4-((4bS,5R,6S,7S,7aR)-6-(((2,2-difluoroethyl)amino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 115F)

To a solution of rac-(4bS,5R,6S,7S,7aR)-7a-(4-bromophenyl)-6-(((2,2-difluoroethyl)amino)methyl)-4-methoxy-7-phenyl-5,6,7,7a-tetrahydro-4bcyclopenta[4,5]furo[2,3-c]pyridine-4b,5-diol (4, 0.6 g, 1.09 mmol) in N,N-dimethylformamide (10 mL), zinc cyanide (0.771 g, 6.59 mmol) and zinc dust (0.0085 g, 0.131 mmol) were added at room temperature and the reaction mixture was degassed with argon for 15 min. 1,1'-Bis(diphenylphosphino)ferrocene (0.012 g, 0.021 mmol) and tris(dibenzylideneacetone) dipalladium (0.030 g, 0.032 mmol) were added to the reaction, degassed for additional 5 min and mixture was heated at 140° C. for 8 h. After completion, the reaction mass was diluted with ethyl acetate and washed with cold water. The organic layer was separated and dried over anhydrous sodium sulphate, filtered and concentrated to give crude. The crude was purified by silica gel column chromatography using 2-3% methanol in dichloromethane as eluent. The desired fractions were concentrated to afford rac-4-((4bS,5R,6S,7S,7aR)-6-(((2,2-difluoroethyl)amino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile as white solid. Yield: 0.230 g, 42% (racemic); MS (ESI) m/z 494.32[M+1]$^+$. The enantiomers were separated by chiral HPLC [Chiralpak IA (4.6×250) mm, 5μ] in hexane/IPA=20/80 (v/v). Peak 1 (Cpd. No. 115F, 113 mg), $[\alpha]_D$+48.6° (c 0.283, $CHCl_3$), $R_t$=6.441 min, ee: 99.66%; MS (ESI) m/z 494.32[M+1]$^+$. $^1$H NMR (400 MHz, DMSO-$d_6$) δ 8.05 (s, 1H), 7.98 (s, 1H), 7.49 (d, J=8.36 Hz, 2H), 7.37 (d, J=8.36 Hz, 2H), 7.08-7.05 (m, 3H), 7.00 (d, J=7.28 Hz, 2H), 6.10-5.70 (m, 1H), 5.70 (s, 1H), 5.19 (d, J=5.16 Hz, 1H), 4.54 (s, 1H), 3.89 (s, 3H), 3.75 (d, J=14.24 Hz, 1H), 3.14 (d, J=12.56 Hz, 1H), 2.88 (t, J=15.42 Hz, 2H), 2.69 (t, J=1.84 Hz, 1H), 2.54 (m, 1H). Peak-2 (117 mg), $[\alpha]_D$−48.9° (c 0.35, $CHCl_3$), $R_t$=19.449 min, ee:99.67%; MS (ESI) m/z 494.32$[M+1]^+$. $^1H$ NMR (400 MHz, DMSO-$d_6$) δ 8.06 (s, 1H), 7.98 (s, 1H), 7.49 (d, J=8.36 Hz, 2H), 7.37 (d, J=8.36 Hz, 2H), 7.08-7.05 (m, 3H), 7.00 (d, J=7.28 Hz, 2H), 6.11-5.70 (m, 1H), 5.70 (s, 1H), 5.19 (d, J=5.16 Hz, 1H), 4.54 (s, 1H), 3.89 (s, 3H), 3.75 (d, J=14.24 Hz, 1H), 3.14 (d, J=12.56 Hz, 1H), 2.88 (t, J=15.42 Hz, 2H), 2.69 (t, J=11.84 Hz, 1H), 2.54 (m, 1H).

Example 116

Rac-(4bS,5R,6R,7S,7aR)-7a-(4-bromophenyl)-N-(2,2-difluoroethyl)-4b,5-dihydroxy-4-methoxy-7-phenyl-4b,6,7,7a-tetrahydro-5H-cyclopenta[4,5]furo[2,3-c]pyridine-6-carboxamide (Cpd. No. 1161F)

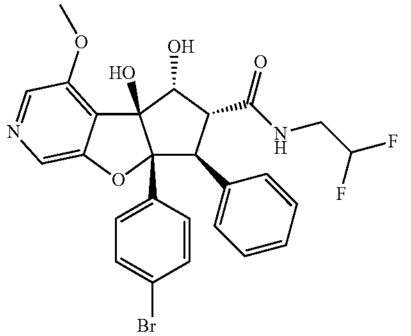

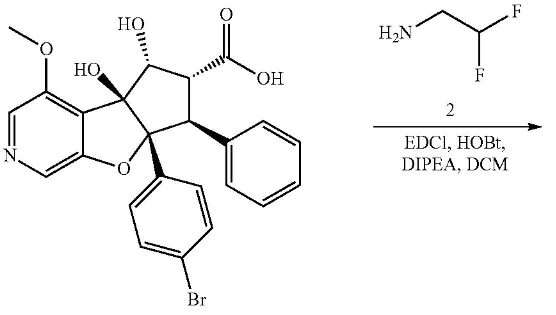

1

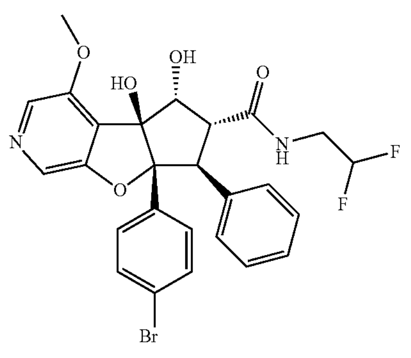

116F

Synthesis of rac-(4aR,5S,6R,7R,7aS)-4a-(4-bromophenyl)-7,7a-dihydroxy-2-(4-methoxybenzyl)-N,N-dimethyl-5-phenyl-2,4a,5,6,7,7a-hexahydrocyclopenta[4,5]furo[3,2-c]pyrazole-6-carboxamide (Cpd. No. 116F)

To a solution of rac-(4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylic acid (1, 0.07 g, 0.14 mmol) in dichloromethane (10 mL), 1-ethyl-3-(3-dimethylaminopropyl)carbodiimide hydrochloride (0.08 g, 0.42 mmol), 1-hydroxybenzotriazole (0.064 g, 0.42 mmol) and N,N-diisopropylethylamine (0.2 mL, 0.98 mmol) were added at 0° C. and stirred the mixture for 5 min. 2,2-difluoroethane-1-amine (0.057 g, 0.70 mmol) was then added at same temperature and the mixture was stirred for 16 h at 40° C. After completion, reaction mass was diluted with dichloromethane and washed with cold water. The organic layer was separated and dried over sodium sulphate, filtered and concentrated to give crude. The crude was purified by silica gel column chromatography eluting with 3% methanol in dichloromethane. The desired fractions were concentrated to afford rac-(4bS,5R,6R,7S,7aR)-7a-(4-bromophenyl)-N-(2,2-difluoroethyl)-4b,5-dihydroxy-4-methoxy-7-phenyl-4b,6,7,7a-tetrahydro-5H-cyclopenta[4,5]furo[2,3-c]pyridine-6-carboxamide (Cpd. No. 116F) as white solid. Yield: 0.05 g, 50.7%; MS (ESI) m/z 561.19$[M+1]^+$; Purity: 98.25%. $^1H$ NMR (400 MHz, DMSO-$d_6$) δ 8.57 (t, J=8.6 Hz, 1H), 8.09 (s, 1H), 7.98 (s, 1H), 7.23 (d, J=8.6 Hz, 2H), 7.06-7.03 (m, 4H), 6.99-6.94 (m, 3H), 6.04-5.76 (m, 1H), 5.06 (d, J=4.72 Hz, 1H), 4.61 (t, J=4.6 Hz, 1H), 4.36 (d, J=14.08 Hz, 1H), 3.94 (dd, J=14.16 & 4.72 Hz, 1H), 3.87 (s, 3H) 3.48-3.36 (m, 2H).

Example 117

Rac-(4bS,5S,6R,7S,7aR)-7a-(4-bromophenyl)-4-methoxy-7-phenyl-6-((2,2,2-trifluoroethyl)sulfonyl)-5,6,7,7a-tetrahydro-4bH-cyclopenta[4,5]furo[2,3-c]pyridine-4b,5-diol (Cpd. No. 117F)

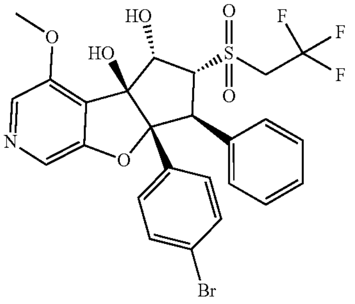

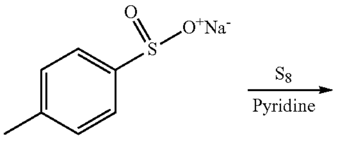

1

-continued

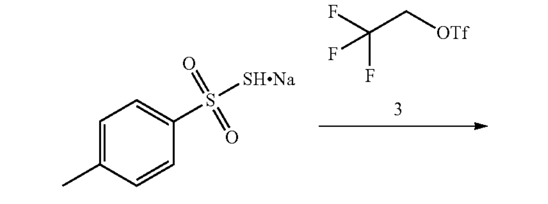

2

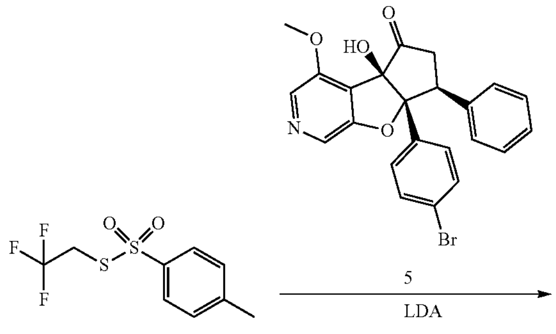

4

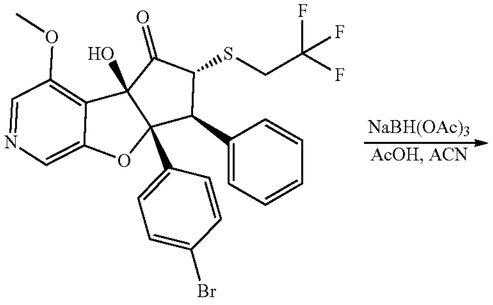

6

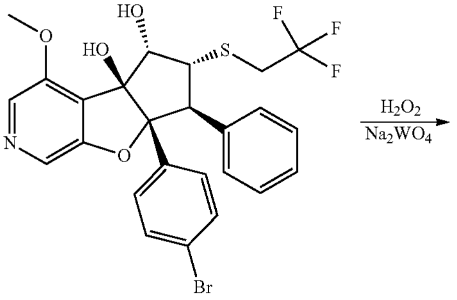

7

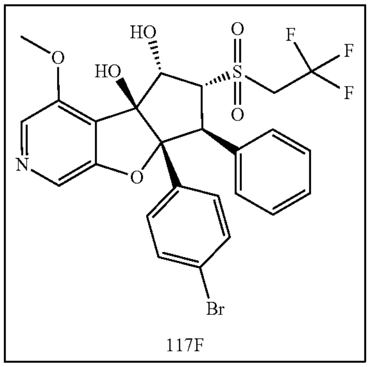 [SMILES: COc1cncc2c1[C@]1(O)[C@H](O)[C@H](S(=O)(=O)CC(F)(F)F)[C@@H](c3ccccc3)[C@]1(c1ccc(Br)cc1)O2]

117F

Synthesis of 4-methylbenzenesulfonothioic S-acid, sodium salt (2)

A solution of sodium 4-methylbenzenesulfinate (1, 50.0 g, 280.6 mmol) and sulfur powder (8.96 g, 59.8 mmol) in pyridine (200 mL) was stirred at room temperature for 16 h. After completion, the solvent was distilled out under reduced pressure to get crude product, which was washed with n-pentane and dried under vacuum to afford 4-methylbenzenesulfonothioic S-acid, sodium salt (2) as brown solid. Yield: 55.0 g, 92.0%; MS (ESI) m/z 186.97[M−1]$^-$.

Synthesis of S-(2,2,2-trifluoroethyl) 4-methylbenzenesulfonothioate (4)

To a solution of 4-methylbenzenesulfonothioic S-acid, sodium salt (2, 10.0 g, 47.39 mmol) in N,N-dimethyl formamide (100 mL) at 0° C., $K_2CO_3$ (6.54 g, 47.39 mmol) and 2,2,2-trifluoroethyl trifluoromethanesulfonate (3, 13.14 g, 56.8 mmol) were added. The reaction mass was stirred for 4 h at room temperature. After completion, the reaction mixture was diluted with ice water and extracted with ethyl acetate. The organic layer was separated and dried over anhydrous sodium sulphate, filtered and concentrated to give crude. The crude was purified by silica gel column chromatography eluting with 5-10% in ethyl acetate in hexane. The desired fractions were concentrated to afford S-(2,2,2-trifluoroethyl) 4-methylbenzenesulfonothioate (4) as colorless liquid. Yield: 2.6 g, 20.0%; $^1$H NMR (400 MHz, DMSO-$d_6$) δ 7.81 (d, J=8.32, 2H), 7.37 (d, J=8.16, 2H), 3.77 (m, 2H), 2.46 (s, 3H);

Synthesis of rac-(4bR,6R,7S,7aR)-7a-(4-bromophenyl)-4b-hydroxy-4-methoxy-7-phenyl-6-((2,2,2-trifluoroethyl)thio)-4b,6,7,7a-tetrahydro-SH-cyclopenta[4,5]furo[2,3-c]pyridin-5-one (6)

To a solution of rac-(4bR,7S,7aR)-7a-(4-bromophenyl)-4b-hydroxy-4-methoxy-7-phenyl-4b,6,7,7a-tetrahydro-5H-cyclopenta[4,5]furo[2,3-c]pyridin-5-one (5, 1.0 g, 2.21 mmol) in dry tetrahydrofuran (20 mL), lithium diisopropyl amide (2.0 M solution in THF) (1.32 mL, 2.65 mmol) was added at −78° C. The reaction mixture was stirred at −78° C. for 1.5 h. A solution of S-(2,2,2-trifluoroethyl) 4-methylbenzenesulfonothioate (4, 1.19 g, 4.42 mmol) in tetrahydrofuran was added at −78° C., then slowly reaction mass was brought to room temperature. The reaction was stirred at room temperature for 16 h. After completion, cooled to 0° C., quenched with saturated ammonium chloride solution, extracted with ethyl acetate, dried over anhydrous sodium sulphate, filtered and concentrated to get crude product which was purified over a plug of silica gel eluting the compound with 5% methanol in dichloromethane. The desired fractions were concentrated under reduced pressure to afford rac-(4bR,6R,7S,7aR)-7a-(4-bromophenyl)-4b-hydroxy-4-methoxy-7-phenyl-6-((2,2,2-trifluoroethyl)thio)-4b,6,7,7a-tetrahydro-5H-cyclopenta[4,5]furo[2,3-c]pyridin-5-one (6) as white solid. Yield: 1.0 g, 80%; MS (ESI) m/z 566.35[M+1]$^+$.

Synthesis of rac-(4bS,5S,6R,7S,7aR)-7a-(4-bromophenyl)-4-methoxy-7-phenyl-6-((2,2,2-trifluoroethyl)thio)-5,6,7,7a-tetrahydro-4bH-cyclopenta[4,5]furo[2,3-c]pyridine-4b, 5-diol (7)

A solution of rac-(4bR,6R,7S,7aR)-7a-(4-bromophenyl)-4b-hydroxy-4-methoxy-7-phenyl-6-((2,2,2-trifluoroethyl)

thio)-4b,6,7,7a-tetrahydro-5H-cyclopenta[4,5]furo[2,3-c] pyridin-5-one (6, 1.0 g, 1.76 mmol) in acetonitrile (20 mL) was cooled at 0° C., to this solution acetic acid (1.06 g, 17.65 mmol) and sodium triacetoxyborohydride (2.25 g, 10.59 mmol) were added. The resulting mixture was stirred for 12 h at room temperature. After completion, the reaction mixture was partitioned between saturated aqueous sodium bicarbonate solution and ethyl acetate. The organic layer was separated and dried over sodium sulphate, filtered and concentrated to give crude. The crude was purified by silica gel column chromatography eluting with 5-6% in methanol in dichloromethane. The desired fractions were concentrated to afford rac-(4bS,5S,6R,7S,7aR)-7a-(4-bromophenyl)-4-methoxy-7-phenyl-6-((2,2,2-trifluoroethyl)thio)-5,6,7,7a-tetrahydro-4bH-cyclopenta[4,5]furo[2,3-c]pyridine-4b,5-diol (7) as white solid. Yield: 0.81 g, 81.0%; MS (ESI) m/z 568.14[M+1]$^+$.

Synthesis of rac-(4bS,5S,6R,7S,7aR)-7a-(4-bromophenyl)-4-methoxy-7-phenyl-6-((2,2,2-trifluoroethyl)sulfonyl)-5,6,7,7a-tetrahydro-4bH-cyclopenta[4,5]furo[2,3-c]pyridine-4b,5-diol (Cpd. No. 117F)

A solution of rac-(4bS,5S,6R,7S,7aR)-7a-(4-bromophenyl)-4-methoxy-7-phenyl-6-((2,2,2-trifluoroethyl)thio)-5,6,7,7a-tetrahydro-4bH-cyclopenta[4,5]furo[2,3-c]pyridine-4b,5-diol (7, 0.1 g, 0.175 mmol) in methanol (2 mL) was cooled at 0° C. then 30% hydrogen peroxide in water (0.1 mL, 0.87 mmol) and sodium tungstate (0.022 g, 0.0875 mmol) were added to the above solution. The resulting mixture was stirred for 12 h at room temperature. After completion, the solvent was concentrated to give crude. The crude was purified by preparative HPLC to afford rac-(4bS,5S,6R,7S,7aR)-7a-(4-bromophenyl)-4-methoxy-7-phenyl-6-((2,2,2-trifluoroethyl)sulfonyl)-5,6,7,7a-tetrahydro-4bH-cyclopenta[4,5]furo[2,3-c]pyridine-4b,5-diol (Cpd. No. 117F) as white solid. Yield: 0.009 g, 9%; MS (ESI) m/z 600.18[M+1]$^+$; $^1$H NMR (400 MHz, DMSO-$d_6$) δ 8.08 (s, 11H), 8.02 (s, 1H), 7.29 (d, J=8.6 Hz, 2H), 7.20 (d, J=9.4 Hz, 2H), 7.06 (m, 5H), 6.28 (d, J=5.8 Hz, 1H), 6.07 (s, 1H), 4.90 (d, J=11.6 Hz, 1H), 4.43 (m, 3H), 3.90 (s, 3H).

Example 118

Rac-4-((4bS,5S,6R,7S,7aR)-4b,5-dihydroxy-4-methoxy-7-phenyl-6-(phenylsulfonyl)-4b,5,6,7-tetrahydro-7aH-cyclopenta[4,5]furo[2,3-c]pyridin-7a-yl) benzonitrile (Cpd. No. 118F)

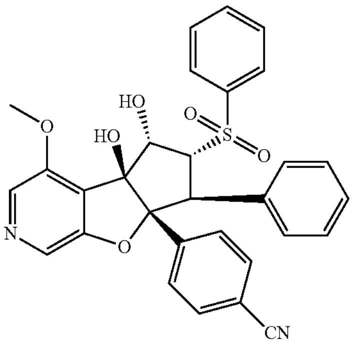

-continued

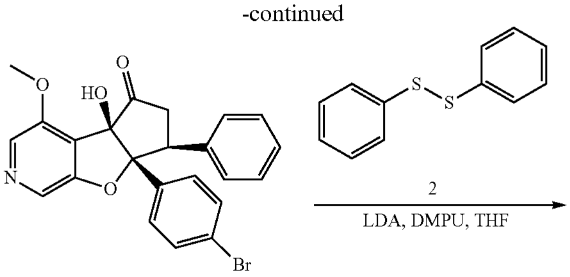

1

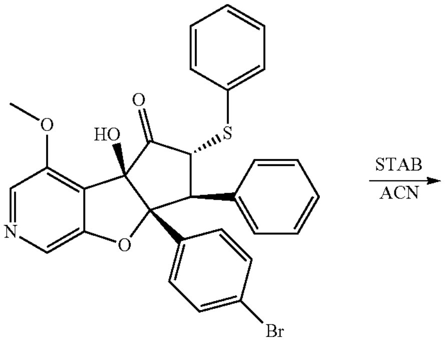

3

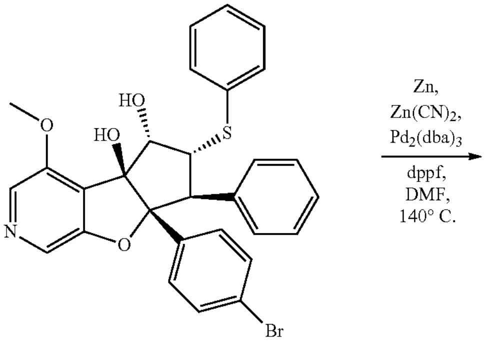

4

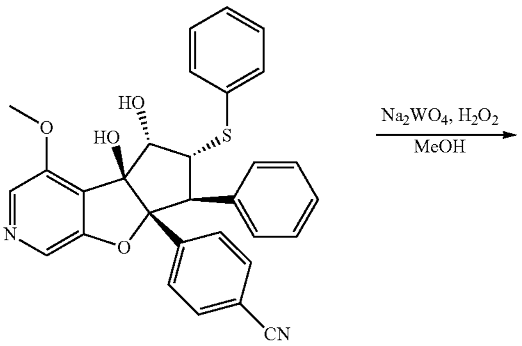

5

-continued

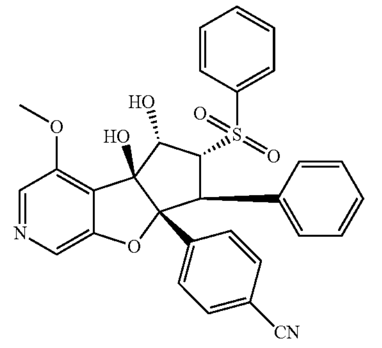

118F

Synthesis of rac-(4bR,6R,7S,7aR)-7a-(4-bromophenyl)-4b-hydroxy-4-methoxy-7-phenyl-6-(phenylthio)-4b,6,7,7a-tetrahydro-5H-cyclopenta[4,5]furo[2,3-c]pyridin-5-one (3)

To a solution of rac-(4bR,7S,7aR)-7a-(4-bromophenyl)-4b-hydroxy-4-methoxy-7-phenyl-4b,6,7,7a-tetrahydro-5H-cyclopenta[4,5]furo[2,3-c]pyridin-5-one (1, 1.0 g, 2.212 mmol) in tetrahydrofuran (20 ml) at −15° C., lithium diisopropylamide 1M in Tetrahydrofuran (4.42 ml, 4.424 mmol) was added and stirred for 30 min. at same temperature followed by addition of 1,2-diphenyldisulfane (2, 0.53 g, 2.433 mmol) and N,N'-Dimethylpropyleneurea (1.1 ml). The reaction mixture was stirred at room temperature for 6 hr. After completion, the mixture was quenched with water and extracted with ethyl acetate. The organic phase was separated, dried over sodium sulphate and concentrated under reduced pressure. The crude was purified by silica gel column chromatography using 45% ethyl acetate in hexanes as eluent. The desired fractions were concentrated to afford rac-(4bR,6R,7S,7aR)-7a-(4-bromophenyl)-4b-hydroxy-4-methoxy-7-phenyl-6-(phenylthio)-4b,6,7,7a-tetrahydro-5H-cyclopenta[4,5]furo[2,3-c]pyridin-5-one (3) as yellow solid. Yield: 0.9 g, 73%; MS (ESI) m/z 560.96[M+1]$^+$.

Synthesis of rac-(4bS,5S,6R,7S,7aR)-7a-(4-bromophenyl)-4-methoxy-7-phenyl-6-(phenylthio)-5,6,7,7a-tetrahydro-4bH-cyclopenta[4,5]furo[2,3-c]pyridine-4b,5-diol (4)

To a solution of rac-(4bR,6R,7S,7aR)-7a-(4-bromophenyl)-4b-hydroxy-4-methoxy-7-phenyl-6-(phenylthio)-4b,6,7,7a-tetrahydro-5H-cyclopenta[4,5]furo[2,3-c]pyridin-5-one (3, 0.9 g, 1.60 mmol) in acetonitrile (36 ml) at 0° C., sodium triacetoxyborohydride (2.04 g, 9.64 mmol) was added portion wise over a period of 5 min followed by addition of acetic acid (0.96 g, 16.01 mmol). The reaction mass was slowly brought to room temperature and stirred for additional 12 h. After completion, the reaction mixture was partitioned between saturated aqueous sodium bicarbonate solution and ethyl acetate. The organic layer was separated, washed with water, dried over anhydrous sodium sulfate, filtered and concentrated under reduced pressure. The crude was purified by silica gel column chromatography using 65% ethyl acetate in hexanes as eluent. The desired fractions were concentrated to afford rac-(4bS,5S,6R,7S,7aR)-7a-(4-bromophenyl)-4-methoxy-7-phenyl-6-(phenylthio)-5,6,7,7a-tetrahydro-4bH-cyclopenta[4,5]furo[2,3-c]pyridine-4b,5-diol (4) as off white solid. Yield: 0.6 g, 67%; MS (ESI) m/z 562.37[M−1]$^+$.

Synthesis of rac-4-((4bS,5S,6R,7S,7aR)-4b,5-dihydroxy-4-methoxy-7-phenyl-6-(phenylthio)-4b,5,6,7-tetrahydro-7aH-cyclopenta[4,5]furo[2,3-c]pyridin-7a-yl)benzonitrile (5)

To a solution of rac-(4bS,5S,6R,7S,7aR)-7a-(4-bromophenyl)-4-methoxy-7-phenyl-6-(phenylthio)-5,6,7,7a-tetrahydro-4bH-cyclopenta[4,5]furo[2,3-c]pyridine-4b,5-diol (4, 0.8 g, 1.42 mmol) in N,N-dimethylformamide (16 mL), zinc cyanide (0.251 g, 2.14 mmol) and zinc dust (0.01 g, 0.14 mmol) were added at room temperature and the reaction mixture was degassed with argon for 15 min. 1,1'-Bis (diphenylphosphino)ferrocene (0.104 g, 0.14 mmol) and tris(dibenzylideneacetone)dipalladium (0.04 g, 0.042 mmol) were added to the reaction, degassed for additional 5 min and mixture was heated at 140° C. for 16 h. After completion, the reaction mass was diluted with ethyl acetate and washed with cold water. The organic layer was separated and dried over anhydrous sodium sulphate, filtered and concentrated to give crude. The crude was purified by silica gel column chromatography using 2-3% methanol in dichloromethane as eluent. The desired fractions were concentrated to afford rac-4-((4bS,5S,6R,7S,7aR)-4b,5-dihydroxy-4-methoxy-7-phenyl-6-(phenylthio)-4b,5,6,7-tetrahydro-7aH-cyclopenta[4,5]furo[2,3-c]pyridin-7a-yl)benzonitrile (5) as yellow solid. Yield: 0.6 g, 83%; MS (ESI) m/z 509.5[M−1]$^-$.

Synthesis of rac-4-((4bS,5S,6R,7S,7aR)-4b,5-dihydroxy-4-methoxy-7-phenyl-6-(phenylsulfonyl)-4b,5,6,7-tetrahydro-7aH-cyclopenta[4,5]furo[2,3-c]pyridin-7a-yl)benzonitrile (Cpd. No. 118F)

To a solution of rac-4-((4bS,5S,6R,7S,7aR)-4b,5-dihydroxy-4-methoxy-7-phenyl-6-(phenylthio)-4b,5,6,7-tetrahydro-7aH-cyclopenta[4,5]furo[2,3-c]pyridin-7a-yl)benzonitrile (5, 0.1 g, 0.196 mmol) in methanol (2.0 mL) at 0° C., 30% aqueous hydrogen peroxide (0.11 mL, 0.984 mmol) was added followed by the addition of sodium tungstate (0.029 g, 0.098 mmol). The reaction mass was stirred for 36 h at room temperature. After completion, the solvent was removed under reduced pressure. The crude was diluted with water and extracted with 10% methanol in dichloromethane. The organic phase was separated, dried over anhydrous sodium sulphate and concentrated under reduced pressure to give crude. The crude was purified by preparative HPLC to afford rac-4-((4bS,5S,6R,7S,7aR)-4b,5-dihydroxy-4-methoxy-7-phenyl-6-(phenylsulfonyl)-4b,5,6,7-tetrahydro-7aH-cyclopenta[4,5]furo[2,3-c]pyridin-7a-yl)benzonitrile (Cpd. No. 118F) as white solid. Yield: 0.025 g, 23.5%; MS (ESI) m/z 541.3 [M+1]$^+$. $^1$H NMR (400 MHz, DMSO-$d_6$) δ 8.13 (s, 1H), 8.04 (s, 1H), 7.60 (t, J=7.2 Hz, 1H), 7.52-7.47 (m, 4H), 7.44-7.38 (m, 4H), 6.97-6.91 (m, 5H), 6.15-6.08 (m, 2H), 5.11 (dd, J=13.8 Hz, 4.0 Hz 1H), 4.69 (d, J=3.2 Hz, 1H), 4.33 (d, J=13.8 Hz, 1H), 3.87 (s, 3H).

Example 119

Rac-4-((4bS,5S,6R,7S,7aR)-4b,5-dihydroxy-4-methoxy-7-phenyl-6-(pyridin-2-ylsulfonyl)-4b,5,6,7-tetrahydro-7aH-cyclopenta[4,5]furo[2,3-c]pyridin-7a-yl)benzonitrile (Cpd. No. 119F)

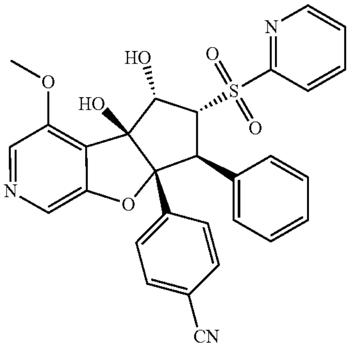

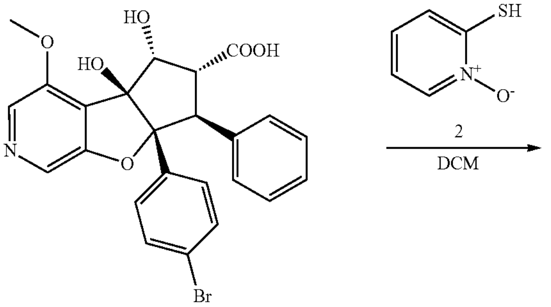

1

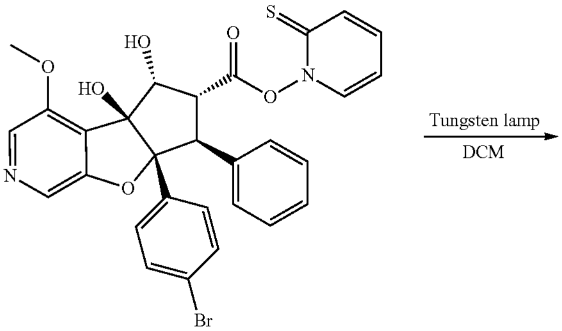

3

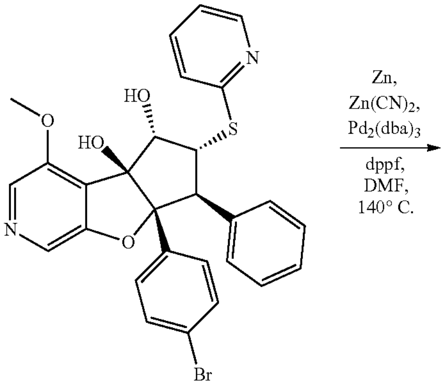

4

-continued

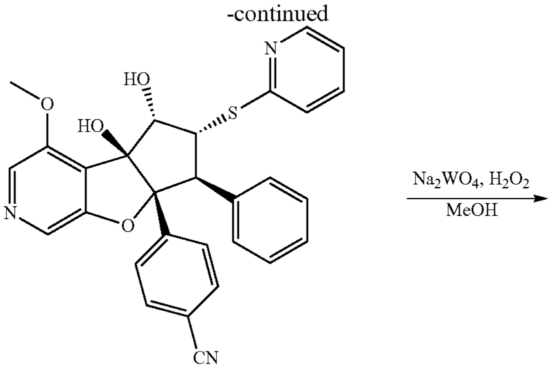

5

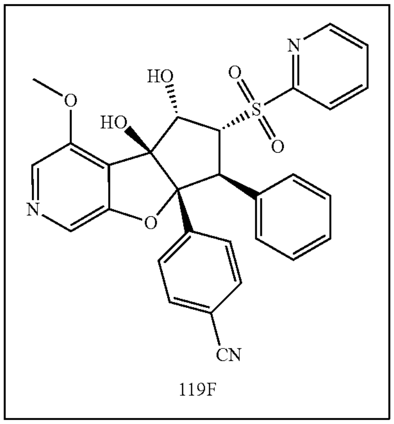

119F

Synthesis of rac-2-thioxopyridin-1(2H)-yl (4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylate (3)

To a solution of rac-(4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylic acid (1, 2.50 g, 5.03 mmol) and 2-mercaptopyridine 1-oxide (2, 0.958 g, 7.54 mmol) in dichloromethane (60 mL) at 0° C., N,N'-dicyclohexylcarbodiimide (1.5 g, 7.54 mmol) was added and the reaction was stirred for 16 h at room temperature in the dark. After completion, solvent was removed under reduced pressure and the residue was diluted with dichloromethane and washed with cold water. The organic layer was separated and dried over anhydrous sodium sulphate, filtered and concentrated to give crude. The crude was purified by triturating with n-pentane and diethyl ether to afford rac-2-thioxopyridin-1(2H)-yl(4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylate (3) as white solid. Yield: 1.80 g, 59%; MS (ESI) m/z 606.42[M+1]$^+$.

Synthesis of rac-(4bS,5S,6R,7S,7aR)-7a-(4-bromophenyl)-4-methoxy-7-phenyl-6-(pyridin-2-ylthio)-5,6,7,7a-tetrahydro-4bH-cyclopenta[4,5]furo[2,3-c]pyridine-4b, 5-diol (4)

To a solution of rac-2-thioxopyridin-1(2H)-yl (4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylate (3, 1.80 g, 2.97 mmol) in dry dichloromethane under nitrogen. The reaction mixture was refluxed by using tungsten lamp (200 W) for 10 h. After completion, solvent was removed under reduced pressure and the residue was purified over a plug of silica gel eluting the compound with 3% methanol in dichloromethane. The desired fractions were concentrated under reduced pressure to afford rac-(4bS,5S,6R,7S,7aR)-7a-(4-bromophenyl)-4-methoxy-7-phenyl-6-(pyridin-2-ylthio)-5,6,7,7a-tetrahydro-4bH-cyclopenta[4,5]furo[2,3-c]pyridine-4b,5-diol (4) as white solid. Yield: 1.66 g, 54%; MS (ESI) m/z 563.36[M+1]$^+$.

Synthesis of rac-4-((4bS,5S,6R,7S,7aR)-4b,5-dihydroxy-4-methoxy-7-phenyl-6-(pyridin-2-ylthio)-4b,5,6,7-tetrahydro-7aH-cyclopenta[4,5]furo[2,3-c]pyridin-7a-yl)benzonitrile (5)

To a solution of rac-(4bS,5S,6R,7S,7aR)-7a-(4-bromophenyl)-4-methoxy-7-phenyl-6-(pyridin-2-ylthio)-5,6,7,7a-tetrahydro-4bH-cyclopenta[4,5]furo[2,3-c]pyridine-4b,5-diol (4, 0.4 g, 0.711 mmol) in N,N-dimethylformamide (10 mL), zinc cyanide (0.499 g, 4.27 mmol) and zinc dust (0.005 g, 0.085 mmol) were added at room temperature and the reaction mixture was degassed with argon for 15 min. 1,1'-Bis(diphenylphosphino)ferrocene (0.008 g, 0.0142 mmol) and tris(dibenzylideneacetone)dipalladium (0.019 g, 0.0213 mmol) were added to the reaction, degassed for additional 5 min. and mixture was heated at 140° C. for 8 h. After completion, the reaction mass was diluted with ethyl acetate and washed with cold water. The organic layer was separated and dried over anhydrous sodium sulphate, filtered and concentrated to give crude. The crude was purified by silica gel column chromatography using 2-3% methanol in dichloromethane as eluent. The desired fractions were concentrated to afford Synthesis of rac-4-((4bS,5S,6R,7S,7aR)-4b,5-dihydroxy-4-methoxy-7-phenyl-6-(pyridin-2-ylthio)-4b,5,6,7-tetrahydro-7aH-cyclopenta[4,5]furo[2,3-c]pyridin-7a-yl)benzonitrile (5) as white solid. Yield: 0.2 g, 55%; MS (ESI) m/z 510.41[M+1]$^+$.

Synthesis of rac-4-((4bS,5S,6R,7S,7aR)-4b,5-dihydroxy-4-methoxy-7-phenyl-6-(pyridin-2-ylsulfonyl)-4b,5,6,7-tetrahydro-7aH-cyclopenta[4,5]furo[2,3-c]pyridin-7a-yl)benzonitrile (Cpd. No. 119F)

To a solution of rac-4-((4bS,5S,6R,7S,7aR)-4b,5-dihydroxy-4-methoxy-7-phenyl-6-(pyridin-2-ylthio)-4b,5,6,7-tetrahydro-7aH-cyclopenta[4,5]furo[2,3-c]pyridin-7a-yl)benzonitrile (5, 0.20 g, 0.392 mmol) in methanol (75 mL) at 0° C., 30% aqueous hydrogen peroxide (0.066 g, 1.96 mmol) was added followed by the addition of sodium tungstate (0.080 g, 0.275 mmol). The reaction mass was stirred for 18 h at room temperature. After completion, the solvent was removed under reduced pressure. The crude was diluted with water and extracted with dichloromethane. The organic phase was separated, dried over anhydrous sodium sulphate and concentrated under reduced pressure to give crude. The crude was purified by preparative HPLC to afford rac-4-((4bS,5S,6R,7S,7aR)-4b,5-dihydroxy-4-methoxy-7-phenyl-6-(pyridin-2-ylsulfonyl)-4b,5,6,7-tetrahydro-7aH-cyclopenta[4,5]furo[2,3-c]pyridin-7a-yl)benzonitrile (Cpd. No. 119F) as white solid Yield: 0.025 g, 11.7%; MS (ESI) m/z 542.28[M+1]$^+$. $^1$H NMR (400 MHz, DMSO-$d_6$) δ 8.79 (d, J=4.12 Hz, 1H), 8.06 (s, 1H), 7.99 (s, 1H), 7.79 (t, J=7.30 Hz, 1H), 7.63 (t, J=5.56 Hz, 1H), 7.51 (d, J=8.0 Hz, 2H), 7.39-7.37 (m, 3H), 6.84 (t, J=7.1 Hz, 1H), 6.74 (t, J=7.28 Hz, 2H), 6.58 (d, J=7.28 Hz, 2H), 6.18 (s, 1H), 6.06 (d, J=5.92 Hz, 1H), 5.24 (dd, J=15.64 Hz, 4.92 Hz, 1H), 4.88 (t, J=9.8 Hz, 1H), 4.56 (d, J=13.8 Hz, 1H), 3.86 (s, 3H).

Example 120

4-((4bR,5R,7S,7aR)-4b-hydroxy-5-(hydroxymethyl)-4-methoxy-7-phenyl-4b,5,6,7-tetrahydro-7aH-cyclopenta[4,5]furo[2,3-c]pyridin-7a-yl)benzonitrile (Cpd. No. 120F)

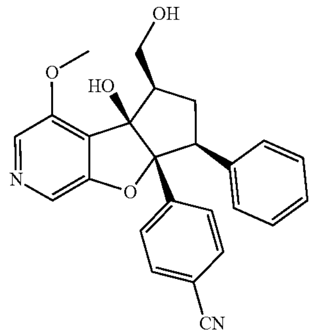

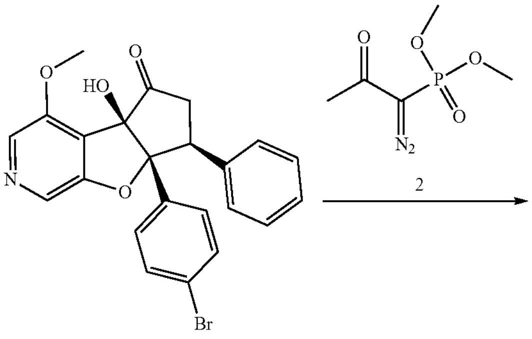

1

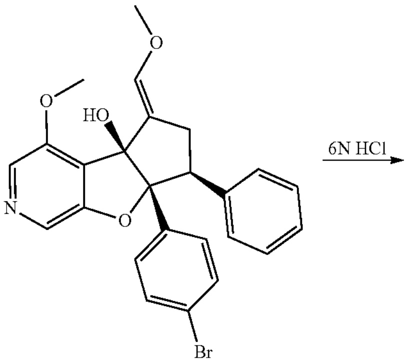

3

-continued

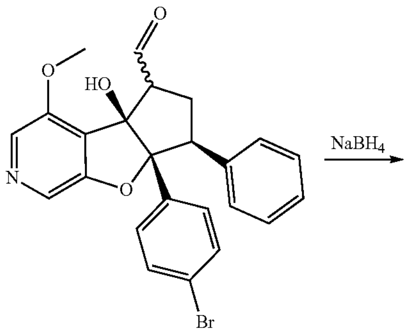

4

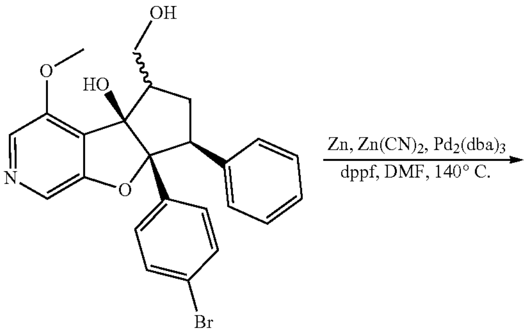

5

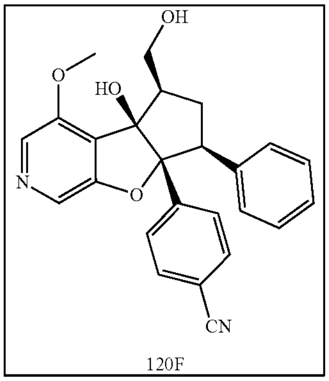 [SMILES: COc1cncc2c1[C@]1(O)[C@@H](CO)C[C@@H](c3ccccc3)[C@]1(c1ccc(C#N)cc1)O2]

120F

Synthesis of rac-(4bR,7S,7aR,E)-7a-(4-bromophenyl)-4-methoxy-5-(methoxymethylene)-7-phenyl-5,6,7,7a-tetrahydro-4bH-cyclopenta[4,5]furo[2,3-c]pyridin-4b-ol (3)

To a solution of rac-(4bR,7S,7aR)-7a-(4-bromophenyl)-4b-hydroxy-4-methoxy-7-phenyl-4b,6,7,7a-tetrahydro-5H-cyclopenta[4,5]furo[2,3-c]pyridin-5-one (1, 0.5 g, 1.105 mmol) in methanol (20 mL) at 0° C. was added dimethyl (1-diazo-2-oxopropyl)phosphonate (2, 0.248 mL, 1.658 mmol) followed by $K_2CO_3$ (0.305 g, 2.210 mmol). The reaction mixture was stirred at 0° C. for 30 min then the reaction mixture was stirred at room temperature for 16 h. After completion of the reaction it was quenched by the addition of saturated sodium bicarbonate solution (30 mL). The precipitated solid was filtered, washed with water, n-pentane and dried under vacuum to afford rac-(4bR,7S,7aR,E)-7a-(4-bromophenyl)-4-methoxy-5-(methoxymethylene)-7-phenyl-5,6,7,7a-tetrahydro-4bH-cyclopenta[4,5]furo[2,3-c]pyridin-4b-ol (3) as white solid. Yield: 0.4 g, 75%; MS (ESI) m/z 480.18[M+1]$^+$; 482.19[M+2]+; LCMS shows desired mass in two peaks (71%+20%).

Synthesis of rac-(4bR,7S,7aR)-7a-(4-bromophenyl)-4b-hydroxy-4-methoxy-7-phenyl-4b,6,7,7a-tetrahydro-5H-cyclopenta[4,5]furo[2,3-c]pyridine-5-carbaldehyde (4)

To a solution of rac-(4bR,7S,7aR,E)-7a-(4-bromophenyl)-4-methoxy-5-(methoxymethylene)-7-phenyl-5,6,7,7a-tetrahydro-4bH-cyclopenta[4,5]furo[2,3-c]pyridin-4b-ol (3, 0.4 g, 0.832 mmol) in THF (6 mL) at 0° C. was added 6N hydrochloric acid (1 mL). The reaction mixture was stirred for 3 h at room temperature. After completion, the reaction mass was cooled and neutralized by the addition of saturated sodium bicarbonate up to pH ~7 and extracted with ethyl acetate. The organic layer was separated and dried over anhydrous sodium sulphate, filtered and concentrated, the crude product obtained was triturated in n-pentane and the solid was filtered off to give rac-(4bR,7S,7aR)-7a-(4-bromophenyl)-4b-hydroxy-4-methoxy-7-phenyl-4b,6,7,7a-tetrahydro-5H-cyclopenta[4,5]furo[2,3-c]pyridine-5-carbaldehyde (4) as pale yellow solid. Yield: 0.3 g, 79%; MS (ESI) m/z 464.12[M−1]$^-$; 466.13[M−2]$^-$. LCMS shows desired mass in two peaks (57%+23%).

Synthesis of rac-(4bR,7S,7aR)-7a-(4-bromophenyl)-5-(hydroxymethyl)-4-methoxy-7-phenyl-5,6,7,7a-tetrahydro-4bH-cyclopenta[4,5]furo[2,3-c]pyridin-4b-ol (5)

To a solution of rac-(4bR,7S,7aR)-7a-(4-bromophenyl)-4b-hydroxy-4-methoxy-7-phenyl-4b,6,7,7a-tetrahydro-5H-cyclopenta[4,5]furo[2,3-c]pyridine-5-carbaldehyde (4, 0.3 g, 0.643 mmol) in methanol (12 mL) at 0° C., sodium borohydride (0.06 g, 1.608 mmol) was added in one portion. The reaction mixture was stirred for 2 h at room temperature. After completion, the reaction mixture was cooled and quenched with ice water. The precipitated solid was filtered off, washed with water, n-pentane and mixture of 10% ether in pentane and dried under vacuum to afford rac-(4bR,7S,7aR)-7a-(4-bromophenyl)-5-(hydroxymethyl)-4-methoxy-7-phenyl-5,6,7,7a-tetrahydro-4bH-cyclopenta[4,5]furo[2,3-c]pyridin-4b-ol (5) as white solid. Yield: 0.2 g, 67%; MS (ESI) m/z 468.17[M+1]$^+$; 470.15[M+2]+. LCMS shows desired mass in two peaks (82%+7%).

Synthesis of 4-((4bR,5R,7S,7aR)-4b-hydroxy-5-(hydroxymethyl)-4-methoxy-7-phenyl-4b,5,6,7-tetrahydro-7aH-cyclopenta[4,5]furo[2,3-c]pyridin-7a-yl)benzonitrile (Cpd. No. 120F)

To a solution of rac-(4bR,7S,7aR)-7a-(4-bromophenyl)-5-(hydroxymethyl)-4-methoxy-7-phenyl-5,6,7,7a-tetrahydro-4bH-cyclopenta[4,5]furo[2,3-c]pyridin-4b-ol (5, 0.30 g, 0.64 mmol) in N,N-dimethylformamide (6.0 mL), zinc cyanide (0.112 g, 0.96 mmol) and zinc dust (0.0041 g, 0.064 mmol) were added at room temperature and mixture was degassed with argon for 15 min. 1,1'-Bis(diphenylphosphino)ferrocene (0.046 g, 0.064 mmol), and tris(dibenzylideneacetone)dipalladium (0.017 g, 0.0192 mmol) were added to the above reaction mixture and the degassing was continued for another 5 minute. The reaction mixture was heated at 140° C. for 3 h. After completion, the reaction mass was diluted with ethyl acetate and washed with cold water. The organic layer was separated and dried over sodium sulphate, filtered and concentrated to give crude.

The crude was purified by silica gel column chromatography eluting with 2-3% methanol in dichloromethane. The desired fractions were concentrated to afford rac-4-((4bR,5R,7S,7aR)-4b-hydroxy-5-(hydroxymethyl)-4-methoxy-7-phenyl-4b,5,6,7-tetrahydro-7aH-cyclopenta[4,5]furo[2,3-c]pyridin-7a-yl)benzonitrile as white solid. Yield: 0.2 g, 75%. (Racemic mixture); MS (ESI) m/z 415.42[M+1]$^+$; The enantiomers were separated by chiral preparative HPLC [chiralpak IC (4.6×250) mm, 5μ] with isocratic 0.1% triethylamine in n-hexane/isopropanol 80/20 v/v. Peak 1 (Cpd. No. 120F, 50 mg), $[\alpha]_D$−74.5° (c 0.22, $CDCl_3$), $R_t$=28.294 min, ee=99.64%; $^1$H NMR (400 MHz, DMSO-$d_6$) δ: 8.16 (s, 1H), 8.08 (s, 1H), 7.58 (d, J=8.28 Hz, 2H), 7.41 (d, J=8.28 Hz, 2H), 7.11 (m, 3H), 6.97 (d, J=7.28 Hz, 2H), 5.49 (s, 1H), 4.60 (t, J=5.16 Hz, 1H), 4.09 (t, J=5.8 Hz, 1H), 3.96 (s, 3H), 3.93 (t, J=6.68 Hz, 1H), 3.54 (dd, J=5.6 Hz, J=5.48 Hz, 1H), 2.71 (d, J=Hz 1H), 2.42 (d, J=7.12 Hz, 1H), 2.25 (t, J=6.12 Hz, 1H); Peak-2 (45 mg), $[\alpha]_D$+75.0° (c 0.20, $CDCl_3$), $R_t$=38.405 min, ee >99% $^1$H NMR (400 MHz, DMSO-$d_6$) δ: 8.16 (s, 1H), 8.08 (s, 1H), 7.58 (d, J=8.36 Hz, 2H), 7.41 (d, J=8.24 Hz, 2H), 7.11 (m, 3H), 6.97 (d, J=7.2 Hz, 2H), 5.49 (s, 1H), 4.60 (t, J=4.12 Hz, 1H), 4.09 (t, J=5.72 Hz, 1H), 3.96 (s, 3H), 3.93 (t, J=6.96 Hz, 1H), 3.54 (dd, J=5.88 Hz, J=5.72 Hz, 1H), 2.75 (t, J=8.08 Hz 1H), 2.45 (d, J=9.4 Hz, 1H), 2.25 (t, J=6.68 Hz, 1H).

Example 121

Rac-((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)(3,3-difluoroazetidin-1-yl)methanone (Cpd. No. 1211F)

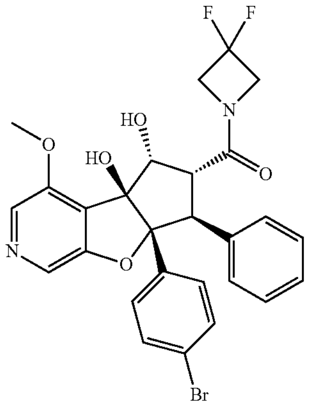

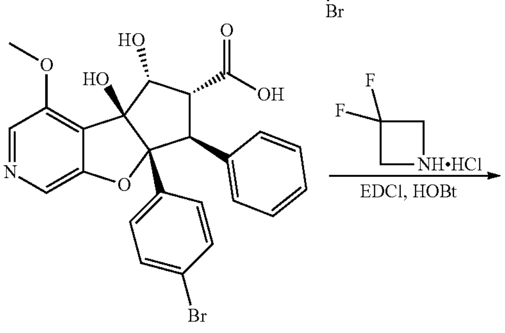

1

-continued

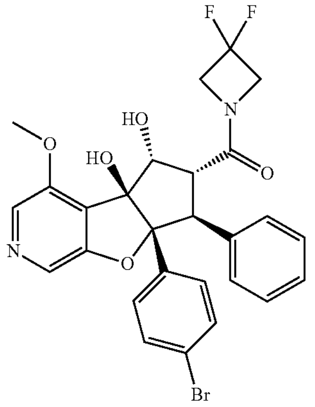

121F

Synthesis of rac-((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)(3,3-difluoroazetidin-1-yl)methanone (Cpd. No. 121F)

To a solution of rac-(4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylic acid (1, 1.50 g, 3.01 mmol) in dichloromethane (20 mL) at 0° C., 1-ethyl-3-(3-dimethylaminopropyl) carbodiimide (1.72 g, 9.05 mmol), hydroxybenzotriazole (1.40 g, 9.045 mmol) and N,N-diisopropylethylamine (3.20 g, 18.1 mmol) were added and the mixture was stirred for 5 minute. 3,3-difluoroazetidine hydrochloride (1.16 g, 9.05 mmol) was then added at the same temperature and the reaction was stirred for 16 h at room temperature. After completion, the reaction mass was diluted with dichloromethane and washed with cold water. The organic layer was separated and dried over anhydrous sodium sulphate, filtered and concentrated to give crude product. The crude product was purified by silica gel column chromatography using 0-5% methanol in dichloromethane as eluent. The desired fractions were concentrated to afford rac-((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)(3,3-difluoroazetidin-1-yl)methanone (Cpd. No. 121F) as white solid. Yield: 1.20 g, 70%; MS (ESI) m/z 573.18[M+1]$^+$; $^1$H NMR (400 MHz, DMSO-$d_6$) δ 8.09 (s, 1H), 7.99 (s, 1H), 7.21 (d, J=8.8 Hz, 2H), 7.08-7.03 (m, 4H), 6.99 (m, 3H), 5.67 (s, 1H), 5.34 (d, J=5.2 Hz, 1H), 5.15 (d, J=11.2 Hz, 1H), 4.75 (m, 2H), 4.36 (d, J=13.6 Hz, 1H), 4.22 (bs, 3H), 4.02 (dd, J=13.6, 5.2 Hz, 1H), 3.88 (s, 3H).

Example 122

4-((4bS,5R,6S,7S,7aR)-6-((3,3-difluoroazetidin-1-yl)methyl)-4b,5-dihydroxy-4-methoxy-7-phenyl-4b,5,6,7-tetrahydro-7aH-cyclopenta[4,5]furo[2,3-c]pyridin-7a-yl) benzonitrile (Cpd. No. 122F)

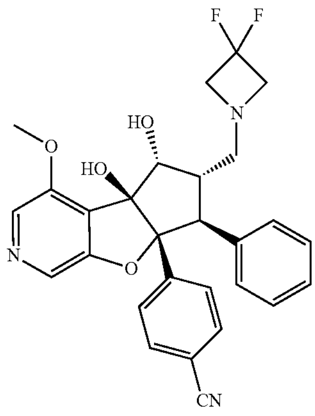

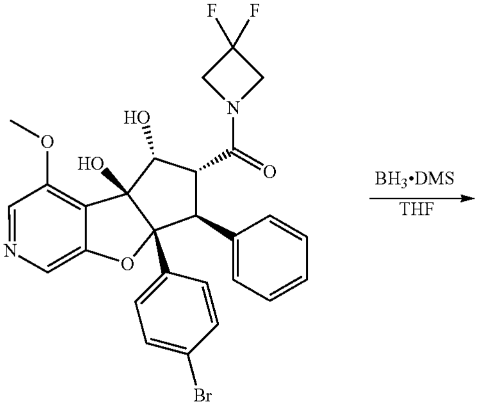

1

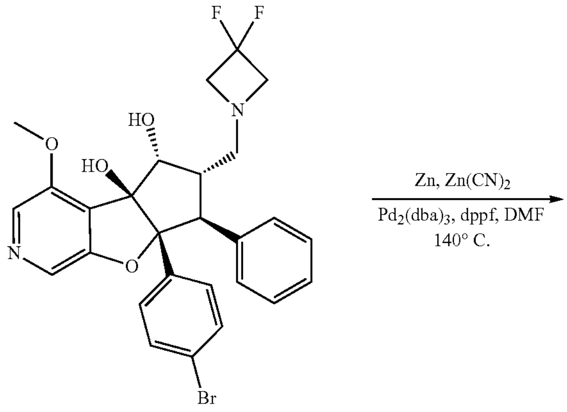

2

-continued

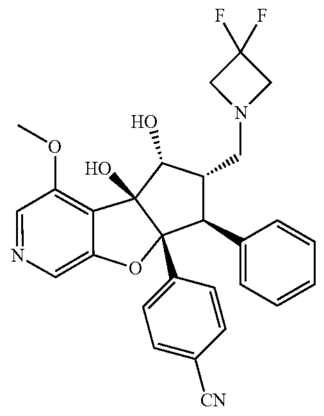

122F

Synthesis of rac-(4bS,5R,6S,7S,7aR)-7a-(4-bromophenyl)-6-((3,3-difluoroazetidin-1-yl)methyl)-4-methoxy-7-phenyl-5,6,7,7a-tetrahydro-4bH-cyclopenta[4,5]furo[2,3-c]pyridine-4b, 5-diol (2)

To a solution of rac-((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)(3,3-difluoroazetidin-1-yl)methanone (1, 1.20 g, 2.09 mmol) in dry tetrahydrofuran (20 mL) at 0° C., borane dimethyl sulphide complex (1.90 ml, 20.9 mmol) was added at the same temperature and the reaction was stirred for 16 h at room temperature. After completion, the reaction mass was diluted with methanol at 0° C. and reflex at 80° C. for 6 h. After completion, the reaction mixture was concentrated to obtain crude product. The crude product was purified by silica gel column chromatography using 0-5% methanol in dichloromethane as eluent. The desired fractions were concentrated under reduced pressure to afford rac-(4bS,5R,6S,7S,7aR)-7a-(4-bromophenyl)-6-((3,3-difluoroazetidin-1-yl)methyl)-4-methoxy-7-phenyl-5,6,7,7a-tetrahydro-4bH-cyclopenta[4,5]furo[2,3-c]pyridine-4b,5-diol (2) as white solid. Yield: 0.60 g, 51%; MS (ESI) m/z 559.24$[M+1]^+$.

Synthesis of 4-((4bS,5R,6S,7S,7aR)-6-((3,3-difluoroazetidin-1-yl)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 122F)

To a solution of rac-(4bS,5R,6S,7S,7aR)-7a-(4-bromophenyl)-6-((3,3-difluoroazetidin-1-yl)methyl)-4-methoxy-7-phenyl-5,6,7,7a-tetrahydro-4bH-cyclopenta[4,5]furo[2,3-c]pyridine-4b,5-diol (2, 0.60 g, 1.04 mmol) in N,N-dimethylformamide (10 mL), zinc cyanide (0.60 g, 5.23 mmol) and zinc dust (0.0079 g, 0.124 mmol) were added at room temperature and the reaction mixture was degassed with argon for 15 minute. 1,1'-Bis(diphenylphosphino)ferrocene (0.012 g, 0.0208 mmol) and tris(dibenzylideneacetone)dipalladium (0.028 g, 0.0312 mmol) were added to the reaction, degassed for additional 5 minute and heated the mixture at 140° C. for 1 h. After completion, the reaction mass was diluted with ethyl acetate and washed with cold water. The organic layer was separated and dried over anhydrous sodium sulphate, filtered and concentrated to give crude product. The crude product was purified by silica gel column chromatography using 2-3% methanol in dichloromethane as eluent. The desired fractions were concentrated to afford rac-4-((4bS,5R,6S,7S,7aR)-6-((3,3-difluoroazetidin-1-yl)methyl)-4b,5-dihydroxy-4-methoxy-7-phenyl-4b,5,6,7-tetrahydro-7aH-cyclopenta[4,5]furo[2,3-c]pyridin-7a-yl)benzonitrile as white solid. Yield: 0.330 g, 61% (racemic), MS (ESI) m/z 506.27 $[M+1]^+$. The enantiomers were separated by chiral preparative HPLC [chiralpak IC (4.6×250) mm, 5μ] in isocratic 0.1% triethylamine in hexane/isopropanol 80/20 v/v. Peak 1 (80 mg), $[\alpha]_D$−8.1° (c 0.43, $CHCl_3$), $R_t$=10.350 min, ee=99.54%, $^1$H NMR (400 MHz, DMSO-$d_6$) δ 8.04 (s, 1H), 7.97 (s, 1H), 7.49 (d, J=8.4 Hz, 2H), 7.37 (d, J=8.4 Hz 2H), 7.10 (m, 2H), 7.02 (m, 3H), 5.74 (s, 1H), 5.23 (d, J=5.2 Hz, 1H), 4.48 (t, J=4.8 Hz, 1H), 3.88 (s, 1H), 3.81 (d, J=14 Hz, 1H), 3.67 (m, 4H), 3.05 (m, 1H), 2.80 (m, 1H), 2.50 (bs, 1H); Peak 2 (Cpd. No. 122F, 85 mg), $[\alpha]_D$+9.0° (c 0.43, $CHCl_3$), $R_t$=14.833 min, ee=99.18%, $^1$H NMR (400 MHz, DMSO-$d_6$) δ 8.04 (s, 1H), 7.97 (s, 1H), 7.49 (d, J=8.4 Hz, 2H), 7.37 (d, J=8.4 Hz, 2H), 7.10 (m, 2H), 7.02 (m, 3H), 5.74 (s, 1H), 5.23 (d, J=5.2 Hz, 1H), 4.48 (t, J=4.8 Hz, 1H), 3.88 (s, 1H), 3.81 (d, J=14 Hz, 1H), 3.67 (m, 4H), 3.05 (m, 1H), 2.80 (m, 1H), 2.50 (bs, 1H).

Example 123

Rac-(5aR,6S,7R,8S,8aS)-3-chloro-5a-(4-cyanophenyl)-8,8a-dihydroxy-N-methyl-6-phenyl-5a,7,8,8a-tetrahydro-6H-cyclopenta[4,5]furo[3,2-b]pyridine-7-sulfonamide (Cpd. No. 123F)

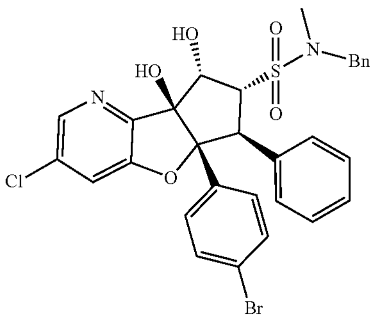

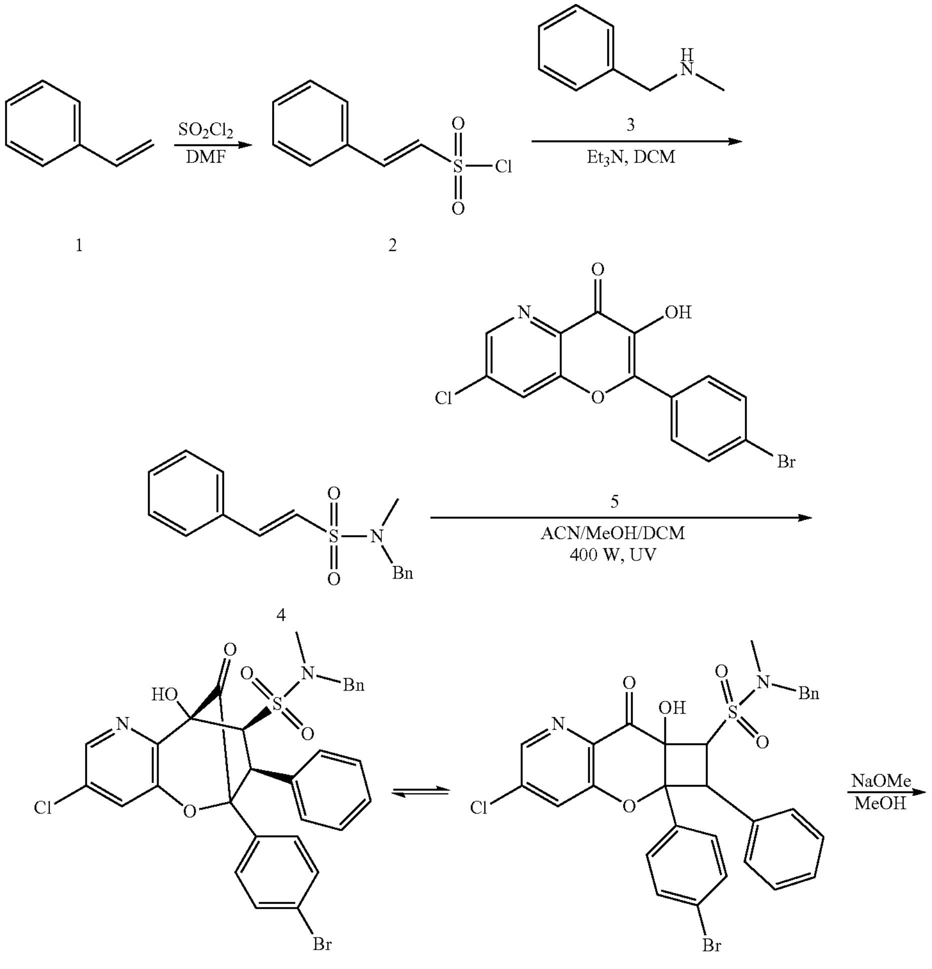

1

2

4

6

6a

-continued

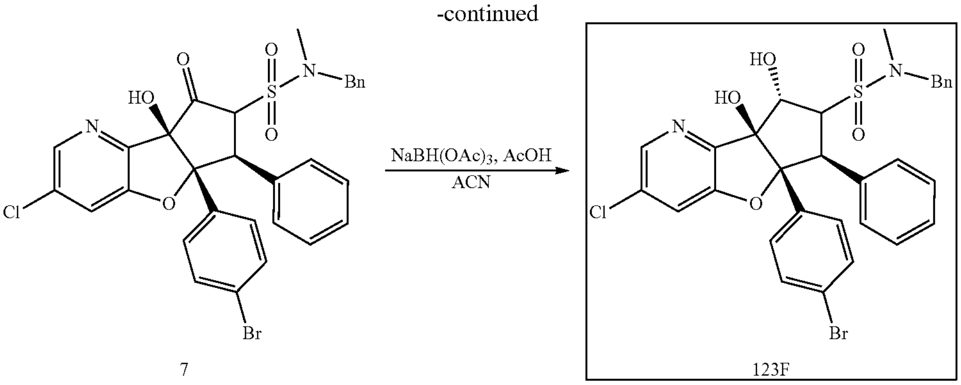

7 123F

Synthesis of ((E)-2-phenylethene-1-sulfonyl chloride (2)

To a solution of styrene (1, 55.00 g, 528.0 mmol) in N,N-dimethylformamide (50 mL) at 0° C., sulfuryl chloride (142.0 g, 1056.1 mmol) was added and the reaction mixture was stirred at room temperature for 2 h. After completion, the mixture was quenched with ice cold water (500 mL) and the mixture was extracted with ethyl acetate (1000 mL). The organic layer was washed with water and brine, separated and dried over anhydrous sodium sulphate, filtered then concentrated under reduced pressure to afford (E)-2-phenylethene-1-sulfonyl chloride (2) as white solid. Yield: 90.0 g, crude.

Synthesis of (E)-N-benzyl-N-methyl-2-phenylethene-1-sulfonamide (4)

To a solution of (E)-2-phenylethene-1-sulfonyl chloride (2, 35.00 g, 173.26 mmol) in dichloromethane (100 mL), triethylamine (25.0 mL, 173.26 mmol) and N-methyl-1-phenylmethanamine (3, 20 mL, 156.0 mmol) were added. The reaction mixture was stirred at room temperature for 16 h. After completion, solvent was removed under reduced pressure. The mixture was quenched with ice cold aqueous solution of sodium bicarbonate (300 mL) and extracted with ethyl acetate (1000 mL). The organic layer was washed with water and brine, dried over anhydrous sodium sulphate, filtered and concentrated under reduced pressure to give crude. The crude was purified by silica gel (100-200 mesh) column chromatography using 50% ethyl acetate in hexanes as eluents. The desired fractions were concentrated under reduced pressure to afford (E)-N-benzyl-N-methyl-2-phenylethene-1-sulfonamide (4) as white solid. Yield: 9.0 g, 18%; MS (ESI) m/z 288.23[M+1]$^+$.

Synthesis of N-benzyl-5a-(4-bromophenyl)-3-chloro-7a-hydroxy-N-methyl-8-oxo-6-phenyl-5a,6,7a,8-tetrahydro-7H-cyclobuta[5,6]pyrano[3,2-b]pyridine-7-sulfonamide (6 & 6a)

A solution of 2-(4-bromophenyl)-7-chloro-3-hydroxy-4H-pyrano[3,2-b]pyridin-4-one (5, 3.0 g, 8.54 mmol) and (E)-N-benzyl-N-methyl-2-phenylethene-1-sulfonamide (4, 7.0 g, 25.64 mmol) in dichloromethane (100 mL), acetonitrile (50 mL) and methanol (50 mL) was placed in a UV reactor flask. The reaction mixture was irradiated under 400 watts UV light for 96 h. After completion, solvent was removed under reduced pressure and the residue was purified over a plug of silica gel (100-200 mesh) eluting the compound with ethyl acetate. The desired fractions were concentrated under reduced pressure to afford N-benzyl-5a-(4-bromophenyl)-3-chloro-7a-hydroxy-N-methyl-8-oxo-6-phenyl-5a,6,7a,8-tetrahydro-7H-cyclobuta[5,6]pyrano[3,2-b]pyridine-7-sulfonamide (6 & 6a) as brown sticky solid. Yield: 1.3 g, crude.

Synthesis of rac-(5aR,6S,8aR)-N-benzyl-5a-(4-bromophenyl)-3-chloro-8a-hydroxy-N-methyl-8-oxo-6-phenyl-5a,7,8,8a-tetrahydro-6H-cyclopenta[4,5]furo[3,2-b]pyridine-7-sulfonamide (7)

The crude compound N-benzyl-5a-(4-bromophenyl)-3-chloro-7a-hydroxy-N-methyl-8-oxo-6-phenyl-5a,6,7a,8-tetrahydro-7H-cyclobuta[5,6]pyrano[3,2-b]pyridine-7-sulfonamide (6 & 6a, 1.30 g) was suspended in methanol (15 mL) and treated with 25% sodium methoxide solution in methanol (15 mL). The reaction was heated at 90° C. for 3 h. After completion, the solvent was removed under reduced pressure. The crude was diluted with ammonium chloride solution and extracted with ethyl acetate. The organic phase was separated, dried over anhydrous sodium sulphate and concentrated under reduced pressure to afford rac-(5aR,6S,8aR)-N-benzyl-5a-(4-bromophenyl)-3-chloro-8a-hydroxy-N-methyl-8-oxo-6-phenyl-5a,7,8,8a-tetrahydro-6H-cyclopenta[4,5]furo[3,2-b]pyridine-7-sulfonamide (7) as brown sticky solid. Yield: 1.3 g, crude.

Synthesis of rac-(5aR,6S,7R,8S,8aS)-N-benzyl-5a-(4-bromophenyl)-3-chloro-8,8a-dihydroxy-N-methyl-6-phenyl-5a, 7,8,8a-tetrahydro-6H-cyclopenta[4,5]furo[3,2-b]pyridine-7-sulfonamide (Cpd. No. 123F)

To a solution of sodium triacetoxyborohydride (1.20 g, 5.64 mmol), rac-(5aR,6S,8aR)-N-benzyl-5a-(4-bromophenyl)-3-chloro-8a-hydroxy-N-methyl-8-oxo-6-phenyl-5a,7,8,8a-tetrahydro-6H-cyclopenta[4,5]furo[3,2-b]pyridine-7-sulfonamide (7, 0.6 g, 0.94 mmol) in acetonitrile (10 mL), acetic acid (0.56 g, 9.40 mmol) was added. The resulting mixture was stirred for 16 h at room temperature. After completion, the reaction mixture was partitioned between saturated aqueous sodium bicarbonate solution and ethyl acetate. The organic layer was separated, dried over anhydrous sodium sulphate, filtered and concentrated under reduced pressure to get the crude. The crude product was purified by Combi-flash (12 g RediSep column) using 50% ethyl acetate in hexanes as eluents. The desired fractions were concentrated under reduced pressure to afford rac-(5aR,6S,7R,8S,8aS)-N-benzyl-5a-(4-bromophenyl)-3-chloro-8,8a-dihydroxy-N-methyl-6-phenyl-5a,7,8,8a-tetrahydro-6H-cyclopenta[4,5]furo[3,2-b]pyridine-7-sulfonamide (Cpd. No. 123F) as brown solid. Yield: 0.23 g, 39.0%; MS (ESI) m/z 641.09[M+1]$^+$; UPLC 98.0%; $^1$H NMR (400 MHz, DMSO-$d_6$)$^8$ 8.21 (d, J=1.9 Hz, 1H), 7.67 (d, J=1.9 Hz. 1H), 7.32-7.29 (m, 3H), 7.26-7.23 (m, 4H), 7.20-7.15 (m, 4H), 7.12-7.02 (m, 3H), 6.36 (s, 1H), 6.02 (s, 1H), 4.99 (dd, J=4.7 Hz, 13.6 Hz, 1H), 4.70 (d, J=3.4 Hz, 1H), 4.59 (d, J=13.7 Hz, 1H), 4.00 (d, J=15.8 Hz, 1H), 3.75 (m, 1H), 2.37 (s, 3H).

Example 124

Rac-(5aR,6S,7R,8S,8aS)-5a-(4-bromophenyl)-3-chloro-8,8a-dihydroxy-N-methyl-6-phenyl-5a,7,8,8a-tetrahydro-6H-cyclopenta[4,5]furo[3,2-b]pyridine-7-sulfonamide (Cpd. No. 124F)

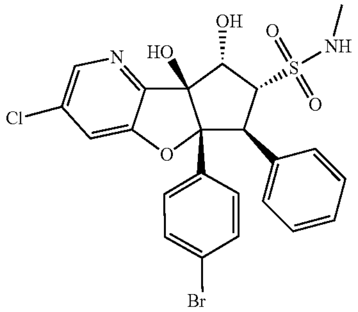

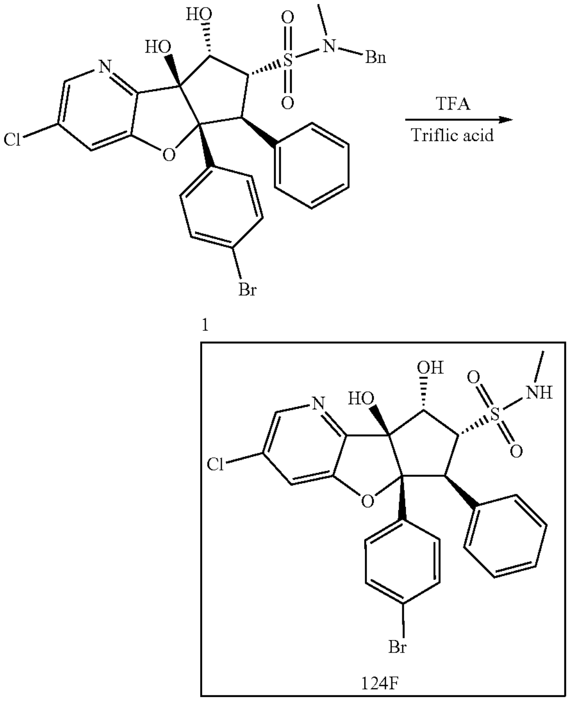

1

124F

Synthesis of rac-(5aR,6S,7R,8S,8aS)-5a-(4-bromophenyl)-3-chloro-8,8a-dihydroxy-N-methyl-6-phenyl-5a,7,8,8a-tetrahydro-6H-cyclopenta[4,5]furo[3,2-b]pyridine-7-sulfonamide (Cpd. No. 124F)

To a solution of rac-(5aR,6S,7R,8S,8aS)-N-benzyl-5a-(4-bromophenyl)-3-chloro-8,8a-dihydroxy-N-methyl-6-phenyl-5a,7,8,8a-tetrahydro-6H-cyclopenta[4,5]furo[3,2-b]pyridine-7-sulfonamide (1, 0.190 g, 0.290 mmol) in dichloromethane (2 mL), trifluoroacetic acid (2.0 mL) and triflic acid (2.0 mL) were added and the reaction was stirred for 3 h at room temperature. After completion, the reaction was diluted with dichloromethane and washed with cold sodium bicarbonate aqueous solution. The organic layer was separated and dried over anhydrous sodium sulphate, filtered and concentrated under reduced pressure to afford rac-(5aR,6S,7R,8S,8aS)-5a-(4-bromophenyl)-3-chloro-8,8a-dihydroxy-N-methyl-6-phenyl-5a,7,8,8a-tetrahydro-6H-cyclopenta[4,5]furo[3,2-b]pyridine-7-sulfonamide (Cpd. No. 124F) as brown solid. Yield: 0.18 g, 92.0%; MS (ESI) m/z 550.9 [M+1]$^+$; UPLC 99.3%; $^1$H NMR (400 MHz, DMSO-$d_6$) δ 8.20 (d, J=1.8 Hz, 1H), 7.66 (d, J=1.8 Hz. 1H), 7.21 (d, J=8.6 Hz, 2H), 7.14 (d, J=8.6 Hz, 4H), 7.08-6.95 (m, 3H), 6.28 (bs. 1H), 6.27-6.25 (m, 1H), 5.84 (bs, 1H), 4.79 (dd, J=4.3 Hz, 13.5 Hz, 1H), 4.69 (m, 1H), 4.55 (d, J=13.6 Hz, 1H), 2.43 (d, J=4.8 Hz, 3H).

Example 125

Rac-(5aR,6S,7R,8S,8aS)-3-chloro-5a-(4-cyanophenyl)-8,8a-dihydroxy-N-methyl-6-phenyl-5a,7,8,8a-tetrahydro-6H-cyclopenta[4,5]furo[3,2-b]pyridine-7-sulfonamide (Cpd No. 125F)

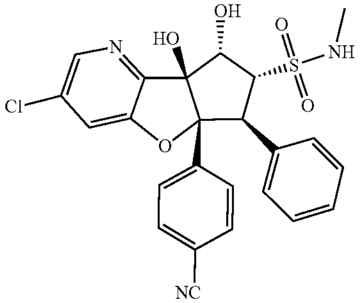

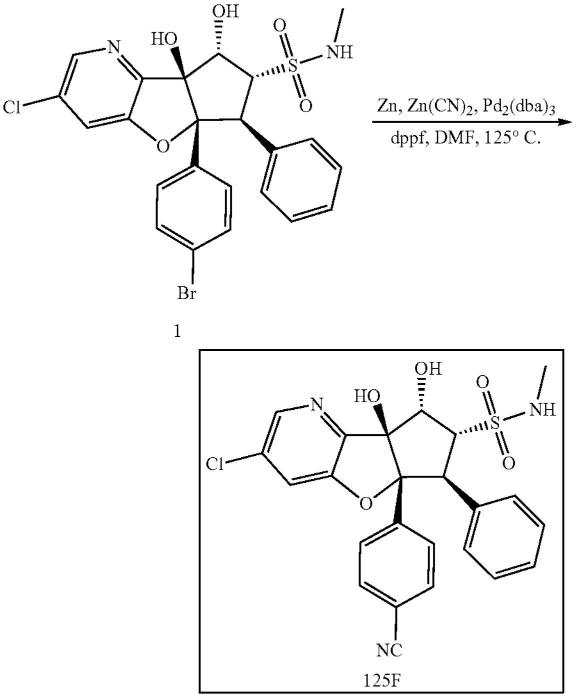

1

125F

Synthesis of rac-(5aR,6S,7R,8S,8aS)-3-chloro-5a-(4-cyanophenyl)-8,8a-dihydroxy-N-methyl-6-phenyl-5a,7,8,8a-tetrahydro-6H-cyclopenta[4,5]furo[3,2-b]pyridine-7-sulfonamide (Cpd. No. 125F)

To a solution of rac-(5aR,6S,7R,8S,8aS)-5a-(4-bromophenyl)-3-chloro-8,8a-dihydroxy-N-methyl-6-phenyl-5a,7,8,8a-tetrahydro-6H-cyclopenta[4,5]furo[3,2-b]pyridine-7-sulfonamide (1, 0.065 g, 0.11 mmol) in N,N-dimethylformamide (3.0 mL), zinc cyanide (0.028 g, 0.23 mmol) and zinc dust (0.031 g, 0.472 mmol) were added at room temperature and the reaction mixture was degassed with argon for 15 min. 1,1'-Bis(diphenylphosphino)ferrocene (1 mg, 0.0024 mmol) and tris(dibenzylideneacetone) dipalladium (2 mg, 0.0024 mmol) were added to the reaction, degassed for additional 5 min and heated the mixture at 125° C. for 6 h. After completion, the reaction mass was diluted with ethyl acetate and washed with cold water. The organic layer was separated and dried over anhydrous sodium sulphate, filtered and concentrated. The crude was purified by Combi-flash (12 g RediSep column) using 3% methanol: dichloromethane as eluent, further it purified by reverse prep HPLC. The desired fractions were lyophilized to afford rac-(5aR,6S,7R,8S,8aS)-3-chloro-5a-(4-cyanophenyl)-8,8a-dihydroxy-N-methyl-6-phenyl-5a,7,8,8a-tetrahydro-6H-cyclopenta[4,5]furo[3,2-b]pyridine-7-sulfonamide (Cpd. No. 125F) as off white solid. Yield: 4 mg, 4% (racemic mixture). MS (ESI) m/z 498.17 $[M+1]^+$; UPLC 98.3%; $^1H$ NMR (400 MHz, DMSO-$d_6$) δ 8.21 (s, 1H), 7.70 (s, 1H), 7.49 (d, J=8.2 Hz, 2H), 7.40 (d, J=8.2 Hz, 2H), 7.16 (d, J=7.4 Hz, 2H), 7.01 (t, J=7.2 Hz, 3H), 6.41 (s, 1H), 6.30 (d, J=4.3 Hz, 1H), 5.90 (d, J=5.9 Hz, 1H), 4.90 (dd, J=4.0 Hz, 13.4 Hz, 1H), 4.69 (m, 1H), 4.60 (d, J=13.8, 1H), 2.50 (s, 3H).

Example 126

4-((4bS,5S,6R,7S,7aR)-4b,5-dihydroxy-4-methoxy-6-(morpholinosulfonyl)-7-phenyl-4b,5,6,7-tetrahydro-7aH-cyclopenta[4,5]furo[2,3-c]pyridin-7a-yl) benzonitrile (Cpd. No. 126F)

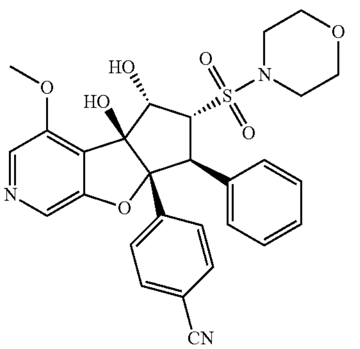

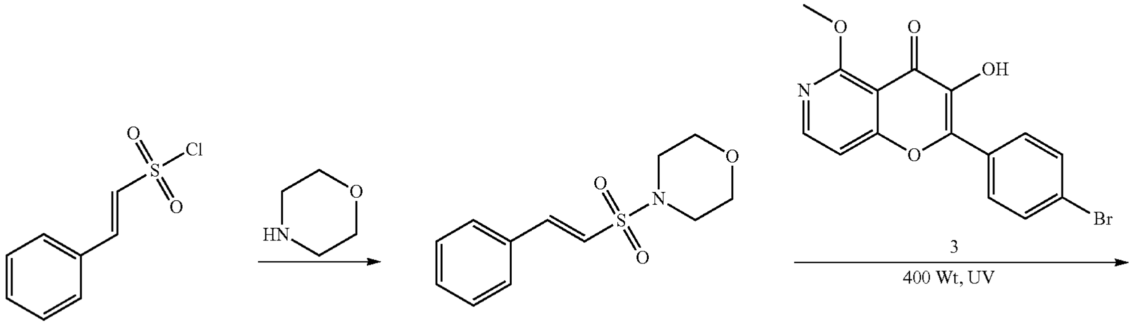

1

2

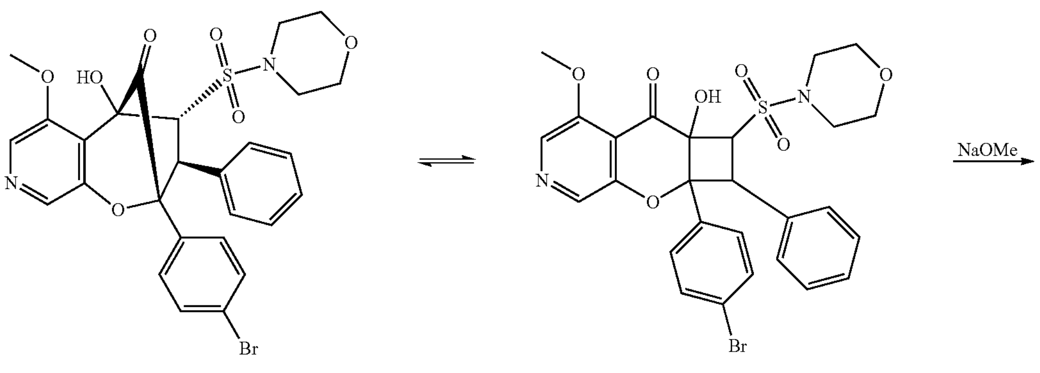

4

4a

-continued

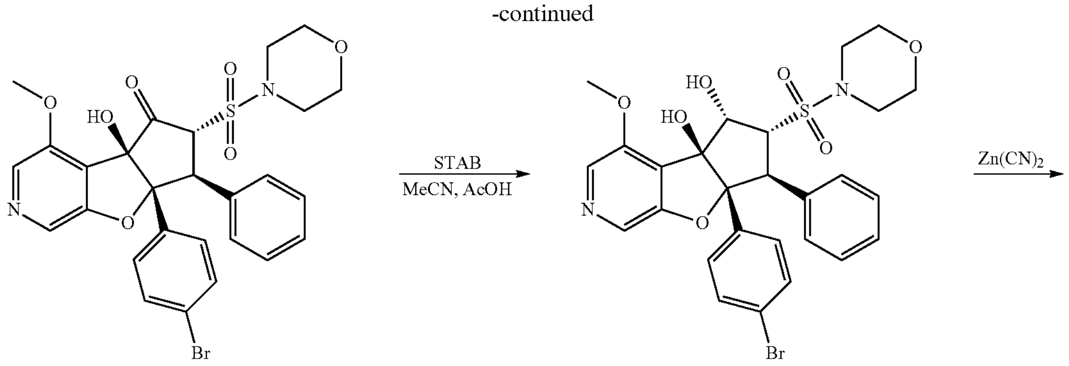

5 6

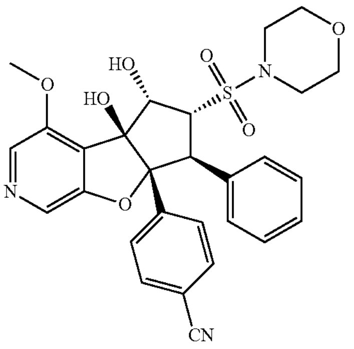

126F

Synthesis of (E)-4-(styrylsulfonyl)morpholine (2)

To a solution of morpholine, (0.65 mL, 355.3 mmol) in dichloromethane (700 mL) at 0° C., triethylamine (109.4 mL, 888.2 mmol) and solution of (E)-2-phenylethene-1-sulfonyl chloride (1, 60.0 mL, 296.0 mmol) in dichloromethane was added drop wise over a period of 15 min. The reaction mass was slowly brought to room temperature and stirred for additional 16 h. After completion, the reaction mass was diluted with dichloromethane (500 mL) and water (250 mL). The organic layer was separated, washed with water, dried over anhydrous sodium sulfate, filtered and concentrated under reduced pressure. The crude was purified by silica gel column chromatography using 20% ethyl acetate in hexanes as eluent. The desired fractions were concentrated to afford (E)-4-(styrylsulfonyl)morpholine (2) as white solid. Yield: 38.0 g, 50.6%; MS (ESI) m/z 254.19 $[M-1]^-$.

Synthesis of rac-(3S,4S,5R)-2-(4-bromophenyl)-5-hydroxy-6-methoxy-4-(morpholinosulfonyl)-3-phenyl-2,3,4,5-tetrahydro-2,5-methanooxepino[2,3-c]pyridin-10-one (4)

A solution of 2-(4-bromophenyl)-3-hydroxy-5-methoxy-4H-pyrano[2,3-c]pyridin-4-one (3, 5.0 g, 14.36 mmol) and (E)-4-(styrylsulfonyl)morpholine (2, 36.86 g, 113.4 mmol) in dichloromethane (150 mL), acetonitrile (150 mL) and methanol (150 mL) was placed in a UV reactor flask. The reaction mixture was irradiated under 400 watts UV light for 72 h. After completion, solvent was removed under reduced pressure and the residue was purified over a plug of silica gel eluting the compound with ethyl acetate. The desired fractions were concentrated under reduced pressure to afford rac-(3S,4S,5R)-2-(4-bromophenyl)-5-hydroxy-6-methoxy-4-(morpholinosulfonyl)-3-phenyl-2,3,4,5-tetrahydro-2,5-methanooxepino[2,3-c]pyridin-10-one (4) as yellow brown solid. Yield: 4.05 g, crude. MS (ESI) m/z 601.42$[M-1]^+$.

Synthesis of rac-(4bR,6R,7S,7aR)-7a-(4-bromophenyl)-4b-hydroxy-4-methoxy-6-(morpholinosulfonyl)-7-phenyl-4b,6,7,7a-tetrahydro-5H-cyclopenta[4,5]furo[2,3-c]pyridin-5-one (5)

A solution of rac-(3S,4S,5R)-2-(4-bromophenyl)-5-hydroxy-6-methoxy-4-(morpholinosulfonyl)-3-phenyl-2,3,4,5-tetrahydro-2,5-methanooxepino[2,3-c]pyridin-10-one (4, 2.0 g, 3.32 mmol) was suspended in methanol (40 mL) and treated with 25% sodium methoxide in methanol (7.1 mL, 33.25). The reaction was heated at 80° C. for 4 h. After completion, the solvent was removed under reduced pressure. The crude was diluted with ammonium chloride solution and extracted with ethyl acetate. The organic phase was separated, dried over anhydrous sodium sulphate and concentrated under reduced pressure to afford rac-(4bR,6R,7S,7aR)-7a-(4-bromophenyl)-4b-hydroxy-4-methoxy-6-(morpholinosulfonyl)-7-phenyl-4b,6,7,7a-tetrahydro-5H-cyclopenta[4,5]furo[2,3-c]pyridin-5-one (5) as brown solid. Yield: 1.8 g, crude; MS (ESI) m/z 601.31 $[M+1]^+$.

Synthesis of rac-(4bS,5S,6R,7S,7aR)-7a-(4-bromophenyl)-4-methoxy-6-(morpholinosulfonyl)-7-phenyl-5,6,7,7a-tetrahydro-4bH-cyclopenta[4,5]furo[2,3-c]pyridine-4b, 5-diol (6)

A solution of rac-(4bR,6R,7S,7aR)-7a-(4-bromophenyl)-4b-hydroxy-4-methoxy-6-(morpholinosulfonyl)-7-phenyl- 4b,6,7,7a-tetrahydro-5H-cyclopenta[4,5]furo[2,3-c]pyridin-5-one (5, 2.0 g, 3.32 mmol) in acetonitrile (40 mL) was cooled at 0° C., acetic acid (1.99 g, 33.25 mmol) and sodium triacetoxyborohydride (7.21 g, 33.25 mmol) were added. The resulting mixture was stirred for 12 h at room temperature. After completion, the reaction mixture was partitioned between saturated aqueous sodium bicarbonate solution and ethyl acetate. The organic layer was separated and dried over sodium sulphate, filtered and concentrated to give crude. The crude was purified by silica gel column chromatography eluting with 2-3% in methanol in dichloromethane. The desired fractions were concentrated to afford rac-(4bS,5S,6R,7S,7aR)-7a-(4-bromophenyl)-4-methoxy-6-(morpholinosulfonyl)-7-phenyl-5,6,7,7a-tetrahydro-4bH-cyclopenta[4,5]furo[2,3-c]pyridine-4b,5-diol (6) as white solid. Yield: 0.4 g, 20%; MS (ESI) m/z 601.41$[M-1]^-$.

Synthesis of 4-((4bR,5R,7S,7aR)-4b-hydroxy-5-(hydroxymethyl)-4-methoxy-7-phenyl-4b,5,6,7-tetrahydro-7aH-cyclopenta[4,5]furo[2,3-c]pyridin-7a-yl)benzonitrile (Cpd. No. 126F)

To a solution of rac-(4bS,5S,6R,7S,7aR)-7a-(4-bromophenyl)-4-methoxy-6-(morpholinosulfonyl)-7-phenyl-5,6,7,7a-tetrahydro-4bH-cyclopenta[4,5]furo[2,3-c]pyridine-4b,5-diol (6, 0.4 g, 0.662 mmol) in N,N-dimethylformamide (8.0 mL), zinc cyanide (0.468 g, 3.97 mmol) and zinc (0.0052 g, 0.079 mmol) were added at room temperature and degassed the mixture with argon for 15 min. 1,1'-Bis(diphenylphosphino)ferrocene (0.0096 g, 0.0132 mmol) and tris (dibenzylideneacetone)dipalladium (0.0018 g, 0.00199 mmol) were added to the reaction and degassing was continued for another 5 min. The reaction mixture was heated at 140° C. for 3 h. After completion, the reaction mass was diluted with ethyl acetate and washed with cold water. The organic layer was separated and dried over sodium sulphate, filtered and concentrated to give crude. The crude was purified by silica gel column chromatography eluting with 2-3% methanol in dichloromethane. The desired fractions were concentrated to afford rac-4-((4bS,5S,6R,7S,7aR)-4b,5-dihydroxy-4-methoxy-6-(morpholinosulfonyl)-7-phenyl-4b,5,6,7-tetrahydro-7aH-cyclopenta[4,5]furo[2,3-c]pyridin-7a-yl)benzonitrile as white solid. Yield: 0.28 g, 77%. (Racemic mixture); MS (ESI) m/z 550.41 $[M+1]^+$; The enantiomers were separated by chiral preparative HPLC [chiralpak IA (4.6×250) mm, 5μ] with isocratic hexane/Ethanol 25/75 v/v to afford Peak 1 (Cpd. No. 126F, 50 mg), $[\alpha]_D$+49.5° (c 0.20, DMSO), $R_t$=8.916 min, ee >99% $^1H$ NMR (400 MHz, DMSO-$d_6$) δ 8.07 (s, 1H), 7.99 (s, 1H), 7.51 (m, 4H), 7.14 (d, J=7.28 Hz, 2H), 7.06 (m, 3H), 6.02 (bs, 2H), 4.96 (dd, J=3.88 Hz, J=3.96 Hz, 1H), 4.72 (d, J=3.72 Hz, 1H), 4.49 (d, J=13.72 Hz, 1H), 3.88 (s, 3H), 3.41 (m, 4H), 2.96 (d, J=12.88 Hz, 2H), 2.86 (d, J=8.4 Hz, 2H); Peak-2 (50 mg), $[\alpha]_D$−47.5° (c 0.29, DMSO), $R_t$=22.074 min, ee >97% $^1H$ NMR (400 MHz, DMSO-$d_6$) δ 8.07 (s, 1H), 7.99 (s, 1H), 7.50 (m, 4H), 7.14 (d, J=7.2 Hz, 2H), 7.05 (m, 3H), 6.02 (bs, 2H), 4.95 (dd, J=9.64 Hz, 1H), 4.72 (d, J=4.04 Hz, 1H), 4.49 (d, J=13.68 Hz, 1H), 3.88 (s, 3H), 3.40 (m, 4H), 2.97 (d, J=9.92 Hz, 2H), 2.86 (d, J=5.76 Hz, 2H).

Example 127

Rac-(5aR,6S,8R,8aS)-5a-(4-bromophenyl)-3-chloro-6-phenyl-5a,6,7,8-tetrahydro-8aH-cyclopenta[4,5]furo[3,2-b]pyridine-8,8a-diol (Cpd. No. 127F)

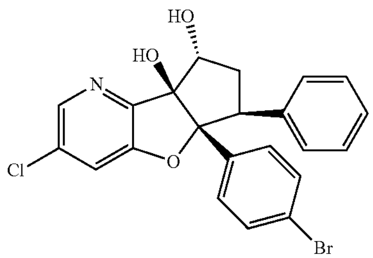

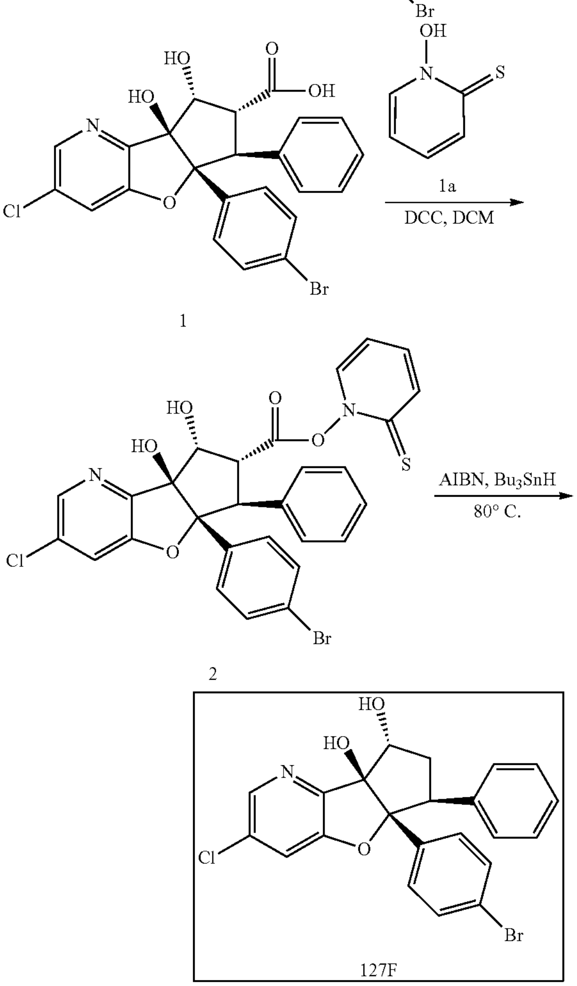

1

2

127F

Synthesis of rac-2-thioxopyridin-1(2H)-yl (5aR,6S,7R,8R,8aS)-5a-(4-bromophenyl)-3-chloro-8,8a-dihydroxy-6-phenyl-5a,7,8,8a-tetrahydro-6H-cyclopenta[4,5]furo[3,2-b]pyridine-7-carboxylate (2)

To a mixture of rac-(5aR,6S,7R,8R,8aS)-5a-(4-bromophenyl)-3-chloro-8,8a-dihydroxy-6-phenyl-5a,7,8,8a-tetrahydro-6H-cyclopenta[4,5]furo[3,2-b]pyridine-7-carboxylic acid (1, 350 mg, 0.70 mmol) and 1-hydroxypyridine-2(1H)-thione (1a, 443 mg, 3.48 mmol) in dichloromethane (10 mL) was added N,N'-Dicyclohexylcarbodiimide (0.16 mL, 1.04 mmol) and stirred vigorously for 4 h. LCMS analysis showed complete consumption of the acid starting material and desired product was observed. The reaction mixture was filtered to remove the urea and concentrated to provide the crude desired product, rac-2-thioxopyridin-1(2H)-yl (5aR,6S,7R,8R,8aS)-5a-(4-bromophenyl)-3-chloro-8,8a-dihydroxy-6-phenyl-5a,7,8,8a-tetrahydro-6H-cyclopenta[4,5]furo[3,2-b]pyridine-7-carboxylate (2). MS (ESI) m/z 611.2[M+1]$^+$. The crude product was used directly in the following step.

Synthesis of rac-(5aR,6S,8R,8aS)-5a-(4-bromophenyl)-3-chloro-6-phenyl-5a,6,7,8-tetrahydro-8aH-cyclopenta[4,5]furo[3,2-b]pyridine-8,8a-diol (Cpd. No. 127F)

The crude material, rac-2-thioxopyridin-1(2H)-yl (5aR,6S,7R,8R,8aS)-5a-(4-bromophenyl)-3-chloro-8,8a-dihydroxy-6-phenyl-5a,7,8,8a-tetrahydro-6H-cyclopenta[4,5]furo[3,2-b]pyridine-7-carboxylate (2) in benzene (50 mL) was treated with tributylstannane (0.55 mL, 2.03 mmol) and azobisisobutyronitrile (22 mg, 0.14 mmol) and heated 80° C. and stirred vigorously in the absence of light for 3 h. After which time the reaction mixture was concentrated in-vacuo, re-dissolved in N,N-dimethylformamide and filtered through a 5 micron membrane. The crude material was purified by reverse phase HPLC to afford rac-(5aR,6S,8R,8aS)-5a-(4-bromophenyl)-3-chloro-6-phenyl-5a,6,7,8-tetrahydro-8aH-cyclopenta[4,5]furo[3,2-b]pyridine-8,8a-diol (Cpd. No. 127F) as a white solid. Yield: 0.031 g, 10%; MS (ESI) m/z 460.1[M+1]$^+$; $^1$H NMR (300 MHz, Chloroform-d) δ 8.23 (s, 1H), 7.69 (s, 1H), 7.30-7.26 (m, 2H), 7.21-7.13 (m, 3H), 7.05-7.01 (m, 4H), 5.01 (dd, J=5.7, 3.4 Hz, 1H), 4.20 (dd, J=11.6, 6.7 Hz, 1H), 2.89-2.78 (m, 1H).

Example 128

Rac-4-((5aR,6S,8R,8aS)-3-chloro-8,8a-dihydroxy-6-phenyl-6,7,8,8a-tetrahydro-5aH-cyclopenta[4,5]furo[3,2-b]pyridin-5a-yl)benzonitrile (Cpd. No. 128F)

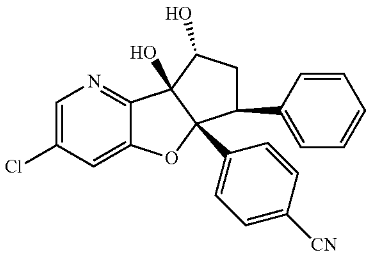

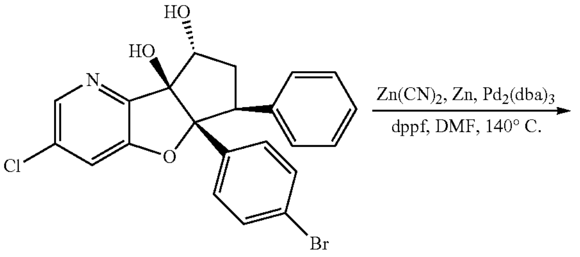

1

-continued

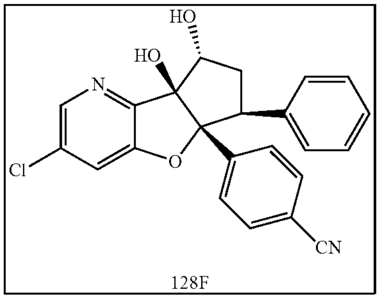

128F

Synthesis of rac-4-((5aR,6S,8R,8aS)-3-chloro-8,8a-dihydroxy-6-phenyl-6,7,8,8a-tetrahydro-5aH-cyclopenta[4,5]furo[3,2-b]pyridin-5a-yl)benzonitrile (Cpd. No. 128F)

To a solution of rac-(5aR,6S,8R,8aS)-5a-(4-bromophenyl)-3-chloro-6-phenyl-5a,6,7,8-tetrahydro-8aH-cyclopenta[4,5]furo[3,2-b]pyridine-8,8a-diol (1, 1a mg, 0.020 mmol) in N,N-dimethylformamide (3 mL), zinc cyanide (17 mg, 0.14 mmol) and zinc (1 mg, 0.015 mmol) were added and degassed the mixture with nitrogen for 15 min. 1,1'-Bis(diphenylphosphino)ferrocene (1 mg, 0.0015 mmol), tris(dibenzylideneacetone)dipalladium (1 mg, 0.0011 mmol) were added to the above reaction and degassing was continued for another 5 min followed by heating the reaction mixture at 140° C. for 1 h. After completion, the reaction was cooled to room temperature and filtered. The filtrate was purified by reverse phase prep HPLC to provide the desired product then purified by preparatory thin layer chromatography (dichloromethane/MeOH) and prep HPLC to afford rac-4-((5aR,6S,8R,8aS)-3-chloro-8,8a-dihydroxy-6-phenyl-6,7,8,8a-tetrahydro-5aH-cyclopenta[4,5]furo[3,2-b]pyridin-5a-yl)benzonitrile (Cpd. No. 128F) as a white powder. Yield: 0.0015 g, 15.6%; MS (ESI) m/z 405.1 [M+1]$^+$; $^1$H NMR (300 MHz, Chloroform-d) δ 8.21 (s, 1H), 7.62 (s, 1H), 7.47-7.38 (m, 2H), 7.36-7.26 (m, 2H), 7.17-7.12 (m, 3H), 7.01-6.97 (m, 2H), 5.00 (dd, J=5.7, 2.7 Hz, 1H), 4.23 (dd, J=12.4, 6.7 Hz, 1H), 2.87 (td, J=13.2, 5.6 Hz, 1H), 2.38-2.30 (m, 1H).

Example 129

Rac-(5aR,6S,8aR)-5a-(4-bromophenyl)-3-chloro-8a-hydroxy-6-phenyl-5a,6,7,8a-tetrahydro-8H-cyclopenta[4,5]furo[3,2-b]pyridin-8-one (Cpd. No. 129F)

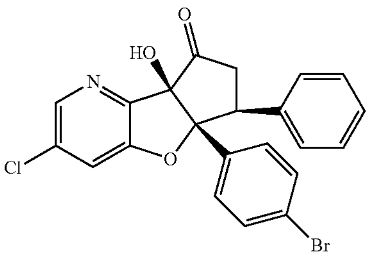

-continued

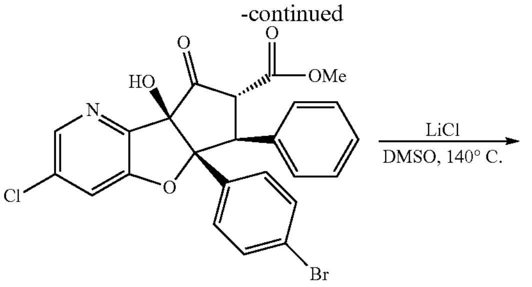

1

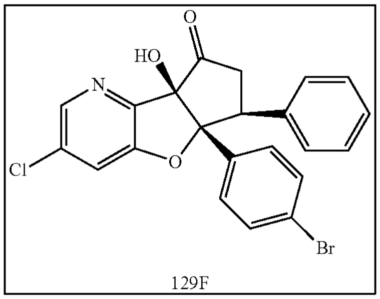

129F

Synthesis of rac-(5aR,6S,8aR)-5a-(4-bromophenyl)-3-chloro-8a-hydroxy-6-phenyl-5a,6,7,8a-tetrahydro-8H-cyclopenta[4,5]furo[3,2-b]pyridin-8-one (Cpd. No. 129F)

A mixture of rac-methyl (5aR,6S,7R,8aR)-5a-(4-bromophenyl)-3-chloro-8a-hydroxy-8-oxo-6-phenyl-5a,7,8,8a-tetrahydro-6H-cyclopenta[4,5]furo[3,2-b]pyridine-7-carboxylate(1, 500 mg, 0.97 mmol) and lithium chloride (0.21 mL, 1.94 mmol) in dimethyl sulfoxide (5 mL) was heated to 140° C. and stirred for 4 h. LCMS analysis of the reaction mixture showed complete conversion to the desired product. The reaction mixture was directly purified by prep HPLC to afford rac-(5aR,6S,8aR)-5a-(4-bromophenyl)-3-chloro-8a-hydroxy-6-phenyl-5a,6,7,8a-tetrahydro-8H-cyclopenta[4,5]furo[3,2-b]pyridin-8-one (Cpd. No. 129F) as a white powder. Yield: 0.350 g, 79%; MS (ESI) m/z 458.1 $[M+1]^+$; $^1H$ NMR (300 MHz, Chloroform-d) δ 8.30 (d, J=1.9 Hz, 1H), 7.52 (d, J=2.0 Hz, 1H), 7.35-7.30 (m, 2H), 7.21-7.16 (m, 3H), 6.99-6.93 (m, 4H), 3.91-3.76 (m, 2H), 3.10 (dd, J=10.9, 1.9 Hz, 2H).

Example 130

Rac-(5aR,6S,8S,8aS)-5a-(4-bromophenyl)-3-chloro-6-phenyl-5a,6,7,8-tetrahydro-8aH-cyclopenta[4,5]furo[3,2-b]pyridine-8,8a-diol (Cpd. No. 130F)

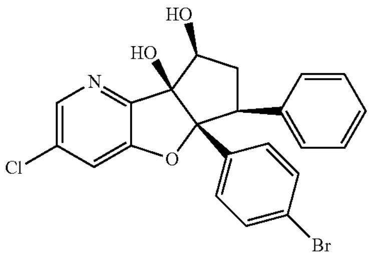

-continued

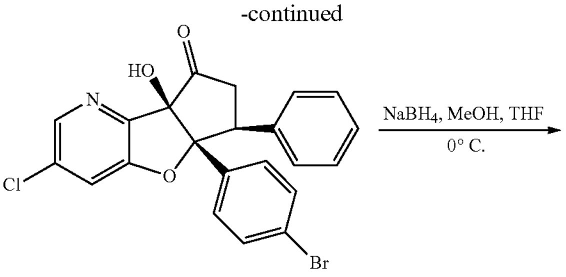

1

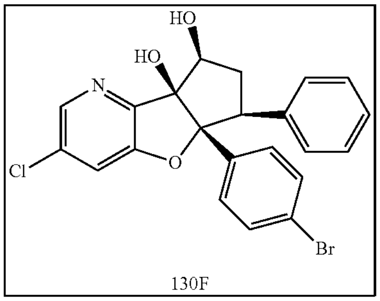

130F

Synthesis of rac-(5aR,6S,8S,8aS)-5a-(4-bromophenyl)-3-chloro-6-phenyl-5a,6,7,8-tetrahydro-8aH-cyclopenta[4,5]furo[3,2-b]pyridine-8,8a-diol (Cpd. No. 130F)

To a solution of rac-(5aR,6S,8aR)-5a-(4-bromophenyl)-3-chloro-8a-hydroxy-6-phenyl-5a,6,7,8a-tetrahydro-8H-cyclopenta[4,5]furo[3,2-b]pyridin-8-one (1, 43 mg, 0.09 mmol) in methanol (1 mL) and THF (1 mL) was added sodium borohydride (11 mg, 0.28 mmol) at 0° C. After stirring for 1 h, the reaction mixture was quenched by addition of saturated aqueous $NH_4Cl$ (50 mL). The mixture was extracted with EtOAc (3×50 mL), washed with brine (50 mL), dried over $Na_2SO_4$. The crude material was purified by prep HPLC to afford rac-(5aR,6S,8S,8aS)-5a-(4-bromophenyl)-3-chloro-6-phenyl-5a,6,7,8-tetrahydro-8aH-cyclopenta[4,5]furo[3,2-b]pyridine-8,8a-diol (Cpd. No. 130F) as a white solid. Yield: 0.023 g, 53%; MS (ESI) m/z 476.35$[M+1]^+$; $^1H$ NMR (300 MHz, Chloroform-d) δ 8.22 (s, 1H), 7.60 (d, J=1.8 Hz, 1H), 7.38-7.25 (m, 2H), 7.19-7.05 (m, 5H), 6.96 (dd, J=6.7, 2.9 Hz, 2H), 4.91-4.79 (m, 1H), 3.37 (dd, J=14.9, 6.5 Hz, 1H), 2.70 (dt, J=13.9, 7.1 Hz, 11H), 2.48 (td, J=14.2, 8.6 Hz, 1H).

Example 131

Rac-4-((5aR,6S,8S,8aS)-3-chloro-8,8a-dihydroxy-6-phenyl-6,7,8,8a-tetrahydro-5aH-cyclopenta[4,5]furo[3,2-b]pyridin-5a-yl)benzonitrile (Cpd. No. 131F)

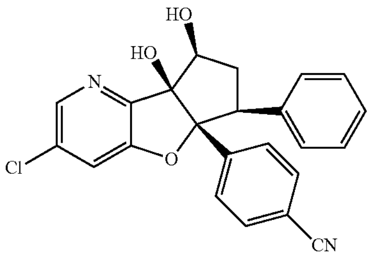

-continued

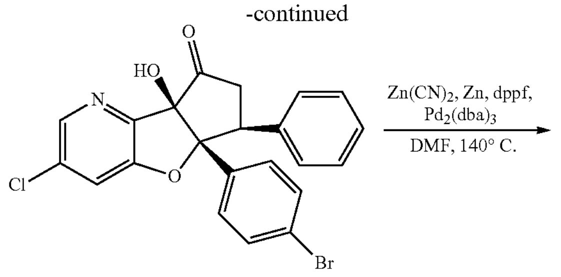

1

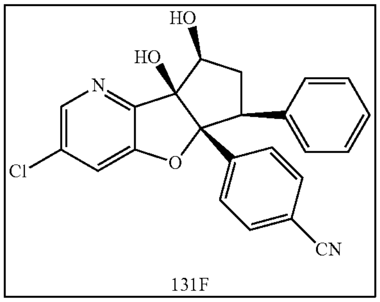

131F

Synthesis of rac-4-((5aR,6S,8S,8aS)-3-chloro-8,8a-dihydroxy-6-phenyl-6,7,8,8a-tetrahydro-5aH-cyclopenta[4,5]furo[3,2-b]pyridin-5a-yl)benzonitrile (Cpd. No. 131F)

A mixture of rac-(5aR,6S,8S,8aS)-5a-(4-bromophenyl)-3-chloro-6-phenyl-5a,6,7,8-tetrahydro-8aH-cyclopenta[4,5]furo[3,2-b]pyridine-8,8a-diol (1, 19.4 mg, 0.04000 mmol), zinc cyanide (29.79 mg, 0.25000 mmol) and zinc (0.41 mg, 0.01000 mmol) in N,N-dimethylformamide (3 mL) was degassed with nitrogen for 15 min. Bis(diphenylphosphino)ferrocene (0.47 mg, 0 mmol), tris(dibenzylideneacetone)-dipalladium (1.16 mg, 0 mmol) were added and degassed for another 5 min followed by heating the reaction mixture at 140° C. for 1 h. After completion, the reaction was cooled to room temperature and filtered. The filtrate was purified by reverse phase prep HPLC to afford rac-4-((5aR,6S,8S,8aS)-3-chloro-8,8a-dihydroxy-6-phenyl-6,7,8,8a-tetrahydro-5aH-cyclopenta[4,5]furo[3,2-b]pyridin-5a-yl)benzonitrile (Cpd. No. 131F) as a white solid. Yield: 0.006 g, 35%; MS (ESI) m/z 405.0[M+1]$^+$; $^1$H NMR (300 MHz, Chloroform-d) δ 8.23 (s, 1H), 7.52 (d, J=1.6 Hz, 1H), 7.41 (d, J=41.6 Hz, 4H), 7.11 (t, J=3.2 Hz, 3H), 6.96-6.88 (m, 2H), 4.86 (t, J=7.7 Hz, 1H), 3.41 (dd, J=14.7, 6.7 Hz, 1H), 2.76-2.63 (m, 1H), 1.25 (s, 1H).

Example 132

Rac-N'-((5aR,6S,8aS)-5a-(4-bromophenyl)-3-chloro-8a-hydroxy-6-phenyl-5a,6,7,8a-tetrahydro-8H-cyclopenta[4,5]furo[3,2-b]pyridin-8-ylidene)-4-methylbenzenesulfonohydrazide (Cpd. No. 132F)

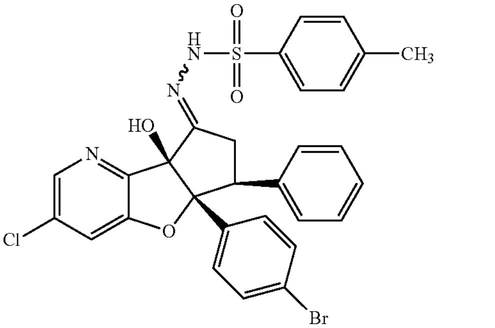

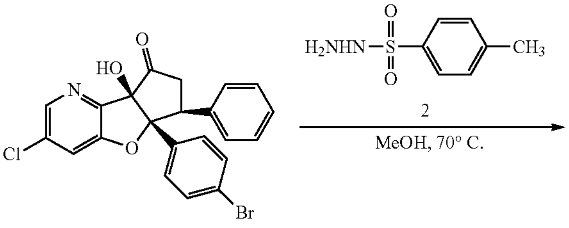

1

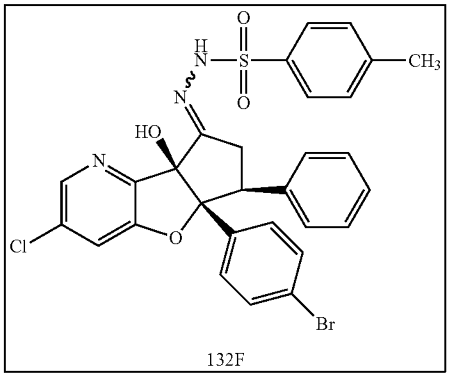

132F

Synthesis of rac-N'-((5aR,6S,8aS)-5a-(4-bromophenyl)-3-chloro-8a-hydroxy-6-phenyl-5a,6,7,8a-tetrahydro-8H-cyclopenta[4,5]furo[3,2-b]pyridin-8-ylidene)-4-methylbenzenesulfonohydrazide (Cpd. No. 132F)

To a solution of rac-(5aR,6S,8aR)-5a-(4-bromophenyl)-3-chloro-8a-hydroxy-6-phenyl-5a,6,7,8a-tetrahydro-8H-cyclopenta[4,5]furo[3,2-b]pyridin-8-one (1, 194. mg, 0.42000 mmol) in methanol (3 mL) was added 4-methylbenzene-sulfonohydrazide (2, 87.01 mg, 0.47000 mmol) and the reaction was allowed to stir for 6 h at 70° C. Upon cooling the product precipitated. The product was filtered and washed with diethyl ether to afford rac-N'-((5aR,6S,8aS)-5a-(4-bromophenyl)-3-chloro-8a-hydroxy-6-phenyl-5a,6,7,8a-tetrahydro-8H-cyclopenta[4,5]furo[3,2-b]pyridin-8-ylidene)-4-methylbenzenesulfonohydrazide (Cpd. No. 132F) as a white solid. Yield: 0.090 g, 34%; MS (ESI) m/z 476.35[M+1]$^+$; $^1$H NMR (300 MHz, DMSO-$d_6$) δ 10.60 (s, 1H), 8.31 (d, J=2.0 Hz, 1H), 7.98-7.83 (m, 3H), 7.48 (d, J=8.1 Hz, 2H), 7.36-7.25 (m, 2H), 7.11 (qd, J=5.4, 4.8, 3.1 Hz, 3H), 6.98-6.81 (m, 4H), 6.26 (s, 1H), 3.57 (dd, J=12.1, 9.6 Hz, 1H), 3.16-2.90 (m, 2H), 2.45 (s, 3H).

Example 133

Rac-(5aR,6S,8aR)-5a-(4-bromophenyl)-3-chloro-6-phenyl-5a,6-dihydro-8aH-cyclopenta[4,5]furo[3,2-b]pyridin-8a-ol (Cpd. No. 133F)

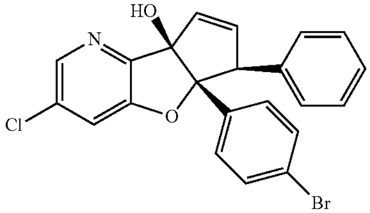

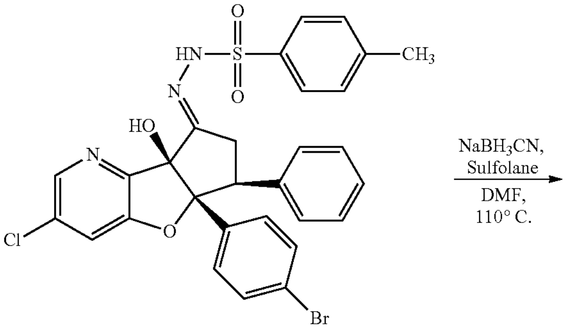

1

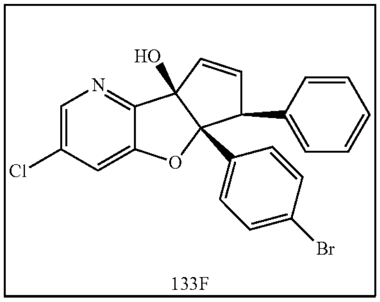

133F

Synthesis of rac-(5aR,6S,8aR)-5a-(4-bromophenyl)-3-chloro-6-phenyl-5a,6-dihydro-8aH-cyclopenta[4,5]furo[3,2-b]pyridin-8a-ol (Cpd. No. 133F)

A solution of rac-N'-((5aR,6S,8aS)-5a-(4-bromophenyl)-3-chloro-8a-hydroxy-6-phenyl-5a,6,7,8a-tetrahydro-8H-cyclopenta[4,5]furo[3,2-b]pyridin-8-ylidene)-4-methylbenzenesulfonohydrazide (1, 50 mg, 0.08000 mmol) in dimethylformide (1 mL) and sulfolane (1 mL, 0.08000 mmol) was treated with sodium cyanoborohydride (24.32 mg, 0.64000 mmol) and the reaction was heated to 110° C. for 4 h. Analysis of the reaction by LCMS showed consumption of the starting material and a mass of the product. Water (0.1 mL) was added and the reaction mixture was directly purified by prep HPLC then normal phase flash column chromatography to afford rac-(5aR,6S,8aR)-5a-(4-bromophenyl)-3-chloro-6-phenyl-5a,6-dihydro-8aH-cyclopenta[4,5]furo[3,2-b]pyridin-8a-ol (Cpd. No. 133F) as a white solid. Yield: 0.002 g, 35%; MS (ESI) m/z 476.35[M+1]$^+$; $^1$H NMR (400 MHz, Chloroform-d) δ 8.11 (d, J=1.9 Hz, 1H), 7.57-7.45 (m, 1H), 7.42-7.09 (m, 5H), 7.06-6.95 (m, 3H), 6.41 (ddd, J=20.7, 5.9, 2.2 Hz, 2H), 5.32 (s, 6H), 4.52 (t, J=2.2 Hz, 1H).

Example 134

Rac-Methyl (4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylate (Cpd. No. 134F)

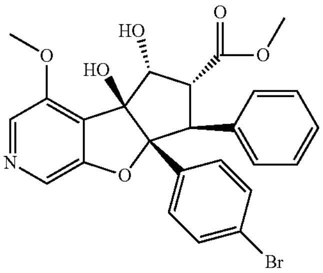

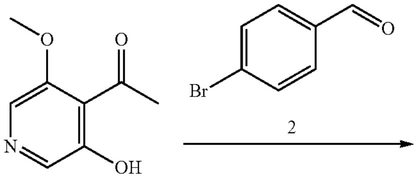

1

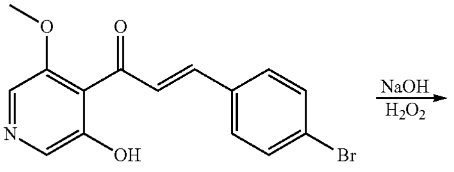

3

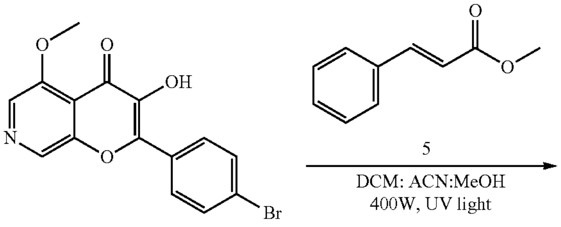

4

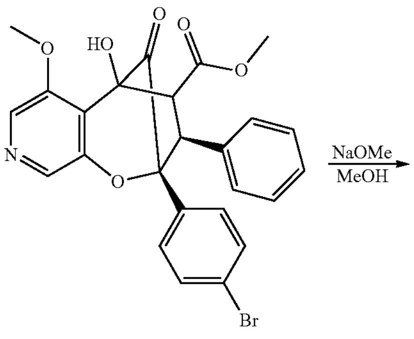

6

-continued

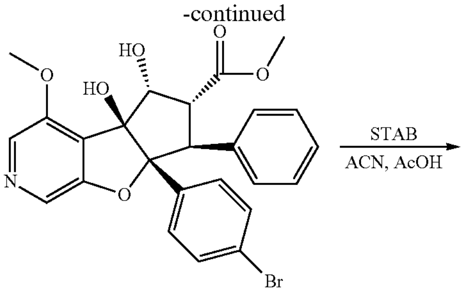

7

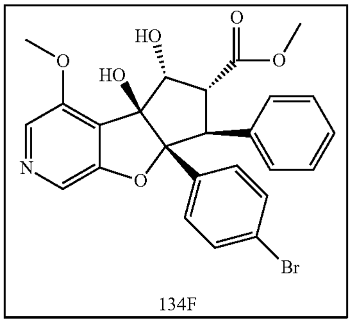 [SMILES: COC(=O)[C@H]1[C@@H](O)[C@@]2(O)c3c(OC)cncc3O[C@@]2(c2ccc(Br)cc2)[C@@H]1c1ccccc1]

134F

Synthesis of (E)-3-(4-bromophenyl)-1-(3-hydroxy-5-methoxypyridin-4-yl)prop-2-en-1-one (3)

To a solution of 1-(3-hydroxy-5-methoxypyridin-4-yl) ethan-1-one (1, 200.0 g, 1.197 mol) in methanol (1000 mL), sodium hydroxide (143.7 g, 3.59 mmol) was added followed by addition of 4-bromobenzaldehyde (2, 221.56 g, 1197.57 mmol). The reaction was heated to reflux for 30 min. After completion, the reaction mass was cooled to room temperature, diluted with water (2000 mL). Solid obtained was filtered and dried. The solid obtained was triturated with pentane, filtered and dried under vacuum to afford (E)-3-(4-bromophenyl)-1-(3-hydroxy-5-methoxypyridin-4-yl)prop-2-en-1-one (3) as yellow solid. Yield: 400.0 g, 96%; MS (ESI) m/z 332.0$[M-1]^-$.

Synthesis of 2-(4-bromophenyl)-3-hydroxy-5-methoxy-4H-pyrano[2,3-c]pyridin-4-one (4)

To a solution of (E)-3-(4-bromophenyl)-1-(3-hydroxy-5-methoxypyridin-4-yl)prop-2-en-1-one (3, 5×40 g, 600.06 mmol) in ethanol (6.0 L) at 0° C., sodium hydroxide (28.8 g, 720.72 mmol) was added followed by the addition of 30% aqueous hydrogen peroxide (429.25 mL, 4204.2 mmol). The reaction mixture was heated at 60° C. for 30 min. After completion, the reaction mixture was cooled and neutralized to pH ~7 by the addition of 6 M hydrogen chloride. The solid obtained was filtered and dried to get crude compound. The crude product obtained was triturated with ethanol, filtered and dried under vacuum to afford 2-(4-bromophenyl)-3-hydroxy-5-methoxy-4H-pyrano[2,3-c]pyridin-4-one (4) as yellow solid. Yield: 54.0 g, 26.0%; MS (ESI) m/z 348.3$[M+1]^+$.

Synthesis of rac-methyl (2R,3R,4R)-2-(4-bromophenyl)-5-hydroxy-6-methoxy-10-oxo-3-phenyl-2,3,4,5-tetrahydro-2,5-methanooxepino[2,3-c]pyridine-4-carboxylate (6)

A solution of 2-(4-bromophenyl)-3-hydroxy-5-methoxy-4H-pyrano[2,3-c]pyridin-4-one (4, 50.0 g, 144.5 mmol) and methyl cinnamate (5, 234.0 g, 1445.0 mmol) in dichloromethane (1200 mL), acetonitrile (600 mL) and methanol (600 mL) was placed in a UV reactor flask. The reaction mixture was irradiated under 400 watts UV light for 48 h. After completion, solvent was removed under reduced pressure and the residue was purified over a plug of silica gel eluting the compound with ethyl acetate. The desired fractions were concentrated under reduced pressure to afford rac-methyl (2R,3R,4R)-2-(4-bromophenyl)-5-hydroxy-6-methoxy-10-oxo-3-phenyl-2,3,4,5-tetrahydro-2,5-methanooxepino[2,3-c]pyridine-4-carboxylate (6) as yellow brown solid. Yield: 70.0 g, crude. MS (ESI) m/z 508.42$[M-1]^-$.

Synthesis of rac-methyl (4bR,6R,7S,7aR)-7a-(4-bromophenyl)-4b-hydroxy-4-methoxy-5-oxo-7-phenyl-4b,6,7,7a-tetrahydro-5H-cyclopenta[4,5]furo[2,3-c]pyridine-6-carboxylate (7)

The crude rac-methyl (2R,3R,4R)-2-(4-bromophenyl)-5-hydroxy-6-methoxy-10-oxo-3-phenyl-2,3,4,5-tetrahydro-2,5-methanooxepino[2,3-c]pyridine-4-carboxylate (6, 70.0 g) was suspended in methanol (700 mL) and treated with 25% sodium methoxide in methanol (222 mL). The reaction was heated at 80° C. for 3 h. After completion, the solvent was removed under reduced pressure. The crude was diluted with ammonium chloride solution, the solid precipitated was filtered off and washed with water and dried under vacuum. The solid obtained was stirred in diethyl ether and filtered off washed with hexane and dried under vacuum to afford rac-methyl (4bR,6R,7S,7aR)-7a-(4-bromophenyl)-4b-hydroxy-4-methoxy-5-oxo-7-phenyl-4b,6,7,7a-tetrahydro-5H-cyclopenta[4,5]furo[2,3-c]pyridine-6-carboxylate (7) as brown solid. Yield: 60.0 g, 85.7%; MS (ESI) m/z 510.3$[M+1]^+$.

Synthesis of rac-methyl (4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylate (Cpd. No. 134F)

To a solution of rac-methyl (4bR,6R,7S,7aR)-7a-(4-bromophenyl)-4b-hydroxy-4-methoxy-5-oxo-7-phenyl-4b,6,7,7a-tetrahydro-5H-cyclopenta[4,5]furo[2,3-c]pyridine-6-carboxylate (7, 60.0 g, 117.6 mmol) in acetonitrile (600 mL) and acetic acid (42.0 ml, 705.0 mmol), sodium triacetoxyborohydride (149.6 g, 705.0 mmol) was added. The resulting mixture was stirred at room temperature for 4 h. After completion, the reaction mixture was partitioned between saturated aqueous sodium bicarbonate solution and ethyl acetate. The organic layer was separated, dried over anhydrous sodium sulphate, filtered and concentrated under reduced pressure to get the crude product. The crude product was purified by silica gel column chromatography using 5% methanol in dichloromethane as eluents. The desired fractions were concentrated under reduced pressure to afford rac-methyl (4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylate (Cpd. No. 134F) as off white solid. Yield: 26.0 g, 43.2%; MS (ESI) m/z 512.18$[M+1]^+$. $^1H$ NMR (400 MHz, DMSO-$d_6$) δ 8.09 (s, 1H), 7.98 (s, 1H), 7.20 (d, J=8.64 Hz, 2H), 7.08-7.04 (m, 4H), 7.0-6.95 (m, 3H), 5.75 (s, 1H), 5.60 (d, J=5.72 Hz, 1H), 4.68 (t, J=6.18 Hz, 1H), 4.33 (d, J=14.36 Hz, 1H), 4.07 (dd, J=14.18, 4.7 Hz, 1H), 3.87 (s, 3H), 3.56 (s, 3H).

Example 135

Rac-((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)(4,4-difluoropiperidin-1-yl)methanone (Cpd. No. 135F)

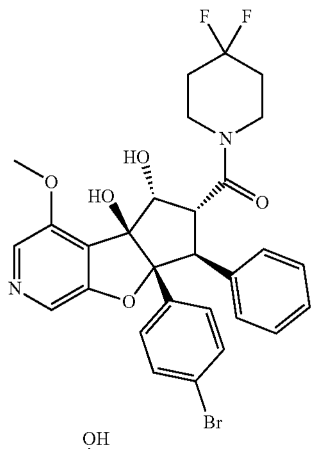

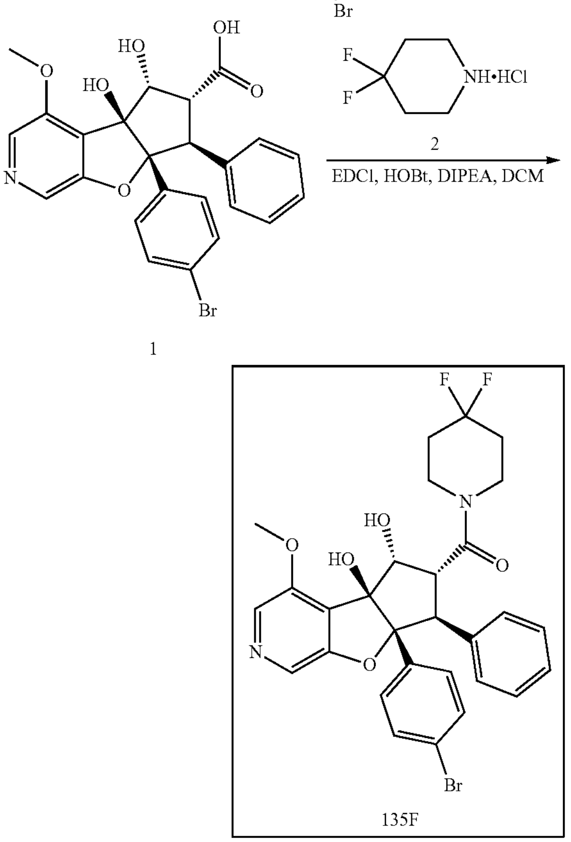

2

1

135F

Synthesis of rac-((4bS,5R,6R,7S,7aR)-7a-(4-bromophenyl)-4b,5-dihydroxy-4-methoxy-7-phenyl-4b,6,7,7a-tetrahydro-SH-cyclopenta[4,5]furo[2,3-c]pyridin-6-yl)(4,4-difluoropiperidin-1-yl)methanone (Cpd. No. 135F)

To a solution of rac-(4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylic acid (1, 0.9 g, 1.8 mmol) in dichloromethane (10 mL), 1-ethyl-3-(3-dimethylaminopropyl)carbodiimide hydrochloride (1.03 g, 5.41 mmol), 1-hydroxybenzotriazole (0.72 g, 5.41 mmol) and N,N-diisopropylethylamine (1.65 mL, 9.12 mmol) were added at 0° C. and stirred for 5 minutes before 4,4-difluoropiperidine hydrochloride (2, 1.4 g, 9.12 mmol) was added at same temperature and the mixture was stirred for 16 h at RT. After completion, reaction mass was diluted with dichloromethane and washed with cold water. The organic layer was separated and dried over anhydrous sodium sulphate, filtered and concentrated to give crude product. The crude product was purified by silica gel column chromatography eluting with 0-4% methanol in dichloromethane. The desired fractions were concentrated to afford rac-((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)(4,4-difluoropiperidin-1-yl)methanone (Cpd. No. 135F) as white solid. Yield: 0.67 g, 67%; MS (ESI) m/z 601.01$[M+1]^+$. $^1H$ NMR (400 MHz, DMSO-$d_6$) δ 8.10 (s, 1H), 8.00 (s, 1H), 7.20 (d, J=8.4 Hz, 2H), 7.08 (d, J=7.8 Hz, 2H), 7.05-7.01 (m, 2H), 6.97-6.91 (m, 3H), 5.73 (s, 1H), 5.29 (d, J=5.6 Hz, 1H), 4.71 (t, J=5.6 Hz, 1H), 4.43 (d, J=13.2 Hz, 1H), 4.26 (dd, J=13.6, 5.6 Hz, 1H), 3.97 (m, 1H), 3.88 (s, 3H), 3.79-3.69 (m, 2H), 3.38 (m, 1H), 2.20 (m, 2H), 1.88 (m, 2H).

Example 136

Rac-Methyl (5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridine-7-carboxylate (Cpd. No. 136F)

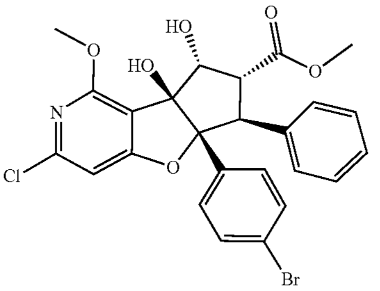

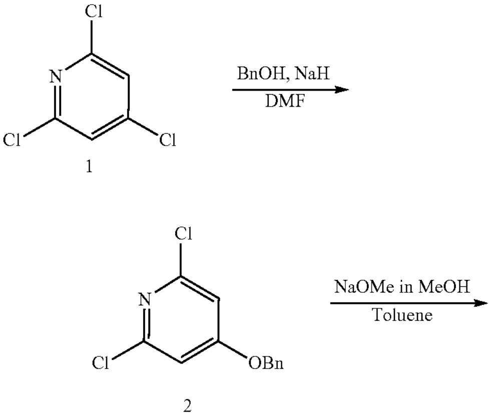

1

2

-continued

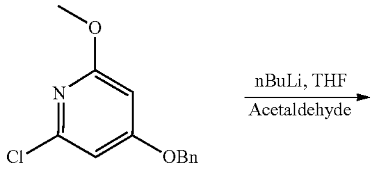

3

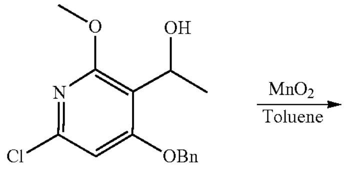

4

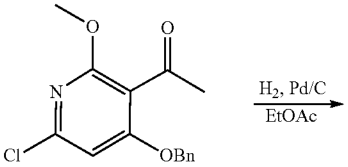

5

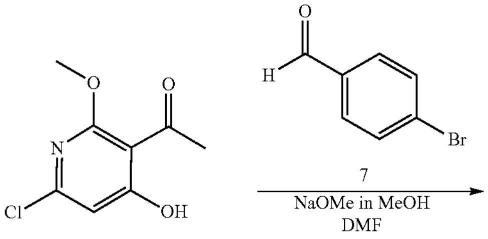

7

6

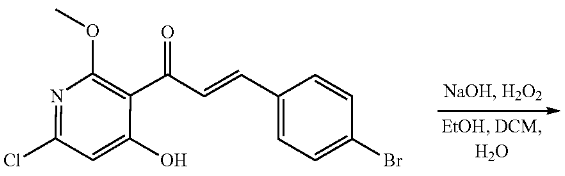

8

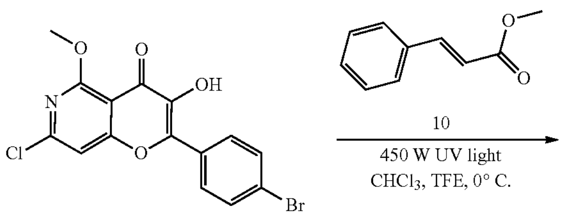

10

9

-continued

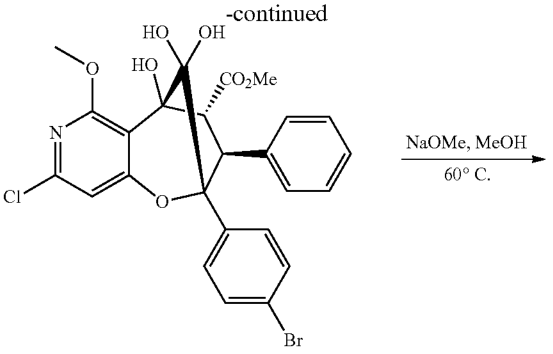

11

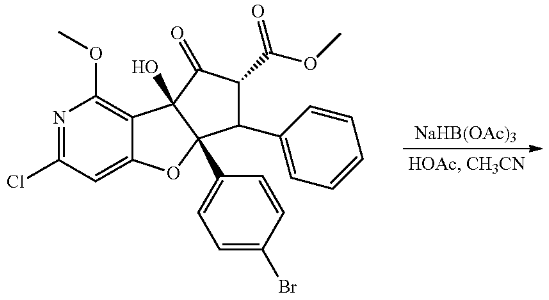

12

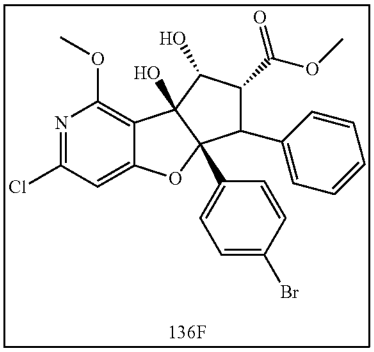

136F

Synthesis of 4-(benzyloxy)-2,6-dichloropyridine (2)

Sodium hydride (60% in mineral oil) (14.22 g, 355.6 mmol) was added in four portions to a stirred solution of 2,4,6-trichloropyridine (1, 58.98 g, 323.3 mmol) in N,N-dimethylformamide (473 mL) at 0° C. under nitrogen. After 5 min benzyl alcohol (33.45 mL, 323.3 mmol) was added dropwise via addition funnel over 1.5 h. The resulting reaction mixture was stirred at 0° C. under nitrogen for 2.5 h. Water (5 mL) was added dropwise very slowly at 0° C., then the reaction mixture was poured into vigorously stirred water (580 mL). Solids were collected by vacuum filtration, washed with water, and air dried overnight to give 65.44 g of an off-white solid. The solids were dissolved in hot EtOAc and filtered. The filtrate was concentrated on a rotary evaporator. The residue was recrystallized from 2% EtOAc in hexanes to afford 4-(benzyloxy)-2,6-dichloropyridine (2) as an off-white solid. Yield: 55.10 g, 67%; MS (ESI) m/z 254.0$[M+1]^+$; $^1H$ NMR (400 MHz, DMSO-$d_6$) δ 7.48-7.34 (m, 5H), 7.29 (s, 2H), 5.27 (s, 2H).

Synthesis of 4-(benzyloxy)-2-chloro-6-methoxypyridine (3)

Sodium methoxide (25 wt % in methanol) (58.04 mL, 253.9 mmol) was added to a stirred solution of 4-benzyloxy-2,6-dichloro-pyridine (2, 54.86 g, 215.9 mmol) in toluene (910 mL) at room temperature under nitrogen. The resulting mixture was stirred vigorously and heated at 70° C. under a reflux condenser under nitrogen for 9 h. The resulting mixture was partitioned between water and diethyl ether. The organics were washed with water and brine, dried over magnesium sulfate, filtered, concentrated on a rotary evaporator, and purified via silica gel chromatography (0.5-1-3% EtOAc in hexanes) to afford 4-(benzyloxy)-2-chloro-6-methoxypyridine (3) as a white solid. Yield: 35.51 g, 66%; Rf=0.33 (10% EtOAc/hexanes); MS (ESI) m/z 250.2[M+1]$^+$; $^1$H NMR (400 MHz, DMSO-$d_6$) δ 7.47-7.32 (m, 5H), 6.81 (d, J=1.9 Hz, 1H), 6.46 (d, J=1.9 Hz, 1H), 5.20 (s, 2H), 3.81 (s, 3H).

Synthesis of 1-(4-(benzyloxy)-6-chloro-2-methoxy-pyridin-3-yl)ethan-1-ol (4)

Anhydrous acetaldehyde from Sigma Aldrich (00070) was dried over 4 Angstrom molecular sieves prior to use. A stirred solution of 4-benzyloxy-2-chloro-6-methoxy-pyridine (3, 31.89 g, 127.7 mmol) in THF (480 mL) was cooled with a dry ice/acetone bath to −75° C. for 15 min. n-Butyllithium (2.5 M in hexanes) (61.3 mL, 153.3 mmol) was added slowly over 10 min.

The resulting dark yellow solution was stirred for 30 min at −75° C. and then acetaldehyde (14.35 mL, 255.4 mmol) was added. After 10 min saturated aqueous ammonium chloride (45 mL) was added and the resulting mixture was partitioned between water and ethyl acetate. The organics were washed with brine, dried over magnesium sulfate, filtered, and concentrated on a rotary evaporator. The crude material was taken up in 10% EtOAc in hexanes and purified via silica gel chromatography (3-6-15% EtOAc in hexanes) to afford 1-(4-(benzyloxy)-6-chloro-2-methoxypyridin-3-yl)ethan-1-ol (4) as a colorless oil which was a 10:1 mixture of regioisomers. Yield: 32.24 g, 83%; MS (ESI) m/z 294.1[M+1]$^+$; $^1$H NMR (400 MHz, DMSO-$d_6$) δ 7.49-7.31 (m, 5H), 6.93 (s, 1H), 5.25 (s, 2H), 5.14 (p, J=6.5 Hz, 1H), 4.61 (d, J=6.1 Hz, 1H), 3.84 (s, 3H), 1.39 (d, J=6.7 Hz, 3H). The regioisomers could be separated by careful chromatography over silica gel.

Synthesis of 1-(4-(benzyloxy)-6-chloro-2-methoxy-pyridin-3-yl)ethan-1-one (5)

Manganese (IV) oxide (26.41 g, 303.8 mmol) was added to a stirred solution of 1-(4-(benzyloxy)-6-chloro-2-methoxypyridin-3-yl)ethan-1-ol (4, 29.75 g, 101.3 mmol) in toluene (400 mL) at room temperature. The resulting mixture was stirred vigorously and heated at 60° C. under a reflux condenser under nitrogen. After 24 h more manganese (IV) oxide (26.41 g, 303.8 mmol) was added and heating was continued at 60° C. At 48 h more manganese (IV) oxide (20.00 g, 230.0 mmol) was added and heating was continued at 60° C. At 73 h more manganese (IV) oxide (10.00 g, 115.0 mmol) was added and heating was continued at 60° C. for a total reaction time of 90 h. After cooling to room temperature the reaction mixture was filtered through Celite and the filter cake washed thoroughly with EtOAc. The filtrate was concentrated on a rotary evaporator and purified via silica gel chromatography (1-4-10% EtOAc/hexanes) to afford 1-(4-(benzyloxy)-6-chloro-2-methoxypyridin-3-yl)ethan-1-one (5) as a white solid. Yield: 23.36 g, 79%; MS (ESI) m/z 292.2[M+1]$^+$; $^1$H NMR (400 MHz, DMSO-$d_6$) δ 7.47-7.32 (m, 5H), 7.11 (s, 1H), 5.28 (s, 2H), 3.85 (s, 3H), 2.38 (s, 3H).

Synthesis of 1-(6-chloro-4-hydroxy-2-methoxypyridin-3-yl)ethan-1-one (6)

1-(4-(benzyloxy)-6-chloro-2-methoxypyridin-3-yl)ethan-1-one (5, 23.35 g, 80.04 mmol) was dissolved in ethyl acetate (600 mL) with stirring in a 2 L round bottom flask. A combination vacuum/nitrogen/hydrogen manifold was attached and the atmosphere in the flask was removed and replaced with argon. 10% palladium on carbon (188 mg, 1.88 mmol) was added and the atmosphere in the flask was removed and replaced with hydrogen. The resulting mixture was stirred vigorously at room temperature under hydrogen for 3 h. The reaction mixture was filtered through Celite and the filter cake washed thoroughly with EtOAc. The filtrate was concentrated on a rotary evaporator and purified via silica gel chromatography (1% ethyl acetate in hexanes isocratic) to afford 1-(6-chloro-4-hydroxy-2-methoxypyridin-3-yl)ethan-1-one (6) as a white solid. Yield: 14.15 g, 88%; MS (ESI) m/z 202.2[M+1]$^+$; $^1$H NMR (400 MHz, DMSO-$d_6$) δ 13.02 (s, 1H), 6.70 (s, 1H), 3.91 (s, 3H), 2.53 (s, 3H).

Synthesis of (E)-3-(4-bromophenyl)-1-(6-chloro-4-hydroxy-2-methoxypyridin-3-yl)prop-2-en-1-one (8)

To a 1 L round bottom flask with a stirbar was added sequentially: 1-(6-chloro-4-hydroxy-2-methoxypyridin-3-yl)ethan-1-one (6, 14.13 g, 70.09 mmol) 4-bromobenzaldehyde (7, 13.34 g, 72.13 mmol), N,N-dimethylformamide (170 mL), and then sodium methoxide (25 wt % in methanol) (48.04 mL, 210.1 mmol). The reaction mixture was stirred vigorously and heated at 50° C. under a reflux condenser for 20 min. The reaction mixture is initially clear and light yellow, but then a lot of solids precipitated. More N,N-dimethylformamide (50 mL) was added to keep the reaction stirring. The reaction mixture was poured onto a vigorously stirred mixture of 1 N hydrochloric acid in water (210 mL, 210 mmol) and ice water (500 mL). The resulting light yellow mixture was stirred vigorously for 10 min and then solids were collected by vacuum filtration. The solids were washed with water and dried under high vacuum to afford (E)-3-(4-bromophenyl)-1-(6-chloro-4-hydroxy-2-methoxypyridin-3-yl)prop-2-en-1-one (8) as a yellow solid. Yield: 25.83 g, 100%; MS (ESI) m/z 368.0, 369.9[M+1]$^+$; $^1$H NMR (400 MHz, DMSO-$d_6$) δ 7.72-7.67 (m, 2H), 7.65-7.59 (m, 2H), 7.40 (d, J=16.2 Hz, 1H), 7.17 (d, J=16.1 Hz, 1H), 6.60 (s, 1H), 3.81 (s, 3H).

Synthesis of 2-(4-bromophenyl)-7-chloro-3-hydroxy-5-methoxy-4H-pyrano[3,2-c]pyridin-4-one (9)

10% aqueous sodium hydroxide (18.1 mL, 49.78 mmol) was added to a stirred mixture (not all dissolved) of (E)-3-(4-bromophenyl)-1-(6-chloro-4-hydroxy-2-methoxypyridin-3-yl)prop-2-en-1-one (8, 8.31 g, 22.54 mmol) in ethanol (160 mL) and dichloromethane (40 mL) cooled with a room temperature water bath. After 1 min 30% aqueous hydrogen peroxide (16.19 mL, 158.5 mmol) was added. The reaction mixture was stirred vigorously while cooled with a room temperature water bath for 1 h. The reaction mixture was diluted with dichloromethane, poured onto saturated aqueous ammonium chloride (250 mL), and extracted three times with dichloromethane. The organics were concentrated on a rotary evaporator. The residual solids were shaken in a separatory funnel with dichloromethane (1 L) and saturated aqueous ammonium chloride (250 mL). The layers were separated and the water layer extracted twice with dichloromethane. The combined organics were dried over $Na_2SO_4$, filtered, and concentrated on a rotary evaporator. 10% ethyl acetate in hexanes (100 mL) was added to the residue and the resulting mixture was heated to reflux with a heat gun. The mixture was capped and let stand 1 h at room temperature. Solids were collected by vacuum filtration, washed with 10% ethyl acetate in hexanes, and dried under high vacuum to afford 2-(4-bromophenyl)-7-chloro-3-hydroxy-5-methoxy-4H-pyrano[3,2-c]pyridin-4-one (9) as an orange solid. Yield: 1.61 g, 19%; MS (ESI) m/z 382.0, 384.0[M+1]$^+$; $^1$H NMR (400 MHz, DMSO-$d_6$) δ 10.01 (s, 1H), 8.15-8.09 (m, 2H), 7.80-7.75 (m, 2H), 7.55 (s, 1H), 4.02 (s, 3H).

Synthesis of rac-methyl (3S,4S,5R)-2-(4-bromophenyl)-8-chloro-5,10,10-trihydroxy-6-methoxy-3-phenyl-2,3,4,5-tetrahydro-2,5-methanooxepino[3,2-c]pyridine-4-carboxylate (11)

To a 500 mL round bottom flask was added sequentially: a stir bar, 2-(4-bromophenyl)-7-chloro-3-hydroxy-5-methoxy-4H-pyrano[3,2-c]pyridin-4-one (9, 1.61 g, 4.21 mmol), methyl cinnamate (10, 6.83 g, 42.1 mmol), chloroform (80 mL), and trifluoroethanol (80 mL). The reaction mixture was stirred vigorously and irradiated with 450 W UV light while being cooled with a 0° C. cold bath for 5 h. The reaction mixture was diluted with 3% triethylamine in ethyl acetate (15 mL), concentrated on a rotary evaporator with silica gel, and dried under high vacuum overnight. The residue was loaded into a loading column and purified via silica gel chromatography (0-5-100% EtOAc/hexanes) (column was pre-equilibrated with 10% EtOAc in hexanes with 3% triethylamine prior to equilibration with 0% hexanes) to afford 1.67 g of impure rac-methyl (3S,4S,5R)-2-(4-bromophenyl)-8-chloro-5,10,10-trihydroxy-6-methoxy-3-phenyl-2,3,4,5-tetrahydro-2,5-methanooxepino[3,2-c]pyridine-4-carboxylate (11) an orange residue which was taken on to the next step without further purification. MS (ESI) m/z 562.3, 564.2 [M]+.

Synthesis of rac-methyl (5aR,6S,7R,8aR)-5a-(4-bromophenyl)-3-chloro-8a-hydroxy-1-methoxy-8-oxo-6-phenyl-5a,7,8,8a-tetrahydro-6H-cyclopenta[4,5]furo[3,2-c]pyridine-7-carboxylate (12)

Sodium methoxide (25 wt. % in methanol) (2.03 mL, 8.89 mmol) was added to a stirred solution of impure rac-methyl (3S,4S,5R)-2-(4-bromophenyl)-8-chloro-5,10,10-trihydroxy-6-methoxy-3-phenyl-2,3,4,5-tetrahydro-2,5-methanooxepino[3,2-c]pyridine-4-carboxylate (11, 1.67 g, 2.97 mmol) in methanol (60 mL) at room temperature under argon. The clear yellow solution changed to dark orange colored. The reaction mixture was heated at 60° C. under a reflux condenser under argon for 40 min and then most of the solvent was removed on a rotary evaporator. The residue was partitioned between saturated aqueous ammonium chloride and ethyl acetate. The organics were washed with brine, dried over magnesium sulfate, filtered, concentrated on a rotary evaporator, and dried under high vacuum to afford impure rac-methyl (5aR,6S,7R,8aR)-5a-(4-bromophenyl)-3-chloro-8a-hydroxy-1-methoxy-8-oxo-6-phenyl-5a,7,8,8a-tetrahydro-6H-cyclopenta[4,5]furo[3,2-c]pyridine-7-carboxylate (12) as an orange residue. Yield: 1.57 g; MS (ESI) m/z 544.0, 546.1[M+1]$^+$. This material was carried on without further purification.

Synthesis of rac-methyl (5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridine-7-carboxylate (Cpd. No. 136F)

To a stirred solution of impure rac-methyl (5aR,6S,7R,8aR)-5a-(4-bromophenyl)-3-chloro-8a-hydroxy-1-methoxy-8-oxo-6-phenyl-5a,7,8,8a-tetrahydro-6H-cyclopenta[4,5]furo[3,2-c]pyridine-7-carboxylate (12, 1.57 g, 2.88 mmol) in MeCN (50 mL) at room temperature was added acetic acid (1.65 mL, 28.8 mmol) and then sodium triacetoxyborohydride (3.05 g, 14.4 mmol). The resulting reaction mixture was stirred vigorously at room temperature under argon for 40 min. Saturated aqueous ammonium chloride (20 mL) was added slowly dropwise and the resulting mixture was partitioned between water and ethyl acetate. The organics were washed with saturated aqueous sodium bicarbonate and then brine, dried over magnesium sulfate, filtered, concentrated on a rotary evaporator and purified via silica gel chromatography (12-22% EtOAc/hexanes) to afford rac-methyl (5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridine-7-carboxylate (Cpd. No. 136F) as a slightly yellow foam-solid. Yield: 631 mg, 27% over three steps; MS (ESI) m/z 546.1, 548.1[M+1]$^+$; $^1$H NMR (400 MHz, DMSO-$d_6$) δ 7.24-7.19 (m, 2H), 7.09-6.92 (m, 8H), 5.70-5.64 (m, 2H), 4.62 (t, J=5.4 Hz, 1H), 4.31 (d, J=13.9 Hz, 1H), 4.09 (dd, J=14.0, 4.9 Hz, 1H), 3.83 (s, 3H), 3.57 (s, 3H).

Example 137

Rac-(5aR,6S,7R,8R,8aS)-5a-(4-bromophenyl)-3-chloro-8,8a-dihydroxy-1-methoxy-N,N-dimethyl-6-phenyl-5a,7,8,8a-tetrahydro-6H-cyclopenta[4,5]furo[3,2-c]pyridine-7-carboxamide (Cpd. No. 137F)

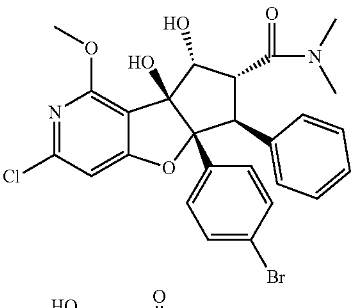

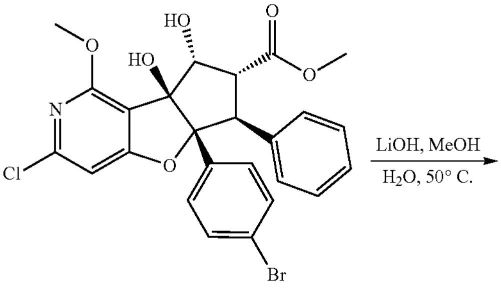

1

-continued

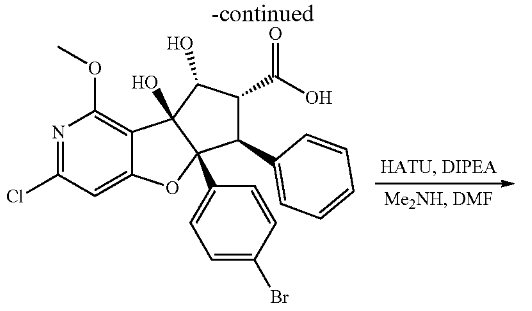

2

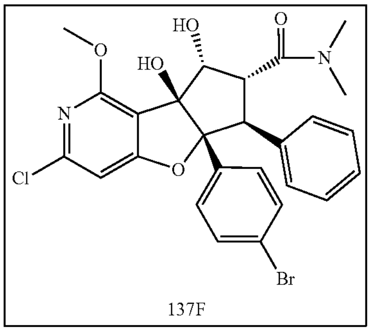

137F

Synthesis of rac-(5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridine-7-carboxylic acid (2)

To a stirred solution of rac-methyl (5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridine-7-carboxylate (1, 1.09 g, 1.99 mmol) in methanol (40 mL) was added water (4 mL) and then lithium hydroxide (477 mg, 19.9 mmol). The resulting yellow reaction mixture was stirred vigorously and heated at 50° C. under a reflux condenser for 4.5 h. The reaction mixture was cooled with a 0° C. cold bath and 1 N hydrochloric acid in water (19.9 mL, 19.9 mmol) was added with vigorous stirring. A few more drops of 1 N hydrochloric acid was added to make the mixture slightly acidic. Most of the methanol was removed on a rotary evaporator. The residue was extracted three times with dichloromethane. The combined organics were washed with brine, dried over magnesium sulfate, filtered, concentrated on a rotary evaporator, and dried under high vacuum at 40° C. overnight to afford crude rac-(5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridine-7-carboxylic acid (2) as a white solid with yellow impurity. Yield: 961 mg, 90%; MS (ESI) m/z 532.1, 534.0 $[M+1]^+$; $^1H$ NMR (400 MHz, DMSO-$d_6$) δ 12.23 (s, 1H), 7.24-7.18 (m, 2H), 7.06 (m, 2H), 7.03-6.94 (m, 5H), 6.93 (s, 1H), 5.62 (d, J=8.3 Hz, 2H), 4.62 (t, J=5.3 Hz, 1H), 4.29 (d, J=13.9 Hz, 1H), 3.95 (dd, J=14.0, 5.0 Hz, 1H), 3.84 (s, 3H).

Synthesis of rac-(5aR,6S,7R,8R,8aS)-5a-(4-bromophenyl)-3-chloro-8,8a-dihydroxy-1-methoxy-N,N-dimethyl-6-phenyl-5a,7,8,8a-tetrahydro-6H-cyclopenta[4,5]furo[3,2-c]pyridine-7-carboxamide (Cpd. No. 137F)

HATU (686 mg, 1.80 mmol) was added to a stirred solution of rac-(5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridine-7-carboxylic acid (2, 915 mg, 1.72 mmol) in N,N-dimethylformamide (15 mL) at room temperature under argon. After 2 min N,N-diisopropylethylamine (0.45 mL, 2.58 mmol) was added. The resulting reaction mixture was stirred at room temperature under argon for 20 min. Dimethylamine (2 M solution in THF) (2.58 mL, 5.15 mmol) was added and the reaction mixture was stirred at room temperature under argon for 3 h. The reaction mixture was diluted with 90% ethyl acetate in hexanes, washed three times with water, once with brine, dried over magnesium sulfate, filtered, concentrated on a rotary evaporator, and purified via silica gel chromatography (30-100% EtOAc/hexanes) to afford rac-(5aR,6S,7R,8R,8aS)-5a-(4-bromophenyl)-3-chloro-8,8a-dihydroxy-1-methoxy-N,N-dimethyl-6-phenyl-5a,7,8,8a-tetrahydro-6H-cyclopenta[4,5]furo[3,2-c]pyridine-7-carboxamide (Cpd. No. 137F) as a white foam-solid. Yield: 917 mg, 95%; MS (ESI) m/z 559.1, 561.1$[M+1]^+$; $^1H$ NMR (400 MHz, DMSO-$d_6$) δ 7.25-7.20 (m, 2H), 7.07-7.00 (m, 4H), 6.99-6.93 (m, 2H), 6.89 (dt, J=8.2, 1.2 Hz, 2H), 5.62 (s, 1H), 5.19 (d, J=5.7 Hz, 1H), 4.69 (t, J=5.5 Hz, 1H), 4.41 (d, J=13.4 Hz, 1H), 4.18 (dd, J=13.5, 5.2 Hz, 1H), 3.84 (s, 3H), 3.27 (s, 3H), 2.77 (s, 3H).

Example 138

Rac-(5aR,6S,7S,8R,8aS)-5a-(4-bromophenyl)-3-chloro-7-((dimethylamino)methyl)-1-methoxy-6-phenyl-5a,6,7,8-tetrahydro-8aH-cyclopenta[4,5]furo[3,2-c]pyridine-8,8a-diol (Cpd. No. 138F)

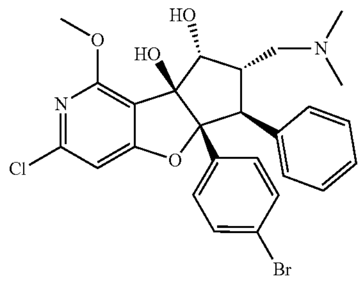

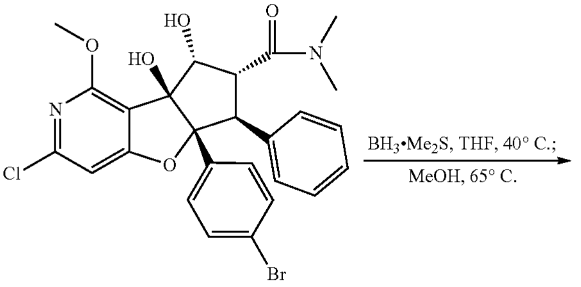

1

-continued

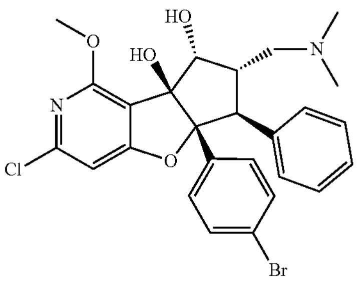

138F

Synthesis of rac-(5aR,6S,7S,8R,8aS)-5a-(4-bromophenyl)-3-chloro-7-((dimethylamino)methyl)-1-methoxy-6-phenyl-5a,6,7,8-tetrahydro-8aH-cyclopenta[4,5]furo[3,2-c]pyridine-8,8a-diol (Cpd. No. 138F)

Borane dimethyl sulfide complex (1.47 mL, 15.5 mmol) was added to a stirred solution of rac-(5aR,6S,7R,8R,8aS)-5a-(4-bromophenyl)-3-chloro-8,8a-dihydroxy-1-methoxy-N,N-dimethyl-6-phenyl-5a,7,8,8a-tetrahydro-6H-cyclopenta[4,5]furo[3,2-c]pyridine-7-carboxamide (1, 866 mg, 1.55 mmol) in THF (30 mL) at room temperature under a reflux condenser under argon. Some bubbling was observed. The reaction mixture was heated at 40° C. under a reflux condenser under argon for 3 h. After cooling to room temperature, wet methanol (20 mL) was added dropwise slowly. The resulting clear colorless reaction mixture was stirred vigorously and heated at 65° C. under a reflux condenser under argon for 36 h. The reaction mixture was loaded onto five 2 g Strata X-C ion exchange columns from Phenomenex. The columns were washed sequentially with acetonitrile, methanol, and then a mixture of 5% ammonium hydroxide in methanol/dichloromethane. Eluent containing the desired product was concentrated on a rotary evaporator and dried under high vacuum at 40° C. to afford rac-(5aR,6S,7S,8R,8aS)-5a-(4-bromophenyl)-3-chloro-7-((dimethylamino)methyl)-1-methoxy-6-phenyl-5a,6,7,8-tetrahydro-8aH-cyclopenta[4,5]furo[3,2-c]pyridine-8,8a-diol (Cpd. No. 138F) as a white solid. Yield: 742 mg, 88%; MS (ESI) m/z 545.2, 547.3; $^{1}H$ NMR (400 MHz, DMSO-$d_6$) δ 7.26-7.21 (m, 2H), 7.13-7.05 (m, 4H), 7.04-6.94 (m, 3H), 6.86 (s, 1H), 5.56 (s, 1H), 5.15 (s, 1H), 4.43 (s, 1H), 3.84 (s, 3H), 3.70 (d, J=14.1 Hz, 1H), 3.08 (ddt, J=14.0, 10.0, 3.6 Hz, 1H), 2.56 (m, 1H), 2.19 (s, 6H), 1.94 (d, J=11.1 Hz, 1H).

Example 139

(5aR,6S,7S,8R,8aS)-5a-(4-cyanophenyl)-7-((dimethylamino)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 1391F)

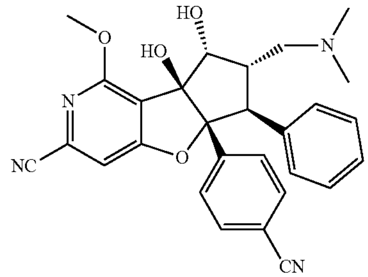

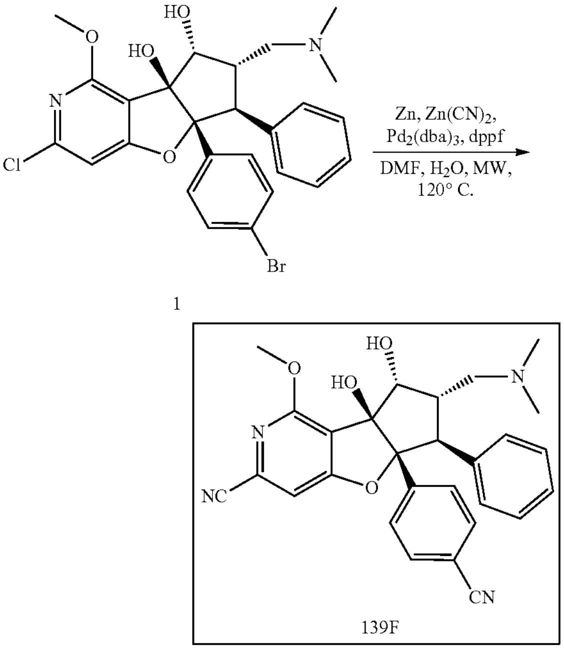

1

139F

Synthesis of rac-(5aR,6S,7S,8R,8aS)-5a-(4-cyanophenyl)-7-((dimethylamino)methyl)-8,8a-dihydroxy-1-methoxy-6-phenyl-5a, 7,8,8a-tetrahydro-6H-cyclopenta[4,5]furo[3,2-c]pyridine-3-carbonitrile (Cpd. No. 139F)

Rac-(5aR,6S,7S,8R,8aS)-5a-(4-bromophenyl)-3-chloro-7-((dimethylamino)methyl)-1-methoxy-6-phenyl-5a,6,7,8-tetrahydro-8aH-cyclopenta[4,5]furo[3,2-c]pyridine-8,8a-diol (1, 165 mg, 0.300 mmol), zinc cyanide (213 mg, 1.81 mmol), zinc powder (19.8 mg, 0.300 mmol), N,N-dimethylformamide (0.9 mL), and water (0.09 mL) were combined in a microwave vial with a stirbar. The resulting mixture was sparged with argon gas for 5 min. $Pd_2dba_3$ (27.7 mg, 0.030 mmol) and dppf (33.5 mg, 0.060 mmol) were added and the resulting mixture was sparged with argon gas for 5 min. The reaction mixture was sealed, stirred, and microwaved at 120° C. for 2 h. The reaction mixture was diluted with DMSO and methanol, filtered, and purified via preparatory HPLC (15-35% acetonitrile in water with 0.1% TFA). Fractions containing the desired product were loaded onto three 2 g Strata X-C ion exchange columns from Phenomenex. The columns were washed sequentially with water, acetonitrile, methanol, and then a mixture of 10% ammonium hydroxide, 20% dichloromethane, and 70% methanol. Fractions containing the desired product were combined, concentrated on a rotary evaporator, and dried under high vacuum at 40° C. to afford rac-(5aR,6S,7S,8R,8aS)-5a-(4-cyanophenyl)-7-((dimethylamino)methyl)-8,8a-dihydroxy-1-methoxy-6-phenyl-5a,7,8,8a-tetrahydro-6H-cyclopenta[4,5]furo[3,2-c]pyridine-3-carbonitrile as a white solid. Yield: 91.6 mg, 63%; The enantiomers were separated by chiral preparative SFC [Chiralpak IG (4.6×250) mm, 5μ] using $CO_2$:EtOH:TEA (60:40:0.1) Mobile phase. Peak 1 (Cpd. No. 139F), $[\alpha]_D$-36.4° (c 0.3, $CHCl_3$), $R_t$=1.52 min, ee >99%. MS (ESI) m/z 483.15[M+1]$^+$; UPLC: 99.75; $^1$H NMR (400 MHz, DMSO-$d_6$) δ 7.61-7.51 (m, 3H), 7.37 (d, J=8.2 Hz, 2H), 7.10-7.06 (m, 2H), 7.02-6.98 (m, 3H), 5.86 (s, 1H), 5.35 (bs, 1H), 4.51 (s, 1H), 3.89 (s, 3H), 3.79 (d, J=13.9 Hz, 1H), 3.17-3.16 (m, 1H), 2.62-2.60 (m, 1H), 2.23 (bs, 6H). 1.98 (bs, 1H). Peak 2, SOR (not recorded, solubility issues) $R_t$=2.04 min, ee >99%. MS (ESI) m/z 483.15 [M+1]$^+$; UPLC: 99.78%. $^1$H NMR (400 MHz, DMSO-$d_6$) δ 7.54-7.50 (m, 3H), 7.35 (d, J=8.2 Hz, 2H), 7.09-7.06 (m, 2H), 7.01-6.88 (m, 3H), 5.85 (s, 1H), 5.42 (bs, 1H), 4.59 (d, J=3.0 Hz, 1H), 3.89 (s, 3H), 3.77 (d, J=14.0 Hz, 1H), 3.18-3.16 (m, 1H), 2.58-2.50 (m, 1H), 2.21 (s, 6H), 1.96 (d, J=10.3 Hz, 1H).

Example 140

4-((5aR,6S,7S,8R,8aS)-3-chloro-7-((dimethylamino)methyl)-8,8a-dihydroxy-1-methoxy-6-phenyl-6,7,8,8a-tetrahydro-5aH-cyclopenta[4,5]furo[3,2-c]pyridin-5a-yl)benzonitrile (Cpd. No. 140F)

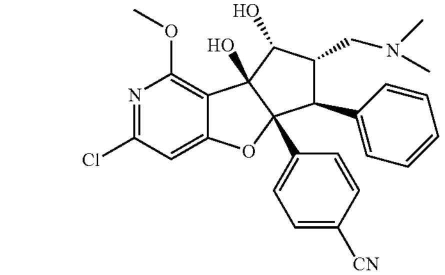

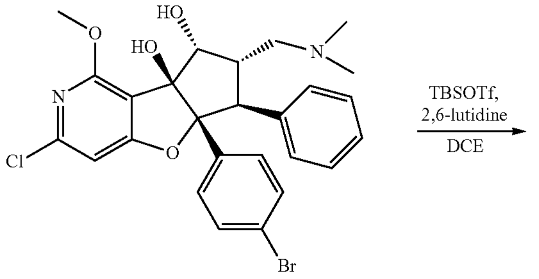

1

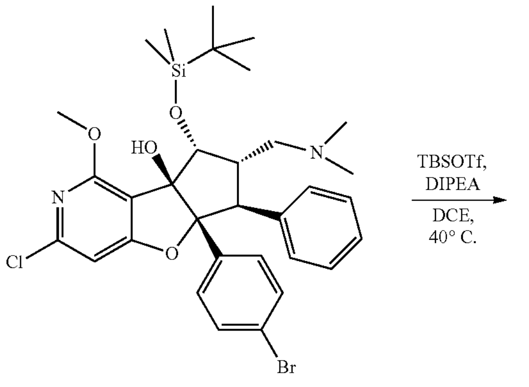

2

-continued

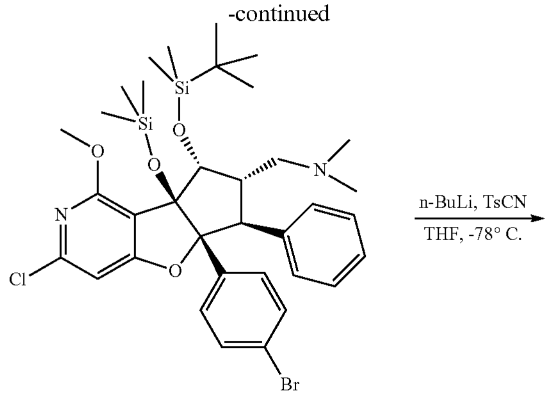

3

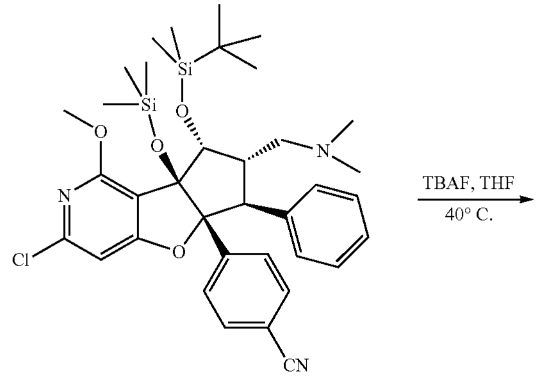

4

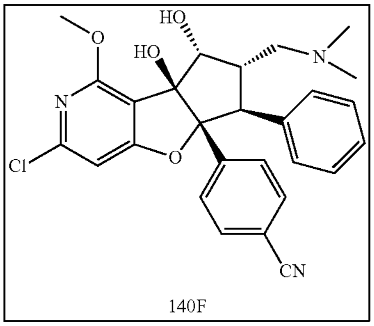

140F

Synthesis of rac-(5aR,6S,7S,8R,8aS)-5a-(4-bromophenyl)-8-((tert-butyldimethylsilyl)oxy)-3-chloro-7-((dimethylamino)methyl)-1-methoxy-6-phenyl-5a,6,7,8-tetrahydro-8aH-cyclopenta[4,5]furo[3,2-c]pyridin-8a-ol (2)

tert-Butyldimethylsilyl trifluoromethanesulfonate (0.82 mL, 3.56 mmol) was added to a stirred mixture (not all dissolved) of rac-(5aR,6S,7S,8R,8aS)-5a-(4-bromophenyl)-3-chloro-7-((dimethylamino)methyl)-1-methoxy-6-phenyl-5a,6,7,8-tetrahydro-8aH-cyclopenta[4,5]furo[3,2-c]pyridine-8,8a-diol (1, 648 mg, 1.19 mmol) and 2,6-lutidine (0.83 mL, 7.12 mmol) in DCE (10 mL) at room temperature under argon. (All solids dissolved) The reaction mixture was sealed and stirred at room temperature for 11 h. The reaction mixture was loaded directly onto a silica gel loading column and purified via silica gel chromatography (10-50% EtOAc/hexanes) to afford rac-(5aR,6S,7S,8R,8aS)-5a-(4-bromophenyl)-8-((tert-butyldimethylsilyl)oxy)-3-chloro-7-((dimethylamino)methyl)-1-methoxy-6-phenyl-5a,6,7,8-tetrahydro-8aH-cyclopenta[4,5]furo[3,2-c]pyridin-8a-ol (2) as a white solid. Yield: 677 mg, 86%; MS (ESI) m/z 661.3[M+1]$^+$; $^1$H NMR (400 MHz, DMSO-$d_6$) δ 7.18 (d, J=8.7 Hz, 2H), 7.12-6.96 (m, 7H), 6.89 (s, 1H), 5.87 (s, 1H), 4.46 (d, J=2.8 Hz, 1H), 4.04-3.97 (m, 1H), 3.79 (s, 3H), 3.25 (t, J=12.1 Hz, 1H), 2.21 (s, 6H), 1.92 (d, J=12.0 Hz, 1H), 0.69 (s, 9H), 0.12 (s, 3H), −0.30 (s, 3H).

Synthesis of rac-1-((5aR,6S,7S,8R,8aS)-5a-(4-bromophenyl)-8-((tert-butyldimethylsilyl)oxy)-3-chloro-1-methoxy-6-phenyl-8a-((trimethylsilyl)oxy)-5a,7,8,8a-tetrahydro-6H-cyclopenta[4,5]furo[3,2-c]pyridin-7-yl)-N,N-dimethylmethanamine (3)

Trimethylsilyl trifluoromethanesulfonate (0.26 mL, 1.45 mmol) was added to a stirred mixture of rac-(5aR,6S,7S,8R,8aS)-5a-(4-bromophenyl)-8-((tert-butyldimethylsilyl)oxy)-3-chloro-7-((dimethylamino)methyl)-1-methoxy-6-phenyl-5a,6,7,8-tetrahydro-8aH-cyclopenta[4,5]furo[3,2-c]pyridin-8a-ol (2, 640 mg, 0.970 mmol) and N,N-diisopropylethylamine (0.51 mL, 2.91 mmol) in DCE (10 mL) at room temperature under argon. The reaction mixture was heated at 40° C. under a reflux condenser under argon for 2.5 h. More N,N-diisopropylethylamine (0.51 mL, 2.91 mmol) was added followed by trimethylsilyl trifluoromethanesulfonate (0.26 mL, 1.45 mmol). The reaction mixture was heated at 40° C. under a reflux condenser under argon for 1.5 h. The reaction mixture was partitioned between dichloromethane and saturated aqueous sodium bicarbonate. The water layer was extracted with dichloromethane. The combined organics were concentrated to dryness and purified via silica gel chromatography (1-20% EtOAc/hexanes) to afford rac-1-((5aR,6S,7S,8R,8aS)-5a-(4-bromophenyl)-8-((tert-butyldimethylsilyl)oxy)-3-chloro-1-methoxy-6-phenyl-8a-((trimethylsilyl)oxy)-5a,7,8,8a-tetrahydro-6H-cyclopenta[4,5]furo[3,2-c]pyridin-7-yl)-N,N-dimethylmethanamine (3) as a white solid at 90% purity. Yield: 649 mg, 81%; MS (ESI) m/z 733.2[M+1]$^+$.

Synthesis of rac-4-((5aR,6S,7S,8R,8aS)-8-((tert-butyldimethylsilyl)oxy)-3-chloro-7-((dimethylamino)methyl)-1-methoxy-6-phenyl-8a-((trimethylsilyl)oxy)-6,7,8,8a-tetrahydro-5aH-cyclopenta[4,5]furo[3,2-c]pyridin-5a-yl)benzonitrile (4)

p-Toluenesulfonyl cyanide from Aldrich (248835) was recrystallized from toluene/hexanes, dissolved in THF, and dried over 4 Angstrom molecular sieves for prior to use. Rac-1-((5aR,6S,7S,8R,8aS)-5a-(4-bromophenyl)-8-((tert-butyldimethylsilyl)oxy)-3-chloro-1-methoxy-6-phenyl-8a-((trimethylsilyl)oxy)-5a,7,8,8a-tetrahydro-6H-cyclopenta[4,5]furo[3,2-c]pyridin-7-yl)-N,N-dimethylmethanamine (3, 467 mg, 0.640 mmol) was dissolved in THF (6 mL) with stirring under argon. The resulting colorless solution was cooled to −78° C. with a dry ice/acetone bath for 15 min. n-Butyllithium (2.5 M in hexane) (0.29 mL, 0.73 mmol) was added dropwise slowly. The reaction mixture was stirred for 30 min at −78° C. under argon. p-Toluenesulfonyl cyanide (2 M in THF) (0.48 mL, 0.96 mmol) was added and the resulting mixture was stirred at −78° C. under argon for 25 min. Saturated aqueous ammonium chloride (2 mL) was added and the resulting mixture was partitioned between water and ethyl acetate. The organics were washed with brine, dried over magnesium sulfate, filtered, concentrated, and purified via silica gel chromatography (10-25% EtOAc/hexanes) to afford impure rac-4-((5aR,6S,7S,8R,8aS)-8-((tert-butyldimethylsilyl)oxy)-3-chloro-7-((dimethylamino)methyl)-1-methoxy-6-phenyl-8a-((trimethylsilyl)oxy)-6,7,8,8a-tetrahydro-5aH-cyclopenta[4,5]furo[3,2-c]pyridin-5a-yl)benzonitrile (4) as a white foam solid. Yield: 296 mg; MS (ESI) m/z 678.4[M+1]$^+$. This material was taken on to the next step without further purification.

Synthesis of 4-((5aR,6S,7S,8R,8aS)-3-chloro-7-((dimethylamino)methyl)-8,8a-dihydroxy-1-methoxy-6-phenyl-6,7,8,8a-tetrahydro-5aH-cyclopenta[4,5]furo[3,2-c]pyridin-5a-yl)benzonitrile (Cpd. No. 140F)

Tetrabutylammonium fluoride (1 M in THF) (2.60 mL, 2.60 mmol) was added to a stirred solution of rac-4-((5aR,6S,7S,8R,8aS)-8-((tert-butyldimethylsilyl)oxy)-3-chloro-7-((dimethylamino)methyl)-1-methoxy-6-phenyl-8a-((trimethylsilyl)oxy)-6,7,8,8a-tetrahydro-5aH-cyclopenta[4,5]furo[3,2-c]pyridin-5a-yl)benzonitrile (4, 294 mg, 0.430 mmol) in THF (5 mL). The reaction mixture was sealed, stirred, and heated at 40° C. for 17 h. The solvent was removed on a rotary evaporator. The residue was taken up in DMSO and methanol, filtered, and purified via preparatory HPLC (25-35% acetonitrile in water with 0.1% TFA). Fractions containing the desired product were loaded onto a Strata X-C ion exchange column from Phenomenex. The column was washed sequentially with water, acetonitrile, methanol, and then 5% ammonium hydroxide in methanol/dichloromethane. Fluent containing the desired product was concentrated on a rotary evaporator. The residue was taken up in 50% acetonitrile in water, sonicated for a few seconds, and then lyophilized to dryness to afford rac-4-((5aR,6S,7S,8R,8aS)-3-chloro-7-((dimethylamino)methyl)-8,8a-dihydroxy-1-methoxy-6-phenyl-6,7,8,8a-tetrahydro-5aH-cyclopenta[4,5]furo[3,2-c]pyridin-5a-yl)benzonitrile as a white solid. Yield: 176 mg, 56% over two steps; The enantiomers were separated by chiral preparative SFC [Chiralpak IG (4.6×250) mm, 5μ] using $CO_2$:EtOH:TEA (60:40:0.2) Mobile phase. Peak 1 (320 mg), $[\alpha]_D$+45° (c 0.3, $CHCl_3$), $R_t$=1.90 min, ee >99%. MS (ESI) m/z 492.2 [M+1]$^+$; UPLC: 99.88%. $^1$H NMR (400 MHz, DMSO-$d_6$) δ 7.51 (d, J=8.2 Hz, 2H), 7.35 (d, J=8.36 Hz, 2H), 7.09-7.05 (m, 2H), 7.01-6.97 (m, 3H), 6.89 (s, 1H), 5.67 (s, 1H), 5.27 (brs, 1H), 4.44 (s, 1H), 3.84 (s, 3H), 3.76 (d, J=14.0 Hz, 1H), 3.18-3.14 (m, 1H), 2.57 (m, 1H), 2.22 (s, 6H), 1.99 (brs, 1H); Peak 2 (Cpd. No. 140F, 478 mg), $[\alpha]_D$−41.0° (c 0.3, $CHCl_3$), $R_t$=3.76 min, ee >99%. MS (ESI) m/z 492.24[M+1]$^+$; UPLC: 99.68%. $^1$H NMR (400 MHz, DMSO-$d_6$) δ 7.50 (d, J=8.48 Hz, 2H), 7.34 (d, J=8.4 Hz, 2H), 7.09-7.05 (m, 2H), 7.01-6.97 (m, 3H), 6.88 (s, 1H), 5.66 (s, 1H), 5.22 (brs, 1H), 4.44 (s, 1H), 3.84 (s, 3H), 3.76 (d, J=14.0 Hz, 1H), 3.17-3.14 (m, 1H), 2.57 (m, 1H), 2.20 (s, 6H), 1.97 (d, J=12.08 HZ, 1H).

Example 141

Rac-4-((5aR,6S,7S,8R,8aS)-7-((dimethylamino)methyl)-8,8a-dihydroxy-1-methoxy-6-phenyl-6,7,8,8a-tetrahydro-5aH-cyclopenta[4,5]furo[3,2-c]pyridin-5a-yl)benzonitrile (Cpd. No. 141F)

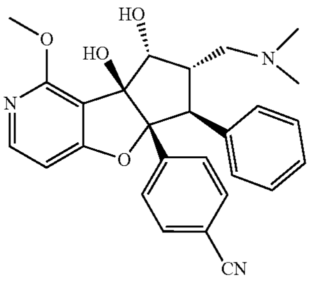

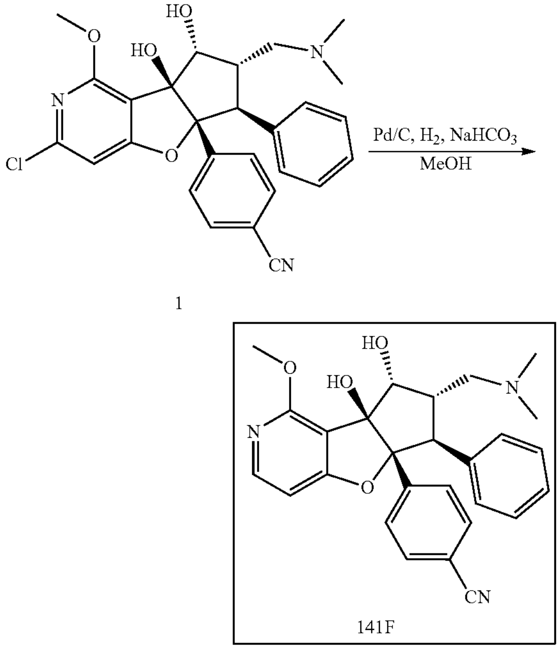

1

141F

Synthesis of rac-4-((5aR,6S,7S,8R,8aS)-7-((dimethylamino)methyl)-8,8a-dihydroxy-1-methoxy-6-phenyl-6,7,8,8a-tetrahydro-5aH-cyclopenta[4,5]furo[3,2-c]pyridin-5a-yl)benzonitrile (Cpd. No. 141F)

Rac-4-((5aR,6S,7S,8R,8aS)-3-chloro-7-((dimethylamino)methyl)-8,8a-dihydroxy-1-methoxy-6-phenyl-6,7,8,8a-tetrahydro-5aH-cyclopenta[4,5]furo[3,2-c]pyridin-5a-yl)benzonitrile (1, 27.2 mg, 0.060 mmol), sodium bicarbonate (9.3 mg, 0.11 mmol), and methanol (7 mL) were combined in a 25 mL round bottom flask with a stirbar. The mixture was sonicated at room temperature for 1 min to dissolve the starting material. A combination vacuum/hydrogen/argon manifold was attached and the atmosphere in the flask was removed and replaced with argon twice. 10% palladium on activated charcoal (5.9 mg, 0.010 mmol) was added and the atmosphere in the flask was removed and replaced with hydrogen twice. The reaction mixture was stirred vigorously at room temperature under a hydrogen balloon for 10 h. The reaction mixture was filtered through a syringe filter and the solvent was removed on a rotary evaporator.

The residue was taken up in DMSO and methanol and purified via preparatory HPLC (10-30% acetonitrile in water with 0.1% TFA). Fractions containing the desired product were loaded onto a Strata X-C ion exchange column from Phenomenex. The column was washed sequentially with water, acetonitrile, methanol, and then 5% ammonium hydroxide in methanol. Fluent containing the desired product was concentrated on a rotary evaporator. The residue was taken up in 50% acetonitrile in water and lyophilized to dryness to afford rac-4-((5aR,6S,7S,8R,8aS)-7-((dimethylamino)methyl)-8,8a-dihydroxy-1-methoxy-6-phenyl-6,7,8,8a-tetrahydro-5aH-cyclopenta[4,5]furo[3,2-c]pyridin-5a-yl)benzonitrile (Cpd. No. 141F) as a white solid. Yield: 11.7 mg, 46%; MS (ESI) m/z 458.5[M+1]$^+$; $^1$H NMR (400 MHz, DMSO-$d_6$) δ 8.00 (d, J=5.7 Hz, 1H), 7.51 (d, J=8.7 Hz, 2H), 7.40-7.34 (m, 2H), 7.12-7.04 (m, 2H), 7.03-6.95 (m, 3H), 6.75 (d, J=5.7 Hz, 1H), 5.58 (s, 1H), 5.11 (s, 1H), 4.50 (d, J=4.1 Hz, 1H), 3.85 (s, 3H), 3.74 (d, J=14.1 Hz, 1H), 3.17 (m, 1H), 2.62 (m, 1H), 2.27 (s, 6H), 2.06 (m, 1H).

Example 142

Rac-(5aR,6S,7S,8R,8aS)-3-chloro-5a-(4-chlorophenyl)-7-((dimethylamino)methyl)-1-methoxy-6-phenyl-5a,6,7,8-tetrahydro-8aH-cyclopenta[4,5]furo[3,2-c]pyridine-8,8a-diol (Cpd. No. 142F)

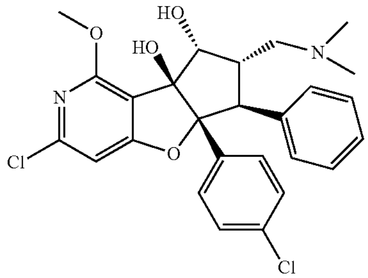

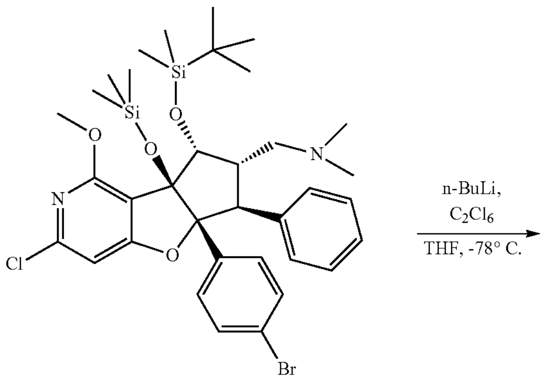

1

-continued

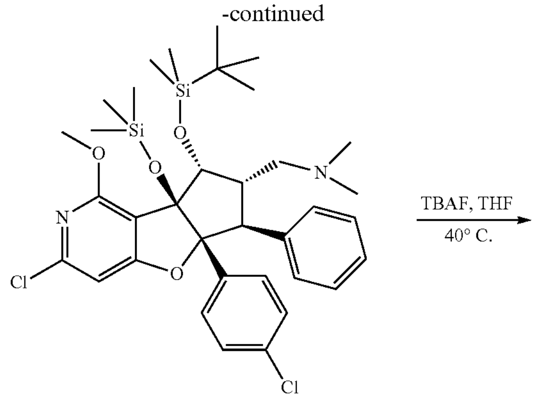

2

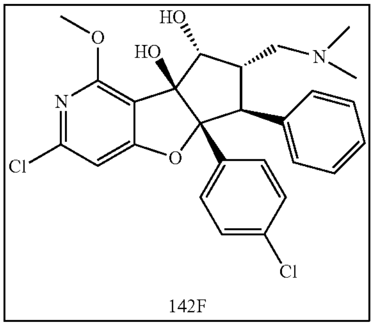

142F

Synthesis of rac-1-((5aR,6S,7S,8R,8aS)-8-((tert-butyldimethylsilyl)oxy)-3-chloro-5a-(4-chlorophenyl)-1-methoxy-6-phenyl-8a-((trimethylsilyl)oxy)-5a,7,8,8a-tetrahydro-6H-cyclopenta[4,5]furo[3,2-c]pyridin-7-yl)-N,N-dimethylmethanamine (2)

Hexachloroethane from Aldrich was dissolved in THF and dried over 4 Angstrom molecular sieves for 2 hours prior to use. Rac-1-((5aR,6S,7S,8R,8aS)-5a-(4-bromophenyl)-8-((tert-butyldimethylsilyl)oxy)-3-chloro-1-methoxy-6-phenyl-8a-((trimethylsilyl)oxy)-5a,7,8,8a-tetrahydro-6H-cyclopenta[4,5]furo[3,2-c]pyridin-7-yl)-N,N-dimethylmethanamine (1, 205 mg, 0.280 mmol) was dissolved in THF (3 mL) with stirring under argon. The resulting colorless solution was cooled to −78° C. with a dry ice/acetone bath for 15 min. n-Butyllithium (2.5 M in hexane) (0.15 mL, 0.36 mmol) was added dropwise slowly. The reaction mixture was stirred for 30 min at −78° C. under argon and then hexachloroethane (0.42 M in THF) (1.07 mL, 0.450 mmol) was added and the resulting mixture was stirred at −78° C. under argon for 45 min.

Saturated aqueous ammonium chloride (1 mL) was added and the reaction mixture was warmed to room temperature with stirring. The resulting mixture was partitioned between water and ethyl acetate. The organics were washed with brine, dried over magnesium sulfate, filtered, concentrated on a rotary evaporator, and purified via silica gel chromatography (5-20% EtOAc/hexanes) to afford rac-1-((5aR,6S,7S,8R,8aS)-8-((tert-butyldimethylsilyl)oxy)-3-chloro-5a-(4-chlorophenyl)-1-methoxy-6-phenyl-8a-((trimethylsilyl)oxy)-5a,7,8,8a-tetrahydro-6H-cyclopenta[4,5]furo[3,2-c]pyridin-7-yl)-N,N-dimethylmethanamine (2) as a white solid. Yield: 154 mg, 80%; MS (ESI) m/z 687.3$[M+1]^+$; $^1H$ NMR (400 MHz, DMSO-$d_6$) δ 7.12-6.95 (m, 1OH), 4.49 (d, J=3.3 Hz, 1H), 3.95 (d, J=13.0 Hz, 1H), 3.79 (s, 3H), 3.19 (m, 1H), 2.18 (s, 6H), 2.00 (m, 1H), 0.67 (s, 9H), 0.11 (s, 3H), −0.16 (s, 9H), −0.26 (s, 3H).

Synthesis of rac-(5aR,6S,7S,8R,8aS)-3-chloro-5a-(4-chlorophenyl)-7-((dimethylamino)methyl)-1-methoxy-6-phenyl-5a,6,7,8-tetrahydro-8aH-cyclopenta[4,5]furo[3,2-c]pyridine-8,8a-diol (Cpd. No. 142F)

Tetrabutylammonium fluoride (1 M in THF) (0.97 mL, 0.97 mmol) was added to a stirred solution of rac-1-((5aR,6S,7S,8R,8aS)-8-((tert-butyldimethylsilyl)oxy)-3-chloro-5a-(4-chlorophenyl)-1-methoxy-6-phenyl-8a-((trimethylsilyl)oxy)-5a,7,8,8a-tetrahydro-6H-cyclopenta[4,5]furo[3,2-c]pyridin-7-yl)-N,N-dimethylmethanamine (2, 111 mg, 0.160 mmol) in THF (3 mL). The reaction mixture was sealed, stirred, and heated at 40° C. for 14 h. The solvent was removed on a rotary evaporator. The residue was taken up in DMSO and methanol, filtered, and purified via preparatory HPLC (15-47% acetonitrile in water with 0.1% TFA). Fractions containing the desired product were loaded onto a Strata X-C ion exchange column from Phenomenex. The column was washed sequentially with water, acetonitrile, methanol, and then 5% ammonium hydroxide in methanol/dichloromethane. Fluent containing the desired product was concentrated on a rotary evaporator, and dried under high vacuum at 40° C. to afford rac-(5aR,6S,7S,8R,8aS)-3-chloro-5a-(4-chlorophenyl)-7-((dimethylamino)methyl)-1-methoxy-6-phenyl-5a,6,7,8-tetrahydro-8aH-cyclopenta[4,5]furo[3,2-c]pyridine-8,8a-diol (Cpd. No. 142F) as a white solid. Yield: 40.0 mg, 49%; MS (ESI) m/z 501.3$[M+1]^+$; $^1H$ NMR (400 MHz, DMSO-d) S 7.16-7.11 (m, 2H), 7.09-7.01 (m, 4H), 7.01-6.90 (m, 3H), 6.83 (s, 1H), 5.54 (s, 1H), 5.17 (s, 1H), 4.41 (d, J=4.1 Hz, 1H), 3.81 (s, 3H), 3.66 (d, J=14.0 Hz, 1H), 3.07 (m, 1H), 2.54 (m, 1H), 2.20 (s, 6H), 1.95 (m, 1H).

Example 143

Rac-(5aR,6S,7S,8R,8aS)-3-chloro-5a-(4-(difluoromethyl)phenyl)-7-((dimethylamino)methyl)-1-methoxy-6-phenyl-5a,6,7,8-tetrahydro-8aH-cyclopenta[4,5]furo[3,2-c]pyridine-8,8a-diol (Cpd. No. 143F)

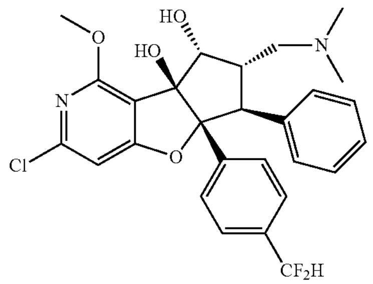

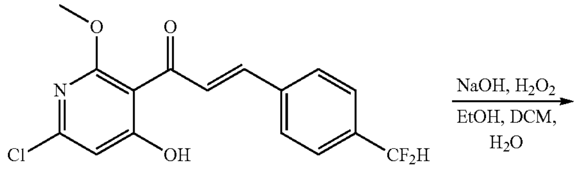

1

-continued

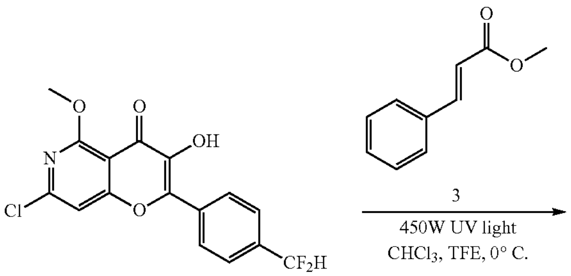

2

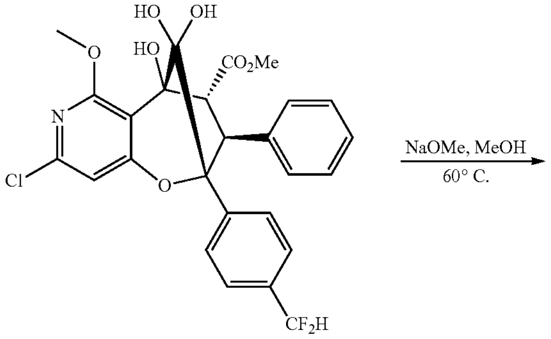

4

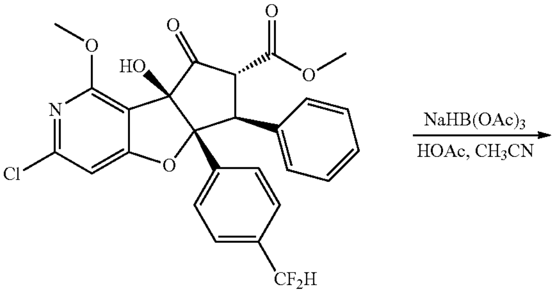

5

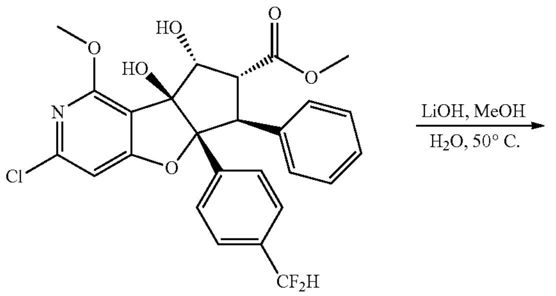

6

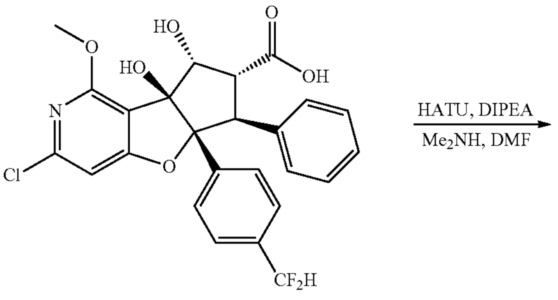

7

-continued

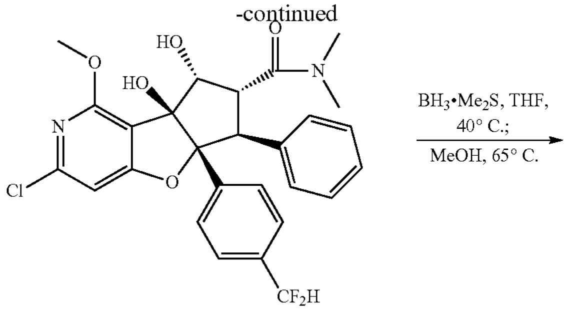

8

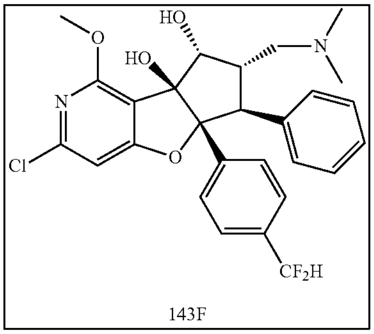

143F

Synthesis of 7-chloro-2-(4-(difluoromethyl)phenyl)-3-hydroxy-5-methoxy-4H-pyrano[3,2-c]pyridin-4-one (2)

10% aqueous sodium hydroxide (3.87 mL, 10.7 mmol) was added to a stirred mixture (not all dissolved) of (E)-1-(6-chloro-4-hydroxy-2-methoxypyridin-3-yl)-3-(4-(difluoromethyl)phenyl)prop-2-en-1-one (1, 1.64 g, 4.83 mmol) in ethanol (32 mL) and dichloromethane (8 mL) cooled with a room temperature water bath. After 1 min 30% aqueous hydrogen peroxide (3.46 mL, 33.9 mmol) was added. The reaction mixture was stirred vigorously while cooled with a room temperature water bath for 1.5 h. The reaction mixture was diluted with dichloromethane, poured onto saturated aqueous ammonium chloride (50 mL), and extracted three times with dichloromethane. The organics were concentrated on a rotary evaporator. The residual solids were shaken in a separatory funnel with dichloromethane (200 mL) and saturated aqueous ammonium chloride (50 mL). The layers were separated and the water layer extracted twice with dichloromethane. The combined organics were dried over $Na_2SO_4$, filtered, and concentrated on a rotary evaporator. The residue was triturated with methanol at room temperature and dried under high vacuum to afford 7-chloro-2-(4-(difluoromethyl)phenyl)-3-hydroxy-5-methoxy-4H-pyrano[3,2-c]pyridin-4-one (2) as a tan solid. Yield: 231 mg, 14%; MS (ESI) m/z 354.2$[M+1]^+$; $^1H$ NMR (400 MHz, DMSO-$d_6$) δ 10.07 (s, 1H), 8.34-8.28 (m, 2H), 7.79-7.73 (m, 2H), 7.56 (s, 1H), 7.12 (t, J=55.7 Hz, 1H), 4.03 (s, 3H).

Synthesis of rac-methyl (3S,4S,5R)-8-chloro-2-(4-(difluoromethyl)phenyl)-5,10,10-trihydroxy-6-methoxy-3-phenyl-2,3,4,5-tetrahydro-2,5-methanooxepino[3,2-c]pyridine-4-carboxylate (4)

To a 100 mL round bottom flask was added sequentially: a stir bar, 7-chloro-2-(4-(difluoromethyl)phenyl)-3-hydroxy-5-methoxy-4H-pyrano[3,2-c]pyridin-4-one (2, 257 mg, 0.730 mmol), methyl cinnamate (3, 1.18 g, 7.27 mmol), chloroform (12 mL), and trifluoroethanol (12 mL). (All material is not dissolved). The reaction mixture was stirred vigorously and irradiated with 450 W UV light while being cooled with a 0° C. cold bath for 3 h.

The reaction mixture was diluted with 3% triethylamine in ethyl acetate (15 mL), concentrated on a rotary evaporator with silica gel, and dried under high vacuum overnight. The residue was loaded into a loading column and purified via silica gel chromatography (0-5-100% EtOAc/hexanes) to afford impure rac-methyl (3S,4S,5R)-8-chloro-2-(4-(difluoromethyl)phenyl)-5,10,10-trihydroxy-6-methoxy-3-phenyl-2,3,4,5-tetrahydro-2,5-methanooxepino[3,2-c]pyridine-4-carboxylate (4) as an orange residue. Yield: 280 mg; MS (ESI) m/z 534.3 [M]+. This material was taken on to the next step without further purification.

Synthesis of rac-methyl (5aR,6S,7R,8aR)-3-chloro-5a-(4-(difluoromethyl)phenyl)-8a-hydroxy-1-methoxy-8-oxo-6-phenyl-5a,7,8,8a-tetrahydro-6H-cyclopenta[4,5]furo[3,2-c]pyridine-7-carboxylate (5)

Sodium methoxide (25 wt. % in methanol) (0.34 mL, 1.49 mmol) was added to a stirred solution of rac-methyl (3S,4S,5R)-8-chloro-2-(4-(difluoromethyl)phenyl)-5,10,10-trihydroxy-6-methoxy-3-phenyl-2,3,4,5-tetrahydro-2,5-methanooxepino[3,2-c]pyridine-4-carboxylate (4, 273 mg, 0.490 mmol) in methanol (10 mL) at room temperature under argon. The clear yellow solution changed to dark orange colored. The reaction mixture was heated at 60° C. under a reflux condenser under argon for 40 min and then most of the solvent was removed on a rotary evaporator. The residue was partitioned between saturated aqueous ammonium chloride and ethyl acetate. The organics were washed with brine, dried over magnesium sulfate, filtered, concentrated on a rotary evaporator, and dried under high vacuum to afford rac-methyl (5aR,6S,7R,8aR)-3-chloro-5a-(4-(difluoromethyl)phenyl)-8a-hydroxy-1-methoxy-8-oxo-6-phenyl-5a,7,8,8a-tetrahydro-6H-cyclopenta[4,5]furo[3,2-c]pyridine-7-carboxylate (5) as a yellow residue. Yield: 240 mg; MS (ESI) m/z 534.1[M+1]$^+$. This material was carried on without further purification.

Synthesis of rac-methyl (5aR,6S,7R,8R,8aS)-3-chloro-5a-(4-(difluoromethyl)phenyl)-8,8a-dihydroxy-1-methoxy-6-phenyl-5a, 7,8,8a-tetrahydro-6H-cyclopenta[4,5]furo[3,2-c]pyridine-7-carboxylate (6)

To a stirred solution of rac-methyl (5aR,6S,7R,8aR)-3-chloro-5a-(4-(difluoromethyl)phenyl)-8a-hydroxy-1-methoxy-8-oxo-6-phenyl-5a,7,8,8a-tetrahydro-6H-cyclopenta[4,5]furo[3,2-c]pyridine-7-carboxylate (5, 264 mg, 0.510 mmol) in MeCN (9 mL) at room temperature was added acetic acid (0.29 mL, 5.12 mmol) and then sodium triacetoxyborohydride (542 mg, 2.56 mmol). The resulting reaction mixture was stirred vigorously at room temperature for 40 min. Saturated aqueous ammonium chloride (5 mL) was added slowly dropwise and the resulting mixture was partitioned between water and ethyl acetate. The organics were washed with saturated aqueous sodium bicarbonate and then brine, dried over magnesium sulfate, filtered, concentrated on a rotary evaporator and purified via silica gel chromatography (12-22% EtOAc/hexanes) to afford rac-methyl (5aR,6S,7R,8R,8aS)-3-chloro-5a-(4-(difluoromethyl)phenyl)-8,8a-dihydroxy-1-methoxy-6-phenyl-5a,7,8,8a-tetrahydro-6H-cyclopenta[4,5]furo[3,2-c]pyridine-7-carboxylate (6) as a slightly yellow solid. Yield: 100 mg, 27% over three steps; MS (ESI) m/z 518.2[M+1]$^+$; $^1$H NMR (400 MHz, DMSO-$d_6$) δ 7.22 (s, 4H), 7.07-7.00 (m, 2H), 6.99-6.92 (m, 4H), 6.80 (t, J=55.9 Hz, 1H), 5.71-5.66 (m, 2H), 4.67-4.62 (m, 1H), 4.33 (d, J=14.1 Hz, 1H), 4.14 (dd, J=14.0, 4.9 Hz, 1H), 3.83 (s, 3H), 3.58 (s, 3H).

Synthesis of rac-(5aR,6S,7R,8R,8aS)-3-chloro-5a-(4-(difluoromethyl)phenyl)-8,8a-dihydroxy-1-methoxy-6-phenyl-5a,7,8,8a-tetrahydro-6H-cyclopenta[4,5]furo[3,2-c]pyridine-7-carboxylic acid (7)

To a stirred mixture (not all dissolved) of rac-methyl (5aR,6S,7R,8R,8aS)-3-chloro-5a-(4-(difluoromethyl)phenyl)-8,8a-dihydroxy-1-methoxy-6-phenyl-5a,7,8,8a-tetrahydro-6H-cyclopenta[4,5]furo[3,2-c]pyridine-7-carboxylate (6, 98.2 mg, 0.190 mmol) in methanol (4 mL) was added water (0.4 mL) and then lithium hydroxide (45.4 mg, 1.90 mmol). The resulting yellow reaction mixture was stirred and heated at 50° C. under a reflux condenser under argon for 3 h. The reaction mixture was cooled with a 0° C. cold bath and 1 N hydrochloric acid in water (1.89 mL, 1.89 mmol) was added with vigorous stirring. A few more drops of 1 N hydrochloric acid was added to make the mixture slightly acidic. Most of the methanol was removed on a rotary evaporator. The residue was extracted three times with dichloromethane. The combined organics were washed with brine, dried over magnesium sulfate, filtered, concentrated on a rotary evaporator and dried under high vacuum at 40° C. overnight to afford crude rac-(5aR,6S,7R,8R,8aS)-3-chloro-5a-(4-(difluoromethyl)phenyl)-8,8a-dihydroxy-1-methoxy-6-phenyl-5a,7,8,8a-tetrahydro-6H-cyclopenta[4,5]furo[3,2-c]pyridine-7-carboxylic acid (7) as a white solid with yellow impurity. Yield: 84.3 mg, 88%; MS (ESI) m/z 504.2[M+1]$^+$.

Synthesis of rac-(5aR,6S,7R,8R,8aS)-3-chloro-5a-(4-(difluoromethyl)phenyl)-8,8a-dihydroxy-1-methoxy-N,N-dimethyl-6-phenyl-5a,7,8,8a-tetrahydro-6H-cyclopenta[4,5]furo[3,2-c]pyridine-7-carboxamide (8)

HATU (66.6 mg, 0.180 mmol) was added to a stirred solution of rac-(5aR,6S,7R,8R,8aS)-3-chloro-5a-(4-(difluoromethyl)phenyl)-8,8a-dihydroxy-1-methoxy-6-phenyl-5a, 7,8,8a-tetrahydro-6H-cyclopenta[4,5]furo[3,2-c]pyridine-7-carboxylic acid (7, 84.1 mg, 0.170 mmol) in N,N-dimethylformamide (1.5 mL) at room temperature under argon. After 2 min N,N-diisopropylethylamine (0.04 mL, 0.250 mmol) was added. The resulting reaction mixture was capped and stirred at room temperature for 20 min. Dimethylamine (2 M solution in THF) (0.25 mL, 0.50 mmol) was added and the reaction mixture was capped and stirred at room temperature for 40 min. The reaction mixture was diluted with ethyl acetate and diethyl ether, washed three times with water, once with brine, dried over magnesium sulfate, filtered, concentrated on a rotary evaporator, and purified via silica gel chromatography (20-100% EtOAc/hexanes) to afford rac-(5aR,6S,7R,8R,8aS)-3-chloro-5a-(4-(difluoromethyl)phenyl)-8,8a-dihydroxy-1-methoxy-N,N-dimethyl-6-phenyl-5a,7,8,8a-tetrahydro-6H-cyclopenta[4,5]furo[3,2-c]pyridine-7-carboxamide (8) as a white foam-solid. Yield: 80.1 mg, 90%; MS (ESI) m/z 531.3 [M+1]$^+$.

Synthesis of rac-(5aR,6S,7S,8R,8aS)-3-chloro-5a-(4-(difluoromethyl)phenyl)-7-((dimethylamino)methyl)-1-methoxy-6-phenyl-5a,6,7,8-tetrahydro-8aH-cyclopenta[4,5]furo[3,2-c]pyridine-8,8a-diol (Cpd. No. 143F)

Borane dimethyl sulfide complex (0.14 mL, 1.51 mmol) was added to a stirred solution of rac-(5aR,6S,7R,8R,8aS)-3-chloro-5a-(4-(difluoromethyl)phenyl)-8,8a-dihydroxy-1-methoxy-N,N-dimethyl-6-phenyl-5a,7,8,8a-tetrahydro-6H-cyclopenta[4,5]furo[3,2-c]pyridine-7-carboxamide (8, 80.1 mg, 0.150 mmol) in THF (3.5 mL) at room temperature under a reflux condenser under argon. Some bubbling was observed. The reaction mixture was heated at 40° C. under a reflux condenser under argon for 3.5 h. After cooling to room temperature, wet methanol (2.5 mL) was added dropwise slowly. The resulting clear colorless reaction mixture was stirred vigorously and heated at 65° C. under a reflux condenser under argon for 43 h. The reaction mixture was loaded onto a 2 g Strata X-C ion exchange column from Phenomenex. The column was washed sequentially with acetonitrile, methanol, and then 5% ammonium hydroxide in dichloromethane/methanol. Eluent containing the desired product was concentrated on a rotary evaporator. The residue was taken up in 50% acetonitrile in water (not all dissolved), sonicated for a few seconds, and then lyophilized to dryness to afford rac-(5aR,6S,7S,8R,8aS)-3-chloro-5a-(4-(difluoromethyl)phenyl)-7-((dimethylamino)methyl)-1-methoxy-6-phenyl-5a,6,7,8-tetrahydro-8aH-cyclopenta[4,5]furo[3,2-c]pyridine-8,8a-diol (Cpd. No. 143F) as a white solid. Yield: 67.8 mg, 87%; MS (ESI) m/z 517.3$[M+1]^+$; $^1$H NMR (400 MHz, DMSO-$d_6$) δ 7.30 (d, J=8.7 Hz, 2H), 7.24 (dt, J=8.6, 1.1 Hz, 2H), 7.09-7.02 (m, 2H), 7.01-6.93 (m, 3H), 6.88 (s, 1H), 6.85 (t, J=55.9 Hz, 1H), 5.58 (s, 1H), 5.16 (s, 1H), 4.46 (d, J=4.2 Hz, 1H), 3.84 (s, 3H), 3.72 (d, J=14.1 Hz, 1H), 3.14 (ddt, J=14.0, 10.1, 3.7 Hz, 1H), 2.60-2.52 (m, 1H), 2.21 (s, 6H), 1.99-1.92 (m, 1H).

Example 144

Rac-(5aR,6S,7S,8R,8aS)-3-chloro-7-((dimethylamino)methyl)-1-methoxy-6-phenyl-5a-(4-(trifluoromethyl)phenyl)-5a,6,7,8-tetrahydro-8aH-cyclopenta[4,5]furo[3,2-c]pyridine-8,8a-diol (Cpd. No. 144F)

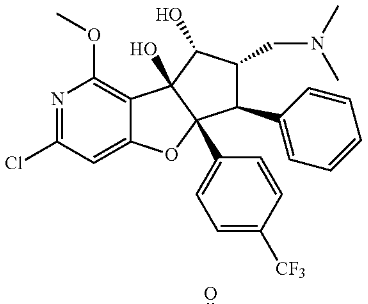

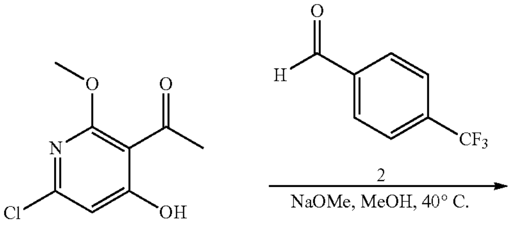

1

-continued

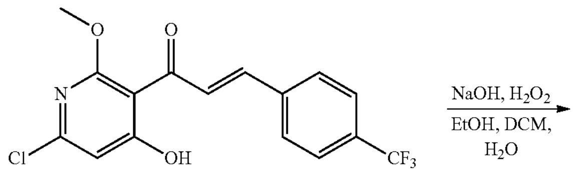

3

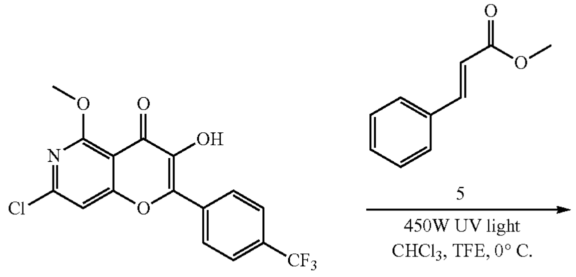

4

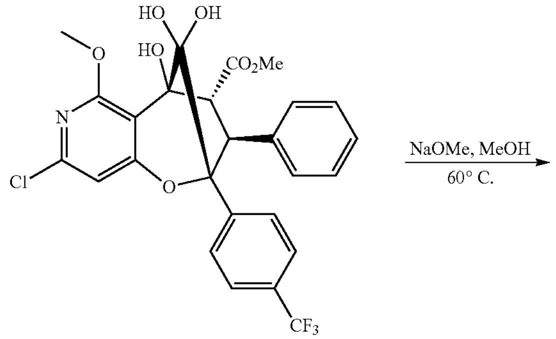

6

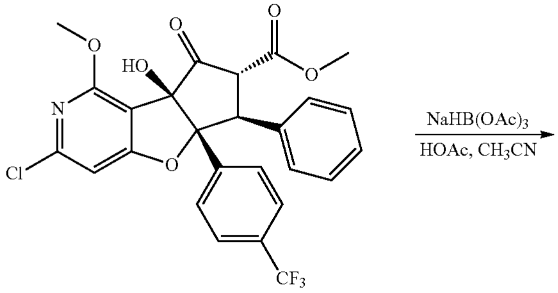

7

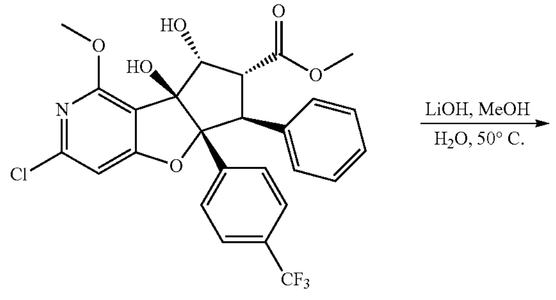

8

-continued

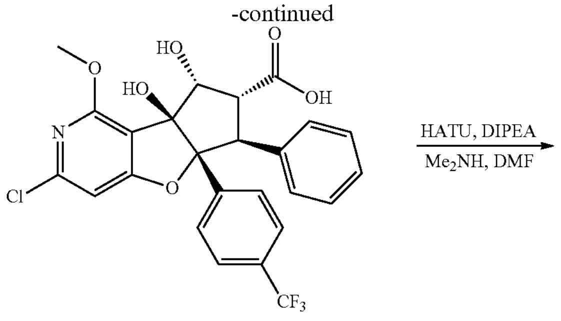

9

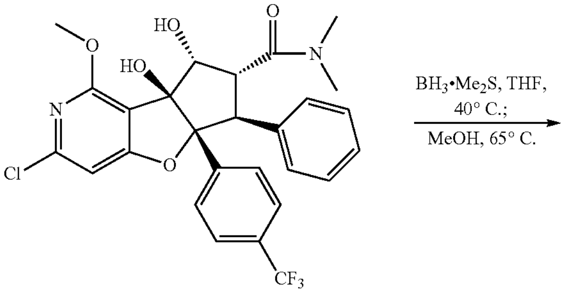

10

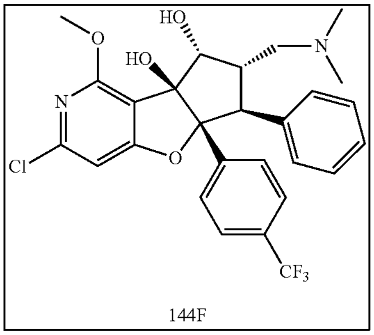

144F

Synthesis of (E)-1-(6-chloro-4-hydroxy-2-methoxypyridin-3-yl)-3-(4-(trifluoromethyl)phenyl)prop-2-en-1-one (3)

Sodium methoxide (25 wt % in methanol) (65.8 mL, 288 mmol) was added to a stirred mixture (not all dissolved) of 1-(6-chloro-4-hydroxy-2-methoxypyridin-3-yl)ethan-1-one (1, 19.33 g, 95.88 mmol) and 4-(trifluoromethyl)benzaldehyde (2, 15.8 mL, 116 mmol) in methanol (300 mL) with stirring at room temperature. The resulting clear yellow reaction mixture was heated at 40° C. under a reflux condenser under argon for 18.5 h. The reaction mixture was poured onto a stirred mixture of 1 N hydrochloric acid in water (288 mL, 288 mmol) and ice water (1 L). The resulting mixture was stirred vigorously for 5 min. Solids were collected by vacuum filtration, washed with water, and then hexanes, and dried under high vacuum to afford (E)-1-(6-chloro-4-hydroxy-2-methoxypyridin-3-yl)-3-(4-(trifluoromethyl)phenyl)prop-2-en-1-one (3) as a light yellow solid. Yield: 29.24 g, 85%; MS (ESI) m/z 358.0[M+1]$^+$; $^1$H NMR (400 MHz, DMSO-$d_6$) δ 7.99-7.93 (m, 2H), 7.81-7.74 (m, 2H), 7.51 (d, J=16.2 Hz, 1H), 7.27 (d, J=16.2 Hz, 1H), 6.61 (s, 1H), 3.82 (s, 3H).

Synthesis of 7-chloro-3-hydroxy-5-methoxy-2-(4-(trifluoromethyl)phenyl)-4H-pyrano[3,2-c]pyridin-4-one (4)

10% aqueous sodium hydroxide (10.2 mL, 27.9 mmol) was added to a stirred mixture (not all dissolved) of (E)-1-(6-chloro-4-hydroxy-2-methoxypyridin-3-yl)-3-(4-(trifluoromethyl)phenyl)prop-2-en-1-one (3, 4.53 g, 12.66 mmol) in ethanol (80 mL) and dichloromethane (20 mL) cooled with a room temperature water bath. After 1 min 30% aqueous hydrogen peroxide (9.07 mL, 88.8 mmol) was added. The reaction mixture was stirred vigorously while cooled with a room temperature water bath for 2 h. The reaction mixture was diluted with dichloromethane, poured onto saturated aqueous ammonium chloride (125 mL), and extracted three times with dichloromethane. The organics were concentrated on a rotary evaporator. The residue was triturated with methanol at room temperature and dried under high vacuum to afford 7-chloro-3-hydroxy-5-methoxy-2-(4-(trifluoromethyl)phenyl)-4H-pyrano[3,2-c]pyridin-4-one (4) as a light yellow solid. Yield: 319 mg, 7%; MS (ESI) m/z 372.1[M+1]$^+$; $^1$H NMR (400 MHz, DMSO-$d_6$) δ 10.24 (s, 1H), 8.41-8.35 (m, 2H), 7.97-7.90 (m, 2H), 7.57 (s, 1H), 4.03 (s, 3H).

Synthesis of rac-methyl (3S,4S,5R)-8-chloro-5,10,10-trihydroxy-6-methoxy-3-phenyl-2-(4-(trifluoromethyl)phenyl)-2,3,4,5-tetrahydro-2,5-methanooxepino[3,2-c]pyridine-4-carboxylate (6)

To a 250 mL round bottom flask was added sequentially: a stir bar, 7-chloro-3-hydroxy-5-methoxy-2-(4-(trifluoromethyl)phenyl)-4H-pyrano[3,2-c]pyridin-4-one (4, 317 mg, 0.850 mmol), methyl cinnamate (5, 1.38 g, 8.53 mmol), chloroform (15 mL), and trifluoroethanol (15 mL). The reaction mixture was stirred vigorously and irradiated with 450 W UV light while being cooled with a 0° C. cold bath for 3 h. The reaction mixture was diluted with 3% triethylamine in ethyl acetate (15 mL), concentrated on a rotary evaporator with silica gel, and dried under high vacuum for 2 h. The residue was loaded into a loading column and purified via silica gel chromatography (0-5-100% EtOAc/hexanes) to afford impure rac-methyl (3S,4S,5R)-8-chloro-5,10,10-trihydroxy-6-methoxy-3-phenyl-2-(4-(trifluoromethyl)phenyl)-2,3,4,5-tetrahydro-2,5-methanooxepino[3,2-c]pyridine-4-carboxylate (6) as an orange residue. Yield: 273 mg; MS (ESI) m/z 552.2 [M]+. This material was taken on to the next step without further purification.

Synthesis of rac-methyl (5aR,6S,7R,8aR)-3-chloro-8a-hydroxy-1-methoxy-8-oxo-6-phenyl-5a-(4-(trifluoromethyl)phenyl)-5a, 7,8,8a-tetrahydro-6H-cyclopenta[4,5]furo[3,2-c]pyridine-7-carboxylate (7)

Sodium methoxide (25 wt. % in methanol) (0.34 mL, 1.49 mmol) was added to a stirred solution of rac-methyl (3S, 4S,5R)-8-chloro-5,10,10-trihydroxy-6-methoxy-3-phenyl-2-(4-(trifluoromethyl)phenyl)-2,3,4,5-tetrahydro-2,5-methanooxepino[3,2-c]pyridine-4-carboxylate (6, 273 mg, 0.490 mmol) in methanol (10 mL) at room temperature under argon. The clear yellow solution changed to dark orange colored. The reaction mixture was heated at 60° C. under a reflux condenser under argon for 40 min and then most of the solvent was removed on a rotary evaporator. The residue was partitioned between saturated aqueous ammonium chloride and ethyl acetate. The organics were washed with brine, dried over magnesium sulfate, filtered, concentrated on a rotary evaporator, and dried under high vacuum to afford impure rac-methyl (5aR,6S,7R,8aR)-3-chloro-8a-hydroxy-1-methoxy-8-oxo-6-phenyl-5a-(4-(trifluoromethyl)phenyl)-5a,7,8,8a-tetrahydro-6H-cyclopenta[4,5]furo[3,2-c]pyridine-7-carboxylate (7) as a yellow residue. Yield: 240 mg; MS (ESI) m/z 534.1[M+1]$^+$. This material was carried on without further purification.

Synthesis of rac-methyl (5aR,6S,7R,8R,8aS)-3-chloro-8,8a-dihydroxy-1-methoxy-6-phenyl-5a-(4-(trifluoromethyl)phenyl)-5a, 7,8,8a-tetrahydro-6H-cyclopenta[4,5]furo[3,2-c]pyridine-7-carboxylate (8)

To a stirred solution of rac-methyl (5aR,6S,7R,8aR)-3-chloro-8a-hydroxy-1-methoxy-8-oxo-6-phenyl-5a-(4-(trifluoromethyl)phenyl)-5a,7,8,8a-tetrahydro-6H-cyclopenta[4,5]furo[3,2-c]pyridine-7-carboxylate (7, 240 mg, 0.450 mmol) in MeCN (9 mL) at room temperature was added acetic acid (0.26 mL, 4.5 mmol) and then sodium triacetoxyborohydride (476 mg, 2.25 mmol). The resulting reaction mixture was stirred vigorously at room temperature for 40 min. Saturated aqueous ammonium chloride (5 mL) was added slowly dropwise and the resulting mixture was partitioned between water and ethyl acetate. The organics were washed with saturated aqueous sodium bicarbonate and then brine, dried over magnesium sulfate, filtered, concentrated on a rotary evaporator and purified via silica gel chromatography (12-22% EtOAc/hexanes) to afford rac-methyl (5aR,6S,7R,8R,8aS)-3-chloro-8,8a-dihydroxy-1-methoxy-6-phenyl-5a-(4-(trifluoromethyl)phenyl)-5a,7,8,8a-tetrahydro-6H-cyclopenta[4,5]furo[3,2-c]pyridine-7-carboxylate (8) as a slightly yellow semi-solid. Yield: 101 mg, 22% over three steps; MS (ESI) m/z 536.2[M+1]$^+$; $^1$H NMR (400 MHz, DMSO-$d_6$) δ 7.38 (d, J=8.6 Hz, 2H), 7.31 (d, J=8.3 Hz, 2H), 7.07-7.01 (m, 2H), 6.99-6.93 (m, 4H), 5.76 (s, 1H), 5.72 (d, J=5.8 Hz, 1H), 4.65 (t, J=5.3 Hz, 1H), 4.37 (d, J=14.0 Hz, 1H), 4.16 (dd, J=14.0, 4.9 Hz, 1H), 3.84 (s, 3H), 3.58 (s, 3H).

Synthesis of rac-(5aR,6S,7R,8R,8aS)-3-chloro-8,8a-dihydroxy-1-methoxy-6-phenyl-5a-(4-(trifluoromethyl)phenyl)-5a, 7,8,8a-tetrahydro-6H-cyclopenta[4,5]furo[3,2-c]pyridine-7-carboxylic acid (9)

To a stirred mixture (not all dissolved) of rac-methyl (5aR,6S,7R,8R,8aS)-3-chloro-8,8a-dihydroxy-1-methoxy-6-phenyl-5a-(4-(trifluoromethyl)phenyl)-5a,7,8,8a-tetrahydro-6H-cyclopenta[4,5]furo[3,2-c]pyridine-7-carboxylate (8, 97.6 mg, 0.180 mmol) in methanol (4 mL) was added water (0.4 mL) and then lithium hydroxide (43.6 mg, 1.82 mmol). The resulting yellow reaction mixture was stirred and heated at 50° C. under a reflux condenser under argon for 3 h. The reaction mixture was cooled with a 0° C. cold bath and 1 N hydrochloric acid in water (1.82 mL, 1.82 mmol) was added with vigorous stirring. A few more drops of 1 N hydrochloric acid was added to make the mixture slightly acidic. Most of the methanol was removed on a rotary evaporator. The residue was extracted three times with dichloromethane. The combined organics were washed with brine, dried over magnesium sulfate, filtered, concentrated on a rotary evaporator and dried under high vacuum at 40° C. overnight to afford crude rac-(5aR,6S,7R,8R,8aS)-3-chloro-8,8a-dihydroxy-1-methoxy-6-phenyl-5a-(4-(trifluoromethyl)phenyl)-5a,7,8,8a-tetrahydro-6H-cyclopenta[4,5]furo[3,2-c]pyridine-7-carboxylic acid (9) as a white solid with yellow impurity. Yield: 84.8 mg, 89%; MS (ESI) m/z 522.3[M+1]$^+$.

Synthesis of rac-(5aR,6S,7R,8R,8aS)-3-chloro-8,8a-dihydroxy-1-methoxy-N,N-dimethyl-6-phenyl-5a-(4-(trifluoromethyl)phenyl)-5a, 7,8,8a-tetrahydro-6H-cyclopenta[4,5]furo[3,2-c]pyridine-7-carboxamide (10)

HATU (64.9 mg, 0.171 mmol) was added to a stirred solution of rac-(5aR,6S,7R,8R,8aS)-3-chloro-8,8a-dihydroxy-1-methoxy-6-phenyl-5a-(4-(trifluoromethyl)phenyl)-5a,7,8,8a-tetrahydro-6H-cyclopenta[4,5]furo[3,2-c]pyridine-7-carboxylic acid (9, 84.8 mg, 0.162 mmol) in N,N-dimethylformamide (1.5 mL) at room temperature. After 2 min N,N-diisopropylethylamine (0.04 mL, 0.24 mmol) was added. The resulting reaction mixture was capped and stirred at room temperature for 20 min. Dimethylamine (2 M solution in THF) (0.24 mL, 0.49 mmol) was added and the reaction mixture was capped and stirred at room temperature for 40 min. The reaction mixture was diluted with ethyl acetate and diethyl ether, washed three times with water, once with brine, dried over magnesium sulfate, filtered, concentrated on a rotary evaporator, and purified via silica gel chromatography (20-100% EtOAc/hexanes) to afford rac-(5aR,6S,7R,8R,8aS)-3-chloro-8,8a-dihydroxy-1-methoxy-N,N-dimethyl-6-phenyl-5a-(4-(trifluoromethyl)phenyl)-5a,7,8,8a-tetrahydro-6H-cyclopenta[4,5]furo[3,2-c]pyridine-7-carboxamide (10) as a white foam-solid. Yield: 83.0 mg, 93%; MS (ESI) m/z 549.2[M+1]$^+$.

Synthesis of rac-(5aR,6S,7S,8R,8aS)-3-chloro-7-((dimethylamino)methyl)-1-methoxy-6-phenyl-5a-(4-(trifluoromethyl)phenyl)-5a,6,7,8-tetrahydro-8aH-cyclopenta[4,5]furo[3,2-c]pyridine-8,8a-diol (Cpd. No. 144F)

Borane dimethyl sulfide complex (0.14 mL, 1.51 mmol) was added to a stirred solution of rac-(5aR,6S,7R,8R,8aS)-3-chloro-8,8a-dihydroxy-1-methoxy-N,N-dimethyl-6-phenyl-5a-(4-(trifluoromethyl)phenyl)-5a,7,8,8a-tetrahydro-6H-cyclopenta[4,5]furo[3,2-c]pyridine-7-carboxamide (10, 83.0 mg, 0.150 mmol) in THF (3.5 mL) at room temperature under a reflux condenser under argon. Some bubbling was observed. The reaction mixture was heated at 40° C. under a reflux condenser under argon for 3.5 h. After cooling to room temperature, wet methanol (2.5 mL) was added dropwise slowly. The resulting clear colorless reaction mixture was stirred vigorously and heated at 65° C. under a reflux condenser under argon for 43 h. The reaction mixture was loaded onto a 2 g Strata X-C ion exchange column from Phenomenex. The column was washed sequentially with acetonitrile, methanol, and then 5% ammonium hydroxide in methanol/dichloromethane. Eluent containing the desired product was concentrated on a rotary evaporator. The residue was taken up in 50% acetonitrile in water (not all dissolved), sonicated for a few seconds, and then lyophilized to dryness to afford rac-(5aR,6S,7S,8R,8aS)-3-chloro-7-((dimethylamino)methyl)-1-methoxy-6-phenyl-5a-(4-(trifluoromethyl)phenyl)-5a,6,7,8-tetrahydro-8aH-cyclopenta[4,5]furo[3,2-c]pyridine-8,8a-diol (Cpd. No. 144F) as a white solid. Yield: 74.0 mg, 91%; MS (ESI) m/z 535.2[M+1]$^+$; $^1$H NMR (400 MHz, DMSO-$d_6$) δ 7.43-7.35 (m, 4H), 7.06 (dd, J=8.3, 6.3 Hz, 2H), 7.02-6.94 (m, 3H), 6.89 (s, 1H), 5.64 (s, 1H), 5.20 (s, 1H), 4.46 (d, J=4.1 Hz, 1H), 3.84 (s, 3H), 3.75 (d, J=14.0 Hz, 1H), 3.14 (ddt, J=13.9, 9.8, 3.7 Hz, 1H), 2.62-2.53 (m, 1H), 2.21 (s, 6H), 1.97 (d, J=12.0 Hz, 1H).

Example 145

(5aR,6S,7S,8R,8aS)-5a-(4-chlorophenyl)-7-((dimethylamino)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 145F)

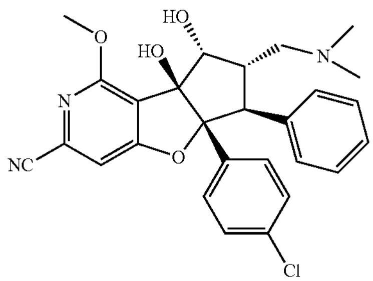

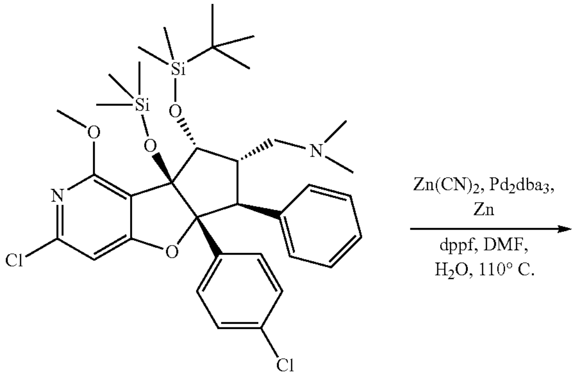

1

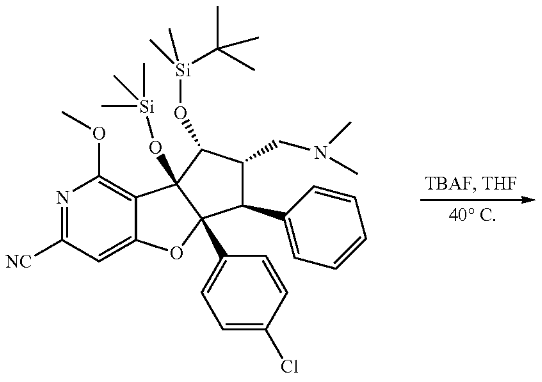

2

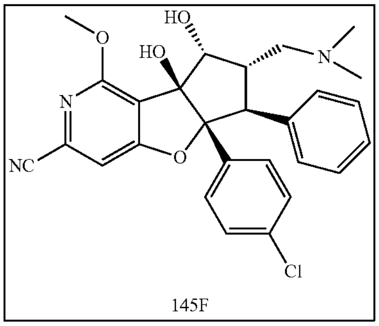

145F

Synthesis of rac-(5aR,6S,7S,8R,8aS)-8-((tert-butyldimethylsilyl)oxy)-5a-(4-chlorophenyl)-7-((dimethylamino)methyl)-1-methoxy-6-phenyl-8a-((trimethylsilyl)oxy)-5a,7,8,8a-tetrahydro-6H-cyclopenta[4,5]furo[3,2-c]pyridine-3-carbonitrile (2)

Rac-1-((5aR,6S,7S,8R,8aS)-8-((tert-butyldimethylsilyl)oxy)-3-chloro-5a-(4-chlorophenyl)-1-methoxy-6-phenyl-8a-((trimethylsilyl)oxy)-5a,7,8,8a-tetrahydro-6H-cyclopenta[4,5]furo[3,2-c]pyridin-7-yl)-N,N-dimethylmethanamine (1, 40.8 mg, 0.059 mmol), zinc powder (4.5 mg, 0.069 mmol), zinc cyanide (20.9 mg, 0.178 mmol), dppf (3.3 mg, 0.006 mmol), $Pd_2dba_3$ (2.7 mg, 0.003 mmol), N,N-dimethylformamide (0.55 mL), and water (0.055 mL) were combined in a 1 dram vial with a stirbar. The mixture was sparged with argon gas for 5 min and then sealed, stirred vigorously, and heated at 100° C. with a block heater for 2.5 h. More of all the reagents was added (including water). The mixture was sparged with argon gas for 5 min and then sealed, stirred vigorously, and heated at 110° C. with a block heater for 5.5 h. After cooling to room temperature the reaction mixture was diluted with methanol, filtered, and purified via preparatory HPLC (30-85% acetonitrile in water with 0.1% TFA). Fractions containing the desired product were combined and lyophilized to dryness to afford rac-(5aR,6S,7S,8R,8aS)-8-((tert-butyldimethylsilyl)oxy)-5a-(4-chlorophenyl)-7-((dimethylamino)methyl)-1-methoxy-6-phenyl-8a-((trimethylsilyl)oxy)-5a,7,8,8a-tetrahydro-6H-cyclopenta[4,5]furo[3,2-c]pyridine-3-carbonitrile (2) as an off-white solid. Yield: 17.6 mg, 44%; MS (ESI) m/z 678.4$[M+1]^+$.

Synthesis of (5aR,6S,7S,8R,8aS)-5a-(4-chlorophenyl)-7-((dimethylamino)methyl)-8,8a-dihydroxy-1-methoxy-6-phenyl-5a, 7,8,8a-tetrahydro-6H-cyclopenta[4,5]furo[3,2-c]pyridine-3-carbonitrile (Cpd. No. 145F)

Tetrabutylammonium fluoride (1 M in THF) (0.15 mL, 0.150 mmol) was added to a stirred solution of rac-(5aR,6S,7S,8R,8aS)-8-((tert-butyldimethylsilyl)oxy)-5a-(4-chlorophenyl)-7-((dimethylamino)methyl)-1-methoxy-6-phenyl-8a-((trimethylsilyl)oxy)-5a,7,8,8a-tetrahydro-6H-cyclopenta[4,5]furo[3,2-c]pyridine-3-carbonitrile (2, 17.0 mg, 0.025 mmol) in THF (1.5 mL). The reaction mixture was sealed, stirred, and heated at 40° C. for 20 h. The solvent was removed on a rotary evaporator. The residue was taken up in DMSO and methanol, filtered, and purified via preparatory HPLC (15-40% acetonitrile in water with 0.1% TFA). Fractions containing the desired product were loaded onto a Strata X-C ion exchange column from Phenomenex. The column was washed sequentially with water, acetonitrile, methanol, and then 5% ammonium hydroxide in methanol/dichloromethane. Fluent containing the desired product was concentrated on a rotary evaporator. The residue was taken up in 50% acetonitrile in water (not all dissolved), sonicated for a few seconds, and then lyophilized to dryness to afford rac-(5aR,6S,7S,8R,8aS)-5a-(4-chlorophenyl)-7-((dimethylamino)methyl)-8,8a-dihydroxy-1-methoxy-6-phenyl-5a,7,8,8a-tetrahydro-6H-cyclopenta[4,5]furo[3,2-c]pyridine-3-carbonitrile as a white solid. Yield: 9.4 mg, 76%; The enantiomers were separated by chiral SFC [Chiralpak IG (4.6×250) mm, 5μ], $CO_2$/0.2% TEA in IPA 60/40 (v/v). Peak 1 (Cpd. No. 145F, 2.60 g), $[\alpha]_D$–71.6° (c 0.35, $CHCl_3$), $R_t$=1.978 min, ee: 99.48% MS (ESI) m/z 492.13$[M+1]^+$; $^1H$ NMR (400 MHz, DMSO-$d_6$) 7.51 (s, 1H), 7.17 (d, J=8.60 Hz, 2H), 7.11-6.96 (m, 7H), 5.74 (s, 1H), 5.29 (bs, 1H), 4.47 (d, J=3.6 Hz, 1H), 3.89 (s, 3H), 3.71 (d, J=14.04 Hz, 1H), 3.10 (t, J=12.0 Hz, 1H), 2.51 (bs, 1H), 2.20 (s, 6H), 1.94 (t, J=12.52 Hz, 1H); Peak 2 (2.54 g), $[\alpha]_D$+77.8° (c 0.30, $CHCl_3$), $R_t$=2.332 min, ee: 99.46% MS (ESI) m/z 492.15[M+1]$^+$; $^1$H NMR (400 MHz, DMSO-$d_6$) 7.51 (s, 1H), 7.17 (d, J=8.72 Hz, 2H), 7.11-6.96 (m, 7H), 5.74 (s, 1H), 5.29 (bs, 1H), 4.47 (d, J=3.76 Hz, 1H), 3.89 (s, 3H), 3.71 (d, J=13.96 Hz, 1H), 3.09 (t, J=10.7 Hz, 1H), 2.53 (bs, 1H), 2.19 (s, 6H), 1.95-1.90 (m, 1H).

Example 146

Rac-(5aR,6S,7S,8R,8aS)-5a-(4-(difluoromethyl)phenyl)-7-((dimethylamino)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 146F)

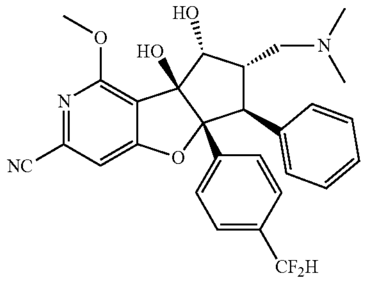

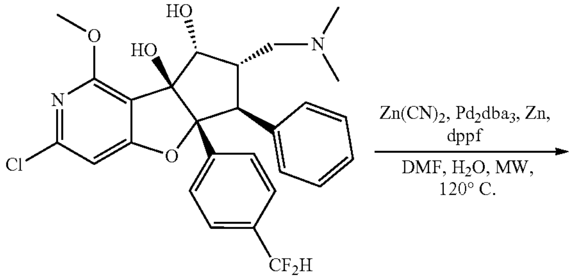

1

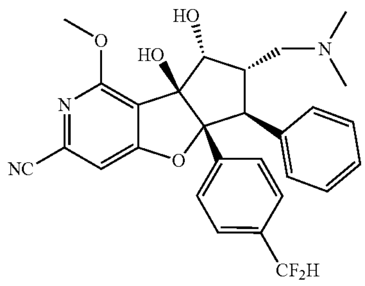

146F

Synthesis of rac-(5aR,6S,7S,8R,8aS)-5a-(4-(difluoromethyl)phenyl)-7-((dimethylamino)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 146F)

Rac-(5aR,6S,7S,8R,8aS)-3-chloro-5a-(4-(difluoromethyl)phenyl)-7-((dimethylamino)methyl)-1-methoxy-6-phenyl-5a,6,7,8-tetrahydro-8aH-cyclopenta[4,5]furo[3,2-c]pyridine-8,8a-diol (1, 22.8 mg, 0.044 mmol), zinc powder (2.9 mg, 0.044 mmol), zinc cyanide (25.9 mg, 0.221 mmol), dppf (4.9 mg, 0.009 mmol), $Pd_2dba_3$ (4.0 mg, 0.004 mmol), N,N-dimethylformamide (0.30 mL), and water (0.03 mL) were combined in a microwave vial with a stirbar. The mixture was sparged with argon gas for 5 min and then sealed, stirred, and microwaved at 110° C. for 1 h. More of all of the reagents and water were added. The mixture was sparged with argon gas for 5 min and then sealed, stirred, and microwaved at 120° C. for 2 h. More of all of the reagents and water were added. The mixture was sparged with argon gas for 5 min and then sealed, stirred, and microwaved at 120° C. for 2 h. The reaction mixture was diluted with DMSO and methanol, filtered, and purified via preparatory HPLC (15-40% acetonitrile in water with 0.1% TFA). Fractions containing the desired product were loaded onto a Strata X-C ion exchange column from Phenomenex. The column was washed sequentially with water, acetonitrile, methanol, and then 5% ammonium hydroxide in methanol/dichloromethane. Fluent containing the desired product was concentrated on a rotary evaporator. The residue was taken up in water/acetonitrile, sonicated for a few seconds, and lyophilized to dryness to afford rac-(5aR,6S,7S,8R,8aS)-5a-(4-(difluoromethyl)phenyl)-7-((dimethylamino)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 146F) as a white solid. Yield: 12.7 mg, 57%; MS (ESI) m/z 508.3[M+1]$^+$; $^1$H NMR (400 MHz, DMSO-$d_6$) δ 7.55 (s, 1H), 7.37-7.21 (m, 4H), 7.03 (dt, J=28.4, 7.6 Hz, 5H), 6.86 (t, J=55.9 Hz, 1H), 5.80 (s, 1H), 5.34 (s, 1H), 4.53 (s, 1H), 3.89 (s, 3H), 3.74 (d, J=14.0 Hz, 1H), 3.19 (m, 1H), 2.24 (s, 6H).

Example 147

(5aR,6S,7S,8R,8aS)-7-((dimethylamino)methyl)-8,8a-dihydroxy-1-methoxy-6-phenyl-5a-(4-(trifluoromethyl)phenyl)-5a,7,8,8a-tetrahydro-6H-cyclopenta[4,5]furo[3,2-c]pyridine-3-carbonitrile (Cpd. No. 147F)

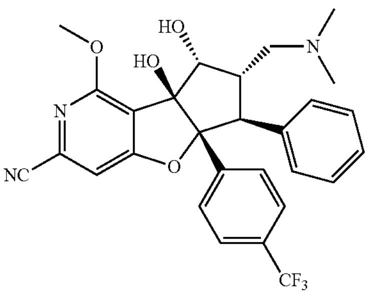

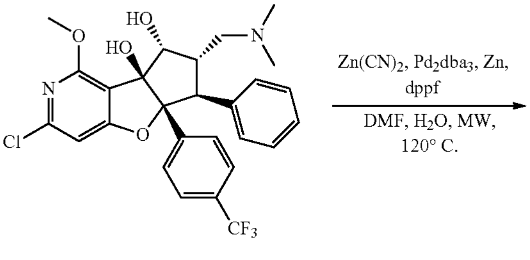

1

-continued

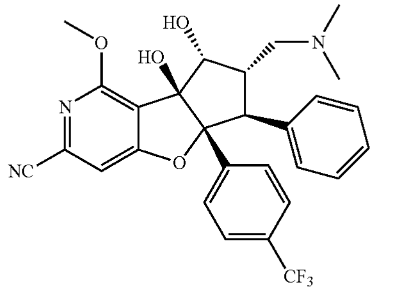

147F

Synthesis of (5aR,6S,7S,8R,8aS)-7-((dimethylamino)methyl)-8,8a-dihydroxy-1-methoxy-6-phenyl-5a-(4-(trifluoromethyl)phenyl)-5a, 7,8,8a-tetrahydro-6H-cyclopenta[4,5]furo[3,2-c]pyridine-3-carbonitrile (Cpd. No. 147F)

Rac-(5aR,6S,7S,8R,8aS)-3-chloro-7-((dimethylamino)methyl)-1-methoxy-6-phenyl-5a-(4-(trifluoromethyl)phenyl)-5a,6,7,8-tetrahydro-8aH-cyclopenta[4,5]furo[3,2-c]pyridine-8,8a-diol (1, 22.6 mg, 0.042 mmol), zinc powder (2.8 mg, 0.042 mmol), zinc cyanide (24.8 mg, 0.211 mmol), dppf (4.7 mg, 0.008 mmol), $Pd_2dba_3$ (3.9 mg, 0.004 mmol), N,N-dimethylformamide (0.40 mL), and water (0.04 mL) were combined in a microwave vial with a stirbar. The mixture was sparged with argon gas for 5 min and then sealed, stirred, and microwaved at 120° C. for 5 h. The reaction mixture was diluted with DMSO and methanol, filtered, and purified via preparatory HPLC (1543% acetonitrile in water with 0.1% TFA). Fractions containing the desired product were loaded onto a Strata X-C ion exchange column from Phenomenex. The column was washed sequentially with water, acetonitrile, methanol, and then 5% ammonium hydroxide in methanol/dichloromethane. Fluent containing the desired product was concentrated on a rotary evaporator. The residue was taken up in water/acetonitrile, sonicated for a few seconds, and lyophilized to dryness to afford rac-(5aR,6S,7S,8R,8aS)-7-((dimethylamino)methyl)-8,8a-dihydroxy-1-methoxy-6-phenyl-5a-(4-(trifluoromethyl)phenyl)-5a,7,8,8a-tetrahydro-6H-cyclopenta[4,5]furo[3,2-c]pyridine-3-carbonitrile as a white solid. Yield: 12.4 mg, 56%; The enantiomers were separated by chiral SFC [CHIRALPAK IG (4.6×250) mm, 5μ] in $CO_2$/MeOH/TEA (80:20:0.2). Peak 1 (650 mg), $R_t$=2.337 min, ee: 99.92%, $[\alpha]_D$+74.10° (c 0.35, chloroform); MS (ESI) m/z 526.16 $[M+1]^+$; $^1H$ NMR (400 MHz, DMSO-$d_6$) 7.55 (s, 1H), 7.42-7.39 (m, 4H), 7.08-6.96 (m, 5H), 5.82 (s, 1H), 5.33 (s, 1H), 4.50 (d, J=3.2 Hz, 1H), 3.89 (s, 3H), 3.76 (d, J=14.12 Hz, 1H), 3.16 (m, 1H), 2.55 (s, 2H), 2.21 (s, 6H), 1.95 (d, J=10.16 Hz, 1H). Peak-2 (Cpd. No. 147F, 650 mg), $R_1$=3.77 min, ee: 99.75%, $[\alpha]^D$−80.4° (c 0.3, chloroform); MS (ESI) m/z 495.16$[M+1]^+$; $^1H$ NMR (400 MHz, DMSO-$d_6$) 7.55 (s, 1H), 7.40 (s, 4H), 7.06-6.97 (m, 5H), 5.83 (s, 1H), 5.33 (s, 1H), 4.51 (s, 1H), 3.89 (s, 3H), 3.76 (d, J=14.0 Hz, 1H), 3.17 (m, 1H), 2.59-2.50 (m, 2H), 2.21 (s, 6H), 1.96 (bs, 1H).

Example 148

Rac-(5aR,6S,7S,8R,8aS)-5a-(4-(difluoromethyl)phenyl)-7-((dimethylamino)methyl)-1-methoxy-6-phenyl-5a,6,7,8-tetrahydro-8aH-cyclopenta[4,5]furo[3,2-c]pyridine-8,8a-diol (Cpd. No. 148F)

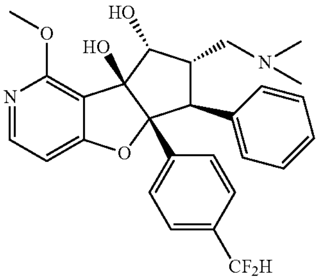

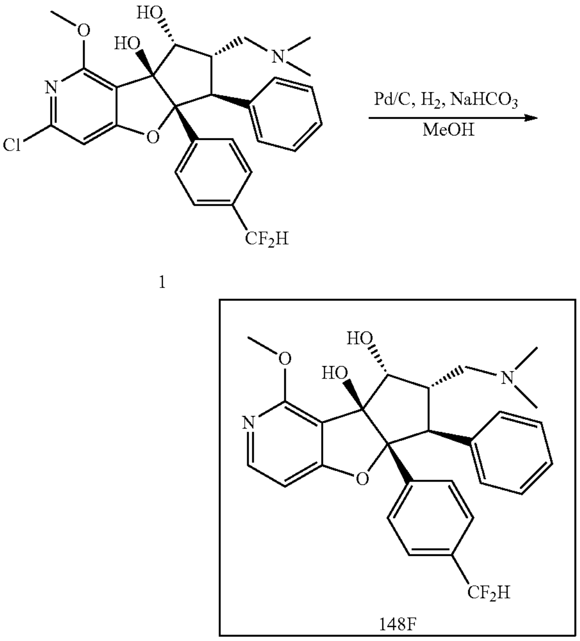

1

148F

Synthesis of rac-(5aR,6S,7S,8R,8aS)-5a-(4-(difluoromethyl)phenyl)-7-((dimethylamino)methyl)-1-methoxy-6-phenyl-5a,6,7,8-tetrahydro-8aH-cyclopenta[4,5]furo[3,2-c]pyridine-8,8a-diol (Cpd. No. 148F)

Rac-(5aR,6S,7S,8R,8aS)-3-chloro-5a-(4-(difluoromethyl)phenyl)-7-((dimethylamino)methyl)-1-methoxy-6-phenyl-5a,6,7,8-tetrahydro-8aH-cyclopenta[4,5]furo[3,2-c]pyridine-8,8a-diol (1, 12.6 mg, 0.024 mmol), sodium bicarbonate (2.3 mg, 0.027 mmol), and methanol (3 mL) were combined in a 10 mL conical flask with a stirbar. A combination vacuum/hydrogen/argon manifold was attached and the atmosphere in the flask was removed and replaced with argon twice. 10% palladium on activated charcoal (5.2 mg, 0.005 mmol) was added and the atmosphere in the flask was removed and replaced with hydrogen twice. The reaction mixture was stirred vigorously at room temperature under a hydrogen balloon for 1.5 h. The reaction mixture was filtered through a syringe filter onto a 1 g Strata X-C ion exchange column from Phenomenex. The column was washed sequentially with water, acetonitrile, methanol, and then 5% ammonium hydroxide in methanol/dichloromethane. Eluent containing the desired product was concentrated on a rotary evaporator. The residue was taken up in water/acetonitrile, sonicated for a few seconds, and lyophilized to dryness to afford rac-(5aR,6S,7S,8R,8aS)-5a-(4-(difluoromethyl)phenyl)-7-((dimethylamino)methyl)-1-methoxy-6-phenyl-5a,6,7,8-tetrahydro-8aH-cyclopenta[4,5]furo[3,2-c]pyridine-8,8a-diol (Cpd. No. 148F) as a white solid. Yield: 11.3 mg, 96%; MS (ESI) m/z 483.3 $[M+1]^+$; $^1H$ NMR (400 MHz, DMSO-$d_6$) δ 7.99 (d, J=5.7 Hz, 1H), 7.33 (d, J=8.3 Hz, 2H), 7.27-7.21 (m, 2H), 7.09-7.01 (m, 2H), 7.01-6.94 (m, 3H), 6.85 (t, J=56.0 Hz), 6.74 (d, J=5.7 Hz, 1H), 5.48 (s, 1H), 5.04 (s, 1H), 4.51 (d, J=4.3 Hz, 1H), 3.85 (s, 3H), 3.69 (d, J=14.1 Hz, 1H), 3.17 (m, 1H), 2.61 (m, 1H), 2.27 (s, 6H), 2.04 (m, 1H).

Example 149

Rac-(5aR,6S,7S,8R,8aS)-7-((dimethylamino)methyl)-1-methoxy-6-phenyl-5a-(4-(trifluoromethyl)phenyl)-5a,6,7,8-tetrahydro-8aH-cyclopenta[4,5]furo[3,2-c]pyridine-8,8a-diol (Cpd. No. 149F)

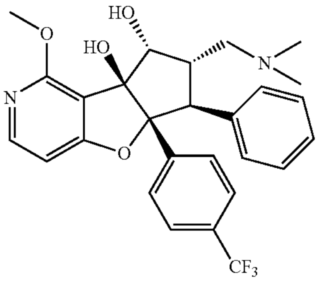

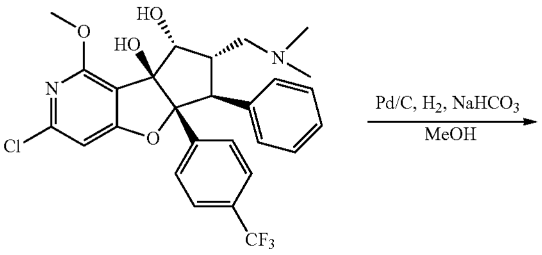

1

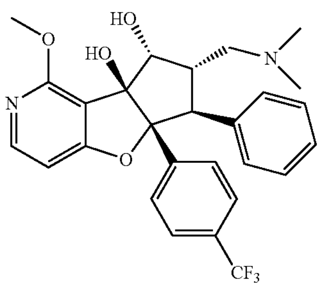

149F

Synthesis of rac-(5aR,6S,7S,8R,8aS)-7-((dimethylamino)methyl)-1-methoxy-6-phenyl-5a-(4-(trifluoromethyl)phenyl)-5a,6,7,8-tetrahydro-8aH-cyclopenta[4,5]furo[3,2-c]pyridine-8,8a-diol (Cpd. No. 149F)

Rac-(5aR,6S,7S,8R,8aS)-3-chloro-7-((dimethylamino)methyl)-1-methoxy-6-phenyl-5a-(4-(trifluoromethyl)phenyl)-5a,6,7,8-tetrahydro-8aH-cyclopenta[4,5]furo[3,2-c]pyridine-8,8a-diol (1, 12.5 mg, 0.023 mmol), sodium bicarbonate (2.2 mg, 0.026 mmol), and methanol (3 mL) were combined in a 15 mL round bottom flask with a stirbar. A combination vacuum/hydrogen/argon manifold was attached and the atmosphere in the flask was removed and replaced with argon twice. 10% palladium on activated charcoal (5.0 mg, 0.005 mmol) was added and the atmosphere in the flask was removed and replaced with hydrogen twice. The reaction mixture was stirred vigorously at room temperature under a hydrogen balloon for 1.5 h. The reaction mixture was filtered through a syringe filter onto a 1 g Strata X-C ion exchange column from Phenomenex. The column was washed sequentially with water, acetonitrile, methanol, and then 5% ammonium hydroxide in methanol/dichloromethane. Eluent containing the desired product was concentrated on a rotary evaporator. The residue was taken up in water/acetonitrile, sonicated for a few seconds, and lyophilized to dryness to afford rac-(5aR,6S,7S,8R,8aS)-7-((dimethylamino)methyl)-1-methoxy-6-phenyl-5a-(4-(trifluoromethyl)phenyl)-5a,6,7,8-tetrahydro-8aH-cyclopenta[4,5]furo[3,2-c]pyridine-8,8a-diol (Cpd. No. 149F) as a white solid. Yield: 10.9 mg, 93%; MS (ESI) m/z 501.3 $[M+1]^+$; $^1H$ NMR (400 MHz, DMSO-$d_6$) δ 8.01 (d, J=5.7 Hz, 1H), 7.40 (m, 4H), 7.10-6.94 (m, 5H), 6.76 (d, J=5.7 Hz, 1H), 5.56 (s, 1H), 5.10 (s, 1H), 4.52 (s, 1H), 3.86 (s, 3H), 3.72 (d, J=14.0 Hz, 1H), 3.18 (m, 1H), 2.28 (s, 6H).

Example 150

Rac-4-((5aR,6S,7S,8R,8aS)-7-((dimethylamino)methyl)-8,8a-dihydroxy-1-methoxy-3-(methylamino)-6-phenyl-6,7,8,8a-tetrahydro-5aH-cyclopenta[4,5]furo[3,2-c]pyridin-5a-yl)benzonitrile (Cpd. No. 150F)

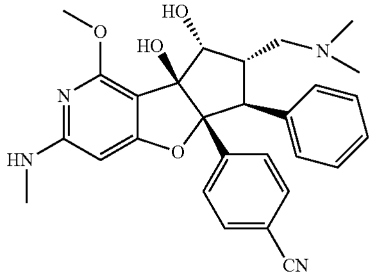

-continued

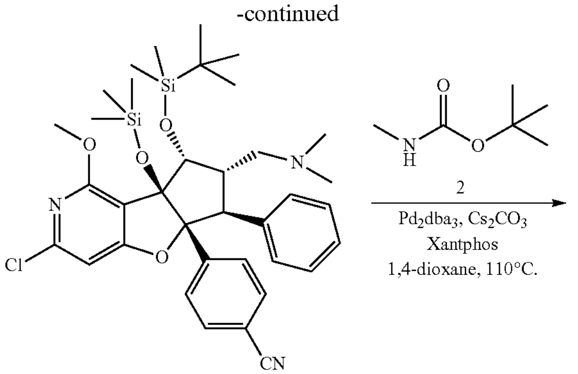

1

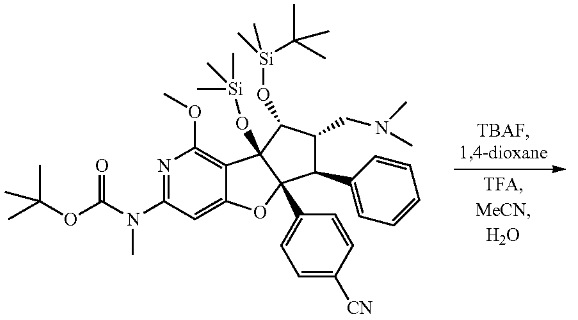

3

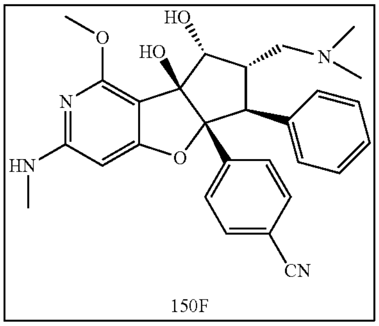

150F

Synthesis of rac-tert-butyl ((5aR,6S,7S,8R,8aS)-8-((tert-butyldimethylsilyl)oxy)-5a-(4-cyanophenyl)-7-((dimethylamino)methyl)-1-methoxy-6-phenyl-8a-((trimethylsilyl)oxy)-5a,7,8,8a-tetrahydro-6H-cyclopenta[4,5]furo[3,2-c]pyridin-3-yl)(methyl) carbamate (3)

Rac-4-((5aR,6S,7S,8R,8aS)-8-((tert-butyldimethylsilyl) oxy)-3-chloro-7-((dimethylamino)methyl)-1-methoxy-6-phenyl-8a-((trimethylsilyl)oxy)-6,7,8,8a-tetrahydro-5aH-cyclopenta[4,5]furo[3,2-c]pyridin-5a-yl)benzonitrile (1, 30.9 mg, 0.046 mmol), Xantphos (5.3 mg, 0.009 mmol), $Pd_2dba_3$ (4.2 mg, 0.005 mmol), cesium carbonate (74.2 mg, 0.228 mmol), tert-butyl-N-methylcarbamate (29.9 mg, 0.227 mmol), and 1,4-dioxane (0.7 mL) were combined in a HPLC vial with a stirbar. The mixture was sparged with argon gas for 5 min and then sealed, stirred vigorously, and heated at 110° C. with a block heater for 2 h. The reaction mixture was loaded directly onto a silica gel loading column and purified via silica gel chromatography (5-50% EtOAc/hexanes) to afford impure rac-tert-butyl ((5aR,6S,7S,8R,8aS)-8-((tert-butyldimethylsilyl)oxy)-5a-(4-cyanophenyl)-7-((dimethylamino)methyl)-1-methoxy-6-phenyl-8a-((trimethylsilyl)oxy)-5a,7,8,8a-tetrahydro-6H-cyclopenta[4,5]furo[3,2-c]pyridin-3-yl)(methyl)carbamate (3) as a yellow foam solid. Yield: 29.6 mg; MS (ESI) m/z 773.6 $[M+1]^+$. This material was carried on to the next step without further purification.

Synthesis of rac-4-((5aR,6S,7S,8R,8aS)-7-((dimethylamino)methyl)-8,8a-dihydroxy-1-methoxy-3-(methylamino)-6-phenyl-6,7,8,8a-tetrahydro-5aH-cyclopenta[4,5]furo[3,2-c]pyridin-5a-yl)benzonitrile (Cpd. No. 150F)

Tetrabutylammonium fluoride (1 M in THF) (0.57 mL, 0.57 mmol) was added to a stirred solution of rac-tert-butyl ((5aR,6S,7S,8R,8aS)-8-((tert-butyldimethylsilyl)oxy)-5a-(4-cyanophenyl)-7-((dimethylamino)methyl)-1-methoxy-6-phenyl-8a-((trimethylsilyl)oxy)-5a,7,8,8a-tetrahydro-6H-cyclopenta[4,5]furo[3,2-c]pyridin-3-yl)(methyl)carbamate (3, 29.6 mg, 0.038 mmol) in 1,4-dioxane (2 mL) in a sealable vial with a stirbar. The reaction mixture was sealed, stirred, and heated at 60° C. for 19 h. The reaction mixture was concentrated, taken up in DMSO and methanol, and purified via preparatory HPLC (15-50% acetonitrile in water with 0.1% TFA). MS (ESI) m/z 587.5 $[M+1]^+$. Fractions containing the desired intermediate were combined and concentrated down to ~15 mL on a rotary evaporator. Acetonitrile (5 mL) was added followed by TFA (1 mL) (total volume ~20 mL). The reaction mixture was stirred and heated at 40° C. under a reflux condenser for 1 h 10 min and then concentrated on a rotary evaporator. The residue was taken up in DMSO/methanol and purified via preparatory HPLC (15-28% acetonitrile in water with 0.1% TFA). Fractions containing the desired product were combined and loaded onto a Strata X-C ion exchange column from Phenomenex. The column was washed sequentially with water, acetonitrile, methanol, and then 5% ammonium hydroxide in methanol/dichloromethane. Fluent containing the desired product was concentrated on a rotary evaporator. The residue was taken up in acetonitrile/water, sonicated for a few seconds, and lyophilized to dryness to afford rac-4-((5aR,6S,7S,8R,8aS)-7-((dimethylamino)methyl)-8,8a-dihydroxy-1-methoxy-3-(methylamino)-6-phenyl-6,7,8,8a-tetrahydro-5aH-cyclopenta[4,5]furo[3,2-c]pyridin-5a-yl)benzonitrile (Cpd. No. 150F) as a white solid. Yield: 8.6 mg, 39% over three steps; MS (ESI) m/z 487.3 $[M+1]^+$; $^1H$ NMR (400 MHz, DMSO-$d_6$) δ 7.52-7.47 (m, 2H), 7.37-7.32 (m, 2H), 7.07 (dd, J=8.0, 6.6 Hz, 2H), 7.03-6.93 (m, 3H), 6.32 (m, 1H), 5.63 (s, 1H), 5.18 (s, 1H), 4.82 (s, 1H), 4.43 (s, 1H), 3.78 (s, 3H), 3.67 (d, J=14.0 Hz, 1H), 3.16 (m, 1H), 2.75 (d, J=4.8 Hz, 3H), 2.33 (br s, 6H).

Example 151

(5aR,6S,7S,8R,8aS)-5a-(4-cyanophenyl)-8,8a-dihydroxy-1-methoxy-7-(morpholinomethyl)-6-phenyl-5a,7,8,8a-tetrahydro-6H-cyclopenta[4,5]furo[3,2-c]pyridine-3-carbonitrile (Cpd. No. 151F)

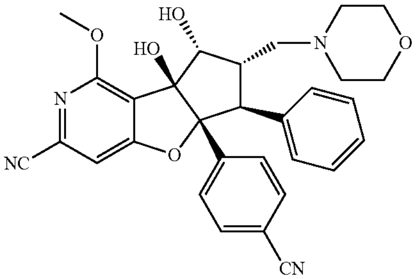

-continued

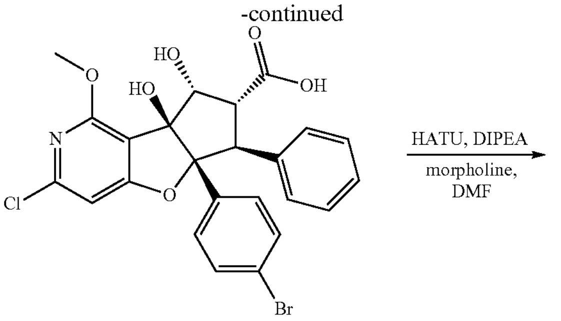

1

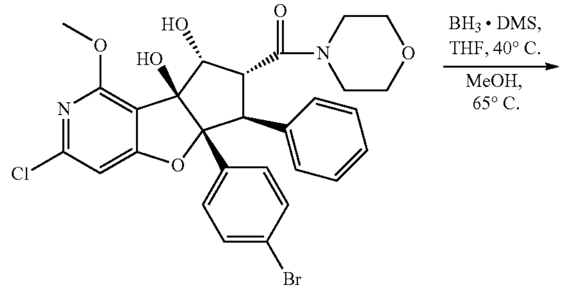

2

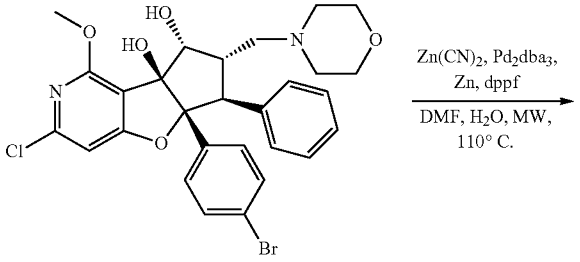

3

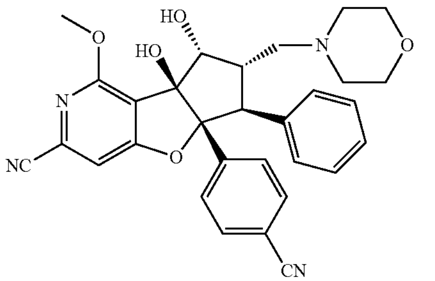

151F

Synthesis of rac-((5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridin-7-yl)(morpholino)methanone (2)

HATU (153 mg, 0.40 mmol) was added to a stirred solution of rac-(5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridine-7-carboxylic acid (1, 204 mg, 0.38 mmol) in N,N-dimethylformamide (3.5 mL) at room temperature under argon. After 2 min N,N-diisopropylethylamine (0.10 mL, 0.57 mmol) was added. The resulting reaction mixture was stirred at room temperature under argon for 20 min. Morpholine (66.7 mg, 0.77 mmol) was added and the reaction mixture was stirred at room temperature under argon for 20 min. The reaction mixture was diluted with diethyl ether, washed three times with water, once with brine, dried over magnesium sulfate, filtered, concentrated on a rotary evaporator, and purified via silica gel chromatography (20-100% EtOAc/hexanes) to afford rac-((5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridin-7-yl)(morpholino)methanone (2) as a white foam-solid. Yield: 186 mg, 81%; MS (ESI) m/z 601.3, 603.3 $[M+1]^+$; $^1H$ NMR (400 MHz, DMSO-$d_6$) δ 7.24-7.19 (m, 2H), 7.08-7.01 (m, 4H), 6.99-6.89 (m, 4H), 5.62 (s, 1H), 5.31 (d, J=5.8 Hz, 1H), 4.63 (t, J=5.5 Hz, 1H), 4.43 (d, J=13.3 Hz, 1H), 4.22 (dd, J=13.4, 5.2 Hz, 1H), 3.90 (m, 1H), 3.84 (s, 3H), 3.82-3.55 (m, 4H), 3.46 (m, 2H).

Synthesis of rac-(5aR,6S,7S,8R,8aS)-5a-(4-bromophenyl)-3-chloro-1-methoxy-7-(morpholinomethyl)-6-phenyl-5a,6,7,8-tetrahydro-8aH-cyclopenta[4,5]furo[3,2-c]pyridine-8,8a-diol (3)

Borane dimethyl sulfide complex (0.29 mL, 3.06 mmol) was added to a stirred solution of rac-((5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridin-7-yl)(morpholino)methanone (2, 184 mg, 0.310 mmol) in THF (5 mL) at room temperature under a reflux condenser under argon. Some bubbling was observed. The reaction mixture was heated at 40° C. under a reflux condenser under argon for 3 h 45 min. After cooling to room temperature, wet methanol (5 mL) was added dropwise slowly. The resulting clear colorless reaction mixture was stirred vigorously and heated at 65° C. under a reflux condenser under argon for 40 h. The reaction mixture was loaded directly onto a five g Strata X-C ion exchange column from Phenomenex. The column was washed sequentially with water, acetonitrile, methanol, and then a mixture of 5% ammonium hydroxide in dichloromethane/methanol. Eluent containing the desired product was concentrated on a rotary evaporator and dried under high vacuum at 40° C. to afford rac-(5aR,6S,7S,8R,8aS)-5a-(4-bromophenyl)-3-chloro-1-methoxy-7-(morpholinomethyl)-6-phenyl-5a,6,7,8-tetrahydro-8aH-cyclopenta[4,5]furo[3,2-c]pyridine-8,8a-diol (3) as a white solid. Yield: 163 mg, 91%; MS (ESI) m/z 587.4, 589.2; $^1H$ NMR (400 MHz, DMSO-$d_6$) δ 7.22 (d, J=8.6 Hz, 2H), 7.13-7.05 (m, 4H), 7.04-6.94 (m, 3H), 6.86 (s, 1H), 5.56 (s, 1H), 5.09 (d, J=5.1 Hz, 1H), 4.44 (t, J=4.4 Hz, 1H), 3.84 (s, 3H), 3.70 (d, J=14.1 Hz, 1H), 3.61 (m, 4H), 3.16 (m, 1H), 2.61-2.53 (m, 2H), 2.31 (m, 2H), 2.03 (d, J=11.2 Hz, 1H).

Synthesis of (5aR,6S,7S,8R,8aS)-5a-(4-cyanophenyl)-8,8a-dihydroxy-1-methoxy-7-(morpholinomethyl)-6-phenyl-5a,7,8,8a-tetrahydro-6H-cyclopenta[4,5]furo[3,2-c]pyridine-3-carbonitrile (Cpd. No. 151F)

Rac-(5aR,6S,7S,8R,8aS)-5a-(4-bromophenyl)-3-chloro-1-methoxy-7-(morpholinomethyl)-6-phenyl-5a,6,7,8-tetrahydro-8aH-cyclopenta[4,5]furo[3,2-c]pyridine-8,8a-diol (3, 30.2 mg, 0.051 mmol), zinc cyanide (36.2 mg, 0.308 mmol), zinc powder (3.4 mg, 0.051 mmol), $Pd_2dba_3$ (4.7 mg, 0.005 mmol), dppf (5.7 mg, 0.010 mmol), N,N-dimethylformamide (0.3 mL), and water (0.03 mL) were combined in a 1 dram vial with a stirbar. The reaction mixture was stirred at room temperature while being sparged with argon gas for 2 min. The reaction mixture was sealed, stirred, and heated at 110° C. with a block heater for 2 h. The reaction mixture was diluted with DMSO and methanol, filtered, and purified via preparatory HPLC (15-38% acetonitrile in water with 0.1% TFA). Fractions containing the desired product were loaded onto a Strata X-C ion exchange column from Phenomenex. The column was washed sequentially with water, acetonitrile, methanol, and then 5% ammonium hydroxide in methanol/dichloromethane. Fluent containing the desired product was concentrated on a rotary evaporator. The residue was taken up in acetonitrile/water, sonicated for a few seconds, and lyophilized to dryness to afford rac-(5aR,6S,7S,8R,8aS)-5a-(4-cyanophenyl)-8,8a-dihydroxy-1-methoxy-7-(morpholinomethyl)-6-phenyl-5a,7,8,8a-tetrahydro-6H-cyclopenta[4,5]furo[3,2-c]pyridine-3-carbonitrile as a white solid. Yield: 19.5 mg, 72%; The enantiomers were separated by chiral SFC [Lux Amylose-1 (4.6×250) mm, 5μ] in CO2/MeOH/TEA (60:40:0.2). Peak 1 (Cpd. No. 151F, 373 mg), $R_t$=1.379 min, ee: 99.86%, $[\alpha]_D$–69.0° (c 0.20, $CHCl_3$); MS (ESI) m/z 525.20[M+1]$^+$. $^1$H NMR (400 MHz, DMSO-$d_6$) 7.55 (s, 1H), 7.51 (d, J=8.36 Hz, 2H), 7.36 (d, J=8.32 Hz, 2H), 7.09-7.06 (m, 2H), 7.00-6.98 (m, 3H), 5.85 (s, 1H), 5.28 (s, 1H), 4.50 (s, 1H), 3.89 (s, 3H), 3.79 (d, J=14.0 Hz, 1H), 3.61 (bs, 4H), 3.25 (bs, 1H), 2.57 (bs, 2H), 2.32 (bs, 2H), 2.07 (bs, 1H). Peak-2 (383 mg), $R_t$=2.578 min, ee: 99.90%, %, $[\alpha]_D$+68.8° (c 0.25, $CHCl_3$); MS (ESI) m/z 525.20[M+1]$^+$; $^1$H NMR (400 MHz, DMSO-$d_6$) 7.55 (s, 1H), 7.51 (d, J=7.2 Hz, 2H), 7.36 (d, J=7.16 Hz, 2H), 7.08-7.01 (m, 5H), 5.85 (s, 1H), 5.29 (bs, 1H), 4.50 (s, 1H), 3.90 (s, 3H), 3.78 (d, J=14.0 Hz, 1H), 3.61 (bs, 3H), 3.50 (s, 1H), 3.26 (s, 1H), 2.57 (bs, 2H), 2.32 (bs, 2H), 2.07 (bs, 1H).

Example 152

Rac-4-((5aR,6S,7S,8R,8aS)-3-chloro-8,8a-dihydroxy-1-methoxy-7-(morpholinomethyl)-6-phenyl-6,7,8,8a-tetrahydro-5aH-cyclopenta[4,5]furo[3,2-c]pyridin-5a-yl)benzonitrile (Cpd. No. 152F)

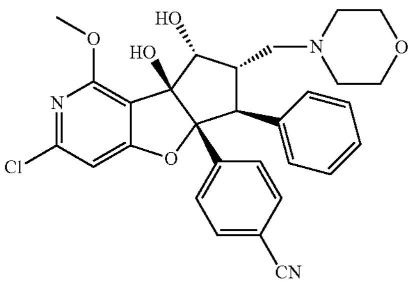

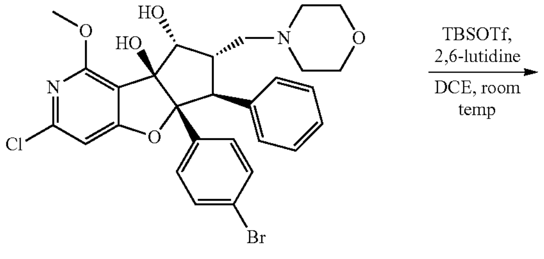

1

-continued

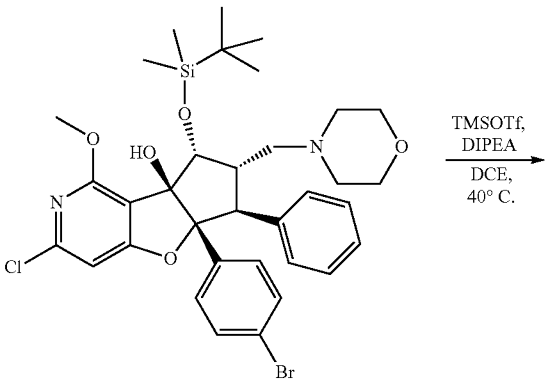

2

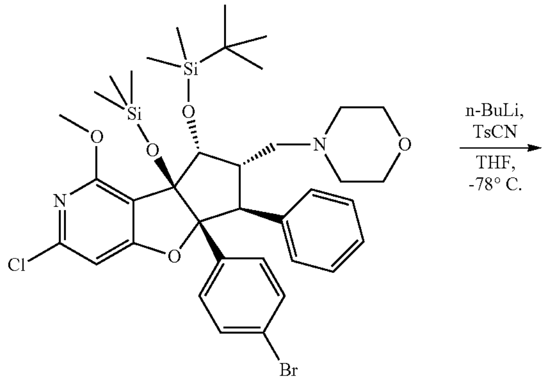

3

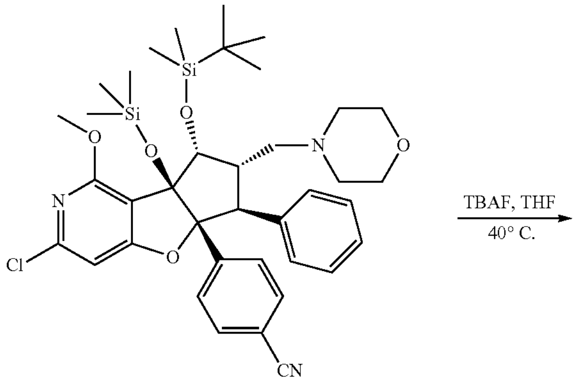

4

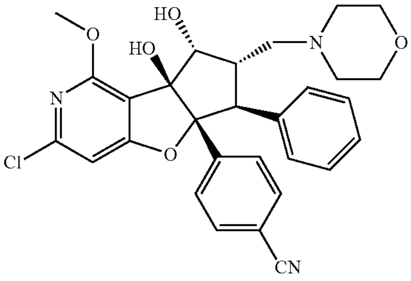

152F

Synthesis of rac-(5aR,6S,7S,8R,8aS)-5a-(4-bromophenyl)-8-((tert-butyldimethylsilyl)oxy)-3-chloro-1-methoxy-7-(morpholinomethyl)-6-phenyl-5a,6,7,8-tetrahydro-8aH-cyclopenta[4,5]furo[3,2-c]pyridin-8a-ol (2)

Rac-tert-Butyldimethylsilyl trifluoromethanesulfonate (0.16 mL, 0.67 mmol) was added to a stirred mixture (not all dissolved) of (5aR,6S,7S,8R,8aS)-5a-(4-bromophenyl)-3-chloro-1-methoxy-7-(morpholinomethyl)-6-phenyl-5a,6,7,8-tetrahydro-8aH-cyclopenta[4,5]furo[3,2-c]pyridine-8,8a-diol (1, 132 mg, 0.225 mmol) and 2,6-lutidine (0.16 mL, 1.35 mmol) in DCE (2 mL) at room temperature under argon. (All solids dissolved) The reaction mixture was sealed and stirred at room temperature for 11 h. The reaction mixture was loaded directly onto a silica gel loading column and purified via silica gel chromatography (5-30% EtOAc/hexanes) to afford rac-(5aR,6S,7S,8R,8aS)-5a-(4-bromophenyl)-8-((tert-butyldimethylsilyl)oxy)-3-chloro-1-methoxy-7-(morpholinomethyl)-6-phenyl-5a,6,7,8-tetrahydro-8aH-cyclopenta[4,5]furo[3,2-c]pyridin-8a-ol (2) as a white foam-solid. Yield: 151 mg, 96%; MS (ESI) m/z 701.3, 703.3 $[M+1]^+$; $^1$H NMR (400 MHz, DMSO-$d_6$) δ 7.20-7.14 (m, 2H), 7.13-6.96 (m, 7H), 6.89 (s, 1H), 5.87 (s, 1H), 4.48 (d, J=2.8 Hz, 1H), 4.02 (d, J=13.8 Hz, 1H), 3.79 (s, 3H), 3.68-3.58 (m, 4H), 3.49-3.34 (m, 1H), 2.63-2.54 (m, 1H), 2.31-2.25 (m, 2H), 2.08 (dd, J=12.2, 2.8 Hz, 1H), 0.69 (s, 9H), 0.13 (s, 3H), −0.30 (s, 3H).

Synthesis of rac-(5aR,6S,7S,8R,8aS)-5a-(4-bromophenyl)-8-((tert-butyldimethylsilyl)oxy)-3-chloro-1-methoxy-7-(morpholinomethyl)-6-phenyl-8a-((trimethylsilyl)oxy)-5a,7,8,8a-tetrahydro-6H-cyclopenta[4,5]furo[3,2-c]pyridine (3)

Trimethylsilyl trifluoromethanesulfonate (0.06 mL, 0.32 mmol) was added to a stirred mixture of rac-(5aR,6S,7S,8R,8aS)-5a-(4-bromophenyl)-8-((tert-butyldimethylsilyl)oxy)-3-chloro-1-methoxy-7-(morpholinomethyl)-6-phenyl-5a,6,7,8-tetrahydro-8aH-cyclopenta[4,5]furo[3,2-c]pyridin-8a-ol (2, 149 mg, 0.21 mmol) and N,N-diisopropylethylamine (0.11 mL, 0.64 mmol) in DCE (2 mL) at room temperature under argon. The reaction mixture was heated at 40° C. under a reflux condenser under argon for 1.5 h. More N,N-diisopropylethylamine (0.11 mL, 0.64 mmol) was added followed by trimethylsilyl trifluoromethanesulfonate (0.06 mL, 0.32 mmol). The reaction mixture was heated at 40° C. under a reflux condenser under argon for 1 h. The reaction mixture was partitioned between dichloromethane and saturated aqueous sodium bicarbonate. The water layer was extracted with dichloromethane. The combined organics were concentrated to dryness and purified via silica gel chromatography (1-20% EtOAc/hexanes) to afford rac-(5aR,6S,7S,8R,8aS)-5a-(4-bromophenyl)-8-((tert-butyldimethylsilyl)oxy)-3-chloro-1-methoxy-7-(morpholinomethyl)-6-phenyl-8a-((trimethylsilyl)oxy)-5a,7,8,8a-tetrahydro-6H-cyclopenta[4,5]furo[3,2-c]pyridine (3) as a white solid. Yield: 155 mg, 94%; MS (ESI) m/z 773.3, 775.3 $[M+1]^+$; $^1$H NMR (400 MHz, DMSO-$d_6$) δ 7.24-7.18 (m, 2H), 7.15-6.94 (m, 4H), 7.05-6.93 (m, 4H), 4.56 (d, J=3.4 Hz, 1H), 3.98 (d, J=13.0 Hz, 1H), 3.66-3.54 (m, 4H), 3.30-3.23 (m, 1H), 2.58-2.52 (m, 1H), 2.35-2.29 (m, 1H), 2.18 (dd, J=12.5, 3.5 Hz, 1H), 0.72 (s, 9H), 0.14 (s, 3H), −0.13 (s, 9H), −0.22 (s, 3H).

Synthesis of rac-4-((5aR,6S,7S,8R,8aS)-8-((tert-butyldimethylsilyl)oxy)-3-chloro-1-methoxy-7-(morpholinomethyl)-6-phenyl-8a-((trimethylsilyl)oxy)-6,7,8,8a-tetrahydro-5aH-cyclopenta[4,5]furo[3,2-c]pyridin-5a-yl)benzonitrile (4)

p-Toluenesulfonyl cyanide from Aldrich (248835) was recrystallized from toluene/hexanes, dissolved in THF, and dried over 4 Angstrom molecular sieves for 3 hours prior to use. Rac-(5aR,6S,7S,8R,8aS)-5a-(4-bromophenyl)-8-((tert-butyldimethylsilyl)oxy)-3-chloro-1-methoxy-7-(morpholinomethyl)-6-phenyl-8a-((trimethylsilyl)oxy)-5a,7,8,8a-tetrahydro-6H-cyclopenta[4,5]furo[3,2-c]pyridine (3, 151 mg, 0.195 mmol) was dissolved in THF (2 mL) with stirring under argon. The resulting colorless solution was cooled to −78° C. with a dry ice/acetone bath for 10 min. n-Butyllithium (2.5 M in hexane) (0.086 mL, 0.215 mmol) was added slowly. The slightly yellow reaction mixture was stirred at −78° C. under argon for 30 min. p-Toluenesulfonyl cyanide (2 M in THF) (0.14 mL, 0.27 mmol) was added and the resulting mixture was stirred at −78° C. under argon for 30 min. Saturated aqueous ammonium chloride (1 mL) was added. After warming to room temperature, the resulting mixture was partitioned between water and ethyl acetate. The organics were washed with brine, dried over magnesium sulfate, filtered, concentrated on a rotary evaporator, and purified via preparatory HPLC (35-82% acetonitrile in water with 0.1% TFA). Fractions containing the desired product were combined, neutralized with saturated aqueous sodium bicarbonate, and the acetonitrile was removed on a rotary evaporator. The residue was extracted twice with dichloromethane. The organics were dried over $Na_2SO_4$, filtered, concentrated on a rotary evaporator, and dried under high vacuum to afford rac-4-((5aR,6S,7S,8R,8aS)-8-((tert-butyldimethylsilyl)oxy)-3-chloro-1-methoxy-7-(morpholinomethyl)-6-phenyl-8a-((trimethylsilyl)oxy)-6,7,8,8a-tetrahydro-5aH-cyclopenta[4,5]furo[3,2-c]pyridin-5a-yl)benzonitrile (4) as a slightly yellow foam solid. Yield: 52.8 mg, 38%; MS (ESI) m/z 720.4 $[M+1]^+$; $^1$H NMR (400 MHz, DMSO-$d_6$) δ 7.53-7.48 (m, 2H), 7.24-7.19 (m, 2H), 7.15-7.08 (m, 4H), 7.03-6.99 (m, 2H), 4.57 (d, J=3.3 Hz, 1H), 4.03 (d, J=13.1 Hz, 1H), 3.83 (s, 3H), 3.67-3.55 (m, 4H), 3.38-3.33 (m, 1H), 2.58-2.52 (m, 1H), 2.37-2.32 (m, 2H), 2.20 (dd, J=12.4, 3.4 Hz, 1H), 0.72 (s, 9H), 0.15 (s, 3H), −0.11 (s, 9H), −0.23 (s, 3H).

Synthesis of rac-4-((5aR,6S,7S,8R,8aS)-3-chloro-8,8a-dihydroxy-1-methoxy-7-(morpholinomethyl)-6-phenyl-6,7,8,8a-tetrahydro-5aH-cyclopenta[4,5]furo[3,2-c]pyridin-5a-yl)benzonitrile (Cpd. No. 152F)

Tetrabutylammonium fluoride (1 M in THF) (0.24 mL, 0.24 mmol) was added to a stirred solution of rac-4-((5aR,6S,7S,8R,8aS)-8-((tert-butyldimethylsilyl)oxy)-3-chloro-1-methoxy-7-(morpholinomethyl)-6-phenyl-8a-((trimethylsilyl)oxy)-6,7,8,8a-tetrahydro-5aH-cyclopenta[4,5]furo[3,2-c]pyridin-5a-yl)benzonitrile (4, 28.9 mg, 0.040 mmol) in THF (2 mL).

The reaction mixture was stirred and heated at 40° C. under a reflux condenser under argon for 14 h. The solvent was removed on a rotary evaporator. The residue was taken up in DMSO and methanol, filtered, and purified via preparatory HPLC (15-38% acetonitrile in water with 0.1% TFA). Fractions containing the desired product were loaded onto a Strata X-C ion exchange column from Phenomenex. The column was washed sequentially with water, acetonitrile, methanol, and then 10% ammonium hydroxide in methanol/dichloromethane. Fluent containing the desired product was concentrated on a rotary evaporator. The residue was taken up in 50% acetonitrile in water, sonicated for a few seconds, and lyophilized to dryness to afford rac-4-((5aR,6S,7S,8R,8aS)-3-chloro-8,8a-dihydroxy-1-methoxy-7-(morpholinomethyl)-6-phenyl-6,7,8,8a-tetrahydro-5aH-cyclopenta[4,5]furo[3,2-c]pyridin-5a-yl)benzonitrile (Cpd. No. 152F) as a white solid. Yield: 15.5 mg, 72%; MS (ESI) m/z 534.3 [M+1]$^+$; $^1$H NMR (400 MHz, DMSO-d) S 7.53-7.47 (m, 2H), 7.38-7.33 (m, 2H), 7.10-7.04 (m, 2H), 7.01-6.97 (m, 3H), 6.89 (s, 1H), 5.66 (s, 1H), 5.15 (d, J=5.2 Hz, 1H), 4.46 (t, J=4.3 Hz, 1H), 3.85 (s, 3H), 3.77 (d, J=14.0 Hz, 1H), 3.68-3.55 (m, 4H), 3.22 (ddt, J=14.0, 10.2, 3.6 Hz, 1H), 2.62-2.56 (m, 2H), 2.34-2.29 (m, 2H), 2.09-2.03 (m, 1H).

Example 153

Rac-(5aR,6S,7S,8R,8aS)-5a-(4-cyanophenyl)-7-((3,3-difluoropyrrolidin-1-yl)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 153F)

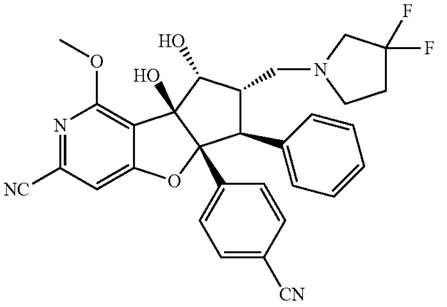

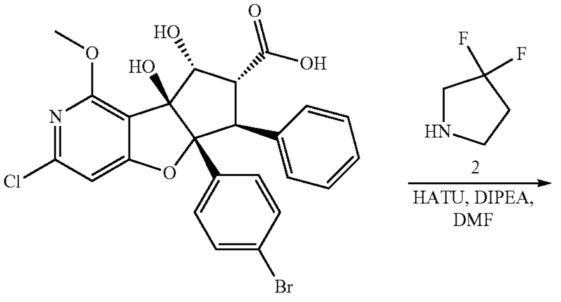

1

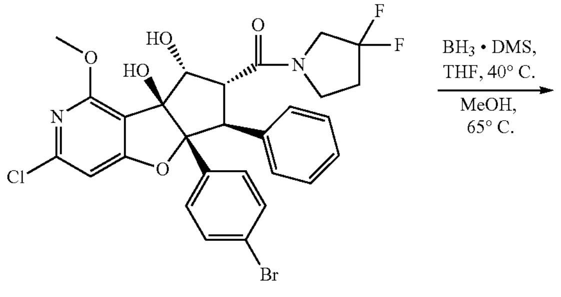

3

-continued

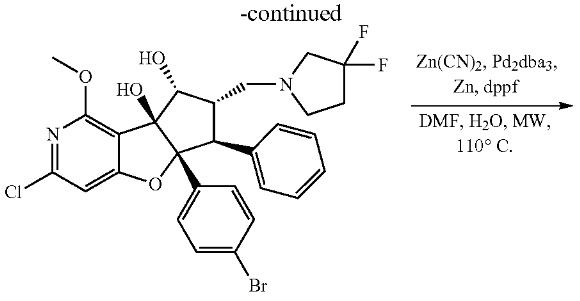

4

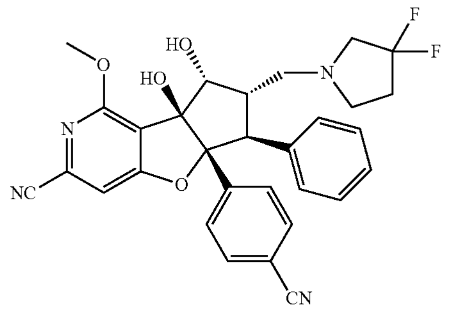

153F

Synthesis of rac-((5aR,6S,7R,8R,8aS)-5a-(4-bromophenyl)-3-chloro-8,8a-dihydroxy-1-methoxy 6-phenyl-5a, 7,8,8a-tetrahydro-6H-cyclopenta[4,5]furo[3,2-c]pyridin-7-yl)(3,3-difluoropyrrolidin-1-yl)methanone (3)

HATU (30.7 mg, 0.081 mmol) was added to a stirred solution of rac-(5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridine-7-carboxylic acid (1, 40.9 mg, 0.077 mmol) in N,N-dimethylformamide (0.70 mL) at room temperature under argon. After 2 min N,N-diisopropylethylamine (0.033 mL, 0.192 mmol) was added. The resulting reaction mixture was stirred at room temperature under argon for 20 min. 3,3-Difluoropyrrolidine hydrochloride (2, 22.1 mg, 0.154 mmol) was added and the reaction mixture was stirred at room temperature under argon for 40 min. The reaction mixture was diluted with ethyl acetate, washed three times with brine, dried over magnesium sulfate, filtered, concentrated on a rotary evaporator, and purified via silica gel chromatography (10-100% EtOAc/hexanes) to afford rac-((5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridin-7-yl)(3,3-difluoropyrrolidin-1-yl)methanone (3) as a white solid. Yield: 47.7 mg, 99.9%; MS (ESI) m/z 621.1, 623.1 [M+1]$^+$.

Synthesis of rac-(5aR,6S,7S,8R,8aS)-5a-(4-bromophenyl)-3-chloro-7-((3,3-difluoropyrrolidin-1-yl)methyl)-1-methoxy-6-phenyl-5a,6,7,8-tetrahydro-8aH-cyclopenta[4,5]furo[3,2-c]pyridine-8,8a-diol (4)

Borane dimethyl sulfide complex (0.109 mL, 1.15 mmol) was added to a stirred solution of rac-((5aR,6S,7R,8R,8aS)-5a-(4-bromophenyl)-3-chloro-8,8a-dihydroxy-1-methoxy- 6-phenyl-5a,7,8,8a-tetrahydro-6H-cyclopenta[4,5]furo[3,2-c]pyridin-7-yl)(3,3-difluoropyrrolidin-1-yl)methanone (3, 47.7 mg, 0.077 mmol) in THF (1 mL) at room temperature under a reflux condenser under argon. Some bubbling was observed. The reaction mixture was heated at 40° C. under a reflux condenser under argon for 7 h. After cooling to room temperature, wet methanol (1 mL) was added dropwise slowly. The resulting clear colorless reaction mixture was stirred vigorously and heated at 65° C. under a reflux condenser under argon for 10 h. The reaction mixture was loaded directly onto a Strata X-C ion exchange column from Phenomenex. The column was washed sequentially with water, acetonitrile, methanol, and then a mixture of 5% ammonium hydroxide in dichloromethane/methanol. Eluent containing the desired product was concentrated on a rotary evaporator and dried under high vacuum at 40° C. to afford rac-(5aR,6S,7S,8R,8aS)-5a-(4-bromophenyl)-3-chloro-7-((3,3-difluoropyrrolidin-1-yl)methyl)-1-methoxy-6-phenyl-5a,6,7,8-tetrahydro-8aH-cyclopenta[4,5]furo[3,2-c]pyridine-8,8a-diol (4) as a white solid. Yield: 37.5 mg, 80%; MS (ESI) m/z 607.1, 609.2 $[M+1]^+$; $^1H$ NMR (400 MHz, DMSO-$d_6$) δ 7.25-7.20 (m, 2H), 7.14-7.06 (m, 4H), 7.03-6.96 (m, 3H), 6.86 (s, 1H), 5.59 (s, 1H), 5.16 (d, J=5.3 Hz, 1H), 4.43 (t, J=4.7 Hz, 1H), 3.84 (s, 3H), 3.70 (d, J=14.1 Hz, 1H), 3.19-3.05 (m, 2H), 2.92-2.65 (m, 4H), 2.31-2.18 (m, 2H), 2.13 (dd, J=11.9, 2.9 Hz, 1H).

Synthesis of rac-(5aR,6S,7S,8R,8aS)-5a-(4-cyano-phenyl)-7-((3,3-difluoropyrrolidin-1-yl)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 153F)

Rac-(5aR,6S,7S,8R,8aS)-5a-(4-bromophenyl)-3-chloro-7-((3,3-difluoropyrrolidin-1-yl)methyl)-1-methoxy-6-phenyl-5a,6,7,8-tetrahydro-8aH-cyclopenta[4,5]furo[3,2-c]pyridine-8,8a-diol (4, 35.2 mg, 0.058 mmol), zinc cyanide (40.8 mg, 0.347 mmol), zinc powder (3.8 mg, 0.058 mmol), $Pd_2dba_3$ (5.3 mg, 0.006 mmol), dppf (6.44 mg, 0.012 mmol), N,N-dimethylformamide (0.30 mL), and water (0.03 mL) were combined in a 1 dram vial with a stirbar. The reaction mixture was stirred at room temperature while being sparged with argon gas for 2 min. The reaction mixture was sealed, stirred, and heated at 110° C. with a block heater for 2 h. The reaction mixture was diluted with DMSO and methanol, filtered, and purified via preparatory HPLC (1540% acetonitrile in water with 0.1% TFA). Fractions containing the desired product were loaded onto a Strata X-C ion exchange column from Phenomenex. The column was washed sequentially with water, acetonitrile, methanol, and then 5% ammonium hydroxide in methanol/dichloromethane. Fluent containing the desired product was concentrated on a rotary evaporator. The residue was taken up in acetonitrile/water, sonicated for a few seconds, and lyophilized to dryness to afford rac-(5aR,6S,7S,8R,8aS)-5a-(4-cyanophenyl)-7-((3,3-difluoropyrrolidin-1-yl)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 153F) as a white solid. Yield: 20.8 mg, 66%; MS (ESI) m/z 545.3 $[M+1]^+$; $^1H$ NMR (400 MHz, DMSO-$d_6$) δ 7.55 (s, 1H), 7.53-7.49 (m, 2H), 7.40-7.35 (m, 2H), 7.11-7.05 (m, 2H), 7.03-6.97 (m, 3H), 5.88 (s, 1H), 5.36 (d, J=5.5 Hz, 1H), 4.50 (dd, J=5.3, 4.1 Hz, 1H), 3.90 (s, 3H), 3.77 (d, J=14.1 Hz, 1H), 3.22-3.12 (m, 2H), 2.91-2.68 (m, 4H), 2.30-2.19 (m, 2H), 2.15 (dd, J=11.9, 2.9 Hz, 1H).

Example 154

Rac-(5aR,6S,7S,8R,8aS)-5a-(4-cyanophenyl)-7-((3,3-difluoropiperidin-1-yl)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 154F)

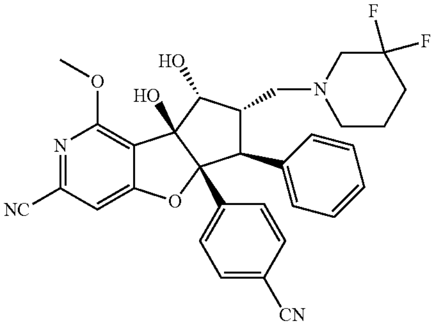

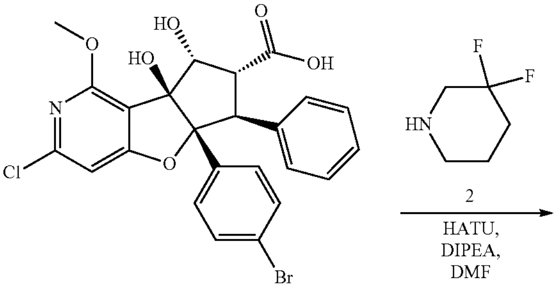

1

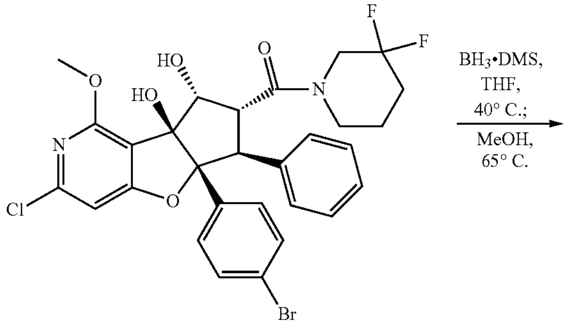

3

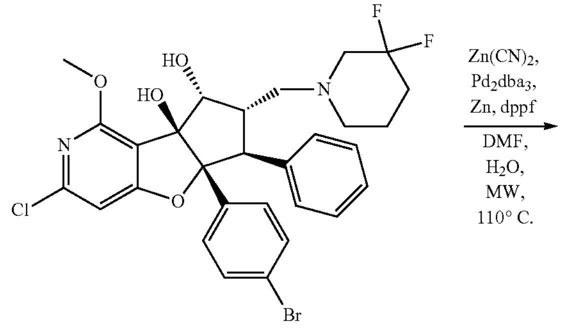

4

-continued

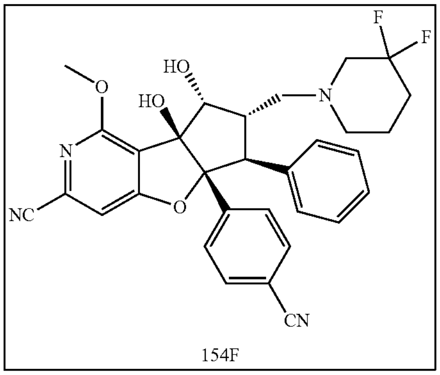

154F

Synthesis of rac-((5aR,6S,7R,8R,8aS)-5a-(4-bromophenyl)-3-chloro-8,8a-dihydroxy-1-methoxy-6-phenyl-5a, 7,8,8a-tetrahydro-6H-cyclopenta[4,5]furo[3,2-c]pyridin-7-yl)(3,3-difluoropiperidin-1-yl) methanone (3)

HATU (29.5 mg, 0.077 mmol) was added to a stirred solution of rac-(5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridine-7-carboxylic acid (1, 39.3 mg, 0.074 mmol) in N,N-dimethylformamide (0.70 mL) at room temperature under argon. After 2 min N,N-diisopropylethylamine (0.032 mL, 0.184 mmol) was added. The resulting reaction mixture was stirred at room temperature under argon for 20 min. 3,3-Difluoropiperidine hydrochloride (2, 23.3 mg, 0.148 mmol) was added and the reaction mixture was stirred at room temperature under argon for 40 min. The reaction mixture was diluted with ethyl acetate, washed three times with brine, dried over magnesium sulfate, filtered, concentrated on a rotary evaporator, and purified via silica gel chromatography (10-100% EtOAc/hexanes) to afford rac-((5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridin-7-yl)(3,3-difluoropiperidin-1-yl)methanone (3) as a white solid. Yield: 42.6 mg, 91%; MS (ESI) m/z 635.3, 637.1 $[M+1]^+$.

Synthesis of rac-(5aR,6S,7S,8R,8aS)-5a-(4-bromophenyl)-3-chloro-7-((3,3-difluoropiperidin-1-yl)methyl)-1-methoxy-6-phenyl-5a,6,7,8-tetrahydro-8aH-cyclopenta[4,5]furo[3,2-c]pyridine-8,8a-diol (4)

Borane dimethyl sulfide complex (0.095 mL, 1.00 mmol) was added to a stirred solution of rac-((5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridin-7-yl)(3,3-difluoropiperidin-1-yl)methanone (3, 42.6 mg, 0.067 mmol) in THF (1 mL) at room temperature under a reflux condenser under argon. Some bubbling was observed. The reaction mixture was heated at 40° C. under a reflux condenser under argon for 7 h. After cooling to room temperature, wet methanol (1 mL) was added dropwise slowly. The resulting clear colorless reaction mixture was stirred vigorously and heated at 65° C. under a reflux condenser under argon for 10 h. The reaction mixture was loaded directly onto a Strata X-C ion exchange column from Phenomenex. The column was washed sequentially with water, acetonitrile, methanol, and then a mixture of 5% ammonium hydroxide in dichloromethane/methanol. Fluent containing the desired product was concentrated on a rotary evaporator and dried under high vacuum at 40° C. to afford rac-(5aR,6S,7S,8R,8aS)-5a-(4-bromophenyl)-3-chloro-7-((3,3-difluoropiperidin-1-yl)methyl)-1-methoxy-6-phenyl-5a,6,7,8-tetrahydro-8aH-cyclopenta[4,5]furo[3,2-c]pyridine-8,8a-diol (4) as a white solid. Yield: 37.5 mg, 90%; MS (ESI) m/z 621.1, 623.2 $[M+1]^+$; $^1$H NMR (400 MHz, DMSO-$d_6$) δ 7.24-7.21 (m, 2H), 7.15-7.05 (m, 4H), 7.02-6.98 (m, 3H), 6.86 (s, 1H), 5.58 (s, 1H), 5.08 (d, J=5.2 Hz, 1H), 4.41 (t, J=4.6 Hz, 1H), 3.85 (s, 3H), 3.71 (d, J=14.0 Hz, 1H), 3.23-3.13 (m, 3H), 2.92 (q, J=11.4 Hz, 1H), 2.70-2.54 (m, 2H), 2.43-2.35 (m, 1H), 2.14 (dd, J=12.7, 2.9 Hz, 1H), 1.93-1.82 (m, 2H), 1.72-1.62 (m, 2H).

Synthesis of rac-(5aR,6S,7S,8R,8aS)-5a-(4-cyanophenyl)-7-((3,3-difluoropiperidin-1-yl)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 154F)

Rac-(5aR,6S,7S,8R,8aS)-5a-(4-bromophenyl)-3-chloro-7-((3,3-difluoropiperidin-1-yl)methyl)-1-methoxy-6-phenyl-5a,6,7,8-tetrahydro-8aH-cyclopenta[4,5]furo[3,2-c]pyridine-8,8a-diol (4, 35.6 mg, 0.057 mmol), zinc cyanide (40.3 mg, 0.343 mmol), zinc powder (3.7 mg, 0.057 mmol), $Pd_2dba_3$ (5.2 mg, 0.006 mmol), dppf (6.4 mg, 0.011 mmol), N,N-dimethylformamide (0.30 mL), and water (0.03 mL) were combined in a 1 dram vial with a stirbar. The reaction mixture was stirred at room temperature while being sparged with argon gas for 2 min. The reaction mixture was sealed, stirred, and heated at 110° C. with a block heater for 2 h. The reaction mixture was diluted with DMSO and methanol, filtered, and purified via preparatory HPLC (15-42% acetonitrile in water with 0.1% TFA). Fractions containing the desired product were loaded onto a Strata X-C ion exchange column from Phenomenex. The column was washed sequentially with water, acetonitrile, methanol, and then 5% ammonium hydroxide in methanol/dichloromethane. Eluent containing the desired product was concentrated on a rotary evaporator. The residue was taken up in acetonitrile/water, sonicated for a few seconds, and lyophilized to dryness to afford rac-(5aR,6S,7S,8R,8aS)-5a-(4-cyanophenyl)-7-((3,3-difluoropiperidin-1-yl)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 154F) as a white solid. Yield: 21.9 mg, 68%; MS (ESI) m/z 559.3 $[M+1]^+$; $^1$H NMR (400 MHz, DMSO-$d_6$) δ 7.55 (s, 1H), 7.53-7.48 (m, 2H), 7.41-7.36 (m, 2H), 7.11-7.05 (m, 2H), 7.04-6.97 (m, 3H), 5.86 (s, 1H), 5.27 (d, J=5.3 Hz, 1H), 4.50-4.45 (m, 1H), 3.90 (s, 3H), 3.78 (d, J=14.0 Hz, 1H), 3.29-3.22 (m, 1H), 2.96 (q, J=11.4 Hz, 1H), 2.71-2.54 (m, 3H), 2.43-2.37 (m, 1H), 2.15 (dd, J=12.6, 2.9 Hz, 1H), 1.93-1.82 (m, 2H), 1.72-1.63 (m, 2H).

Example 155

Rac-(5aR,6S,7S,8R,8aS)-7-((tert-butylamino)methyl)-5a-(4-cyanophenyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 155F)

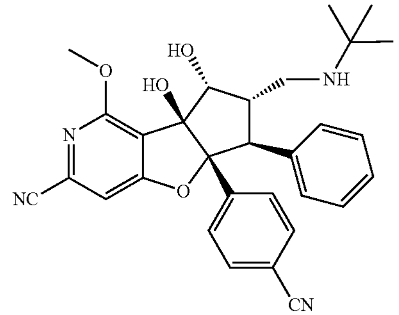

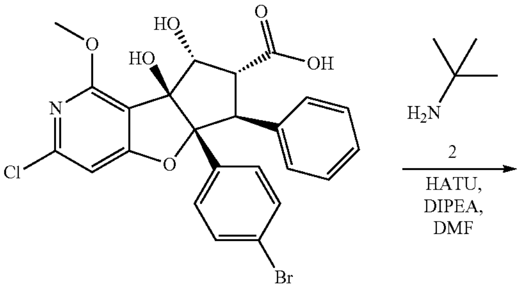

1

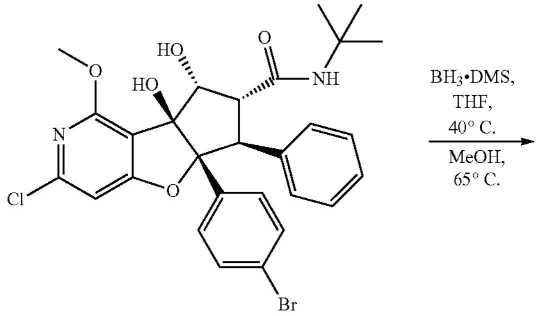

3

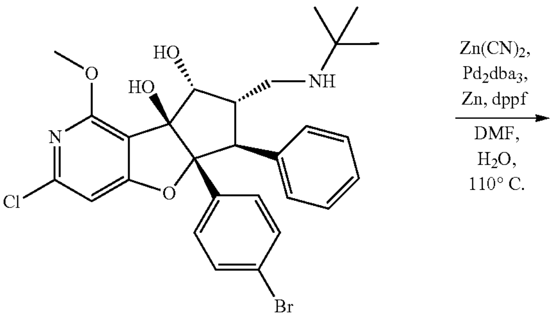

4

-continued

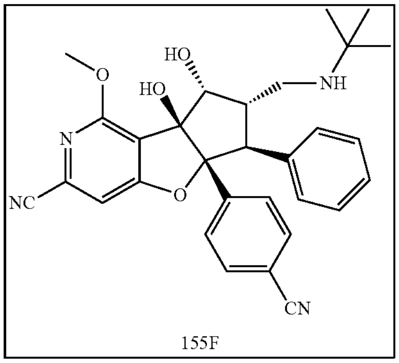

155F

Synthesis of rac-(5aR,6S,7R,8R,8aS)-5a-(4-bromophenyl)-N-(tert-butyl)-3-chloro-8,8a-dihydroxy-1-methoxy-6-phenyl-5a, 7,8,8a-tetrahydro-6H-cyclopenta[4,5]furo[3,2-c]pyridine-7-carboxamide (3)

HATU (46.4 mg, 0.122 mmol) was added to a stirred solution of rac-(5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridine-7-carboxylic acid (1, 61.9 mg, 0.116 mmol) in N,N-dimethylformamide (1 mL) at room temperature. After 2 min N,N-diisopropylethylamine (0.030 mL, 0.174 mmol) was added. The resulting reaction mixture was capped and stirred at room temperature for 20 min. 2-methylpropan-2-amine (2, 0.24 mL, 2.32 mmol) was added and the reaction mixture was capped and stirred at room temperature for 1 h. The reaction mixture was diluted with ethyl acetate, washed three times with brine, dried over magnesium sulfate, filtered, concentrated on a rotary evaporator, and purified via silica gel chromatography (20-60% EtOAc/hexanes) to afford rac-(5aR,6S,7R,8R,8aS)-5a-(4-bromophenyl)-N-(tert-butyl)-3-chloro-8,8a-dihydroxy-1-methoxy-6-phenyl-5a,7,8,8a-tetrahydro-6H-cyclopenta[4,5]furo[3,2-c]pyridine-7-carboxamide (3) as a white solid. Yield: 61.7 mg, 90%; MS (ESI) m/z 587.3, 589.1 $[M+1]^+$.

Synthesis of rac-(5aR,6S,7S,8R,8aS)-5a-(4-bromophenyl)-7-((tert-butylamino)methyl)-3-chloro-1-methoxy-6-phenyl-5a,6,7,8-tetrahydro-8aH-cyclopenta[4,5]furo[3,2-c]pyridine-8,8a-diol (4)

Borane dimethyl sulfide complex (0.049 mL, 0.512 mmol) was added to a stirred solution of rac-(5aR,6S,7R,8R,8aS)-5a-(4-bromophenyl)-N-(tert-butyl)-3-chloro-8,8a-dihydroxy-1-methoxy-6-phenyl-5a,7,8,8a-tetrahydro-6H-cyclopenta[4,5]furo[3,2-c]pyridine-7-carboxamide (3, 30.1 mg, 0.051 mmol) in THF (1.5 mL) at room temperature under a reflux condenser under argon. Some bubbling was observed. The reaction mixture was heated at 40° C. under a reflux condenser under argon for 6 h. After cooling to room temperature, wet methanol (1 mL) was added dropwise slowly. The resulting clear colorless reaction mixture was stirred vigorously and heated at 65° C. under a reflux condenser under argon for 9.5 h. The reaction mixture was loaded directly onto a Strata X-C ion exchange column from Phenomenex. The column was washed sequentially with water, acetonitrile, methanol, and then a mixture of 5% ammonium hydroxide in dichloromethane/methanol. Fluent containing the desired product was concentrated on a rotary evaporator and dried under high vacuum at 40° C. to afford rac-(5aR,6S,7S,8R,8aS)-5a-(4-bromophenyl)-7-((tert-butylamino)methyl)-3-chloro-1-methoxy-6-phenyl-5a,6,7,8-tetrahydro-8aH-cyclopenta[4,5]furo[3,2-c]pyridine-8,8a-diol (4) as a white solid. Yield: 23.7 mg, 81%; MS (ESI) m/z 573.2, 575.1 $[M+1]^+$.

Synthesis of rac-(5aR,6S,7S,8R,8aS)-7-((tert-butylamino)methyl)-5a-(4-cyanophenyl)-8,8a-dihydroxy-1-methoxy-6-phenyl-5a, 7,8,8a-tetrahydro-6H-cyclopenta[4,5]furo[3,2-c]pyridine-3-carbonitrile (Cpd. No. 155F)

Rac-(5aR,6S,7S,8R,8aS)-5a-(4-bromophenyl)-7-((tert-butylamino)methyl)-3-chloro-1-methoxy-6-phenyl-5a,6,7,8-tetrahydro-8aH-cyclopenta[4,5]furo[3,2-c]pyridine-8,8a-diol (4, 20.8 mg, 0.036 mmol), zinc cyanide (25.5 mg, 0.217 mmol), zinc powder (2.4 mg, 0.036 mmol), $Pd_2dba_3$ (3.3 mg, 0.004 mmol), dppf (4.0 mg, 0.007 mmol), N,N-dimethylformamide (0.30 mL), and water (0.03 mL) were combined in a 1 dram vial with a stirbar. The reaction mixture was stirred at room temperature while being sparged with argon gas for 2 min. The reaction mixture was sealed, stirred, and heated at 110° C. with a block heater for 2 h. The reaction mixture was diluted with DMSO and methanol, filtered, and purified via preparatory HPLC (15-43% acetonitrile in water with 0.1% TFA). Fractions containing the desired product were loaded onto a Strata X-C ion exchange column from Phenomenex. The column was washed sequentially with water, acetonitrile, methanol, and then 5% ammonium hydroxide in methanol/dichloromethane. Fluent containing the desired product was concentrated on a rotary evaporator. The residue was taken up in acetonitrile/water, sonicated for a few seconds, and lyophilized to dryness to afford rac-(5aR,6S,7S,8R,8aS)-7-((tert-butylamino)methyl)-5a-(4-cyanophenyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 155F) as a white solid. Yield: 12.6 mg, 68%; MS (ESI) m/z 511.2 $[M+1]^+$; $^1H$ NMR (400 MHz, DMSO-$d_6$) δ 7.56 (s, 1H), 7.55-7.49 (m, 2H), 7.37-7.30 (m, 2H), 7.12-7.05 (m, 2H), 7.04-6.95 (m, 3H), 5.88 (s, 1H), 5.78 (s, 1H), 4.55 (d, J=4.3 Hz, 1H), 3.90 (s, 3H), 3.85 (d, J=14.3 Hz, 1H), 3.09-3.02 (m, 1H), 2.63 (d, J=9.2 Hz, 1H), 2.58-2.53 (m, 1H), 0.96 (s, 9H).

Example 156

Rac-(5aR,6S,7S,8R,8aS)-5a-(4-bromophenyl)-7-((4-fluoropiperidin-1-yl)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 156aF)

Rac-4-((5aR,6S,7S,8R,8aS)-3-chloro-7-((4-fluoropiperidin-1-yl)methyl)-8,8a-dihydroxy-1-methoxy-6-phenyl-6,7,8,8a-tetrahydro-5aH-cyclopenta[4,5]furo[3,2-c]pyridin-5a-yl)benzonitrile (Cpd. No. 156bF)

Rac-(5aR,6S,7S,8R,8aS)-5a-(4-cyanophenyl)-7-((4-fluoropiperidin-1-yl)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 156cF)

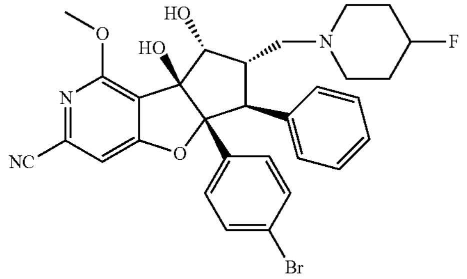

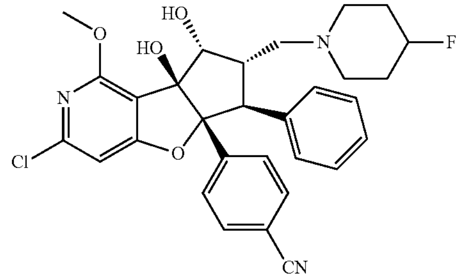

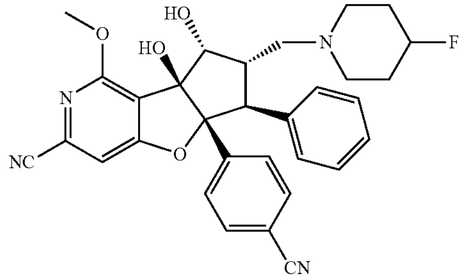

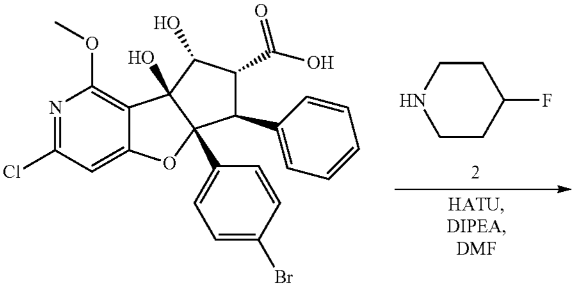

1

-continued

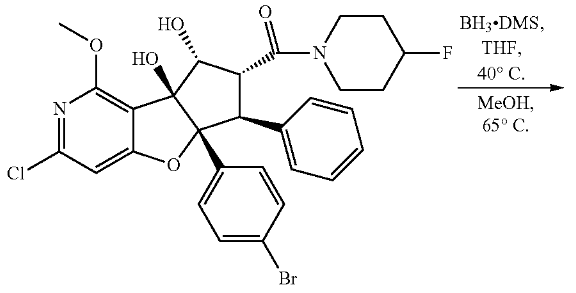

3

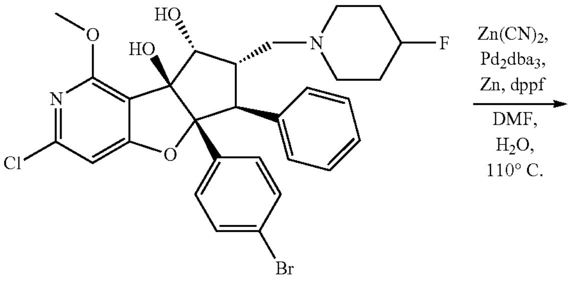

4

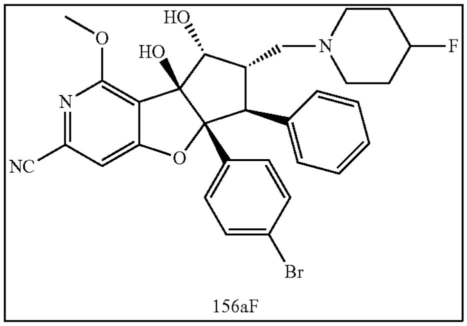

156aF

+

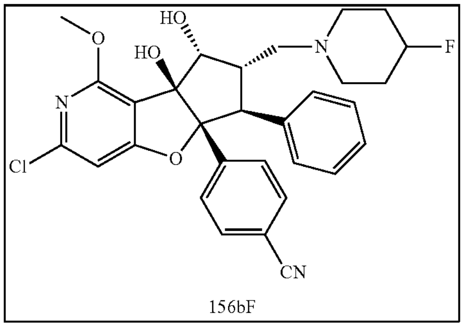

156bF

+

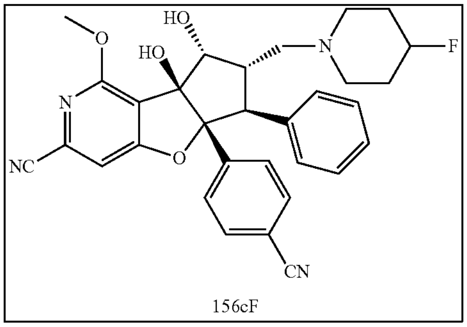

156cF

Synthesis of rac-((5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridin-7-yl)(4-fluoropiperidin-1-yl)methanone (3)

HATU (75.2 mg, 0.198 mmol) was added to a stirred solution of rac-(5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridine-7-carboxylic acid (1, 100.4 mg, 0.188 mmol) in N,N-dimethylformamide (1.5 mL) at room temperature under argon. After 2 min N,N-diisopropylethylamine (0.082 mL, 0.471 mmol) was added. The resulting reaction mixture was stirred at room temperature under argon for 20 min. 4-fluoropiperidine hydrochloride (2, 52.6 mg, 0.377 mmol) was added and the reaction mixture was stirred at room temperature under argon for 1 h. The reaction mixture was diluted with ethyl acetate, washed three times with brine, dried over magnesium sulfate, filtered, concentrated on a rotary evaporator, and purified via silica gel chromatography (10-100% EtOAc/hexanes) to afford rac-((5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridin-7-yl)(4-fluoropiperidin-1-yl)methanone (3) as a white foam-solid. Yield: 107.6 mg, 92%; MS (ESI) m/z 617.3, 619.3 [M+1]$^+$.

Synthesis of rac-(5aR,6S,7S,8R,8aS)-5a-(4-bromophenyl)-3-chloro-7-((4-fluoropiperidin-1-yl)methyl)-1-methoxy-6-phenyl-5a,6,7,8-tetrahydro-8aH-cyclopenta[4,5]furo[3,2-c]pyridine-8,8a-diol (4)

Borane dimethyl sulfide complex (0.165 mL, 1.74 mmol) was added to a stirred solution of rac-((5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridin-7-yl)(4-fluoropiperidin-1-yl)methanone (3, 107.6 mg, 0.174 mmol) in THF (2.5 mL) at room temperature under a reflux condenser under argon. Some bubbling was observed. The reaction mixture was heated at 40° C. under a reflux condenser under argon for 11.5 h. After cooling to room temperature, wet methanol (2 mL) was added dropwise slowly. The resulting clear colorless reaction mixture was stirred vigorously and heated at 65° C. under a reflux condenser under argon for 3 h 45 min. The reaction mixture was loaded directly onto a Strata X-C ion exchange column from Phenomenex. The column was washed sequentially with water, acetonitrile, methanol, and then a mixture of 5% ammonium hydroxide in dichloromethane/methanol. Eluent containing the desired product was concentrated on a rotary evaporator and dried under high vacuum at 40° C. to afford rac-(5aR,6S,7S,8R,8aS)-5a-(4-bromophenyl)-3-chloro-7-((4-fluoropiperidin-1-yl)methyl)-1-methoxy-6-phenyl-5a,6,7,8-tetrahydro-8aH-cyclopenta[4,5]furo[3,2-c]pyridine-8,8a-diol (4) as a white solid. Yield: 102.4 mg, 97%; MS (ESI) m/z 603.4, 605.2 [M+1]$^+$.

Synthesis of rac-(5aR,6S,7S,8R,8aS)-5a-(4-bromophenyl)-7-((4-fluoropiperidin-1-yl)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 156aF)

Rac-4-((5aR,6S,7S,8R,8aS)-3-chloro-7-((4-fluoropiperidin-1-yl)methyl)-8,8a-dihydroxy-1-methoxy-6-phenyl-6,7,8,8a-tetrahydro-5aH-cyclopenta[4,5]furo[3,2-c]pyridin-5a-yl)benzonitrile (Cpd. No. 156bF)

Rac-(5aR,6S,7S,8R,8aS)-5a-(4-cyanophenyl)-7-((4-fluoropiperidin-1-yl)methyl)-8,8a-dihydroxy-1-methoxy-6-phenyl-5a, 7,8,8a-tetrahydro-6H-cyclopenta[4,5]furo[3,2-c]pyridine-3-carbonitrile (Cpd. No. 156cF)

Rac-(5aR,6S,7S,8R,8aS)-5a-(4-bromophenyl)-3-chloro-7-((4-fluoropiperidin-1-yl)methyl)-1-methoxy-6-phenyl-5a,6,7,8-tetrahydro-8aH-cyclopenta[4,5]furo[3,2-c]pyridine-8,8a-diol (4, 25.1 mg, 0.042 mmol), zinc cyanide (24.4 mg, 0.208 mmol), zinc powder (0.3 mg, 0.004 mmol, $Pd_2dba_3$ (3.8 mg, 0.004 mmol), dppf (4.6 mg, 0.008 mmol), N,N-dimethylformamide (0.60 mL), and water (0.06 mL) were combined in a 1 dram vial with a stirbar. The reaction mixture was stirred at room temperature while being sparged with argon gas for 2 min. The reaction mixture was sealed, stirred, and heated at 110° C. with a block heater for 22 min. The reaction mixture was diluted with DMSO and methanol, filtered, and purified via preparatory HPLC (1544% acetonitrile in water with 0.1% TFA). Fractions containing the desired product were loaded onto a Strata X-C ion exchange column from Phenomenex. The column was washed sequentially with water, acetonitrile, methanol, and then 5% ammonium hydroxide in methanol/dichloromethane. Fluent containing the desired product was concentrated on a rotary evaporator. The residue was taken up in acetonitrile/water, sonicated for a few seconds, and lyophilized to dryness to afford the desired product as a white solid.

Rac-(5aR,6S,7S,8R,8aS)-5a-(4-bromophenyl)-7-((4-fluoropiperidin-1-yl)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 156aF): Yield: 2.6 mg, 11%; MS (ESI) m/z 594.2, 596.2 $[M+1]^+$; $^1H$ NMR (400 MHz, DMSO-$d_6$) δ 7.52 (s, 1H), 7.25-7.22 (m, 2H), 7.14-7.05 (m, 4H), 7.04-6.96 (m, 3H), 5.74 (s, 1H), 5.21 (s, 1H), 4.76-4.58 (m, 1H), 4.47 (d, J=4.0 Hz, 1H), 3.89 (s, 3H), 3.71 (d, J=14.1 Hz, 1H), 3.20-3.12 (m, 1H), 2.80-2.71 (m, 1H), 2.57 (dd, J=12.7, 10.2 Hz, 2H), 2.48-2.38 (m, 1H), 2.30-2.17 (m, 1H), 2.04 (dd, J=12.6, 3.1 Hz, 2H), 1.99-1.60 (m, 4H).

Rac-4-((5aR,6S,7S,8R,8aS)-3-chloro-7-((4-fluoropiperidin-1-yl)methyl)-8,8a-dihydroxy-1-methoxy-6-phenyl-6,7,8,8a-tetrahydro-5aH-cyclopenta[4,5]furo[3,2-c]pyridin-5a-yl)benzonitrile (Cpd. No. 156bF): Yield: 5.7 mg, 25%; MS (ESI) m/z 550.3 $[M+1]^+$; $^1H$ NMR (400 MHz, DMSO-$d_6$) δ 7.53-7.47 (m, 2H), 7.38-7.33 (m, 2H), 7.10-7.04 (m, 2H), 7.02-6.96 (m, 3H), 6.89 (s, 1H), 5.67 (s, 1H), 5.16 (s, 1H), 4.67 (ddt, J=49.0, 7.3, 3.7 Hz, 1H), 4.44 (d, J=4.1 Hz, 1H), 3.84 (s, 3H), 3.76 (d, J=14.0 Hz, 1H), 3.25-3.17 (m, 1H), 2.81-2.70 (m, 1H), 2.59 (dd, J=12.6, 10.1 Hz, 1H), 2.26-2.19 (m, 1H), 2.10-2.03 (m, 1H), 1.98-1.62 (m, 4H).

Rac-(5aR,6S,7S,8R,8aS)-5a-(4-cyanophenyl)-7-((4-fluoropiperidin-1-yl)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 156cF): Yield: 5.6 mg, 25%; MS (ESI) m/z 541.3 $[M+1]^+$; $^1H$ NMR (400 MHz, DMSO-$d_6$) δ 7.55 (s, 1H), 7.53-7.49 (m, 2H), 7.39-7.34 (m, 2H), 7.10-7.04 (m, 2H), 7.02-6.97 (m, 3H), 5.85 (s, 1H), 5.28 (s, 1H), 4.76-4.58 (m, 1H), 4.49 (d, J=4.0 Hz, 1H), 3.90 (s, 3H), 3.77 (d, J=14.0 Hz, 1H), 3.27-3.17 (m, 1H), 2.81-2.70 (m, 1H), 2.59 (dd, J=12.6, 10.1 Hz, 1H), 2.25-2.19 (m, 1H), 2.11-2.03 (m, 1H), 1.98-1.65 (m, 4H).

Example 157

Rac-(5aR,6S,7S,8R,8aS)-5a-(4-bromophenyl)-7-((4,4-difluoropiperidin-1-yl)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 157aF)

Rac-4-((5aR,6S,7S,8R,8aS)-3-chloro-7-((4,4-difluoropiperidin-1-yl)methyl)-8,8a-dihydroxy-1-methoxy-6-phenyl-6,7,8,8a-tetrahydro-5aH-cyclopenta[4,5]furo[3,2-c]pyridin-5a-yl)benzonitrile (Cpd. No. 157bF)

Rac-(5aR,6S,7S,8R,8aS)-5a-(4-cyanophenyl)-7-((4,4-difluoropiperidin-1-yl)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 157cF)

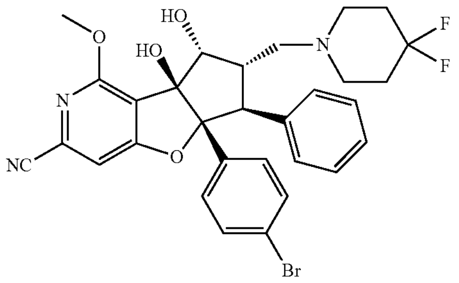

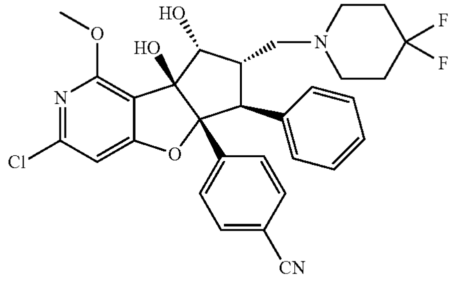

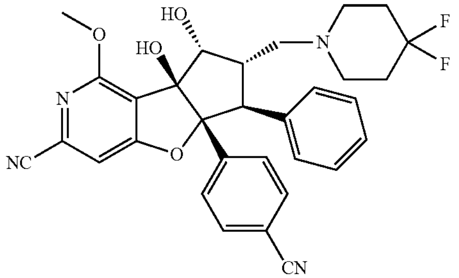

-continued

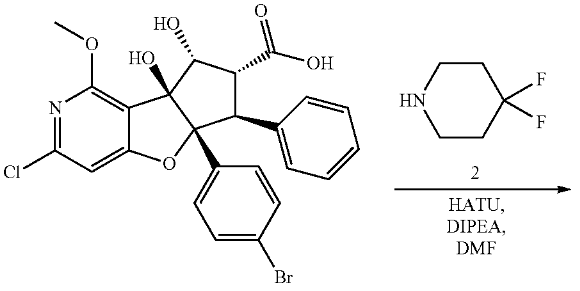

1

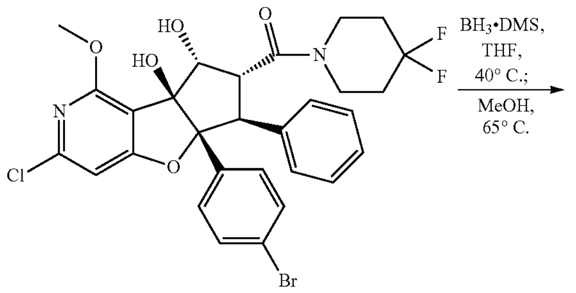

3

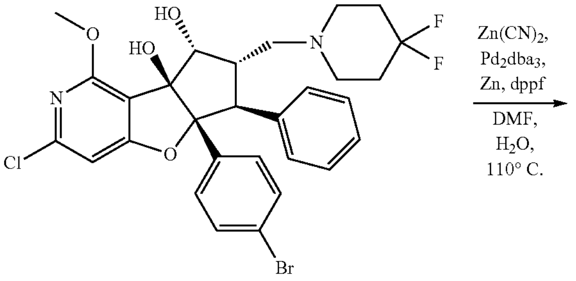

4

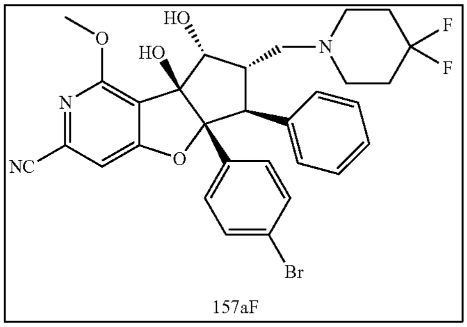

157aF

+

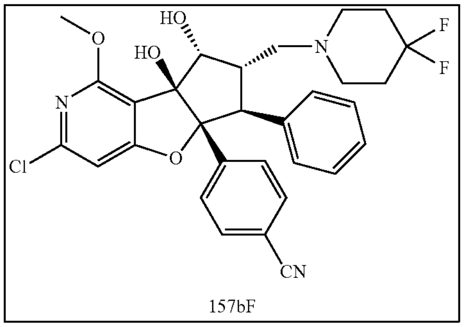

157bF

+

-continued

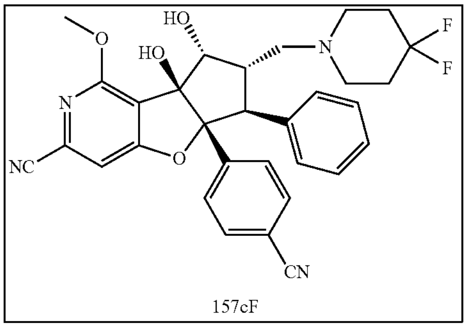

157cF

Synthesis of rac-((5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridin-7-yl)(4,4-difluoropiperidin-1-yl)methanone (3)

HATU (74.9 mg, 0.197 mmol) was added to a stirred solution of rac-(5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridine-7-carboxylic acid (1, 99.9 mg, 0.188 mmol) in N,N-dimethylformamide (1.5 mL) at room temperature. After 2 min N,N-diisopropylethylamine (0.049 mL, 0.281 mmol) was added. The resulting reaction mixture was capped and stirred at room temperature for 20 min. 4,4-Difluoropiperidine (2, 45.4 mg, 0.375 mmol) was added and the reaction mixture was capped and stirred at room temperature for 40 min. The reaction mixture was diluted with ethyl acetate, washed once with water, twice with brine, dried over magnesium sulfate, filtered, concentrated on a rotary evaporator, and purified via silica gel chromatography (10-80% EtOAc/hexanes) to afford rac-((5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridin-7-yl)(4,4-difluoropiperidin-1-yl)methanone (3) as a white solid. Yield: 113.7 mg, 95%; MS (ESI) m/z 635.3, 637.2 $[M+1]^+$.

Synthesis of rac-(5aR,6S,7S,8R,8aS)-5a-(4-bromophenyl)-3-chloro-7-((4,4-difluoropiperidin-1-yl)methyl)-1-methoxy-6-phenyl-5a,6,7,8-tetrahydro-8aH-cyclopenta[4,5]furo[3,2-c]pyridine-8,8a-diol (4)

Borane dimethyl sulfide complex (0.254 mL, 2.68 mmol) was added to a stirred solution of rac-((5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridin-7-yl)(4,4-difluoropiperidin-1-yl)methanone (3, 113.7 mg, 0.179 mmol) in THF (3 mL) at room temperature under a reflux condenser under argon. Some bubbling was observed. The reaction mixture was heated at 40° C. under a reflux condenser under argon for 17 h. After cooling to room temperature, wet methanol (2 mL) was added dropwise slowly. The resulting clear colorless reaction mixture was stirred vigorously and heated at 65° C. under a reflux condenser under argon for 2.5 h. The reaction mixture was loaded directly onto a Strata X-C ion exchange column from Phenomenex. The column was washed sequentially with water, acetonitrile, methanol, and then a mixture of 5% ammonium hydroxide in dichloromethane/methanol. Eluent containing the desired product was concentrated on a rotary evaporator and dried under high vacuum at 40° C. to afford rac-(5aR,6S,7S,8R,8aS)-5a-(4-bromophenyl)-3-chloro-7-((4,4-difluoropiperidin-1-yl)methyl)-1-methoxy-6-phenyl-5a,6,7,8-tetrahydro-8aH-cyclopenta[4,5]furo[3,2-c]pyridine-8,8a-diol (4) as a white solid. Yield: 102.6 mg, 92%; MS (ESI) m/z 621.2, 623.2 $[M+1]^+$.

Synthesis of rac-(5aR,6S,7S,8R,8aS)-5a-(4-bromophenyl)-7-((4,4-difluoropiperidin-1-yl)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 157aF)

Rac-4-((5aR,6S,7S,8R,8aS)-3-chloro-7-((4,4-difluoropiperidin-1-yl)methyl)-8,8a-dihydroxy-1-methoxy-6-phenyl-6,7,8,8a-tetrahydro-5aH-cyclopenta[4,5]furo[3,2-c]pyridin-5a-yl)benzonitrile (Cpd. No. 157bF)

Rac-(5aR,6S,7S,8R,8aS)-5a-(4-cyanophenyl)-7-((4,4-difluoropiperidin-1-yl)methyl)-8,8a-dihydroxy-1-methoxy-6-phenyl-5a, 7,8,8a-tetrahydro-6H-cyclopenta[4,5]furo[3,2-c]pyridine-3-carbonitrile (Cpd. No. 157cF)

Rac-(5aR,6S,7S,8R,8aS)-5a-(4-bromophenyl)-3-chloro-7-((4,4-difluoropiperidin-1-yl)methyl)-1-methoxy-6-phenyl-5a,6,7,8-tetrahydro-8aH-cyclopenta[4,5]furo[3,2-c]pyridine-8,8a-diol (4, 39.9 mg, 0.064 mmol), zinc cyanide (37.7 mg, 0.321 mmol), zinc powder (0.4 mg, 0.006 mmol), $Pd_2dba_3$ (5.9 mg, 0.006 mmol), dppf (7.1 mg, 0.013 mmol), N,N-dimethylformamide (0.90 mL), and water (0.09 mL) were combined in a 1 dram vial with a stirbar. The reaction mixture was stirred at room temperature while being sparged with argon gas for 2 min. The reaction mixture was sealed, stirred, and heated at 110° C. with a block heater for 25 min. The reaction mixture was diluted with DMSO and methanol, filtered, and purified via preparatory HPLC (1546% acetonitrile in water with 0.1% TFA). Fractions containing the desired product were loaded onto a Strata X-C ion exchange column from Phenomenex. The column was washed sequentially with water, acetonitrile, methanol, and then 5% ammonium hydroxide in methanol/dichloromethane. Fluent containing the desired product was concentrated on a rotary evaporator. The residue was taken up in acetonitrile/water, sonicated for a few seconds, and lyophilized to dryness to afford the desired product as a white solid. Rac-(5aR,6S,7S,8R,8aS)-5a-(4-bromophenyl)-7-((4,4-difluoropiperidin-1-yl)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 157aF): Yield: 3.2 mg, 8%; MS (ESI) m/z 612.2, 614.1 $[M+1]^+$; $^1H$ NMR (400 MHz, DMSO-$d_6$) δ 7.52 (s, 1H), 7.25-7.22 (m, 2H), 7.15-7.06 (m, 4H), 7.04-6.96 (m, 3H), 5.75 (s, 1H), 5.19 (s, 1H), 4.49 (s, 1H), 3.90 (s, 3H), 3.70 (d, J=14.1 Hz, 1H), 3.21-3.13 (m, 1H), 2.74-2.58 (m, 3H), 2.47-2.39 (m, 2H), 2.10 (dd, J=12.5, 3.1 Hz, 1H), 2.05-1.90 (m, 4H).

Rac-4-((5aR,6S,7S,8R,8aS)-3-chloro-7-((4,4-difluoropiperidin-1-yl)methyl)-8,8a-dihydroxy-1-methoxy-6-phenyl-6,7,8,8a-tetrahydro-5aH-cyclopenta[4,5]furo[3,2-c]pyridin-5a-yl)benzonitrile (Cpd. No. 157bF): Yield: 8.2 mg, 23%; MS (ESI) m/z 568.3 $[M+1]^+$; $^1H$ NMR (400 MHz, DMSO-$d_6$) δ 7.53-7.48 (m, 2H), 7.39-7.34 (m, 2H), 7.11-7.04 (m, 2H), 7.02-6.96 (m, 3H), 6.90 (s, 1H), 5.67 (s, 1H), 5.14 (d, J=5.2 Hz, 1H), 4.46 (t, J=4.6 Hz, 1H), 3.85 (s, 3H), 3.76 (d, J=14.0 Hz, 1H), 3.26-3.17 (m, 1H), 2.76-2.60 (m, 3H), 2.48-2.42 (m, 2H), 2.13 (dd, J=12.7, 3.1 Hz, 1H), 2.04-1.91 (m, 4H).

Rac-(5aR,6S,7S,8R,8aS)-5a-(4-cyanophenyl)-7-((4,4-difluoropiperidin-1-yl)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 157cF): Yield: 6.7 mg, 19%; MS (ESI) m/z 559.3 $[M+1]^+$; $^1H$ NMR (400 MHz, DMSO-$d_6$) δ 7.55 (s, 1H), 7.54-7.49 (m, 2H), 7.40-7.35 (m, 2H), 7.10-7.04 (m, 2H), 7.03-6.97 (m, 3H), 5.85 (s, 1H), 5.26 (d, J=5.4 Hz, 1H), 4.50 (t, J=4.6 Hz, 1H, 3.90 (s, 3H), 3.77 (d, J=14.0 Hz, 1H), 3.28-3.20 (m, 1H), 2.76-2.59 (m, 3H), 2.47-2.41 (m, 2H), 2.13 (dd, J=12.5, 3.1 Hz, 1H), 2.04-1.91 (m, 4H).

Example 158

Rac-(5aR,6S,7S,8R,8aS)-5a-(4-bromophenyl)-8,8a-dihydroxy-1-methoxy-6-phenyl-7-(pyrrolidin-1-ylmethyl)-5a,7,8,8a-tetrahydro-6H-cyclopenta[4,5]furo[3,2-c]pyridine-3-carbonitrile (Cpd. No. 158aF)

Rac-4-((5aR,6S,7S,8R,8aS)-3-chloro-8,8a-dihydroxy-1-methoxy-6-phenyl-7-(pyrrolidin-1-ylmethyl)-6,7,8,8a-tetrahydro-5aH-cyclopenta[4,5]furo[3,2-c]pyridin-5a-yl)benzonitrile (Cpd. No. 158bF)

Rac-(5aR,6S,7S,8R,8aS)-5a-(4-cyanophenyl)-8,8a-dihydroxy-1-methoxy-6-phenyl-7-(pyrrolidin-1-ylmethyl)-5a,7,8,8a-tetrahydro-6H-cyclopenta[4,5]furo[3,2-c]pyridine-3-carbonitrile (Cpd. No. 158cF)

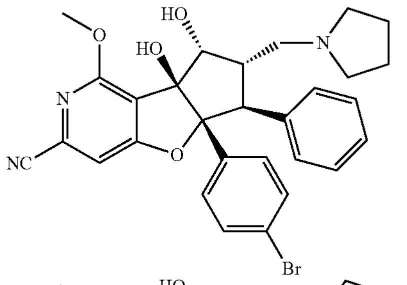

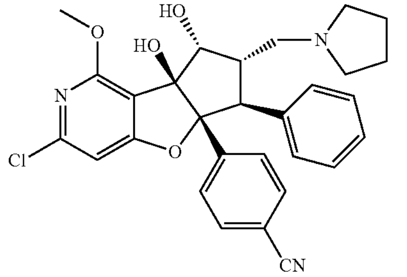

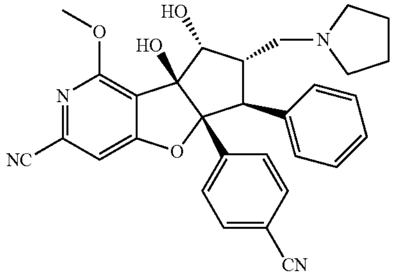

-continued

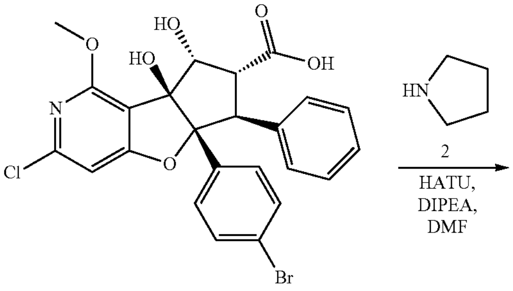

1

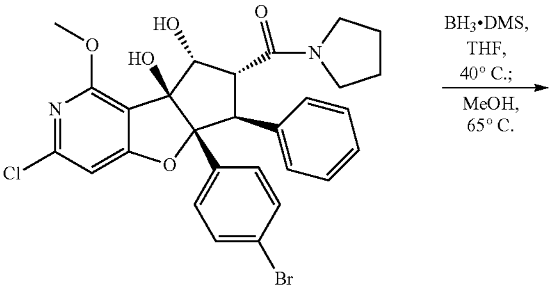

3

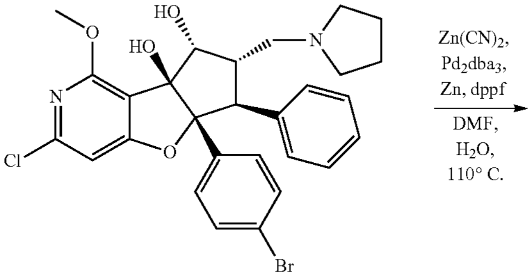

4

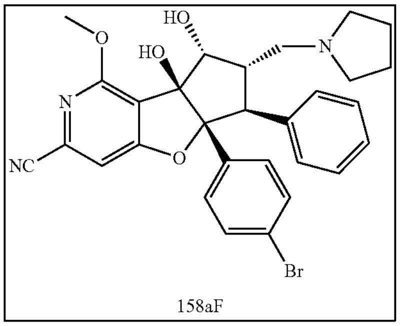

158aF

+

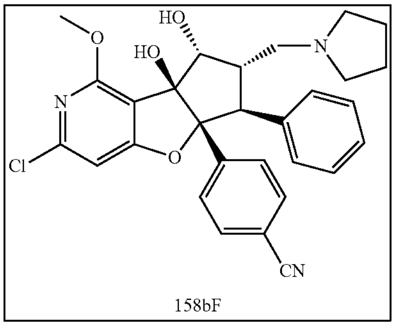

158bF

+

-continued

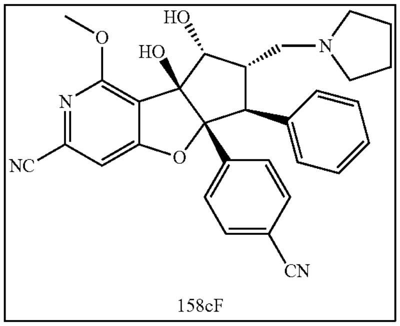

158cF

Synthesis of rac-((5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridin-7-yl)(pyrrolidin-1-yl)methanone (3)

HATU (75.2 mg, 0.198 mmol) was added to a stirred solution of rac-(5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridine-7-carboxylic acid (1, 100.4 mg, 0.188 mmol) in N,N-dimethylformamide (1.5 mL) at room temperature under argon. After 2 min N,N-diisopropylethylamine (0.082 mL, 0.471 mmol) was added. The resulting reaction mixture was stirred at room temperature under argon for 20 min. Pyrrolidine (2, 26.8 mg, 0.377 mmol) was added and the reaction mixture was stirred at room temperature under argon for 25 min. The reaction mixture was diluted with ethyl acetate, washed three times with brine, dried over magnesium sulfate, filtered, concentrated on a rotary evaporator, and purified via silica gel chromatography (10-100% EtOAc/hexanes) to afford rac-((5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridin-7-yl)(pyrrolidin-1-yl)methanone (3) as a white foam-solid. Yield: 110 mg, 99.9%; MS (ESI) m/z 585.2, 587.3 $[M+1]^+$.

Synthesis of rac-(5aR,6S,7S,8R,8aS)-5a-(4-bromophenyl)-3-chloro-1-methoxy-6-phenyl-7-(pyrrolidin-1-ylmethyl)-5a,6,7,8-tetrahydro-8aH-cyclopenta[4,5]furo[3,2-c]pyridine-8,8a-diol (4)

Borane dimethyl sulfide complex (0.178 mL, 1.88 mmol) was added to a stirred solution of rac-((5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridin-7-yl)(pyrrolidin-1-yl)methanone (3, 110 mg, 0.188 mmol) in THF (3 mL) at room temperature under a reflux condenser under argon. Some bubbling was observed. The reaction mixture was heated at 40° C. under a reflux condenser under argon for 8 h 45 min. After cooling to room temperature, wet methanol (2 mL) was added dropwise slowly. The resulting clear colorless reaction mixture was stirred vigorously and heated at 65° C. under a reflux condenser under argon for 34 h. The reaction mixture was loaded directly onto a Strata X-C ion exchange column from Phenomenex. The column was washed sequentially with water, acetonitrile, methanol, and then a mixture of 5% ammonium hydroxide in dichloromethane/methanol. Eluent containing the desired product was concentrated on a rotary evaporator and dried under high vacuum at 40° C. to afford rac-(5aR,6S,7S,8R,8aS)-5a-(4-bromophenyl)-3-chloro-1-methoxy-6-phenyl-7-(pyrrolidin-1-ylmethyl)-5a,6,7,8-tetrahydro-8aH-cyclopenta[4,5]furo[3,2-c]pyridine-8,8a-diol (4) as a white solid. Yield: 92.9 mg, 87%; MS (ESI) m/z 571.4, 573.1.

Synthesis of rac-(5aR,6S,7S,8R,8aS)-5a-(4-bromophenyl)-8,8a-dihydroxy-1-methoxy-6-phenyl-7-(pyrrolidin-1-ylmethyl)-5a,7,8,8a-tetrahydro-6H-cyclopenta[4,5]furo[3,2-c]pyridine-3-carbonitrile (Cpd. No. 158aF)

Rac-4-((5aR,6S,7S,8R,8aS)-3-chloro-8,8a-dihydroxy-1-methoxy-6-phenyl-7-(pyrrolidin-1-ylmethyl)-6,7,8,8a-tetrahydro-5aH-cyclopenta[4,5]furo[3,2-c]pyridin-5a-yl)benzonitrile (Cpd. No. 158bF)

Rac-(5aR,6S,7S,8R,8aS)-5a-(4-cyanophenyl)-8,8a-dihydroxy-1-methoxy-6-phenyl-7-(pyrrolidin-1-ylmethyl)-5a,7,8,8a-tetrahydro-6H-cyclopenta[4,5]furo[3,2-c]pyridine-3-carbonitrile (Cpd. No. 158cF)

Rac-(5aR,6S,7S,8R,8aS)-5a-(4-bromophenyl)-3-chloro-1-methoxy-6-phenyl-7-(pyrrolidin-1-ylmethyl)-5a,6,7,8-tetrahydro-8aH-cyclopenta[4,5]furo[3,2-c]pyridine-8,8a-diol (4, 39.5 mg, 0.069 mmol), zinc cyanide (40.6 mg, 0.345 mmol), zinc powder (0.5 mg, 0.007 mmol), $Pd_2dba_3$ (6.3 mg, 0.007 mmol), dppf (7.7 mg, 0.014 mmol), N,N-dimethylformamide (0.90 mL), and water (0.09 mL) were combined in a 1 dram vial with a stirbar. The reaction mixture was stirred at room temperature while being sparged with argon gas for 2 min. The reaction mixture was sealed, stirred, and heated at 110° C. with a block heater for 22 min. The reaction mixture was diluted with DMSO and methanol, filtered, and purified via preparatory HPLC (15-42% acetonitrile in water with 0.1% TFA). Fractions containing the desired product were loaded onto a Strata X-C ion exchange column from Phenomenex. The column was washed sequentially with water, acetonitrile, methanol, and then 5% ammonium hydroxide in methanol/dichloromethane. Fluent containing the desired product was concentrated on a rotary evaporator. The residue was taken up in acetonitrile/water, sonicated for a few seconds, and lyophilized to dryness to afford the desired product as a white solid.

Rac-(5aR,6S,7S,8R,8aS)-5a-(4-bromophenyl)-8,8a-dihydroxy-1-methoxy-6-phenyl-7-(pyrrolidin-1-ylmethyl)-5a,7,8,8a-tetrahydro-6H-cyclopenta[4,5]furo[3,2-c]pyridine-3-carbonitrile (Cpd. No. 158aF): Yield: 4.7 mg, 12%; MS (ESI) m/z 562.2, 564.2 $[M+1]^+$; $^1H$ NMR (400 MHz, DMSO-$d_6$) δ 7.52 (s, 1H), 7.27-7.22 (m, 2H), 7.12-7.06 (m, 4H), 7.04-6.95 (m, 3H), 5.74 (s, 1H), 5.43 (br s, 1H), 4.50 (d, J=4.1 Hz, 1H), 3.89 (s, 3H), 3.74 (d, J=14.1 Hz, 1H), 3.16-3.06 (m, 1H), 2.80-2.73 (m, 1H), 2.58-2.53 (m, 2H), 2.46-2.39 (m, 2H), 2.15 (dd, J=12.0, 3.0 Hz, 1H), 1.71-1.66 (m, 4H).

Rac-4-((5aR,6S,7S,8R,8aS)-3-chloro-8,8a-dihydroxy-1-methoxy-6-phenyl-7-(pyrrolidin-1-ylmethyl)-6,7,8,8a-tetrahydro-5aH-cyclopenta[4,5]furo[3,2-c]pyridin-5a-yl)benzonitrile (Cpd. No. 158bF): Yield: 8.9 mg, 25%; MS (ESI) m/z 518.3 $[M+1]^+$; $^1H$ NMR (400 MHz, DMSO-$d_6$) δ 7.53-7.49 (m, 2H), 7.37-7.32 (m, 2H), 7.10-7.05 (m, 2H), 7.02-6.96 (m, 3H), 6.89 (s, 1H), 5.67 (s, 1H), 5.38 (br s, 1H), 4.48 (d, J=4.1 Hz, 1H), 3.84 (s, 3H), 3.79 (d, J=14.1 Hz, 1H), 3.19-3.12 (m, 1H), 2.80 (t, J=11.0 Hz, 1H), 2.62-2.56 (m, 2H), 2.48-2.42 (m, 2H), 2.19 (d, J=12.0 Hz, 1H), 1.73-1.67 (m, 4H).

Rac-(5aR,6S,7S,8R,8aS)-5a-(4-cyanophenyl)-8,8a-dihydroxy-1-methoxy-6-phenyl-7-(pyrrolidin-1-ylmethyl)-5a,7,8,8a-tetrahydro-6H-cyclopenta[4,5]furo[3,2-c]pyridine-3-carbonitrile (Cpd. No. 158cF): Yield: 4.1 mg, 12%; MS (ESI) m/z 509.3 $[M+1]^+$; $^1H$ NMR (400 MHz, DMSO-$d_6$) δ 7.55 (s, 1H), 7.54-7.49 (m, 2H), 7.37-7.32 (m, 2H), 7.11-7.05 (m, 2H), 7.03-6.97 (m, 3H), 5.86 (s, 1H), 4.53 (d, J=4.1 Hz, 1H), 3.89 (s, 3H), 3.81 (d, J=14.1 Hz, 1H), 3.22-3.14 (m, 1H), 2.85-2.78 (m, 1H), 2.65-2.58 (m, 2H), 2.21 (d, J=12.1 Hz, 1H), 1.74-1.67 (m, 4H).

Example 159

Rac-(5aR,6S,7S,8R,8aS)-5a-(4-bromophenyl)-7-((diethylamino)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 159aF)

Rac-4-((5aR,6S,7S,8R,8aS)-3-chloro-7-((diethylamino)methyl)-8,8a-dihydroxy-1-methoxy-6-phenyl-6,7,8,8a-tetrahydro-5aH-cyclopenta[4,5]furo[3,2-c]pyridin-5a-yl)benzonitrile (Cpd. No. 159bF)

Rac-(5aR,6S,7S,8R,8aS)-5a-(4-cyanophenyl)-7-((diethylamino)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 159cF)

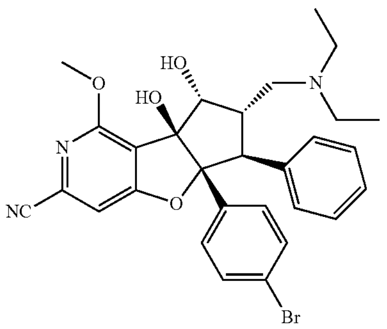

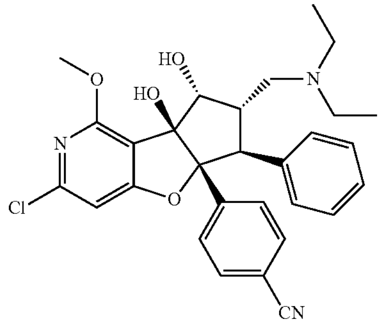

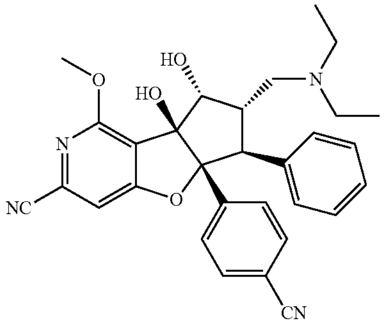

-continued

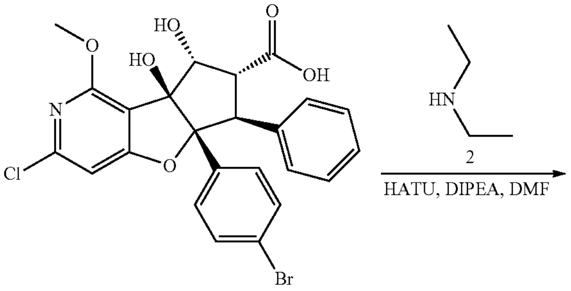

1

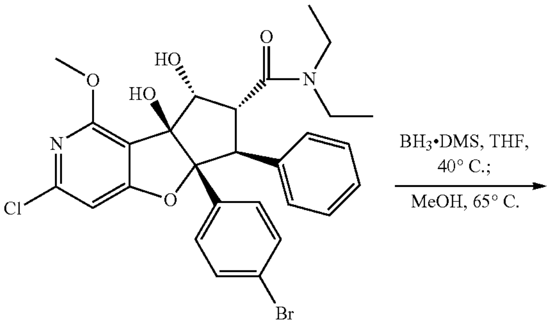

3

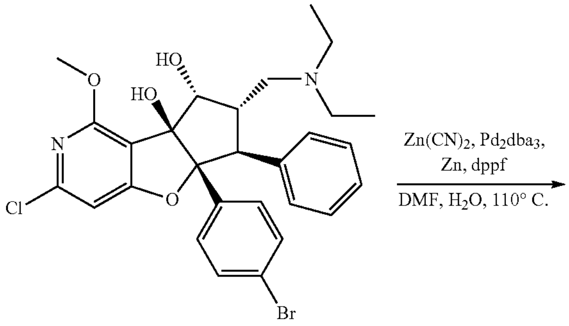

4

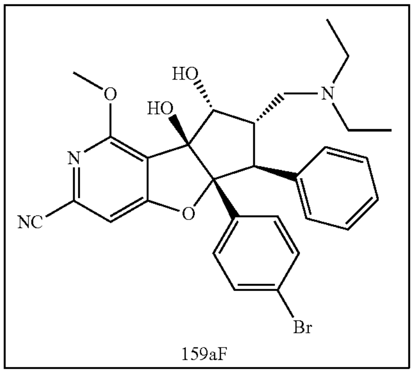

159aF

+

-continued

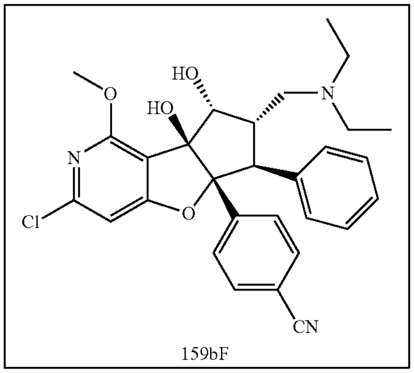

159bF

+

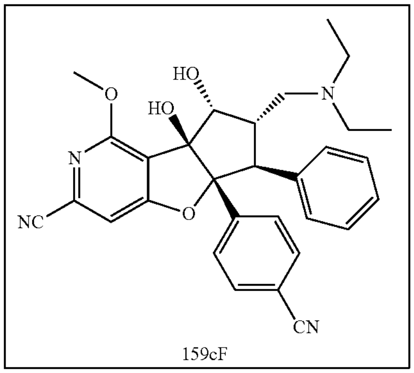

159cF

Synthesis of rac-(5aR,6S,7R,8R,8aS)-5a-(4-bromophenyl)-3-chloro-N,N-diethyl-8,8a-dihydroxy-1-methoxy-6-phenyl-5a, 7,8,8a-tetrahydro-6H-cyclopenta[4,5]furo[3,2-c]pyridine-7-carboxamide (3)

HATU (75.4 mg, 0.198 mmol) was added to a stirred solution of rac-(5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridine-7-carboxylic acid (1, 100.6 mg, 0.189 mmol) in N,N-dimethylformamide (1.5 mL) at room temperature under argon. After 2 min N,N-diisopropylethylamine (0.082 mL, 0.472 mmol) was added. The resulting reaction mixture was stirred at room temperature under argon for 20 min. Diethylamine (2, 0.039 mL, 0.378 mmol) was added and the reaction mixture was stirred at room temperature under argon for 20 min. More diethylamine (2, 0.50 mL, 4.83 mmol) was added. The resulting reaction mixture was stirred at room temperature under argon for 20 min. The reaction mixture was diluted with ethyl acetate, washed three times with brine, dried over magnesium sulfate, filtered, concentrated on a rotary evaporator, and purified via silica gel chromatography (10-100% EtOAc/hexanes) to afford rac-(5aR,6S,7R,8R,8aS)-5a-(4-bromophenyl)-3-chloro-N,N-diethyl-8,8a-dihydroxy-1-methoxy-6-phenyl-5a,7,8,8a-tetrahydro-6H-cyclopenta[4,5]furo[3,2-c]pyridine-7-carboxamide (3) as a white foam-solid. Yield: 90.1 mg, 81%; MS (ESI) m/z 587.4, 589.2 $[M+1]^+$.

Synthesis of rac-(5aR,6S,7S,8R,8aS)-5a-(4-bromophenyl)-3-chloro-7-((diethylamino)methyl)-1-methoxy-6-phenyl-5a,6,7,8-tetrahydro-8aH-cyclopenta[4,5]furo[3,2-c]pyridine-8,8a-diol (4)

Borane dimethyl sulfide complex (0.145 mL, 1.53 mmol) was added to a stirred solution of rac-(5aR,6S,7R,8R,8aS)-

5a-(4-bromophenyl)-3-chloro-N,N-diethyl-8,8a-dihydroxy-1-methoxy-6-phenyl-5a,7,8,8a-tetrahydro-6H-cyclopenta[4,5]furo[3,2-c]pyridine-7-carboxamide (3, 90.1 mg, 0.153 mmol) in THF (2.5 mL) at room temperature under a reflux condenser under argon. Some bubbling was observed. The reaction mixture was heated at 40° C. under a reflux condenser under argon for 8 h 45 min. After cooling to room temperature, wet methanol (2 mL) was added dropwise slowly. The resulting clear colorless reaction mixture was stirred vigorously and heated at 65° C. under a reflux condenser under argon for 11.5 h. The reaction mixture was loaded directly onto a Strata X-C ion exchange column from Phenomenex. The column was washed sequentially with water, acetonitrile, methanol, and then a mixture of 5% ammonium hydroxide in dichloromethane/methanol. Eluent containing the desired product was concentrated on a rotary evaporator and dried under high vacuum at 40° C. to afford rac-(5aR,6S,7S,8R,8aS)-5a-(4-bromophenyl)-3-chloro-7-((diethylamino)methyl)-1-methoxy-6-phenyl-5a,6,7,8-tetrahydro-8aH-cyclopenta[4,5]furo[3,2-c]pyridine-8,8a-diol (4) as a white solid. Yield: 72.3 mg, 82%; MS (ESI) m/z 573.2, 575.2 $[M+1]^+$.

Synthesis of rac-(5aR,6S,7S,8R,8aS)-5a-(4-bromophenyl)-7-((diethylamino)methyl)-8,8a-dihydroxy-1-methoxy-6-phenyl-5a, 7,8,8a-tetrahydro-6H-cyclopenta[4,5]furo[3,2-c]pyridine-3-carbonitrile (Cpd. No. 159aF)

Rac-4-((5aR,6S,7S,8R,8aS)-3-chloro-7-((diethylamino)methyl)-8,8a-dihydroxy-1-methoxy-6-phenyl-6,7,8,8a-tetrahydro-5aH-cyclopenta[4,5]furo[3,2-c]pyridin-5a-yl)benzonitrile (Cpd. No. 159bF)

Rac-(5aR,6S,7S,8R,8aS)-5a-(4-cyanophenyl)-7-((diethylamino)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 159cF)

Rac-(5aR,6S,7S,8R,8aS)-5a-(4-bromophenyl)-3-chloro-7-((diethylamino)methyl)-1-methoxy-6-phenyl-5a,6,7,8-tetrahydro-8aH-cyclopenta[4,5]furo[3,2-c]pyridine-8,8a-diol (4, 39.9 mg, 0.070 mmol), zinc cyanide (40.8 mg, 0.348 mmol), zinc powder (0.5 mg, 0.007 mmol), $Pd_2dba_3$ (6.4 mg, 0.007 mmol), dppf (7.7 mg, 0.014 mmol), N,N-dimethylformamide (0.90 mL), and water (0.09 mL) were combined in a 1 dram vial with a stirbar. The reaction mixture was stirred at room temperature while being sparged with argon gas for 2 min. The reaction mixture was sealed, stirred, and heated at 110° C. with a block heater for 25 min. The reaction mixture was diluted with DMSO and methanol, filtered, and purified via preparatory HPLC (15-43% acetonitrile in water with 0.1% TFA). Fractions containing the desired product were loaded onto a Strata X-C ion exchange column from Phenomenex. The column was washed sequentially with water, acetonitrile, methanol, and then 5% ammonium hydroxide in methanol/dichloromethane. Fluent containing the desired product was concentrated on a rotary evaporator. The residue was taken up in acetonitrile/water, sonicated for a few seconds, and lyophilized to dryness to afford the desired product as a white solid.

Rac-(5aR,6S,7S,8R,8aS)-5a-(4-bromophenyl)-7-((diethylamino)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 159aF): Yield: 5.2 mg, 13%; MS (ESI) m/z 564.2, 566.2 $[M+1]^+$; $^1H$ NMR (400 MHz, DMSO-$d_6$) δ 7.52 (s, 1H), 7.28-7.22 (m, 2H), 7.13-7.06 (m, 4H), 7.04-6.96 (m, 3H), 5.74 (s, 1H), 4.48 (d, J=4.1 Hz, 1H), 3.90 (s, 3H), 3.76 (d, J=14.1 Hz, 1H), 3.14-3.07 (m, 1H), 2.66-2.58 (m, 3H), 2.47-2.40 (m, 2H), 2.22 (d, J=12.7 Hz, 1H), 0.94 (t, J=7.0 Hz, 6H).

Rac-4-((5aR,6S,7S,8R,8aS)-3-chloro-7-((diethylamino)methyl)-8,8a-dihydroxy-1-methoxy-6-phenyl-6,7,8,8a-tetrahydro-5aH-cyclopenta[4,5]furo[3,2-c]pyridin-5a-yl)benzonitrile (Cpd. No. 159bF): Yield: 9.4 mg, 26%; MS (ESI) m/z 520.3 $[M+1]^+$; $^1H$ NMR (400 MHz, DMSO-$d_6$) δ 7.54-7.49 (m, 2H), 7.37-7.32 (m, 2H), 7.10-7.04 (m, 2H), 7.02-6.97 (m, 3H), 6.89 (s, 1H), 5.66 (s, 1H), 5.28 (s, 1H), 4.45 (d, J=4.1 Hz, 1H), 3.85 (s, 3H), 3.81 (d, J=14.0 Hz, 1H), 3.18-3.10 (m, 1H), 2.69-2.56 (m, 3H), 2.47-2.40 (m, 2H), 2.27-2.19 (m, 1H), 0.94 (t, J=7.1 Hz, 6H).

Rac-(5aR,6S,7S,8R,8aS)-5a-(4-cyanophenyl)-7-((diethylamino)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 159cF): Yield: 5.9 mg, 17%; MS (ESI) m/z 511.3 $[M+1]^+$; $^1H$ NMR (400 MHz, DMSO-$d_6$) δ 7.55 (s, 1H), 7.54-7.49 (m, 2H), 7.38-7.33 (m, 2H), 7.11-7.05 (m, 2H), 7.03-6.97 (m, 3H), 5.84 (s, 1H), 4.50 (d, J=4.1 Hz, 1H), 3.90 (s, 3H), 3.83 (d, J=14.0 Hz, 1H), 3.21-3.12 (m, 1H), 2.67-2.59 (m, 3H), 2.48-2.40 (m, 2H), 2.24 (d, J=12.7 Hz, 1H), 0.95 (t, J=7.0 Hz, 6H).

Example 160

Rac-(5aR,6S,7R,8S,8aS)-5a-(4-bromophenyl)-3-chloro-6-phenyl-7-(pyridin-2-ylthio)-5a,6,7,8-tetrahydro-8aH-cyclopenta[4,5]furo[3,2-b]pyridine-8,8a-diol (Cpd. No. 160aF)

Rac-(5aR,6S,7R,8R,8aS)-5a-(4-bromophenyl)-3-chloro-6-phenyl-7-(pyridin-2-ylthio)-5a,6,7,8-tetrahydro-8aH-cyclopenta[4,5]furo[3,2-b]pyridine-8,8a-diol (Cpd. No. 160bF)

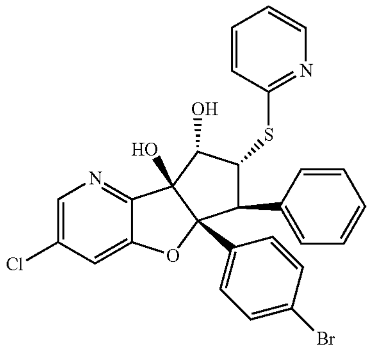

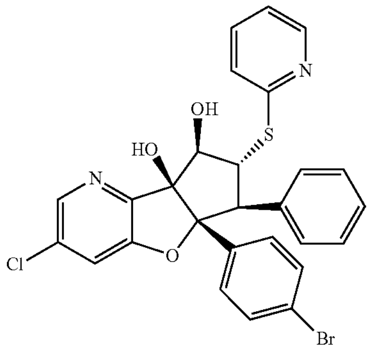

-continued

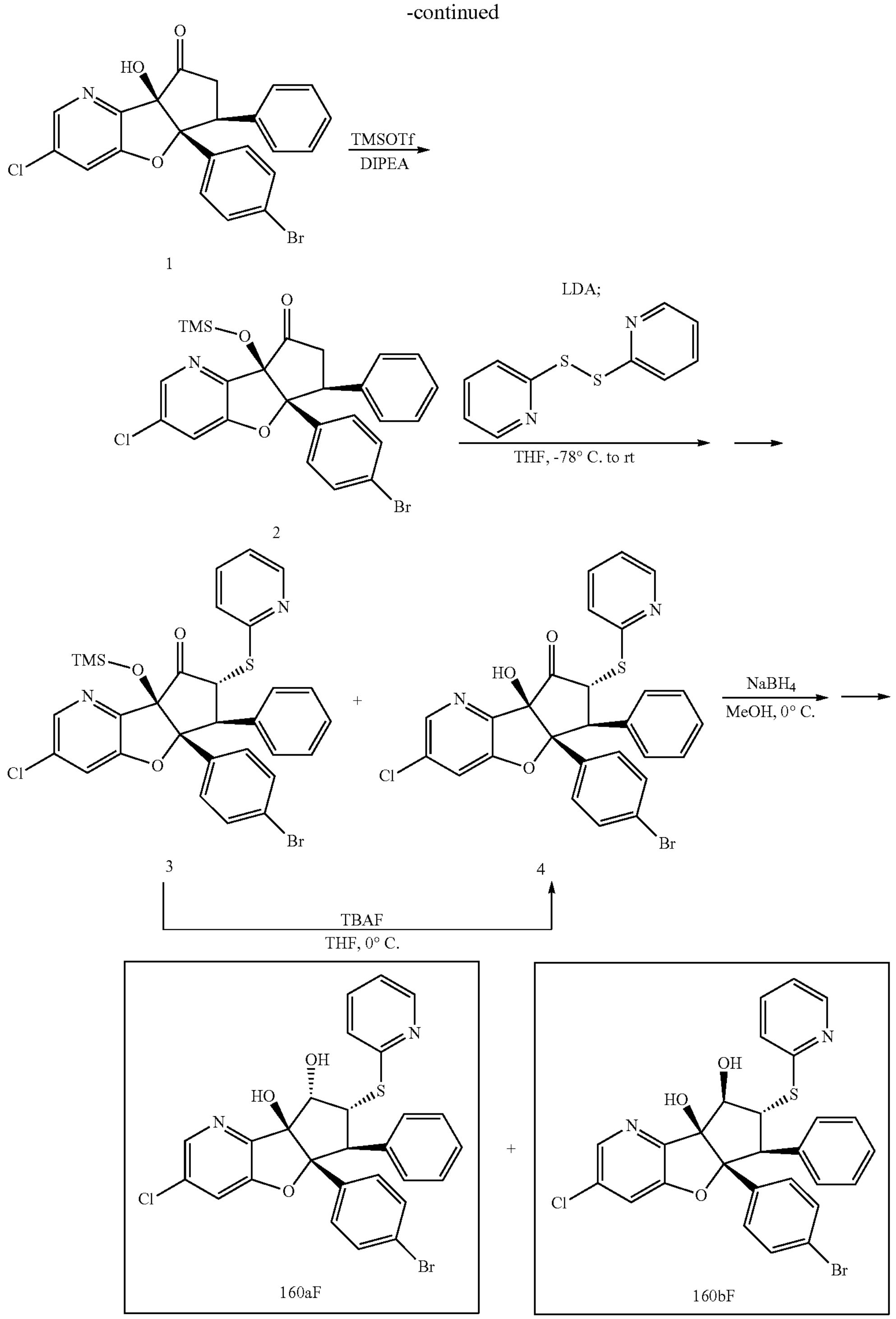

1, 2, 3, 4, 160aF, 160bF

Synthesis of rac-(5aR,6S,8aR)-5a-(4-bromophenyl)-3-chloro-6-phenyl-8a-((trimethylsilyl)oxy)-5a,6,7,8a-tetrahydro-8H-cyclopenta[4,5]furo[3,2-b]pyridin-8-one (2)

In a flame dried flask, rac-(5aR,6S,8aR)-5a-(4-bromophenyl)-3-chloro-8a-hydroxy-6-phenyl-5a,6,7,8a-tetrahydro-8H-cyclopenta[4,5]furo[3,2-b]pyridin-8-one (1, 300 mg, 0.657 mmol) was dissolved in dichloromethane (4.4 mL) and cooled to 0° C. Diisopropylethylamine (0.24 mL, 1.4 mmol) and trimethylsilyl trifluoromethanesulfonate (0.15 mL, 0.83 mmol) were added and the mixture was stirred at 0° C. After 20 min full conversion was observed. Water was added, the phases were separated, and the aq. phase was extracted (3×dichloromethane). The combined organic phases were then dried ($Na_2SO_4$), filtered, and concentrated. Purification by column chromatography ($SiO_2$, 0-20% ethyl acetate/hexane) to afford rac-(5aR,6S,8aR)-5a-(4-bromophenyl)-3-chloro-6-phenyl-8a-((trimethylsilyl)oxy)-5a,6,7,8a-tetrahydro-8H-cyclopenta[4,5]furo[3,2-b]pyridin-8-one (2) as a white solid. Yield: 292 mg, 84%; MS (ESI) m/z 527.9 [M+1]$^+$.

Synthesis of rac-(5aR,6S,7R,8aR)-5a-(4-bromophenyl)-3-chloro-6-phenyl-7-(pyridin-2-ylthio)-8a-((trimethylsilyl)oxy)-5a,6,7,8a-tetrahydro-8H-cyclopenta[4,5]furo[3,2-b]pyridin-8-one (3) and rac-(5aR,6S,7R,8aR)-5a-(4-bromophenyl)-3-chloro-8a-hydroxy-6-phenyl-7-(pyridin-2-ylthio)-5a,6,7,8a-tetrahydro-8H-cyclopenta[4,5]furo[3,2-b]pyridin-8-one (4)

In a flame-dried flask, N,N-diisopropylamine (0.06 mL, 0.4 mmol) was dissolved in THF (2.5 mL) and cooled to 0° C. n-Butyllithium solution (2.5 M in hexane, 0.15 mL, 0.38 mmol) was added, and the mixture was stirred for 10 min, then cooled down to −78° C. Then rac-(5aR,6S,8aR)-5a-(4-bromophenyl)-3-chloro-6-phenyl-8a-((trimethylsilyl)oxy)-5a,6,7,8a-tetrahydro-8H-cyclopenta[4,5]furo[3,2-b]pyridin-8-one (2, 188 mg, 0.355 mmol) in 1.5 mL THF was added, and the mixture was stirred at −78° C. for 1.5 h. A solution of 2-(2-pyridyldisulfanyl)pyridine (102 mg, 0.462 mmol) in 1 mL THF was added, and the mixture was allowed to slowly warm up to rt overnight. Then the reaction was quenched with $NH_4Cl$ (aq). The mixture was extracted with dichloromethane thrice, and the combined organic phases were dried ($Na_2SO_4$), filtered and concentrated. Purification by column chromatography ($SiO_2$, 0-40% ethyl acetate/hexane) to afford rac-(5aR,6S,7R,8aR)-5a-(4-bromophenyl)-3-chloro-6-phenyl-7-(pyridin-2-ylthio)-8a-((trimethylsilyl)oxy)-5a,6,7,8a-tetrahydro-8H-cyclopenta[4,5]furo[3,2-b]pyridin-8-one (3). Yield: (87 mg, 0.14 mmol, 39%); MS (ESI) m/z 637.0 [M+1]$^+$, and rac-(5aR,6S,7R,8aR)-5a-(4-bromophenyl)-3-chloro-8a-hydroxy-6-phenyl-7-(pyridin-2-ylthio)-5a,6,7,8a-tetrahydro-8H-cyclopenta[4,5]furo[3,2-b]pyridin-8-one (4).Yield: 46 mg (0.081 mmol), 23%; MS (ESI) m/z 565.0 [M+1]$^+$.

Synthesis of rac-(5aR,6S,7R,8aR)-5a-(4-bromophenyl)-3-chloro-8a-hydroxy-6-phenyl-7-(pyridin-2-ylthio)-5a,6,7,8a-tetrahydro-8H-cyclopenta[4,5]furo[3,2-b]pyridin-8-one (4) via desilylation of (3)

The starting material rac-(5aR,6S,7R,8aR)-5a-(4-bromophenyl)-3-chloro-6-phenyl-7-(pyridin-2-ylthio)-8a-((trimethylsilyl)oxy)-5a,6,7,8a-tetrahydro-8H-cyclopenta[4,5]furo[3,2-b]pyridin-8-one (3, 79.3 mg, 0.124 mmol) was dissolved in THF (2.5 mL), cooled to 0° C., and treated with tetrabutylammonium fluoride (1.0 M in THF, 0.14 mL, 0.14 mmol). The mixture was stirred at rt. After 15 min frill and clean conversion was observed by TLC. The reaction was quenched ($NH_4Cl$(aq)) and the mixture was extracted with dichloromethane (3×). The combined organic phases were dried ($Na_2SO_4$), filtered and concentrated. The crude product was combined with the crude product from an analogously conducted reaction with 5.3 mg (0.0083 mmol) starting material for purification purposes. Purification by column chromatography ($SiO_2$, 0-50% ethyl acetate/hexane) to afford rac-(5aR,6S,7R,8aR)-5a-(4-bromophenyl)-3-chloro-8a-hydroxy-6-phenyl-7-(pyridin-2-ylthio)-5a,6,7,8a-tetrahydro-8H-cyclopenta[4,5]furo[3,2-b]pyridin-8-one (4) as a white solid. Yield: 74.2 mg (0.131 mmol, 99%); MS (ESI) m/z 565 [M+1]$^+$.

Synthesis of rac-(5aR,6S,7R,8S,8aS)-5a-(4-bromophenyl)-3-chloro-6-phenyl-7-(pyridin-2-ylthio)-5a,6,7,8-tetrahydro-8aH-cyclopenta[4,5]furo[3,2-b]pyridine-8,8a-diol (Cpd. No. 160aF) and rac-(5aR,6S,7R,8R,8aS)-5a-(4-bromophenyl)-3-chloro-6-phenyl-7-(pyridin-2-ylthio)-5a,6,7,8-tetrahydro-8aH-cyclopenta[4,5]furo[3,2-b]pyridine-8,8a-diol (Cpd. No. 160bF)

The starting material rac-(5aR,6S,7R,8aR)-5a-(4-bromophenyl)-3-chloro-8a-hydroxy-6-phenyl-7-(pyridin-2-ylthio)-5a,6,7,8a-tetrahydro-8H-cyclopenta[4,5]furo[3,2-b]pyridin-8-one (4, 33 mg, 0.058 mmol) was dissolved in methanol (1 mL) and cooled to 0° C. $NaBH_4$ (22 mg, 0.58 mmol) was added, and the mixture was stirred at 0° C. After 10 min complete conversion was observed; LCMS showed rather clean conversion to a mixture of diastereomeric alcohols 5:6 (ratio 5:6 ca. 1:9). The mixture was directly subjected to column chromatography ($SiO_2$, 0-40% ethyl acetate/hexane) to give 12.3 mg of slightly impure syn-diol (Cpd. No. 160bF) and 3 mg of slightly impure anti-diol (Cpd. No. 160aF). Syn-diol (Cpd. No. 160bF) was re-purified by reverse phase HPLC (C18, MeCN/water+0.1% TFA) and finally preparative TLC to afford pure rac-(5aR,6S,7R,8R,8aS)-5a-(4-bromophenyl)-3-chloro-6-phenyl-7-(pyridin-2-ylthio)-5a,6,7,8-tetrahydro-8aH-cyclopenta[4,5]furo[3,2-b]pyridine-8,8a-diol (Cpd. No. 160bF) as a white solid. Yield: 4.1 mg; MS (ESI) m/z 567.0 [M+1]$^+$; $^1$H NMR (400 MHz, DMSO-$d_6$) δ 8.35 (d, J=2.0 Hz, 1H), 8.13-8.10 (m, 1H), 7.83 (d, J=2.0 Hz, 1H), 7.56 (ddd, J=7.6, 7.6, 2.0 Hz, 1H), 7.40 (d, J=8.7 Hz, 2H), 7.22 (d, J=8.7 Hz, 2H), 7.07 (ddd, J=7.6, 4.9, 1.0 Hz, 1H), 7.04-6.97 (m, 4H), 6.82-6.77 (m, 2H), 6.65 (d, J=5.1 Hz, 1H), 5.60 (s, 1H), 4.90 (dd, J=6.8, 5.1 Hz, 1H), 4.46 (dd, J=14.2, 6.8 Hz, 1H), 3.73 (d, J=14.2 Hz, 1H). Anti-diol (Cpd. No. 160aF) was repurified by preparative TLC ($SiO_2$, dichloromethane/MeOH=19/1) to afford pure rac-(5aR,6S,7R,8S,8aS)-5a-(4-bromophenyl)-3-chloro-6-phenyl-7-(pyridin-2-ylthio)-5a,6,7,8-tetrahydro-8aH-cyclopenta[4,5]furo[3,2-b]pyridine-8,8a-diol (Cpd. No. 160aF) as a white solid. Yield: 1.2 mg; MS (ESI) m/z 567.1 [M+1]$^+$; $^1$H NMR (400 MHz, DMSO-$d_6$) δ 8.61 (bd, J=5.1 Hz, 1H), 8.19 (d, J=2.1 Hz, 1H), 7.66 (d, J=2.1 Hz, 1H), 7.63 (ddd, J=7.9, 7.9, 2.1 Hz, 1H), 7.29-7.23 (m, 3H), 7.18 (bdd, J=7.9 Hz, 5.1 Hz, 1H), 7.14 (d, J=8.6 Hz, 2H), 7.03-6.94 (m, 5H), 6.26 (s, 1H), 5.93 (d, J=5.9 Hz, 1H), 5.50 (dd, J=14.7, 4.0 Hz, 1H), 4.47 (dd, J=5.9, 4.0 Hz, 1H), 4.29 (d, J=14.7 Hz, 1H).

Example 161

Rac-methyl (1aS,2R,3S,3aR,8bS)-3a-(4-bromophenyl)-6-chloro-3-phenyl-1a,2,3,3a-tetrahydro-oxireno[2",3":1',5']cyclopenta[1',2':4,5]furo[3,2-b]pyridine-2-carboxylate (Cpd. No. 161F)

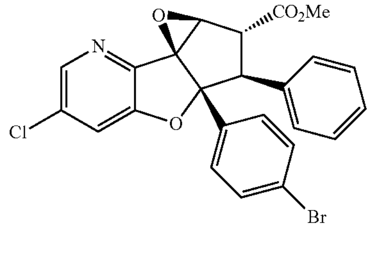

-continued

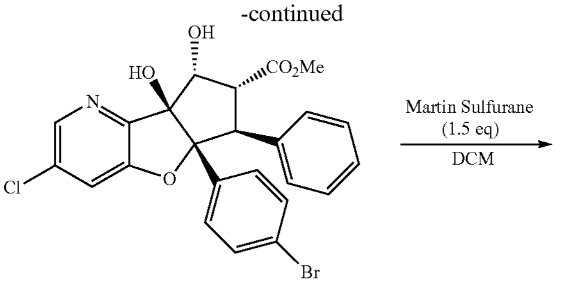

1

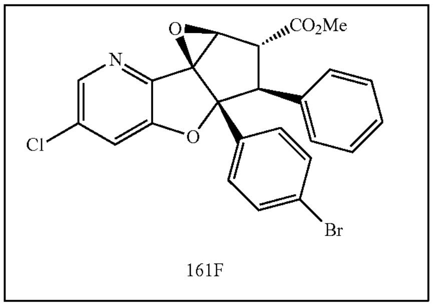

161F

Synthesis of rac-methyl (1aS,2R,3S,3aR,8bS)-3a-(4-bromophenyl)-6-chloro-3-phenyl-1a,2,3,3a-tetra-hydro-oxireno[2",3":1',5']cyclopenta[1',2':4,5]furo[3,2-b]pyridine-2-carboxylate (Cpd. No. 161F)

Rac-methyl (5aR,6S,7R,8R,8aS)-5a-(4-bromophenyl)-3-chloro-8,8a-dihydroxy-6-phenyl-5a,7,8,8a-tetrahydro-6H-cyclopenta[4,5]furo[3,2-b]pyridine-7-carboxylate (1, 42 mg, 0.081 mmol) was dissolved in dichloromethane (0.6 mL) under argon. Martin sulfurane (82 mg, 0.12 mmol) was added, and the mixture was stirred at rt. The mixture turned dark red. After 6 h the reaction was quenched with $NH_4Cl$ (aq). The mixture was extracted with dichloromethane (3×), and the combined organic phases were dried ($Na_2SO_4$), filtered and concentrated. Purification by repeated column chromatography ($SiO_2$, 0-30% ethyl acetate/hexane, then 0-20% ethyl acetate/hexane) to afford rac-methyl (1aS,2R,3S,3aR,8bS)-3a-(4-bromophenyl)-6-chloro-3-phenyl-1a,2,3,3a-tetrahydro-oxireno[2",3":1',5']cyclopenta[1',2':4,5]furo[3,2-b]pyridine-2-carboxylate (Cpd. No. 161F) as a light orange solid. Yield: 29.6 mg (0.0594 mmol), 73%; MS (ESI) m/z 498.0 $[M+1]^+$; $^1H$ NMR (400 MHz, $CDCl_3$) δ 8.17 (d, J=1.9 Hz, 1H), 7.29 (d, J=1.9 Hz, 1H), 7.23-7.19 (m, 2H), 7.15-7.10 (m, 5H), 7.05-7.00 (m, 2H), 4.91 (d, J=11.8 Hz, 1H), 4.37 (d, J=0.6 Hz, 1H), 3.72 (s, 3H), 3.72 (dd, J=11.8, 0.6 Hz, 1H).

Example 162

Rac-(5aR,6S,8R,8aR)-5a-(4-bromophenyl)-3-chloro-8-(hydroxymethyl)-6-phenyl-5a,6,7,8-tetrahydro-8aH-cyclopenta[4,5]furo[3,2-b]pyridin-8a-ol (Cpd. No. 162F)

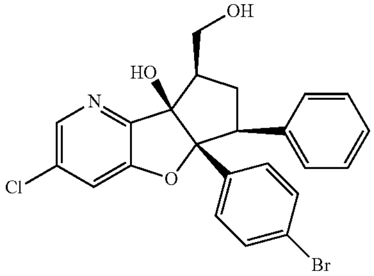

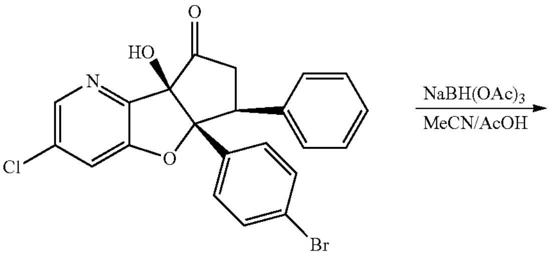

1

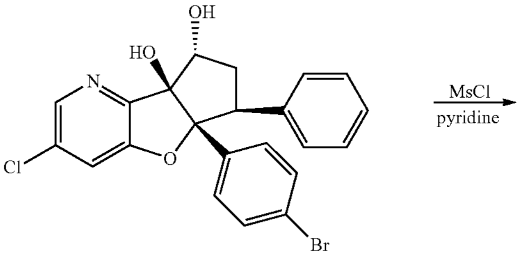

2

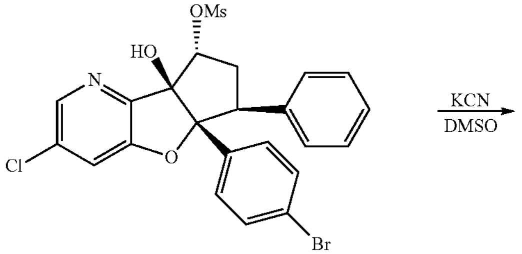

3

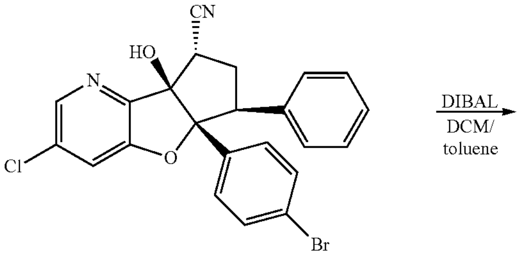

4

-continued

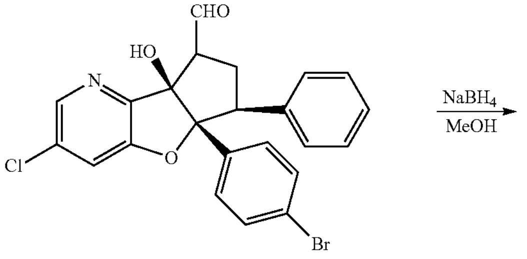

5

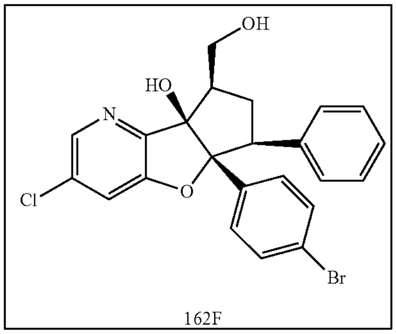

162F

+

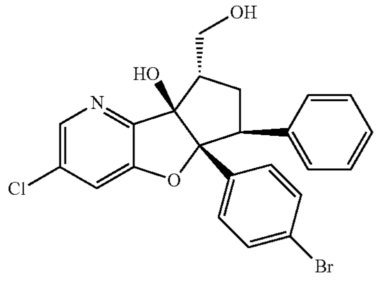

6

Synthesis of rac-(5aR,6S,8R,8aS)-5a-(4-bromophenyl)-3-chloro-6-phenyl-5a,6,7,8-tetrahydro-8aH-cyclopenta[4,5]furo[3,2-b]pyridine-8,8a-diol (2)

The starting material rac-(5aR,6S,8aR)-5a-(4-bromophenyl)-3-chloro-8a-hydroxy-6-phenyl-6,7-dihydrocyclopenta[4,5]furo[1,2-b]pyridin-8-one (1, 209 mg, 0.458 mmol) was dissolved in acetic acid (2 mL) and MeCN (2 mL), and sodium triacetoxyborohydride (0.97 g, 4.6 mmol) was added. After stirring for 20 min water was carefully added. The mixture was extracted with dichloromethane thrice, and the combined organic phases were dried ($Na_2SO_4$), filtered and concentrated. Purification by column chromatography ($SiO_2$, 0-30% ethyl acetate/hexane) to afford rac-(5aR,6S,8R,8aS)-5a-(4-bromophenyl)-3-chloro-6-phenyl-5a,6,7,8-tetrahydro-8aH-cyclopenta[4,5]furo[3,2-b]pyridine-8,8a-diol (2). Yielded: 196 mg (0.427 mmol), 93%; MS (ESI) m/z 458.1 $[M+1]^+$.

Synthesis of rac-(5aR,6S,8R,8aS)-5a-(4-bromophenyl)-3-chloro-8a-hydroxy-6-phenyl-5a, 7,8,8a-tetrahydro-6H-cyclopenta[4,5]furo[3,2-b]pyridin-8-yl methanesulfonate (3)

To a solution of rac-(5aR,6S,8R,8aS)-5a-(4-bromophenyl)-3-chloro-6-phenyl-5a,6,7,8-tetrahydro-8aH-cyclopenta[4,5]furo[3,2-b]pyridine-8,8a-diol (2, 196 mg, 0.427 mmol) in pyridine (4.5 mL) was added methanesulfonyl chloride (0.04 mL, 0.5 mmol) and the mixture was stirred at rt After stirring over night the reaction was quenched with $NH_4Cl$ (aq) and the mixture was extracted with dichloromethane thrice. The combined organic phases were dried ($Na_2SO_4$), filtered and concentrated. Purification by column chromatography ($SiO_2$, 0-50% ethyl acetate/hexane) to afford rac-(5aR,6S,8R,8aS)-5a-(4-bromophenyl)-3-chloro-8a-hydroxy-6-phenyl-5a,7,8,8a-tetrahydro-6H-cyclopenta[4,5]furo[3,2-b]pyridin-8-yl methanesulfonate (3) as a white solid. Yield:185 mg (0.345 mmol), 81%; MS (ESI) m/z 535.9 $[M+1]^+$.

Synthesis of rac-(5aR,6S,8S,8aR)-5a-(4-bromophenyl)-3-chloro-8a-hydroxy-6-phenyl-5a, 7,8,8a-tetrahydro-6H-cyclopenta[4,5]furo[3,2-b]pyridine-8-carbonitrile (4)

To a solution of rac-(5aR,6S,8R,8aS)-5a-(4-bromophenyl)-3-chloro-8a-hydroxy-6-phenyl-5a,7,8,8a-tetrahydro-6H-cyclopenta[4,5]furo[3,2-b]pyridin-8-yl methanesulfonate (3, 185 mg, 0.345 mmol) in DMSO (3.5 mL) was added potassium cyanide (45 mg, 0.69 mmol) and the mixture was stirred at rt under argon. After 1.5 h the mixture was diluted with ethyl acetate and washed with water and brine, then dried ($Na_2SO_4$), filtered and concentrated. Purification by column chromatography ($SiO_2$, 0-45% ethyl acetate/hexane) to afford rac-(5aR,6S,8S,8aR)-5a-(4-bromophenyl)-3-chloro-8a-hydroxy-6-phenyl-5a,7,8,8a-tetrahydro-6H-cyclopenta[4,5]furo[3,2-b]pyridine-8-carbonitrile (4) as off-white solid. Yield: 149 mg (0.319 mmol), 92%; MS (ESI) m/z 467.1 $[M+1]^+$.

Synthesis of rac-(5aR,6S,8aR)-5a-(4-bromophenyl)-3-chloro-8a-hydroxy-6-phenyl-5a,7,8,8a-tetrahydro-6H-cyclopenta[4,5]furo[3,2-b]pyridine-8-carbaldehyde (5)

The starting material rac-(5aR,6S,8S,8aR)-5a-(4-bromophenyl)-3-chloro-8a-hydroxy-6-phenyl-5a,7,8,8a-tetrahydro-6H-cyclopenta[4,5]furo[3,2-b]pyridine-8-carbonitrile (4, 20 mg, 0.043 mmol) was dissolved in dichloromethane (0.4 mL) and cooled to −78° C. DIBAL (1 M sln. in toluene) (0.1 mL, 0.1 mmol) was added, and the mixture was stirred at −78° C. After 2.5 h another 0.05 mL DIBAL sln (1 M in toluene, 0.05 mmol) were added. After another 30 min the mixture was allowed to warm up to −20° C. within 1 h. Then MeOH (0.1 mL) was added, followed by ca. 2 mL aq. sat. Rochelle-salt sln. The mixture was stirred for 1 h at rt, then extracted (3×dichloromethane). The combined organic phases were dried ($Na_2SO_4$), filtered and concentrated. The crude product, which contained a diastereomeric mixture of the C1-aldehydes (5), was directly used in the next step.

Synthesis of rac-(5aR,6S,8R,8aR)-5a-(4-bromophenyl)-3-chloro-8-(hydroxymethyl)-6-phenyl-5a,6,7,8-tetrahydro-8aH-cyclopenta[4,5]furo[3,2-b]pyridin-8a-ol (Cpd. No. 162F)

Crude rac-(5aR,6S,8aR)-5a-(4-bromophenyl)-3-chloro-8a-hydroxy-6-phenyl-5a,7,8,8a-tetrahydro-6H-cyclopenta[4,5]furo[3,2-b]pyridine-8-carbaldehyde (5) from the previous step was dissolved in methanol (1 mL) under argon and cooled to 0° C. Sodium borohydride (16 mg, 0.42 mmol) was added and the mixture was stirred at 0° C. for 20 min, then at rt. After 45 min total reaction time the reaction was quenched with water, and the resulting mixture was extracted thrice with ethyl acetate. The combined organic phases were dried ($Na_2SO_4$), filtered and concentrated. Purification by preparative TLC ($SiO_2$, EtOAC/Hexane=1/1) over 2 steps to afford primary alcohol of rac-(5aR,6S,8R,8aR)-5a-(4-bromophenyl)-3-chloro-8-(hydroxymethyl)-6-phenyl-5a,6,7,8-tetrahydro-8aH-cyclopenta[4,5]furo[3,2-b]pyridin-8a-ol (Cpd. No. 162F) as a white solid. Yield: 1.3 mg (0.0028 mmol), 6%; MS (ESI) m/z 472.1 $[M+1]^+$; $^1H$ NMR (400 MHz, DMSO-$d_6$) δ 8.25 (d, J=2.1 Hz, 1H), 7.75 (d, J=2.1 Hz, 1H), 7.31 (d, J=8.7 Hz, 1H), 7.14 (d, J=8.7 Hz, 1H), 7.13-7.07 (m, 3H), 7.00-6.97 (m, 2H), 5.57 (s, 1H), 4.55 (bt, J=5.4 Hz, 1H), 4.07-4.01 (m, 1H), 3.85-3.76 (m, 1H), 3.55 (dd, J=14.0, 6.2 Hz, 1H), 2.73-2.63 (m, 1H), 2.35 (ddd, J=13, 13, 13 Hz, 1H), 2.24 (ddd, J=13, 6.5, 6.5 Hz, 1H).

Example 163

Rac-(5aR,6S,7R,8S,8aS)-5a-(4-bromophenyl)-3-chloro-6-phenyl-7-(pyridin-2-ylsulfonyl)-5a,6,7,8-tetrahydro-8aH-cyclopenta[4,5]furo[3,2-b]pyridine-8,8a-diol (Cpd. No. 163F)

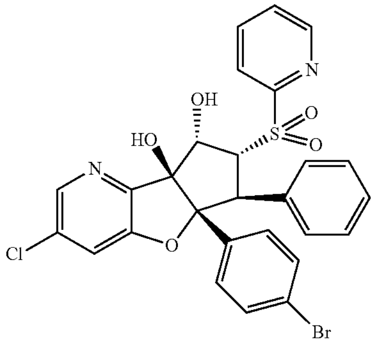

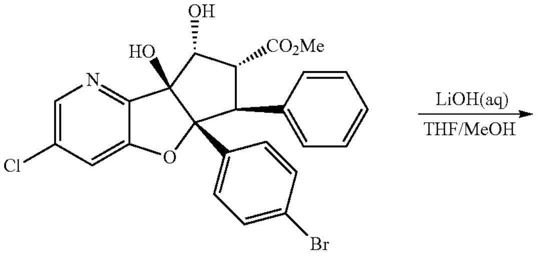

1

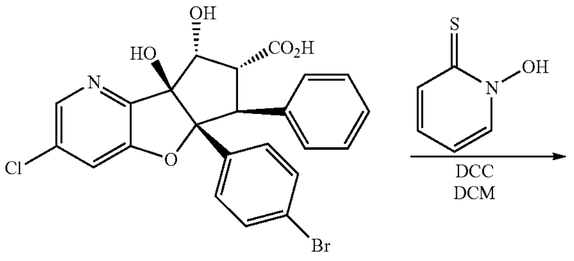

2

-continued

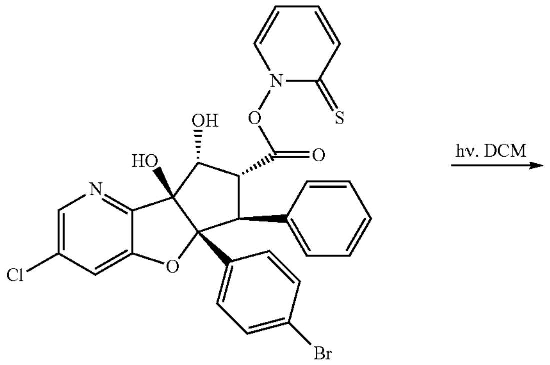

3

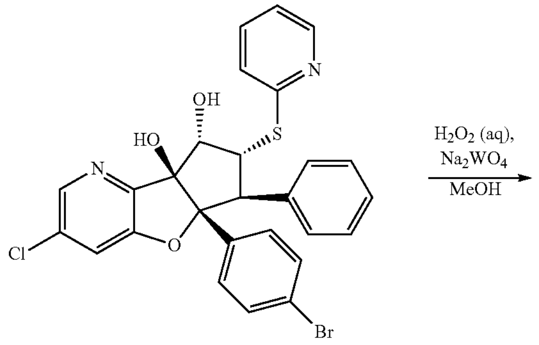

4

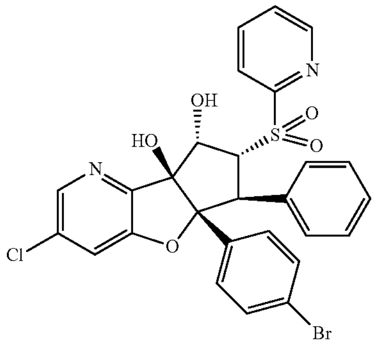

163F

Synthesis of rac-(5aR,6S,7R,8R,8aS)-5a-(4-bromophenyl)-3-chloro-8,8a-dihydroxy-6-phenyl-5a, 7,8,8a-tetrahydro-6H-cyclopenta[4,5]furo[3,2-b]pyridine-7-carboxylic acid (2)

To rac-methyl (5aR,6S,7R,8R,8aS)-5a-(4-bromophenyl)-3-chloro-8,8a-dihydroxy-6-phenyl-5a,7,8,8a-tetrahydro-6H-cyclopenta[4,5]furo[3,2-b]pyridine-7-carboxylate, (1, 400 mg, 0.774 mmol) in methanol (3 mL) and THF (3 mL) at rt was added LiOH (aq) (2 M, 6 mL, 12 mmol) and the mixture was stirred at 40° C. After 1 h the mixture was cooled down to rt, stirred for another 1.5 h, acidified with 2M hydrochloric acid (aq) (6.5 mL) and diluted with EtOAc and water. The aq. phase was extracted thrice (EtOAc), and the combined organic phases were dried ($Na_2SO_4$), filtered and concentrated to afford the crude acid of rac-(5aR,6S,7R,8R,8aS)-5a-(4-bromophenyl)-3-chloro-8,8a-dihydroxy-6-phenyl-5a,7,8,8a-tetrahydro-6H-cyclopenta[4,5]furo[3,2-b]pyridine-7-carboxylic acid (2). Yield: 416 mg; MS (ESD) m/z 502.0 $[M+1]^+$. The crude product was used in the next step without further purification.

Synthesis of rac-2-thioxopyridin-1(2H)-yl (5aR,6S,7R,8R,8aS)-5a-(4-bromophenyl)-3-chloro-8,8a-dihydroxy-6-phenyl-5a,7,8,8a-tetrahydro-6H-cyclopenta[4,5]furo[3,2-b]pyridine-7-carboxylate (3)

To a solution of rac-(5aR,6S,7R,8R,8aS)-5a-(4-bromophenyl)-3-chloro-8,8a-dihydroxy-6-phenyl-5a,7,8,8a-tetrahydro-6H-cyclopenta[4,5]furo[3,2-b]pyridine-7-carboxylic acid (2, 416 mg of the crude product obtained in the previous step) and 1-hydroxypyridine-2-thione (112 mg, 0.881 mmol) in dichloromethane (7.5 mL) in a vial shielded from light was added DCC (176 mg, 0.851 mmol) and the mixture was stirred at r.t. overnight. After 17.5 h the mixture was concentrated and the residue was taken up in MeCN and filtered through celite. The filtrate was concentrated. Purification by column chromatography ($SiO_2$, 0-50% ethyl acetate/hexane; column was covered in aluminum foil) yielded 464 mg (0.758 mmol, 98% over 2 steps) of rac-2-thioxopyridin-1(2H)-yl (5aR,6S,7R,8R,8aS)-5a-(4-bromophenyl)-3-chloro-8,8a-dihydroxy-6-phenyl-5a,7,8,8a-tetrahydro-6H-cyclopenta[4,5]furo[3,2-b]pyridine-7-carboxylate (3) as a yellow/green solid; MS (ESI) m/z 611 $[M+1]^+$.

Synthesis of rac-(5aR,6S,7R,8S,8aS)-5a-(4-bromophenyl)-3-chloro-6-phenyl-7-(pyridin-2-ylthio)-5a,6,7,8-tetrahydro-8aH-cyclopenta[4,5]furo[3,2-b]pyridine-8,8a-diol (4)

Rac-2-thioxopyridin-1(2H)-yl (5aR,6S,7R,8R,8aS)-5a-(4-bromophenyl)-3-chloro-8,8a-dihydroxy-6-phenyl-5a,7,8,8a-tetrahydro-6H-cyclopenta[4,5]furo[3,2-b]pyridine-7-carboxylate (3, 56 mg, 0.092 mmol) was dissolved in dichloromethane (2.5 mL) in a 5 mL MW vial under argon. The vial was sealed and the mixture was stirred and irradiated (HDX XG-1026 lamp, 250 W halogen bulb, 1 h). After 20 min complete conversion was observed by LCMS. The mixture was concentrated and the crude product was purified by column chromatography ($SiO_2$, 0-50% ethyl acetate/hexane) to yield 42.3 mg (0.0745 mmol, 81%) of rac-(5aR,6S,7R,8S,8aS)-5a-(4-bromophenyl)-3-chloro-6-phenyl-7-(pyridin-2-ylthio)-5a,6,7,8-tetrahydro-8aH-cyclopenta[4,5]furo[3,2-b]pyridine-8,8a-diol (4) as a white solid; MS (ESI) m/z 566.9 $[M+1]^+$.

Synthesis of rac-(5aR,6S,7R,8S,8aS)-5a-(4-bromophenyl)-3-chloro-6-phenyl-7-(pyridin-2-ylsulfonyl)-5a,6,7,8-tetrahydro-8aH-cyclopenta[4,5]furo[3,2-b]pyridine-8,8a-diol (Cpd. No. 163F)

Rac-(5aR,6S,7R,8S,8aS)-5a-(4-bromophenyl)-3-chloro-6-phenyl-7-(pyridin-2-ylthio)-5a,6,7,8-tetrahydro-8aH-cyclopenta[4,5]furo[3,2-b]pyridine-8,8a-diol (4, 42.3 mg, 0.0745 mmol) was dissolved in methanol (2 mL) and cooled to 0° C. Hydrogen peroxide (30% in water, 0.07 mL, 0.7 mmol) was added, followed by sodium tungstate dihydrate (12.3 mg, 0.0373 mmol), and the mixture was stirred at rt. After 25 h water was added, and the mixture was extracted with dichloromethane thrice. The combined organic phases were dried ($Na_2SO_4$), filtered and concentrated. Purification by column chromatography ($SiO_2$, 0-50% ethyl acetate/dichloromethane) yielded product contaminated with the sulfoxide intermediate (inseparable). The material was re-subjected to the same reaction conditions. After 9 h 1 mL N,N-dimethylformamide was added to improve solubility. After another 1.5 h another 0.07 mL hydrogen peroxide (30% in water, 0.7 mmol) were added and the mixture was stirred overnight. Then another 0.07 mL hydrogen peroxide (30% in water, 0.7 mmol) were added. After 2 days total the reaction was complete as judged by LCMS. The mixture was diluted with water and extracted with dichloromethane (3×). The combined organic phases were dried ($Na_2SO_4$), filtered and concentrated. Purification by column chromatography ($SiO_2$, 0-40% ethyl acetate/dichloromethane) yielded 18.4 mg (41%) of Rac-(5aR,6S,7R,8S,8aS)-5a-(4-bromophenyl)-3-chloro-6-phenyl-7-(pyridin-2-ylsulfonyl)-5a,6,7,8-tetrahydro-8aH-cyclopenta[4,5]furo[3,2-b]pyridine-8,8a-diol (Cpd. No. 163F) as white solid; MS (ESI) m/z 598.9 $[M+1]^+$; $^1H$ NMR (400 MHz, DMSO-$d_6$) δ 8.80 (ddd, J=4.7, 1.7, 1.0 Hz, 1H), 8.19 (d, J=2.0 Hz, 1H), 7.79 (ddd, J=7.7, 7.7, 1.7, 1H), 7.67 (d, J=2.0 Hz, 1H), 7.64 (ddd, J=7.7, 4.7, 1.0 Hz, 1H), 7.40 (ddd, J=7.7, 1.0, 1.0 Hz, 1H), 7.24 (d, J=8.8 Hz, 2H), 7.13 (d, J=8.8 Hz, 2H), 6.89-6.83 (m, 1H), 6.77 (t, J=7.3 Hz, 2H), 6.65 (d, J=7.3 Hz, 2H), 6.50 (s, 1H), 6.11 (d, J=6.2 Hz, 1H), 5.26 (dd, J=13.7, 4.3 Hz, 1H), 4.80 (dd, J=6.2, 4.3 Hz, 1H), 4.69 (d, J=13.7 Hz).

Example 164

Rac-4-((5aR,6S,7R,8S,8aS)-3-chloro-8,8a-dihydroxy-6-phenyl-7-(pyridin-2-ylsulfonyl)-6,7,8,8a-tetrahydro-5aH-cyclopenta[4,5]furo[3,2-b]pyridin-5a-yl)benzonitrile (Cpd. No. 164F)

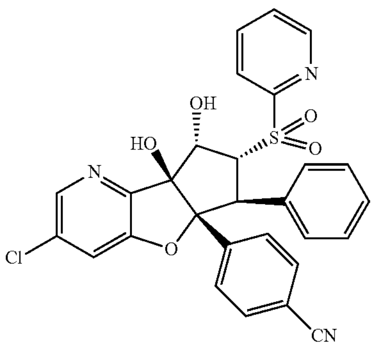

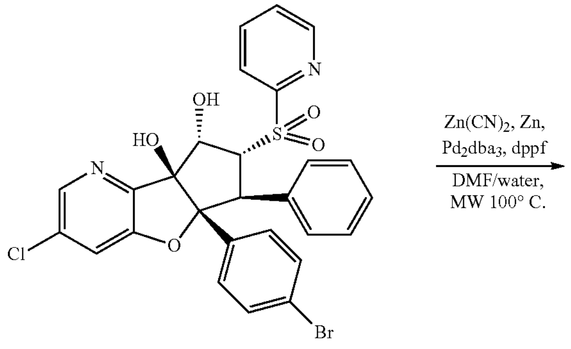

1

-continued

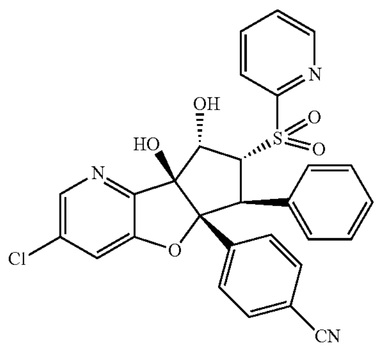

164F

Synthesis of rac-4-((5aR,6S,7R,8S,8aS)-3-chloro-8,8a-dihydroxy-6-phenyl-7-(pyridin-2-ylsulfonyl)-6,7,8,8a-tetrahydro-5aH-cyclopenta[4,5]furo[3,2-b]pyridin-5a-yl)benzonitrile (Cpd. No. 164F)

In a 0.5-2 mL microwave vial rac-(5aR,6S,7R,8S,8aS)-5a-(4-bromophenyl)-3-chloro-6-phenyl-7-(pyridin-2-ylsulfonyl)-5a,6,7,8-tetrahydro-8aH-cyclopenta[4,5]furo[3,2-b]pyridine-8,8a-diol (1, 50 mg, 0.083 mmol) was dissolved in N,N-dimethylformamide (0.8 mL) and water (0.08 mL). Zinc cyanide (33 mg, 0.28 mmol) and zinc (3 mg, 0.05 mmol) were added, and the mixture was degassed by bubbling argon through it for 5 min. Dppf (14 mg, 0.025 mmol) and Tris(dibenzylideneacetone)dipalladium(0) (11 mg, 0.012 mmol) were added, and the mixture was degassed for another 5 min, then incubated at 100° C. for 1 h 15 min in total. Then the mixture was diluted with dichloromethane and washed with water. The aq. phase was extracted with dichloromethane twice. Then the combined organic phases were dried ($Na_2SO_4$), filtered and concentrated. Purification by column chromatography ($SiO_2$, 0-50% ethyl acetate/dichloromethane) yielded 16.3 mg of rac-4-((5aR,6S,7R,8S,8aS)-3-chloro-8,8a-dihydroxy-6-phenyl-7-(pyridin-2-ylsulfonyl)-6,7,8,8a-tetrahydro-5aH-cyclopenta[4,5]furo[3,2-b]pyridin-5a-yl)benzonitrile (Cpd. No. 164) containing traces of SM. This material was repurified by HPLC (C18, MeCN/water+0.1% TFA) to give 10 mg (0.018 mmol, 22%) of pure rac-4-((5aR,6S,7R,8,8aS)-3-chloro-8,8a-dihydroxy-6-phenyl-7-(pyridin-2-ylsulfonyl)-6,7,8,8a-tetrahydro-5aH-cyclopenta[4,5]furo[3,2-b]pyridin-5a-yl)benzonitrile (Cpd. No. 164F) as a white solid; MS (ESI) m/z 546.2 $[M+1]^+$; $^1H$ NMR (400 MHz, DMSO-$d_6$) δ 8.80 (ddd, J=4.7, 1.7, 1.0 Hz, 1H), 8.20 (d, J=2.0 Hz, 1H), 7.81 (ddd, J=7.8, 7.8, 1.7 Hz, 1H), 7.70 (d, J=2.0 Hz, 11H), 7.65 (ddd, J=7.8, 4.7, 1.0 Hz, 1H), 7.50 (d, J=8.7 Hz, 2H), 7.43 (ddd, J=7.8, 1.0, 1.0 Hz, 1H), 7.38 (d, J=8.7 Hz, 2H), 6.89-6.84 (m, 1H), 6.78 (t, J=7.5 Hz, 2H), 6.71-6.67 (m, 2H), 6.59 (b, 1H), 6.14 (b, 1H), 5.33 (dd, J=13.8, 4.3, 1H), 4.80 (d, J=4.3 Hz, 1H), 4.75 (d, J=13.8 Hz, 1H).

Example 165

Rac-(5aR,6S,8S,8aR)-8-(aminomethyl)-5a-(4-bromophenyl)-3-chloro-6-phenyl-5a,6,7,8-tetra-hydro-8aH-cyclopenta[4,5]furo[3,2-b]pyridin-8a-ol (Cpd. No. 165)

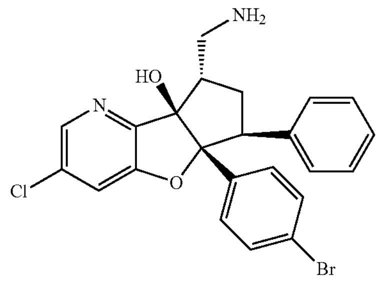

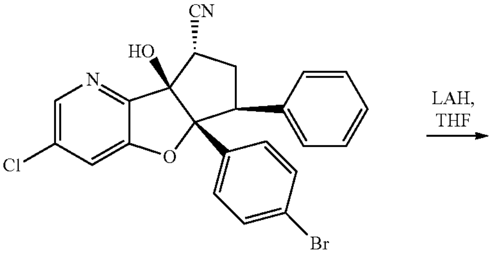

1

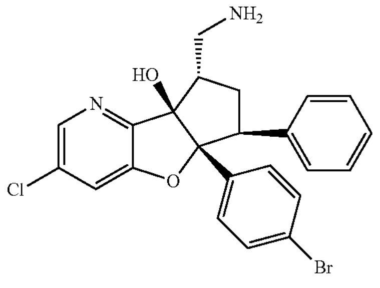

165F

Synthesis of rac-(5aR,6S,8S,8aR)-8-(aminomethyl)-5a-(4-bromophenyl)-3-chloro-6-phenyl-5a,6,7,8-tetra-hydro-8aH-cyclopenta[4,5]furo[3,2-b]pyridin-8a-ol (Cpd. No. 165F)

To a solution of rac-(5aR,6S,8S,8aR)-5a-(4-bromophenyl)-3-chloro-8a-hydroxy-6-phenyl-5a,7,8,8a-tetrahydro-6H-cyclopenta[4,5]furo[3,2-b]pyridine-8-carbonitrile (1, 20 mg, 0.043 mmol) in THF (0.5 mL) at 0° C. was added LAH (3.4 mg, 0.090 mmol) and the mixture was stirred at rt. After 1 h 0.02 mL water were added at 0° C., followed by 0.02 mL 12.5% NaOH (aq) and ca. 60 mg of $Na_2SO_4$. The mixture was stirred for 10 min at rt, then filtered through celite (rinsed with dichloromethane) and concentrated. The crude product (ca. 19 mg, yellow foam) was purified by repeated HPLC (C18, MeCN/$H_2O$+0.1% TFA) to yield 5.3 mg (0.0091 mmol, 21%) of the TFA salt of rac-(5aR,6S,8S,8aR)-8-(aminomethyl)-5a-(4-bromophenyl)-3-chloro-6-phenyl-5a,6,7,8-tetra-hydro-8aH-cyclopenta[4,5]furo[3,2-b]pyridin-8a-ol (Cpd. No. 165F) as a white solid; MS (ESI) m/z 470.9 $[M+1]^+$; $^1H$ NMR (400 MHz, DMSO-$d_6$) δ 8.30

(d, J=2.0 Hz, 1H), 8.01 (b, 3H), 7.88 (d, J=2.0 Hz, 1H), 7.38 (d, J=8.8 Hz, 2H), 7.16-7.08 (m, 5H), 6.96-6.92 (m, 2H), 6.01 (s, 1H), 3.74 (dd, J=9.9, 8.5 Hz, 1H), 3.56-3.47 (m, 1H), 3.20-3.10 (m, 1H), 3.08-2.97 (m, 1H), 2.60 (ddd, J=14.0, 9.9, 9.9 Hz, 1H), 1.86 (ddd, J=14.0, 8.5, 6.2, 1H).

Example 166

Rac-(5aR,6S,8S,8aR)-5a-(4-bromophenyl)-3-chloro-8-(hydroxymethyl)-6-phenyl-5a,6,7,8-tetrahydro-8aH-cyclopenta[4,5]furo[3,2-b]pyridin-8a-ol (Cpd. No. 166F)

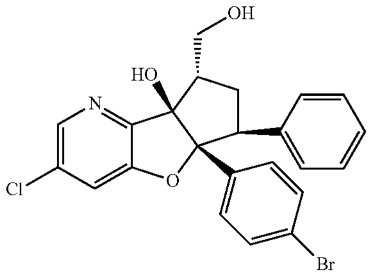

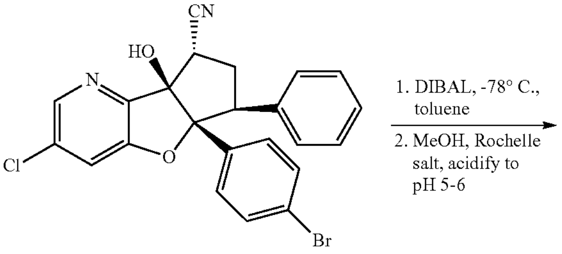

1

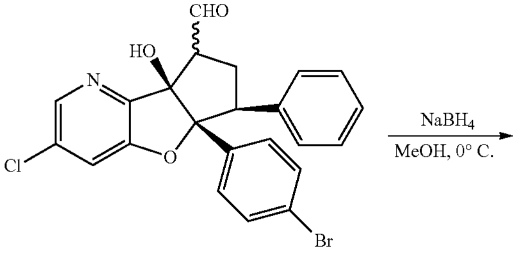

2

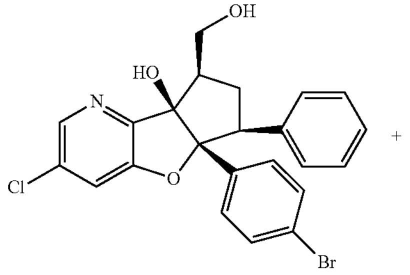

3

-continued

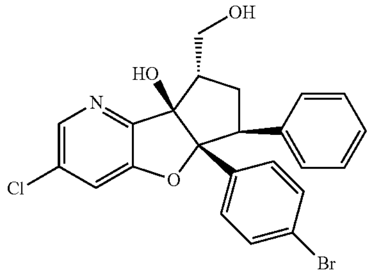

166F

Synthesis of rac-(5aR,6S,8aR)-5a-(4-bromophenyl)-3-chloro-8a-hydroxy-6-phenyl-5a,7,8,8a-tetrahydro-6H-cyclopenta[4,5]furo[3,2-b]pyridine-8-carbaldehyde (2)

The starting material rac-(5aR,6S,8S,8aR)-5a-(4-bromophenyl)-3-chloro-8a-hydroxy-6-phenyl-5a,7,8,8a-tetrahydro-6H-cyclopenta[4,5]furo[3,2-b]pyridine-8-carbonitrile (1, 84 mg, 0.18 mmol) was dissolved in dichloromethane (1.8 mL) and cooled to −78° C. DIBAL (1.0 M sln. in toluene, 0.39 mL, 0.39 mmol) was added, and the mixture was stirred at −78° C. for 30 min, then warmed up to 0° C. within 30 min and stirred for another 30 min. Then 2M aq. hydrochloric acid (0.7 mL) was added dropwise, and the mixture was diluted with saturated aq. Rochelle salt solution and dichloromethane and vigorously stirred for 30 min. Then the mixture was extracted with dichloromethane thrice. The combined organic phases were washed with brine, dried ($Na_2SO_4$), filtered and concentrated. The crude product (mixture of epimers) of rac-(5aR,6S,8aR)-5a-(4-bromophenyl)-3-chloro-8a-hydroxy-6-phenyl-5a,7,8,8a-tetrahydro-6H-cyclopenta[4,5]furo[3,2-b]pyridine-8-carbaldehyde (2) was directly used in the next step without further purification.

Synthesis of rac-(5aR,6S,8S,8aR)-5a-(4-bromophenyl)-3-chloro-8-(hydroxymethyl)-6-phenyl-5a,6,7,8-tetrahydro-8aH-cyclopenta[4,5]furo[3,2-b]pyridin-8a-ol (Cpd. No. 166F)

The starting material rac-(5aR,6S,8aR)-5a-(4-bromophenyl)-3-chloro-8a-hydroxy-6-phenyl-5a,7,8,8a-tetrahydro-6H-cyclopenta[4,5]furo[3,2-b]pyridine-8-carbaldehyde (2) (crude product from previous step) was dissolved in methanol (1.8 mL) under argon and cooled to 0° C. Sodium borohydride (34 mg, 0.90 mmol) was added and the mixture was stirred at 0° C. for 20 min, then at rt for 5 min. Complete conversion was observed by TLC (hexane/EtOAc=1/1). The reaction was quenched at 0° C. (water), and the mixture was extracted (3×dichloromethane). The combined organic phases were dried ($Na_2SO_4$), filtered and concentrated. Purification by column chromatography ($SiO_2$, 0-10% ethyl acetate/dichloromethane) yielded 14.6 mg (ca. 0.03 mmol, ca. 17%) of slightly impure product, which was repurified by HPLC (C18, MeCN/water+0.1% TFA) and finally preparative TLC ($SiO_2$, EtOAc/Hexane=1/1) to give 3.7 mg (0.0078 mmol) of pure rac-(5aR,6S,8S,8aR)-5a-(4-bromophenyl)-3-chloro-8-(hydroxymethyl)-6-phenyl-5a,6,7,8-tetrahydro-8aH-cyclopenta[4,5]furo[3,2-b]pyridin-8a-ol (Cpd. No. 166F) as a white solid; MS (ESI) m/z 472.0 $[M+1]^+$; $^1H$ NMR (400 MHz, DMSO-$d_6$) δ 8.26 (d, J=2.0 Hz, 1H), 7.76

(d, J=2.0 Hz, 1H), 7.35 (d, J=8.8 Hz, 1H), 7.14 (d, J=8.8 Hz, 2H), 7.12-7.07 (m, 3H), 6.97-6.92 (m, 2H), 5.98 (s, 1H), 4.79 (dd, J=6.9, 4.4 Hz, 1H), 4.05 (ddd, J=10.8, 5.9, 4.4 Hz, 1H), 3.61 (dd, J=12.0, 7.6 Hz, 1H), 3.48-3.40 (m, 1H), 2.95-2.84 (m, 1H), 2.60-2.47 (m, 1H), 1.89 (ddd, J=13.5, 7.6, 3.6 Hz, 1H).

Example 167

Rac-4-((5aR,6S,8R,8aR)-3-chloro-8a-hydroxy-8-(hydroxymethyl)-6-phenyl-6,7,8,8a-tetrahydro-5aH-cyclopenta[4,5]furo[3,2-b]pyridin-5a-yl)benzonitrile (Cpd. No. 167F)

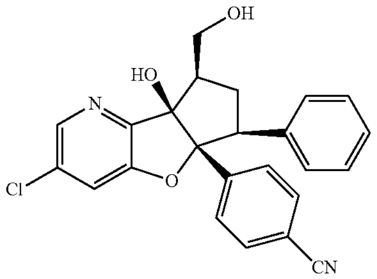

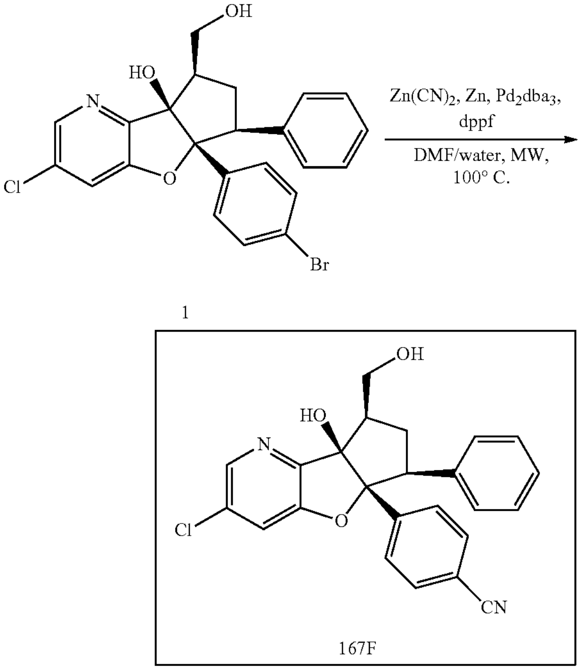

1

167F

Synthesis of rac-4-((5aR,6S,8R,8aR)-3-chloro-8a-hydroxy-8-(hydroxymethyl)-6-phenyl-6,7,8,8a-tetrahydro-5aH-cyclopenta[4,5]furo[3,2-b]pyridin-5a-yl) benzonitrile (Cpd. No. 167F)

In a 0.5-2 mL microwave vial rac-(5aR,6S,8R,8aR)-5a-(4-bromophenyl)-3-chloro-8-(hydroxymethyl)-6-phenyl-5a,6,7,8-tetrahydro-8aH-cyclopenta[4,5]furo[3,2-b]pyridin-8a-ol (1, 12.7 mg, 0.0269 mmol) was dissolved in N,N-dimethylformamide (0.5 mL) and water (0.05 mL). Zinc cyanide (11 mg, 0.094 mmol) and zinc (1 mg, 0.02 mmol) were added, and the mixture was degassed by bubbling argon through it for 5 min. Dppf (4.6 mg, 0.0083 mmol) and Tris(dibenzylideneacetone)dipalladium(0) (3.5 mg, 0.0039 mmol) were added and the mixture was degassed for another 5 min, then incubated at 100° C. for 1 h 10 min. Then the mixture was diluted with dichloromethane and washed with water. The aq. phase was extracted with dichloromethane twice. The combined organic phases were dried ($Na_2SO_4$), filtered and concentrated. Purification by column chromatography ($SiO_2$, 0-50% ethyl acetate/hexane) yielded 3.8 mg (0.0091 mmol, 34%) of rac-4-((5aR,6S,8R,8aR)-3-chloro-8a-hydroxy-8-(hydroxymethyl)-6-phenyl-6,7,8,8a-tetrahydro-5aH-cyclopenta[4,5]furo[3,2-b]pyridin-5a-yl)benzonitrile (Cpd. No. 167F) as a white solid; MS (ESI) m/z 419.2 $[M+1]^+$; $^1$H NMR (400 MHz, DMSO-$d_6$) δ 8.27 (d, J=2.0 Hz, 1H), 7.78 (d, J=2.0 Hz, 1H), 7.59 (d, J=8.7 Hz, 2H), 7.39 (d, J=8.7 Hz, 2H), 7.12-7.03 (m, 3H), 7.00-6.96 (m, 2H), 5.66 (s, 1H), 4.59 (dd, J=6.1, 4.8 Hz, 1H), 4.06 (ddd, J=11.0, 4.8, 4.8 Hz, 1H), 3.84 (ddd, J=11.0, 7.8, 6.1 Hz, 1H), 3.63 (dd, J=14.0, 6.2 Hz, 1H), 2.74-2.65 (m, 1H), 2.40 (b ddd, J=13, 13, 13 Hz, 1H), 2.26 (b ddd, J=13, 6.5, 6.5 Hz, 1H).

Example 168

Rac-4-((5aR,6S,8S,8aR)-3-chloro-8a-hydroxy-8-(hydroxymethyl)-6-phenyl-6,7,8,8a-tetrahydro-5aH-cyclopenta[4,5]furo[3,2-b]pyridin-5a-yl)benzonitrile (Cpd. No. 168F)

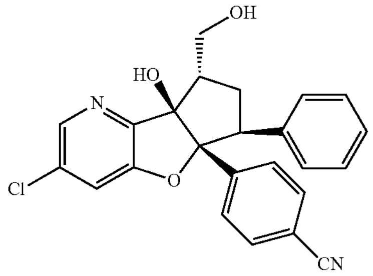

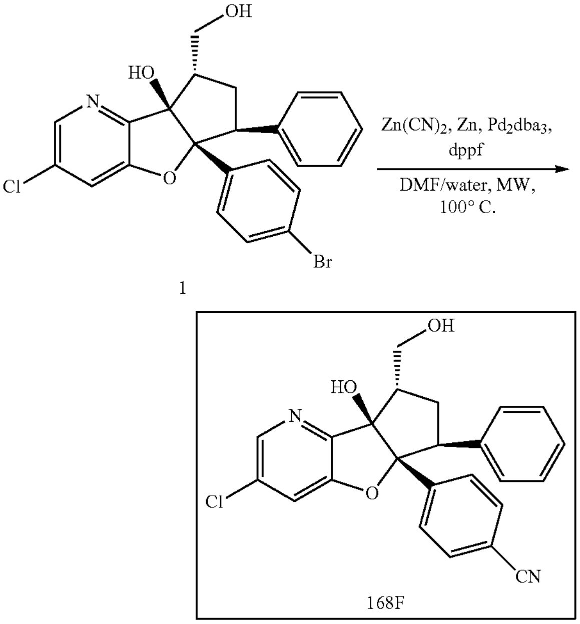

1

168F

Synthesis of rac-4-((5aR,6S,8S,8aR)-3-chloro-8a-hydroxy-8-(hydroxymethyl)-6-phenyl-6,7,8-tetrahydro-5aH-cyclopenta[4,5]furo[3,2-b]pyridin-5a-yl) benzonitrile (Cpd. No. 168F)

In a 0.5-2 mL microwave vial rac-(5aR,6S,8S,8aR)-5a-(4-bromophenyl)-3-chloro-8-(hydroxymethyl)-6-phenyl-5a,6,7,8-tetrahydro-8aH-cyclopenta[4,5]furo[3,2-b]pyridin-8a-ol (1, 12.4 mg, 0.0262 mmol) was dissolved in N,N-dimethylformamide (0.5 mL) and water (0.05 mL). Zinc cyanide (10.5 mg, 0.0894 mmol) and zinc (1 mg, 0.02 mmol) were added, and the mixture was degassed by bubbling argon through it for 5 min. Dppf (4.5 mg, 0.0081 mmol) and Tris(dibenzylideneacetone)dipalladium(0) (3.5 mg, 0.0038 mmol) were added and the mixture was degassed for another 5 min, then incubated at 100° C. for 45 min in total. Then the mixture was diluted with dichloromethane and washed with water. The aq. phase was extracted with dichloromethane twice. Then the combined organic phases were dried ($Na_2SO_4$), filtered and concentrated. Purification by column chromatography ($SiO_2$, 0-50% ethyl acetate/hexane) and preparative TLC ($SiO_2$, EtOAC/Hexane=2/1) yielded 3.8 mg (0.0091 mmol, 35%) of rac-4-((5aR,6S,8S,8aR)-3-chloro-8a-hydroxy-8-(hydroxymethyl)-6-phenyl-6,7,8,8a-tetrahydro-5aH-cyclopenta[4,5]furo[3,2-b]pyridin-5a-yl)benzonitrile (Cpd. No. 168F) as a white solid; MS (ESI) m/z 419.1 $[M+1]^+$; $^1$H NMR (400 MHz, DMSO-$d_6$) δ 8.28 (d, J=2.0 Hz, 1H), 7.79 (d, J=2.0 Hz, 1H), 7.63 (d, J=8.8 Hz, 2H), 7.38 (d, J=8.8 Hz, 2H), 7.13-7.06 (m, 3H), 6.96-6.92 (m, 2H), 5.77 (s, 1H), 4.79 (dd, J=6.9, 4.4 Hz, 1H), 4.07-4.01 (m, 1H), 3.69 (dd, J=12.1, 7.7 Hz, 1H), 3.49-3.41 (m, 1H), 2.98-2.89 (m, 1H), 2.65-2.54 (m, 1H), 1.93 (ddd, J=13.4, 7.7, 3.6 Hz, 1H).

Example 169

Rac-(2aR,3S,3aR,8bS,8cR)-3a-(4-bromophenyl)-6-chloro-8b-hydroxy-3-phenyl-3,3a,8b,8c-tetrahydrooxeto[3",2":4',5']cyclopenta[1',2':4,5]furo[3,2-b]pyridin-2(2aH)-one (Cpd. No. 169F)

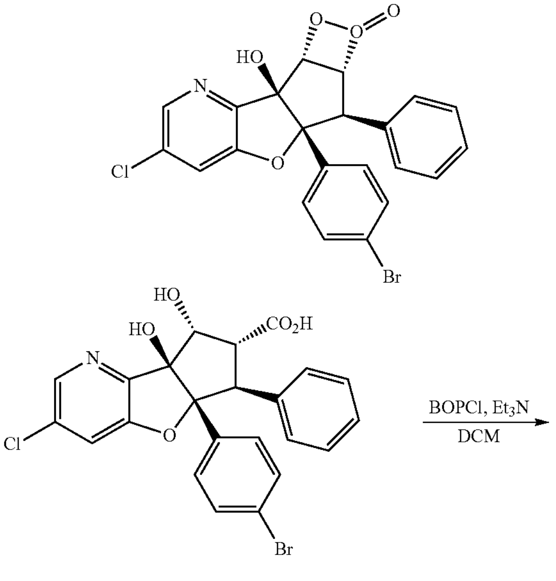

1

-continued

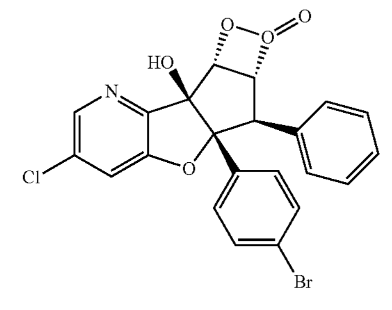

169F

Synthesis of rac-(2aR,3S,3aR,8bS,8cR)-3a-(4-bromophenyl)-6-chloro-8b-hydroxy-3-phenyl-3,3a,8b,8c-tetrahydrooxeto[3",2":4',5']cyclopenta[1',2':4,5]furo[3,2-b]pyridin-2(2aH)-one (Cpd. No. 169F)

The starting material rac-(5aR,6S,7R,8R,8aS)-5a-(4-bromophenyl)-3-chloro-8,8a-dihydroxy-6-phenyl-5a,7,8,8a-tetrahydro-6H-cyclopenta[4,5]furo[3,2-b]pyridine-7-carboxylic acid (1, 106 mg, 0.211 mmol) was dissolved in dichloromethane (3.8 mL) under argon and cooled to 0° C. Triethylamine (0.09 mL, 0.6 mmol) and 3-[chloro-(2-oxooxazolidin-3-yl)phosphoryl]oxazolidin-2-one (70 mg, 0.27 mmol) were added, and the mixture was stirred at rt. After 1 h 15 min water and brine were added, and the mixture was extracted with dichloromethane thrice. The combined organic phases were dried ($Na_2SO_4$), filtered and concentrated. Purification by column chromatography ($SiO_2$, 0-30% ethyl acetate/hexane) yielded 53.9 mg (0.111 mmol, 53%) of rac-(2aR,3S,3aR,8bS,8cR)-3a-(4-bromophenyl)-6-chloro-8b-hydroxy-3-phenyl-3,3a,8b,8c-tetrahydrooxeto[3",2":4',5']cyclopenta[1',2':4,5]furo[3,2-b]pyridin-2(2aH)-one (Cpd. No. 169F) as a white solid; MS (ESI) m/z 484.2 $[M+1]^+$; $^1$H NMR (400 MHz, DMSO-$d_6$) δ 8.24 (d, J=2.0 Hz, 1H), 7.72 (d, J=2.0 Hz, 1H), 7.36 (s, 1H), 7.24 (d, J=8.9 Hz, 2H), 7.21-7.16 (m, 3H), 7.10-7.05 (m, 4H), 5.46 (d, J=5.0 Hz, 1H), 4.89 (dd, J=5.0, 2.9 Hz, 1H), 4.26 (d, J=2.9 Hz, 1H).

Example 170

Rac-(4bR,5R,6R,7S,7aR)-5-(aminomethyl)-7a-(4-bromophenyl)-6-(hydroxymethyl)-4-methoxy-7-phenyl-5,6,7,7a-tetrahydro-4bH-cyclopenta[4,5]furo[2,3-c]pyridin-4b-ol (Cpd. No. 170F)

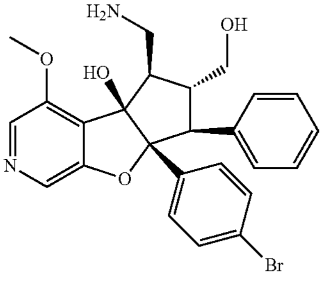

-continued

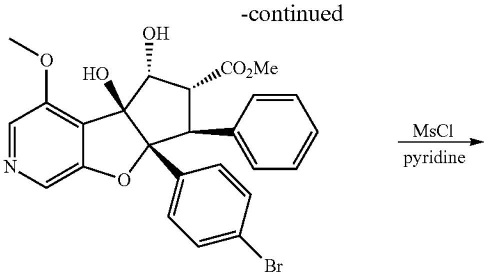

1

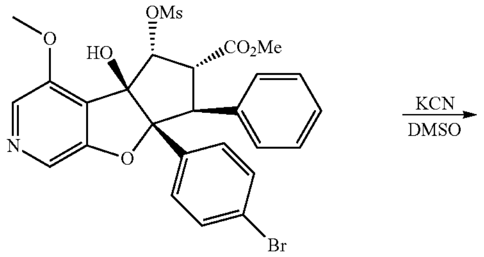

2

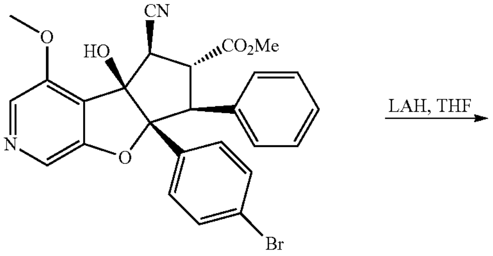

3

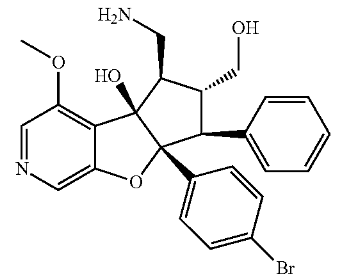

170F

Synthesis of rac-methyl (4bS,5R,6R,7S,7aR)-7a-(4-bromophenyl)-4b-hydroxy-4-methoxy-5-((methylsulfonyl)oxy)-7-phenyl-4b,6,7,7a-tetrahydro-5H-cyclopenta[4,5]furo[2,3-c]pyridine-6-carboxylate (2)

To a solution of rac-methyl (4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylate (1, 800 mg, 1.56 mmol) in pyridine (15 mL) was added methanesulfonyl chloride (0.14 mL, 1.8 mmol) and the mixture was stirred at rt. After 24 h, another 0.03 mL (0.4 mmol) methanesulfonyl chloride added, and the mixture was stirred for another 1 h. Then the reaction was quenched with $NH_4Cl$(aq) and the mixture was extracted with dichloromethane thrice. The combined organic phases were dried ($Na_2SO_4$), filtered and concentrated. The crude product rac-methyl (4bS,5R,6R,7S,7aR)-7a-(4-bromophenyl)-4b-hydroxy-4-methoxy-5-((methylsulfonyl)oxy)-7-phenyl-4b,6,7,7a-tetrahydro-5H-cyclopenta[4,5]furo[2,3-c]pyridine-6-carboxylate (2); MS (ESI) m/z 589.9 $[M+1]^+$; was dried under vacuum overnight and then directly used in the next step.

Synthesis of rac-methyl (4bR,5R,6R,7S,7aR)-7a-(4-bromophenyl)-5-cyano-4b-hydroxy-4-methoxy-7-phenyl-4b,6,7,7a-tetrahydro-5H-cyclopenta[4,5]furo[2,3-c]pyridine-6-carboxylate (3)

To a solution of rac-methyl (4bS,5R,6R,7S,7aR)-7a-(4-bromophenyl)-4b-hydroxy-4-methoxy-5-((methylsulfonyl)oxy)-7-phenyl-4b,6,7,7a-tetrahydro-5H-cyclopenta[4,5]furo[2,3-c]pyridine-6-carboxylate (2, crude product from previous step) in DMSO (15 mL) was added potassium cyanide (226 mg, 3.47 mmol) and the mixture was stirred at rt under argon. After 6 h the mixture was diluted with EtOAc and washed brine twice, then dried ($Na_2SO_4$), filtered and concentrated. Purification by column chromatography yielded 755 mg (1.45 mmol, 93% over 2 steps) of rac-methyl (4bR,5R,6R,7S,7aR)-7a-(4-bromophenyl)-5-cyano-4b-hydroxy-4-methoxy-7-phenyl-4b,6,7,7a-tetrahydro-5H-cyclopenta[4,5]furo[2,3-c]pyridine-6-carboxylate (3); MS (ESI) m/z 521.3 $[M+1]^+$.

Synthesis of rac-(4bR,5R,6R,7S,7aR)-5-(aminomethyl)-7a-(4-bromophenyl)-6-(hydroxymethyl)-4-methoxy-7-phenyl-5,6,7,7a-tetrahydro-4bH-cyclopenta[4,5]furo[2,3-c]pyridin-4b-ol (Cpd. No. 170F)

To a solution of rac-methyl (4bR,5R,6R,7S,7aR)-7a-(4-bromophenyl)-5-cyano-4b-hydroxy-4-methoxy-7-phenyl-4b,6,7,7a-tetrahydro-5H-cyclopenta[4,5]furo[2,3-c]pyridine-6-carboxylate (3, 40 mg, 0.077 mmol) in THF (0.8 mL) at 0° C. was added LAH (11.7 mg, 0.306 mmol) and the mixture was stirred at rt. After 1 h 0.05 mL water were added at 0° C., followed by 0.05 mL 12.5% NaOH (aq) and ca. 150 mg of $Na_2SO_4$. The mixture was stirred for 10 min at rt, then filtered through celite (rinsed with dichloromethane) and concentrated. The crude product (ca. 34 mg, white solid) was purified by HPLC (C18, MeCN/$H_2O$+0.1% TFA) to yield 32.5 mg (0.0532 mmol, 69%) of rac-(4bR,5R,6R,7S,7aR)-5-(aminomethyl)-7a-(4-bromophenyl)-6-(hydroxymethyl)-4-methoxy-7-phenyl-5,6,7,7a-tetrahydro-4bH-cyclopenta[4,5]furo[2,3-c]pyridin-4b-ol (Cpd. No. 170F) as the TFA salt; MS (ESI) m/z 497.2 $[M+1]^+$; $^1$H NMR (400 MHz, DMSO-$d_6$) δ 8.21 (s, 1H), 8.14 (s, 1H), 7.72 (s, 3H), 7.36 (d, J=8.7 Hz, 2H), 7.15-7.06 (m, 5H), 6.83-6.77 (m, 2H), 6.30 (s, 1H), 4.90 (b, 1H), 4.01 (s, 3H), 3.54-3.41 (m, 1H), 3.46 (dd, J=11.3, 2.9 Hz, 1H), 3.35-3.28 (m, 1H), 3.29 (d, J=13.7 Hz, 1H), 3.17 (dd, J=11.3, 5.5 Hz, 1H), 2.99 (ddd, J=9.9, 9.9, 4.0 Hz, 1H), 2.64-2.54 (m, 1H).

Example 171

Rac-4-((4bR,5R,6R,7S,7aR)-5-(aminomethyl)-4b-hydroxy-6-(hydroxymethyl)-4-methoxy-7-phenyl-4b,5,6,7-tetrahydro-7aH-cyclopenta[4,5]furo[2,3-c]pyridin-7a-yl)benzonitrile (Cpd. No. 171F)

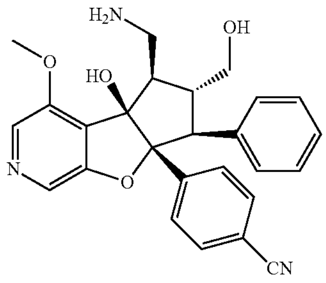

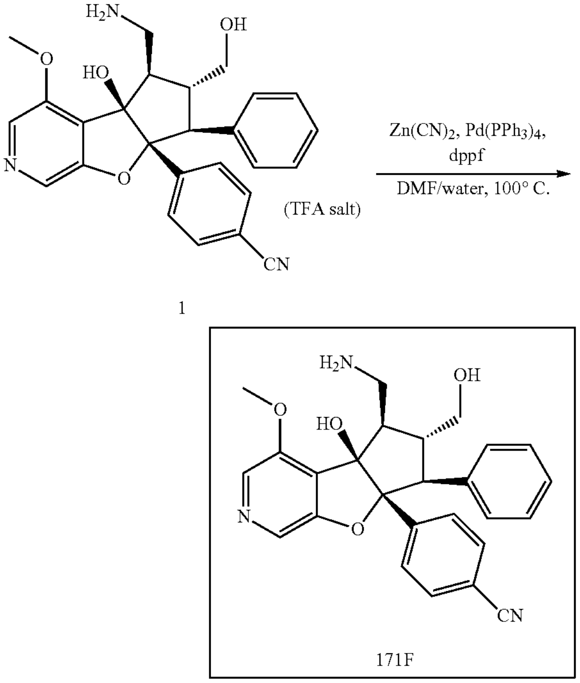

1

171F

Synthesis of rac4-((4bR,5R,6R,7S,7aR)-5-(aminomethyl)-4b-hydroxy-6-(hydroxymethyl)-4-methoxy-7-phenyl-4b,5,6,7-tetrahydro-7aH-cyclopenta[4,5]furo[2,3-c]pyridin-7a-yl)benzonitrile (Cpd. No. 171F)

In a 0.5-2 mL microwave vial rac-(4bR,5R,6R,7S,7aR)-5-(aminomethyl)-7a-(4-bromophenyl)-6-(hydroxymethyl)-4-methoxy-7-phenyl-5,6,7,7a-tetrahydro-4bH-cyclopenta[4,5]furo[2,3-c]pyridin-4b-ol (1, 91 mg, 0.18 mmol) was dissolved in N,N-dimethylformamide (3.3 mL) and water (0.33 mL). Zinc cyanide (90 mg, 0.77 mmol) and zinc (4.8 mg, 0.073 mmol) were added, and the mixture was degassed by bubbling argon through it for 5 min. Dppf (31 mg, 0.056 mmol) and Tris(dibenzylideneacetone)dipalladium(0) (24.1 mg, 0.0263 mmol) were added and the mixture was degassed for another 5 min, then incubated at 100° C. for 1.5 h. Then the mixture was filtered (rinsed with MeCN) and concentrated. The crude product was purified by HPLC (C18, MeCN/water+0.1% TFA) to yield 46.1 mg (0.0827 mmol), 45% of rac-4-((4bR,5R,6R,7S,7aR)-5-(aminomethyl)-4b-hydroxy-6-(hydroxymethyl)-4-methoxy-7-phenyl-4b,5,6,7-tetrahydro-7aH-cyclopenta[4,5]furo[2,3-c]pyridin-7a-yl)benzonitrile (Cpd. No. 171F) as the TFA salt (white solid); MS (ESI) m/z 444.2 $[M+1]^+$; $^1H$ NMR (400 MHz, DMSO-$d_6$) δ 8.22 (s, 1H), 8.15 (s, 1H), 7.68 (b, 3H), 7.63 (d, J=8.3 Hz, 2H), 7.36 (d, J=8.3 Hz, 2H), 7.12-7.06 (m, 3H), 6.83-6.78 (m, 2H), 6.36 (s, 1H), 4.88 (b, 1H), 4.01 (s, 3H), 3.56-3.49 (m, 1H), 3.49-3.44 (m, 1H), 3.35 (d, J=13.5 Hz, 1H), 3.37-3.27 (m, 1H), 3.19 (dd, J=11.4, 5.4, 1H), 3.00 (ddd, J=10.0, 10.0, 4.0, 1H), 2.70-2.61 (m, 1H).

Example 172

Rac-(4bR,5R,7S,7aR)-5-(aminomethyl)-7a-(4-bromophenyl)-4-methoxy-7-phenyl-5,6,7,7a-tetrahydro-4bH-cyclopenta[4,5]furo[2,3-c]pyridin-4b-ol (Cpd. No. 172F)

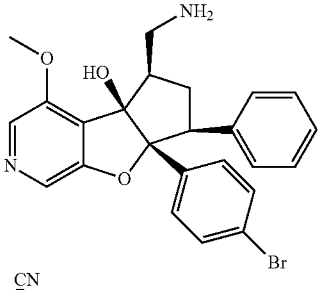

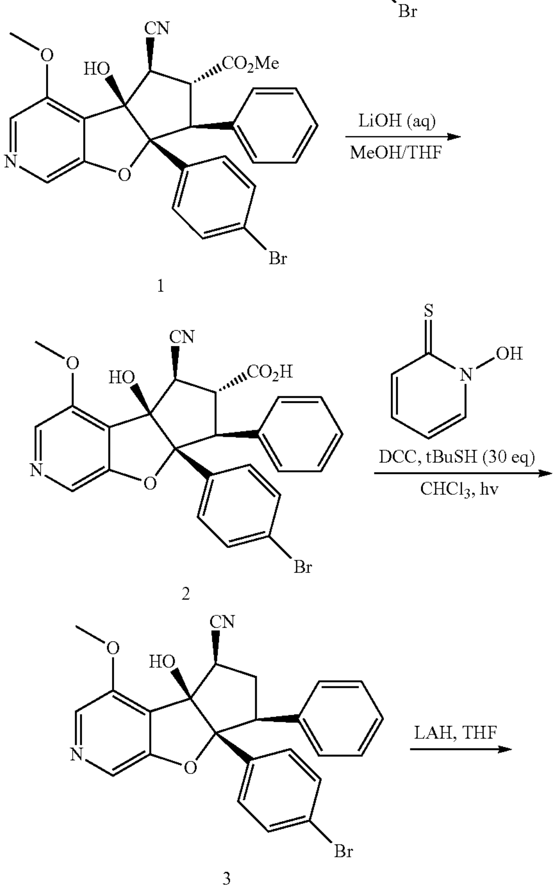

1

2

3

-continued

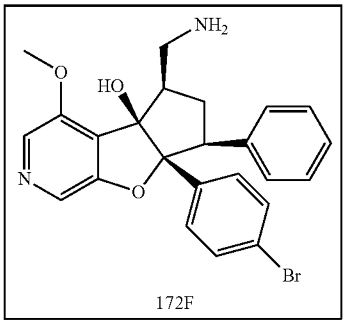

172F

Synthesis of rac-(4bR,5R,6R,7S,7aR)-7a-(4-bromophenyl)-5-cyano-4b-hydroxy-4-methoxy-7-phenyl-4b,6,7,7a-tetrahydro-5H-cyclopenta[4,5]furo[2,3-c]pyridine-6-carboxylic acid (2)

To rac-methyl (4bR,5R,6R,7S,7aR)-7a-(4-bromophenyl)-5-cyano-4b-hydroxy-4-methoxy-7-phenyl-4b,6,7,7a-tetrahydro-5H-cyclopenta[4,5]furo[2,3-c]pyridine-6-carboxylate (1, 467 mg, 0.896 mmol) in methanol (4.5 mL) and THF (4.5 mL) at rt was added LiOH (aq) (2M, 6.5 mL, 13 mmol) and the mixture was stirred at 40° C. After 40 min the mixture was cooled down to rt, acidified with 2M hydrochloric acid (aq) (7 mL) and diluted with EtOAc and water. The aq. phase was extracted thrice, and the combined organic phases were dried ($Na_2SO_4$), filtered and concentrated to afford crude rac-(4bR,5R,6R,7S,7aR)-7a-(4-bromophenyl)-5-cyano-4b-hydroxy-4-methoxy-7-phenyl-4b,6,7,7a-tetrahydro-5H-cyclopenta[4,5]furo[2,3-c]pyridine-6-carboxylic acid (2) as an orange solid. Yield: 457 mg; MS (ESI) m/z 507.2 $[M+1]^-$. The crude material was pure by LCMS and was used without further purification.

Synthesis of rac-(4bR,5R,7S,7aR)-7a-(4-bromophenyl)-4b-hydroxy-4-methoxy-7-phenyl-4b,6,7,7a-tetrahydro-SH-cyclopenta[4,5]furo[2,3-c]pyridine-5-carbonitrile (3)

In an 8-mL-vial, crude rac-(4bR,5R,6R,7S,7aR)-7a-(4-bromophenyl)-5-cyano-4b-hydroxy-4-methoxy-7-phenyl-4b,6,7,7a-tetrahydro-5H-cyclopenta[4,5]furo[2,3-c]pyridine-6-carboxylic acid (2, 100 mg) and 1-hydroxypyridine-2-thione (37.3 mg, 0.294 mmol) were suspended in chloroform (2.8 mL). 2-methylpropane-2-thiol (0.67 mL, 0.56 g, 5.9 mmol) was added, the mixture was irradiated (HDX XG-1026 lamp, 250 W halogen bulb), and a solution of DCC (46 mg, 0.22 mmol) in 2 mL $CHCl_3$ was added dropwise under argon. The mixture was irradiated with vigorous stirring without additional external heating. After 10 min complete conversion was observed. The mixture was concentrated and dried in vacuo. The crude product was combined with the crude product of an analogously conducted experiment utilizing 15 mg (0.030 mmol) of starting material for purification purposes. Purification by HPLC (C18, MeCN/water+0.1% TFA) yielded 73 mg (0.16 mmol, 69%) of rac-(4bR,5R,7S,7aR)-7a-(4-bromophenyl)-4b-hydroxy-4-methoxy-7-phenyl-4b,6,7,7a-tetrahydro-5H-cyclopenta[4,5]furo[2,3-c]pyridine-5-carbonitrile (3) as a white foam; MS (ESI) m/z 463.1 $[M+1]^+$.

Synthesis of rac-(4bR,5R,7S,7aR)-5-(aminomethyl)-7a-(4-bromophenyl)-4-methoxy-7-phenyl-5,6,7,7a-tetrahydro-4bH-cyclopenta[4,5]furo[2,3-c]pyridin-4b-ol (Cpd. No. 172F)

To a solution of rac-(4bR,5R,7S,7aR)-7a-(4-bromophenyl)-4b-hydroxy-4-methoxy-7-phenyl-4b,6,7,7a-tetrahydro-5H-cyclopenta[4,5]furo[2,3-c]pyridine-5-carbonitrile (3, 73 mg, 0.16 mmol) in THF (1.6 mL) at 0° C. was added LAH (16.5 mg, 0.435 mmol) and the mixture was stirred at rt. After 30 min 0.05 mL water were added at 0° C., followed by 0.05 mL 12.5% NaOH (aq) and ca. 100 mg of $Na_2SO_4$. The mixture was stirred for 10 min at rt, then filtered through celite (rinsed with dichloromethane) and concentrated. Purification of the crude product by HPLC (C18, $MeCN/H_2O$+ 0.1% TFA) yielded 61.4 mg (ca. 93% pure by $^1$H-NMR, 0.0982 mmol, 62% yield) of rac-(4bR,5R,7S,7aR)-5-(aminomethyl)-7a-(4-bromophenyl)-4-methoxy-7-phenyl-5,6,7,7a-tetrahydro-4bH-cyclopenta[4,5]furo[2,3-c]pyridin-4b-ol (Cpd. No. 172F) as the TFA salt. An analytically pure sample could be obtained by repurification of 12 mg of this material by reverse phase HPLC; MS (ESI) m/z 467.3 $[M+1]^+$; $^1$H NMR (400 MHz, DMSO-$d_6$) δ 8.21 (s, 1H), 8.12 (s, 1H), 7.72 (b, 3H), 7.33 (d, J=8.8 Hz, 2H), 7.15-7.05 (m, 5H), 6.96-6.92 (m, 2H), 6.05 (s, 1H), 3.99 (s, 3H), 3.56-3.40 (m, 2H), 3.22-3.12 (m, 1H), 2.96-2.86 (m, 1H), 2.29-2.22 (m, 2H).

Example 173

Rac-4-((4bR,5R,7S,7aR)-5-(aminomethyl)-4b-hydroxy-4-methoxy-7-phenyl-4b,5,6,7-tetrahydro-7aH-cyclopenta[4,5]furo[2,3-c]pyridin-7a-yl)benzonitrile (Cpd. No. 173F)

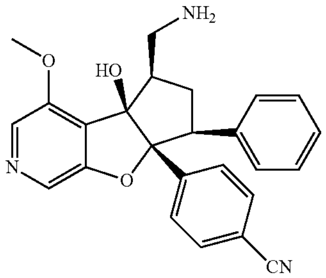

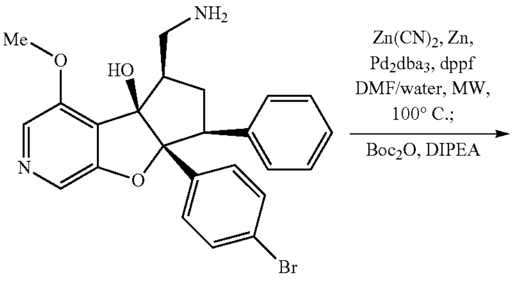

1
(TFA salt)

-continued

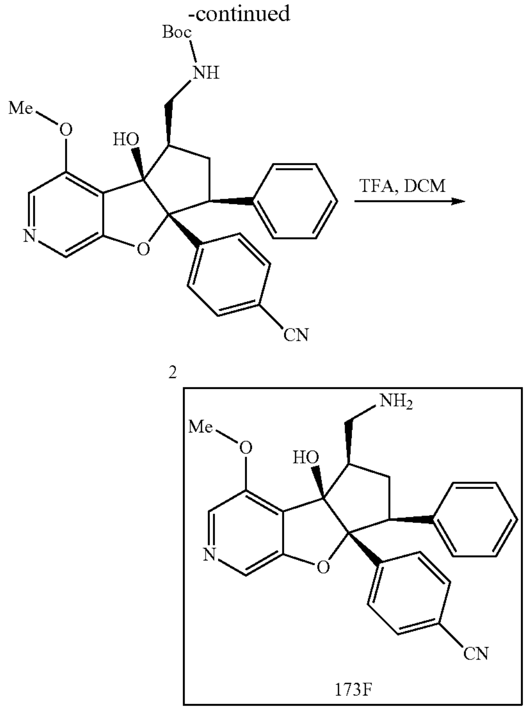

2

173F

Synthesis of rac-tert-butyl (((4bR,5R,7S,7aR)-7a-(4-cyanophenyl)-4b-hydroxy-4-methoxy-7-phenyl-4b,6,7,7a-tetrahydro-5H-cyclopenta[4,5]furo[2,3-c]pyridin-5-yl)methyl)carbamate (2)

In a 0.5-2 mL microwave vial rac-(4bR,5R,7S,7aR)-5-(aminomethyl)-7a-(4-bromophenyl)-4-methoxy-7-phenyl-5,6,7,7a-tetrahydro-4bH-cyclopenta[4,5]furo[2,3-c]pyridin-4b-ol (1, 35.6 mg, 0.06000 mmol) was dissolved in N,N-dimethylformamide (1.5 mL) and water (0.15 mL). Zinc cyanide (30 mg, 0.26 mmol) and zinc (2.1 mg, 0.032 mmol) were added, and the mixture was degassed by bubbling argon through it for 5 min. Dppf (10.5 mg, 0.0189 mmol) and Tris(dibenzylideneacetone)dipalladium(0) (8.1 mg, 0.0088 mmol) were added and the mixture was degassed for another 5 min, then incubated at 100° C. for 1 h. Then the mixture was filtered and concentrated. The crude product was dissolved in dichloromethane (0.6 mL), and N,N-diisopropylethylamine (0.06 mL, 0.3 mmol) and tert-butoxycarbonyl tert-butyl carbonate (22 mg, 0.10 mmol) were added at 0° C. The mixture was stirred at rt. After 1 h 45 min water was added. The mixture was extracted with dichloromethane thrice, and the combined organic phases were dried ($Na_2SO_4$), filtered and concentrated. Purification by HPLC (C18, MeCN/$H_2O$+0.1% TFA) yielded 13 mg (0.025 mmol, 41% over 2 steps) of rac-tert-butyl (((4bR,5R,7S,7aR)-7a-(4-cyanophenyl)-4b-hydroxy-4-methoxy-7-phenyl-4b,6,7,7a-tetrahydro-5H-cyclopenta[4,5]furo[2,3-c]pyridin-5-yl)methyl)carbamate (2) as a white solid; MS (ESI) m/z 514.4 $[M+1]^+$.

Synthesis of rac-4-((4bR,5R,7S,7aR)-5-(aminomethyl)-4b-hydroxy-4-methoxy-7-phenyl-4b,5,6,7-tetrahydro-7aH-cyclopenta[4,5]furo[2,3-c]pyridin-7a-yl)benzonitrile (Cpd. No. 173F)

To a solution of rac-tert-butyl N-[[(5aR,6S,8R,8aR)-5a-(4-cyanophenyl)-8a-hydroxy-1-methoxy-6-phenyl-7,8-dihydro-6H-cyclopenta[4,5]furo[1,2-b]pyridin-8-yl]methyl]carbamate (2, 13 mg, 0.025 mmol) in dichloromethane (0.8 mL) at rt was added trifluoroacetic acid (0.04 mL, 0.06 g, 0.5 mmol) and the mixture was stirred at rt. After 1.5 h another 0.04 mL (0.06 g, 0.5 mmol) trifluoroacetic acid were added. After another 30 min another 0.02 mL (0.03 g, 0.3 mmol) trifluoroacetic acid were added, and the mixture was stirred for another 45 min, after which the reaction was complete as judged by LCMS. The mixture was concentrated, taken up in MeCN and water, frozen and lyophilized to yield 11.7 mg (0.0222 mmol, 87%) of the TFA salt of rac-4-((4bR,5R,7S,7aR)-5-(aminomethyl)-4b-hydroxy-4-methoxy-7-phenyl-4b,5,6,7-tetrahydro-7aH-cyclopenta[4,5]furo[2,3-c]pyridin-7a-yl)benzonitrile (Cpd. No. 173F) as a white solid; MS (ESI) m/z 414.3 $[M+1]^+$; $^1H$ NMR (400 MHz, DMSO-$d_6$) δ 8.23 (s, 1H), 8.14 (s, 1H), 7.72 (b, 3H), 7.61 (d, J=8.0 Hz, 2H), 7.36 (d, J=8.0 Hz, 2H), 7.15-7.04 (m, 3H), 6.97-6.92 (m, 2H), 6.12 (s, 1H), 3.99 (s, 3H), 3.65-3.55 (m, 1H), 3.52-3.42 (m, 1H), 3.26-3.14 (m, 1H), 2.98-2.87 (m, 1H), 2.36-2.25 (m, 2H).

Example 174

Rac-(5aR,6S,8R,8aR)-8-(aminomethyl)-5a-(4-bromophenyl)-3-chloro-6-phenyl-5a,6,7,8-tetrahydro-8aH-cyclopenta[4,5]furo[3,2-b]pyridin-8a-ol (Cpd. No. 174F)

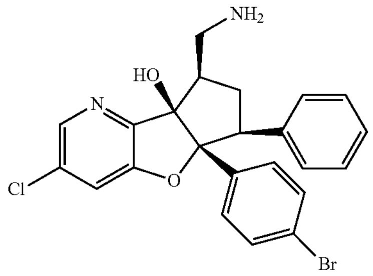

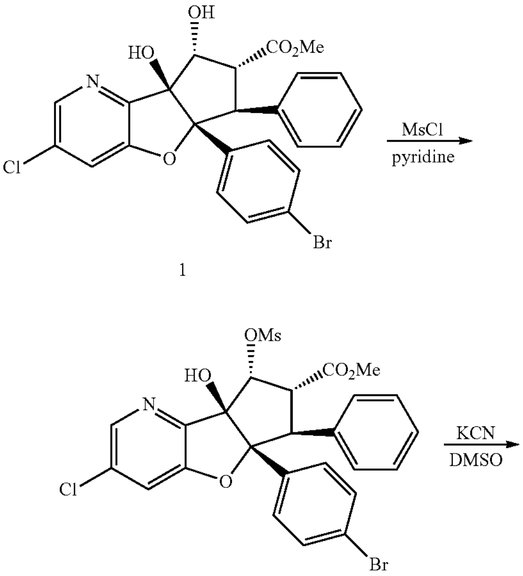

1

2

-continued

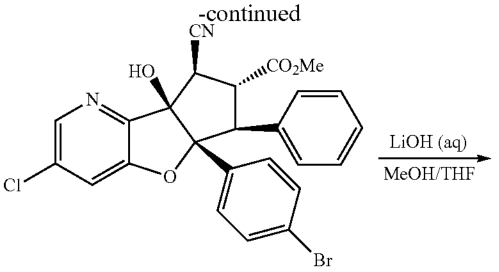

3

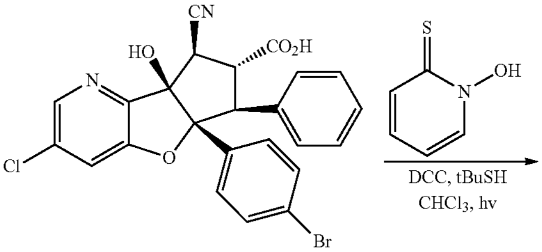

4

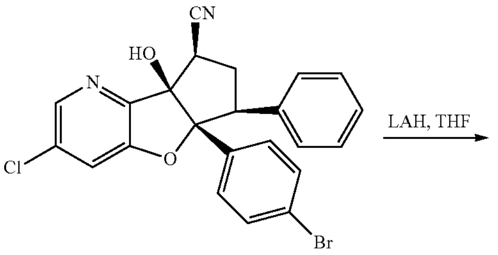

5

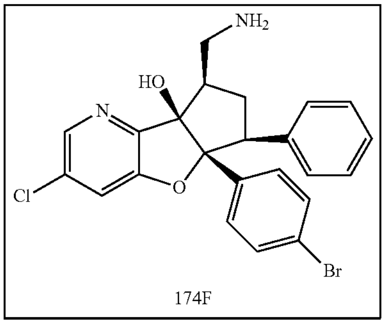 [SMILES: NC[C@H]1C[C@@H](c2ccccc2)[C@]2(c3ccc(Br)cc3)Oc3cc(Cl)cnc3[C@]12O]

174F

Synthesis of rac-methyl (5aR,6S,7R,8R,8aS)-5a-(4-bromophenyl)-3-chloro-8a-hydroxy-8-((methylsulfonyl)oxy)-6-phenyl-5a,7,8,8a-tetrahydro-6H-cyclopenta[4,5]furo[3,2-b]pyridine-7-carboxylate (2)

To a solution of rac-methyl (5aR,6S,7R,8R,8aS)-5a-(4-bromophenyl)-3-chloro-8,8a-dihydroxy-6-phenyl-5a,7,8,8a-tetrahydro-6H-cyclopenta[4,5]furo[3,2-b]pyridine-7-carboxylate (1, 800 mg, 1.55 mmol) in pyridine (15 mL) was added methanesulfonyl chloride (0.15 mL, 0.22 g, 1.9 mmol) and the mixture was stirred at rt. After 23.5 h another 0.08 mL (0.1 g, 1 mmol) methanesulfonyl chloride added, and the mixture was stirred for another 3.5 h. Another 0.1 mL (0.1 g, 1 mmol) methanesulfonyl chloride were added, and the mixture was stirred for ca. another 1 h. Then the reaction was quenched with $NH_4Cl$ (aq) and the mixture was extracted with dichloromethane thrice. The combined organic phases were dried ($Na_2SO_4$), filtered and concentrated. The crude product was purified by column chromatography ($SiO_2$, 0-50% ethyl acetate/hexane) to yield 775 mg (1.30 mmol, 84%) of rac-methyl (5aR,6S,7R,8R,8aS)-5a-(4-bromophenyl)-3-chloro-8a-hydroxy-8-((methylsulfonyl)oxy)-6-phenyl-5a,7,8,8a-tetrahydro-6H-cyclopenta[4,5]furo[3,2-b]pyridine-7-carboxylate (2) as a yellowish foam; MS (ESI) m/z 594.1 $[M+1]^+$.

Synthesis of rac-methyl (5aR,6S,7R,8R,8aR)-5a-(4-bromophenyl)-3-chloro-8-cyano-8a-hydroxy-6-phenyl-5a,7,8,8a-tetrahydro-6H-cyclopenta[4,5]furo[3,2-b]pyridine-7-carboxylate (3)

To a solution of rac-methyl (5aR,6S,7R,8R,8aS)-5a-(4-bromophenyl)-3-chloro-8a-hydroxy-8-((methylsulfonyl)oxy)-6-phenyl-5a,7,8,8a-tetrahydro-6H-cyclopenta[4,5]furo[3,2-b]pyridine-7-carboxylate (2, 775 mg, 1.30 mmol) in DMSO (13 mL) was added potassium cyanide (189 mg, 2.90 mmol) and the mixture was stirred at rt under argon. After stirring for 16 h the mixture was diluted with EtOAc and washed brine (2×), then dried ($Na_2SO_4$), filtered and concentrated. Purification by column chromatography ($SiO_2$, 0-45% ethyl acetate/hexane) yielded 469 mg (0.892 mmol, 68%) of rac-methyl (5aR,6S,7R,8R,8aR)-5a-(4-bromophenyl)-3-chloro-8-cyano-8a-hydroxy-6-phenyl-5a,7,8,8a-tetrahydro-6H-cyclopenta[4,5]furo[3,2-b]pyridine-7-carboxylate (3) as a yellowish foam; MS (ESI) m/z 525.2 $[M+1]^+$.

Synthesis of rac-(5aR,6S,7R,8R,8aR)-5a-(4-bromophenyl)-3-chloro-8-cyano-8a-hydroxy-6-phenyl-5a,7,8,8a-tetrahydro-6H-cyclopenta[4,5]furo[3,2-b]pyridine-7-carboxylic acid (4)

To rac-methyl (5aR,6S,7R,8R,8aR)-5a-(4-bromophenyl)-3-chloro-8-cyano-8a-hydroxy-6-phenyl-5a,7,8,8a-tetrahydro-6H-cyclopenta[4,5]furo[3,2-b]pyridine-7-carboxylate (3, 460 mg, 0.875 mmol) in methanol (4.5 mL) and THF (4.5 mL) at rt was added LiOH (aq) (2M, 6.3 mL, 12.6 mmol) and the mixture was stirred at 40° C. After 1 h the mixture was cooled down to rt, and stirred for another 15 min, then acidified with 2M hydrochloric acid (aq) (7 mL) and diluted with EtOAc and water. The aq. phase was extracted thrice, and the combined organic phases were dried ($Na_2SO_4$), filtered and concentrated to give 417 mg (0.815 mmol, 93%) of rac-(5aR,6S,7R,8R,8aR)-5a-(4-bromophenyl)-3-chloro-8-cyano-8a-hydroxy-6-phenyl-5a,7,8,8a-tetrahydro-6H-cyclopenta[4,5]furo[3,2-b]pyridine-7-carboxylic acid (4); MS (ESI) m/z 511.1 $[M+1]^+$.

Synthesis of rac-(5aR,6S,8R,8aR)-5a-(4-bromophenyl)-3-chloro-8a-hydroxy-6-phenyl-5a, 7,8,8a-tetrahydro-6H-cyclopenta[4,5]furo[3,2-b]pyridine-8-carbonitrile (5)

In a screw-cap vial, rac-(5aR,6S,7R,8R,8aR)-5a-(4-bromophenyl)-3-chloro-8-cyano-8a-hydroxy-6-phenyl-5a,7,8,8a-tetrahydro-6H-cyclopenta[4,5]furo[3,2-b]pyridine-7-carboxylic acid (4, 387 mg, 0.756 mmol) and 1-hydroxypyridine-2-thione (144 mg, 1.13 mmol) were suspended in Chloroform (7.5 mL). 2-methylpropane-2-thiol (2.1 mL, 0.168 g, 18.6 mmol) was added, the mixture was irradiated, and DCC (175 mg, 0.848 mmol) in 1.5 mL $CHCl_3$ was added dropwise under argon. The mixture was irradiated for 15 min with vigorous stirring without additional external heating. The mixture was then concentrated and dried in vacuo. Purification by repeated column chromatography (first column: $SiO_2$, 0-25% ethyl acetate/hexane; second column: $SiO_2$, 0-20% ethyl acetate/hexane) yielded 136 mg (0.291 mmol, 38%) of rac-(5aR,6S,8R,8aR)-5a-(4-bromophenyl)-3-chloro-8a-hydroxy-6-phenyl-5a,7,8,8a-tetrahydro-6H-cyclopenta[4,5]furo[3,2-b]pyridine-8-carbonitrile (5) as an off-white foam; MS (ESI) m/z 467.2 $[M+1]^+$.

Synthesis of rac-(5aR,6S,8R,8aR)-8-(aminomethyl)-5a-(4-bromophenyl)-3-chloro-6-phenyl-5a,6,7,8-tetrahydro-8aH-cyclopenta[4,5]furo[3,2-b]pyridin-8a-ol (Cpd. No. 174F)

To a solution of rac-(5aR,6S,8R,8aR)-5a-(4-bromophenyl)-3-chloro-8a-hydroxy-6-phenyl-5a,7,8,8a-tetrahydro-6H-cyclopenta[4,5]furo[3,2-b]pyridine-8-carbonitrile (5, 134 mg, 0.286 mmol) in THF (2.9 mL) at 0° C. was added LAH (27 mg, 0.72 mmol) and the mixture was stirred at rt. After 30 min 0.1 mL water were added at 0° C., followed by 0.1 mL 12.5% NaOH (aq) and ca. 200 mg of $Na_2SO_4$. The mixture was stirred for 10 min at rt, then filtered through celite (rinsed with dichloromethane) and concentrated. The crude product was taken up in 2 mL dichloromethane and treated with trifluoroacetic acid (0.03 mL, 0.04 g, 0.4 mmol), then concentrated to yield 176 mg of crude TFA salt of (Cpd. No. 174F). Ca. 96 mg of this material were used without purification for further derivatization. The rest was purified by HPLC (C18, MeCN/water+0.1% TFA), providing 22 mg of pure rac-(5aR,6S,8R,8aR)-8-(aminomethyl)-5a-(4-bromophenyl)-3-chloro-6-phenyl-5a,6,7,8-tetrahydro-8aH-cyclopenta[4,5]furo[3,2-b]pyridin-8a-ol (Cpd. No. 174F) as the TFA salt as a white solid; MS (ESI) m/z 471.2 $[M+1]^+$; $^1H$ NMR (400 MHz, DMSO-$d_6$) δ 8.29 (d, J=2.0 Hz, 1H), 7.84 (d, J=2.0 Hz, 1H), 7.81 (b, 3H), 7.33 (d, J=8.7 Hz, 2H), 7.15-7.05 (m, 5H), 6.99-6.95 (m, 2H), 6.15 (s, 1H), 3.66 (dd, J=13.5, 6.4 Hz, 1H), 3.44-3.35 (m, 1H), 3.22-3.13 (m, 1H), 2.86-2.76 (m, 1H), 2.38-2.24 (m, 2H).

Example 175

Rac-4-((5aR,6S,8R,8aR)-8-(aminomethyl)-3-chloro-8a-hydroxy-6-phenyl-6,7,8,8a-tetrahydro-5aH-cyclopenta[4,5]furo[3,2-b]pyridin-5a-yl)benzonitrile (Cpd. No. 175F)

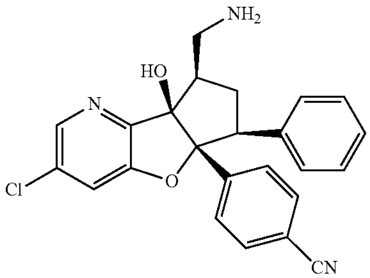

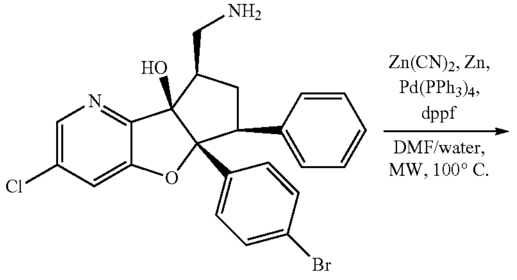

1
(TFA salt)

-continued

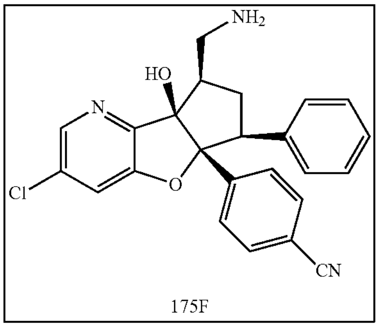

175F

Synthesis of rac-4-((5aR,6S,8R,8aR)-8-(aminomethyl)-3-chloro-8a-hydroxy-6-phenyl-6,7,8,8a-tetrahydro-5aH-cyclopenta[4,5]furo[3,2-b]pyridin-5a-yl)benzonitrile (Cpd. No. 175F)

In a 0.5-2 mL microwave vial rac-(5aR,6S,8R,8aR)-8-(aminomethyl)-5a-(4-bromophenyl)-3-chloro-6-phenyl-5a,6,7,8-tetrahydro-8aH-cyclopenta[4,5]furo[3,2-b]pyridin-8a-ol (1, 48 mg, 0.082 mmol) was dissolved in N,N-dimethylformamide (0.7 mL) and water (0.07 mL). Zinc cyanide (39 mg, 0.33 mmol) and zinc (3 mg, 0.05 mmol) were added, and the mixture was degassed by bubbling argon through it for 5 min. Dppf (14.0 mg, 0.0253 mmol) and Tris(dibenzylideneacetone)dipalladium(0) (10.8 mg, 0.0118 mmol) were added and the mixture was degassed for another 5 min, then incubated at 100° C. for 2.25 h in total. The mixture was filtered, diluted with MeCN, DMSO and water and subjected to purification by HPLC (C18 MeCN/water+0.1% TFA) to provide 13.8 mg (32%) of the TFA salt of rac-4-((5aR,6S,8R,8aR)-8-(aminomethyl)-3-chloro-8a-hydroxy-6-phenyl-6,7,8,8a-tetrahydro-5aH-cyclopenta[4,5]furo[3,2-b]pyridin-5a-yl)benzonitrile (Cpd. No. 175F) as a white solid; MS (ESI) m/z 418.4 $[M+1]^+$; $^1H$ NMR (400 MHz, DMSO-$d_6$) δ 8.31 (d, J=2.0 Hz, 1H), 7.87 (d, J=2.0 Hz, 1H), 7.82 (b, 3H), 7.61 (d, J=8.8 Hz, 2H), 7.37 (d, J=8.8 Hz, 2H), 7.15-7.03 (m, 3H), 6.99-6.94 (m, 2H), 6.22 (s, 1H), 3.74 (dd, J=13.7, 6.1 Hz, 1H), 3.45-3.38 (m, 1H), 3.24-3.15 (m, 1H), 2.86-2.77 (m, 1H), 2.46-2.36 (m, 1H), 2.36-2.23 (m, 11H).

Example 176

Rac-(5aR,6S,8R,8aR)-8-(aminomethyl)-5a-(4-cyanophenyl)-8a-hydroxy-6-phenyl-5a,7,8,8a-tetrahydro-6H-cyclopenta[4,5]furo[3,2-b]pyridine-3-carbonitrile (Cpd. No. 176F)

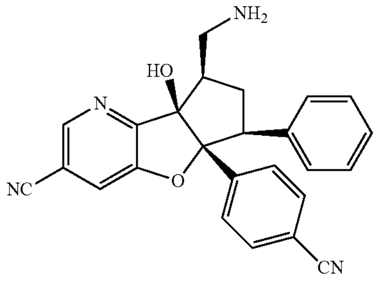

-continued

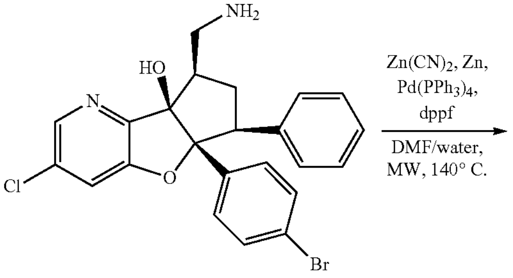

1
(TFA salt)

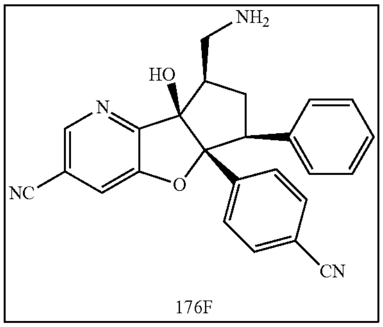

176F

Synthesis of rac-(5aR,6S,8R,8aR)-8-(aminomethyl)-5a-(4-cyanophenyl)-8a-hydroxy-6-phenyl-5a,7,8,8a-tetrahydro-6H-cyclopenta[4,5]furo[3,2-b]pyridine-3-carbonitrile (Cpd. No. 176F)

In a 0.5-2 mL MW vial rac-(5aR,6S,8R,8aR)-8-(aminomethyl)-5a-(4-bromophenyl)-3-chloro-6-phenyl-5a,6,7,8-tetrahydro-8aH-cyclopenta[4,5]furo[3,2-b]pyridin-8a-ol (1, 48 mg, 0.08000 mmol) was dissolved in N,N-dimethylformamide (0.7 mL) and water (0.07 mL). Zinc cyanide (39 mg, 0.33 mmol) and zinc (3 mg, 0.05 mmol) were added, and the mixture was degassed by bubbling argon through it for 5 min. Dppf (14.0 mg, 0.0253 mmol) and Tris(dibenzylideneacetone)dipalladium(0) (10.8 mg, 0.0118 mmol) were added and the mixture was degassed for another 5 min, then incubated at 140° C. for 1 h. Then the mixture was filtered, diluted with DMSO and MeCN, and directly subjected to purification by HPLC (C18, MeCN/water+0.1% TFA) to yield 3.6 mg (ca. 90% pure by $^1$H-NMR, 8%) of the TFA salt of rac-(5aR,6S,8R,8aR)-8-(aminomethyl)-5a-(4-cyanophenyl)-8a-hydroxy-6-phenyl-5a,7,8,8a-tetrahydro-6H-cyclopenta[4,5]furo[3,2-b]pyridine-3-carbonitrile (Cpd. No. 176F) as white solid; MS (ESI) m/z 409.2 $[M+1]^+$; $^1$H NMR (400 MHz, DMSO-$d_6$) d 8.75 (d, J=1.7 Hz, 1H), 8.21 (d, J=1.7 Hz, 1H), 7.86 (b, 3H), 7.62 (d, J=8.7 Hz, 2H), 7.38 (d, J=8.7 Hz, 2H), 7.15-7.04 (m, 3H), 6.98-6.94 (m, 2H), 6.39 (s, 1H), 3.75 (dd, J=14.0, 6.3 Hz, 1H), 3.47-3.37 (m, 1H), 3.26-3.16 (m, 1H), 2.89-2.80 (m, 1H), 2.42 (b ddd, J=13, 13, 13 Hz, 1H), 2.34-2.26 (m, 1H).

Example 177

Rac-(5aR,6S,8R,8aR)-5a-(4-bromophenyl)-3-chloro-8-(morpholinomethyl)-6-phenyl-5a,6,7,8-tetrahydro-8aH-cyclopenta[4,5]furo[3,2-b]pyridin-8a-ol (Cpd. No. 177F)

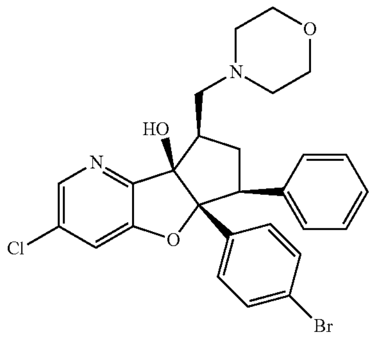

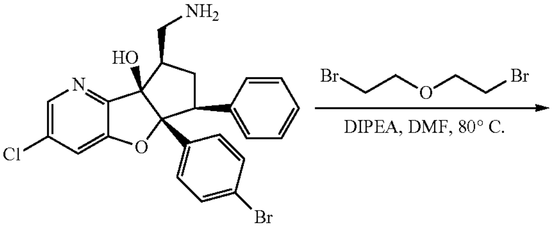

1

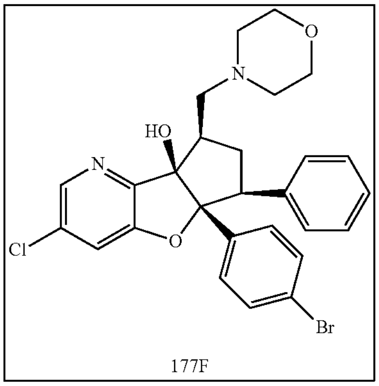

177F

Synthesis of rac-(5aR,6S,8R,8aR)-5a-(4-bromophenyl)-3-chloro-8-(morpholinomethyl)-6-phenyl-5a,6,7,8-tetrahydro-8aH-cyclopenta[4,5]furo[3,2-b]pyridin-8a-ol (Cpd. No. 177F)

To a solution of rac-(5aR,6S,8R,8aR)-8-(aminomethyl)-5a-(4-bromophenyl)-3-chloro-6-phenyl-5a,6,7,8-tetrahydro-8aH-cyclopenta[4,5]furo[3,2-b]pyridin-8a-ol (1, 49 mg, 0.10 mmol) in N,N-dimethylformamide (0.7 mL) were added N,N-Diisopropylethylamine (0.06 mL, 0.04 g, 0.3 mmol) and 1-bromo-2-(2-bromoethoxy)ethane (15 mL, 28 mg, 0.12 mmol) and the mixture was stirred at 80° C. After 1.5 h another 5 uL bis(bromoethyl)ether (9 mg, 0.04 mmol) were added at rt, and stirring at 80° C. was continued for another 30 min. Then the mixture was cooled to 0° C., diluted with water and treated with trifluoroacetic acid (0.04 mL, 0.06 g, 0.5 mmol). The mixture was then diluted with MeCN and subjected to HPLC purification (C18, MeCN/water+0.1% TFA) to yield 28.6 mg (42%) of rac-(5aR,6S,8R,8aR)-5a-(4-bromophenyl)-3-chloro-8-(morpholinomethyl)-6-phenyl-5a,6,7,8-tetrahydro-8aH-cyclopenta[4,5]furo[3,2-b]pyridin-8a-ol (Cpd. No. 177F) as its TFA salt, white solid; MS (ESI) m/z 541.2 $[M+1]^+$; $^1$H NMR (400 MHz, DMSO-$d_6$) δ 9.33 (b, 1H), 8.31 (d, J=2.0 Hz, 1H), 7.85 (d, J=2.0 Hz, 1H), 7.33 (d, J=8.8 Hz, 2H), 7.16-7.07 (m, 5H), 7.00-6.96 (m, 2H), 6.21 (s, 1H), 4.09-3.97 (m, 2H), 3.84-3.28 (m, 8H, partially obscured by water peak), 3.25-3.13 (m, 1H), 3.12-3.01 (m, 1H), 2.44-2.32 (m, 2H).

Example 178

Rac-4-((5aR,6S,8R,8aR)-3-chloro-8a-hydroxy-8-(morpholinomethyl)-6-phenyl-6,7,8,8a-tetrahydro-5aH-cyclopenta[4,5]furo[3,2-b]pyridin-5a-yl)benzonitrile (Cpd. No. 178F)

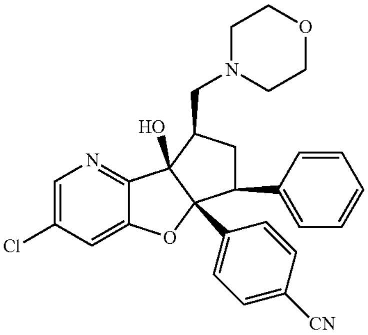

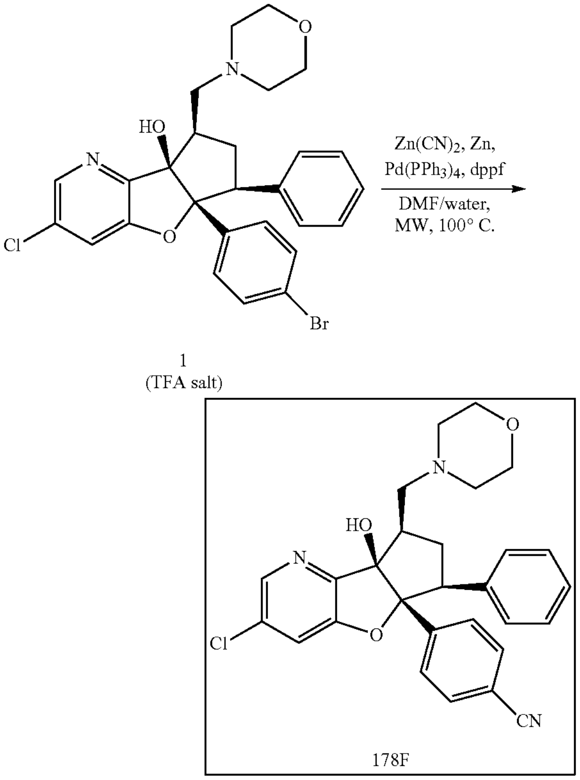

1
(TFA salt)

178F

Synthesis of rac-4-((5aR,6S,8R,8aR)-3-chloro-8a-hydroxy-8-(morpholinomethyl)-6-phenyl-6,7,8,8a-tetrahydro-5aH-cyclopenta[4,5]furo[3,2-b]pyridin-5a-yl)benzonitrile (Cpd. No. 178F)

In a 0.5-2 mL microwave vial rac-(5aR,6S,8R,8aR)-5a-(4-bromophenyl)-3-chloro-8-(morpholinomethyl)-6-phenyl-5a,6,7,8-tetrahydro-8aH-cyclopenta[4,5]furo[3,2-b]pyridin-8a-ol (1, 24 mg, 0.037 mmol) was dissolved in N,N-dimethylformamide (0.5 mL) and water (0.05 mL). Zinc cyanide (18.8 mg, 0.160 mmol) and zinc (1.3 mg, 0.020 mmol) were added, and the mixture was degassed by bubbling argon through it for 5 min. Dppf (6.3 mg, 0.011 mmol) and Tris(dibenzylideneacetone)dipalladium(0) (4.8 mg, 0.0053 mmol) were added and the mixture was degassed for another 5 min, then incubated at 100° C. for 2 h in total. Then the mixture was filtered, diluted with MeCN, DMSO and water and subjected to purification by HPLC (C18, MeCN/water+0.1% TFA) to yield 10.6 mg (0.0176 mmol, 48%) of rac-4-((5aR,6S,8R,8aR)-3-chloro-8a-hydroxy-8-(morpholinomethyl)-6-phenyl-6,7,8,8a-tetrahydro-5aH-cyclopenta[4,5]furo[3,2-b]pyridin-5a-yl)benzonitrile (Cpd. No. 178F) as TFA salt, white solid; MS (ESI) m/z 488.3 $[M+1]^+$; $^1$H NMR (400 MHz, DMSO-$d_6$) δ 9.41 (b, 1H), 8.32 (d, J=2.0 Hz, 1H), 7.88 (d, J=2.0 Hz, 1H), 7.61 (d, J=8.6 Hz, 2H), 7.36 (d, J=8.6H, 2H), 7.15-7.04 (m, 3H), 7.00-6.95 (m, 2H), 6.28 (s, 1H), 4.09-3.98 (m, 2H), 3.85-3.42 (m, 7H, partially obscured by water peak), 3.42-3.30 (m, 1H), 3.25-3.14 (m, 1H), 3.14-3.02 (m, 1H), 2.47-2.38 (m, 2H).

Example 179

Rac-(4bR,5R,6R,7S,7aR)-7a-(4-bromophenyl)-6-(hydroxymethyl)-4-methoxy-5-(morpho-linomethyl)-7-phenyl-5,6,7,7a-tetrahydro-4bH-cyclopenta[4,5]furo[2,3-c]pyridin-4b-ol (Cpd. No. 179F)

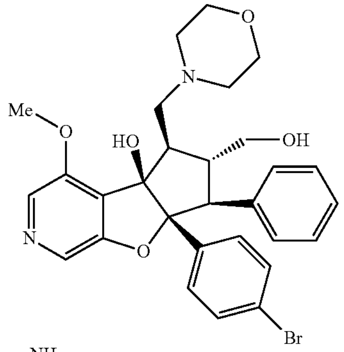

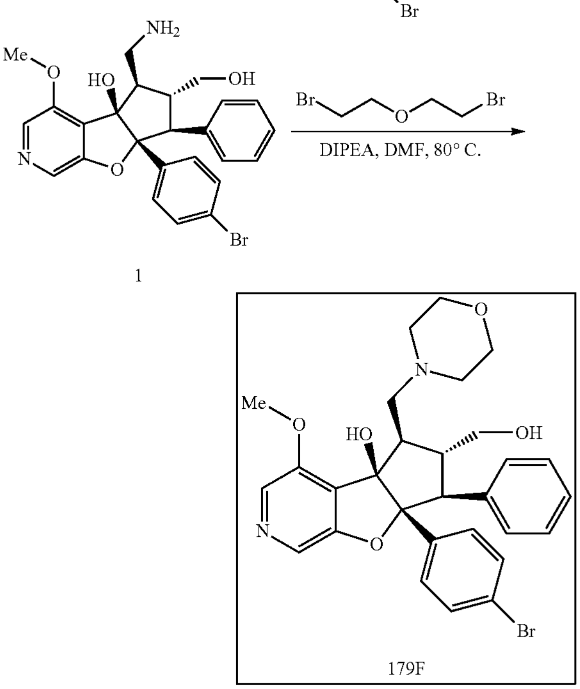

1

179F

Synthesis of rac-(4bR,5R,6R,7S,7aR)-7a-(4-bromophenyl)-6-(hydroxymethyl)-4-methoxy-5-(morpholinomethyl)-7-phenyl-5,6,7,7a-tetrahydro-4bH-cyclopenta[4,5]furo[2,3-c]pyridin-4b-ol (Cpd. No. 179F)

To a solution of crude rac-(4bR,5R,6R,7S,7aR)-5-(aminomethyl)-7a-(4-bromophenyl)-6-(hydroxymethyl)-4-methoxy-7-phenyl-5,6,7,7a-tetrahydro-4bH-cyclopenta[4,5]furo[2,3-c]pyridin-4b-ol (1, 53 mg, 0.11000 mmol) in toluene (0.5 mL) and N,N-dimethylformamide (0.2 mL) at rt were added sodium bicarbonate (21 mg, 0.25 mmol) and 1-bromo-2-(2-bromoethoxy)ethane (15 uL, 28 mg, 0.12 mmol) and the mixture was stirred at 50° C. After 1 h partial product formation observed and the mixture was warmed up to 70° C. After another 1 h the mixture was warmed up to 90° C. After another 2 h at this temperature the mixture was allowed to cool to rt, then the reaction was quenched with $NaHCO_3$(aq). The mixture was extracted with dichloromethane (3×); and the organic phases were dried ($Na_2SO_4$), filtered and concentrated. The material was taken up in DMSO/MeCN/water for HPLC purification (C18, MeCN/water+0.1% TFA) to yield 7.9 mg (0.012 mmol, 11%) of rac-(4bR,5R,6R,7S,7aR)-7a-(4-bromophenyl)-6-(hydroxymethyl)-4-methoxy-5-(morpho-linomethyl)-7-phenyl-5,6,7,7a-tetrahydro-4bH-cyclopenta[4,5]furo[2,3-c]pyridin-4b-ol (Cpd. No. 179F) as its TFA salt, white solid; MS (ESI) m/z 567.4 $[M+1]^+$; $^1H$ NMR (400 MHz, DMSO-$d_6$) δ 9.95 (b, 1H), 8.19 (s, 1H), 8.15 (s, 1H), 7.34 (d, J=8.5 Hz, 2H), 7.18-7.08 (m, 5H), 6.81-6.76 (m, 2H), 6.05 (s, 1H), 4.18-4.07 (m, 1H), 4.03 (s, 3H), 3.93-3.83 (m, 1H), 3.82-3.11 (m, 11H, partially obscured by water peak), 3.09 (d, J=13.4 Hz, 1H), 2.97-2.86 (m, 1H).

Example 180

Rac-4-((4bR,5R,6R,7S,7aR)-4b-hydroxy-6-(hydroxymethyl)-4-methoxy-5-(morpholino-methyl)-7-phenyl-4b,5,6,7-tetrahydro-7aH-cyclopenta[4,5]furo[2,3-c]pyridin-7a-yl)benzonitrile (Cpd. No. 180F)

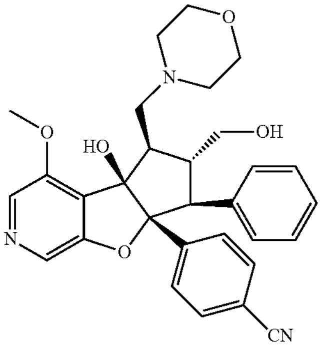

-continued

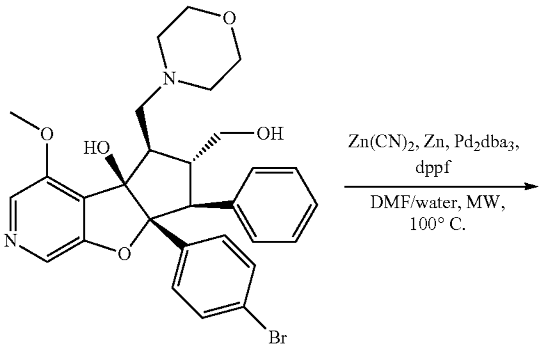

1
(TFA salt)

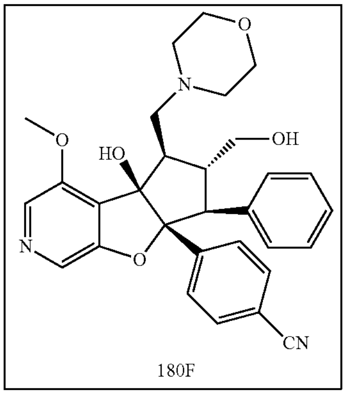

180F

Synthesis of rac-4-((4bR,5R,6R,7S,7aR)-4b-hydroxy-6-(hydroxymethyl)-4-methoxy-5-(morpholino-methyl)-7-phenyl-4b,5,6,7-tetrahydro-7aH-cyclopenta[4,5]furo[2,3-c]pyridin-7a-yl)benzonitrile (Cpd. No. 180F)

In a 0.5-2 mL microwave vial rac-(4bR,5R,6R,7S,7aR)-7a-(4-bromophenyl)-6-(hydroxymethyl)-4-methoxy-5-(morpholinomethyl)-7-phenyl-5,6,7,7a-tetrahydro-4bH-cyclopenta[4,5]furo[2,3-c]pyridin-4b-ol (1, 26 mg, 0.038 mmol) was dissolved in N,N-dimethylformamide (0.6 mL) and water (0.06 mL). Zinc cyanide (20 mg, 0.17 mmol) and zinc (1.5 mg, 0.023 mmol) were added, and the mixture was degassed by bubbling argon through it for 5 min. Dppf (6.9 mg, 0.012 mmol) and Tris(dibenzylideneacetone)dipalladium(0) (5.2 mg, 0.0057 mmol) were added and the mixture was degassed for another 5 min, then incubated at 100° C. for 1.5 h in total. The mixture was filtered, diluted with MeCN, DMSO and water and subjected to purification by HPLC (C18, MeCN/water+0.1% TFA) to yield 6.1 mg (0.0097 mmol, 25%), of the TFA salt of rac-4-((4bR,5R,6R,7S,7aR)-4b-hydroxy-6-(hydroxymethyl)-4-methoxy-5-(morpholino-methyl)-7-phenyl-4b,5,6,7-tetrahydro-7aH-cyclopenta[4,5]furo[2,3-c]pyridin-7a-yl)benzonitrile (Cpd. No. 180F) as a white, hygroscopic solid; MS (ESI) m/z 514.3 $[M+1]^+$; $^1H$ NMR (400 MHz, DMSO-$d_6$) δ 10.02 (b, 1H), 8.21 (s, 1H), 8.16 (s, 1H), 7.63 (d, J=8.2 Hz, 2H), 7.39 (bd, 2H), 7.14-7.08 (m, 3H), 6.81-6.76 (m, 2H), 6.12 (s, 1H), 4.20-4.07 (m, 1H), 4.04 (s, 3H), 3.94-3.83 (m, 1H), 3.83-3.11 (m, 11H, partially obscured by water peak), 3.15 (d, J=13.5 Hz, 1H), 3.04-2.94 (m, 1H).

Example 181

Rac-(4bR,5R,6R,7S,7aR)-7a-(4-bromophenyl)-5-(((2,2-difluoroethyl)amino)methyl)-6-(hydroxymethyl)-4-methoxy-7-phenyl-5,6,7,7a-tetrahydro-4bH-cyclopenta[4,5]furo[2,3-c]pyridin-4b-ol (Cpd. No. 181F)

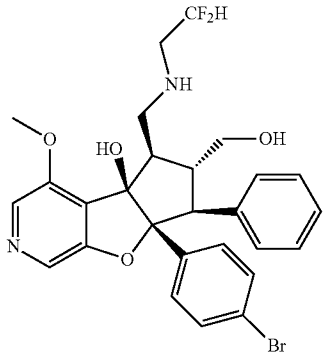

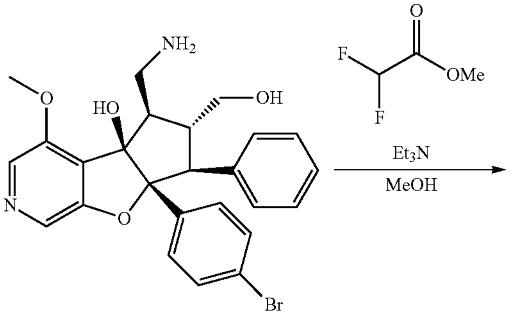

1

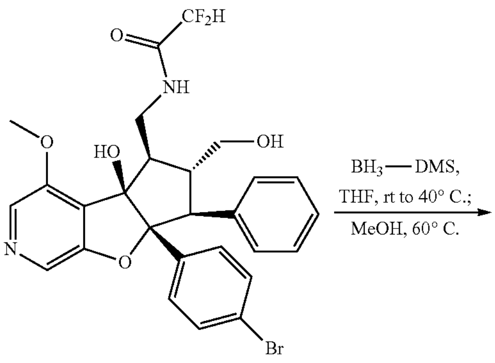

2

-continued

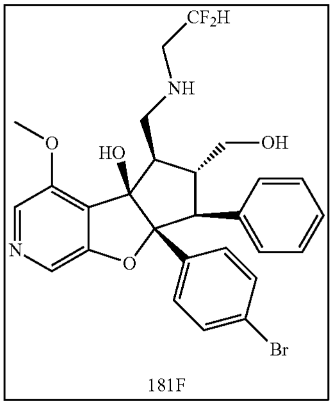

181F

Synthesis of rac-N-(((4bR,5R,6R,7S,7aR)-7a-(4-bromophenyl)-4b-hydroxy-6-(hydroxymethyl)-4-methoxy-7-phenyl-4b,6,7,7a-tetrahydro-5H-cyclopenta[4,5]furo[2,3-c]pyridin-5-yl)methyl)-2,2-difluoroacetamide (2)

To a solution of crude rac-(4bR,5R,6R,7S,7aR)-5-(aminomethyl)-7a-(4-bromophenyl)-6-(hydroxymethyl)-4-methoxy-7-phenyl-5,6,7,7a-tetrahydro-4bH-cyclopenta[4,5]furo[2,3-c]pyridin-4b-ol (1, 40 mg, 0.080 mmol) in methanol (0.8 mL) at rt were added triethylamine (24 mL, 17 mg, 0.17 mmol) and methyl 2,2-difluoroacetate (0.2 mL, 0.3 g, 2 mmol) and the mixture was stirred at rt. After 30 min the mixture was concentrated in vacuo. The crude product rac-N-(((4bR,5R,6R,7S,7aR)-7a-(4-bromophenyl)-4b-hydroxy-6-(hydroxymethyl)-4-methoxy-7-phenyl-4b,6,7,7a-tetrahydro-5H-cyclopenta[4,5]furo[2,3-c]pyridin-5-yl)methyl)-2,2-difluoroacetamide (2) (MS (ESI) m/z 575.1 [M+1]*) was used without further purification.

Synthesis of rac-(4bR,5R,6R,7S,7aR)-7a-(4-bromophenyl)-5-(((2,2-difluoroethyl)amino) methyl)-6-(hydroxymethyl)-4-methoxy-7-phenyl-5,6,7,7a-tetrahydro-4bH-cyclopenta-[4,5]-furo-[2,3-c]pyridin-4b-ol (Cpd. No. 181F)

To a solution of crude rac-N-(((4bR,5R,6R,7S,7aR)-7a-(4-bromophenyl)-4b-hydroxy-6-(hydroxymethyl)-4-methoxy-7-phenyl-4b,6,7,7a-tetrahydro-5H-cyclopenta[4,5]furo[2,3-c]pyridin-5-yl)methyl)-2,2-difluoroacetamide (2, 12 mg, 0.021 mmol) in THF (0.4 mL) at 0° C. was added $BH_3$-DMS complex in THF (0.07 mL, 0.14 mmol) and the mixture was stirred at 0° C. to 45 min, then at rt. After 2 h total reaction time warmed up to 40° C. and stirred for another 7 h, then over night at rt. 0.4 mL MeOH were added and the mixture was stirred at 60° C. for 3.5 h, then at 70° C. for 30 min. Then the mixture was concentrated, redissolved in MeCN/DMSO/water+a few drops of TFA and purified by HPLC (C18, MeCN/water+0.1% TFA) to yield 4.7 mg (0.0070 mmol, 33%) of rac-(4bR,5R,6R,7S,7aR)-7a-(4-bromophenyl)-5-(((2,2-difluoroethyl)amino) methyl)-6-(hydroxymethyl)-4-methoxy-7-phenyl-5,6,7,7a-tetrahydro-4bH-cyclopenta-[4,5]-furo-[2,3-c]pyridin-4b-ol (Cpd. No. 181F) as its TFA salt as a white solid; MS (ESI) m/z 561.2 $[M+1]^+$; $^1H$ NMR (400 MHz, DMSO-$d_6$) δ 9.56 (b, 1H), 8.48 (b, 1H), 8.20 (s, 1H), 8.14 (s, 1H), 7.34 (d, J=8.6 Hz, 2H), 7.16-7.08 (m, 5H), 6.83-6.78 (m, 2H), 6.57 (tt, J=53.8, 3.2 Hz, 1H), 6.37 (s, 1H), 5.57 (b, 1H), 4.00 (s, 3H), 3.86-3.48 (m, 4H, partially obscured by water peak), 3.47-3.42 (m, 1H), 3.26 (d, J=13.7 Hz, 1H), 3.20 (dd, J=11.1, 6.5 Hz, 1H), 3.08-3.00 (m, 1H), 2.72-2.63 (m, 1H).

Example 182

Rac-4-((4bR,5R,6R,7S,7aR)-5-(((2,2-difluoroethyl)amino)methyl)-4b-hydroxy-6-(hydroxyl-methyl)-4-methoxy-7-phenyl-4b,5,6,7-tetrahydro-7aH-cyclopenta[4,5]furo[2,3-c]pyridin-7a-yl)benzonitrile (Cpd. No. 1821F)

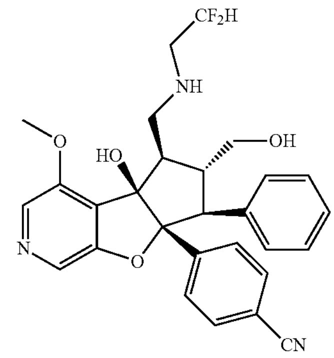

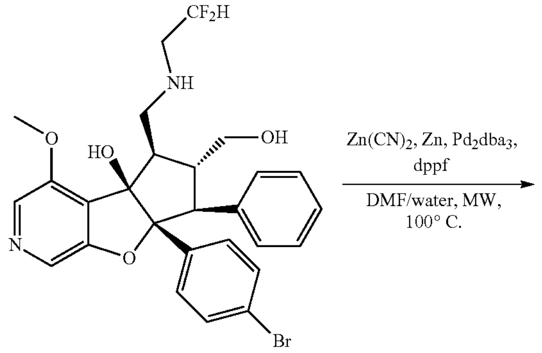

1
(TFA salt)

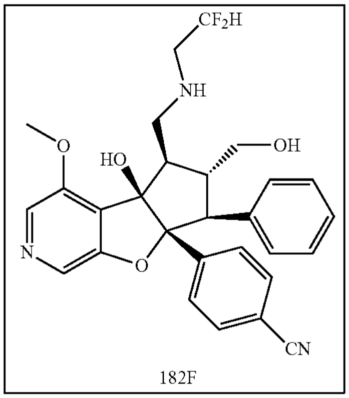

182F

Synthesis of rac-4-((4bR,5R,6R,7S,7aR)-5-(((2,2-difluoroethyl)amino)methyl)-4b-hydroxy-6-(hydroxyl-methyl)-4-methoxy-7-phenyl-4b,5,6,7-tetrahydro-7aH-cyclopenta[4,5]furo[2,3-c]pyridin-7a-yl)benzonitrile (Cpd. No. 182F)

In a 0.5-2 mL microwave vial rac-(4bR,5R,6R,7S,7aR)-7a-(4-bromophenyl)-5-(((2,2-difluoroethyl)amino)methyl)-

6-(hydroxymethyl)-4-methoxy-7-phenyl-5,6,7,7a-tetrahydro-4bH-cyclopenta[4,5]furo[2,3-c]pyridin-4b-ol (1, 65 mg, 0.096 mmol) was dissolved in N,N-dimethylformamide (0.9 mL) and water (0.09 mL). Zinc cyanide (51 mg, 0.43 mmol) and zinc (3.1 mg, 0.047 mmol) were added, and the mixture was degassed by bubbling argon through it for 5 min. Dppf (16 mg, 0.029 mmol) and Tris(dibenzylideneacetone)dipalladium(0) (13 mg, 0.014 mmol) were added and the mixture was degassed for another 5 min, then incubated at 100° C. for 2 h in total. The mixture was filtered, diluted with MeCN, DMSO and water and subjected to purification by HPLC (C18 MeCN/water+0.1% TFA) to yield 31 mg (93% pure, 48%) of the TAF salt of rac-4-((4bR,5R,6R,7S,7aR)-5-(((2,2-difluoroethyl)amino)methyl)-4b-hydroxy-6-(hydroxyl-methyl)-4-methoxy-7-phenyl-4b,5,6,7-tetrahydro-7aH-cyclopenta[4,5]furo[2,3-c]pyridin-7a-yl)benzonitrile) (Cpd. No. 182F) as a white solid. This material was 93% pure by $^1$H-NMR (the major impurity appeared to be the reductive debromination product, i. e. H instead of CN in the 4' position). A part of this material was re-subjected to HPLC purification (C18, MeCN/water+0.1% TFA) to yield material of 95% purity; MS (ESI) m/z 508.4 $[M+1]^+$; $^1$H NMR (400 MHz, DMSO-$d_6$) δ 9.58 (b, 1H), 8.55 (b, 1H), 8.23 (s, 1H), 8.16 (s, 1H), 7.62 (d, J=8.5 Hz, 2H), 7.37 (bd, J=8.5 Hz, 2H), 7.13-7.07 (m, 3H), 6.83-6.79 (m, 2H), 6.57 (tt, J=53.6, 3.0 Hz, 1H), 6.43 (s, 1H), 5.64 (b, 1H), 4.01 (s, 3H), 4.00-3.70 (m, 3H, partially obscured by water peak), 3.62-3.52 (m, 1H), 3.46 (dd, J=11.1, 2.3 Hz, 1H), 3.33 (d, J=13.6 Hz, 1H), 3.21 (dd, J=11.1, 6.7 Hz, 1H), 3.10-3.02 (m, 1H), 2.81-2.70 (m, 1H).

Example 183

Rac-(4bR,5R,6R,7S,7aR)-7a-(4-bromophenyl)-6-(hydroxymethyl)-4-methoxy-5-((4-methylpiperazin-1-yl)methyl)-7-phenyl-5,6,7,7a-tetrahydro-4bH-cyclopenta[4,5]furo[2,3-c]pyridin-4b-ol (Cpd. No. 183F)

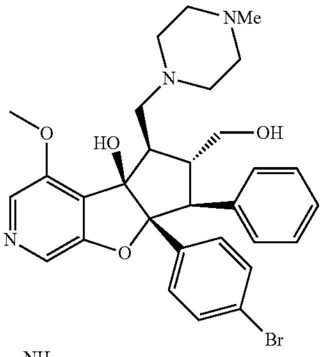

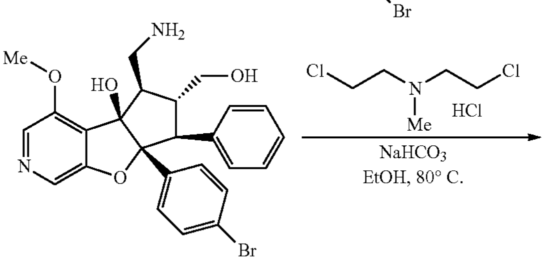

-continued

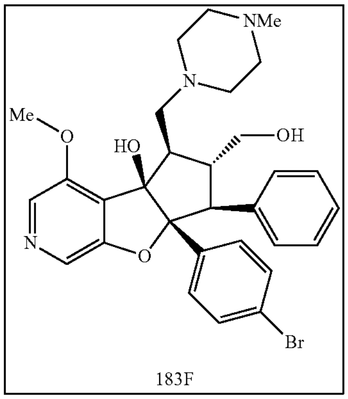

183F

Synthesis of rac-(4bR,5R,6R,7S,7aR)-7a-(4-bromophenyl)-6-(hydroxymethyl)-4-methoxy-5-((4-methylpiperazin-1-yl)methyl)-7-phenyl-5,6,7,7a-tetrahydro-4bH-cyclopenta[4,5]furo[2,3-c]pyridin-4b-ol (Cpd. No. 183F)

To a solution of rac-(4bR,5R,6R,7S,7aR)-5-(aminomethyl)-7a-(4-bromophenyl)-6-(hydroxymethyl)-4-methoxy-7-phenyl-5,6,7,7a-tetrahydro-4bH-cyclopenta[4,5]furo[2,3-c]pyridin-4b-ol (1, 103 mg, 0.207 mmol) in ethanol (0.7 mL) at rt were added sodium bicarbonate (97.5 mg, 1.16 mmol) and mechlorethamine hydrochloride (46 mg, 0.24 mmol) and the mixture was stirred at 80° C. After 1 h The mixture was concentrated to approximately a third of its original volume, treated with 5 mL water, cooled down to 0° C., and acidified with trifluoroacetic acid (0.14 mL, 0.21 g, 1.8 mmol), then diluted with MeCN/water and subjected to HPLC purification (C18, MeCN/water+0.1% TFA) to yield 41.3 mg (0.0595 mmol, 29%) of the TFA salt of rac-(4bR,5R,6R,7S,7aR)-7a-(4-bromophenyl)-6-(hydroxymethyl)-4-methoxy-5-((4-methylpiperazin-1-yl)methyl)-7-phenyl-5,6,7,7a-tetrahydro-4bH-cyclopenta[4,5]furo[2,3-c]pyridin-4b-ol (Cpd. No. 183F) as a white solid; MS (ESI) m/z 580.4 $[M+1]^+$; $^1H$ NMR (400 MHz, DMSO-$d_6$) δ 8.18 (s, 1H), 8.13 (s, 1H), 7.33 (d, J=8.7 Hz, 2H), 7.15 (bd, J=8.7 Hz, 2H), 7.13-7.07 (m, 3H), 6.81-6.77 (m, 2H), 5.84 (b, 1H), 4.00 (s, 3H), 3.53 (bd, J=11 Hz, 1H), 3.20 (bdd, J=11, 6 Hz, 1H), 3.18 (d, J=13.7 Hz, 1H), 3.00-2.93 (m, 1H) [The remaining protons appeared as very broad signals, partially obscured be the water peak, in the range of 4.1-2.6 pm].

Example 184

Rac-4-((4bR,5R,6R,7S,7aR)-4b-hydroxy-6-(hydroxymethyl)-4-methoxy-5-((4-methyl-piperazin-1-yl)methyl)-7-phenyl-4b,5,6,7-tetrahydro-7aH-cyclopenta[4,5]furo[2,3-c]pyridin-7a-yl)benzonitrile (Cpd. No. 184F)

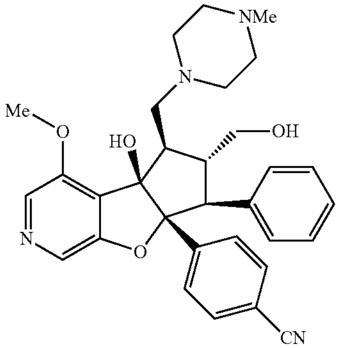

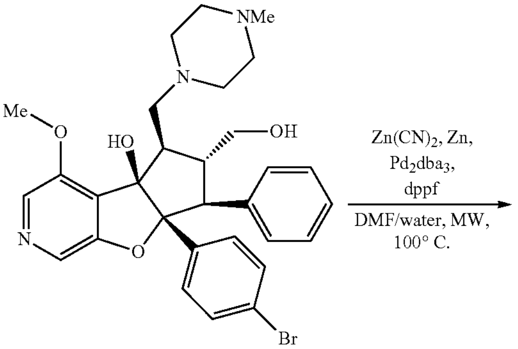

1
(TFA salt)

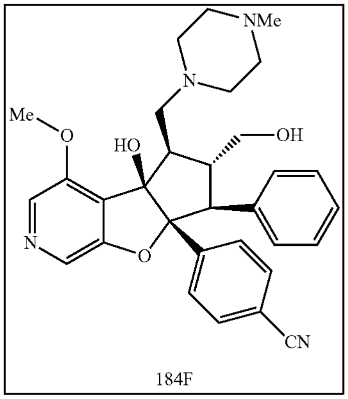

184F

Synthesis of rac-4-((4bR,5R,6R,7S,7aR)-4b-hydroxy-6-(hydroxymethyl)-4-methoxy-5-((4-methylpiperazin-1-yl)methyl)-7-phenyl-4b,5,6,7-tetrahydro-7aH-cyclopenta[4,5]furo[2,3-c]pyridin-7a-yl) benzonitrile (Cpd. No. 184F)

In a 0.5-2 mL microwave vial rac-(4bR,5R,6R,7S,7aR)-7a-(4-bromophenyl)-6-(hydroxymethyl)-4-methoxy-5-((4-methylpiperazin-1-yl)methyl)-7-phenyl-5,6,7,7a-tetrahydro-4bH-cyclopenta[4,5]furo[2,3-c]pyridin-4b-ol (1, 36.6 mg, 0.0527 mmol) was dissolved in N,N-dimethylformamide (0.9 mL) and water (0.09 mL). Zinc cyanide (29 mg, 0.25 mmol) and zinc (1.4 mg, 0.021 mmol) were added, and the mixture was degassed by bubbling argon through it for 5 min. Dppf (8.8 mg, 0.016 mmol) and Tris(dibenzylideneacetone)dipalladium(0) (7.2 mg, 0.0079 mmol) were added and the mixture was degassed for another 5 min, then incubated at 100° C. for 2 h in total. The mixture was filtered, diluted with MeCN, DMSO and water, filtered again, and subjected to purification by HPLC (C18, MeCN/water+0.1% TFA) to yield 14.5 mg (0.0226 mol, 43%) of the TFA salt of rac-4-((4bR,5R,6R,7S,7aR)-4b-hydroxy-6-(hydroxymethyl)-4-methoxy-5-((4-methyl-piperazin-1-yl)methyl)-7-phenyl-4b,5,6,7-tetrahydro-7aH-cyclopenta[4,5]furo[2,3-c]pyridin-7a-yl)benzonitrile (Cpd. No. 184F) as a white solid; MS (ESI) m/z 527.4 $[M+1]^+$; $^1H$ NMR (400 MHz, DMSO-$d_6$) δ 8.24 (s, 1H), 8.17 (s, 1H), 7.62 (d, J=8.5 Hz, 2H), 7.39 (bd, J=8.5 Hz, 2H), 7.13-7.04 (m, 3H), 6.83-6.76 (m, 2H), 4.02 (s, 3H), 3.55 (dd, J=11.0, 2.5 Hz, 1H), 3.41-3.33 (m, 1H), 3.26-3.22 (m, 1H), 3.23 (d, J=13.2 Hz, 1H), 3.08-3.00 (m, 1H), 2.88-2.77 (m, 1H), 2.83 (s, 3H) [The remaining protons appeared as very broad signals in the ranges of 6.4-4.1 ppm and 3.83-2.77 ppm (partially obscured by the water peak)].

Example 185

Rac-(4bR,5R,6R,7S,7aR)-7a-(4-bromophenyl)-6-(hydroxymethyl)-4-methoxy-5-((oxetan-3-ylamino)methyl)-7-phenyl-5,6,7,7a-tetrahydro-4bH-cyclopenta[4,5]furo[2,3-c]pyridin-4b-ol (Cpd. No. 185F)

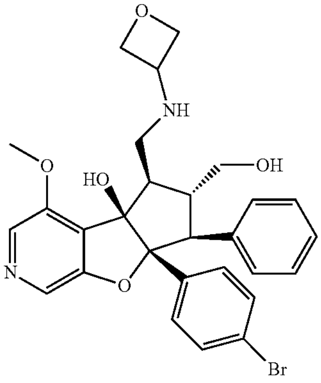

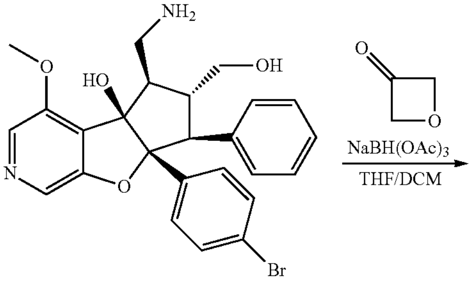

1

-continued

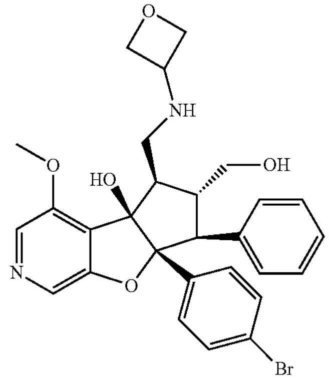

185F

Synthesis of rac-(4bR,5R,6R,7S,7aR)-7a-(4-bromophenyl)-6-(hydroxymethyl)-4-methoxy-5-((oxetan-3-ylamino)methyl)-7-phenyl-5,6,7,7a-tetrahydro-4bH-cyclopenta[4,5]furo[2,3-c]pyridin-4b-ol (Cpd. No. 185F)

To a suspension of rac-(4bR,5R,6R,7S,7aR)-5-(aminomethyl)-7a-(4-bromophenyl)-6-(hydroxymethyl)-4-methoxy-7-phenyl-5,6,7,7a-tetrahydro-4bH-cyclopenta[4,5]furo[2,3-c]pyridin-4b-ol (1, 50 mg, 0.10 mmol) in dichloromethane (1.5 mL) were added oxetan-3-one (7.0 mL, 8.6 mg, 0.12 mmol), acetic acid (1.2 mL, 1.3 mg, 0.021 mmol) and molecular sieves (ca. 60 mg). After 5 min THF (1 mL) was added for solubility reasons, and the mixture was stirred for another 25 min. Sodium triacetoxyborohydride (89 mg, 0.42 mmol) (STAB) was added. After 15 min another 0.03 mL (0.04 g, 0.6 mmol) 3-oxetanone were added. 2 h after STAB addition virtually full conversion was observed by LCMS. The reaction was quenched by addition of $NaHCO_3$(aq) and brine and extracted (3×dichloromethane). The combined organic phases were dried ($Na_2SO_4$), filtered and concentrated. Purification by HPLC (C18, MeCN/water+0.1% TFA) yielded 32.8 mg (0.049 mmol, 49%) of the TFA salt of rac-(4bR,5R,6R,7S,7aR)-7a-(4-bromophenyl)-6-(hydroxymethyl)-4-methoxy-5-((oxetan-3-ylamino)methyl)-7-phenyl-5,6,7,7a-tetrahydro-4bH-cyclopenta[4,5]furo[2,3-c]pyridin-4b-ol (Cpd. No. 185F) as a white solid; MS (ESI) m/z 553.3 $[M+1]^+$; $^1H$ NMR (400 MHz, DMSO-$d_6$) δ 9.33 (b, 1H), 8.67 (b, 1H), 8.21 (s, 1H), 8.14 (s, 1H), 7.34 (d, J=8.5 Hz, 2H), 7.15-7.07 (m, 5H), 6.81-6.77 (m, 2H), 6.29 (s, 1H), 5.12 (b, 1H), 4.82-4.76 (m, 3H), 4.67 (dd, J=7.6, 5.8, 1H), 4.62-4.53 (m, 1H), 4.00 (s, 3H), 3.62-3.49 (m, 1H), 3.51 (dd, J=11.4, 2.8 Hz, 1H), 3.38-3.28 (m, 1H), 3.30 (d, J=13.6 Hz, 1H), 3.20 (dd, J=11.4, 5.8 Hz, 1H), 3.07-2.99 (m, 1H), 2.64-2.55 (m, 1H).

Example 186

Rac-4-((4bR,5R,6R,7S,7aR)-4b-hydroxy-6-(hydroxymethyl)-4-methoxy-5-((oxetan-3-ylamino)-methyl)-7-phenyl-4b,5,6,7-tetrahydro-7aH-cyclopenta[4,5]furo[2,3-c]pyridin-7a-yl)-benzonitrile (Cpd. No. 1861)

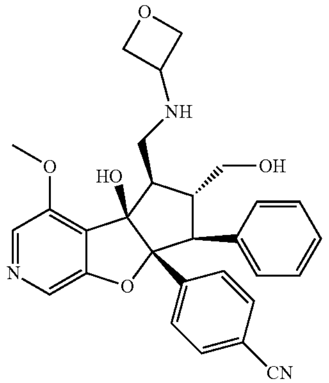

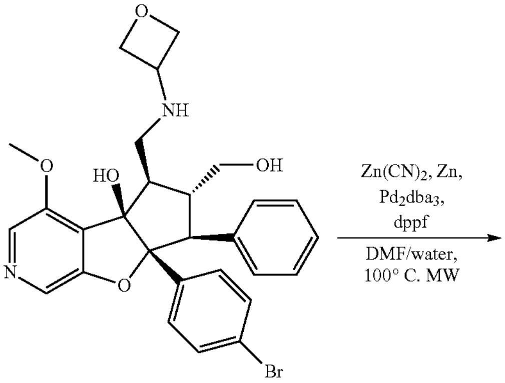

1
(TFA salt)

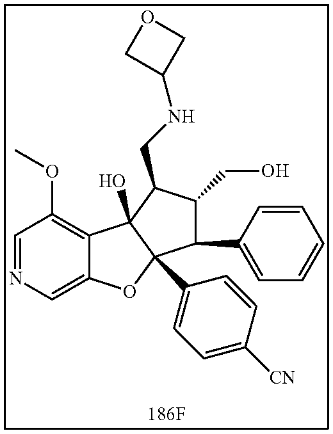

186F

Synthesis of rac-4-((4bR,5R,6R,7S,7aR)-4b-hydroxy-6-(hydroxymethyl)-4-methoxy-5-((oxetan-3-ylamino)-methyl)-7-phenyl-4b,5,6,7-tetrahydro-7aH-cyclopenta[4,5]furo[2,3-c]pyridin-7a-yl)-benzonitrile (Cpd. No. 186F)

In a 0.5-2 mL microwave vial rac-(4bR,5R,6R,7S,7aR)-7a-(4-bromophenyl)-6-(hydroxymethyl)-4-methoxy-5-((oxetan-3-ylamino)methyl)-7-phenyl-5,6,7,7a-tetrahydro-4bH-cyclopenta[4,5]furo[2,3-c]pyridin-4b-ol (1, 25 mg, 0.037 mmol) was dissolved in N,N-dimethylformamide (0.7 mL) and water (0.07 mL). Zinc cyanide (20.5 mg, 0.175 mmol) and zinc (1 mg, 0.02 mmol) were added, and the mixture was degassed by bubbling argon through it for 5 min. Dppf (6 mg, 0.01 mmol) and Tris(dibenzylideneacetone)dipalladium(0) (5 mg, 0.01 mmol) were added and the mixture was degassed for another 5 min, then incubated at 100° C. for 2 h in total. The mixture was filtered, diluted with MeCN, DMSO and water, filtered again, and subjected to purification by HPLC (C18, MeCN/water+0.1% TFA) to yield 11.3 mg (0.0184 mmol, 49%) of the TFA salt of rac-4-((4bR,5R,6R,7S,7aR)-4b-hydroxy-6-(hydroxymethyl)-4-methoxy-5-((oxetan-3-ylamino)-methyl)-7-phenyl-4b,5,6,7-tetrahydro-7aH-cyclopenta[4,5]furo[2,3-c]pyridin-7a-yl)-benzonitrile (Cpd. No. 186F) as a white solid; MS (ESI) m/z 500.3 $[M+1]^+$; $^1$H NMR (400 MHz, DMSO-$d_6$) δ 9.45 (b, 1H), 8.83 (b, 1H), 8.23 (s, 1H), 8.16 (s, 1H), 7.62 (d, J=8.4 Hz, 2H), 7.36 (bd, J=8.4 Hz, 2H), 7.13-7.06 (m, 3H), 6.83-6.77 (m, 2H), 6.36 (s, 1H), 5.17 (b, 1H), 4.86-4.76 (m, 3H), 4.69 (dd, J=7.7, 5.8 Hz, 1H), 4.63-4.54 (m, 1H), 4.00 (s, 3H), 3.64-3.54 (m, 1H), 3.53 (dd, J=11.5, 2.8 Hz, 1H), 3.37 (d, J=13.6 Hz, 1H), 3.40-3.31 (m, 1H), 3.22 (dd, J=11.5, 5.8 Hz, 1H), 3.10-3.00 (m, 1H), 2.75-2.64 (m, 1H).

Example 187

Rac-(4bR,5R,6R,7S,7aR)-7a-(4-bromophenyl)-6-(hydroxymethyl)-4-methoxy-7-phenyl-5-(((pyridin-4-ylmethyl)amino)methyl)-5,6,7,7a-tetrahydro-4bH-cyclopenta[4,5]furo[2,3-c]pyridin-4b-ol (Cpd. No. 187F)

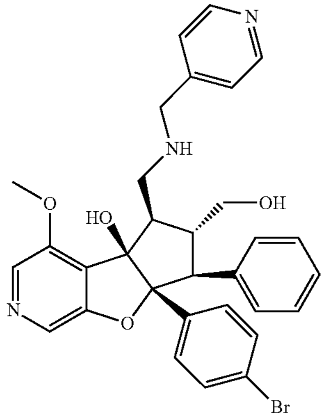

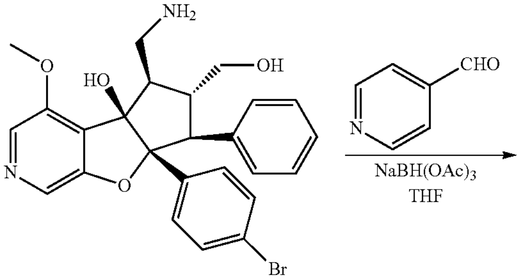

1

-continued

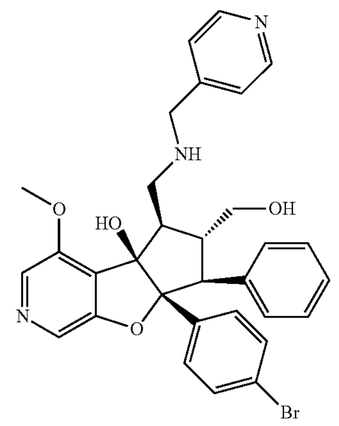

187F

Synthesis of rac-(4bR,5R,6R,7S,7aR)-7a-(4-bromophenyl)-6-(hydroxymethyl)-4-methoxy-7-phenyl-5-(((pyridin-4-ylmethyl)amino)methyl)-5,6,7,7a-tetrahydro-4bH-cyclopenta[4,5]furo[2,3-c]pyridin-4b-ol (Cpd. No. 187F)

To a solution of rac-(4bR,5R,6R,7S,7aR)-5-(aminomethyl)-7a-(4-bromophenyl)-6-(hydroxymethyl)-4-methoxy-7-phenyl-5,6,7,7a-tetrahydro-4bH-cyclopenta[4,5]furo[2,3-c]pyridin-4b-ol (1, 50 mg, 0.10 mmol) in THF (1 mL) were added pyridine-4-carbaldehyde (13 mL, 15 mg, 0.14 mmol), acetic acid (1.2 mL, 1.3 mg, 0.021 mmol) and molecular sieves (ca. 80 mg). The mixture was stirred for 30 min. Sodium triacetoxyborohydride (85 mg, 0.40 mmol) was added. After 1 h the reaction was quenched with $NaHCO_3$ (aq), and the mixture was extracted (3×dichloromethane). The combined organic phases were dried ($Na_2SO_4$), filtered and concentrated. The crude product was taken up in MeCN/DMSO/water and subjected to purification by HPLC (C18, MeCN/water+0.1% TFA) to yield 52.6 mg (0.0749 mmol, 74%) of the TFA salt of rac-(4bR,5R,6R,7S,7aR)-7a-(4-bromophenyl)-6-(hydroxymethyl)-4-methoxy-7-phenyl-5-(((pyridin-4-ylmethyl)amino)methyl)-5,6,7,7a-tetrahydro-4bH-cyclopenta[4,5]furo[2,3-c]pyridin-4b-ol (Cpd. No. 187F) as a white solid; MS (ESI) m/z 588.3 $[M+1]^+$; $^1H$ NMR (400 MHz, DMSO-$d_6$) δ 9.29 (b, 1H), 8.76-8.73 (m, 2H), 8.72 (b, 1H), 8.22 (s, 1H), 8.14 (s, 1H), 7.66-7.63 (m, 2H), 7.32 (d, J=8.8 Hz, 2H), 7.14-7.04 (m, 5H), 6.84-6.79 (m, 2H), 6.32 (s, 1H), 5.49 (b, 1H), 4.51-4.45 (m, 2H), 3.91 (s, 3H), 3.75-3.61 (m, 1H), 3.50-3.41 (m, 1H), 3.44 (dd, J=11.2, 2.7 Hz, 1H), 3.26 (d, J=13.5 Hz, 1H), 3.21 (dd, J=11.2, 6.7 Hz, 1H), 3.11-3.04 (m, 1H), 2.76-2.65 (m, 1H).

Example 188

Rac-4-((4bR,5R,6R,7S,7aR)-4b-hydroxy-6-(hydroxymethyl)-4-methoxy-7-phenyl-5-(((pyridin-4-ylmethyl)amino)methyl)-4b,5,6,7-tetrahydro-7aH-cyclopenta[4,5]furo[2,3-c]pyridin-7a-yl)benzonitrile (Cpd. No. 188F)

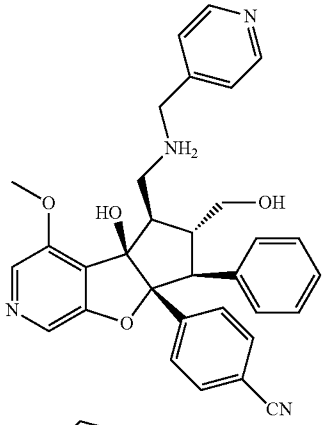

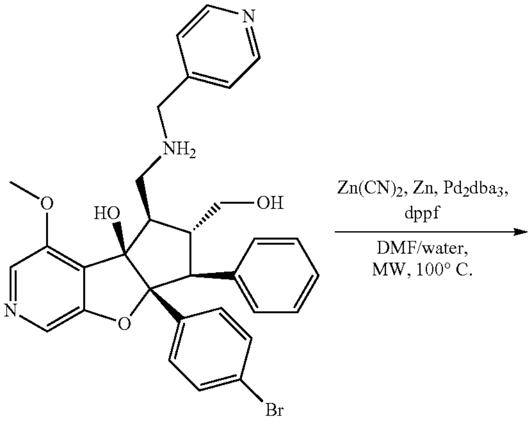

1

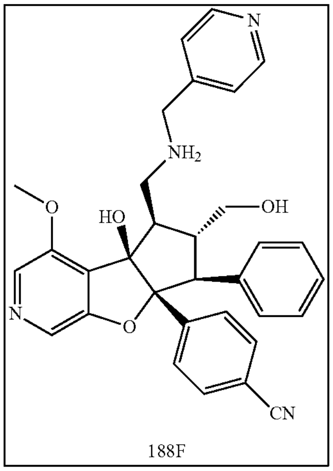

188F

Synthesis of rac-4-((4bR,5R,6R,7S,7aR)-4b-hydroxy-6-(hydroxymethyl)-4-methoxy-7-phenyl-(((pyridin-4-ylmethyl)amino)methyl)-4b,5,6,7-tetrahydro-7aH-cyclopenta[4,5]furo[2,3-c]pyridin-7a-yl) benzonitrile (Cpd. No. 188F)

In a 0.5-2 mL microwave vial rac-(4bR,5R,6R,7S,7aR)-7a-(4-bromophenyl)-6-(hydroxymethyl)-4-methoxy-7-phenyl-5-(((pyridin-4-ylmethyl)amino)methyl)-5,6,7,7a-tetrahydro-4bH-cyclopenta[4,5]furo[2,3-c]pyridin-4b-ol (1, 39.7 mg, 0.0565 mmol) was dissolved in N,N-dimethylformamide (0.7 mL) and water (0.07 mL). Zinc cyanide (32 mg, 0.27 mmol) and zinc (1.5 mg, 0.023 mmol) were added, and the mixture was degassed by bubbling argon through it for 5 min. Dppf (9.4 mg, 0.017 mmol) and Tris(dibenzylideneacetone)dipalladium(0) (7.5 mg, 0.0082 mmol) were added and the mixture was degassed for another 5 min, then incubated at 100° C. for 2 h in total. The mixture was filtered, diluted with MeCN, DMSO and water, filtered again, and subjected to purification by HPLC (C18, MeCN/water+0.1% TFA) to afford rac-4-((4bR,5R,6R,7S,7aR)-4b-hydroxy-6-(hydroxymethyl)-4-methoxy-7-phenyl-5-(((pyridin-4-ylmethyl)amino)methyl)-4b,5,6,7-tetrahydro-7aH-cyclopenta[4,5]furo[2,3-c]pyridin-7a-yl)benzonitrile (Cpd. No. 188F). Yield: 11.3 mg (0.0174 mmol, 31%); MS (ESI) m/z 535.3 $[M+1]^+$; $^1$H NMR (400 MHz, DMSO-$d_6$) δ 9.31 (b, 1H), 8.80 (b, 1H), 8.75-8.73 (m, 2H), 8.23 (s, 1H), 8.15 (s, 1H), 7.67-7.64 (m, 2H), 7.61 (d, J=8.4 Hz, 2H), 7.34 (bd, J=8.4 Hz, 2H), 7.13-7.06 (m, 3H), 6.84-6.80 (m, 2H), 6.37 (s, 1H), 5.58 (b, 1H), 4.52-4.45 (m, 2H), 3.91 (s, 3H), 3.76-3.65 (m, 1H), 3.52-3.42 (m, 1H), 3.46 (dd, J=11.0, 2.4 Hz, 1H), 3.33 (d, J=13.5 Hz, 1H), 3.23 (dd, J=11.0, 6.7 Hz, 1H), 3.12-3.05 (m, 1H), 2.84-2.73 (m, 1H).

Example 189

Rac-4-((5aR,6S,7R,8S,8aS)-3-chloro-8,8a-dihydroxy-6-phenyl-7-(pyridin-2-ylthio)-6,7,8,8a-tetrahydro-5aH-cyclopenta[4,5]furo[3,2-b]pyridin-5a-yl) benzonitrile (Cpd. No. 189F)

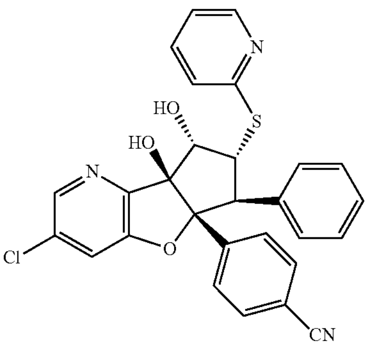

-continued

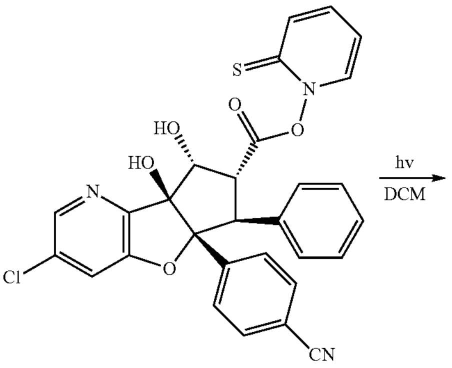

1

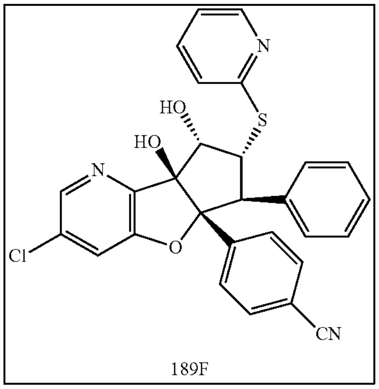

189F

Synthesis of rac-4-((5aR,6S,7R,8S,8aS)-3-chloro-8,8a-dihydroxy-6-phenyl-7-(pyridin-2-ylthio)-6,7,8,8a-tetrahydro-5aH-cyclopenta[4,5]furo[3,2-b]pyridin-5a-yl)benzonitrile (Cpd. No. 189F)

Rac-2-thioxopyridin-1(2H)-yl (5aR,6S,7R,8R,8aS)-3-chloro-5a-(4-cyanophenyl)-8,8a-dihydroxy-6-phenyl-5a,7,8,8a-tetrahydro-6H-cyclopenta[4,5]furo[3,2-b]pyridine-7-carboxylate (1, 34 mg, 0.060 mmol) was dissolved in dichloromethane (1.8 mL) in a microwave vial. The vial was sealed then irradiated with 250 watt halogen lamp and the lamp and vial were enveloped in a sheet of aluminum foil. After stirring under irradiating conditions overnight all solvent had evaporated. LCMS of this residue indicated that the thiopyridine product was the major component. This residue was purified by RP HPLC to afford rac-4-((5aR,6S,7R,8S,8aS)-3-chloro-8,8a-dihydroxy-6-phenyl-7-(pyridin-2-ylthio)-6,7,8,8a-tetrahydro-5aH-cyclopenta[4,5]furo[3,2-b]pyridin-5a-yl)benzonitrile (Cpd. No. 189F). Yield: 17.9 mg, 57%; MS (ESI) m/z 514.2 (M+H) $^1$H NMR (400 MHz, methanol-$d_4$) δ 8.53 (m, 1H), 8.17 (s, 1H), 7.73 (dd, 1H), 7.56 (s, 1H). 7/52 (d, 2H), 7.43 (d, 2H), 7.41 (dd, 1H), 7.27 (dd, 1H), 7.04-6.97 (m, 5H), 5.45 (m, 1H), 4.35 (d, 1H), 4.37 (d, 1H).

Example 190

Rac-(5aR,6S,8aS)-5a-(4-bromophenyl)-3-chloro-8-ethynyl-8,8a-dihydroxy-N,N-dimethyl-6-phenyl-5a,7,8,8a-tetrahydro-6H-cyclopenta[4,5]furo[3,2-b]pyridine-7-carboxamide (Cpd. No. 190F)

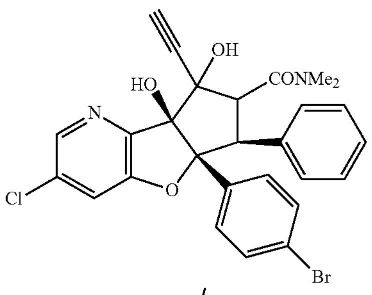

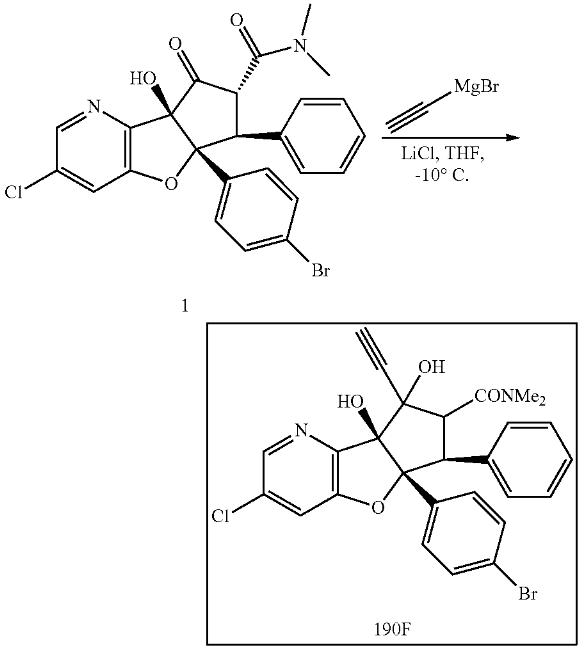

1

190F

Synthesis of rac-(5aR,6S,8aS)-5a-(4-bromophenyl)-3-chloro-8-ethynyl-8,8a-dihydroxy-N,N-dimethyl-6-phenyl-5a,7,8,8a-tetrahydro-6H-cyclopenta[4,5]furo[3,2-b]pyridine-7-carboxamide (Cpd. No. 190F)

Rac-(5aR,6S,7R,8aR)-5a-(4-bromophenyl)-3-chloro-8a-hydroxy-N,N-dimethyl-8-oxo-6-phenyl-5a,7,8,8a-tetrahydro-6H-cyclopenta[4,5]furo[3,2-b]pyridine-7-carboxamide (1, 40.8 mg, 0.080 mmol) and flame dried lithium chloride (26 mg, 0.62 mmol) were dissolved in THF (1 mL) in a flame dried vial. The mixture was cooled to −10° C. and ethynyl magnesium bromide (0.97 mL 0.48 mmol) was added dropwise. The reaction was monitored by LCMS. After 1 hr the desired product constituted a major component of reaction mixture. The reaction was quenched after 1 hr at −10+ C. with sat $NH_4Cl$, EtOAc was added, the layers separated and the aqueous layer was extracted with more EtOAc ×2. The combined organic material was washed with brine and dried over magnesium sulfate. The mixture was purified by RP-HPLC to afford rac-(5aR,6S,8aS)-5a-(4-bromophenyl)-3-chloro-8-ethynyl-8,8a-dihydroxy-N,N-dimethyl-6-phenyl-5a,7,8,8a-tetrahydro-6H-cyclopenta[4,5]furo[3,2-b]pyridine-7-carboxamide (Cpd. No. 190F). Yield: 33%; MS (ESI) m/z 553.3, 555.3 (M+H) $^1H$ NMR (400 MHz, Chloroform-d) δ 8.13 (s, 1H), 7.44 (bs, 1H), 7.32 (s, 1H), 7.17 (d, J=8 Hz, 2H)), 7.09-7.03 (m, 5H), 2H), 6.91 (d, J=8 Hz, 2H), 4.86 (d, J=13.3 Hz, 1H), 4.48 (d, J=13.3 Hz, 1H), 3.44 (s, 3H), 3.02 (s, 3H), 2.73 (s, 1H).

Example 191

Rac-(5aR,6S,8aS)-5a-(4-bromophenyl)-3-chloro-8,8a-dihydroxy-N,N-dimethyl-6-phenyl-8-(prop-1-yn-1-yl)-5a,7,8,8a-tetrahydro-6H-cyclopenta[4,5]furo[3,2-b]pyridine-7-carboxamide (Cpd. No. 191F)

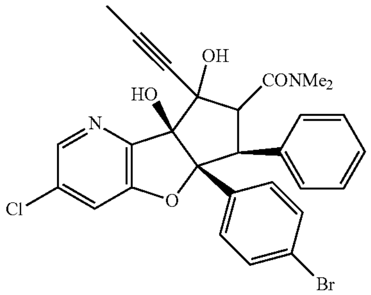

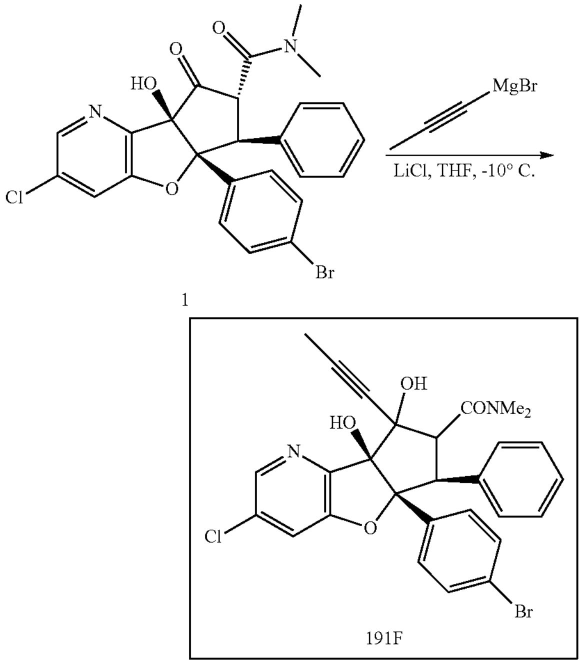

1

191F

Synthesis of rac-(5aR,6S,8aS)-5a-(4-bromophenyl)-3-chloro-8,8a-dihydroxy-N,N-dimethyl-6-phenyl-8-(prop-1-yn-1-yl)-5a,7,8,8a-tetrahydro-6H-cyclopenta[4,5]furo[3,2-b]pyridine-7-carboxamide (Cpd. No. 191F)

Rac-(5aR,6S,7R,8aR)-5a-(4-bromophenyl)-3-chloro-8a-hydroxy-N,N-dimethyl-8-oxo-6-phenyl-5a,7,8,8a-tetrahydro-6H-cyclopenta[4,5]furo[3,2-b]pyridine-7-carboxamide (1, 39 mg, 0.060 mmol) and flame dried lithium chloride (21.3 mg, 0.5 mmol) in THF (1 mL) to −10° C. 1-propynyl magnesium bromide (0.78 mL, 0.39 mmol) was added dropwise. After 1 hr the desired product constituted a major component of reaction mixture. The reaction was quenched after 1 hr at −10° C. with sat $NH_4Cl$, EtOAc was added, the layers separated and the aqueous layer was extracted with more EtOAc ×2. The combined organic material was washed with brine and dried over magnesium sulfate. The mixture was purified by RP-HPLC to afford rac-(5aR,6S,8aS)-5a-(4-bromophenyl)-3-chloro-8,8a-dihydroxy-N,N-dimethyl-6-phenyl-8-(prop-1-yn-1-yl)-5a,7,8,8a-tetrahydro-6H-cyclopenta[4,5]furo[3,2-b]pyridine-7-carboxamide (Cpd. No. 191F) as a white solid. MS (ESI) m/z 567.1, 569.1 (M+H) $^1$H NMR (400 MHz, DMSO-$d_6$) δ 8.13 (d, J=2.0 Hz, 1H), 7.62 (d, J=2.0 Hz, 1H), 7.14 (d, J=8 Hz, 2H), 7.10-7.00 (m, 4H), 6.96 (t, J=7.3 Hz, 1H), 6.94-6.86 (m, 2H), 6.48 (s, 1H), 6.22 (s, 1H), 5.40 (s, 1H), 4.71 (d, J=13.2 Hz, 1H), 4.48 (d, J=13.3 Hz, 1H), 3.43 (s, 3H), 2.86 (s, 3H), 1.89 (s, 3H).

Example 192

Rac-(4bR,7S,7aR)-7a-(4-bromophenyl)-4b-hydroxy-4-methoxy-N,N-dimethyl-5-oxo-7-phenyl-4b,6,7,7a-tetrahydro-5H-cyclopenta[4,5]furo[2,3-c]pyridine-6-carboxamide (Cpd. No. 192F)

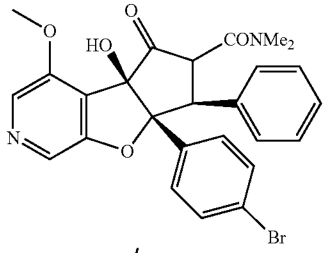

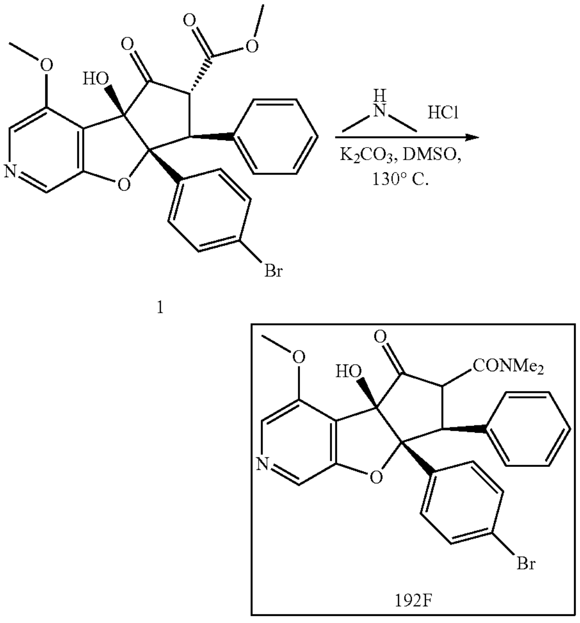

1

192F

Synthesis of rac-(4bR,7S,7aR)-7a-(4-bromophenyl)-4b-hydroxy-4-methoxy-N,N-dimethyl-5-oxo-7-phenyl-4b,6,7,7a-tetrahydro-5H-cyclopenta[4,5]furo[2,3-c]pyridine-6-carboxamide (Cpd. No. 192F)

Rac-methyl (4bR,6R,7S,7aR)-7a-(4-bromophenyl)-4b-hydroxy-4-methoxy-5-oxo-7-phenyl-4b,6,7,7a-tetrahydro-5H-cyclopenta[4,5]furo[2,3-c]pyridine-6-carboxylate (1, 250 mg, 0.49 mmol) and potassium carbonate (1.596 g, 4.9 mmol) were placed in vial and then DMSO (5 mL) was added. Dimethylamine hydrochloride salt (0.04 mL) 1.47 mmol) was added to the solution and the mixture heated to 130° C. After 5 hr LCMS indicated full consumption of the starting material. The pot was cooled to rt and the solution was dissolved in EtOAc and sat. aq. $NH_4Cl$. The layers were separated and aqueous material extracted with EtOAc ×3; the combined organic material was washed with brine and dried over magnesium sulfate. Purification by automated flash chromatography (eluting twice dichloromethane and MeOH) led to isolation of product in good purity. A small portion was further purified by semiprep RP-HPLC to afford rac-(4bR,7S,7aR)-7a-(4-bromophenyl)-4b-hydroxy-4-methoxy-N,N-dimethyl-5-oxo-7-phenyl-4b,6,7,7a-tetrahydro-5H-cyclopenta[4,5]furo[2,3-c]pyridine-6-carboxamide (Cpd. No. 192F) as a white solid. MS (ESI) m/z 523.1, 525.1 (M+H) $^1$H NMR (400 MHz, DMSO-$d_6$) δ 8.30 (d, J=0.4 Hz, 1H), 8.12 (d, J=0.4 Hz, 1H), 7.33 (d, J=8 Hz, 2H), 7.14-7.01 (m, 5H), 6.97-6.90 (m, 2H), 6.59 (s, 1H), 4.72 (d, J=13.2 Hz, 1H), 4.18 (d, J=13.2 Hz, 1H), 3.86 (s, 3H), 2.74 (s, 3H).

Example 193

Rac-Methyl (4bS,5R,6R,7aR)-4b,5-dihydroxy-7a-(4-iodophenyl)-4-methoxy-7-phenyl-4b,6,7,7a-tetrahydro-5H-cyclopenta[4,5]furo[2,3-c]pyridine-6-carboxylate (Cpd. No. 193F)

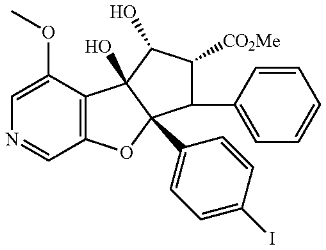

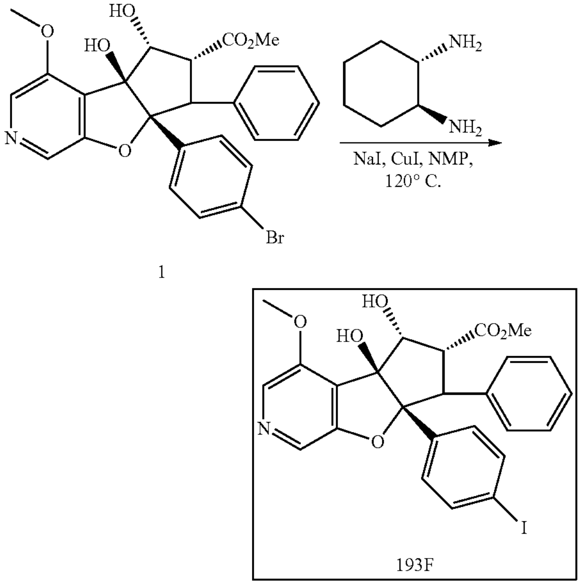

1

193F

Synthesis of rac-methyl (4bS,5R,6R,7aR)-4b,5-dihydroxy-7a-(4-iodophenyl)-4-methoxy-7-phenyl-4b,6,7,7a-tetrahydro-5H-cyclopenta[4,5]furo[2,3-c]pyridine-6-carboxylate (Cpd. No. 193F)

Cyclohexane-1,2-diamine (11 mg, 0.10000 mmol) was placed in a vial with NMP (1 mL). Sodium iodide (52.66 mg, 0.35 mmol) and rac-methyl (4bS,5R,6R,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylate (1, 90 mg, 0.18000 mmol) were added, followed by copper (D) iodide (10.04 mg, 0.05000 mmol). The mixture was degassed by sparging with an argon balloon for 10 min. The vial was sealed and heated to 120° C. The reaction was monitored by LCMS. After heating for 23 hr the reaction was cooled to rt and diluted with 10 mL dichloromethane and filtered through celite. The filtrate was rotavapped and then the residue was taken up in EtOAc. Saturated aq $NH_4Cl$ was added, the layers separated and aqueous layer extracted with EtOAc ×3. The combined organic material was washed with brine and dried over magnesium sulfate. In order to remove any residual copper the residue was taken up in EtOAc. Water and 1 mL 3M $NH_3$ in dioxane were added and the aqueous layer was extracted with EtOAc ×3. The combined organic material was washed with brine and dried over magnesium sulfate. The crude material was purified on semiprep RP-HPLC to afford rac-methyl (4bS,5R,6R,7aR)-4b,5-dihydroxy-7a-(4-iodophenyl)-4-methoxy-7-phenyl-4b,6,7,7a-tetrahydro-5H-cyclopenta[4,5]furo[2,3-c]pyridine-6-carboxylate (Cpd. No. 193F) as a white solid. Yield 43%; MS (ESI) m/z 560.2 (M+H)$^1$H NMR (400 MHz, DMSO-$d_6$) δ 8.19 (s, 1H), 8.04 (s, 1H), 7.34 (d, J=8 Hz, 2H), 7.08-6.99 (m, 2H), 7.01-6.90 (m, 3H), 6.87 (d, J 8 Hz, 2H), 5.84 (s, 1H), 5.67 (s, 1H), 4.67 (d, J=4.8 Hz, 1H), 4.30 (d, J=13.9 Hz, 1H), 4.07 (dd, J=14.0, 4.9 Hz, 1H), 3.86 (d, J=1.1 Hz, 3H), 1.21 (s, 1H).

Example 194

Rac-4-((4bS,5R,6S,7S,7aR)-6-((4-acetylpiperazin-1-yl)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 194F)

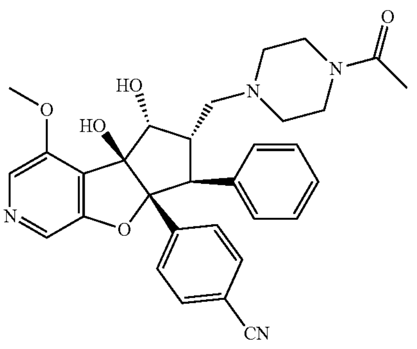

-continued

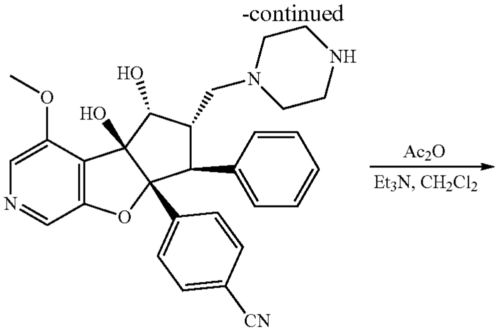

1

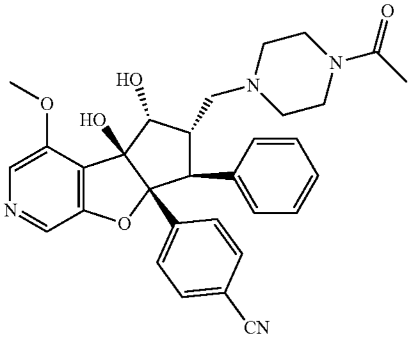

194F

Synthesis of rac-4-((4bS,5R,6S,7S,7aR)-6-((4-acetylpiperazin-1-yl)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 194F)

Rac-4-((4bS,5R,6S,7S,7aR)-4b,5-dihydroxy-4-methoxy-7-phenyl-6-(piperazin-1-ylmethyl)-4b,5,6,7-tetrahydro-7aH-cyclopenta[4,5]furo[2,3-c]pyridin-7a-yl)benzonitrile (1, 25 mg, 0.05 mmol) was dissolved in dichloromethane (0.5 mL) in a microwave vial. Triethylamine (0.03 mL, 0.2 mL) was then added, followed by acetic anhydride (0.01 mL, 0.06 mmol). The vial was sealed and stirred at rt. LCMS at 30 min indicated complete conversion to product. The reaction mixture was poured onto saturated aqueous $NaHCO_3$ and diluted with dichloromethane. The aqueous layer was extracted with dichloromethane ×3, the combined organic material was washed with brine and dried over magnesium sulfate. The crude material was purified by RP-HPLC to afford rac-4-((4bS,5R,6S,7S,7aR)-6-((4-acetylpiperazin-1-yl)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 194F) as a fluffy white solid after lyophilization. Yield 59%; MS (ESI) m/z 494.0, 496.0 (M+H)$^1$H NMR (400 MHz, DMSO-$d_6$) δ 9.41 (s, 1H), 8.08 (dd, J=28, 2.7 Hz, 1H), 7.51 (d, J=8.6 Hz, 1H), 7.40 (d, J=8.5 Hz, 1H), 7.13-6.95 (m, 3H), 5.90 (bs, 1H), 5.45 (bs, 1H), 4.72 (bs, 1H), 4.44 (bs, 1H), 3.98 (bs, 1H), 3.89 (d, J=0.7 Hz, 3H), 3.85-3.72 (m, 2H), 3.85-3.72 (m, 2H), 3.29 (m, 1H), 3.07-2.9 (m, 3H), 2.02 (d, J=8.3 Hz, 2H).

Example 195

Rac-(5aR,6S,7S,8R,8aS)-5a-(4-bromophenyl)-3-chloro-7-(((2,2-difluoroethyl)amino)methyl)-1-methoxy-6-phenyl-5a,6,7,8-tetrahydro-8aH-cyclopenta[4,5]furo[3,2-c]pyridine-8,8a-diol (Cpd. No. 195F)

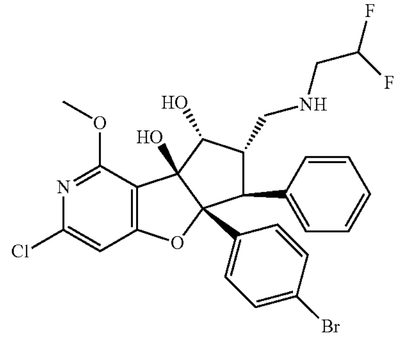

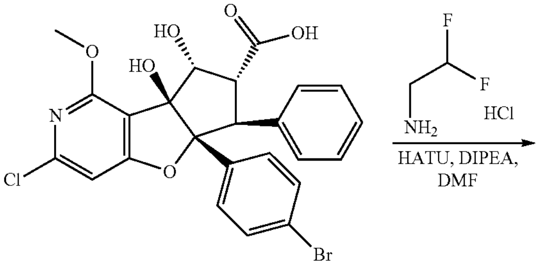

1

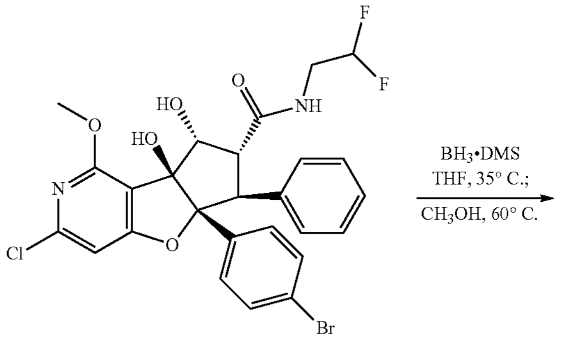

2

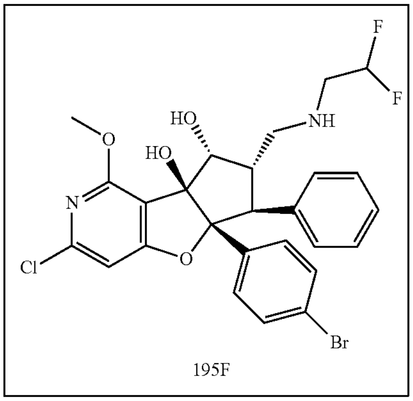

195F

Synthesis of rac-(5aR,6S,7R,8R,8aS)-5a-(4-bromophenyl)-3-chloro-N-(2,2-difluoroethyl)-8,8a-dihydroxy-1-methoxy-6-phenyl-5a, 7,8,8a-tetrahydro-6H-cyclopenta[4,5]furo[3,2-c]pyridine-7-carboxamide (2)

Rac-(5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridine-7-carboxylic acid (1, 80 mg, 0.15 mmol) was dissolved in N,N-dimethylformamide (3 mL in a vial under argon. Added HATU (60 mg, 0.16 mmol) After 30 min DIPEA (0.08 mL, 0.45 mmol) was added with automated pipette and the solution stirred at rt 45 min then 2,2 difluoroethylamine hydrochloride salt (0.45 mmol) was added in one portion. LCMS at 3 hr looks like >90% conversion to product. The reaction mixture was diluted with 90% EtOAc:Hexanes and washed with water 3×, then brine and dried over magnesium sulfate. The crude product was purified by automated flash chromatography to afford rac-(5aR,6S,7R,8R,8aS)-5a-(4-bromophenyl)-3-chloro-N-(2,2-difluoroethyl)-8,8a-dihydroxy-1-methoxy-6-phenyl-5a,7,8,8a-tetrahydro-6H-cyclopenta[4,5]furo[3,2-c]pyridine-7-carboxamide (2) as a white solid, which was carried on to the next step. MS (ESI) m/z 593.2, 595.2 (M+H).

Synthesis of rac-(5aR,6S,7S,8R,8aS)-5a-(4-bromophenyl)-3-chloro-7-(((2,2-difluoroethyl)amino)methyl)-1-methoxy-6-phenyl-5a,6,7,8-tetrahydro-8aH-cyclopenta[4,5]furo[3,2-c]pyridine-8,8a-diol (Cpd. No. 195F)

Rac-(5aR,6S,7R,8R,8aS)-5a-(4-bromophenyl)-3-chloro-N-(2,2-difluoroethyl)-8,8a-dihydroxy-1-methoxy-6-phenyl-5a,7,8,8a-tetrahydro-6H-cyclopenta[4,5]furo[3,2-c]pyridine-7-carboxamide (2, 96 mg, 1.6 mmol) was stirred in THF (3 mL) under argon. Borane dimethylsulfide complex (0.15 mL, 1.59 mmol) was added dropwise and subsequently attached a reflux condenser and warmed to 35° C. LCMS of an aliquot at 5 hours looks like almost all SM has been consumed, so the reaction was quenched very slowly with 2 mL MeOH. It was then heated to 60° C. for 3 hr then cooled to rt overnight (14 hr) and then heated an additional 6 hr at 60° C. at which time LCMS looks like full conversion to product. Solvent was rotavapped and purification was carried out with phenomonex ion exchange column: the column was wetted with water, then the crude residue was loaded as a solution in DMSO/MeCN. The column was washed 2× each with Water, MeCN, and Methanol, and the product was eluted with a 75:20:5 MeOH:dichloromethane: NH4OH solution (column washed with this solution ×3. these combined washes were rotavapped and the product rac-(5aR,6S,7S,8R,8aS)-5a-(4-bromophenyl)-3-chloro-7-(((2,2-difluoroethyl)amino)methyl)-1-methoxy-6-phenyl-5a,6,7,8-tetrahydro-8aH-cyclopenta[4,5]furo[3,2-c]pyridine-8,8a-diol (Cpd. No. 195F) was isolated with high purity as a white solid. Yield: 82.6 mg, 82% (over 2 steps); MS (ESI) m/z 581.2, 583.1 (M+H) $^1$H NMR (400 MHz, DMSO-$d_6$) δ 7.29-7.15 (m, 3H), 7.11-6.90 (m, 10H), 6.84 (s, 1H), 5.93 (t, J=4.3 Hz, 1H), 5.50 (s, 1H), 5.15 (d, J=5.5 Hz, 1H), 4.44 (t, J=4.9 Hz, 1H), 3.82 (s, 4H), 3.63 (d, J=14.3 Hz, 1H), 3.06 (s, 2H), 3.05 (dd, J=14.0, 10.1 Hz, OH), 2.83 (t, J=16.1 Hz, 3H), 2.63 (t, J=10.8 Hz, 2H), 1.20 (s, 1H).

Example 196

Rac-4-((5aR,6S,7S,8R,8aS)-3-chloro-7-(((2,2-difluoroethyl)amino)methyl)-8,8a-dihydroxy-1-methoxy-6-phenyl-6,7,8,8a-tetrahydro-5aH-cyclopenta[4,5]furo[3,2-c]pyridin-5a-yl)benzonitrile (Cpd. No. 196F)

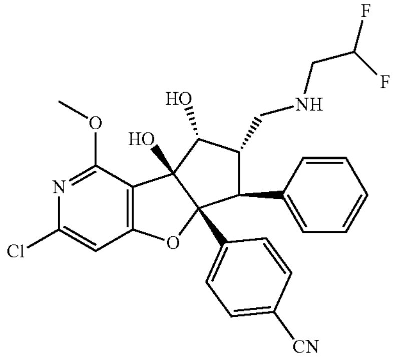

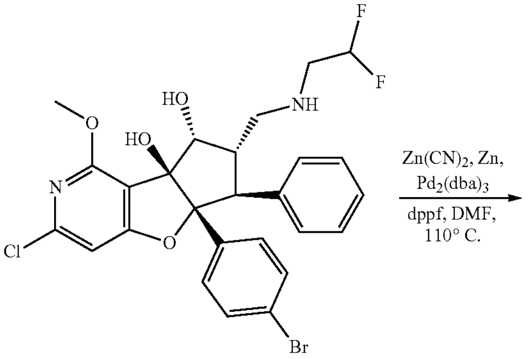

1

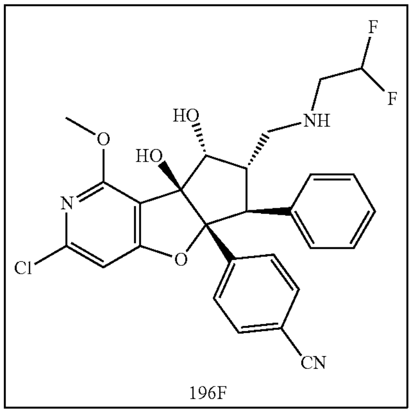

196F

Synthesis of rac-4-((5aR,6S,7S,8R,8aS)-3-chloro-7-(((2,2-difluoroethyl)amino)methyl)-8,8a-dihydroxy-1-methoxy-6-phenyl-6,7,8,8a-tetrahydro-5aH-cyclopenta[4,5]furo[3,2-c]pyridin-5a-yl)benzonitrile (Cpd. No. 196F)

Rac-(5aR,6S,7S,8R,8aS)-5a-(4-bromophenyl)-3-chloro-7-(((2,2-difluoroethyl)amino)methyl)-1-methoxy-6-phenyl-5a,6,7,8-tetrahydro-8aH-cyclopenta[4,5]furo[3,2-c]pyridine-8,8a-diol (1, 27 mg, 0.046 mmol) was dissolved in in N,N-dimethylformamide (0.60 mL) and water (0.060 mL)

and the solution was sparged with argon for 10 minutes. Zinc cyanide (33 mg, 0.278 mmol), zinc (3.0 mg, 0.0464 mmol), Tris(dibenzylideneacetone)dipalladium(0) (3.3 mg, 0.0037 mmol), and dppf (4.1 mg 0.0074 mmol) were added and the mixture heated at 110° C. for 2 hours, at which point LCMS modest conversion to product. The mixture was immediately cooled to rt, filtered through celite, and the filtrate was purified by RP-HPLC to afford rac-4-((5aR,6S,7S,8R,8aS)-3-chloro-7-(((2,2-difluoroethyl)amino)methyl)-8,8a-dihydroxy-1-methoxy-6-phenyl-6,7,8,8a-tetrahydro-5aH-cyclopenta[4,5]furo[3,2-c]pyridin-5a-yl)benzonitrile (Cpd. No. 196F) as a fluffy white solid. Yield 10%; LCMS (ESI) m/z528.2, 530.3 (M+H) $^1$H NMR (400 MHz, DMSO-$d_6$) δ 9.19 (s, 1H), 8.94 (s, 1H), 7.55 (d, J=8.3 Hz, 2H), 7.28 (d, J=8.5 Hz, 2H), 7.14-6.98 (m, 2H), 7.00-6.90 (m, 2H), 6.37 (t, J=48 Hz, 1H), 5.78 (s, 1H), 5.28 (d, J=6.2 Hz, 1H), 4.63 (s, 1H), 3.84 (s, 2H), 3.76 (d, J=14.1 Hz, 1H), 3.55 (bs, 1H), 3.12 (bs, 1H), 2.94 (bs, 1H), 2.81 (bs, 1H).

Example 197

Rac-(5aR,6S,7S,8R,8aS)-5a-(4-cyanophenyl)-7-(((2,2-difluoroethyl)amino)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 197F)

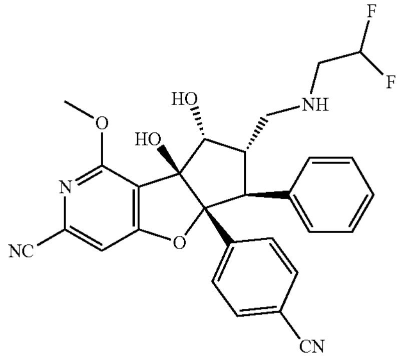

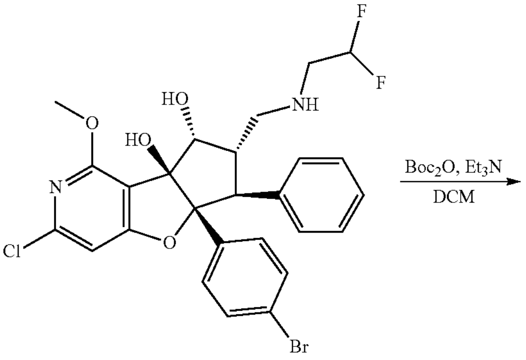

1

-continued

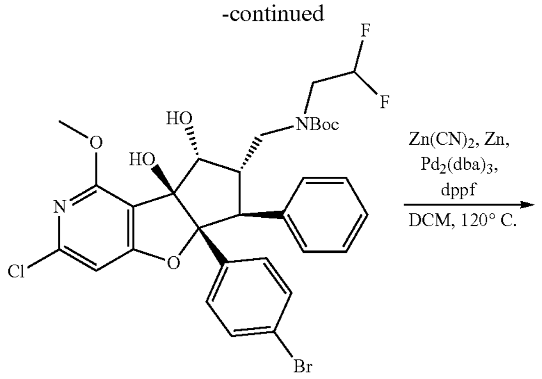

2

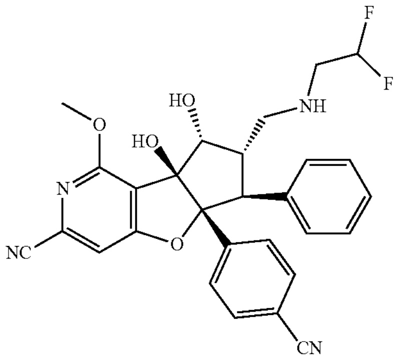

197F

Synthesis of rac-tert-butyl (((5aR,6S,7S,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridin-7-yl)methyl)(2,2-difluoroethyl)carbamate (2)

Rac-(5aR,6S,7S,8R,8aS)-5a-(4-bromophenyl)-3-chloro-7-(((2,2-difluoroethyl)amino)methyl)-1-methoxy-6-phenyl-5a,6,7,8-tetrahydro-8aH-cyclopenta[4,5]furo[3,2-c]pyridine-8,8a-diol (1, 20.2 mg, 0.029 mmol, 1 eq.) was stirred in dichloromethane (0.6 mL) and N,N-dimethylformamide (0.7 mL). Triethylamine (0.012 mL, 0.085 mmol) was added, followed by di-tert-butyl dicarbonate (10.0 mg, 0.0458 mmol) and the mixture stirred at rt fir 40 and subsequently warmed to 35° C. for 8 hr, at which point complete consumption of starting material was observed by LCMS. The solvent was removed in vacuo and the residue was purified by flash chromatography eluting with hexanes and ethyl acetate to afford rac-tert-butyl (((5aR,6S,7S,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridin-7-yl)methyl)(2,2-difluoroethyl)carbamate (2) as a white residue that was carried on to the next step. LCMS (ESI) m/z 681.3, 683.4 (M+H)

Synthesis of rac-(5aR,6S,7S,8R,8aS)-5a-(4-cyanophenyl)-7-(((2,2-difluoroethyl)amino)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 197F)

Rac-tert-butyl (((5aR,6S,7S,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridin-7-yl)methyl)(2,2-difluoroethyl)carbamate (2, 21 mg, 0.03000 mmol) was dissolved in N,N-dimethylformamide (0.70 mL) and water (0.070 mL). Zinc dust (2.0 mg), zinc cyanide (23.5 mg, 0.2006 mmol) Tris(dibenzylideneacetone)dipalladium(0) (1.7 mg, 0.00185 mmol), and dppf (2.05 mg, 0.0037 mmol) were added and the mixture sparged with argon for 5 min. The vial was sealed and then heated to 120° C. for 40 min and then cooled to rt. LCMS-rapid conversion to product and moncyano compound (ca 9:1 product:monocyano after 20 min). After 40 minutes the reaction mixture was diluted with 2.5 mL dichloromethane and filtered with syringe filter. TFA (0.03 mL) was added and the mixture stirred at rt for 1 hr then at 40° C. for 18 hr. The reaction was cooled to rt and passed through an ion exchange column, eluting with water, MeCN, and MeOH, (3× each) and then the produce was washed off column with a 75:20:5 solution of MeOH:dichloromethane:$NH_4OH$. The material was further purified by RP-HPLC to afford rac-(5aR,6S,7S,8R,8aS)-5a-(4-cyanophenyl)-7-(((2,2-difluoroethyl)amino)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 197F). Yield: 25%; LCMS (ESI) m/z 519.3 (M+H) $^1$H NMR (400 MHz, DMSO-$d_6$) δ 9.04 (s, 1H), 7.56 (d, J=8.9 Hz, 2H), 7.29 (d, J=8.5 Hz, 11H), 7.13-6.95 (m, 4H), 6.38, t, J=52 Hz, 1H), 5.94 (s, 1H), 5.43 (s, 1H), 4.69 (s, 1H), 3.89 (s, 2H), 3.76 (d, J=14.2 Hz, 11H), 3.64-3.54 (bs, 3H), 3.50-3.21 (bs, 3H), 3.10 (s, 1H), 2.84 (bs, 1H).

Example 198

4-((5aR,6S,7S,8R,8aS)-3-chloro-8,8a-dihydroxy-1-methoxy-7-((4-methylpiperazin-1-yl)methyl)-6-phenyl-6,7,8,8a-tetrahydro-5aH-cyclopenta[4,5]furo[3,2-c]pyridin-5a-yl)benzonitrile (Cpd. No. 198aF)

Rac-(5aR,6S,7S,8R,8aS)-5a-(4-cyanophenyl)-8,8a-dihydroxy-1-methoxy-7-((4-methylpiperazin-1-yl)methyl)-6-phenyl-5a,7,8,8a-tetrahydro-6H-cyclopenta[4,5]furo[3,2-c]pyridine-3-carbonitrile (Cpd. No. 198bF)

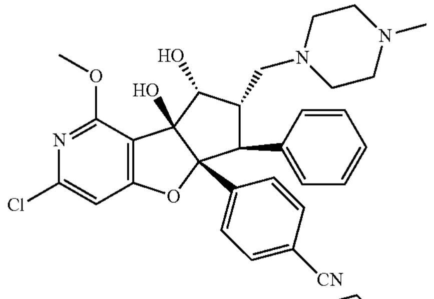

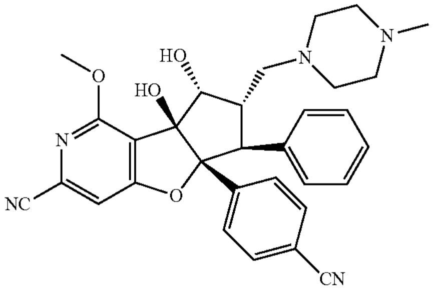

-continued

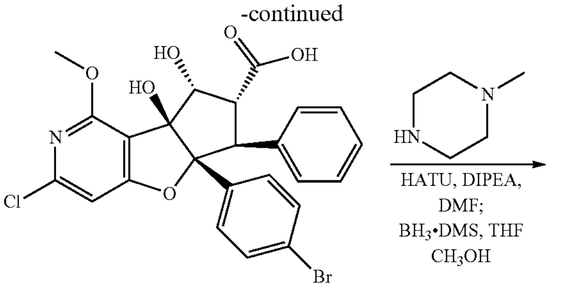

1

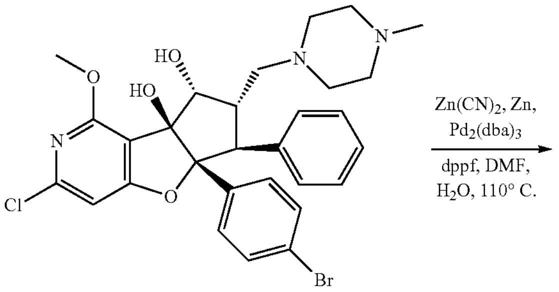

2

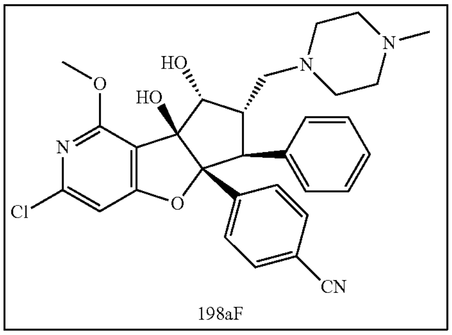

198aF

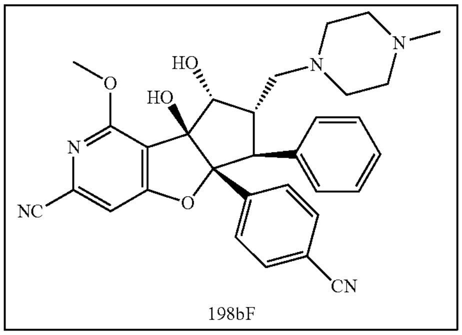 [SMILES: COc1nc(C#N)cc2c1[C@]1(O)[C@H](O)[C@H](CN3CCN(C)CC3)[C@@H](c3ccccc3)[C@]1(c1ccc(C#N)cc1)O2]

198bF

Synthesis of rac-(5aR,6S,7S,8R,8aS)-5a-(4-bromophenyl)-3-chloro-1-methoxy-7-((4-methylpiperazin-1-yl)methyl)-6-phenyl-5a,6,7,8-tetrahydro-8aH-cyclopenta[4,5]furo[3,2-c]pyridine-8,8a-diol (2)

Rac-(5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridine-7-carboxylic acid (1) was dissolved in N,N-dimethylformamide (2.8 mL) under an atmosphere of argon. HATU (124 mg, 0.33 mmol) was added in one portion and 2 minutes later Hunig's base (0.08 mmol, 0.45 mmol) was added dropwise. After 20 min LCMS (taken in MeOH) looks like complete consumption of (1). 1-methylpiperizine (0.1 mL, 0.93 mmol) was added and the reaction mixture stirred another 40 min, at which time LCMS shows complete conversion to product. The reaction mixture was cooled, poured onto water, diluted with 90% EtOAc/hexanes, and the organic material was washed an additional 3× with water. It was then washed with brine and dried over magnesium sulfate. The product was purified by flash chromatography to provide a solid of sufficient purity for the next step.

The intermediate amide was dissolved in THF (3 mL) and a solution of borane dimethyl sulfide complex (0.151 mL, 1.59 mmol) was added dropwise and the mixture subsequently warmed to 35° C. under a reflux condenser. LCMS of an aliquot at 5 hours looks like almost all starting material has been consumed, so the reaction was quenched very slowly with 2 mL of methanol. It was then heated to 60° C. for 3 hr then cooled to room temperature and stirred overnight (14 hr) and then heated an additional 6 hr at 60° C. at which time LCMS looks like full conversion to product. Solvent was rotavapped and purification was carried out with phenomonex ion exchange column: the column was wetted with water, then the crude residue was loaded as a solution in DMSO/MeCN. The column was washed 2×each with Water, MeCN, and Methanol, and the product was eluted with a 75:20:5 MeOH:dichloromethane:$NH_4OH$ solution (column washed with this solution ×3. these combined washes were rotavapped and the product was isolated with high purity.

Synthesis of 4-((5aR,6S,7S,8R,8aS)-3-chloro-8,8a-dihydroxy-1-methoxy-7-((4-methylpiperazin-1-yl)methyl)-6-phenyl-6,7,8,8a-tetrahydro-5aH-cyclopenta[4,5]furo[3,2-c]pyridin-5a-yl)benzonitrile (Cpd. No. 198aF)

Rac-(5aR,6S,7S,8R,8aS)-5a-(4-cyanophenyl)-8,8a-dihydroxy-1-methoxy-7-((4-methylpiperazin-1-yl)methyl)-6-phenyl-5a,7,8,8a-tetrahydro-6H-cyclopenta[4,5]furo[3,2-c]pyridine-3-carbonitrile (Cpd. No. 198bF)

Rac-(5aR,6S,7S,8R,8aS)-5a-(4-bromophenyl)-3-chloro-1-methoxy-7-((4-methylpiperazin-1-yl)methyl)-6-phenyl-5a,6,7,8-tetrahydro-8aH-cyclopenta[4,5]furo[3,2-c]pyridine-8,8a-diol (2, 28 mg, 0.046 mmol) was dissolved in N,N-dimethylformamide (0.80 mL) and water (0.080 mL) and the solution was sparged with argon for 10 minutes. Zinc cyanide (35 mg, 0.30 mol), zinc dust (3 mg, 0.047 mmol), Tris(dibenzylideneacetone)dipalladium(0) (2.6 mg, 0.003 mmol), and dppf (3 mg, 0.005 mmol) were added and the mixture heated at 110° C. for 30 minutes, at which point LCMS indicated conversion to a mixture of starting material, mono- and bis-cyanated compounds. The mixture was immediately cooled to rt, filtered through celite, and the filtrate was purified by RP-HPLC to afford the both mono- and bis-cyanated products as white solids. Combined yield 11%

4-((5aR,6S,7S,8R,8aS)-3-Chloro-8,8a-dihydroxy-1-methoxy-7-((4-methylpiperazin-1-yl)methyl)-6-phenyl-6,7,8,8a-tetrahydro-5aH-cyclopenta[4,5]furo[3,2-c]pyridin-5a-yl)benzonitrile: The enantiomers were separated by chiral SFC [CHHIALPAK IG (4.6 ×250)mm, 5μ], Mobile Phase: $CO_2$/MeOH/TEA (60:40:0.2)], Peak 1 (1.56 g), $R_t$=2.833 min, ee: 99.92%, $[\alpha]_D$+47.10 (c 0.25, $CHCl_3$); MS (ESI) m/z 547.24[M+1]$^+$; $^1H$ NMR (400 MHz, DMSO-d) 7.49 (d, J=8.52 Hz, 2H), 7.34 (d, J=8.48 Hz, 2H), 7.08-7.05 (m, 2H), 7.00-6.97 (m, 3H), 6.88 (s, 1H), 5.66 (s, 1H), 5.14 (bs, 1H), 4.42 (d, J=3.72 Hz, 1H), 3.84 (s, 3H), 3.77 (d, J=14.04 Hz, 1H), 3.22-3.20 (m, 1H), 2.62-2.56 (m, 2H), 2.49-2.32 (m, 7H), 2.15 (s, 3H), 2.05 (d, J=9.92 Hz, 1H); Peak-2 (Cpd. No. 198aF, 1.55 g), $R_t$=3.83 min, ee: 99.36%, $[\alpha]_D$-29.2° (c 0.30, $CHCl_3$); MS (ESI) m/z 547.24[M+1]$^+$; $^1$H NMR (400 MHz, DMSO-$d_6$) 7.49 (d, J=8.52 Hz, 2H), 7.34 (d, J=8.48 Hz, 2H), 7.08-7.05 (m, 2H), 7.00-6.97 (m, 3H), 6.88 (s, 1H), 5.66 (s, 1H), 5.15 (bs, 1H), 4.43 (bs, 1H), 3.84 (s, 3H), 3.77 (d, J=14.12, Hz, 1H), 3.22-3.20 (m, 1H), 2.62-2.56 (m, 2H), 2.49-2.32 (m, 7H), 2.15 (s, 3H), 2.05 (d, J=9.92 Hz, 1H).

Rac-(5aR,6S,7S,8R,8aS)-5a-(4-cyanophenyl)-8,8a-dihydroxy-1-methoxy-7-((4-methylpiperazin-1-yl)methyl)-6-phenyl-5a,7,8,8a-tetrahydro-6H-cyclopenta[4,5]furo[3,2-c]pyridine-3-carbonitrile (Cpd. No. 198bF): MS (ESI) m/z 538.7 (M+H)$^1$H NMR (400 MHz, DMSO-$d_6$) δ 7.54 (s, 1H), 7.49 (d, J=8.6 Hz, 1H), 7.35 (d, J=8.6 Hz, 1H), 7.07-6.95 (m, 5H) 5.81 (s, 1H), 4.48 (s, 1H), 3.87 (s, 3H), 3.73 (d, J=14.1 Hz, 1H), 2.96 (bs, 5H), 2.77 (bs, 3H).

Example 199

Rac-(5aR,6S,7R,8R,8aR)-5a-(4-bromophenyl)-3-chloro-7-(hydroxymethyl)-1-methoxy-8-(morpholinomethyl)-6-phenyl-5a,6,7,8-tetrahydro-8aH-cyclopenta[4,5]furo[3,2-c]pyridin-8a-ol (Cpd. No. 199F)

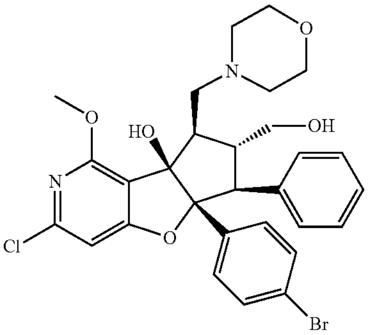

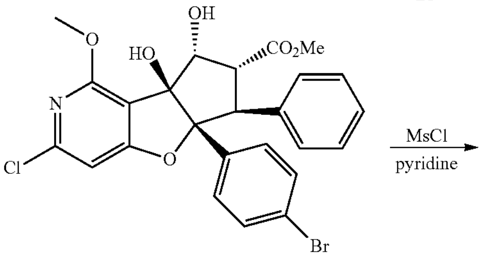

1

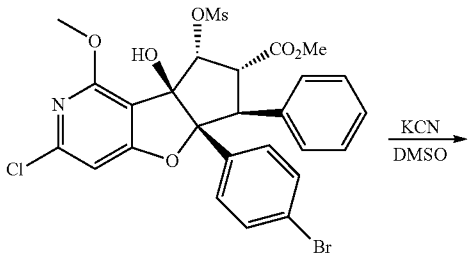

2

-continued

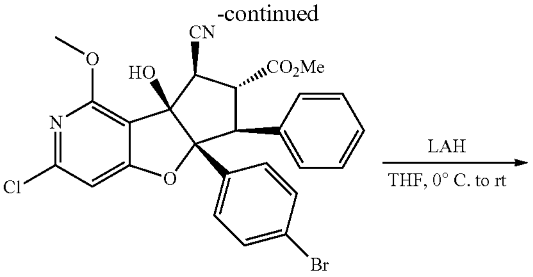

3

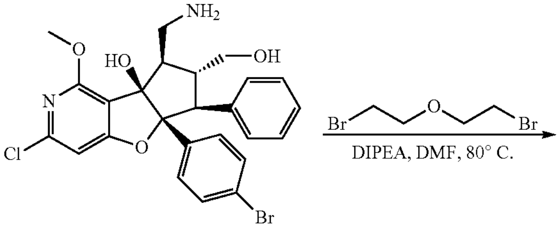

4

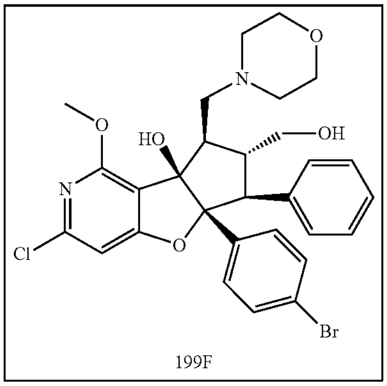

199F

Synthesis of rac-methyl (5aR,6S,7R,8R,8aS)-5a-(4-bromophenyl)-3-chloro-8a-hydroxy-1-methoxy-8-((methylsulfonyl)oxy)-6-phenyl-5a,7,8,8a-tetrahydro-6H-cyclopenta[4,5]furo[3,2-c]pyridine-7-carboxylate (2)

To a solution of rac-methyl (5aR,6S,7R,8R,8aS)-5a-(4-bromophenyl)-3-chloro-8,8a-dihydroxy-1-methoxy-6-phenyl-7,8-dihydro-6H-cyclopenta[4,5]furo[1,2-d]pyridine-7-carboxylate (1, 20 mg, 0.037 mmol) in pyridine (0.40 mL) was added methanesulfonyl chloride (4 mL, 6 mg, 0.05 mmol) and the mixture was stirred at rt overnight. After 18 h another 2 mL (3 mg, 0.03 mmol) methanesulfonyl chloride were added, followed by another 3 mL (4 mg, 0.04 mmol) methanesulfonyl chloride. After 2 days total reaction time the reaction was quenched with $NH_4Cl$(aq) and the mixture was extracted with dichloromethane thrice. The combined organic phases were dried ($Na_2SO_4$), filtered and concentrated to afford rac-methyl (5aR,6S,7R,8R,8aS)-5a-(4-bromophenyl)-3-chloro-8a-hydroxy-1-methoxy-8-((methylsulfonyl)oxy)-6-phenyl-5a,7,8,8a-tetrahydro-6H-cyclopenta[4,5]furo[3,2-c]pyridine-7-carboxylate (2). The crude product [MS (ESI) m/z 624.2 [M+1]$^+$] was used without further purification in the next step.

Synthesis of rac-methyl (5aR,6S,7R,8R,8aR)-5a-(4-bromophenyl)-3-chloro-8-cyano-8a-hydroxy-1-methoxy-6-phenyl-5a, 7,8,8a-tetrahydro-6H-cyclopenta[4,5]furo[3,2-c]pyridine-7-carboxylate (3)

To a solution of rac-methyl (5aR,6S,7R,8R,8aS)-5a-(4-bromophenyl)-3-chloro-8a-hydroxy-1-methoxy-8-((methylsulfonyl)oxy)-6-phenyl-5a,7,8,8a-tetrahydro-6H-cyclopenta[4,5]furo[3,2-c]pyridine-7-carboxylate (2, 22.9 mg, 0.0367 mmol) in DMSO (0.50 mL) was added potassium cyanide (5.3 mg, 0.082 mmol) and the mixture was stirred at rt under argon. After 17 h the mixture was diluted with EtOAc and washed brine. The aq. phase was re-extracted with EtOAc, and the combined organic phases were dried ($Na_2SO_4$), filtered and concentrated. Purification by column chromatography ($SiO_2$, 0-35% ethyl acetate/hexane) provided the desired product rac-methyl (5aR,6S,7R,8R,8aR)-5a-(4-bromophenyl)-3-chloro-8-cyano-8a-hydroxy-1-methoxy-6-phenyl-5a,7,8,8a-tetrahydro-6H-cyclopenta[4,5]furo[3,2-c]pyridine-7-carboxylate (3) as a white foam. Yield: 15.9 mg (0.0286 mmol, 77% over 2 steps); MS (ESI) m/z 555.2 $[M+1]^+$.

Synthesis of rac-(5aR,6S,7R,8R,8aR)-8-(aminomethyl)-5a-(4-bromophenyl)-3-chloro-7-(hydroxymethyl)-1-methoxy-6-phenyl-5a,6,7,8-tetrahydro-8aH-cyclopenta[4,5]furo[3,2-c]pyridin-8a-ol (4)

To a solution of rac-methyl (5aR,6S,7R,8R,8aR)-5a-(4-bromophenyl)-3-chloro-8-cyano-8a-hydroxy-1-methoxy-6-phenyl-5a,7,8,8a-tetrahydro-6H-cyclopenta[4,5]furo[3,2-c]pyridine-7-carboxylate (3, 15.9 mg, 0.0286 mmol) in THF (0.50 mL) at 0° C. was added lithium aluminum hydride (4.3 mg, 0.11 mmol) and the mixture was stirred at rt. After 45 min 0.02 mL water were added at 0° C., followed by 0.02 mL 12.5% NaOH (aq) and ca. 50 mg of $Na_2SO_4$. The mixture was stirred for 10 min at rt, then filtered (rinsed with THF and dichloromethane) and concentrated to give 15.8 mg of the crude desired amino alcohol of rac-(5aR,6S,7R,8R,8aR)-8-(aminomethyl)-5a-(4-bromophenyl)-3-chloro-7-(hydroxymethyl)-1-methoxy-6-phenyl-5a,6,7,8-tetrahydro-8aH-cyclopenta[4,5]furo[3,2-c]pyridin-8a-ol (4) as a white solid; MS (ESI) m/z 531.2 $[M+1]^+$. The crude material was used in the next step without further purification.

Synthesis of rac-(5aR,6S,7R,8R,8aR)-5a-(4-bromophenyl)-3-chloro-7-(hydroxymethyl)-1-methoxy-8-(morpholinomethyl)-6-phenyl-5a,6,7,8-tetrahydro-8aH-cyclopenta[4,5]furo[3,2-c]pyridin-8a-ol (Cpd. No. 199F)

To a solution of crude rac-(5aR,6S,7R,8R,8aR)-8-(aminomethyl)-5a-(4-bromophenyl)-3-chloro-7-(hydroxymethyl)-1-methoxy-6-phenyl-5a,6,7,8-tetrahydro-8aH-cyclopenta[4,5]furo[3,2-c]pyridin-8a-ol (4, 15.8 mg) in N,N-dimethylformamide (0.50 mL) were added N,N-diisopropylethylamine (18 mL, 13 mg, 0.10 mmol) and 1-bromo-2-(2-bromoethoxy)ethane (4.5 mL, 8.3 mg, 0.036 mmol) and the mixture was stirred at 80° C. After 1 h 45 min and 2.5 h another 1.5 mL (2.8 mg, 0.012 mmol) bis(bromoethyl)ether were added, and stirring at 80° C. was continued. After 3.75 h total reaction time the mixture was allowed to cool down to rt, then diluted with MeCN/DMSO/water and acidified with trifluoroacetic acid (20 mL, 30 mg, 0.26 mmol). The so obtained mixture was subjected to repeated HPLC purification (C18, MeCN/water+0.1% TFA) to provide the desired product rac-(5aR,6S,7R,8R,8aR)-5a-(4-bromophenyl)-3-chloro-7-(hydroxymethyl)-1-methoxy-8-(morpholinomethyl)-6-phenyl-5a,6,7,8-tetrahydro-8aH-cyclopenta[4,5]furo[3,2-c]pyridin-8a-ol (Cpd. No. 199F) as its TFA salt. Yield: 2.5 mg (0.0035 mmol, 12% over 2 steps), white solid; MS (ESI) m/z 601.4 $[M+1]^+$; $^1$H NMR (400 MHz, DMSO-$d_6$) δ 9.91 (b, 1H), 7.35 (d, J=8.5 Hz, 2H), 7.16-7.06 (m, 5H), 7.03 (s, 1H), 6.82-6.74 (m, 2H), 5.95 (s, 1H), 4.21-4.06 (m, 1H), 3.99 (s, 3H), 3.90-3.19 (m, 12H; partially obscured by water peak), 3.17-3.10 (m, 1H), 3.14 (d, J=13.6 Hz, 1H), 2.94-2.84 (m, 1H).

Example 200

Rac-(5aR,6S,7R,8R,8aR)-5a-(4-cyanophenyl)-8a-hydroxy-7-(hydroxymethyl)-1-methoxy-8-(morpholinomethyl)-6-phenyl-5a,7,8,8a-tetrahydro-6H-cyclopenta[4,5]furo[3,2-c]pyridine-3-carbonitrile (Cpd. No. 200F)

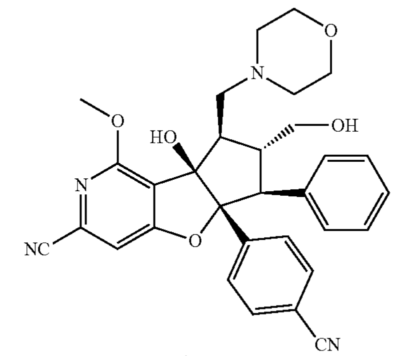

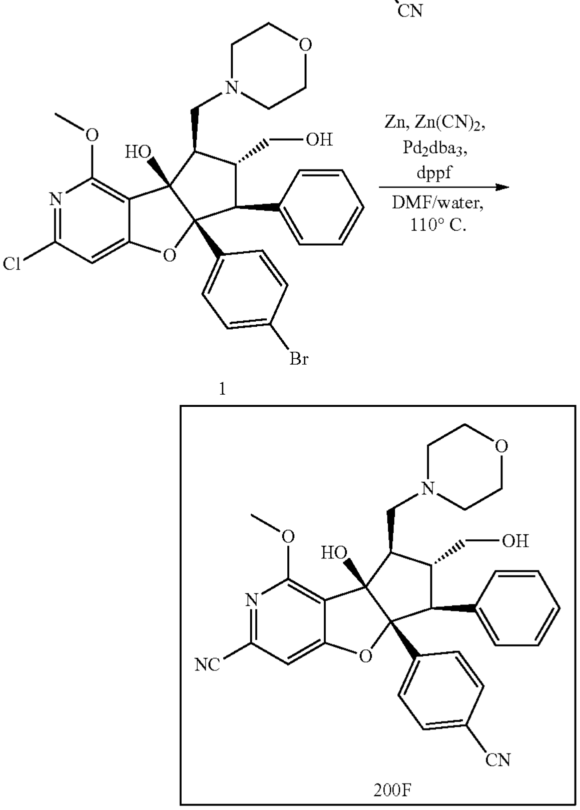

1

200F

Synthesis of rac-(5aR,6S,7R,8R,8aR)-5a-(4-cyanophenyl)-8a-hydroxy-7-(hydroxymethyl)-1-methoxy-8-(morpholinomethyl)-6-phenyl-5a,7,8,8a-tetrahydro-6H-cyclopenta[4,5]furo[3,2-c]pyridine-3-carbonitrile (Cpd. No. 200F)

In a vial, rac-(5aR,6S,7R,8R,8aR)-5a-(4-bromophenyl)-3-chloro-7-(hydroxymethyl)-1-methoxy-8-(morpholinomethyl)-6-phenyl-5a,6,7,8-tetrahydro-8aH-cyclopenta[4,5]furo[3,2-c]pyridin-8a-ol (1, 29.4 mg, 0.0411 mmol) was dissolved in N,N-dimethylformamide (0.40 mL) and water (0.04 mL), and zinc (0.8 mg, 0.01 mmol) and zinc cyanide (24.5 mg, 0.209 mmol) were added. The mixture was degassed by bubbling argon through it for 5 min. Then dppf (6.8 mg, 0.012 mmol) and $Pd_2dba_3$ (5.6 mg, 0.0062 mmol) were added. The mixture was degassed by bubbling argon through it for another 5 min, then the vial was sealed and placed in a preheated heating block (110° C.). The mixture was stirred for 2 h. Then the mixture was filtered, diluted with MeCN, DMSO and water, and filtered again. The filtrate and the precipitate were separately subjected to HPLC purification (C18, MeCN/water+0.1% TFA) to afford the TFA salt of the desired product rac-(5aR,6S,7R,8R,8aR)-5a-(4-cyanophenyl)-8a-hydroxy-7-(hydroxymethyl)-1-methoxy-8-(morpholinomethyl)-6-phenyl-5a,7,8,8a-tetrahydro-6H-cyclopenta[4,5]furo[3,2-c]pyridine-3-carbonitrile (Cpd. No. 200F) as a white solid. Yield: 7.0 mg, 26%; MS (ESI) m/z 539.4 $[M+1]^+$; $^1$H NMR (400 MHz, DMSO-$d_6$) δ 9.95 (b, 1H), 7.72 (s, 1H), 7.65 (bd, 2H), 7.36 (b, 2H), 7.15-7.06 (m, 3H), 6.821□6.75 (m, 2H), 6.17 (s, 1H), 4.23-4.02 (m, 1H), 4.05 (s, 3H), 3.88-3.79 (m, 1H), 3.79-3.24 (m, 11H; partially obscured by water peak), 3.22-3.15 (m, 1H), 3.19 (d, J=13.6 Hz, 1H), 3.04-2.93 (m, 1H).

Example 201

Rac-(4bR,5R,6R,7S,7aR)-5-((2-oxa-6-azaspiro[3.3]heptan-6-yl)methyl)-7a-(4-bromophenyl)-6-(hydroxymethyl)-4-methoxy-7-phenyl-5,6,7,7a-tetrahydro-4bH-cyclopenta[4,5]furo[2,3-c]pyridin-4b-ol (Cpd. No. 201F)

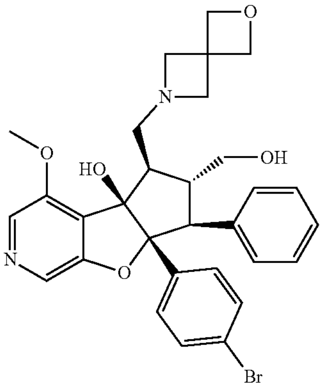

-continued

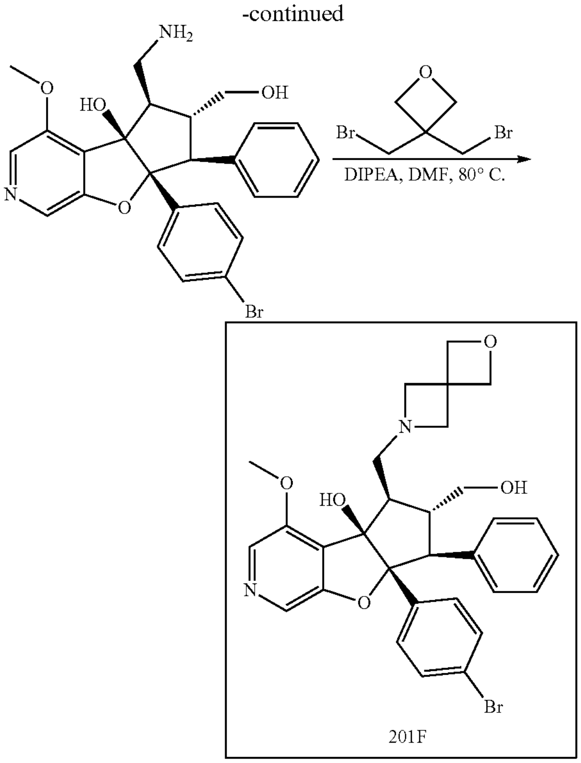

201F

Synthesis of rac-(4bR,5R,6R,7S,7aR)-5-((2-oxa-6-azaspiro[3.3]heptan-6-yl)methyl)-7a-(4-bromophenyl)-6-(hydroxymethyl)-4-methoxy-7-phenyl-5,6,7,7a-tetrahydro-4bH-cyclopenta[4,5]furo[2,3-c]pyridin-4b-ol (Cpd. No. 201F)

To a solution of rac-(5aR,6S,7R,8R,8aR)-8-(aminomethyl)-5a-(4-bromophenyl)-7-(hydroxyl-methyl)-1-methoxy-6-phenyl-7,8-dihydro-6H-cyclopenta[4,5]furo[1,2-b]pyridin-8a-ol (1, 51 mg, 0.10 mmol) in N,N-dimethylformamide (0.60 mL) were added N,N-diisopropylethylamine (0.060 mL, 45 mg, 0.34 mmol) and 3,3-bis(bromomethyl)oxetane (17 □L, 32 mg, 0.13 mmol) in 0.2 mL N,N-dimethylformamide and the mixture was stirred at 80° C. After 3 h another 6 µL (0.01 g, 0.05 mmol) bis(bromoethyl)oxetane were added. After another 1 h another 3 µL (6 mg, 0.02 mmol) bis(bromoethyl)oxetane were added. After another 30 min the mixture was allowed to cool down to rt, then diluted with MeCN/water and acidified with trifluoroacetic acid (0.08 mL, 0.1 g, 1 mmol). Purification by HPLC (C18, MeCN/water+0.1% TFA) provided the TFA salt of rac-(4bR,5R,6R,7S,7aR)-5-((2-oxa-6-azaspiro[3.3]heptan-6-yl)methyl)-7a-(4-bromophenyl)-6-(hydroxymethyl)-4-methoxy-7-phenyl-5,6,7,7a-tetrahydro-4bH-cyclopenta[4,5]furo[2,3-c]pyridin-4b-ol (Cpd. No. 201F) as a white solid. Yield: 31.8 mg, 45%; MS (ESI) m/z 579.4 $[M+1]^+$; $^1$H NMR (400 MHz, DMSO-$d_6$) δ 8.92 (b, 1H), 8.21 (s, 1H), 8.17 (s, 1H), 7.35 (d, J=8.7 Hz, 2H), 7.13-7.06 (m, 5H), 6.81-6.76 (m, 2H), 6.24 (s, 1H), 5.12 (b, 1H), 4.83 (d, J=7.1 Hz, 1H), 4.76 (d, J=7.1 Hz, 1H), 4.73-4.69 (m, 2H), 4.61-4.50 (m, 2H), 4.40 (dd, J=11.0, 5.8 Hz, 1H), 4.21 (dd, J=11.0, 5.8 Hz, 1H). 4.07 (s, 3H), 3.89-3.81 (m, 1H), 3.60-3.51 (m, 1H), 3.49 (dd, J=11.4, 2.6 Hz, 1H), 3.26 (d, J=13.4 Hz, 1H), 3.16 (dd, J=11.4 Hz, 5.1 Hz, 1H), 2.95-2.88 (m, 1H), 2.51-2.42 (m, 1H).

Example 202

Rac-4-((4bR,5R,6R,7S,7aR)-5-((2-oxa-6-azaspiro[3.3]heptan-6-yl)methyl)-4b-hydroxy-6-(hydroxymethyl)-4-methoxy-7-phenyl-4b,5,6,7-tetrahydro-7aH-cyclopenta[4,5]furo[2,3-c]pyridin-7a-yl)benzonitrile (Cpd. No. 202F)

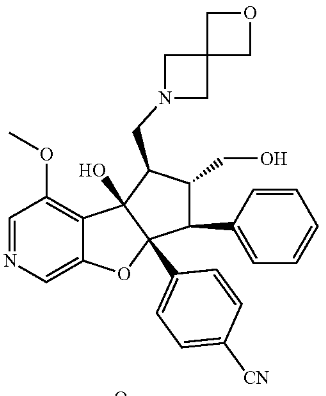

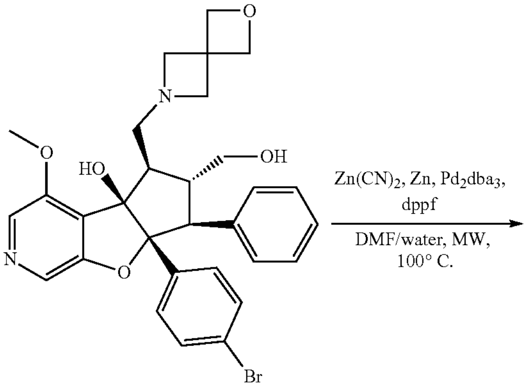

1
(TFA salt)

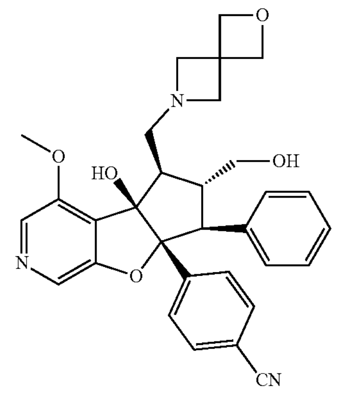

202F

Synthesis of rac-4-((4bR,5R,6R,7S,7aR)-5-((2-oxa-6-azaspiro[3.3]heptan-6-yl)methyl)-4b-hydroxy-6-(hydroxymethyl)-4-methoxy-7-phenyl-4b,5,6,7-tetrahydro-7aH-cyclopenta[4,5]furo[2,3-c]pyridin-7a-yl)benzonitrile (Cpd. No. 202F)

In microwave vial rac-(4bR,5R,6R,7S,7aR)-5-((2-oxa-6-azaspiro[3.3]heptan-6-yl)methyl)-7a-(4-bromophenyl)-6-(hydroxymethyl)-4-methoxy-7-phenyl-5,6,7,7a-tetrahydro-4bH-cyclopenta[4,5]furo[2,3-c]pyridin-4b-ol (1, 24.5 mg, 0.0353 mmol) was dissolved in N,N-dimethylformamide (0.70 mL) and Water (0.07 mL). Zinc cyanide (21 mg, 0.18 mmol) and zinc (0.9 mg, 0.01 mmol) were added, and the mixture was degassed by bubbling argon through it for 5 min. Dppf (5.7 mg, 0.010 mmol) and tris(dibenzylideneacetone)dipalladium(0) (4.7 mg, 0.0052 mmol) were added and the mixture was degassed for another 5 min, then incubated at 100° C. for 2 h in total. The mixture was filtered, diluted with MeCN, DMSO and water, filtered again, and subjected to purification by HPLC (C18, MeCN/water+0.1% TFA) to provide compound rac-4-((4bR,5R,6R,7S,7aR)-5-((2-oxa-6-azaspiro[3.3]heptan-6-yl)methyl)-4b-hydroxy-6-(hydroxymethyl)-4-methoxy-7-phenyl-4b,5,6,7-tetrahydro-7aH-cyclopenta[4,5]furo[2,3-c]pyridin-7a-yl) benzonitrile (Cpd. No. 202F) as the corresponding TFA salt. Yield: 7.4 mg, 33%, white solid; MS (ESI) m/z 526.4 $[M+1]^+$; $^1$H NMR (400 MHz, DMSO-$d_6$) δ 9.00 (b, 1H), 8.23 (s, 1H), 8.18 (s, 1H), 7.62 (d, J=8.7 Hz, 2H), 7.34 (d, J=8.7 Hz, 2H), 7.13-7.05 (m, 3H), 6.82-6.74 (m, 2H), 6.32 (s, 1H), 5.20 (b, 1H), 4.83 (d, J=7.2 Hz, 1H), 4.76 (d, J=7.2 Hz, 1H), 4.74-4.68 (m, 2H), 4.61-4.51 (m, 2H), 4.42 (dd, J=11.1, 5.8 Hz, 1H), 4.21 (dd, J=10.7, 5.4 Hz, 1H), 4.07 (s, 3H), 3.92-3.84 (m, 1H), 3.62-3.55 (m, 1H), 3.50 (dd, J=11.5, 2.7 Hz, 1H), 3.32 (d, J=13.6 Hz, 1H), 3.16 (dd, J=11.5, 5.4 Hz, 1H), 2.97-2.89 (m, 1H), 2.60-2.50 (m, 1H).

Example 203

Rac-(4bR,5R,6R,7S,7aR)-7a-(4-bromophenyl)-6-(hydroxymethyl)-4-methoxy-5-((((1-methyl-1H-pyrazol-5-yl)methyl)amino)methyl)-7-phenyl-5,6,7,7a-tetrahydro-4bH-cyclopenta[4,5]furo[2,3-c]pyridin-4b-ol (Cpd. No. 203F)

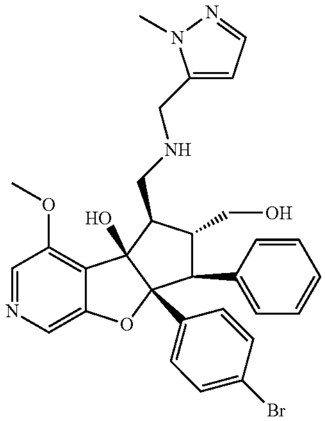

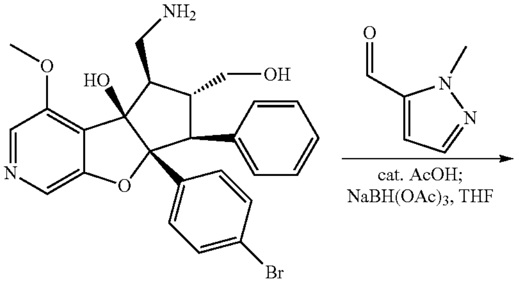

1

-continued

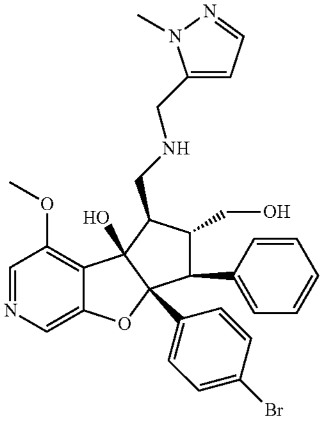

203F

Synthesis of rac-(4bR,5R,6R,7S,7aR)-7a-(4-bromophenyl)-6-(hydroxymethyl)-4-methoxy-5-((((1-methyl-1H-pyrazol-5-yl)methyl)amino)methyl)-7-phenyl-5,6,7,7a-tetrahydro-4bH-cyclopenta[4,5]furo[2,3-c]pyridin-4b-ol (Cpd. No. 203F)

To a solution of rac-(4bR,5R,6R,7S,7aR)-5-(aminomethyl)-7a-(4-bromophenyl)-6-(hydroxymethyl)-4-methoxy-7-phenyl-5,6,7,7a-tetrahydro-4bH-cyclopenta[4,5]furo[2,3-c]pyridin-4b-ol (1, 50 mg, 0.10 mmol) in THF (1 mL) were added 2-methylpyrazole-3-carbaldehyde (12 μL, 13 mg, 0.12 mmol), acetic acid (1.2 μL, 1.3 mg, 0.021 mmol) and molecular sieves (ca. 80 mg). The mixture was stirred for 30 min. Then sodium triacetoxyborohydride (85 mg, 0.40 mmol) was added, and the mixture was stirred for 30 min. Another 3 μL (3 mg, 0.03 mmol) 2-methylpyrazole-3-carbaldehyde were added. After another 30 min the reaction was quenched with $NaHCO_3$(aq), and the mixture was extracted (3×dichloromethane). The combined organic phases were dried ($Na_2SO_4$), filtered and concentrated. The crude product was taken up in MeCN/DMSO/water. And subjected to HPLC purification (C18, MeCN/$H_2O$+0.1% TFA) to provide product rac-(4bR,5R,6R,7S,7aR)-7a-(4-bromophenyl)-6-(hydroxymethyl)-4-methoxy-5-((((1-methyl-1H-pyrazol-5-yl)methyl)amino)methyl)-7-phenyl-5,6,7,7a-tetrahydro-4bH-cyclopenta[4,5]furo[2,3-c]pyridin-4b-ol (Cpd. No. 203F) as its TFA salt. Yield: 40.5 mg (0.0574 mmol, 57%), white solid; MS (ESI) m/z 591.3 $[M+1]^+$; $^1H$ NMR (400 MHz, DMSO-$d_6$) δ 9.14 (b, 1H), 8.52 (b, 1H), 8.21 (s, 1H), 8.13 (s, 1H), 7.52 (d, J=1.9 Hz, 1H), 7.34 (d, J=8.6 Hz, 2H), 7.14-7.08 (m, 5H), 6.85-6.80 (m, 2H), 6.53 (d, J=1.9 Hz, 1H), 6.35 (s, 1H), 5.52 (b, 1H), 4.63-4.48 (m, 2H), 3.92 (s, 3H), 3.91 (s, 3H), 3.78-3.68 (m, 1H), 3.54-3.44 (m, 1H), 3.45 (dd, J=11.1, 2.5 Hz, 1H), 3.27 (d, J=13.6 Hz, 1H), 3.21 (dd, J=11.4, 6.8 Hz, 1H), 3.10-3.02 (m, 1H), 2.76-2.66 (m, 1H).

Example 204

Rac-4-((4bR,5R,6R,7S,7aR)-4b-hydroxy-6-(hydroxymethyl)-4-methoxy-5-((((1-methyl-1H-pyrazol-5-yl)methyl)amino)methyl)-7-phenyl-4b,5,6,7-tetrahydro-7aH-cyclopenta[4,5]furo[2,3-c]pyridin-7a-yl)benzonitrile (Cpd. No. 204F)

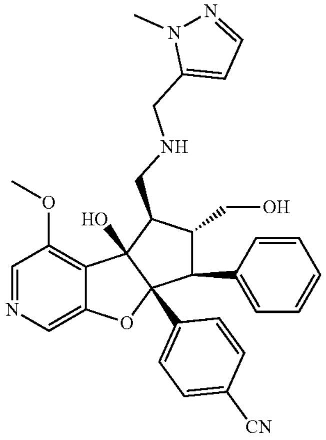

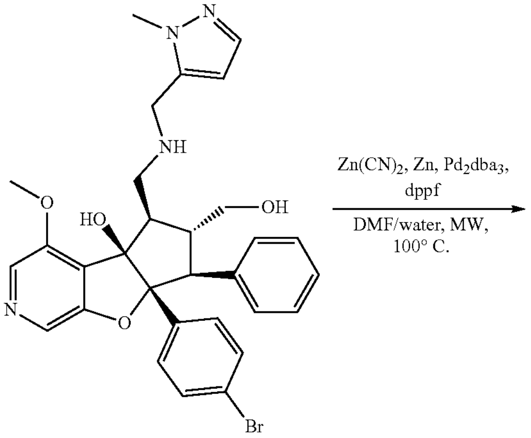

1
(TFA salt)

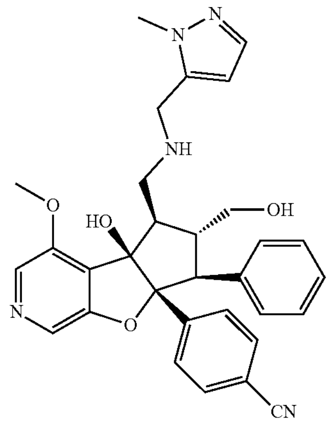

204F

Synthesis of rac-4-((4bR,5R,6R,7S,7aR)-4b-hydroxy-6-(hydroxymethyl)-4-methoxy-5-((((1-methyl-1H-pyrazol-5-yl)methyl)amino)methyl)-7-phenyl-4b,5,6,7-tetrahydro-7aH-cyclopenta[4,5]furo[2,3-c]pyridin-7a-yl)benzonitrile (Cpd. No. 204F)

In a microwave vial rac-(4bR,5R,6R,7S,7aR)-7a-(4-bromophenyl)-6-(hydroxymethyl)-4-methoxy-5-((((1-methyl-1H-pyrazol-5-yl)methyl)amino)methyl)-7-phenyl-5,6,7,7a-tetrahydro-4bH-cyclopenta[4,5]furo[2,3-c]pyridin-4b-ol (1, 29.7 mg, 0.0421 mmol) was dissolved in N,N-dimethylformamide (0.70 mL) and water (0.07 mL). Zinc cyanide (25 mg, 0.21 mmol) and zinc (1 mg, 0.02 mmol) were added, and the mixture was degassed by bubbling argon through it for 5 min. Dppf (6.6 mg, 0.012 mmol) and Tris(dibenzylideneacetone)dipalladium(0) (5.5 mg, 0.0060 mmol) were added and the mixture was degassed for another 5 min, then incubated at 100° C. for 2 h in total. The mixture was filtered, diluted with MeCN, DMSO and water, filtered again, and subjected to purification by HPLC (C18, MeCN/water+0.1% TFA) to provide compound rac-4-((4bR,5R,6R,7S,7aR)-4b-hydroxy-6-(hydroxymethyl)-4-methoxy-5-((((1-methyl-1H-pyrazol-5-yl)methyl)amino)methyl)-7-phenyl-4b,5,6,7-tetrahydro-7aH-cyclopenta[4,5]furo[2,3-c]pyridin-7a-yl)benzonitrile (Cpd. No. 204F) as its TFA salt. Yield: 13.3 mg, 48%, white solid; MS (ESI) m/z 538.6 $[M+1]^+$; $^1H$ NMR (400 MHz, DMSO-$d_6$) δ 9.23 (b, 1H), 8.66 (b, 1H), 8.24 (s, 1H), 8.15 (s, 1H), 7.62 (d, J=8.4 Hz, 2H), 7.52 (d, J=1.9 Hz, 1H), 7.36 (bd, J=8.4 Hz, 2H), 7.13-7.04 (m, 3H), 6.85-6.79 (m, 2H), 6.53 (d, J=1.9 Hz, 1H), 6.41 (s, 1H), 5.59 (b, 1H), 4.64-4.47 (m, 2H), 3.92 (s, 3H), 3.91 (s, 3H), 3.83-3.70 (m, 1H), 3.57-3.47 (m, 1H), 3.47 (dd, J=11.2, 2.6, 1H), 3.34 (d, J=13.5 Hz, 1H), 3.22 (dd, J=11.2, 6.6 Hz, 1H), 3.121D3.03 (m, 1H), 2.84-2.74 (m, 1H).

Example 205

Rac-(4bR,5R,6R,7S,7aR)-7a-(4-bromophenyl)-5-((dimethylamino)methyl)-6-(hydroxymethyl)-4-methoxy-7-phenyl-5,6,7,7a-tetrahydro-4bH-cyclopenta[4,5]furo[2,3-c]pyridin-4b-ol (Cpd. No. 205F)

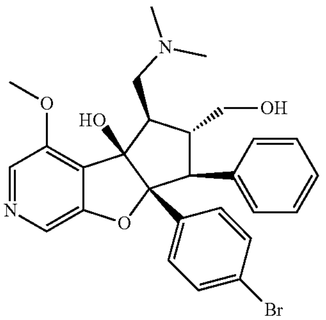

-continued

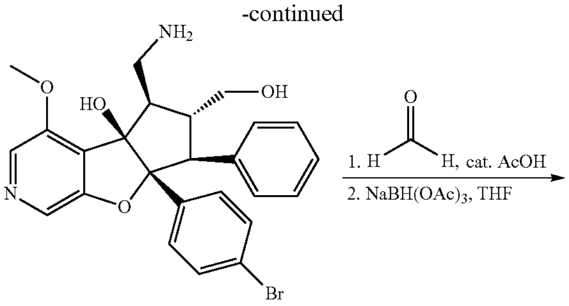

1

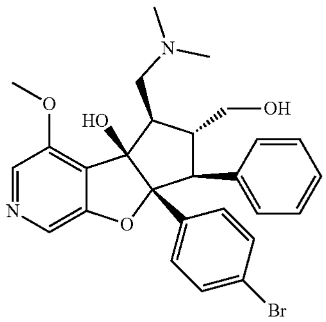

205F

Synthesis of rac-(4bR,5R,6R,7S,7aR)-7a-(4-bromophenyl)-5-((dimethylamino)methyl)-6-(hydroxymethyl)-4-methoxy-7-phenyl-5,6,7,7a-tetrahydro-4bH-cyclopenta[4,5]furo[2,3-c]pyridin-4b-ol (Cpd. No. 205F)

To a solution of crude rac-(5aR,6S,7R,8R,8aR)-8-(aminomethyl)-5a-(4-bromophenyl)-7-(hydroxymethyl)-1-methoxy-6-phenyl-7,8-dihydro-6H-cyclopenta[4,5]furo[1,2-b]pyridin-8a-ol (1, 50 mg, 0.10 mmol) in THF (1 mL) were added formaldehyde (37% solution in water, 30 μL, 33 mg, 0.41 mmol), acetic acid (1.2 μL, 1.3 mg, 0.021 mmol) and molecular sieves (ca. 80 mg). The mixture was stirred for 30 min. Sodium triacetoxyborohydride (85 mg, 0.40 mmol) was added, and the mixture was stirred for another 30 min. Then the reaction was quenched with $NaHCO_3$(aq), and the mixture was extracted (3×dichloromethane). The combined organic phases were dried ($Na_2SO_4$), filtered and concentrated. The crude product was taken up in MeCN/DMSO/water+a few drops of TFA. Purification by prep-HPLC (C18, MeCN/$H_2O$+0.1% TFA) provided rac-(4bR,5R,6R,7S,7aR)-7a-(4-bromophenyl)-5-((dimethylamino)methyl)-6-(hydroxymethyl)-4-methoxy-7-phenyl-5,6,7,7a-tetrahydro-4bH-cyclopenta[4,5]furo[2,3-c]pyridin-4b-ol (Cpd. No. 205F) as the TFA salt. Yield: 25.1 mg (0.0393 mmol, 39%), white solid; MS (ESI) m/z 525.2 $[M+1]^+$; $^1H$ NMR (400 MHz, DMSO-$d_6$) δ 8.81 (b, 1H), 8.20 (s, 1H), 8.15 (s, 1H), 7.34 (d, J=8.8 Hz, 2H), 7.17-7.08 (m, 5H), 6.81-6.75 (m, 2H), 6.20 (s, 1H), 5.91 (b, 1H), 4.03 (s, 3H), 3.84-3.76 (m, 1H), 3.57-3.48 (m, 1H), 3.46-3.40 (m, 1H), 3.23 (dd, J=11.0, 7.5 Hz, 1H), 3.18 (d, J=13.7 Hz, 1H), 3.16-3.09 (m, 1H), 3.08 (d, J=4.9 Hz, 3H), 2.98 (d, J=4.9 Hz, 3H), 2.75-2.66 (m, 1H).

Example 206

Rac-4-((4bR,5R,6R,7S,7aR)-5-((dimethylamino)methyl)-4b-hydroxy-6-(hydroxymethyl)-4-methoxy-7-phenyl-4b,5,6,7-tetrahydro-7aH-cyclopenta[4,5]furo[2,3-c]pyridin-7a-yl)benzonitrile (Cpd. No. 206F)

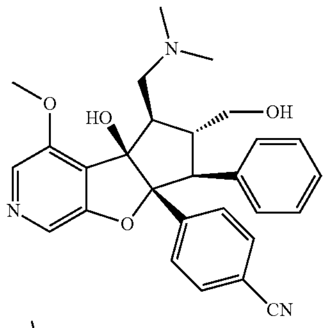

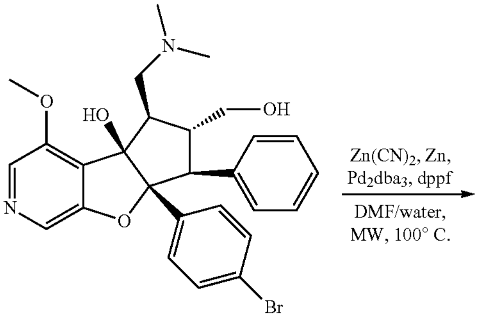

1
(TFA salt)

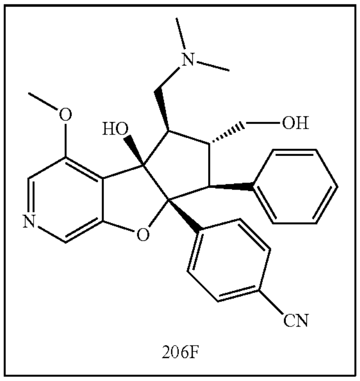

206F

Synthesis of rac-4-((4bR,5R,6R,7S,7aR)-5-((dimethylamino)methyl)-4b-hydroxy-6-(hydroxymethyl)-4-methoxy-7-phenyl-4b,5,6,7-tetrahydro-7aH-cyclopenta[4,5]furo[2,3-c]pyridin-7a-yl)benzonitrile (Cpd. No. 206F)

In a microwave vial rac-(4bR,5R,6R,7S,7aR)-7a-(4-bromophenyl)-5-((dimethylamino)methyl)-6-(hydroxymethyl)-4-methoxy-7-phenyl-5,6,7,7a-tetrahydro-4bH-cyclopenta[4,5]furo[2,3-c]pyridin-4b-ol (1, 19.4 mg, 0.0303 mmol) was dissolved in N,N-dimethylformamide (0.70 mL) and water (0.07 mL). Zinc cyanide (18 mg, 0.15 mmol) and zinc (0.8 mg, 0.01 mmol) were added, and the mixture was degassed by bubbling argon through it for 5 min. Dppf (4.9 mg, 0.0088 mmol) and Tris(dibenzylideneacetone)dipalladium (0) (4.1 mg, 0.0044 mmol) were added and the mixture was degassed for another 5 min, then incubated at 100° C. for 2 h in total. The mixture was filtered, diluted with MeCN, DMSO and water, and filtered again. The filtrate and the precipitate both contained the desired product and were separately subjected to HPLC purification (C18, MeCN/water+0.1% TFA) to provide the desired product rac-4-((4bR,5R,6R,7S,7aR)-5-((dimethylamino)methyl)-4b-hydroxy-6-(hydroxymethyl)-4-methoxy-7-phenyl-4b,5,6,7-tetrahydro-7aH-cyclopenta[4,5]furo[2,3-c]pyridin-7a-yl)benzonitrile (Cpd. No. 206F) as its TFA salt. Overall yield: 11.6 mg, 65%, white solid; MS (ESI) m/z 472.4 $[M+1]^+$; $^1H$ NMR (400 MHz, DMSO-$d_6$) δ 8.88 (b, 1H), 8.22 (s, 1H), 8.17 (s, 1H), 7.62 (d, J=8.6 Hz, 2H), 7.39 (bd, 2H), 7.13-7.07 (m, 3H), 6.82-6.76 (m, 2H), 6.27 (s, 1H), 5.98 (s, 1H), 4.04 (s, 3H), 3.86-3.78 (m, 1H), 3.61-3.51 (m, 1H), 3.44 (dd, J=11.0, 3.1 Hz, 1H), 3.28-3.21 (m, 1H), 3.23 (d, J=13.3 Hz, 1H), 3.18-3.10 (m, 1H), 3.08 (d, J=4.8 Hz, 3H), 2.98 (d, J=4.8 Hz, 3H), 2.83-2.73 (m, 1H).

Example 207

Rac-(5aR,6S,7S,8R,8aS)-5a-(4-cyanophenyl)-7-((3,3-difluoroazetidin-1-yl)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 207aF)

Rac-4-((5aR,6S,7S,8R,8aS)-3-chloro-7-((3,3-difluoroazetidin-1-yl)methyl)-8,8a-dihydroxy-1-methoxy-6-phenyl-6,7,8,8a-tetrahydro-5aH-cyclopenta[4,5]furo[3,2-c]pyridin-5a-yl)benzonitrile (Cpd. No. 207bF)

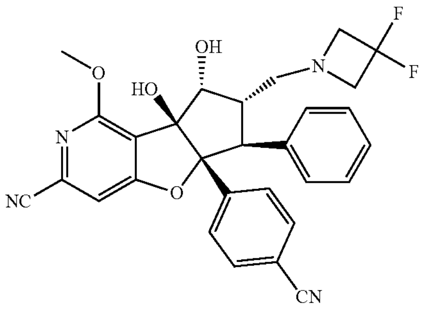

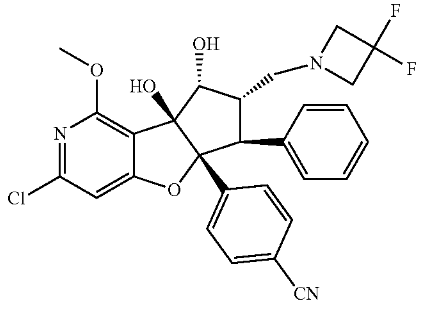

-continued

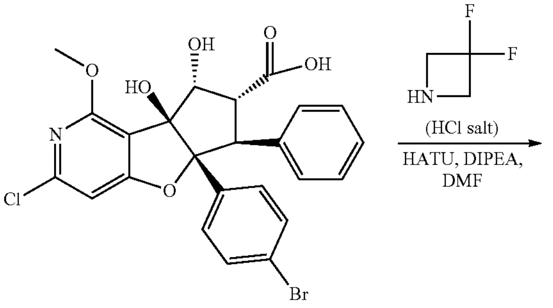

1

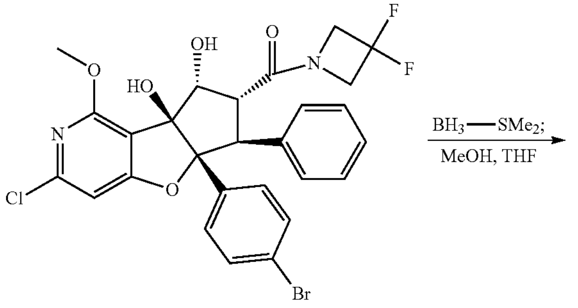

2

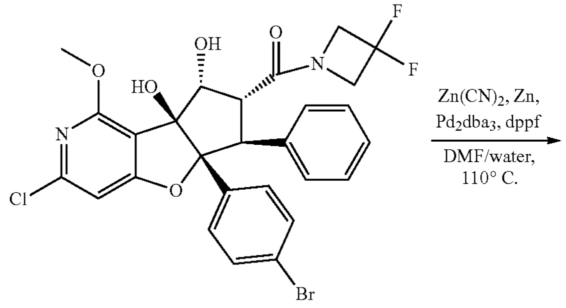

3

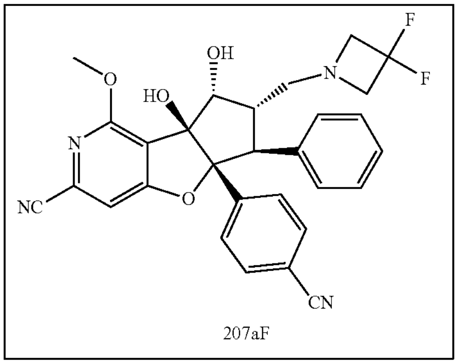

207aF

+

-continued

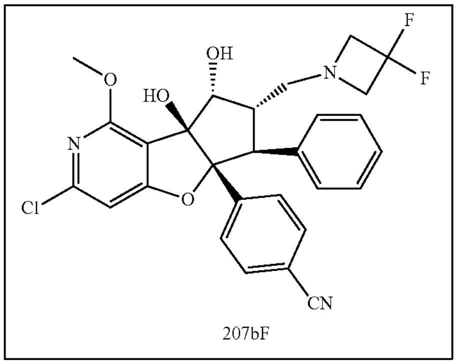

207bF

Synthesis of rac-((5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridin-7-yl)(3,3-difluoroazetidin-1-yl)methanone (2)

To a solution of rac-(5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridine-7-carboxylic acid (1, 41 mg, 0.077 mmol) in N,N-dimethylformamide (0.70 mL) at rt under argon was added HATU (32 mg, 0.084 mmol). After 2 min N,N-diisopropylethylamine (34 uL, 25 mg, 0.20 mmol) was added, and the mixture was stirred for 15 min. Another 34 uL (25 mg, 0.20 mmol) DIPEA were added, followed by 3,3-difluoroazetidine hydrochloride (30 mg, 0.23 mmol) and the mixture was stirred at rt for 45 min. Then the mixture was diluted with ethyl acetate and washed with brine. The aq. phase was re-extracted with EtOAc once. Then the combined organic phases were dried ($Na_2SO_4$), filtered and concentrated. Purification by column chromatography ($SiO_2$, 0-5.5% MeOH in dichloromethane) gave 53.5 mg of rac-((5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridin-7-yl)(3,3-difluoroazetidin-1-yl)methanone (2) as a yellow foam, which was used in the next step without further purification; MS (ESI) m/z 607.2 $[M+1]^+$.

Synthesis of rac-(5aR,6S,7S,8R,8aS)-5a-(4-bromophenyl)-3-chloro-7-((3,3-difluoroazetidin-1-yl)methyl)-1-methoxy-6-phenyl-5a,6,7,8-tetrahydro-8aH-cyclopenta[4,5]furo[3,2-c]pyridine-8,8a-diol (3)

To a solution of rac-((5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridin-7-yl)(3,3-difluoroazetidin-1-yl)methanone (2) (impure material obtained in previous step, 53.5 mg) in THF (0.80 mL) at 0° C. was added $BH_3$-DMS complex in THF (2M, 0.23 mL, 0.46 mmol) and the mixture was stirred at 40° C. for 4 h. Borane adducts of desired product observed. 1 mL MeOH was carefully added at 0° C. and the mixture was stirred at 60° C. for 1.5 h. The product was isolated using ion-exchange extraction [Phenomenex Strata™-X-C; column was washed with water, product solution loaded, washed with water (3×), MeCN (3×), MeOH (3×), then product was eluted with 5% $NH_4OH$(aq) in MeOH (3×)] to afford rac-(5aR,6S,7S,8R,8aS)-5a-(4-bromophenyl)-3-chloro-7-((3,3-difluoroazetidin-1-yl)methyl)-1-methoxy-6-phenyl-5a,6,7,8-tetrahydro-8aH-cyclopenta[4,5]furo[3,2-c]pyridine-8,8a-diol (3). Yield: 27.4 mg (0.0461 mmol, 60% over 2 steps); MS (ESI) m/z 593.3 $[M+1]^+$.

Synthesis of rac-(5aR,6S,7S,8R,8aS)-5a-(4-cyanophenyl)-7-((3,3-difluoroazetidin-1-yl)methyl)-8,8a-dihydroxy-1-methoxy-6-phenyl-5a,7,8,8a-tetrahydro-6H-cyclopenta[4,5]furo[3,2-c]-pyridine-3-carbonitrile (Cpd. No. 207aF)

Rac-4-((5aR,6S,7S,8R,8aS)-3-chloro-7-((3,3-difluoroazetidin-1-yl)methyl)-8,8a-dihydroxy-1-methoxy-6-phenyl-6,7,8,8a-tetrahydro-5aH-cyclopenta[4,5]furo-[3,2-c]pyridin-5a-yl)benzonitrile (Cpd. No. 207bF)

In a screw-cap-vial, rac-(5aR,6S,7S,8R,8aS)-5a-(4-bromophenyl)-3-chloro-7-((3,3-difluoroazetidin-1-yl)methyl)-1-methoxy-6-phenyl-5a,6,7,8-tetrahydro-8aH-cyclopenta[4,5]furo[3,2-c]pyridine-8,8a-diol (3, 27.4 mg, 0.0461 mmol) was dissolved in N,N-dimethylformamide (0.40 mL) and water (0.04 mL), and zinc (0.9 mg, 0.01 mmol) and zinc cyanide (27 mg, 0.23 mmol) were added. The mixture was degassed by bubbling argon through it for 5 min. Then dppf (7.7 mg, 0.014 mmol) and $Pd_2dba_3$ (6.3 mg, 0.0069 mmol) were added. The mixture was degassed by bubbling argon through it for another 5 min, then the vial was sealed and placed in a preheated heating block (110° C.). The mixture was stirred for 2 h. Then the mixture was filtered, diluted with MeCN, DMSO and water, filtered again, and subjected to purification by HPLC (C18, MeCN/water+0.1% TFA) to provide the TFA salts of desired products (Cpd. No. 207aF and Cpd. No. 207bF) as white solids. Yields and analytical data: (Cpd. No. 207aF): 17.6 mg (0.0273 mmol, 59%); MS (ESI) m/z 531.4 $[M+1]^+$. $^1H$ NMR (400 MHz, DMSO-$d_6$) δ 7.60 (s, 1H), 7.56 (d, J=8.7 Hz, 2H), 7.34 (d, J=8.7 Hz, 2H), 7.14-6.99 (m, 5H), 5.97 (bs, 1H), 5.55 (b, 1H), 4.84-4.36 (m, 4H), 4.54-4.51 (m, 1H), 3.92 (s, 3H), 3.79 (d, J=13.6 Hz, 1H), 3.37-3.21 (m, 2H), 3.07-2.81 (m, 1H). (Cpd. No. 207bF): 5.1 mg (0.0078 mmol, 17%); MS (ESI) m/z 540.2 $[M+1]^+$. $^1H$ NMR (400 MHz, DMSO-$d_6$) δ 7.55 (d, J=8.6 Hz, 2H), 7.33 (d, J=8.6 Hz, 2H), 7.14□6.98 (m, 5H), 6.94 (s, 1H), 5.79 (bs, 1H), 5.43 (b, 1H), 4.99-4.02 (b, 4H), 4.47 (bs, 1H), 3.86 (s, 3H), 3.78 (d, J=13.5 Hz, 1H), 3.32-3.13 (b, 2H), 3.04-2.77 (b, 1H).

Example 208

Rac-(5aR,6S,7S,8R,8aS)-5a-(4-cyanophenyl)-7-(((2,2-difluoroethyl)(methyl)amino)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 208aF)

Rac-4-((5aR,6S,7S,8R,8aS)-3-chloro-7-(((2,2-difluoroethyl)(methyl)amino)methyl)-8,8a-dihydroxy-1-methoxy-6-phenyl-6,7,8,8a-tetrahydro-5aH-cyclopenta[4,5]furo[3,2-c]pyridin-5a-yl)benzonitrile (Cpd. No. 208bF)

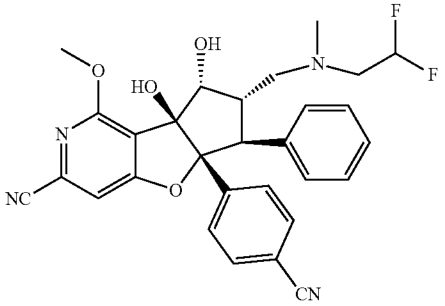

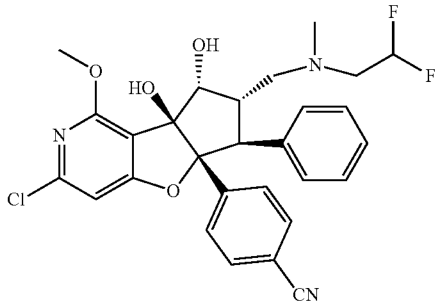

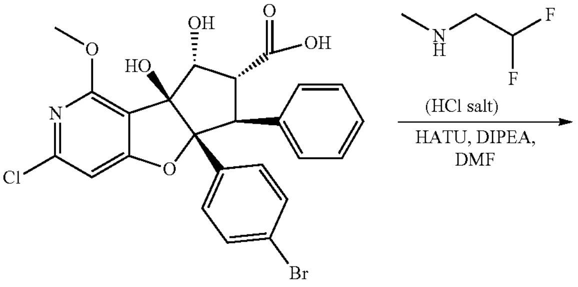

1

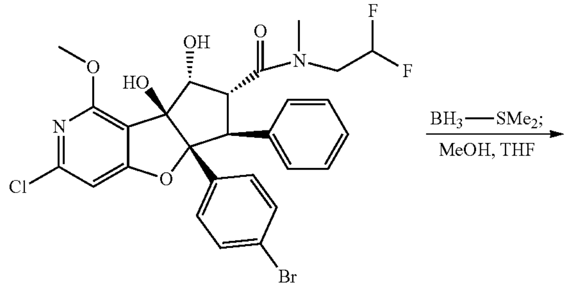

2

-continued

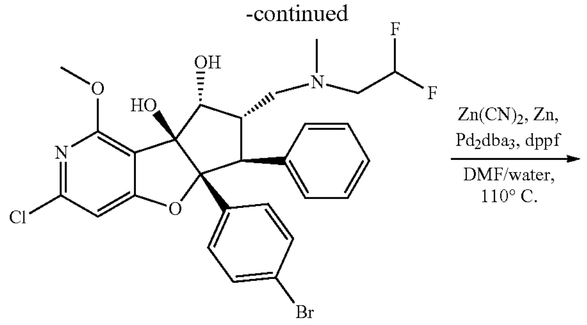

3

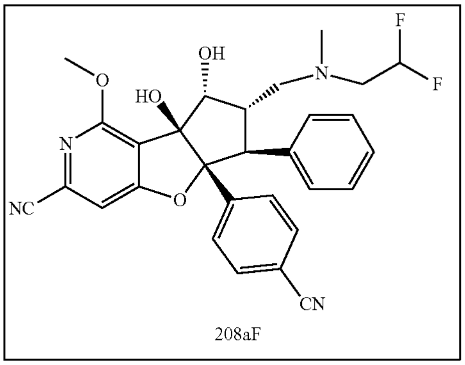

208aF

+

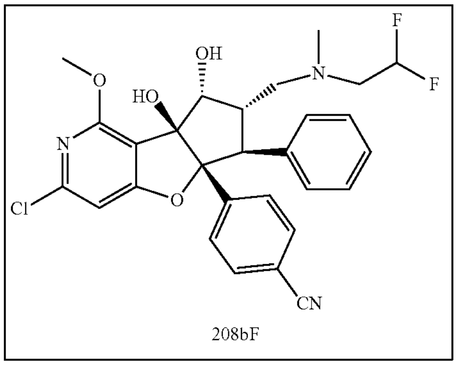

208bF

Synthesis of rac-(5aR,6S,7R,8R,8aS)-5a-(4-bromophenyl)-3-chloro-N-(2,2-difluoroethyl)-8,8a-dihydroxy-1-methoxy-N-methyl-6-phenyl-5a, 7,8,8a-tetrahydro-6H-cyclopenta[4,5]furo[3,2-c]pyridine-7-carboxamide (2)

To a solution of rac-(5aR,6S,7R,8R,8aS)-5a-(4-bromophenyl)-3-chloro-8,8a-dihydroxy-1-methoxy-6-phenyl-5a, 7,8,8a-tetrahydro-6H-cyclopenta[4,5]furo[3,2-c]pyridine-7-carboxylic acid (1, 40 mg, 0.075 mmol) in N,N-dimethylformamide (0.70 mL) at rt under argon was added HATU (31 mg, 0.082 mmol). After 2 min N,N-diisopropylethylamine (33 µL, 24 mg, 0.19 mmol) was added, and the mixture was stirred for 15 min. Then another 33 µL (24 mg, 0.19 mmol) DIPEA were added, followed by 2,2-difluoro-N-methyl-ethanamine hydrochloride (29.6 mg, 0.225 mmol), and the mixture was stirred for 2 h, then diluted with EtOAc and washed with brine. The aq. phase was re-extracted with EtOAc once, and the combined organic phases were dried, filtered and concentrated. Purification by column chromatography ($SiO_2$, 0-5% MeOH in dichloromethane) gave 49 mg of material containing the product rac-(5aR,6S,7R,8R,8aS)-5a-(4-bromophenyl)-3-chloro-N-(2,2-difluoroethyl)-8,8a-dihydroxy-1-methoxy-N-methyl-6-phenyl-5a,7,8,8a-tetrahydro-6H-cyclopenta[4,5]furo[3,2-c]pyridine-7-carboxamide (2) as an orange foam, which was used in the next step without further purification; MS (ESI) m/z 609.3 $[M+1]^+$.

Synthesis of rac-(5aR,6S,7S,8R,8aS)-5a-(4-bromophenyl)-3-chloro-7-(((2,2-difluoroethyl)(methyl)amino)methyl)-1-methoxy-6-phenyl-5a,6,7,8-tetrahydro-8aH-cyclopenta[4,5]furo[3,2-c]pyridine-8,8a-diol (3)

To a solution of rac-(5aR,6S,7R,8R,8aS)-5a-(4-bromophenyl)-3-chloro-N-(2,2-difluoroethyl)-8,8a-dihydroxy-1-methoxy-N-methyl-6-phenyl-5a,7,8,8a-tetrahydro-6H-cyclopenta[4,5]furo[3,2-c]pyridine-7-carboxamide (2) (impure material obtained in previous step, 49 mg) in THF (0.75 mL) at 0° C. was added $BH_3$-DMS complex in THF (2M, 0.22 mL, 0.44 mmol) and the mixture was stirred at 40° C. for 4 h. Then 1 mL MeOH was carefully added at 0° C. and the mixture was stirred at 60° C. for 1 h. The product was isolated using ion-exchange extraction [Phenomenex Strata™-X-C; column was washed with water, product solution loaded, washed with water (3×), MeCN (3×), MeOH (3×), then product was eluted with 5% $NH_4OH$ in MeOH (3×)] to provide the desired product of rac-(5aR,6S,7S,8R,8aS)-5a-(4-bromophenyl)-3-chloro-7-(((2,2-difluoroethyl)(methyl)amino)methyl)-1-methoxy-6-phenyl-5a,6,7,8-tetrahydro-8aH-cyclopenta[4,5]furo[3,2-c]pyridine-8,8a-diol (3). Yield: 30.6 mg (0.0514 mmol, 69% over 2 steps), white solid; MS (ESI) m/z 595.3 $[M+1]^+$.

Synthesis of rac-(5aR,6S,7S,8R,8aS)-5a-(4-cyanophenyl)-7-(((2,2-difluoroethyl)(methyl)amino)-methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 208aF)

rac-4-((5aR,6S,7S,8R,8aS)-3-chloro-7-(((2,2-difluoroethyl) (methyl)amino)methyl)-8,8a-dihydroxy-1-methoxy-6-phenyl-6,7,8,8a-tetrahydro-5aH-cyclopenta[4,5]furo[3,2-c]pyridin-5a-yl)benzonitrile (Cpd. No. 208bF)

In a microwave vial, rac-(5aR,6S,7S,8R,8aS)-5a-(4-bromophenyl)-3-chloro-7-(((2,2-difluoroethyl)(methyl)amino)methyl)-1-methoxy-6-phenyl-5a,6,7,8-tetrahydro-8aH-cyclopenta[4,5]furo[3,2-c]pyridine-8,8a-diol (3, 30.6 mg, 0.0514 mmol) was dissolved in N,N-dimethylformamide (0.40 mL) and water (0.04 mL) and zinc (1.2 mg, 0.018 mmol) and zinc cyanide (30.2 mg, 0.257 mmol) were added. The mixture was degassed by bubbling argon through it for 5 min. Dppf (8.6 mg, 0.016 mmol) and $Pd_2dba_3$ (7.3 mg, 0.0080 mmol) were added. The mixture was degassed by bubbling argon through it for another 5 min, then the vial was sealed, then placed in a preheated heating block (110° C.). The mixture was stirred for 2 h. Then the mixture was filtered, diluted with MeCN, DMSO and water, filtered again, and subjected to purification by HPLC (C18, MeCN/water+0.1% TFA) to provide the desired products rac-(5aR,6S,7S,8R,8aS)-5a-(4-cyanophenyl)-7-(((2,2-difluoroethyl)(methyl)amino)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 208aF and Cpd. No. 208bF) as the corresponding TFA salts. Yields and analytical data: (Cpd. No. 208aF): 17.2 mg (0.0266 mmol, 52%), white solid; MS (ESI) m/z 533.3 $[M+1]^+$. $^1H$ NMR (400 MHz, DMSO-$d_6$) δ 7.60 (s, 1H), 7.55 (d, J=8.8 Hz, 2H), 7.41 (d, J=8.8 Hz, 2H), 7.15-6.99 (m, 5H), 6.43 (bt, J=54 Hz, 1H), 5.97 (bs, 1H), 5.59 (b, 1H), 5.20-4.00 (b, 2H), 4.66 (b, 1H), 3.92 (s, 3H), 3.79 (d, J=13.9 Hz, 1H). [Remaining protons appear as broad signals between 3.75 and 2.50 ppm, partially overlapping with water peak]. (Cpd. No. 208bF): 4.4 mg (0.0067 mmol, 13%), white solid; MS (ESI) m/z 542.2 $[M+1]^+$. $^1$H NMR (400 MHz, DMSO-$d_6$) δ 7.54 (d, J=8.5 Hz, 2H), 7.39 (d, J=8.5 Hz, 2H), 7.14116.98 (m, 5H), 6.94 (s, 1H), 6.70-6.10 (b, 1H), 5.77 (bs, 1H), 5.70-5.00 (b, 1H), 4.58 (b, 1H), 3.89 (s, 3H), 3.78 (d, J=13.9 Hz, 1H). [Remaining protons appear as broad signals between 5.00 and 2.50 ppm, partially overlapping with water peak].

Example 209

Rac-(5aR,6S,7R,8R,8aR)-5a-(4-bromophenyl)-3-chloro-8-((dimethylamino)methyl)-7-(hydroxymethyl)-1-methoxy-6-phenyl-5a,6,7,8-tetrahydro-8aH-cyclopenta[4,5]furo[3,2-c]pyridin-8a-ol (Cpd. No. 209F)

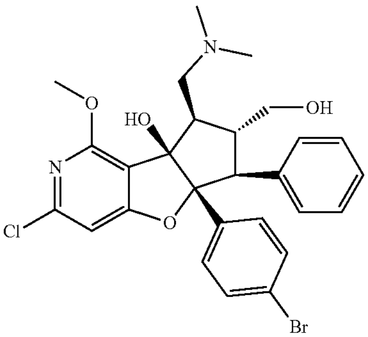

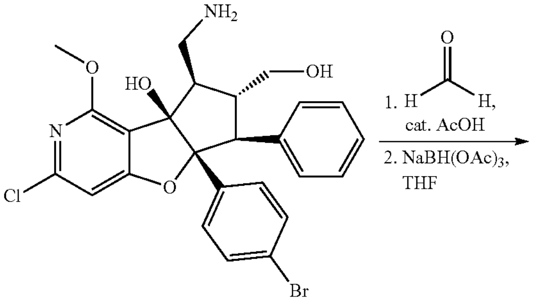

1

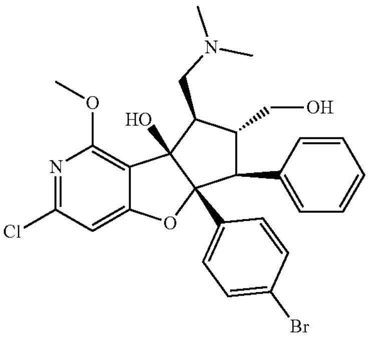

209F

Synthesis of rac-(5aR,6S,7R,8R,8aR)-5a-(4-bromophenyl)-3-chloro-8-((dimethylamino)methyl)-7-(hydroxymethyl)-1-methoxy-6-phenyl-5a,6,7,8-tetrahydro-8aH-cyclopenta[4,5]furo[3,2-c]pyridin-8a-ol (Cpd. No. 209F)

To a solution of rac-(5aR,6S,7R,8R,8aR)-8-(aminomethyl)-5a-(4-bromophenyl)-3-chloro-7-(hydroxymethyl)-1-methoxy-6-phenyl-5a,6,7,8-tetrahydro-8aH-cyclopenta[4,5]furo[3,2-c]pyridin-8a-ol (1, 224 mg, 0.421 mmol) in THF (5 mL) were added formaldehyde (37% sln. in water) (0.34 mL, 1.7 mmol), acetic acid (9 μL, 9 mg, 0.2 mmol) and molecular sieves (ca. 0.5 g). The mixture was stirred for 30 min. Sodium triacetoxyborohydride (358 mg, 1.69 mmol) was added, and the mixture was stirred for another 30 min. Then the reaction was quenched with $NaHCO_3$(aq), and the mixture was extracted (3×dichloromethane). The combined organic phases were dried ($Na_2SO_4$), filtered and concentrated. Purification by prep HPLC (C18, MeCN/water+0.1% TFA; product fractions were combined and lyophilized; the so obtained fluffy white solid was taken up in a few mL of MeCN, frozen and lyophilized again to remove water) provided rac-(5aR,6S,7R,8R,8aR)-5a-(4-bromophenyl)-3-chloro-8-((dimethylamino)methyl)-7-(hydroxymethyl)-1-methoxy-6-phenyl-5a,6,7,8-tetrahydro-8aH-cyclopenta[4,5]furo[3,2-c]pyridin-8a-ol (Cpd. No. 209F) as the TFA salt. Yield: 143 mg, 50%, white solid; MS (ESI) m/z 559.2 $[M+1]^+$. $^1$H NMR (400 MHz, DMSO-$d_6$) δ 8.63 (b, 1H), 7.36 (d, J=8.8 Hz, 2H), 7.15-7.07 (m, 5H), 7.04 (s, 1H), 6.81-6.76 (m, 2H), 6.11 (s, 1H), 6.10-5.70 (b, 1H), 3.99 (s, 3H), 3.81-3.71 (m, 1H), 3.51 (ddd, J=12.5, 7.5, 4.5 Hz, 1H), 3.43 (dd, J=11.1, 2.9 Hz, 1H), 3.27-3.20 (m, 1H), 3.21 (d, J=13.5 Hz, 1H), 3.15-3.07 (m, 1H), 3.07 (d, J=4.7 Hz, 3H), 2.98 (d, J=4.7 Hz, 3H), 2.76-2.65 (m, 1H).

Example 210

Rac-(5aR,6S,7R,8R,8aR)-5a-(4-cyanophenyl)-8-((dimethylamino)methyl)-8a-hydroxy-7-(hydroxymethyl)-1-methoxy-6-phenyl-5a,7,8,8a-tetrahydro-6H-cyclopenta[4,5]furo[3,2-c]pyridine-3-carbonitrile (Cpd. No. 210F)

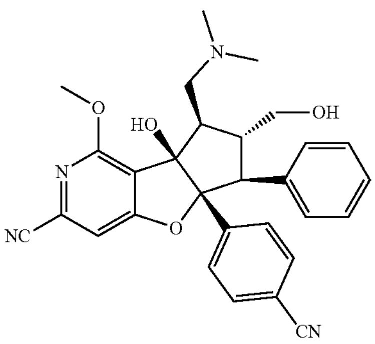

-continued

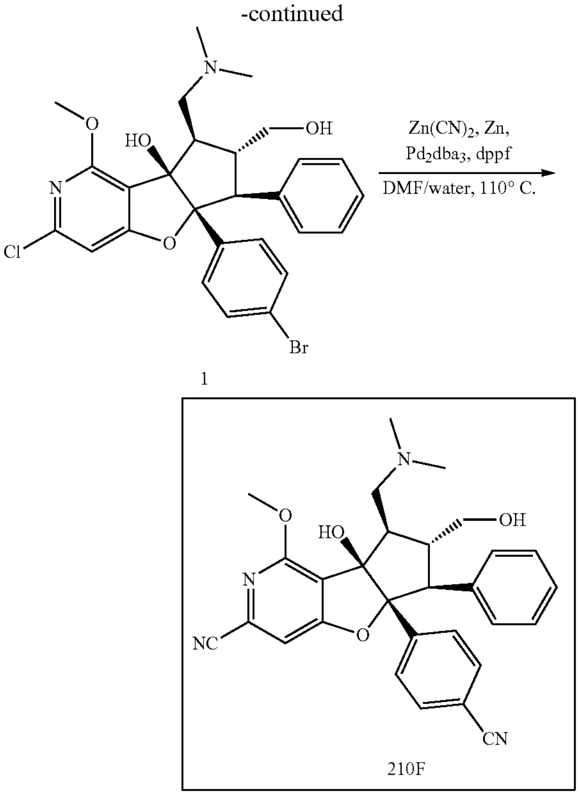

Synthesis of rac-(5aR,6S,7R,8R,8aR)-5a-(4-cyanophenyl)-8-((dimethylamino)methyl)-8a-hydroxy-7-(hydroxymethyl)-1-methoxy-6-phenyl-5a,7,8,8a-tetrahydro-6H-cyclopenta[4,5]furo[3,2-c]pyridine-3-carbonitrile (Cpd. No. 210F)

In a vial, rac-(5aR,6S,7R,8R,8aR)-5a-(4-bromophenyl)-3-chloro-8-((dimethylamino)methyl)-7-(hydroxymethyl)-1-methoxy-6-phenyl-5a,6,7,8-tetrahydro-8aH-cyclopenta[4,5]furo[3,2-c]pyridin-8a-ol (1) (ca. 86% pure by LCMS, 18.7 mg, 0.0287 mmol) was dissolved in N,N-dimethylformamide (0.40 mL) and water (0.04 mL), and zinc (1 mg, 0.02 mmol) and zinc cyanide (20.8 mg, 0.177 mmol) were added. The mixture was degassed by bubbling argon through it for 5 min. Then dppf (5.6 mg, 0.010 mmol) and $Pd_2dba_3$ (4.7 mg, 0.0051 mmol) were added. The mixture was degassed by bubbling argon through it for another 5 min, then the vial was sealed, then placed in a preheated heating block (110° C.). The mixture was stirred for 2 h. Then the mixture was cooled down to rt, diluted with DMSO and filtered. The filtrate contained some of the bis-CN product and a CN/proteo impurity (judged by LCMS—resulting from proteodebromination or proteodechlorination). The precipitate largely consisted of product (judged by LCMS). Precipitate and filtrate were separately subjected to HPLC purification (C18, MeCN/water+0.1% TFA). HPLC purification of the filtrate provided 9.1 mg of a mixture of the desired product and the CN/proteo impurity as TFA salts (inseparable) as a white solid. HPLC purification of the precipitate provided 1.5 mg of a mixture of the desired product and the CN/proteo impurity as TFA salts (inseparable) as a white solid in addition to 6.2 mg (0.010 mmol, 35%) of the pure TFA salt of rac-(5aR,6S,7R,8R,8aR)-5a-(4-cyanophenyl)-8-((dimethylamino)methyl)-8a-hydroxy-7-(hydroxymethyl)-1-methoxy-6-phenyl-5a,7,8,8a-tetrahydro-6H-cyclopenta[4,5]furo[3,2-c]pyridine-3-carbonitrile (Cpd. No. 210F) as a white hygroscopic solid; MS (ESI) m/z 497.3 $[M+1]^+$; $^1H$ NMR (400 MHz, DMSO-$d_6$) δ 8.95 (b, 1H), 7.73 (s, 1H), 7.65 (d, J=8.5 Hz, 2H), 7.36 (bd, 2H), 7.15-7.06 (m, 3H), 6.82-6.74 (m, 2H), 6.30 (s, 1H), 6.06 (b, 1H), 4.04 (s, 3H), 2.84-3.74 (m, 1H), 3.62-3.52 (m, 1H), 3.16 (d, J=13.4 Hz, 1H), 3.19-3.12 (m, 1H), 3.08 (d, J=4.7 Hz, 3H), 2.98 (d, J=4.7 Hz, 3H), 2.86-2.76 (m, 1H). [Remaining protons are obscured by water peak.]

Example 211

Rac-(5aR,6S,7S,8R,8aS)-5a-(4-cyanophenyl)-7-((3-fluoroazetidin-1-yl)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 211aF)

Rac-4-((5aR,6S,7S,8R,8aS)-3-chloro-7-((3-fluoroazetidin-1-yl)methyl)-8,8a-dihydroxy-1-methoxy-6-phenyl-6,7,8,8a-tetrahydro-5aH-cyclopenta[4,5]furo[3,2-c]pyridin-5a-yl)benzonitrile (Cpd. No. 211bF)

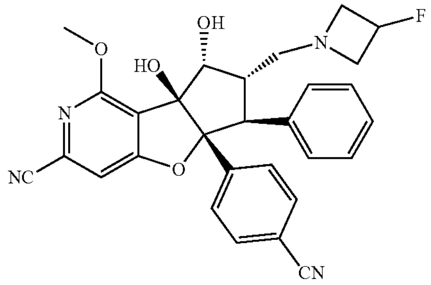

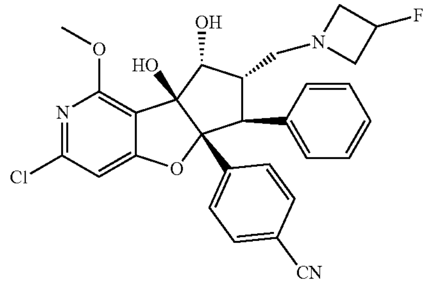

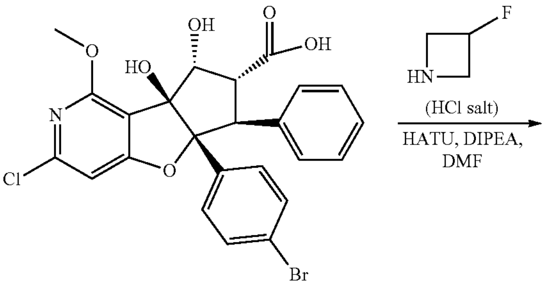

1

-continued

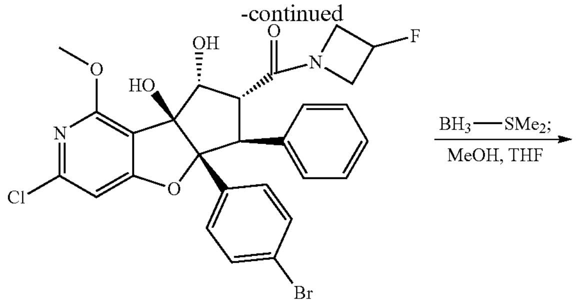

2

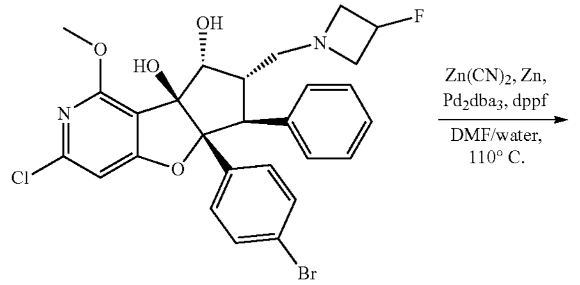

3

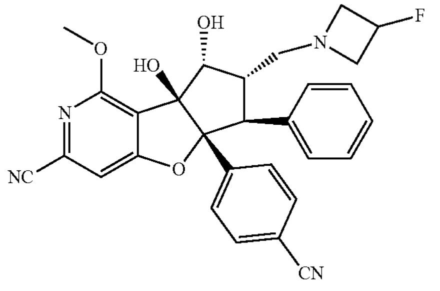

211aF

+

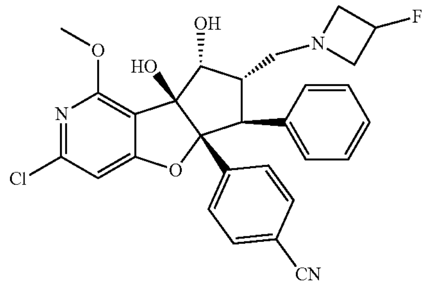

211bF

Synthesis of rac-((5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridin-7-yl)(3-fluoroazetidin-1-yl)methanone (2)

To a solution of rac-(5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridine-7-carboxylic acid (1, 50 mg, 0.094 mmol) in N,N-dimethylformamide (1 mL) at rt under argon was added HATU (40 mg, 0.11 mmol). After 2 min N,N-diisopropylethylamine (42 μL, 31 mg, 0.24 mmol) was added, and the mixture was stirred at rt. After 15 min another 42 μL (31 mg, 0.24 mmol) DIPEA were added, followed by 3-fluoroazetidine hydrochloride (31 mg, 0.28 mmol) and the mixture was stirred at rt for 10 min. Then the mixture was diluted with ethyl acetate and washed with brine. The aq. phase was re-extracted with EtOAc once. Then the combined organic phases were dried ($Na_2SO_4$), filtered and concentrated. Purification by column chromatography ($SiO_2$, 0-5% MeOH/dichloromethane) provided 63.6 mg of the still impure product of rac-((5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridin-7-yl)(3-fluoroazetidin-1-yl)methanone (2) as a white foam, which was used without further purification. MS (ESI) m/z 589.1 $[M+1]^+$.

Synthesis of rac-(5aR,6S,7S,8R,8aS)-5a-(4-bromophenyl)-3-chloro-7-((3-fluoroazetidin-1-yl)methyl)-1-methoxy-6-phenyl-5a,6,7,8-tetrahydro-8aH-cyclopenta[4,5]furo[3,2-c]pyridine-8,8a-diol (3)

To a solution of rac-((5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridin-7-yl)(3-fluoroazetidin-1-yl)methanone (2, 63.6 mg of the impure product of the previous step) in THF (0.80 mL) at 0° C. was added $BH_3$-DMS complex in THF (2M, 0.28 mL, 0.56 mmol) and the mixture was stirred at 40 C for 4 h. Borane adducts of desired product observed by LCMS. 1 mL MeOH was carefully added at 0° C. and the mixture was stirred at 60° C. for 8 h, then at rt for another 1 h. The product was isolated using ion-exchange extraction [Phenomenex Strata™-X-C; column was washed with water, product solution loaded, washed with water (3×), MeCN (3×), MeOH (3×), then product was eluted with 5% $NH_4H$ in MeOH (3×)]. The so-obtained product of rac-(5aR,6S,7S,8R,8aS)-5a-(4-bromophenyl)-3-chloro-7-((3-fluoroazetidin-1-yl)methyl)-1-methoxy-6-phenyl-5a,6,7,8-tetrahydro-8aH-cyclopenta[4,5]furo[3,2-c]pyridine-8,8a-diol (3) was purified by column chromatography ($SiO_2$, 0-5% MeOH/dichloromethane). Yield: 34.7 mg (0.060 mmol, 64% over 2 steps); MS (ESI) m/z 575.1 $[M+1]^+$.

Synthesis of rac-(5aR,6S,7S,8R,8aS)-5a-(4-cyanophenyl)-7-((3-fluoroazetidin-1-yl)methyl)-8,8a-dihydroxy-1-methoxy-6-phenyl-5a, 7,8,8a-tetrahydro-6H-cyclopenta[4,5]furo[3,2-c]pyridine-3-carbonitrile (Cpd. No. 211aF)

Rac-4-((5aR,6S,7S,8R,8aS)-3-chloro-7-((3-fluoroazetidin-1-yl)methyl)-8,8a-dihydroxy-1-methoxy-6-phenyl-6,7,8,8a-tetrahydro-5aH-cyclopenta[4,5]furo[3,2-c]pyridin-5a-yl)benzonitrile (Cpd. No. 211bF)

In a vial, rac-(5aR,6S,7S,8R,8aS)-5a-(4-bromophenyl)-3-chloro-7-((3-fluoroazetidin-1-yl)methyl)-1-methoxy-6-phenyl-5a,6,7,8-tetrahydro-8aH-cyclopenta[4,5]furo[3,2-c]pyridine-8,8a-diol (3, 31.8 mg, 0.0552 mmol) was dissolved in N,N-dimethylformamide (0.50 mL) and Water (0.05 mL), and zinc (1.2 mg, 0.018 mmol) and zinc cyanide (33 mg, 0.28 mmol) were added. The mixture was degassed by bubbling argon through it for 5 min. Then dppf (9.2 mg, 0.017 mmol) and $Pd_2dba_3$ (7.6 mg, 0.0083 mmol) were added. The mixture was degassed by bubbling argon through it for another 5 min, then the vial was sealed and placed in a preheated heating block (110° C.). The mixture was stirred for 2 h. Then the mixture was diluted with DMSO/MeCN and filtered, and the filtrate was subjected to purification by HPLC (C18, MeCN/water+0.1% TFA; product fractions combined and lyophilized) to provide the desired products of rac-(5aR,6S,7S,8R,8aS)-5a-(4-cyanophenyl)-7-((3-fluoroazetidin-1-yl)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 211aF) and rac-4-((5aR,6S,7S,8R,8aS)-3-chloro-7-((3-fluoroazetidin-1-yl)methyl)-8,8a-dihydroxy-1-methoxy-6-phenyl-6,7,8,8a-tetrahydro-5aH-cyclopenta[4,5]furo[3,2-c]pyridin-5a-yl)benzonitrile (Cpd. No. 211bF) as their diastereomeric TFA salts (cis/trans ammonium-H relative to F, dr ca. 1:1). Yields and analytical data: (Cpd. No. 211aF) (ca. 1:1 mixture of diastereomeric TFA salts): 20.1 mg (0.0321 mmol, 58%), white solid; MS (ESI) m/z 513.3 $[M+1]^+$. Compounds 211aF and 211bF appear to exist as diastereomeric TFA salts (dr ca. 1:1, i. e. ammonium-proton cis and trans relative to F in each case). In addition to this, the observed signal broadening hampered the detailed analysis of the $^1$H-NMRs. Therefore, in the following only selected characteristic NMR signals are listed. $^1$H NMR (400 MHz, DMSO-$d_6$) δ 10.56 (b, 0.5H), 9.90 (b, 0.5H), 7.61 (s, 1H), 7.57 (d, J=8.6 Hz, 2H), 7.34 (d, J=8.6 Hz, 2H), 7.16-6.97 (m, 5H), 6.01 (s, 0.5H), 5.99 (s, 0.5H), 5.70 (b, 0.5H), 5.59 (b, 0.5H), 5.52-5.26 (m, 1H), 3.92 (s, 3H). [Remaining protons appear as broad signals between 4.80 and 2.60 ppm.]. (Cpd. No. 211bF) (ca. 1:1 mixture of diastereomeric TFA salts): 2.3 mg (0.0036 mmol, 7%), white solid; MS (ESI) m/z 522.4 $[M+1]^+$. $^1$H NMR (400 MHz, DMSO-$d_6$) δ 10.44 (b, 0.5H), 9.72 (b, 0.5H), 7.57 (d, J=8.4 Hz, 2H), 7.36-7.31 (m, 2H), 7.17-6.93 (m, 6H), 5.84 (bs, 0.5H), 5.82 (s, 0.5H), 5.53 (bd, J=6.3 Hz, 0.5H), 5.43 (d, J=6.3 Hz, 0.5H), 5.52-5.25 (m, 1H), 3.87 (s, 3H). [Remaining protons appear as broad signals between 4.75 and 2.80 ppm.]

Example 212

(5aR,6S,7S,8R,8aS)-7-(azetidin-1-ylmethyl)-5a-(4-cyanophenyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 212F)

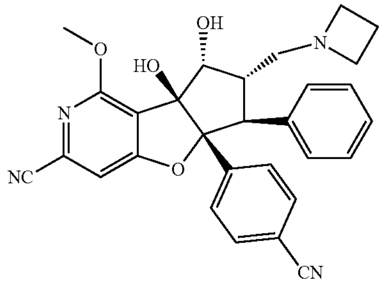

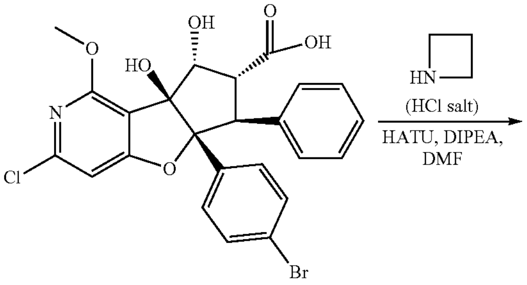

1

-continued

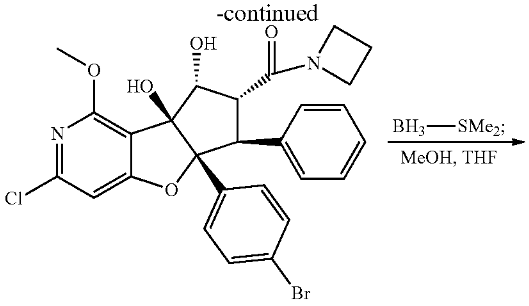

2

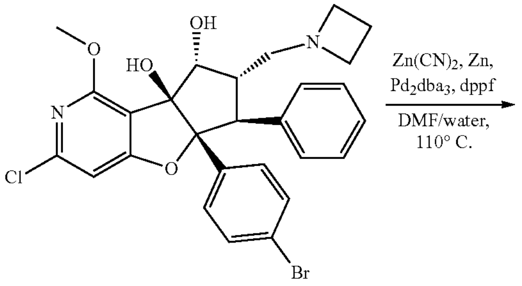

3

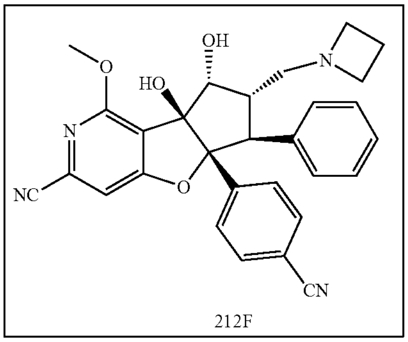

212F

Synthesis of rac-azetidin-1-yl((5aR,6S,7R,8R,8aS)-5a-(4-bromophenyl)-3-chloro-8,8a-dihydroxy-1-methoxy-6-phenyl-5a, 7,8,8a-tetrahydro-6H-cyclopenta[4,5]furo[3,2-c]pyridin-7-yl)methanone (2)

To a solution of rac-(5aR,6S,7R,8R,8aS)-5a-(4-bromophenyl)-3-chloro-8,8a-dihydroxy-1-methoxy-6-phenyl-5a, 7,8,8a-tetrahydro-6H-cyclopenta[4,5]furo[3,2-c]pyridine-7-carboxylic acid (1, 50 mg, 0.094 mmol) in N,N-dimethylformamide (1 mL) at rt under argon was added HATU (40 mg, 0.11 mmol). After 2 min N,N-diisopropylethylamine (42 μL, 31 mg, 0.24 mmol) was added, and the mixture was stirred for 15 min. Then another 42 μL (31 mg, 0.24 mmol) DIPEA were added, followed by azetidine hydrochloride (26 mg, 0.28 mmol) and the mixture was stirred at rt for 45 min. Then the mixture was diluted with ethyl acetate and washed with brine. The aq. phase was re-extracted with EtOAc once. Then the combined organic phases were dried ($Na_2SO_4$), filtered and concentrated. Purification by column chromatography ($SiO_2$, 0-5% MeOH/dichloromethane) yielded 58.7 mg of the still impure product of rac-azetidin-1-yl((5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridin-7-yl)methanone (2) as a white foam; MS (ESI) m/z 571.2 $[M+1]^+$. This material was used without further purification.

Synthesis of rac-(5aR,6S,7S,8R,8aS)-7-(azetidin-1-ylmethyl)-5a-(4-bromophenyl)-3-chloro-1-methoxy-6-phenyl-5a,6,7,8-tetrahydro-8aH-cyclopenta[4,5]furo[3,2-c]pyridine-8,8a-diol (3)

To a solution of rac-azetidin-1-yl((5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridin-7-yl)methanone (2, 58.7 mg of impure product of the previous step) in THF (0.80 mL) at 0° C. was added $BH_3$-DMS complex in THF (2M, 0.28 mL, 0.56 mmol) and the mixture was stirred at 40° C. for 4 h. Borane adducts of desired product observed by LCMS. 1 mL MeOH was carefully added at 0° C. and the mixture was stirred at 60° C. for 8 h, then at rt for another 2 h. Then product was isolated using ion-exchange extraction [Phenomenex Strata™-X-C; column was washed with water, product solution loaded, washed with water (3×), MeCN (3×), MeOH (3×), then product was eluted with 5% $NH_4OH$ in MeOH (3×)]. The so-obtained material was repurified by column chromatography ($SiO_2$, 0-10% MeOH/dichloromethane) to provide the desired product of rac-(5aR,6S,7S,8R,8aS)-7-(azetidin-1-ylmethyl)-5a-(4-bromophenyl)-3-chloro-1-methoxy-6-phenyl-5a,6,7,8-tetrahydro-8aH-cyclopenta[4,5]furo[3,2-c]pyridine-8,8a-diol (3) as a white solid. Yield: 14.1 mg (0.0253 mmol, 27%, 2 steps); MS (ESI) m/z 557.3 $[M+1]^+$.

Synthesis of (5aR,6S,7S,8R,8aS)-7-(azetidin-1-ylmethyl)-5a-(4-cyanophenyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 212F)

In a vial, rac-(5aR,6S,7S,8R,8aS)-7-(azetidin-1-ylmethyl)-5a-(4-bromophenyl)-3-chloro-1-methoxy-6-phenyl-5a,6,7,8-tetrahydro-8aH-cyclopenta[4,5]furo[3,2-c]pyridine-8,8a-diol (3, 14.1 mg, 0.0253 mmol) was dissolved in N,N-dimethylformamide (0.40 mL) and water (0.04 mL) and zinc (0.8 mg, 0.01 mmol) and zinc cyanide (15 mg, 0.13 mmol) were added. The mixture was degassed by bubbling argon through it for 5 min. Then dppf (4.2 mg, 0.0076 mmol) and $Pd_2dba_3$ (3.5 mg, 0.0038 mmol) were added. The mixture was degassed by bubbling argon through it for another 5 min, then the vial was sealed and placed in a preheated heating block (110° C.). The mixture was stirred for 2 h Then the mixture was diluted with DMSO/MeCN and filtered, and the filtrate was subjected to purification by HPLC (C18, MeCN/water+0.1% TFA; product fractions were combined and lyophilized) to provide 4.8 mg of slightly impure product of rac-(5aR,6S,7S,8R,8aS)-7-(azetidin-1-ylmethyl)-5a-(4-cyanophenyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 14) as the TFA salt containing small amounts (ca. 10%) of the monocyanated product, and 4.7 mg (31%) of the pure TFA salt of rac-(5aR,6S,7S,8R,8aS)-7-(azetidin-1-ylmethyl)-5a-(4-cyanophenyl)-8,8a-dihydroxy-1-methoxy-6-phenyl-5a,7,8,8a-tetrahydro-6H-cyclopenta[4,5]furo[3,2-c]pyridine-3-carbonitrile as a white solid; The enantiomers were separated by chiral HPLC [CHIRALPAK IG (4.6×250) mm, 5μ] in $CO_2$/IPA/TEA (60:40:0.2). Peak 1 (Cpd. No. 212F, 505 mg), $R_t$=2.03 min, ee: 98.76%, $[\alpha]_D$−101° (c 0.40, $CHCl_3$); MS (ESI) m/z 495.16$[M+1]^+$; $^1H$ NMR (400 MHz, DMSO-$d_6$) 7.54-7.50 (m, 3H), 7.32 (d, J=7.6 Hz, 2H), 7.08-7.07 (m, 2H), 7.02-6.96 (m, 3H), 5.82 (s, 1H), 4.46 (s, 1H), 3.89 (s, 3H), 3.80 (d, J=14.0 Hz, 1H), 3.10 (bs, 4H), 2.95 (bs, 1H), 2.62-2.59 (m, 1H), 2.32 (d, J=5.2 Hz, 1H), 1.92-1.90 (m, 2H), 1.03 (bs, 1H). Peak-2 (455 mg), $R_t$=3.77 min, ee: 99.50%, $[\alpha]_D$+120.2° (c 0.25, $CHCl_3$); MS (ESI) m/z 495.16 $[M+1]^+$; $^1H$ NMR (400 MHz, DMSO-$d_6$) 7.54-7.50 (m, 3H), 7.32 (d, J=7.6 Hz, 2H), 7.10-7.07 (m, 2H), 7.02-6.97 (m, 3H), 5.82 (s, 1H), 4.46 (s, 1H), 3.89 (s, 3H), 3.80 (d, J=14.0 Hz, 1H), 3.10 (bs, 4H), 2.95 (bs, 1H), 2.62-2.59 (m, 1H), 2.32 (d, J=5.2 Hz, 1H), 1.92-1.90 (m, 2H), 1.04-1.02 (m, 1H).

Example 213

Rac-(5aR,6S,7R,8R,8aR)-5a-(4-cyanophenyl)-8-((4,4-difluoropiperidin-1-yl)methyl)-8a-hydroxy-7-(hydroxymethyl)-1-methoxy-6-phenyl-5a,7,8,8a-tetrahydro-6H-cyclopenta[4,5]furo[3,2-c]pyridine-3-carbonitrile (Cpd. No. 213F)

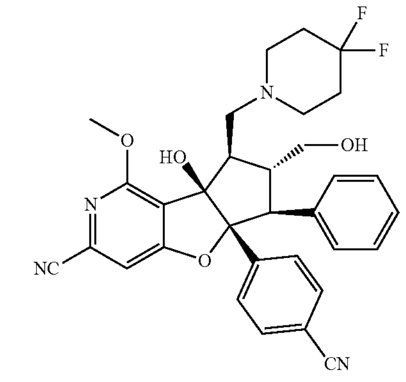

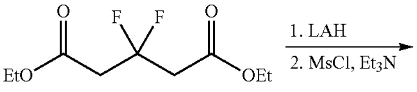

1

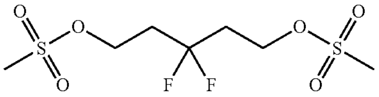

2

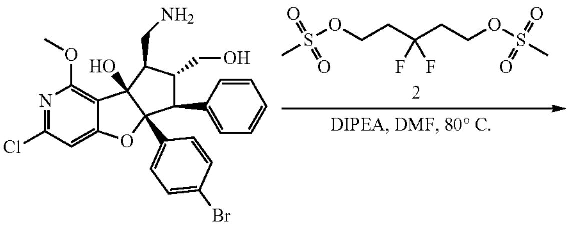

3

-continued

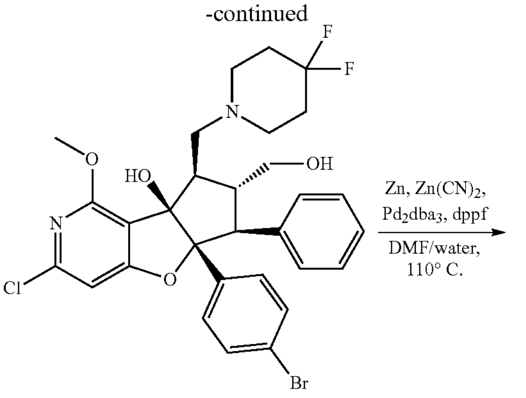

4

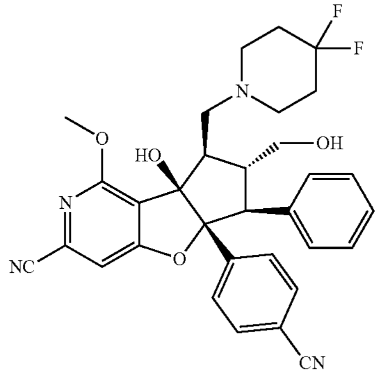

213F

Synthesis of 3,3-difluoropentane-1,5-diyl dimethanesulfonate (2)

[1] Ester reduction: To a solution of diethyl 3,3-difluoropentanedioate (1, 142 mg, 0.632 mmol) in THF (7 mL) at 0° C. was added LAH (57 mg, 1.5 mmol) and the mixture was stirred at rt. After 2.5 h 0.3 mL water were added at 0° C., followed by 0.3 mL 12.5% NaOH (aq) and ca. 500 mg of $Na_2SO_4$. The mixture was stirred for 10 min at rt, then filtered (rinsed with THF) and concentrated to give 103 mg of 3,3-difluoropentane-1,5-diol as a cloudy oil, which was used without further purification. $^1H$ NMR (400 MHz, DMSO-$d_6$) δ 4.64 (t, J=5.1 Hz, 2H), 3.56 (dt, J=6.9, 5.1 Hz, 4H), 2.06 (tt, J=17.0, 6.9 Hz, 4H).

[2] Mesylation: To a solution of 3,3-difluoropentane-1,5-diol (103 mg of the crude product obtained in the previous step) in dichloromethane (4.2 mL) at −78° C. were added triethylamine (0.35 mL, 0.25 g, 2.5 mmol) and methanesulfonyl chloride (0.12 mL, 0.18 g, 1.6 mmol) and the mixture was stirred at −78° C. for 30 min, then warmed up to 0° C. and stirred for another 1.5 h. Then the reaction was quenched (water) and the mixture was extracted (3×dichloromethane). The combined organic phases were dried ($Na_2SO_4$), filtered and concentrated. The residue was taken up in EtOAc and washed with water and brine. The organic phase was dried ($Na_2SO_4$), filtered and concentrated to give 192 mg of 3,3-difluoropentane-1,5-diyl dimethanesulfonate (2) as a yellowish oil, which was used without further purification. $^1H$ NMR (400 MHz, $CDCl_3$) δ 4.44 (t, J=6.4 Hz, 4H), 3.05 (s, 6H), 2.41 (tt, J=16.1, 6.4 Hz, 4H).

Synthesis of rac-(5aR,6S,7R,8R,8aR)-5a-(4-bromophenyl)-3-chloro-8-((4,4-difluoropiperidin-1-yl)methyl)-7-(hydroxymethyl)-1-methoxy-6-phenyl-5a,6,7,8-tetrahydro-8aH-cyclopenta[4,5]furo[3,2-c]pyridin-8a-ol (4)

A solution of rac-(5aR,6S,7R,8R,8aR)-8-(aminomethyl)-5a-(4-bromophenyl)-3-chloro-7-(hydroxymethyl)-1-methoxy-6-phenyl-5a,6,7,8-tetrahydro-8aH-cyclopenta[4,5]furo[3,2-c]pyridin-8a-ol (3, 30 mg, 0.056 mmol), N,N-diisopropylethylamine (36 μL, 27 mg, 0.21 mmol) and (3,3-difluoro-5-methylsulfonyloxy-pentyl) methanesulfonate (2, 22 mg, 0.074 mmol) in N,N-dimethylformamide (0.60 mL) was stirred at 80° C. After 5 h another 36 μL (27 mg, 0.21 mmol) DIPEA and 20 mg (0.067 mmol) bis-mesylate (2) in 0.30 mL N,N-dimethylformamide were added, and stirring at 80 C was continued. After 7 h total, the mixture was cooled down to rt. The product was isolated by ion-exchange extraction as a mixture with the SM and other amines [Phenomenex Strata™-X-C; column was washed with water, product solution loaded, washed with water (3×), MeCN (3×), MeOH (3×), then product was eluted with 5% $NH_4OH$ in MeOH (3×)]. The so-obtained product mixture (23 mg) of rac-(5aR,6S,7R,8R,8aR)-5a-(4-bromophenyl)-3-chloro-8-((4,4-difluoropiperidin-1-yl)methyl)-7-(hydroxymethyl)-1-methoxy-6-phenyl-5a,6,7,8-tetrahydro-8aH-cyclopenta[4,5]furo[3,2-c]pyridin-8a-ol (4), was used in the next step without further purification.

Synthesis of rac-(5aR,6S,7R,8R,8aR)-5a-(4-cyanophenyl)-8-((4,4-difluoropiperidin-1-yl)methyl)-8a-hydroxy-7-(hydroxymethyl)-1-methoxy-6-phenyl-5a,7,8,8a-tetrahydro-6H-cyclopenta[4,5]furo[3,2-c]pyridine-3-carbonitrile (Cpd. No. 213F)

In a vial, crude rac-(5aR,6S,7R,8R,8aR)-5a-(4-bromophenyl)-3-chloro-8-((4,4-difluoropiperidin-1-yl)methyl)-7-(hydroxymethyl)-1-methoxy-6-phenyl-5a,6,7,8-tetrahydro-8aH-cyclopenta[4,5]furo[3,2-c]pyridin-8a-ol (4, 23 mg obtained in the previous step) was dissolved in N,N-dimethylformamide (0.40 mL) and water (0.04 mL), and zinc (0.9 mg, 0.01 mmol) and zinc cyanide (22 mg, 0.19 mmol) were added. The mixture was degassed by bubbling argon through it for 5 min. Then dppf (6.1 mg, 0.011 mmol) and $Pd_2dba_3$ (5.1 mg, 0.0056 mmol) were added. The mixture was degassed by bubbling argon through it for another 5 min, then the vial was sealed, then placed in a preheated heating block (110° C.). The mixture was stirred for 2 h. Then the mixture was filtered, diluted with MeCN, DMSO and water, filtered again, and subjected to repeated purification by HPLC (C18, MeCN/water+0.1% TFA). The so-obtained product (free base) was finally purified by preparative TLC ($SiO_2$, dichloromethane/2% MeOH) to provide the pure desired product rac-(5aR,6S,7R,8R,8aR)-5a-(4-cyanophenyl)-8-((4,4-difluoropiperidin-1-yl)methyl)-8a-hydroxy-7-(hydroxymethyl)-1-methoxy-6-phenyl-5a,7,8,8a-tetrahydro-6H-cyclopenta[4,5]furo[3,2-c]pyridine-3-carbonitrile (Cpd. No. 213F). Yield: 2.0 mg (6%, 2 steps), white solid; MS (ESI) m/z 573.4 $[M+1]^+$; $^1H$ NMR (400 MHz, DMSO-$d_6$) δ 7.66 (s, 1H), 7.61 (d, J=8.5 Hz, 2H), 7.36 (bd, 2H), 7.12-7.03 (m, 3H), 6.82-6.75 (m, 2H), 6.10-5.90 (b, 1H), 5.88 (b, 1H), 4.00 (s, 3H), 3.47-3.38 (m, 1H), 3.24 (d, J=13.6 Hz, 1H), 3.20-3.12 (m, 1H), 3.15-2.63 (b, 8H), 2.14-1.92 (b, 4H).

Example 214

Rac-(5aR,6S,7S,8R,8aS)-5a-(4-bromophenyl)-3-chloro-7-((3,3-dimethylmorpholino)methyl)-6-phenyl-5a,6,7,8-tetrahydro-8aH-cyclopenta[4,5]furo[3,2-b]pyridine-8,8a-diol (Cpd. No. 214F)

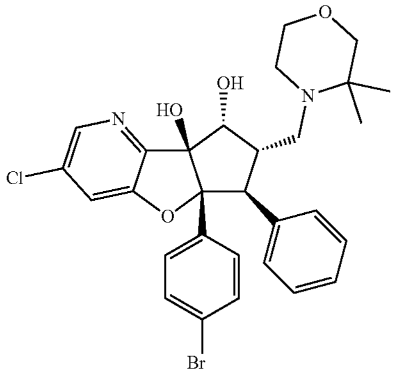

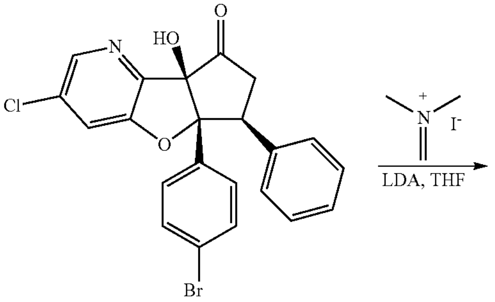

1

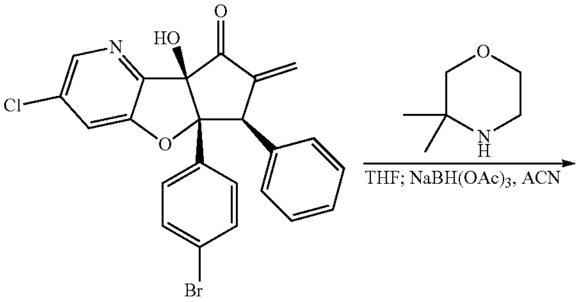

2

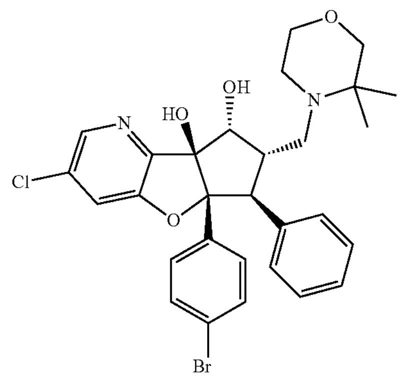

214F

Synthesis of rac-(5aR,6R,8aR)-5a-(4-bromophenyl)-3-chloro-8a-hydroxy-7-methylene-6-phenyl-5a,6,7,8a-tetrahydro-8H-cyclopenta[4,5]furo[3,2-b]pyridin-8-one (2)

A stirred solution of rac-(5aR,6S,8aR)-5a-(4-bromophenyl)-3-chloro-8a-hydroxy-6-phenyl-5a,6,7,8a-tetrahydro-8H-cyclopenta[4,5]furo[3,2-b]pyridin-8-one (1, 95 mg, 0.008 mmol) in THF (3 mL) was cooled to −78° C. and lithium diisopropyl amide (1.95 M in THF, 0.43 mL, 0.85 mmol) was added slowly. After 15 minutes dimethyl(methylene) ammonium iodide (192 mg, 1.04 mmol) was added in 1 portion. The reaction mixture was allowed to gradually warm to room temperature. After stirring at room temperature for 3 hours the reaction mixture was diluted with 10 mL of ethyl acetate and 10 mL of saturated aqueous sodium bicarbonate. The layers were separated and the aqueous phase extracted with ethyl acetate three times. The combined organic material was washed with brine and dried over magnesium sulfate. Purification by silica gel chromatography eluting with hexanes and ethyl acetate afforded rac-(5aR,6R,8aR)-5a-(4-bromophenyl)-3-chloro-8a-hydroxy-7-methylene-6-phenyl-5a,6,7,8a-tetrahydro-8H-cyclopenta[4,5]furo[3,2-b]pyridin-8-one (2) as a tan solid. Yield: 55 mg, 56%; LCMS (ESI) m/z 469.5 $[M+1]^+$.

Synthesis of rac-(5aR,6S,7S,8R,8aS)-5a-(4-bromophenyl)-3-chloro-7-((3,3-dimethylmorpholino)methyl)-6-phenyl-5a,6,7,8-tetrahydro-8aH-cyclopenta[4,5]furo[3,2-b]pyridine-8,8a-diol (Cpd. No. 214F)

Rac-(5aR,6R,8aR)-5a-(4-bromophenyl)-3-chloro-8a-hydroxy-7-methylene-6-phenyl-5a,6,7,8a-tetrahydro-8H-cyclopenta[4,5]furo[3,2-b]pyridin-8-one (2, 26.0 mg, 0.07 mmol) was dissolved in THF (0.3 mL) and the mixture was stirred for 3 h. The solvent was then removed under a stream of nitrogen. The oily residue was taken up in acetonitrile (0.3 mL) and stirred at rt while sodium triacetoxyborohydride (44 mg, 0.21 mmol) was added. After 2 hr the mixture was diluted with ethyl acetate and saturated aqueous ammonium chloride was added. The aqueous material was extracted with ethyl acetate 3 times, and the combined organic material was washed with brine and dried over magnesium sulfate. The solvent was removed in vacuo and residue purified by RP-HPLC. The fractions containing product were then passed through an ion exchange column, washing the material first with water, then methanol, then acetonitrile. The product was then eluted with a solution of methanol:dichloromethane:aqueous $NH_4OH$ (75:20:5), and the solvent rotavapped. The residue was taken up in a water/acetonitrile mixture, frozen and lyophilized to afford rac-(5aR,6S,7S,8R,8aS)-5a-(4-bromophenyl)-3-chloro-7-((3,3-dimethylmorpholino)methyl)-6-phenyl-5a,6,7,8-tetrahydro-8aH-cyclopenta[4,5]furo[3,2-b]pyridine-8,8a-diol (Cpd. No. 214F) as a white solid. Yield: 4.9 mg, 17%; LCMS (ESI) m/z 586.5 $[M+1]^+$; $^1H$ NMR (400 MHz, DMSO-$d_6$) δ 8.12 (s, 1H), 7.55 (s, 1H), 7.17 (d, J=8 Hz, 2H), 7.09-7.00 (m, 7H), 5.92 (s, 1H), 4.39 (d, J=6H), 3.88 (d, J=12 Hz, 1H), 3.67-3.65 (m, 1H), 3.57-3.55 (m, 1H), 3.16-3.09 (m, 4H), 2.73-2.62 (m, 2H), 2.02-1.99 (m, 1H), 0.83 (s, 3H), 0.76 (s, 3H).

Example 215

Rac-((5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridin-7-yl)(3-(difluoromethyl)azetidin-1-yl)methanone (Cpd. No. 215N)

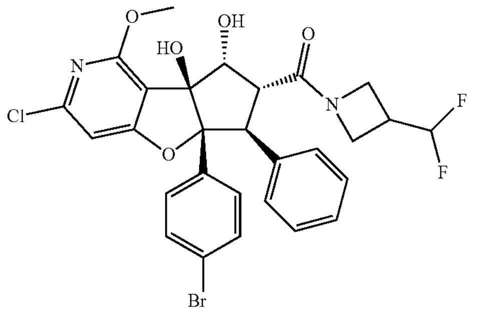

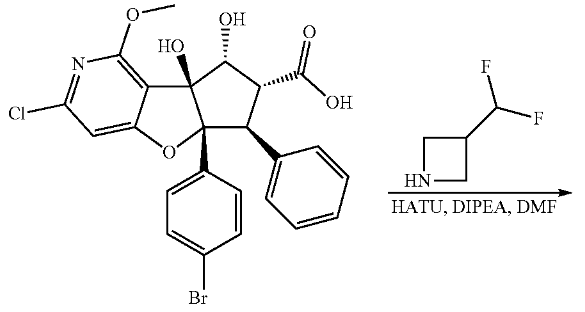

1

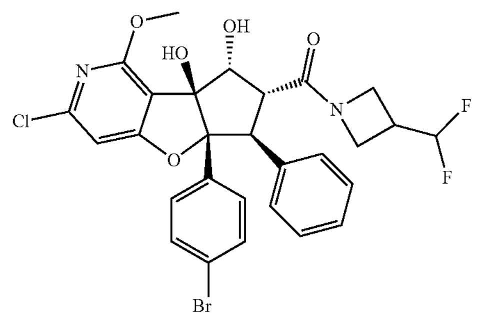

215F

Synthesis of rac-((5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridin-7-yl)(3-(difluoromethyl)azetidin-1-yl)methanone (Cpd. No. 215F)

To a stirred solution of rac-(5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridine-7-carboxylic acid (1, 0.08 g, 0.14 mmol) in N,N-dimethylformamide (1.76 mL) was added HATU (55.8 mg, 0.14 mmol) and then N,N diisopropylamine (0.12 mL, 0.70 mmol) dropwise 2 minutes later. 3-(difluoromethyl)azetidine hydrochloride (60.2 mg, 0.42 mmol) was added in 1 portion. After 65 minutes the mixture was diluted with water and EtOAc and washed organic phase with water 2× and brine 1×. The organic material was dried over magnesium sulfate, filtered, and rotavapped. The crude material was purified by by silica gel column chromatography eluting with hexanes and ethyl acetate to afford rac-((5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridin-7-yl)(3-(difluoromethyl)azetidin-1-yl)methanone (Cpd. No. 215F) as a white solid. Yield: 82 mg, 94%; LCMS (ESI) m/z 621.3, 623.3 $[M+1]^+$; $^1H$ NMR (400 MHz, DMSO-$d_6$) δ 7.15 (d, J=8.3 Hz, 2H), 7.04-6.93 (m, 5H), 6.93-6.84 (m, 3H), 6.30 (t, J=56 Hz, 1H) 5.57 (d, J=13.1 Hz, 1H), 5.18 (s, 1H), 4.68-4.58 (m, 2H), 4.53-4.22 (m, 3H), 3.87 (d, J=8.7 Hz, 1H), 3.84-3.66 (m, 6H).

Example 216

Rac-((5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridin-7-yl)(3-(difluoromethyl)azetidin-1-yl)methanone (Cpd. No. 216F)

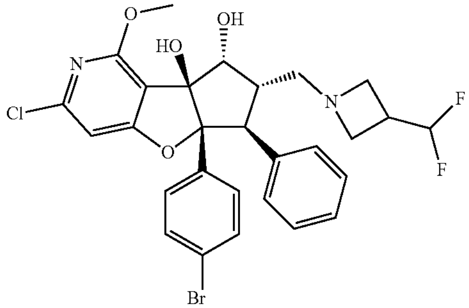

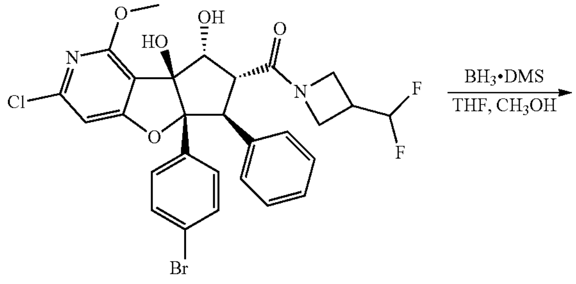

1

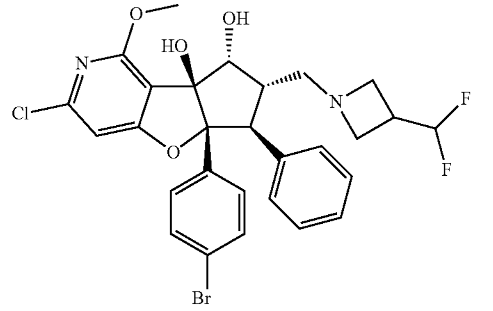

216F

Synthesis of rac-((5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridin-7-yl)(3-(difluoromethyl)azetidin-1-yl)methanone (Cpd. No. 216F)

To a stirred solution of rac-[(5aR,6S,7R,8R,8aS)-5a-(4-bromophenyl)-3-chloro-8,8a-dihydroxy-1-methoxy-6-phenyl-7,8-dihydro-6H-cyclopenta[4,5]furo[1,2-d]pyridin-7-yl]-[3-(difluoromethyl)azetidin-1-yl]methanone (0.08 g, 0.13200 mmol) in THF (2 mL) was added borane methylsulfanylmethane (2.0 M in THF, 0.66 mL, 1.32 mmol). After 10 min the reaction was warmed to 40° C. After 14 the reaction was cooled to room temperature and methanol (1.7 mL) was slowly added. Subsequently the reaction was heated to 70° C. After 3.5 hours the pot was cooled to rt. The solvent was rotavapped and the residue was purified via ion exchange chromatography, eluting with methanol twice, acetonitrile twice, and then eluting the product with a MeOH:$NH_4$OH:dichloromethane (75:5:20) solvent system. The solvent was removed in vacuum to afford Rac-((5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridin-7-yl)(3-(difluoromethyl)azetidin-1-yl)methanone (Cpd. No. 216F) as a white foam. Yield: 57 mg, 71%; LCMS (ESI) m/z 607.1 609.2 $[M+1]^+$; $^1$H NMR (400 MHz, DMSO-$d_6$) δ 7.24-7.15 (m, 2H), 7.10-7.02 (m, 5H), 7.02-6.89 (m, 3H), 6.82 (s, 1H), 6.16 (td, J=60 Hz, 5.3 Hz, 1H), 5.52 (s, 1H), 5.32 (s, 1H), 4.35 (d, J=4.1 Hz, 1H), 3.80 (s, 3H), 3.66 (d, J=14.2 Hz, 1H), 3.28-3.18 (m, 10H), 3.05 (t, J=6.7 Hz, 2H), 2.92-2.73 (m, 2H), 2.63-2.54 (m, 2H), 2.30-2.21 (m, 1H).

Example 217

Rac-4-((5aR,6S,7S,8R,8aS)-3-chloro-7-((3-(difluoromethyl)azetidin-1-yl)methyl)-8,8a-dihydroxy-1-methoxy-6-phenyl-6,7,8,8a-tetrahydro-5aH-cyclopenta[4,5]furo[3,2-c]pyridin-5a-yl)benzonitrile (Cpd. No. 217F)

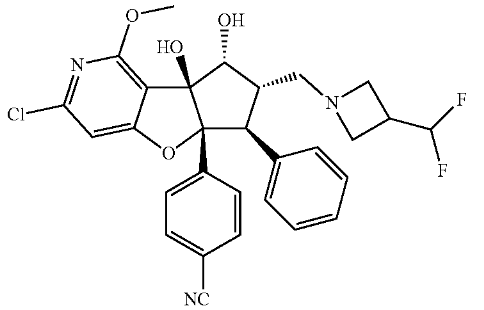

-continued

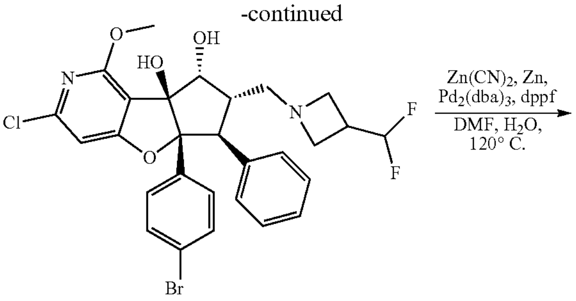

1

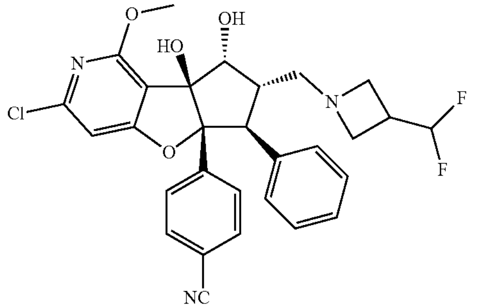

217F

Synthesis of rac-4-((5aR,6S,7S,8R,8aS)-3-chloro-7-((3-(difluoromethyl)azetidin-1-yl)methyl)-8,8a-dihydroxy-1-methoxy-6-phenyl-6,7,8,8a-tetrahydro-5aH-cyclopenta[4,5]furo[3,2-c]pyridin-5a-yl)benzonitrile (Cpd. No. 217F)

Rac-(5aR,6S,7S,8R,8aS)-5a-(4-bromophenyl)-3-chloro-7-((3-(difluoromethyl)azetidin-1-yl)methyl)-1-methoxy-6-phenyl-5a,6,7,8-tetrahydro-8aH-cyclopenta[4,5]furo[3,2-c]pyridine-8,8a-diol (1, 0.03 g, 0.046 mmol), dicyanozinc (32.45 mg, 0.276 mmol), dppf (20.4 mg, 0.037 mmol), and zinc (2.9 mg, 0.046 mmol) were dissolved in N,N-dimethylformamide (0.460 mL) and water (0.040 mL). The mixture was sparged with an argon balloon for 5 min then tris(dibenzylideneacetone)dipalladium(0) (16.8 mg, 0.018 mmol) was added and the reaction was stirred in heating block at 120° C. After 90 minutes the pot was cooled to room temperature. The mixture was diluted with methanol, filtered through celite and the volatile solvent removed in vacuo. The residue was taken up in DMSO and purified by RP-HPLC to afford rac-4-((5aR,6S,7S,8R,8aS)-3-chloro-7-((3-(difluoromethyl)azetidin-1-yl)methyl)-8,8a-dihydroxy-1-methoxy-6-phenyl-6,7,8,8a-tetrahydro-5aH-cyclopenta[4,5]furo[3,2-c]pyridin-5a-yl)benzonitrile (Cpd. No. 217F). Yield: 3.8 mg, 13%; LCMS (ESI) m/z 554.4, 556.3 $[M+1]^+$; $^1$H NMR (400 MHz, Methanol-$d_4$) δ 7.13-6.99 (m, 6H), 6.99-6.92 (m, 3H), 6.75 (s, 2H), 6.03 (td, J=56 Hz, 4.2 Hz, 1H), 4.61-4.53 (m, 3H), 3.94 (s, 3H), 3.87-3.77 (m, 2H), 3.75 (bs, 1H), 3.57 (bs, 1H), 3.03 (bs, 1H), 2.74 (bs, 1H).

Example 218

Rac-(5aR,6S,7S,8R,8aS)-5a-(4-cyanophenyl)-7-((3-(difluoromethyl)azetidin-1-yl)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 218F)

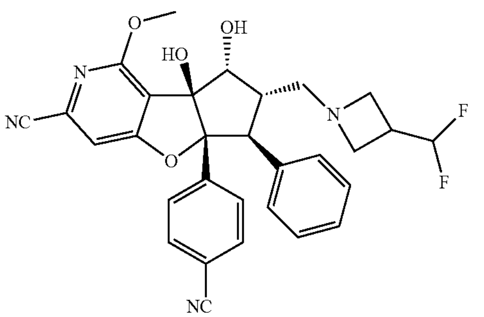

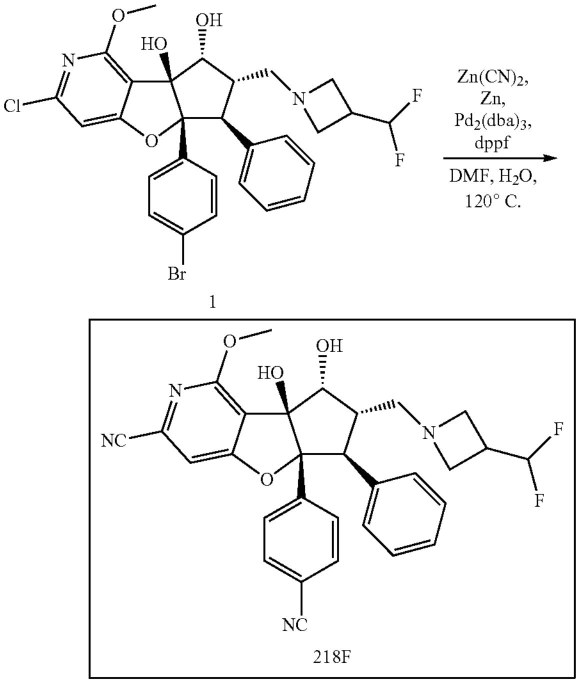

1

218F

Synthesis of rac-(5aR,6S,7S,8R,8aS)-5a-(4-cyanophenyl)-7-((3-(difluoromethyl)azetidin-1-yl)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 218F)

Rac-(5aR,6S,7S,8R,8aS)-5a-(4-bromophenyl)-3-chloro-7-((3-(difluoromethyl)azetidin-1-yl)methyl)-1-methoxy-6-phenyl-5a,6,7,8-tetrahydro-8aH-cyclopenta[4,5]furo[3,2-c]pyridine-8,8a-diol (1, 0.03 g, 0.04600 mmol), dicyanozinc (32.4 mg, 0.276 mmol), dppf (20.4 mg, 0.037 mmol), and zinc (2.9 mg, 0.046 mmol) were dissolved in N,N-dimethylformamide (0.460 mL) and water (0.040 mL). The mixture was sparged with an argon balloon for 5 min then Tris (dibenzylideneacetone)dipalladium(0) (16.8 mg, 0.0180 mmol) was added and the reaction was stirred in heating block at 120° C. After 90 minutes the pot was cooled to room temperature. The mixture was diluted with methanol, filtered through celite and the volatile solvent removed in vacuo. The residue was taken up in DMSO and purified by RP-HPLC to afford rac-(5aR,6S,7S,8R,8aS)-5a-(4-cyanophenyl)-7-((3-(difluoromethyl)azetidin-1-yl)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 218F). Yield: 5.3 mg, 21%; LCMS (ESI) m/z 545.5 $[M+1]^+$; $^1H$ NMR (400 MHz, Methanol-$d_4$) δ 7.46-7.35 (m, 4H), 7.24 (d, J=0.5 Hz, 1H), 7.11-6.93 (m, 5H), 5.98 (td, J=60.0, 4.0 Hz, 1H), 4.81-4.67 (m, 2H), 4.63-4.53 (m, 2H), 3.98 (s, 3H), 3.82 (d, J=14.4 Hz, 1H), 3.47-3.28 (m, 3H), 3.30-3.15 (m, 2H), 3.05 (t, J=11.8 Hz, 1H), 2.88-2.73 (m, 1H), 2.52 (dd, J=12.5, 3.0 Hz, 1H), 1.27 (s, 1H).

Example 219

Rac-((5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridin-7-yl)(1,1-difluoro-4-azaspiro[2.3]hexan-4-yl)methanone (Cpd. No. 219F)

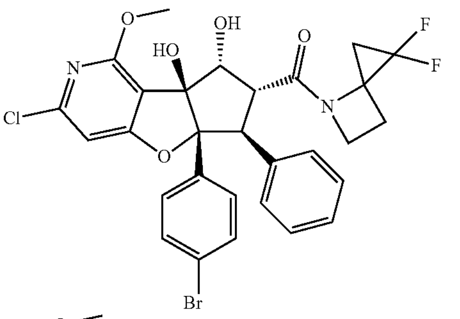

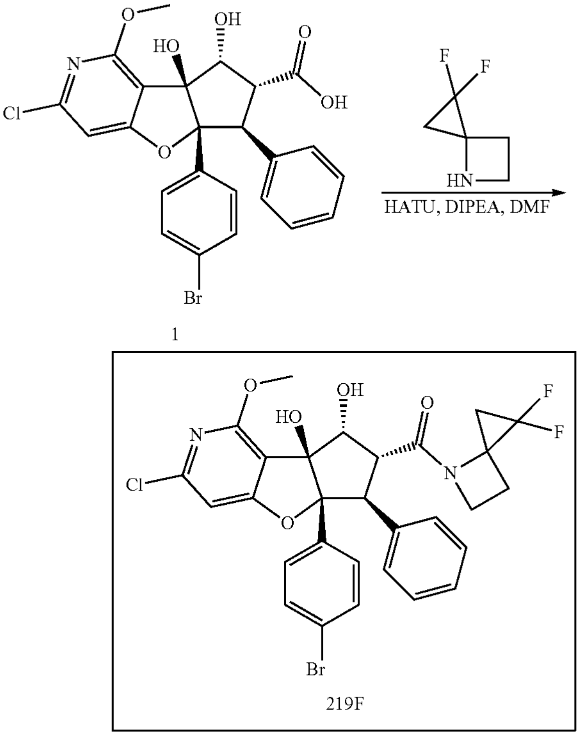

1

219F

Synthesis of rac-((5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridin-7-yl)(1,1-difluoro-4-azaspiro[2.3]hexan-4-yl)methanone (Cpd. No. 219F)

To a stirred solution of rac-(5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridine-7-carboxylic acid (1, 0.09 g, 0.169 mmol) in N,N-dimethylformamide (1.76 mL) was added HATU (67.4 mg, 0.177 mmol) and then N, N diisopropylamine (0.15 mL, 0.84 mmol) was dropwise 2 minutes later. After 20 minutes 2,2-difluoro-5-azaspiro[2.3]hexane hydrochloride (78.8 mg, 0.510 mmol) was added in 1 portion. After 30 min the mixture was diluted with water and EtOAc and the organic material was washed with water twice and with brine once. The organic material was dried over magnesium sulfate, filtered, and rotavapped. The crude material was purified by silica gel chromatography eluting with hexanes and EtOAc to afford the product rac-((5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridin-7-yl)(1,1-difluoro-4-azaspiro[2.3]hexan-4-yl)methanone (Cpd. No. 219F). Yield: 83 mg, 78%; LCMS (ESI) m/z 633.3, 635.3[M+1]$^+$; $^1$H NMR (400 MHz, DMSO-$d_6$) δ 7.21-7.14 (m, 2H), 7.07-6.88 (m, 8H), 5.60 (s, 1H), 5.55 (s, 1H), 5.37-5.29 (m, 1H), 4.77 (d, J=8.5 Hz, 1H), 4.70-4.58 (m, 2H), 4.46 (d, J=9.5 Hz, 1H), 4.32 (d, J=13.7 Hz, 1H), 3.98-3.83 (m, 3H), 3.81 (d, J=1.8 Hz, 3H), 1.80-1.74 (m, 2H).

Example 220

Rac-(5aR,6S,7S,8R,8aS)-5a-(4-bromophenyl)-3-chloro-7-((1,1-difluoro-4-azaspiro[2.3]hexan-4-yl)methyl)-1-methoxy-6-phenyl-5a,6,7,8-tetrahydro-8aH-cyclopenta[4,5]furo[3,2-c]pyridine-8,8a-diol (Cpd. No. 220F)

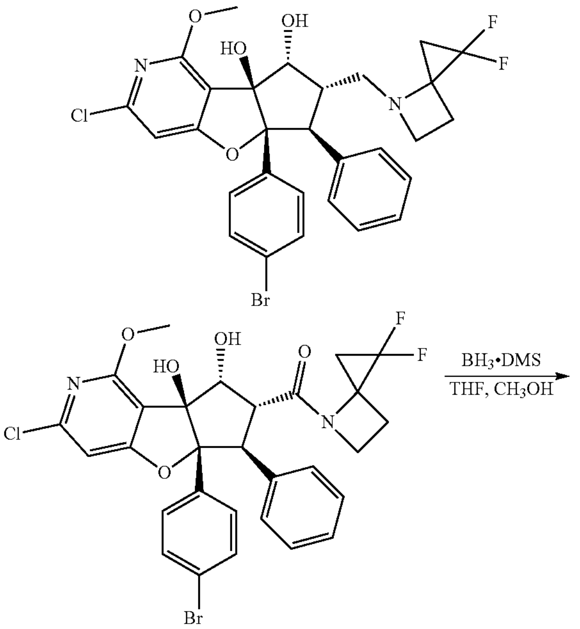

1

-continued

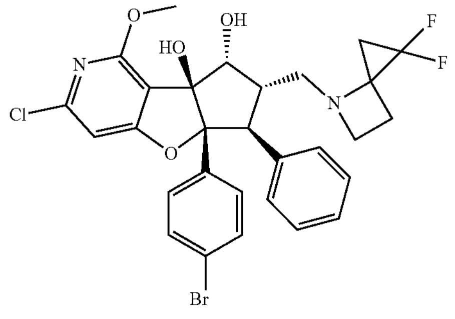

220F

Synthesis of rac-(5aR,6S,7S,8R,8aS)-5a-(4-bromophenyl)-3-chloro-7-((1,1-difluoro-4-azaspiro[2.3]hexan-4-yl)methyl)-1-methoxy-6-phenyl-5a,6,7,8-tetrahydro-8aH-cyclopenta[4,5]furo[3,2-c]pyridine-8,8a-diol (Cpd. No. 220F)

To a stirred solution of rac-((5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridin-7-yl)(1,1-difluoro-4-azaspiro[2.3]hexan-4-yl)methanone (1, 0.08 g, 0.126 mmol) in THF (1.76 mL) borane dimethylsulfide solution (2.0 M in THF, 0.50 mL, 1 mmol) was added. After 2 minutes the pot was warmed to 40° C. The reaction was stirred 12 hr and then cooled to rt and added methanol (1.7 mL) was added over 5 min to quench reaction. The mixture was then warmed to 60° C. for 8 hours and the reaction was cooled to room temperature and the solvent removed in vacuo. The residue was taken up in acetonitrile and purified by ion exchange chromatography, washing the column sequentially with water, acetonitrile, and methanol, and subsequently eluting product with a solution of 75:25:5 methanol:dichloromethane:ammonium hydroxide. The solvent was removed in vacuo and the residue was taken up in a mixture of acetonitrile and water, frozen, and lyophilized to afford rac-(5aR,6S,7S,8R,8aS)-5a-(4-bromophenyl)-3-chloro-7-((1,1-difluoro-4-azaspiro[2.3]hexan-4-yl)methyl)-1-methoxy-6-phenyl-5a,6,7,8-tetrahydro-8aH-cyclopenta[4,5]furo[3,2-c]pyridine-8,8a-diol (Cpd. No. 220F) as a fluffy white solid. Yield: 61 mg, 78%; LCMS (ESI) m/z 619.3, 621.1 [M+1]$^+$; $^1$H NMR (400 MHz, DMSO-$d_6$) δ 7.19 (d, J=8.7 Hz, 2H), 7.11-6.98 (m, 3H), 7.01-6.91 (m, 3H), 6.82 (s, 1H), 5.53 (bs, 1H), 5.20 (bs, 1H), 4.37 (bs, 1H), 3.81 (s, 3H), 3.67 (d, J=14.2 Hz, 1H), 3.44-3.41 (m, 1H). 3.28-3.17 (m, 2H), 2.91 (bs, 1H), 2.69 (bs, 1H), 2.34 (bs, 1H), 1.50 (m, 2H).

Example 221

Rac-(5aR,6S,7S,8R,8aS)-5a-(4-cyanophenyl)-7-((1,1-difluoro-4-azaspiro[2.3]hexan-4-yl)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 221F)

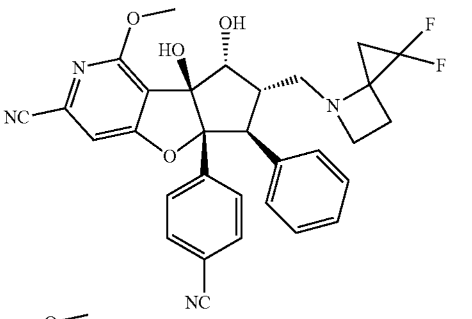

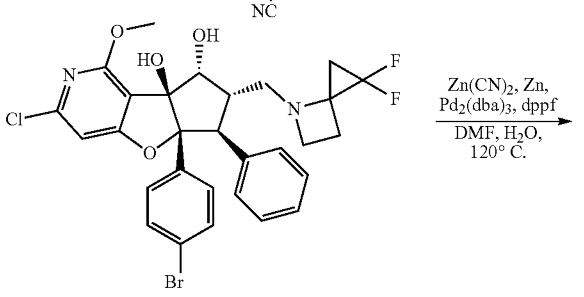

1

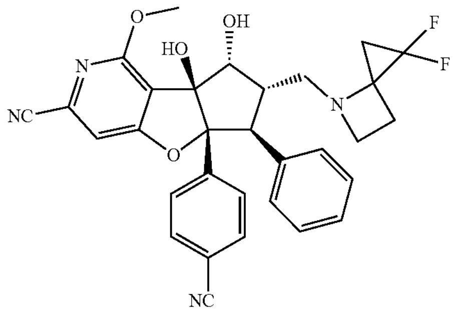

221F

Synthesis of rac-(5aR,6S,7S,8R,8aS)-5a-(4-cyanophenyl)-7-((1,1-difluoro-4-azaspiro[2.3]hexan-4-yl)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 221F)

Rac-(5aR,6S,7S,8R,8aS)-5a-(4-bromophenyl)-3-chloro-7-((1,1-difluoro-4-azaspiro[2.3]hexan-4-yl)methyl)-1-methoxy-6-phenyl-5a,6,7,8-tetrahydro-8aH-cyclopenta[4,5]furo[3,2-c]pyridine-8,8a-diol (1, 0.040 g, 0.061 mmol), dicyanozinc (50.3 mg, 0.43 mmol), dppf (27.1 mg, 0.049 mmol), and zinc (3.9 mg, 0.061 mmol) were dissolved in N,N-dimethylformamide (0.61 mL) and water (0.06 mL). The solution was sparged with an argon balloon for 10 minutes then Tris(dibenzylideneacetone)dipalladium(0) (22.4 mg, 0.024 mmol) was added. The vial was sealed and stirred at 120° C. for 1 hr and the reaction was cooled to rt.

The mixture was diluted with methanol and a few drops of DMSO and filtered through celite, washing the pad several times with methanol. The volatile solvent was removed in vacuo and the residue taken up in DMSO, filtered through a syringe filter then purified on RP-HPLC to afford rac-(5aR,6S,7S,8R,8aS)-5a-(4-cyanophenyl)-7-((1,1-difluoro-4-azaspiro[2.3]hexan-4-yl)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 221F). Yield: 3.5 mg, 11%; LCMS (ESI) m/z 557.3 $[M+1]^+$; $^1H$ NMR (400 MHz, DMSO-$d_6$) δ 7.51 (s, 1H), 7.48 (d, J=8.7 Hz, 2H), 7.31 (d, J=8.7 Hz, 3H), 7.10-6.93 (m, 7H), 5.82 (s, 1H), 5.48 (s, 1H), 4.47-4.41 (m, 2H), 3.86 (s, 4H), 3.74 (d, J=14.2 Hz, 1H), 3.39 (dd, J=20.5, 7.4 Hz, 3H), 3.25 (dd, J=14.5, 7.5 Hz, 3H), 3.04-2.88 (m, 1H), 2.77-2.64 (m, 3H), 2.44-2.31 (m, 2H), 2.25-2.17 (m, 2H), 1.71-1.53 (m, 3H), 1.50 (dd, J=9.9, 7.2 Hz, 3H).

Example 222

Rac-4-((5aR,6S,7S,8R,8aS)-3-chloro-7-((1,1-difluoro-4-azaspiro[2.3]hexan-4-yl)methyl)-8,8a-dihydroxy-1-methoxy-6-phenyl-6,7,8,8a-tetrahydro-5aH-cyclopenta[4,5]furo[3,2-c]pyridin-5a-yl)benzonitrile (Cpd. No. 222F)

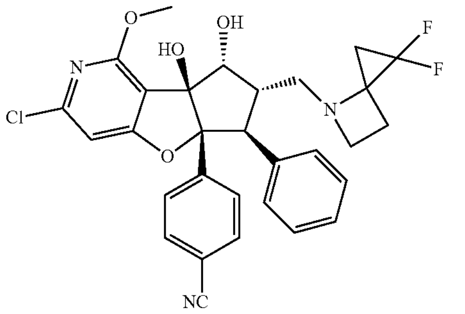

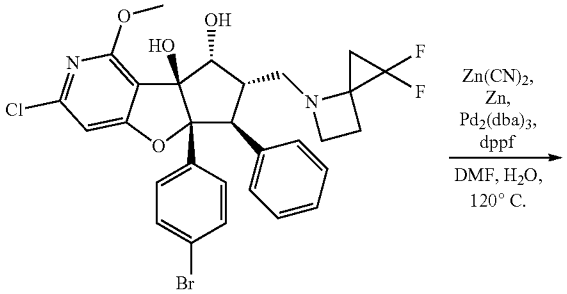

1

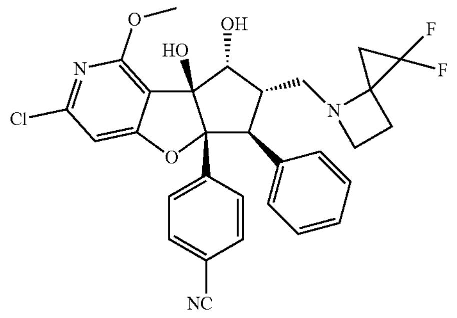

222F

Synthesis of rac-4-((5aR,6S,7S,8R,8aS)-3-chloro-7-((1,1-difluoro-4-azaspiro[2.3]hexan-4-yl)methyl)-8,8a-dihydroxy-1-methoxy-6-phenyl-6,7,8,8a-tetrahydro-5aH-cyclopenta[4,5]furo[3,2-c]pyridin-5a-yl)benzonitrile (Cpd. No. 222F)

Rac-(5aR,6S,7S,8R,8aS)-5a-(4-bromophenyl)-3-chloro-7-((1,1-difluoro-4-azaspiro[2.3]hexan-4-yl)methyl)-1-methoxy-6-phenyl-5a,6,7,8-tetrahydro-8aH-cyclopenta[4,5]furo[3,2-c]pyridine-8,8a-diol (1, 0.04 g, 0.061 mmol), dicyanozinc (50.3 mg, 0.43 mmol), dppf (27.1 mg, 0.049 mmol), and zinc (3.9 g, 0.061 mmol) were dissolved in N,N-dimethylformamide (0.61 mL) and water (0.06 mL). The solution was sparged with an argon balloon for 10 min then Tris(dibenzylideneacetone)dipalladium(0) (22.4 mg, 0.024 mmol) was added. The vial was sealed and stirred at 120° C. for 1 hr and the reaction was cooled to rt. The mixture was diluted with methanol and a few drops of DMSO and filtered through celite, washing the pad several times with methanol. The volatile solvent was removed in vacuo and the residue taken up in DMSO, filtered through a syringe filter then purified on RP-HPLC to afford rac-4-((5aR,6S,7S,8R,8aS)-3-chloro-7-((1,1-difluoro-4-azaspiro[2.3]hexan-4-yl)methyl)-8,8a-dihydroxy-1-methoxy-6-phenyl-6,7,8,8a-tetrahydro-5aH-cyclopenta[4,5]furo[3,2-c]pyridin-5a-yl)benzonitrile (Cpd. No. 222F). Yield: 3.3 mg, 9%; LCMS (ESI) m/z 566.3, 568.4 $[M+1]^+$; $^1H$ NMR (400 MHz, DMSO-$d_6$) δ 7.50-7.43 (m, 2H), 7.34-7.27 (m, 2H), 7.05 (t, J=7.3 Hz, 3H), 6.97 (dd, J=9.7, 7.4 Hz, 3H), 6.85 (s, 1H), 5.64 (s, 1H), 5.35 (s, 1H), 4.39 (d, J=4.0 Hz, 1H), 3.81 (s, 4H), 3.73 (d, J=14.1 Hz, 1H), 3.38 (dd, J=19.6, 7.5 Hz, 3H), 3.01-2.90 (m, 2H), 2.78-2.65 (m, 3H), 2.44-2.32 (m, 2H), 2.21 (t, J=6.3 Hz, 2H), 1.59 (s, OH), 1.50 (dd, J=9.7, 7.4 Hz, 2H).

Example 223

Rac-(5aR,6S,7S,8R,8aS)-5a-(4-bromophenyl)-3-chloro-1-methoxy-7-((methylamino)methyl)-6-phenyl-5a,6,7,8-tetrahydro-8aH-cyclopenta[4,5]furo[3,2-c]pyridine-8,8a-diol (Cpd. No. 223F)

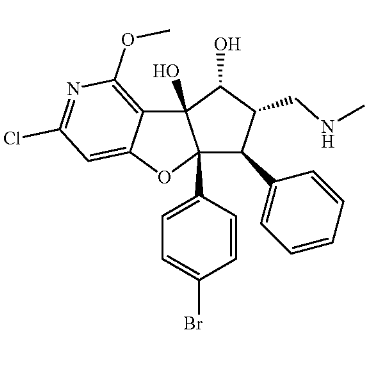

-continued

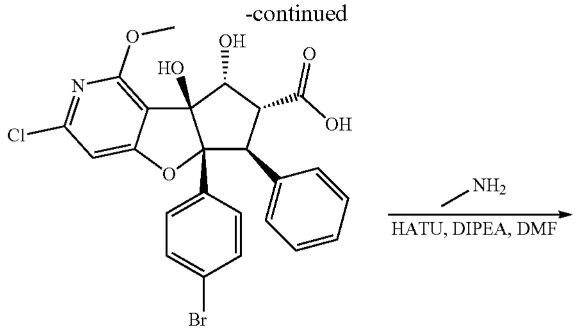

1

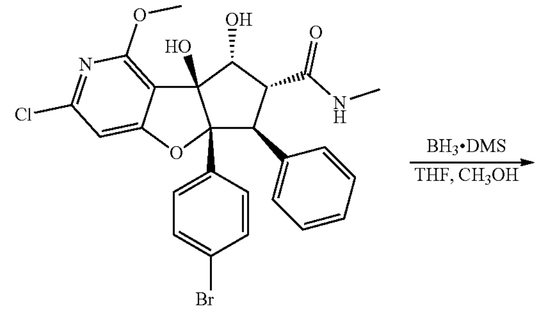

2

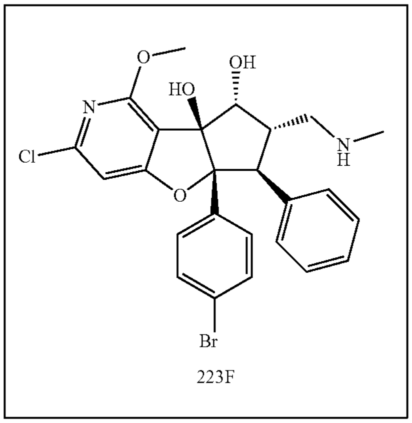

223F

Synthesis of rac-(5aR,6S,7R,8R,8aS)-5a-(4-bromophenyl)-3-chloro-8,8a-dihydroxy-1-methoxy-N-methyl-6-phenyl-5a,7,8,8a-tetrahydro-6H-cyclopenta[4,5]furo[3,2-c]pyridine-7-carboxamide (2)

To a stirred solution of rac-(5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridine-7-carboxylic acid (1, 0.1 g, 0.175 mmol) in N,N-dimethylformamide (1.0 mL) was added HATU (69.7 mg, 0.183 mmol) and then N,N diisopropylamine (0.15 mL, 0.87 mmol). After 30 minutes methyl amine (2.0 M solution, 0.90 mL, 1.8 mmol) was added slowly. After 2 hr the reaction mixture was diluted with ethyl acetate and washed sequentially with saturated aqueous $NH_4Cl$, water, and brine, and then dried over magnesium sulfate. Purification was carried out via silica gel chromatography eluting with dichloromethane and ethyl acetate to afford pure product rac-(5aR,6S,7R,8R,8aS)-5a-(4-bromophenyl)-3-chloro-8,8a-dihydroxy-1-methoxy-N-methyl-6-phenyl-5a,7,8,8a-tetrahydro-6H-cyclopenta[4,5]furo[3,2-c]pyridine-7-carboxamide (2). Yield: 97 mg, 99%; LCMS (ESI) m/z 547.3 $[M+1]^+$.

Synthesis of rac-(5aR,6S,7S,8R,8aS)-5a-(4-bromophenyl)-3-chloro-1-methoxy-7-((methylamino) methyl)-6-phenyl-5a,6,7,8-tetrahydro-8aH-cyclopenta[4,5]furo[3,2-c]pyridine-8,8a-diol (Cpd. No. 223F)

To a stirred solution of rac-(5aR,6S,7R,8R,8aS)-5a-(4-bromophenyl)-3-chloro-8,8a-dihydroxy-1-methoxy-N-methyl-6-phenyl-5a,7,8,8a-tetrahydro-6H-cyclopenta[4,5]furo[3,2-c]pyridine-7-carboxamide (2, 0.09 g, 0.166 mmol) in THF (4.0 mL) was added borane methylsulfanylmethane (2.0 M in THF, 0.85 mL, 1.71 mmol) dropwise and the reaction was warmed to 35° C. After 4.5 hr the reaction was cooled to rt and methanol (1 mL) was added slowly while stirring vigorously until bubbling ceased, and then the mixture was heated to 65° C. for 19 hours. The vial was cooled to room temperature and solvent removed in vacuo. The residue was taken up in a mixture of dichloromethane and methanol, then purified on strata ion exchange column, washing first with acetonitrile and methanol, then eluting the product with several washes with a solution of 75:25:5 methanol: dichloromethane: ammonium hydroxide. The solvent was removed in vacuo, the residue was taken up in a mixture of acetonitrile and water, and the mixture was then frozen and lyophilized to afford rac-(5aR,6S,7S,8R,8aS)-5a-(4-bromophenyl)-3-chloro-1-methoxy-7-((methylamino) methyl)-6-phenyl-5a,6,7,8-tetrahydro-8aH-cyclopenta[4,5]furo[3,2-c]pyridine-8,8a-diol (Cpd. No. 223F) as a fluffy white powder. Yield: 68 mg, 76%; LCMS (ESI) m/z 531.3, 533.1 $[M+1]^+$; $^1H$ NMR (400 MHz, Methanol-$d_4$) δ 7.22-7.14 (m, 2H), 7.17-6.94 (m, 8H), 6.74 (s, 1H), 4.70 (dd, J=5.0, 0.5 Hz, 1H), 4.40 (d, J=14.2 Hz, 1H), 3.92 (s, 3H), 3.97-3.86 (m, 1H), 2.97 (d, J=0.5 Hz, 1H), 2.87-2.76 (m, 1H), 2.79 (s, 4H), 2.01 (s, 1H).

Example 224

Rac-4-((5aR,6S,7S,8R,8aS)-3-chloro-8,8a-dihydroxy-1-methoxy-7-((methylamino)methyl)-6-phenyl-6,7,8,8a-tetrahydro-5aH-cyclopenta[4,5]furo[3,2-c]pyridin-5a-yl)benzonitrile (Cpd. No. 224F)

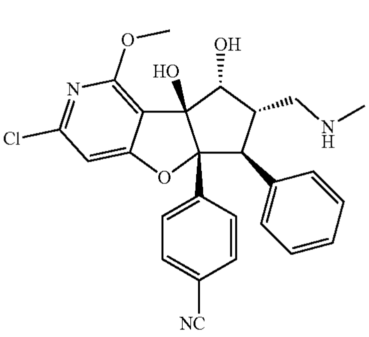

-continued

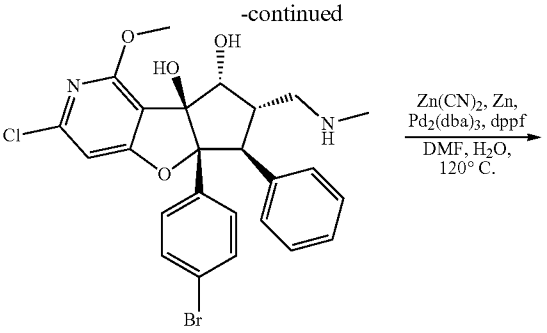

1

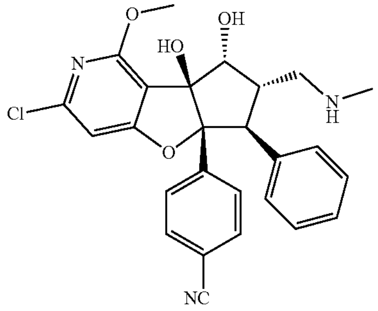

224F

Synthesis of rac-4-((5aR,6S,7S,8R,8aS)-3-chloro-8,8a-dihydroxy-1-methoxy-7-((methylamino)methyl)-6-phenyl-6,7,8,8a-tetrahydro-5aH-cyclopenta[4,5]furo[3,2-c]pyridin-5a-yl)benzonitrile (Cpd. No. 224F)

Rac-(5aR,6S,7S,8R,8aS)-5a-(4-bromophenyl)-3-chloro-1-methoxy-7-((methylamino)methyl)-6-phenyl-5a,6,7,8-tetrahydro-8aH-cyclopenta[4,5]furo[3,2-c]pyridine-8,8a-diol (1, 0.03 g, 0.056 mmol), dicyanozinc (46.0 mg, 0.39 mmol), dppf (31.0 mg, 0.056 mmol), and zinc (3.6 mg, 0.056 mmol) were dissolved in water (0.056 mL) and N,N-dimethylformamide (0.56 mL) that had been previously sparged with argon for 1 hr. Tris(dibenzylideneacetone)dipalladium(0) (22.4 mg, 0.024 mmol) was added, the vial was sealed and stirred at 120° C. After 45 minutes the reaction was cooled to room temperature, diluted with methanol and filtered through celite, washing the pad several times with more methanol. The filtrate was rotavapped, taken up in DMSO and purified via RP-HPLC to afford rac-4-((5aR,6S,7S,8R,8aS)-3-chloro-8,8a-dihydroxy-1-methoxy-7-((methylamino)methyl)-6-phenyl-6,7,8,8a-tetrahydro-5aH-cyclopenta[4,5]furo[3,2-c]pyridin-5a-yl)benzonitrile (Cpd. No. 224F). Yield: 3.2 g, 12%; LCMS (ESI) m/z 522.4, 524.2 $[M+1]^+$; $^1H$ NMR (400 MHz, DMSO-$d_6$) δ 7.49 (d, J=8.7 Hz, 2H), 7.34-7.27 (m, 2H), 7.04 (dd, J=7.9, 6.5 Hz, 2H), 7.01-6.91 (m, 4H), 6.87 (s, 1H), 5.60 (s, 1H), 4.46 (d, J=4.4 Hz, 1H), 3.81 (s, 3H), 3.76 (d, J=15 Hz, 1H), 3.16-3.08 (m, 1H), 2.77-2.69 (m, 1H), 2.69-2.56 (m, 1H), 2.48-2.30 (m, 1H), 2.23 (s, 4H), 2.19 (d, J=6.2 Hz, 1H), 1.63-1.52 (m, 1H).

Example 225

Rac-(5aR,6S,7S,8R,8aS)-5a-(4-cyanophenyl)-8,8a-dihydroxy-1-methoxy-7-((methylamino)methyl)-6-phenyl-5a,7,8,8a-tetrahydro-6H-cyclopenta[4,5]furo[3,2-c]pyridine-3-carbonitrile (Cpd. No. 225F)

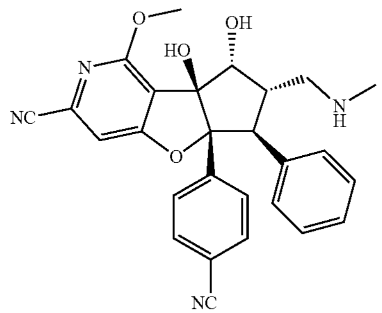

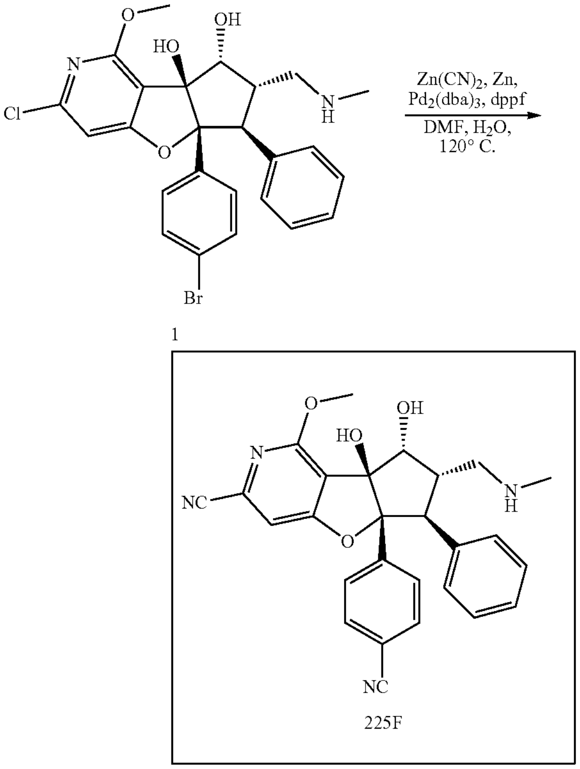

1

225F

Synthesis of rac-(5aR,6S,7S,8R,8aS)-5a-(4-cyanophenyl)-8,8a-dihydroxy-1-methoxy-7-((methylamino)methyl)-6-phenyl-5a,7,8,8a-tetrahydro-6H-cyclopenta[4,5]furo[3,2-c]pyridine-3-carbonitrile (Cpd. No. 225F)

Rac-(5aR,6S,7S,8R,8aS)-5a-(4-bromophenyl)-3-chloro-1-methoxy-7-((methylamino)methyl)-6-phenyl-5a,6,7,8-tetrahydro-8aH-cyclopenta[4,5]furo[3,2-c]pyridine-8,8a-diol (1, 0.03 g, 0.056 mmol), dicyanozinc (46.0 mg, 0.39 mmol), dppf (31.0 mg, 0.056 mmol), and zinc (3.6 mg, 0.056 mmol) were dissolved in water (0.056 mL) and N,N-dimethylformamide (0.560 mL) that had previously been sparged with argon for 1 hour. Tris(dibenzylideneacetone)dipalladium(0) (22.4 mg, 0.024 mmol) was added, the vial was sealed and stirred at 120° C. for 45 minutes. The reaction was cooled to room temperature, diluted with methanol and filtered through celite, washing the pad several times with more methanol. The filtrate was rotavapped, taken up in DMSO and purified via RP-HPLC to afford rac-(5aR,6S,7S,8R,8aS)-5a-(4-cyanophenyl)-8,8a-dihydroxy-1-methoxy-7-((methylamino)methyl)-6-phenyl-5a,7,8,8a-tetrahydro-6H-cyclopenta[4,5]furo[3,2-c]pyridine-3-carbonitrile (Cpd. No. 225F). Yield 15.3 mg (58%). LCMS (ESI) m/z 469.2 $[M+1]^+$. $^1H$ NMR (400 MHz, DMSO-$d_6$) δ 7.52 (s, 1H), 7.51-7.47 (m, 2H), 7.35-7.27 (m, 2H), 7.09-6.92 (m, 6H), 5.77 (s, 1H), 4.51 (d, J=4.3 Hz, 1H), 3.86 (s, 3H), 3.77 (d, J=14.3 Hz, 1H), 3.10 (ddt, J=13.3, 8.2, 3.7 Hz, 1H), 2.60 (dd, J=12.0, 8.6 Hz, 1H), 2.42 (dd, J=11.8, 3.1 Hz, 1H), 2.20 (s, 3H), 2.18 (d, J=7.3 Hz, 1H).

Example 226

Rac-(4bR,5R,6R,7S,7aR)-7a-(4-bromophenyl)-5-((tert-butylamino)methyl)-6-(hydroxymethyl)-4-methoxy-7-phenyl-5,6,7,7a-tetrahydro-4bH-cyclopenta[4,5]furo[2,3-c]pyridin-4b-ol (Cpd. No. 226F)

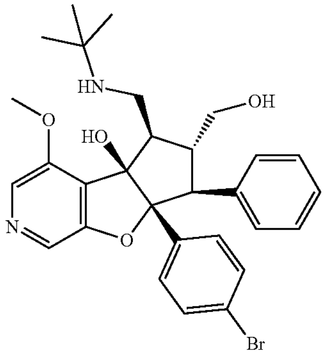

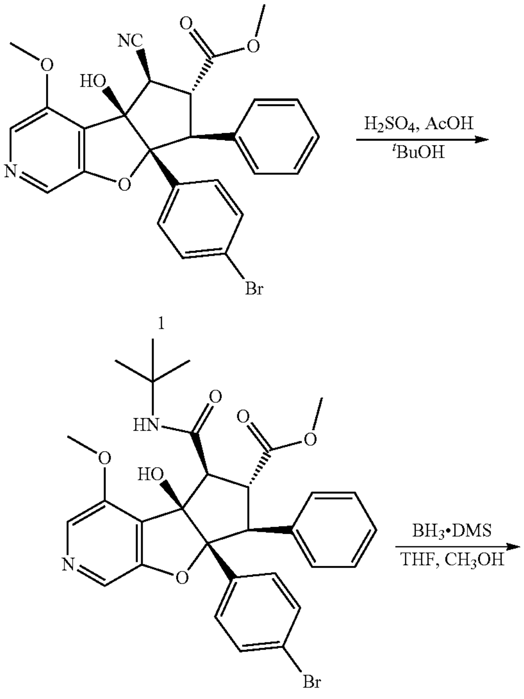

1

2

-continued

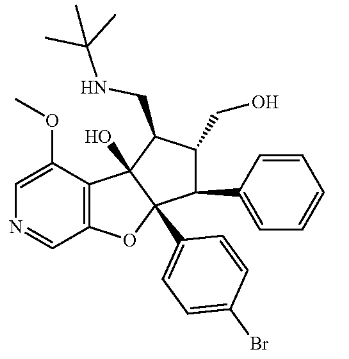

226F

Synthesis of rac-methyl (4bR,5S,6R,7S,7aR)-7a-(4-bromophenyl)-5-(tert-butylcarbamoyl)-4b-hydroxy-4-methoxy-7-phenyl-4b,6,7,7a-tetrahydro-5H-cyclopenta[4,5]furo[2,3-c]pyridine-6-carboxylate (2)

Rac-methyl (4bR,5R,6R,7S,7aR)-7a-(4-bromophenyl)-5-cyano-4b-hydroxy-4-methoxy-7-phenyl-4b,6,7,7a-tetrahydro-5H-cyclopenta[4,5]furo[2,3-c]pyridine-6-carboxylate (1, 100 mg, 0.192 mmol) was dissolved in acetic acid (2.0 mL) and 2-methylpropan-2-ol (1.99 mL, 20.9 mmol). The solution was stirred vigorously at room temperature while $H_2SO_4$ (0.06 mL) was added dropwise. The reaction was then warmed to 40° C. for 17 hours and more $H_2SO_4$ (0.01 mL) was added. After 30 hours the reaction was cooled to room temperature and saturated aqueous $NaHCO_3$ (5 mL) was added slowly and this material was extracted with ethyl acetate three times, the organic material was then dried over magnesium sulfate, filtered and solvent removed in vacuo. The crude residue was purified by RP-HPLC to afford rac-methyl (4bR,5S,6R,7S,7aR)-7a-(4-bromophenyl)-5-(tert-butylcarbamoyl)-4b-hydroxy-4-methoxy-7-phenyl-4b,6,7,7a-tetrahydro-5H-cyclopenta[4,5]furo[2,3-c]pyridine-6-carboxylate (2). Yield: 70.6 mg, 62%; LCMS (ESI) m/z 591.3, 593.2 $[M+1]^+$; $^1H$ NMR (400 MHz, DMSO-$d_6$) δ 8.22 (s, 1H), 8.19 (s, 1H), 7.35-7.28 (m, 3H), 7.25-7.17 (m, 2H), 7.09-7.03 (m, 4H), 6.94 (s, 1H), 6.78 (dd, J=6.7, 3.0 Hz, 3H), 5.99 (s, 1H), 4.08 (dd, J=13.9, 10.5 Hz, 1H), 4.04 (s, 1H), 3.55 (d, J=10.5 Hz, 1H), 3.47 (d, J=13.9 Hz, 1H), 3.39 (s, 3H), 1.35 (s, 9H).

Synthesis of rac-(4bR,5R,6R,7S,7aR)-7a-(4-bromophenyl)-5-((tert-butylamino)methyl)-6-(hydroxymethyl)-4-methoxy-7-phenyl-5,6,7,7a-tetrahydro-4bH-cyclopenta[4,5]furo[2,3-c]pyridin-4b-ol (Cpd. No. 226F)

Rac-methyl (4bR,5S,6R,7S,7aR)-7a-(4-bromophenyl)-5-(tert-butylcarbamoyl)-4b-hydroxy-4-methoxy-7-phenyl-4b,6,7,7a-tetrahydro-5H-cyclopenta[4,5]furo[2,3-c]pyridine-6-carboxylate (2, 65.0 mg, 0.109 mmol) was dissolved in THF (2.7 mL). Borane; methylsulfanylmethane (1.5 6 mL, 3.12 mmol) was added dropwise and the reaction warmed to 35° C. After stirring 12 hours, the reaction was cooled to room temperature and methanol (1.3 mL) was added over 5 minutes to quench the reaction, and the mixture then warmed to 60° C. After stirring for 6 hours the pot was cooled to room temperature and solvent removed in vacuo. The residue was then purified via RP-HPLC to afford rac-(4bR,5R,6R,7S,7aR)-7a-(4-bromophenyl)-5-((tert-butylamino)methyl)-6-(hydroxymethyl)-4-methoxy-7-phenyl-5,6,7,7a-tetrahydro-4bH-cyclopenta[4,5]furo[2,3-c]pyridin-4b-ol (Cpd. No. 226F). Yield: 18.0 mg, 30%; LCMS (ESI) m/z 553.4, 555.5 $[M+1]^+$; $^1H$ NMR (400 MHz, DMSO-$d_6$) δ 8.17 (d, J=2.4 Hz, 1H), 8.11 (s, 1H), 7.31 (d, J=8.2 Hz, 3H), 7.14-7.04 (m, 7H), 6.78 (d, J=6.6 Hz, 3H), 6.49 (d, J=0.5 Hz, 1H), 3.98 (s, 3H), 3.98 (d, J=1.9 Hz, 1H), 3.66 (m, 2H), 3.47 (d, J=11.1 Hz, 1H), 3.28 (d, J=13.6 Hz, 2H), 3.17 (dd, J=11.2, 6.0 Hz, 1H), 2.87 (m, 2H), 2.68-2.62 (m, 1H), 1.37 (s, 9H).

Example 227

Rac-(5aR,6S,7R,8S,8aR)-5a-(4-bromophenyl)-3-chloro-7-((dimethylamino)methyl)-8a-hydroxy-6-phenyl-5a,7,8,8a-tetrahydro-6H-cyclopenta[4,5]furo[3,2-b]pyridine-8-carbonitrile (Cpd. No. 227F)

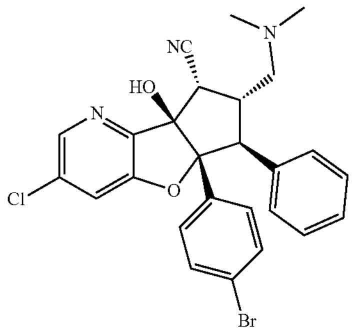

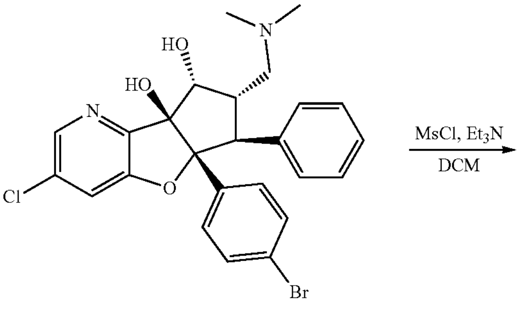

1

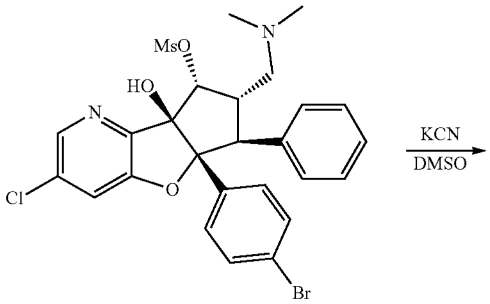

2

-continued

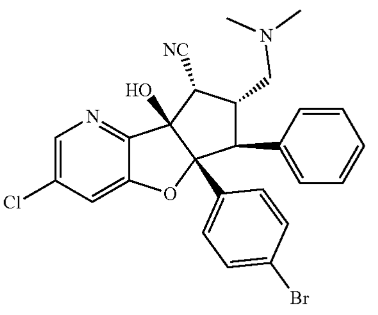

227F

Synthesis of rac-(5aR,6S,7S,8R,8aS)-5a-(4-bromophenyl)-3-chloro-7-((dimethylamino)methyl)-8a-hydroxy-6-phenyl-5a, 7,8,8a-tetrahydro-6H-cyclopenta[4,5]furo[3,2-b]pyridin-8-yl methanesulfonate (2)

To a solution of rac-(5aR,6S,7S,8R,8aS)-5a-(4-bromophenyl)-3-chloro-7-((dimethylamino)methyl)-6-phenyl-5a,6,7,8-tetrahydro-8aH-cyclopenta[4,5]furo[3,2-b]pyridine-8,8a-diol (1, 46 mg, 0.089 mmol) in dichloromethane (1 mL) was added trimethylamine (37 □L, 0.27 mmol) and methanesulfonyl chloride (10 μL, 0.13 mmol) dropwise. The reaction was stirred at room temperature for 2 h. The resulting mixture was diluted with methanol and purified via RP-HPLC (C18, 0.1% trifluoroacetic acid in acetonitrile/water=15-50%) to afford rac-(5aR,6S,7S,8R,8aS)-5a-(4-bromophenyl)-3-chloro-7-((dimethylamino)methyl)-8a-hydroxy-6-phenyl-5a,7,8,8a-tetrahydro-6H-cyclopenta[4,5]furo[3,2-b]pyridin-8-yl methanesulfonate (2, trifluoroacetic acid salt) as a white solid. Yield: 34 mg, 64%; MS (ESI) m/z 595.4[M+1]$^+$.

Synthesis of rac-(5aR,6S,7R,8S,8aR)-5a-(4-bromophenyl)-3-chloro-7-((dimethylamino)methyl)-8a-hydroxy-6-phenyl-5a,7,8,8a-tetrahydro-6H-cyclopenta[4,5]furo[3,2-b]pyridine-8-carbonitrile (Cpd. No. 227F)

Rac-(5aR,6S,7S,8R,8aS)-5a-(4-bromophenyl)-3-chloro-7-((dimethylamino)methyl)-8a-hydroxy-6-phenyl-5a,7,8,8a-tetrahydro-6H-cyclopenta[4,5]furo[3,2-b]pyridin-8-yl methanesulfonate (2, trifluoroacetic acid salt, 32 mg, 0.054 mmol) and potassium cyanide (7 mg, 0.11 mmol) were dissolved in dimethylsulfoxide (1 mL). The reaction was stirred at room temperature overnight. The mixture was purified on RP-HPLC (C18, 0.1% trifluoroacetic acid in acetonitrile/water=15-50%) to afford rac-(5aR,6S,7R,8S,8aR)-5a-(4-bromophenyl)-3-chloro-7-((dimethylamino)methyl)-8a-hydroxy-6-phenyl-5a,7,8,8a-tetrahydro-6H-cyclopenta[4,5]furo[3,2-b]pyridine-8-carbonitrile (Cpd. No. 227F, trifluoroacetic acid salt) as a white solid. Yield: 17 mg, 61%; MS (ESI) m/z 526.1[M+1]$^+$; $^1$H NMR (400 MHz, DMSO-$d_6$) δ 9.79 (s, 1H), 8.40 (d, J=2.0 Hz, 1H), 7.88 (d, J=2.0 Hz, 1H), 7.34 (d, J=8.8 Hz, 2H), 7.23 (d, J=8.7 Hz, 2H), 7.16 (d, J=1.8 Hz, 1H), 7.15 (d, J=1.8 Hz, 2H), 6.98-6.95 (m, 2H), 6.78 (s, 1H), 4.44 (d, J=7.1 Hz, 1H), 3.77-3.63 (m, 1H), 3.23 (t, J=11.9 Hz, 2H), 3.01 (dd, J=14.4, 7.3 Hz, 1H), 2.93 (d, J=4.5 Hz, 3H), 2.86 (d, J=4.5 Hz, 3H).

Example 228

Rac-(5aR,6S,7R,8S,8aR)-3-chloro-5a-(4-cyanophenyl)-7-((dimethylamino)methyl)-8a-hydroxy-6-phenyl-5a,7,8,8a-tetrahydro-6H-cyclopenta[4,5]furo[3,2-b]pyridine-8-carbonitrile (Cpd. No. 228F)

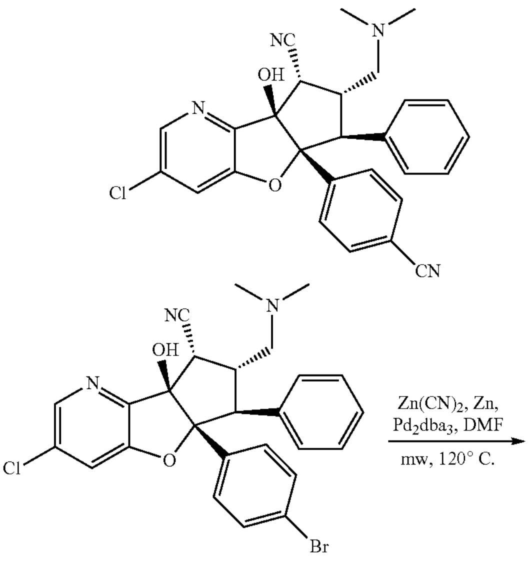

1

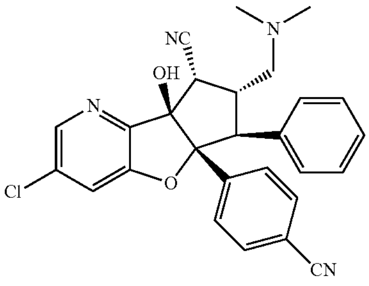

228F

Synthesis of rac-(5aR,6S,7R,8S,8aR)-3-chloro-5a-(4-cyanophenyl)-7-((dimethylamino)methyl)-8a-hydroxy-6-phenyl-5a,7,8,8a-tetrahydro-6H-cyclopenta[4,5]furo[3,2-b]pyridine-8-carbonitrile (Cpd. No. 228F)

A suspension of rac-(5aR,6S,7R,8S,8aR)-5a-(4-bromophenyl)-3-chloro-7-((dimethylamino)methyl)-8a-hydroxy-6-phenyl-5a,7,8,8a-tetrahydro-6H-cyclopenta[4,5]furo[3,2-b]pyridine-8-carbonitrile (1, trifluoroacetic acid salt, 11 mg, 0.021 mmol), zinc (1 mg, 0.011 mmol) and zinc cyanide (8 mg, 0.067 mmol) in N,N-dimethylformamide (0.5 mL) and water (0.05 mL) was purged with argon for 5 min. Dppf (1 mg, 0.002 mmol) and tris(dibenzylideneacetone)dipalladium(0) (1 mg, 0.001 mmol) were added. The reaction was microwaved at 120° C. for 0.5 h. The mixture was filtered through a pad of celite and purified via RP-HPLC (C18, 0.1% trifluoroacetic acid in acetonitrile/water=15-45%) to afford rac-(5aR,6S,7R,8S,8aR)-3-chloro-5a-(4-cyanophenyl)-7-((dimethylamino)methyl)-8a-hydroxy-6-phenyl-5a, 7,8,8a-tetrahydro-6H-cyclopenta[4,5]furo[3,2-b]pyridine-8-carbonitrile (Cpd. No. 228F, trifluoroacetic acid salt) as a white solid. Yield: 2.5 mg, 25%; MS (ESI) m/z 471.1[M+1]$^+$; $^1$H NMR (400 MHz, DMSO-$d_6$) δ 10.05 (s, 1H), 8.42 (d, J=2.0 Hz, 1H), 7.91 (d, J=2.0 Hz, 1H), 7.62 (d, J=8.7 Hz, 2H), 7.49 (d, J=8.5 Hz, 2H), 7.17-7.11 (m, 3H), 7.02-6.96 (m, 2H), 6.88 (s, 1H), 4.53 (d, J=7.1 Hz, 11H), 3.85-3.72 (m, 1H), 3.29-3.17 (m, 2H), 3.03 (dd, J=14.4, 7.7 Hz, 1H), 2.94 (d, J=4.6 Hz, 3H), 2.85 (d, J=4.6 Hz, 3H).

Example 229

Rac-(5aR,6S,7R,8R,8aS)-5a-(4-bromophenyl)-8,8a-dihydroxy-1,3-dimethoxy-N,N-dimethyl-6-phenyl-5a,7,8,8a-tetrahydro-6H-cyclopenta[4,5]furo[3,2-c]pyridine-7-carboxamide (Cpd. No. 229F)

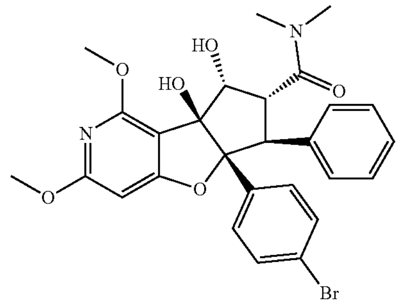

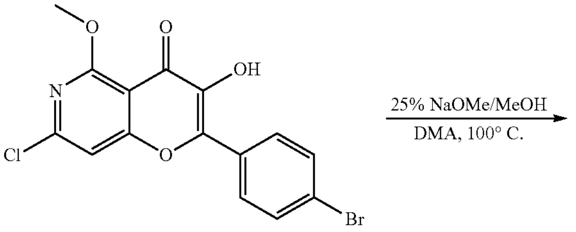

1

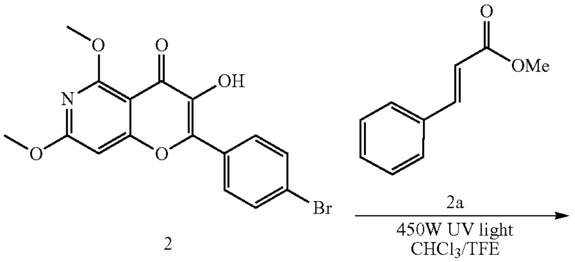

2

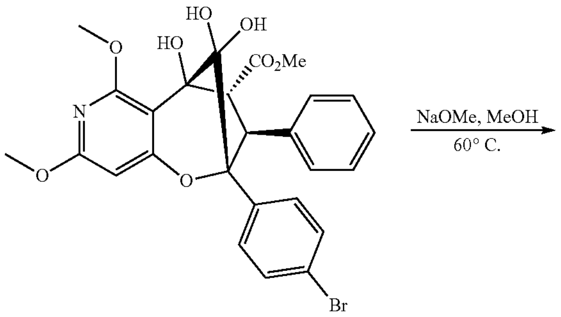

3

-continued

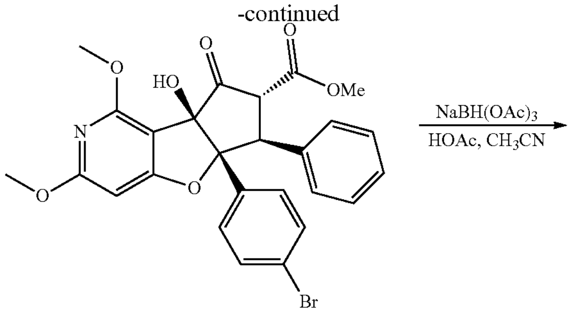

4

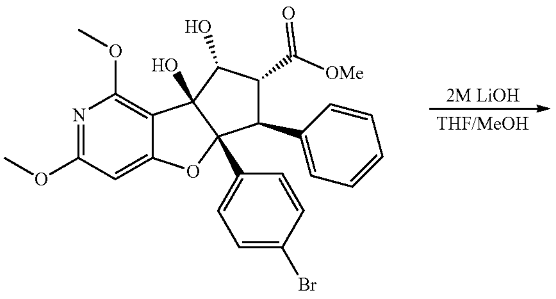

5

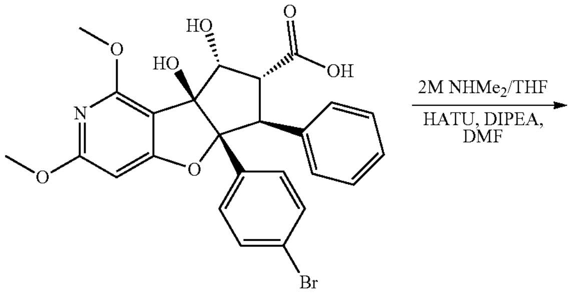

6

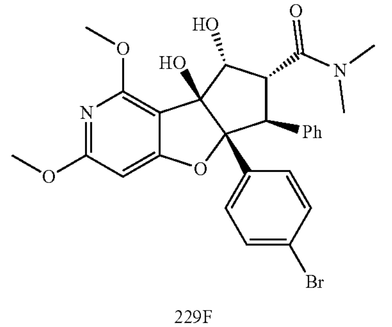

229F

Synthesis of 2-(4-bromophenyl)-3-hydroxy-5,7-dimethoxy-4H-pyrano[3,2-c]pyridin-4-one (2)

To a solution of 2-(4-bromophenyl)-7-chloro-3-hydroxy-5-methoxy-4H-pyrano[3,2-c]pyridin-4-one (1, 399 mg, 1.04 mmol) in N,N-dimethylacetamide (9 mL) was added sodium methoxide (25% in methanol, 0.72 mL, 3.13 mmol) drop-wise. The reaction was stirred at 100° C. for 2 h. The resulting mixture was cooled to room temperature and quenched via the addition of saturated ammonium chloride solution. The precipitate was filtered, washed with water and dried under vacuum to afford 2-(4-bromophenyl)-3-hydroxy-5,7-dimethoxy-4H-pyrano[3,2-c]pyridin-4-one (2) as a yellow solid. Yield: 226 mg, 57%; MS (ESI) m/z 380.1 $[M+1]^+$.

Synthesis of rac-methyl (3S,4S,5R)-2-(4-bromophenyl)-5,10,10-trihydroxy-6,8-dimethoxy-3-phenyl-2,3,4,5-tetrahydro-2,5-methanooxepino[3,2-c]pyridine-4-carboxylate (3)

2-(4-Bromophenyl)-3-hydroxy-5,7-dimethoxy-4H-pyrano[3,2-c]pyridin-4-one (2, 80 mg, 0.21 mmol) and methyl cinnamate (2a, 343 mg, 2.12 mmol) were dissolved in chloroform (3.5 mL) and trifluoroethanol (2.8 mL). The reaction mixture was stirred vigorously and irradiated with 450 W UV light at 0° C. for 2 h. The reaction mixture was concentrated and purified via column chromatography (silica, ethyl acetate/hexanes=0-5% then 100%) to remove the cinnamate. The crude was used directly for the next step. Yield: 130 mg, crude; MS (ESI) m/z 540.2$[M+1]^+$.

Synthesis of rac-methyl (5aR,6S,7R,8aR)-5a-(4-bromophenyl)-8a-hydroxy-1,3-dimethoxy-8-oxo-6-phenyl-5a,7,8,8a-tetrahydro-6H-cyclopenta[4,5]furo[3,2-c]pyridine-7-carboxylate (4)

Sodium methoxide (25% in methanol, 0.16 mL, 0.70 mmol) was added to a stirred solution of rac-methyl (3S,4S,5R)-2-(4-bromophenyl)-5,10,10-trihydroxy-6,8-dimethoxy-3-phenyl-2,3,4,5-tetrahydro-2,5-methanooxepino[3,2-c]pyridine-4-carboxylate (3, 130 mg, 0.23 mmol) in methanol (4 mL) at room temperature. The reaction mixture was heated at 60° C. for 40 min and then the solvent was removed. The residue was partitioned between saturated aqueous ammonium chloride and dichloromethane. The organics were combined, dried over magnesium sulfate, filtered and concentrated to afford the crude product. Yield: 126 mg, crude; MS (ESI) m/z 540.2$[M+1]^+$.

Synthesis of rac-methyl (5aR,6S,7R,8R,8aS)-5a-(4-bromophenyl)-8,8a-dihydroxy-1,3-dimethoxy-6-phenyl-5a,7,8,8a-tetrahydro-6H-cyclopenta[4,5]furo[3,2-c]pyridine-7-carboxylate (5)

To a stirred solution of rac-methyl (5aR,6S,7R,8aR)-5a-(4-bromophenyl)-8a-hydroxy-1,3-dimethoxy-8-oxo-6-phenyl-5a,7,8,8a-tetrahydro-6H-cyclopenta[4,5]furo[3,2-c]pyridine-7-carboxylate (126 mg, 0.23 mmol) in acetonitrile (4 mL) at room temperature was added acetic acid (0.13 mL, 2.33 mmol) and then sodium triacetoxyborohydride (247 mg, 1.17 mmol). The reaction was stirred at room temperature for 40 min. Saturated aqueous ammonium chloride (30 mL) was added slowly and the resulting mixture was partitioned between water and dichloromethane. The organics were combined, dried over magnesium sulfate, filtered and concentrated. The crude was purified via column chromatography (silica, ethyl acetate/hexanes=0-45%) to afford rac-methyl (5aR,6S,7R,8R,8aS)-5a-(4-bromophenyl)-8,8a-dihydroxy-1,3-dimethoxy-6-phenyl-5a,7,8,8a-tetrahydro-6H-cyclopenta[4,5]furo[3,2-c]pyridine-7-carboxylate as a yellow solid. Yield: 74 mg, 58%; MS (ESI) m/z 542.1$[M+1]^+$.

Synthesis of rac-(5aR,6S,7R,8R,8aS)-5a-(4-bromophenyl)-8,8a-dihydroxy-1,3-dimethoxy-6-phenyl-5a, 7,8,8a-tetrahydro-6H-cyclopenta[4,5]furo[3,2-c]pyridine-7-carboxylic acid (6)

To a solution of rac-methyl (5aR,6S,7R,8R,8aS)-5a-(4-bromophenyl)-8,8a-dihydroxy-1,3-dimethoxy-6-phenyl-5a,7,8,8a-tetrahydro-6H-cyclopenta[4,5]furo[3,2-c]pyridine-7-carboxylate (68 mg, 0.12 mmol) in tetrahydrofuran (2 mL) and methanol (2 mL) was added 2 M lithium hydroxide solution (2 mL, 4 mmol). The reaction was stirred at room temperature for 2 h. The reaction was acidified with 1 M hydrochloric acid. The mixture was extracted with water and dichloromethane. The combined organics were dried over magnesium sulfate, filtered and concentrated. The crude was used directly for next step. Yield: 71 mg, crude; MS (ESI) m/z 530.2$[M+1]^+$.

Synthesis of rac-(5aR,6S,7R,8R,8aS)-5a-(4-bromophenyl)-8,8a-dihydroxy-1,3-dimethoxy-N,N-dimethyl-6-phenyl-5a,7,8,8a-tetrahydro-6H-cyclopenta[4,5]furo[3,2-c]pyridine-7-carboxamide (Cpd. No. 229F)

To a stirred solution of rac-(5aR,6S,7R,8R,8aS)-5a-(4-bromophenyl)-8,8a-dihydroxy-1,3-dimethoxy-6-phenyl-5a, 7,8,8a-tetrahydro-6H-cyclopenta[4,5]furo[3,2-c]pyridine-7-carboxylic acid (71 mg, 0.13 mmol) in N,N-dimethylformamide (2 mL) at room temperature were added HATU (54 mg, 0.14 mmol) and N,N-diisopropylethylamine (0.04 mL, 0.20 mmol). The reaction was stirred at room temperature for 15 min. Dimethylamine (2 M solution in tetrahydrofuran) (0.2 mL, 0.40 mmol) was added and the reaction was stirred at room temperature for 1 h. The reaction mixture was diluted with dichloromethane and washed with water. The combined organics were dried over magnesium sulfate, filtered and concentrated. The crude was purified via column chromatography (silica, ethyl acetate/hexanes=0-90%) to afford rac-(5aR,6S,7R,8R,8aS)-5a-(4-bromophenyl)-8,8a-dihydroxy-1,3-dimethoxy-N,N-dimethyl-6-phenyl-5a,7,8,8a-tetrahydro-6H-cyclopenta[4,5]furo[3,2-c]pyridine-7-carboxamide (Cpd. No. 229F) as a light yellow solid. Yield: 64 mg, 86%; MS (ESI) m/z 557.3$[M+1]^+$; $^1$H NMR (400 MHz, DMSO-$d_6$) δ 7.25-7.18 (m, 2H), 7.08-6.99 (m, 4H), 6.99-6.91 (m, 1H), 6.87 (dd, J=7.8, 1.4 Hz, 2H), 6.11 (s, 1H), 4.70 (d, J=5.6 Hz, 1H), 4.35 (d, J=13.5 Hz, 1H), 4.13 (dd, J=13.5, 5.6 Hz, 2H), 3.85 (s, 3H), 3.85 (s, 3H), 3.26 (s, 3H), 2.76 (s, 3H).

Example 230

Rac-(5aR,6S,7S,8R,8aS)-5a-(4-bromophenyl)-7-((dimethylamino)methyl)-1,3-dimethoxy-6-phenyl-5a,6,7,8-tetrahydro-8aH-cyclopenta[4,5]furo[3,2-c]pyridine-8,8a-diol (Cpd. No. 230F)

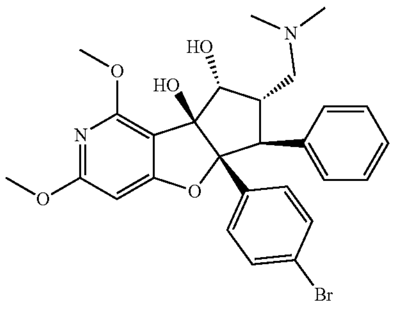

-continued

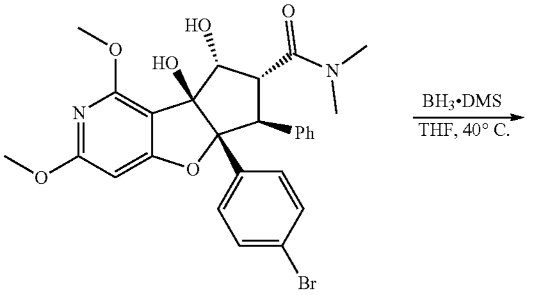

1

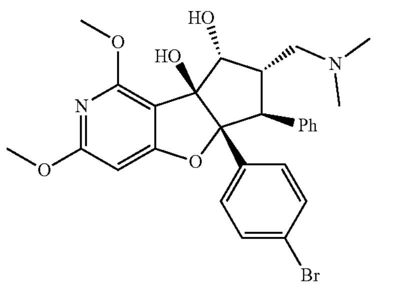

230F

Synthesis of rac-(5aR,6S,7S,8R,8aS)-5a-(4-bromophenyl)-7-((dimethylamino)methyl)-1,3-dimethoxy-6-phenyl-5a,6,7,8-tetrahydro-8aH-cyclopenta[4,5]furo[3,2-c]pyridine-8,8a-diol (Cpd. No. 230F)

Borane dimethyl sulfide complex (0.08 mL, 0.86 mmol) was added to a stirred solution of rac-(5aR,6S,7R,8R,8aS)-5a-(4-bromophenyl)-8,8a-dihydroxy-1,3-dimethoxy-N,N-dimethyl-6-phenyl-5a,7,8,8a-tetrahydro-6H-cyclopenta[4,5]furo[3,2-c]pyridine-7-carboxamide (48 mg, 0.086 mmol) in tetrahydrofuran (3 mL) at room temperature. The reaction was heated at 40° C. After cooling to room temperature, methanol (3 mL) was added dropwise. The resulting clear colorless reaction mixture was stirred vigorously and heated at 70° C. overnight. The reaction mixture was cooled to room temperature and purified via Phenomenex Strata ion exchange column to afford rac-(5aR,6S,7S,8R,8aS)-5a-(4-bromophenyl)-7-((dimethylamino)methyl)-1,3-dimethoxy-6-phenyl-5a,6,7,8-tetrahydro-8aH-cyclopenta[4,5]furo[3,2-c]pyridine-8,8a-diol (Cpd. No. 230F) as a white solid. Yield: 35 mg, 75%; MS (ESI) m/z 543.2[M+1]$^+$; $^1$H NMR (400 MHz, DMSO-$d_6$) δ 7.27-7.17 (m, 2H), 7.12-7.05 (m, 3H), 7.02-6.97 (m, 1H), 6.97-6.92 (m, 2H), 6.02 (s, 1H), 5.29 (s, 1H), 4.90 (s, 1H), 4.41 (s, 1H), 3.84 (s, 3H), 3.83 (s, 3H), 3.66 (d, J=14.0 Hz, 1H), 3.10-3.00 (m, 1H), 2.55 (d, J=11.9 Hz, 1H), 2.19 (s, 6H), 1.94 (dd, J=12.4, 3.1 Hz, 1H), 1.24 (s, 1H).

Example 231

4-((5aR,6S,7S,8R,8aS)-7-((dimethylamino)methyl)-8,8a-dihydroxy-1,3-dimethoxy-6-phenyl-6,7,8,8a-tetrahydro-5aH-cyclopenta[4,5]furo[3,2-c]pyridin-5a-yl)benzonitrile (Cpd. No. 231F)

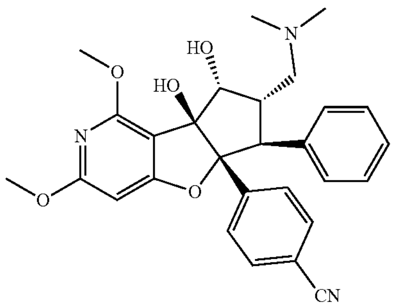

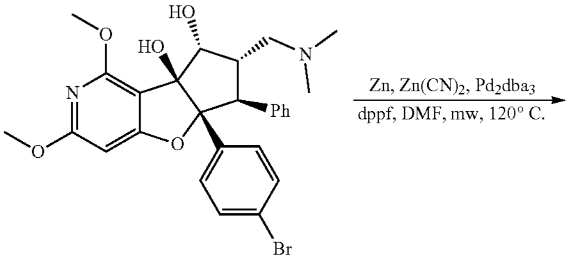

1

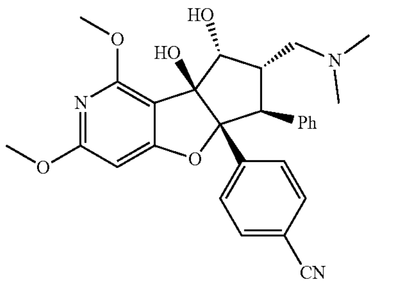

231F

Synthesis of 4-((5aR,6S,7S,8R,8aS)-7-((dimethylamino)methyl)-8,8a-dihydroxy-1,3-dimethoxy-6-phenyl-6,7,8,8a-tetrahydro-5aH-cyclopenta[4,5]furo[3,2-c]pyridin-5a-yl)benzonitrile (Cpd. No. 231F)

A mixture of rac-(5aR,6S,7S,8R,8aS)-5a-(4-bromophenyl)-7-((dimethylamino)methyl)-1,3-dimethoxy-6-phenyl-5a,6,7,8-tetrahydro-8aH-cyclopenta[4,5]furo[3,2-c]pyridine-8,8a-diol (30 mg, 0.055 mmol), zinc cyanide (20 mg, 0.17 mmol) and zinc powder (4 mg, 0.055 mmol) in N,N-dimethylformamide (0.50 mL) and water (0.05 mL) was purged with argon for 5 min. Tris(dibenzylideneacetone) dipalladium(0) (5 mg, 0.0055 mmol) and dppf (6 mg, 0.011 mmol) were added. The reaction was microwaved at 120° C. for 1.5 h. The mixture was cooled to room temperature, filtered and purified via RP-HPLC (C18, acetonitrile/water=15-35%) to afford rac-4-((5aR,6S,7S,8R,8aS)-7-((dimethylamino)methyl)-8,8a-dihydroxy-1,3-dimethoxy-6-phenyl-6,7,8,8a-tetrahydro-5aH-cyclopenta[4,5]furo[3,2-c]

pyridin-5a-yl)benzonitrile as a white solid. Yield: 11 mg, 41%; The enantiomers were separated by chiral SFC [CHHIALPAK IG (4.6×250)mm, 5μ] in $CO_2$/MeOH/TEA (60:40:0.2), Peak 1 (Cpd. No. 231F, 1.56 g), $R_t$=1.958 min, ee: 99.74%, $[\alpha]_D$ −38.8° (c 0.25, $CHCl_3$); MS (ESI) m/z 488.20[M+1]$^+$; $^1$H NMR (400 MHz, DMSO-$d_6$) 7.49 (d, J=8.32 Hz, 2H), 7.34 (d, J=8.36 Hz, 2H), 7.08-7.04 (m, 2H), 7.00-6.95 (m, 3H), 6.04 (s, 1H), 5.40 (s, 1H), 5.03 (bs, 1H), 4.42 (d, J=3.8 Hz, 1H), 3.84 (s, 6H), 3.73 (d, J=14.0 Hz, 1H), 3.14-3.08 (m, 1H), 2.58-2.56 (m, 1H), 2.20 (s, 6H), 1.96 (d, J=10.7 Hz, 1H). Peak-2 (1.55 g), $R_t$=3.90 min, ee: 99.66%, $[\alpha]_D$+34.5° (c 0.20, $CHCl_3$); MS (ESI) m/z 488.20[M+1]$^+$; $^1$H NMR (400 MHz, DMSO-$d_6$) 7.49 (d, J=8.48 Hz, 2H), 7.34 (d, J=8.48 Hz, 2H), 7.08-7.04 (m, 2H), 7.00-6.95 (m, 3H), 6.04 (s, 1H), 5.40 (s, 1H), 5.03 (bs, 1H), 4.42 (d, J=4.12 Hz, 1H), 3.84 (s, 6H), 3.73 (d, J=14.12 Hz, 1H), 3.14-3.08 (m, 1H), 2.58-2.56 (m, 1H), 2.20 (s, 6H), 1.97 (d, J=9.68 Hz, 1H).

Example 232

Rac-4-((5aR,6S,7S,8R,8aS)-7-((diethylamino)methyl)-8,8a-dihydroxy-1,3-dimethoxy-6-phenyl-6,7,8,8a-tetrahydro-5aH-cyclopenta[4,5]furo[3,2-c]pyridin-5a-yl)benzonitrile (Cpd. No. 232F)

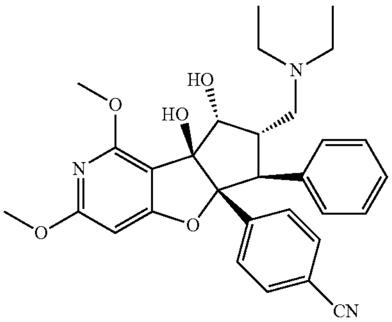

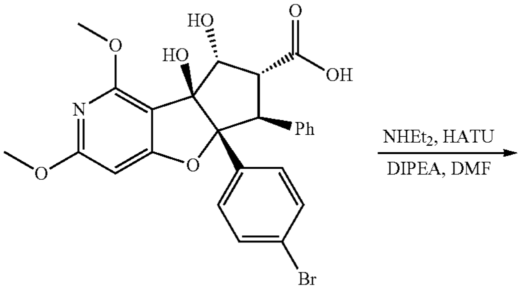

1

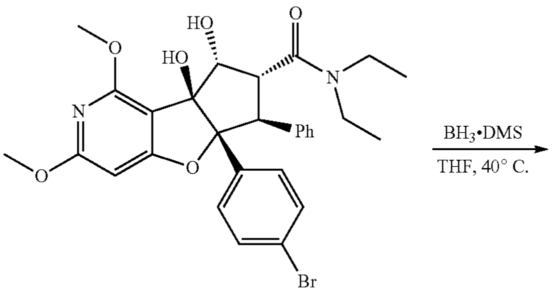

2

-continued

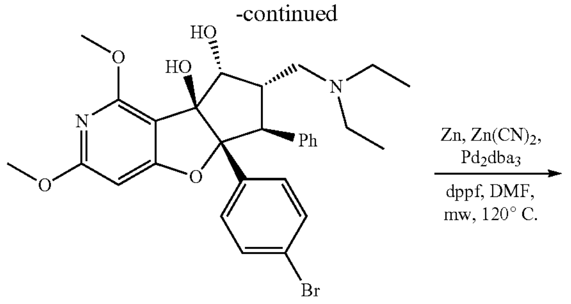

3

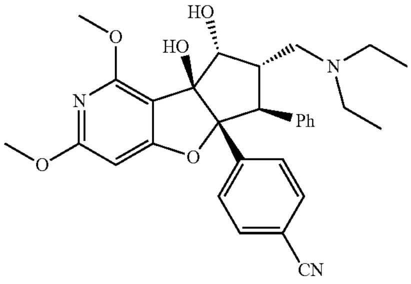

232F

Synthesis of rac-(5aR,6S,7R,8R,8aS)-5a-(4-bromophenyl)-N,N-diethyl-8,8a-dihydroxy-1,3-dimethoxy-6-phenyl-5a,7,8,8a-tetrahydro-6H-cyclopenta[4,5]furo[3,2-c]pyridine-7-carboxamide (2)

HATU (19 mg, 0.050 mmol) was added to a stirred solution of rac-(5aR,6S,7R,8R,8aS)-5a-(4-bromophenyl)-8,8a-dihydroxy-1,3-dimethoxy-6-phenyl-5a,7,8,8a-tetrahydro-6H-cyclopenta[4,5]furo[3,2-c]pyridine-7-carboxylic acid (25 mg, 0.047 mmol) in N,N-dimethylformamide (2 mL) at room temperature. After 2 min, N,N-diisopropylethylamine (0.01 mL, 0.071 mmol) was added. The reaction was stirred for 15 min at room temperature. Diethylamine (0.15 mL, 1.42 mmol) was added and the reaction was stirred at room temperature overnight. The reaction mixture was diluted with dichloromethane and washed with water. The combined organics were dried over magnesium sulfate, filtered, concentrated on a rotary evaporator, and purified via column chromatography (silica, ethyl acetate/hexanes=0-90%) to afford rac-(5aR,6S,7R,8R,8aS)-5a-(4-bromophenyl)-N,N-diethyl-8,8a-dihydroxy-1,3-dimethoxy-6-phenyl-5a,7,8,8a-tetrahydro-6H-cyclopenta[4,5]furo[3,2-c]pyridine-7-carboxamide (2) as a light yellow solid. Yield: 30 mg, 100%; MS (ESI) m/z 585.4[M+1]$^+$.

Synthesis of rac-(5aR,6S,7S,8R,8aS)-5a-(4-bromophenyl)-7-((diethylamino)methyl)-1,3-dimethoxy-6-phenyl-5a,6,7,8-tetrahydro-8aH-cyclopenta[4,5]furo[3,2-c]pyridine-8,8a-diol (3)

Borane dimethyl sulfide complex (0.05 mL, 0.51 mmol) was added to a stirred solution of rac-(5aR,6S,7R,8R,8aS)-5a-(4-bromophenyl)-N,N-diethyl-8,8a-dihydroxy-1,3-dimethoxy-6-phenyl-5a,7,8,8a-tetrahydro-6H-cyclopenta[4,5]furo[3,2-c]pyridine-7-carboxamide (2, 30 mg, 0.051 mmol) in tetrahydrofuran (3 mL) at room temperature. The reaction mixture was heated at 40° C. for 5 h. After cooling to room temperature, methanol (3 mL) was added dropwise. The resulting clear colorless reaction mixture was stirred vigorously and heated at 70° C. overnight. The reaction mixture was cooled to room temperature and purified via Phenomenex Strata ion exchange column to afford rac-(5aR,6S,7S,8R,8aS)-5a-(4-bromophenyl)-7-((diethylamino)methyl)-1,3-dimethoxy-6-phenyl-5a,6,7,8-tetrahydro-8aH-cyclopenta[4,5]furo[3,2-c]pyridine-8,8a-diol (3) as a light yellow solid. Yield: 35 mg, 100%; MS (ESI) m/z 569.4[M+1]$^+$;

Synthesis of rac-4-((5aR,6S,7S,8R,8aS)-7-((diethylamino)methyl)-8,8a-dihydroxy-1,3-dimethoxy-6-phenyl-6,7,8,8a-tetrahydro-5aH-cyclopenta[4,5]furo[3,2-c]pyridin-5a-yl)benzonitrile (Cpd. No. 232F)

A mixture of rac-(5aR,6S,7S,8R,8aS)-5a-(4-bromophenyl)-7-((diethylamino)methyl)-1,3-dimethoxy-6-phenyl-5a,6,7,8-tetrahydro-8aH-cyclopenta[4,5]furo[3,2-c]pyridine-8,8a-diol (10 mg, 0.018 mmol), zinc cyanide (6 mg, 0.053 mmol) and zinc powder (1 mg, 0.018 mmol) in N,N-dimethylformamide (0.50 mL) and water (0.050 mL) was purged with argon for 5 min. Tris(dibenzylideneacetone)dipalladium(0) (2 mg, 0.0018 mmol) and dppf (2 mg, 0.0035 mmol) were added. The reaction was microwaved at 120° C. for 2 h. The mixture was cooled to room temperature, filtered and purified via RP-HPLC (C18, acetonitrile/water=15-35%) to afford rac-4-((5aR,6S,7S,8R,8aS)-7-((diethylamino)methyl)-8,8a-dihydroxy-1,3-dimethoxy-6-phenyl-6,7,8,8a-tetrahydro-5aH-cyclopenta[4,5]furo[3,2-c]pyridin-5a-yl)benzonitrile (Cpd. No. 232F) as a white solid. Yield: 4 mg, 44%; MS (ESI) m/z 516.3[M+1]$^+$; $^1$H NMR (400 MHz, DMSO-$d_6$) δ 8.95 (s, 1H), 7.54 (d, J=8.8 Hz, 2H), 7.41 (d, J=8.5 Hz, 2H), 7.15-6.94 (m, 5H), 6.11 (s, 1H), 5.58 (s, 1H), 5.33 (d, J=6.8 Hz, 1H), 4.65-4.56 (m, 1H), 3.87 (s, 3H), 3.86 (s, 3H), 3.80 (d, J=13.9 Hz, 1H), 3.52-3.42 (m, 2H), 3.19-3.08 (m, 2H), 2.71-2.62 (m, 1H), 1.19 (t, J=7.1 Hz, 6H).

Example 233

4-((4bS,5R,6S,7S,7aR)-4b,5-dihydroxy-4-methoxy-6-((methyl(2,2,2-trifluoroethyl)amino)methyl)-7-phenyl-4b,5,6,7-tetrahydro-7aH-cyclopenta[4,5]furo[2,3-c]pyridin-7a-yl)benzonitrile (Cpd. No. 233F)

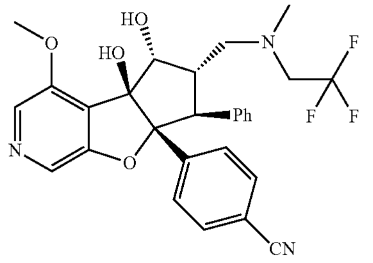

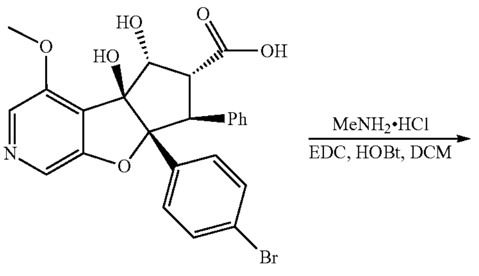

1

-continued

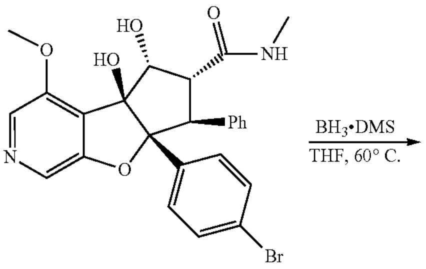

2

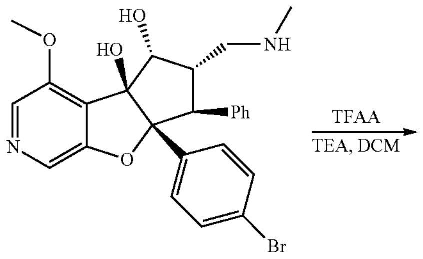

3

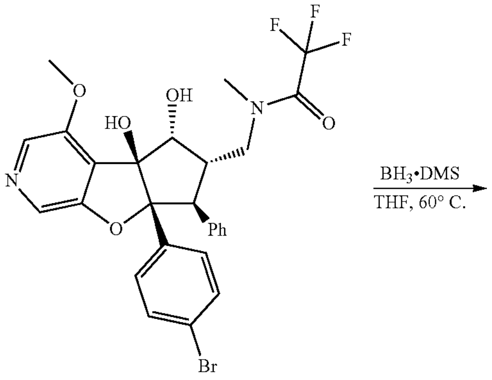

4

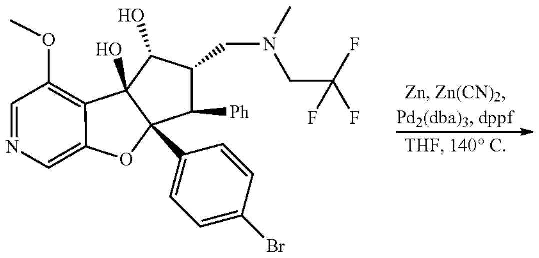

5

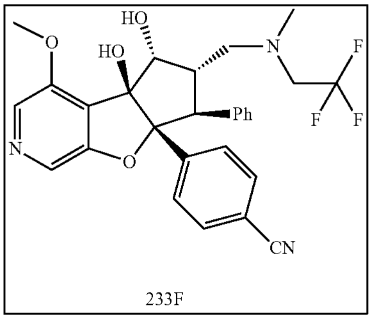

233F

Synthesis of rac-(4bS,5R,6R,7S,7aR)-7a-(4-bromophenyl)-4b,5-dihydroxy-4-methoxy-N-methyl-7-phenyl-4b,6,7,7a-tetrahydro-5H-cyclopenta[4,5]furo[2,3-c]pyridine-6-carboxamide (2)

To a solution of rac-(4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylic acid (1, 0.65 g, 1.3 mmol) in dichloromethane (10.0 mL), 1-ethyl-3-(3-dimethylaminopropyl)carbodiimide (0.3 g, 1.9 mmol), hydroxybenzotriazole (0.26 g, 1.9 mmol) and N,N-diisopropylethylamine (0.7 mL, 3.9 mmol) were added at 0° C. and stirred the mixture for 5 min. Methylamine hydrochloride (0.26 g, 3.9 mmol) was then added at same temperature and the reaction was stirred at room temperature for 5 h. After completion, reaction mass was diluted with dichloromethane (20 mL) and washed with cold water. The organic layer was separated and dried over anhydrous sodium sulphate, filtered and concentrated under reduced pressure. The crude product was purified by Combi-flash (12 g RediSep column) using 30% ethyl acetate in hexanes as eluent. The desired fraction were concentrated to afford rac-(4bS,5R,6R,7S,7aR)-7a-(4-bromophenyl)-4b,5-dihydroxy-4-methoxy-N-methyl-7-phenyl-4b,6,7,7a-tetrahydro-5H-cyclopenta[4,5]furo[2,3-c]pyridine-6-carboxamide (2) as white solid. Yield: 0.6 g, 90%; MS (ESI) m/z 511.36 $[M+1]^+$, UPLC: 97.28%.

Synthesis of rac-(4bS,5R,6S,7S,7aR)-7a-(4-bromophenyl)-4-methoxy-6-((methylamino)methyl)-7-phenyl-5,6,7,7a-tetrahydro-4bH-cyclopenta[4,5]furo[2,3-c]pyridine-4b, 5-diol (3)

To a solution of rac-(4bS,5R,6R,7S,7aR)-7a-(4-bromophenyl)-4b,5-dihydroxy-4-methoxy-N-methyl-7-phenyl-4b,6,7,7a-tetrahydro-5H-cyclopenta[4,5]furo[2,3-c]pyridine-6-carboxamide (2, 0.6 g, 1.2 mmol) in tetrahydrofuran (30 mL), borane dimethylsulfide (1.0 ml, 11.7 mmol) was added at 0° C. The reaction mixture was heated at 60° C. for 3 h. After completion, reaction mass was quenched with methanol at 0° C. and then heated at 80° C. for 16 h. The solvents were concentrated and the solid obtained was dried to afford rac-(4bS,5R,6S,7S,7aR)-7a-(4-bromophenyl)-4-methoxy-6-((methylamino)methyl)-7-phenyl-5,6,7,7a-tetrahydro-4bH-cyclopenta[4,5]furo[2,3-c]pyridine-4b,5-diol (3) as white solid. Yield: 0.45 g, 77%; MS (ESI) m/z 496.37 $[M-1]^-$, UPLC: 93.46%

Synthesis of rac-N-(((4bS,5R,6S,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)methyl)-2,2,2-trifluoro-N-methylacetamide (4)

To a solution of rac-(4bS,5R,6S,7S,7aR)-7a-(4-bromophenyl)-4-methoxy-6-((methylamino)methyl)-7-phenyl-5,6,7,7a-tetrahydro-4bH-cyclopenta[4,5]furo[2,3-c]pyridine-4b,5-diol (3, 0.8 g, 1.6 mmol) in dichloromethane (5.0 mL), trifluoro acetic anhydride (0.4 g, 1.9 mmol), and triethylamine (0.7 mL, 4.8 mmol) were added at 0° C. and stirred the mixture for 5 minute and then reaction was stirred at room temperature for 30 min. After completion, reaction mixture was diluted with dichloromethane (20 mL) and washed with cold water. The organic layer was separated and dried over anhydrous sodium sulphate, filtered and concentrated under reduced pressure. The crude product was purified by Combi-flash (12 g RediSep column) using 30% ethyl acetate in hexanes as eluent. The desired fractions were concentrated to afford rac-N-(((4bS,5R,6S,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)methyl)-2,2,2-trifluoro-N-methylacetamide (4) as yellow solid. Yield: 0.4 g, 43%; MS (ESI) m/z 579.20$[M+1]^+$, UPLC: 82.36%.

Synthesis of rac-(4bS,5R,6S,7S,7aR)-7a-(4-bromophenyl)-4-methoxy-6-((methyl(2,2,2-trifluoroethyl)amino)methyl)-7-phenyl-5,6,7,7a-tetrahydro-4bH-cyclopenta[4,5]furo[2,3-c]pyridine-4b,5-diol (5)

To a solution of rac-N-(((4bS,5R,6S,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)methyl)-2,2,2-trifluoro-N-methylacetamide (4, 0.2 g, 0.3 mmol) in tetrahydrofuran (20 mL), borane dimethylsulfide (0.3 ml, 3.7 mmol) was added at 0° C. The reaction mixture was heated at 60° C. for 6 h. After completion, reaction mass was quenched with methanol at 0° C. and then heated at 90° C. for 16 h. The solvents were concentrated and the solid obtained was dried to afford rac-(4bS,5R,6S,7S,7aR)-7a-(4-bromophenyl)-4-methoxy-6-((methyl(2,2,2-trifluoroethyl)amino)methyl)-7-phenyl-5,6,7,7a-tetrahydro-4bH-cyclopenta[4,5]furo[2,3-c]pyridine-4b,5-diol (5) as yellow solid. Yield: 0.15 g, 77%; MS (ESI) m/z 579.2$[M+1]^+$, UPLC: 89.22%.

Synthesis of 4-((4bS,5R,6S,7S,7aR)-4b,5-dihydroxy-4-methoxy-6-((methyl(2,2,2-trifluoroethyl)amino)methyl)-7-phenyl-4b,5,6,7-tetrahydro-7aH-cyclopenta[4,5]furo[2,3-c]pyridin-7a-yl)benzonitrile (Cpd. No. 233F)

To a mixture of rac-(4bS,5R,6S,7S,7aR)-7a-(4-bromophenyl)-4-methoxy-6-((methyl(2,2,2-trifluoroethyl)amino)methyl)-7-phenyl-5,6,7,7a-tetrahydro-4bH-cyclopenta[4,5]furo[2,3-c]pyridine-4b,5-diol (5, 0.15 g, 0.26 mmol) in N,N-dimethylformamide (10.0 mL) at room temperature, zinc cyanide (182 mg, 1.55 mmol) and zinc (3 mg, 0.05 mmol) were added at room temperature and mixture was degassed with argon for 15 min. 1,1'-Bis(diphenylphosphino) ferrocene (4.0 mg, 0.008 mmol) and tris(dibenzylideneacetone)dipalladium (7.0 mg, 0.08 mmol) were added to the reaction mixture and degassing was continued for another 5 min. The reaction mixture was heated at 140° C. for 16 h. After completion, the reaction was cooled to room temperature and passed through celite bed. The filtrate was concentrated and treated with ice-cold water, the solid precipitated was filtered. The crude solid was purified by Combi-flash (12 g RediSep column) using 30% ethyl acetate in hexanes as eluent. Then it was submitted for reverse prep HPLC. The desired fractions were lyophilized to afford rac-4-((4bS,5R,6S,7S,7aR)-4b,5-dihydroxy-4-methoxy-6-((methyl(2,2,2-trifluoroethyl)amino)methyl)-7-phenyl-4b,5,6,7-tetrahydro-7aH-cyclopenta[4,5]furo[2,3-c]pyridin-7a-yl)benzonitrile as white solid. Yield: 0.10 g, 73%. The enantiomers were separated by chiral preparative HPLC [chiralpak IB (4.6×250) mm] using n-Hexane/EtOH (90/10) (v/v) Mobile phase. Peak 1 (21 mg), $[\alpha]_D$−13.0° (c 0.2, $CHCl_3$), $R_t$=12.65 min, ee >99%. MS (ESI) m/z 526.45$[M+1]^+$; UPLC: 99.29%; $^1$H NMR (400 MHz, DMSO-$d_6$) δ 8.05 (s, 1H), 7.97 (s, 1H), 7.49 (d, J=8.4 Hz, 2H), 7.39 (d, J=8.4 Hz, 2H), 7.09-6.97 (m, 5H), 5.72 (s, 1H), 5.11 (d, J=5.7 Hz, 1H), 4.59 (t, J=5.0 Hz, 1H), 3.88 (s, 3H), 3.77 (d, J=14.0 Hz, 1H), 3.42-2.75 (m, 4H), 2.46 (s, 3H), 2.39 (d, J=11.0 Hz, 1H). Peak 2 (Cpd. No. 233F, 22 mg), $[\alpha]_D$+14.5° (c 0.2, $CHCl_3$), $R_t$=17.019 min, ee >99%. MS (ESI) m/z 526.42 $[M+1]^+$; UPLC: 99.42%; $^1H$ NMR (400 MHz, DMSO-$d_6$) δ 8.04 (s, 1H), 7.97 (s, 1H), 7.49 (d, J=8.4 Hz, 2H), 7.39 (d, J=8.4 Hz, 2H), 7.09-6.97 (m, 5H), 5.71 (s, 1H), 5.11 (d, J=5.4 Hz, 1H), 4.50 (t, J=5.0 Hz, 1H), 3.88 (s, 3H), 3.77 (d, J=14.0, 1H), 3.42-2.73 (m, 4H), 2.46 (s, 3H), 2.39 (d, J=11.5 Hz, 1H).

Example 234

Rac-(4bR,5R,7S,7aR)-7a-(4-(aminomethyl)phenyl)-5-(hydroxymethyl)-4-methoxy-7-phenyl-5,6,7,7a-tetrahydro-4bH-cyclopenta[4,5]furo[2,3-c]pyridin-4b-ol (Cpd. No. 234F)

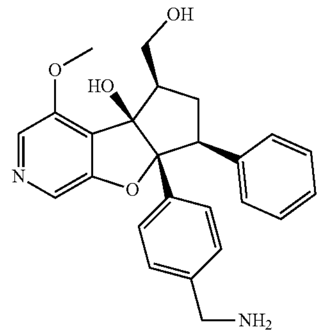

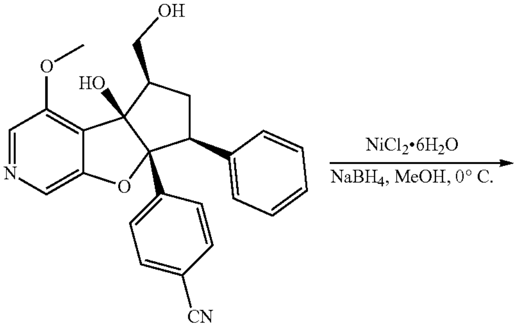

1

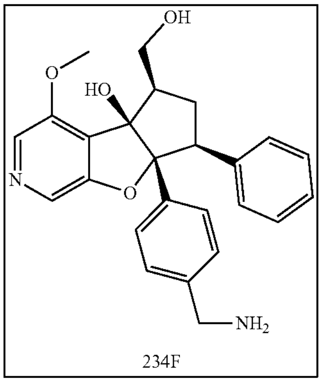

234F

Synthesis of rac-(4bR,5R,7S,7aR)-7a-(4-(aminomethyl)phenyl)-5-(hydroxymethyl)-4-methoxy-7-phenyl-5,6,7,7a-tetrahydro-4bH-cyclopenta[4,5]furo[2,3-c]pyridin-4b-ol (Cpd. No. 234F)

To a solution of rac-4-((4bR,5R,7S,7aR)-4b-hydroxy-5-(hydroxymethyl)-4-methoxy-7-phenyl-4b,5,6,7-tetrahydro-7aH-cyclopenta[4,5]furo[2,3-c]pyridin-7a-yl)benzonitrile (1, 0.050 g, 0.120 mmol) in methanol (1 mL) at 0° C., was added nickel (II) chloride hexa hydrate (0.028 g, 0.12 mmol) followed by sodium borohydride (0.0091 g, 0.24 mmol) at the same temperature. The reaction was stirred for 2 h at room temperature. After completion, the reaction mass was quenched with ice water extracted with ethyl acetate and washed with cold water. The organic layer was separated and dried over anhydrous sodium sulphate, filtered and concentrated to give crude. The crude was purified by reverse phase prep-HPLC and desired fractions were lyophilized to afford rac-(4bR,5R,7S,7aR)-7a-(4-(aminomethyl)phenyl)-5-(hydroxymethyl)-4-methoxy-7-phenyl-5,6,7,7a-tetrahydro-4bH-cyclopenta[4,5]furo[2,3-c]pyridin-4b-ol (Cpd. No. 234F) as white solid. Yield: 0.005 g, 10% (racemic); MS (ESI) m/z 419.29$[M+1]^+$; $^1H$ NMR (400 MHz, DMSO-$d_6$) 8.13 (s, 1H), 8.05 (s, 1H), 7.16 (d, J=8.2 Hz, 2H), 7.09-7.02 (m, 5H), 7.00 (d, J=7.3 Hz, 2H), 5.23 (s, 1H), 4.59 (bs, 1H), 4.05-4.02 (dd, J=6.8, 10.8 Hz, 1H), 3.95 (s, 3H), 3.88 (t, J=10.5 Hz, 1H), 3.58 (s, 2H), 2.77 (m, 1H), 2.42 (d, J=14.9 Hz, 1H), 2.22 (m, 1H).

Example 235

Rac-((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)(2-oxa-6-azaspiro[3.3]heptan-6-yl)methanone (Cpd. No. 235F)

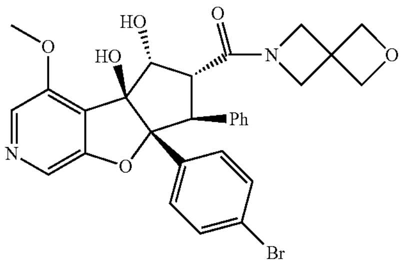

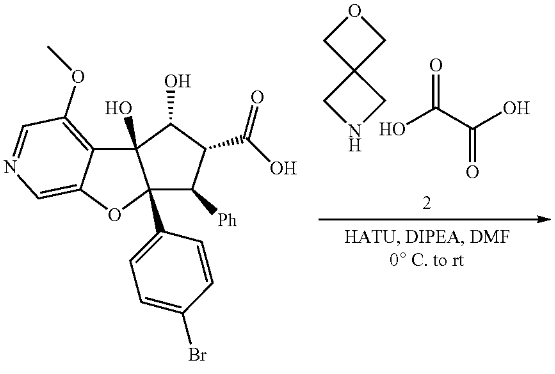

1

-continued

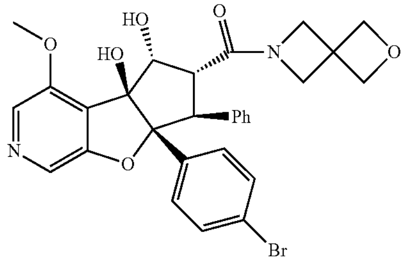

235F

Synthesis of rac-((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)(2-oxa-6-azaspiro[3.3]heptan-6-yl) methanone (Cpd. No. 235F)

To a solution of rac-(4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylic acid (1, 1.0 g, 2.0 mmol) in N,N-dimethylformamide (20 mL), HATU (2.29 g, 6.0 mmol) and N,N-diisopropylethylamine (1.80 ml, 10.0 mmol) were added at 0° C. and stirred the mixture for 5 min. 2-oxa-6-azaspiro[3.3]heptane oxalate (2, 1.44 g, 5.0 mmol) was then added and the reaction mixture was stirred for 2 h at room temperature. After completion, reaction mass was diluted with ethyl acetate and washed with cold water. The organic layer was dried over anhydrous sodium sulphate, filtered and concentrated to give crude product. The crude product was purified by combi-flash (12 g, RedisSep column) using 6% methanol in dichloromethane as eluent. The desired fractions were concentrated to afford rac-((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)(2-oxa-6-azaspiro[3.3]heptan-6-yl)methanone (Cpd. No. 235F) as white solid. Yield: 0.85 g, 73%; MS (ESI) m/z 579.25$[M+1]^+$ $^1$H NMR (400 MHz, DMSO-$d_6$) δ 8.08 (s, 1H), 7.98 (s, 1H), 7.20 (d, J=8.6 Hz, 2H), 7.04-7.01 (m, 4H), 6.97-6.90 (m, 3H), 5.68 (s, 1H), 5.16 (d, J=5.3 Hz, 1H), 4.77 (t, J=6.8 Hz, 2H), 4.73-4.70 (m, 2H), 4.67 (d, J=5.4 Hz, 2H), 4.49 (d, J=8.9 Hz, 1H), 4.33 (d, J=13.6 Hz, 1H), 3.97 (s, 2H), 3.87 (s, 3H), 3.83-3.79 (dd, J=5.2 Hz, 13.9 Hz, 1H).

Example 236

Rac-4-((4bS,5R,6S,7S,7aR)-6-((2-oxa-6-azaspiro[3.3]heptan-6-yl)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 236F)

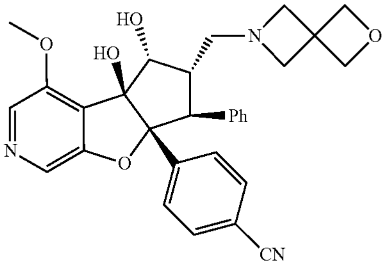

-continued

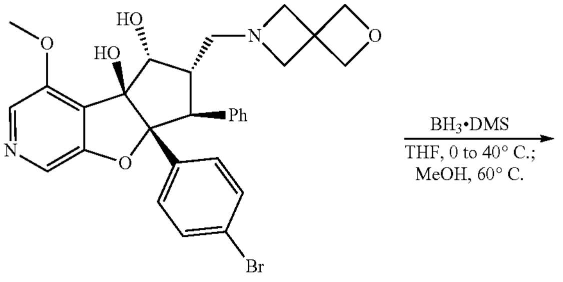

1

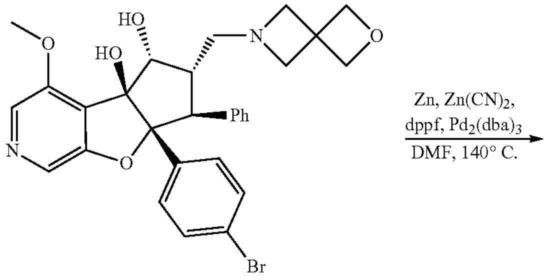

2

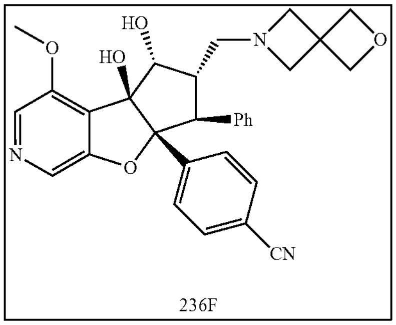

236F

Synthesis of rac-(4bS,5R,6S,7S,7aR)-6-((2-oxa-6-azaspiro[3.3]heptan-6-yl)methyl)-7a-(4-bromophenyl)-4-methoxy-7-phenyl-5,6,7,7a-tetrahydro-4bH-cyclopenta[4,5]furo[2,3-c]pyridine-4b,5-diol (2)

To a solution of rac-((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)(2-oxa-6-azaspiro[3.3]heptan-6-yl)methanone (1, 0.89 g, 1.0 mmol) in tetrahydrofuran (15 mL), borane dimethylsulfide (0.23 ml, 3.0 mmol) was added at 0° C. The reaction mixture was stirred for 3 h at room temperature. After completion, reaction mass was quenched with methanol at 0° C. and then heated at 60° C. for 4 h. The solvents were concentrated to give crude product. The crude product was purified by combi-flash (4 g, RediSep column) using 7% methanol in dichloromethane as eluent. The desired fractions were concentrated to afford rac-(4bS,5R,6S,7S,7aR)-6-((2-oxa-6-azaspiro[3.3]heptan-6-yl)methyl)-7a-(4-bromophenyl)-4-methoxy-7-phenyl-5,6,7,7a-tetrahydro-4bH-cyclopenta[4,5]furo[2,3-c]pyridine-4b,5-diol (2) as white solid. Yield: 0.55 g, 64%; MS (ESI) m/z 565.72$[M+1]^+$

Synthesis of rac-4-((4bS,5R,6S,7S,7aR)-6-((2-oxa-6-azaspiro[3.3]heptan-6-yl)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 236F)

To a mixture of rac-(4bS,5R,6S,7S,7aR)-6-((2-oxa-6-azaspiro[3.3]heptan-6-yl)methyl)-7a-(4-bromophenyl)-4-methoxy-7-phenyl-5,6,7,7a-tetrahydro-4bH-cyclopenta[4,5]furo[2,3-c]pyridine-4b,5-diol (2, 0.55 g, 0.97 mmol) in N,N-dimethylformamide (10.0 mL) at room temperature, zinc cyanide (670 mg, 5.89 mmol) and zinc dust (62 mg, 0.97 mmol) were added at room temperature and degassed the mixture with argon for 15 min. 1,1'-Bis(diphenylphosphino) ferrocene (139 mg, 0.19 mmol) and tris(dibenzylideneacetone)dipalladium (266 mg, 0.29 mmol) were added to the reaction mixture and degassing was continued for another 5 min. The reaction mixture was heated at 140° C. for 2.5 h. After completion, the reaction was cooled to room temperature and passed through celite bed. The filtrate was diluted with ethyl acetate and washed with water. The organic layer was separated, dried over anhydrous sodium sulphate and concentrated under reduced pressure to give the crude. The crude product was purified by reverse phase prep HPLC. The desired fractions were lyophilized to afford rac-4-((4bS,5R,6S,7S,7aR)-6-((2-oxa-6-azaspiro[3.3]heptan-6-yl)methyl)-4b,5-dihydroxy-4-methoxy-7-phenyl-4b,5,6,7-tetrahydro-7aH-cyclopenta[4,5]furo[2,3-c]pyridin-7a-yl)benzonitrile as white solid. Yield: 0.15 g, 30%. The enantiomers were separated by chiral preparative HPLC [chiralpak IA (4.6×250) mm] using n-Hexane/EtOH=50/50 (v/v) Mobile phase. Peak 1 (Cpd. No. 236F, 40 mg); $[\alpha]_D$−99.1° (c 0.29, $CHCl_3$), $R_t$=5.661 min, ee 99.90%. MS (ESI) m/z 512.28$[M+1]^+$. $^1$H NMR (400 MHz, DMSO-d6) δ 8.03 (s, 1H), 7.96 (s, 1H), 7.48 (d, J=8.2 Hz, 2H), 7.34 (d, J=8.2 Hz, 2H), 7.09-7.06 (m, 2H), 7.01-6.97 (m, 3H), 5.72 (s, 1H), 5.40 (brs, 1H), 4.58 (d, J=3.2 Hz, 4H), 4.44 (d, J=2.5 Hz, 1H), 3.87 (s, 3H), 3.78 (d, J=14.1 Hz, 1H), 3.29 (s, 4H), 2.94 (s, 1H), 2.69-2.49 (m, 1H), 2.25-2.17 (m, 1H). Peak-2 (34 mg); $[\alpha]_D$+23.0° (c 0.259, $CHCl_3$), $R_t$=22.48 min, ee 99.30%. MS (ESI) m/z 512.24 $[M+1]^+$; $^1$H NMR (400 MHz, DMSO-d) δ 8.03 (s, 1H), 7.96 (s, 1H), 7.48 (d, J=8.2 Hz, 2H), 7.34 (d, J=8.2 Hz, 2H), 7.09-7.06 (m, 2H), 7.01-6.97 (m, 3H), 5.72 (s, 1H), 5.39 (bs, 1H), 4.60-4.56 (m, 4H), 4.44 (d, J=2.5 Hz, 1H), 3.87 (s, 3H), 3.78 (d, J=14.1 Hz, 1H), 3.29 (s, 4H), 2.94 (s, 1H), 2.69-2.50 (m, 1H), 2.25-2.17 (m, 1H).

Example 237

Rac-(4bS,5R,6R,7S,7aR)-7a-(4-bromophenyl)-4b,5-dihydroxy-4-methoxy-N-methyl-N-(oxetan-3-yl)-7-phenyl-4b,6,7,7a-tetrahydro-5H-cyclopenta[4,5]furo[2,3-c]pyridine-6-carboxamide (Cpd. No. 237F)

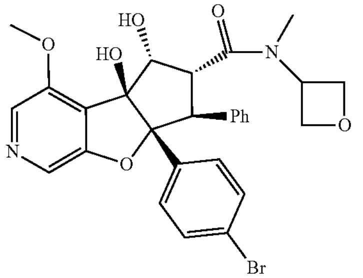

-continued

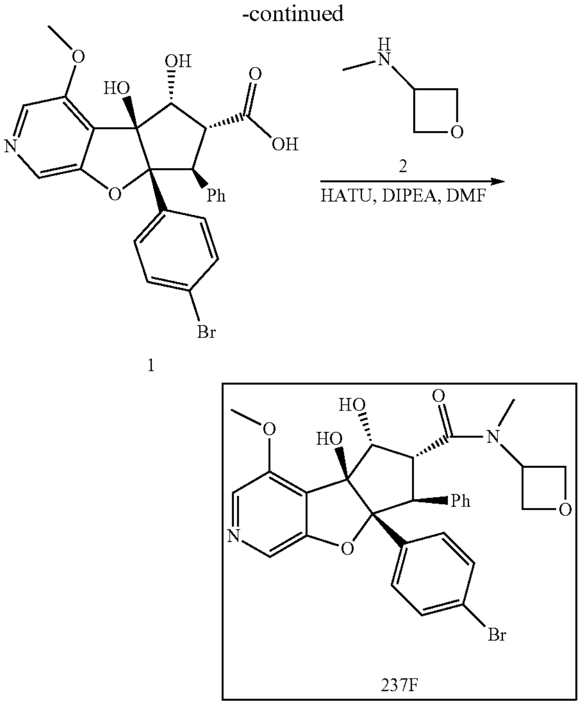

1

237F

Synthesis of rac-(4bS,5R,6R,7S,7aR)-7a-(4-bromophenyl)-4b,5-dihydroxy-4-methoxy-N-methyl-N-(oxetan-3-yl)-7-phenyl-4b,6,7,7a-tetrahydro-5H-cyclopenta[4,5]furo[2,3-c]pyridine-6-carboxamide (Cpd. No. 237F)

To a solution of rac-(4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylic acid (1, 1.0 g, 2.0 mmol) in N,N-dimethylformamide (10 mL), 0-(7-Azabenzotriazol-1-yl)-N,N,N',N'-tetramethyluronium hexafluorophosphate (2.29 g, 6.0 mmol) and N,N-diisopropylethylamine (1.80 ml, 10.0 mmol) were added at 0° C. and stirred the mixture for 5 min. N-methyloxetan-3-amine (2, 1.44 g, 5.0 mmol) was then added and the reaction mixture was stirred for 2 h at room temperature. After completion, reaction mixture was diluted with ethyl acetate and washed with cold water. The organic layer was dried over anhydrous sodium sulphate, filtered and concentrated to give crude product. The crude product was purified by combi-flash (12 g, RediSep column) using 6% methanol in dichloromethane as eluent. The desired fractions were concentrated to afford rac-(4bS,5R,6R,7S,7aR)-7a-(4-bromophenyl)-4b,5-dihydroxy-4-methoxy-N-methyl-N-(oxetan-3-yl)-7-phenyl-4b,6,7,7a-tetrahydro-5H-cyclopenta[4,5]furo[2,3-c]pyridine-6-carboxamide (Cpd. No. 237F) as white solid. Yield: 0.94 g, 83%; MS (ESI) m/z 567.25$[M+1]^+$; $^1$H NMR (400 MHz, DMSO-d6) (8.10 (s, 1H), 7.99 (s, 1H), 7.22-7.20 (m, 2H), 7.12-7.07 (m, 2H), 7.04-7.01 (m, 2H), 6.96-6.86 (m, 3H), 5.71 (d, J=11.3 Hz, 1H), 5.24 (d, J=5.3 Hz, 1H), 5.09-5.06 (m, 1H), 4.97-4.75 (m, 2H), 4.63-4.53 (m, 3H), 4.36 (d, J=13.6 Hz, 1H), 4.25-4.20 (m, 1H), 3.87 (s, 3H), 3.43 (s, 2H), 2.96 (s, 1H).

Example 238

Rac-4-((4bS,5R,6S,7S,7aR)-4b,5-dihydroxy-4-methoxy-6-((methyl(oxetan-3-yl)amino)methyl)-7-phenyl-4b,5,6,7-tetrahydro-7aH-cyclopenta[4,5]furo[2,3-c]pyridin-7a-yl)benzonitrile (Cpd. No. 238F)

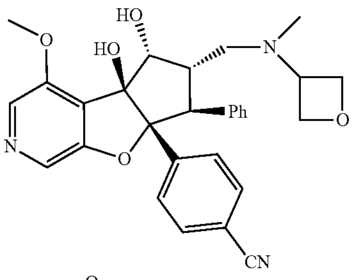

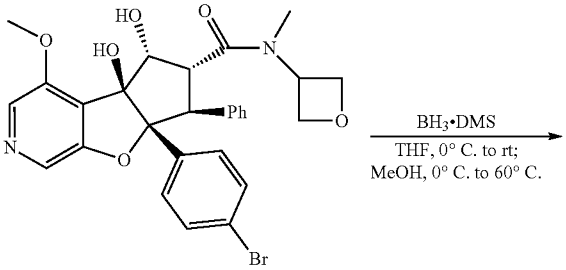

1

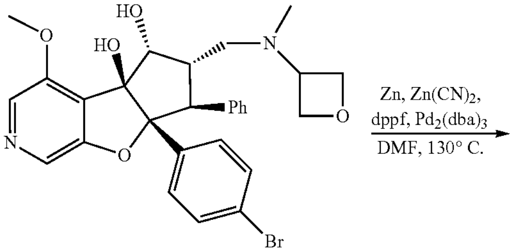

2

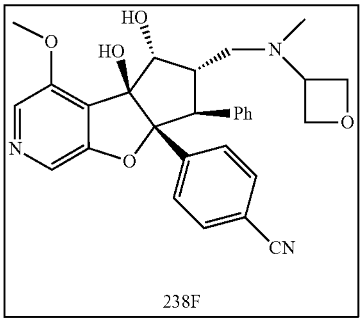

238F

Synthesis of rac-(4bS,5R,6S,7S,7aR)-7a-(4-bromophenyl)-4-methoxy-6-((methyl(oxetan-3-yl)amino)methyl)-7-phenyl-5,6,7,7a-tetrahydro-4bH-cyclopenta[4,5]furo[2,3-c]pyridine-4b,5-diol (2)

To a solution of rac-(4bS,5R,6R,7S,7aR)-7a-(4-bromophenyl)-4b,5-dihydroxy-4-methoxy-N-methyl-N-(oxetan-3-yl)-7-phenyl-4b,6,7,7a-tetrahydro-5H-cyclopenta[4,5]furo[2,3-c]pyridine-6-carboxamide (1, 0.55 g, 0.97 mmol) in tetrahydrofuran (15 mL), borane dimethyl sulfide (0.18 ml, 1.94 mmol) was added at 0° C. The reaction mixture was stirred for 3 h at room temperature. After completion, reaction mixture was quenched with methanol at 0° C. and then heated at 60° C. for 4 h. The solvents were concentrated to give crude product. The crude product was purified by combi-flash (4 g, RediSep column) using 0-7% methanol in dichloromethane as eluent. The desired fractions were concentrated to afford rac-(4bS,5R,6S,7S,7aR)-7a-(4-bromophenyl)-4-methoxy-6-((methyl(oxetan-3-yl)amino)methyl)-7-phenyl-5,6,7,7a-tetrahydro-4bH-cyclopenta[4,5]furo[2,3-c]pyridine-4b,5-diol (2) as white solid. Yield: 0.16 g, 29%; MS (ESI) m/z 553.12[M+1]$^+$.

Synthesis of rac-4-((4bS,5R,6S,7S,7aR)-4b,5-dihydroxy-4-methoxy-6-((methyl(oxetan-3-yl)amino)methyl)-7-phenyl-4b,5,6,7-tetrahydro-7aH-cyclopenta[4,5]furo[2,3-c]pyridin-7a-yl)benzonitrile (Cpd. No. 238F)

To a mixture of rac-(4bS,5R,6S,7S,7aR)-7a-(4-bromophenyl)-4-methoxy-6-((methyl(oxetan-3-yl)amino)methyl)-7-phenyl-5,6,7,7a-tetrahydro-4bH-cyclopenta[4,5]furo[2,3-c]pyridine-4b,5-diol (2, 0.31 g, 0.56 mmol) in N,N-dimethylformamide (5.0 mL) at room temperature, zinc cyanide (0.656 g, 5.61 mmol) and zinc (0.003 g, 0.05 mmol) were added and the mixture was degassed with argon for 15 min. 1,1'-Bis(diphenylphosphino) ferrocene (0.093 g, 0.168 mmol) and tris(dibenzylideneacetone)dipalladium (0.154 g, 0.168 mmol) were added to the reaction mixture and degassing was continued for another 5 min. The reaction mixture was heated at 130° C. for 2.5 h. After completion, the reaction was cooled to room temperature and passed through celite bed. The filtrate was diluted with ethyl acetate and washed with water. The organic layer was separated, dried over anhydrous sodium sulphate and concentrated under reduced pressure to give the crude product. The crude product was purified by combi-flash (12 g, RediSep column) using 0-10% methanol in dichloromethane as eluent. The product obtained was further purified by reverse phase prep HPLC. The desired fractions were lyophilized to afford rac-4-((4bS,5R,6S,7S,7aR)-4b,5-dihydroxy-4-methoxy-6-((methyl(oxetan-3-yl)amino)methyl)-7-phenyl-4b,5,6,7-tetrahydro-7aH-cyclopenta[4,5]furo[2,3-c]pyridin-7a-yl)benzonitrile as white solid. Yield: 0.036 g, 13%. The enantiomers were separated by chiral preparative HPLC [chiralpak IA (4.6×250) mm] using n-Hexane/EtOH=70/30 (v/v) Mobile phase. Peak 1 (9 mg); $R_t$=7.54, ee >99%; MS (ESI) m/z 500.33[M+1]$^+$. $^1$H NMR (400 MHz, DMSO-$d_6$) δ 8.04 (s, 1H), 7.97 (s, 1H), 7.48 (d, J=8.2 Hz, 2H), 7.38 (d, J=8.2 Hz, 2H), 7.09-7.05 (m, 2H), 7.0-6.98 (m, 3H), 5.76 (s, 1H), 5.22 (d, J=5.7 Hz, 1H), 4.50-4.45 (m, 3H), 4.43-4.36 (m, 2H), 3.89 (s, 3H), 3.79 (d, J=14.1 Hz, 1H), 3.41 (t, J=5.92 Hz, 1H), 3.19 (bs, 1H), 2.56 (bs, 1H) 2.20 (s, 3H), 1.84 (d, J=11.6 Hz, 1H); Peak 2 (Cpd. No. 238F, 8 mg); $R_t$=11.54, ee >99%; MS (ESI) m/z 500.30[M+1]$^+$; $^1$H NMR (400 MHz, DMSO-$d_6$) δ 8.04 (s, 1H), 7.97 (s, 1H), 7.48 (d, J=8.2 Hz, 2H), 7.38 (d, J=8.2 Hz, 2H), 7.09-7.05 (m, 2H), 7.0-6.98 (m, 3H), 5.76 (s, 1H), 5.22 (d, J=5.3 Hz, 1H), 4.48-4.42 (m, 3H), 4.40-4.36 (m, 2H), 3.89 (s, 3H), 3.80 (d, J=14.2 Hz, 1H), 3.41 (t, J=6.7 Hz, 1H), 3.19 (t, J=14.0 Hz, 1H), 2.56 (brs, 1H), 2.20 (s, 3H), 1.84 (d, J=11.2 Hz, 1H).

Example 239

Rac-(4bS,5R,6R,7S,7aR)-7a-(4-bromophenyl)-4b,5-dihydroxy-4-methoxy-N-(oxetan-3-yl)-7-phenyl-4b,6,7,7a-tetrahydro-5H-cyclopenta[4,5]furo[2,3-c]pyridine-6-carboxamide (Cpd. No. 239F)

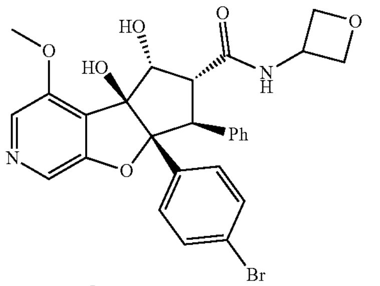

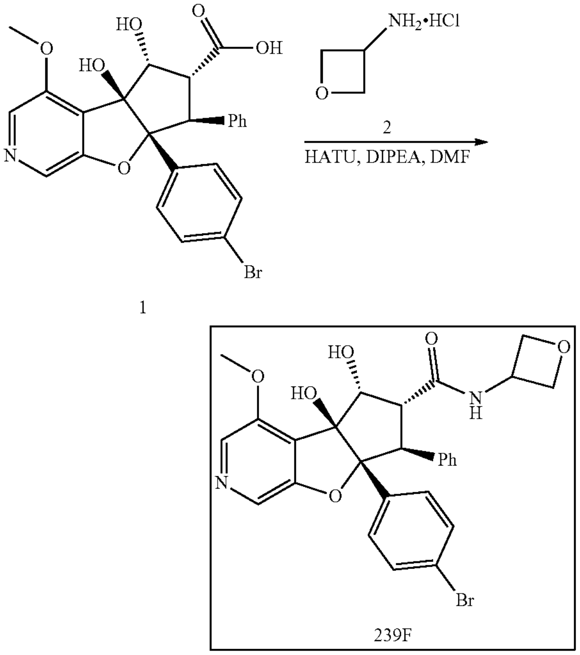

1

239F

Synthesis of rac-(4bS,5R,6R,7S,7aR)-7a-(4-bromophenyl)-4b,5-dihydroxy-4-methoxy-N-(oxetan-3-yl)-7-phenyl-4b,6,7,7a-tetrahydro-5H-cyclopenta[4,5]furo[2,3-c]pyridine-6-carboxamide (Cpd. No. 239F)

To a solution of rac-(4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylic acid (1, 1.5 g, 3.0 mmol) in N,N-dimethylformamide (20 mL), 1-[Bis(dimethylamino)methylene]-1H-1,2,3-triazolo[4,5-b]pyridinium 3-oxide hexafluorophosphate (3.43 g, 9.0 mmol) and N,N-diisopropyl ethylamine (2.7 ml, 15.0 mmol) were added at 0° C. and stirred the mixture for 5 min. oxetan-3-amine hydrochloride (2, 0.82 g, 7.5 mmol) was then added and the reaction mixture was stirred for 4 h at room temperature. After completion, reaction mass was diluted with ethyl acetate and washed with cold water. The organic layer was dried over anhydrous sodium sulphate, filtered and concentrated to give crude product. The crude product was purified by Combi-flash (12 g RediSep column) using 0-3% methanol in dichloromethane as eluent. The product obtained was repurified by reverse phase prep HPLC. The desired fractions were lyophilized to afford rac-(4bS,5R,6R,7S,7aR)-7a-(4-bromophenyl)-4b,5-dihydroxy-4-methoxy-N-(oxetan-3-yl)-7-phenyl-4b,6,7,7a-tetrahydro-5H-cyclopenta[4,5]furo[2,3-c]pyridine-6-carboxamide (Cpd. No. 239F) as brown solid. Yield: 1.1 g, 66%; MS (ESI) m/z 553.19$[M+1]^+$, UPLC: 99.82%, $^1H$ NMR (400 MHz, DMSO-d6) δ 8.88 (d, J=6.2 Hz, 1H), 8.08 (s, 1H), 7.98 (s, 1H), 7.23 (d, J=8.6 Hz, 2H), 7.07-6.94 (m, 7H), 5.67 (s, 1H), 5.14 (d, J=4.7 Hz, 1H), 4.71-4.64 (m, 4H), 4.42 (t, J=5.8 Hz, 1H), 4.34-4.31 (m, 2H), 3.87 (s, 3H), 3.84 (d, J=4.8 Hz, 1H).

Example 240

Rac-4-((4bS,5R,6S,7S,7aR)-4b,5-dihydroxy-4-methoxy-6-((oxetan-3-ylamino)methyl)-7-phenyl-4b,5,6,7-tetrahydro-7aH-cyclopenta[4,5]furo[2,3-c]pyridin-7a-yl)benzonitrile (Cpd. No. 240F)

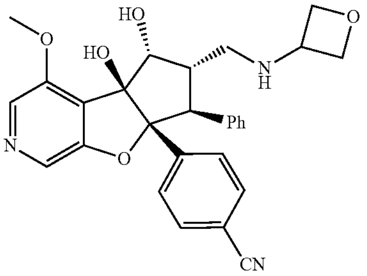

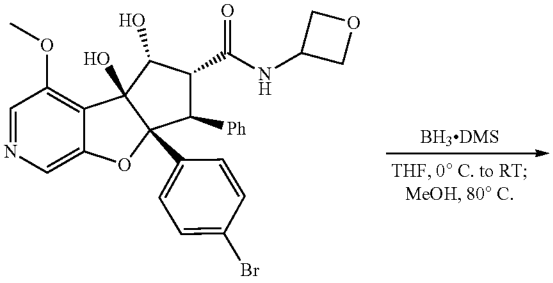

1

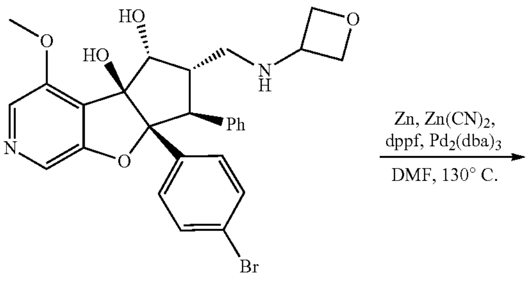

2

-continued

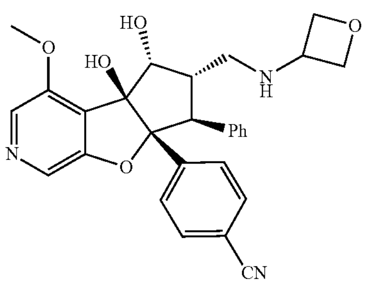

240F

Synthesis of rac-(4bS,5R,6S,7S,7aR)-7a-(4-bromophenyl)-4-methoxy-6-((oxetan-3-ylamino)methyl)-7-phenyl-5,6,7,7a-tetrahydro-4bH-cyclopenta[4,5]furo[2,3-c]pyridine-4b,5-diol (2)

To a solution of rac-(4bS,5R,6R,7S,7aR)-7a-(4-bromophenyl)-4b,5-dihydroxy-4-methoxy-N-(oxetan-3-yl)-7-phenyl-4b,6,7,7a-tetrahydro-5H-cyclopenta[4,5]furo[2,3-c]pyridine-6-carboxamide (1, 1.0 g, 1.8 mmol) in tetrahydrofuran (30 mL), borane dimethylsulfide (0.5 ml, 5.4 mmol) was added at 0° C. Then reaction mixture was stirred at room temperature for 16 h. After completion, reaction mass was quenched with methanol at 0° C. and then heated at 80° C. for 6 h. The solvents were concentrated and the residue was purified by flash column chromatography by eluting with gradient of 1-5% methanol in dichloromethane. The fractions containing desired product was concentrated and dried under vacuum to afford rac-(4bS,5R,6S,7S,7aR)-7a-(4-bromophenyl)-4-methoxy-6-((oxetan-3-ylamino)methyl)-7-phenyl-5,6,7,7a-tetrahydro-4bH-cyclopenta[4,5]furo[2,3-c]pyridine-4b,5-diol (2) as brown solid. Yield: 0.12 g, 12%; MS (ESI) m/z 539.37[M+1]$^+$, UPLC: 50.27% Synthesis of rac-4-((4bS,5R,6S,7S,7aR)-4b,5-dihydroxy-4-methoxy-6-((oxetan-3-ylamino)methyl)-7-phenyl-4b,5,6,7-tetrahydro-7aH-cyclopenta[4,5]furo[2,3-c]pyridin-7a-yl)benzonitrile (Cpd. No. 240F)

To a mixture of rac-(4bS,5R,6S,7S,7aR)-7a-(4-bromophenyl)-4-methoxy-6-((oxetan-3-ylamino)methyl)-7-phenyl-5,6,7,7a-tetrahydro-4bH-cyclopenta[4,5]furo[2,3-c]pyridine-4b,5-diol (2, 0.12 g, 0.2 mmol) in N,N-dimethylformamide (5.0 mL) at room temperature, zinc cyanide (26 mg, 2.2 mmol) and zinc (14 mg, 0.2 mmol) were added at room temperature and degassed the mixture with argon for 15 min. 1,1'-Bis(diphenylphosphino) ferrocene (36.0 mg, 0.06 mmol) and tris(dibenzylideneacetone)dipalladium (61.0 mg, 0.06 mmol) were added to the reaction mixture and degassing was continued for another 5 min. The reaction mixture was heated at 140° C. for 3 h. After completion, the reaction mass was cooled to room temperature and passed through celite bed. Filtrate was concentrated and treated with ice-cold water, the solid precipitated was filtered. The crude product was purified by Combi-flash (12 g RediSep column) using 30% ethyl acetate: hexanes as eluent. The product obtained was repurified by reverse phase prep HPLC. The desired fractions were lyophilized to afford rac-4-((4bS,5R,6S,7S,7aR)-4b,5-dihydroxy-4-methoxy-6-((oxetan-3-ylamino)methyl)-7-phenyl-4b,5,6,7-tetrahydro-7aH-cyclopenta[4,5]furo[2,3-c]pyridin-7a-yl)benzonitrile (Cpd. No. 240F) as white solid. Yield: 0.02 g, 18%, MS (ESI) m/z 486.24[M+1]$^+$; UPLC: 94.57%; $^1$H NMR (400 MHz, DMSO-$d_6$) δ 8.03 (s, 1H), 7.96 (s, 1H), 7.46 (d, J=8.34 Hz, 2H), 7.34 (d, J=8.36 Hz, 2H), 7.05-6.94 (m, 5H), 5.69 (s, 1H), 5.30 (s, 1H), 4.59-4.52 (m, 3H), 4.29-4.22 (m, 2H), 3.87 (s, 3H), 3.80-3.70 (m, 2H), 3.06 (d, J=3.72 Hz, 1H), 2.53-1.78 (m, 2H), 1.78 (s, 1H).

Example 241

Rac-4-((4bS,5R,6S,7S,7aR)-4b,5-dihydroxy-4-methoxy-6-((((1-methyl-1H-pyrazol-5-yl)methyl)amino)methyl)-7-phenyl-4b,5,6,7-tetrahydro-7aH-cyclopenta[4,5]furo[2,3-c]pyridin-7a-yl)benzonitrile (Cpd. No. 241F)

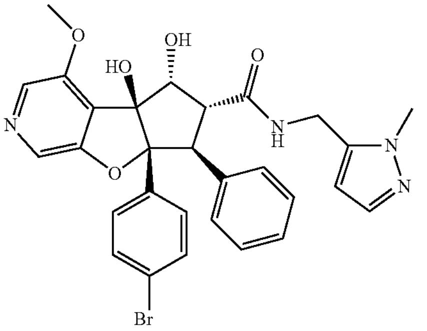

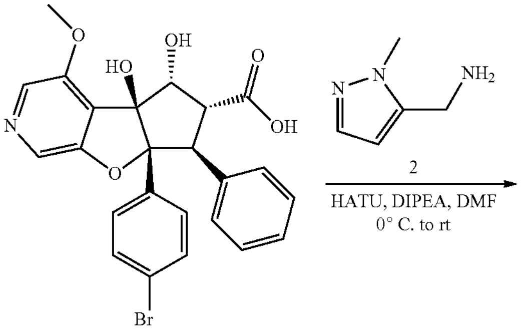

1

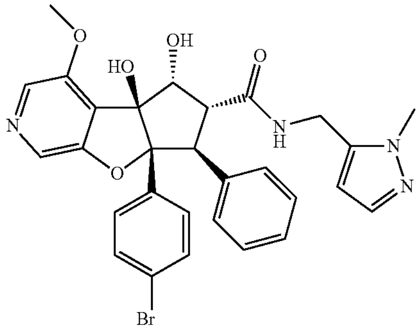

241F

Synthesis of rac-(4bS,5R,6R,7S,7aR)-7a-(4-bromophenyl)-4b,5-dihydroxy-4-methoxy-N-((1-methyl-1H-pyrazol-5-yl)methyl)-7-phenyl-4b,6,7,7a-tetrahydro-5H-cyclopenta[4,5]furo[2,3-c]pyridine-6-carboxamide. (Cpd. No. 241F)

To the solution of rac-(4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylic acid (1, 1.00 g, 2.01 mmol) in N,N-dimethylformamide (5 mL) at 0° C., HATU (1.14 g, 3.01 mmol) and N,N-diisopropylethylamine (1.04 ml, 6.02 mmol) were added and the mixture was stirred for 5 min. (1-methyl-1H-pyrazol-5-yl)methanamine (2, 0.27 ml, 3.01 mmol) was added at the same temperature and the reaction was stirred for 16 h at room temperature. After completion, the reaction mixture was diluted with dichloromethane and washed with cold water. The organic layer was separated and dried over anhydrous sodium sulphate, filtered and concentrated to give crude product. The crude product was purified by silica gel (100-200 mesh size) column chromatography using 0-3% methanol in dichloromethane as eluent. The desired fractions were concentrated to afford rac-(4bS,5R,6R,7S,7aR)-7a-(4-bromophenyl)-4b,5-dihydroxy-4-methoxy-N-((1-methyl-1H-pyrazol-5-yl)methyl)-7-phenyl-4b,6,7,7a-tetrahydro-5H-cyclopenta[4,5]furo[2,3-c]pyridine-6-carboxamide (Cpd. No. 241F) as white solid. Yield: 0.85 g, 83%; MS (ESI) m/z 591.41[M+1]$^+$. $^1$H NMR (400 MHz, DMSO-$d_6$); $^1$H NMR (400 MHz, DMSO-d) 8.62 (t, J=5.2 Hz, 1H), 8.27 (s, 1H), 8.11 (s, 1H), 7.24 (d, J=9.0 Hz, 3H), 7.10-7.04 (m, 4H), 7.01-6.96 (m, 3H), 6.06 (s, 1H), 5.86 (s, 1H), 5.27 (bs, 1H), 4.63 (d, J=4.4 Hz, 1H), 4.40 (d, J=14.0 Hz, 1H), 4.35-4.21 (m, 2H), 3.97 (d, J=4.6 Hz, 1H), 3.91 (s, 3H), 3.61 (s, 3H).

Example 242

Rac-4-((4bS,5R,6S,7S,7aR)-4b,5-dihydroxy-4-methoxy-6-((((1-methyl-1H-pyrazol-5-yl)methyl)amino)methyl)-7-phenyl-4b,5,6,7-tetrahydro-7aH-cyclopenta[4,5]furo[2,3-c]pyridin-7a-yl)benzonitrile (Cpd. No. 242F)

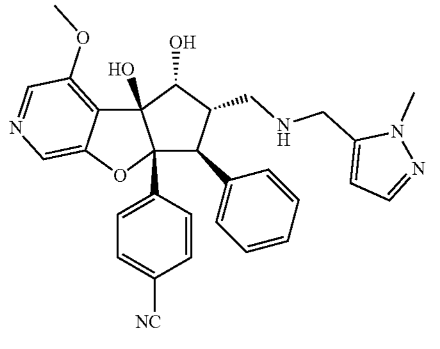

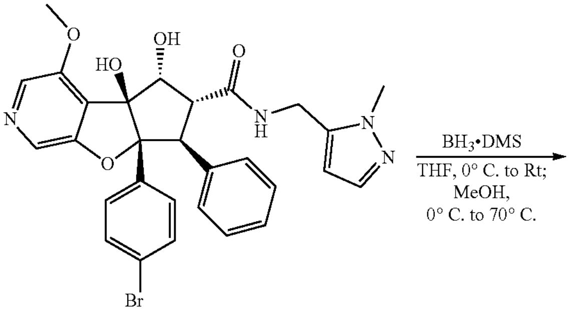

1

-continued

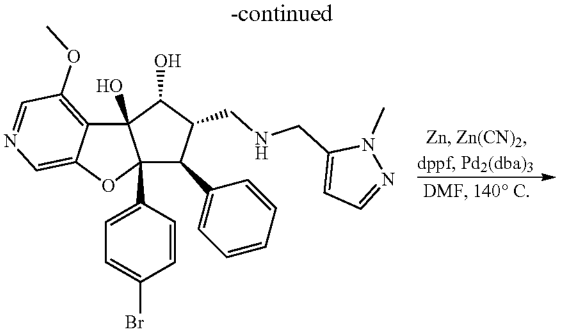

2

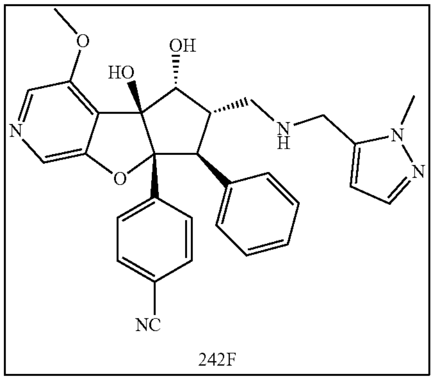

242F

Synthesis of rac-(4bS,5R,6S,7S,7aR)-7a-(4-bromophenyl)-4-methoxy-6-((((1-methyl-1H-pyrazol-5-yl)methyl)amino)methyl)-7-phenyl-5,6,7,7a-tetrahydro-4bH-cyclopenta[4,5]furo[2,3-c]pyridine-4b,5-diol (2)

To a solution of rac-(4bS,5R,6R,7S,7aR)-7a-(4-bromophenyl)-4b,5-dihydroxy-4-methoxy-N-((1-methyl-1H-pyrazol-5-yl)methyl)-7-phenyl-4b,6,7,7a-tetrahydro-5H-cyclopenta[4,5]furo[2,3-c]pyridine-6-carboxamide (1, 0.85 g, 1.43 mmol) in dry tetrahydrofuran (30 ml) at 0° C., borane dimethyl sulphide complex (1.36 ml, 14.37 mmol) was added drop wise over a period of 5 min. The reaction mixture was slowly brought to room temperature and stirred for additional 16 h. After completion, the reaction mixture was quenched with methanol at 0° C. and heated to reflux for 24 h. After completion, solvent was removed under reduced pressure and the residue was purified over a plug of silica gel (100-200 mesh size) using 5% methanol in dichloromethane as a eluent. The desired fractions were concentrated under reduced pressure to afford rac-(4bS,5R,6S,7S,7aR)-7a-(4-bromophenyl)-4-methoxy-6-((((1-methyl-1H-pyrazol-5-yl)methyl)amino)methyl)-7-phenyl-5,6,7,7a-tetrahydro-4bH-cyclopenta[4,5]furo[2,3-c]pyridine-4b,5-diol (2) as a white solid. Yield: 0.65 g, 72%; MS (ESI) m/z 577.28[M+1]$^+$.

Synthesis of rac-4-((4bS,5R,6S,7S,7aR)-4b,5-dihydroxy-4-methoxy-6-((((1-methyl-1H-pyrazol-5-yl)methyl)amino)methyl)-7-phenyl-4b,5,6,7-tetrahydro-7aH-cyclopenta[4,5]furo[2,3-c]pyridin-7a-yl)benzonitrile (Cpd. No. 242F)

To a solution of rac-(4bS,5R,6S,7S,7aR)-7a-(4-bromophenyl)-4-methoxy-6-((((1-methyl-1H-pyrazol-5-yl)methyl)amino)methyl)-7-phenyl-5,6,7,7a-tetrahydro-4bH-cyclopenta[4,5]furo[2,3-c]pyridine-4b,5-diol (2, 0.65 g, 1.12 mmol) in N,N-dimethylformamide (10 mL), zinc cyanide (1.3 g, 11.2 mmol) and zinc dust (0.0085 g, 0.131 mmol) were added at room temperature and the reaction mixture was degassed with argon for 15 min. 1,1'-Bis (diphenylphosphino)ferrocene (0.012 g, 0.021 mmol) and tetrakis(triphenylphosphine)palladium (0.693 g, 0.6 mmol) were added to the reaction mixture, degassed for additional 5 min and mixture was heated at 140° C. for 8 h. After completion, the reaction mixture was diluted with ethyl acetate and washed with cold water. The organic layer was separated and dried over anhydrous sodium sulphate, filtered and concentrated to give crude product. The crude product was purified by silica gel (100-200 mesh size) column chromatography using 2-3% methanol in dichloromethane as eluent. The desired fractions were concentrated to afford rac-4-((4bS,5R,6S,7S,7aR)-4b,5-dihydroxy-4-methoxy-6-((((1-methyl-1H-pyrazol-5-yl)methyl)amino)methyl)-7-phenyl-4b,5,6,7-tetrahydro-7aH-cyclopenta[4,5]furo[2,3-c]pyridin-7a-yl)benzonitrile (Cpd. No. 242F) as a white solid. Yield: 0.59 g, 54% (racemic); The enantiomers were separated by chiral HPLC [Chiralpak IA (4.6 ×250) mm, 5μ] in Hexane/Ethanol=40/60 (v/v). Peak 1 (70 mg), $[\alpha]_D$+24.2° (c 0.252, $CHCl_3$), $R_t$=5.47 min, ee: 99.60%; MS (ESI) m/z 524.28[M+1]$^+$; $^1$H NMR (400 MHz, DMSO-$d_6$) 8.05 (s, 1H), 7.98 (s, 1H), 7.49 (d, J=8.52 Hz, 2H), 7.36 (d, J=8.40 Hz, 2H), 7.25 (bs, 1H), 7.05-7.03 (m, 2H), 6.98-6.92 (m, 4H), 6.09 (s, 1H), 5.70 (s, 1H), 5.29 (bs, 1H), 4.55 (s, 1H), 3.88 (s, 4H), 3.84-3.69 (m, 7H). 3.17 (bs, 1H). Peak-2 (64 mg), $[\alpha]_D$−21.0° (c 0.27, $CHCl_3$), $R_t$=10.36 min, ee:99.52%; MS (ESI) m/z 524.28[M+1]$^+$; $^1$H NMR (400 MHz, DMSO-$d_6$) 8.05 (s, 1H), 7.98 (s, 1H), 7.53-7.48 (m, 2H), 7.36 (d, J=7.56 Hz, 2H), 7.25 (bs, 1H), 7.05-7.03 (m, 2H), 6.98 (bs, 4H), 6.09 (s, 1H), 5.70 (s, 1H), 5.28 (bs, 1H), 4.55 (s, 1H), 3.89 (s, 4H), 3.80-3.69 (m, 7H). 3.17 (bs, 1H).

Example 243

4-((4bS,5R,6S,7S,7aR)-6-((tert-butyl(methyl)amino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 243F)

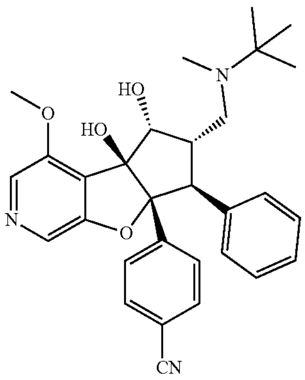

-continued

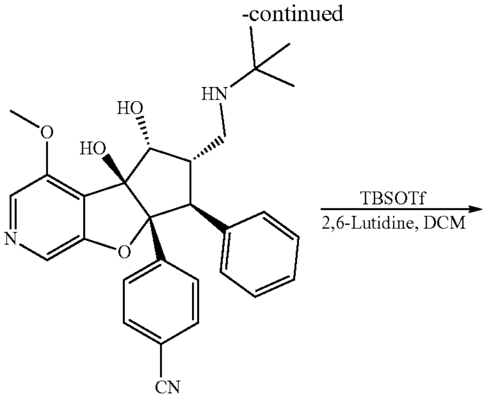

1

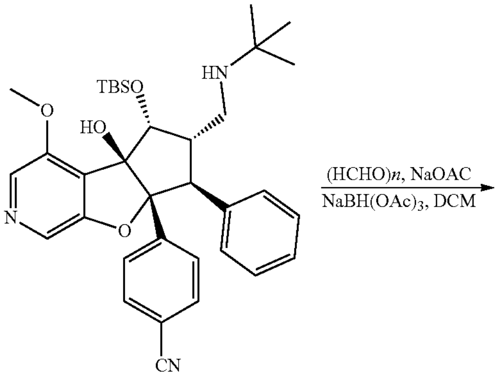

2

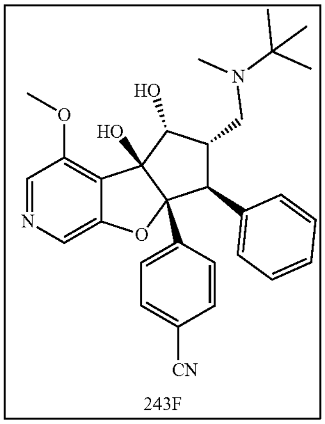

243F

Synthesis of rac-4-((4bS,5R,6S,7S,7aR)-6-((tert-butylamino)methyl)-5-((tert-butyldimethylsilyl)oxy)-4b-hydroxy-4-methoxy-7-phenyl-4b,5,6,7-tetrahydro-7aH-cyclopenta[4,5]furo[2,3-c]pyridin-7a-yl)benzonitrile (2)

To a solution of rac-4-((4bS,5R,6S,7S,7aR)-6-((tert-butylamino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (1, 0.41 g, 0.84 mmol) in dichloromethane (10 mL) at 0° C., 2,6-Lutidine (0.24 mL, 2.10 mmol) and tert-Butyldimethylsilyl trifluoromethanesulfonate (0.30 mL, 1.26 mmol) were added and reaction mixture was stirred for 1 h at room temperature. The reaction was monitored by TLC. After completion, the crude reaction mixture was used as such for next step.

Synthesis of rac-4-((4bS,5R,6S,7S,7aR)-6-((tert-butyl(methyl)amino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 243F)

A solution of rac-4-((4bS,5R,6S,7S,7aR)-6-((tert-butylamino)methyl)-5-((tert-butyldimethylsilyl)oxy)-4b-hydroxy-4-methoxy-7-phenyl-4b,5,6,7-tetrahydro-7aH-cyclopenta[4,5]furo[2,3-c]pyridin-7a-yl)benzonitrile (2) (obtained from previous step) in dichloromethane (10 mL) at 0° C., p-formaldehyde (0.100 g, 3.36 mmol), sodium acetate (0.68 g, 0.84 mmol) and sodium triacetoxyborohydride (0.711 g, 3.36 mmol) were added and reaction mixture was stirred at room temperature for 2 h. After completion, the reaction mixture was diluted with water, neutralized with sodium bicarbonate solution and extracted with 10% methanol in dichloromethane. The organic layer was dried over anhydrous sodium sulphate, filtered and concentrated to give crude. The crude was purified by column chromatography using silica gel (100-200 mesh) and 0-6% 7M methanolic ammonia in dichloromethane as eluent. The desired fractions were concentrated under reduced pressure to afford rac-4-((4bS,5R,6S,7S,7aR)-6-((tert-butyl(methyl)amino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile as white solid. Yield: 0.230 g, 55%; MS (ESI) m/z 500.52[M+1]$^+$. The enantiomers were separated by chiral HPLC [Chiralpak IC (4.6×250)mm, 5μ], 0.1% TEA in n-Hexane/IPA=70/30(v/v) Peak 1 (50 mg), $[\alpha]_D$+33.2° (c 0.28, $CHCl_3$), $R_t$=7.94 min, ee: 99.88%; MS (ESI) m/z 500.37[M+1]$^+$; $^1$H NMR (400 MHz, DMSO-$d_6$) □ 8.04 (s, 1H), 7.96 (s, 1H), 7.48 (d, J=8.5 Hz, 2H), 7.36 (d, J=8.4 Hz, 2H), 7.08-7.05 (m, 2H), 7.02-6.96 (m, 3H), 5.72 (s, 1H), 5.32 (bs, 1H), 4.50 (s, 1H), 3.93 (s, 1H), 3.87 (s, 3H), 3.13 (bs, 1H), 2.73 (bs, 1H), 2.25-2.19 (m, 3H), 1.25-1.22 (m, 1H), 0.94 (s, 9H). Peak-2 (Cpd. No. 243F, 52 mg) $[\alpha]_D$−35.2° (c 0.25, $CHCl_3$), $R_t$=14.67 min, ee: 99.74%; MS (ESI) m/z 500.40[M+1]$^+$; $^1$H NMR (400 MHz, DMSO-$d_6$) □ 8.04 (s, 1H), 7.96 (s, 1H), 7.48 (d, J=8.5 Hz, 2H), 7.36 (d, J=8.44 Hz, 2H), 7.08-7.05 (m, 2H), 7.02-6.98 (m, 3H), 5.72 (s, 1H), 5.32 (bs, 1H), 4.50 (s, 1H), 3.93 (s, 1H), 3.87 (s, 3H), 3.13 (bs, 1H), 2.73 (bs, 1H), 2.25-2.19 (m, 3H), 1.25-1.22 (m, 1H), 0.94 (s, 9H).

Example 244

Rac-4-((4bS,5R,6S,7S,7aR)-6-((cyclopropylamino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 244F)

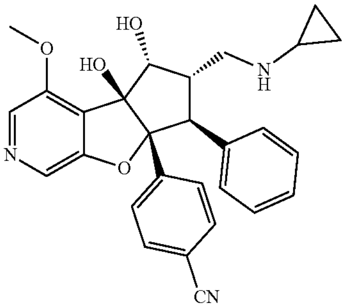

-continued

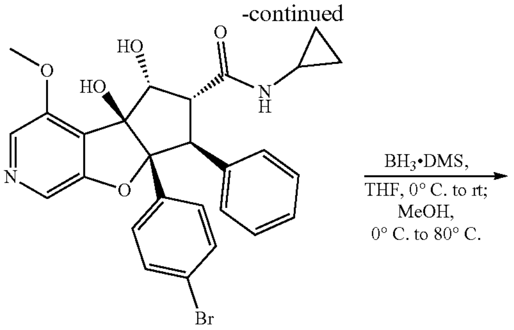

1

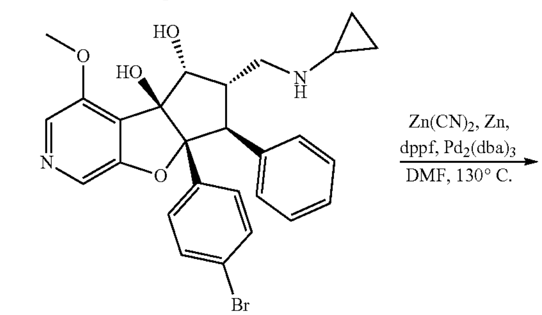

2

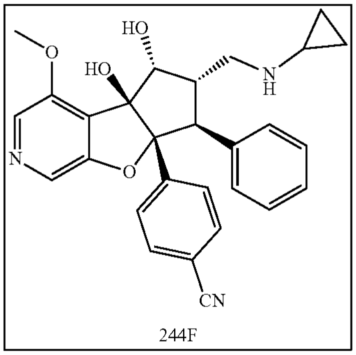

244F

Synthesis of rac-(4bS,5R,6S,7S,7aR)-7a-(4-bromophenyl)-6-((cyclopropylamino)methyl)-4-methoxy-7-phenyl-5,6,7,7a-tetrahydro-4bH-cyclopenta[4,5]furo[2,3-c]pyridine-4b,5-diol (2)

To a solution of rac-(4bS,5R,6R,7S,7aR)-7a-(4-bromophenyl)-N-cyclopropyl-4b,5-dihydroxy-4-methoxy-7-phenyl-4b,6,7,7a-tetrahydro-5H-cyclopenta[4,5]furo[2,3-c]pyridine-6-carboxamide (1, 1.20 g, 22.3 mmol) in dry tetrahydrofuran (25 ml) at 0° C., borane dimethyl sulphide complex (2.1 ml, 22.3 mmol) was added drop wise over a period of 5 min. The reaction mass was slowly brought to room temperature and stirred for additional 18 h. After completion, the reaction mixture was quenched with methanol at 0° C. and heated to reflux for 3 h. After completion, solvent was removed under reduced pressure and the residue was purified over a plug of silica gel (100-200 mesh size) eluting the compound with 5% methanol in dichloromethane as eluent. The desired fractions were concentrated under reduced pressure to afford rac-(4bS,5R,6S,7S,7aR)-7a-(4-bromophenyl)-6-((cyclopropylamino)methyl)-4-methoxy-7-phenyl-5,6,7,7a-tetrahydro-4bH-cyclopenta[4,5]furo[2,3-c]pyridine-4b,5-diol (2) as white solid. Yield: 0.8 g, 68%; MS (ESI) 523.34 m/z [M+1]$^+$.

Synthesis of rac-4-((4bS,5R,6S,7S,7aR)-6-((cyclopropylamino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 244F)

To a solution of rac-(4bS,5R,6S,7S,7aR)-7a-(4-bromophenyl)-6-((cyclopropylamino)methyl)-4-methoxy-7-phenyl-5,6,7,7a-tetrahydro-4bH-cyclopenta[4,5]furo[2,3-c]pyridine-4b,5-diol (2, 0.3 g, 0.57 mmol) in N,N-dimethylformamide (5 mL), zinc cyanide (0.40 g, 3.4 mmol) and zinc dust (0.0044 g, 0.068 mmol) were added at room temperature and the reaction mixture was degassed with argon for 15 min. 1,1'-Bis(diphenylphosphino)ferrocene (0.0063 g, 0.011 mmol) and tris(dibenzylideneacetone)dipalladium (0.015 g, 0.017 mmol) were added to the reaction, degassed for additional 5 min and mixture was heated at 130° C. for 25 min. After completion, the reaction mass was diluted with ethyl acetate and washed with cold water. The organic layer was separated and dried over anhydrous sodium sulphate, filtered and concentrated to give crude. The crude was purified by silica gel (100-200 mesh size) column chromatography using 2-3% methanol in dichloromethane as eluent. The product obtained was repurified by reverse phase HPLC. The desired fractions were lyophilized to afford rac-4-((4bS,5R,6S,7S,7aR)-6-((cyclopropylamino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 244F) as white solid. Yield: 0.004 g, 14%; MS (ESI) m/z 470.35[M+1]$^+$. $^1$H NMR (400 MHz, DMSO-$d_6$) 8.05 (s, 1H), 7.98 (s, 1H), 7.50 (d, J=8.0 Hz, 2H), 7.35 (d, J=8.1 Hz, 2H), 7.09 (t, J=6.96 Hz, 2H), 7.01-6.98 (m, 3H), 5.70 (s, 1H), 5.27 (d, J=4.4 Hz, 1H), 4.51 (d, J=4.4 Hz, 1H), 3.89 (s, 3H), 3.78 (d, J=14.0 Hz, 1H), 3.14 (bs, 1H), 2.74 (bs, 1H), 2.69-2.59 (m, 2H), 2.10 (bs, 1H), 0.38 (bs, 2H), 0.25 (bs, 2H).

Example 245

Rac-(4bS,5R,6R,7S,7aR)-7a-(4-bromophenyl)-N-cyclopropyl-4b,5-dihydroxy-4-methoxy-N-methyl-7-phenyl-4b,6,7,7a-tetrahydro-5H-cyclopenta[4,5]furo[2,3-c]pyridine-6-carboxamide (Cpd. No. 245F)

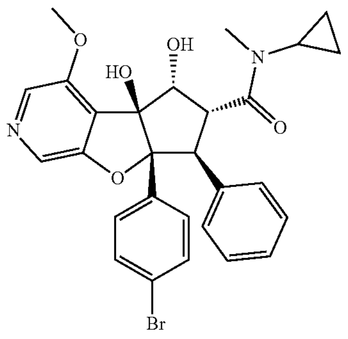

-continued

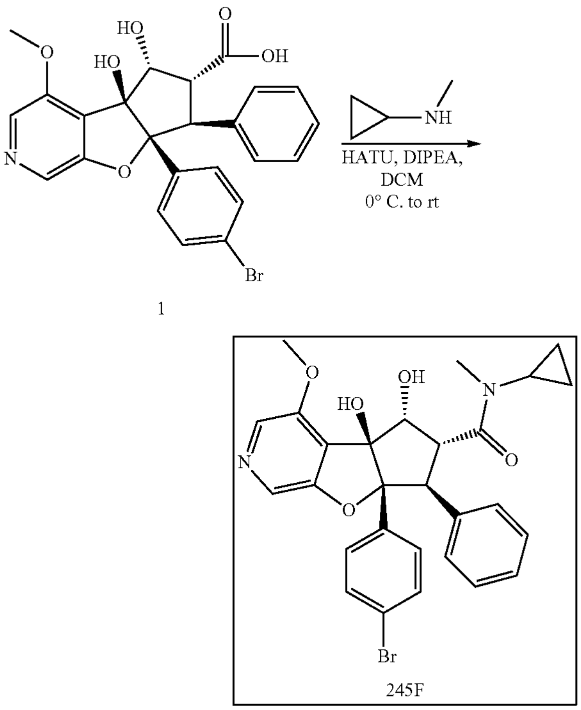

1

245F

Synthesis of rac-(4bS,5R,6R,7S,7aR)-7a-(4-bromophenyl)-N-cyclopropyl-4b,5-dihydroxy-4-methoxy-N-methyl-7-phenyl-4b,6,7,7a-tetrahydro-5H-cyclopenta[4,5]furo[2,3-c]pyridine-6-carboxamide (Cpd. No. 245F)

To a solution of rac-(4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylic acid (1, 1.5 g, 3.02 mmol) in dichloromethane (20 mL) at 0° C., 1-[Bis(dimethylamino)methylene]-1H-1,2,3-triazolo[4,5-b]pyridinium 3-oxide hexafluorophosphate (1.71 g, 4.52 mmol) and N,N-diisopropylethylamine (3.2 ml, 18.4 mmol) were added and the mixture was stirred for 5 min. N-methylcyclopropanamine (0.97 g, 9.0 mmol) was then added at the same temperature and the reaction was stirred for 16 h at room temperature. After completion, the reaction mixture was diluted with dichloromethane and washed with cold water. The organic layer was separated and dried over anhydrous sodium sulphate, filtered and concentrated to give crude product. The crude product was purified by silica gel (100-200 mesh size) column chromatography using 0-5% methanol in dichloromethane as eluent. The desired fractions were concentrated to afford rac-(4bS,5R,6R,7S,7aR)-7a-(4-bromophenyl)-N-cyclopropyl-4b,5-dihydroxy-4-methoxy-N-methyl-7-phenyl-4b,6,7,7a-tetrahydro-5H-cyclopenta[4,5]furo[2,3-c]pyridine-6-carboxamide (Cpd. No. 245F) as white solid. Yield: 1.3 g, 78%; MS (ESI) m/z 551.25[M+1]$^+$; $^1$H NMR (400 MHz, DMSO-$d_6$) 8.11 (s, 1H), 8.01 (s, 1H), 7.28 (d, J=8.4 Hz, 2H), 7.06-6.95 (m, 5H), 6.80 (d, J=7.2 Hz, 2H), 5.73 (s, 1H), 5.11 (d, J=5.2 Hz, 1H), 4.94 (t, J=5.6 Hz, 1H), 4.46 (dd, J=13.7, 4.7 Hz, 1H), 4.31 (d, J=13.6 Hz, 1H), 3.89 (s, 3H), 3.35 (bs, 1H), 3.20 (bs, 1H), 3.02 (s, 1H), 2.73 (s, 3H), 1.33-1.23 (m, 2H).

Example 246

Rac-4-((4bS,5R,6S,7S,7aR)-6-((cyclopropyl(methyl)amino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 246F)

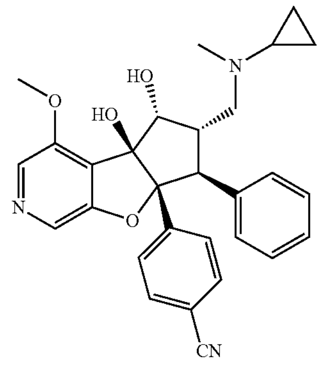

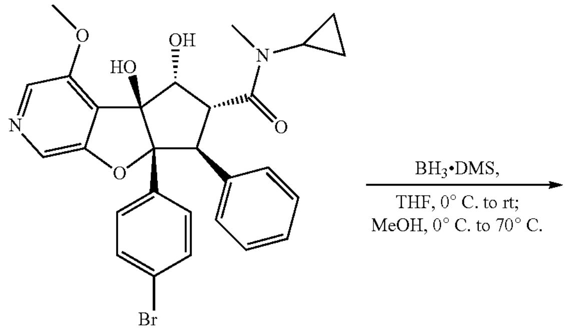

1

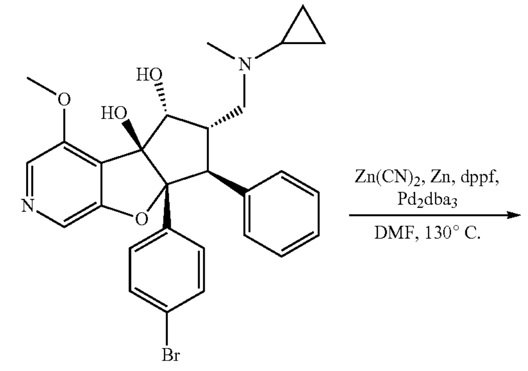

2

-continued

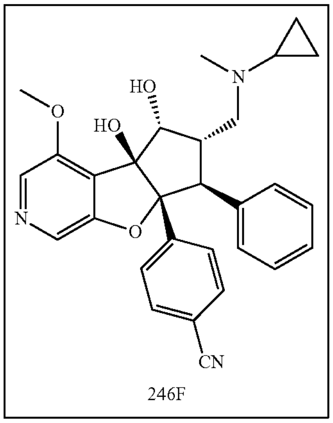

246F

Synthesis of rac-(4bS,5R,6S,7S,7aR)-7a-(4-bromophenyl)-6-((cyclopropyl(methyl)amino)methyl)-4-methoxy-7-phenyl-5,6,7,7a-tetrahydro-4bH-cyclopenta[4,5]furo[2,3-c]pyridine-4b,5-diol (2)

To a solution of rac-(4bS,5R,6R,7S,7aR)-7a-(4-bromophenyl)-N-cyclopropyl-4b,5-dihydroxy-4-methoxy-N-methyl-7-phenyl-4b,6,7,7a-tetrahydro-5H-cyclopenta[4,5]furo[2,3-c]pyridine-6-carboxamide (1, 1.20 g, 2.17 mmol) in dry tetrahydrofuran (20 ml) at 0° C., borane dimethyl sulphide complex (2.06 ml, 21.7 mmol) was added drop wise over a period of 5 min. The reaction mixture was slowly brought to room temperature and stirred for additional 16 h. After completion, the reaction mixture was quenched with methanol at 0° C. and heated to reflux for 5 h. After completion, solvent was removed under reduced pressure and the residue was purified by silica gel (100-200 mesh size) column chromatography eluting the compound with 5% methanol in dichloromethane as eluent. The desired fractions were concentrated under reduced pressure to afford rac-(4bS,5R,6S,7S,7aR)-7a-(4-bromophenyl)-6-((cyclopropyl(methyl)amino)methyl)-4-methoxy-7-phenyl-5,6,7,7a-tetrahydro-4bH-cyclopenta[4,5]furo[2,3-c]pyridine-4b,5-diol (2) as white solid. Yield: 0.8 g, 64%; MS (ESI) 538.38 m/z $[M+1]^+$.

Synthesis of rac-4-((4bS,5R,6S,7S,7aR)-6-((cyclopropyl(methyl)amino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 246F)

To a solution of rac-(4bS,5R,6S,7S,7aR)-7a-(4-bromophenyl)-6-((cyclopropyl(methyl)amino)methyl)-4-methoxy-7-phenyl-5,6,7,7a-tetrahydro-4bH-cyclopenta[4,5]furo[2,3-c]pyridine-4b,5-diol (2, 0.5 g, 0.93 mmol) in N,N-dimethylformamide (5 mL), zinc cyanide (0.53 g, 4.6 mmol) and zinc dust (0.0071 g, 0.12 mmol) were added at room temperature and the reaction mixture was degassed with argon for 15 min. 1,1'-Bis(diphenylphosphino)ferrocene (0.010 g, 0.019 mmol) and tris(dibenzylideneacetone)dipalladium (0.026 g, 0.028 mmol) were added to the reaction, degassed for additional 5 min and mixture was heated at 130° C. for 3 h. After completion, the reaction mixture was diluted with ethyl acetate and washed with cold water. The organic layer was separated and dried over anhydrous sodium sulphate, filtered and concentrated to give crude product. The crude product was purified by silica gel (100-200 mesh size) column chromatography using 2-3% methanol in dichloromethane as eluent. The desired fractions were concentrated to afford rac-4-((4bS,5R,6S,7S,7aR)-6-((cyclopropyl(methyl)amino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 246F) as white solid. Yield: 0.08 g, 17%; MS (ESI) m/z 484.34[M+1]$^+$; $^1$H NMR (400 MHz, DMSO-$d_6$) 8.04 (s, 1H), 7.96 (s, 1H), 7.50 (d, J=8.4 Hz, 2H), 7.36 (d, J=8.4 Hz, 2H), 7.09 (t, J=14.8 Hz, 2H), 7.01 (d, J=6.4 Hz, 3H), 5.72 (s, 1H), 5.07 (d, J=6.4 Hz, 1H), 4.43-4.41 (t, J=5.5 Hz, 1H), 3.87 (s, 3H), 3.80 (d, J=14.1 Hz, 1H), 3.25-3.22 (m, 1H), 2.83 (t, J=12.2 Hz, 1H), 2.36 (s, 3H), 2.27 (d, J=10.4 Hz, 1H), 1.62 (m, 1H), 0.49-0.36 (m, 4H).

Example 247

Rac-(4bS,5R,6R,7S,7aR)-7a-(4-bromophenyl)-N-(2-fluoroethyl)-4b,5-dihydroxy-4-methoxy-N-methyl-7-phenyl-4b,6,7,7a-tetrahydro-5H-cyclopenta[4,5]furo[2,3-c]pyridine-6-carboxamide (Cpd. No. 247F)

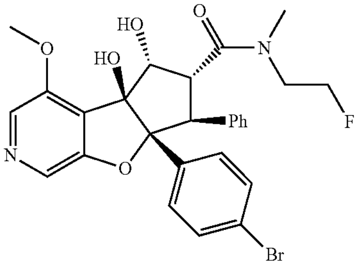

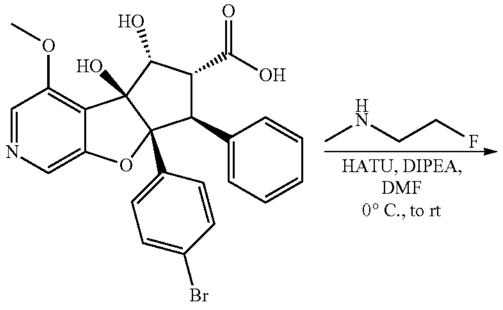

1

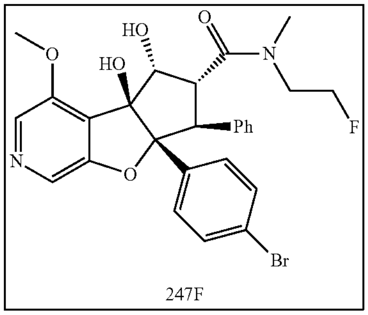

247F

Synthesis of rac-(4bS,5R,6R,7S,7aR)-7a-(4-bromophenyl)-N-(2-fluoroethyl)-4b,5-dihydroxy-4-methoxy-N-methyl-7-phenyl-4b,6,7,7a-tetrahydro-5H-cyclopenta[4,5]furo[2,3-c]pyridine-6-carboxamide (Cpd. No. 247F)

To a solution of rac-(4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylic acid (1, 1.50 g, 3.01 mmol) in N,N-dimethylformamide (15 mL) at 0° C., were added HATU (1.71 g, 4.51 mmol), N,N-diisopropylethylamine (1.66 mL, 9.03 mmol) and the mixture was stirred for 5 min. 2-fluoro-N-methylethan-1-amine (1a, 0.510 g, 4.51 mmol) was then added at the same temperature and the reaction was stirred for 24 h at room temperature. After completion, the reaction mixture was diluted with cold water. The solid precipitated was filtered and dried to afford rac-(4bS,5R,6R,7S,7aR)-7a-(4-bromophenyl)-N-(2-fluoroethyl)-4b,5-dihydroxy-4-methoxy-N-methyl-7-phenyl-4b,6,7,7a-tetrahydro-5H-cyclopenta[4,5]furo[2,3-c]pyridine-6-carboxamide (Cpd. No. 247F) as white solid. Yield: 1.15 g, 69%; MS (ESI) m/z 557.41[M+1]$^+$; $^1$H NMR (400 MHz, DMSO-$d_6$) 8.10 (s, 1H), 7.99 (s, 1H), 7.21 (d, J=7.9 Hz, 2H), 7.08-7.01 (m, 4H), 6.98-6.89 (m, 3H), 5.73 (d, J=16.5 Hz, 1H), 5.15 (dd, J=5.5, 17.4 Hz, 1H), 4.85-4.65 (m, 2H), 4.52-4.41 (m, 2H), 4.25-4.15 (m, 1H), 3.88 (s, 3H), 3.57-3.52 (m, 2H), 3.35 (s, 2H), 2.80 (s, 1H).

Example 248

4-((4bS,5R,6S,7S,7aR)-6-(((2-fluoroethyl)(methyl)amino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 248F)

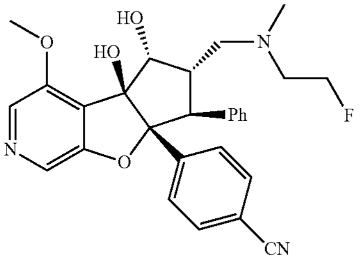

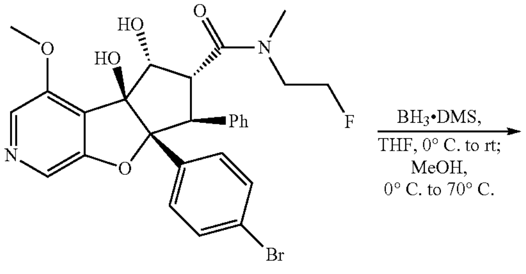

1

-continued

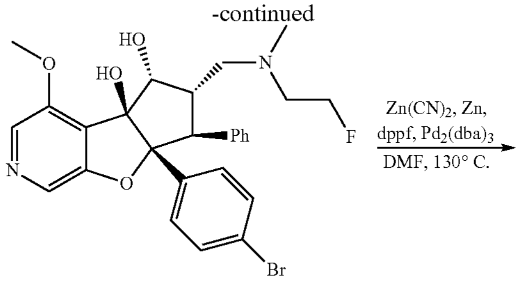

2

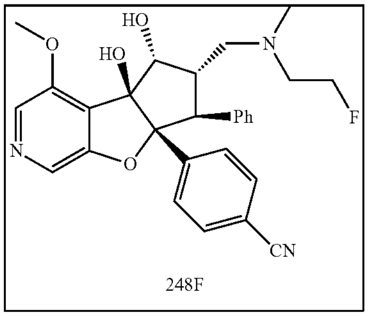

248F

Synthesis of rac-(4bS,5R,6S,7S,7aR)-7a-(4-bromophenyl)-6-(((2-fluoroethyl)(methyl)amino)methyl)-4-methoxy-7-phenyl-5,6,7,7a-tetrahydro-4bH-cyclopenta[4,5]furo[2,3-c]pyridine-4b,5-diol (2)

To a solution of rac-(4bS,5R,6R,7S,7aR)-7a-(4-bromophenyl)-N-(2-fluoroethyl)-4b,5-dihydroxy-4-methoxy-N-methyl-7-phenyl-4b,6,7,7a-tetrahydro-5H-cyclopenta[4,5]furo[2,3-c]pyridine-6-carboxamide (1, 1.15 g, 2.06 mmol) in dry tetrahydrofuran (20 ml) at 0° C., borane dimethyl sulphide complex (1.56 g, 20.63 mmol) was added drop wise over a period of 5 min.

The reaction mass was slowly brought to room temperature and stirred for additional 16 h. After completion, the reaction mass was quenched with methanol at 0° C. and heated to reflux for 16 h. After completion, solvent was removed under reduced pressure and the residue was purified over a plug of silica gel eluting the compound with 5% methanol in dichloromethane. The desired fractions were concentrated under reduced pressure to afford rac-(4bS,5R,6S,7S,7aR)-7a-(4-bromophenyl)-6-(((2-fluoroethyl)(methyl)amino)methyl)-4-methoxy-7-phenyl-5,6,7,7a-tetrahydro-4bH-cyclopenta[4,5]furo[2,3-c]pyridine-4b,5-diol (2) as white solid. Yield: 0.60 g, (crude), MS (ESI) m/z 543.25 $[M+1]^+$.

Synthesis of 4-((4bS,5R,6S,7S,7aR)-6-(((2-fluoroethyl)(methyl)amino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 248F)

To a solution of rac-(4bS,5R,6S,7S,7aR)-7a-(4-bromophenyl)-6-(((2-fluoroethyl)(methyl)amino)methyl)-4-methoxy-7-phenyl-5,6,7,7a-tetrahydro-4bH-cyclopenta[4,5]furo[2,3-c]pyridine-4b,5-diol (2, 1.20 g, 2.20 mmol) in N,N-dimethylformamide (24 mL), zinc cyanide (1.56 g, 13.24 mmol) and zinc dust (0.017 g, 0.264 mmol) were added at room temperature and the reaction mixture was degassed with argon for 15 min. 1,1'-Bis(diphenylphosphino)ferrocene (0.032 g, 0.044 mmol) and tris(dibenzylideneacetone)dipalladium (0.060 g, 0.066 mmol) were added to the reaction, degassed for additional 5 min and mixture was heated at 140° C. for 3 h. After completion, the reaction mass was diluted with ethyl acetate and washed with cold water. The organic layer was separated and dried over anhydrous sodium sulphate, filtered and concentrated to give crude. The crude was purified by Prep-HPLC to afford rac-4-((4bS,5R,6S,7S,7aR)-6-(((2-fluoroethyl)(methyl)amino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile as white solid. Yield: 0.180 g, 18%; MS (ESI) m/z 490.52$[M+1]^+$; The enantiomers were separated by chiral SFC [chiralpak ID (4.6 ×250) mm, 5μ], $CO_2$/0.1% TEA in EtOH 80/20 V/V. Peak 1 (40 mg), $[\alpha]_D$−17.3° (c 0.25, $CHCl_3$), $R_t$=4.970 min, ee: 99.54% MS (ESI) m/z 490.24 $[M+1]^+$. $^1H$ NMR (400 MHz, DMSO-$d_6$) 8.04 (s, 1H), 7.97 (s, 1H), 7.48 (d, J=8.44 Hz, 2H), 7.37 (d, J=8.40 Hz, 2H), 7.09-6.97 (m, 5H), 5.73 (s, 1H), 5.06 (d, J=4.96 Hz 1H), 4.57 (bs, 1H), 4.50 (bs, 1H), 4.45 (bs, 1H), 3.88 (s, 3H), 3.80 (d, J=13.92 Hz, 1H), 3.22-3.19 (m, 1H), 2.85-2.78 (m, 1H), 2.67-2.55 (m, 2H), 2.32 (s, 3H), 2.18-2.12 (m, 1H). Peak 2 (Cpd. No. 248F, 57 mg), $[\alpha]_D$+18.6° (c 0.276, $CHCl_3$), $R_t$=5.948 min, ee: 95.18% MS (ESI) m/z 490.31 $[M+1]^+$. H NMR (400 MHz, DMSO-$d_6$) 8.04 (s, 1H), 7.97 (s, 1H), 7.49 (d, J=8.4 Hz, 2H), 7.37 (d, J=8.4 Hz, 2H), 7.09-6.97 (m, 5H), 5.73 (s, 1H), 5.06 (d, J=4.9 Hz 1H), 4.57 (bs, 1H), 4.50 (bs, 1H), 4.45 (bs, 1H), 3.88 (s, 3H), 3.80 (d, J=13.9 Hz, 1H), 3.22-3.19 (m, 1H), 2.85-2.78 (m, 1H), 2.67-2.55 (m, 2H), 2.32 (s, 3H), 2.19-2.16 (m, 1H).

Example 249

Rac-(4bS,5R,6R,7S,7aR)-7a-(4-bromophenyl)-4b,5-dihydroxy-4-methoxy-N-methyl-N-((1-methyl-1H-pyrazol-5-yl)methyl)-7-phenyl-4b,6,7,7a-tetrahydro-5H-cyclopenta[4,5]furo[2,3-c]pyridine-6-carboxamide (Cpd. No. 249F)

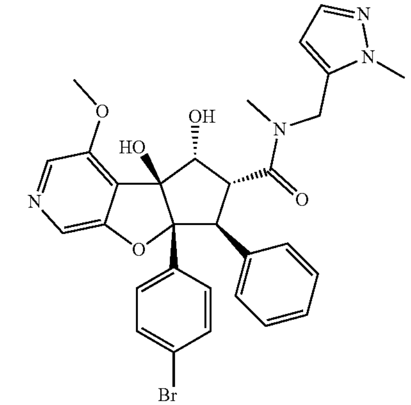

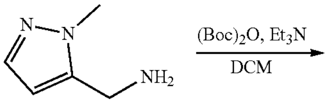

1

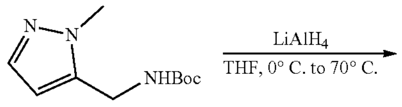

2

-continued

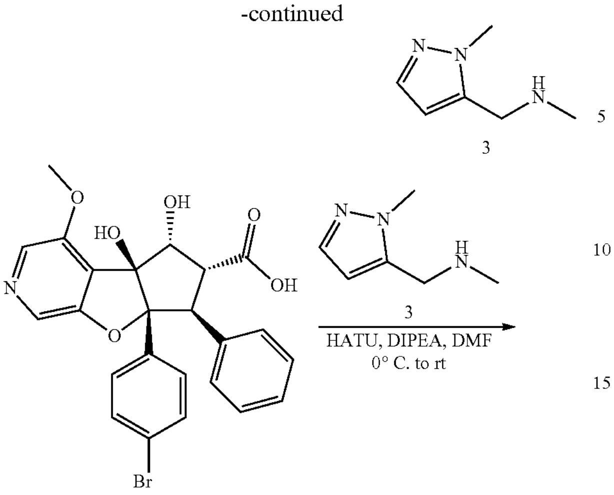

4

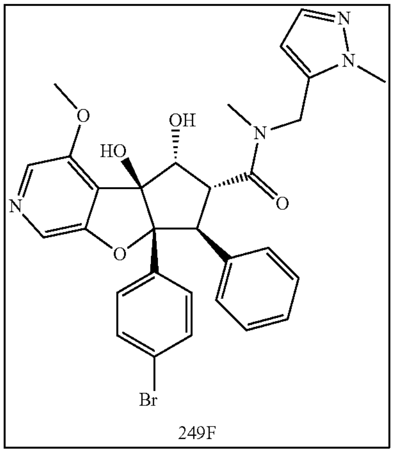

249F

Synthesis of tert-butyl ((1-methyl-1H-pyrazol-5-yl) methyl)carbamate (2)

To a solution of (1-methyl-1H-pyrazol-5-yl)methanamine (1, 0.5 g, 4.5 mmol) in dichloromethane (10 mL) and triethylamine (0.627 ml, 4.5 mmol) at 0° C., di-tert-butyl dicarbonate (0.982 g, 4.5 mmol) was added dropwise and reaction mixture stirred at room temperature for 2 h. The reaction mixture was concentrated and crude obtained was purified by combi-flash (4 g, RediSep column) using 30% ethyl acetate in hexane as a eluent. The combined pure fractions were concentrated to afford tert-butyl ((1-methyl-1H-pyrazol-5-yl) methyl)carbamate (2) as a colourless liquid. Yield: 0.61 g, 67%; MS (ESI) m/z 212.31[M+1]$^+$.

Synthesis of N-methyl-1-(1-methyl-1H-pyrazol-5-yl)methanamine (3)

To a solution of compound tert-butyl (1-methyl-1H-pyrazol-5-yl)methyl)carbamate (2, 0.6 g, 2.84 mmol) in tetrahydrofuran at 0° C. was added drop wise lithium aluminum hydride (11.36 ml, 11.36 mmol, 1M in THF) and reaction mixture was heated at 70° C. for 4 h. The reaction mixture was cooled to 0° C. and quenched slowly by addition of aqueous sodium hydroxide slowly over a period of 15 to 20 minutes. The resulting suspension was diluted with Ethyl acetate & passed through celite pad. The filtrate obtained was dried over anhydrous sodium sulphate filtered and concentrated to get pure N-methyl-1-(1-methyl-1H-pyrazol-5-yl)methanamine (3). Yield 0.305 g, 85.9%.

Synthesis of rac-(4bS,5R,6R,7S,7aR)-7a-(4-bromophenyl)-4b,5-dihydroxy-4-methoxy-N-methyl-N-((1-methyl-1H-pyrazol-5-yl)methyl)-7-phenyl-4b,6,7,7a-tetrahydro-5H-cyclopenta[4,5]furo[2,3-c]pyridine-6-carboxamide (Cpd. No. 249F)

To the solution of rac-(4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylic acid (4, 1.00 g, 2.01 mmol) in N,N-dimethylformamide (20 ml) at 0° C., HATU (2.29 g, 6.03 mmol) and N,N-diisopropylethylamine (1.81 g, 14.0 mmol) were added and the mixture was stirred for 5 min. N-methyl-1-(1-methyl-1H-pyrazol-5-yl)methanamine (3, 1.24 g, 10.06 mmol) was then added at the same temperature and then reaction mixture was stirred for 16 h. at room temperature. After completion, the reaction mixture was diluted with cold water to get solid. Solid obtained was filtered, dried and triturated with pentane to afford rac-(4bS,5R,6R,7S,7aR)-7a-(4-bromophenyl)-4b,5-dihydroxy-4-methoxy-N-methyl-N-((1-methyl-1H-pyrazol-5-yl)methyl)-7-phenyl-4b,6,7,7a-tetrahydro-5H-cyclopenta[4,5]furo[2,3-c]pyridine-6-carboxamide (Cpd. No. 249F) as a white solid. Yield: 0.90 g, 74%; MS (ESI) m/z 605.26[M+1]$^+$; $^1$H NMR (400 MHz, DMSO-d6) □ 8.11 (s, 1H), 8.00 (s, 1H), 7.30 (s, 1H), 7.20 (d, J=8.4 Hz, 2H), 7.09 (d, J=8.8 Hz, 2H), 7.05-6.93 (m, 5H), 6.21 (s, 1H), 5.70 (s, 1H), 5.23 (bs, 1H), 4.78 (t, J=4.8 Hz, 1H), 4.60 (d, J=15.2 Hz, 1H), 4.49-4.41 (m, 2H), 4.26-4.21 (m, 1H), 3.88 (s, 3H), 3.56 (s, 3H), 3.20 (s, 3H).

Example 250

4-((4bS,5R,6S,7S,7aR)-4b,5-dihydroxy-4-methoxy-6-((methyl((1-methyl-1H-pyrazol-5-yl)methyl)amino)methyl)-7-phenyl-4b,5,6,7-tetrahydro-7aH-cyclopenta[4,5]furo[2,3-c]pyridin-7a-yl)benzonitrile (Cpd. No. 250F)

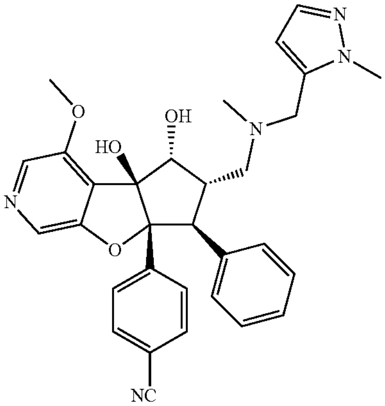

-continued

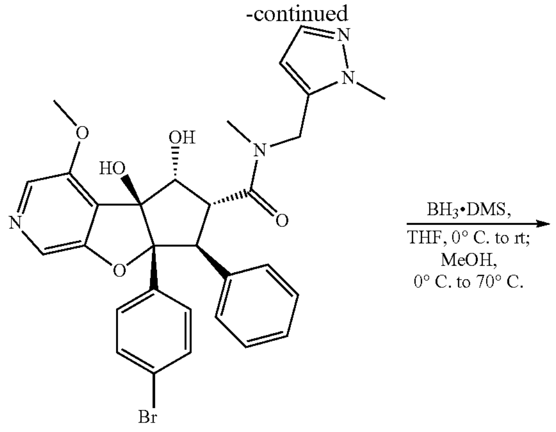

1

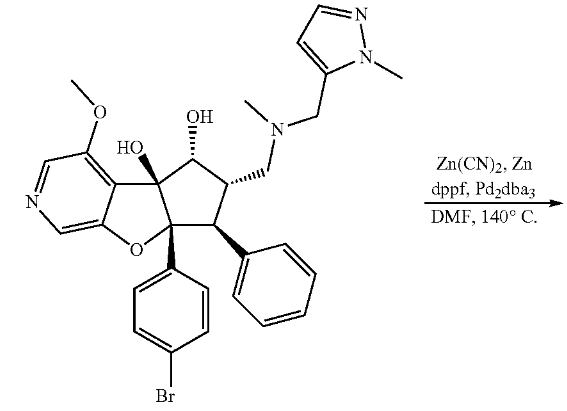

2

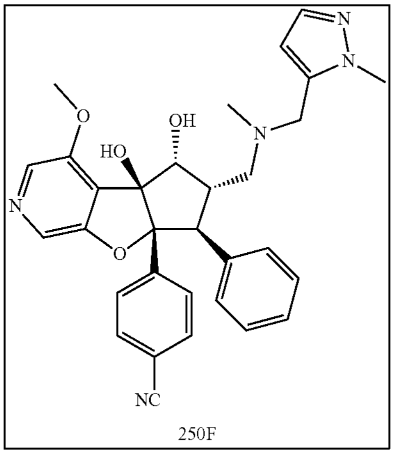

250F

Synthesis of rac-(4bS,5R,6S,7S,7aR)-7a-(4-bromophenyl)-4-methoxy-6-((methyl((1-methyl-1H-pyrazol-5-yl)methyl)amino)methyl)-7-phenyl-5,6,7,7a-tetrahydro-4bH-cyclopenta[4,5]furo[2,3-c]pyridine-4b,5-diol (2)

To a solution of rac-(4bS,5R,6R,7S,7aR)-7a-(4-bromophenyl)-4b,5-dihydroxy-4-methoxy-N-methyl-N-((1-methyl-1H-pyrazol-5-yl)methyl)-7-phenyl-4b,6,7,7a-tetrahydro-5H-cyclopenta[4,5]furo[2,3-c]pyridine-6-carboxamide (1, 1.20 g, 1.98 mmol) in dry tetrahydrofuran (20 ml) at 0° C., borane dimethyl sulphide complex (2.7 mL, 29.8 mmol) was added drop wise over a period of 5 min. The reaction mixture was slowly brought to room temperature and stirred for additional 16 h. After completion, the reaction mixture was quenched with methanol (40 ml) at 0° C. and heated to reflux for 24 h. After completion, solvent was removed under reduced pressure and crude obtained was purified by silica gel (100-200 mesh size) column chromatography using 2% methanol in dichloromethane as eluent. The desired fractions were concentrated under reduced pressure to afford rac-(4bS,5R,6S,7S,7aR)-7a-(4-bromophenyl)-4-methoxy-6-((methyl((1-methyl-1H-pyrazol-5-yl)methyl)amino)methyl)-7-phenyl-5,6,7,7a-tetrahydro-4bH-cyclopenta[4,5]furo[2,3-c]pyridine-4b,5-diol (2) Yield: 0.75 g, 64%; MS (ESI) m/z 589.51[M+1]$^+$.

Synthesis of 4-((4bS,5R,6S,7S,7aR)-4b,5-dihydroxy-4-methoxy-6-((methyl((1-methyl-1H-pyrazol-5-yl)methyl)amino)methyl)-7-phenyl-4b,5,6,7-tetrahydro-7aH-cyclopenta[4,5]furo[2,3-c]pyridin-7a-yl)benzonitrile (Cpd. No. 250F)

To a solution of rac-((4bS,5R,6S,7S,7aR)-7a-(4-bromophenyl)-4-methoxy-6-((methyl((1-methyl-1H-pyrazol-5-yl)methyl)amino)methyl)-7-phenyl-5,6,7,7a-tetrahydro-4bH-cyclopenta[4,5]furo[2,3-c]pyridine-4b,5-diol (2, 0.75 g, 1.27 mmol) in N,N-dimethylformamide (10 mL), zinc cyanide (1.48 g, 12.7 mmol) and zinc dust (0.009 g, 0.131 mmol) were added at room temperature and the reaction mixture was degassed with argon for 15 minutes. 1,1'-Bis(diphenylphosphino)ferrocene (0.014 g, 0.025 mmol) and tetrakis(triphenylphosphine) palladium (0.044 g, 0.038 mmol) were added to the reaction mixture, degassed for additional 5 min and mixture was heated at 140° C. for 8 h. After completion, the reaction mixture was diluted with ethyl acetate and washed with cold water. The organic layer was separated and dried over anhydrous sodium sulphate, filtered and concentrated to give crude product. The crude product was purified by silica gel (100-200 mesh size) column chromatography using 6% methanol in dichloromethane as eluent. The desired fractions were concentrated to afford rac-4-((4bS,5R,6S,7S,7aR)-4b,5-dihydroxy-4-methoxy-6-((methyl((1-methyl-1H-pyrazol-5-yl)methyl)amino)methyl)-7-phenyl-4b,5,6,7-tetrahydro-7aH-cyclopenta[4,5]furo[2,3-c]pyridin-7a-yl)benzonitrile as white solid. Yield: 0.28 g, 41%; The enantiomers were separated by chiral SFC [CHIRALPAK ID (4.6×250)mm, 5μ] in C2/0.1% TEA in EtOH=(60/40) Peak 1 (Cpd. No. 250F, 83 mg), $[\alpha]_D$–46.0° (c 0.25, $CHCl_3$), $R_t$=2.15 min, ee 99.76%; MS (ESI) m/z 538.36[M+1]$^+$. $^1$H NMR (400 MHz, DMSO-$d_6$) 8.04 (s, 1H), 7.98 (s, 1H), 7.47 (d, J=8.0 Hz, 2H), 7.34 (d, J=8.0 Hz, 2H), 7.30 (s, 1H), 7.07-7.03 (m, 2H), 6.99-6.96 (m, 3H), 6.11 (s, 1H), 5.75 (s, 1H), 5.10 (d, J=4.4 Hz, 1H), 4.52 (bs, 1H), 3.89 (s, 3H), 3.84 (s, 3H), 3.78 (d, J=14.0 Hz, 1H), 3.62 (d, J=13.6 Hz, 1H), 3.43 (d, J=13.8 Hz, 1H), 3.17 (bs, 1H), 2.73-2.66 (m, 1H), 2.21 (s, 3H), 2.14 (d, J=11.2 Hz, 1H); Peak-2 (94 mg), $[\alpha]_D$+39.0° (c 0.309, $CHCl_3$), $R_t$=2.59 min, ee 98.04%; MS (ESI) m/z 538.36 [M+1]$^+$. $^1$H NMR (400 MHz, DMSO-$d_6$) 8.04 (s, 1H), 7.98 (s, 1H), 7.47 (d, J=8.0 Hz, 2H), 7.34 (d, J=8.0 Hz, 2H), 7.30 (s, 1H), 7.07-7.03 (m, 2H), 6.99-6.96 (m, 3H), 6.11 (s, 1H), 5.75 (s, 1H), 5.10 (d, J=4.40 Hz, 1H), 4.52 (bs, 1H), 3.89 (s, 3H), 3.84 (s, 3H), 3.78 (d, J=14.0 Hz, 1H), 3.63 (d, J=13.6 Hz, 1H), 3.43 (d, J=13.8 Hz, 1H), 3.18 (bs, 1H), 2.73-2.66 (m, 1H), 2.21 (s, 3H), 2.14 (d, J=11.2 Hz, 1H).

Example 251

Rac-(4bS,5R,6R,7S,7aR)-7a-(4-bromophenyl)-4b,5-dihydroxy-N-(2-hydroxy-2-methylpropyl)-4-methoxy-N-methyl-7-phenyl-4b,6,7,7a-tetrahydro-5H-cyclopenta[4,5]furo[2,3-c]pyridine-6-carboxamide (Cpd. No. 2511)

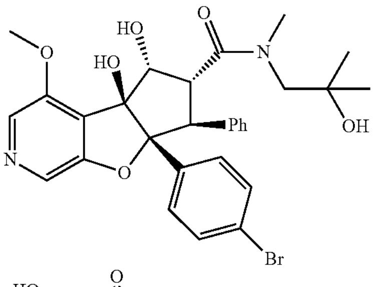

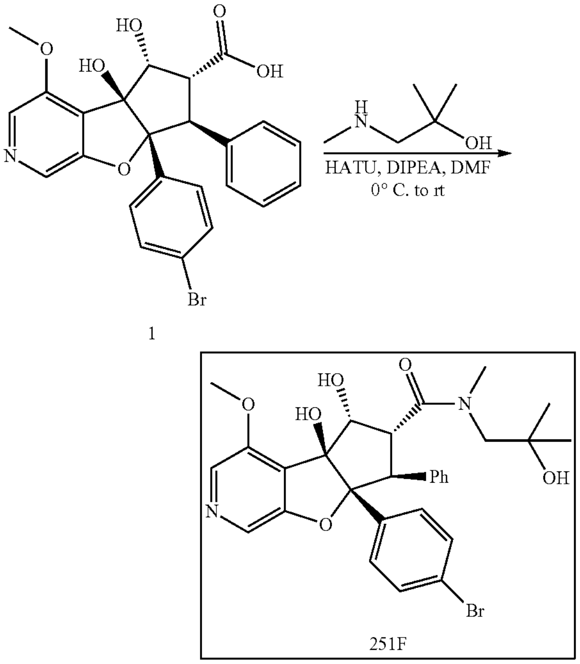

1

251F

Synthesis of rac-(4bS,5R,6R,7S,7aR)-7a-(4-bromophenyl)-4b,5-dihydroxy-N-(2-hydroxy-2-methylpropyl)-4-methoxy-N-methyl-7-phenyl-4b,6,7,7a-tetrahydro-5H-cyclopenta[4,5]furo[2,3-c]pyridine-6-carboxamide (Cpd. No. 251F)

To a solution of rac-(4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylic acid (1, 1.50 g, 3.01 mmol) in N,N-dimethylformamide (15 mL) at 0° C., 1-[Bis(dimethylamino)methylene] 1H-1,2,3-triazolo[4,5-b]pyridinium3-oxide hexafluorophosphate (1.71 g, 4.51 mmol), N,N-diisopropylethylamine (1.66 mL, 9.03 mmol) were added and the reaction mixture was stirred for 5 min. 2-methyl-1-(methylamino)propan-2-ol (1.550 g, 15.05 mmol) was then added at the same temperature and the reaction was stirred for 24 h at room temperature. After completion, the reaction mixture was diluted with cold water. The solid precipitated was filtered and dried to afford rac-(4bS,5R,6R,7S,7aR)-7a-(4-bromophenyl)-4b,5-dihydroxy-N-(2-hydroxy-2-methylpropyl)-4-methoxy-N-methyl-7-phenyl-4b,6,7,7a-tetrahydro-5H-cyclopenta[4,5]furo[2,3-c]pyridine-6-carboxamide (Cpd. No. 251F) as white solid. Yield: 1.315 g, 82%; MS (ESI) m/z 583.38[M+1]$^+$; $^1$H NMR (400 MHz, DMSO-$d_6$) 8.10 (s, 1H), 7.99 (s, 1H), 7.22 (d, J=8.44 Hz, 2H), 7.14-6.91 (m, 7H), 5.09-4.96 (m, 1H), 4.79 (bs, 1H), 4.59-4.40 (m, 2H), 4.22 (dd, J=4.84, 13.48 Hz, 1H), 3.88 (bs, 4H), 3.40 (s, 3H), 3.12 (d, J=7.4 Hz, 1H), 2.82 (s, 1H), 0.99 (s, 3H), 0.93 (s, 3H).

Example 252

4-((4bS,5R,6S,7S,7aR)-4b,5-dihydroxy-6-(((2-hydroxy-2-methylpropyl)(methyl)amino)methyl)-4-methoxy-7-phenyl-4b,5,6,7-tetrahydro-7aH-cyclopenta[4,5]furo[2,3-c]pyridin-7a-yl)benzonitrile (Cpd. No. 252F)

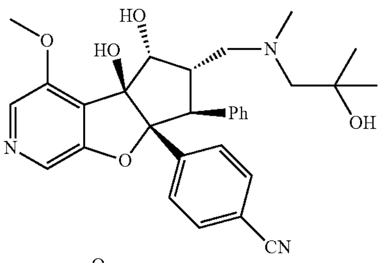

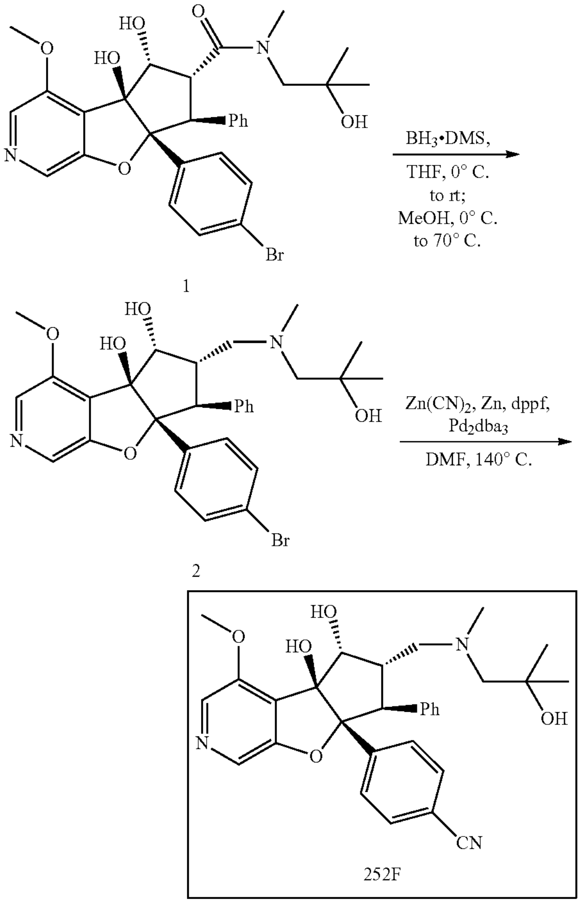

1

2

252F

Synthesis of rac-(4bS,5R,6S,7S,7aR)-7a-(4-bromophenyl)-6-(((2-hydroxy-2-methylpropyl)(methyl)amino)methyl)-4-methoxy-7-phenyl-5,6,7,7a-tetrahydro-4bH-cyclopenta[4,5]furo[2,3-c]pyridine-4b,5-diol (2)

To a solution of rac-(4bS,5R,6R,7S,7aR)-7a-(4-bromophenyl)-4b,5-dihydroxy-N-(2-hydroxy-2-methylpropyl)-4-methoxy-N-methyl-7-phenyl-4b,6,7,7a-tetrahydro-5H-cyclopenta[4,5]furo[2,3-c]pyridine-6-carboxamide (1, 1.2 g, 2.05 mmol) in dry tetrahydrofuran (20 ml) at 0° C., borane dimethyl sulphide complex (2.34 g, 30.85 mmol) was added drop wise over a period of 5 min. The reaction mixture was slowly brought to room temperature and stirred for additional 16 h. After completion, the reaction mixture was quenched with methanol at 0° C. and heated to reflux for 16 h. After completion, solvent was removed under reduced pressure and the residue was purified by silica gel (100-200 mesh size) column chromatography using 5% methanol in dichloromethane as eluent. The desired fractions were concentrated under reduced pressure to afford rac-(4bS,5R,6S,7S,7aR)-7a-(4-bromophenyl)-6-(((2-hydroxy-2-methylpropyl)(methyl)amino)methyl)-4-methoxy-7-phenyl-5,6,7,7a-tetrahydro-4bH-cyclopenta[4,5]furo[2,3-c]pyridine-4b,5-diol (2) as white solid. Yield: 1.0 g, (crude), MS (ESI) m/z 569.46[M+1]$^+$.

Synthesis of 4-((4bS,5R,6S,7S,7aR)-4b,5-dihydroxy-6-(((2-hydroxy-2-methylpropyl)(methyl)amino)methyl)-4-methoxy-7-phenyl-4b,5,6,7-tetrahydro-7aH-cyclopenta[4,5]furo[2,3-c]pyridin-7a-yl)benzonitrile (Cpd. No. 252F)

To a solution of rac-(4bS,5R,6S,7S,7aR)-7a-(4-bromophenyl)-6-(((2-hydroxy-2-methylpropyl)(methyl)amino)methyl)-4-methoxy-7-phenyl-5,6,7,7a-tetrahydro-4bH-cyclopenta[4,5]furo[2,3-c]pyridine-4b,5-diol (2, 1.0 g, 1.75 mmol) in N,N-dimethylformamide (10 mL), zinc cyanide (1.23 g, 10.53 mmol) and zinc dust (0.057 g, 0.875 mmol) were added at room temperature and the reaction mixture was degassed with argon for 15 min. 1,1'-Bis(diphenylphosphino)ferrocene (0.097 g, 0.175 mmol) and tris(dibenzylideneacetone)dipalladium (0.080 g, 0.087 mmol) were added to the reaction mixture, degassed for additional 5 min and reaction mixture was heated at 140° C. for 7 h. After completion, the reaction mixture was diluted with ethyl acetate and washed with cold water. The organic layer was separated and dried over anhydrous sodium sulphate, filtered and concentrated to give crude product. The crude product was purified by Preparative HPLC to afford rac-4-((4bS,5R,6S,7S,7aR)-4b,5-dihydroxy-6-(((2-hydroxy-2-methylpropyl)(methyl)amino)methyl)-4-methoxy-7-phenyl-4b,5,6,7-tetrahydro-7aH-cyclopenta[4,5]furo[2,3-c]pyridin-7a-yl)benzonitrile as white solid. Yield: 0.273 g, 30%; MS (ESI) m/z 516.53[M+1]$^+$. The enantiomers were separated by chiral SFC [chiralpak IG (4.6×250) mm, 5μ], $CO_2$/0.1% TEA in MeOH (60/40).

Peak 1 (88 mg), $[\alpha]_D$–34.4° (c 0.45, $CHCl_3$), $R_t$=1.929 min, ee: 99.92% MS (ESI) m/z 490.24 [M+1]$^+$; $^1$H NMR (400 MHz, DMSO-$d_6$) 8.04 (s, 1H), 7.96 (s, 1H), 7.48 (d, J=8.3 Hz, 2H), 7.37 (d, J=8.4 Hz, 2H), 7.08-6.98 (m, 5H), 5.72 (s, 1H), 5.15 (s, 1H), 4.61 (d, J=6.4 Hz, 2H), 3.89 (s, 3H), 3.79 (d, J=13.8 Hz, 1H), 3.23-3.16 (m, 1H), 2.66-2.60 (m, 1H), 2.43 (s, 3H), 2.29 (bs, 1H), 2.20 (s, 2H), 1.13 (s, 3H), 1.02 (s, 3H). Peak 2 (Cpd. No. 252F, 95 mg), $[\alpha]_D$+32.0° (c 0.30, $CHCl_3$), $R_t$=3.157 min, ee: 98.9% MS (ESI) m/z 516.53 [M+1]$^+$. $^1$H NMR (400 MHz, DMSO-d6) □ 8.04 (s, 1H), 7.96 (s, 1H), 7.48 (d, J=8.3 Hz, 2H), 7.37 (d, J=8.3 Hz, 2H), 7.09-6.97 (m, 5H), 5.72 (s, 1H), 5.15 (s, 1H), 4.61 (bs, 2H), 3.89 (s, 3H), 3.79 (d, J=13.8 Hz, 1H), 3.22-3.20 (m, 1H), 2.66-2.60 (m, 1H), 2.43 (s, 3H), 2.29 (bs, 1H), 2.20 (s, 2H), 1.13 (s, 3H), 1.02 (s, 3H).

Example 253

Rac-(4bS,5R,6R,7S,7aR)-7a-(4-bromophenyl)-4b,5-dihydroxy-N-(2-hydroxy-2-methylpropyl)-4-methoxy-7-phenyl-4b,6,7,7a-tetrahydro-5H-cyclopenta[4,5]furo[2,3-c]pyridine-6-carboxamide (Cpd. No. 253F)

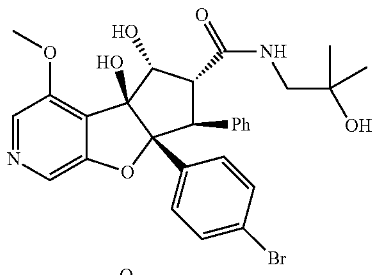

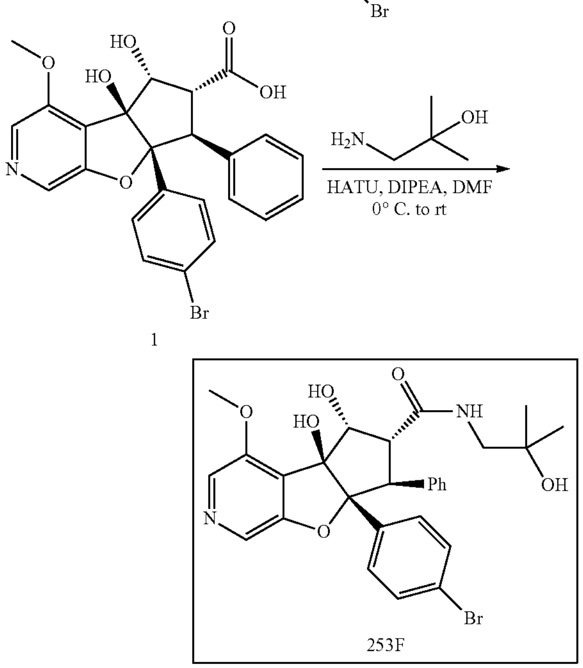

1

253F

Synthesis of rac-(4bS,5R,6R,7S,7aR)-7a-(4-bromophenyl)-4b,5-dihydroxy-N-(2-hydroxy-2-methylpropyl)-4-methoxy-7-phenyl-4b, 6,7,7a-tetrahydro-5H-cyclopenta[4,5]furo[2,3-c]pyridine-6-carboxamide (Cpd. No. 253F)

To a solution of rac-(4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylic acid (1, 1.50 g, 3.01 mmol) in N,N-dimethylformamide (30 mL) at 0° C., 1-[Bis(dimethylamino)methylene] 1H-1,2,3-triazolo[4,5-b]pyridinium3-oxide hexafluorophosphate (1.71 g, 4.51 mmol), N,N-diisopropylethylamine (1.16 g, 9.03 mmol) were added and the mixture was stirred for 5 min. 1-amino-2-methylpropan-2-ol (0.804 g, 9.03 mmol) was then added at the same temperature and the reaction was stirred for 24 h at room temperature. After completion, the reaction mass was diluted with cold water. The solid precipitated was filtered and dried to afford rac-(4bS,5R,6R,7S,7aR)-7a-(4-bromophenyl)-4b,5-dihydroxy-N-(2-hydroxy-2-methylpropyl)-4-methoxy-7-phenyl-4b,6,7,7a-tetrahydro-5H-cyclopenta[4,5]furo[2,3-c]pyridine-6-carboxamide (Cpd. No. 253F) as white solid. Yield: 0.80 g, 46%; MS (ESI) m/z 569.23[M+1]$^+$; $^1$H NMR (400 MHz, DMSO-d$_6$) 8.23 (bs, 1H), 8.08 (s, 1H), 7.98 (s, 1H), 7.23 (d, J=8.5 Hz, 2H), 7.10 (d, J=8.5 Hz, 2H), 7.05-6.99 (m, 5H), 5.67 (s, 1H), 5.03 (d, J=3.4 Hz, 1H), 4.57 (bs, 1H), 4.43 (s, 1H), 4.33 (d, J=14.16 Hz, 1H), 4.10-4.06 (m, 1H), 3.87 (s, 3H), 2.99 (d, J=5.88 Hz, 2H), 0.98 (s, 3H), 0.93 (s, 3H).

Example 254

4-((4bS,5R,6S,7S,7aR)-4b,5-dihydroxy-6-(((2-hydroxy-2-methylpropyl)amino)methyl)-4-methoxy-7-phenyl-4b,5,6,7-tetrahydro-7aH-cyclopenta[4,5]furo[2,3-c]pyridin-7a-yl)benzonitrile (Cpd. No. 254F)

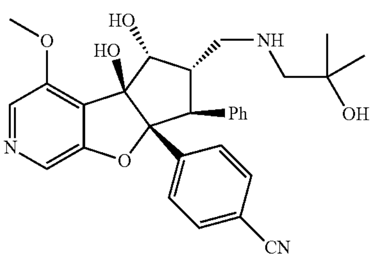

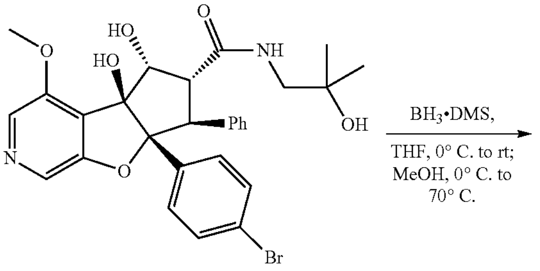

1

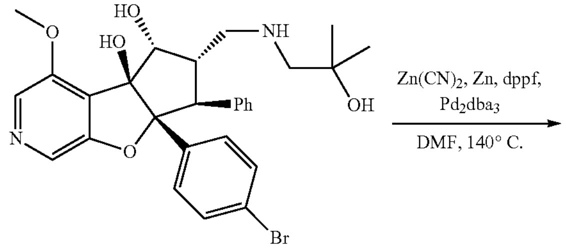

2

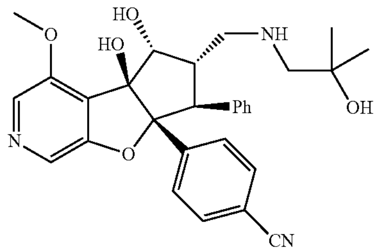

254F

Synthesis of rac-((4bS,5R,6S,7S,7aR)-7a-(4-bromophenyl)-6-(((2-hydroxy-2-methylpropyl)amino)methyl)-4-methoxy-7-phenyl-5,6,7,7a-tetrahydro-4bH-cyclopenta[4,5]furo[2,3-c]pyridine-4b,5-diol (2)

To a solution of rac-(4bS,5R,6R,7S,7aR)-7a-(4-bromophenyl)-4b,5-dihydroxy-N-(2-hydroxy-2-methylpropyl)-4-methoxy-7-phenyl-4b,6,7,7a-tetrahydro-5H-cyclopenta[4,5]furo[2,3-c]pyridine-6-carboxamide (1, 0.7 g, 1.22 mmol) in dry tetrahydrofuran (14 ml) at 0° C., borane dimethyl sulphide complex (0.933 g, 12.29 mmol) was added drop wise over a period of 5 min.

The reaction mixture was slowly brought to room temperature and stirred for additional 16 h. After completion, the reaction mixture was quenched with methanol at 0° C. and heated to reflux for 16 h. After completion, solvent was removed under reduced pressure and the residue was purified over a plug of silica gel (100-200 mesh size) eluting the compound with 5% methanol in dichloromethane as eluent. The desired fractions were concentrated under reduced pressure to afford rac-(4bS,5R,6S,7S,7aR)-7a-(4-bromophenyl)-6-(((2-hydroxy-2-methylpropyl)amino)methyl)-4-methoxy-7-phenyl-5,6,7,7a-tetrahydro-4bH-cyclopenta[4,5]furo[2,3-c]pyridine-4b,5-diol (2) as white solid. Yield: 0.559 g, 82%; MS (ESI) m/z 555.47[M+1]$^+$.

Synthesis of 4-((4bS,5R,6S,7S,7aR)-4b,5-dihydroxy-6-(((2-hydroxy-2-methylpropyl)amino)methyl)-4-methoxy-7-phenyl-4b,5,6,7-tetrahydro-7aH-cyclopenta[4,5]furo[2,3-c]pyridin-7a-yl)benzonitrile (Cpd. No. 254F)

To a solution of rac-(4bS,5R,6S,7S,7aR)-7a-(4-bromophenyl)-6-(((2-hydroxy-2-methylpropyl)amino)methyl)-4-methoxy-7-phenyl-5,6,7,7a-tetrahydro-4bH-cyclopenta[4,5]furo[2,3-c]pyridine-4b,5-diol (2, 0.55 g, 0.99 mmol) in N,N-dimethylformamide (10 mL), zinc cyanide (0.175 g, 1.48 mmol) and zinc dust (0.0064 g, 0.099 mmol) were added at room temperature and the reaction mixture was degassed with argon for 15 min. 1,1'-Bis(diphenylphosphino)ferrocene (0.072 g, 0.099 mmol) and tris(dibenzylideneacetone)dipalladium (0.027 g, 0.029 mmol) were added to the reaction, degassed for additional 5 min and mixture was heated at 140° C. for 3 h. After completion, the reaction mixture was diluted with ethyl acetate and washed with cold water. The organic layer was separated and dried over anhydrous sodium sulphate, filtered and concentrated to give crude product. The crude product was purified by silica gel (100-200 mesh size) column chromatography using 3-5% methanol in dichloromethane as eluent. The desired fractions were concentrated to afford rac-4-((4bS,5R,6S,7S,7aR)-4b,5-dihydroxy-6-(((2-hydroxy-2-methylpropyl)amino)methyl)-4-methoxy-7-phenyl-4b,5,6,7-tetrahydro-7aH-cyclopenta[4,5]furo[2,3-c]pyridin-7a-yl)benzonitrile as white solid. Yield: 0.250 g, 51%; MS (ESI) m/z 502.29 [M+1]$^+$. The enantiomers were separated by chiral HPLC [Chiralpak IA (4.6×250) mm, 5μ] in 0.1% TEA in n-Hexane/EtOH=85/15 (V/V). Peak 1 (Cpd. No. 254F, 40 mg), $[\alpha]_D$+5.20° (c 0.257, CHCl$_3$), R$_t$=13.139 min, ee: 99.88%; MS (ESI) m/z 502.28[M+1]$^+$. $^1$H NMR (400 MHz, DMSO-d$_6$) 8.04 (s, 1H), 7.96 (s, 1H), 7.48 (d, J=8.40 Hz, 2H), 7.35 (d, J=8.4 Hz, 2H), 7.07-6.95 (m, 5H), 5.68 (s, 1H), 5.48 (bs, 1H), 4.55 (d, J=3.76 Hz, 1H), 4.19 (s, 1H), 3.86 (s, 3H), 3.82 (d, J=14.4 Hz, 1H), 3.18 (bs, 1H), 2.74-2.69 (m, 1H), 2.55 (bs, 2H), 2.41 (s, 1H), 2.30 (s, 1H), 1.05 (s, 6H). Peak-2 (30 mg), $[\alpha]_D$−9.2° (c 0.23, CHCl$_3$), R$_t$=27.70 min, ee:99.16%;

MS (ESI) m/z 502.28[M+1]$^+$. $^1$H NMR (400 MHz, DMSO-$d_6$) 8.04 (s, 1H), 7.96 (s, 1H), 7.48 (d, J=8.40 Hz, 2H), 7.35 (d, J=8.4 Hz, 2H), 7.07-6.98 (m, 5H), 5.68 (s, 1H), 5.48 (bs, 1H), 4.55 (bs, 1H), 4.18 (s, 1H), 3.86 (s, 3H), 3.82 (d, J=14.28 Hz, 1H), 3.17 (bs, 1H), 2.73-2.68 (m, 1H), 2.55 (bs, 2H), 2.43 (bs, 1H), 2.30 (s, 1H), 1.05 (s, 6H).
Example 255
Rac-(4bS,5R,6S,7S,7aR)-6-((dimethylamino)methyl)-4-methoxy-7-phenyl-7a-(p-tolyl)-5,6,7,7a-tetrahydro-4bH-cyclopenta[4,5]furo[2,3-c]pyridine-4b,5-diol (Cpd. No. 255F)
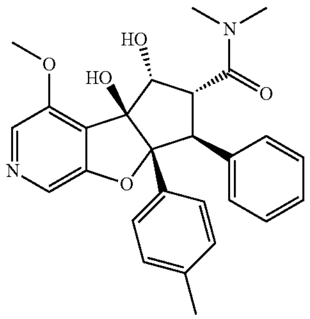
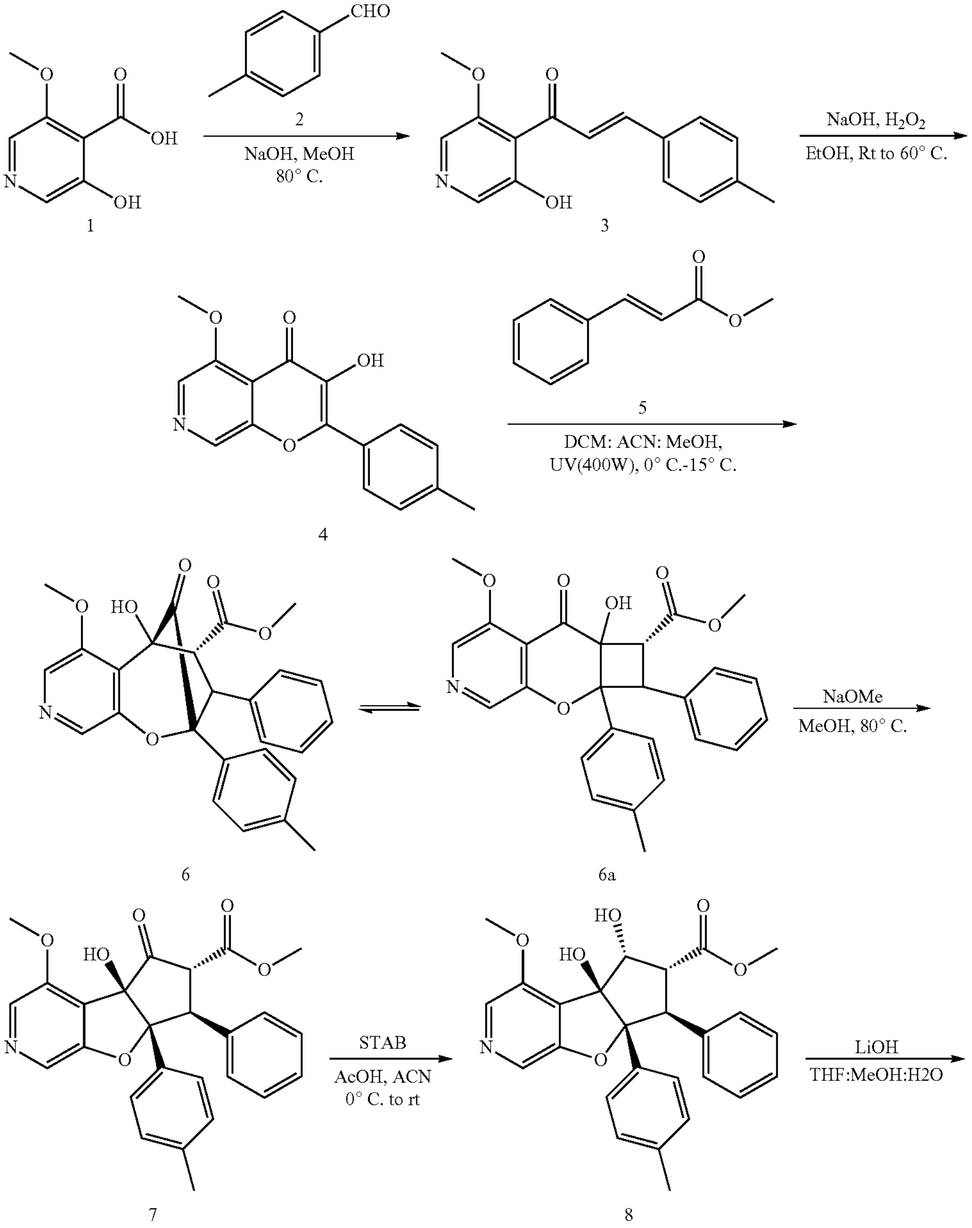

-continued

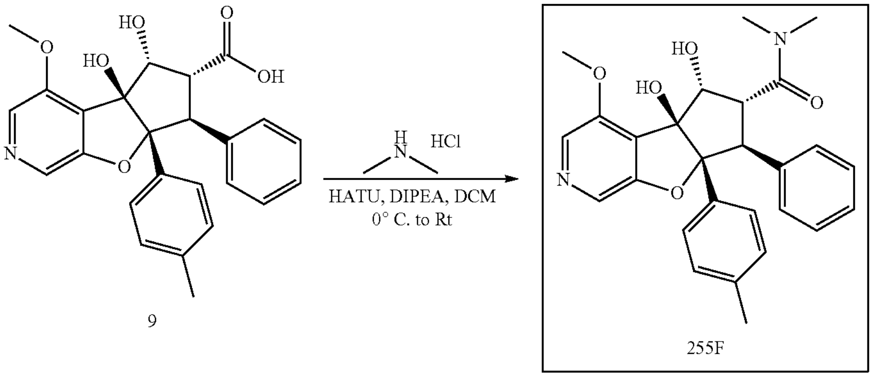

9

255F

Synthesis of (E)-1-(3-hydroxy-5-methoxypyridin-4-yl)-3-(p-tolyl)prop-2-en-1-one (3)

To a solution of 1-(3-hydroxy-5-methoxypyridin-4-yl) ethan-1-one (1, 10.0 g, 59.8 mmol) in methanol (250 mL), sodium hydroxide (7.1 g, 179.6 mmol) was added followed by addition of 4-methylbenzaldehyde (2, 7.1 g, 59.8 mmol). The reaction was heated to reflux for 1 h. After completion, the reaction mixture was cooled to room temperature, diluted with water (200 mL) The solid precipited out was filtered and dried over vacuum to get the crude product. The crude product was triturated with pentane, and dried under vacuum to afford (E)-1-(3-hydroxy-5-methoxypyridin-4-yl)-3-(p-tolyl)prop-2-en-1-one (3) as yellow solid. Yield: 16.0 g, 99%; MS (ESI) m/z 270.12[M+1]$^+$.

Synthesis of 3-hydroxy-5-methoxy-2-(p-tolyl)-4H-pyrano[2,3-c]pyridin-4-one (4)

To a solution of (E)-1-(3-hydroxy-5-methoxypyridin-4-yl)-3-(p-tolyl)prop-2-en-1-one (3, 16.0 g, 59.4 mmol) in ethanol (480 mL) at 0° C., sodium hydroxide (2.8 g, 71.3 mmol) was added followed by the addition of 30% aqueous hydrogen peroxide (47.1 mL, 416.2 mmol). The reaction mass was stirred for 30 min at 60° C. After completion, the reaction mass was cooled and neutralized to pH ~7 by the addition of 6 M hydrogen chloride. Then filtered and dried. The solid obtained was triturated with ethanol, filtered and dried under vacuum to afford 3-hydroxy-5-methoxy-2-(p-tolyl)-4H-pyrano[2,3-c]pyridin-4-one (4) as yellow solid. Yield: 3.8 g, 23.0%; MS (ESI) m/z 284.32[M+1]$^+$.

Synthesis of rac-methyl (3S,4S,5R)-5-hydroxy-6-methoxy-10-oxo-3-phenyl-2-(p-tolyl)-2,3,4,5-tetrahydro-2,5-methanooxepino[2,3-c]pyridine-4-carboxylate (6)

To a solution of 3-hydroxy-5-methoxy-2-(p-tolyl)-4H-pyrano[2,3-c]pyridin-4-one (4, 3.80 g, 13.5 mmol) and methyl cinnamate (5, 21.93 g, 135.2 mmol) in dichloromethane (300 mL), acetonitrile (150 mL) and methanol (150 mL) was placed in a UV reactor flask. The reaction mixture was irradiated under 400 watts UV light for 12 h. After completion, solvent was removed under reduced pressure and the residue was purified by silica gel (100-200 mesh size) using ethyl acetate as eluent. The desired fractions were concentrated under reduced pressure to afford rac-methyl (3S,4S,5R)-5-hydroxy-6-methoxy-10-oxo-3-phenyl-2-(p-tolyl)-2,3,4,5-tetrahydro-2,5-methanooxepino[2,3-c]pyridine-4-carboxylate (6) as yellow brown solid. Yield: 5.0 g, crude. MS (ESI) m/z 446.46 [M+1]$^+$.

Synthesis of rac-methyl (4bR,6R,7S,7aR)-4b-hydroxy-4-methoxy-5-oxo-7-phenyl-7a-(p-tolyl)-4b,6,7,7a-tetrahydro-5H-cyclopenta[4,5]furo[2,3-c]pyridine-6-carboxylate (7)

The crude compound rac-methyl (3S,4S,5R)-5-hydroxy-6-methoxy-10-oxo-3-phenyl-2-(p-tolyl)-2,3,4,5-tetrahydro-2,5-methanooxepino[2,3-c]pyridine-4-carboxylate (6, 5.0 g) was suspended in methanol (50 mL) and treated with 25% sodium methoxide in methanol (24 mL). The reaction was heated at 80° C. for 3 h. After completion, the solvent was removed under reduced pressure. The crude residue was diluted with aqueous ammonium chloride solution and extracted with ethyl acetate. The organic phase was separated, dried over sodium sulphate and concentrated under reduced pressure to afford of rac-methyl (4bR,6R,7S,7aR)-4b-hydroxy-4-methoxy-5-oxo-7-phenyl-7a-(p-tolyl)-4b,6,7,7a-tetrahydro-5H-cyclopenta[4,5]furo[2,3-c]pyridine-6-carboxylate (7) as off white solid. Yield: 4.5 g, crude. MS (ESI) m/z 446.46 [M+1]$^+$.

Synthesis of rac-methyl (4bS,5R,6R,7S,7aR)-4b,5-dihydroxy-4-methoxy-7-phenyl-7a-(p-tolyl)-4b,6,7,7a-tetrahydro-5H-cyclopenta[4,5]furo[2,3-c]pyridine-6-carboxylate (8)

To a solution of rac-methyl (4bR,6R,7S,7aR)-4b-hydroxy-4-methoxy-5-oxo-7-phenyl-7a-(p-tolyl)-4b,6,7,7a-tetrahydro-5H-cyclopenta[4,5]furo[2,3-c]pyridine-6-carboxylate (7, 4.50 g, 10.11 mmol) in acetonitrile (45 mL) at 0° C. were added sodium triacetoxyborohydride (21.93 g, 101.1 mmol), and acetic acid (5 ml, 101.1 mmol). The resulting mixture was stirred for 4 h at room temperature. After completion, the reaction mixture was partitioned between saturated aqueous sodium bicarbonate solution and ethyl acetate. The organic layer was separated, dried over sodium sulphate, filtered and concentrated under reduced pressure to get the crude. The crude was purified by silica gel column chromatography using 0-5% methanol in dichloromethane as eluents. The desired fractions were concentrated under reduced pressure to afford rac-methyl (4bS,5R,6R,7S,7aR)-4b,5-dihydroxy-4-methoxy-7-phenyl-7a-(p-tolyl)-4b,6,7,7a-tetrahydro-5H-cyclopenta[4,5]furo[2,3-c]pyridine-6-carboxylate (8) as off white solid. Yield: 2.5 g, 55.3%; MS (ESI) m/z 448.43[M+1]$^+$.

Synthesis of rac-(4bS,5R,6R,7S,7aR)-4b,5-dihydroxy-4-methoxy-7-phenyl-7a-(p-tolyl)-4b,6,7,7a-tetrahydro-5H-cyclopenta[4,5]furo[2,3-c]pyridine-6-carboxylic acid (9)

To a solution of rac-methyl (4bS,5R,6R,7S,7aR)-4b,5-dihydroxy-4-methoxy-7-phenyl-7a-(p-tolyl)-4b,6,7,7a-tetrahydro-5H-cyclopenta[4,5]furo[2,3-c]pyridine-6-carboxylate (8, 2.50 g, 5.59 mmol) in methanol:tetrahydrofuran:water (2:1:1, 50 mL), lithium hydroxide (1.34 g, 55.9 mmol) was added and the reaction was stirred for 3 h at room temperature. After completion, the reaction mixture was cooled to 0° C. and acidified with 1 M hydrochloric acid to pH ~2-3. The precipitate obtained was filtered and dried under vacuum to afford rac-(4bS,5R,6R,7S,7aR)-4b,5-dihydroxy-4-methoxy-7-phenyl-7a-(p-tolyl)-4b,6,7,7a-tetrahydro-5H-cyclopenta[4,5]furo[2,3-c]pyridine-6-carboxylic acid (9) as white solid. Yield: 2.0 g, 83%; MS (ESI) m/z 434.26[M+1]$^+$.

Synthesis of rac-(4bS,5R,6R,7S,7aR)-4b,5-dihydroxy-4-methoxy-N,N-dimethyl-7-phenyl-7a-(p-tolyl)-4b,6,7,7a-tetrahydro-5H-cyclopenta[4,5]furo[2,3-c]pyridine-6-carboxamide (Cpd. No. 255F)

To a solution of rac-(4bS,5R,6R,7S,7aR)-4b,5-dihydroxy-4-methoxy-7-phenyl-7a-(p-tolyl)-4b,6,7,7a-tetrahydro-5H-cyclopenta[4,5]furo[2,3-c]pyridine-6-carboxylic acid (9, 0.5 g, 1.15 mmol) in dichloromethane (15 mL) at 0° C., 1-[Bis (dimethylamino)methylene]-1H-1,2,3-triazolo[4,5-b]pyridinium3-oxide hexafluorophosphate, (1.31 g, 3.77 mmol) and N,N-diisopropylethylamine (1.23 ml, 6.90 mmol) were added and the mixture was stirred for 5 min. Dimethylamine hydrochloride (0.470 g, 5.77 mmol) was added at the same temperature and the reaction was stirred for 16 h at room temperature. After completion, the reaction mixture was diluted with dichloromethane and washed with ice cold water. The organic layer was separated and dried over sodium sulphate, filtered and concentrated to give crude product. The crude product was purified by silica gel (100-200 mesh size) column chromatography using 0-5% methanol in dichloromethane as eluent. The desired fractions were concentrated to afford rac-(4bS,5R,6R,7S,7aR)-4b,5-dihydroxy-4-methoxy-N,N-dimethyl-7-phenyl-7a-(p-tolyl)-4b,6,7,7a-tetrahydro-5H-cyclopenta[4,5]furo[2,3-c]pyridine-6-carboxamide (Cpd. No. 255F) as white solid. Yield: 0.5 g, 94%; MS (ESI) m/z 461.29[M+1]$^+$. $^1$H NMR (400 MHz, DMSO-$d_6$) δ 8.09 (s, 1H), 7.98 (s, 1H), 7.02-6.91 (m, 5H), 6.88-6.83 (m, 4H), 5.52 (s, 1H), 5.01 (d, J=5.08 Hz, 1H), 4.78 (t, J=5.32 Hz, 1H), 4.33 (d, J=13.44 Hz, 1H), 4.14 (dd, J=5.56 Hz, J=13.48 Hz, 1H), 3.87 (s, 3H), 3.26 (s, 3H), 2.76 (s, 3H), 2.11 (s, 3H).

Example 256

(4bS,5R,6S,7S,7aR)-6-((dimethylamino)methyl)-4-methoxy-7-phenyl-7a-(p-tolyl)-5,6,7,7a-tetrahydro-4bH-cyclopenta[4,5]furo[2,3-c]pyridine-4b,5-diol (Cpd. No. 256F)

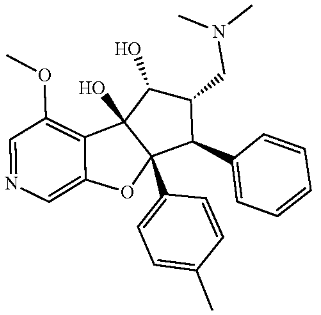

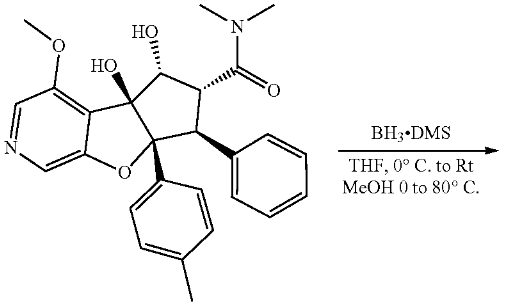

1

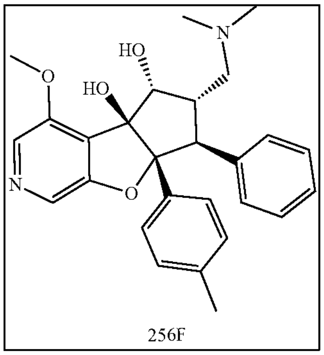

256F

Synthesis of (4bS,5R,6S,7S,7aR)-6-((dimethylamino)methyl)-4-methoxy-7-phenyl-7a-(p-tolyl)-5,6,7,7a-tetrahydro-4bH-cyclopenta[4,5]furo[2,3-c]pyridine-4b,5-diol (Cpd. No. 256F)

To a solution of rac-(4bS,5R,6R,7S,7aR)-4b,5-dihydroxy-4-methoxy-N,N-dimethyl-7-phenyl-7a-(p-tolyl)-4b,6,7,7a-tetrahydro-5H-cyclopenta[4,5]furo[2,3-c]pyridine-6-carboxamide (1, 0.6 g, 1.3 mmol) in dry tetrahydrofuran (20 ml) at 0° C., borane dimethyl sulphide complex (1.48 ml, 19.5 mmol) was added drop wise over a period of 5 min. The reaction mixture was slowly brought to room temperature and stirred for additional 16 h. After completion, the reaction mixture was quenched with methanol at 0° C. and heated to reflux for 10 h. After completion, solvent was removed under reduced pressure and the residue was purified by silica gel (100-200 mesh size) eluting the compound with 0-5% methanol in dichloromethane as eluent. The desired fractions were concentrated under reduced pressure to afford rac-(4bS,5R,6S,7S,7aR)-6-((dimethylamino)methyl)-4-methoxy-7-phenyl-7a-(p-tolyl)-5,6,7,7a-tetrahydro-4bH-cyclopenta[4,5]furo[2,3-c]pyridine-4b,5-diol as white solid. Yield: 0.330 g. The enantiomers were separated by chiral SFC [CHIRALPAK IG (4.6×150) mm, 5p] in $CO_2$/0.1% TEA in EtOH=(60/40). Peak 1 (Cpd. No. 256F, 86 mg), $[\alpha]_D$−32.0° (c 0.51, $CHCl_3$), $R_t$=3.302 min, ee: 99.86%; MS (ESI) m/z 447.28[M+1]$^+$. $^1$H NMR (400 MHz, DMSO-$d_6$) δ 8.00 (s, 1H), 7.93 (s, 1H), 7.07-7.03 (m, 4H), 6.99-6.93 (m, 3H), 6.84 (d, J=7.76 Hz, 2H), 5.46 (s, 1H), 5.01 (s, 1H), 4.49 (s, 1H), 3.87 (s, 3H), 3.65 (d, J=13.84 Hz, 1H), 3.17-3.06 (m, 1H), 2.55 (s, 1H), 2.18 (s, 6H), 2.10 (s, 3H), 1.92 (d, J=11.92 Hz, 1H); Peak-2 (87 mg), $[\alpha]_D$+35.2° (c 0.269, $CHCl_3$), $R_t$=4.149 min, ee: 99.90%; MS (ESI) m/z 447.28[M+1]$^+$; $^1$H NMR (400 MHz, DMSO-$d_6$) δ 8.00 (s, 1H), 7.93 (s, 1H), 7.07-7.03 (m, 4H), 6.99-6.93 (m, 3H), 6.84 (d, J=7.76 Hz, 2H), 5.46 (s, 1H), 5.01 (s, 1H), 4.49 (s, 1H), 3.87 (s, 3H), 3.65 (d, J=13.84 Hz, 1H), 3.17-3.06 (m, 1H), 2.55 (s, 1H), 2.18 (s, 6H), 2.10 (s, 3H), 1.92 (d, J=11.92 Hz, 1H).

Example 257

Rac-((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)(piperidin-1-yl)methanone (Cpd. No. 257F)

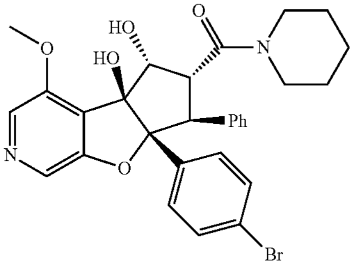

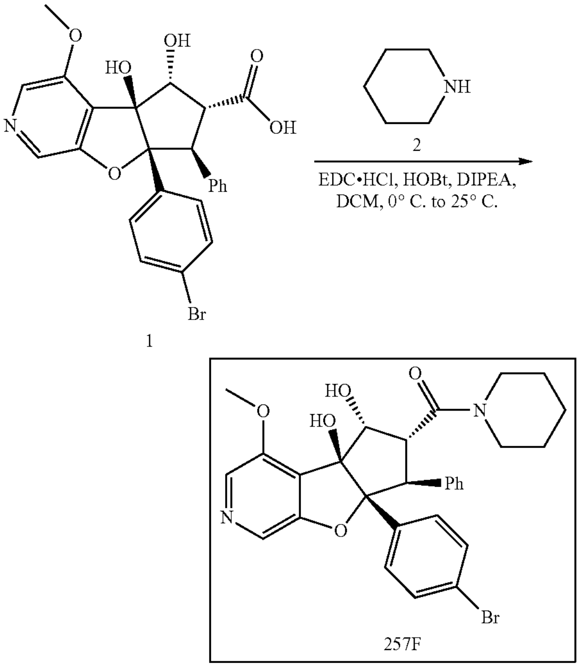

1
2
257F

Synthesis of rac-((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)(piperidin-1-yl)methanone (Cpd. No. 257F)

To a solution of rac-(4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylic acid (1, 1.0 g, 2.0 mmol) in dichloromethane (25.0 mL), 1-ethyl-3-(3-dimethylaminopropyl) carbodiimide (1.16 g, 6.0 mmol), hydroxybenzotriazole (0.82 g, 6.0 mmol) and N,N-diisopropylethylamine (1.5 mL, 12.2 mmol) were added at 0° C. and stirred the mixture for 5 min. piperidine (2, 0.297 g, 10.1 mmol) was then added at same temperature and the reaction was stirred at room temperature for 5 h. After completion, reaction mass was diluted with dichloromethane (20 mL) and washed with cold water. The organic layer was separated and dried over anhydrous sodium sulphate, filtered and concentrated under reduced pressure. The crude was purified by reverse phase HPLC to afford rac-((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)(piperidin-1-yl) methanone (Cpd. No. 257F) as white solid. Yield: 0.80 g, 70%; MS (ESI) m/z 565.26[M+1]$^+$, UPLC: 99.79%; $^1$H NMR (400 MHz, DMSO-d6) δ 8.09 (s, 1H), 7.98 (s, 1H), 7.20 (d, J=8.0 Hz, 2H), 7.07-7.02 (m, 4H), 6.97-6.93 (m, 1H), 6.90 (d, J=8.1 Hz, 2H), 5.71 (s, 1H), 5.11 (d, J=5.4 Hz, 1H), 4.67 (t, J=5.1 Hz, 1H), 4.47 (d, J=13.3 Hz, 1H), 4.18 (dd, J=4.9 Hz, 13.2 Hz, 1H), 3.87 (s, 3H), 3.73 (bs, 2H), 3.35 (m, 2H), 1.75-1.64 (m, 4H), 1.46-1.34 (m, 2H).

Example 258

4-((4bS,5R,6S,7S,7aR)-4b,5-dihydroxy-4-methoxy-7-phenyl-6-(piperidin-1-ylmethyl)-4b,5,6,7-tetrahydro-7aH-cyclopenta[4,5]furo[2,3-c]pyridin-7a-yl)benzonitrile (Cpd. No. 258F)

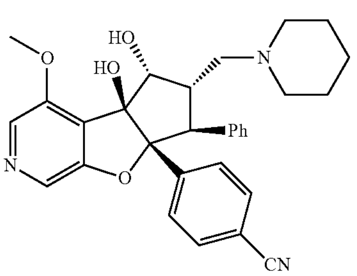

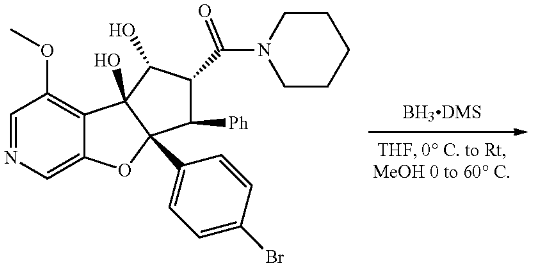

1

-continued

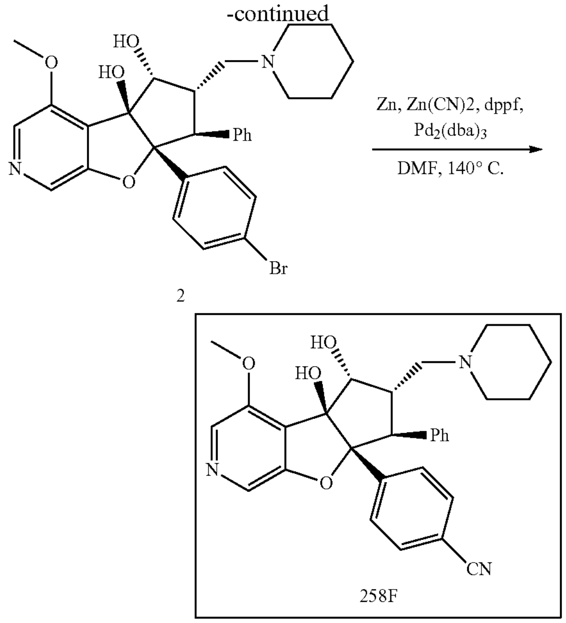

2

258F

Synthesis of rac-(4bS,5R,6S,7S,7aR)-7a-(4-bromophenyl)-4-methoxy-7-phenyl-6-(piperidin-1-ylmethyl)-5,6,7,7a-tetrahydro-4bH-cyclopenta[4,5]furo[2,3-c]pyridine-4b,5-diol (2)

To a solution of rac-((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)(piperidin-1-yl)methanone (1, 0.80 g, 1.6 mmol) in tetrahydrofuran, borane dimethylsulfide (1.2 ml, 16.0 mmol) was added at 0° C. The reaction mixture was stirred for 3 h at room temperature. After completion, reaction mass was quenched with methanol at 0° C. and then heated at 60° C. for 4 h. The solvents were concentrated give crude. The crude was purified by Combi-flash (4 g, RediSep column) using 7% methanol in dichloromethane as eluent. The desired fractions were concentrated to afford rac-(4bS,5R,6S,7S,7aR)-7a-(4-bromophenyl)-4-methoxy-7-phenyl-6-(piperidin-1-ylmethyl)-5,6,7,7a-tetrahydro-4bH-cyclopenta[4,5]furo[2,3-c]pyridine-4b,5-diol (2) as white solid. Yield: 0.4 g, 60%; MS (ESI) m/z 551.1[M+1]$^+$.

Synthesis of 4-((4bS,5R,6S,7S,7aR)-4b,5-dihydroxy-4-methoxy-7-phenyl-6-(piperidin-1-ylmethyl)-4b,5,6,7-tetrahydro-7aH-cyclopenta[4,5]furo[2,3-c]pyridin-7a-yl)benzonitrile (Cpd. No. 258F)

To a mixture of rac-(4bS,5R,6S,7S,7aR)-7a-(4-bromophenyl)-4-methoxy-7-phenyl-6-(piperidin-1-ylmethyl)-5,6,7,7a-tetrahydro-4bH-cyclopenta[4,5]furo[2,3-c]pyridine-4b,5-diol (2, 0.4 g, 0.72 mmol) in N,N-dimethylformamide (3.0 mL) at room temperature, zinc cyanide (0.508 g, 4.34 mmol) and zinc (0.047 g, 0.72 mmol) were added at room temperature and degassed the mixture with argon for 15 min. 1,1'-Bis(diphenylphosphino) ferrocene (0.092 g, 0.166 mmol) and tris(dibenzylideneacetone)dipalladium (0.152 g, 0.166 mmol) were added to the reaction mixture and degassing was continued for another 5 min. The reaction mixture was heated at 140° C. for 2.5 h. After completion, the reaction was cooled to room temperature and passed through celite bed. The filtrate was diluted with ethyl acetate and washed with water. The organic layer was separated, dried over anhydrous sodium sulphate and concentrated under reduced pressure to give the crude. The crude was purified by combi-flash (12 g, RediSep column) using 0-10% methanol in dichloromethane as eluent. The product obtained was repurified by reverse phase prep HPLC. The desired fractions were lyophilized to afford rac-4-((4bS,5R,6S,7S,7aR)-4b,5-dihydroxy-4-methoxy-7-phenyl-6-(piperidin-1-ylmethyl)-4b,5,6,7-tetrahydro-7aH-cyclopenta[4,5]furo[2,3-c]pyridin-7a-yl)benzonitrile as white solid. Yield: 0.350 g, 82%. The enantiomers were separated by chiral preparative HPLC [Chiralpak IA (4.6×250) mm] using 0.1% TEA in n-Hexane/IPA (80/20) (v/v) mobile phase. Peak 1 (31 mg); $[\alpha]_D$+11.50 (c 0.34, $CHCl_3$), $R_t$=14.5, ee >99%; MS (ESI) m/z 498.32 [M+1]$^+$; UPLC: 97.70%. $^1$H NMR (400 MHz, DMSO-d6) δ 8.04 (s, 1H), 7.96 (s, 1H), 7.51 (d, J=8.2 Hz, 2H), 7.37 (d, J=8.2 Hz, 2H), 7.12-7.07 (m, 2H), 7.05-6.99 (m, 3H), 5.72 (s, 1H), 4.50 (d, J=3.6 Hz, 1H), 3.87 (s, 3H), 3.81 (d, J=13.8 Hz, 1H), 2.32-2.27 (m, 3H), 2.09 (d, J=11.6 Hz, 1H), 1.64 (s, 2H), 1.52-1.50 (m, 5H), 1.37 (s, 3H). Peak-2 (Cpd. No. 258F, 17 mg); $[\alpha]_D$-10.4° (c 0.23, $CHCl_3$), $R_t$=22.8, ee >99%; MS (ESI) m/z 497.91 [M+1]$^+$; UPLC: 99.60%; $^1$H NMR (400 MHz, DMSO-$d_6$) δ 8.04 (s, 1H), 7.96 (s, 1H), 7.48 (d, J=8.2 Hz, 2H), 7.36 (d, J=8.2 Hz, 2H), 7.08-7.05 (m, 2H), 7.01-6.96 (m, 3H), 5.72 (s, 1H), 5.38 (bs, 1H), 4.50 (d, J=3.4 Hz, 1H), 3.87 (s, 3H), 3.80 (d, J=14.0 Hz, 1H), 2.28-2.24 (m, 2H), 2.06 (d, J=11.2 Hz, 1H), 1.88 (s, 4H), 1.59-1.51 (m, 4H), 1.40-1.37 (m, 2H).

Example 259

Rac-4-((4bS,5R,6S,7S,7aR)-6-(((2-fluoroethyl)amino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 259F)

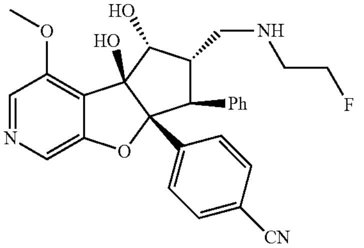

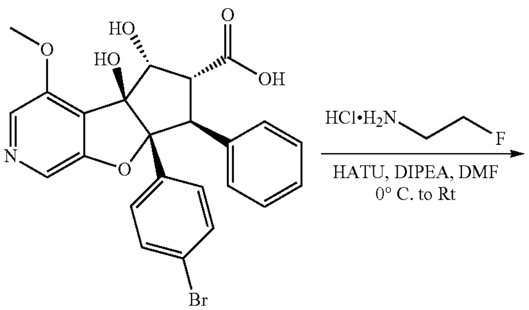

1

-continued

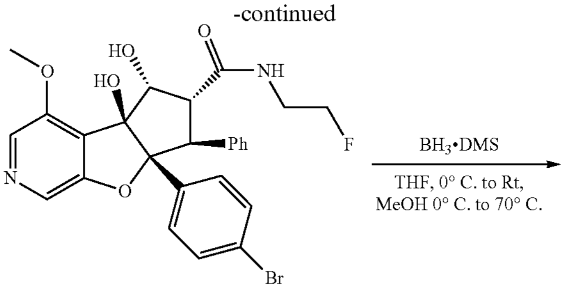

2

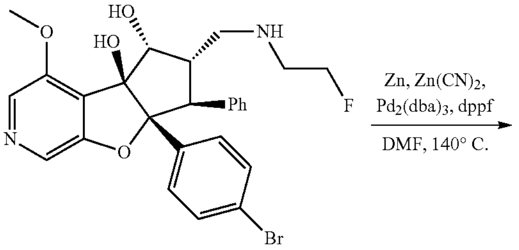

3

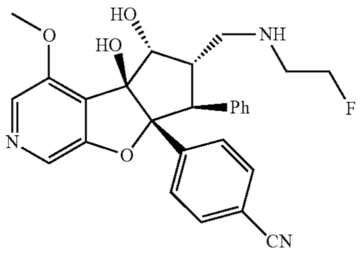

259F

Synthesis of rac-(4bS,5R,6R,7S,7aR)-7a-(4-bromophenyl)-N-(2-fluoroethyl)-4b,5-dihydroxy-4-methoxy-7-phenyl-4b,6,7,7a-tetrahydro-5H-cyclopenta[4,5]furo[2,3-c]pyridine-6-carboxamide (2)

To a solution of rac-(4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylic acid (1, 0.350 g, 0.702 mmol) in N,N-dimethylformamide (3.5 mL) at 0° C., 1-[Bis(dimethylamino)methylene]-1H-1,2,3-triazolo[4,5-b]pyridinium-3-oxide hexafluorophosphate (0.40 g, 1.05 mmol), and N,N-diisopropylethylamine (0.34 mL, 2.10 mmol) were added at 0° C. The reaction mixture was stirred for 5 min at and 2-fluoroethan-1-amine hydrochloride (0.349 g, 3.51 mmol) was then added at the same temperature and the reaction was stirred for 24 h at room temperature. After completion, the reaction mixture was diluted with cold water. The solid precipitated was filtered and dried to afford rac-(4bS,5R,6R,7S,7aR)-7a-(4-bromophenyl)-N-(2-fluoroethyl)-4b,5-dihydroxy-4-methoxy-7-phenyl-4b,6,7,7a-tetrahydro-5H-cyclopenta[4,5]furo[2,3-c]pyridine-6-carboxamide (2) as white solid. Yield: 0.34 g, 89%; MS (ESI) m/z 543.39[M+1]$^+$.

Synthesis of rac-(4bS,5R,6S,7S,7aR)-7a-(4-bromophenyl)-6-(((2-fluoroethyl)amino)methyl)-4-methoxy-7-phenyl-5,6,7,7a-tetrahydro-4bH-cyclopenta[4,5]furo[2,3-c]pyridine-4b,5-diol (3)

To a solution of rac-(4bS,5R,6R,7S,7aR)-7a-(4-bromophenyl)-N-(2-fluoroethyl)-4b,5-dihydroxy-4-methoxy-7-phenyl-4b,6,7,7a-tetrahydro-5H-cyclopenta[4,5]furo[2,3-c]pyridine-6-carboxamide (2, 0.34 g, 0.626 mmol) in dry tetrahydrofuran (10 ml) at 0° C., borane dimethyl sulphide complex (0.951 g, 12.52 mmol) was added drop wise over a period of 5 min. The reaction mixture was slowly brought to room temperature and stirred for additional 16 h. After completion, the reaction mixture was quenched with methanol at 0° C. and heated to reflux for 16 h. After completion, solvent was removed under reduced pressure and the crude product was by silica gel (100-200 mesh size) column chromatography using 5% methanol in dichloromethane as eluent. The desired fractions were concentrated under reduced pressure to afford rac-(4bS,5R,6S,7S,7aR)-7a-(4-bromophenyl)-6-(((2-fluoroethyl)amino)methyl)-4-methoxy-7-phenyl-5,6,7,7a-tetrahydro-4bH-cyclopenta[4,5]furo[2,3-c]pyridine-4b,5-diol (3) as white solid. Yield: 0.250 g, 76%; MS (ESI) m/z 529.42[M+1]$^+$.

Synthesis of rac-4-((4bS,5R,6S,7S,7aR)-6-(((2-fluoroethyl)amino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 259F)

To a solution of rac-(4bS,5R,6S,7S,7aR)-7a-(4-bromophenyl)-6-(((2-fluoroethyl)amino)methyl)-4-methoxy-7-phenyl-5,6,7,7a-tetrahydro-4bH-cyclopenta[4,5]furo[2,3-c]pyridine-4b,5-diol (3, 0.25 g, 0.472 mmol) in N,N-dimethylformamide (6 mL), zinc cyanide (0.083 g, 0.708 mmol) and zinc dust (0.003 g, 0.047 mmol) were added at room temperature and the reaction mixture was degassed with argon for 15 min. 1,1'-Bis(diphenylphosphino)ferrocene (0.034 g, 0.047 mmol) and tris(dibenzylideneacetone)dipalladium (0.012 g, 0.014 mmol) were added to the reaction, degassed for additional 5 min and mixture was heated at 140° C. for 3 h. After completion, the reaction mixture was diluted with ethyl acetate and washed with cold water. The organic layer was separated and dried over anhydrous sodium sulphate, filtered and concentrated to give crude. The crude product was purified by reverse phase Preparative HPLC to afford rac-4-((4bS,5R,6S,7S,7aR)-6-(((2-fluoroethyl)amino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 259F) as white solid. Yield: 0.015 g, 7%; MS (ESI) m/z 476.25[M+1]$^+$; $^1$H NMR (400 MHz, DMSO-$d_6$) D 8.13 (s, 1H), 8.06 (s, 1H), 7.58 (d, J=8.32 Hz, 2H), 7.35 (d, J=8.3 Hz, 2H), 7.12-7.01 (m, 5H), 5.92 (s, 1H), 5.27 (d, J=4.8 Hz, 1H), 4.77 (s, 1H), 4.71 (s, 1H), 4.65 (s, 1H), 3.91 (s, 3H), 3.84 (d, J=14.2 Hz, 1H), 3.42-3.30 (m, 4H), 3.15-3.10 (t, J=9.0 Hz, 1H), 2.85 (d, J=7.6 Hz, 1H).

Example 260

Rac-((4bS,5R,6R,7S,7aR)-7a-(4-bromophenyl)-4b,5-dihydroxy-4-methoxy-N-(2-methoxyethyl)-N-methyl-7-phenyl-4b,6,7,7a-tetrahydro-5H-cyclopenta[4,5]furo[2,3-c]pyridine-6-carboxamide (Cpd. No. 260F)

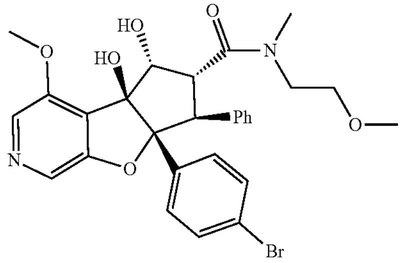

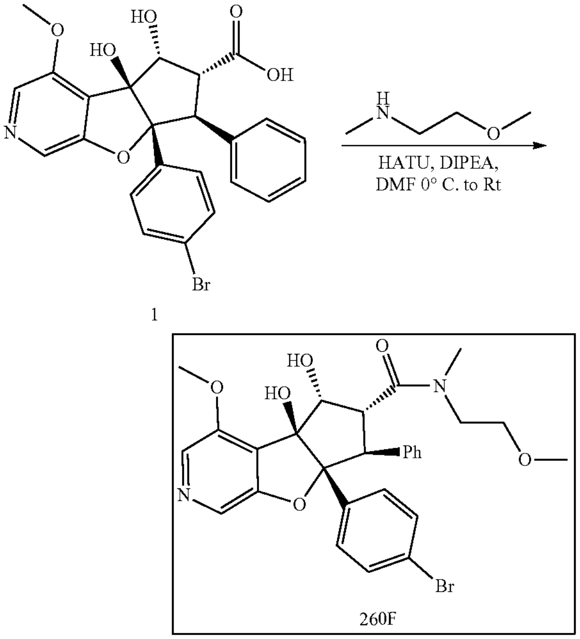

1

260F

Synthesis of rac-((4bS,5R,6R,7S,7aR)-7a-(4-bromophenyl)-4b,5-dihydroxy-4-methoxy-N-(2-methoxyethyl)-N-methyl-7-phenyl-4b,6,7,7a-tetrahydro-5H-cyclopenta[4,5]furo[2,3-c]pyridine-6-carboxamide (Cpd. No. 260F)

To a solution of rac-(4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylicacid (1, 1.50 g, 3.01 mmol) in N,N-dimethylformamide (15 mL) at 0° C., 1-[Bis(dimethylamino)methylene]-1H-1,2,3-triazolo[4,5-b]pyridinium-3-oxide hexafluorophosphate (1.71 g, 4.51 mmol), N,N-diisopropylethylamine (1.66 mL, 9.03 mmol) were added and the mixture was stirred for 5 min. 2-methoxy-N-methylethan-1-amine (1.340 g, 15.05 mmol) was then added at the same temperature and the reaction was stirred for 24 h at room temperature. After completion, the reaction mixture was diluted with cold water. The solid precipitated was filtered and dried to afford rac-(4bS,5R,6R,7S,7aR)-7a-(4-bromophenyl)-4b,5-dihydroxy-4-methoxy-N-(2-methoxyethyl)-N-methyl-7-phenyl-4b,6,7,7a-tetrahydro-5H-cyclopenta[4,5]furo[2,3-c]pyridine-6-carboxamide (Cpd. No. 260F) as white solid. Yield: 1.315 g, 82%; MS (ESI) m/z 569.38[M+1]$^+$. $^1$H NMR (400 MHz, DMSO-$d_6$) 8.10 (d, J=3.56 Hz, 1H), 7.99 (d, J=3.76 Hz, 1H), 7.24 (d, J=17.24 Hz, 2H), 7.07-6.89 (m, 7H), 5.72 (s, 1H), 5.70 (d, J=7.24 Hz, 1H), 5.09 (dd, J=5.32, 13.08 Hz, 1H), 4.74-4.69 (m, 1H), 4.46-4.35 (m, 1H), 4.19-4.13 (m, 1H), 3.88 (d, J=3.56 Hz, 3H), 3.71-3.60 (m, 2H), 3.66 (t, J=10.36 Hz, 1H), 3.44 (s, 2H), 3.20 (s, 1H), 2.78 (s, 3H).

Example 261

4-((4bS,5R,6S,7S,7aR)-4b,5-dihydroxy-4-methoxy-6-(((2-methoxyethyl)(methyl)amino)methyl)-7-phenyl-4b,5,6,7-tetrahydro-7aH-cyclopenta[4,5]furo[2,3-c]pyridin-7a-yl)benzonitrile (Cpd. No. 2611)

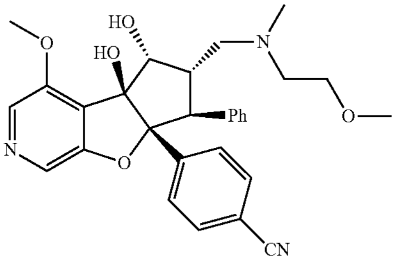

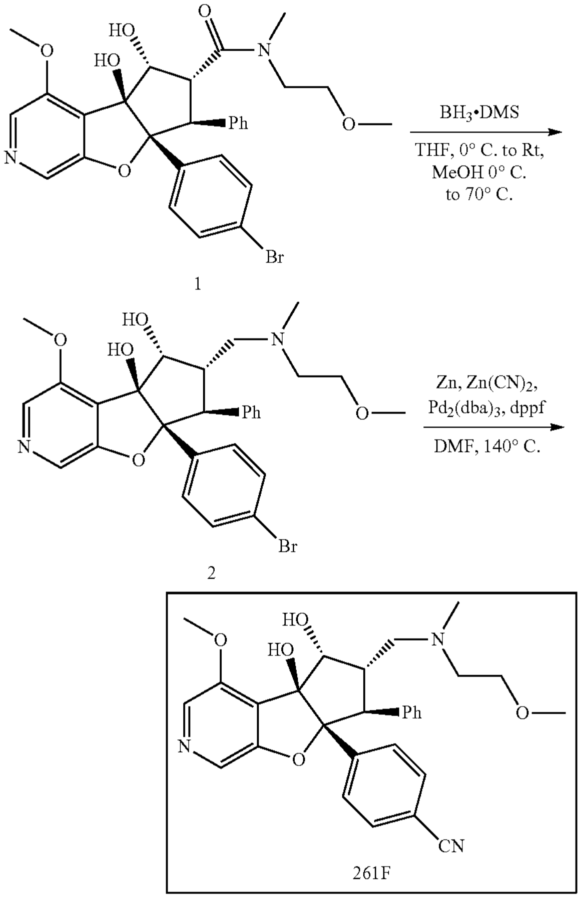

1

2

261F

Synthesis of rac-(4bS,5R,6S,7S,7aR)-7a-(4-bromophenyl)-4-methoxy-6-(((2-methoxyethyl)(methyl)amino)methyl)-7-phenyl-5,6,7,7a-tetrahydro-4bH-cyclopenta[4,5]furo[2,3-c]pyridine-4b,5-diol (2)

To a solution of rac-(4bS,5R,6R,7S,7aR)-7a-(4-bromophenyl)-4b,5-dihydroxy-4-methoxy-N-(2-methoxyethyl)-N-methyl-7-phenyl-4b,6,7,7a-tetrahydro-5H-cyclopenta[4,5]furo[2,3-c]pyridine-6-carboxamide (1, 1.100 g, 1.93 mmol) in dry tetrahydrofuran (20 ml) at 0° C., borane dimethyl sulphide complex (2.19 g, 28.95 mmol) was added drop wise over a period of 5 min. The reaction mass was slowly brought to room temperature and stirred for additional 16 h. After completion, the reaction mass was quenched with methanol at 0° C. and heated to reflux for 16 h. After completion, solvent was removed under reduced pressure and the residue was purified over a plug of silica gel eluting the compound with 5% methanol in dichloromethane. The desired fractions were concentrated under reduced pressure to afford rac-(4bS,5R,6S,7S,7aR)-7a-(4-bromophenyl)-4-methoxy-6-(((2-methoxyethyl)(methyl)amino)methyl)-7-phenyl-5,6,7,7a-tetrahydro-4bH-cyclopenta[4,5]furo[2,3-c]pyridine-4b,5-diol (2) as white solid. Yield: 0.39 g, 69%; MS (ESI) m/z 555.46[M+1]$^+$.

Synthesis of 4-((4bS,5R,6S,7S,7aR)-4b,5-dihydroxy-4-methoxy-6-(((2-methoxyethyl)(methyl)amino)methyl)-7-phenyl-4b,5,6,7-tetrahydro-7aH-cyclopenta[4,5]furo[2,3-c]pyridin-7a-yl)benzonitrile (Cpd. No. 261F)

To a solution of rac-(4bS,5R,6S,7S,7aR)-7a-(4-bromophenyl)-4-methoxy-6-(((2-methoxyethyl)(methyl)amino)methyl)-7-phenyl-5,6,7,7a-tetrahydro-4bH-cyclopenta[4,5]furo[2,3-c]pyridine-4b,5-diol (2, 0.39 g, 0.70 mmol) in N,N-dimethylformamide (4 mL), zinc cyanide (0.494 g, 4.21 mmol) and zinc dust (0.022 g, 0.35 mmol) were added at room temperature and the reaction mixture was degassed with argon for 15 min. 1,1'-Bis(diphenylphosphino)ferrocene (0.038 g, 0.07 mmol) and tris(dibenzylideneacetone)dipalladium (0.032 g, 0.035 mmol) were added to the reaction, degassed for additional 5 min and mixture was heated at 140° C. for 9 h. After completion, the reaction mass was diluted with ethyl acetate and washed with cold water. The organic layer was separated and dried over anhydrous sodium sulphate, filtered and concentrated to give crude. The crude was purified by Preparative HPLC to afford rac-4-((4bS,5R,6S,7S,7aR)-4b,5-dihydroxy-4-methoxy-6-(((2-methoxyethyl)(methyl)amino)methyl)-7-phenyl-4b,5,6,7-tetrahydro-7aH-cyclopenta[4,5]furo[2,3-c]pyridin-7a-yl)benzonitrile as white solid. Yield: 0.137 g, 39%; MS (ESI) m/z 502.26[M+1]$^+$. The enantiomers were separated by chiral SFC [chiralpak IC (4.6 ×250) mm, 5μ], $CO_2$/0.1% TEA in ethanol 80/20 (v/v). Peak 1 (44 mg), $[\alpha]_D$−44.1° (c 0.27, $CHCl_3$), $R_t$=6.220 min, ee: 99.64% MS (ESI) m/z 502.26 [M+1]$^+$. $^1$H NMR (400 MHz, DMSO-$d_6$) 8.04 (s, 1H), 7.97 (s, 1H), 7.49 (d, J=8.28 Hz, 2H), 7.37 (d, J=8.40 Hz, 2H), 7.07-7.00 (m, 5H), 5.72 (s, 1H), 5.0 (bs, 1H), 4.50 (bs, 1H), 3.88 (s, 3H), 3.80 (d, J=13.8 Hz, 1H), 3.40 (s, 2H), 3.22 (s, 4H), 2.64-2.57 (m, 2H), 2.41-2.39 (m, 1H), 2.29 (s, 3H), 2.17 (d, J=10.72 Hz, 1H). Peak 2 (Cpd. No. 261F, 44 mg), $[\alpha]_D$+31.4° (c 0.265, $CHCl_3$), $R_t$=7.523 min, ee: 97.28% MS (ESI) m/z 502.29 [M+1]$^+$. $^1$H NMR (400 MHz, DMSO-$d_6$) 8.04 (s, 1H), 7.97 (s, 1H), 7.50 (d, J=8.28 Hz, 2H), 7.38 (d, J=8.40 Hz, 2H), 7.09-7.00 (m, 5H), 5.72 (s, 1H), 5.0 (bs, 1H), 4.50 (bs, 1H), 3.88 (s, 3H), 3.81 (d, J=13.8 Hz, 1H), 3.40 (s, 2H), 3.22 (s, 4H), 2.64-2.57 (m, 2H), 2.41-2.39 (m, 1H), 2.29 (s, 3H), 2.17 (d, J=10.72 Hz, 1H).

Example 262

Rac-(4bS,5R,6R,7S,7aR)-7a-(4-bromophenyl)-4b,5-dihydroxy-4-methoxy-N-(2-methoxyethyl)-7-phenyl-4b,6,7,7a-tetrahydro-5H-cyclopenta[4,5]furo[2,3-c]pyridine-6-carboxamide (Cpd. No. 262F)

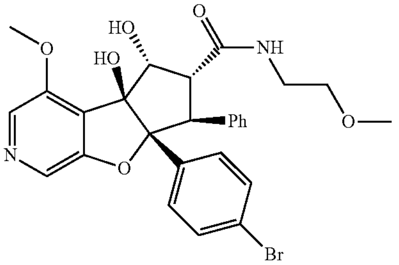

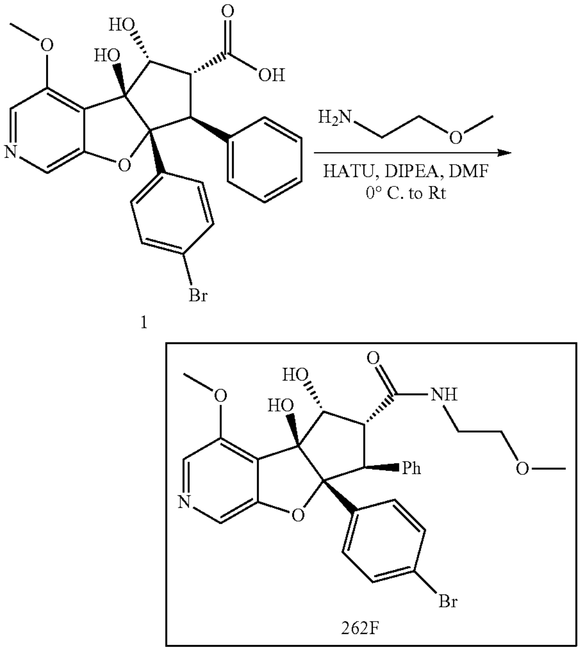

1

262F

Synthesis of rac-(4bS,5R,6R,7S,7aR)-7a-(4-bromophenyl)-4b,5-dihydroxy-4-methoxy-N-(2-methoxyethyl)-7-phenyl-4b,6,7,7a-tetrahydro-5H-cyclopenta[4,5]furo[2,3-c]pyridine-6-carboxamide (Cpd. No. 262F)

To a solution of rac-(4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylic acid (1, 2.0 g, 4.01 mmol) in N,N-dimethylformamide (20 mL) at 0° C., 1-[Bis(dimethylamino)methylene]-1H-1,2,3-triazolo[4,5-b]pyridinium-3-oxidhexafluorophosphate (2.28 g, 6.02 mmol), N,N-diisopropylethylamine (1.98 mL, 12.03 mmol) were added and the mixture was stirred for 5 min. 2-methoxyethan-1-amine (1.50 g, 20.05 mmol) was then added at the same temperature and the reaction was stirred for 24 h at room temperature. After completion, the reaction mixture was diluted with cold water. The solid precipitated was filtered and dried to afford rac-(4bS,5R,6R,7S,7aR)-7a-(4-bromophenyl)-4b,5-dihydroxy-4-methoxy-N-(2-methoxyethyl)-7-phenyl-4b,6,7,7a-tetrahydro-5H-cyclopenta[4,5]furo[2,3-c]pyridine-6-carboxamide (Cpd. No. 262F) as white solid. Yield: 1.55 g, 70%; MS (ESI) m/z 555.21[M+1]$^+$; $^1$H NMR (400 MHz, DMSO-$d_6$) 8.38 (t, J=5.12 Hz, 1H), 8.08 (s, 1H), 7.98 (s, 1H), 7.24 (d, J=8.52 Hz, 2H), 7.08-6.96 (m, 7H), 5.66 (s, 1H), 5.03 (d, J=3.88 Hz, 1H), 4.55 (t, J=4.08 Hz, 1H), 4.34 (d, J=14.24 Hz, 1H), 3.95 (dd, J=14.4, 4.4 Hz, 1H), 3.87 (s, 3H), 3.29-3.15 (m, 7H).

Example 263

4-((4bS,5R,6S,7S,7aR)-4b,5-dihydroxy-4-methoxy-6-(((2-methoxyethyl)amino)methyl)-7-phenyl-4b,5,6,7-tetrahydro-7aH-cyclopenta[4,5]furo[2,3-c]pyridin-7a-yl)benzonitrile hydrochloride (Cpd. No. 263F)

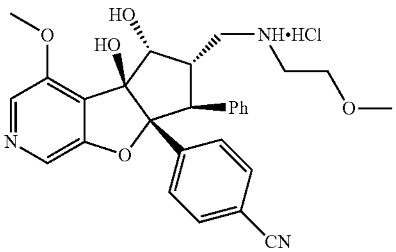

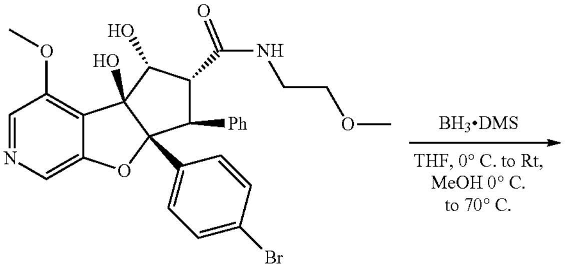

1

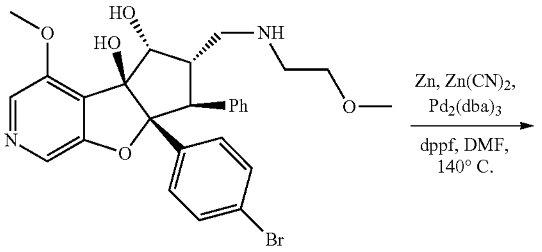

2

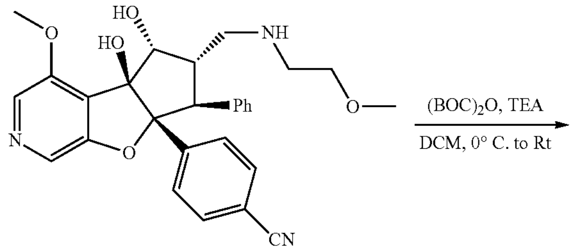

3

-continued

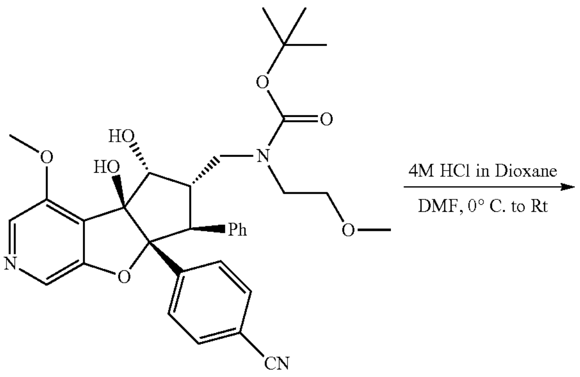

4

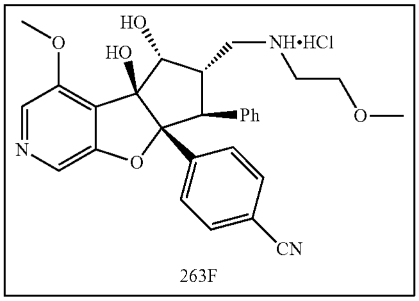

263F

Synthesis of rac-(4bS,5R,6S,7S,7aR)-7a-(4-bromophenyl)-4-methoxy-6-(((2-methoxyethyl)amino)methyl)-7-phenyl-5,6,7,7a-tetrahydro-4bH-cyclopenta[4,5]furo[2,3-c]pyridine-4b,5-diol (2)

To a solution of rac-(4bS,5R,6R,7S,7aR)-7a-(4-bromophenyl)-4b,5-dihydroxy-4-methoxy-N-(2-methoxyethyl)-7-phenyl-4b,6,7,7a-tetrahydro-5H-cyclopenta[4,5]furo[2,3-c]pyridine-6-carboxamide (1, 1.50 g, 2.70 mmol) in dry tetrahydrofuran (20 ml) at 0° C., borane dimethyl sulphide complex (3.07 g, 40.5 mmol) was added drop wise over a period of 5 min. The reaction mixture was slowly brought to room temperature and stirred for additional 16 h. After completion, the reaction mixture was quenched with methanol at 0° C. and heated to reflux for 16 h. After completion, solvent was removed under reduced pressure and the residue was purified by silica gel (100-200 mesh size) using 0-10% methanolic ammonia in dichloromethane as eluent. The desired fractions were concentrated under reduced pressure to afford rac-(4bS,5R,6S,7S,7aR)-7a-(4-bromophenyl)-4-methoxy-6-(((2-methoxyethyl)amino) methyl)-7-phenyl-5,6,7,7a-tetrahydro-4bH-cyclopenta[4,5]furo[2,3-c]pyridine-4b,5-diol (2) as white solid. Yield: 1.00 g, 69%, MS (ESI) m/z 541.21[M+1]$^+$.

Synthesis of rac-4-((4bS,5R,6S,7S,7aR)-4b,5-dihydroxy-4-methoxy-6-(((2-methoxyethyl)amino) methyl)-7-phenyl-4b,5,6,7-tetrahydro-7aH-cyclopenta[4,5]furo[2,3-c]pyridin-7a-yl)benzonitrile (3)

To a solution of rac-(4bS,5R,6S,7S,7aR)-7a-(4-bromophenyl)-4-methoxy-6-(((2-methoxyethyl)amino)methyl)-7-phenyl-5,6,7,7a-tetrahydro-4bH-cyclopenta[4,5]furo[2,3-c]pyridine-4b,5-diol (2, 0.950 g, 1.75 mmol) in N,N-dimethylformamide (10 mL), zinc cyanide (1.23 g, 10.52 mmol) and zinc dust (0.057 g, 0.875 mmol) were added at room temperature and the reaction mixture was degassed with argon for 15 min. 1,1'-Bis(diphenylphosphino)ferrocene (0.097 g, 0.175 mmol) and tris(dibenzylideneacetone) dipalladium (0.080 g, 0.0875 mmol) were added to the reaction, degassed for additional 5 min and mixture was heated at 140° C. for 16 h. After completion, the reaction mixture was diluted with ethyl acetate and washed with cold water. The organic layer was separated and dried over anhydrous sodium sulphate, filtered and concentrated to give crude product. The crude product was purified by Preparative HPLC to afford rac-4-((4bS,5R,6S,7S,7aR)-4b,5-dihydroxy-4-methoxy-6-(((2-methoxyethyl)amino) methyl)-7-phenyl-4b,5,6,7-tetrahydro-7aH-cyclopenta[4,5]furo[2,3-c] pyridin-7a-yl)benzonitrile (3) as white solid. Yield: 0.163 g, 19%; MS (ESI) m/z 488.32[M+1]$^+$.

Synthesis of tert-butyl-(((4bS,5R,6S,7S,7aR)-7a-(4-cyanophenyl)-4b,5-dihydroxy-4-methoxy-7-phenyl-4b,6,7,7a-tetrahydro-5H-cyclopenta[4,5]furo[2,3-c] pyridin-6-yl)methyl)(2-methoxyethyl)carbamate (4)

To a solution of rac-4-((4bS,5R,6S,7S,7aR)-4b,5-dihydroxy-4-methoxy-6-(((2-methoxyethyl)amino)methyl)-7-phenyl-4b,5,6,7-tetrahydro-7aH-cyclopenta[4,5]furo[2,3-c] pyridin-7a-yl)benzonitrile (3, 0.15 g, 0.37 mmol) in dichloromethane (3 mL) at 0° C., triethylamine (0.08 mL, 0.61 mmol), Boc anhydride (0.1 mL, 0.45 mmol) were added at same temperature and the mixture was stirred for 1 h at room temperature. After completion, the reaction mixture was diluted with cold water, extracted with dichloromethane. The organic layer was separated and dried over anhydrous sodium sulphate, filtered and concentrated to give crude product. The crude product was washed with n-pentane to afford rac-tert-butyl (((4bS,5R,6S,7S,7aR)-7a-(4-cyanophenyl)-4b,5-dihydroxy-4-methoxy-7-phenyl-4b,6,7,7a-tetrahydro-5H-cyclopenta[4,5]furo[2,3-c]pyridin-6-yl) methyl)(2-methoxyethyl)carbamate as white solid. Yield: 0.15 g, 83%; MS (ESI) m/z 588.56 [M+1]$^+$. The enantiomers were separated by chiral HPLC [chiralpak IC (4.6×250) mm, 5μ], n-Hexane/Isopropanol=70/30 (v/v). Peak 1 (48 mg) and Peak 2 (4, 45 mg).

Synthesis of 4-((4bS,5R,6S,7S,7aR)-4b,5-dihydroxy-4-methoxy-6-(((2-methoxyethyl)amino) methyl)-7-phenyl-4b,5,6,7-tetrahydro-7aH-cyclopenta[4,5]furo[2,3-c]pyridin-7a-yl)benzonitrile hydrochloride (Cpd. No. 263F)

To a solution of tert-butyl (((4bR,5S,6R,7R,7aS)-7a-(4-cyanophenyl)-4b,5-dihydroxy-4-methoxy-7-phenyl-4b,6,7,7a-tetrahydro-5H-cyclopenta[4,5]furo[2,3-c]pyridin-6-yl) methyl)(2-methoxyethyl)carbamate (4, 0.045 g, 0.076 mmol) in dichloromethane (2 mL) at 0° C., 4M hydrochloric acid in 1,4-Dioxane (1 mL), was added at same temperature and the mixture was stirred for 3 h at room temperature. After completion, the reaction mixture was concentrated to give residue. The residue obtained was triturated with mixture of ether and n-pentane filtered and dried to afford 4-((4bS,5R,6S,7S,7aR)-4b,5-dihydroxy-4-methoxy-6-(((2-methoxyethyl)amino)methyl)-7-phenyl-4b,5,6,7-tetrahydro-7aH-cyclopenta[4,5]furo[2,3-c]pyridin-7a-yl)benzonitrile hydrochloride (Cpd. No. 263F) as white solid. Yield: 0.032 g, 84%; Peak 1 (32 mg), $[\alpha]_D$−12.0° (c 0.20, $CHCl_3$), $R_t$=9.10 min [CHIRALPAK IG (4.6×250)mm, 5μ]$CO_2$/0.2% Triethylamine in methanol=(80/20)], ee: 99.56% MS (ESI) m/z 488.26 [M+1]$^+$; $^1$H NMR (400 MHz, DMSO-$d_6$) 8.24 (s, 1H), 8.13 (s, 1H), 7.57 (d, J=8.44 Hz, 2H), 7.34 (d, J=8.4 Hz, 2H), 7.13-7.04 (m, 5H), 6.02 (bs, 1H), 5.44 (bs, 1H), 4.74 (s, 1H), 3.94 (s, 3H), 3.81 (d, J=14.08 Hz, 1H), 3.61 (bs, 3H), 3.31 (s, 3H), 3.15-3.05 (m, 4H), 2.77 (bs, 1H).

Example 264

Rac-((1R,5S)-3-oxa-8-azabicyclo[3.2.1]octan-8-yl) ((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl) methanone (Cpd. No. 264F)

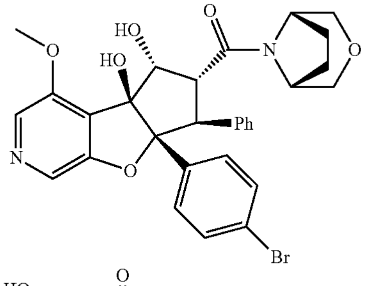

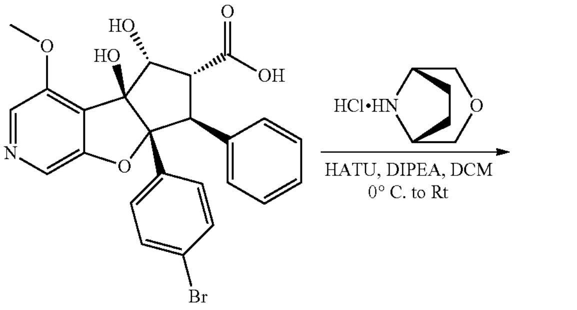

1

264F

Synthesis of rac-((1R,5S)-3-oxa-8-azabicyclo[3.2.1] octan-8-yl)((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)methanone (Cpd. No. 264F)

To a solution of rac-(4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylic acid (1, 1.5 g, 3.02 mmol) in dichloromethane (20 mL) at 0° C., were added 1-[Bis(dimethylamino)methylene]-1H-1,2,3-triazolo[4,5-b]pyridinium3-oxide hexafluorophosphate (1.71 g, 4.52 mmol) and N,N-diisopropylethylamine (3.28 ml, 18.4 mmol). The resulting reaction mixture was stirred for 5 min. (1R,5S)-3-oxa-8-azabicyclo [3.2.1]octane hydrochloride (0.9 g, 6.03 mmol) was then added at the same temperature and the reaction mixture was stirred for 16 h at room temperature. After completion, the reaction mixture was diluted with dichloromethane and washed with cold water. The organic layer was separated, dried over anhydrous sodium sulphate, filtered and concentrated to give crude product. The crude product was purified by silica gel (100-200 mesh size) column chromatography using 0-5% methanol in dichloromethane as eluent. The desired fractions were concentrated to afford rac-((1R,5S)-3-oxa-8-azabicyclo[3.2.1]octan-8-yl)((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)methanone (Cpd. No. 264F) as white solid. Yield: 1.70 g, 95%; MS (ESI) m/z 593.21 $[M+1]^+$; $^1$H NMR (400 MHz, DMSO-$d_6$) δ 8.10 (s, 1H), 7.99 (s, 1H), 7.19 (d, J=8.0 Hz, 2H), 7.08-6.97 (m, 6H), 6.88 (d, J=7.2 Hz, 1H), 5.73 (d, J=6.8 Hz, 1H), 5.20 (m, 1H), 4.71-4.63 (m, 2H), 4.52-4.46 (m, 1H), 4.31 (bs, 1H), 4.10-4.05 (m, 1H), 3.88 (s, 3H), 3.79-3.70 (m, 2H), 3.52 (bs, 2H), 2.08 (bs, 2H), 1.78-1.63 (m, 2H).

Example 265

4-((4bS,5R,6S,7S,7aR)-6-(((1R,5S)-3-oxa-8-azabicyclo[3.2.1]octan-8-yl) methyl)-4b,5-dihydroxy-4-methoxy-7-phenyl-4b,5,6,7-tetrahydro-7aH-cyclopenta [4,5]furo[2,3-c]pyridin-7a-yl)benzonitrile (Cpd. No. 265F)

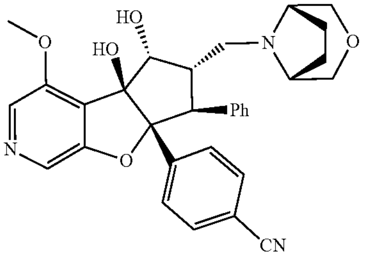

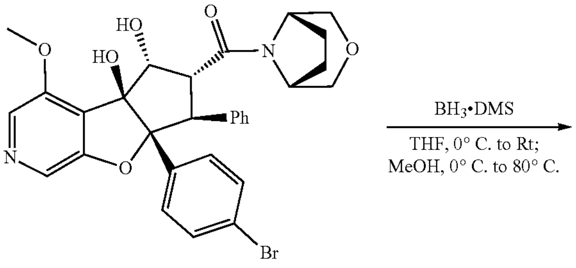

1

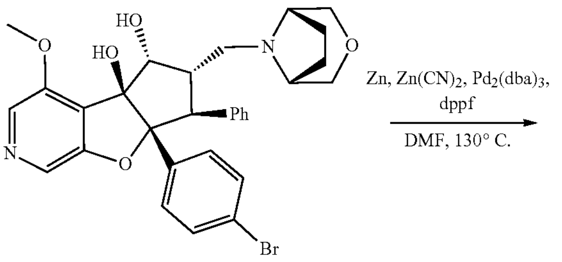

2

-continued

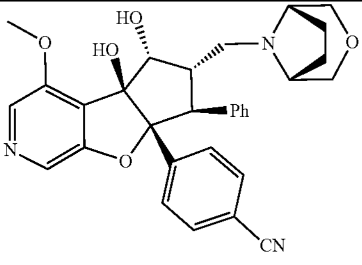

265F

Synthesis of rac-(4bS,5R,6S,7S,7aR)-6-(((JR,5S)-3-oxa-8-azabicyclo[3.2.1]octan-8-yl)methyl)-7a-(4-bromophenyl)-4-methoxy-7-phenyl-5,6,7,7a-tetrahydro-4bH-cyclopenta[4,5]furo[2,3-c]pyridine-4b,5-diol (2)

To a solution of rac-((1R,5S)-3-oxa-8-azabicyclo[3.2.1]octan-8-yl)((4bS,5R,6R,7S,7aR)-7a-(4-bromophenyl)-4b,5-dihydroxy-4-methoxy-7-phenyl-4b,6,7,7a-tetrahydro-5H-cyclopenta [4,5]furo[2,3-c]pyridin-6-yl)methanone (1, 1.20 g, 2.02 mmol) in dry tetrahydrofuran (20 ml) at 0° C., borane dimethyl sulfide complex (1.90 ml, 20.2 mmol) was added drop wise over a period of 5 min. The reaction mass was slowly brought to room temperature and stirred for additional 16 h. After completion, the reaction mixture was quenched with methanol at 0° C. and heated to reflux for 10 h. After completion, solvent was removed under reduced pressure and the residue was purified by silica gel (100-200 mesh size) column chromatography using 0-5% methanol in dichloromethane as eluent. The desired fractions were concentrated under reduced pressure to afford rac-(4bS,5R,6S,7S,7aR)-6-(((1R,5S)-3-oxa-8-azabicyclo[3.2.1]octan-8-yl)methyl)-7a-(4-bromophenyl)-4-methoxy-7-phenyl-5,6,7,7a-tetrahydro-4bH-cyclopenta[4,5]furo[2,3-c]pyridine-4b,5-diol (2) as white solid. Yield: 1.0 g, (crude); MS (ESI) 579.21 m/z $[M+1]^+$.

Synthesis of 4-((4bS,5R,6S,7S,7aR)-6-(((JR,5S)-3-oxa-8-azabicyclo[3.2.1]octan-8-yl) methyl)-4b,5-dihydroxy-4-methoxy-7-phenyl-4b,5,6,7-tetrahydro-7aH-cyclopenta [4,5]furo[2,3-c]pyridin-7a-yl) benzonitrile (Cpd. No. 265F)

To a solution of rac-(4bS,5R,6S,7S,7aR)-6-(((1R,5S)-3-oxa-8-azabicyclo[3.2.1]octan-8-yl)methyl)-7a-(4-bromophenyl)-4-methoxy-7-phenyl-5,6,7,7a-tetrahydro-4bH-cyclopenta[4,5]furo[2,3-c]pyridine-4b,5-diol (2, 1.0 g, 0.17 mmol) in N,N-dimethylformamide (10 mL), zinc cyanide (0.98 g, 0.86 mmol) and zinc dust (0.013 g, 0.020 mmol) were added at room temperature and the reaction mixture was degassed with argon for 15 min. 1,1'-Bis(diphenylphosphino)ferrocene (0.019 g, 0.035 mmol) and tris(dibenzylideneacetone)dipalladium (0.047 g, 0.052 mmol) were added to the reaction, degassed for additional 5 min and mixture was heated at 130° C. for 2 h. After completion, the reaction mixture was diluted with ethyl acetate and washed with cold water. The organic layer was separated, dried over anhydrous sodium sulphate, filtered and concentrated to give crude product. The crude product was purified by silica gel (100-200 mesh size) column chromatography using 2-3% methanol in dichloromethane as eluent. The desired fractions were concentrated to afford rac-4-((4bS,5R,6S,7S, 7aR)-6-(((1R,5S)-3-oxa-8-azabicyclo[3.2.1]octan-8-yl)methyl)-4b,5-dihydroxy-4-methoxy-7-phenyl-4b,5,6,7-tetrahydro-7aH-cyclopenta[4,5]furo[2,3-c]pyridin-7a-yl)benzonitrile as white solid. Yield: 0.30 g; MS (ESD) m/z 526.36[M+1]$^+$. The enantiomers were separated by chiral SFC [CHIRALPAK IA (4.6×250) mm, 5μ] in CO2/0.1% TEA in MeOH (80/20). Peak 1 (Cpd. No. 265F, 72 mg), $[\alpha]_D$–26.5° (c 0.25, $CHCl_3$), $R_t$=6.077 min, ee: 99.84%; MS (ESI) m/z 526.26[M+1]$^+$; $^1H$ NMR (400 MHz, DMSO-$d_6$) 8.05 (s, 1H), 7.97 (s, 1H), 7.48 (d, J=8.4 Hz, 2H), 7.39 (d, J=8.4 Hz, 2H), 7.09-6.96 (m, 5H), 5.71 (s, 1H), 5.38 (s, 1H), 4.61 (s, 1H), 3.88 (s, 3H), 3.82 (d, J=14.2 Hz, 1H), 3.56 (d, J=7.6 Hz, 2H), 3.50 (t, J=12.0 Hz, 1H), 3.38 (s, 1H), 3.15 (bs, 1H), 2.94 (s, 1H), 2.44-2.41 (m, 2H), 2.23 (d, J=11.2 Hz, 1H), 1.69-1.62 (m, 4H). Peak-2 (104 mg), $[\alpha]_D$+39.2° (c 0.258, $CHCl_3$), $R_t$=7.813 min, ee: 99.68%; MS (ESI) m/z 526.26[M+1]$^+$; $^1H$ NMR (400 MHz, DMSO-$d_6$) □ 8.05 (s, 1H), 7.97 (s, 1H), 7.48 (d, J=8.4 Hz, 2H), 7.39 (d, J=8.4 Hz, 2H), 7.11-6.96 (m, 5H), 5.71 (s, 1H), 5.38 (bs, 1H), 4.61 (s, 1H), 3.88 (s, 3H), 3.84 (d, J=13.6 Hz, 1H), 3.56 (d, J=7.6 Hz, 2H), 3.50 (t, J=12.0 Hz, 1H), 3.37 (s, 1H), 3.17 (bs, 1H), 3.02 (s, 1H), 2.44-2.41 (m, 2H), 2.23 (d, J=11.2 Hz, 1H), 1.69-1.62 (m, 4H).

Example 266

Rac-((1R,5S)-3-oxa-6-azabicyclo[3.1.1]heptan-6-yl)((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)methanone (Cpd. No. 266F)

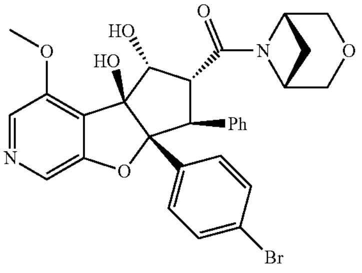

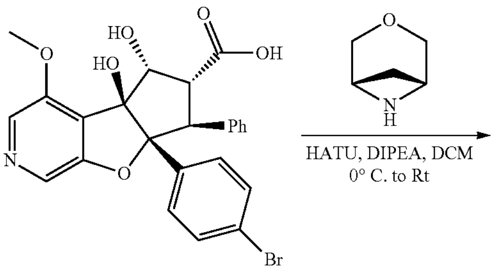

1

-continued

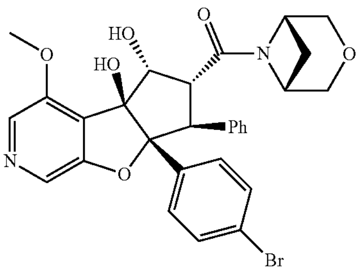

266F

Synthesis of rac-((R,5S)-3-oxa-6-azabicyclo[3.1.1]heptan-6-yl)((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)methanone (Cpd. No. 266F)

To a solution of rac-(4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylic acid (1, 1.0 g, 2.0 mmol) in dichloromethane (15 mL), 1-[Bis(dimethylamino)methylene]-1H-1,2,3-triazolo[4,5-b]pyridinium3-oxide hexafluorophosphate (1.14 g, 6.0 mmol) and NN-diisopropylethylamine (1.37 ml, 8.0 mmol) were added at 0° C. and stirred the reaction mixture for 5 min. (1R,5S)-3-oxa-6-azabicyclo[3.1.1]heptane (0.39 g, 4.0 mmol) was then added and the reaction mixture was stirred for 2 h at room temperature. After completion, reaction mixture was concentrated and the solid obtained was taken in ice cold water, filtered and dried to afford rac-((1R,5S)-3-oxa-6-azabicyclo[3.1.1]heptan-6-yl)((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)methanone (Cpd. No. 266F) as off white solid. Yield: 0.92 g, 79%; MS (ESI) m/z 579.25[M+1]$^+$; $^1H$ NMR (400 MHz, DMSO-$d_6$) b 8.08 (s, 1H), 7.98 (s, 1H), 7.19 (d, J=8.7 Hz, 2H), 7.10-6.93 (m, 7H), 5.74-4.73 (m, 3H), 4.65-4.16 (m, 4H), 4.01-3.73 (m, 7H), 2.57 (bs, 1H), 1.93-1.82 (m, 1H).

Example 267

Rac-4-((4bS,5R,6S,7S,7aR)-6-(((1R,5S)-3-oxa-6-azabicyclo[3.1.1]heptan-6-yl)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 267F)

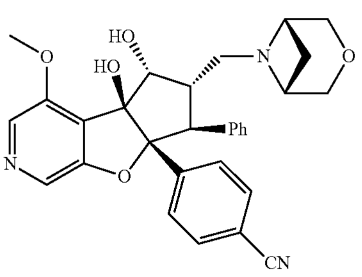

-continued

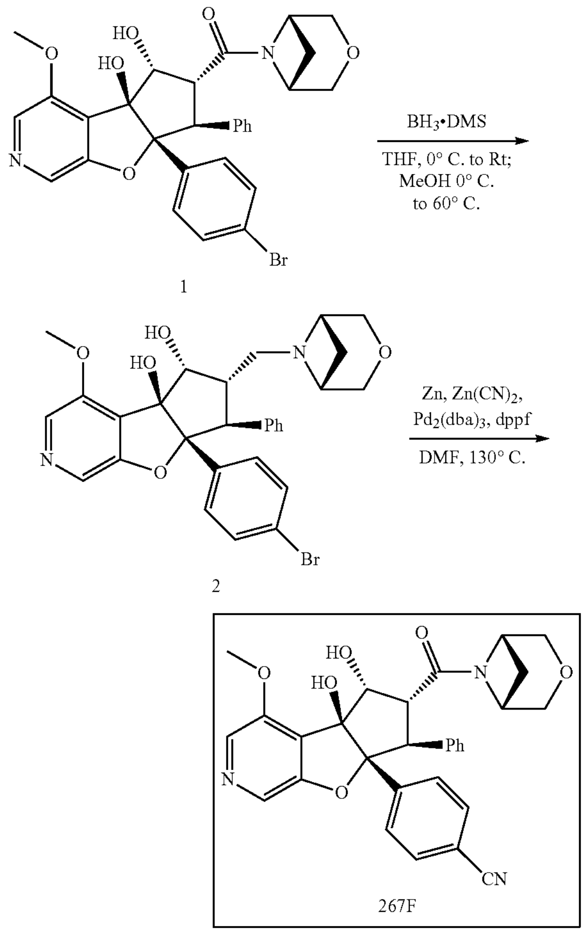

1

2

267F

Synthesis of rac-(4bS,5R,6S,7S,7aR)-6-(((1R,5S)-3-oxa-6-azabicyclo[3.1.1]heptan-6-yl)methyl)-7a-(4-bromophenyl)-4-methoxy-7-phenyl-5,6,7,7a-tetrahydro-4bH-cyclopenta[4,5]furo[2,3-c]pyridine-4b,5-diol (2)

To a solution of rac-((1R,5S)-3-oxa-6-azabicyclo[3.1.1]heptan-6-yl)((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)methanone (1, 0.35 g, 1.0 mmol) in tetrahydrofuran (15 mL), borane dimethyl sulfide (0.57 ml, 6.0 mmol) was added at 0° C. The reaction mixture was stirred for 6 h at room temperature. After completion, reaction mixture was quenched with methanol at 0° C. and then heated at 60° C. for 16 h. The reaction mixture was loaded directly onto two 2 g Strata X-C ion exchange columns from Phenomenex. The columns were washed with acetonitrile and then methanol. Then the product was eluted with a 1:2:7 mixture of ammonium hydroxide: dichloromethane:methanol. The eluent containing the desired product was concentrated to afford rac-(4bS,5R,6S,7S,7aR)-6-(((1R,5S)-3-oxa-6-azabicyclo[3.1.1]heptan-6-yl)methyl)-7a-(4-bromophenyl)-4-methoxy-7-phenyl-5,6,7,7a-tetrahydro-4bH-cyclopenta[4,5]furo[2,3-c]pyridine-4b,5-diol (2) as white solid. Yield: 0.11 g, 32%; MS (ESI) m/z 565.25$[M+1]^+$.

Synthesis of rac-4-((4bS,5R,6S,7S,7aR)-6-(((1R,5S)-3-oxa-6-azabicyclo[3.1.1]heptan-6-yl)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 267F)

To a mixture of rac-(4bS,5R,6S,7S,7aR)-6-(((1R,5S)-3-oxa-6-azabicyclo[3.1.1]heptan-6-yl)methyl)-7a-(4-bromophenyl)-4-methoxy-7-phenyl-5,6,7,7a-tetrahydro-4bH-cyclopenta[4,5]furo[2,3-c]pyridine-4b,5-diol (2, 0.15 g, 2.6 mmol) in N,N-dimethylformamide (3.0 mL) at room temperature, zinc cyanide (186 mg, 1.59 mmol) and zinc (16 mg, 0.26 mmol) were added at room temperature and degassed the mixture with argon for 15 min. 1,1'-Bis(diphenylphosphino) ferrocene (43 mg, 0.059 mmol) and tris (dibenzylideneacetone)dipalladium (53 mg, 0.059 mmol) were added to the reaction mixture and degassing was continued for another 5 min. The reaction mixture was heated at 130° C. for 1.5 h. After completion, the reaction was cooled to room temperature and passed through celite bed. The filtrate was diluted with ethyl acetate and washed with water. The organic layer was separated, dried over anhydrous sodium sulphate and concentrated under reduced pressure to give the crude product. The crude product was purified by combi-flash (12 g, RediSep column) using 0-10% methanol in dichloromethane as eluent. The product obtained was repurified by reverse phase preparative HPLC. The desired fractions were lyophilized to afford rac-4-((4bS,5R,6S,7S,7aR)-6-(((1R,5S)-3-oxa-6-azabicyclo[3.1.1]heptan-6-yl)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 267F) as white solid. Yield: 0.075 g, 55%; MS (ESI) m/z 512.30$[M+1]^+$; $^1H$ NMR (400 MHz, DMSO-$d_6$) δ 8.05 (s, 1H), 7.96 (s, 1H), 7.48 (d, J=8.44 Hz, 2H), 7.38 (d, J=8.52 Hz, 2H), 7.10-7.07 (m, 2H), 7.03-7.01 (m, 3H), 6.18 (bs, 1H), 5.71 (s, 1H), 4.53 (d, J=3.84 Hz, 1H), 3.98 (d, J=10.84 Hz, 1H), 3.87 (bs, 4H), 3.60 (d, J=10.16 Hz, 1H), 3.55-3.45 (m, 2H), 3.09-3.06 (m, 1H), 2.81 (dd, J=7.9 Hz, 12.8 Hz, 1H), 2.66 (d, J=10.64 Hz, 1H), 2.50-2.43 (m, 2H), 1.88 (s, 1H) 1.62 (d, J=7.88 Hz, 1H).

Example 268

4-((4bS,5R,6S,7S,7aR)-6-(((1R,5S)-8-azabicyclo[3.2.1]octan-8-yl)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 268F)

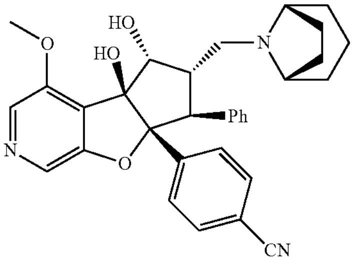

-continued

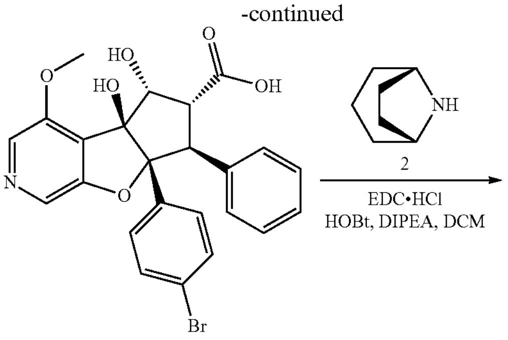

1

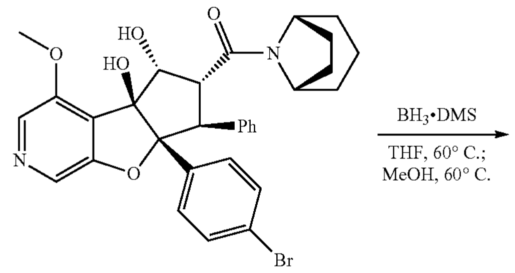

3

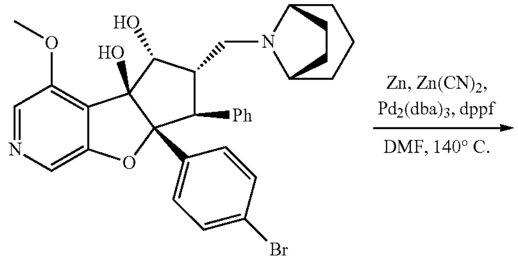

4

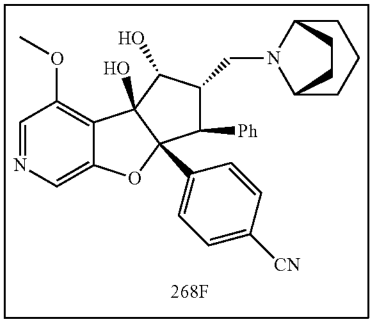

268F

Synthesis of rac-((1R,5S)-8-azabicyclo[3.2.1]octan-8-yl)((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)methanone (3)

To a solution of rac-(4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylic acid (1, 0.05 g, 0.10 mmol) in dichloromethane (5.0 mL), 1-ethyl-3-(3-dimethylaminopropyl) carbodiimide (0.043 g, 0.32 mmol), hydroxybenzotriazole (0.04 g, 0.3 mmol) and N,N-diisopropylethylamine (0.09 mL, 0.5 mmol) were added at 0° C. and stirred the mixture for 5 min. (1R,5S)-8-azabicyclo[3.2.1]octane (2, 0.016 g, 0.15 mmol) was then added at same temperature and the reaction was stirred at room temperature for 5 h. After completion, reaction mass was diluted with dichloromethane (20 mL) and washed with cold water. The organic layer was separated and dried over anhydrous sodium sulphate, filtered and concentrated under reduced pressure. The crude was purified by reverse phase HPLC to afford rac-((1R,5S)-8-azabicyclo[3.2.1]octan-8-yl)((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)methanone (3) as white solid. Yield: 23.0 mg, 43%. MS (ESI) m/z 591.18[M+1]$^+$; UPLC 99.6%; $^1$H NMR (400 MHz, DMSO-$d_6$, at High temperature VT (373K) δ: 8.11 (s, 1H), 8.01 (s, 1H), 7.21 (d, J=8.6 Hz, 2H), 7.11 (d, J=8.1 Hz, 2H), 7.05-6.94 (m, 5H), 4.70 (d, J=4.8 Hz, 1H), 4.52 (d, J=13.2 Hz, 1H), 4.09-4.05 (m, 1H), 3.92 (s, 3H), 2.01-1.78 (m, 8H), 1.60-1.55 (m, 4H).

Synthesis of rac-(4bS,5R,6S,7S,7aR)-6-(((1R,5S)-8-azabicyclo[3.2.1]octan-8-yl)methyl)-7a-(4-bromophenyl)-4-methoxy-7-phenyl-5,6,7,7a-tetrahydro-4bH-cyclopenta[4,5]furo[2,3-c]pyridine-4b,5-diol (4)

To a solution of rac-((1R,5S)-8-azabicyclo[3.2.1]octan-8-yl)((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)methanone (3, 0.50 g, 0.84 mmol) in tetrahydrofuran (10 mL), Borane dimethyl sulphide (0.2 mL, 2.1 mmol), was added at 0° C. and stirred the mixture for 3 h at room temperature. After completion, reaction mass was quenched with methanol (5.0 mL) and again heated for 10 h at 60° C. The reaction mixture was concentrated to give crude. The crude was purified by combi-flash (12 g, RediSep column) using 5-20% methanol in dichloromethane as eluent. The desired fractions were concentrated to afford rac-(4bS,5R,6S,7S,7aR)-6-(((1R,5S)-8-azabicyclo[3.2.1]octan-8-yl)methyl)-7a-(4-bromophenyl)-4-methoxy-7-phenyl-5,6,7,7a-tetrahydro-4bH-cyclopenta[4,5]furo[2,3-c]pyridine-4b,5-diol (4) as off white solid. Yield: 0.45 g, 92%; MS (ESI) m/z 577.4[M+1]$^+$.

Synthesis of 4-((4bS,5R,6S,7S,7aR)-6-(((1R,5S)-8-azabicyclo[3.2.1]octan-8-yl)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 268F)

To a solution of rac-(4bS,5R,6S,7S,7aR)-6-(((1R,5S)-8-azabicyclo[3.2.1]octan-8-yl)methyl)-7a-(4-bromophenyl)-4-methoxy-7-phenyl-5,6,7,7a-tetrahydro-4bH-cyclopenta[4,5]furo[2,3-c]pyridine-4b,5-diol (4, 0.450 g, 0.78 mmol) in N,N-dimethylformamide (5.0 mL), zinc cyanide (0.543 g, 4.6 mmol) and zinc (0.005 g, 0.078 mmol) were added at room temperature and degassed the mixture with argon for 15 min. 1,1'-Bis(diphenylphosphino)ferrocene (0.130 g, 0.23 mmol), tris(dibenzylideneacetone)dipalladium (0.214 g, 0.023 mmol) were added to the reaction and degassing was continued for another 5 min. The reaction mixture was heated at 140° C. for 3 h. After completion, the reaction was cooled to room temperature and passed through celite bed. The filtrate was diluted with ethyl acetate and washed with water. The organic layer was separated, dried over anhydrous sodium sulphate and concentrated under reduced pressure to give the crude. The crude was purified by combi-flash (4 g, RediSep column) using 0-15% methanol in dichloromethane as eluent. The desired fractions were concentrated under reduced pressure. The crude was purified by reverse phase preparative HPLC and desired fractions were lyophilized to give rac-4-((4bS,5R,6S,7S,7aR)-6-(((1R,5S)-8-azabicyclo[3.2.1]octan-8-yl)methyl)-4b,5-dihydroxy-4-methoxy-7-phenyl-4b,5,6,7-tetrahydro-7aH-cyclopenta[4,5]furo[2,3-c]pyridin-7a-yl)benzonitrile as white solid. Yield: 140 mg, 35%. The enantiomers were separated by chiral preparative HPLC [Chiralpak IA (4.6×250) mm, 5]; 0.1% TEA in n-Hexane/IPA=60/40 (V/V); Peak 1 (9 mg), $[\alpha]_D$+33.10 (c 0.27, $CHCl_3$), $R_t$=9.36, ee >99%; MS (ESI) m/z 523.93[M+1]$^+$; UPLC: 98.8%; $^1$H NMR (400 MHz, DMSO-$d_6$) δ 8.06 (s, 1H), 7.97 (s, 1H), 7.47 (d, J=8.4 Hz, 2H), 7.37 (d, J=8.4 Hz, 2H), 7.09-6.97 (m, 5H), 5.68 (s, 1H), 4.6 (d, J=3.5 Hz, 1H), 3.95 (d, J=13.9 Hz, 1H), 3.88 (s, 3H), 3.13-3.11 (m, 1H), 2.97 (bs, 1H), 1.90 (s, 2H), 1.76 (m, 1H), 1.74-1.31 (m, 1OH); Peak 2 (Cpd. No. 268F, 8 mg), $[\alpha]_D$ −58.9° (c 0.25, $CHCl_3$), $R_t$=14.22, ee >99%; MS (ESI) m/z 524.31 [M+1]$^+$; UPLC: 97.3%; $^1$H NMR (400 MHz, DMSO-$d_6$) δ 8.06 (s, 1H), 7.97 (s, 1H), 7.48 (d, J=8.4 Hz, 2H), 7.37 (d, J=8.4 Hz, 2H), 7.07-6.98 (m, 5H), 6.05 (s, 1H), 5.69 (s, 1H), 4.6 (s, 1H), 3.95 (m, 1H), 3.88 (s, 3H), 3.12 (bs, 1H), 2.95 (bs, 1H), 2.60 (bs, 2H), 1.76 (m, 1H), 1.59-1.14 (m, 1OH).

Example 269

Rac-(3aR,4R,4aR,9bS,9cR)-4a-(4-(difluoromethyl)phenyl)-9b-hydroxy-9-methoxy-4-phenyl-3,3a,4,4a,9b,9c-hexahydro-2H-oxazolo[4",5":4',5']cyclopenta[1',2':4,5]furo[2,3-c]pyridin-2-one (Cpd. No. 269F)

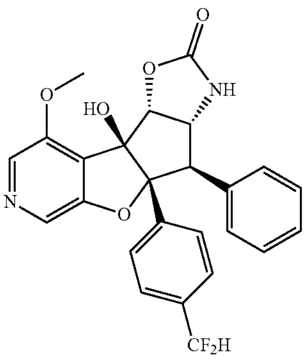

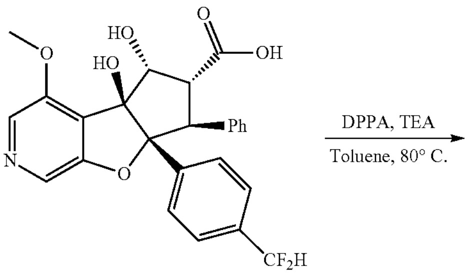

1

-continued

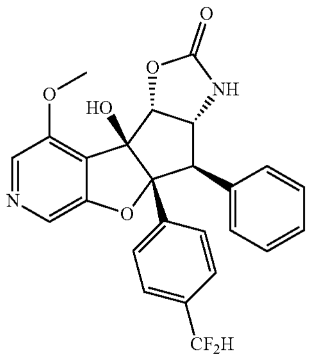

269F

Synthesis of rac-(3aR,4R,4aR,9bS,9cR)-4a-(4-(difluoromethyl)phenyl)-9b-hydroxy-9-methoxy-4-phenyl-3,3a,4,4a,9b,9c-hexahydro-2H-oxazolo[4",5":4',5]cyclopenta[1',2':4,5]furo[2,3-c]pyridin-2-one (Cpd. No. 269F)

To a solution of rac-(4bS,5R,6R,7S,7aR)-7a-(4-(difluoromethyl)phenyl)-4b,5-dihydroxy-4-methoxy-7-phenyl-4b,6,7,7a-tetrahydro-5H-cyclopenta[4,5]furo[2,3-c]pyridine-6-carboxylic acid (1, 0.5 g, 1.0 mmol) in toluene (10 mL), triethylamine (0.2 mL, 1.5 mmol) and diphenylphosphoryl azide (0.29 ml, 1.3 mmol) were added. The reaction mixture was stirred for 16 h at 80° C. After completion, reaction mass was diluted with water (10 mL) and solid precipitated was filtered and washed with pentane then dried to give rac-(3aR,4R,4aR,9bS,9cR)-4a-(4-(difluoromethyl)phenyl)-9b-hydroxy-9-methoxy-4-phenyl-3,3a,4,4a,9b,9c-hexahydro-2H-oxazolo[4",5":4',5']cyclopenta[1',2':4,5]furo[2,3-c]pyridin-2-one (Cpd. No. 269F) as off white solid. Yield: 0.36 g, 73%; MS (ESI) m/z 467.24[M+1]$^+$, UPLC: 95.03%; $^1$H NMR (400 MHz, DMSO-d6) δ 8.31 (s, 1H), 8.21 (s, 1H), 8.15 (s, 1H), 7.36 (d, J=8.0 Hz, 2H), 7.26 (d, J=8.0 Hz, 2H), 7.10-6.79 (m, 6H), 6.03 (s, 1H), 5.43 (d, J=8.3 Hz, 1H), 4.97 (t, J=9.5 Hz, 1H), 3.97 (s, 3H), 3.46 (d, J=10.8 Hz, 1H).

Example 270

Rac-(4bS,5R,6R,7R,7aR)-6-amino-7a-(4-(difluoromethyl)phenyl)-4-methoxy-7-phenyl-5,6,7,7a-tetrahydro-4bH-cyclopenta[4,5]furo[2,3-c]pyridine-4b,5-diol (Cpd. No. 270F)

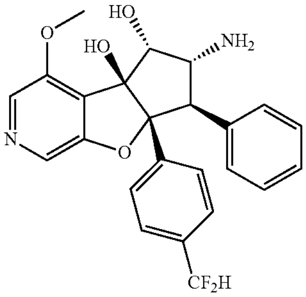

-continued

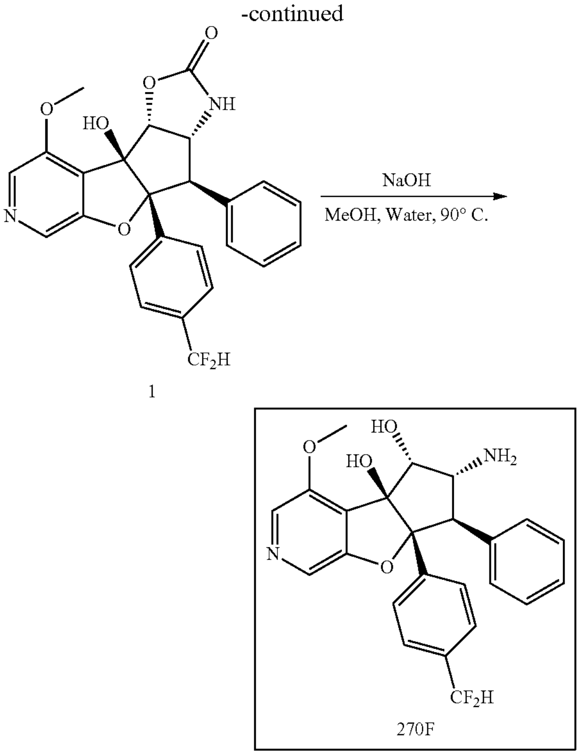

1

270F

Synthesis of rac-(4bS,5R,6R,7R, 7aR)-6-amino-7a-(4-(difluoromethyl)phenyl)-4-methoxy-7-phenyl-5,6,7,7a-tetrahydro-4bH-cyclopenta[4,5]furo[2,3-c]pyridine-4b,5-diol (Cpd. No. 270F)

To a solution of rac-(3aR,4R,4aR,9bS,9cR)-4a-(4-(difluoromethyl)phenyl)-9b-hydroxy-9-methoxy-4-phenyl-3,3a,4,4a,9b,9c-hexahydro-2H-oxazolo[4",5":4',5']cyclopenta[1',2':4,5]furo[2,3-c]pyridin-2-one (1, 0.35 g, 0.74 mmol) in methanol:water (1:1), sodium hydroxide (0.089 g, 2.2 mmol) was added. The reaction mixture was stirred for 16 h at 90° C. After completion, methanol was concentrated and the solid obtained was filtered and washed with diethyl ether, dried under vacuum to afford rac-(4bS,5R,6R,7R,7aR)-6-amino-7a-(4-(difluoromethyl)phenyl)-4-methoxy-7-phenyl-5,6,7,7a-tetrahydro-4bH-cyclopenta[4,5]furo[2,3-c]pyridine-4b,5-diol (Cpd. No. 270F) as white solid. Yield: 0.19 g, 58%; MS (ESI) m/z 441.19 $[M+1]^+$, UPLC: 97.71%; $^1H$ NMR (400 MHz, DMSO-d) δ 8.06 (s, 1H), 7.91 (s, 1H), 7.35-6.68 (m, 10H), 5.54 (bs, 1H), 5.16 (bs, 1H), 4.21 (m, 2H), 3.88 (s, 3H), 3.70 (d, J=9.8 Hz, 1H), 1.53 (brs, 2H).

Example 271

Rac-((4bS,5R,6R,7S,7aR)-7a-(4-chlorophenyl)-4b,5-dihydroxy-4-methoxy-N,N-dimethyl-7-phenyl-4b,6,7,7a-tetrahydro-5H-cyclopenta[4,5]furo[2,3-c]pyridine-6-carboxamide (Cpd. No. 271F)

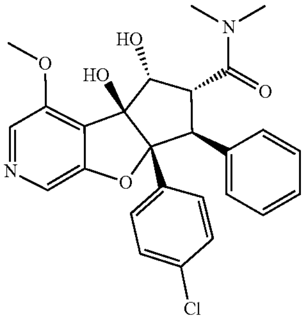

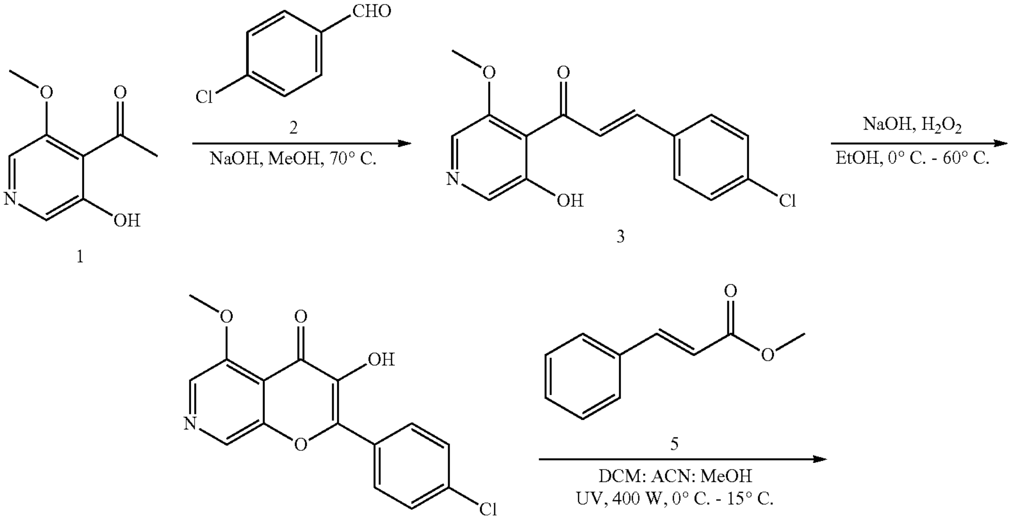

1

2

3

4

5

-continued

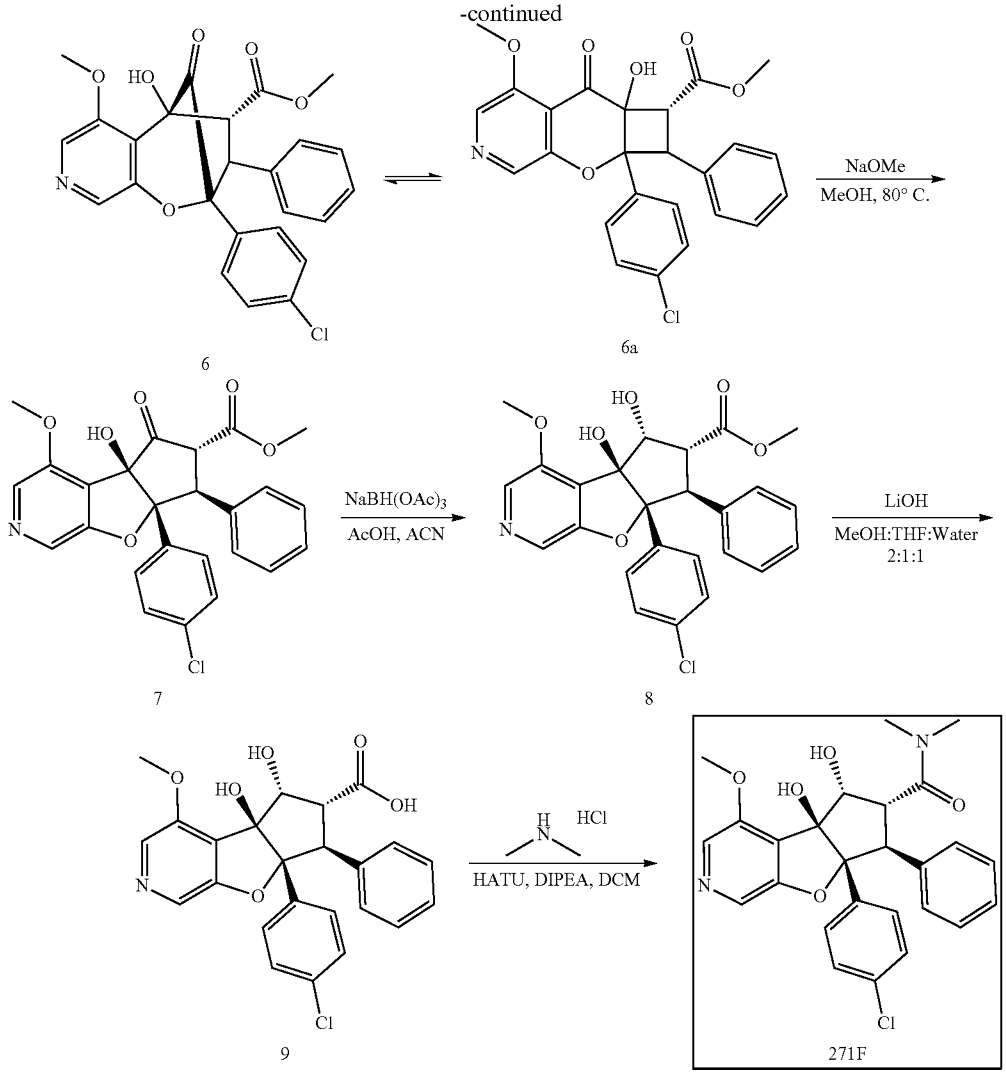

6 6a 7 8 9 271F

Synthesis of (E)-3-(4-chlorophenyl)-1-(3-hydroxy-5-methoxypyridin-4-yl)prop-2-en-1-one (3)

To a solution of 1-(3-hydroxy-5-methoxypyridin-4-yl) ethan-1-one (1, 5.0 g, 29.9 mmol) and 4-chlorobenzaldehyde (2, 4.2 g, 29.9 mmol) in methanol (50 mL), sodium hydroxide (3.60 g, 89.8 mmol) was added and the mixture was heated to reflux for 30 min. After completion, the reaction mixture was cooled to room temperature, The precipitated solid was filtered, washed with water, n-pentane and dried under high vacuum to afford (E)-3-(4-chlorophenyl)-1-(3-hydroxy-5-methoxypyridin-4-yl)prop-2-en-1-one (3) as yellow solid. Yield: 8.0 g, 92.0%; MS (ESI) m/z 290.39[M+1]$^+$.

Synthesis of 2-(4-chlorophenyl)-3-hydroxy-5-methoxy-4H-pyrano[2,3-c]pyridin-4-one (4)

To a solution of (E)-3-(4-chlorophenyl)-1-(3-hydroxy-5-methoxypyridin-4-yl)prop-2-en-1-one (3, 20.0 g, 69.2 mmol) in ethanol (500 mL) at 0° C., sodium hydroxide (3.30 g, 83.0 mmol) and 30% aqueous hydrogen peroxide (55.0 mL, 48.4 mmol) were added dropwise. The reaction mass was stirred for 30 min at 60° C. After completion, the reaction mass was cooled and neutralized by the addition of 6 M hydrogen chloride to pH ~7. The solid obtained was filtered, washed with cold ethanol, pentane and dried under high vacuum to afford 2-(4-chlorophenyl)-3-hydroxy-5-methoxy-4H-pyrano[2,3-c]pyridin-4-one (4) as pale yellow solid. Yield: 4.8 g, 23%; MS (ESI) m/z 304.09[M+1]$^+$.

Synthesis of rac-methyl (6R)-7a-(4-chlorophenyl)-5a-hydroxy-4-methoxy-5-oxo-7-phenyl-5a,6,7,7a-tetrahydro-5H-cyclobuta[5,6]pyrano[2,3-c]pyridine-6-carboxylate (6)

A solution of 2-(4-chlorophenyl)-3-hydroxy-5-methoxy-4H-pyrano[2,3-c]pyridin-4-one (4, 4.80 g, 15.80 mmol) and methyl cinnamate (5, 25.60 g, 158.0 mmol) in dichloromethane (200 mL), acetonitrile (100 mL) and methanol (100 mL) was placed in a UV reactor flask. The reaction mixture was irradiated under 400 watts UV light for 16 h at 0° C.-15° C. After completion, solvent was removed under reduced pressure and the residue was purified over a plug of silica gel eluting the compound with ethyl acetate. The desired fractions were concentrated under reduced pressure to afford rac-methyl (6R)-7a-(4-chlorophenyl)-5a-hydroxy-4-methoxy-5-oxo-7-phenyl-5a,6,7,7a-tetrahydro-5H-cyclobuta[5,6]pyrano[2,3-c]pyridine-6-carboxylate (6) as yellow brown solid. Yield: 6.10 g, crude; MS (ESI) m/z 466.82[M+1]$^+$.

Synthesis of rac-methyl (4bR,6R,7S,7aR)-7a-(4-chlorophenyl)-4b-hydroxy-4-methoxy-5-oxo-7-phenyl-4b,6,7,7a-tetrahydro-5H-cyclopenta[4,5]furo[2,3-c]pyridine-6-carboxylate (7)

The crude compound rac-methyl (6R)-7a-(4-chlorophenyl)-5a-hydroxy-4-methoxy-5-oxo-7-phenyl-5a,6,7,7a-tetrahydro-5H-cyclobuta[5,6]pyrano[2,3-c]pyridine-6-carboxylate (6, 6.10 g, 12.90 mmol) was suspended in methanol (60.0 mL) and treated with 25% sodium methoxide in methanol (30.0 mL). The reaction was heated at 80° C. for 3 h. After completion, the solvent was removed under reduced pressure. The crude was diluted with ammonium chloride solution and extracted with ethyl acetate. The organic phase was separated, dried over anhydrous sodium sulphate and concentrated under reduced pressure to afford rac-methyl (4bR,6R,7S,7aR)-7a-(4-chlorophenyl)-4b-hydroxy-4-methoxy-5-oxo-7-phenyl-4b,6,7,7a-tetrahydro-5H-cyclopenta[4,5]furo[2,3-c]pyridine-6-carboxylate (7) Yield: 5.56 g, crude.

Synthesis of rac-methyl (4bS,5R,6R,7S,7aR)-7a-(4-chlorophenyl)-4b,5-dihydroxy-4-methoxy-7-phenyl-4b,6,7,7a-tetrahydro-5H-cyclopenta[4,5]furo[2,3-c]pyridine-6-carboxylate (8)

To a solution of rac-methyl (4bR,6R,7S,7aR)-7a-(4-chlorophenyl)-4b-hydroxy-4-methoxy-5-oxo-7-phenyl-4b,6,7,7a-tetrahydro-5H-cyclopenta[4,5]furo[2,3-c]pyridine-6-carboxylate (7, 5.50 g, 11.80 mmol) in acetonitrile (55 mL), sodium triacetoxyborohydride (15.0 g, 70.09 mmol), and acetic acid (7.0 ml, 118.0 mmol) were added. The resulting mixture was stirred for 4 h at room temperature. After completion, the reaction mixture was partitioned between saturated aqueous sodium bicarbonate solution and ethyl acetate. The organic layer was separated, dried over anhydrous sodium sulphate, filtered and concentrated under reduced pressure to get the crude. The crude was purified by silica gel (100-200 mesh size) column chromatography using 1-5% methanol in dichloromethane as eluent. The desired fractions were concentrated under reduced pressure to afford rac-methyl (4bS,5R,6R,7S,7aR)-7a-(4-chlorophenyl)-4b,5-dihydroxy-4-methoxy-7-phenyl-4b,6,7,7a-tetrahydro-5H-cyclopenta[4,5]furo[2,3-c]pyridine-6-carboxylate (8) as off white solid. Yield: 3.90 g, 71.0%; MS (ESI) m/z 468.40[M+1]$^+$.

Synthesis of rac-(4bS,5R,6R,7S,7aR)-7a-(4-chlorophenyl)-4b,5-dihydroxy-4-methoxy-7-phenyl-4b,6,7,7a-tetrahydro-5H-cyclopenta[4,5]furo[2,3-c]pyridine-6-carboxylic acid (9)

To a solution of rac-methyl (4bS,5R,6R,7S,7aR)-7a-(4-chlorophenyl)-4b,5-dihydroxy-4-methoxy-7-phenyl-4b,6,7,7a-tetrahydro-5H-cyclopenta[4,5]furo[2,3-c]pyridine-6-carboxylate (8, 2.30 g, 4.92 mmol) in methanol: tetrahydrofuran:water (2:1:1, 40 mL), lithium hydroxide (1.18 g, 49.20 mmol) was added and the reaction was stirred for 2 h at room temperature. After completion, the reaction mass was cooled to 0° C. and acidified with 1 M hydrochloric acid to pH ~2-3. The precipitate was filtered and washed with n-pentane and dried under vacuum to afford rac-(4bS,5R,6R,7S,7aR)-7a-(4-chlorophenyl)-4b,5-dihydroxy-4-methoxy-7-phenyl-4b,6,7,7a-tetrahydro-5H-cyclopenta[4,5]furo[2,3-c]pyridine-6-carboxylic acid (9) as white solid. Yield: 1.90 g, 85%; MS (ESI) m/z 454.19[M+1]$^+$.

Synthesis of rac-((4bS,5R,6R,7S,7aR)-7a-(4-chlorophenyl)-4b,5-dihydroxy-4-methoxy-N,N-dimethyl-7-phenyl-4b,6,7,7a-tetrahydro-SH-cyclopenta[4,5]furo[2,3-c]pyridine-6-carboxamide (Cpd. No. 271F)

To a solution of rac-(4bS,5R,6R,7S,7aR)-7a-(4-chlorophenyl)-4b,5-dihydroxy-4-methoxy-7-phenyl-4b,6,7,7a-tetrahydro-5H-cyclopenta[4,5]furo[2,3-c]pyridine-6-carboxylic acid (9, 0.90 g, 1.98 mmol) in dichloromethane (20 mL) at 0° C., 1-[Bis(dimethylamino)methylene]-1H-1,2,3-triazolo[4,5-b]pyridinium3-oxidhexafluorophosphate (1.12 g, 2.97 mmol) and N,N-diisopropylethylamine (2.20 mL, 11.88 mmol) were added and the mixture was stirred for 5 min. N,N-dimethylamine hydrochloride (0.80 g, 9.90 mmol) was then added at the same temperature and the reaction was stirred for 16 h at room temperature. After completion, the reaction mass was diluted with water, extracted with dichloromethane, dried with anhydrous sodium sulphate, filtered, concentrated to give crude product. The crude product was washed with n-pentane and dried to afford rac-(4bS,5R,6R,7S,7aR)-7a-(4-chlorophenyl)-4b,5-dihydroxy-4-methoxy-N,N-dimethyl-7-phenyl-4b,6,7,7a-tetrahydro-5H-cyclopenta[4,5]furo[2,3-c]pyridine-6-carboxamide (Cpd. No. 271F) as white solid. Yield: 0.91 g, 81%; MS (ESI) m/z 481.20[M+1]$^+$.

Example 272

(4bS,5R,6S,7S,7aR)-7a-(4-chlorophenyl)-6-((dimethylamino)methyl)-4-methoxy-7-phenyl-5,6,7,7a-tetrahydro-4bH-cyclopenta[4,5]furo[2,3-c]pyridine-4b,5-diol (Cpd. No. 272F)

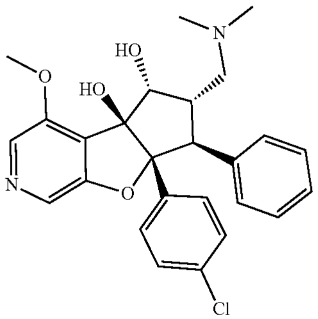

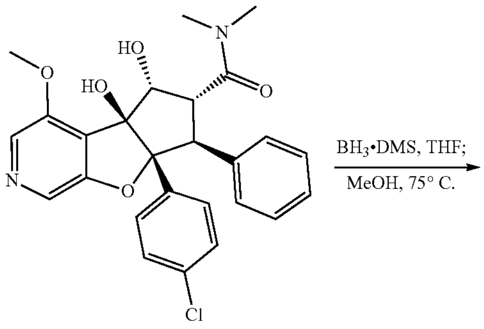

1

-continued

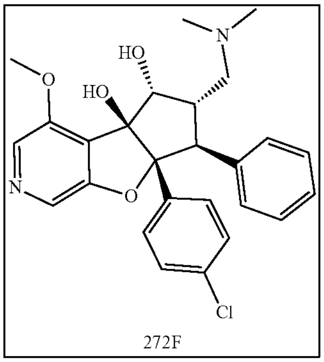

272F

Synthesis of (4bS,5R,6S,7S,7aR)-7a-(4-chlorophenyl)-6-((dimethylamino)methyl)-4-methoxy-7-phenyl-5,6,7,7a-tetrahydro-4bH-cyclopenta[4,5]furo[2,3-c]pyridine-4b,5-diol (Cpd. No. 272F)

To a solution of rac-(4bS,5R,6R,7S,7aR)-7a-(4-chlorophenyl)-4b,5-dihydroxy-4-methoxy-N,N-dimethyl-7-phenyl-4b,6,7,7a-tetrahydro-5H-cyclopenta[4,5]furo[2,3-c]pyridine-6-carboxamide (1, 0.40 g, 0.83 mmol) in dry tetrahydrofuran (8 ml) at 0° C., borane dimethyl sulphide complex (1.60 mL, 16.6 mmol) was added drop wise over a period of 5 min. The reaction mass was slowly brought to room temperature and stirred for additional 16 h. After completion, the reaction mass was quenched with methanol at 0° C. and heated to reflux for 48 h. After completion, solvent was removed under reduced pressure and the residue was purified over a plug of silica gel eluting the compound with 1-5% methanol in dichloromethane. The desired fractions were concentrated under reduced pressure to afford rac-(4bS,5R,6S,7S,7aR)-7a-(4-chlorophenyl)-6-((dimethylamino)methyl)-4-methoxy-7-phenyl-5,6,7,7a-tetrahydro-4bH-cyclopenta[4,5]furo[2,3-c]pyridine-4b,5-diol as white solid. Yield: 0.30 g 85%; MS (ESI) m/z 467.42[M+1]$^+$. The enantiomers were separated by chiral SFC [Chiralpak IA (4.6×150) mm, 5], $CO_2$/EtOH 60/40 V/V. Peak 1 (Cpd. No. 272F, 120 mg), $[\alpha]_D$–30.0° (c 0.26, $CHCl_3$), $R_t$=2.977 min, ee: 99.9% MS (ESI) m/z 467.28[M+1]$^+$; $^1$H NMR (400 MHz, DMSO-$d_6$) δ 8.01 (s, 1H), 7.95 (s, 1H), 7.20 (d, J=8.56 Hz, 2H), 7.09-7.06 (m, 4H), 7.01-6.97 (m, 3H), 5.63 (s, 1H), 5.09 (s, 1H), 4.48 (s, 1H), 3.87 (s, 3H), 3.72 (d, J=14.12 Hz 1H), 3.10 (bs, 1H), 2.57 (s, 1H), 2.19 (s, 6H), 1.96 (d, J=9.88 Hz, 1H); Peak-2 (110 mg), $[\alpha]_D$+28.4° (c 0.30, $CHCl_3$), $R_t$=3.483 min, ee: 99.78%, MS (ESI) m/z 467.27[M+1]$^+$. $^1$H NMR (400 MHz, DMSO-$d_6$) δ 8.01 (s, 1H), 7.95 (s, 1H), 7.19 (d, J=8.56 Hz, 2H), 7.09-7.06 (m, 4H), 7.01-6.97 (m, 3H), 5.63 (s, 1H), 5.09 (s, 1H), 4.48 (s, 1H), 3.87 (s, 3H), 3.72 (d, J=14.12 Hz 1H), 3.10 (bs, 1H), 2.57 (s, 1H), 2.19 (s, 6H), 1.96 (d, J=9.88 Hz, 1H).

Example 273

Rac-(6-oxa-3-azabicyclo[3.1.1]heptan-3-yl)((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)methanone (Cpd. No. 273F)

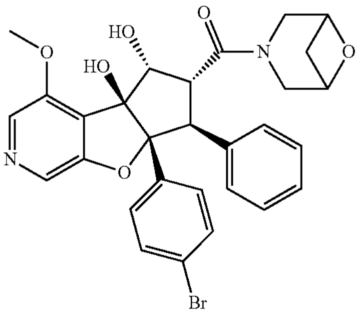

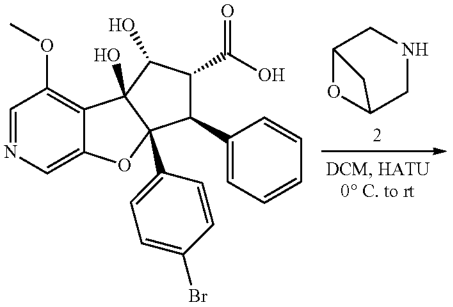

1

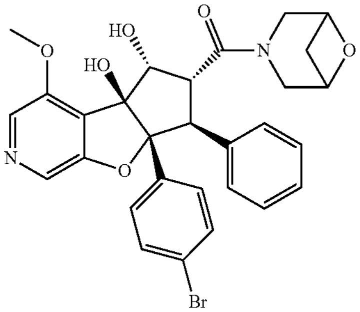

273F

Synthesis of rac-(6-oxa-3-azabicyclo[3.1.1]heptan-3-yl)((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)methanone (Cpd. No. 273F)

To a solution of rac-(4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylic acid (1, 1.50 g, 3.02 mmol) in dichloromethane (20 mL) at 0° C., 1-[Bis(dimethylamino)methylene]-1H-1,2,3-triazolo[4,5-b]pyridinium3-oxide hexafluorophosphate (1.71 g, 4.52 mmol) and N,N-diisopropylethylamine (3.2 ml, 18.4 mmol) were added and the mixture was stirred for 5 min. 6-oxa-3-azabicyclo[3.1.1]heptane (2, 0.613 g, 4.52 mmol) was then added at the same temperature and the reaction was stirred for 16 h at room temperature. After completion, the reaction mixture was diluted with dichloromethane and washed with cold water. The organic layer was separated and dried over anhydrous sodium sulphate, filtered and concentrated to give crude product. The crude product was purified by silica gel (100-200 mesh size)

column chromatography using 0-5% methanol in dichloromethane as eluent. The desired fractions were concentrated to afford rac-(6-oxa-3-azabicyclo[3.1.1]heptan-3-yl)((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)methanone (Cpd. No. 273F) as white solid. Yield: 1.5 g, 88%; MS (ESI) m/z 579.21[M+1]$^+$; $^1$H NMR (400 MHz, DMSO-$d_6$) 8.11 (s, 1H), 8.05 (s, 1H), 7.22-7.19 (m, 2H), 7.11-7.00 (m, 4H), 6.99-6.93 (m, 3H), 5.70 (d, J=15.8 Hz, 1H), 5.23-5.20 (m, 1H), 4.85-4.79 (m, 1H), 4.74-4.69 (m, 1H), 4.59-4.50 (m, 2H), 4.45 (t, J=26.8 Hz, 1H), 4.15-4.04 (m, 1H), 4.01-3.92 (m, 1H), 3.87 (d, J=5.32 Hz, 3H), 3.57 (d, J=13.92 Hz, 1H), 3.40-3.37 (m, 1H), 3.10 (t, J=7.24 Hz, 1H), 1.88 (m, 1H).

Example 274

4-((4bS,5R,6S,7S,7aR)-6-((6-oxa-3-azabicyclo[3.1.1]heptan-3-yl)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 274 F)

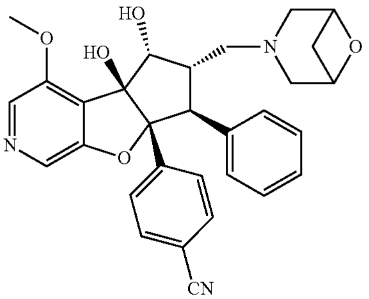

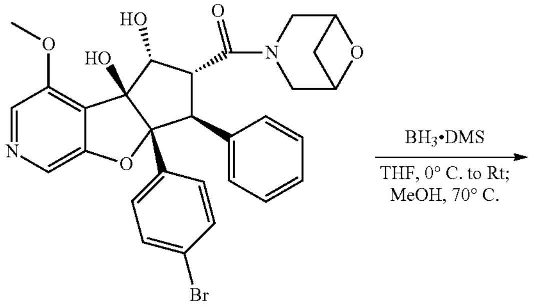

1

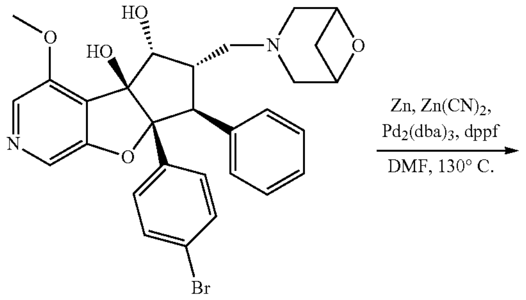

2

-continued

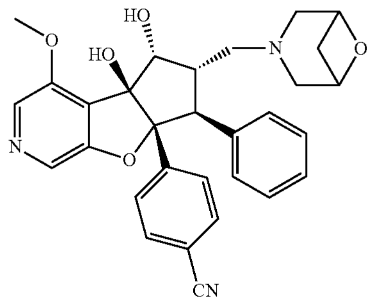

274F

Synthesis of rac-(4bS,5R,6S,7S,7aR)-6-((6-oxa-3-azabicyclo[3.1.1]heptan-3-yl)methyl)-7a-(4-bromophenyl)-4-methoxy-7-phenyl-5,6,7,7a-tetrahydro-4bH-cyclopenta[4,5]furo[2,3-c]pyridine-4b,5-diol (2)

To a solution of rac-(6-oxa-3-azabicyclo[3.1.1]heptan-3-yl)((4bS,5R,6R,7S,7aR)-7a-(4-bromophenyl)-4b,5-dihydroxy-4-methoxy-7-phenyl-4b,6,7,7a-tetrahydro-5Hcyclopenta[4,5]furo[2,3-c]pyridin-6-yl)methanone (1, 1.30 g, 2.22 mmol) in dry tetrahydrofuran (20 ml) at 0° C., borane dimethyl sulphide complex (5.0 ml, 44.9 mmol) was added dropwise over a period of 5 min. The reaction mixture was slowly brought to room temperature and stirred for additional 16 h. After completion, the reaction mixture was quenched with methanol at 0° C. and heated to reflux for 5 h. After completion, solvent was removed under reduced pressure and the residue was purified by silica gel (100-200 mesh size) using 5% methanol in dichloromethane as eluent. The desired fractions were concentrated under reduced pressure to afford rac-(4bS,5R,6S,7S,7aR)-6-((6-oxa-3-azabicyclo[3.1.1]heptan-3-yl)methyl)-7a-(4-bromophenyl)-4-methoxy-7-phenyl-5,6,7,7a-tetrahydro-4bH-cyclopenta[4,5]furo[2,3-c]pyridine-4b,5-diol (2) as white solid. Yield: 0.3 g, (crude); MS (ESI) m/z 567.39[M+1]$^+$.

Synthesis of 4-((4bS,5R,6S,7S,7aR)-6-((6-oxa-3-azabicyclo[3.1.1]heptan-3-yl)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 274F)

To a solution of rac-(4bS,5R,6S,7S,7aR)-6-((6-oxa-3-azabicyclo[3.1.1]heptan-3-yl)methyl)-7a-(4-bromophenyl)-4-methoxy-7-phenyl-5,6,7,7a-tetrahydro-4bH-cyclopenta[4,5]furo[2,3-c]pyridine-4b,5-diol (2, 0.3 g, 0.53 mmol) in N,N-dimethylformamide (3 mL), zinc cyanide (0.3 g, 2.65 mmol) and zinc dust (0.004 g, 0.063 mmol) were added at room temperature and the reaction mixture was degassed with argon for 15 min. 1,1'-Bis(diphenylphosphino)ferrocene (0.006 g, 0.0106 mmol) and tris(dibenzylideneacetone) dipalladium (0.015 g, 0.016 mmol) were added to the reaction, degassed for additional 5 min and mixture was heated at 130° C. for 4 h. After completion, the reaction mixture was diluted with ethyl acetate and washed with cold water. The organic layer was separated and dried over anhydrous sodium sulphate, filtered and concentrated to give crude product. The crude product was purified by silica gel (100-200 mesh size) column chromatography using 2-3% methanol in dichloromethane as eluent. The desired fractions were concentrated to afford rac-4-((4bS,5R,6S,7S,7aR)-6-((6-oxa-3-azabicyclo[3.1.1]heptan-3-yl)methyl)-4b,5-dihydroxy-4-methoxy-7-phenyl-4b,5,6,7-tetrahydro-7aH-cyclopenta[4,5]furo[2,3-c]pyridin-7a-yl)benzonitrile as white solid. Yield: 0.04 g, 15%; MS (ESI) m/z 511.86[M+1]$^+$. The enantiomers were separated by chiral HPLC [Chiralpak IG (4.6 ×250) mm, 5 pm] in hexane/EtOH=50/50 (v/v). Peak 1 (Cpd. No. 274F, 3 mg), $R_t$=8.073 min, ee: 99.86%; MS (ESI) m/z 511.86[M+1]$^+$. $^1$H NMR (400 MHz, DMSO-$d_6$) 8.05 (s, 1H), 7.97 (s, 1H), 7.49 (d, J=8.4 Hz, 2H), 7.37 (d, J=8.4 Hz, 2H), 7.10-6.98 (m, 5H), 5.75 (s, 1H), 5.13 (d, J=5.2 Hz, 1H), 4.53 (bs, 1H), 4.49 (bs, 1H), 4.39 (s, 1H), 3.87 (s, 3H), 3.82 (s, 1H), 3.33 (s, 2H), 3.09 (d, J=11.6 Hz, 1H), 2.89-2.77 (m, 2H), 2.64-2.54 (m, 2H), 2.40-2.24 (m, 2H). Peak-2 (3 mg), $R_t$=11.833 min, ee: 99.94%; MS (ESI) m/z 512.27[M+1]$^+$. $^1$H NMR (400 MHz, DMSO-$d_6$) 8.05 (s, 1H), 7.97 (s, 1H), 7.49 (d, J=8.4 Hz, 2H), 7.37 (d, J=8.4 Hz, 2H), 7.10-6.98 (m, 5H), 5.75 (s, 1H), 5.13 (d, J=5.2 Hz, 1H), 4.53 (bs, 1H), 4.49 (bs, 1H), 4.39 (s, 1H), 3.87 (s, 3H), 3.82 (s, 1H), 3.33 (s, 2H), 3.09 (d, J=11.6 Hz, 1H), 2.89-2.77 (m, 2H), 2.64-2.54 (m, 2H), 2.40-2.24 (m, 2H).

Example 275

Rac-(3aR,4S,4aR,9bS,9cR)-4a-(4-bromophenyl)-9b-hydroxy-9-methoxy-4-phenyl-3,3a,4,4a,9b,9c-hexahydro-2H-furo[3",2":4',5']cyclopenta[1',2':4,5]furo[2,3-c]pyridin-2-one (Cpd. No. 275F)

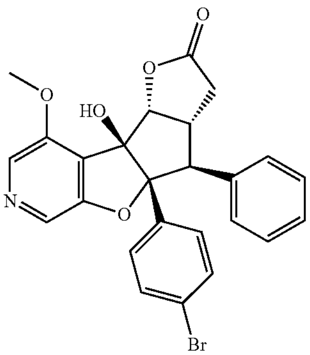

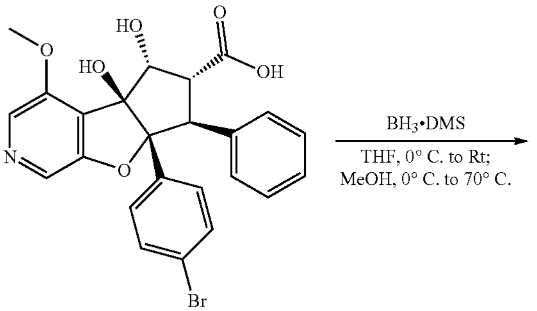

1

-continued

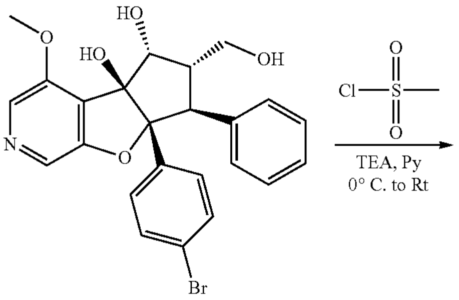

2

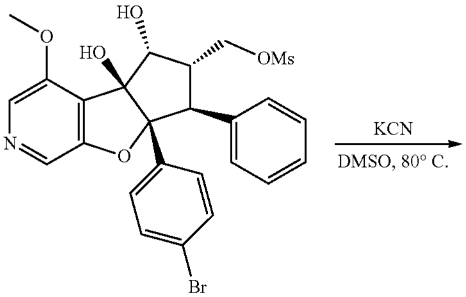

3

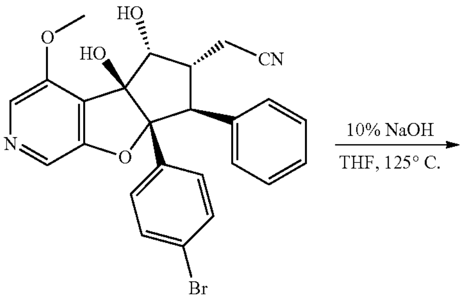

4

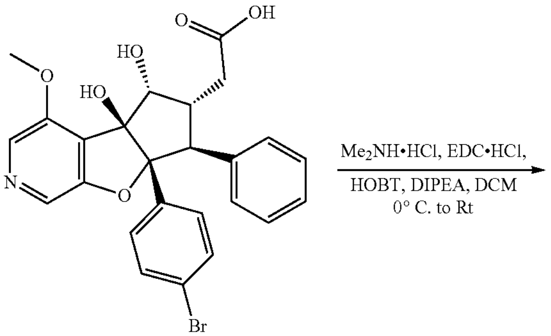

5

-continued

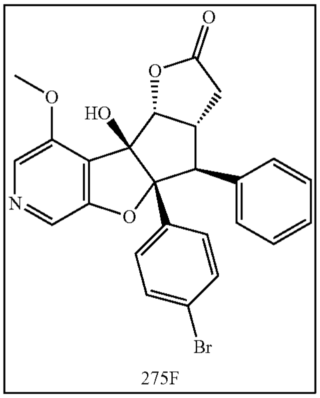

275F

Synthesis of rac-(4bS,5R,6S,7S,7aR)-7a-(4-bromophenyl)-6-(hydroxymethyl)-4-methoxy-7-phenyl-5,6,7,7a-tetrahydro-4bH-cyclopenta[4,5]furo[2,3-c]pyridine-4b, 5-diol (2)

To a solution of rac-(4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylic acid (1, 5.0 g, 10.03 mol) in dry tetrahydrofuran (100 mL) at 0° C., borane dimethyl sulphide complex (9.52 mL, 100.33 mmol) was added drop wise over a period of 5 min. The reaction mixture was heated at 60° C. for 6 h. After completion, the reaction mass was quenched with methanol at 0° C. and heated to reflux for 16 h. After completion, solvent was removed under reduced pressure to get the crude. The crude product obtained was triturated with diethyl ether, filtered and dried under vacuum to afford rac-(4bS,5R,6S,7S,7aR)-7a-(4-bromophenyl)-6-(hydroxymethyl)-4-methoxy-7-phenyl-5,6,7,7a-tetrahydro-4bH-cyclopenta[4,5]furo[2,3-c]pyridine-4b,5-diol (2) as white solid. Yield: 4.5 g, 93%; MS (ESI) m/z 484.3[M+1]$^+$.

Synthesis of rac-((4bS,5R,6S,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)methyl methanesulfonate (3)

To a solution of rac-(4bS,5R,6S,7S,7aR)-7a-(4-bromophenyl)-6-(hydroxymethyl)-4-methoxy-7-phenyl-5,6,7,7a-tetrahydro-4bH-cyclopenta[4,5]furo[2,3-c]pyridine-4b,5-diol (2, 4.5 g, 9.29 mmol) in pyridine (90 mL) at 0° C., methane sulfonyl chloride (1.60 g, 19.93 mmol) was added. The resulting mixture was stirred at room temperature for 16 h. After completion, the solvent was removed under reduced pressure. The crude was diluted with water and extracted with ethyl acetate. The organic layer was separated, dried over anhydrous sodium sulphate and concentrated under reduced pressure to afford crude product. The crude product was purified by silica gel (100-200 mesh size) column chromatography using 5% methanol in dichloromethane as eluents. The desired fractions were concentrated under reduced pressure to afford rac-((4bS,5R,6S,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl) methyl methanesulfonate (3) as white solid. Yield: 4.20 g, 80.0%; MS (ESI) m/z 562.3 [M+1]$^+$.

Synthesis of rac-2-((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)acetonitrile (4)

To a solution of rac-((4bS,5R,6S,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl) methyl methanesulfonate (3, 4.20 g, 7.47 mmol) in dimethylsulfoxide (84 mL), potassium cyanide (4.86 g, 74.6 mmol) was added. The resulting mixture was heated at 80° C. for 16 h. After completion, the reaction mixture was diluted with water and extracted with ethyl acetate. The organic layer was washed with ice cold water and brine. The organic layer was separated, dried over anhydrous sodium sulphate and concentrated under reduced pressure to afford crude product.

The crude product was purified by silica gel (100-200 mesh size) column chromatography using 5% methanol in dichloromethane as eluents. The desired fractions were concentrated under reduced pressure to afford rac-2-((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)acetonitrile (4) as yellow brown solid. Yield: 2.1 g, 58%. MS (ESI) m/z 493.33[M+1]$^+$.

Synthesis of rac-2-((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)acetic acid (5)

In a sealed tube to a solution of rac-2-((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)acetonitrile (4, 0.8 g, 1.6 mol) in tetrahydrofuran (4 mL), 10% aqueous sodium hydroxide solution (16 mL) was added. The reaction mixture was heated at 125° C. for 36 h. After completion, the reaction mixture was acidified using 1N hydrochloric acid, the solid was precipitated and filtered. The crude product obtained was triturated with diethyl ether and dried under vacuum to afford rac-2-((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)acetic acid (5) as white solid. Yield: 0.75 g, 90%; MS (ESI) m/z 512.3[M+1]$^+$.

Synthesis of rac-(3aR,4S,4aR,9bS,9cR)-4a-(4-bromophenyl)-9b-hydroxy-9-methoxy-4-phenyl-3,3a,4,4a,9b,9c-hexahydro-2H-furo[3",2":4',5']cyclopenta[1',2':4,5]furo[2,3-c]pyridin-2-one (Cpd. No. 275F)

To a solution of rac-2-((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)acetic acid (5, 0.45 g, 0.88 mmol) in dichloromethane (9 mL) at 0° C., 1-ethyl-3-(3-dimethylaminopropyl) carbodiimide (0.50 g, 2.63 mmol), hydroxybenzotriazole (0.40 g, 2.63 mmol) and N,N-diisopropylethylamine (1.09 mL, 6.15 mmol) were added and the mixture was stirred for 5 min. dimethylamine hydrochloride (0.358 g, 4.39 mmol) was then added at the same temperature and the reaction was stirred for 16 h at room temperature. After completion, the reaction mass was diluted with dichloromethane and washed with cold water. The organic layer was separated and dried over sodium sulphate, filtered and concentrated to give crude. The crude was purified by silica gel 100-200 mesh size) column chromatography using 3% methanol in dichloromethane as eluent. The desired fractions were concentrated to afford rac-3aR,4S,4aR,9bS,9cR)-4a-(4-bromophenyl)-9b-hydroxy-9-methoxy-4-phenyl-3,3a,4,4a,9b,9c-hexahydro-2H-furo[3",2":4',5']cyclopenta[1',2':4,5]furo[2,3-c]pyridin-2-one (Cpd. No. 275F) as off white solid. Yield: 0.40 g, 66.0%; MS (ESI) m/z 494.31[M+1]$^+$. $^1$H NMR (400 MHz, DMSO-$d_6$) δ 8.17 (s, 1H), 8.12 (s, 1H), 7.35 (d, J=8.36 Hz, 2H), 7.12-7.10 (m, 5H), 6.96 (d, J=5.04, 2H), 6.02 (s, 1H), 5.36 (d, J=6.48 Hz, 1H), 3.96 (s, 3H), 3.80-3.74 (m, 1H), 3.37 (s, 1H), 2.90 (dd, J=17.88 Hz, 7.94 Hz, 1H), 1.99 (d, J=17.8, 1H).

Example 276

Rac-4-((4bS,5R,6R,7S,7aR)-6-(2-(dimethylamino)ethyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 276F)

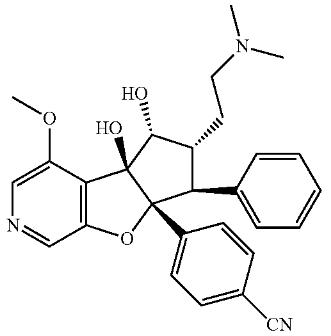

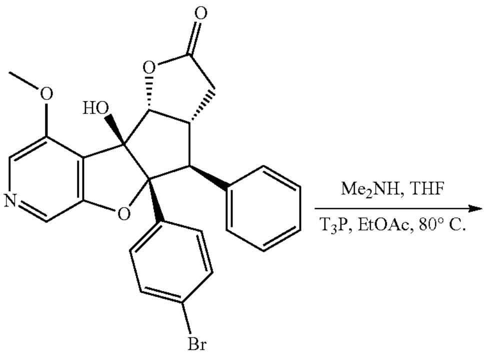

1

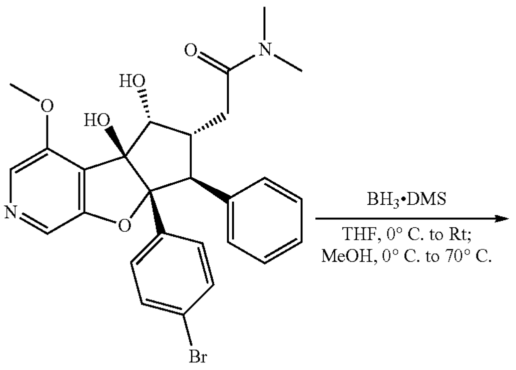

2

-continued

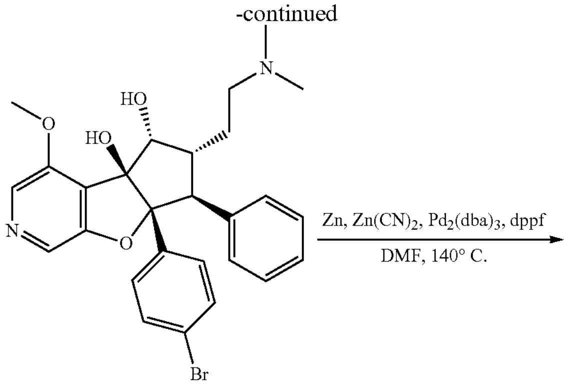

3

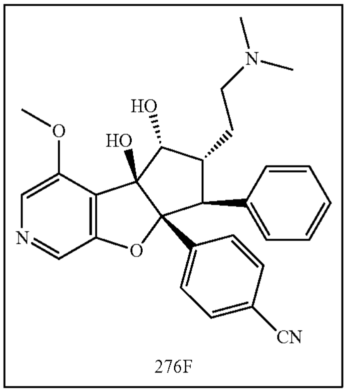 [SMILES: COc1cncc2c1[C@]1(O)[C@H](O)[C@H](CCN(C)C)[C@@H](c3ccccc3)[C@]1(c1ccc(C#N)cc1)O2]

276F

Synthesis of rac-2-((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)-N,N-dimethylacetamide (2)

To a solution of rac-(3aR,4S,4aR,9bS,9cR)-4a-(4-bromophenyl)-9b-hydroxy-9-methoxy-4-phenyl-3,3a,4,4a,9b,9c-hexahydro-2H-furo[3",2":4',5']cyclopenta[1',2':4,5]furo[2,3-c]pyridin-2-one (1, 0.25 g, 0.506 mol) in 2M solution of dimethyl amine (20 mL) in tetrahydrofuran, 50% propylphosphonicanhydride solution in ethyl acetate (3.2 mL, 5.05 mmol) was added. The reaction mixture was heated at 80° C. for 16 h. After completion the reaction mixture was diluted with water and extracted with ethyl acetate. The organic layer was washed with brine. The organic layer was separated, dried over anhydrous sodium sulphate and concentrated under reduced pressure to afford crude product. The crude product was purified by silica gel (100-200 mesh size) column chromatography using 5% methanol in dichloromethane as eluent. The desired fractions were concentrated under reduced pressure to afford rac-2-((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)-N,N-dimethylacetamide (2) as white solid. Yield: 0.13 g, 48%. MS (ESI) m/z 539.43[M+1]$^+$.

Synthesis of rac-(4bS,5R,6R,7S,7aR)-7a-(4-bromophenyl)-6-(2-(dimethylamino)ethyl)-4-methoxy-7-phenyl-5,6,7,7a-tetrahydro-4bH-cyclopenta[4,5]furo[2,3-c]pyridine-4b,5-diol (3)

To a solution of rac-2-((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)-N, N-dimethylacetamide (2, 0.13 g, 0.24 mmol) in dry tetrahydrofuran (5.2 ml) at 0° C., borane dimethyl sulphide complex (0.23 ml, 2.4 mmol) was added drop wise over a period of 5 min. The reaction mixture was slowly brought to room temperature and stirred for additional 16 h. After completion, the reaction mixture was quenched with methanol (40 ml) at 0° C. and heated to reflux for 24 h. After completion, solvent was removed under reduced pressure and crude obtained was purified by silica gel (100-200 mesh size) column chromatography using 10% methanol in dichloromethane as eluent. The desired fractions were concentrated under reduced pressure to afford rac-(4bS,5R,6R,7S,7aR)-7a-(4-bromophenyl)-6-(2-(dimethylamino)ethyl)-4-methoxy-7-phenyl-5,6,7,7a-tetrahydro-4bH-cyclopenta[4,5]furo[2,3-c]pyridine-4b,5-diol (3). Yield: 0.09 g, 69%; MS (ESI) m/z 525.4[M+1]+.

Synthesis of rac-4-((4bS,5R,6R,7S,7aR)-6-(2-(dimethylamino)ethyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 276F)

To a solution of rac-(4bS,5R,6R,7S,7aR)-7a-(4-bromophenyl)-6-(2-(dimethylamino)ethyl)-4-methoxy-7-phenyl-5,6,7,7a-tetrahydro-4bH-cyclopenta[4,5]furo[2,3-c]pyridine-4b,5-diol (3, 0.09 g, 0.171 mmol) in N,N-dimethylformamide (4 mL), zinc cyanide (0.12 g, 1.03 mmol) and zinc dust (0.00013 g, 0.002 mmol) were added at room temperature and the reaction mixture was degassed with argon for 15 minutes. 1,1'-Bis(diphenylphosphino) ferrocene (0.0018 g, 0.00342 mmol) and Tetrakis(triphenylphosphine)palladium (0.0046 g, 0.00513 mmol) were added to the reaction mixture, degassed for additional 5 min and mixture was heated at 140° C. for 8 h. After completion, the reaction mixture was diluted with ethyl acetate and washed with cold water. The organic layer was separated and dried over anhydrous sodium sulphate, filtered and concentrated to give crude product. The crude product was purified by silica gel (100-200 mesh size) column chromatography using 6% methanol in dichloromethane as eluent. The desired fractions were concentrated to afford rac-4-((4bS,5R,6R,7S,7aR)-6-(2-(dimethylamino)ethyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 276F) as white solid. Yield: 0.015 g, 18%; MS (ESI) m/z 472.28[M+1]+; $^1$H NMR (400 MHz, DMSO-$d_6$) 8.05 (s, 1H), 7.97 (s, 1H), 7.50 (d, J=8.4 Hz, 2H), 7.36 (d, J=8.4 Hz, 2H), 7.09-7.05 (m, 2H), 7.01-6.96 (m, 3H), 5.68 (s, 1H), 4.42 (d, J=4.04 Hz, 1H), 3.88 (s, 3H), 3.76 (d, J=14.1 Hz, 1H), 3.03 (bs, 1H), 2.41-2.37 (m, 1H), 2.32-2.26 (m, 1H), 2.12 (s, 6H), 1.48 (bs, 1H), 1.41 (bs, 1H).

Example 277

Rac-(4bS,5R,6R,7S,7aR)-7a-(4-bromophenyl)-4b,5-dihydroxy-4-methoxy-N-methyl-7-phenyl-N-(pyridin-3-ylmethyl)-4b,6,7,7a-tetrahydro-5H-cyclopenta[4,5]furo[2,3-c]pyridine-6-carboxamide (Cpd. No. 277F)

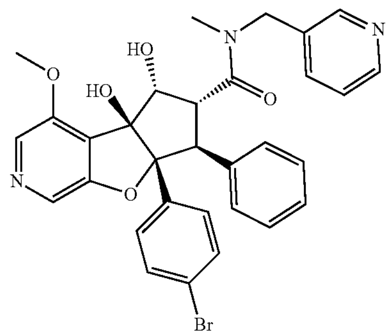

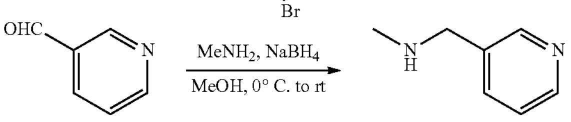

1

2

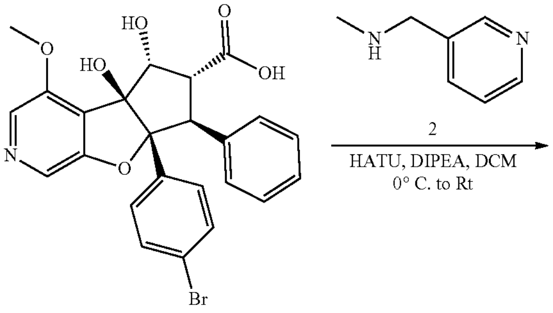

3

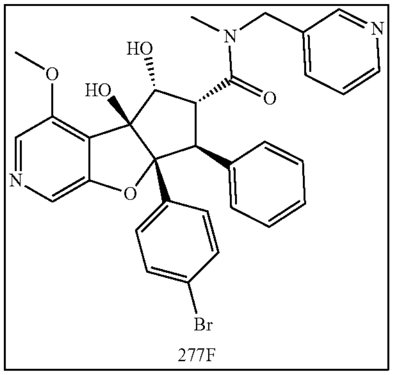

277F

Synthesis of N-methyl-1-(pyridin-3-yl)methanamine (2)

To a solution of nicotinaldehyde (1, 1.50 g, 14 mmol) in methanol (30 ml) 2.0 M methylamine (21 ml, 42 mmol) in tetrahydrofuran was added and the reaction was stirred for 16 h at room temperature. Sodium borohydride (0.53 g, 14 mmol) was added portion wise at 0° C. and the reaction was stirred for 6 h at room temperature. After completion, the reaction mass was concentrated to give crude product. The crude product was triturated with pentane, supernent layer was decanted off at 0° C. and the residue was dried under vacuum to afford N-methyl-1-(pyridin-3-yl) methanamine (2) as brown oil. Yield: 1.4 g (Crude) MS (ESI) m/z 123.05[M+1]$^+$.

Synthesis of rac-(4bS,5R,6R,7S,7aR)-7a-(4-bromophenyl)-4b,5-dihydroxy-4-methoxy-N-methyl-7-phenyl-N-(pyridin-3-ylmethyl)-4b,6,7,7a-tetrahydro-5H-cyclopenta[4,5]furo[2,3-c]pyridine-6-carboxamide (Cpd. No. 277F)

To a solution of rac-(4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylic acid (3, 1.50 g, 3.02 mmol) in N,N-dimethylformamide (20 mL) at 0° C., 1-[Bis (dimethylamino)methylene]-1H-1,2,3-triazolo[4,5-b] pyridinium3-oxide hexafluorophosphate (1.71 g, 4.52 mmol), and N,N-diisopropylethylamine (3.20 ml, 18.4 mmol) were added and the mixture was stirred for 5 min. N-methyl-1-(pyridin-3-yl)methanamine (2, 1.1 g, 9.03 mmol) was then added at the same temperature and the reaction was stirred for 16 h at room temperature. After completion, the reaction mixture was diluted with dichloromethane and washed with cold water. The organic layer was separated and dried over anhydrous sodium sulphate, filtered and concentrated to give crude. The crude was purified by silica gel (100-200 mesh size) column chromatography using 0-5% methanol in dichloromethane as eluent. The desired fractions were concentrated to afford rac-(4bS,5R,6R,7S,7aR)-7a-(4-bromophenyl)-4b,5-dihydroxy-4-methoxy-N-methyl-7-phenyl-N-(pyridin-3-ylmethyl)-4b,6,7,7a-tetrahydro-5H-cyclopenta[4,5]furo[2,3-c]pyridine-6-carboxamide (Cpd. No. 277F) as white solid. Yield: 1.30 g, 72%; MS (ESI) m/z 602.37[M+1]$^+$; $^1$H NMR (400 MHz, DMSO-$d_6$)(Compound exist in rotameric form) 8.65-8.42 (m, 2H), 8.11 (d, J=7.6 Hz, 1H), 8.01 (s, 1H), 7.80-7.54 (m, 1H), 7.31-6.68 (m, 9H), 5.77-5.71 (m, 1H), 5.29-5.23 (m, 1H), 4.86-4.80 (m, 1H), 4.58-4.40 (m, 2H), 4.28 (dd, J=13.72 Hz, 5.32 Hz, 1H), 3.89 (s, 3H), 3.26-2.77 (m, 4H).

Example 278

4-((4bS,5R,6S,7S,7aR)-4b,5-dihydroxy-4-methoxy-6-((methyl(pyridin-3-ylmethyl)amino)methyl)-7-phenyl-4b,5,6,7-tetrahydro-7aH-cyclopenta[4,5]furo[2,3-c]pyridin-7a-yl)benzonitrile (Cpd. No. 278F)

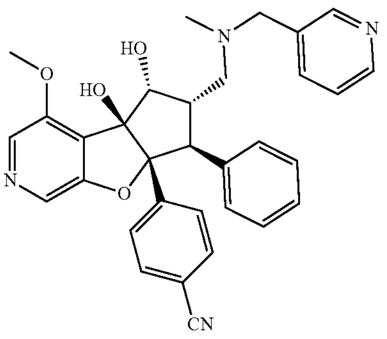

-continued

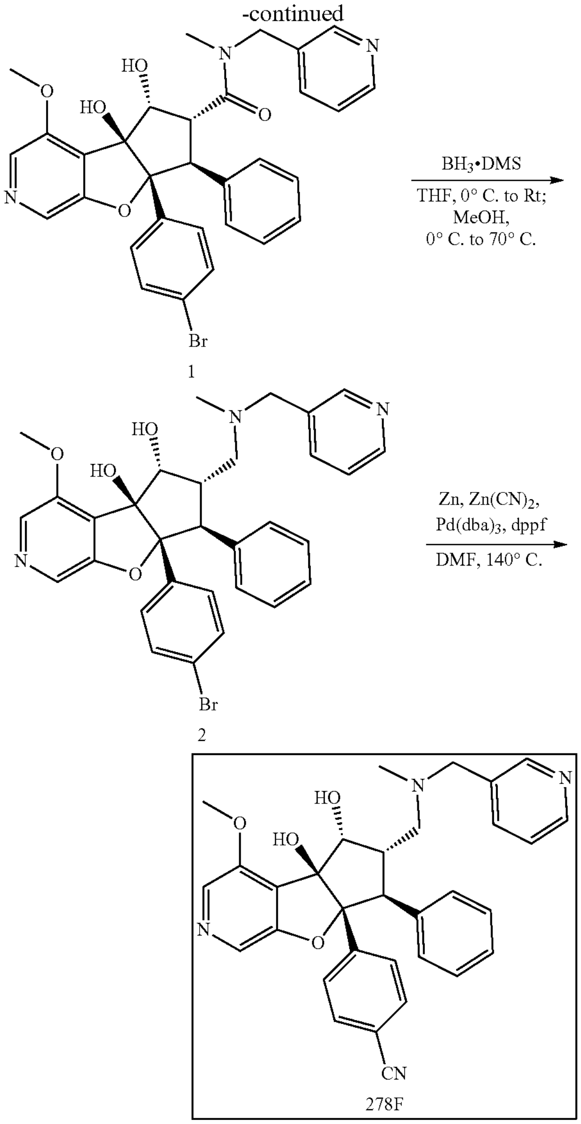

1

2

278F

Synthesis of rac-(4bS,5R,6S,7S,7aR)-7a-(4-bromophenyl)-4-methoxy-6-((methyl(pyridin-3-ylmethyl)amino)methyl)-7-phenyl-5,6,7,7a-tetrahydro-4bH-cyclopenta[4,5]furo[2,3-c]pyridine-4b,5-diol (2)

To a solution of rac-(4bS,5R,6R,7S,7aR)-7a-(4-bromophenyl)-4b,5-dihydroxy-4-methoxy-N-methyl-7-phenyl-N-(pyridin-3-ylmethyl)-4b,6,7,7a-tetrahydro-5H-cyclopenta[4,5]furo[2,3-c]pyridine-6-carboxamide (1, 1.25 g, 2.07 mmol) in dry tetrahydrofuran (25 ml) at 0° C., borane dimethyl sulphide complex (2.0 ml, 20.7 mmol) was added drop wise over a period of 5 min. The reaction mass was slowly brought to room temperature and stirred for additional 6 h. After completion, the reaction mass was quenched with methanol at 0° C. and heated to reflux for 5 h. After completion, solvent was removed under reduced pressure and the residue was purified over a plug of silica gel (100-200 mesh size) using 5% methanol in dichloromethane as eluent. The desired fractions were concentrated under reduced pressure to afford rac-(4bS,5R,6S,7S,7aR)-7a-(4-bromophenyl)-4-methoxy-6-((methyl(pyridin-3-ylmethyl)amino)methyl)-7-phenyl-5,6,7,7a-tetrahydro-4bH-cyclopenta[4,5]furo[2,3-c]pyridine-4b,5-diol (2) as white solid. Yield: 0.65 g; MS (ESI) m/z 588.45[M+1]$^+$.

Synthesis of 4-((4bS,5R,6S,7S,7aR)-4b,5-dihydroxy-4-methoxy-6-((methyl(pyridin-3-ylmethyl)amino)methyl)-7-phenyl-4b,5,6,7-tetrahydro-7aH-cyclopenta[4,5]furo[2,3-c]pyridin-7a-yl)benzonitrile (Cpd. No. 278F)

To a solution of rac-(4bS,5R,6S,7S,7aR)-7a-(4-bromophenyl)-4-methoxy-6-((methyl(pyridin-3-ylmethyl)amino)methyl)-7-phenyl-5,6,7,7a-tetrahydro-4bH-cyclopenta[4,5]furo[2,3-c]pyridine-4b,5-diol (2, 0.650 g, 0.72 mmol) in N,N-dimethylformamide (5 mL), zinc cyanide (0.127 g, 1.079 mmol) and zinc dust (0.005 g, 0.072 mmol) were added at room temperature and the reaction mixture was degassed with argon for 15 min. 1,1'-Bis(diphenylphosphino)ferrocene (0.053 g, 0.072 mmol) and tris(dibenzylideneacetone)dipalladium (0.020 g, 0.021 mmol) were added to the reaction mixture, degassed for additional 5 min and mixture was heated at 140° C. for 3 h. After completion, the reaction mixture was diluted with ethyl acetate and washed with cold water. The organic layer was separated and dried over anhydrous sodium sulphate, filtered and concentrated to give crude product. The crude product was purified by silica gel (100-200 mesh size) column chromatography using 5-10% methanol in dichloromethane as eluent. The desired fractions were concentrated to afford rac-4-((4bS,5R,6S,7S,7aR)-4b,5-dihydroxy-4-methoxy-6-((methyl(pyridin-3-ylmethyl)amino)methyl)-7-phenyl-4b,5,6,7-tetrahydro-7aH-cyclopenta[4,5]furo[2,3-c]pyridin-7a-yl)benzonitrile as white solid. Yield: 0.350 g, 47%; The enantiomers were separated by chiral HPLC [Chiralpak IG (4.6x250) mm, 5 pm] in n-hexane/EtOH=50/50 (v/v). Peak 1 (77 mg), $[\alpha]_D$–539° (c 0.11, $CHCl_3$), $R_t$=7.188 min, ee: 99.60%; MS (ESI) m/z 534.99[M+1]$^+$; $^1$H NMR (400 MHz, DMSO-$d_6$) 8.55 (s, 1H), 8.47 (d, J=3.3 Hz, 1H), 8.05 (s, 1H), 7.98 (s, 1H), 7.75 (d, J=8.04 Hz, 1H), 7.47 (d, J=8.5 Hz, 2H), 7.37-7.35 (m, 3H), 7.06-6.96 (m, 5H), 5.77 (s, 1H), 5.16 (d, J=5.2 Hz, 1H), 4.59 (t, J=4.0 Hz, 1H), 3.90 (s, 3H), 3.78 (d, J=14.24 Hz, 1H), 3.68 (d, J=13.4 Hz, 1H), 3.42 (d, J=13.44 Hz, 1H), 3.32-3.23 (m, 1H), 2.72-2.66 (m, 1H), 2.19 (s, 4H); Peak-2 (Cpd. No. 278F, 85 mg), $[\alpha]_D$+554.1° (c 0.11, $CHCl_3$) $R_t$=13.72 min, ee: 99.84%; MS (ESI) m/z 534.90 [M+1]$^+$; $^1$H NMR (400 MHz, DMSO-$d_6$) 8.55 (s, 1H), 8.46 (d, J=3.3 Hz, 1H), 8.05 (s, 1H), 7.98 (s, 1H), 7.75 (d, J=8.04 Hz, 1H), 7.47 (d, J=8.5 Hz, 2H), 7.37-7.35 (m, 3H), 7.06-6.96 (m, 5H), 5.77 (s, 1H), 5.16 (d, J=5.2 Hz, 1H), 4.60 (t, J=4.0 Hz, 1H), 3.90 (s, 3H), 3.78 (d, J=14.24 Hz, 1H), 3.68 (d, J=13.4 Hz, 1H), 3.42 (d, J=13.44 Hz, 1H), 3.32-3.23 (m, 1H), 2.72-2.66 (m, 1H), 2.19 (s, 4H).

Example 279

Rac-((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)(3,3-difluoropyrrolidin-1-yl)methanone (Cpd. No. 279F)

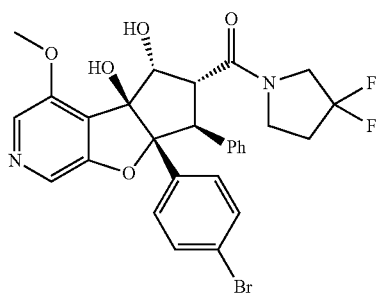

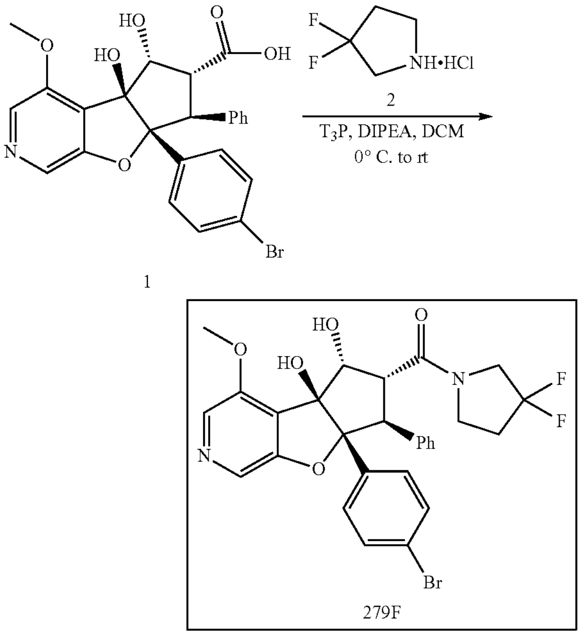

1

2

279F

Synthesis of rac-((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)(3,3-difluoropyrrolidin-1-yl)methanone (Cpd. No. 279F)

To a solution of rac-(4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylic acid (1, 2.0 g, 4.0 mmol) in dichloromethane (50 mL) at 0° C. were added 3,3-difluoropyrrolidine hydrochloride (2, 0.86 g, 6.0 mmol) N,N-diisopropylethylamine (2.5 ml, 16.0 mmol) and propylphosphonic anhydride ($T_3P$, 6 ml, 10 mmol). The reaction mixture was stirred at room temperature for overnight. After completion, saturated solution of sodium bicarbonate was added to reaction mixture and concentrated to remove dichloromethane. The solid precipitated was filtered off. The crude product was purified by combi-flash (12 g, RediSep column) using 0-5% methanol in dichloromethane as eluent. The desired fractions were concentrated under reduced pressure to afford rac-((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)(3,3-difluoropyrrolidin-1-yl)methanone (Cpd. No. 279F) as white solid. Yield: 0.64 g, 34%; MS (ESI) m/z 587.4 $[M+1]^+$; $^1H$ NMR (400 MHz, DMSO-$d_6$) δ 8.10 (s, 1H), 7.99 (s, 1H), 7.20-7.18 (m, 2H), 7.11-7.02 (m, 4H), 6.93 (bs, 3H), 5.69 (d, J=10.0 Hz, 1H), 5.21 (bs, 1H), 4.80-4.76 (m, 1H), 4.65-4.30 (m, 2H), 4.13-4.02 (m, 2H), 3.88 (s, 3H), 3.68-3.57 (m, 1H), 3.47 (t, J=7.3 Hz, 1H), 2.65 (bs, 1H), 2.38 (bs, 1H).

Example 280

4-((4bS,5R,6S,7S,7aR)-6-((3,3-difluoropyrrolidin-1-yl)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 280F)

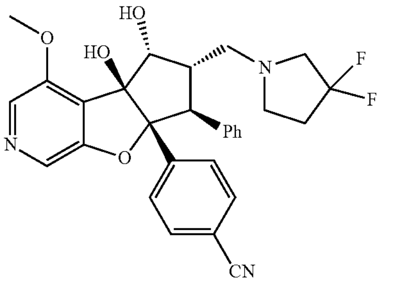

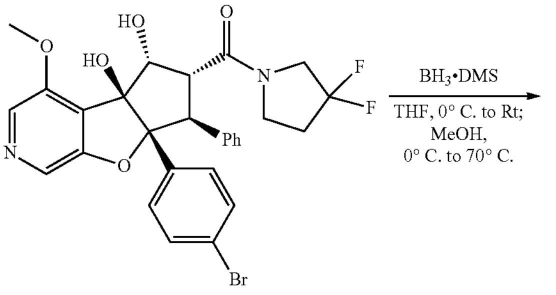

1

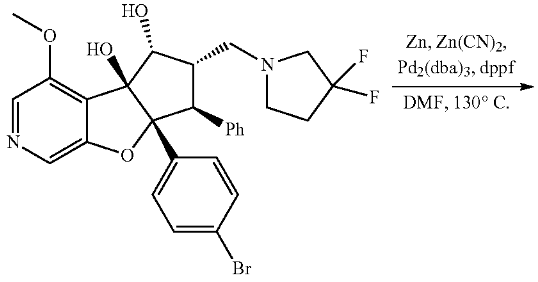

2

-continued

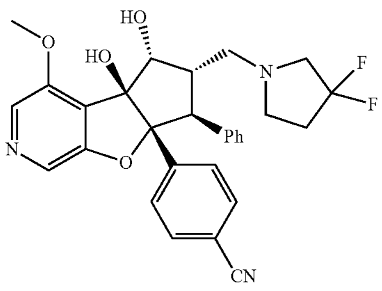

280F

Synthesis of rac-(4bS,5R,6S,7S,7aR)-7a-(4-bromophenyl)-6-((3,3-difluoropyrrolidin-1-yl)methyl)-4-methoxy-7-phenyl-5,6,7,7a-tetrahydro-4bH-cyclopenta[4,5]furo[2,3-c]pyridine-4b,5-diol (2)

To a solution of rac-((4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridin-6-yl)(3,3-difluoropyrrolidin-1-yl)methanone (1, 0.630 g, 1.0 mmol) in tetrahydrofuran (15 ml) at 0° C., borane dimethylsulfide (1.02 mL, 10.0 mmol) was added. The reaction mixture was stirred at room temperature for overnight. After completion, reaction mixture was quenched with methanol at 0° C. and then heated at 70° C. for 6 h. The solvents were concentrated and the residue was purified by flash column chromatography by eluting with gradient of 0-5% methanol in dichloromethane to afford rac-((4bS,5R,6S,7S,7aR)-7a-(4-bromophenyl)-6-((3,3-difluoropyrrolidin-1-yl)methyl)-4-methoxy-7-phenyl-5,6,7,7a-tetrahydro-4bH-cyclopenta[4,5]furo[2,3-c]pyridine-4b,5-diol) (2) as white solid. Yield: 0.4 g, 65%; MS (ESI) m/z 573.4$[M+1]^+$.

Synthesis of 4-((4bS,5R,6S,7S,7aR)-6-((3,3-difluoropyrrolidin-1-yl)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 280F)

To a mixture of rac-(4bS,5R,6S,7S,7aR)-7a-(4-bromophenyl)-6-((3,3-difluoropyrrolidin-1-yl)methyl)-4-methoxy-7-phenyl-5,6,7,7a-tetrahydro-4bH-cyclopenta[4,5]furo[2,3-c]pyridine-4b,5-diol (2, 0.4 g, 0.69 mmol) in N,N-dimethylformamide (5.0 mL) at room temperature were added, zinc cyanide (245 mg, 2.09 mmol) and zinc (65 mg, 0.69 mmol), and degassed the mixture with argon for 15 min. 1,1'-Bis(diphenylphosphino) ferrocene (38 mg, 0.07 mmol) and tris(dibenzylideneacetone)dipalladium (32 mg, 0.035 mmol) were added to the reaction mixture and degassing was continued for another 5 min. The reaction mixture was heated at 140° C. for 6 h. After completion, the reaction mixture was cooled to room temperature and passed through celite bed. The filtrate was concentrated and treated with ice-cold water, the solid precipitated was filtered. The crude product was purified by combi-flash (12 g RediSep column) using 5% methanol and dichloromethane as eluent. The product obtained was repurified by reverse phase preparative HPLC. The desired fractions were lyophilized to afford rac-4-((4bS,5R,6S,7S,7aR)-6-((3,3-difluoropyrrolidin-1-yl)methyl)-4b,5-dihydroxy-4-methoxy-7-phenyl-4b,5,6,7-tetrahydro-7aH-cyclopenta[4,5]furo[2,3-c]pyridin-7a-yl)benzonitrile as white solid. Yield: 0.20 g, 55%. The enantiomers were separated by chiral SFC [Chiralpak IA (4.6×250) mm, 5μ] using $CO_2$/MeOH=(80/20), Peak 1 (Cpd. No. 280F, 50 mg), $[\alpha]_D$+22.9° (c 0.27, $CHCl_3$), $R_t$=3.73 min, ee 99.66%; MS (ESI) m/z 520.30 $[M+1]^+$; $^1H$ NMR (400 MHz, DMSO-$d_6$) δ 8.04 (s, 1H), 7.97 (s, 1H), 7.48 (d, J=8.3 Hz, 2H), 7.38 (d, J=8.4 Hz, 2H), 7.09-6.97 (m, 5H), 5.77 (s, 1H), 5.18 (d, J=5.3 Hz, 1H), 4.50 (t, J=4.52 Hz, 1H), 3.87 (s, 3H), 3.78 (d, J=14.0 Hz, 1H), 3.18-3.12 (m, 2H), 2.91-2.61 (m, 4H), 2.32-2.17 (m, 3H). Peak-2 (49 mg), $[\alpha]_D$-15.0° (c 0.25, $CHCl_3$), $R_t$=6.34 min, ee 99.84%; MS (ESI) m/z 520.28 $[M+1]^+$; $^1H$ NMR (400 MHz, DMSO-$d_6$) δ 8.04 (s, 1H), 7.97 (s, 1H), 7.48 (d, J=8.3 Hz, 2H), 7.38 (d, J=8.4 Hz, 2H), 7.09-6.97 (m, 5H), 5.77 (s, 1H), 5.18 (d, J=5.2 Hz, 1H), 4.50 (t, J=4.72 Hz, 1H), 3.87 (s, 3H), 3.78 (d, J=14.2 Hz, 1H), 3.19-3.11 (m, 2H), 2.91-2.66 (m, 4H), 2.30-2.19 (m, 3H).

Example 281

Rac-((4bS,5R,6R,7S,7aR)-4b,5-dihydroxy-4-methoxy-7-phenyl-7a-(4-(trifluoromethyl)phenyl)-4b,6,7,7a-tetrahydro-5H-cyclopenta[4,5]furo[2,3-c]pyridin-6-yl)(morpholino)methanone (Cpd. No. 2811)

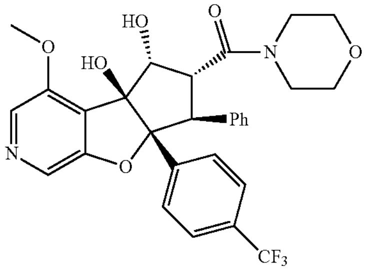

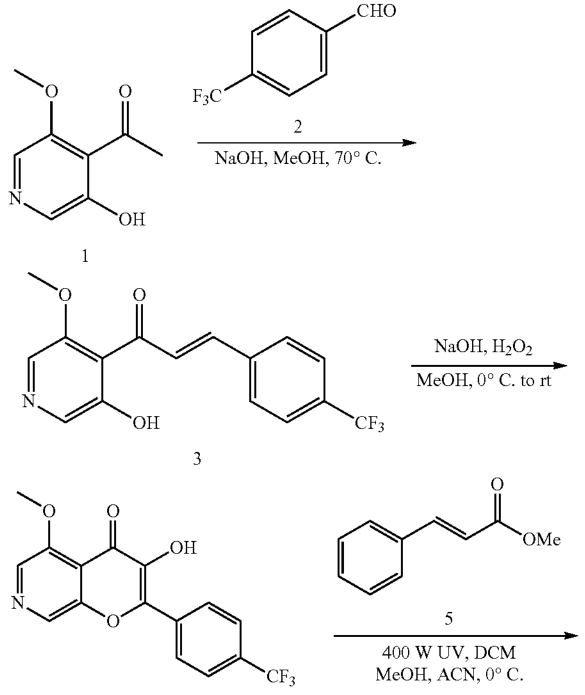

1

3

4

-continued

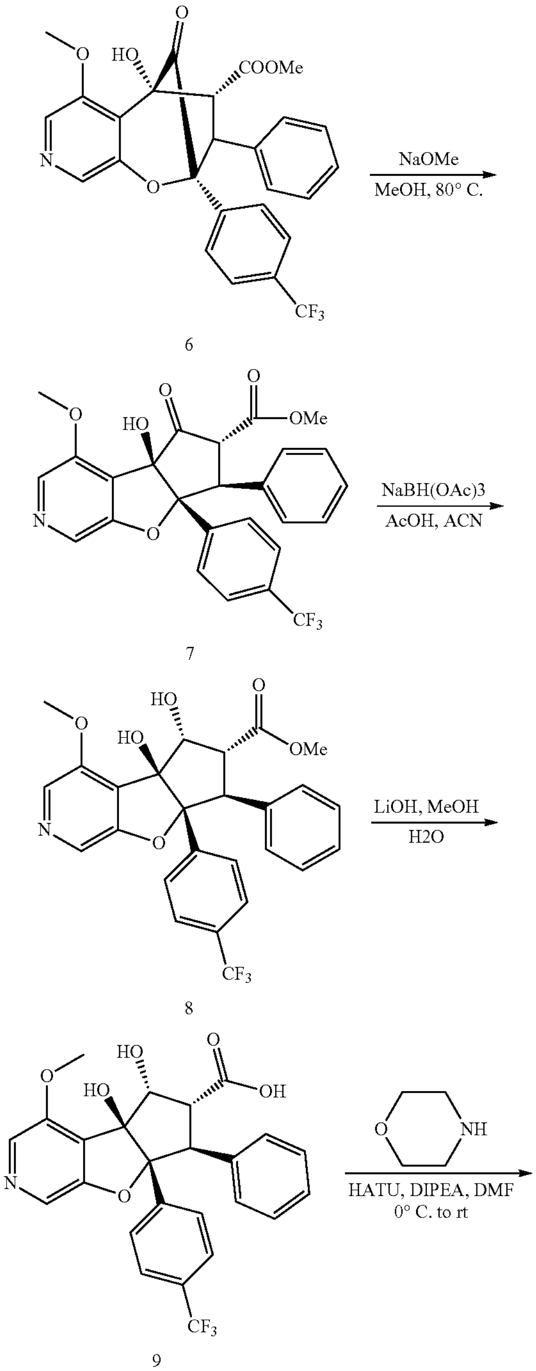

6

7

8

9

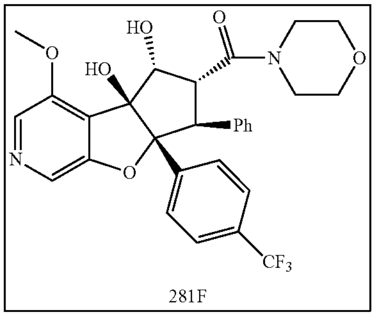

281F

Synthesis of (E)-1-(3-hydroxy-5-methoxypyridin-4-yl)-3-(4-(trifluoromethyl)phenyl)prop-2-en-1-one (3)

To a solution of 1-(3-hydroxy-5-methoxypyridin-4-yl) ethan-1-one (1, 20.0 g, 11.97 mmol) in methanol (100 mL) at 0° C. were added sodium hydroxide (5.70 g, 14.37 mmol) and 4-(trifluoromethyl)benzaldehyde (2, 20.8 g, 11.97 mmol). The reaction mixture was then stirred at 70° C. for 15 min. After completion, reaction mixture was cooled to 0° C. and water was added and neutralized to pH ~7 with 6 M aqueous hydrogen chloride. The solid obtained was filtered, washed with excess of water and dried under vacuum to afford (E)-1-(3-hydroxy-5-methoxypyridin-4-yl)-3-(4-(trifluoromethyl)phenyl)prop-2-en-1-one (3) as yellow solid. Yield: 31.0 g; MS (ESI) m/z 322.18[M−1]$^-$.

Synthesis of 3-hydroxy-5-methoxy-2-(4-(trifluoromethyl)phenyl)-4H-pyrano[2,3-c]pyridin-4-one (4)

To a solution of (E)-1-(3-hydroxy-5-methoxypyridin-4-yl)-3-(4-(trifluoromethyl)phenyl)prop-2-en-1-one (3, 25.0 g, 77.4 mmol) in methanol (250 mL) was added crushed sodium hydroxide (3.71 g, 92.8 mmol) followed by addition of hydrogen peroxide (44.0 mL, 387.0 mmol) at 0° C. The reaction mixture was stirred for 45 min at room temperature. After completion, reaction mixture was neutralized with 6 M hydrogen chloride to pH ~7. The solid obtained was filtered and dried under vacuum to afford 3-hydroxy-5-methoxy-2-(4-(trifluoromethyl)phenyl)-4H-pyrano[2,3-c]pyridin-4-one (4) as pale yellow solid. Yield: 5.50 g, 21%; MS (ESI) m/z 336.18[M−1]$^-$.

Synthesis of rac-methyl (2S,3S,4S,5R)-5-hydroxy-6-methoxy-10-oxo-3-phenyl-2-(4-(trifluoromethyl)phenyl)-2,3,4,5-tetrahydro-2,5-methanooxepino[2,3-c]pyridine-4-carboxylate (6)

A solution of 3-hydroxy-5-methoxy-2-(4-(trifluoromethyl) phenyl)-4H-pyrano [2,3-c]pyridin-4-one (4, 5.50 g, 16.3 mmol) and methyl cinnamate (5, 26.4 g, 163.3 mmol) in dichloromethane (200 mL), acetonitrile (100 mL) and methanol (100 mL) was placed in a UV reactor flask. The reaction mixture was irradiated for 16 h under 400 watts UV light at 0-15° C. After completion, the solvent was removed under reduced pressure and the crude residue was purified by Combi-flash (40 g, RediSep column) by using ethyl acetate as eluent. The desired fractions were concentrated under reduced pressure to afford rac-methyl (2S,3S,4S,5R)-5-hydroxy-6-methoxy-10-oxo-3-phenyl-2-(4-(trifluoromethyl)phenyl)-2,3,4,5-tetrahydro-2,5-methanooxepino[2,3-c]pyridine-4-carboxylate (6) as brown solid. Yield: 6.0 g, crude.

Synthesis of rac-methyl (4bR,6R,7S,7aR)-4b-hydroxy-4-methoxy-5-oxo-7-phenyl-7a-(4-(trifluoromethyl)phenyl)-4b,6,7,7a-tetrahydro-5H-cyclopenta[4,5]furo[2,3-c]pyridine-6-carboxylate (7)

The crude rac-methyl (2S,3S,4S,5R)-5-hydroxy-6-methoxy-10-oxo-3-phenyl-2-(4-(trifluoromethyl)phenyl)-2,3,4,5-tetrahydro-2,5-methanooxepino[2,3-c]pyridine-4-carboxylate (6, 6.0 g) was suspended in methanol (60 mL) and treated with sodium methoxide (25% in methanol, 60 mL) and heated the mixture to 80° C. for 3 h. After completion, the solvent was removed under reduced pressure and mixture was diluted with ammonium chloride solution and extracted with ethyl acetate. The organic phase was separated, dried over anhydrous sodium sulphate, filtered and concentrated under reduced pressure to afford rac-methyl (4bR,6R,7S,7aR)-4b-hydroxy-4-methoxy-5-oxo-7-phenyl-7a-(4-(trifluoromethyl)phenyl)-4b,6,7,7a-tetrahydro-5H-cyclopenta[4,5]furo[2,3-c]pyridine-6-carboxylate (7) as brown solid. Yield: 5.90 g, crude.

Synthesis of rac-methyl (4bS,5R,6R,7S,7aR)-4b,5-dihydroxy-4-methoxy-7-phenyl-7a-(4-(trifluoromethyl)phenyl)-4b,6,7,7a-tetrahydro-5H-cyclopenta[4,5]furo[2,3-c]pyridine-6-carboxylate (8)

To a solution of rac-methyl (4bR,6R,7S,7aR)-4b-hydroxy-4-methoxy-5-oxo-7-phenyl-7a-(4-(trifluoromethyl) phenyl)-4b,6,7,7a-tetrahydro-5H-cyclopenta[4,5]furo[2,3-c]pyridine-6-carboxylate (7, 5.9 g, 11.8 mmol) in acetonitrile (60 mL) and acetic acid (7.1 mL, 118.0 mmol) was added sodium triacetoxyborohydride (15.0 g, 70.8 mmol). The resulting mixture was stirred at room temperature for 4 h. After completion, reaction mixture was partitioned between saturated aqueous sodium bicarbonate solution and ethyl acetate. The organic layer was separated, dried over anhydrous sodium sulphate and concentrated under reduced pressure to get the crude residue. The crude residue was purified by combi-flash (40 g, RediSep) using 30-50% ethyl acetate in hexane as eluent. The desired fractions were concentrated under reduced pressure to afford rac-methyl (4bS,5R,6R,7S,7aR)-4b,5-dihydroxy-4-methoxy-7-phenyl-7a-(4-(trifluoromethyl)phenyl)-4b,6,7,7a-tetrahydro-5H-cyclopenta[4,5]furo[2,3-c]pyridine-6-carboxylate (8) as off white solid. Yield: 3.50 g, 58.10%; MS (ESI) m/z 500.55 [M−1]$^-$.

Synthesis of rac-(4bS,5R,6R,7S,7aR)-4b,5-dihydroxy-4-methoxy-7-phenyl-7a-(4-(trifluoromethyl) phenyl)-4b,6,7,7a-tetrahydro-5H-cyclopenta[4,5]furo [2,3-c]pyridine-6-carboxylic acid (9)

To a solution of rac-methyl (4bS,5R,6R,7S,7aR)-4b,5-dihydroxy-4-methoxy-7-phenyl-7a-(4-(trifluoromethyl)phenyl)-4b,6,7,7a-tetrahydro-5H-cyclopenta[4,5]furo[2,3-c] pyridine-6-carboxylate (8, 3.50 g, 6.18 mmol) in methanol and water (3:1, 30 mL), lithium hydroxide (1.48 g, 61.8 mmol) was added and the reaction was stirred at room temperature for 1 h. After completion, methanol was distilled off and reaction mixture was cooled to 0° C., acidified with 1 M hydrogen chloride to pH ~6. The precipitated solid was filtered and dried under vacuum to afford rac-(4bS,5R,6R,7S,7aR)-4b,5-dihydroxy-4-methoxy-7-phenyl-7a-(4-(trifluoromethyl)phenyl)-4b,6,7,7a-tetrahydro-5H-cyclopenta[4,5]furo[2,3-c]pyridine-6-carboxylic acid (9) as off white solid. Yield: 2.80 g, 82%; MS (ESI) m/z 486.47[M−1]$^-$.

Synthesis of rac-((4bS,5R,6R,7S,7aR)-4b,5-dihydroxy-4-methoxy-7-phenyl-7a-(4-(trifluoromethyl) phenyl)-4b,6,7,7a-tetrahydro-5H-cyclopenta[4,5]furo [2,3-c]pyridin-6-yl)(morpholino)methanone (Cpd. No. 281F)

To a solution of rac-(4bS,5R,6R,7S,7aR)-4b,5-dihydroxy-4-methoxy-7-phenyl-7a-(4-(trifluoromethyl)phenyl)-4b,6,7,7a-tetrahydro-5H-cyclopenta[4,5]furo[2,3-c]pyridine-6-carboxylic acid (9, 0.65 g, 1.3 mmol) in N,N-dimethylformamide (5 mL), 1-[Bis(dimethylamino) methylene]-1H-1,2,3-triazolo[4,5-b]pyridinium-3-oxide hexafluorophosphate (1.0 g, 2.6 mmol) and N,N-diisopropylethylamine (0.7 ml, 4.0 mmol) were added at 0° C. and stirred the mixture for 5 min. morpholine (0.17 g, 2.0 mmol) was then added and the reaction mixture was stirred for 3 h at 25° C. After completion, reaction mixture was diluted with ethyl acetate and washed with cold water. The organic layer was dried over anhydrous sodium sulphate, filtered and concentrated to give crude product. The crude product was purified by Combi-flash (12 g, RediSep column) using 6% methanol in dichloromethane as eluent. The desired fractions were concentrated to afford rac-((4bS,5R,6R,7S,7aR)-4b,5-dihydroxy-4-methoxy-7-phenyl-7a-(4-(trifluoromethyl)phenyl)-4b,6,7,7a-tetrahydro-5H-cyclopenta[4,5]furo[2,3-c]pyridin-6-yl)(morpholino)methanone (Cpd. No. 281F) as off white solid. Yield: 0.7 g, 94%; MS (ESI) m/z 556.89 $[M+1]^+$; $^1H$ NMR (400 MHz, DMSO-$d_6$) δ 8.13 (s, 1H), 8.01 (s, 1H), 7.36 (s, 4H), 7.03-7.00 (m, 2H), 6.95-6.92 (m, 3H), 5.78 (s, 1H), 5.29 (d, J=5.4 Hz, 1H), 4.72 (t, J=5.2 Hz, 1H), 4.50 (d, J=13.4 Hz, 1H), 4.26 (dd, J=5.08, 13.2 Hz, 1H), 3.88 (s, 4H), 3.79-3.47 (m, 7H).

Example 282

(4bS,5R,6S,7S,7aR)-4-methoxy-6-(morpholinomethyl)-7-phenyl-7a-(4-(trifluoromethyl)phenyl)-5,6,7,7a-tetrahydro-4bH-cyclopenta[4,5]furo[2,3-c]pyridine-4b,5-diol (Cpd. No. 282F)

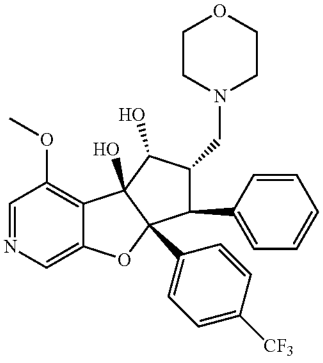

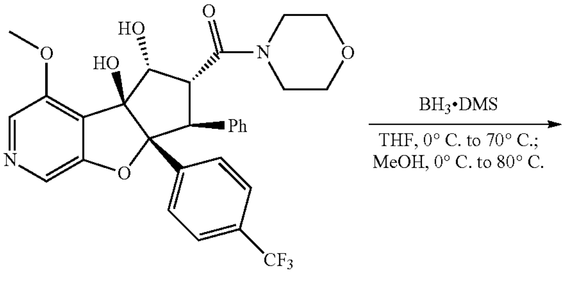

1

-continued

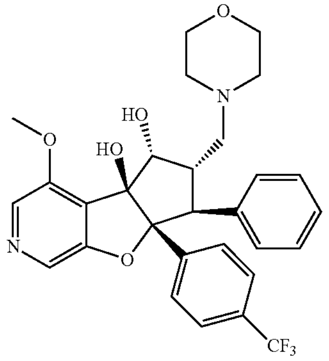

282F

Synthesis of (4bS,5R,6S,7S,7aR)-4-methoxy-6-(morpholinomethyl)-7-phenyl-7a-(4-(trifluoromethyl)phenyl)-5,6,7,7a-tetrahydro-4bH-cyclopenta[4,5]furo[2,3-c]pyridine-4b,5-diol (Cpd. No. 282F)

To a solution of rac-((4bS,5R,6R,7S,7aR)-4b,5-dihydroxy-4-methoxy-7-phenyl-7a-(4-(trifluoromethyl)phenyl)-4b,6,7,7a-tetrahydro-5H-cyclopenta[4,5]furo[2,3-c]pyridin-6-yl)(morpholino)methanone (1, 0.7 g, 1.25 mmol) in tetrahydrofuran (10 mL), Borane dimethyl sulphide (1.0 mL, 12.5 mmol) was added at 0° C. and stirred the mixture for 6 h at 70° c. After completion, reaction mixture was quenched with methanol (10.0 mL) at 0° C. and again heated for 10 h at 80° C. The reaction mixture was concentrated to give crude product. The crude product was purified by combi-flash (12 g, RediSep column) using 20% methanol in dichloromethane as eluent. The desired fractions were concentrated under reduced pressure. The compound was again re-purified by reverse phase preparative HPLC and desired fractions were lyophilized to give rac-(4bS,5R,6S,7S,7aR)-4-methoxy-6-(morpholinomethyl)-7-phenyl-7a-(4-(trifluoromethyl)phenyl)-5,6,7,7a-tetrahydro-4bH-cyclopenta[4,5]furo[2,3-c]pyridine-4b,5-diol as white solid. Yield: 50 mg, 7%. The enantiomers were separated by chiral SFC [Chiralpak IG (4.6×250) mm, 5μ]; $CO_2$/0.1% TEA in EtOH=(80/20) Peak 1 (Cpd. No. 282F, 12 mg), $[\alpha]_D$−70.0° (c 0.26, $CHCl_3$), $R_t$=5.19 min, ee: 99.76%; MS (ESI) m/z 543.31 $[M+1]^+$; $^1H$ NMR (400 MHz, DMSO-$d_6$) δ 8.04 (s, 1H), 7.96 (s, 1H), 7.39 (bs, 4H), 7.04-7.00 (m, 5H), 5.70 (s, 1H), 5.08 (bs, 1H), 4.52 (s, 1H), 3.87 (s, 3H), 3.78 (d, J=14.7 Hz, 1H), 3.61-3.50 (m, 6H), 2.32-1.89 (m, 5H); Peak 2 (8 mg), $[\alpha]_D$+50.2° (c 0.25, $CHCl_3$), $R_t$=7.89 min, ee: 99.70%; MS (ESI) m/z 543.31 $[M+1]^+$; $^1H$ NMR (400 MHz, DMSO-$d_6$) δ: 8.04 (s, 1H), 7.96 (s, 1H), 7.39 (d, J=7.88 Hz, 4H), 7.06-7.00 (m, 5H), 5.70 (s, 1H), 5.08 (bs, 1H), 4.52 (s, 1H), 3.88 (s, 3H), 3.78 (d, J=14.0 Hz, 1H), 3.61-3.22 (m, 6H), 2.62-2.05 (m, 5H).

Example 283

Rac-(4bS,5R,6S,7S,7aR)-4-methoxy-6-((4-methylpiperazin-1-yl)methyl)-7-phenyl-7a-(4-(trifluoromethyl)phenyl)-5,6,7,7a-tetrahydro-4bH-cyclopenta[4,5]furo[2,3-c]pyridine-4b,5-diol (Cpd. No. 283F)

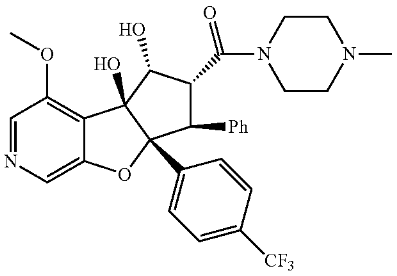

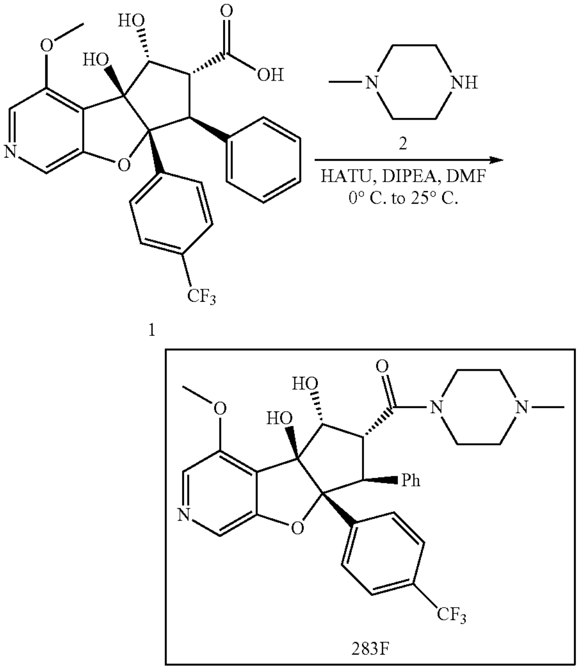

1

2

283F

Synthesis of rac-((4bS,5R,6R,7S,7aR)-4b,5-dihydroxy-4-methoxy-7-phenyl-7a-(4-(trifluoromethyl)phenyl)-4b,6,7,7a-tetrahydro-5H-cyclopenta[4,5]furo[2,3-c]pyridin-6-yl)(4-methylpiperazin-1-yl)methanone (Cpd. No. 283F)

To a solution of rac-(4bS,5R,6R,7S,7aR)-4b,5-dihydroxy-4-methoxy-7-phenyl-7a-(4-(trifluoromethyl)phenyl)-4b,6,7,7a-tetrahydro-5H-cyclopenta[4,5]furo[2,3-c]pyridine-6-carboxylic acid (1, 1.0 g, 1.0 mmol) in N,N-dimethylformamide (20 mL) at 0° C. were added 1-[Bis(dimethylamino)methylene]-1H-1,2,3-triazolo[4,5-b]pyridinium3-oxide hexafluorophosphate (1.2 g, 3.0 mmol) and N,N-diisopropylethylamine (0.8 ml, 5.1 mmol) and reaction mixture stirred for 5 min. 1-methylpiperazine (2, 0.25 g, 2.5 mmol) was then added and the reaction mixture was stirred for 2 h at 25° C. After completion, reaction mixture was diluted with ethyl acetate and washed with cold water. The organic layer was dried over anhydrous sodium sulphate, filtered and concentrated to give crude product. The crude product was purified by combi-flash (12 g, RediSep column) using 6% methanol in dichloromethane as eluent. The desired fractions were concentrated to afford rac-((4bS,5R,6R,7S,7aR)-4b,5-dihydroxy-4-methoxy-7-phenyl-7a-(4-(trifluoromethyl)phenyl)-4b,6,7,7a-tetrahydro-5H-cyclopenta[4,5]furo[2,3-c]pyridin-6-yl)(4-methylpiperazin-1-yl)methanone (Cpd. No. 283F) as white solid. Yield: 0.55 g, 94%; MS (ESI) m/z 570.29 $[M+1]^+$; $^1H$ NMR (400 MHz, DMSO-$d_6$) δ 8.12 (s, 1H), 8.00 (s, 1H), 7.35 (s, 4H), 7.03-7.00 (m, 2H), 6.95-6.90 (m, 3H), 5.79 (s, 1H), 5.22 (d, J=5.3 Hz, 1H), 4.70 (t, J=5.1 Hz, 1H), 4.52 (d, J=13.4 Hz, 1H), 4.26 (dd, J=4.7, 13.2 Hz, 1H), 3.87 (s, 4H), 3.67 (bs, 1H), 3.48 (bs, 1H), 3.32 (bs, 1H), 2.54 (bs, 1H), 2.37-2.32 (m, 2H), 2.23 (s, 3H), 2.11 (bs, 1H).

Example 284

(4bS,5R,6S,7S,7aR)-4-methoxy-6-((4-methylpiperazin-1-yl)methyl)-7-phenyl-7a-(4-(trifluoromethyl)phenyl)-5,6,7,7a-tetrahydro-4bH-cyclopenta[4,5]furo[2,3-c]pyridine-4b,5-diol (Cpd. No. 284F)

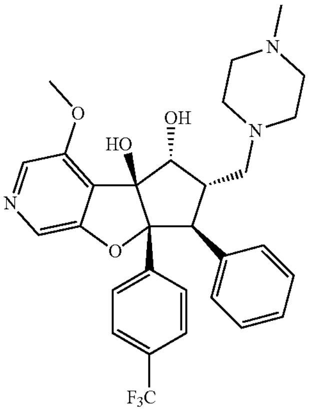

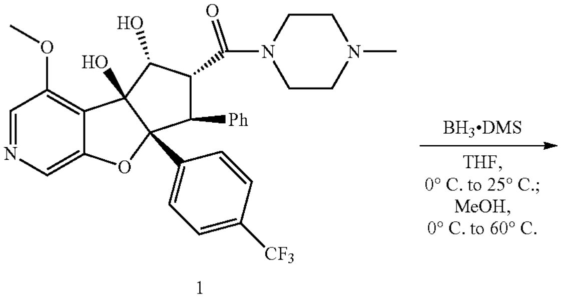

1

-continued

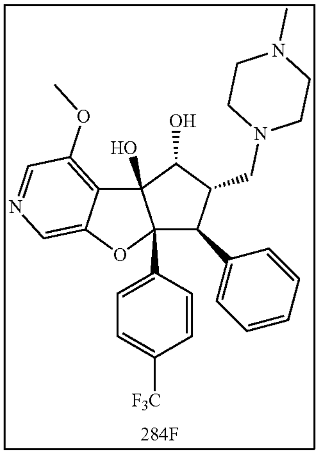

284F

Synthesis of (4bS,5R,6S,7S,7aR)-4-methoxy-6-((4-methylpiperazin-1-yl)methyl)-7-phenyl-7a-(4-(trifluoromethyl)phenyl)-5,6,7,7a-tetrahydro-4bH-cyclopenta[4,5]furo[2,3-c]pyridine-4b,5-diol (Cpd. No. 284F)

To a solution of rac-((4bS,5R,6R,7S,7aR)-4b,5-dihydroxy-4-methoxy-7-phenyl-7a-(4-(trifluoromethyl)phenyl)-4b,6,7,7a-tetrahydro-5H-cyclopenta[4,5]furo[2,3-c]pyridin-6-yl)(4-methylpiperazin-1-yl)methanone (1, 0.5 g, 0.87 mmol) in tetrahydrofuran (10 mL) at 0° C., borane dimethyl sulphide (0.7 mL, 8.7 mmol) was added and reaction mixture was stirred for 3 h at room temperature. After completion, reaction mixture was quenched with methanol (5.0 mL) at 0° C. and heated for 10 h at 60° C. The reaction mixture was concentrated to give crude product. The crude product was purified by combi-flash (12 g, RediSep column) using 20% methanol in dichloromethane as eluent. The desired fractions were concentrated under reduced pressure. The compound was re-purified by reverse phase preparative HPLC and desired fractions were lyophilized to give rac-(4bS,5R,6S,7S,7aR)-4-methoxy-6-((4-methylpiperazin-1-yl)methyl)-7-phenyl-7a-(4-(trifluoromethyl)phenyl)-5,6,7,7a-tetrahydro-4bH-cyclopenta[4,5]furo[2,3-c]pyridine-4b,5-diol as white solid. Yield: 0.210, 48%. The enantiomers were separated by chiral SFC [Chiralpak IA (4.6×250) mm, 5μ]; $CO_2$/0.1% TEA in MeOH=60/40], Peak 1 (Cpd. No. 284F, 17 mg), $[\alpha]_D$−48.1° (c 0.27, $CHCl_3$), $R_t$=1.54, ee 99.90%; MS (ESI) m/z 556.33 $[M+1]^+$. $^1$H NMR (400 MHz, DMSO-$d_6$) δ: 8.02 (s, 1H), 7.94 (s, 1H), 7.39-7.34 (m, 4H), 7.05-7.02 (m, 2H), 6.98-6.96 (m, 3H), 5.68 (s, 1H), 5.06 (bs, 1H), 4.47 (s, 1H), 3.85 (s, 3H), 3.76 (d, J=14.2, 1H), 3.22-3.19 (m, 1H), 2.60-2.57 (m, 4H), 2.30 (m, 5H), 2.15 (s, 3H), 2.06 (d, J=11.48 Hz, 1H); Peak 2 (16 mg), $[\alpha]_D$+1$^4$0.8° (c 0.25, $CHCl_3$), $R_t$=2.55, ee 99.9%; MS (ESI) m/z 556.32 $[M+1]^+$; $^1$H NMR (400 MHz, DMSO-$d_6$) δ: 8.04 (s, 1H), 7.96 (s, 1H), 7.41-7.36 (m, 4H), 7.07-7.04 (m, 2H), 7.00-6.98 (m, 3H), 5.70 (s, 1H), 5.08 (bs, 1H), 4.49 (s, 1H), 3.87 (s, 3H), 3.78 (d, J=14.2, 1H), 3.24-3.22 (m, 1H), 2.59-2.56 (m, 4H), 2.32 (bs, 5H), 2.16 (s, 3H), 2.02 (d, J=11.12 Hz, 1H).

Example 285

Rac-(4bS,5R,6R,7S,7aR)-N-(2,2-difluoroethyl)-4b,5-dihydroxy-4-methoxy-7-phenyl-7a-(4-(trifluoromethyl)phenyl)-4b,6,7,7a-tetrahydro-5H-cyclopenta[4,5]furo[2,3-c]pyridine-6-carboxamide (Cpd. No. 285F)

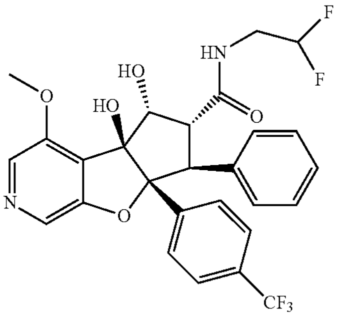

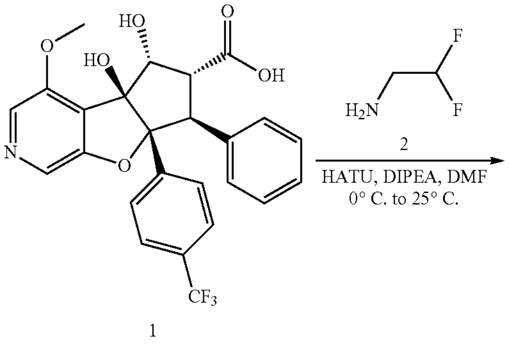

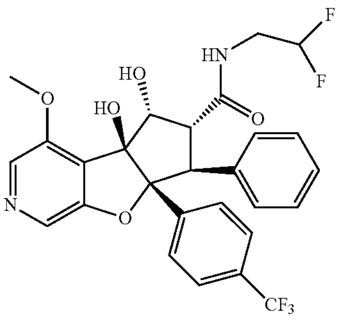

285F

Synthesis of rac-(4bS,5R,6R,7S,7aR)-N-(2,2-difluoroethyl)-4b,5-dihydroxy-4-methoxy-7-phenyl-7a-(4-(trifluoromethyl)phenyl)-4b,6,7,7a-tetrahydro-5H-cyclopenta[4,5]furo[2,3-c]pyridine-6-carboxamide (Cpd. No. 285F)

To a solution of rac-(4bS,5R,6R,7S,7aR)-4b,5-dihydroxy-4-methoxy-7-phenyl-7a-(4-(trifluoromethyl)phenyl)-4b,6,7,7a-tetrahydro-5H-cyclopenta[4,5]furo[2,3-c]pyridine-6-carboxylic acid (1, 0.7 g, 1.0 mmol) in N,N-dimethylformamide (5.0 mL), 1-[Bis(dimethylamino)methylene]-1H-1,2,3-triazolo[4,5-b]pyridinium-3-oxide hexafluorophosphate (1.60 g, 4.3 mmol) and N,N-diisopropylethylamine (1.25 ml, 7.1 mmol) were added at 0° C. and stirred the mixture for 5 min. 2,2-Difluoroethan-1-amine (2, 0.20 mL, 2.8 mmol) was then added and the reaction mixture was stirred for 2 h at 25° C. After completion, reaction mixture was diluted with ethyl acetate and washed with cold water. The organic layer was dried over anhydrous sodium sulphate, filtered and concentrated to give crude product. The crude product was purified by combi-flash (12 g, RediSep column) using 6% methanol in dichloromethane as eluent. The desired fractions were concentrated to afford rac-(4bS,5R,6R,7S,7aR)-N-(2,2-difluoroethyl)-4b,5-dihydroxy-4-methoxy-7-phenyl-7a-(4-(trifluoromethyl)phenyl)-4b,6,7,7a-tetrahydro-5H-cyclopenta[4,5]furo[2,3-c]pyridine-6-carboxamide (Cpd. No. 285F) as white solid. Yield: 0.66 g, 83%; MS (ESI) m/z 551.18 [M+1]$^+$; $^1$H NMR (400 MHz, DMSO-$d_6$) δ 8.59 (t, J=5.5 Hz, 1H), 8.12 (s, 1H), 7.99 (s, 1H), 7.40 (d, J=8.4 Hz, 2H), 7.32 (d, J=8.2 Hz, 2H), 7.04-7.01 (m, 2H), 6.96 (bs, 3H), 6.05-5.75 (m, 2H), 5.13 (d, J=4.5 Hz, 1H), 4.64 (t, J=4.9 Hz, 1H), 4.41 (d, J=14.3 Hz, 1H), 4.01 (dd, J=4.4, 14.0 Hz, 1H), 3.87 (s, 3H), 3.50-3.40 (m, 1H).

Example 286

(4bS,5R,6S,7S,7aR)-6-(((2,2-difluoroethyl)amino)methyl)-4-methoxy-7-phenyl-7a-(4-(trifluoromethyl)phenyl)-5,6,7,7a-tetrahydro-4bH-cyclopenta[4,5]furo[2,3-c]pyridine-4b,5-diol (Cpd. No. 286F)

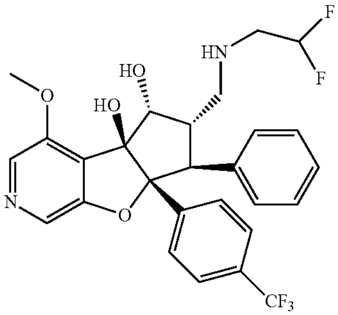

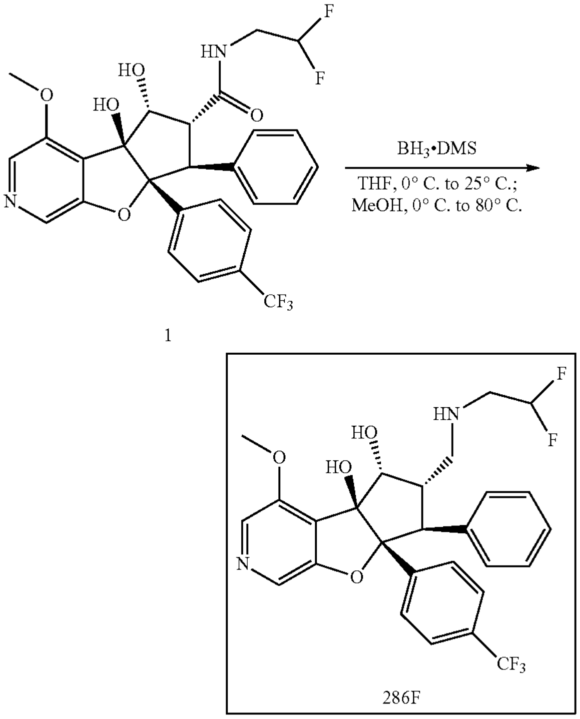

1

286F

Synthesis of (4bS,5R,6S,7S,7aR)-6-(((2,2-difluoroethyl)amino)methyl)-4-methoxy-7-phenyl-7a-(4-(trifluoromethyl)phenyl)-5,6,7,7a-tetrahydro-4bH-cyclopenta[4,5]furo[2,3-c]pyridine-4b,5-diol (Cpd. No. 286F)

To a solution of rac-(4bS,5R,6R,7S,7aR)-N-(2,2-difluoroethyl)-4b,5-dihydroxy-4-methoxy-7-phenyl-7a-(4-(trifluoromethyl)phenyl)-4b,6,7,7a-tetrahydro-5H-cyclopenta[4,5]furo[2,3-c]pyridine-6-carboxamide (1, 0.650 g, 1.18 mmol) in tetrahydrofuran (10 mL), Borane dimethyl sulphide (1.1 mL, 11.8 mmol), was added at 0° C. and stirred the mixture for 3 h at room temperature. After completion, reaction mixture was quenched with methanol (5.0 mL) and again heated for 12 h at 80° C. The reaction mixture was concentrated to give crude product. The crude product was purified by combi-flash (12 g, RediSep column) using 20% methanol in dichloromethane as eluent. The desired fractions were concentrated under reduced pressure. The compound was re-purified by reverse phase prep HPLC, desired fractions were lyophilized to give rac-(4bS,5R,6S,7S,7aR)-6-(((2,2-difluoroethyl)amino)methyl)-4-methoxy-7-phenyl-7a-(4-(trifluoromethyl)phenyl)-5,6,7,7a-tetrahydro-4bH-cyclopenta[4,5]furo[2,3-c]pyridine-4b,5-diol as white solid. Yield: 365 mg, 57%. The enantiomers were separated by chiral preparative HPLC [Chiralpak IG (4.6×250) mm, 5μ]; n-Hexane/EtOH=85/15 (V/V) Peak 1 (Cpd. No. 286F, 19 mg), $[\alpha]_D$−9.3° (c 0.23, $CHCl_3$), $R_t$=14.7, ee 99.52%; MS (ESI) m/z 537.23 [M+1]$^+$; $^1$H NMR (400 MHz, DMSO-$d_6$) δ 8.06 (s, 1H), 7.98 (s, 1H), 7.39 (s, 4H), 7.07-6.98 (m, 5H), 5.83 (t, J=56.8 Hz, 1H), 5.68 (s, 1H), 5.19 (d, J=5.0 Hz, 1H), 4.56 (s, 1H), 3.89 (s, 3H), 3.76 (d, J=14.2, 1H), 3.17 (bs, 1H), 2.89 (bs, 2H), 2.69 (bs, 2H), 2.03 (bs, 1H). Peak 2 (19 mg), $[\alpha]_D$+9.0° (c 0.26, $CHCl_3$), $R_t$=20.05, ee:98.48%; MS (ESI) m/z 537.22 [M+1]$^+$; $^1$H NMR (400 MHz, DMSO-$d_6$) δ: 8.06 (s, 1H), 7.98 (s, 1H), 7.39 (s, 4H), 7.05-6.98 (m, 5H), 5.97 (t, J=56.8 Hz, 1H), 5.68 (s, 1H), 5.19 (d, J=4.5 Hz, 1H), 4.56 (s, 1H), 3.89 (s, 3H), 3.74 (d, J=14.1, 1H), 3.18 (bs, 1H), 2.89 (bs, 2H), 2.69-2.66 (m, 2H), 2.13 (bs, 1H).

Example 287

Rac-4-((4bS,5R,7S,7aR)-4b,5-dihydroxy-4-methoxy-5-(morpholinomethyl)-7-phenyl-4b,5,6,7-tetrahydro-7aH-cyclopenta[4,5]furo[2,3-c]pyridin-7a-yl)benzonitrile (Cpd. No. 287F)

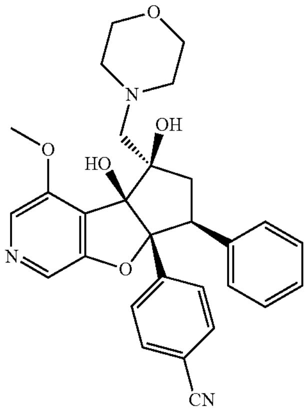

-continued

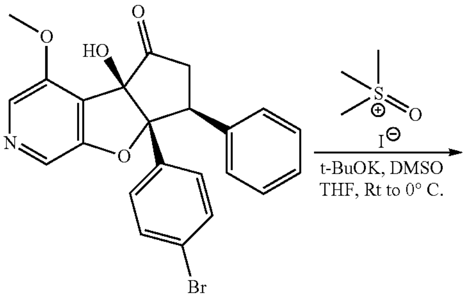

1

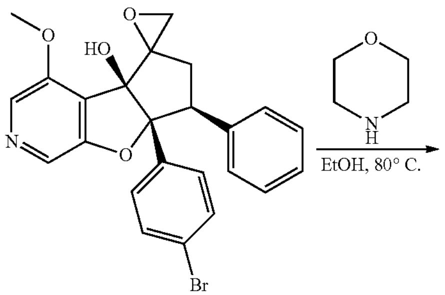

2

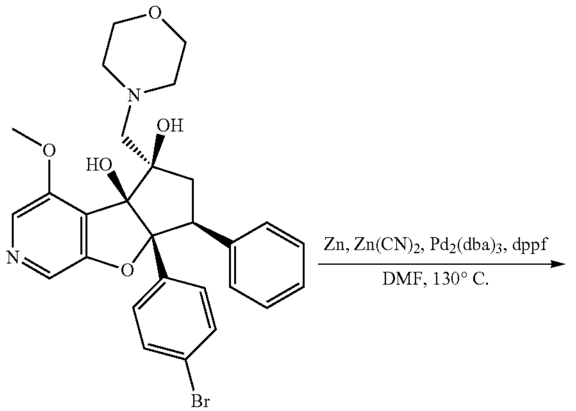

3

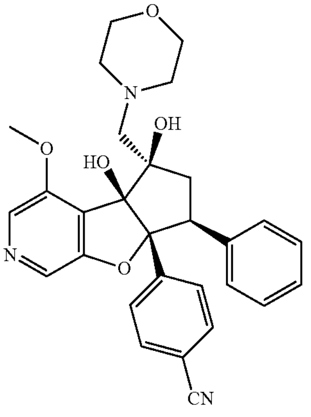

287F

Synthesis of rac-(4bR,7S,7aR)-7a-(4-bromophenyl)-4-methoxy-7-phenyl-7,7a-dihydrospiro[cyclopenta[4,5]furo[2,3-c]pyridine-5,2'-oxiran]-4b(6H)-ol (2)

To a solution of trimethylsulfoxonium iodide (0.38 g, 1.76 mmol) in dimethyl sulfoxide (2 ml) was added 1.0 M potassium tert-butoxide (1.65 ml, 1.65 mmol) in tetrahydrofuran at room temperature and reaction mixture stirred for 1 h. Reaction mixture then cooled to −5° C., and rac-(4bR,7S,7aR)-7a-(4-bromophenyl)-4b-hydroxy-4-methoxy-7-phenyl-4b,6,7,7a-tetrahydro-5H-cyclopenta[4,5]furo[2,3-c]pyridin-5-one (1, 0.50 g, 1.10 mmol) in mixture of dimethyl sulfoxide (2 ml) and tetrahydrofuran (2 ml) was added slowly over a period of 5 min. The reaction mixture then stirred at 0° C. for 2 h. The reaction mixture was quenched by addition of cold water and extracted with ethyl acetate. The organic layer was washed with cold water, brine, dried over anhydrous sodium sulphate and concentrated under reduced pressure to get crude. The crude obtained was purified by silica gel (100-200 mesh size) column chromatography using 2% methanol in dichloromethane as eluent. The desired fractions were concentrated to afford rac-(4bR,7S,7aR)-7a-(4-bromophenyl)-4-methoxy-7-phenyl-7,7a-dihydrospiro[cyclopenta[4,5]furo[2,3-c]pyridine-5,2'-oxiran]-4b(6H)-ol (2). Yield: 0.17 g, 33%; MS (ESI) m/z 466.10 $[M+1]^+$.

Synthesis of rac-(4bS,5R,7S,7aR)-7a-(4-bromophenyl)-4-methoxy-5-(morpholinomethyl)-7-phenyl-5,6,7,7a-tetrahydro-4bH-cyclopenta[4,5]furo[2,3-c]pyridine-4b, 5-diol (3)

In a sealed vial a solution of compound rac-(4bR,7S,7aR)-7a-(4-bromophenyl)-4-methoxy-7-phenyl-7,7a-dihydrospiro[cyclopenta[4,5]furo[2,3-c]pyridine-5,2'-oxiran]-4b(6H)-ol (2, 0.1 g, 0.215 mmol), and morpholine (0.092 ml, 1.07 mmol) in ethanol was heated at 80° C. for 5 h. The reaction mixture was concentrated under reduced pressure. The crude obtained was triturated with diethyl ether. The solid obtained was again triturated with pentane and dried to afford rac-(4bS,5R,7S,7aR)-7a-(4-bromophenyl)-4-methoxy-5-(morpholinomethyl)-7-phenyl-5,6,7,7a-tetrahydro-4bH-cyclopenta[4,5]furo[2,3-c]pyridine-4b,5-diol (3). Yield 0.040 g, 34.0%; MS (ESI) m/z 553.28$[M+1]^+$.

Synthesis of rac-4-((4bS,5R,7S,7aR)-4b,5-dihydroxy-4-methoxy-5-(morpholinomethyl)-7-phenyl-4b,5,6,7-tetrahydro-7aH-cyclopenta[4,5]furo[2,3-c]pyridin-7a-yl)benzonitrile (Cpd. No. 287F)

To the solution of rac-(4bS,5R,7S,7aR)-7a-(4-bromophenyl)-4-methoxy-5-(morpholinomethyl)-7-phenyl-5,6,7,7a-tetrahydro-4bH-cyclopenta[4,5]furo[2,3-c]pyridine-4b,5-diol (3, 0.050 g, 0.090 mmol) in N,N-dimethylformamide (3 ml), zinc cyanide (0.064 g, 0.54 mmol) and zinc dust (0.001 g, 0.01 mmol) were added at room temperature and the reaction mixture was degassed with argon for 15 minutes, tris(dibenzylideneacetone)dipalladium (0.0024 g, 0.0027 mmol) and 1,1'-Bis(diphenylphosphino) ferrocene (0.001 g, 0.0018 mmol) were added and reaction mixture was heated at 140° C. for 5 h. After completion, the reaction mixture was diluted with ethyl acetate and washed with cold water. The organic layer was separated and dried over anhydrous sodium sulphate, filtered and concentrated to give crude product. The crude product was purified by preparative HPLC After purification compound was loaded on Phenomenex (strata-X-C) column and eluted in 5% methanolic ammonia to get pure rac-4-((4bS,5R,7S,7aR)-4b,5-dihydroxy-4-methoxy-5-(morpholinomethyl)-7-phenyl-4b,5,6,7-tetrahydro-7aH-cyclopenta[4,5]furo[2,3-c]pyridin-7a-yl)benzonitrile (Cpd. No. 287F) as a white solid. Yield: 0.01 g, 22%; MS (ESI) m/z 500.3[M+1]$^+$; $^1$H NMR (400 MHz, DMSO-$d_6$) 8.16 (s, 1H), 8.05 (s, 1H), 7.52 (d, J=8.4 Hz, 2H), 7.30 (d, J=8.4 Hz, 2H), 7.12-7.03 (m, 5H), 5.57 (s, 1H), 5.52 (s, 1H), 3.90 (s, 3H), 3.70 (dd, J=5.6, 14.8 Hz, 1H), 3.49 (bs, 4H), 2.93-2.89 (m, 1H), 2.66-2.51 (m, 3H), 2.39-1.90 (m, 4H).

Example 288

(5aR,6S,7S,8R,8aS)-5a-(4-cyanophenyl)-7-((3,3-difluoroazetidin-1-yl)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 288F)

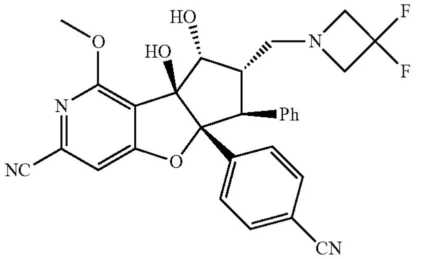

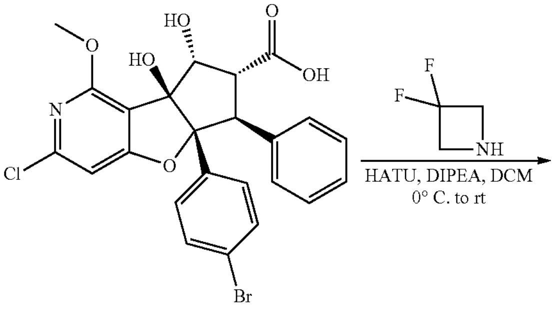

1

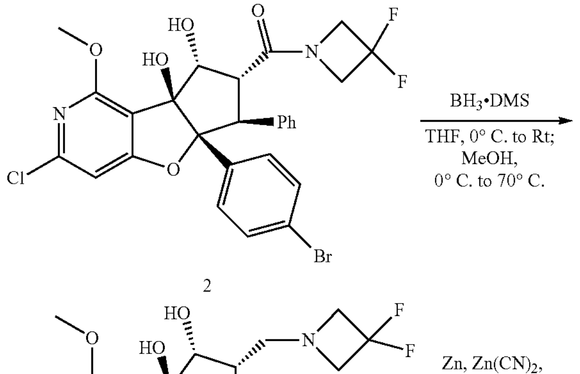

2

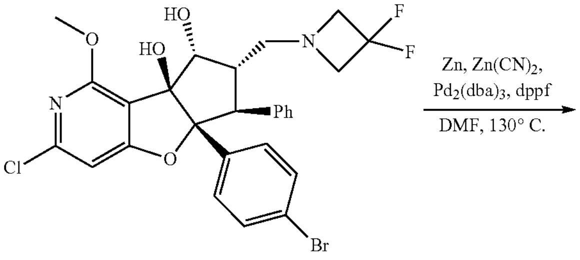

3

-continued

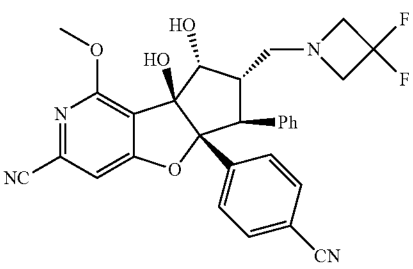

288F

Synthesis of rac-((5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridin-7-yl)(3,3-difluoroazetidin-1-yl)methanone (2)

To a solution of rac-(5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridine-7-carboxylic acid (1, 2.0 g, 3.76 mmol) in dichloromethane (20 mL) at 0° C. were added 1-[Bis(dimethylamino)methylene]-1H-1,2,3-triazolo[4,5-b]pyridinium 3-oxide hexafluorophosphate (2.14 g, 5.64 mmol), and N,N-diisopropylethylamine (4.0 ml, 22.1 mmol), and reaction mixture was stirred for 5 min. 3,3-difluoroazetidine hydrochloride (1.43 g, 11.2 mmol) was then added at the same temperature and the reaction mixture was stirred for 16 h at room temperature. After completion, the reaction mixture was diluted with dichloromethane and washed with cold water. The organic layer was separated and dried over anhydrous sodium sulphate, filtered and concentrated to give crude product. The crude product was purified by silica gel (100-200 mesh size) column chromatography using 0-5% methanol in dichloromethane as eluent. The desired fractions were concentrated to afford rac-((5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridin-7-yl)(3,3-difluoroazetidin-1-yl)methanone (2) as yellow solid. Yield: 2.00 g, 90%; MS (ESI) m/z 605.10[M+1]$^+$.

Synthesis of rac-(5aR,6S,7S,8R,8aS)-5a-(4-bromophenyl)-3-chloro-7-((3,3-difluoroazetidin-1-yl)methyl)-1-methoxy-6-phenyl-5a,6,7,8-tetrahydro-8aH-cyclopenta[4,5]furo[3,2-c]pyridine-8,8a-diol (3)

To a solution of rac-((5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridin-7-yl)(3,3-difluoroazetidin-1-yl)methanone (2, 2.00 g, 3.6 mmol) in dry tetrahydrofuran (20 ml) at 0° C., borane dimethyl sulphide complex (3.5 ml, 36.4 mmol) was added drop wise over a period of 5 min. The reaction mixture was slowly brought to room temperature and stirred for additional 16 h. After completion, the reaction mass was quenched with methanol at 0° C. and heated to reflux for 10 h. After completion, solvent was removed under reduced pressure and the residue was purified by silica gel (100-200 mesh size) column chromatography using 5% methanol in dichloromethane as eluent. The desired fractions were concentrated under reduced pressure to afford rac-(5aR,6S,7S, 8R,8aS)-5a-(4-bromophenyl)-3-chloro-7-((3,3-difluoroazetidin-1-yl)methyl)-1-methoxy-6-phenyl-5a,6,7,8-tetrahydro-8aH-cyclopenta[4,5]furo[3,2-c]pyridine-8,8a-diol (3) as white solid. Yield: 1.0 g, 51%; MS (ESI) m/z 593.19[M+1]$^+$.

Synthesis of (5aR,6S,7S,8R,8aS)-5a-(4-cyanophenyl)-7-((3,3-difluoroazetidin-1-yl)methyl)-8,8a-dihydroxy-1-methoxy-6-phenyl-5a, 7,8,8a-tetrahydro-6H-cyclopenta[4,5]furo[3,2-c]pyridine-3-carbonitrile (Cpd. No. 288F)

To a solution of rac-(5aR,6S,7S,8R,8aS)-5a-(4-bromophenyl)-3-chloro-7-((3,3-difluoroazetidin-1-yl)methyl)-1-methoxy-6-phenyl-5a,6,7,8-tetrahydro-8aH-cyclopenta[4,5]furo[3,2-c]pyridine-8,8a-diol (3, 1.0 g, 1.68 mmol) in N,N-dimethylformamide (10 mL), zinc cyanide (1.15 g, 10.1 mmol) and zinc dust (0.011 g, 0.168 mmol) were added at room temperature and the reaction mixture was degassed with argon for 15 min. 1,1'-Bis(diphenylphosphino)ferrocene (0.186 g, 0.336 mmol) and tris(dibenzylideneacetone) dipalladium (0.153 g, 0.168 mmol) were added to the reaction mixture, degassed for additional 5 min and mixture was heated at 130° C. for 2 h. After completion, the reaction mixture was diluted with ethyl acetate and washed with cold water. The organic layer was separated and dried over anhydrous sodium sulphate, filtered and concentrated to give crude product. The crude product was purified by silica gel (100-200 mesh size) column chromatography using 2-3% methanol in dichloromethane as eluent. The desired fractions were concentrated to afford rac-(5aR,6S,7S,8R,8aS)-5a-(4-cyanophenyl)-7-((3,3-difluoroazetidin-1-yl)methyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 288F) as white solid. Yield: 0.50 g, MS (ESI) m/z 531.23[M+1]$^+$. The enantiomers were separated by chiral SFC [CHRIALPAK IA (4.6×250)mm, 5μ]: $CO_2$/MeOH/TEA (80:20:0.2)]. Peak 1 (160 mg), $R_t$=2.416 min, ee: 99.78%, $[\alpha]_D$−89.4° (c 0.25, $CHCl_3$); MS (ESI) m/z 531.23 [M+1]$^+$; $^1$H NMR (400 MHz, DMSO-d) 7.56-7.51 (m, 3H), 7.34 (d, J=8.4 Hz, 2H), 7.11-7.07 (m, 2H), 7.01 (d, J=7.6 Hz, 3H), 5.88 (s, 1H), 5.42 (s, 1H), 4.46 (s, 1H), 3.89 (s, 3H), 3.79 (d, J=14.0 Hz, 1H), 3.64 (bs, 3H), 3.06-2.99 (m, 1H), 2.79-2.74 (m, 1H), 2.58-2.37 (m, 2H). Peak-2 (170 mg), $R_t$=4.573 min, ee: 99.32%, $[\alpha]_D$+71.9° (c 0.35, $CHCl_3$) MS (ESI) m/z 531.23[M+1]$^+$; $^1$H NMR (400 MHz, DMSO-d) 7.55-7.50 (m, 3H), 7.34 (d, J=8.4 Hz, 2H), 7.08-7.07 (m, 2H), 7.01 (d, J=6.8 Hz, 3H), 5.87 (s, 1H), 5.42 (s, 1H), 4.46 (s, 1H), 3.89 (s, 3H), 3.79 (d, J=14.0 Hz, 1H), 3.64 (bs, 3H), 3.03-2.98 (m, 1H), 2.80-2.73 (m, 1H), 2.58-2.38 (m, 2H).

Example 289

Rac-(4bR,7S,7aR)-4-methoxy-5-(morpholinomethyl)-7-phenyl-7a-(4-(trifluoromethyl)phenyl)-5,6,7,7a-tetrahydro-4bH-cyclopenta[4,5]furo[2,3-c]pyridin-4b-ol (Cpd. No. 289F)

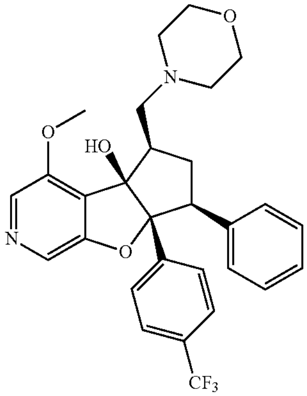

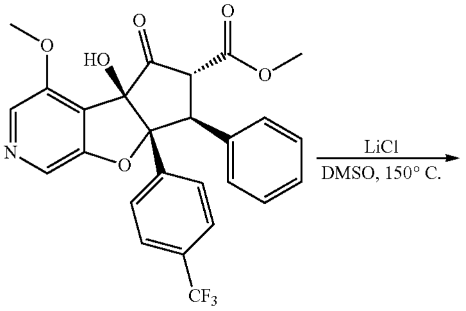

1

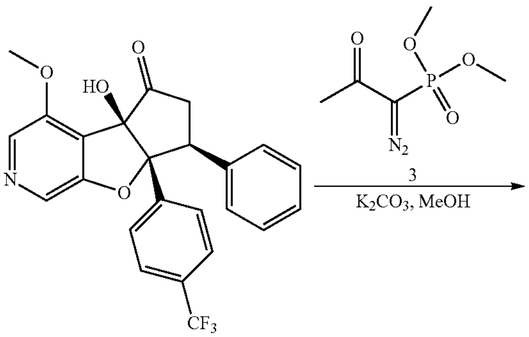

2

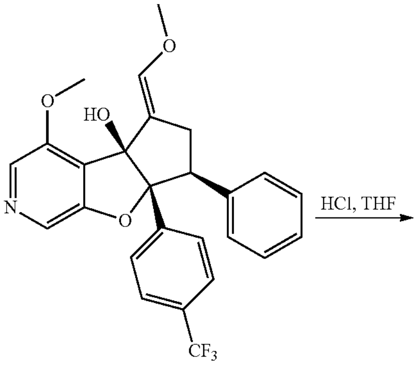

4

-continued

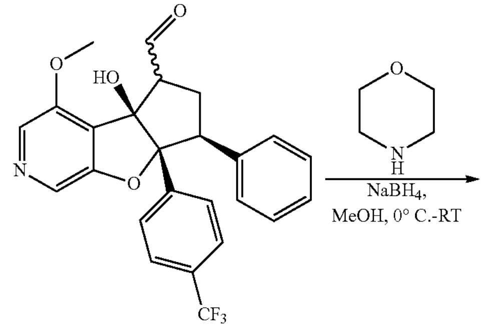

5

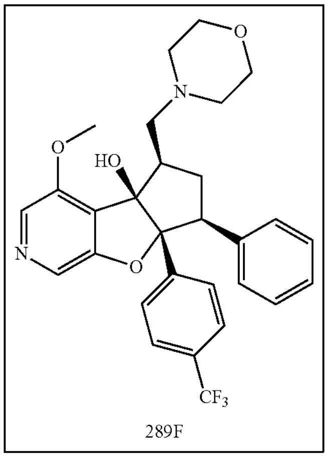

289F

Synthesis of rac-(4bR,7S,7aR)-4b-hydroxy-4-methoxy-7-phenyl-7a-(4-(trifluoromethyl)phenyl)-4b,6,7,7a-tetrahydro-5H-cyclopenta[4,5]furo[2,3-c]pyridin-5-one (2)

To a solution of rac-methyl (4bR,6R,7S,7aR)-4b-hydroxy-4-methoxy-5-oxo-7-phenyl-7a-(4-(trifluoromethyl)phenyl)-4b,6,7,7a-tetrahydro-5H-cyclopenta[4,5]furo[2,3-c]pyridine-6-carboxylate (1, 2.0 g, 3.98 mmol) in dimethyl sulphoxide (20 mL), lithium chloride (0.50 g, 11.9 mmol) was added. The reaction mixture was stirred at 150° C. for 15 min. After completion, the reaction mass was cooled to room temperature and quenched with cold water. The solid obtained was filtered, washed with water and then dissolved in dichloromethane. The dichloromethane layer was dried over anhydrous sodium sulphate, filtered and concentrated under reduced pressure to get crude product. The crude product was purified by silica gel (100-200 mesh) column chromatography eluting with dichloromethane to afford rac-(4bR,7S,7aR)-4b-hydroxy-4-methoxy-7-phenyl-7a-(4-(trifluoromethyl)phenyl)-4b,6,7,7a-tetrahydro-5H-cyclopenta[4,5]furo[2,3-c]pyridin-5-one (2) as white solid. Yield: 1.15 g, 75%; MS (ESI) m/z 442.2[M+1]$^+$.

Synthesis of rac-(4bR,7S,7aR,E)-4-methoxy-5-(methoxymethylene)-7-phenyl-7a-(4-(trifluoromethyl)phenyl)-5,6,7,7a-tetrahydro-4bH-cyclopenta[4,5]furo[2,3-c]pyridin-4b-ol (4)

To a solution of rac-(4bR,7S,7aR)-4b-hydroxy-4-methoxy-7-phenyl-7a-(4-(trifluoromethyl)phenyl)-4b,6,7,7a-tetrahydro-5H-cyclopenta[4,5]furo[2,3-c]pyridin-5-one (2, 1.30 g, 2.94 mmol) in methanol (15 mL) at 0° C. was added dimethyl(1-diazo-2-oxopropyl)phosphonate (3, 0.84 g, 4.42 mmol) followed by potassium carbonate (0.81 g, 5.88 mmol). The reaction mixture was stirred at 0° C. for 30 min, then the reaction mixture was stirred at room temperature for 16 h. After completion, saturated solution of sodium bicarbonate (30 mL) was added. The precipitated solid was filtered, washed with water, n-pentane and dried under vacuum to afford rac-(4bR,7S,7aR,E)-4-methoxy-5-(methoxymethylene)-7-phenyl-7a-(4-(trifluoromethyl)phenyl)-5,6,7,7a-tetrahydro-4bH-cyclopenta[4,5]furo[2,3-c]pyridin-4b-ol (4) as white solid. Yield: 1.1 g, 79.7%; MS (ESI) m/z 470.25[M+1]$^+$.

Synthesis of rac-(4bR,7S,7aR)-4b-hydroxy-4-methoxy-7-phenyl-7a-(4-(trifluoromethyl)phenyl)-4b,6,7,7a-tetrahydro-5H-cyclopenta[4,5]furo[2,3-c]pyridine-5-carbaldehyde (5)

To a solution of rac-(4bR,7S,7aR,E)-4-methoxy-5-(methoxymethylene)-7-phenyl-7a-(4-(trifluoromethyl)phenyl)-5,6,7,7a-tetrahydro-4bH-cyclopenta[4,5]furo[2,3-c]pyridin-4b-ol (4, 1.0 g, 2.13 mmol) in tetrahydrofuran (20 mL) at 0° C. was added 6 N hydrochloric acid (10 mL). The reaction mixture was stirred for 18 h at room temperature. After completion, the reaction mass was cooled and neutralized by the addition of saturated sodium bicarbonate up to pH ~7 and extracted with ethyl acetate, The organic layer was separated and dried over anhydrous sodium sulphate, filtered and concentrated, the crude product obtained was triturated in n-pentane and filtered off to give rac-(4bR,7S,7aR)-4b-hydroxy-4-methoxy-7-phenyl-7a-(4-(trifluoromethyl)phenyl)-4b,6,7,7a-tetrahydro-5H-cyclopenta[4,5]furo[2,3-c]pyridine-5-carbaldehyde (5) as pale yellow solid. Yield: 0.62 g, 64%; MS (ESI) m/z 454.26[M−1]$^-$.

Synthesis of rac-(4bR,5R,7S,7aR)-4-methoxy-5-(morpholinomethyl)-7-phenyl-7a-(4-(trifluoromethyl)phenyl)-5,6,7,7a-tetrahydro-4bH-cyclopenta[4,5]furo[2,3-c]pyridin-4b-ol (Cpd. No. 289F)

To a solution of rac-(4bR,7S,7aR)-4b-hydroxy-4-methoxy-7-phenyl-7a-(4-(trifluoromethyl)phenyl)-4b,6,7,7a-tetrahydro-5H-cyclopenta[4,5]furo[2,3-c]pyridine-5-carbaldehyde (5, 0.61 g, 1.34 mmol) in methanol (20 mL) at 0° C., morpholine (0.68 mL, 6.7 mmol) and acetic acid (catalytic) was added. The reaction mixture was stirred for 18 h at room temperature. Then sodium borohydride (0.05 g, 1.34 mmol) was added at 0° C. and reaction mixture was stirred for another 3 h at room temperature. After completion, the reaction mixture was quenched with ice water and extracted with dichloromethane. The organic layer was separated and dried over anhydrous sodium sulphate, filtered and concentrated to give crude product. The crude product was purified by preparative HPLC to afford rac-(4bR,5R,7S,7aR)-4-methoxy-5-(morpholinomethyl)-7-phenyl-7a-(4-(trifluoromethyl)phenyl)-5,6,7,7a-tetrahydro-4bH-cyclopenta[4,5]furo[2,3-c]pyridin-4b-ol (Cpd. No. 289F) as white solid. Yield: 10 mg, 1.4%; MS (ESI) m/z 527.27[M+1]$^+$; $^1$H NMR (400 MHz, DMSO-$d_6$) 8.17 (s, 1H), 8.07 (s, 1H), 7.47 (d, J=8.36 Hz, 2H), 7.40 (d, J=8.20 Hz, 2H), 7.07-6.95 (m, 5H), 5.70 (s, 1H), 3.96 (m, 4H), 3.80-3.52 (m, 6H), 3.08-2.58 (m, 5H), 2.28 (m, 2H).

Example 290

4-((4bS,5R,6S,7S,7aR)-6-((tert-butylamino)methyl)-4b,5-dihydroxy-4-methoxy-7-phenyl-4b,5,6,7-tetrahydro-7aH-cyclopenta[4,5]furo[2,3-c]pyridin-7a-yl) benzonitrile (Cpd. No. 290F)

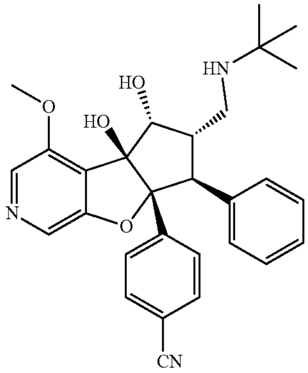

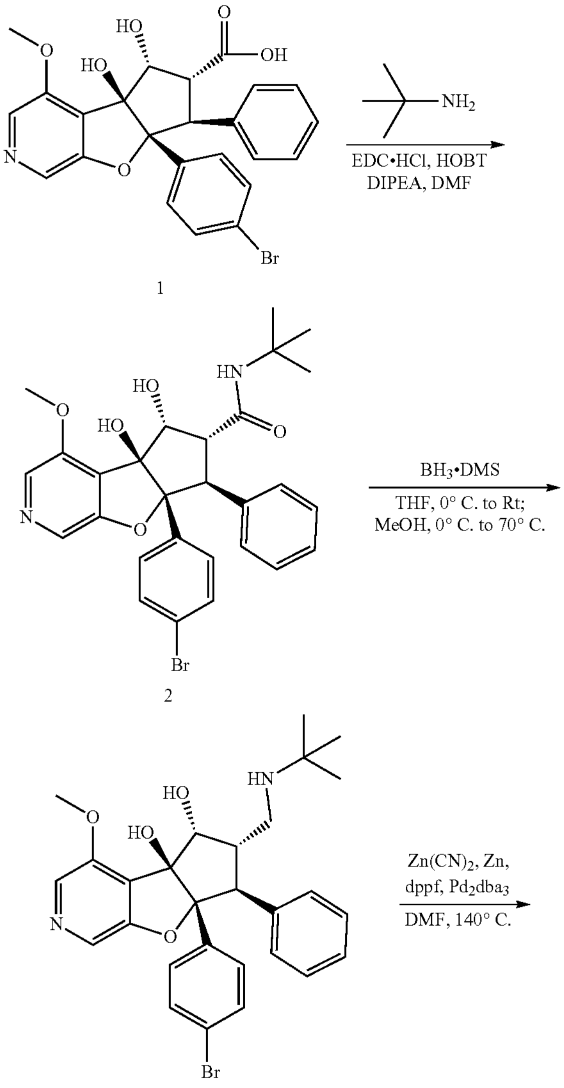

1

2

3

-continued

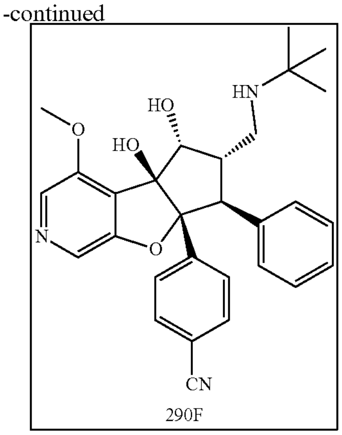

290F

Synthesis of rac-(4bS,5R,6R,7S,7aR)-7a-(4-bromophenyl)-N-(tert-butyl)-4b,5-dihydroxy-4-methoxy-7-phenyl-4b,6,7,7a-tetrahydro-5H-cyclopenta[4,5]furo[2,3-c]pyridine-6-carboxamide (2)

To a solution of rac-(4bS,5R,6R,7S,7aR)-7a-(4-bromophenyl)-4b,5-dihydroxy-4-methoxy-7-phenyl-4b,6,7,7a-tetrahydro-5H-cyclopenta[4,5]furo[2,3-c]pyridine-6-carboxylic acid (1, 5.0 g, 10.0 mmol) in N,N-dimethylformamide (50 mL) at 0° C., 2-methylpropan-2-amine (6.0 g, 50.0 mmol), N,N-diisopropylethylamine (11.0 mL, 60.0 mmol), N-(3-Dimethylaminopropyl)-N'-ethylcarbodiimide hydrochloride (5.70 g, 30.0 mmol) and 1-Hydroxybenzotriazole (4.50 g, 30.0 mmol) were added and reaction mixture was stirred for 16 h at room temperature. After completion, the reaction mixture was diluted with ice cold water to obtain solid. This solid was filtered off and the cake was dissolved in 10% methanol in dichloromethane. The organic layer was dried over anhydrous sodium sulphate, filtered and concentrated to give crude. The crude was purified by column chromatography using silica gel (100-200 mesh) and 0-4% methanol in dichloromethane as eluent. The desired fractions were concentrated to afford rac-(4bS,5R,6R,7S,7aR)-7a-(4-bromophenyl)-N-(tert-butyl)-4b,5-dihydroxy-4-methoxy-7-phenyl-4b,6,7,7a-tetrahydro-5H-cyclopenta[4,5]furo[2,3-c]pyridine-6-carboxamide (2) as white solid. Yield: 1.80 g, 32%; MS (ESI) m/z 553.41[M+1]$^+$.

Synthesis of rac-(4bS,5R,6S,7S,7aR)-7a-(4-bromophenyl)-6-((tert-butylamino)methyl)-4-methoxy-7-phenyl-5,6,7,7a-tetrahydro-4bH-cyclopenta[4,5]furo[2,3-c]pyridine-4b,5-diol (3)

To a solution of rac-(4bS,5R,6R,7S,7aR)-7a-(4-bromophenyl)-N-(tert-butyl)-4b,5-dihydroxy-4-methoxy-7-phenyl-4b,6,7,7a-tetrahydro-5H-cyclopenta[4,5]furo[2,3-c]pyridine-6-carboxamide (2, 1.8 g, 3.20 mmol) in dry tetrahydrofuran (20 mL) at 0° C., borane dimethyl sulphide complex (4.50 mL, 48.0 mmol) was added drop wise and reaction mixture was stirred at room temperature 16 h. After completion, the reaction mass was quenched with methanol at 0° C. and heated to reflux for 6 h. After completion, solvent was removed under reduced pressure to give crude which was purified by column chromatography using silica gel (100-200 mesh) and 0-15% methanol in dichloromethane as eluent. The desired fractions were concentrated under reduced pressure to afford rac-(4bS,5R,6S,7S,7aR)-7a-(4-bromophenyl)-6-((tert-butylamino)methyl)-4-methoxy-7-phenyl-5,6,7,7a-tetrahydro-4bH-cyclopenta[4,5]furo[2,3-c]pyridine-4b,5-diol (3) as white solid. Yield: 1.40 g, 82.3%; MS (ESI) m/z 539.45 $[M+1]^+$.

Synthesis of 4-((4bS,5R,6S,7S,7aR)-6-((tert-butylamino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile (Cpd. No. 290F)

To a solution of rac-(4bS,5R,6S,7S,7aR)-7a-(4-bromophenyl)-6-((tert-butylamino)methyl)-4-methoxy-7-phenyl-5,6,7,7a-tetrahydro-4bH-cyclopenta[4,5]furo[2,3-c]pyridine-4b,5-diol (3, 1.40 g, 2.50 mmol) in N,N-dimethylformamide (20.0 mL), zinc cyanide (1.70 g, 15.0 mmol) and zinc dust (0.081 g, 1.25 mmol) were added and the reaction mixture was degassed under argon for 15 min. 1,1'-Bis(diphenylphosphino)ferrocene (0.114 g, 0.125 mmol) and tris(dibenzylideneacetone)dipalladium (0.14 g, 0.25 mmol) were added to the reaction, degassed for additional 5 min and mixture was heated at 140° C. for 16 h. After completion, the reaction mass was diluted ice cold water and extracted with ethyl acetate. The organic layer was washed with water, dried over anhydrous sodium sulphate, filtered and concentrated to give crude which was purified by column chromatography using silica gel (100-200 mesh) and 0-15% methanol in dichloromethane as eluent. The desired fractions were concentrated to afford rac-4-((4bS,5R,6S,7S,7aR)-6-((tert-butylamino)methyl)-4b,5-dihydroxy-4-methoxy-7-phenyl-4b,5,6,7-tetrahydro-7aH-cyclopenta[4,5]furo[2,3-c]pyridin-7a-yl)benzonitrile as white solid. Yield: 0.820 g, 65% (racemic); MS (ESI) m/z 486.49 $[M+1]^+$. The enantiomers were separated by chiral SFC [chiralpak IG (4.6×150) mm, 5μ], $CO_2$/0.1% TEA in EtOH=(60/40) Peak 1 (Cpd. No. 290F, 55 mg), $[\alpha]_D$−34.2° (c 0.25, $CHCl_3$), $R_t$=1.73 min, ee: 99.9%; MS (ESI) m/z 486.36$[M+1]^+$. $^1H$ NMR (400 MHz, DMSO-$d_6$) 8.05 (s, 1H), 7.97 (s, 1H), 7.48 (d, J=8.7 Hz, 2H), 7.35 (d, J=8.4 Hz, 2H), 7.09-7.05 (m, 2H), 7.00-6.98 (m, 3H), 5.76 (s, 1H), 5.65 (s, 1H), 4.54 (s, 1H), 3.88 (s, 3H), 3.85 (s, 1H), 3.05-3.01 (m, 1H), 2.62-2.57 (m, 2H), 1.57-1.52 (s, 1H), 0.98 (s, 9H). Peak-2 (58 mg) $[\alpha]_D$+28.5° (c 0.27, $CHCl_3$), $R_t$=2.42 min, ee: 99.88%; MS (ESI) m/z 486.32$[M+1]^+$; $^1H$ NMR (400 MHz, DMSO-$d_6$) 8.05 (s, 1H), 7.97 (s, 1H), 7.49 (d, J=8.44 Hz, 2H), 7.35 (d, J=8.5 Hz, 2H), 7.09-7.05 (m, 2H), 7.00-6.98 (m, 3H), 5.77 (s, 1H), 5.66 (s, 1H), 4.54 (s, 1H), 3.88 (s, 3H), 3.85 (s, 1H), 3.15-3.10 (m, 1H), 2.62-2.56 (m, 2H), 1.64 (s, 1H), 0.94 (s, 9H).

Example 291

4-((4bS,5R,6S,7S,7aR)-4b,5-dihydroxy-4-methoxy-7-phenyl-6-(((2,2,2-trifluoroethyl)amino)methyl)-4b,5,6,7-tetrahydro-7aH-cyclopenta[4,5]furo[2,3-c]pyridin-7a-yl)benzonitrile (Cpd. No. 291F)

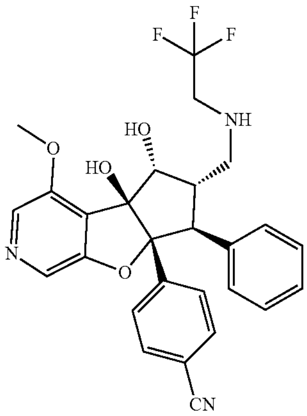

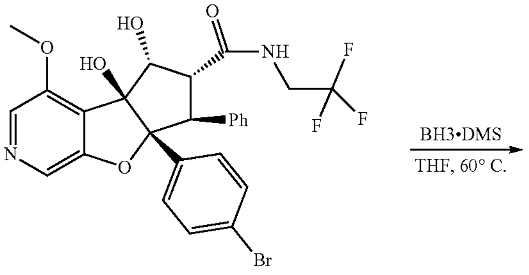

1

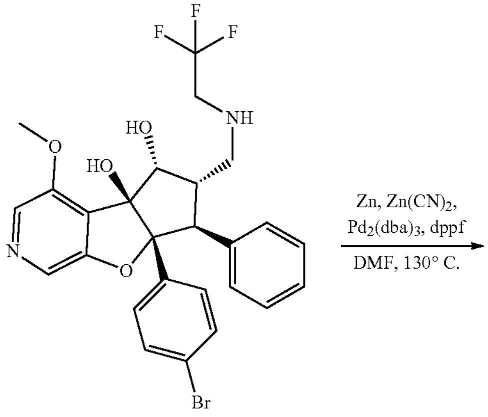

3

-continued

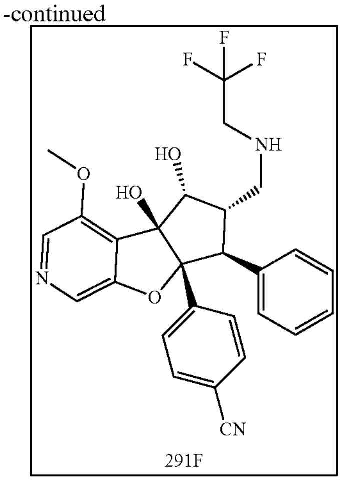

291F

Synthesis of rac-(4bS,5R,6S,7S,7aR)-7a-(4-bromophenyl)-4-methoxy-7-phenyl-6-(((2,2,2-trifluoroethyl)amino)methyl)-5,6,7,7a-tetrahydro-4bH-cyclopenta[4,5]furo[2,3-c]pyridine-4b,5-diol (3)

To a solution of rac-(4bS,5R,6R,7S,7aR)-7a-(4-bromophenyl)-4b,5-dihydroxy-4-methoxy-7-phenyl-N-(2,2,2-trifluoroethyl)-4b,6,7,7a-tetrahydro-5H-cyclopenta[4,5]furo[2,3-c]pyridine-6-carboxamide (1, 1.20 g, 1.9 mmol) in tetrahydrofuran (20 mL), borane dimethyl sulphide (1.90 mL, 19.0 mmol) was added at 0° C. and mixture was stirred at 60° C. for 3 h. After completion, reaction mass was quenched with methanol (10.0 mL) and again heated for 16 h at 60° C. The reaction mixture was concentrated to give rac-(4bS,5R,6S,7S,7aR)-7a-(4-bromophenyl)-4-methoxy-7-phenyl-6-(((2,2,2-trifluoroethyl)amino)methyl)-5,6,7,7a-tetrahydro-4bH-cyclopenta[4,5]furo[2,3-c]pyridine-4b,5-diol (3) as off white solid. Yield: 1.0 g, 85%; MS (ESI) m/z 565.1[M+1]$^+$ Synthesis of 4-((4bS,5R,6S,7S,7aR)-4b,5-dihydroxy-4-methoxy-7-phenyl-6-(((2,2,2-trifluoroethyl)amino)methyl)-4b,5,6,7-tetrahydro-7aH-cyclopenta[4,5]furo[2,3-c]pyridin-7a-yl)benzonitrile (Cpd. No. 291F)

To a solution of rac-(4bS,5R,6S,7S,7aR)-7a-(4-bromophenyl)-4-methoxy-7-phenyl-6-(((2,2,2-trifluoroethyl)amino)methyl)-5,6,7,7a-tetrahydro-4bH-cyclopenta[4,5]furo[2,3-c]pyridine-4b,5-diol (3, 1.0 g, 1.7 mmol) in N,N-dimethylformamide (15.0 mL), zinc cyanide (1.24 g, 10.6 mmol) and zinc (0.115 g, 1.7 mmol) were added at room temperature and degassed the mixture with argon for 15 min. 1,1'-Bis(diphenylphosphino)ferrocene (0.029 g, 0.05 mmol), tris(dibenzylideneacetone)dipalladium (0.048 g, 0.05 mmol) were added to the reaction and degassing was continued for another 5 min. The reaction mixture was heated at 140° C. for 16 h. After completion, the reaction was cooled to room temperature and passed through celite bed. The filtrate was diluted with ethyl acetate and washed with water. The organic layer was separated, dried over anhydrous sodium sulphate and concentrated under reduced pressure to give the crude. The crude was purified by combi-flash (4.0 g, RediSep column) using 30-70% ethyl acetate in hexane as eluent. The desired fractions were concentrated under reduced pressure. The compound was again re-purified by reverse phase prep and desired fractions were lyophilized to give rac-4-((4bS,5R,6S,7S,7aR)-4b,5-dihydroxy-4-methoxy-7-phenyl-6-(((2,2,2-trifluoroethyl)amino)methyl)-4b,5,6,7-tetrahydro-7aH-cyclopenta[4,5]furo[2,3-c]pyridin-7a-yl)benzonitrile (Cpd. No. 291F) as white solid. Yield: 513 mg, 56%. The enantiomers were separated by chiral SFC [Chiralpak IG (4.6 ×250)mm, 5μ]; $CO_2$/0.1% TEA in EtOH=(60/40); Peak 1 (108 mg), $[\alpha]_D$+29.5° (c 0.26, $CHCl_3$), $R_t$=1.84, ee >99%; MS (ESI) m/z 512.27 [M+1]$^+$; UPLC: 98.7%; $^1$H NMR (400 MHz, DMSO-$d_6$) δ 8.06 (s, 1H), 7.98 (s, 1H), 7.51 (d, J=8.4 Hz, 2H), 7.37 (d, J=8.1 Hz, 2H), 7.08-6.97 (m, 5H), 5.71 (s, 1H), 5.14 (d, J=5.6 Hz, 1H), 4.54 (t, J=4.7 Hz, 1H), 3.89 (s, 3H), 3.73 (d, J=14.1 Hz, 1H), 3.27-3.14 (m, 3H), 2.75-2.70 (m, 1H), 2.39 (bs, 1H). Peak 2 (117 mg), $[\alpha]_D$−30.7° (c 0.27, $CHCl_3$), $R_t$=2.23, ee >95%; MS (ESI) m/z 512.27 [M+1]$^+$; UPLC: 95.7%; $^1$H NMR (400 MHz, DMSO-$d_6$) δ 8.06 (s, 1H), 7.98 (s, 1H), 7.50 (d, J=8.5 Hz, 2H), 7.37 (d, J=8.3 Hz, 2H), 7.08-6.97 (m, 5H), 5.71 (s, 1H), 5.14 (d, J=5.6 Hz, 1H), 4.54 (t, J=4.8 Hz, 1H), 3.89 (s, 3H), 3.73 (d, J=14.1 Hz, 1H), 3.27-3.14 (m, 3H), 2.75-2.70 (m, 1H), 2.38 (bs, 1H).

Example 292

Rac-(5aR,6S,7S,8R,8aS)-7-(aminomethyl)-5a-(4-bromophenyl)-3-chloro-1-methoxy-6-phenyl-5a,6,7,8-tetrahydro-8aH-cyclopenta[4,5]furo[3,2-c]pyridine-8,8a-diol (Cpd. No. 292F)

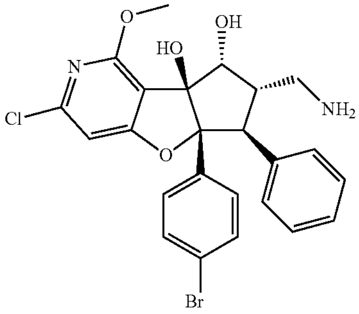

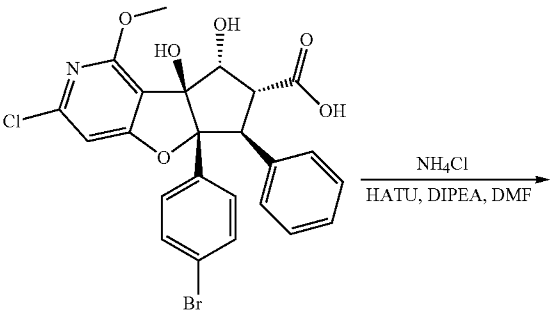

1

-continued

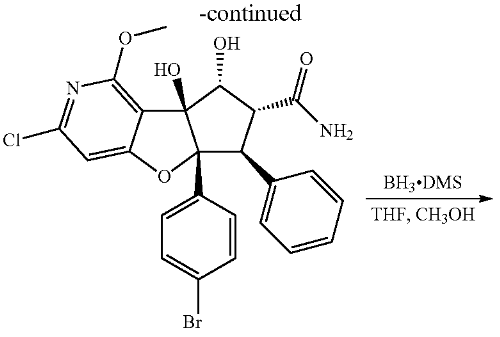

2

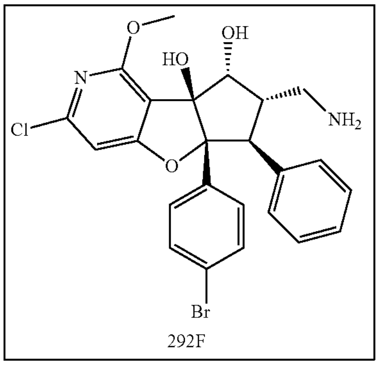

292F

Synthesis of rac-(5aR,6S,7R,8R,8aS)-5a-(4-bromophenyl)-3-chloro-8,8a-dihydroxy-1-methoxy-6-phenyl-5a, 7,8,8a-tetrahydro-6H-cyclopenta[4,5]furo [3,2-c]pyridine-7-carboxamide (2)

To a stirred solution of rac-(5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c] pyridine-7-carboxylic acid (1, 0.1 g, 0.18 mmol) in N,N-dimethylformamide (1 mL) was added HATU (69.77 mg, 0.18300 mmol) and then DIPEA (0.15 mL, 0.87000 mmol). After 1 hr LCMS (taken in methanol) indicated complete consumption of the SM, so ammonium chloride was added in one portion. The reaction was allowed to stir for an additional 65 hr, at which point the mixture was poured onto water and diluted with ethyl acetate. The organic material was washed with sat ammonium chloride, water, and brine, then dried over magnesium sulfate, filtered, and solvent removed in vacuum to afford rac-(5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c] pyridine-7-carboxamide (2). This material was carried on to the subsequent step without further purification. LCMS (ESI) m/z 531.1, 533.1 $[M+1]^+$.

Synthesis of rac-(5aR,6S,7S,8R,8aS)-7-(aminomethyl)-5a-(4-bromophenyl)-3-chloro-1-methoxy-6-phenyl-5a,6,7,8-tetrahydro-8aH-cyclopenta[4,5]furo [3,2-c]pyridine-8,8a-diol (Cpd. No. 292F)

To a stirred solution of rac-(5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c] pyridine-7-carboxamide (2, 0.09 g, 0.16300 mmol) in THF (2.5 mL) was added borane dimethylsulfide (0.84 mL, 1.68 mmol) dropwise. After 3.5 hr the reaction was cooled to rt and MeOH (1 mL) was added slowly with vigorous evolution of gas. The reaction was then heated to 60° C. and monitored by LCMS. 20 hr after the addition of methanol, the vial was cooled to rt and solvent removed in vacuo. The residue was taken up in a mixture of dichloromethane and methanol, then purified on strata ion exchange column, washing first with acetonitrile and MeOH (twice with each), then eluting the product with several washes with a solution of 5% $NH_4OH$, 20% dichloromethane, and 75% MeOH. The solvent was removed in vacuo, and the residue was taken up in a mixture of water and acetonitrile. This solution was frozen and lyophilized to afford rac-(5aR,6S,7S,8R,8aS)-7-(aminomethyl)-5a-(4-bromophenyl)-3-chloro-1-methoxy-6-phenyl-5a,6,7,8-tetrahydro-8aH-cyclopenta[4,5]furo[3,2-c] pyridine-8,8a-diol (Cpd. No. 292F) as a white solid. Yield: 69 mg, 81%. LCMS (ESI) m/z 517.1, 519.1 [M+1]; $^1H$ NMR (400 MHz, DMSO-$d_6$) δ 7.21 (d, J=8.6 Hz, 2H), 7.10-7.00 (m, 4H), 6.99 (d, J=7.0 Hz, 1H), 6.93 (d, J=7.3 Hz, 2H), 6.84 (s, 1H), 5.48 (s, 1H), 4.50 (s, 1H), 3.63 (d, J=14.4 Hz, 1H), 2.95 (s, 2H), 2.59 (d, J=9.8 Hz, 1H), 2.52 (dd, J=12.7, 3.5 Hz, 1H).

Example 293

Rac-(5aR,6S,7S,8R,8aS)-7-(aminomethyl)-5a-(4-cyanophenyl)-8,8a-dihydroxy-1-methoxy-6-phenyl-5a,7,8,8a-tetrahydro-6H-cyclopenta[4,5]furo[3,2-c] pyridine-3-carbonitrile (Cpd. No. 293F)

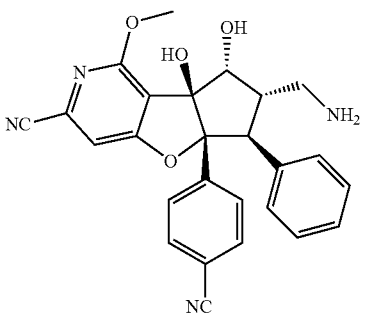

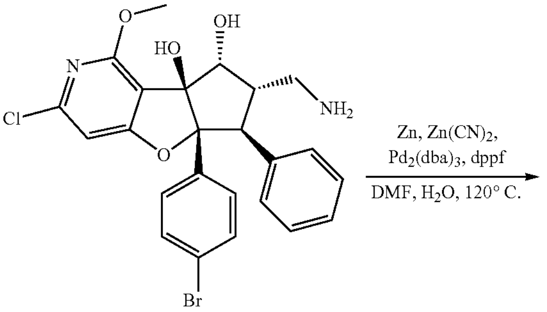

1

-continued

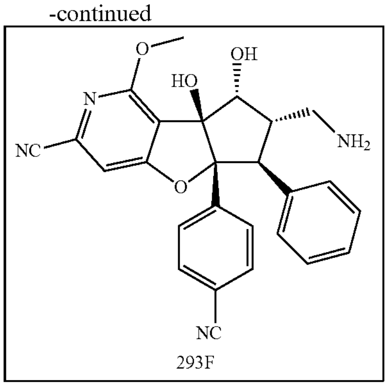

293F

Synthesis of rac-(5aR,6S,7S,8R,8aS)-7-(aminomethyl)-5a-(4-cyanophenyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 293F)

Rac-(5aR,6S,7S,8R,8aS)-7-(aminomethyl)-5a-(4-bromophenyl)-3-chloro-1-methoxy-6-phenyl-5a,6,7,8-tetrahydro-8aH-cyclopenta[4,5]furo[3,2-c]pyridine-8,8a-diol (1, 0.03 g, 0.056 mmol), dicyanozinc (46 mg, 0.39 mmol), dppf (31 mg, 0.056 mmol) and zinc (4 mg, 0.056 mmol) in N,N-dimethylformamide (0.56 mL) and 0.056 mL water. Tris(dibenzylideneacetone)dipalladium(0) (22 mg, 0.024 mmol) was added, the vial was sealed and stirred at 120° C. After 45 min LCMS indicated the product and chlorocyano product were major components. The mixture was cooled to rt after 1 h, diluted with methanol and a few drops of DMSO then filtered through celite. The pad was washed several times with methanol containing a small amount of DMSO. The volatile solvents were removed in vacuo, the residue was diluted with DMSO and purified via RP-HPLC to afford rac-(5aR,6S,7S,8R,8aS)-7-(aminomethyl)-5a-(4-cyanophenyl)-8,8a-dihydroxy-1-methoxy-6-phenyl-5a,7,8,8a-tetrahydro-6H-cyclopenta[4,5]furo[3,2-c]pyridine-3-carbonitrile (Cpd. No. 293F). Yield: 6.0 mg, 23%. LCMS (ESI) m/z 455.1 $[M+1]^+$; H NMR (400 MHz, DMSO-$d_6$) δ 7.58 (s, 1H), 7.56 (d, J=8.6 Hz, 2H), 7.27 (d, J=8.5 Hz, 2H), 7.13-7.01 (m, 4H), 7.00-6.91 (m, 4H), 6.49 (s, 1H), 5.32 (s, 1H), 4.68-4.55 (m, 1H), 3.89 (s, 2H), 3.83-3.73 (m, 1H), 2.90 (s, 1H).

Example 294

Rac-4-((5aR,6S,7S,8R,8aS)-7-(aminomethyl)-3-chloro-8,8a-dihydroxy-1-methoxy-6-phenyl-6,7,8,8a-tetrahydro-5aH-cyclopenta[4,5]furo[3,2-c]pyridin-5a-yl)benzonitrile (Cpd. No. 294F)

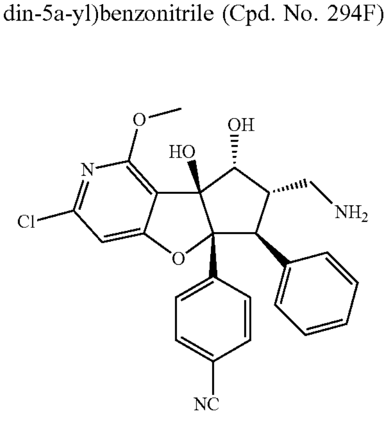

-continued

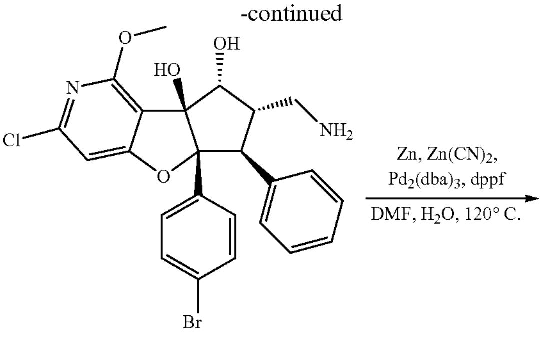

1

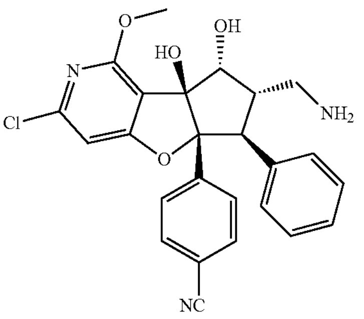

294F

Synthesis of rac-4-((5aR,6S,7S,8R,8aS)-7-(aminomethyl)-3-chloro-8,8a-dihydroxy-1-methoxy-6-phenyl-6,7,8,8a-tetrahydro-5aH-cyclopenta[4,5]furo[3,2-c]pyridin-5a-yl)benzonitrile (Cpd. No. 294F)

Rac-(5aR,6S,7S,8R,8aS)-7-(aminomethyl)-5a-(4-bromophenyl)-3-chloro-1-methoxy-6-phenyl-5a,6,7,8-tetrahydro-8aH-cyclopenta[4,5]furo[3,2-c]pyridine-8,8a-diol (1, 0.03 g, 0.056 mmol), dicyanozinc (46 mg, 0.39 mmol), dppf (31 mg, 0.056 mmol) and zinc (4 mg, 0.056 mmol) in N,N-dimethylformamide (0.56 mL) and water (0.056 mL). Tris(dibenzylideneacetone)dipalladium(0) (22 mg, 0.024 mmol) was added, the vial was sealed and stirred at 120° C. After 45 min LCMS indicated the product and bis-cyanated product were major components. The mixture was cooled to room temperature after 1 h, diluted with methanol and a few drops of DMSO then filtered through celite. The pad was washed several times with methanol containing a small amount of DMSO. The volatile solvents were removed in vacuo, the residue was diluted with DMSO and purified via RP-HPLC to afford rac-4-((5aR,6S,7S,8R,8aS)-7-(aminomethyl)-3-chloro-8,8a-dihydroxy-1-methoxy-6-phenyl-6,7,8,8a-tetrahydro-5aH-cyclopenta[4,5]furo[3,2-c]pyridin-5a-yl) benzonitrile (Cpd. No. 294F). Yield: 7.5 mg, 28%. LCMS (ESI) m/z 464.2, 466.4 $[M+1]^+$; $^1H$ NMR (400 MHz, DMSO-$d_6$) δ 7.55 (d, J=8.4 Hz, 2H), 7.26 (d, J=8.6 Hz, 2H), 7.06 (dq, J=13.4, 7.1 Hz, 4H), 7.00-6.89 (m, 2H), 6.49 (s, 1H), 5.23 (s, 1H), 4.61-4.52 (m, 1H), 3.83 (s, 3H), 3.79 (d, J=14.5 Hz, 1H), 2.91 (bs, 1H).

Example 295

Rac-(5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridine-7-carboxylic acid (Cpd. No. 295F)

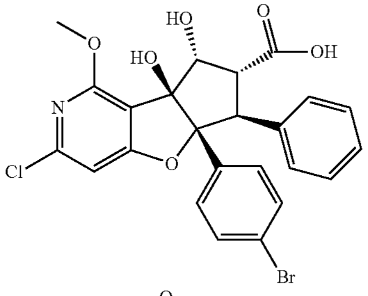

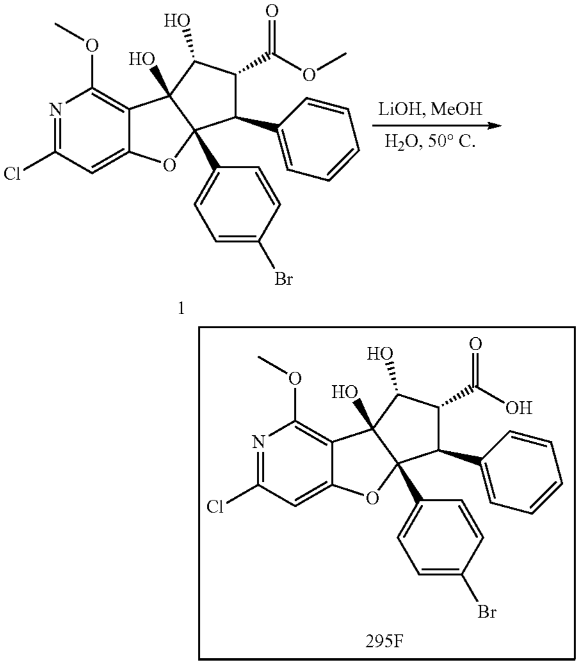

1

295F

Synthesis of rac-(5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridine-7-carboxylic acid (Cpd. No. 295F)

To a stirred solution of rac-methyl (5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridine-7-carboxylate (1, 1.09 g, 1.99 mmol) in methanol (40 mL) was added water (4 mL) and then lithium hydroxide (477 mg, 19.9 mmol). The resulting yellow reaction mixture was stirred vigorously and heated at 50° C. under a reflux condenser for 4.5 h. The reaction mixture was cooled with a 0° C. cold bath and 1 N hydrochloric acid in water (19.9 mL, 19.9 mmol) was added with vigorous stirring. A few more drops of 1 N hydrochloric acid was added to make the mixture slightly acidic. Most of the methanol was removed on a rotary evaporator. The residue was extracted three times with dichloromethane. The combined organics were washed with brine, dried over magnesium sulfate, filtered, concentrated on a rotary evaporator, and dried under high vacuum at 40° C. overnight to afford crude rac-(5aR,6S,7R,8R,8aS)-5a-(4-bromophenyl)-3-chloro-8,8a-dihydroxy-1-methoxy-6-phenyl-5a,7,8,8a-tetrahydro-6H-cyclopenta[4,5]furo[3,2-c]pyridine-7-carboxylic acid (Cpd. No. 295F) as a white solid. Yield: 961 mg, 90%; MS (ESI) m/z 532.1, 534.0[M+1]$^+$; $^1$H NMR (400 MHz, DMSO-$d_6$) δ 12.23 (s, 1H), 7.24-7.18 (m, 2H), 7.06 (m, 2H), 7.03-6.94 (m, 5H), 6.93 (s, 1H), 5.62 (d, J=8.3 Hz, 2H), 4.62 (t, J=5.3 Hz, 1H), 4.29 (d, J=13.9 Hz, 1H), 3.95 (dd, J=14.0, 5.0 Hz, 1H), 3.84 (s, 3H).

Example 296

The following compounds, denoted below as compounds A through DQ, can be synthesized by one of skill in the art according to the procedures provided in the indicated general methods ("GM") and/or the individual examples ("EXP"). The compounds contain substituents Ra, Rb and Rc, which are defined in Table 1. For example, the first compound below is Compound A, and it can be made from the appropriate starting materials according to the procedures described in general method ("GM") 3 or GM3.

Compounds A-DQ

A

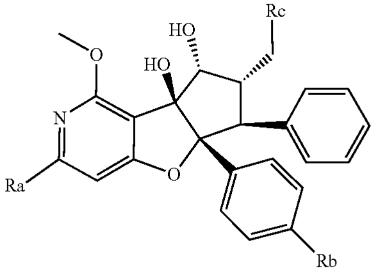

GM3

B

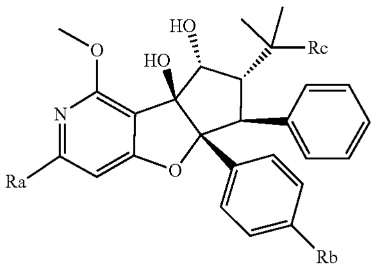

GM8

C

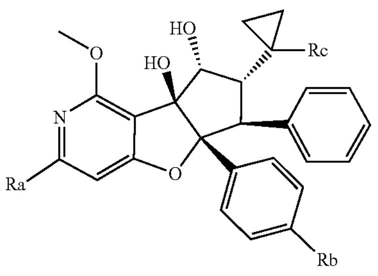

GM9

-continued
D
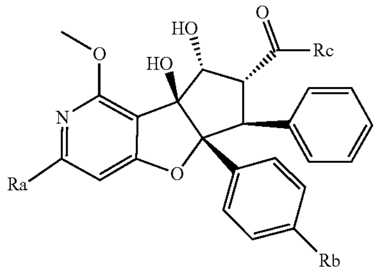
GM3
E
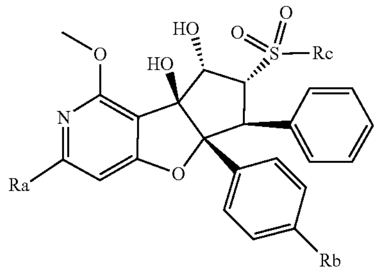
GM6,7
F
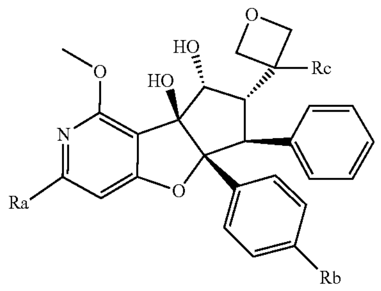
GM10
G
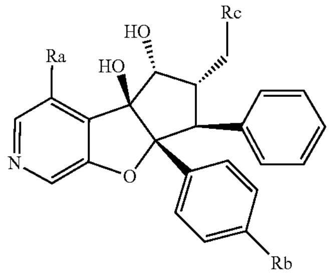
GM3
H
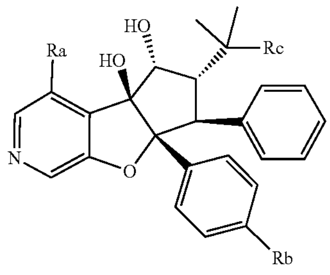
GM8
-continued
I
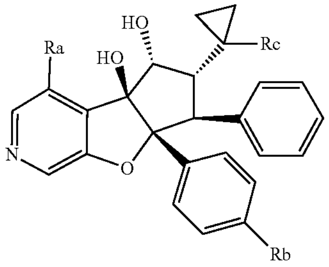
GM9
J
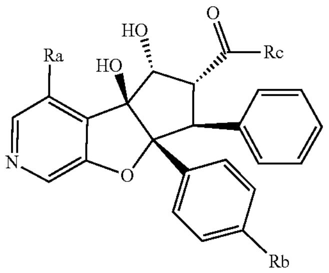
GM3
K
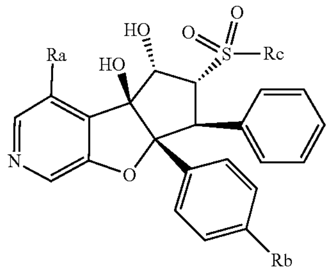
GM6,7
L
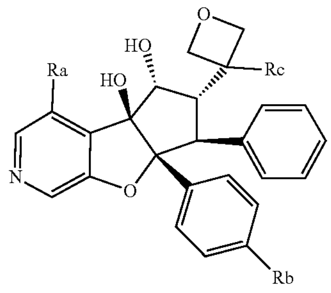
GM10
M
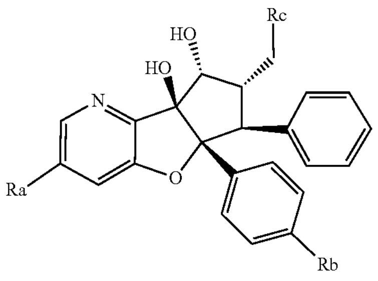
GM3

-continued
N
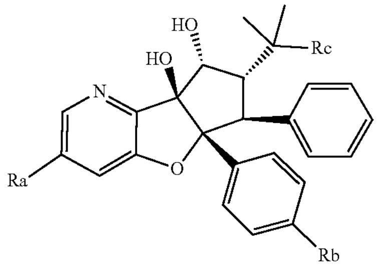
GM8
O
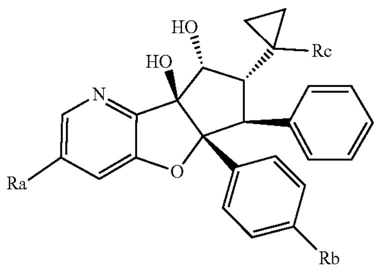
GM9
P
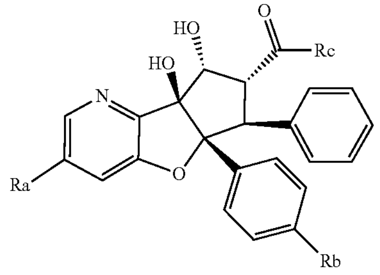
GM3
Q
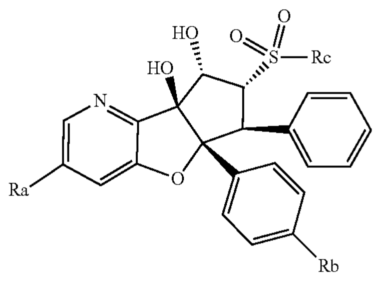
GM6,7
R
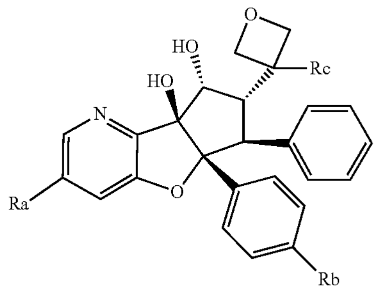
GM10
-continued
S
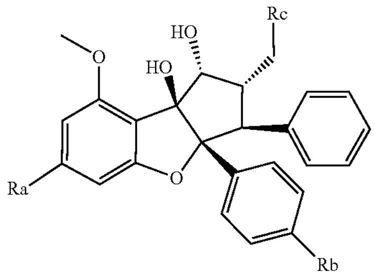
GM3
T
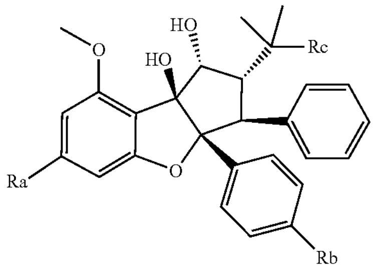
GM8
U
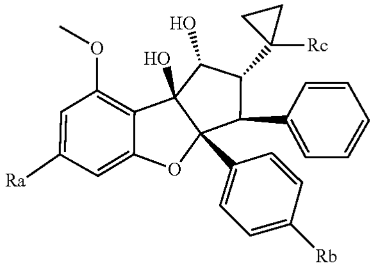
GM9
V
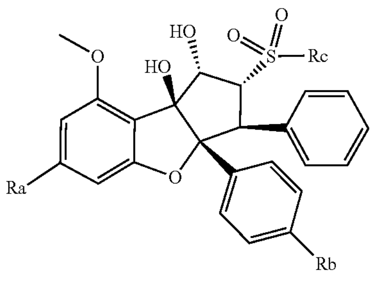
GM6,7
W
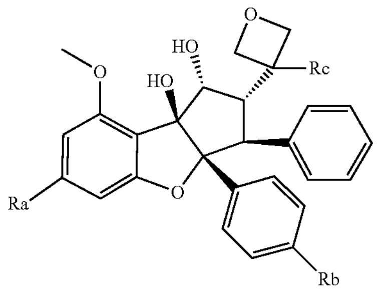
GM10

-continued
X
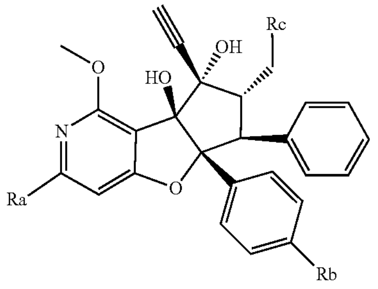
EXP190
Y
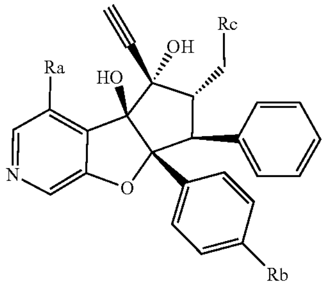
EXP190
Z
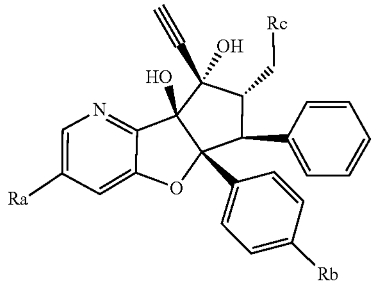
EXP190
AA
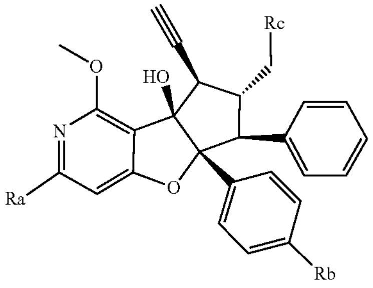
EXP48
AB
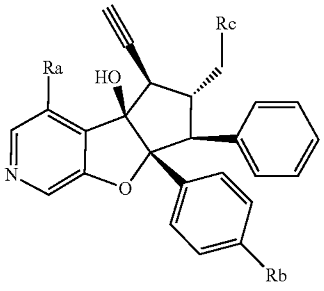
EXP48
-continued
AC
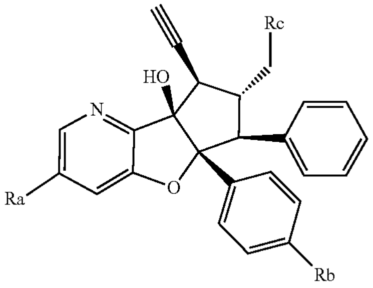
EXP48
AD
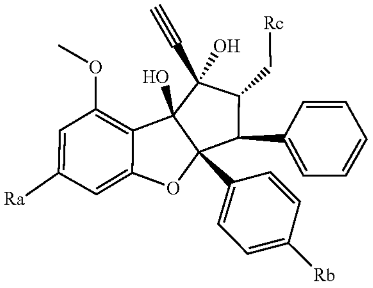
EXP190
AE
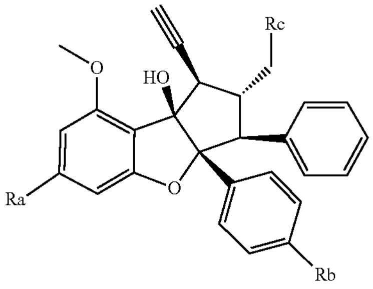
EXP48
AF
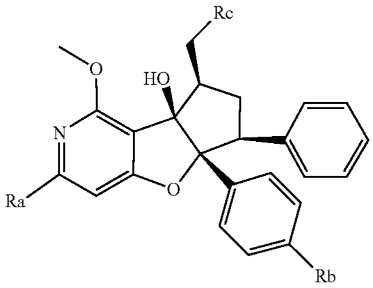
GM4
AG
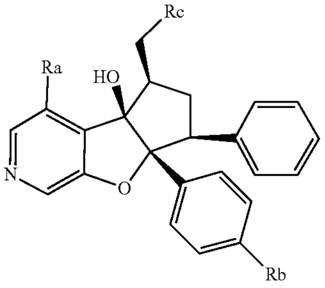
GM4

-continued
AH
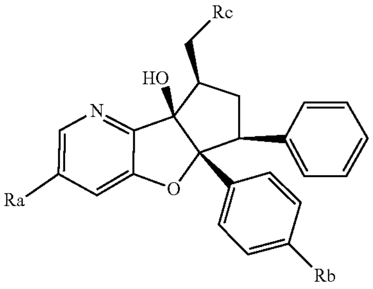
GM4
AI
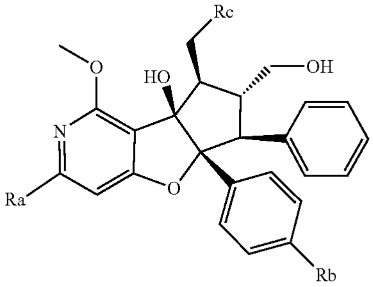
GM5
AJ
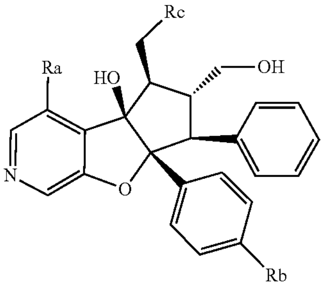
GM5
AK
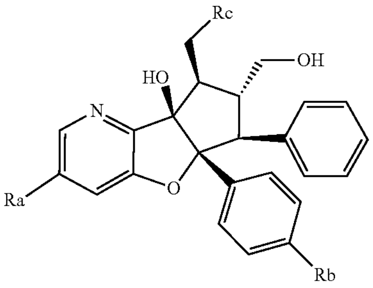
GM5
AL
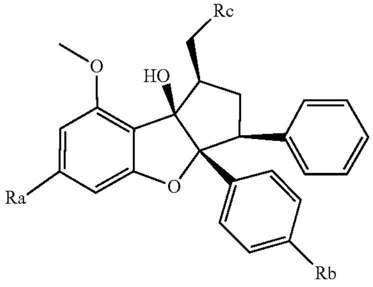
GM4
-continued
AM
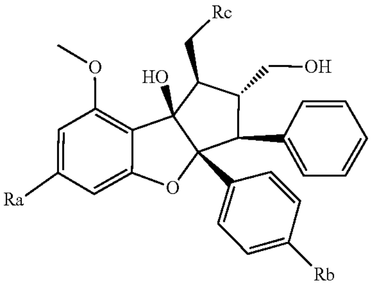
GM5
AN
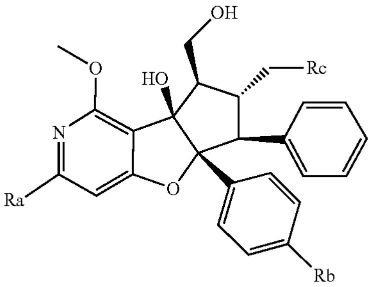
GM3
AO
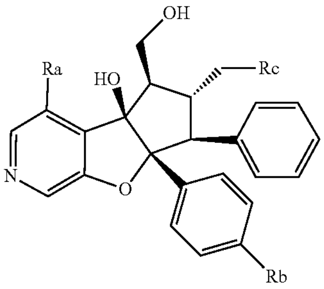
GM3
AP
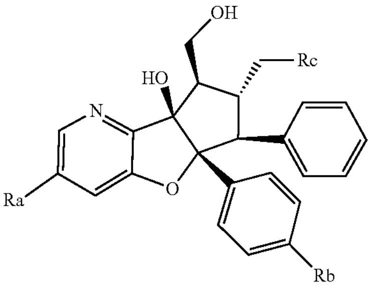
GM3
AQ
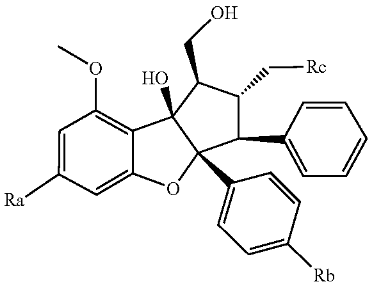
GM3

-continued
AR
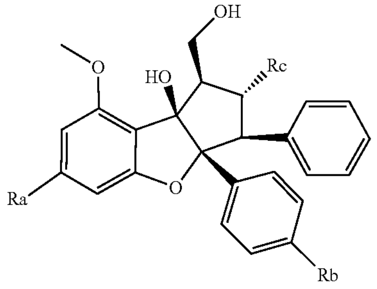
EXP270
AS
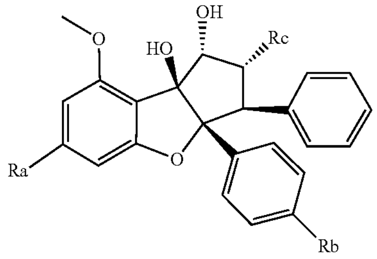
EXP270
AT
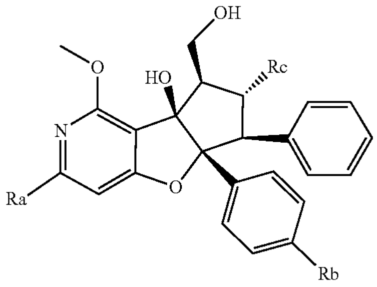
EXP270
AU
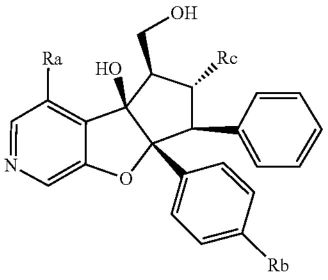
EXP270
AV
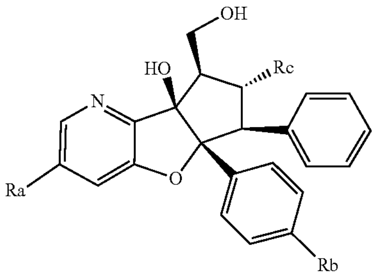
EXP270
-continued
AW
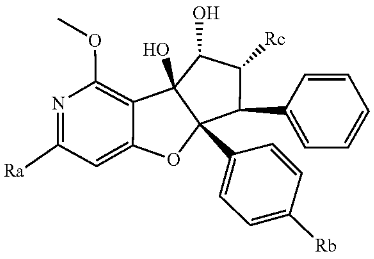
EXP270
AX
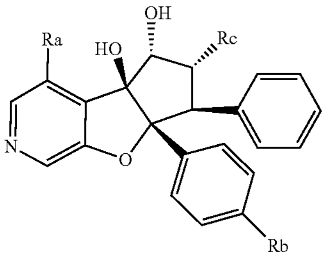
EXP270
AY
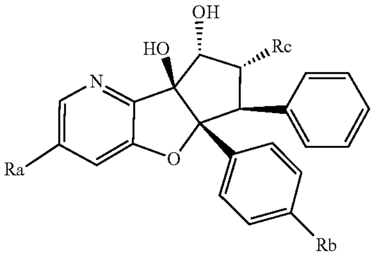
EXP270
AZ
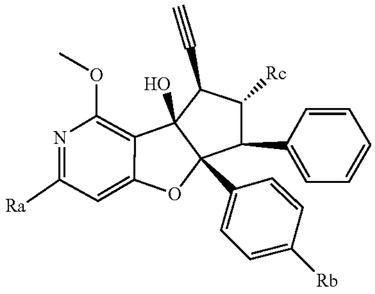
EXP48,270
BA
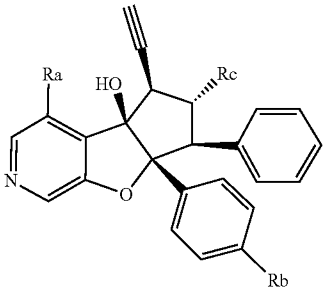
EXP48,270

-continued
BB
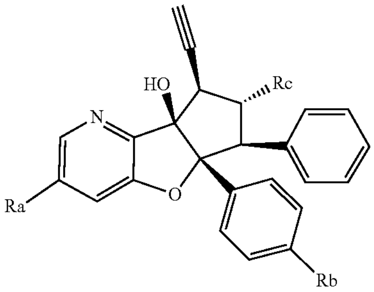
EXP48,270
BC
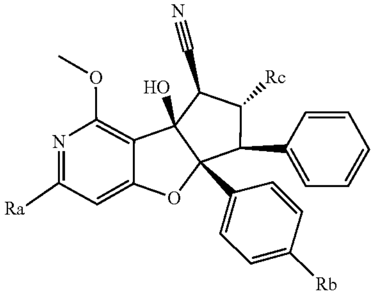
GM4, EXP270
BD
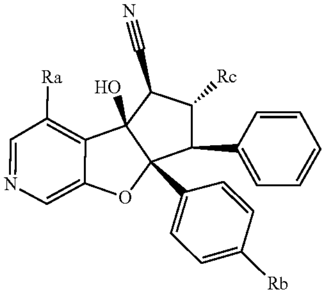
GM4, EXP270
BE
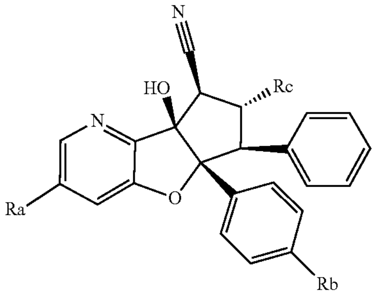
GM4, EXP270
-continued
BF
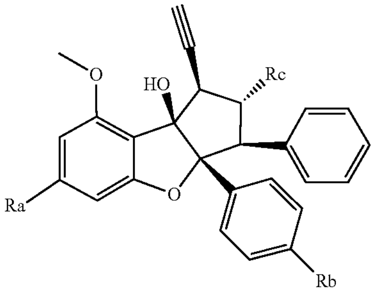
EXP48,270
BG
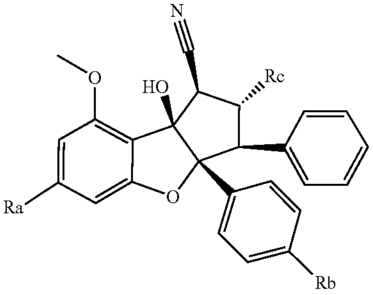
GM4, EXP270
BH
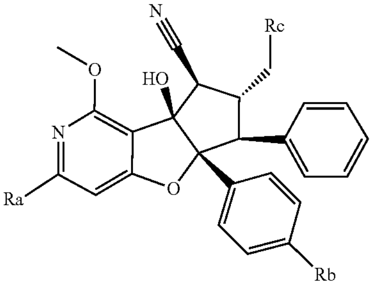
GM3,4
BI
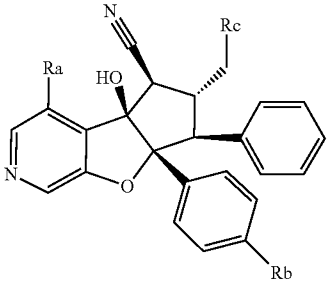
GM3,4
BJ
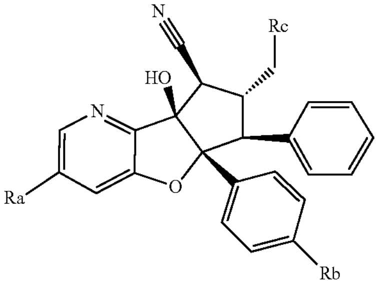
GM3,4

-continued
BK
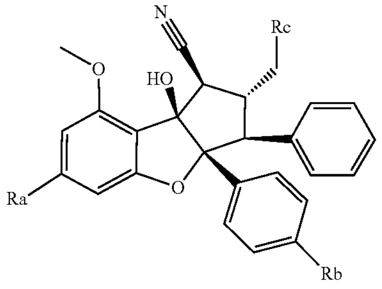
GM3,4
BL
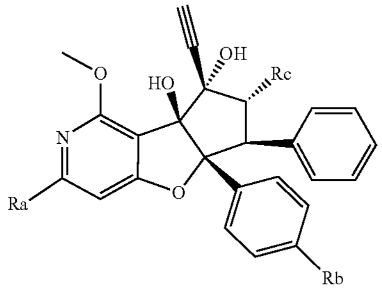
EXP190,270
BM
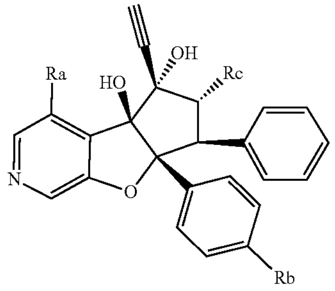
EXP190,270
BN
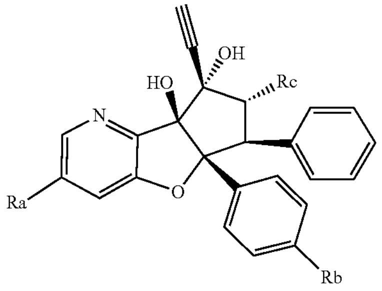
EXP190,270
BO
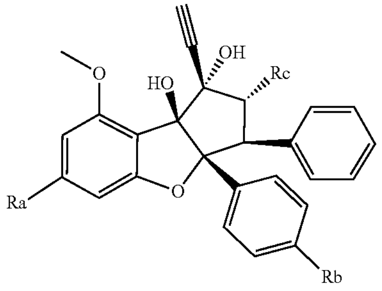
EXP190,270
-continued
BP
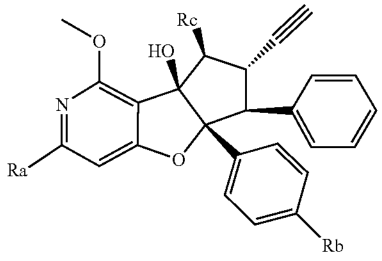
GM3
BQ
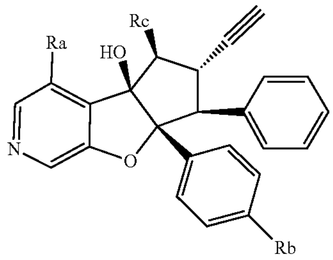
GM3
BR
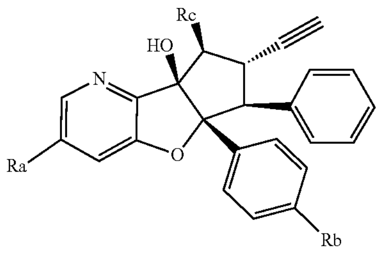
GM3
BS
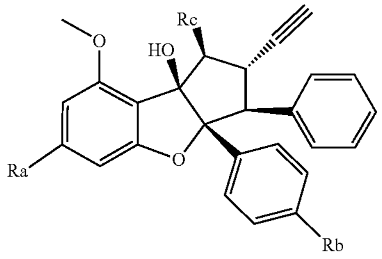
GM3
BT
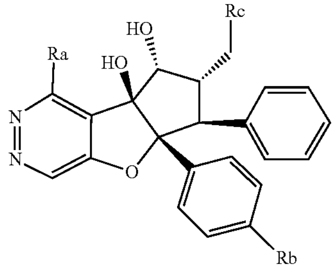
GM3

-continued
BU
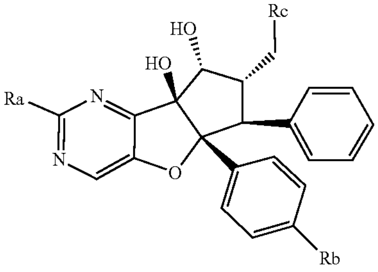
GM3
BV
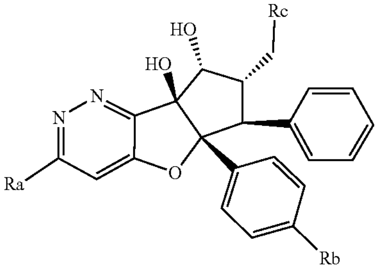
GM3
BW
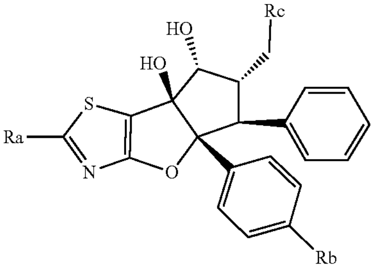
GM3
BX
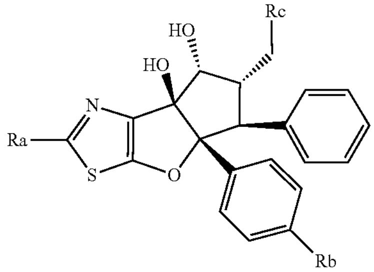
GM3
BY
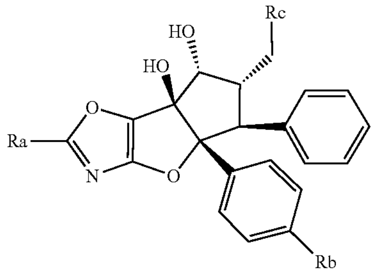
GM3
-continued
BZ
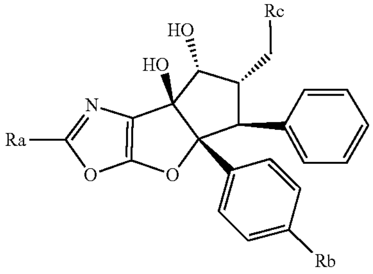
GM3
CA
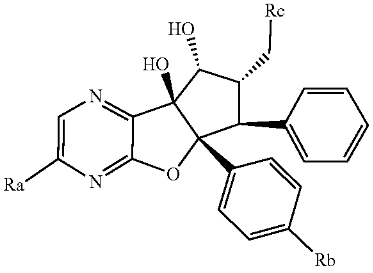
GM3
CB
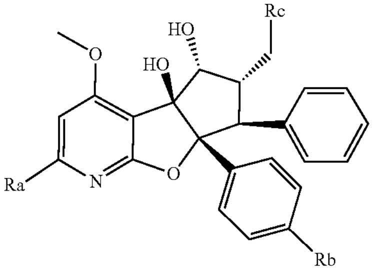
GM3
CC
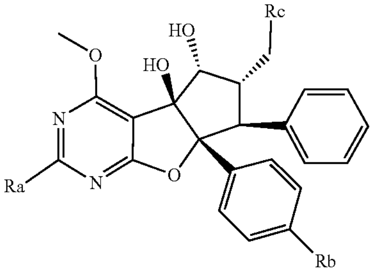
GM3
CD
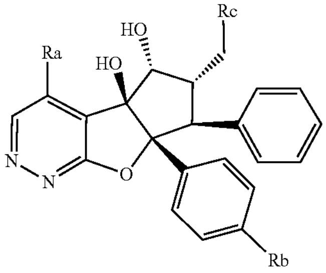
GM3

-continued
CE
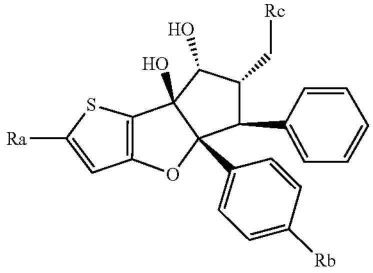
GM3
CF
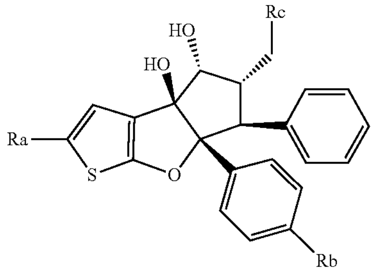
GM3
CG
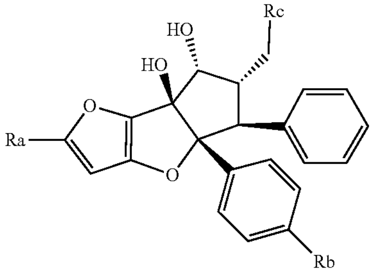
GM3
CH
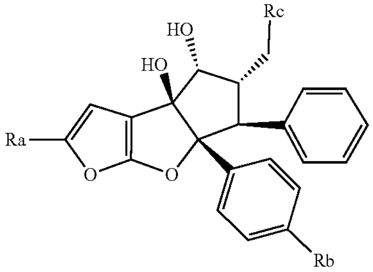
GM3
CI
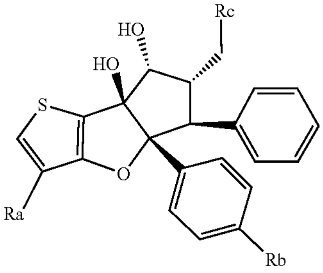
GM3
-continued
CJ
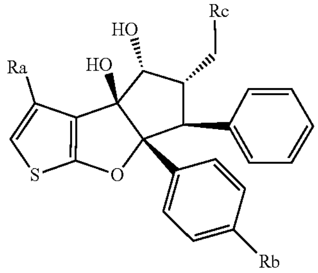
GM3
CK
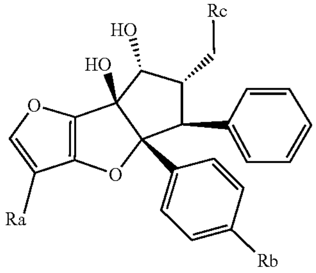
GM3
CL
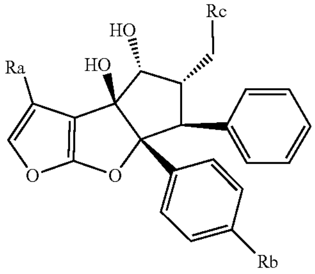
GM3
CM
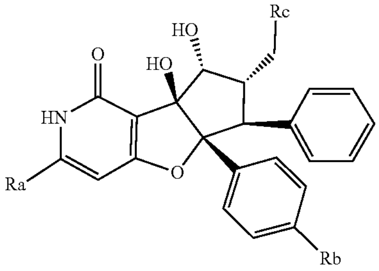
GM3
CN
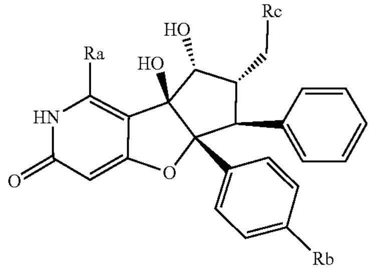
GM3

-continued
CO
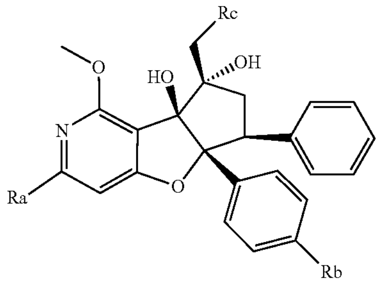
GM12
CP
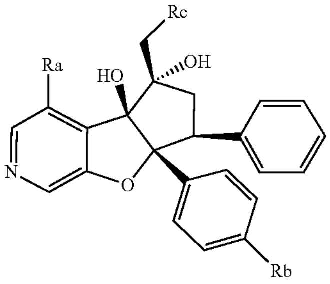
GM12
CQ
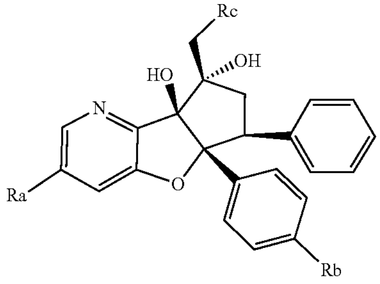
GM12
CR
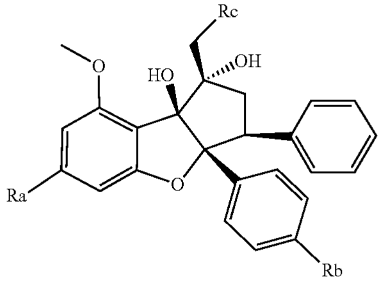
GM12
CS
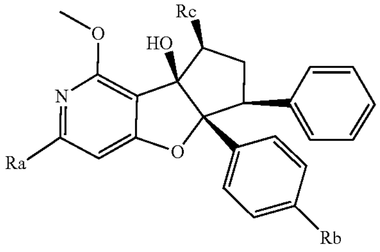
GM3
-continued
CT
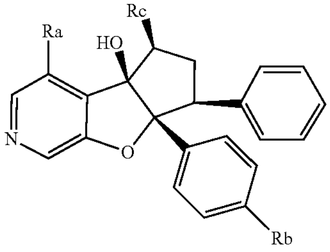
GM3
CU
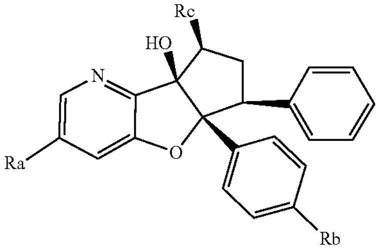
GM3
CV
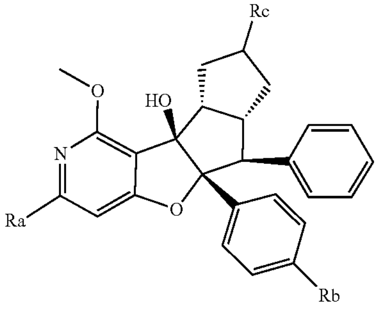
GM11
CW
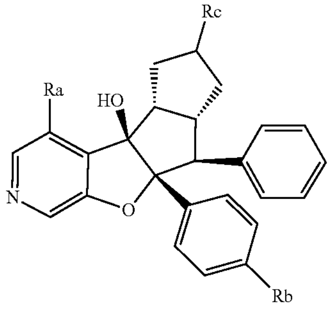
GM11
CX
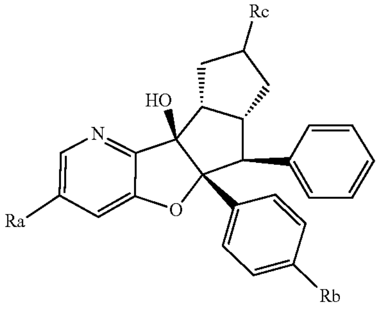
GM11

-continued
CY
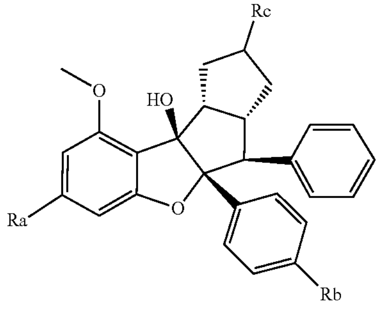
GM11
CZ
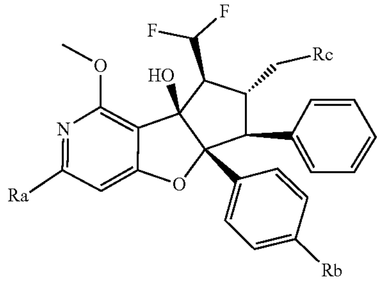
GM3
DA
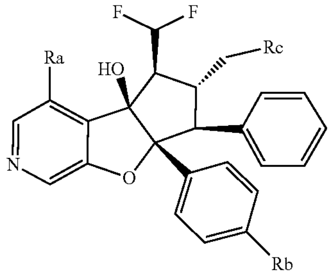
GM3
DB
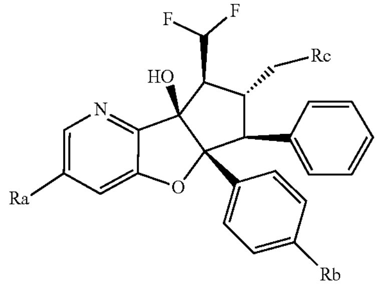
GM3
DC
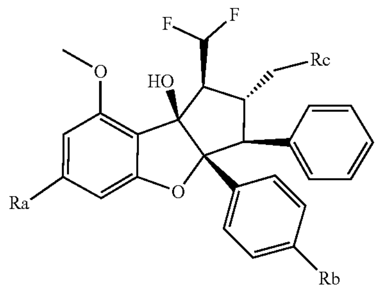
GM3
-continued
DD
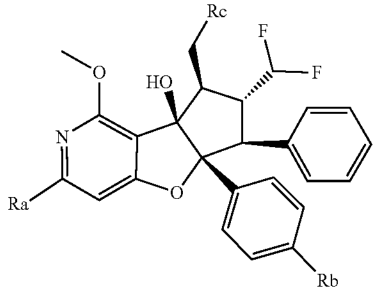
GM5
DE
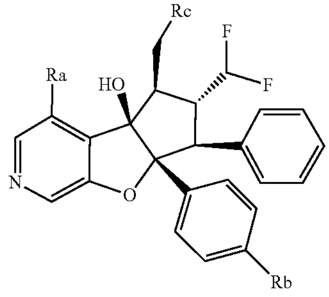
GM5
DF
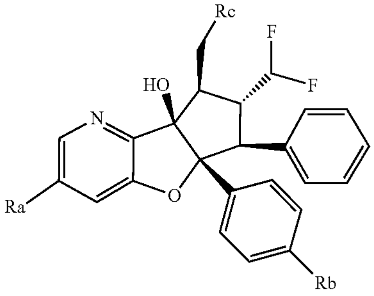
GM5
DG
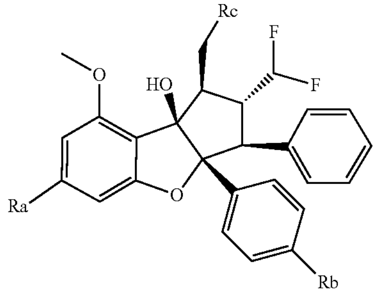
GM5

-continued
DH
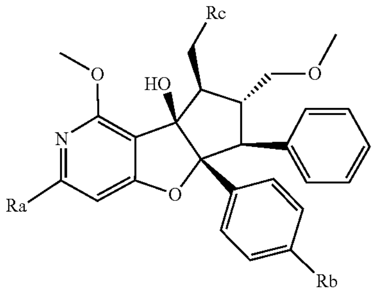
GM5
DI
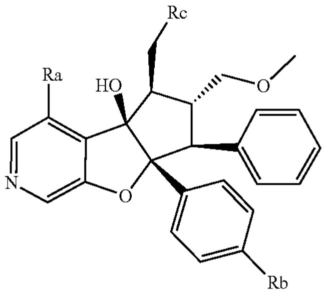
GM5
DJ
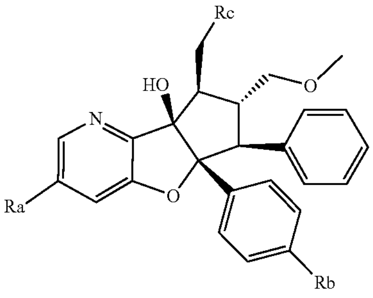
GM5
DK
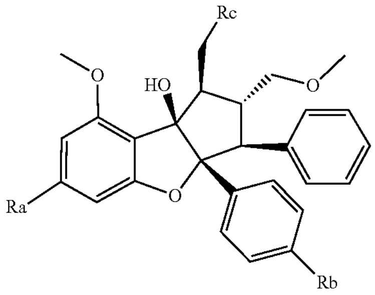
GM5
-continued
DL
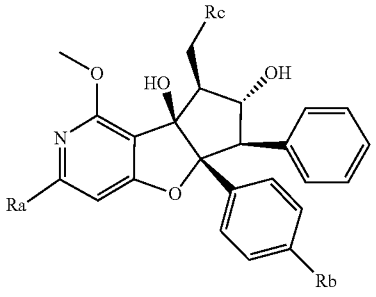
GM5
DM
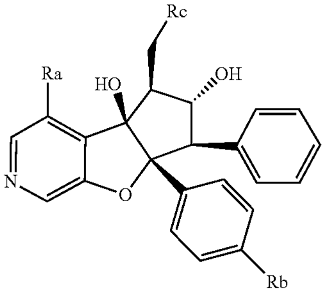
GM5
DN
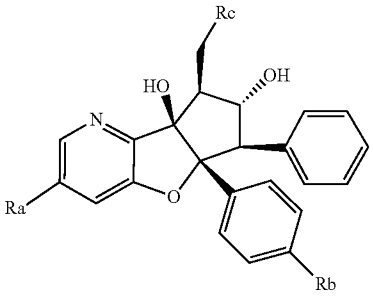
GM5
DO
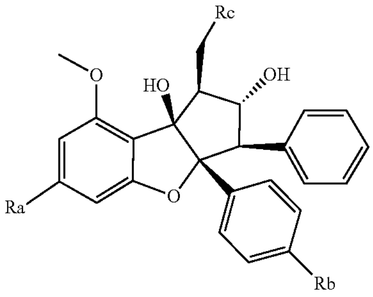
GM5
DP
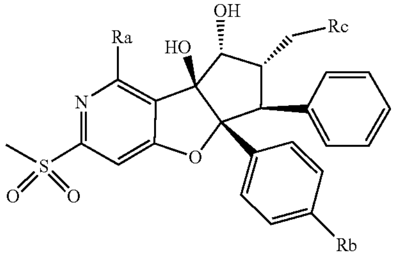
GM3

-continued
DQ
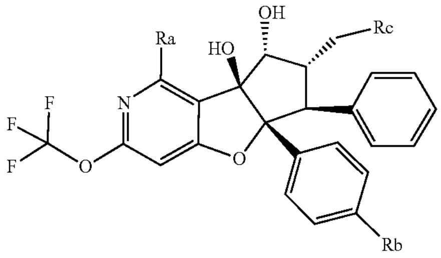
GM3
TABLE 1
| Ra | Rb | Rc |
|---|---|---|
| Cl | Cl | 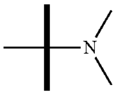 |
| Cl | CN | 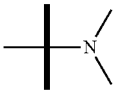 |
| Cl | $CF_2H$ | 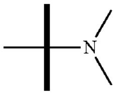 |
| Cl | $CF_3$ | 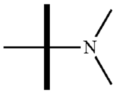 |
| Cl | Cl | 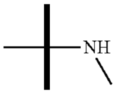 |
| Cl | CN | 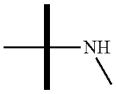 |
| Cl | $CF_2H$ | 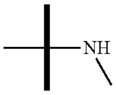 |
| Cl | $CF_3$ | 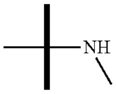 |
| Cl | Cl | 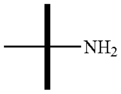 |
| Cl | CN | 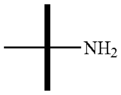 |
| Cl | $CF_2H$ | 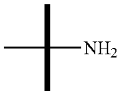 |
TABLE 1-continued
| Ra | Rb | Rc |
|---|---|---|
| Cl | $CF_3$ | 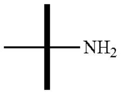 |
| Cl | Cl | 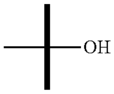 |
| Cl | CN | 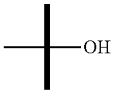 |
| Cl | $CF_2H$ | 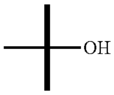 |
| Cl | $CF_3$ | 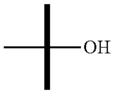 |
| Cl | Cl | 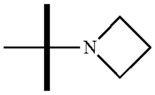 |
| Cl | CN | 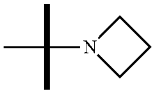 |
| Cl | $CF_2H$ | 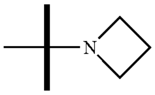 |
| Cl | $CF_3$ | 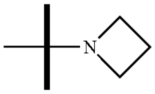 |
| Cl | Cl | 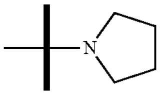 |
| Cl | CN | 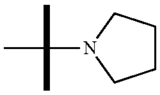 |
| Cl | $CF_2H$ | 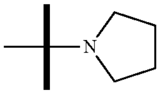 |
| Cl | $CF_3$ | 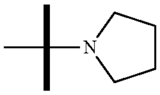 |
| Cl | Cl | 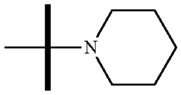 |

TABLE 1-continued
| Ra | Rb | Rc |
|---|---|---|
| Cl | CN | 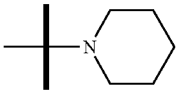 |
| Cl | $CF_2H$ | 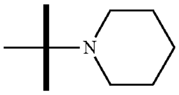 |
| Cl | $CF_3$ | 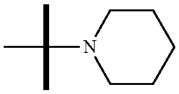 |
| Cl | Cl | 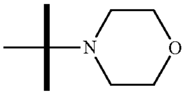 |
| Cl | CN | 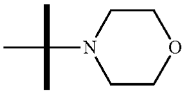 |
| Cl | $CF_2H$ | 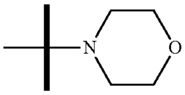 |
| Cl | $CF_3$ | 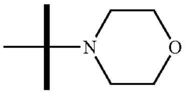 |
| Cl | Cl | 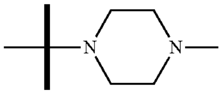 |
| Cl | CN | 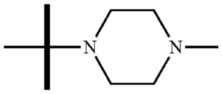 |
| Cl | $CF_2H$ | 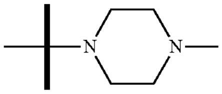 |
| Cl | $CF_3$ | 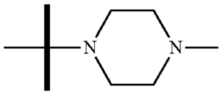 |
| Cl | Cl | 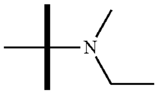 |
| Cl | CN | 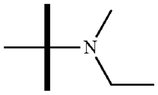 |
| Cl | $CF_2H$ | 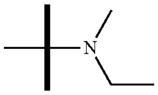 |
TABLE 1-continued
| Ra | Rb | Rc |
|---|---|---|
| Cl | $CF_3$ | 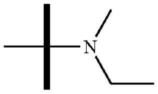 |
| Cl | Cl | 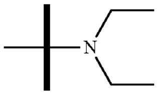 |
| Cl | CN | 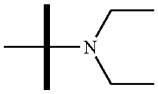 |
| Cl | $CF_2H$ | 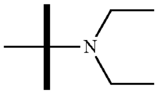 |
| Cl | $CF_3$ | 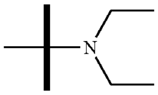 |
| Cl | Cl | 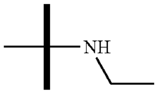 |
| Cl | CN | 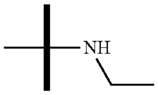 |
| Cl | $CF_2H$ | 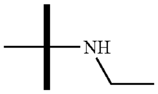 |
| Cl | $CF_3$ | 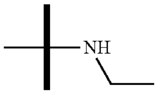 |
| Cl | Cl | 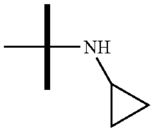 |
| Cl | CN | 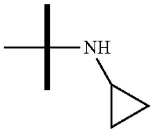 |
| Cl | $CF_2H$ | 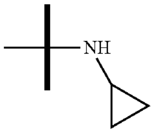 |
| Cl | $CF_3$ | 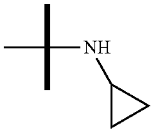 |

TABLE 1-continued
| Ra | Rb | Rc |
|---|---|---|
| Cl | Cl | 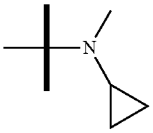 |
| Cl | CN | 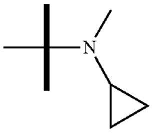 |
| Cl | $CF_2H$ | 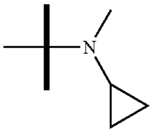 |
| Cl | $CF_3$ | 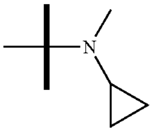 |
| Cl | Cl | 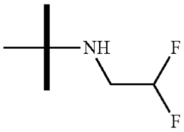 |
| Cl | CN | 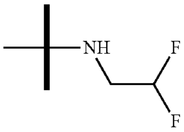 |
| Cl | $CF_2H$ | 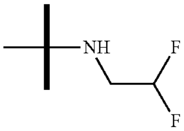 |
| Cl | $CF_3$ | 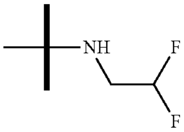 |
| Cl | Cl | 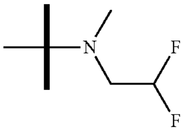 |
| Cl | CN | 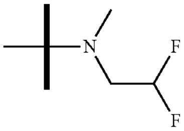 |
| Cl | $CF_2H$ | 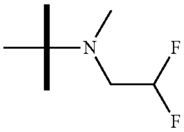 |
TABLE 1-continued
| Ra | Rb | Rc |
|---|---|---|
| Cl | $CF_3$ | 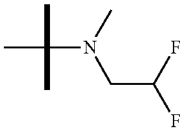 |
| Cl | Cl | 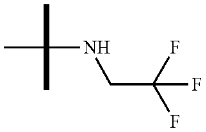 |
| Cl | CN | 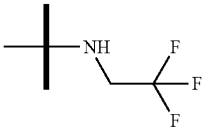 |
| Cl | $CF_2H$ | 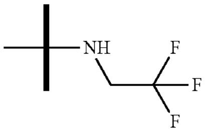 |
| Cl | $CF_3$ | 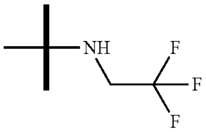 |
| Cl | Cl | 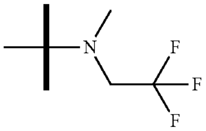 |
| Cl | CN | 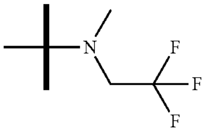 |
| Cl | $CF_2H$ | 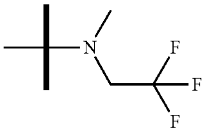 |
| Cl | $CF_3$ | 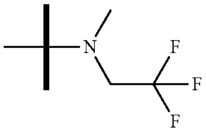 |
| Cl | Cl | 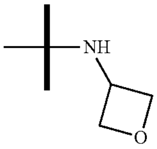 |

TABLE 1-continued
| Ra | Rb | Rc |
|---|---|---|
| Cl | CN | 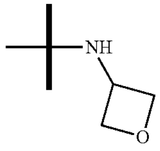 |
| Cl | $CF_2H$ | 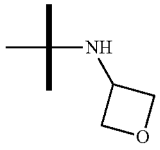 |
| Cl | $CF_3$ | 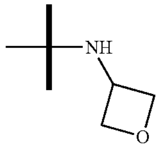 |
| Cl | Cl | 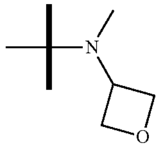 |
| Cl | CN | 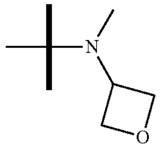 |
| Cl | $CF_2H$ | 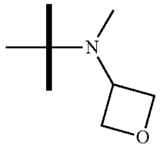 |
| Cl | $CF_3$ | 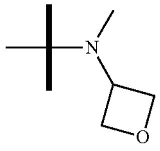 |
| Cl | Cl | 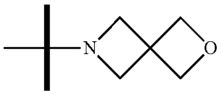 |
| Cl | CN | 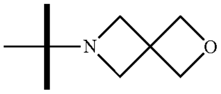 |
| Cl | $CF_2H$ | 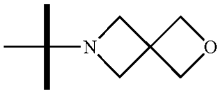 |
| Cl | $CF_3$ | 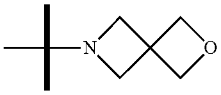 |
TABLE 1-continued
| Ra | Rb | Rc |
|---|---|---|
| Cl | Cl | 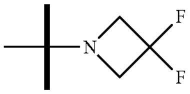 |
| Cl | CN | 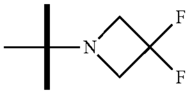 |
| Cl | $CF_2H$ | 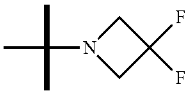 |
| Cl | $CF_3$ | 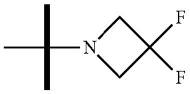 |
| Cl | Cl | 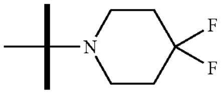 |
| Cl | CN | 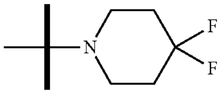 |
| Cl | $CF_2H$ | 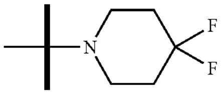 |
| Cl | $CF_3$ | 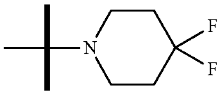 |
| Cl | Cl | 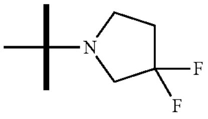 |
| Cl | CN | 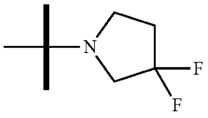 |
| Cl | $CF_2H$ | 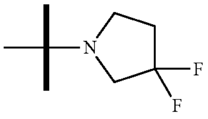 |
| Cl | $CF_3$ | 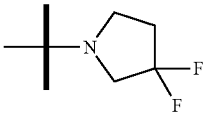 |
| Cl | Cl | 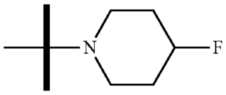 |

TABLE 1-continued
| Ra | Rb | Rc |
|---|---|---|
| Cl | CN | 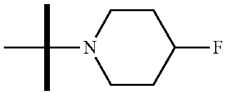 |
| Cl | $CF_2H$ | 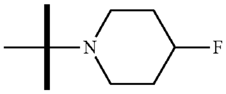 |
| Cl | $CF_3$ | 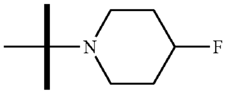 |
| Cl | Cl | 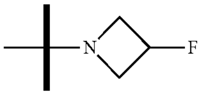 |
| Cl | CN | 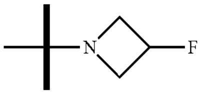 |
| Cl | $CF_2H$ | 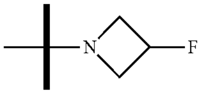 |
| Cl | $CF_3$ | 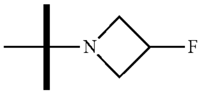 |
| Cl | Cl | 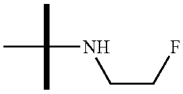 |
| Cl | CN | 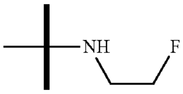 |
| Cl | $CF_2H$ | 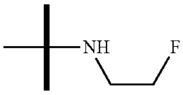 |
| Cl | $CF_3$ | 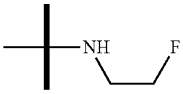 |
| Cl | Cl | 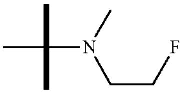 |
| Cl | CN | 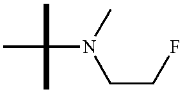 |
| Cl | $CF_2H$ | 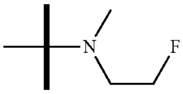 |
TABLE 1-continued
| Ra | Rb | Rc |
|---|---|---|
| Cl | $CF_3$ | 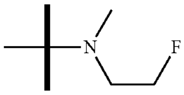 |
| Cl | Cl | 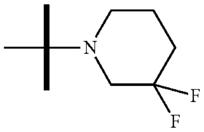 |
| Cl | CN | 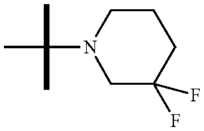 |
| Cl | $CF_2H$ | 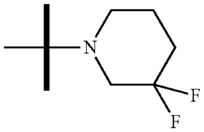 |
| Cl | $CF_3$ | 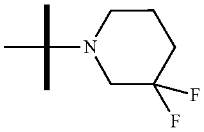 |
| Cl | Cl | 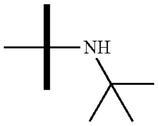 |
| Cl | CN | 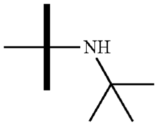 |
| Cl | $CF_2H$ | 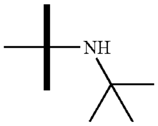 |
| Cl | $CF_3$ | 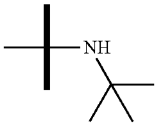 |
| Cl | Cl | 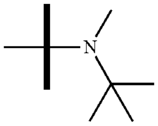 |
| Cl | CN | 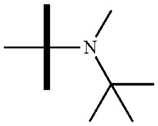 |

TABLE 1-continued
| Ra | Rb | Rc |
|---|---|---|
| Cl | $CF_2H$ | 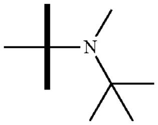 |
| Cl | $CF_3$ | 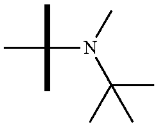 |
| Cl | Cl | 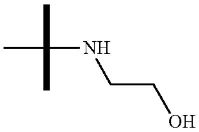 |
| Cl | CN | 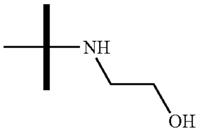 |
| Cl | $CF_2H$ | 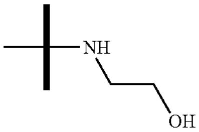 |
| Cl | $CF_3$ | 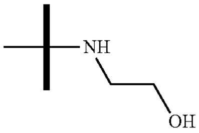 |
| Cl | Cl | 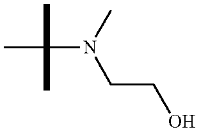 |
| Cl | CN | 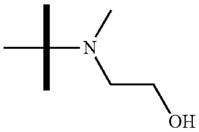 |
| Cl | $CF_2H$ | 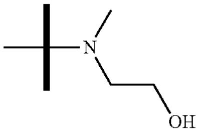 |
| Cl | $CF_3$ | 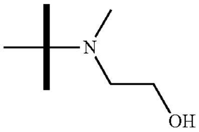 |
| Cl | Cl | 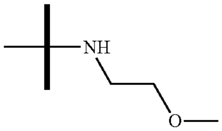 |
TABLE 1-continued
| Ra | Rb | Rc |
|---|---|---|
| Cl | CN | 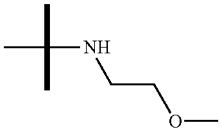 |
| Cl | $CF_2H$ | 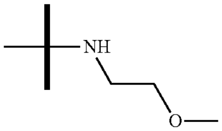 |
| Cl | $CF_3$ | 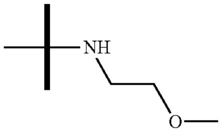 |
| Cl | Cl | 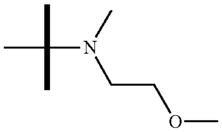 |
| Cl | CN | 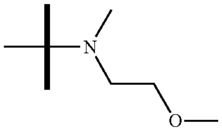 |
| Cl | $CF_2H$ | 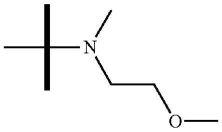 |
| Cl | $CF_3$ | 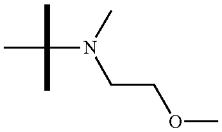 |
| Cl | Cl | 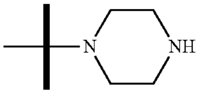 |
| Cl | CN | 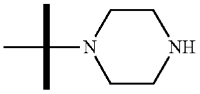 |
| Cl | $CF_2H$ | 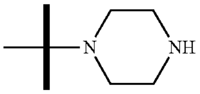 |
| Cl | $CF_3$ | 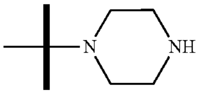 |
| Cl | Cl | 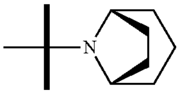 |

TABLE 1-continued
| Ra | Rb | Rc |
|---|---|---|
| Cl | CN | 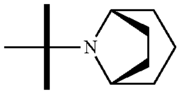 |
| Cl | $CF_2H$ | 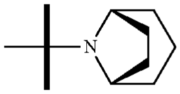 |
| Cl | $CF_3$ | 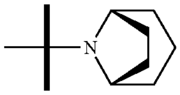 |
| Cl | Cl | 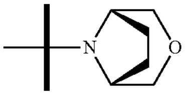 |
| Cl | CN | 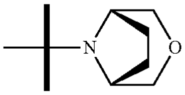 |
| Cl | $CF_2H$ | 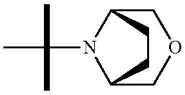 |
| Cl | $CF_3$ | 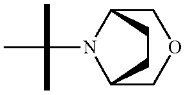 |
| Cl | Cl | 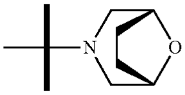 |
| Cl | CN | 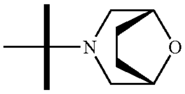 |
| Cl | $CF_2H$ | 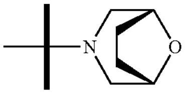 |
| Cl | $CF_3$ | 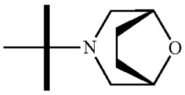 |
| Cl | Cl | 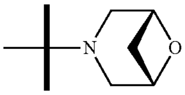 |
| Cl | CN | 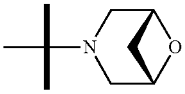 |
| Cl | $CF_2H$ | 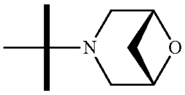 |
TABLE 1-continued
| Ra | Rb | Rc |
|---|---|---|
| Cl | $CF_3$ | 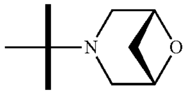 |
| Cl | Cl | 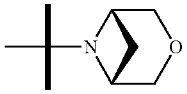 |
| Cl | CN | 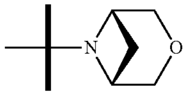 |
| Cl | $CF_2H$ | 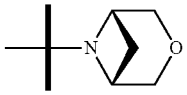 |
| Cl | $CF_3$ | 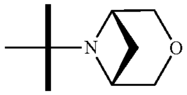 |
| Cl | Cl | 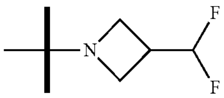 |
| Cl | CN | 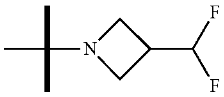 |
| Cl | $CF_2H$ | 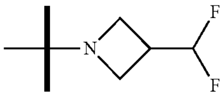 |
| Cl | $CF_3$ | 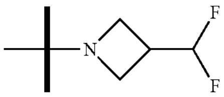 |
| Cl | Cl | 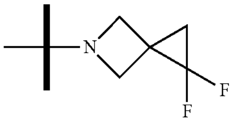 |
| Cl | CN | 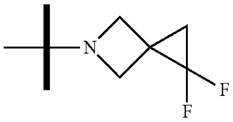 |
| Cl | $CF_2H$ | 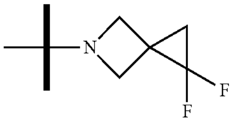 |
| Cl | $CF_3$ | 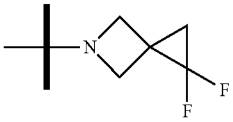 |

TABLE 1-continued
| Ra | Rb | Rc |
|---|---|---|
| Cl | Cl | 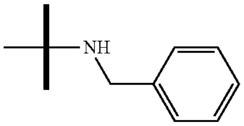 |
| Cl | CN | 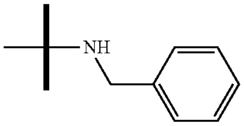 |
| Cl | $CF_2H$ | 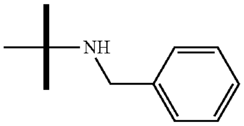 |
| Cl | $CF_3$ | 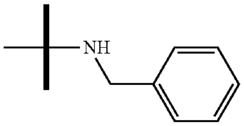 |
| Cl | Cl | 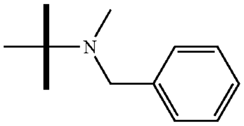 |
| Cl | CN | 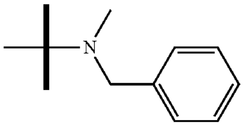 |
| Cl | $CF_2H$ | 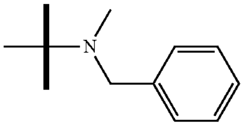 |
| Cl | $CF_3$ | 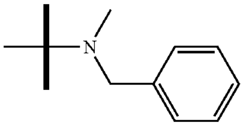 |
| Cl | Cl | 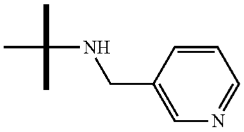 |
| Cl | CN | 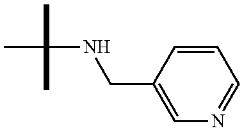 |
| Cl | $CF_2H$ | 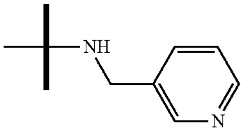 |
TABLE 1-continued
| Ra | Rb | Rc |
|---|---|---|
| Cl | $CF_3$ | 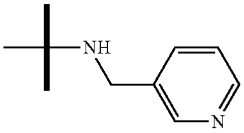 |
| Cl | Cl | 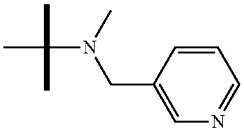 |
| Cl | CN | 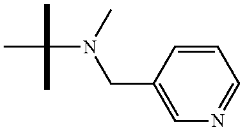 |
| Cl | $CF_2H$ | 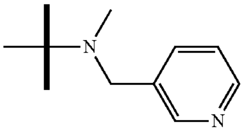 |
| Cl | $CF_3$ | 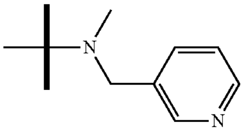 |
| Cl | Cl | 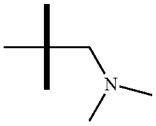 |
| Cl | CN | 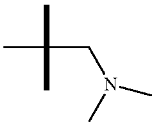 |
| Cl | $CF_2H$ | 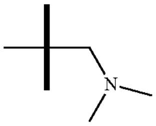 |
| Cl | $CF_3$ | 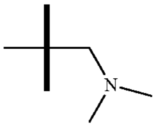 |
| Cl | Cl | 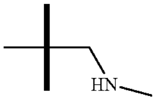 |
| Cl | CN | 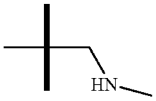 |

TABLE 1-continued
| Ra | Rb | Rc |
|---|---|---|
| Cl | $CF_2H$ | 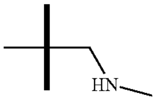 |
| Cl | $CF_3$ | 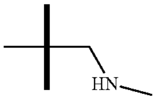 |
| Cl | Cl | 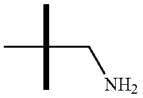 |
| Cl | CN | 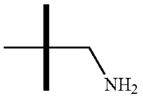 |
| Cl | $CF_2H$ | 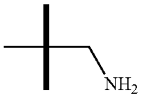 |
| Cl | $CF_3$ | 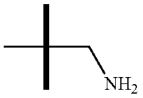 |
| Cl | Cl | 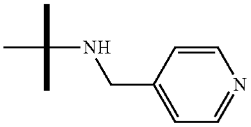 |
| Cl | CN | 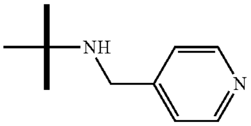 |
| Cl | $CF_2H$ | 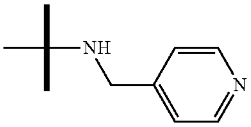 |
| Cl | $CF_3$ | 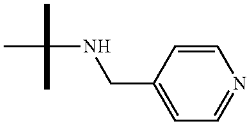 |
| Cl | Cl | 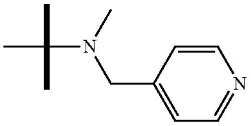 |
| Cl | CN | 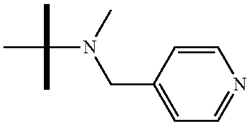 |
TABLE 1-continued
| Ra | Rb | Rc |
|---|---|---|
| Cl | $CF_2H$ | 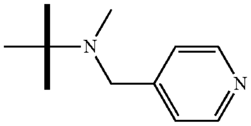 |
| Cl | $CF_3$ | 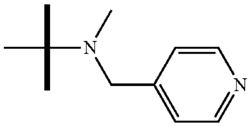 |
| Cl | Cl | 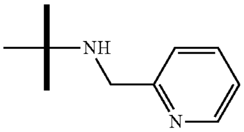 |
| Cl | CN | 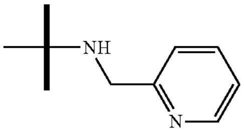 |
| Cl | $CF_2H$ | 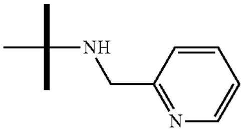 |
| Cl | $CF_3$ | 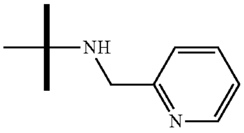 |
| Cl | Cl | 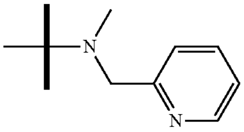 |
| Cl | CN | 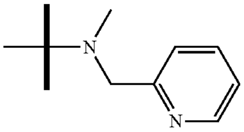 |
| Cl | $CF_2H$ | 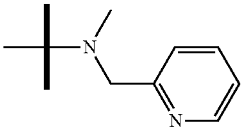 |
| Cl | $CF_3$ | 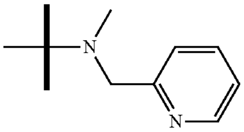 |
| Cl | Cl | 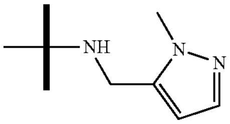 |

TABLE 1-continued
| Ra | Rb | Rc |
|---|---|---|
| Cl | CN | 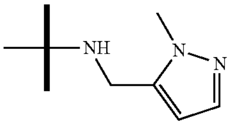 |
| Cl | $CF_2H$ | 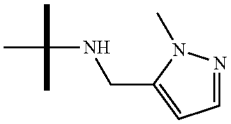 |
| Cl | $CF_3$ | 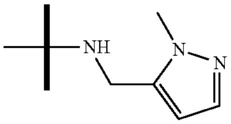 |
| Cl | Cl | 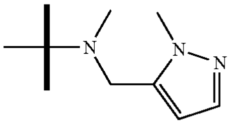 |
| Cl | CN | 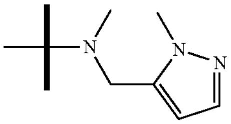 |
| Cl | $CF_2H$ | 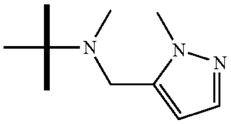 |
| Cl | $CF_3$ | 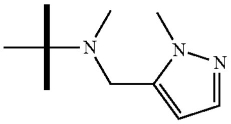 |
| Cl | Cl | 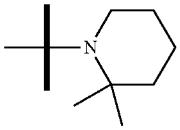 |
| Cl | CN | 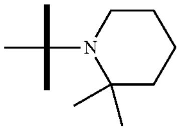 |
| Cl | $CF_2H$ | 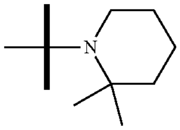 |
| Cl | $CF_3$ | 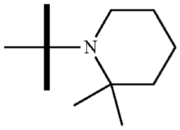 |
TABLE 1-continued
| Ra | Rb | Rc |
|---|---|---|
| Cl | Cl | 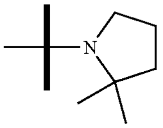 |
| Cl | CN | 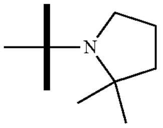 |
| Cl | $CF_2H$ | 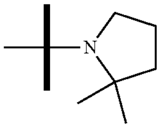 |
| Cl | $CF_3$ | 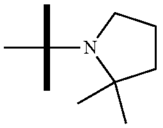 |
| Cl | Cl | 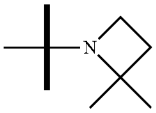 |
| Cl | CN | 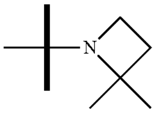 |
| Cl | $CF_2H$ | 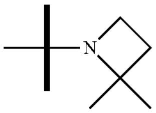 |
| Cl | $CF_3$ | 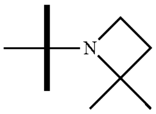 |
| Cl | Cl | 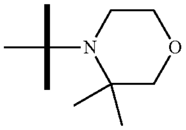 |
| Cl | CN | 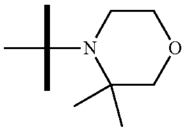 |
| Cl | $CF_2H$ | 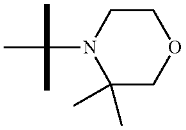 |

TABLE 1-continued
| Ra | Rb | Rc |
|---|---|---|
| Cl | $CF_3$ | 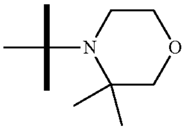 |
| Cl | Cl | 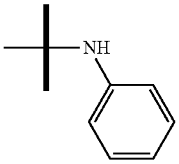 |
| Cl | CN | 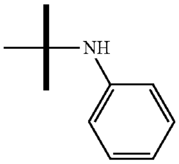 |
| Cl | $CF_2H$ | 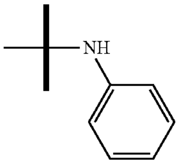 |
| Cl | $CF_3$ | 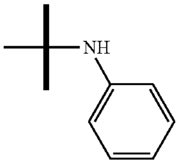 |
| Cl | Cl | 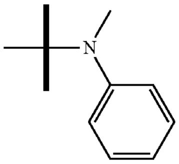 |
| Cl | CN | 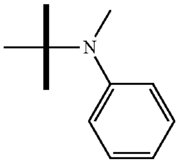 |
| Cl | $CF_2H$ | 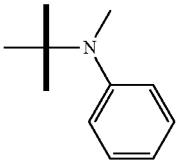 |
| Cl | $CF_3$ | 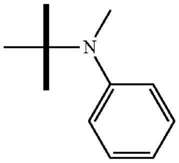 |
TABLE 1-continued
| Ra | Rb | Rc |
|---|---|---|
| Cl | Cl | 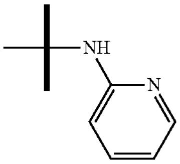 |
| Cl | CN | 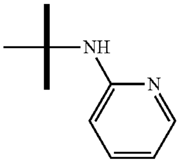 |
| Cl | $CF_2H$ | 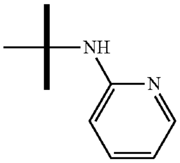 |
| Cl | $CF_3$ | 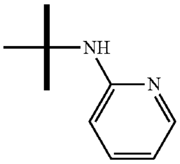 |
| Cl | Cl | 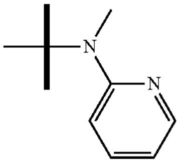 |
| Cl | CN | 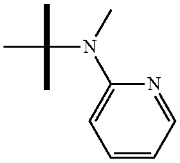 |
| Cl | $CF_2H$ | 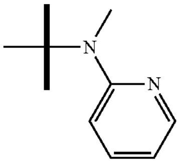 |
| Cl | $CF_3$ | 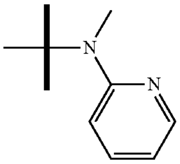 |
| Cl | Cl | 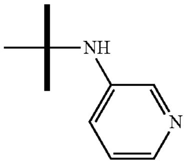 |

TABLE 1-continued
| Ra | Rb | Rc |
|---|---|---|
| Cl | CN | 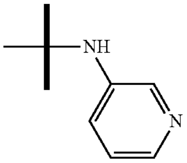 |
| Cl | $CF_2H$ | 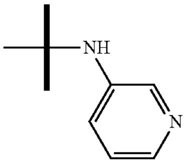 |
| Cl | $CF_3$ | 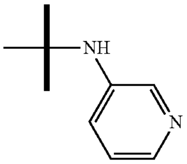 |
| Cl | Cl | 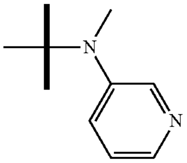 |
| Cl | CN | 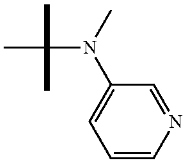 |
| Cl | $CF_2H$ | 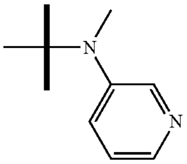 |
| Cl | $CF_3$ | 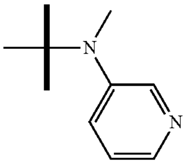 |
| Cl | Cl | 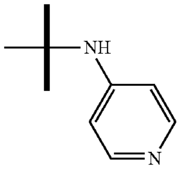 |
| Cl | CN | 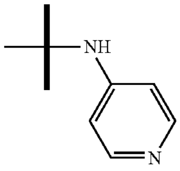 |
TABLE 1-continued
| Ra | Rb | Rc |
|---|---|---|
| Cl | $CF_2H$ | 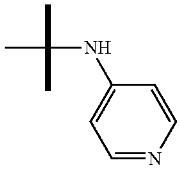 |
| Cl | $CF_3$ | 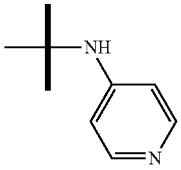 |
| Cl | Cl | 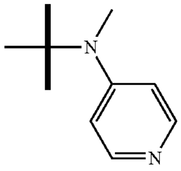 |
| Cl | CN | 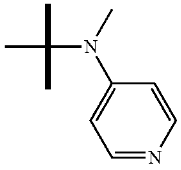 |
| Cl | $CF_2H$ | 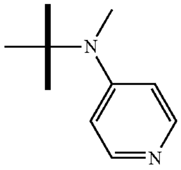 |
| Cl | $CF_3$ | 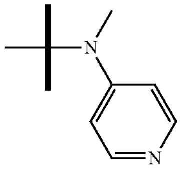 |
| Cl | Cl | 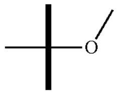 |
| Cl | CN | 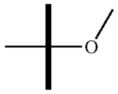 |
| Cl | $CF_2H$ | 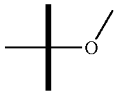 |
| Cl | $CF_3$ | 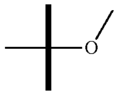 |

TABLE 1-continued
| Ra | Rb | Rc |
|---|---|---|
| Cl | Cl | 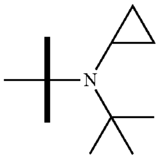 |
| Cl | CN | 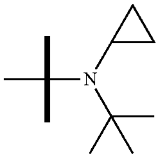 |
| Cl | $CF_2H$ | 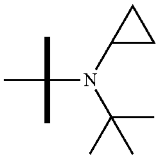 |
| Cl | $CF_3$ | 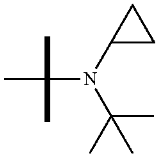 |
| Cl | Cl | 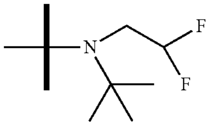 |
| Cl | CN | 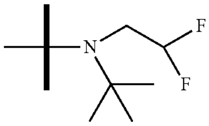 |
| Cl | $CF_2H$ | 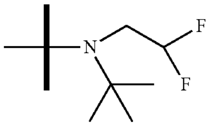 |
| Cl | $CF_3$ | 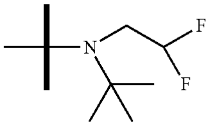 |
| Cl | Cl | 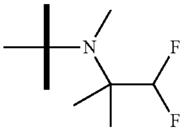 |
| Cl | CN | 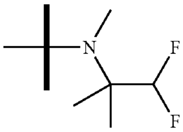 |
TABLE 1-continued
| Ra | Rb | Rc |
|---|---|---|
| Cl | $CF_2H$ | 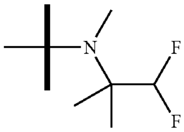 |
| Cl | $CF_3$ | 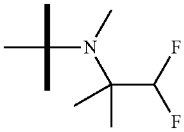 |
| Cl | Cl | 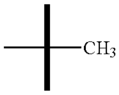 |
| Cl | CN | 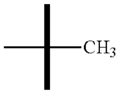 |
| Cl | $CF_2H$ | 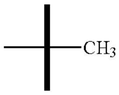 |
| Cl | $CF_3$ | 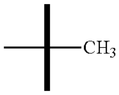 |
| Cl | Cl | 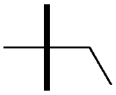 |
| Cl | CN | 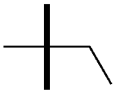 |
| Cl | $CF_2H$ | 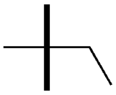 |
| Cl | $CF_3$ | 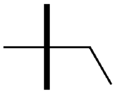 |
| Cl | Cl | 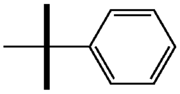 |
| Cl | CN | 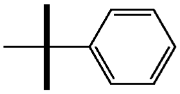 |
| Cl | $CF_2H$ | 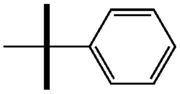 |
| Cl | $CF_3$ | 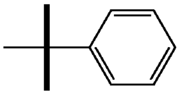 |

TABLE 1-continued
| Ra | Rb | Rc |
|---|---|---|
| Cl | Cl | 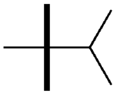 |
| Cl | CN | 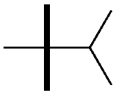 |
| Cl | $CF_2H$ | 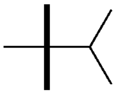 |
| Cl | $CF_3$ | 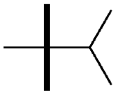 |
| Cl | Cl | 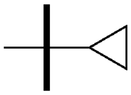 |
| Cl | CN | 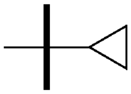 |
| Cl | $CF_2H$ | 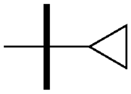 |
| Cl | $CF_3$ | 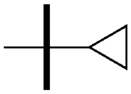 |
| Cl | Cl | 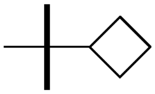 |
| Cl | CN | 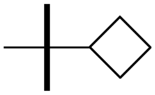 |
| Cl | $CF_2H$ | 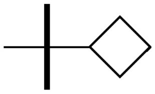 |
| Cl | $CF_3$ | 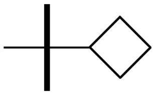 |
| Cl | Cl | 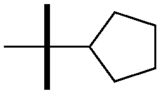 |
| Cl | CN | 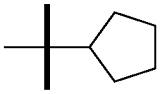 |
TABLE 1-continued
| Ra | Rb | Rc |
|---|---|---|
| Cl | $CF_2H$ | 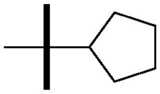 |
| Cl | $CF_3$ | 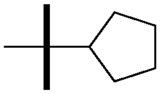 |
| Cl | Cl | 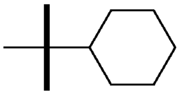 |
| Cl | CN | 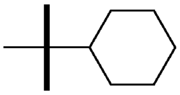 |
| Cl | $CF_2H$ | 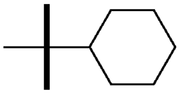 |
| Cl | $CF_3$ | 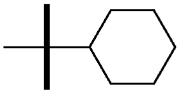 |
| Cl | Cl | 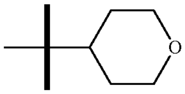 |
| Cl | CN | 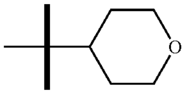 |
| Cl | $CF_2H$ | 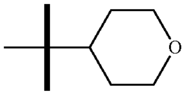 |
| Cl | $CF_3$ | 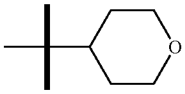 |
| Cl | Cl | 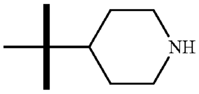 |
| Cl | CN | 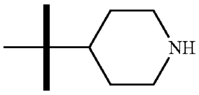 |
| Cl | $CF_2H$ | 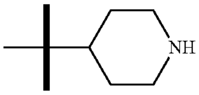 |
| Cl | $CF_3$ | 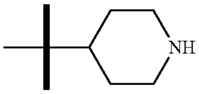 |

TABLE 1-continued
| Ra | Rb | Rc |
|---|---|---|
| Cl | Cl | 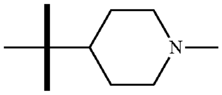 |
| Cl | CN | 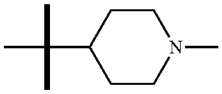 |
| Cl | $CF_2H$ | 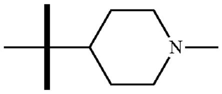 |
| Cl | $CF_3$ | 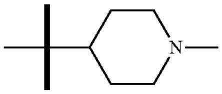 |
| Cl | Cl | 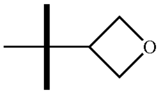 |
| Cl | CN | 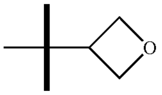 |
| Cl | $CF_2H$ | 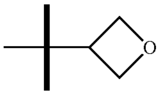 |
| Cl | $CF_3$ | 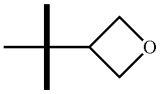 |
| Cl | Cl | 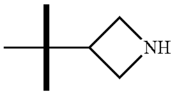 |
| Cl | CN | 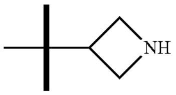 |
| Cl | $CF_2H$ | 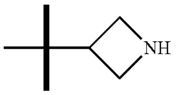 |
| Cl | $CF_3$ | 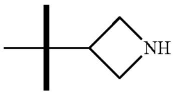 |
| Cl | Cl | 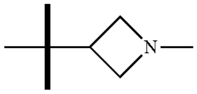 |
| Cl | CN | 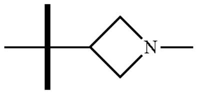 |
TABLE 1-continued
| Ra | Rb | Rc |
|---|---|---|
| Cl | $CF_2H$ | 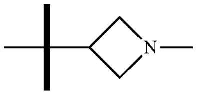 |
| Cl | $CF_3$ | 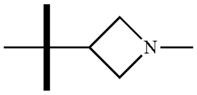 |
| Cl | Cl | 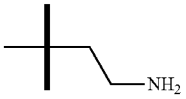 |
| Cl | CN | 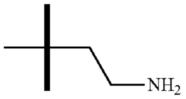 |
| Cl | $CF_2H$ | 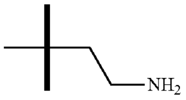 |
| Cl | $CF_3$ | 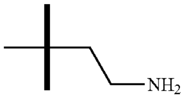 |
| Cl | Cl | 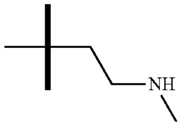 |
| Cl | CN | 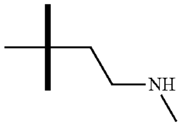 |
| Cl | $CF_2H$ | 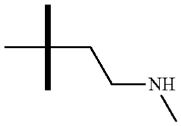 |
| Cl | $CF_3$ | 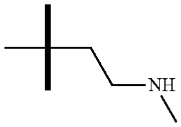 |
| Cl | Cl | 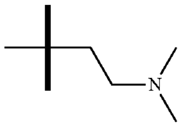 |
| Cl | CN | 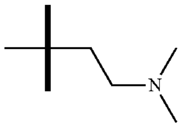 |

TABLE 1-continued
| Ra | Rb | Rc |
|---|---|---|
| Cl | $CF_2H$ | 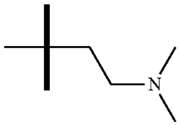 |
| Cl | $CF_3$ | 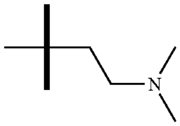 |
| Cl | Cl | 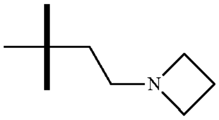 |
| Cl | CN | 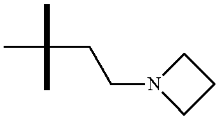 |
| Cl | $CF_2H$ | 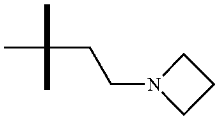 |
| Cl | $CF_3$ | 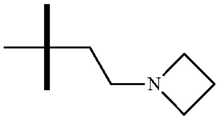 |
| Cl | Cl | 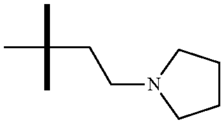 |
| Cl | CN | 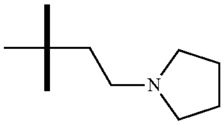 |
| Cl | $CF_2H$ | 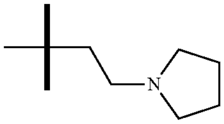 |
| Cl | $CF_3$ | 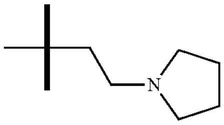 |
| Cl | Cl | 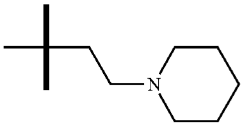 |
TABLE 1-continued
| Ra | Rb | Rc |
|---|---|---|
| Cl | CN | 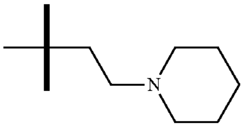 |
| Cl | $CF_2H$ | 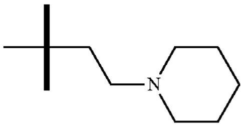 |
| Cl | $CF_3$ | 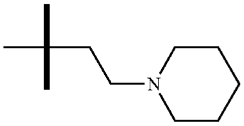 |
| Cl | Cl | 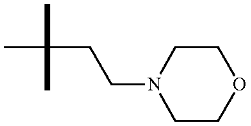 |
| Cl | CN | 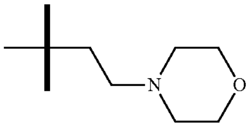 |
| Cl | $CF_2H$ | 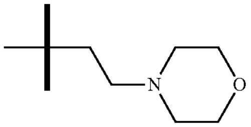 |
| Cl | $CF_3$ | 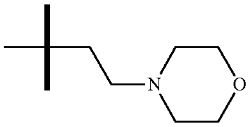 |
| Cl | Cl | 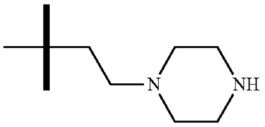 |
| Cl | CN | 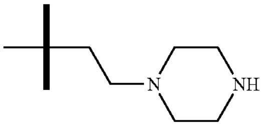 |
| Cl | $CF_2H$ | 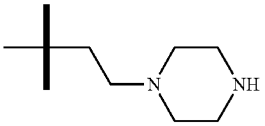 |
| Cl | $CF_3$ | 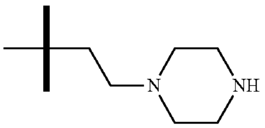 |

TABLE 1-continued
| Ra | Rb | Rc |
|---|---|---|
| Cl | Cl | 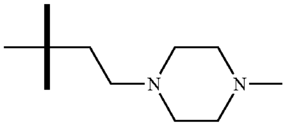 |
| Cl | CN | 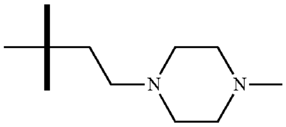 |
| Cl | $CF_2H$ | 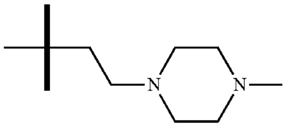 |
| Cl | $CF_3$ | 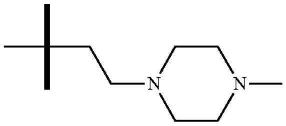 |
| CN | Cl | 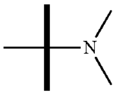 |
| CN | CN | 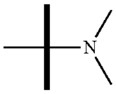 |
| CN | $CF_2H$ | 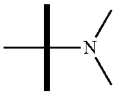 |
| CN | $CF_3$ | 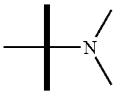 |
| CN | Cl | 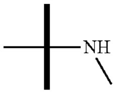 |
| CN | CN | 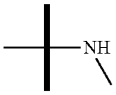 |
| CN | $CF_2H$ | 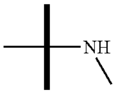 |
| CN | $CF_3$ | 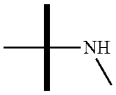 |
| CN | Cl | 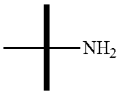 |
TABLE 1-continued
| Ra | Rb | Rc |
|---|---|---|
| CN | CN | 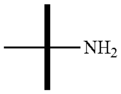 |
| CN | $CF_2H$ | 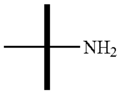 |
| CN | $CF_3$ | 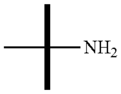 |
| CN | Cl | 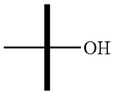 |
| CN | CN | 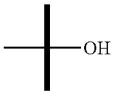 |
| CN | $CF_2H$ | 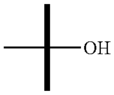 |
| CN | $CF_3$ | 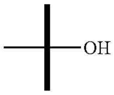 |
| CN | Cl | 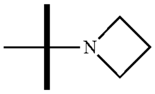 |
| CN | CN | 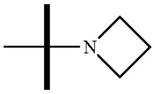 |
| CN | $CF_2H$ | 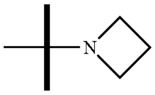 |
| CN | $CF_3$ | 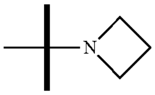 |
| CN | Cl | 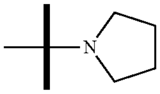 |
| CN | CN | 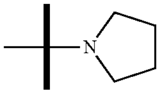 |
| CN | $CF_2H$ | 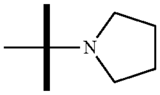 |

TABLE 1-continued
| Ra | Rb | Rc |
|---|---|---|
| CN | $CF_3$ | 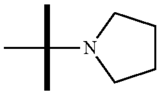 |
| CN | Cl | 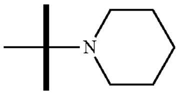 |
| CN | CN | 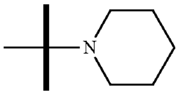 |
| CN | $CF_2H$ | 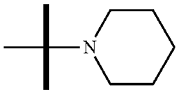 |
| CN | $CF_3$ | 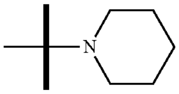 |
| CN | Cl | 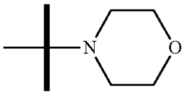 |
| CN | CN | 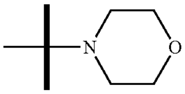 |
| CN | $CF_2H$ | 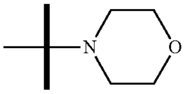 |
| CN | $CF_3$ | 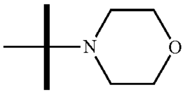 |
| CN | Cl | 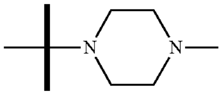 |
| CN | CN | 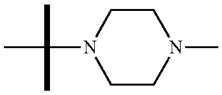 |
| CN | $CF_2H$ | 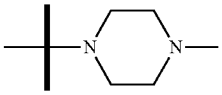 |
| CN | $CF_3$ | 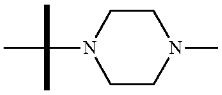 |
| CN | Cl | 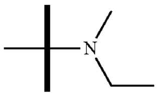 |
| CN | CN | 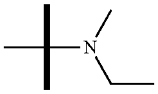 |
| CN | $CF_2H$ | 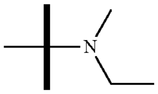 |
| CN | $CF_3$ | 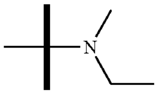 |
| CN | Cl | 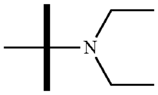 |
| CN | CN | 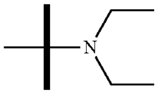 |
| CN | $CF_2H$ | 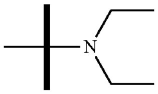 |
| CN | $CF_3$ | 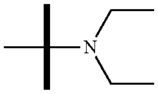 |
| CN | Cl | 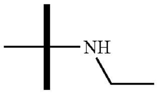 |
| CN | CN | 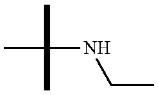 |
| CN | $CF_2H$ | 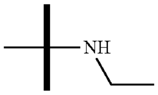 |
| CN | $CF_3$ | 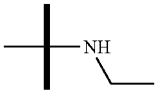 |
| CN | Cl | 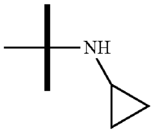 |
| CN | CN | 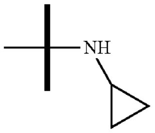 |

TABLE 1-continued
| Ra | Rb | Rc |
|---|---|---|
| CN | $CF_2H$ | 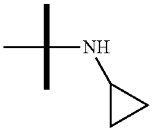 |
| CN | $CF_3$ | 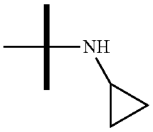 |
| CN | Cl | 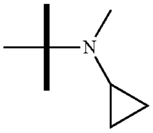 |
| CN | CN | 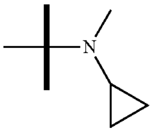 |
| CN | $CF_2H$ | 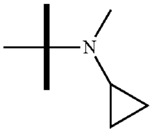 |
| CN | $CF_3$ | 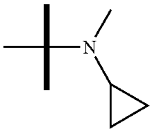 |
| CN | Cl | 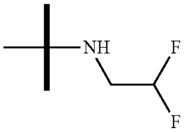 |
| CN | CN | 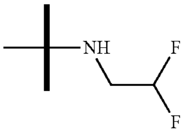 |
| CN | $CF_2H$ | 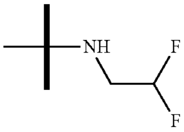 |
| CN | $CF_3$ | 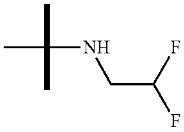 |
| CN | Cl | 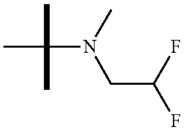 |
TABLE 1-continued
| Ra | Rb | Rc |
|---|---|---|
| CN | CN | 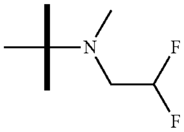 |
| CN | $CF_2H$ | 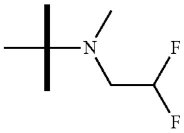 |
| CN | $CF_3$ | 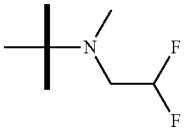 |
| CN | Cl | 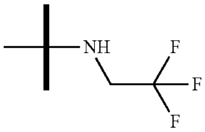 |
| CN | CN | 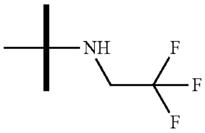 |
| CN | $CF_2H$ | 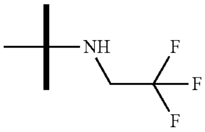 |
| CN | $CF_3$ | 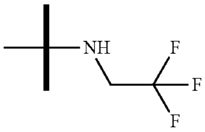 |
| CN | Cl | 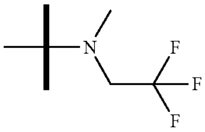 |
| CN | CN | 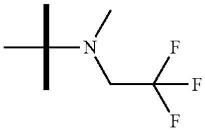 |
| CN | $CF_2H$ | 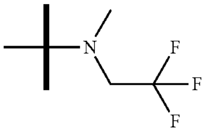 |

TABLE 1-continued
| Ra | Rb | Rc |
|---|---|---|
| CN | $CF_3$ | 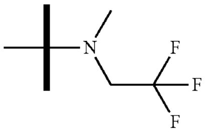 |
| CN | Cl | 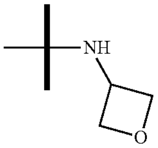 |
| CN | CN | 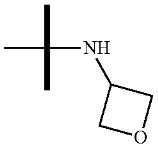 |
| CN | $CF_2H$ | 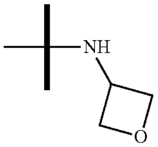 |
| CN | $CF_3$ | 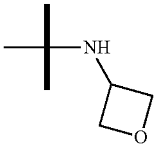 |
| CN | Cl | 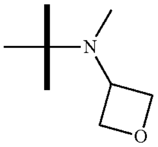 |
| CN | CN | 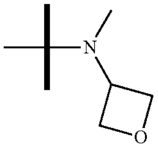 |
| CN | $CF_2H$ | 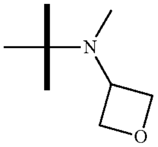 |
| CN | $CF_3$ | 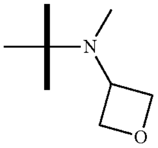 |
| CN | Cl | 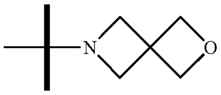 |
TABLE 1-continued
| Ra | Rb | Rc |
|---|---|---|
| CN | CN | 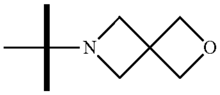 |
| CN | $CF_2H$ | 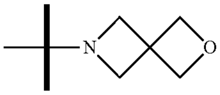 |
| CN | $CF_3$ | 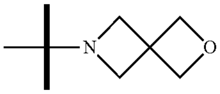 |
| CN | Cl | 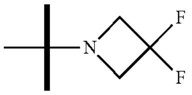 |
| CN | CN | 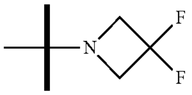 |
| CN | $CF_2H$ | 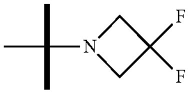 |
| CN | $CF_3$ | 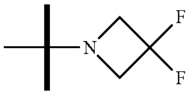 |
| CN | Cl | 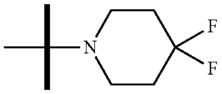 |
| CN | CN | 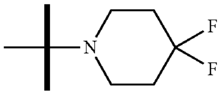 |
| CN | $CF_2H$ | 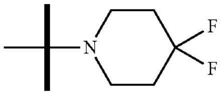 |
| CN | $CF_3$ | 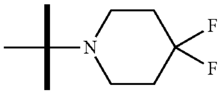 |
| CN | Cl | 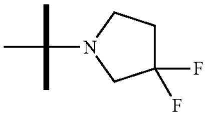 |
| CN | CN | 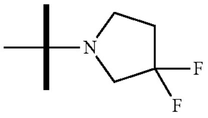 |
| CN | $CF_2H$ | 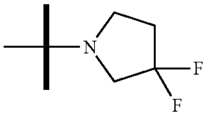 |

| Ra | Rb | Rc |
|---|---|---|
| CN | $CF_3$ | 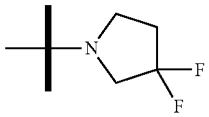 |
| CN | Cl | 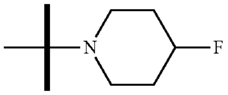 |
| CN | CN | 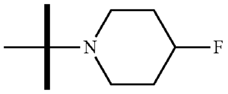 |
| CN | $CF_2H$ | 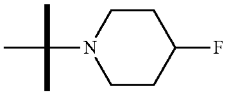 |
| CN | $CF_3$ | 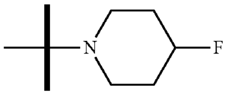 |
| CN | Cl | 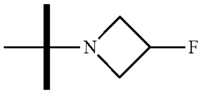 |
| CN | CN | 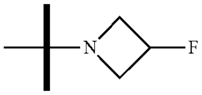 |
| CN | $CF_2H$ | 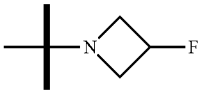 |
| CN | $CF_3$ | 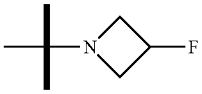 |
| CN | Cl | 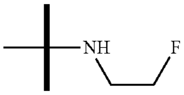 |
| CN | CN | 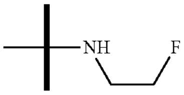 |
| CN | $CF_2H$ | 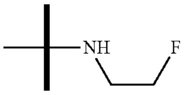 |
| CN | $CF_3$ | 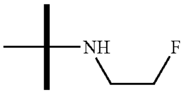 |
| CN | Cl | 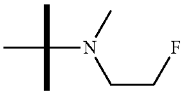 |
| Ra | Rb | Rc |
|---|---|---|
| CN | CN | 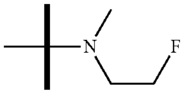 |
| CN | $CF_2H$ | 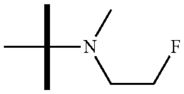 |
| CN | $CF_3$ | 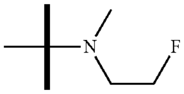 |
| CN | Cl | 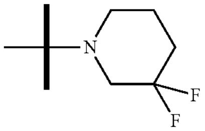 |
| CN | CN | 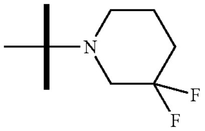 |
| CN | $CF_2H$ | 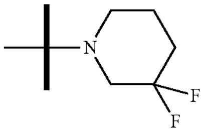 |
| CN | $CF_3$ | 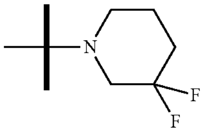 |
| CN | Cl | 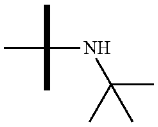 |
| CN | CN | 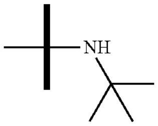 |
| CN | $CF_2H$ | 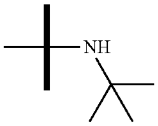 |
| CN | $CF_3$ | 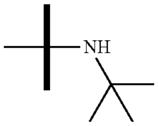 |
| CN | Cl | 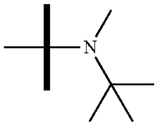 |

TABLE 1-continued
| Ra | Rb | Rc |
|---|---|---|
| CN | CN | 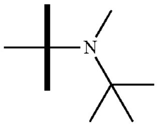 |
| CN | $CF_2H$ | 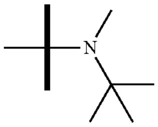 |
| CN | $CF_3$ | 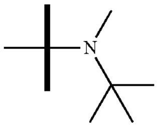 |
| CN | Cl | 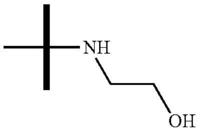 |
| CN | CN | 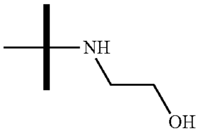 |
| CN | $CF_2H$ | 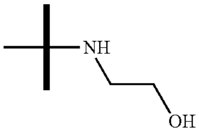 |
| CN | $CF_3$ | 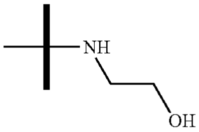 |
| CN | Cl | 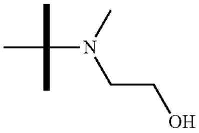 |
| CN | CN | 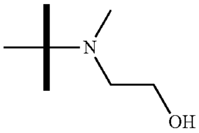 |
| CN | $CF_2H$ | 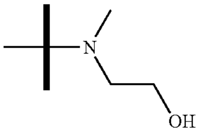 |
| CN | $CF_3$ | 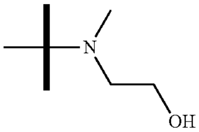 |
TABLE 1-continued
| Ra | Rb | Rc |
|---|---|---|
| CN | Cl | 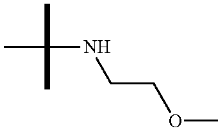 |
| CN | CN | 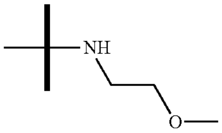 |
| CN | $CF_2H$ | 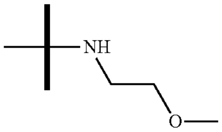 |
| CN | $CF_3$ | 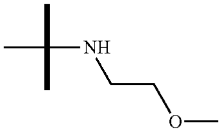 |
| CN | Cl | 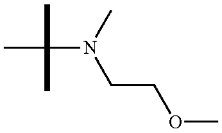 |
| CN | CN | 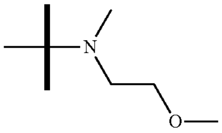 |
| CN | $CF_2H$ | 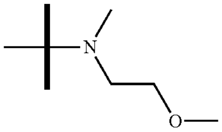 |
| CN | $CF_3$ | 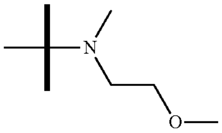 |
| CN | Cl | 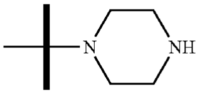 |
| CN | CN | 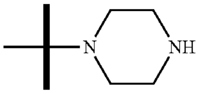 |
| CN | $CF_2H$ | 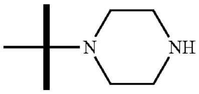 |

TABLE 1-continued
| Ra | Rb | Rc |
|---|---|---|
| CN | $CF_3$ | 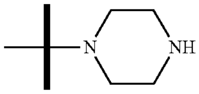 |
| CN | Cl | 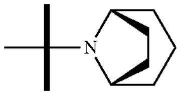 |
| CN | CN | 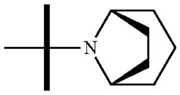 |
| CN | $CF_2H$ | 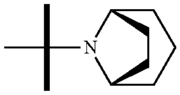 |
| CN | $CF_3$ | 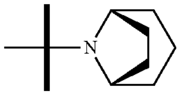 |
| CN | Cl | 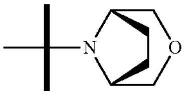 |
| CN | CN | 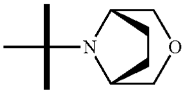 |
| CN | $CF_2H$ | 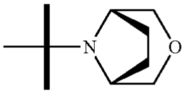 |
| CN | $CF_3$ | 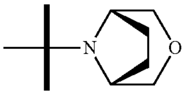 |
| CN | Cl | 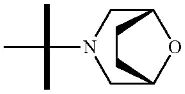 |
| CN | CN | 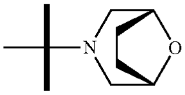 |
| CN | $CF_2H$ | 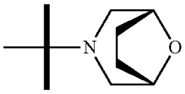 |
| CN | $CF_3$ | 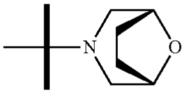 |
| CN | Cl | 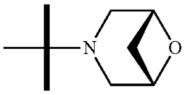 |
TABLE 1-continued
| Ra | Rb | Rc |
|---|---|---|
| CN | CN | 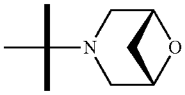 |
| CN | $CF_2H$ | 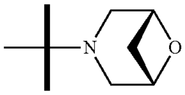 |
| CN | $CF_3$ | 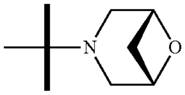 |
| CN | Cl | 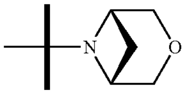 |
| CN | CN | 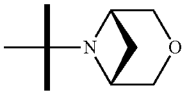 |
| CN | $CF_2H$ | 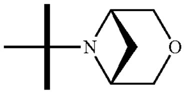 |
| CN | $CF_3$ | 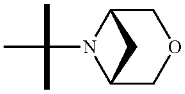 |
| CN | Cl | 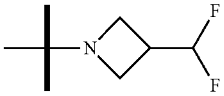 |
| CN | CN | 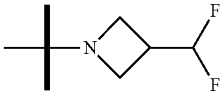 |
| CN | $CF_2H$ | 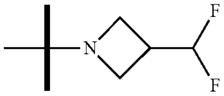 |
| CN | $CF_3$ | 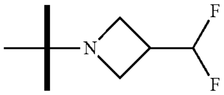 |
| CN | Cl | 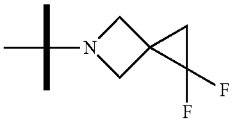 |
| CN | CN | 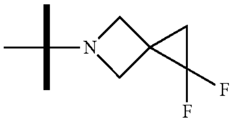 |

TABLE 1-continued
| Ra | Rb | Rc |
|---|---|---|
| CN | $CF_2H$ | 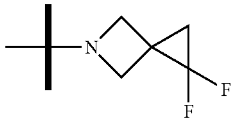 |
| CN | $CF_3$ | 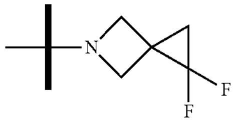 |
| CN | Cl | 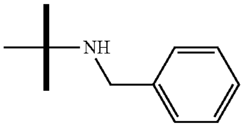 |
| CN | CN | 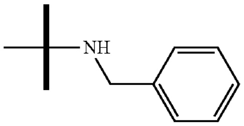 |
| CN | $CF_2H$ | 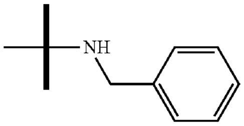 |
| CN | $CF_3$ | 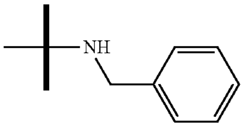 |
| CN | Cl | 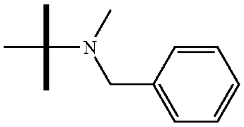 |
| CN | CN | 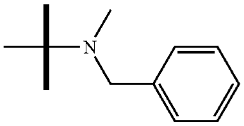 |
| CN | $CF_2H$ | 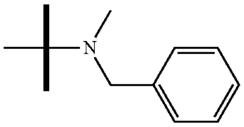 |
| CN | $CF_3$ | 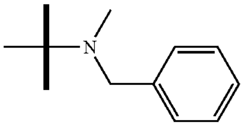 |
| CN | Cl | 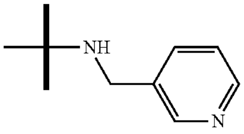 |
TABLE 1-continued
| Ra | Rb | Rc |
|---|---|---|
| CN | CN | 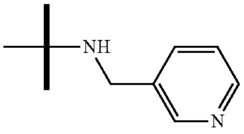 |
| CN | $CF_2H$ | 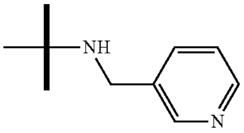 |
| CN | $CF_3$ | 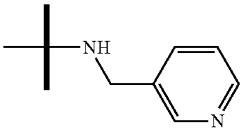 |
| CN | Cl | 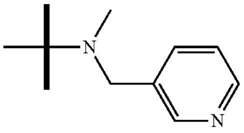 |
| CN | CN | 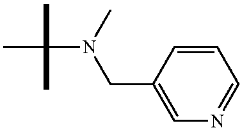 |
| CN | $CF_2H$ | 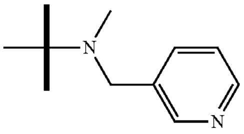 |
| CN | $CF_3$ | 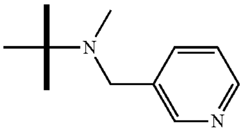 |
| CN | Cl | 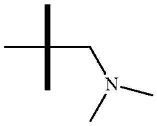 |
| CN | CN | 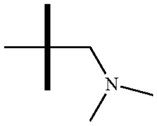 |
| CN | $CF_2H$ | 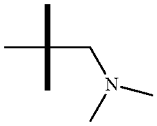 |
| CN | $CF_3$ | 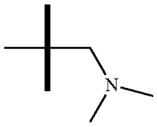 |

TABLE 1-continued
| Ra | Rb | Rc |
|---|---|---|
| CN | Cl | 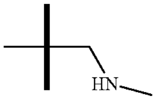 |
| CN | CN | 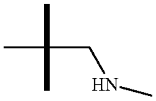 |
| CN | $CF_2H$ | 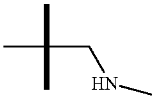 |
| CN | $CF_3$ | 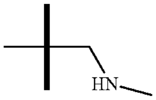 |
| CN | Cl | 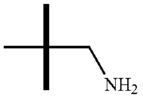 |
| CN | CN | 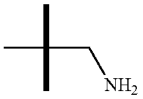 |
| CN | $CF_2H$ | 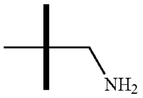 |
| CN | $CF_3$ | 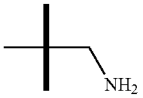 |
| CN | Cl | 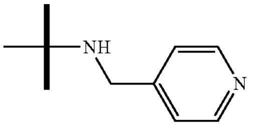 |
| CN | CN | 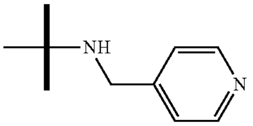 |
| CN | $CF_2H$ | 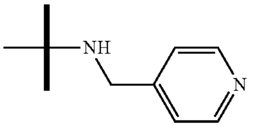 |
| CN | $CF_3$ | 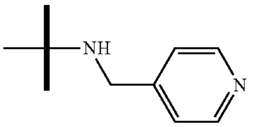 |
TABLE 1-continued
| Ra | Rb | Rc |
|---|---|---|
| CN | Cl | 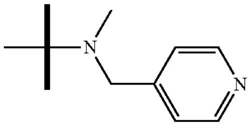 |
| CN | CN | 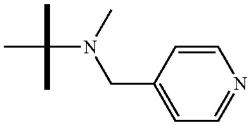 |
| CN | $CF_2H$ | 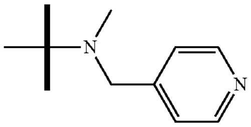 |
| CN | $CF_3$ | 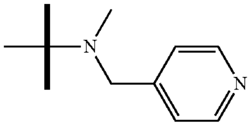 |
| CN | Cl | 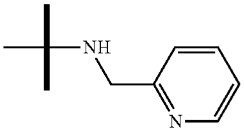 |
| CN | CN | 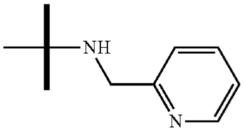 |
| CN | $CF_2H$ | 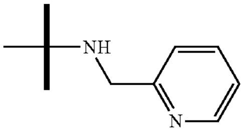 |
| CN | $CF_3$ | 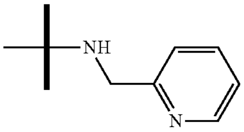 |
| CN | Cl | 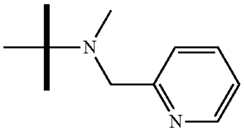 |
| CN | CN | 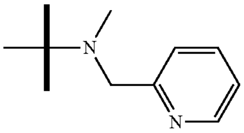 |
| CN | $CF_2H$ | 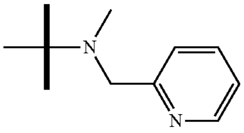 |

TABLE 1-continued
| Ra | Rb | Rc |
|---|---|---|
| CN | $CF_3$ | 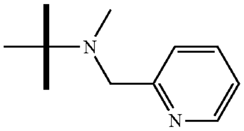 |
| CN | Cl | 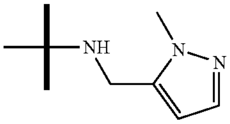 |
| CN | CN | 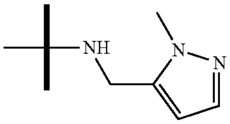 |
| CN | $CF_2H$ | 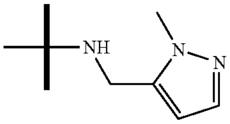 |
| CN | $CF_3$ | 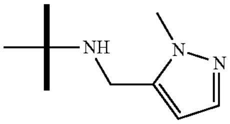 |
| CN | Cl | 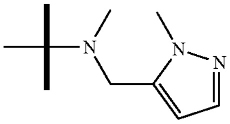 |
| CN | CN | 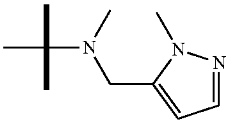 |
| CN | $CF_2H$ | 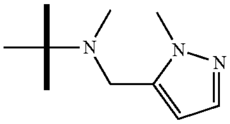 |
| CN | $CF_3$ | 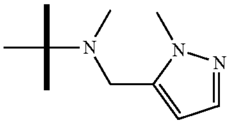 |
| CN | Cl | 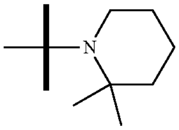 |
| CN | CN | 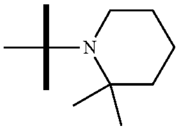 |
TABLE 1-continued
| Ra | Rb | Rc |
|---|---|---|
| CN | $CF_2H$ | 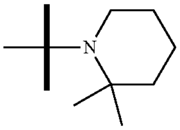 |
| CN | $CF_3$ | 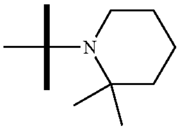 |
| CN | Cl | 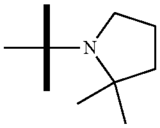 |
| CN | CN | 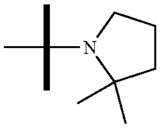 |
| CN | $CF_2H$ | 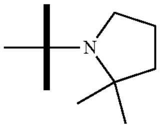 |
| CN | $CF_3$ | 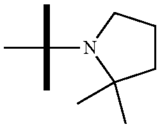 |
| CN | Cl | 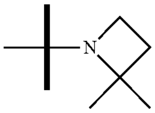 |
| CN | CN | 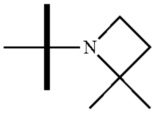 |
| CN | $CF_2H$ | 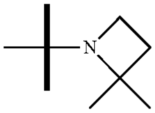 |
| CN | $CF_3$ | 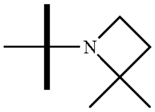 |
| CN | Cl | 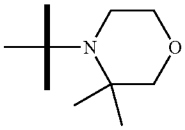 |

TABLE 1-continued
| Ra | Rb | Rc |
|---|---|---|
| CN | CN | 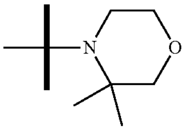 |
| CN | $CF_2H$ | 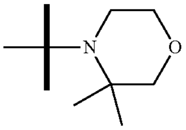 |
| CN | $CF_3$ | 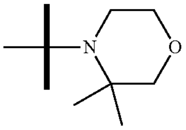 |
| CN | Cl | 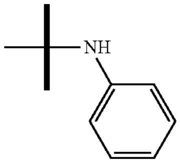 |
| CN | CN | 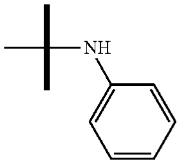 |
| CN | $CF_2H$ | 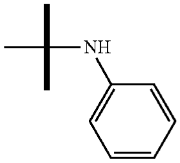 |
| CN | $CF_3$ | 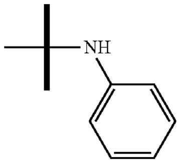 |
| CN | Cl | 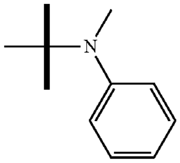 |
| CN | CN | 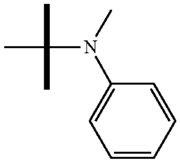 |
TABLE 1-continued
| Ra | Rb | Rc |
|---|---|---|
| CN | $CF_2H$ | 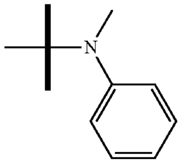 |
| CN | $CF_3$ | 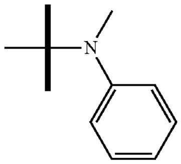 |
| CN | Cl | 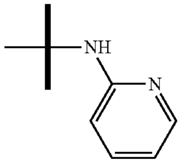 |
| CN | CN | 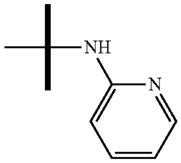 |
| CN | $CF_2H$ | 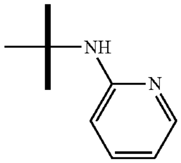 |
| CN | $CF_3$ | 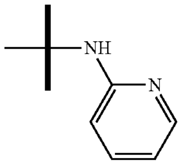 |
| CN | Cl | 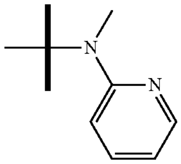 |
| CN | CN | 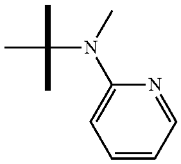 |
| CN | $CF_2H$ | 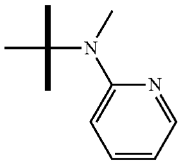 |

TABLE 1-continued
| Ra | Rb | Rc |
|---|---|---|
| CN | $CF_3$ | 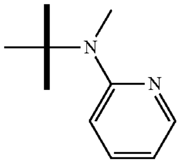 |
| CN | Cl | 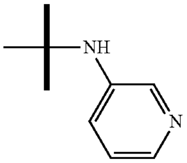 |
| CN | CN | 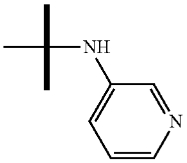 |
| CN | $CF_2H$ | 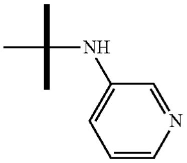 |
| CN | $CF_3$ | 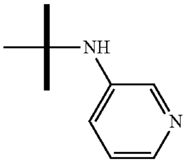 |
| CN | Cl | 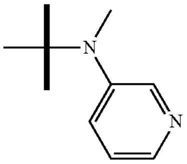 |
| CN | CN | 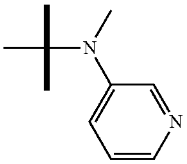 |
| CN | $CF_2H$ | 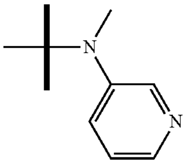 |
| CN | $CF_3$ | 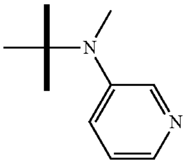 |
TABLE 1-continued
| Ra | Rb | Rc |
|---|---|---|
| CN | Cl | 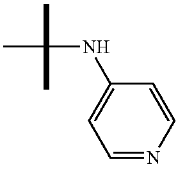 |
| CN | CN | 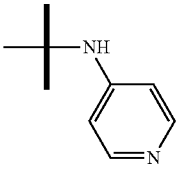 |
| CN | $CF_2H$ | 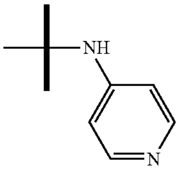 |
| CN | $CF_3$ | 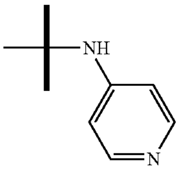 |
| CN | Cl | 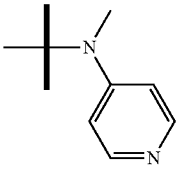 |
| CN | CN | 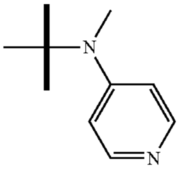 |
| CN | $CF_2H$ | 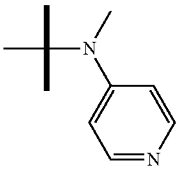 |
| CN | $CF_3$ | 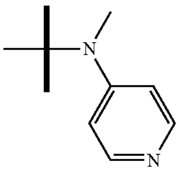 |
| CN | Cl | 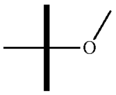 |

TABLE 1-continued
| Ra | Rb | Rc |
|---|---|---|
| CN | CN | 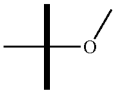 |
| CN | $CF_2H$ | 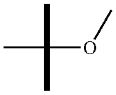 |
| CN | $CF_3$ | 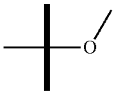 |
| CN | Cl | 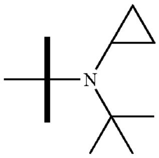 |
| CN | CN | 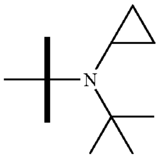 |
| CN | $CF_2H$ | 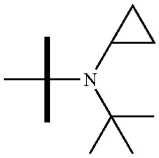 |
| CN | $CF_3$ | 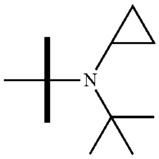 |
| CN | Cl | 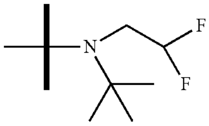 |
| CN | CN | 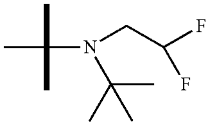 |
| CN | $CF_2H$ | 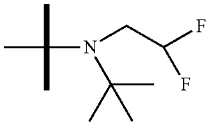 |
| CN | $CF_3$ | 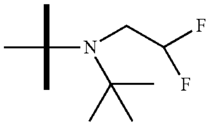 |
TABLE 1-continued
| Ra | Rb | Rc |
|---|---|---|
| CN | Cl | 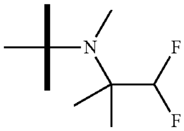 |
| CN | CN | 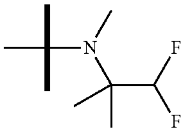 |
| CN | $CF_2H$ | 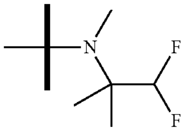 |
| CN | $CF_3$ | 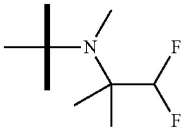 |
| CN | Cl | 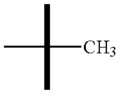 |
| CN | CN | 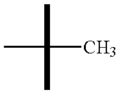 |
| CN | $CF_2H$ | 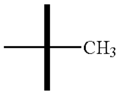 |
| CN | $CF_3$ | 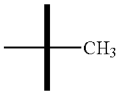 |
| CN | Cl | 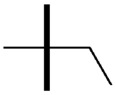 |
| CN | CN | 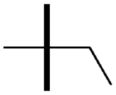 |
| CN | $CF_2H$ | 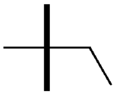 |
| CN | $CF_3$ | 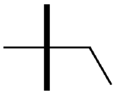 |
| CN | Cl | 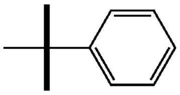 |

TABLE 1-continued
| Ra | Rb | Rc |
|---|---|---|
| CN | CN | 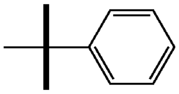 |
| CN | $CF_2H$ | 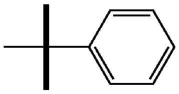 |
| CN | $CF_3$ | 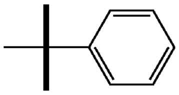 |
| CN | Cl | 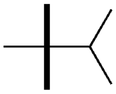 |
| CN | CN | 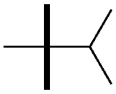 |
| CN | $CF_2H$ | 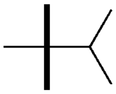 |
| CN | $CF_3$ | 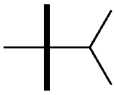 |
| CN | Cl | 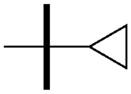 |
| CN | CN | 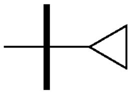 |
| CN | $CF_2H$ | 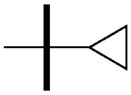 |
| CN | $CF_3$ | 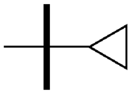 |
| CN | Cl | 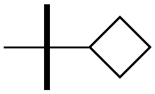 |
| CN | CN | 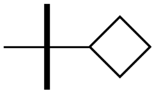 |
| CN | $CF_2H$ | 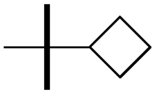 |
TABLE 1-continued
| Ra | Rb | Rc |
|---|---|---|
| CN | $CF_3$ | 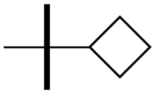 |
| CN | Cl | 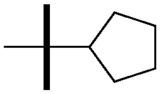 |
| CN | CN | 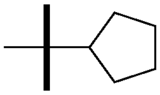 |
| CN | $CF_2H$ | 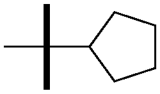 |
| CN | $CF_3$ | 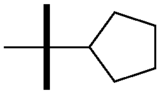 |
| CN | Cl | 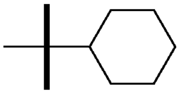 |
| CN | CN | 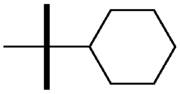 |
| CN | $CF_2H$ | 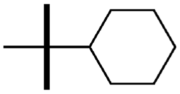 |
| CN | $CF_3$ | 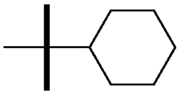 |
| CN | Cl | 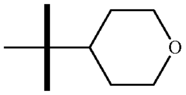 |
| CN | CN | 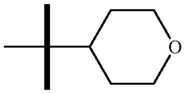 |
| CN | $CF_2H$ | 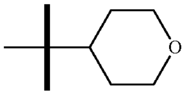 |
| CN | $CF_3$ | 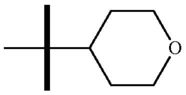 |
| CN | Cl | 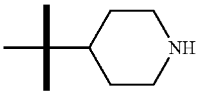 |

TABLE 1-continued
| Ra | Rb | Rc |
|---|---|---|
| CN | CN | 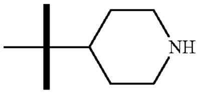 |
| CN | $CF_2H$ | 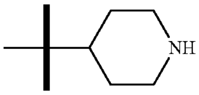 |
| CN | $CF_3$ | 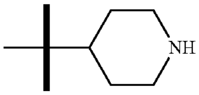 |
| CN | Cl | 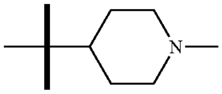 |
| CN | CN | 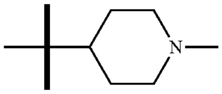 |
| CN | $CF_2H$ | 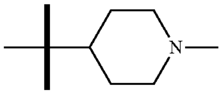 |
| CN | $CF_3$ | 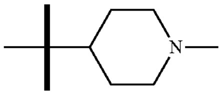 |
| CN | Cl | 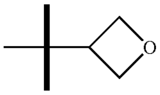 |
| CN | CN | 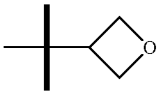 |
| CN | $CF_2H$ | 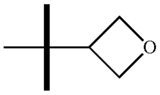 |
| CN | $CF_3$ | 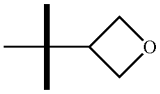 |
| CN | Cl | 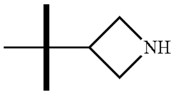 |
| CN | CN | 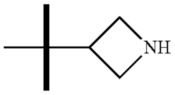 |
| CN | $CF_2H$ | 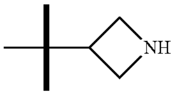 |
TABLE 1-continued
| Ra | Rb | Rc |
|---|---|---|
| CN | $CF_3$ | 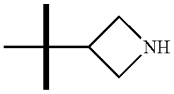 |
| CN | Cl | 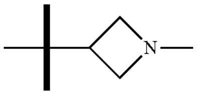 |
| CN | CN | 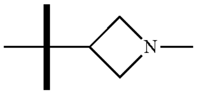 |
| CN | $CF_2H$ | 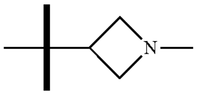 |
| CN | $CF_3$ | 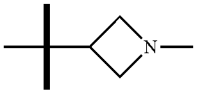 |
| CN | Cl | 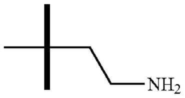 |
| CN | CN | 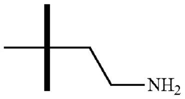 |
| CN | $CF_2H$ | 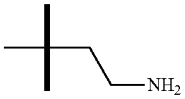 |
| CN | $CF_3$ | 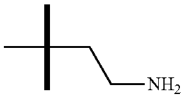 |
| CN | Cl | 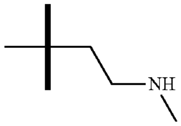 |
| CN | CN | 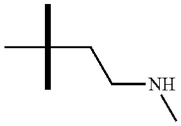 |
| CN | $CF_2H$ | 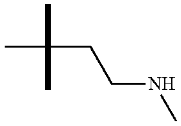 |
| CN | $CF_3$ | 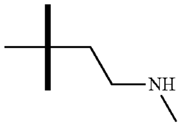 |

TABLE 1-continued
| Ra | Rb | Rc |
|---|---|---|
| CN | Cl | 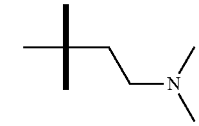 |
| CN | CN | 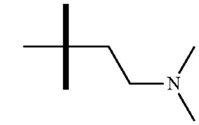 |
| CN | $CF_2H$ | 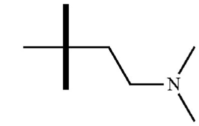 |
| CN | $CF_3$ | 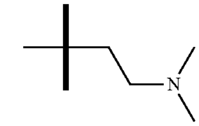 |
| CN | Cl | 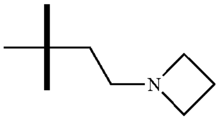 |
| CN | CN | 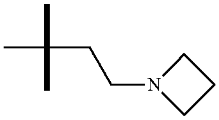 |
| CN | $CF_2H$ | 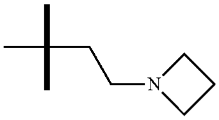 |
| CN | $CF_3$ | 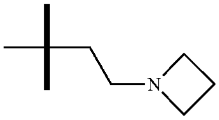 |
| CN | Cl | 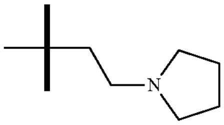 |
| CN | CN | 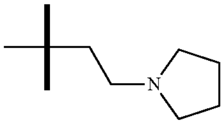 |
| CN | $CF_2H$ | 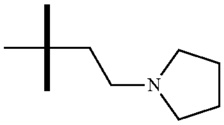 |
TABLE 1-continued
| Ra | Rb | Rc |
|---|---|---|
| CN | $CF_3$ | 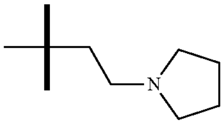 |
| CN | Cl | 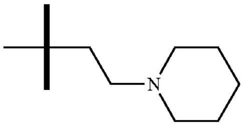 |
| CN | CN | 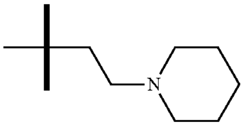 |
| CN | $CF_2H$ | 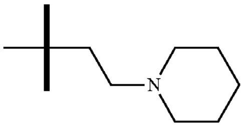 |
| CN | $CF_3$ | 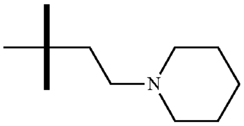 |
| CN | Cl | 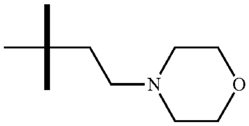 |
| CN | CN | 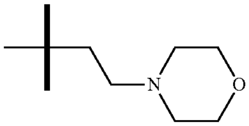 |
| CN | $CF_2H$ | 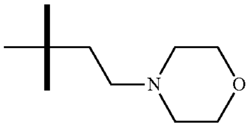 |
| CN | $CF_3$ | 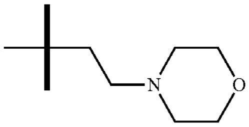 |
| CN | Cl | 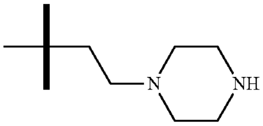 |
| CN | CN | 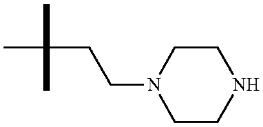 |

TABLE 1-continued
| Ra | Rb | Rc |
|---|---|---|
| CN | $CF_2H$ | 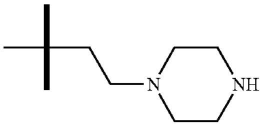 |
| CN | $CF_3$ | 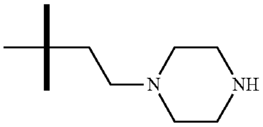 |
| CN | Cl | 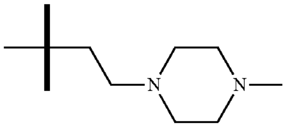 |
| CN | CN | 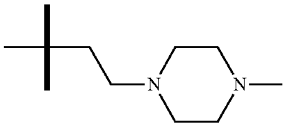 |
| CN | $CF_2H$ | 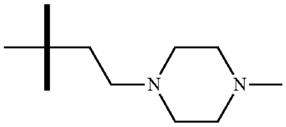 |
| CN | $CF_3$ | 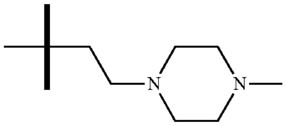 |
| OMe | Cl | 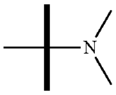 |
| OMe | CN | 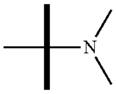 |
| OMe | $CF_2H$ | 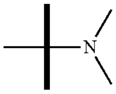 |
| OMe | $CF_3$ | 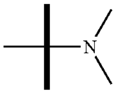 |
| OMe | Cl | 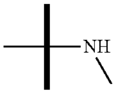 |
| OMe | CN | 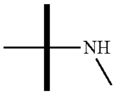 |
| OMe | $CF_2H$ | 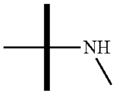 |
TABLE 1-continued
| Ra | Rb | Rc |
|---|---|---|
| OMe | $CF_3$ | 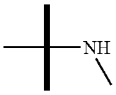 |
| OMe | Cl | 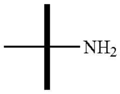 |
| OMe | CN | 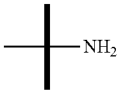 |
| OMe | $CF_2H$ | 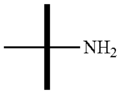 |
| OMe | $CF_3$ | 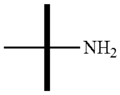 |
| OMe | Cl | 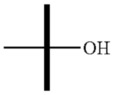 |
| OMe | CN | 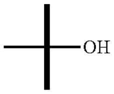 |
| OMe | $CF_2H$ | 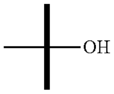 |
| OMe | $CF_3$ | 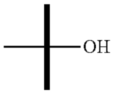 |
| OMe | Cl | 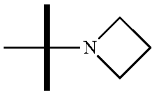 |
| OMe | CN | 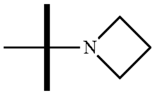 |
| OMe | $CF_2H$ | 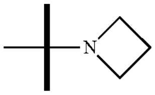 |
| OMe | $CF_3$ | 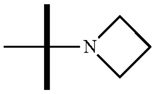 |
| OMe | Cl | 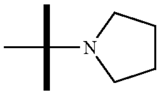 |

TABLE 1-continued
| Ra | Rb | Rc |
|---|---|---|
| OMe | CN | 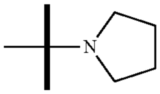 |
| OMe | $CF_2H$ | 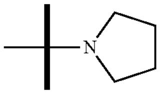 |
| OMe | $CF_3$ | 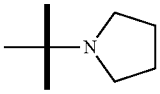 |
| OMe | Cl | 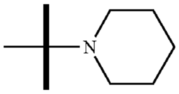 |
| OMe | CN | 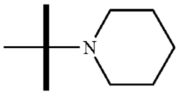 |
| OMe | $CF_2H$ | 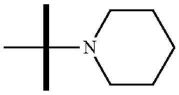 |
| OMe | $CF_3$ | 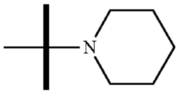 |
| OMe | Cl | 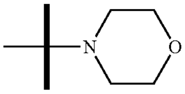 |
| OMe | CN | 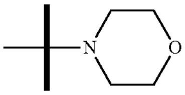 |
| OMe | $CF_2H$ | 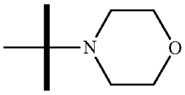 |
| OMe | $CF_3$ | 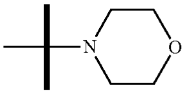 |
| OMe | Cl | 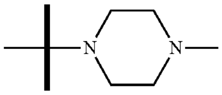 |
| OMe | CN | 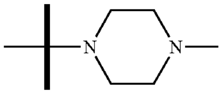 |
| OMe | $CF_2H$ | 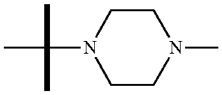 |
TABLE 1-continued
| Ra | Rb | Rc |
|---|---|---|
| OMe | $CF_3$ | 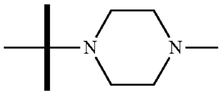 |
| OMe | Cl | 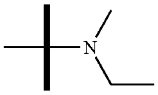 |
| OMe | CN | 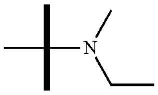 |
| OMe | $CF_2H$ | 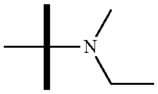 |
| OMe | $CF_3$ | 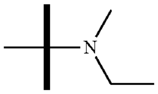 |
| OMe | Cl | 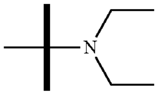 |
| OMe | CN | 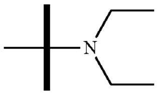 |
| OMe | $CF_2H$ | 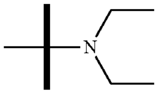 |
| OMe | $CF_3$ | 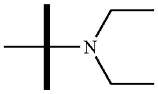 |
| OMe | Cl | 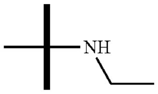 |
| OMe | CN | 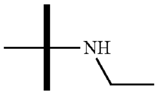 |
| OMe | $CF_2H$ | 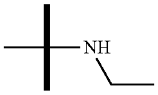 |
| OMe | $CF_3$ | 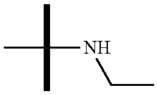 |
| OMe | Cl | 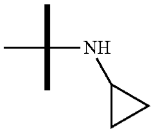 |

TABLE 1-continued
| Ra | Rb | Rc |
|---|---|---|
| OMe | CN | 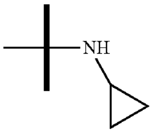 |
| OMe | $CF_2H$ | 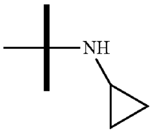 |
| OMe | $CF_3$ | 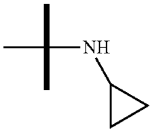 |
| OMe | Cl | 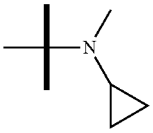 |
| OMe | CN | 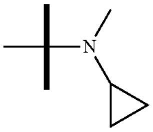 |
| OMe | $CF_2H$ | 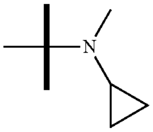 |
| OMe | $CF_3$ | 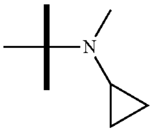 |
| OMe | Cl | 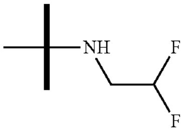 |
| OMe | CN | 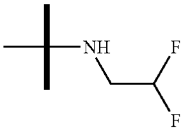 |
| OMe | $CF_2H$ | 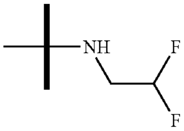 |
| OMe | $CF_3$ | 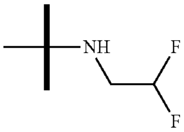 |
TABLE 1-continued
| Ra | Rb | Rc |
|---|---|---|
| OMe | Cl | 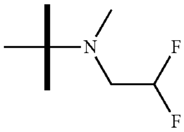 |
| OMe | CN | 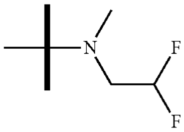 |
| OMe | $CF_2H$ | 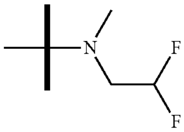 |
| OMe | $CF_3$ | 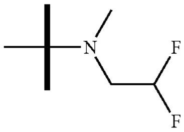 |
| OMe | Cl | 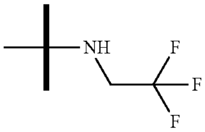 |
| OMe | CN | 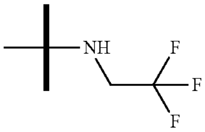 |
| OMe | $CF_2H$ | 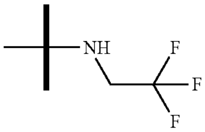 |
| OMe | $CF_3$ | 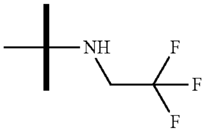 |
| OMe | Cl | 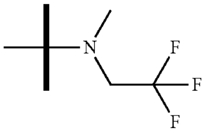 |
| OMe | CN | 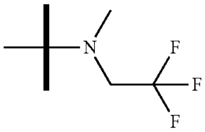 |

TABLE 1-continued
| Ra | Rb | Rc |
|---|---|---|
| OMe | $CF_2H$ | 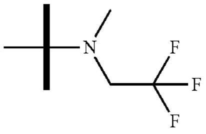 |
| OMe | $CF_3$ | 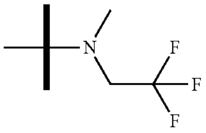 |
| OMe | Cl | 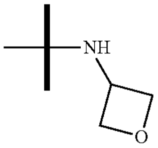 |
| OMe | CN | 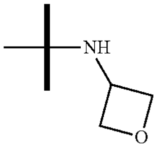 |
| OMe | $CF_2H$ | 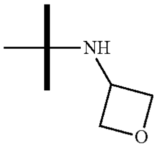 |
| OMe | $CF_3$ | 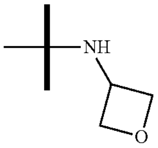 |
| OMe | Cl | 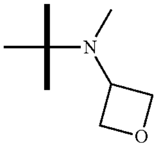 |
| OMe | CN | 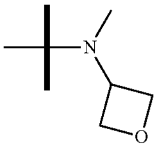 |
| OMe | $CF_2H$ | 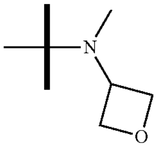 |
| OMe | $CF_3$ | 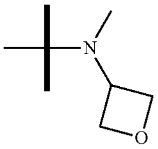 |
TABLE 1-continued
| Ra | Rb | Rc |
|---|---|---|
| OMe | Cl | 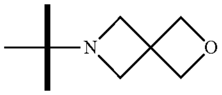 |
| OMe | CN | 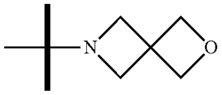 |
| OMe | $CF_2H$ | 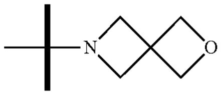 |
| OMe | $CF_3$ | 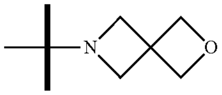 |
| OMe | Cl | 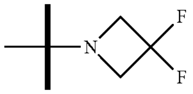 |
| OMe | CN | 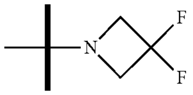 |
| OMe | $CF_2H$ | 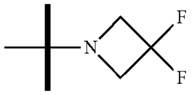 |
| OMe | $CF_3$ | 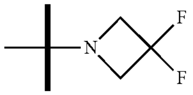 |
| OMe | Cl | 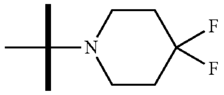 |
| OMe | CN | 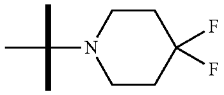 |
| OMe | $CF_2H$ | 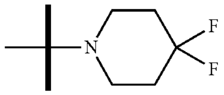 |
| OMe | $CF_3$ | 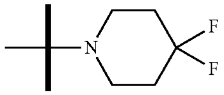 |
| OMe | Cl | 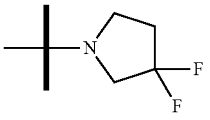 |
| OMe | CN | 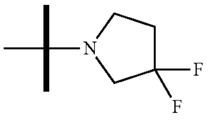 |

TABLE 1-continued
| Ra | Rb | Rc |
|---|---|---|
| OMe | $CF_2H$ | 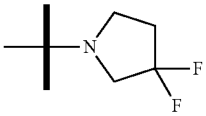 |
| OMe | $CF_3$ | 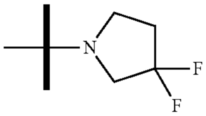 |
| OMe | Cl | 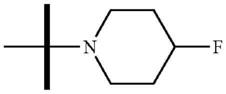 |
| OMe | CN | 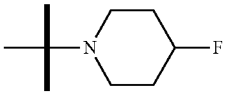 |
| OMe | $CF_2H$ | 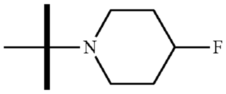 |
| OMe | $CF_3$ | 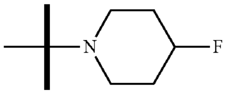 |
| OMe | Cl | 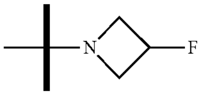 |
| OMe | CN | 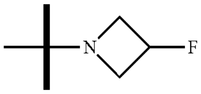 |
| OMe | $CF_2H$ | 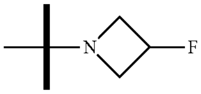 |
| OMe | $CF_3$ | 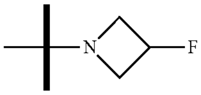 |
| OMe | Cl | 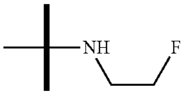 |
| OMe | CN | 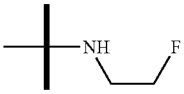 |
| OMe | $CF_2H$ | 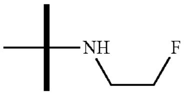 |
| OMe | $CF_3$ | 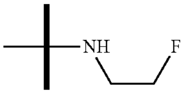 |
TABLE 1-continued
| Ra | Rb | Rc |
|---|---|---|
| OMe | Cl | 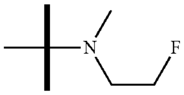 |
| OMe | CN | 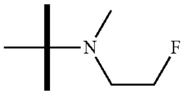 |
| OMe | $CF_2H$ | 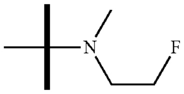 |
| OMe | $CF_3$ | 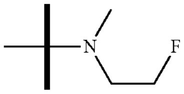 |
| OMe | Cl | 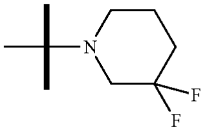 |
| OMe | CN | 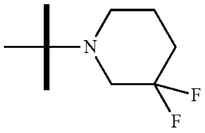 |
| OMe | $CF_2H$ | 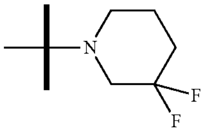 |
| OMe | $CF_3$ | 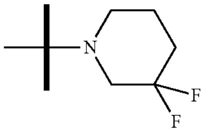 |
| OMe | Cl | 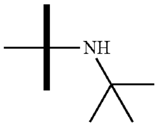 |
| OMe | CN | 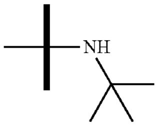 |
| OMe | $CF_2H$ | 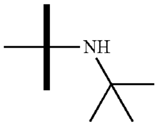 |
| OMe | $CF_3$ | 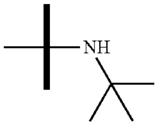 |

TABLE 1-continued
| Ra | Rb | Rc |
|---|---|---|
| OMe | Cl | 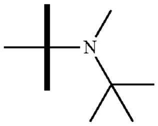 |
| OMe | CN | 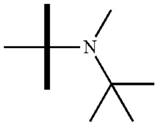 |
| OMe | $CF_2H$ | 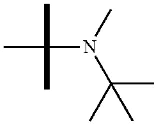 |
| OMe | $CF_3$ | 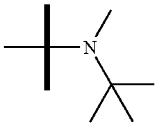 |
| OMe | Cl | 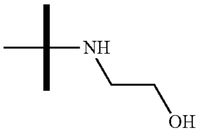 |
| OMe | CN | 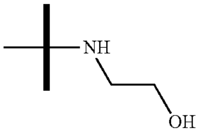 |
| OMe | $CF_2H$ | 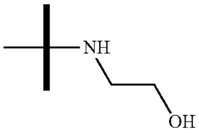 |
| OMe | $CF_3$ | 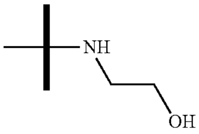 |
| OMe | Cl | 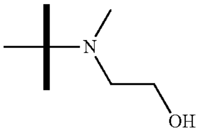 |
| OMe | CN | 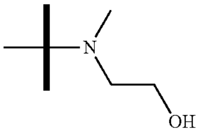 |
| OMe | $CF_2H$ | 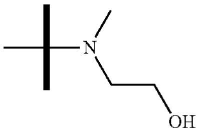 |
TABLE 1-continued
| Ra | Rb | Rc |
|---|---|---|
| OMe | $CF_3$ | 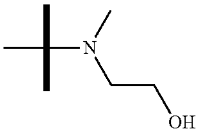 |
| OMe | Cl | 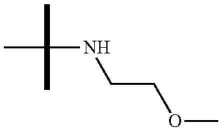 |
| OMe | CN | 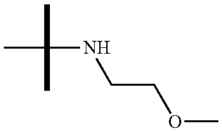 |
| OMe | $CF_2H$ | 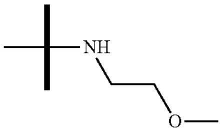 |
| OMe | $CF_3$ | 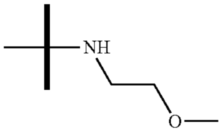 |
| OMe | Cl | 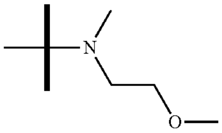 |
| OMe | CN | 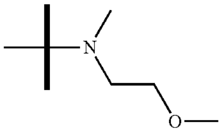 |
| OMe | $CF_2H$ | 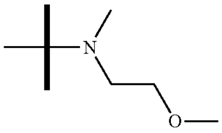 |
| OMe | $CF_3$ | 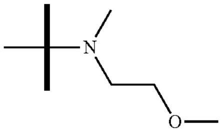 |
| OMe | Cl | 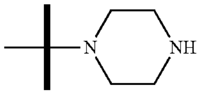 |
| OMe | CN | 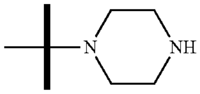 |

TABLE 1-continued
| Ra | Rb | Rc |
| --- | --- | --- |
| OMe | $CF_2H$ | 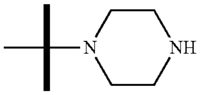 |
| OMe | $CF_3$ | 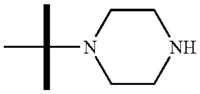 |
| OMe | Cl | 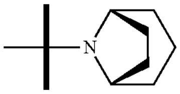 |
| OMe | CN | 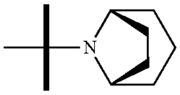 |
| OMe | $CF_2H$ | 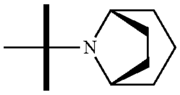 |
| OMe | $CF_3$ | 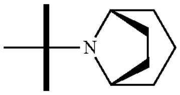 |
| OMe | Cl | 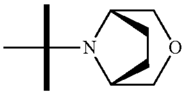 |
| OMe | CN | 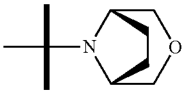 |
| OMe | $CF_2H$ | 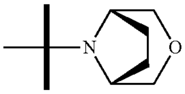 |
| OMe | $CF_3$ | 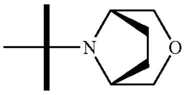 |
| OMe | Cl | 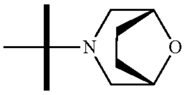 |
| OMe | CN | 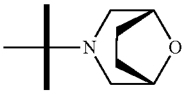 |
| OMe | $CF_2H$ | 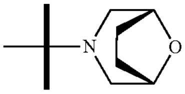 |
| OMe | $CF_3$ | 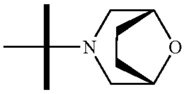 |
TABLE 1-continued
| Ra | Rb | Rc |
| --- | --- | --- |
| OMe | Cl | 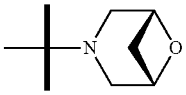 |
| OMe | CN | 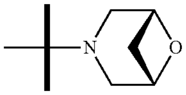 |
| OMe | $CF_2H$ | 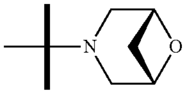 |
| OMe | $CF_3$ | 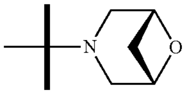 |
| OMe | Cl | 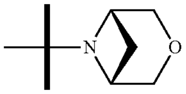 |
| OMe | CN | 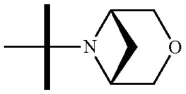 |
| OMe | $CF_2H$ | 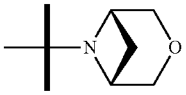 |
| OMe | $CF_3$ | 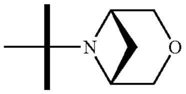 |
| OMe | Cl | 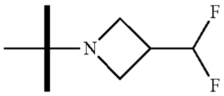 |
| OMe | CN | 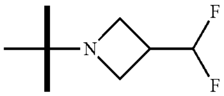 |
| OMe | $CF_2H$ | 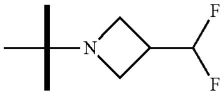 |
| OMe | $CF_3$ | 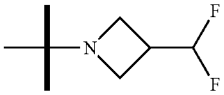 |
| OMe | Cl | 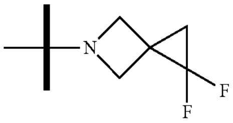 |
| OMe | CN | 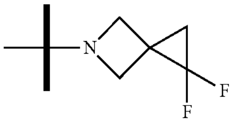 |

TABLE 1-continued
| Ra | Rb | Rc |
|---|---|---|
| OMe | $CF_2H$ | 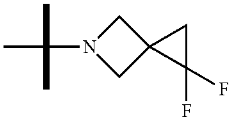 |
| OMe | $CF_3$ | 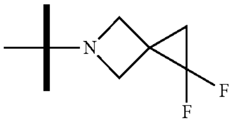 |
| OMe | Cl | 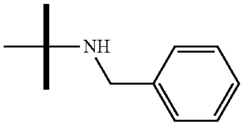 |
| OMe | CN | 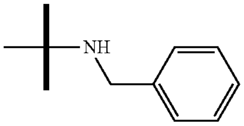 |
| OMe | $CF_2H$ | 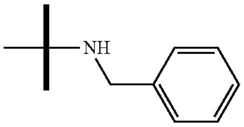 |
| OMe | $CF_3$ | 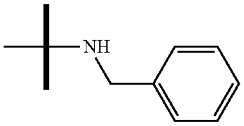 |
| OMe | Cl | 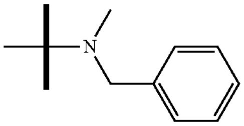 |
| OMe | CN | 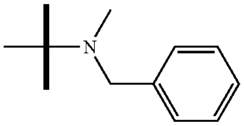 |
| OMe | $CF_2H$ | 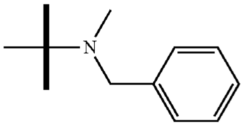 |
| OMe | $CF_3$ | 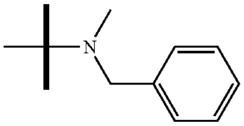 |
| OMe | Cl | 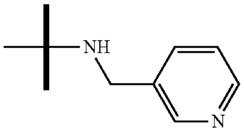 |
TABLE 1-continued
| Ra | Rb | Rc |
|---|---|---|
| OMe | CN | 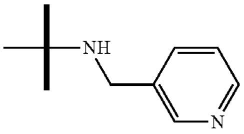 |
| OMe | $CF_2H$ | 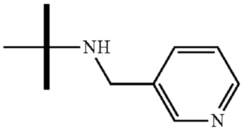 |
| OMe | $CF_3$ | 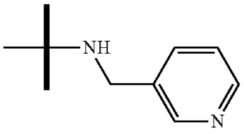 |
| OMe | Cl | 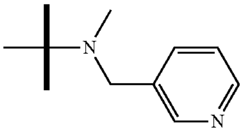 |
| OMe | CN | 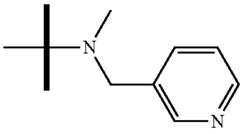 |
| OMe | $CF_2H$ | 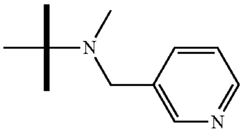 |
| OMe | $CF_3$ | 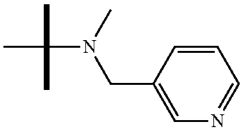 |
| OMe | Cl | 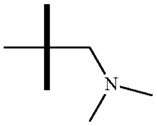 |
| OMe | CN | 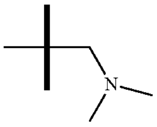 |
| OMe | $CF_2H$ | 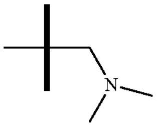 |
| OMe | $CF_3$ | 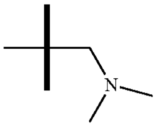 |

TABLE 1-continued
| Ra | Rb | Rc |
|---|---|---|
| OMe | Cl | 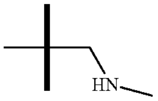 |
| OMe | CN | 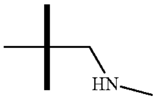 |
| OMe | $CF_2H$ | 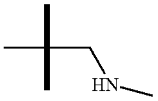 |
| OMe | $CF_3$ | 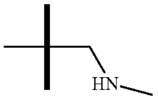 |
| OMe | Cl | 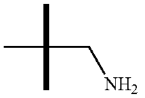 |
| OMe | CN | 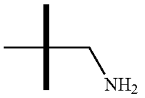 |
| OMe | $CF_2H$ | 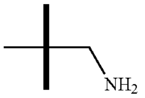 |
| OMe | $CF_3$ | 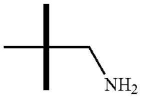 |
| OMe | Cl | 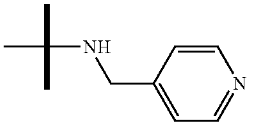 |
| OMe | CN | 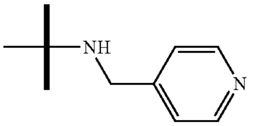 |
| OMe | $CF_2H$ | 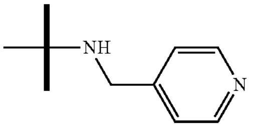 |
| OMe | $CF_3$ | 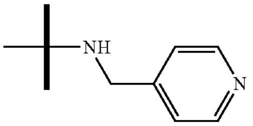 |
TABLE 1-continued
| Ra | Rb | Rc |
|---|---|---|
| OMe | Cl | 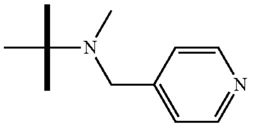 |
| OMe | CN | 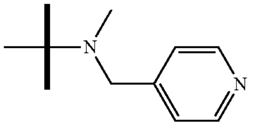 |
| OMe | $CF_2H$ | 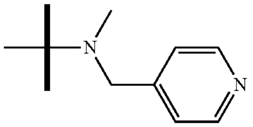 |
| OMe | $CF_3$ | 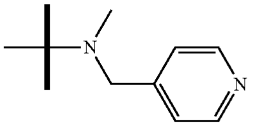 |
| OMe | Cl | 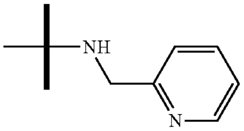 |
| OMe | CN | 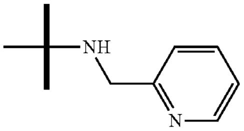 |
| OMe | $CF_2H$ | 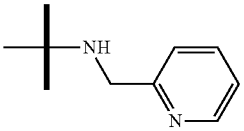 |
| OMe | $CF_3$ | 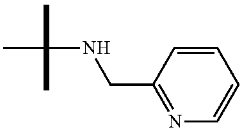 |
| OMe | Cl | 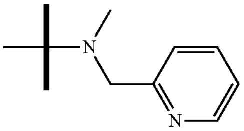 |
| OMe | CN | 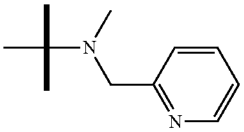 |
| OMe | $CF_2H$ | 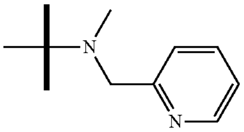 |

TABLE 1-continued
| Ra | Rb | Rc |
|---|---|---|
| OMe | $CF_3$ | 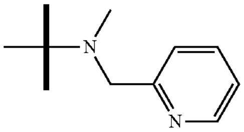 |
| OMe | Cl | 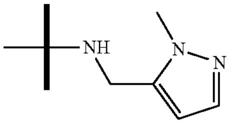 |
| OMe | CN | 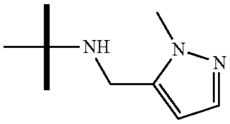 |
| OMe | $CF_2H$ | 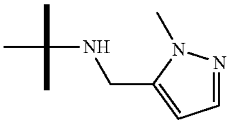 |
| OMe | $CF_3$ | 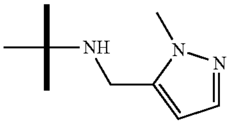 |
| OMe | Cl | 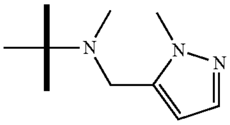 |
| OMe | CN | 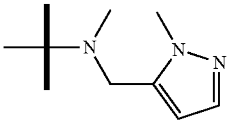 |
| OMe | $CF_2H$ | 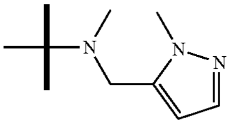 |
| OMe | $CF_3$ | 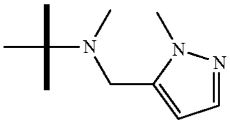 |
| OMe | Cl | 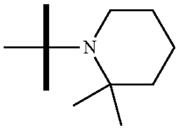 |
| OMe | CN | 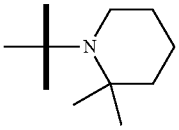 |
TABLE 1-continued
| Ra | Rb | Rc |
|---|---|---|
| OMe | $CF_2H$ | 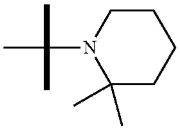 |
| OMe | $CF_3$ | 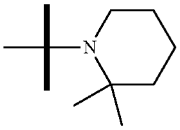 |
| OMe | Cl | 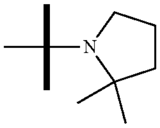 |
| OMe | CN | 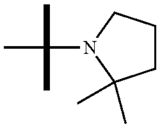 |
| OMe | $CF_2H$ | 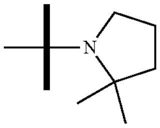 |
| OMe | $CF_3$ | 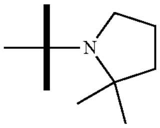 |
| OMe | Cl | 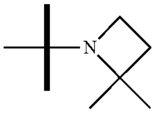 |
| OMe | CN | 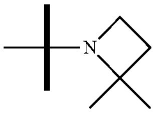 |
| OMe | $CF_2H$ | 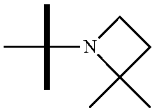 |
| OMe | $CF_3$ | 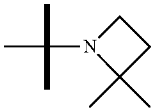 |
| OMe | Cl | 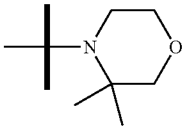 |

TABLE 1-continued
| Ra | Rb | Rc |
|---|---|---|
| OMe | CN | 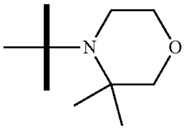 |
| OMe | $CF_2H$ | 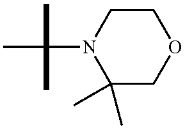 |
| OMe | $CF_3$ | 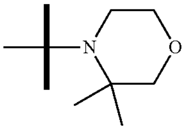 |
| OMe | Cl | 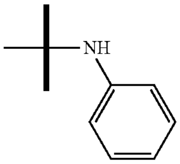 |
| OMe | CN | 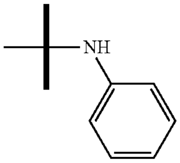 |
| OMe | $CF_2H$ | 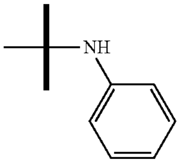 |
| OMe | $CF_3$ | 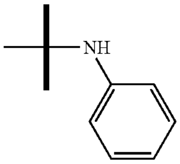 |
| OMe | Cl | 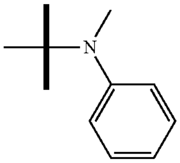 |
| OMe | CN | 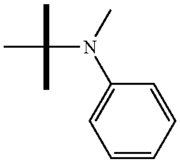 |
TABLE 1-continued
| Ra | Rb | Rc |
|---|---|---|
| OMe | $CF_2H$ | 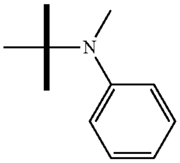 |
| OMe | $CF_3$ | 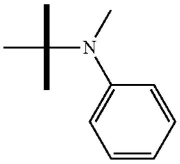 |
| OMe | Cl | 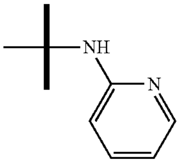 |
| OMe | CN | 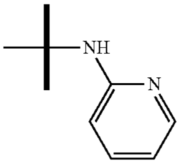 |
| OMe | $CF_2H$ | 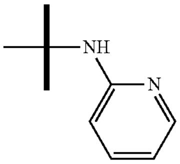 |
| OMe | $CF_3$ | 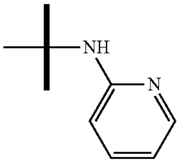 |
| OMe | Cl | 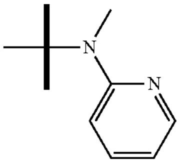 |
| OMe | CN | 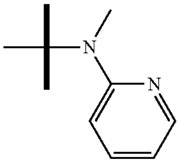 |
| OMe | $CF_2H$ | 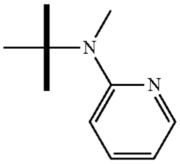 |

TABLE 1-continued
| Ra | Rb | Rc |
|---|---|---|
| OMe | $CF_3$ | 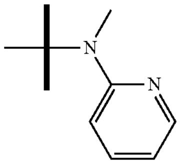 |
| OMe | Cl | 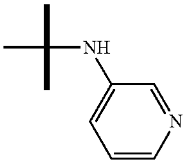 |
| OMe | CN | 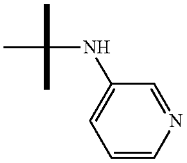 |
| OMe | $CF_2H$ | 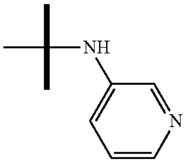 |
| OMe | $CF_3$ | 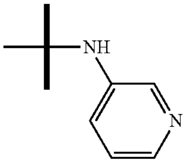 |
| OMe | Cl | 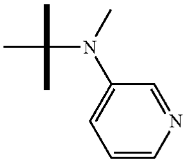 |
| OMe | CN | 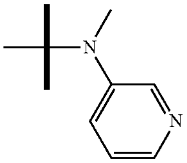 |
| OMe | $CF_2H$ | 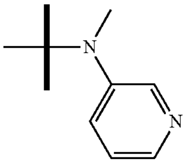 |
| OMe | $CF_3$ | 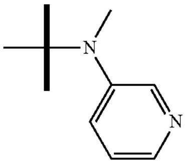 |
TABLE 1-continued
| Ra | Rb | Rc |
|---|---|---|
| OMe | Cl | 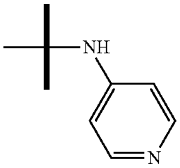 |
| OMe | CN | 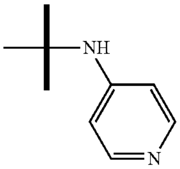 |
| OMe | $CF_2H$ | 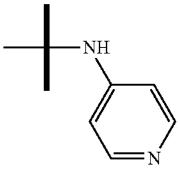 |
| OMe | $CF_3$ | 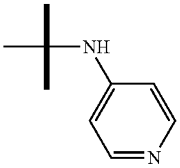 |
| OMe | Cl | 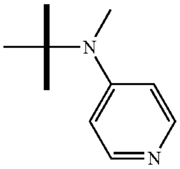 |
| OMe | CN | 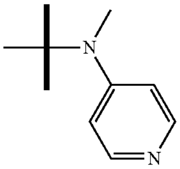 |
| OMe | $CF_2H$ | 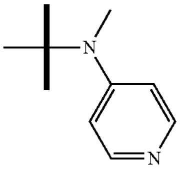 |
| OMe | $CF_3$ | 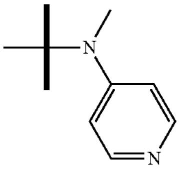 |
| OMe | Cl | 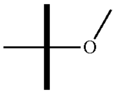 |

TABLE 1-continued
| Ra | Rb | Rc |
|---|---|---|
| OMe | CN | 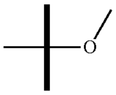 |
| OMe | $CF_2H$ | 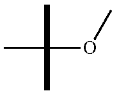 |
| OMe | $CF_3$ | 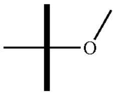 |
| OMe | Cl | 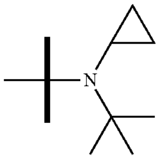 |
| OMe | CN | 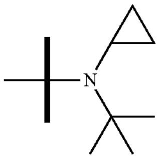 |
| OMe | $CF_2H$ | 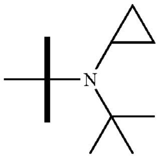 |
| OMe | $CF_3$ | 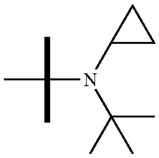 |
| OMe | Cl | 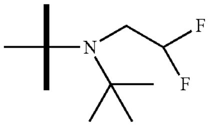 |
| OMe | CN | 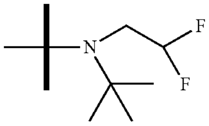 |
| OMe | $CF_2H$ | 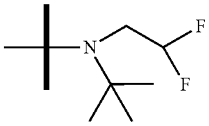 |
| OMe | $CF_3$ | 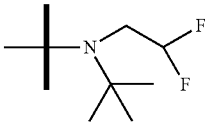 |
TABLE 1-continued
| Ra | Rb | Rc |
|---|---|---|
| OMe | Cl | 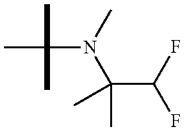 |
| OMe | CN | 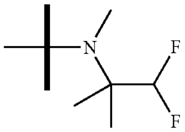 |
| OMe | $CF_2H$ | 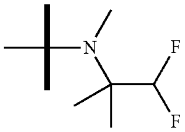 |
| OMe | $CF_3$ | 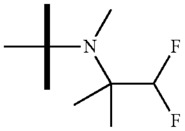 |
| OMe | Cl | 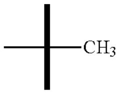 |
| OMe | CN | 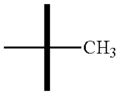 |
| OMe | $CF_2H$ | 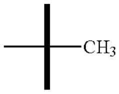 |
| OMe | $CF_3$ | 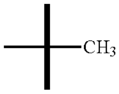 |
| OMe | Cl | 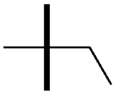 |
| OMe | CN | 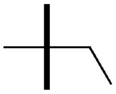 |
| OMe | $CF_2H$ | 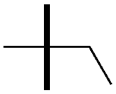 |
| OMe | $CF_3$ | 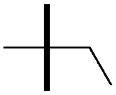 |
| OMe | Cl | 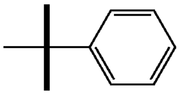 |

TABLE 1-continued
| Ra | Rb | Rc |
|---|---|---|
| OMe | CN | 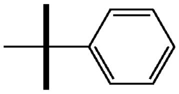 |
| OMe | $CF_2H$ | 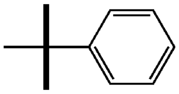 |
| OMe | $CF_3$ | 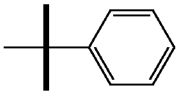 |
| OMe | Cl | 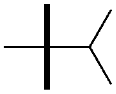 |
| OMe | CN | 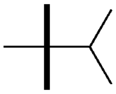 |
| OMe | $CF_2H$ | 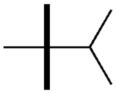 |
| OMe | $CF_3$ | 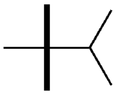 |
| OMe | Cl | 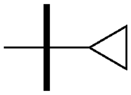 |
| OMe | CN | 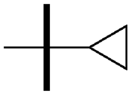 |
| OMe | $CF_2H$ | 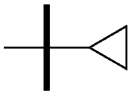 |
| OMe | $CF_3$ | 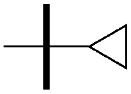 |
| OMe | Cl | 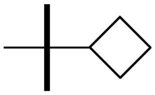 |
| OMe | CN | 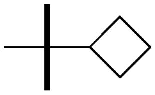 |
| OMe | $CF_2H$ | 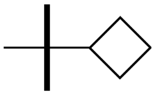 |
TABLE 1-continued
| Ra | Rb | Rc |
|---|---|---|
| OMe | $CF_3$ | 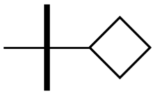 |
| OMe | Cl | 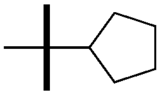 |
| OMe | CN | 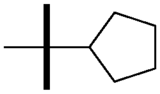 |
| OMe | $CF_2H$ | 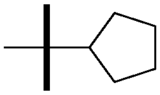 |
| OMe | $CF_3$ | 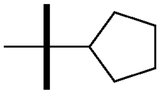 |
| OMe | Cl | 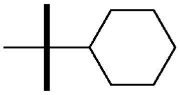 |
| OMe | CN | 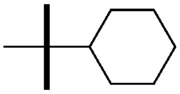 |
| OMe | $CF_2H$ | 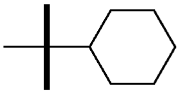 |
| OMe | $CF_3$ | 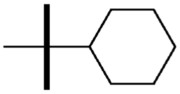 |
| OMe | Cl | 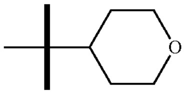 |
| OMe | CN | 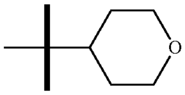 |
| OMe | $CF_2H$ | 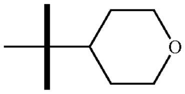 |
| OMe | $CF_3$ | 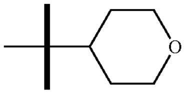 |
| OMe | Cl | 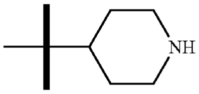 |

TABLE 1-continued
| Ra | Rb | Rc |
|---|---|---|
| OMe | CN | 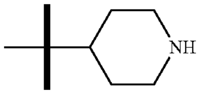 |
| OMe | $CF_2H$ | 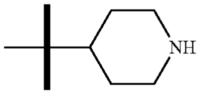 |
| OMe | $CF_3$ | 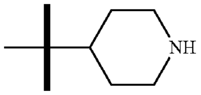 |
| OMe | Cl | 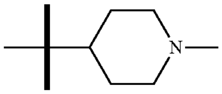 |
| OMe | CN | 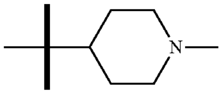 |
| OMe | $CF_2H$ | 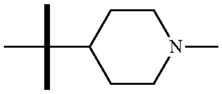 |
| OMe | $CF_3$ | 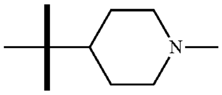 |
| OMe | Cl | 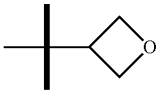 |
| OMe | CN | 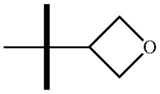 |
| OMe | $CF_2H$ | 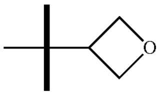 |
| OMe | $CF_3$ | 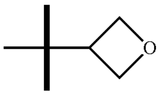 |
| OMe | Cl | 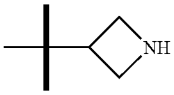 |
| OMe | CN | 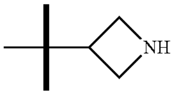 |
| OMe | $CF_2H$ | 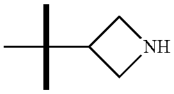 |
TABLE 1-continued
| Ra | Rb | Rc |
|---|---|---|
| OMe | $CF_3$ | 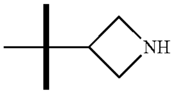 |
| OMe | Cl | 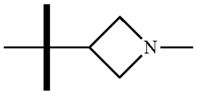 |
| OMe | CN | 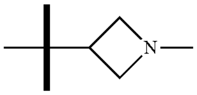 |
| OMe | $CF_2H$ | 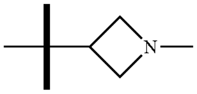 |
| OMe | $CF_3$ | 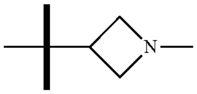 |
| OMe | Cl | 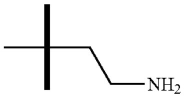 |
| OMe | CN | 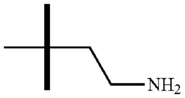 |
| OMe | $CF_2H$ | 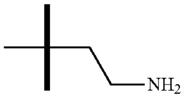 |
| OMe | $CF_3$ | 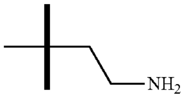 |
| OMe | Cl | 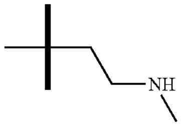 |
| OMe | CN | 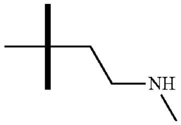 |
| OMe | $CF_2H$ | 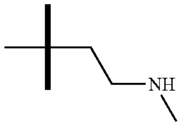 |
| OMe | $CF_3$ | 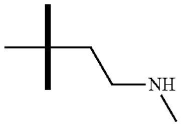 |

TABLE 1-continued
| Ra | Rb | Rc |
|---|---|---|
| OMe | Cl | 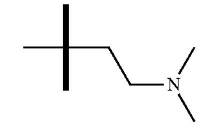 |
| OMe | CN | 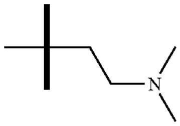 |
| OMe | $CF_2H$ | 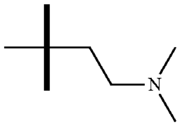 |
| OMe | $CF_3$ | 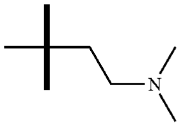 |
| OMe | Cl | 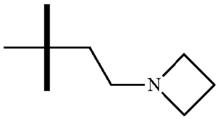 |
| OMe | CN | 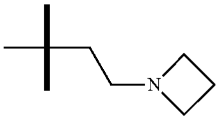 |
| OMe | $CF_2H$ | 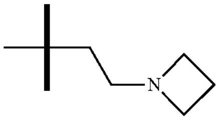 |
| OMe | $CF_3$ | 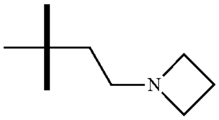 |
| OMe | Cl | 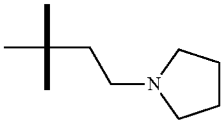 |
| OMe | CN | 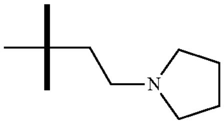 |
| OMe | $CF_2H$ | 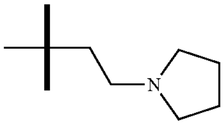 |
TABLE 1-continued
| Ra | Rb | Rc |
|---|---|---|
| OMe | $CF_3$ | 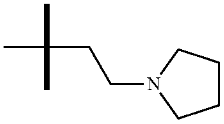 |
| OMe | Cl | 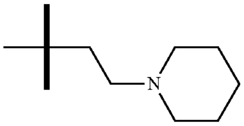 |
| OMe | CN | 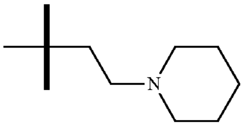 |
| OMe | $CF_2H$ | 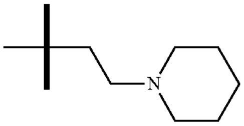 |
| OMe | $CF_3$ | 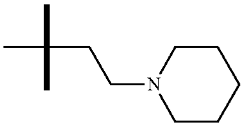 |
| OMe | Cl | 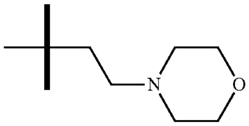 |
| OMe | CN | 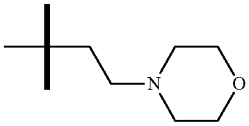 |
| OMe | $CF_2H$ | 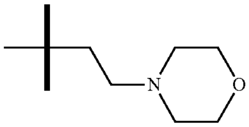 |
| OMe | $CF_3$ | 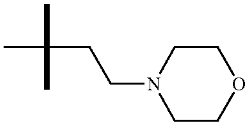 |
| OMe | Cl | 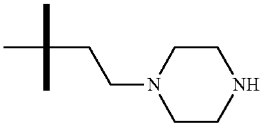 |
| OMe | CN | 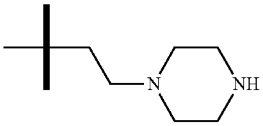 |

TABLE 1-continued
| Ra | Rb | Rc |
|---|---|---|
| OMe | $CF_2H$ | 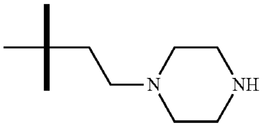 |
| OMe | $CF_3$ | 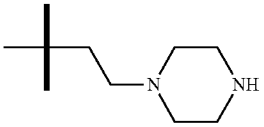 |
| OMe | Cl | 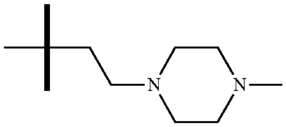 |
| OMe | CN | 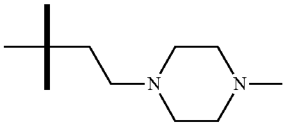 |
| OMe | $CF_2H$ | 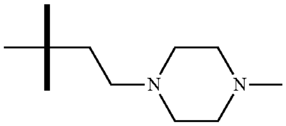 |
| OMe | $CF_3$ | 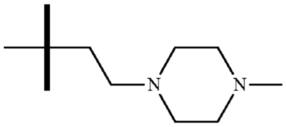 |
| H | Cl | 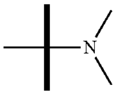 |
| H | CN | 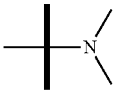 |
| H | $CF_2H$ | 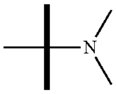 |
| H | $CF_3$ | 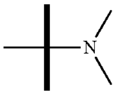 |
| H | Cl | 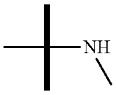 |
| H | CN | 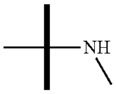 |
| H | $CF_2H$ | 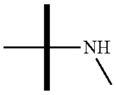 |
TABLE 1-continued
| Ra | Rb | Rc |
|---|---|---|
| H | $CF_3$ | 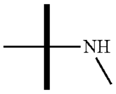 |
| H | Cl | 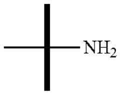 |
| H | CN | 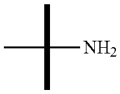 |
| H | $CF_2H$ | 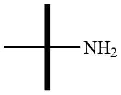 |
| H | $CF_3$ | 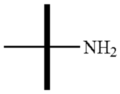 |
| H | Cl | 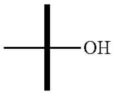 |
| H | CN | 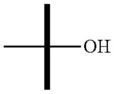 |
| H | $CF_2H$ | 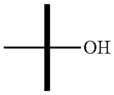 |
| H | $CF_3$ | 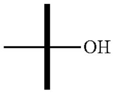 |
| H | Cl | 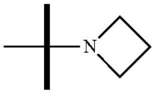 |
| H | CN | 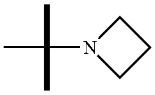 |
| H | $CF_2H$ | 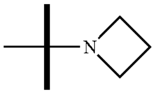 |
| H | $CF_3$ | 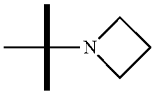 |
| H | Cl | 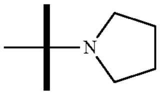 |

TABLE 1-continued
| Ra | Rb | Rc |
|---|---|---|
| H | CN | 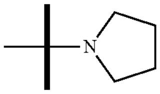 |
| H | $CF_2H$ | 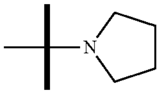 |
| H | $CF_3$ | 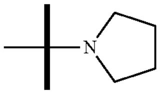 |
| H | Cl | 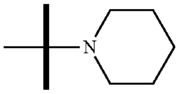 |
| H | CN | 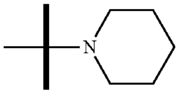 |
| H | $CF_2H$ | 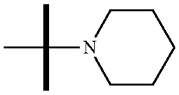 |
| H | $CF_3$ | 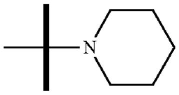 |
| H | Cl | 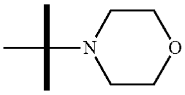 |
| H | CN | 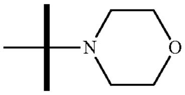 |
| H | $CF_2H$ | 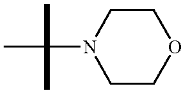 |
| H | $CF_3$ | 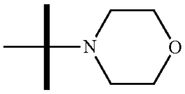 |
| H | Cl | 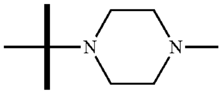 |
| H | CN | 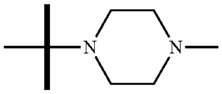 |
| H | $CF_2H$ | 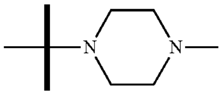 |
TABLE 1-continued
| Ra | Rb | Rc |
|---|---|---|
| H | $CF_3$ | 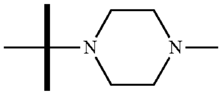 |
| H | Cl | 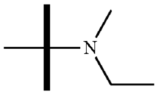 |
| H | CN | 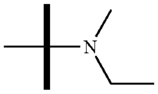 |
| H | $CF_2H$ | 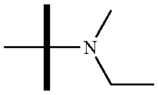 |
| H | $CF_3$ | 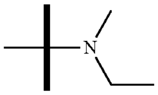 |
| H | Cl | 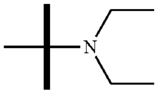 |
| H | CN | 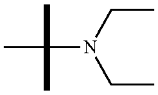 |
| H | $CF_2H$ | 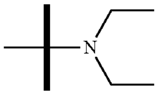 |
| H | $CF_3$ | 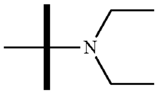 |
| H | Cl | 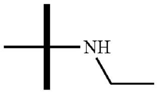 |
| H | CN | 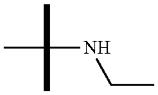 |
| H | $CF_2H$ | 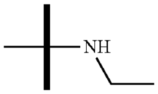 |
| H | $CF_3$ | 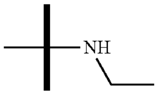 |
| H | Cl | 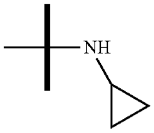 |

TABLE 1-continued
| Ra | Rb | Rc |
|---|---|---|
| H | CN | 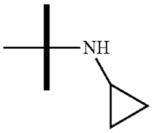 |
| H | $CF_2H$ | 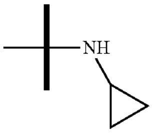 |
| H | $CF_3$ | 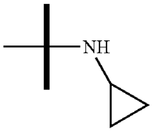 |
| H | Cl | 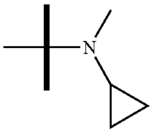 |
| H | CN | 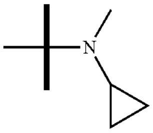 |
| H | $CF_2H$ | 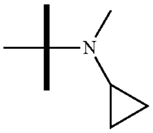 |
| H | $CF_3$ | 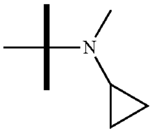 |
| H | Cl | 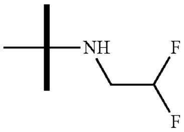 |
| H | CN | 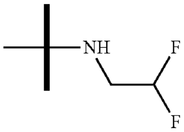 |
| H | $CF_2H$ | 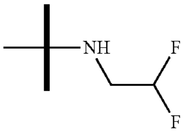 |
| H | $CF_3$ | 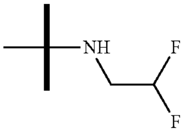 |
TABLE 1-continued
| Ra | Rb | Rc |
|---|---|---|
| H | Cl | 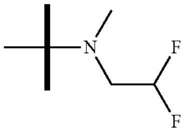 |
| H | CN | 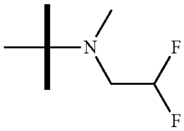 |
| H | $CF_2H$ | 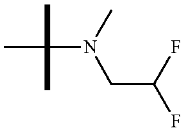 |
| H | $CF_3$ | 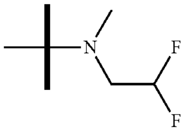 |
| H | Cl | 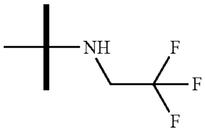 |
| H | CN | 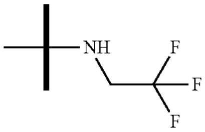 |
| H | $CF_2H$ | 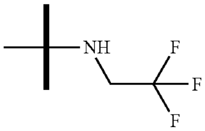 |
| H | $CF_3$ | 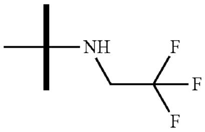 |
| H | Cl | 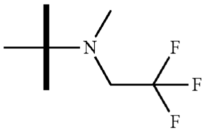 |
| H | CN | 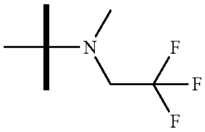 |

TABLE 1-continued
| Ra | Rb | Rc |
|---|---|---|
| H | $CF_2H$ | 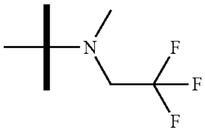 |
| H | $CF_3$ | 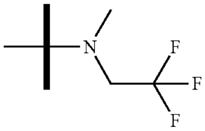 |
| H | Cl | 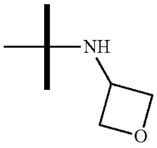 |
| H | CN | 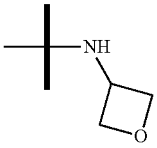 |
| H | $CF_2H$ | 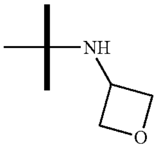 |
| H | $CF_3$ | 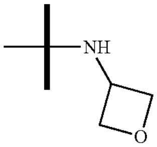 |
| H | Cl | 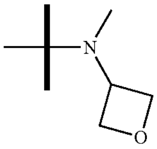 |
| H | CN | 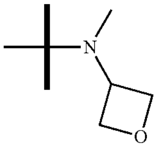 |
| H | $CF_2H$ | 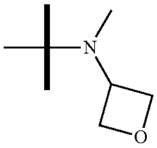 |
| H | $CF_3$ | 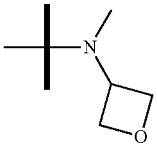 |
TABLE 1-continued
| Ra | Rb | Rc |
|---|---|---|
| H | Cl | 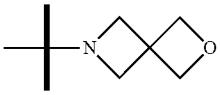 |
| H | CN | 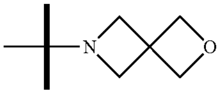 |
| H | $CF_2H$ | 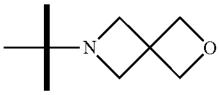 |
| H | $CF_3$ | 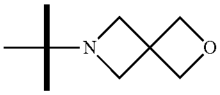 |
| H | Cl | 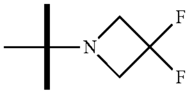 |
| H | CN | 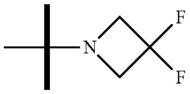 |
| H | $CF_2H$ | 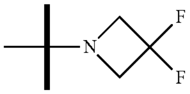 |
| H | $CF_3$ | 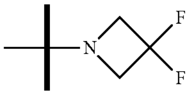 |
| H | Cl | 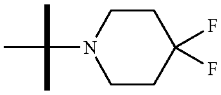 |
| H | CN | 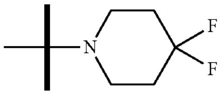 |
| H | $CF_2H$ | 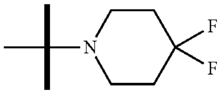 |
| H | $CF_3$ | 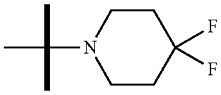 |
| H | Cl | 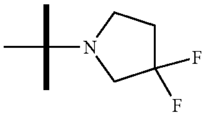 |
| H | CN | 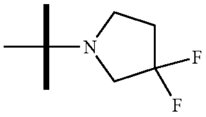 |

TABLE 1-continued
| Ra | Rb | Rc |
| --- | --- | --- |
| H | $CF_2H$ | 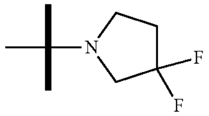 |
| H | $CF_3$ | 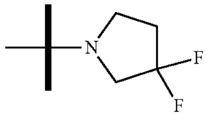 |
| H | Cl | 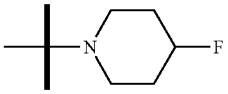 |
| H | CN | 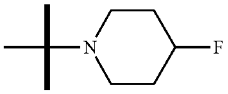 |
| H | $CF_2H$ | 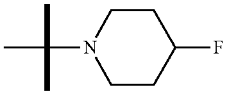 |
| H | $CF_3$ | 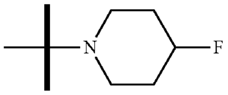 |
| H | Cl | 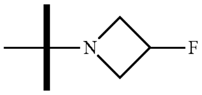 |
| H | CN | 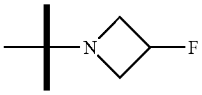 |
| H | $CF_2H$ | 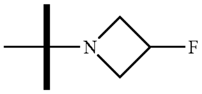 |
| H | $CF_3$ | 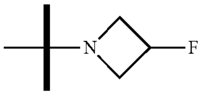 |
| H | Cl | 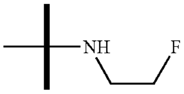 |
| H | CN | 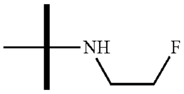 |
| H | $CF_2H$ | 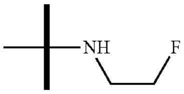 |
| H | $CF_3$ | 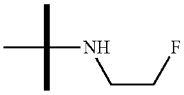 |
TABLE 1-continued
| Ra | Rb | Rc |
| --- | --- | --- |
| H | Cl | 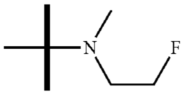 |
| H | CN | 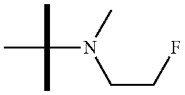 |
| H | $CF_2H$ | 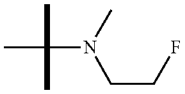 |
| H | $CF_3$ | 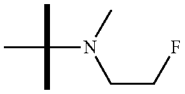 |
| H | Cl | 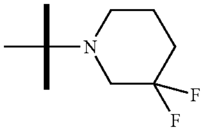 |
| H | CN | 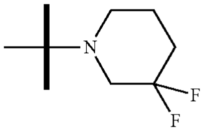 |
| H | $CF_2H$ | 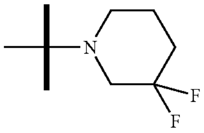 |
| H | $CF_3$ | 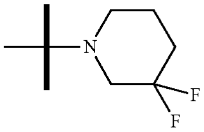 |
| H | Cl | 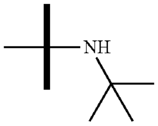 |
| H | CN | 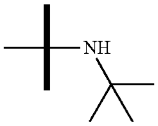 |
| H | $CF_2H$ | 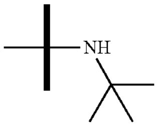 |
| H | $CF_3$ | 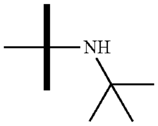 |

TABLE 1-continued
| Ra | Rb | Rc |
|---|---|---|
| H | Cl | 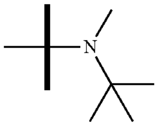 |
| H | CN | 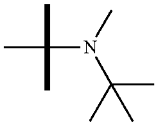 |
| H | $CF_2H$ | 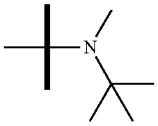 |
| H | $CF_3$ | 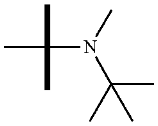 |
| H | Cl | 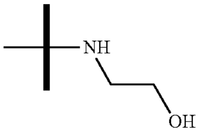 |
| H | CN | 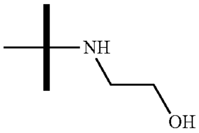 |
| H | $CF_2H$ | 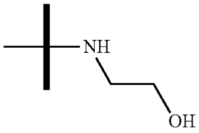 |
| H | $CF_3$ | 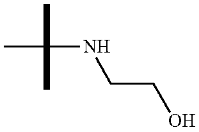 |
| H | Cl | 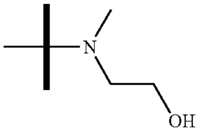 |
| H | CN | 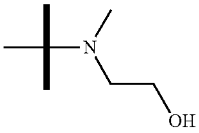 |
| H | $CF_2H$ | 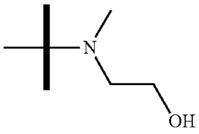 |
| H | $CF_3$ | 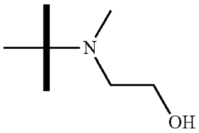 |
| H | Cl | 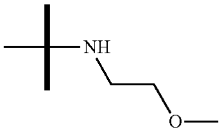 |
| H | CN | 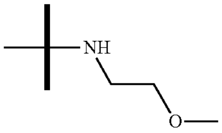 |
| H | $CF_2H$ | 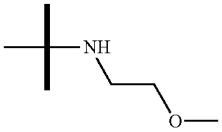 |
| H | $CF_3$ | 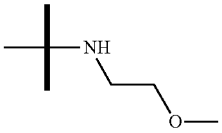 |
| H | Cl | 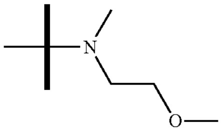 |
| H | CN | 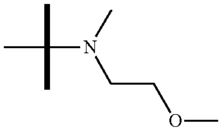 |
| H | $CF_2H$ | 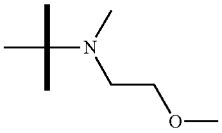 |
| H | $CF_3$ | 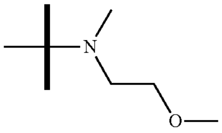 |
| H | Cl | 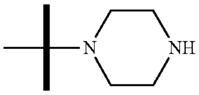 |
| H | CN | 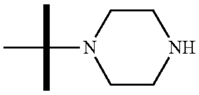 |

TABLE 1-continued
| Ra | Rb | Rc |
|---|---|---|
| H | $CF_2H$ | 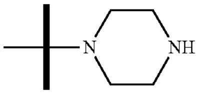 |
| H | $CF_3$ | 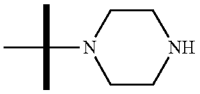 |
| H | Cl | 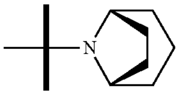 |
| H | CN | 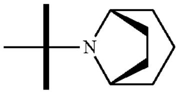 |
| H | $CF_2H$ | 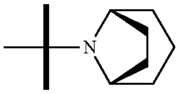 |
| H | $CF_3$ | 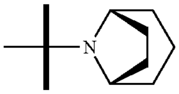 |
| H | Cl | 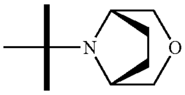 |
| H | CN | 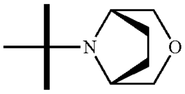 |
| H | $CF_2H$ | 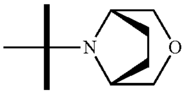 |
| H | $CF_3$ | 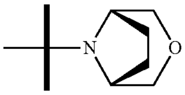 |
| H | Cl | 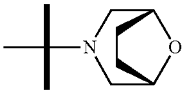 |
| H | CN | 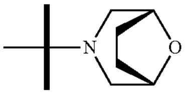 |
| H | $CF_2H$ | 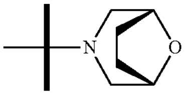 |
| H | $CF_3$ | 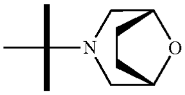 |
TABLE 1-continued
| Ra | Rb | Rc |
|---|---|---|
| H | Cl | 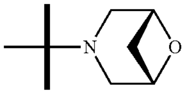 |
| H | CN | 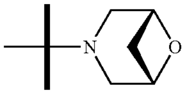 |
| H | $CF_2H$ | 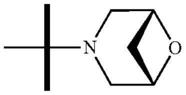 |
| H | $CF_3$ | 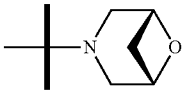 |
| H | Cl | 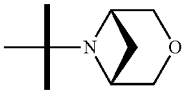 |
| H | CN | 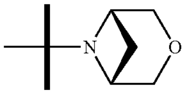 |
| H | $CF_2H$ | 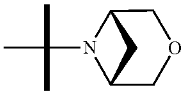 |
| H | $CF_3$ | 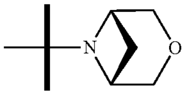 |
| H | Cl | 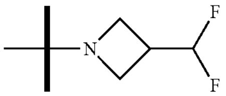 |
| H | CN | 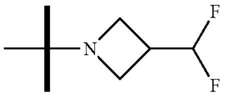 |
| H | $CF_2H$ | 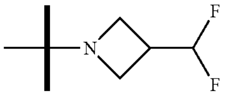 |
| H | $CF_3$ | 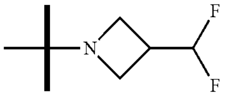 |
| H | Cl | 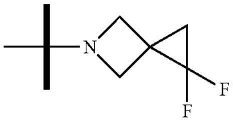 |
| H | CN | 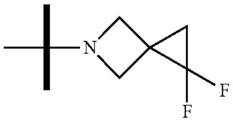 |

TABLE 1-continued
| Ra | Rb | Rc |
|---|---|---|
| H | $CF_2H$ | 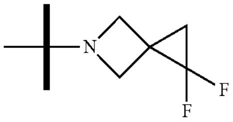 |
| H | $CF_3$ | 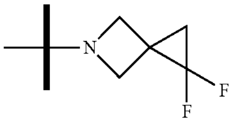 |
| H | Cl | 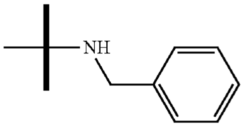 |
| H | CN | 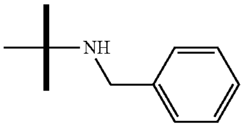 |
| H | $CF_2H$ | 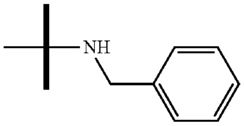 |
| H | $CF_3$ | 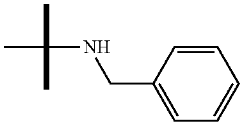 |
| H | Cl | 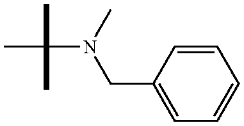 |
| H | CN | 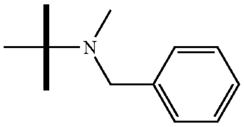 |
| H | $CF_2H$ | 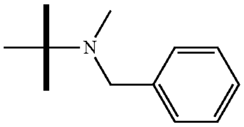 |
| H | $CF_3$ | 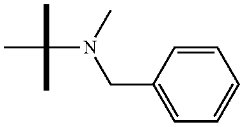 |
| H | Cl | 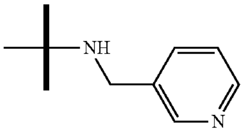 |
TABLE 1-continued
| Ra | Rb | Rc |
|---|---|---|
| H | CN | 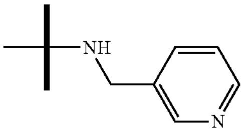 |
| H | $CF_2H$ | 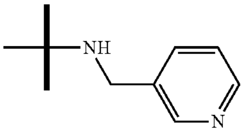 |
| H | $CF_3$ | 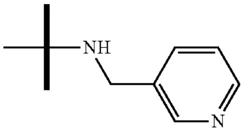 |
| H | Cl | 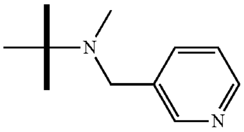 |
| H | CN | 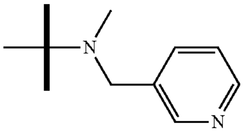 |
| H | $CF_2H$ | 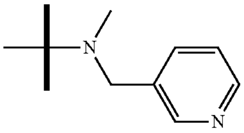 |
| H | $CF_3$ | 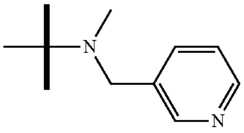 |
| H | Cl | 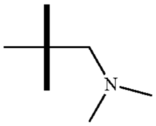 |
| H | CN | 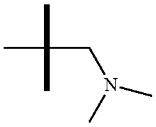 |
| H | $CF_2H$ | 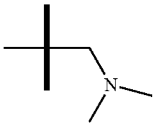 |
| H | $CF_3$ | 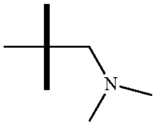 |

TABLE 1-continued
| Ra | Rb | Rc |
|---|---|---|
| H | Cl | 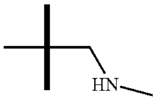 |
| H | CN | 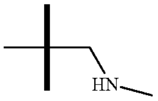 |
| H | $CF_2H$ | 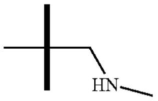 |
| H | $CF_3$ | 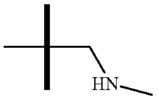 |
| H | Cl | 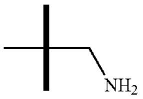 |
| H | CN | 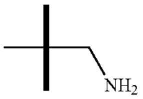 |
| H | $CF_2H$ | 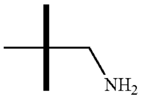 |
| H | $CF_3$ | 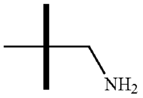 |
| H | Cl | 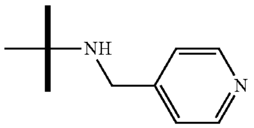 |
| H | CN | 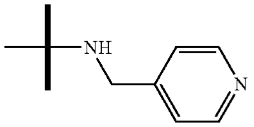 |
| H | $CF_2H$ | 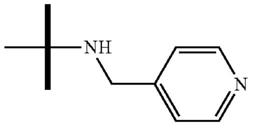 |
| H | $CF_3$ | 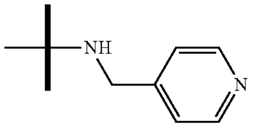 |
TABLE 1-continued
| Ra | Rb | Rc |
|---|---|---|
| H | Cl | 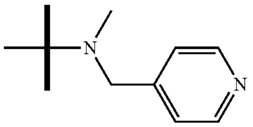 |
| H | CN | 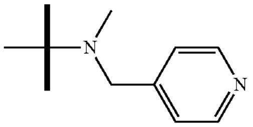 |
| H | $CF_2H$ | 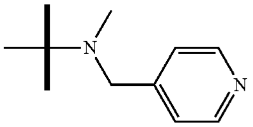 |
| H | $CF_3$ | 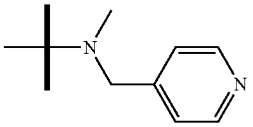 |
| H | Cl | 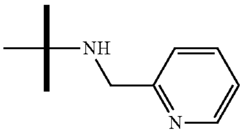 |
| H | CN | 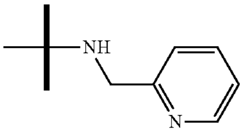 |
| H | $CF_2H$ | 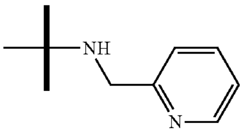 |
| H | $CF_3$ | 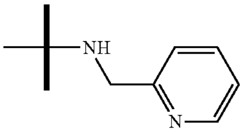 |
| H | Cl | 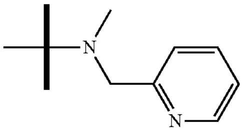 |
| H | CN | 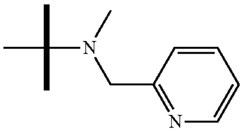 |
| H | $CF_2H$ | 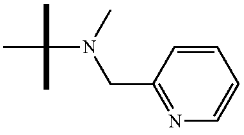 |

TABLE 1-continued
| Ra | Rb | Rc |
|---|---|---|
| H | $CF_3$ | 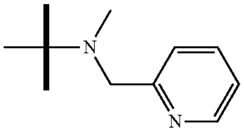 |
| H | Cl | 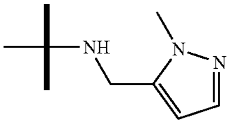 |
| H | CN | 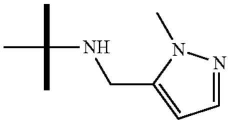 |
| H | $CF_2H$ | 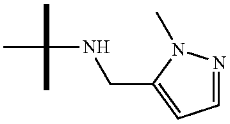 |
| H | $CF_3$ | 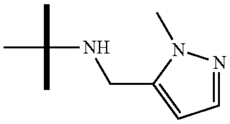 |
| H | Cl | 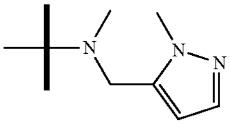 |
| H | CN | 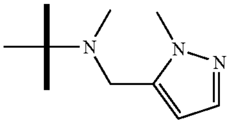 |
| H | $CF_2H$ | 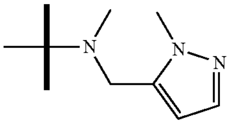 |
| H | $CF_3$ | 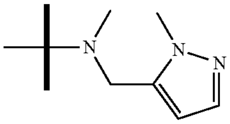 |
| H | Cl | 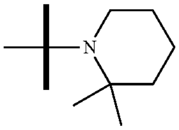 |
| H | CN | 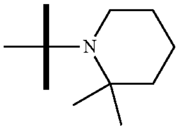 |
TABLE 1-continued
| Ra | Rb | Rc |
|---|---|---|
| H | $CF_2H$ | 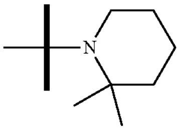 |
| H | $CF_3$ | 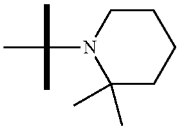 |
| H | Cl | 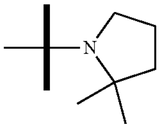 |
| H | CN | 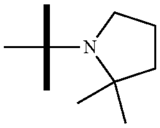 |
| H | $CF_2H$ | 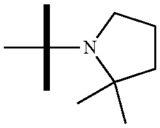 |
| H | $CF_3$ | 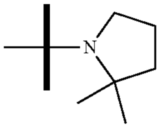 |
| H | Cl | 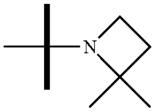 |
| H | CN | 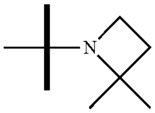 |
| H | $CF_2H$ | 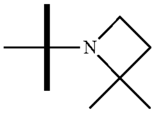 |
| H | $CF_3$ | 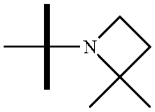 |
| H | Cl | 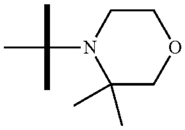 |

TABLE 1-continued
| Ra | Rb | Rc |
|---|---|---|
| H | CN | 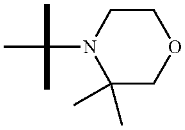 |
| H | $CF_2H$ | 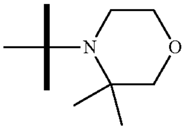 |
| H | $CF_3$ | 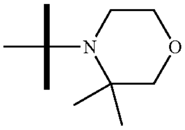 |
| H | Cl | 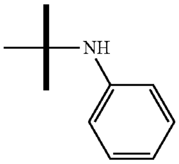 |
| H | CN | 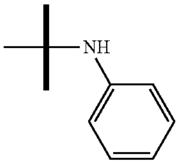 |
| H | $CF_2H$ | 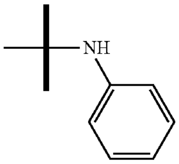 |
| H | $CF_3$ | 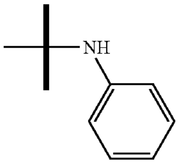 |
| H | Cl | 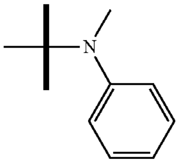 |
| H | CN | 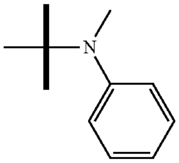 |
TABLE 1-continued
| Ra | Rb | Rc |
|---|---|---|
| H | $CF_2H$ | 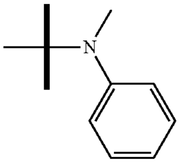 |
| H | $CF_3$ | 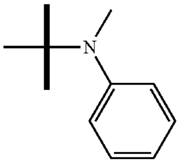 |
| H | Cl | 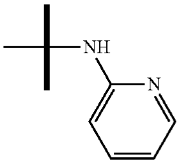 |
| H | CN | 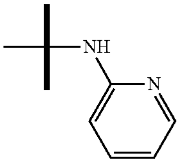 |
| H | $CF_2H$ | 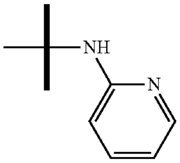 |
| H | $CF_3$ | 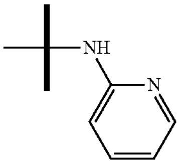 |
| H | Cl | 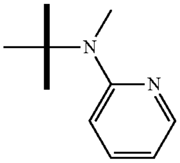 |
| H | CN | 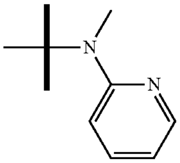 |
| H | $CF_2H$ | 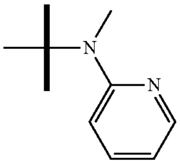 |

TABLE 1-continued
| Ra | Rb | Rc |
|---|---|---|
| H | $CF_3$ | 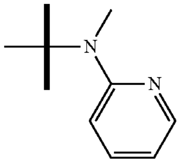 |
| H | Cl | 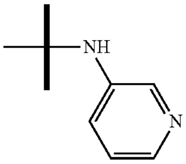 |
| H | CN | 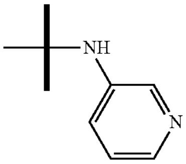 |
| H | $CF_2H$ | 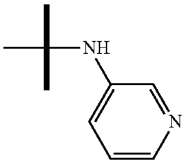 |
| H | $CF_3$ | 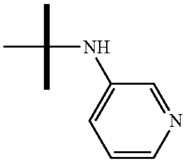 |
| H | Cl | 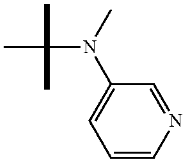 |
| H | CN | 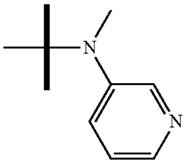 |
| H | $CF_2H$ | 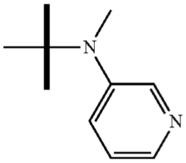 |
| H | $CF_3$ | 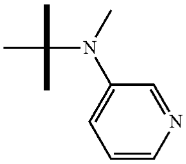 |
TABLE 1-continued
| Ra | Rb | Rc |
|---|---|---|
| H | Cl | 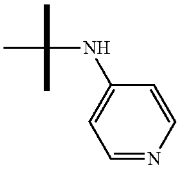 |
| H | CN | 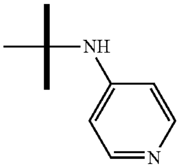 |
| H | $CF_2H$ | 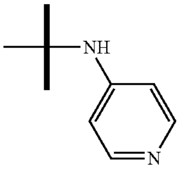 |
| H | $CF_3$ | 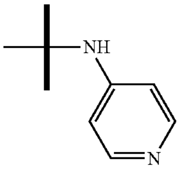 |
| H | Cl | 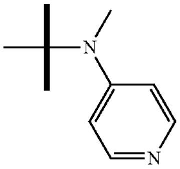 |
| H | CN | 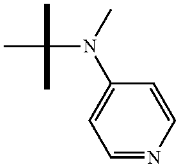 |
| H | $CF_2H$ | 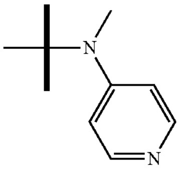 |
| H | $CF_3$ | 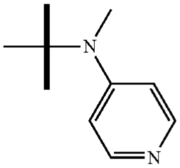 |
| H | Cl | 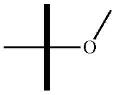 |

TABLE 1-continued
| Ra | Rb | Rc |
|---|---|---|
| H | CN | 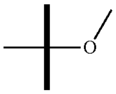 |
| H | $CF_2H$ | 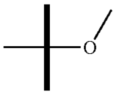 |
| H | $CF_3$ | 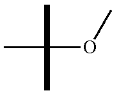 |
| H | Cl | 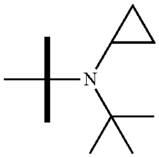 |
| H | CN | 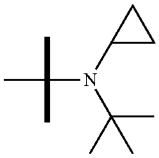 |
| H | $CF_2H$ | 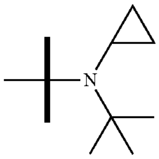 |
| H | $CF_3$ | 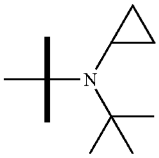 |
| H | Cl | 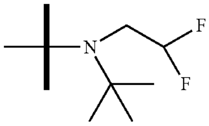 |
| H | CN | 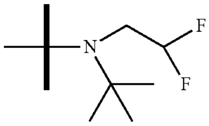 |
| H | $CF_2H$ | 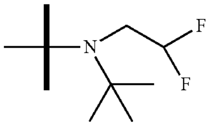 |
| H | $CF_3$ | 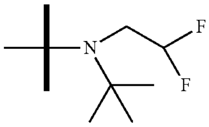 |
TABLE 1-continued
| Ra | Rb | Rc |
|---|---|---|
| H | Cl | 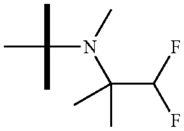 |
| H | CN | 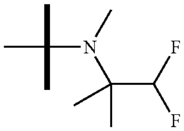 |
| H | $CF_2H$ | 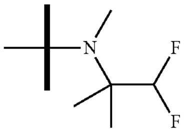 |
| H | $CF_3$ | 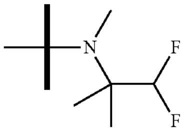 |
| H | Cl | 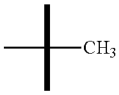 |
| H | CN | 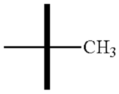 |
| H | $CF_2H$ | 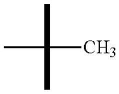 |
| H | $CF_3$ | 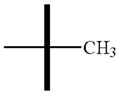 |
| H | Cl | 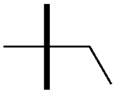 |
| H | CN | 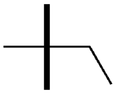 |
| H | $CF_2H$ | 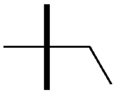 |
| H | $CF_3$ | 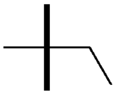 |
| H | Cl | 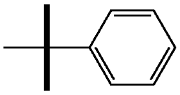 |

TABLE 1-continued
| Ra | Rb | Rc |
|---|---|---|
| H | CN | 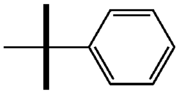 |
| H | $CF_2H$ | 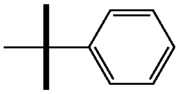 |
| H | $CF_3$ | 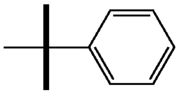 |
| H | Cl | 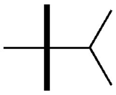 |
| H | CN | 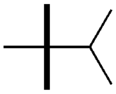 |
| H | $CF_2H$ | 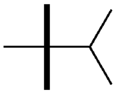 |
| H | $CF_3$ | 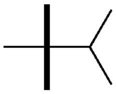 |
| H | Cl | 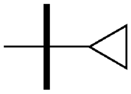 |
| H | CN | 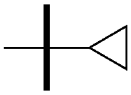 |
| H | $CF_2H$ | 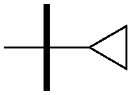 |
| H | $CF_3$ | 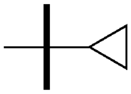 |
| H | Cl | 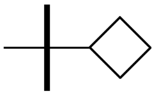 |
| H | CN | 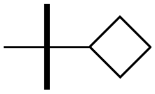 |
| H | $CF_2H$ | 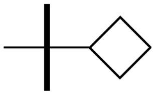 |
TABLE 1-continued
| Ra | Rb | Rc |
|---|---|---|
| H | $CF_3$ | 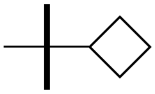 |
| H | Cl | 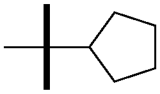 |
| H | CN | 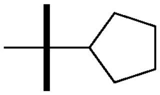 |
| H | $CF_2H$ | 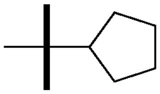 |
| H | $CF_3$ | 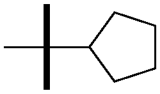 |
| H | Cl | 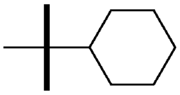 |
| H | CN | 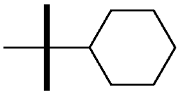 |
| H | $CF_2H$ | 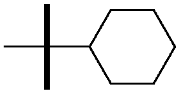 |
| H | $CF_3$ | 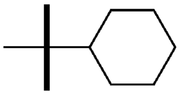 |
| H | Cl | 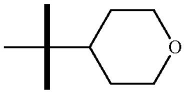 |
| H | CN | 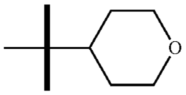 |
| H | $CF_2H$ | 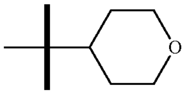 |
| H | $CF_3$ | 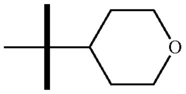 |
| H | Cl | 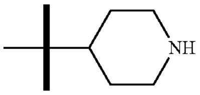 |

TABLE 1-continued
| Ra | Rb | Rc |
|---|---|---|
| H | CN | 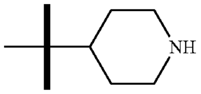 |
| H | $CF_2H$ | 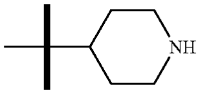 |
| H | $CF_3$ | 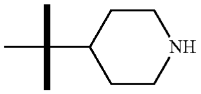 |
| H | Cl | 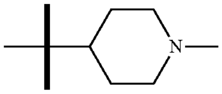 |
| H | CN | 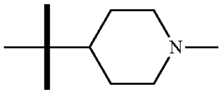 |
| H | $CF_2H$ | 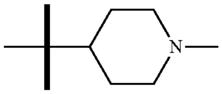 |
| H | $CF_3$ | 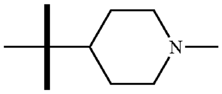 |
| H | Cl | 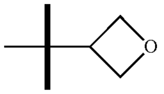 |
| H | CN | 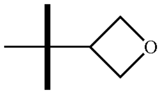 |
| H | $CF_2H$ | 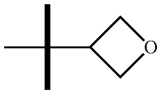 |
| H | $CF_3$ | 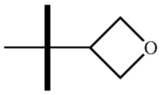 |
| H | Cl | 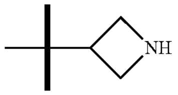 |
| H | CN | 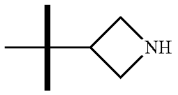 |
| H | $CF_2H$ | 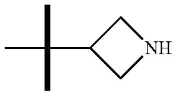 |
TABLE 1-continued
| Ra | Rb | Rc |
|---|---|---|
| H | $CF_3$ | 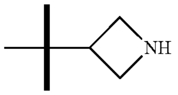 |
| H | Cl | 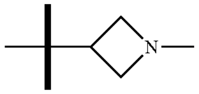 |
| H | CN | 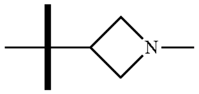 |
| H | $CF_2H$ | 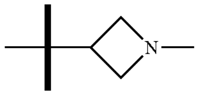 |
| H | $CF_3$ | 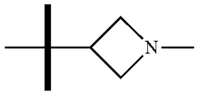 |
| H | Cl | 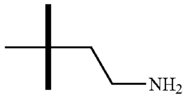 |
| H | CN | 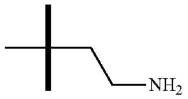 |
| H | $CF_2H$ | 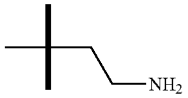 |
| H | $CF_3$ | 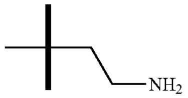 |
| H | Cl | 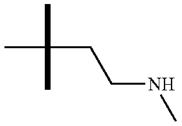 |
| H | CN | 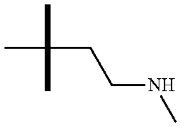 |
| H | $CF_2H$ | 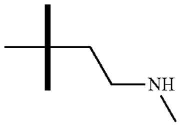 |
| H | $CF_3$ | 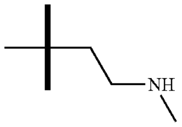 |

TABLE 1-continued
| Ra | Rb | Rc |
|---|---|---|
| H | Cl | 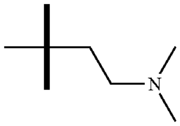 |
| H | CN | 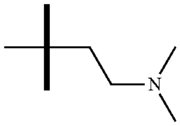 |
| H | $CF_2H$ | 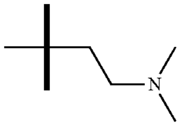 |
| H | $CF_3$ | 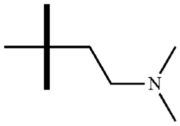 |
| H | Cl | 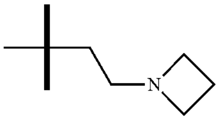 |
| H | CN | 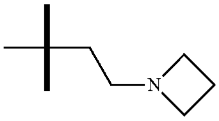 |
| H | $CF_2H$ | 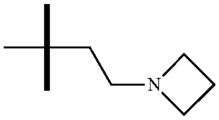 |
| H | $CF_3$ | 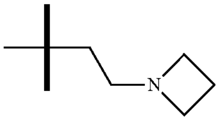 |
| H | Cl | 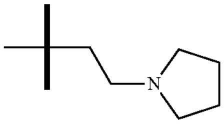 |
| H | CN | 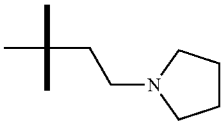 |
| H | $CF_2H$ | 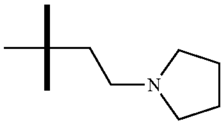 |
TABLE 1-continued
| Ra | Rb | Rc |
|---|---|---|
| H | $CF_3$ | 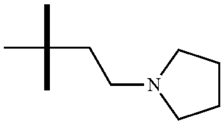 |
| H | Cl | 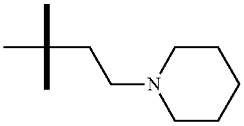 |
| H | CN | 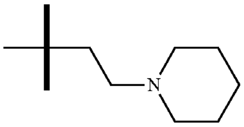 |
| H | $CF_2H$ | 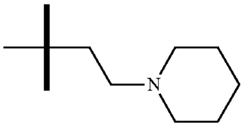 |
| H | $CF_3$ | 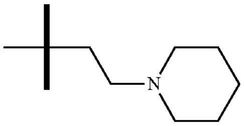 |
| H | Cl | 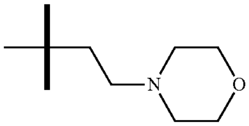 |
| H | CN | 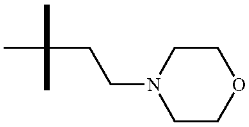 |
| H | $CF_2H$ | 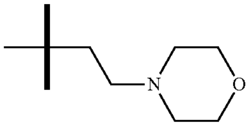 |
| H | $CF_3$ | 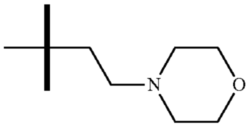 |
| H | Cl | 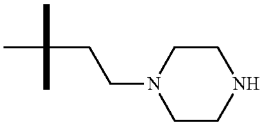 |
| H | CN | 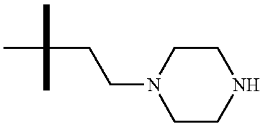 |

TABLE 1-continued

| Ra | Rb | Rc |
|---|---|---|
| H | $CF_2H$ | 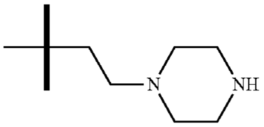 |
| H | $CF_3$ | 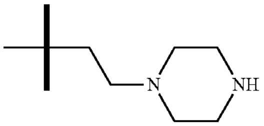 |
| H | Cl | 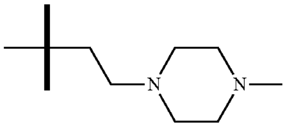 |
| H | CN | 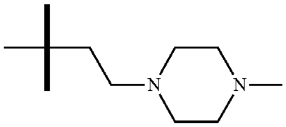 |
| H | $CF_2H$ | 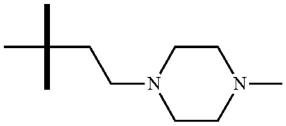 |
| H | $CF_3$ | 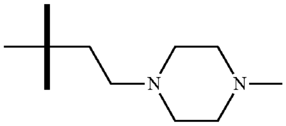 |

Example 297

Cell Proliferation

Human tumor cell lines were cultured in the appropriate media (DMEM and RPMI) supplemented with penicillin G (100 U/ml), streptomycin (100 μg/ml), 10% FBS in a humidified atmosphere of 5% $CO_2$ maintained at 37° C. Exponentially growing cells were seeded at 2,500 cells/well in 96 well plates prior to drug treatment. The following day, cells were treated with either DMSO (vehicle control) or eIF4A inhibitors at the appropriate dose for 72 hours at 37° C. Following compound treatment, cell proliferation was assessed by CellTiter-Glo assay (Promega, Madison WI) according to the manufacturer's protocol. Dose-response curves were fitted by non-linear regression (sigmoidal dose response model) using KaleidaGraph (Synergy Software, Reading PA) and $IC_{50}$ values were calculated.

The results of these assays with MDA-MB-231 human breast cancer cells are set forth in Table 2 below. To this end, $IC_{50}$ values of less than 100 nM are labelled as "+++", from 100 nM to 1000 nM are labelled as "++", and greater than 1000 nM are labelled as "+" (NA means "not available").

TABLE 2

| MDA-MB-231 cell proliferation assay ($IC_{50}$) | | | |
|---|---|---|---|
| Cpd. No. | $IC_{50}$ | Cpd. No. | $IC_{50}$ |
| 1F | ++ | 2F | ++ |
| 3F | +++ | 4F | ++ |
| 5F | ++ | 6F | ++ |
| 7F | ++ | 8F | ++ |
| 9F | + | 10F | + |
| 11F | ++ | 12F | + |
| 13F | + | 14F | ++ |
| 15F | + | 16F | ++ |
| 17F | ++ | 18F | +++ |
| 19F | ++ | 20F | +++ |
| 21F | + | 22F | ++ |
| 23F | + | 24F | + |
| 25F | + | 26F | ++ |
| 27F | ++ | 28F | ++ |
| 29F | + | 30F | ++ |
| 31F | + | 32F | + |
| 33Fa | ++ | 33Fb | + |
| 34F | + | 35F | + |
| 36F | + | 37F | + |
| 38F | + | 39F | ++ |
| 40Fa | NA | 40Fb | ++ |
| 40Fc | NA | 41Fa | + |
| 41Fb | ++ | 41Fc | + |
| 42F | ++ | 43F | + |
| 44F | + | 45F | + |
| 46F | + | 47F | + |
| 48F | + | 49F | ++ |
| 50F | ++ | 51F | ++ |
| 52F | ++ | 53F | +++ |
| 54F | ++ | 55F | ++ |
| 56F | + | 57F | + |
| 58F | + | 59F | + |
| 60F | + | 61F | + |
| 62F | ++ | 63F | + |
| 64F | +++ | 65F | ++ |
| 66F | +++ | 67F | ++ |
| 68F | ++ | 69F | ++ |
| 70F | ++ | 71F | +++ |
| 72F | ++ | 73F | +++ |
| 74F | +++ | 75F | ++ |
| 76F | +++ | 77F | +++ |
| 78F | ++ | 79F | + |
| 80F | + | 81F | +++ |
| 82F | + | 83F | +++ |
| 84F | + | 85F | + |
| 86F | + | 87F | +++ |
| 88F | +++ | 89F | +++ |
| 90F | +++ | 91F | + |
| 92F | + | 93F | + |
| 94F | + | 95F | ++ |
| 96F | + | 97F | ++ |
| 98F | ++ | 99F | + |
| 100F | + | 101F | ++ |
| 102F | ++ | 103F | +++ |
| 104F | ++ | 105F | + |
| 106F | ++ | 107F | ++ |
| 108F | ++ | 109F | ++ |
| 110F | ++ | 111F | +++ |
| 112F | ++ | 113F | ++ |
| 114F | +++ | 115F | ++ |
| 116F | +++ | 117F | + |
| 118F | ++ | 119F | ++ |
| 120F | +++ | 121F | ++ |
| 122F | ++ | 123F | ++ |
| 124F | ++ | 125F | + |
| 126F | ++ | 127F | ++ |
| 128F | ++ | 129F | + |
| 130F | + | 131F | + |
| 132F | + | 133F | + |
| 134F | NA | 135F | +++ |
| 136F | +++ | 137F | +++ |
| 138F | +++ | 139F | +++ |
| 140F | +++ | 141F | ++ |
| 142F | +++ | 143F | +++ |
| 144F | +++ | 145F | +++ |
| 146F | +++ | 147F | +++ |

TABLE 2-continued

| MDA-MB-231 cell proliferation assay ($IC_{50}$) | | | |
|---|---|---|---|
| Cpd. No. | $IC_{50}$ | Cpd. No. | $IC_{50}$ |
| 148F | + | 149F | + |
| 150F | +++ | 151F | +++ |
| 152F | +++ | 153F | ++ |
| 154F | ++ | 155F | ++ |
| 156Fa | +++ | 156Fb | +++ |
| 156Fc | +++ | 157Fa | ++ |
| 157Fb | ++ | 157Fc | ++ |
| 158Fa | +++ | 158Fb | +++ |
| 158Fc | +++ | 159Fa | +++ |
| 159Fb | +++ | 159Fc | +++ |
| 160Fa | ++ | 160Fb | + |
| 161F | + | 162F | ++ |
| 163F | ++ | 164F | ++ |
| 165F | ++ | 166F | ++ |
| 167F | ++ | 168F | + |
| 169F | + | 170F | +++ |
| 171F | ++ | 172F | +++ |
| 173F | +++ | 174F | +++ |
| 175F | +++ | 176F | ++ |
| 177F | ++ | 178F | +++ |
| 179F | +++ | 180F | +++ |
| 181F | +++ | 182F | +++ |
| 183F | +++ | 184F | +++ |
| 185F | +++ | 186F | +++ |
| 187F | +++ | 188F | +++ |
| 189F | ++ | 190F | ++ |
| 191F | ++ | 192F | + |
| 193F | ++ | 194F | + |
| 195F | ++ | 196F | +++ |
| 197F | ++ | 198Fa | +++ |
| 198Fb | +++ | 199F | +++ |
| 200F | +++ | 201 | +++ |
| 202F | +++ | 203F | +++ |
| 204F | +++ | 205F | +++ |
| 206F | +++ | 207Fa | ++ |
| 207Fb | ++ | 208Fa | ++ |
| 208Fb | ++ | 209F | +++ |
| 210F | +++ | 211Fa | +++ |
| 211Fb | +++ | 212F | +++ |
| 213F | +++ | 214F | ++ |
| 215F | +++ | 216F | +++ |
| 217F | +++ | 218F | +++ |
| 219F | +++ | 220F | +++ |
| 221F | +++ | 222F | +++ |
| 223F | NA | 224F | +++ |
| 225F | +++ | 226F | +++ |
| 227F | + | 228F | + |
| 229F | +++ | 230F | +++ |
| 231F | +++ | 232F | +++ |
| 233F | ++ | 234F | + |
| 235F | +++ | 236F | ++ |
| 237F | +++ | 238F | ++ |
| 239F | +++ | 240F | ++ |
| 241F | +++ | 242F | ++ |
| 243F | ++ | 244F | +++ |
| 245F | ++ | 246F | ++ |
| 247F | +++ | 248F | +++ |
| 249F | +++ | 250F | + |
| 251F | +++ | 252F | +++ |
| 253F | +++ | 254F | +++ |
| 255F | ++ | 256F | +++ |
| 257F | +++ | 256F | +++ |
| 257F | +++ | 258F | +++ |
| 259F | ++ | 260F | +++ |
| 261F | +++ | 262F | +++ |
| 263F | +++ | 264F | +++ |
| 265F | ++ | 266F | +++ |
| 267F | ++ | 268F | ++ |
| 269F | +++ | 270F | ++ |
| 271F | ++ | 272F | +++ |
| 273F | +++ | 274F | ++ |
| 275F | +++ | 276F | ++ |
| 277F | +++ | 278F | ++ |
| 279F | +++ | 280F | ++ |
| 281F | ++ | 282F | ++ |
| 283F | ++ | 284F | ++ |

TABLE 2-continued

| MDA-MB-231 cell proliferation assay ($IC_{50}$) | | | |
|---|---|---|---|
| Cpd. No. | $IC_{50}$ | Cpd. No. | $IC_{50}$ |
| 285F | ++ | 286F | ++ |
| 287F | + | 288F | +++ |
| 289F | ++ | 290F | ++ |
| 291F | ++ | 292F | +++ |
| 293F | +++ | 294F | +++ |
| 295F | +++ | | |

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled.

The invention claimed is:

1. A compound having the structure:

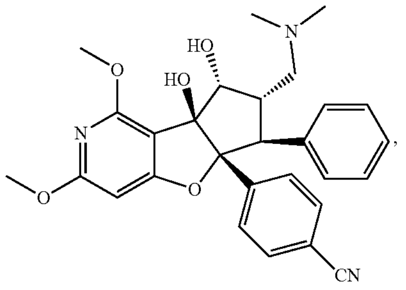 [SMILES: COc1cc2c(c(OC)n1)[C@]1(O)[C@H](O)[C@H](CN(C)C)[C@@H](c3ccccc3)[C@]1(c1ccc(C#N)cc1)O2]

or a pharmaceutically acceptable salt thereof.

2. A compound having the structure:

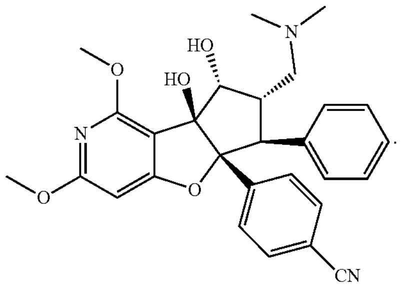 [SMILES: COc1cc2c(c(OC)n1)[C@]1(O)[C@H](O)[C@H](CN(C)C)[C@@H](c3ccccc3)[C@]1(c1ccc(C#N)cc1)O2]

3. A method for treating an eIF4A dependent condition in a mammal in need thereof comprising administering to the mammal a therapeutically effective amount of a compound having the structure:

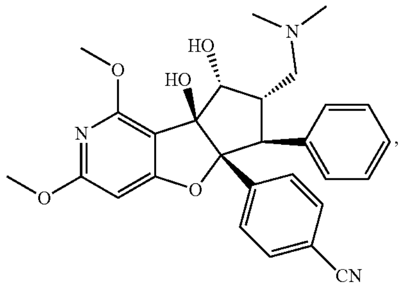 [SMILES: COc1cc2c(c(OC)n1)[C@]1(O)[C@H](O)[C@H](CN(C)C)[C@@H](c3ccccc3)[C@]1(c1ccc(C#N)cc1)O2]
or a pharmaceutically acceptable salt thereof,
wherein the eIF4A dependent condition is breast cancer.
4. The method of claim 3, wherein the eIF4A dependent condition is triple-negative breast cancer, HER2 positive breast cancer, or a hormone receptor positive breast cancer.
* * * * *